(12) United States Patent
Guzi et al.

(10) Patent No.: US 8,673,924 B2
(45) Date of Patent: *Mar. 18, 2014

(54) SUBSTITUTED PYRAZOLO[1,5-A]PYRIMIDINES AS CYCLIN DEPENDENT KINASE INHIBITORS

(75) Inventors: Timothy J. Guzi, Chatham, NJ (US); Kamil Paruch, Garwood, NJ (US); Michael P. Dwyer, Scotch Plains, NJ (US); Ronald J. Doll, Convent Station, NJ (US); Viyyoor M. Girijavallabhan, Parsippany, NJ (US); Alan Mallams, Hackettstown, NJ (US); Carmen S. Alvarez, Livingston, NJ (US); Kartik M. Keertikar, East Windsor, NJ (US); Jocelyn Rivera, Monmouth Junction, NJ (US); Tin-Yau Chan, Edison, NJ (US); Vincent S. Madison, Mountain Lakes, NJ (US); Thierry O. Fischmann, Scotch Plains, NJ (US); Lawrence W. Dillard, Skillman, NJ (US); Vinh D. Tran, Fountain Valley, CA (US); Zhenmin He, Shanghai (CN); Ray Anthony James, Bensalem, PA (US); Haengsoon Park, Plainsboro, NJ (US); Vidyadhar M. Paradkar, Somerville, NJ (US); Douglas Walsh Hobbs, Yardley, PA (US); Paul Kirschmeier, Basking Ridge, NJ (US); Rajat Bannerji, Morristown, NJ (US)

(73) Assignees: Merck Sharp & Dohme Corp., Rahway, NJ (US); Pharmacopeia, LLC, San Diego, CA (US)

( * ) Notice: Subject to any disclaimer, the term of this patent is extended or adjusted under 35 U.S.C. 154(b) by 550 days.

This patent is subject to a terminal disclaimer.

(21) Appl. No.: 11/788,847

(22) Filed: Apr. 20, 2007

(65) Prior Publication Data

US 2008/0050384 A1 Feb. 28, 2008

Related U.S. Application Data

(60) Continuation-in-part of application No. 11/396,079, filed on Mar. 31, 2006, now abandoned, which is a division of application No. 10/776,988, filed on Feb. 11, 2004, now Pat. No. 7,119,200, which is a continuation-in-part of application No. 10/654,546, filed on Sep. 3, 2003, now Pat. No. 7,161,003.

(60) Provisional application No. 60/421,959, filed on Oct. 29, 2002, provisional application No. 60/408,027, filed on Sep. 4, 2002.

(51) Int. Cl.
*C07D 487/04* (2006.01)
*A61K 31/519* (2006.01)
*A61P 35/00* (2006.01)

(52) U.S. Cl.
USPC ............................ 514/259.3; 544/281

(58) Field of Classification Search
USPC .............. 544/281, 117, 61; 514/259.3, 233.2, 514/218, 228.5; 540/575
See application file for complete search history.

(56) References Cited

U.S. PATENT DOCUMENTS

| 3,907,799 A | 9/1975 | O'Brien et al. |
| 5,571,813 A | 11/1996 | Rühter et al. |
| 5,602,136 A | 2/1997 | Rühter et al. |

(Continued)

FOREIGN PATENT DOCUMENTS

| DE | 10223917 | 12/2003 |
| EP | 0628559 | 4/2002 |

(Continued)

OTHER PUBLICATIONS

Fischer, P.M.; Gianella-Borrador A.; CDK inhibitors in clinical development for the treatment of cancer, Expert. Opin. Investig. Drugs; 2003; 12(6); 955-970.*

(Continued)

*Primary Examiner* — Susanna Moore
(74) *Attorney, Agent, or Firm* — Richard S. Parr; Laura M. Ginkel

(57) ABSTRACT

In its many embodiments, the present invention provides a method of inhibiting one or more cyclin dependent kinases in a patient comprising administering to said patient a therapeutically effective amount of at least one pyrazolo[1,5-a]pyrimidine compound or a pharmaceutical composition comprising such compound, and methods of treatment, prevention, inhibition, or amelioration of one or more diseases associated with the CDKs using such compounds or pharmaceutical compositions. An example pyrazolo[1,5-a]pyrimidine compound useful in the present invention is shown below:

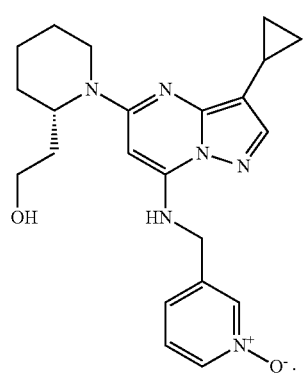

25 Claims, No Drawings

(56) References Cited

U.S. PATENT DOCUMENTS

| | | | |
|---|---|---|---|
| 5,602,137 | A | 2/1997 | Rühter et al. |
| 6,107,305 | A | 8/2000 | Misra et al. |
| 6,180,627 | B1 | 1/2001 | Blagg et al. |
| 6,383,790 | B1 | 5/2002 | Shokat |
| 6,413,974 | B1 | 7/2002 | Dumont et al. |

FOREIGN PATENT DOCUMENTS

| | | |
|---|---|---|
| WO | WO 91/18904 | 12/1991 |
| WO | WO 92/18504 | 10/1992 |
| WO | WO 95/35298 | 12/1995 |
| WO | WO 99/10325 | 3/1999 |
| WO | WO 00/26210 | 5/2000 |
| WO | WO 02/10162 | 2/2002 |
| WO | WO 02/22610 | 3/2002 |
| WO | WO 02/32893 | 4/2002 |
| WO | WO 02/40485 | 5/2002 |
| WO | WO 02/50079 | 6/2002 |
| WO | WO 02/64211 | 8/2002 |
| WO | WO 03/091256 | 11/2003 |
| WO | WO 03/101993 | 12/2003 |
| WO | WO 2007/044449 | 4/2007 |

OTHER PUBLICATIONS

Fischer, P.M.; Gianella-Borradori, A.; Recent progress in the discovery and development of cyclin-dependent kinase inhibitors, I Expert. Opin. Investig. Drugs; 2005; 14(4); 457-477. I.*
Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Vippagunta et. al., "Crystalline Solids," Advanced Drug Delivery Reviews, vol. 48, pp. 3-26 (2001).*
Gavezzotti, "Are Crystal Structures Predicatable?" Acc. Chem. Res., vol. 27, pp. 309-314 (1994).*
Anderson et al, "Preparation of Water-Soluble Compounds Through Salt Formation", The Practice of Medicinal Chemistry, pp. 739-754 (1996).
Berge et al, "Pharmaceutical Salts", Journal of Pharmaceutical Sciences, vol. 66, No. 1, pp. 1-19 (1977).
Bible et al., "Cytotoxic Synergy Between Flavopiridol (NSC 649890, L86-8275) and Various Antineoplastic Agents: The Importance of Sequence of Administration", Cancer Research, vol. 57, pp. 3375-3380 (Aug. 15, 1997).
Feng et al, "Discovery of a Novel, Selective, and Orally Bioavailable Class of Thrombin Inhibitors Incorporating Aminopyridyl Moieties at the P1 Position", J. Med. Chem., vol. 40, pp. 3726-3733 (1997).
Gennaro (ed.), "Remington's Pharmaceutical Sciences", 18th Edition, Mack Publishing Co., Easton, Pennsylvania (1990).
Gould, "Salt Selection for Basic Drugs", International J. of Pharmaceutics, vol. 33, pp. 201-217 (1986).
Greene et al, Protective Groups in Organic Synthesis, Wiley, New York (1981).
Gudmundsson et al, Synthesis of Novel Imidazo[1,2-α]pyridines with Potent Activity Against Herpesviruses, Organic Letters, vol. 5, No. 8, pp. 1369-1372 (2003).
Gupton et al, An Alternative Preparation of the 2-Dimethylaminomethylene-1,3-bis (dimethylimmonio)propane Salt from Phosphonoacetic Acids and Some Applications in Heterocyclic Synthesis, J. Heterocyclic Chem., vol. 28, pp. 1281-1285 (1991).
Heinisch et al, "Synthesen und Reaktionen von Pyridazinderivaten, 3. Mitt.", Monatschefte fur Chemie, vol. 104, pp. 1372-1382 (1973).
Higuchi et al, "Pro-Drugs as Novel Delivery Systems", vol. 14, A.C.S. Symposium Series (1987).
Hosoi et al, "Evidence for cdk5 as a Major Activity Phosphorylating Tau Protein in Porcine Brain Extract", J. Biochem., vol. 117, pp. 741-749 (1995).
Kim et al, "Discovery of Aminothiazole Inhibitors of Cyclin-Dependent Kinase 2: Synthesis, X-ray Crystallographic Analysis, and Biological Activities", Journal of Medical Chemistry, vol. 45, pp. 3905-3927 (2002).
López-Rodriguez et al, Design, Synthesis and Biological Evaluation of Novel Arachidonic Acid Derivatives as Highly Potent and Selective Endocannabinoid Transporter Inhibitors, J. Med. Chem., vol. 44, pp. 4505-4508 (2001).
Makisumi, "Studies on the Azaindolizine Compounds. XI. Synthesis of 6,7-Disubstituted Pyrazolo[1,5-α]pyrimidines", Chem. Pharm. Bull., vol. 10, pp. 620-626 (1962).
Meijer et al, "Biochemical and Cellular Effects of Roscovitine, a Potent and Selective Inhibitor of the Cyclin-Dependent Kinases CDC2, CDK2 and CDK5", Eur. J. Biochem, vol. 243, pp. 527-536 (1997).
Novinson et al, "Synthesis and Antimicrobial Activity of Some Novel Heterocycles. Azolo-αs-triazines[1]" Journal of Medicinal Chemistry, vol. 19, No. 4, pp. 517-520 (1976).
Novinson et al, "Synthesis and Antifungal Properties of Certain 7-Alkylaminopyrazolo[1,5-α]pyrimidines", J. Med. Chem., vol. 20, No. 2, pp. 296-299 (1977).
Ongkeko et al, "Inactivation of Cdc2 Increases the Level of Apoptosis Induced by DNA Damage", J. Cell Sci., vol. 108, p. 2897 (1995).
Ragan et al, "Shock Sensitivity of a Vinamidinium Bis-Perchlorate Reagent and Demonstration of a Lower Energy Alternative", Synlett, vol. 8, pp. 1172-1174 (2000).
Roche, "Bioreversible Carriers in Drug Design", American Pharmaceutical Association and Pergamon Press (1987).
Senderowicz et al, "Phase I Trial of Continous Infusion Flavopiridol, a Novel Cyclin-Dependent Kinase Inhibitor, in Patients with Refractory Neoplasmns", Journal of Clinical Oncology, vol. 16, No. 9, pp. 2986-2999 (Sep. 1998).
Shiota et al, "Synthesis and Structure-Activity Relationship of a New Series of Potent Angiotensin II Receptor Antagonists: Pyrazolo [1,5-α]pyrimidine Derivatives", Chem. Pharm. Bull., vol. 47, No. 7, pp. 928-938 (1999).
Shiota et al, "Regioselective Reactions of Organozinc Reagents with 2,4-Dichloroquinoline and 5,7-Dichloropyrazolo[1,5-α]pyrimidine", Journal of Organic Chemistry, vol. 64, pp. 453-457 (1999).
Vesely et al, "Inhibition of Cyclin-Dependent Kinases by Purine Analogues", Eur. J. Biochem, vol. 224, pp. 771-786 (1994).
The Orange Book (Food & Drug Administration, Washington, DC (http://www.accessdata.fda.gov/scripts/cder/ob/default.cfm, May 6, 2010.
International Search Report for related case PCT/US2008/004907, mailed Jul. 1, 2008.
Brief Report: Randomized Phase 2 Study of the Cyclin-Dependent Kinase Inhibitor Dinaciclib (MK-7965) Versus Erlotinib in Patients with Non-Small Cell Lung Cancer, 18 pages.

* cited by examiner

SUBSTITUTED PYRAZOLO[1,5-A]PYRIMIDINES AS CYCLIN DEPENDENT KINASE INHIBITORS

REFERENCE TO RELATED APPLICATIONS

This application is a Continuation-in-Part of U.S. patent application Ser. No. 11/396,079 filed Mar. 31, 2006, which is a divisional of U.S. patent application Ser. No. 10/776,988 filed Feb. 11, 2004 (now U.S. Pat. No. 7,119,200) which is a continuation-in-part of Ser. No. 10/654,546 filed Sep. 3, 2003 (now U.S. Pat. No. 7,161,003), which claims priority to U.S. provisional patent applications, Ser. Nos. 60/408,027 filed Sep. 4, 2002 and 60/421,959 filed Oct. 29, 2002.

FIELD OF THE INVENTION

The present invention relates to pyrazolo[1,5-a]pyrimidine compounds useful as protein kinase inhibitors (such as for example, the inhibitors of the cyclin-dependent kinases, mitogen-activated protein kinase (MAPK/ERK), glycogen synthase kinase 3(GSK3beta) and the like), pharmaceutical compositions containing the compounds, and methods of treatment using the compounds and compositions to treat diseases such as, for example, cancer, inflammation, arthritis, viral diseases, neurodegenerative diseases such as Alzheimer's disease, cardiovascular diseases, and fungal diseases. This application claims benefit of priority from U.S. provisional patent applications, Ser. No. 60/408,027 filed Sep. 4, 2002, and Ser. No. 60/421,959 filed Oct. 29, 2002.

BACKGROUND OF THE INVENTION

Protein kinase inhibitors include kinases such as, for example, the inhibitors of the cyclin-dependent kinases (CDKs), mitogen activated protein kinase (MAPK/ERK), glycogen synthase kinase 3 (GSK3beta), and the like. Protein kinase inhibitors are described, for example, by M. Hale et al in WO02/22610 A1 and by Y. Mettey et al in *J. Med. Chem.*, (2003) 46 222-236. The cyclin-dependent kinases are serine/threonine protein kinases, which are the driving force behind the cell cycle and cell proliferation. Individual CDK's, such as, CDK1, CDK2, CDK3, CDK4, CDK5, CDK6 and CDK7, CDK8 and the like, perform distinct roles in cell cycle progression and can be classified as either G1, S, or G2M phase enzymes. Uncontrolled proliferation is a hallmark of cancer cells, and misregulation of CDK function occurs with high frequency in many important solid tumors. CDK2 and CDK4 are of particular interest because their activities are frequently misregulated in a wide variety of human cancers. CDK2 activity is required for progression through G1 to the S phase of the cell cycle, and CDK2 is one of the key components of the G1 checkpoint. Checkpoints serve to maintain the proper sequence of cell cycle events and allow the cell to respond to insults or to proliferative signals, while the loss of proper checkpoint control in cancer cells contributes to tumorgenesis. The CDK2 pathway influences tumorgenesis at the level of tumor suppressor function (e.g. p52, RB, and p27) and oncogene activation (cyclin E). Many reports have demonstrated that both the coactivator, cyclin E, and the inhibitor, p27, of CDK2 are either over- or underexpressed, respectively, in breast, colon, nonsmall cell lung, gastric, prostate, bladder, non-Hodgkin's lymphoma, ovarian, and other cancers. Their altered expression has been shown to correlate with increased CDK2 activity levels and poor overall survival. This observation makes CDK2 and its regulatory pathways compelling targets for the development years, a number of adenosine 5'-triphosphate (ATP) competitive small organic molecules as well as peptides have been reported in the literature as CDK inhibitors for the potential treatment of cancers. U.S. Pat. No. 6,413,974, col. 1, line 23-col. 15, line 10 offers a good description of the various CDKs and their relationship to various types of cancer.

CDK inhibitors are known. For example, flavopiridol (Formula I) is a nonselective CDK inhibitor that is currently undergoing human clinical trials, A. M. Sanderowicz et al, *J. Clin. Oncol.* (1998) 16, 2986-2999.

Formula I

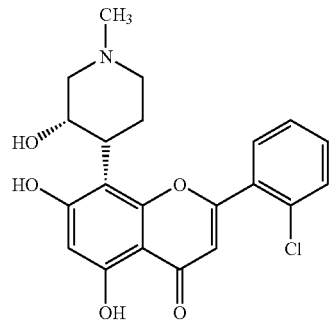

Other known inhibitors of the CDKs include, for example, olomoucine (J. Vesely et al, *Eur. J. Biochem.*, (1994) 224, 771-786) and roscovitine (I. Meijer et al, *Eur. J. Biochem.*, (1997) 243, 527-536). U.S. Pat. No. 6,107,305 describes certain pyrazolo[3,4-b]pyridine compounds as CDK inhibitors. An illustrative compound from the '305 patent has the Formula II:

Formula II

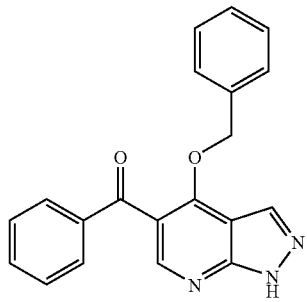

K. S. Kim et al, *J. Med. Chem.* 45 (2002) 3905-3927 and WO 02/10162 disclose certain aminothiazole compounds as CDK inhibitors.

Pyrazolopyrimidines are known. For Example, WO92/18504, WO02/50079, WO95/35298, WO02/40485, EP94304104.6, EP0628559 (equivalent to U.S. Pat. Nos. 5,602,136, 5,602,137 and 5,571,813), U.S. Pat. No. 6,383,790, *Chem. Pharm. Bull.*, (1999) 47 928, *J. Med. Chem.*, (1977) 20, 296, *J. Med. Chem.*, (1976) 19 517 and *Chem. Pharm. Bull.*, (1962) 10 620 disclose various pyrazolopyrimidines. Other publications of interest are: WO 03/101993 (published Dec. 11, 2003), WO 03/091256 (published Nov. 6, 2003), and DE 10223917 (published Dec. 11, 2003).

There is a need for new compounds, formulations, treatments and therapies to treat diseases and disorders associated with CDKs. It is, therefore, an object of this invention to provide compounds useful in the treatment or prevention or amelioration of such diseases and disorders.

SUMMARY OF THE INVENTION

In its many embodiments, the present invention provides a novel class of pyrazolo[1,5-a]pyrimidine compounds as inhibitors of cyclin dependent kinases, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the CDKs using such compounds or pharmaceutical compositions.

In one aspect, the present application discloses a compound, or pharmaceutically acceptable salts or solvates of said compound, said compound having the general structure shown in Formula III:

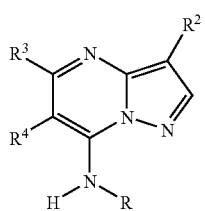

Formula III wherein:

R is H, alkyl, alkenyl, alkynyl, arylalkyl, arylalkenyl, cycloalkyl, cycloalkylalkyl, alkenylalkyl, alkynylalkyl, heterocyclyl, heterocyclylalkyl, heteroarylalkyl (including N-oxide of said heteroaryl), —(CHR$^5$)$_n$-aryl, —(CHR$^5$)$_n$—heteroaryl,

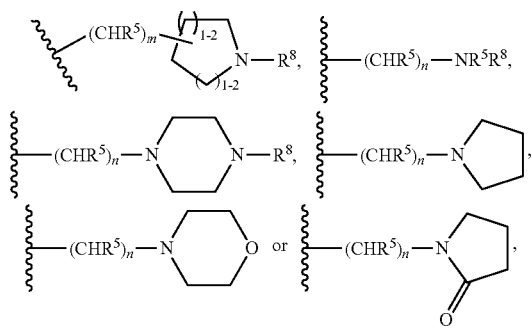

wherein each of said alkyl, alkenyl, alkynyl, aryl, cycloalkyl, heterocyclyl, and heteroaryl can be unsubstituted or optionally substituted with one or more moieties which can be the same or different, each moiety being independently selected from the group consisting of halogen, alkyl, aryl, cycloalkyl, heterocyclylalkyl, CF$_3$, OCF$_3$, CN, —OR$^5$, —NR$^5$R$^{10}$, —C(R$^4$R$^5$)$_p$—R$^9$, —N(R$^5$)Boc, —(CR$^4$R$^5$)$_p$OR$^5$, —C(O$_2$)R$^5$, —C(O)R$^5$, —C(O)NR$^5$R$^{10}$, —SO$_3$H, —SR$^{10}$, —S(O$_2$)R$^7$, —S(O$_2$)NR$^5$R$^{10}$, —N(R$^5$)S(O$_2$)R$^7$, —N(R$^5$)C(O)R$^7$ and —N(R$^5$)C(O)NR$^5$R';

R$^2$ is selected from the group consisting of R$^9$, alkyl, alkenyl, alkynyl, CF$_3$, heterocyclyl, heterocyclylalkyl, halogen, haloalkyl, aryl, arylalkyl, heteroarylalkyl, alkynylalkyl, cycloalkyl, heteroaryl, alkyl substituted with 1-6 R$^9$ groups which can be the same or different and are independently selected from the list of R$^9$ shown below, aryl substituted with 1-3 aryl or heteroaryl groups which can be the same or different and are independently selected from phenyl, pyridyl, thiophenyl, furanyl and thiazolo groups, aryl fused with an aryl or heteroaryl group, heteroaryl substituted with 1-3 aryl or heteroaryl groups which can be the same or different and are independently selected from phenyl, pyridyl, thiophenyl, furanyl and thiazolo groups, heteroaryl fused with an aryl or heteroaryl group,

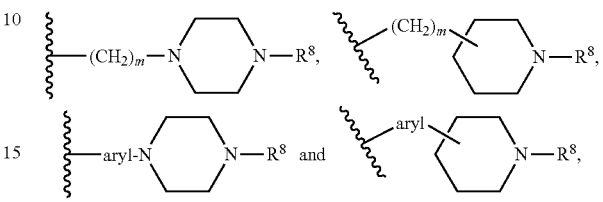

wherein one or more of the aryl and/or one or more of the heteroaryl in the above-noted definitions for R$^2$ can be unsubstituted or optionally substituted with one or more moieties which can be the same or different, each moiety being independently selected from the group consisting of halogen, —CN, —OR$^5$, —SR$^5$, —S(O$_2$)R$^6$, —S(O$_2$)NR$^5$R$^5$, —NR$^5$R$^5$, —C(O)NR$^5$R$^6$, CF$_3$, alkyl, aryl and OCF$_3$;

R$^3$ is selected from the group consisting of H, halogen, —NR$^5$R$^6$, —OR$^6$, —SR$^6$, —C(O)N(R$^5$R$^6$), alkyl, alkynyl, cycloalkyl, aryl, arylalkyl, heterocyclyl, heterocyclylalkyl, heteroaryl and heteroarylalkyl,

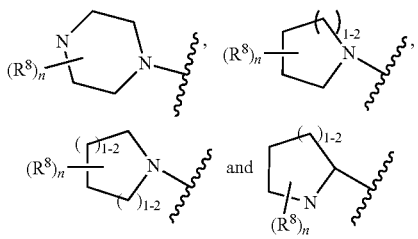

wherein each of said alkyl, cycloalkyl, aryl, arylalkyl, heterocyclyl, heterocyclylalkyl, heteroaryl and heteroarylalkyl for R$^3$ and the heterocyclyl moieties whose structures are shown immediately above for R$^3$ can be unsubstituted or optionally independently substituted with one or more moieties which can be the same or different, each moiety being independently selected from the group consisting of halogen, alkyl, aryl, cycloalkyl, CF$_3$, CN, —OCF$_3$, —(CR$^4$R$^5$)$_p$OR$^5$, —OR$^5$, —NR$^5$R$^6$, —(CR$^4$R$^5$)$_p$NR$^5$R$^6$, —C(O$_2$)R$^5$, —C(O)R$^5$, —C(O)NR$^5$R$^6$, —SR$^6$, —S(O$_2$)R$^6$, —S(O$_2$)NR$^5$R$^6$, —N(R$^5$)S(O$_2$)R$^7$, —N(R$^5$)C(O)R$^7$ and —N(R$^5$)C(O)NR$^5$R$^6$, with the proviso that no carbon adjacent to a nitrogen atom on a heterocyclyl ring carries a —OR$^5$ moiety;

R$^4$ is H, halo or alkyl;

R$^5$ is H, alkyl, aryl or cycloalkyl;

R$^6$ is selected from the group consisting of H, alkyl, alkenyl, aryl, arylalkyl, arylalkenyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, heterocyclylalkyl, CF$_3$, OCF$_3$, CN, —OR$^5$, —NR$^5$R$^{10}$, —C(R$^4$R$^5$)$_p$—R$^9$, —N(R$^5$)Boc, —(CR$^4$R$^5$)$_p$OR$^5$, —C(O$_2$)R$^5$, —C(O)R$^5$, —C(O)NR$^5$R$^{10}$, —SO$_3$H, —SR$^{10}$, —S(O$_2$)R$^7$, —S(O$_2$)NR$^5$R$^{10}$, —N(R$^5$)S(O$_2$)R$^7$, —N(R$^5$)C(O)R$^7$ and —N(R$^5$)C(O)NR$^5$R$^{10}$;

R$^{10}$ is selected from the group consisting of H, alkyl, aryl, arylalkyl, cycloalkyl, heterocyclyl, heterocyclylalkyl, heteroaryl, and heteroarylalkyl, wherein each of said alkyl, aryl, arylalkyl, cycloalkyl, heterocyclyl, heterocyclylalkyl, heteroaryl, and heteroarylalkyl can be unsubstituted or optionally substituted with one or more moieties which can be the same or different, each moiety being independently selected from the group consisting of halogen, alkyl, aryl, cycloalkyl, heterocyclylalkyl, CF$_3$, OCF$_3$, CN, —OR$^5$, —NR$^4$R$^5$, —C(R$^4$R$^5$)$_p$—R$^9$, —N(R$^5$)Boc, —(CR$^4$R$^5$) pOR$^5$, —C(O$_2$)R$^5$, —C(O)NR$^4$R$^5$, —C(O)R$^5$, —SO$_3$H, —SR$^5$, —S(O$_2$)R$^7$, —S(O$_2$)NR$^4$R$^5$, —N(R$^5$)S(O$_2$)R$^7$, —N(R$^5$)C(O)R$^7$ and —N(R$^5$)C(O)NR$^4$R$^5$;

or optionally (i) R$^5$ and R$^{10}$ in the moiety —NR$^5$R$^{10}$, or (ii) R$^5$ and R$^6$ in the moiety —NR$^5$R$^6$, may be joined together to form a cycloalkyl or heterocyclyl moiety, with each of said cycloalkyl or heterocyclyl moiety being unsubstituted or optionally independently being substituted with one or more R$^9$ groups;

R$^7$ is selected from the group consisting of alkyl, cycloalkyl, aryl, arylalkenyl, heteroaryl, arylalkyl, heteroarylalkyl, heteroarylalkenyl, and heterocyclyl, wherein each of said alkyl, cycloalkyl, heteroarylalkyl, aryl, heteroaryl and arylalkyl can be unsubstituted or optionally independently substituted with one or more moieties which can be the same or different, each moiety being independently selected from the group consisting of halogen, alkyl, aryl, cycloalkyl, CF$_3$, OCF$_3$, CN, —OR$^5$, —NR$^5$R$^{10}$, —CH$_2$OR$^5$, —C(O$_2$)R$^5$, —C(O)NR$^5$R$^{10}$, —C(O)R$^5$, —SR$^{10}$, —S(O$_2$)R$^{10}$, —S(O$_2$)NR$^5$R$^{10}$, —N(R$^5$)S(O$_2$)R$^{10}$, —N(R$^5$)C(O)R$^{10}$ and —N(R$^5$)C(O)NR$^5$R$^{10}$;

R$^8$ is selected from the group consisting of R$^6$, —OR$^6$—C(O)NR$^5$R$^{10}$, —S(O$_2$)NR$^5$R$^{10}$, —C(O)R$^7$, —C(=N—CN)—NH$_2$, —C(=NH)—NHR$^5$, heterocyclyl, and —S(O$_2$) R$^7$;

R$^9$ is selected from the group consisting of halogen, —CN, —NR$^5$R$^{10}$, —C(O$_2$)R$^6$, —C(O)NR$^5$R$^{10}$, —OR$^6$, —SR$^6$, —S(O$_2$)R$^7$, —S(O$_2$)NR$^5$R$^{10}$, —N(R$^5$)S(O$_2$)R$^7$, —N(R$^5$)C(O)R$^7$ and —N(R$^5$)C(O)NR$^5$R$^{10}$;

m is 0 to 4;
n is 1 to 4; and
p is 1 to 4, with the proviso that when R$^2$ is phenyl, R$^3$ is not alkyl, alkynyl or halogen, and that when R$^2$ is aryl, R is not

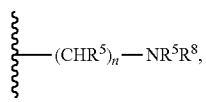

and with the further proviso that when R is arylalkyl, then any heteroaryl substituent on the aryl of said arylalkyl contains at least three heteroatoms.

The compounds of Formula III can be useful as protein kinase inhibitors and can be useful in the treatment and prevention of proliferative diseases, for example, cancer, inflammation and arthritis. They may also be useful in the treatment of neurodegenerative diseases such Alzheimer's disease, cardiovascular diseases, viral diseases and fungal diseases.

DETAILED DESCRIPTION

In one embodiment, the present invention discloses pyrazolo[1,5-a]pyrimidine compounds which are represented by structural Formula III, or a pharmaceutically acceptable salt or solvate thereof, wherein the various moieties are as described above.

In another embodiment, R is —(CHR$^5$)$_n$-aryl, —(CHR$^5$)$_n$-heteroaryl, —(CHR$^5$)$_n$-heteroaryl (with said heteroaryl being substituted with an additional, same or different, heteroaryl), —(CHR$^5$)$_n$-heterocyclyl (with said heterocyclyl being substituted with an additional, same or different, heterocyclyl), or

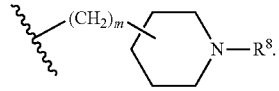

In another embodiment, R$^2$ is halogen, CF$_3$, CN, lower alkyl, alkyl substituted with —OR$^6$, alkynyl, aryl, heteroaryl or heterocyclyl.

In another embodiment, R$^3$ is H, lower alkyl, aryl, heteroaryl, cycloalkyl, —NR$^5$R$^6$,

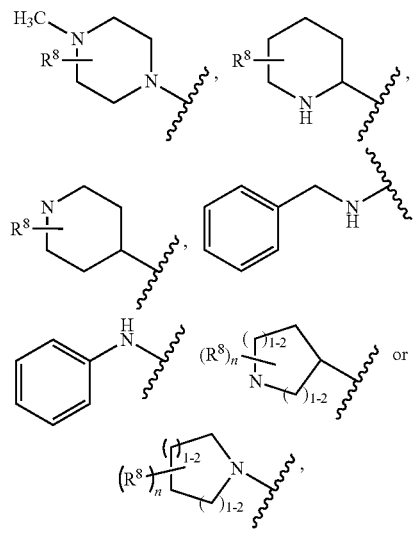

wherein said alkyl, aryl, heteroaryl, cycloalkyl and the heterocyclyl structures shown immediately above for R$^3$ are optionally substituted with one or more moieties which can be the same or different, each moiety being independently selected from the group consisting of halogen, CF$_3$, OCF$_3$, lower alkyl, CN, —C(O)R$^5$, —S(O$_2$)R$^5$, —C(=NH)—NH$_2$, —C(=CN)—NH$_2$, hydroxyalkyl, alkoxycarbonyl, —SR$^5$, and OR$^5$, with the proviso that no carbon adjacent to a nitrogen atom on a heterocyclyl ring carries a —OR$^5$ moiety.

In another embodiment, R$^4$ is H or lower alkyl.

In another embodiment, R$^5$ is H, lower alkyl or cycloalkyl.

In another embodiment, n is 1 to 2.

In an additional embodiment, R is —(CHR$^5$)$_n$-aryl, —(CHR$^5$)$_n$-heteroaryl.

In an additional embodiment, R$^2$ is halogen, CF$_3$, CN, lower alkyl, alkynyl, or alkyl substituted with —OR$^6$.

In an additional embodiment, R$^2$ is lower alkyl, alkynyl or Br.

In an additional embodiment, R$^3$ is H, lower alkyl, aryl,

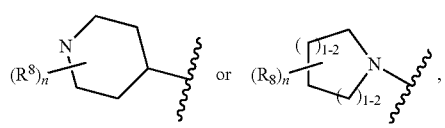

wherein said alkyl, aryl and the heterocyclyl moieties shown immediately above for $R^3$ are optionally substituted with one or more moieties which can be the same or different, each moiety being independently selected from the group consisting of halogen, $CF_3$, lower alkyl, hydroxyalkyl, alkoxy, —$S(O_2)R^5$, and CN.

In an additional embodiment, $R^4$ is H.

In an additional embodiment, $R^5$ is H, ethyl, cyclopropyl, cyclobutyl, cyclopentyl or cyclohexyl.

In an additional embodiment, $R^8$ is alkyl or hydroxyalkyl.

In an additional embodiment, n is 1.

In an additional embodiment, p is 1 or 2.

Another embodiment discloses the inventive compounds shown in Table 1, which exhibited CDK2 inhibitory activity of about 0.0001 μM to > about 5 μM. The assay methods are described later (from page 333 onwards).

TABLE 1

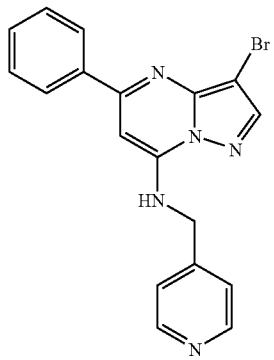 [SMILES: Brc1cnn2c(NCc3ccncc3)cc(-c3ccccc3)nc12]

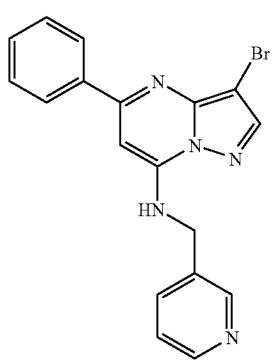 [SMILES: Brc1cnn2c(NCc3cccnc3)cc(-c3ccccc3)nc12]

TABLE 1-continued

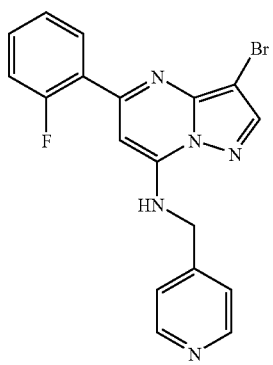 [SMILES: Fc1ccccc1-c1cc(NCc2ccncc2)n2ncc(Br)c2n1]

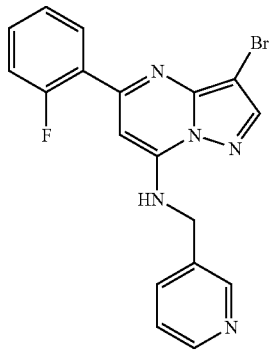 [SMILES: Fc1ccccc1-c1cc(NCc2cccnc2)n2ncc(Br)c2n1]

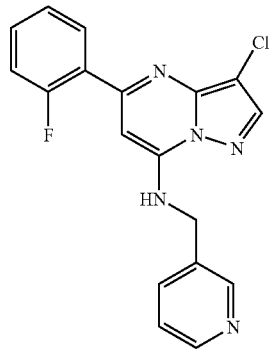 [SMILES: Fc1ccccc1-c1cc(NCc2cccnc2)n2ncc(Cl)c2n1]

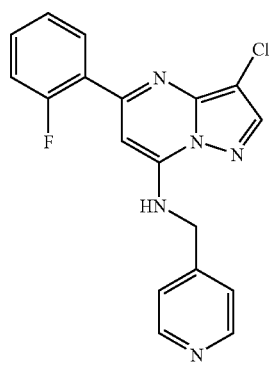 [SMILES: Fc1ccccc1-c1cc(NCc2ccncc2)n2ncc(Cl)c2n1]

TABLE 1-continued
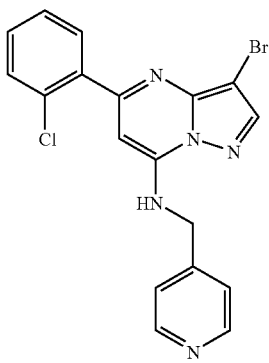 [SMILES: Clc1ccccc1-c1cc(NCc2ccncc2)n2ncc(Br)c2n1]
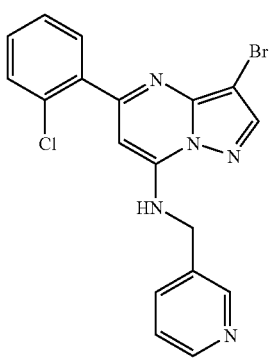 [SMILES: Clc1ccccc1-c1cc(NCc2cccnc2)n2ncc(Br)c2n1]
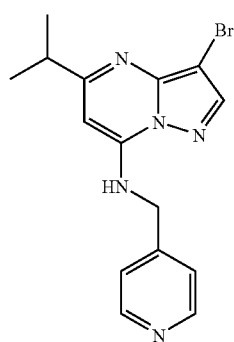
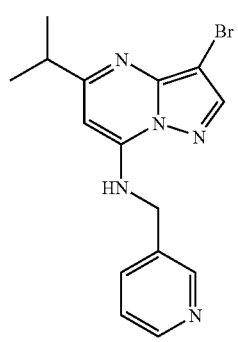 [SMILES: CC(C)c1cc(NCc2cccnc2)n2ncc(Br)c2n1]
TABLE 1-continued
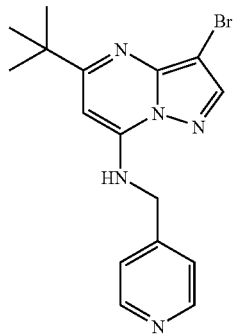 [SMILES: CC(C)(C)c1cc(NCc2ccncc2)n2ncc(Br)c2n1]
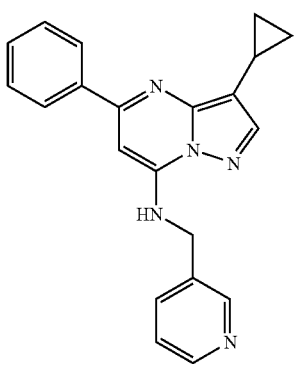 [SMILES: c1ccc(-c2cc(NCc3cccnc3)n3ncc(C4CC4)c3n2)cc1]
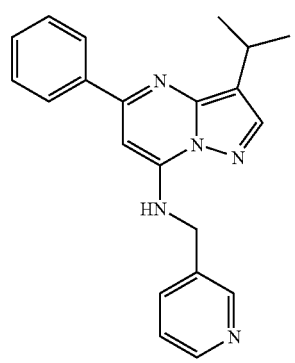 [SMILES: CC(C)c1cnn2c(NCc3cccnc3)cc(-c3ccccc3)nc12]
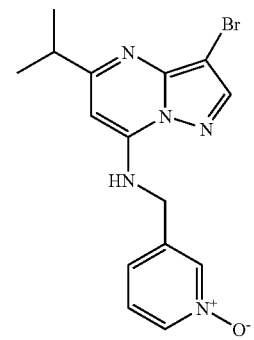 [SMILES: CC(C)c1cc(NCc2ccc[n+]([O-])c2)n2ncc(Br)c2n1]

TABLE 1-continued
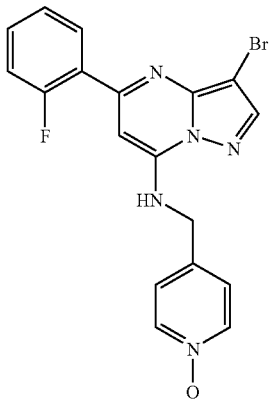
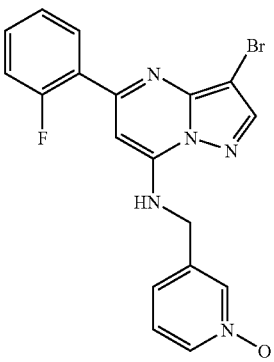
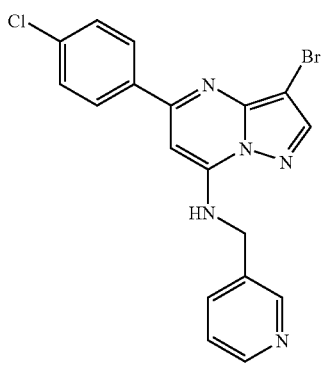 [SMILES: Clc1ccc(-c2cc(NCc3cccnc3)n3ncc(Br)c3n2)cc1]
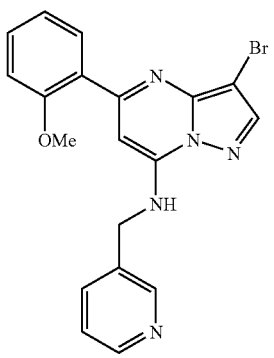 [SMILES: COc1ccccc1-c1cc(NCc2cccnc2)n2ncc(Br)c2n1]
TABLE 1-continued
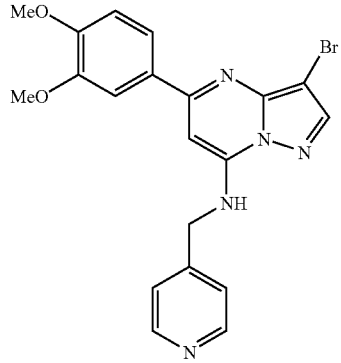 [SMILES: COc1ccc(-c2cc(NCc3ccncc3)n3ncc(Br)c3n2)cc1OC]
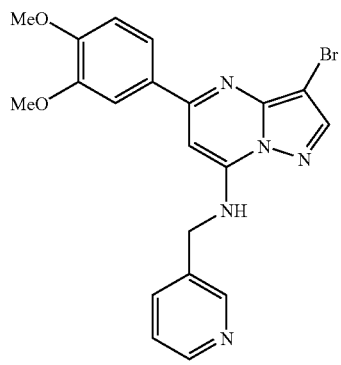 [SMILES: COc1ccc(-c2cc(NCc3cccnc3)n3ncc(Br)c3n2)cc1OC]
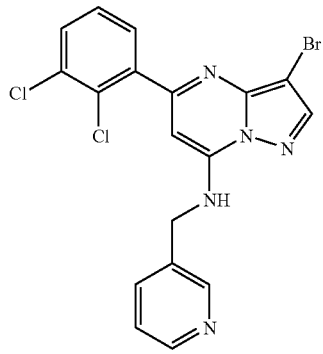 [SMILES: Clc1cccc(-c2cc(NCc3cccnc3)n3ncc(Br)c3n2)c1Cl]
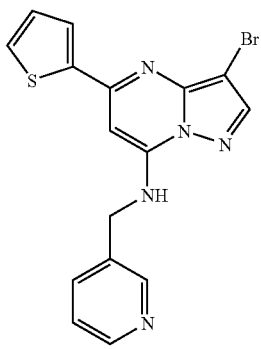 [SMILES: Brc1cnn2c(NCc3cccnc3)cc(-c3cccs3)nc12]

TABLE 1-continued
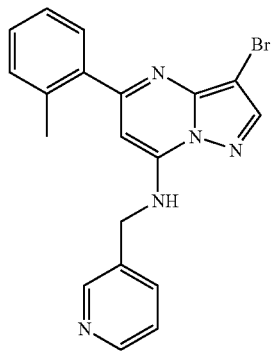 [SMILES: Cc1ccccc1-c1cc(NCc2cccnc2)n2ncc(Br)c2n1]
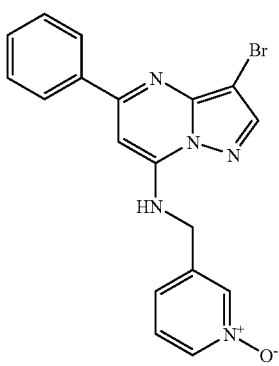 [SMILES: [O-][n+]1cccc(CNc2cc(-c3ccccc3)nc3c(Br)cnn23)c1]
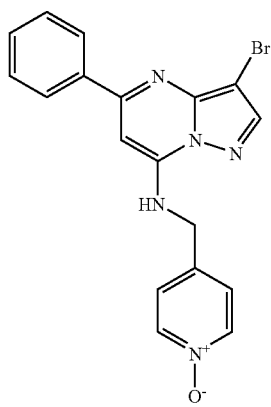 [SMILES: [O-][n+]1ccc(CNc2cc(-c3ccccc3)nc3c(Br)cnn23)cc1]
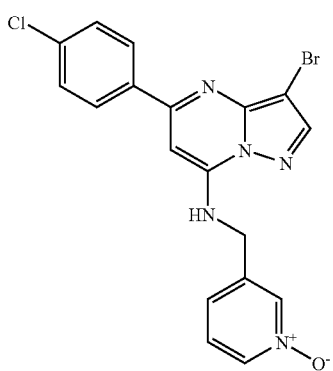 [SMILES: [O-][n+]1cccc(CNc2cc(-c3ccc(Cl)cc3)nc3c(Br)cnn23)c1]
TABLE 1-continued
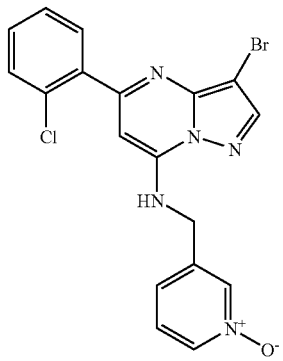 [SMILES: [O-][n+]1cccc(CNc2cc(-c3ccccc3Cl)nc3c(Br)cnn23)c1]
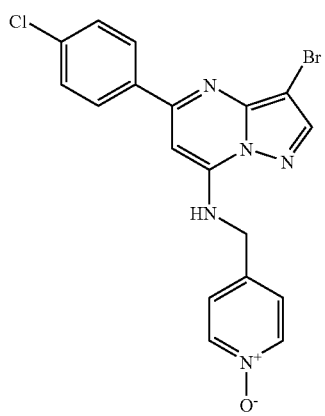 [SMILES: [O-][n+]1ccc(CNc2cc(-c3ccc(Cl)cc3)nc3c(Br)cnn23)cc1]
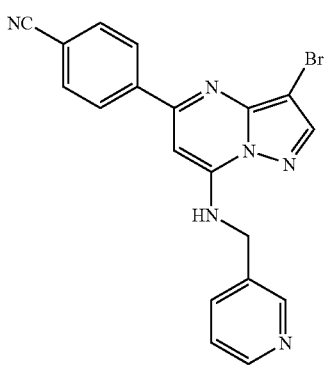
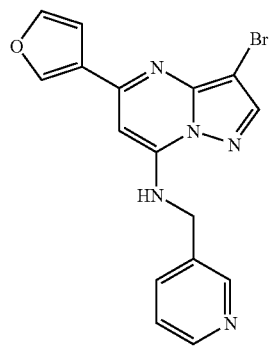 [SMILES: Brc1cnn2c(NCc3cccnc3)cc(-c3ccoc3)nc12]

TABLE 1-continued
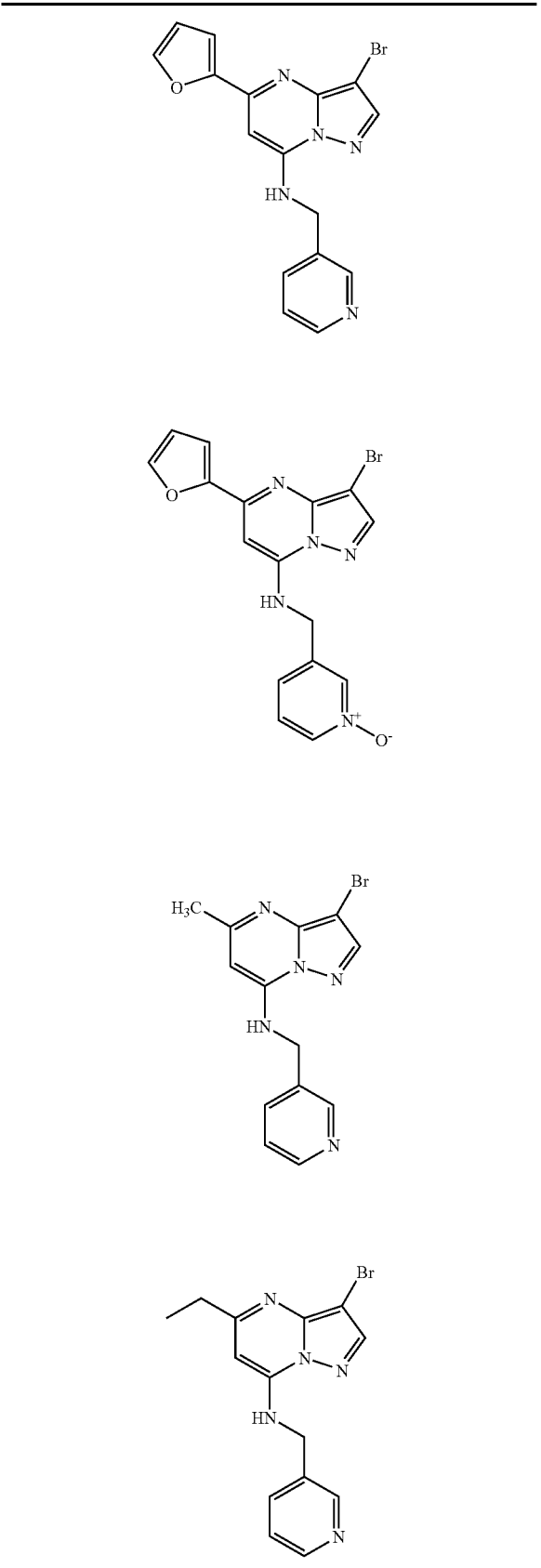
TABLE 1-continued
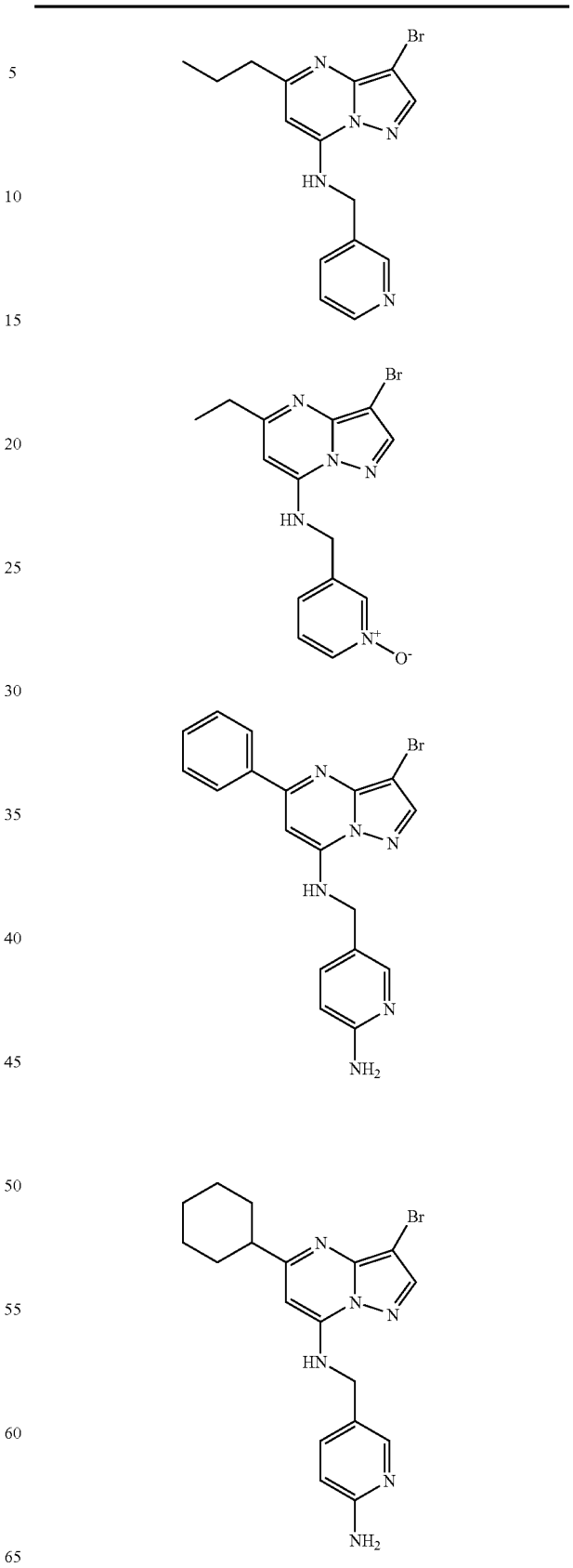

TABLE 1-continued
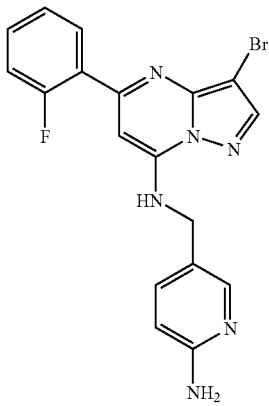
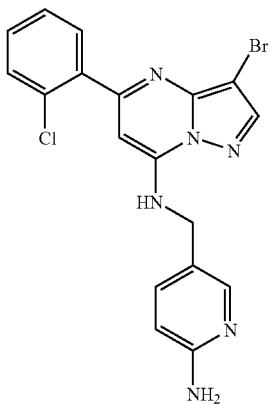
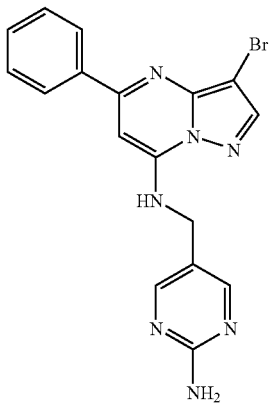 [SMILES: Nc1ncc(CNc2cc(-c3ccccc3)nc3c(Br)cnn23)cn1]
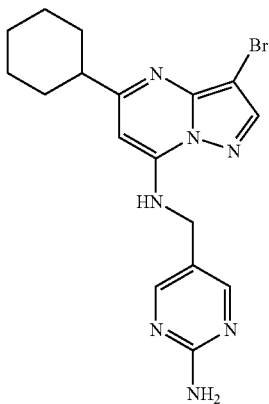 [SMILES: Nc1ncc(CNc2cc(C3CCCCC3)nc3c(Br)cnn23)cn1]
TABLE 1-continued
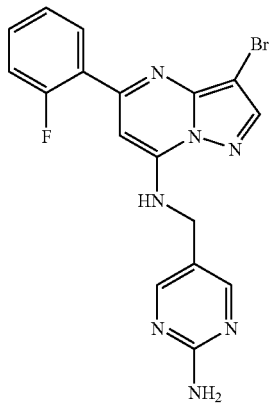
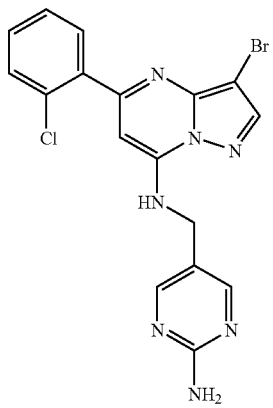
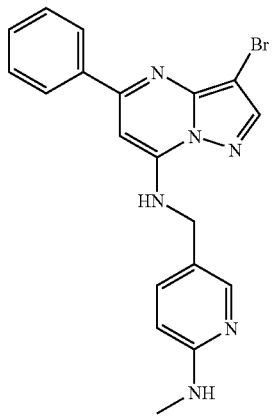 [SMILES: CNc1ccc(CNc2cc(-c3ccccc3)nc3c(Br)cnn23)cn1]
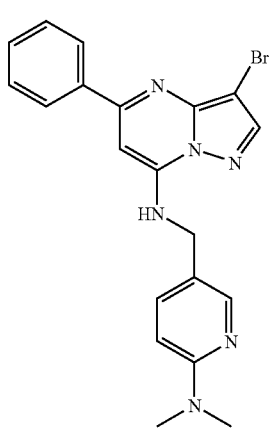 [SMILES: CN(C)c1ccc(CNc2cc(-c3ccccc3)nc3c(Br)cnn23)cn1]

TABLE 1-continued
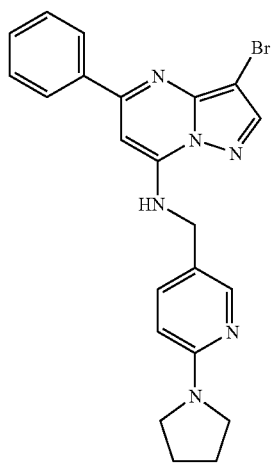 [SMILES: Brc1cnn2c(NCc3ccc(N4CCCC4)nc3)cc(-c3ccccc3)nc12]
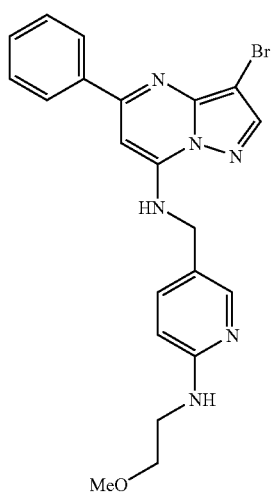 [SMILES: COCCNc1ccc(CNc2cc(-c3ccccc3)nc3c(Br)cnn23)cn1]
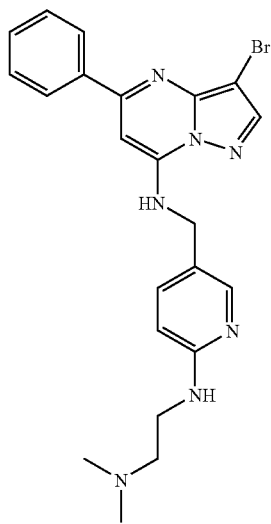 [SMILES: CN(C)CCNc1ccc(CNc2cc(-c3ccccc3)nc3c(Br)cnn23)cn1]
TABLE 1-continued
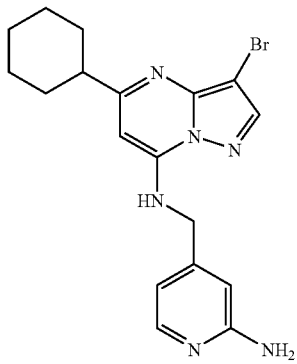 [SMILES: Nc1cc(CNc2cc(C3CCCCC3)nc3c(Br)cnn23)ccn1]
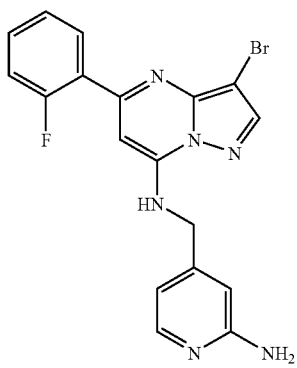
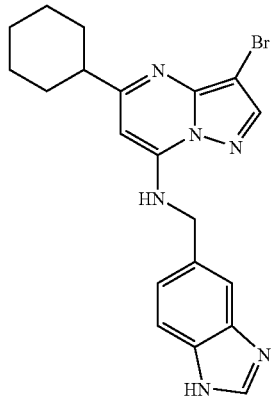 [SMILES: Brc1cnn2c(NCc3ccc4[nH]cnc4c3)cc(C3CCCCC3)nc12]
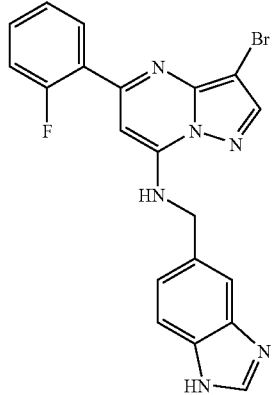 [SMILES: Fc1ccccc1-c1cc(NCc2ccc3[nH]cnc3c2)n2ncc(Br)c2n1]

TABLE 1-continued
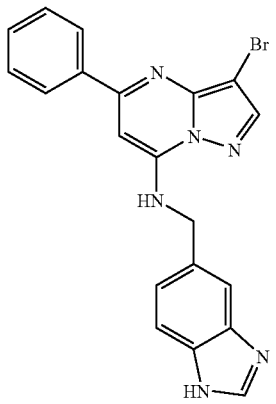 [SMILES: Brc1cnn2c(NCc3ccc4[nH]cnc4c3)cc(-c3ccccc3)nc12]
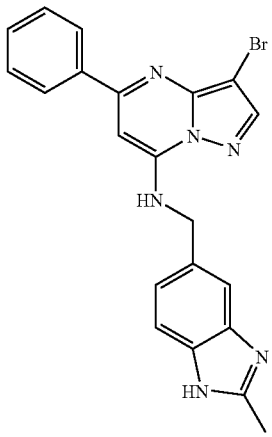
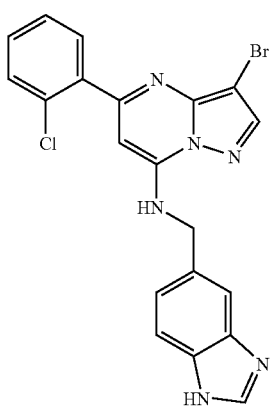 [SMILES: Clc1ccccc1-c1cc(NCc2ccc3[nH]cnc3c2)n2ncc(Br)c2n1]
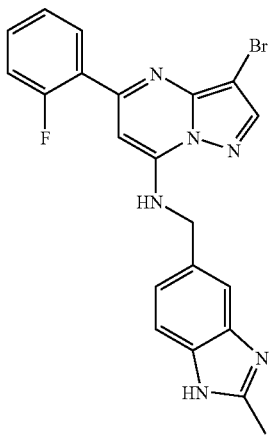
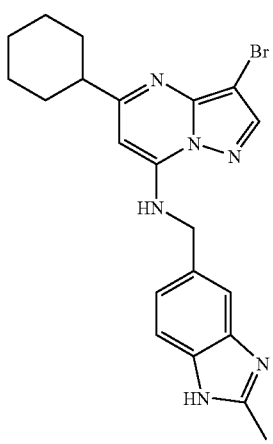 [SMILES: Cc1nc2cc(CNc3cc(C4CCCCC4)nc4c(Br)cnn34)ccc2[nH]1]
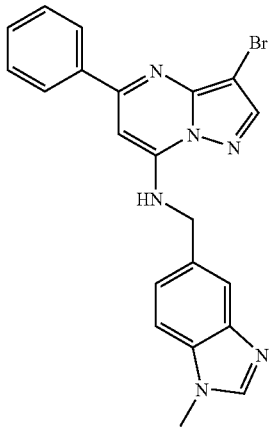 [SMILES: Cn1cnc2cc(CNc3cc(-c4ccccc4)nc4c(Br)cnn34)ccc21]

TABLE 1-continued
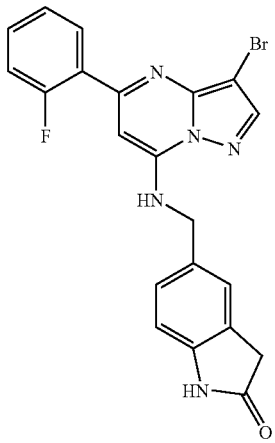 [SMILES: O=C1Cc2cc(CNc3cc(-c4ccccc4F)nc4c(Br)cnn34)ccc2N1]
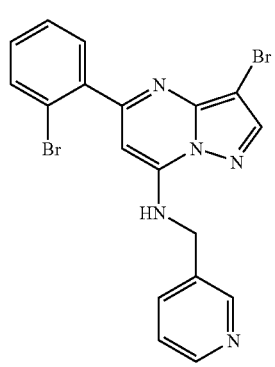 [SMILES: Brc1ccccc1-c1cc(NCc2cccnc2)n2ncc(Br)c2n1]
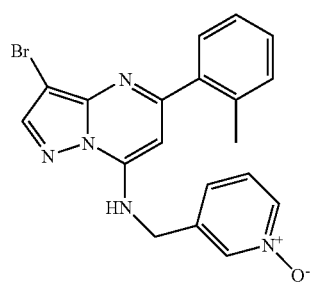 [SMILES: Cc1ccccc1-c1cc(NCc2ccc[n+]([O-])c2)n2ncc(Br)c2n1]
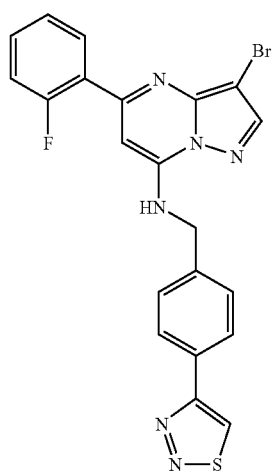 [SMILES: Fc1ccccc1-c1cc(NCc2ccc(-c3csnn3)cc2)n2ncc(Br)c2n1]
TABLE 1-continued
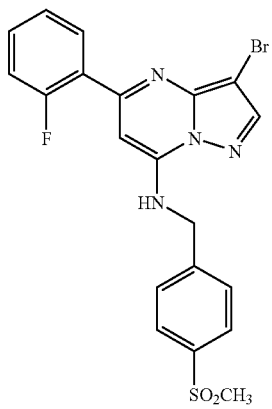 [SMILES: CS(=O)(=O)c1ccc(CNc2cc(-c3ccccc3F)nc3c(Br)cnn23)cc1]
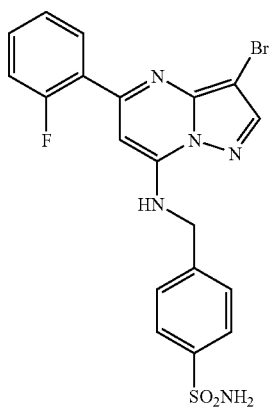 [SMILES: NS(=O)(=O)c1ccc(CNc2cc(-c3ccccc3F)nc3c(Br)cnn23)cc1]
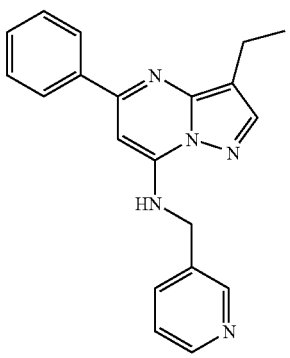 [SMILES: CCc1cnn2c(NCc3cccnc3)cc(-c3ccccc3)nc12]
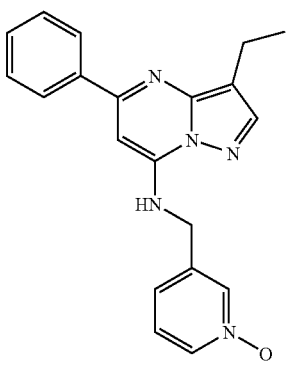

TABLE 1-continued
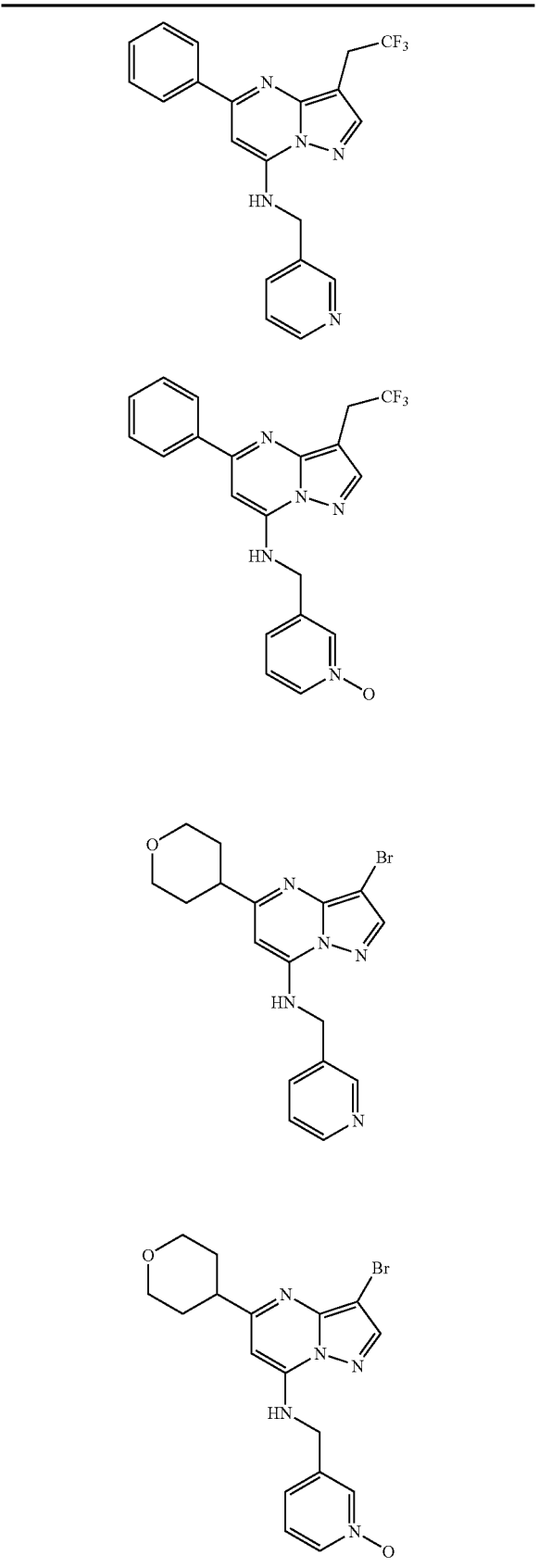
TABLE 1-continued
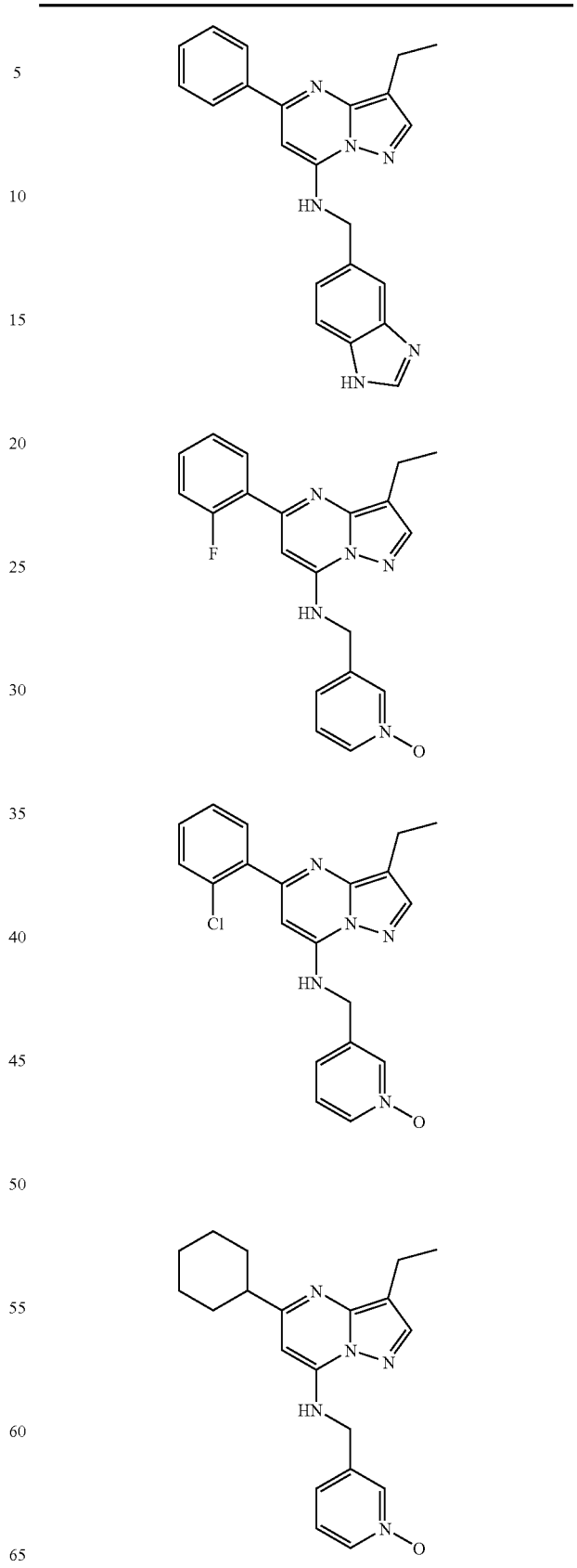

TABLE 1-continued
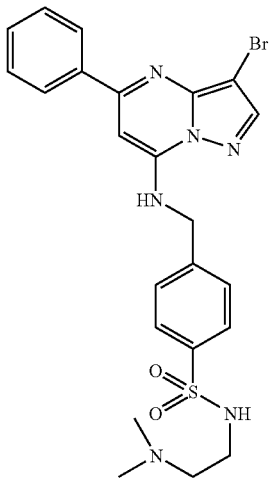 [SMILES: CN(C)CCNS(=O)(=O)c1ccc(CNc2cc(-c3ccccc3)nc3c(Br)cnn23)cc1]
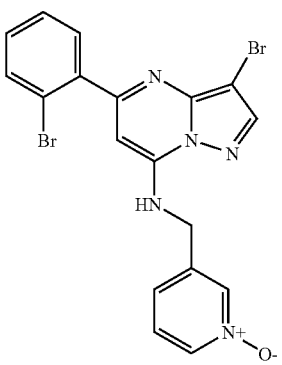 [SMILES: [O-][n+]1cccc(CNc2cc(-c3ccccc3Br)nc3c(Br)cnn23)c1]
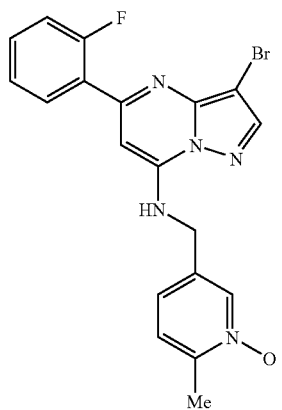
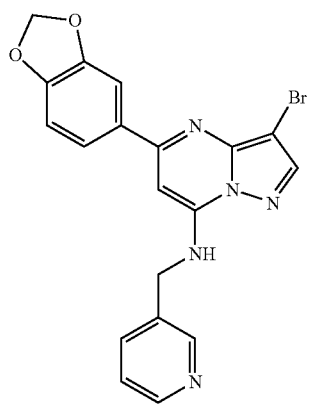 [SMILES: Brc1cnn2c(NCc3cccnc3)cc(-c3ccc4c(c3)OCO4)nc12]
TABLE 1-continued
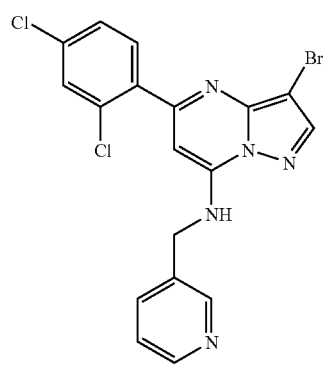 [SMILES: Clc1ccc(-c2cc(NCc3cccnc3)n3ncc(Br)c3n2)c(Cl)c1]
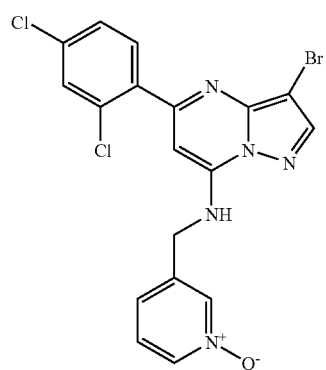 [SMILES: [O-][n+]1cccc(CNc2cc(-c3ccc(Cl)cc3Cl)nc3c(Br)cnn23)c1]
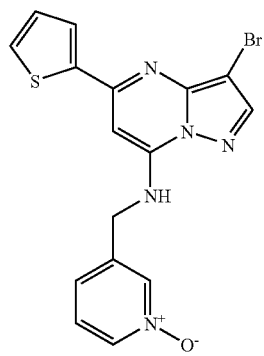 [SMILES: [O-][n+]1cccc(CNc2cc(-c3cccs3)nc3c(Br)cnn23)c1]
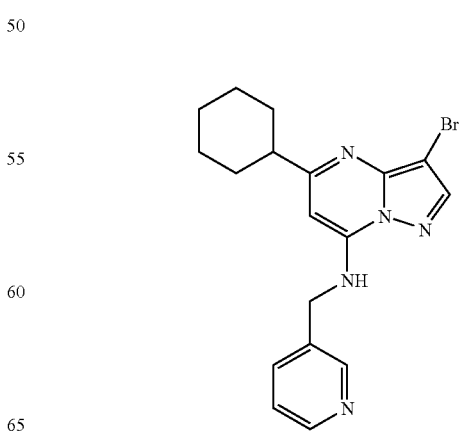

TABLE 1-continued
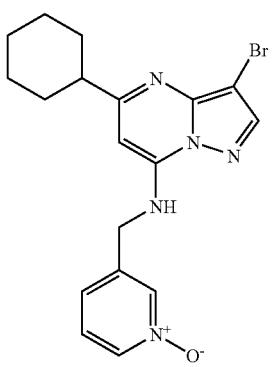 [SMILES: [O-][n+]1cccc(CNc2cc(C3CCCCC3)nc3c(Br)cnn23)c1]
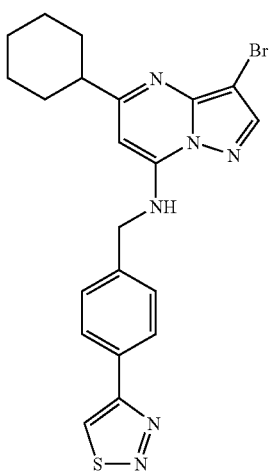 [SMILES: Brc1cnn2c(NCc3ccc(-c4csnn4)cc3)cc(C3CCCCC3)nc12]
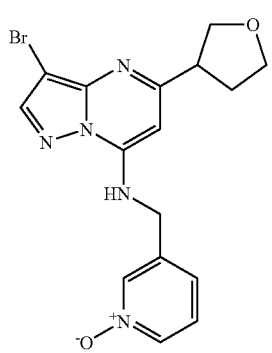
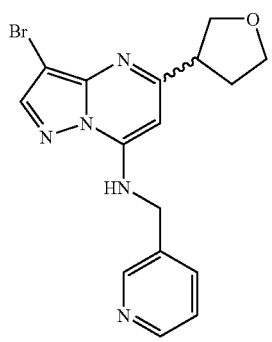
TABLE 1-continued
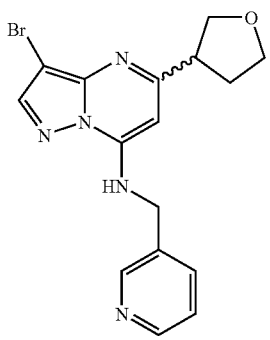 [SMILES: Brc1cnn2c(NCc3cccnc3)cc(C3CCOC3)nc12]
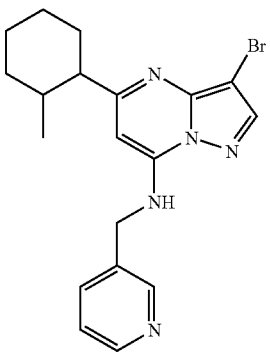 [SMILES: CC1CCCCC1c1cc(NCc2cccnc2)n2ncc(Br)c2n1]
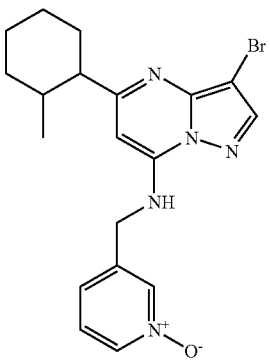 [SMILES: CC1CCCCC1c1cc(NCc2ccc[n+]([O-])c2)n2ncc(Br)c2n1]
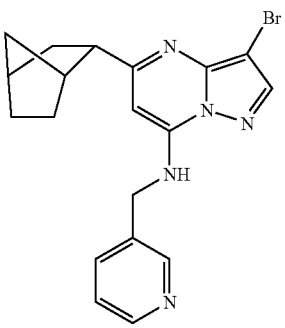 [SMILES: Brc1cnn2c(NCc3cccnc3)cc(C3CC4CCC3C4)nc12]

TABLE 1-continued
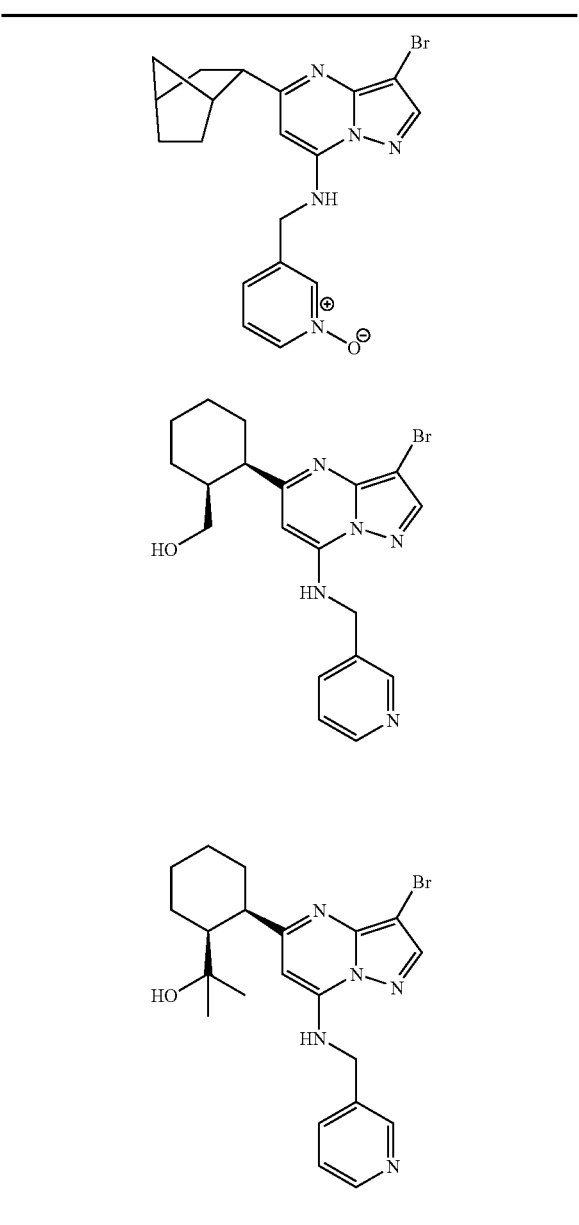
TABLE 1-continued
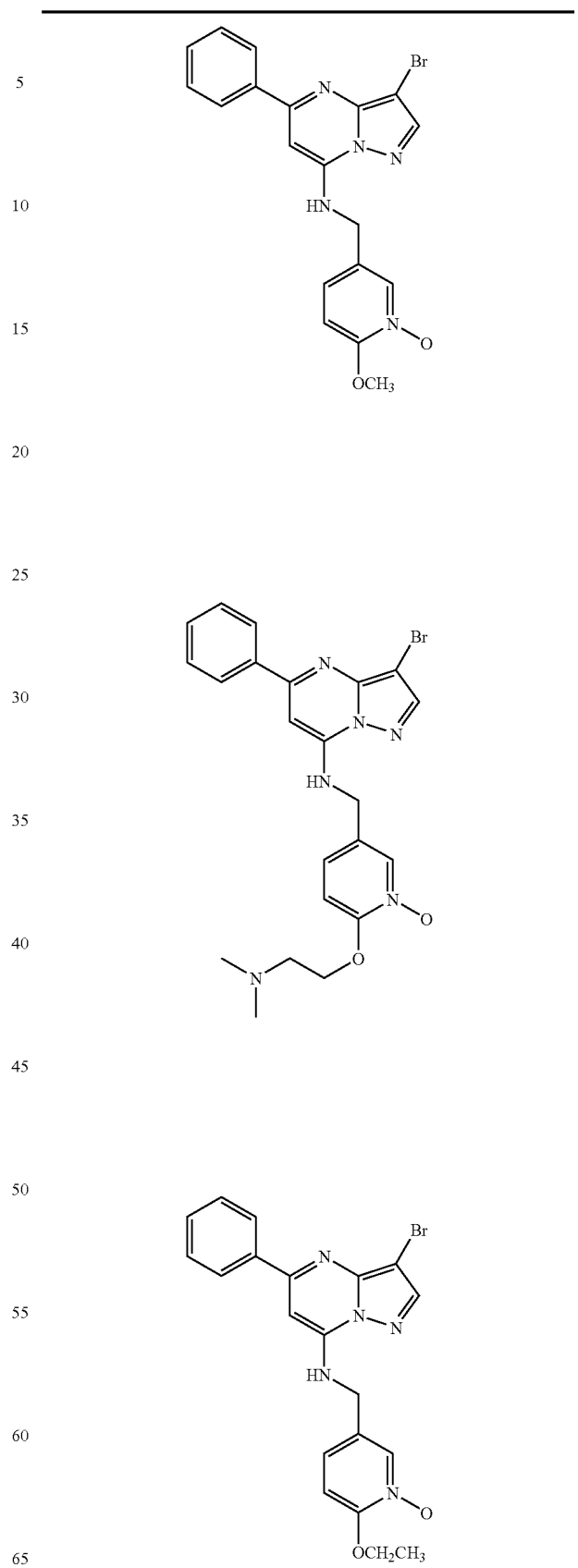

TABLE 1-continued
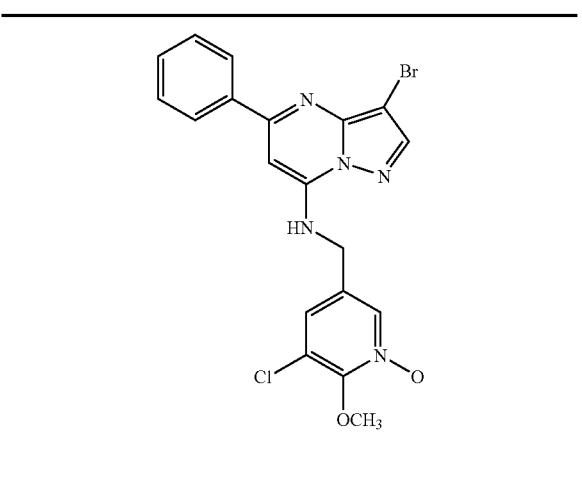
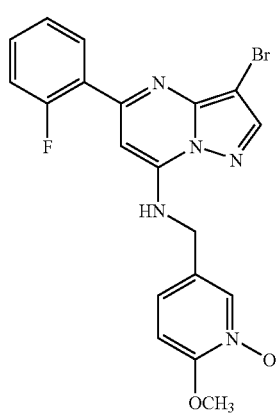
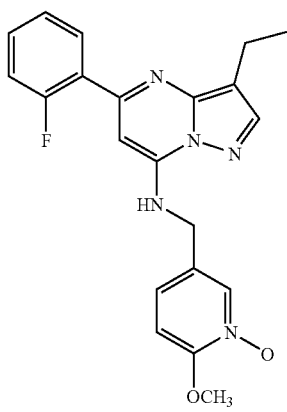
TABLE 1-continued
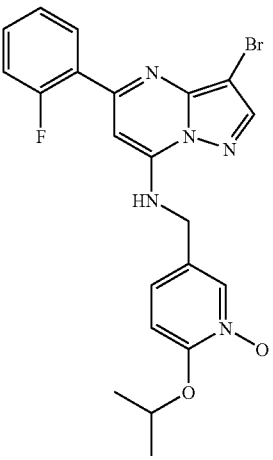
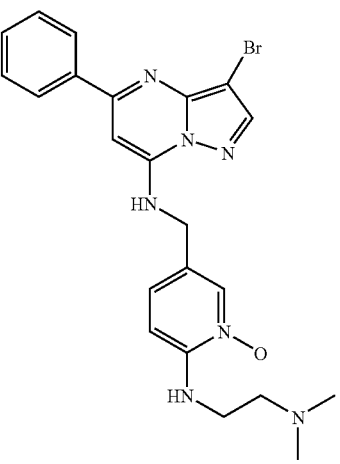
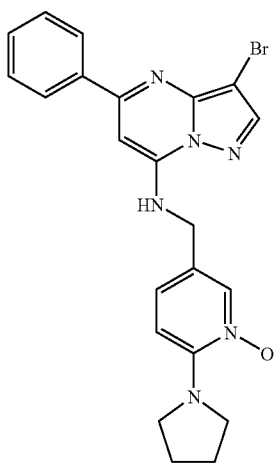

TABLE 1-continued
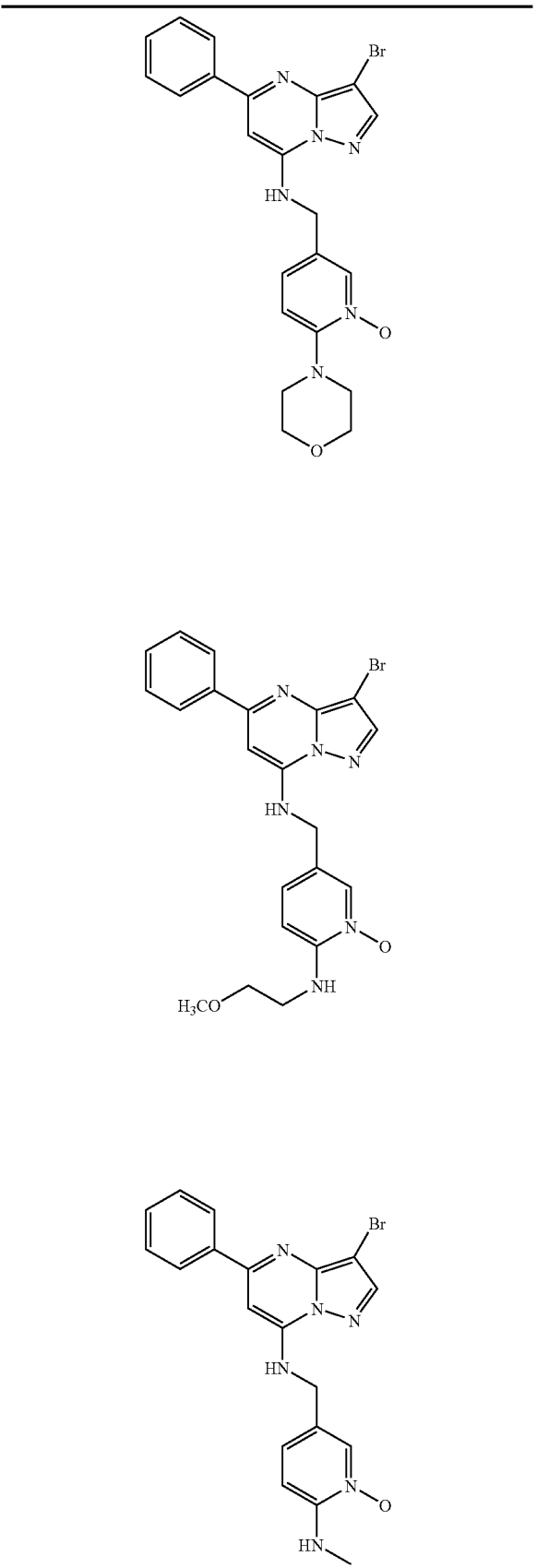
TABLE 1-continued
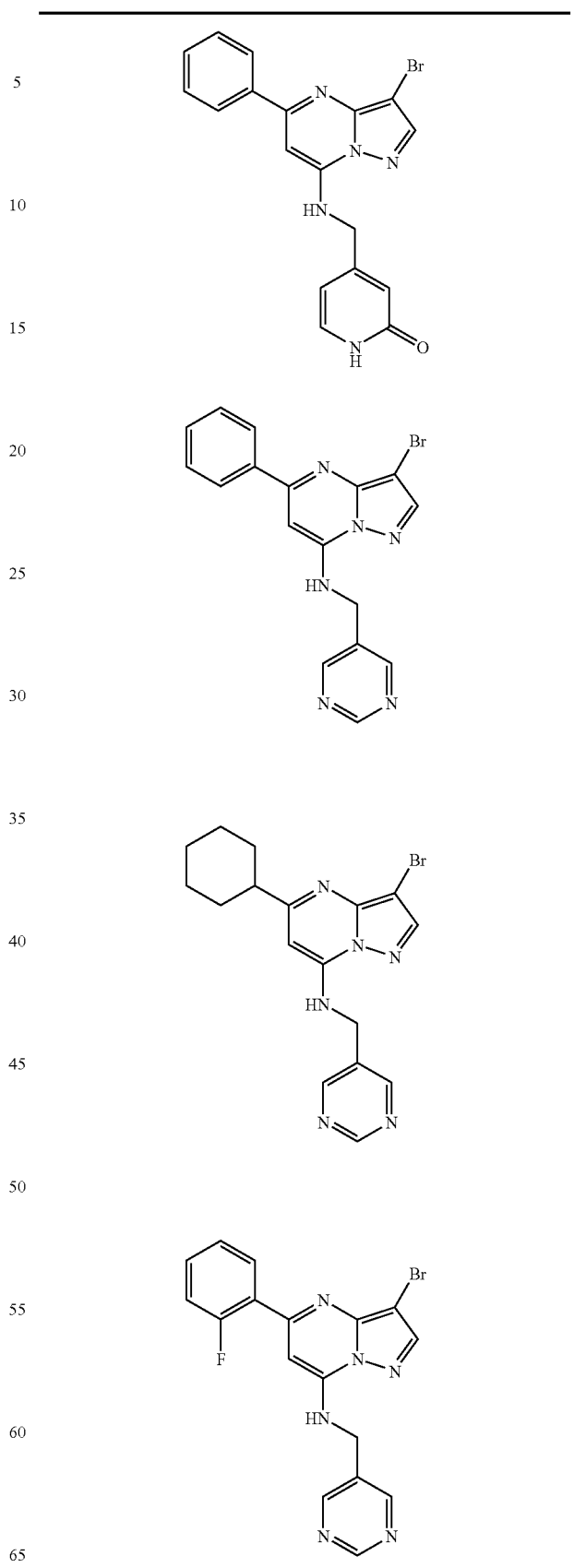

TABLE 1-continued
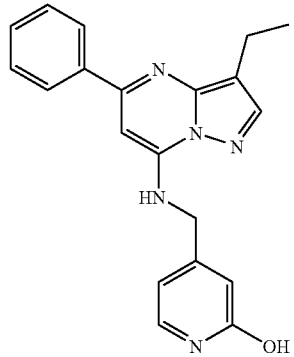 [SMILES: CCc1cnn2c(NCc3ccnc(O)c3)cc(-c3ccccc3)nc12]
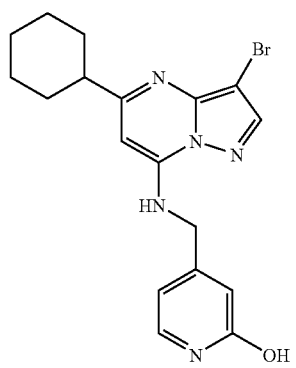 [SMILES: Oc1cc(CNc2cc(C3CCCCC3)nc3c(Br)cnn23)ccn1]
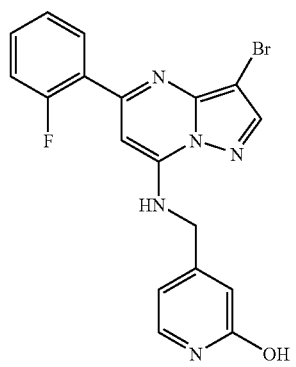 [SMILES: Oc1cc(CNc2cc(-c3ccccc3F)nc3c(Br)cnn23)ccn1]
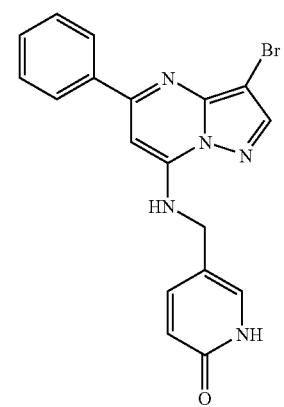 [SMILES: O=c1ccc(CNc2cc(-c3ccccc3)nc3c(Br)cnn23)c[nH]1]
TABLE 1-continued
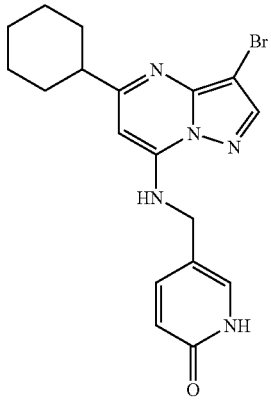 [SMILES: O=c1ccc(CNc2cc(C3CCCCC3)nc3c(Br)cnn23)c[nH]1]
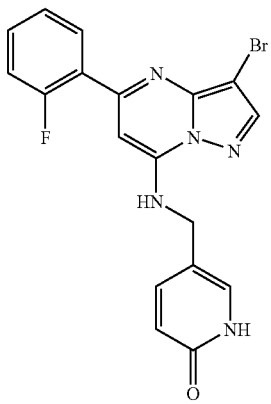 [SMILES: O=c1ccc(CNc2cc(-c3ccccc3F)nc3c(Br)cnn23)c[nH]1]
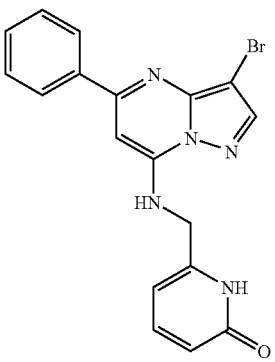 [SMILES: O=c1cccc(CNc2cc(-c3ccccc3)nc3c(Br)cnn23)[nH]1]
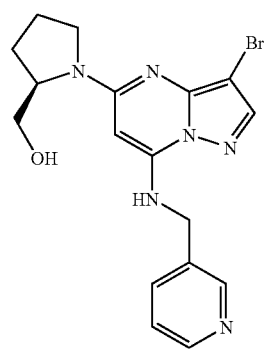 [SMILES: OC[C@H]1CCCN1c1cc(NCc2cccnc2)n2ncc(Br)c2n1]

TABLE 1-continued
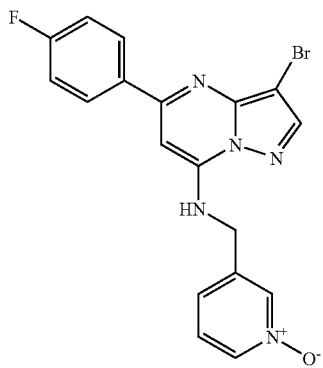 [SMILES: [O-][n+]1cccc(CNc2cc(-c3ccc(F)cc3)nc3c(Br)cnn23)c1]
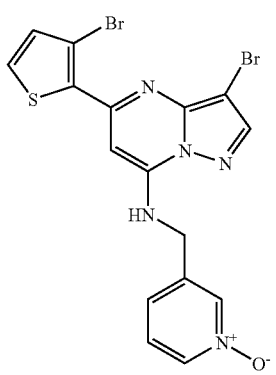
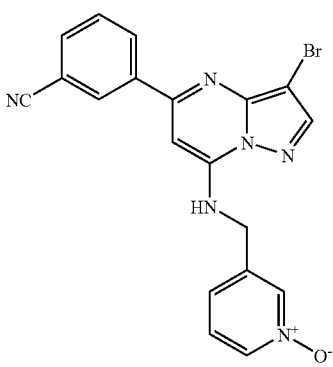
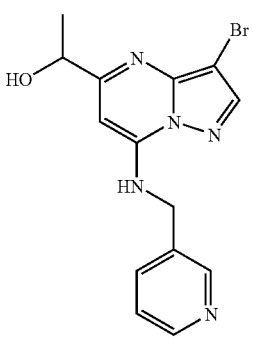
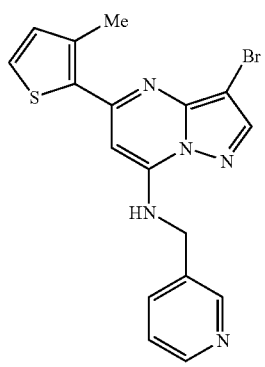 [SMILES: Cc1ccsc1-c1cc(NCc2cccnc2)n2ncc(Br)c2n1]
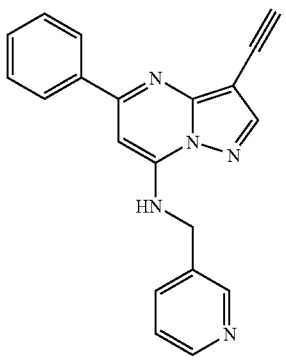
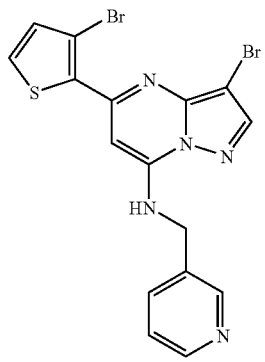 [SMILES: Brc1ccsc1-c1cc(NCc2cccnc2)n2ncc(Br)c2n1]
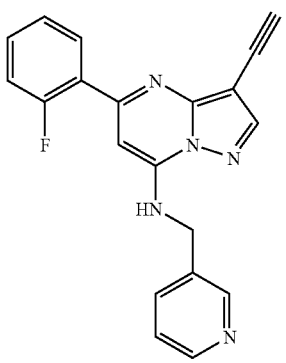 [SMILES: C#Cc1cnn2c(NCc3cccnc3)cc(-c3ccccc3F)nc12]

TABLE 1-continued
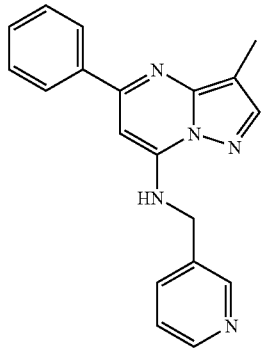 [SMILES: Cc1cnn2c(NCc3cccnc3)cc(-c3ccccc3)nc12]
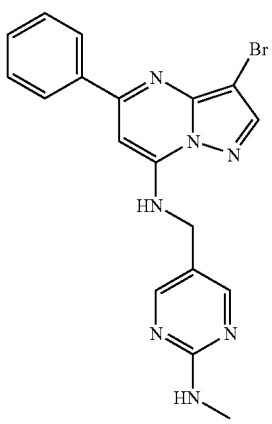 [SMILES: CNc1ncc(CNc2cc(-c3ccccc3)nc3c(Br)cnn23)cn1]
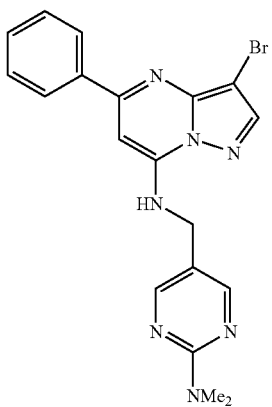
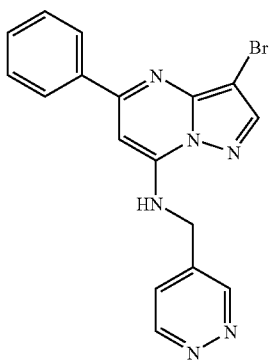 [SMILES: Brc1cnn2c(NCc3ccnnc3)cc(-c3ccccc3)nc12]
TABLE 1-continued
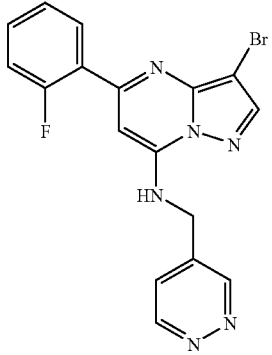 [SMILES: Fc1ccccc1-c1cc(NCc2ccnnc2)n2ncc(Br)c2n1]
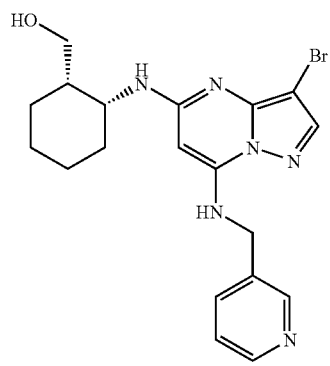 [SMILES: OC[C@H]1CCCC[C@H]1Nc1cc(NCc2cccnc2)n2ncc(Br)c2n1]
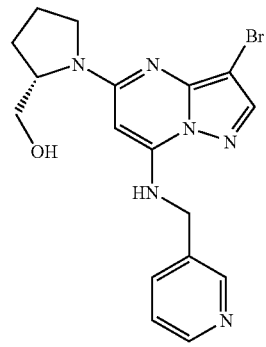 [SMILES: OC[C@@H]1CCCN1c1cc(NCc2cccnc2)n2ncc(Br)c2n1]
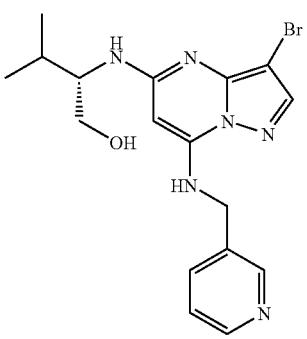 [SMILES: CC(C)[C@@H](CO)Nc1cc(NCc2cccnc2)n2ncc(Br)c2n1]

TABLE 1-continued
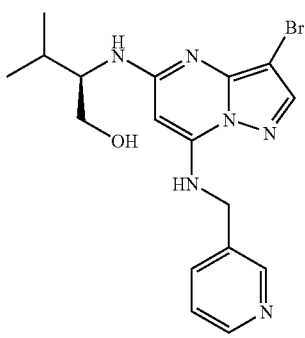
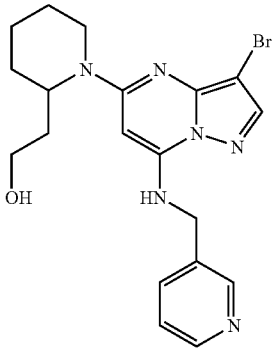
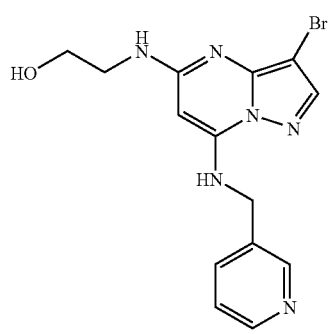 [SMILES: OCCNc1cc(NCc2cccnc2)n2ncc(Br)c2n1]
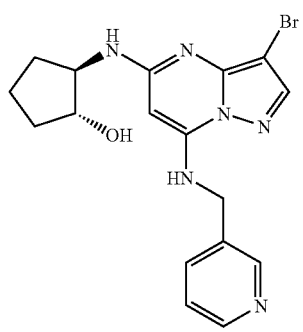
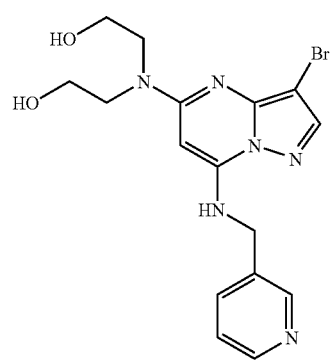 [SMILES: OCCN(CCO)c1cc(NCc2cccnc2)n2ncc(Br)c2n1]
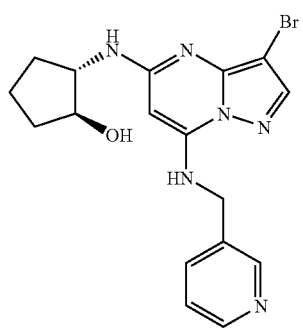
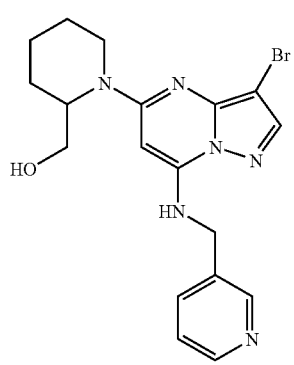 [SMILES: OCC1CCCCN1c1cc(NCc2cccnc2)n2ncc(Br)c2n1]
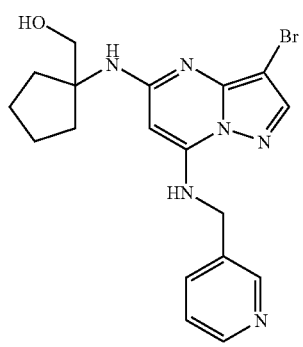 [SMILES: OCC1(Nc2cc(NCc3cccnc3)n3ncc(Br)c3n2)CCCC1]

TABLE 1-continued
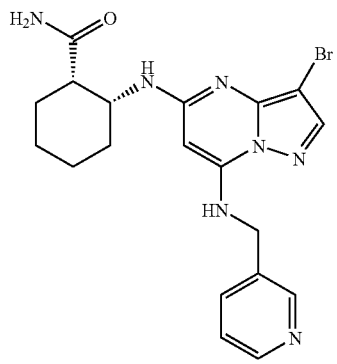 [SMILES: NC(=O)[C@H]1CCCC[C@H]1Nc1cc(NCc2cccnc2)n2ncc(Br)c2n1]
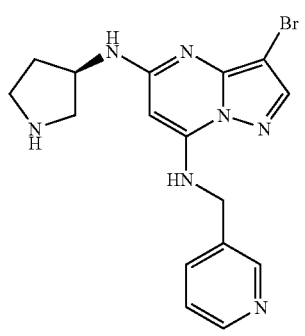 [SMILES: Brc1cnn2c(NCc3cccnc3)cc(N[C@@H]3CCNC3)nc12]
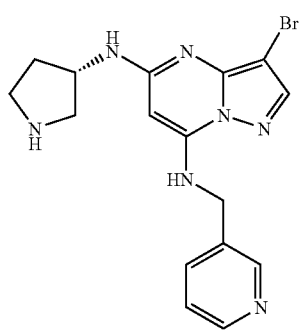 [SMILES: Brc1cnn2c(NCc3cccnc3)cc(N[C@H]3CCNC3)nc12]
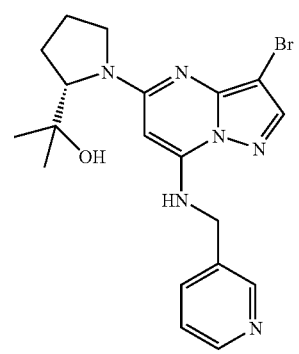 [SMILES: CC(C)(O)[C@@H]1CCCN1c1cc(NCc2cccnc2)n2ncc(Br)c2n1]
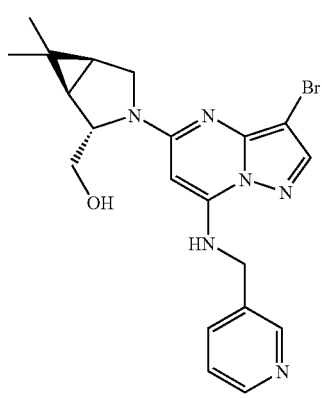 [SMILES: CC1(C)[C@@H]2[C@@H](CO)N(c3cc(NCc4cccnc4)n4ncc(Br)c4n3)C[C@@H]21]

TABLE 1-continued
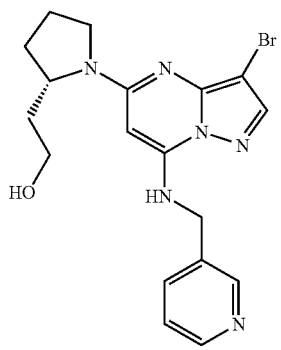 [SMILES: OCC[C@@H]1CCCN1c1cc(NCc2cccnc2)n2ncc(Br)c2n1]
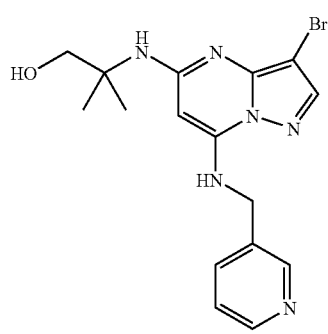 [SMILES: CC(C)(CO)Nc1cc(NCc2cccnc2)n2ncc(Br)c2n1]
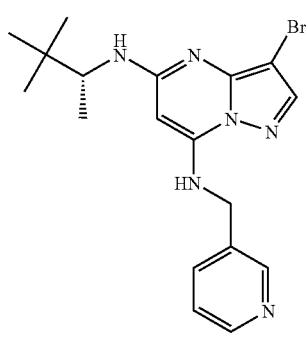 [SMILES: C[C@@H](Nc1cc(NCc2cccnc2)n2ncc(Br)c2n1)C(C)(C)C]
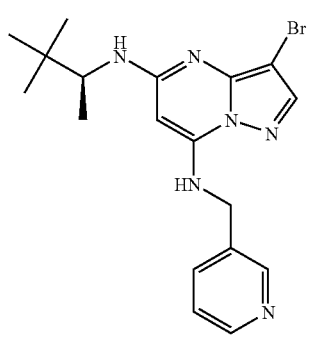
TABLE 1-continued
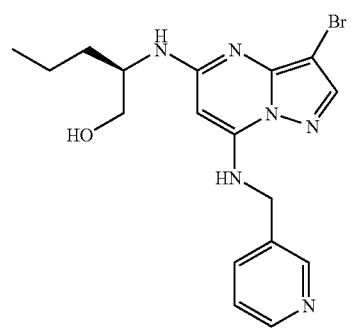 [SMILES: CCC[C@H](CO)Nc1cc(NCc2cccnc2)n2ncc(Br)c2n1]
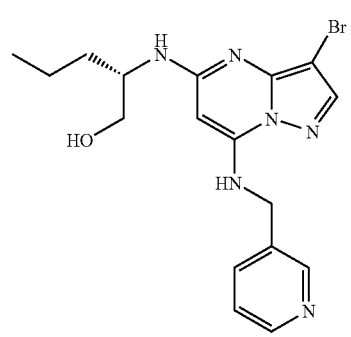 [SMILES: CCC[C@@H](CO)Nc1cc(NCc2cccnc2)n2ncc(Br)c2n1]
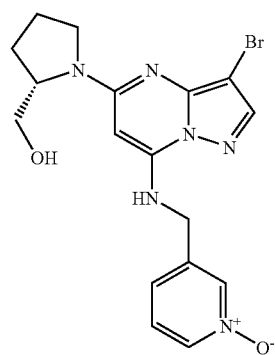 [SMILES: [O-][n+]1cccc(CNc2cc(N3CCC[C@H]3CO)nc3c(Br)cnn23)c1]
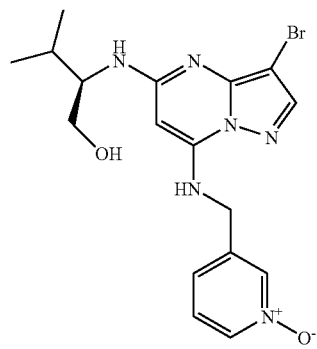 [SMILES: CC(C)[C@H](CO)Nc1cc(NCc2ccc[n+]([O-])c2)n2ncc(Br)c2n1]

TABLE 1-continued
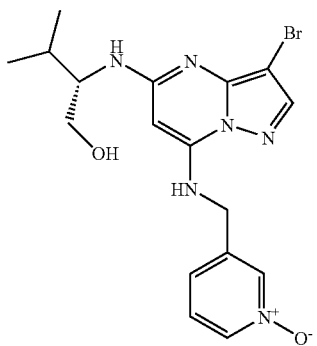 [SMILES: CC(C)[C@@H](CO)Nc1cc(NCc2ccc[n+]([O-])c2)n2ncc(Br)c2n1]
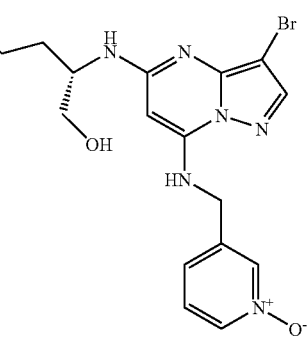
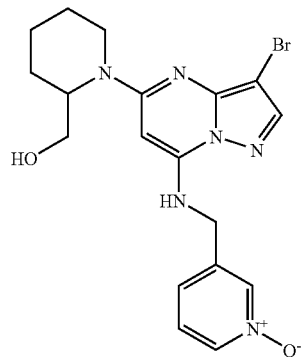 [SMILES: [O-][n+]1cccc(CNc2cc(N3CCCCC3CO)nc3c(Br)cnn23)c1]
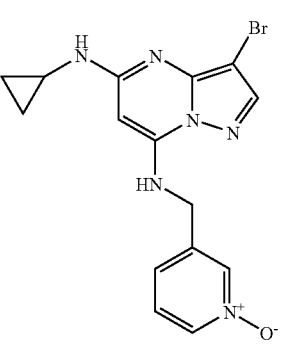
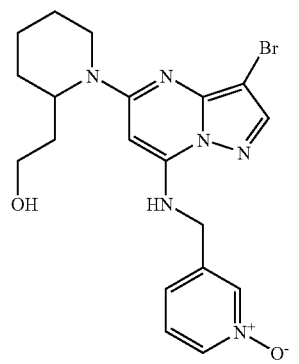 [SMILES: [O-][n+]1cccc(CNc2cc(N3CCCCC3CCO)nc3c(Br)cnn23)c1]
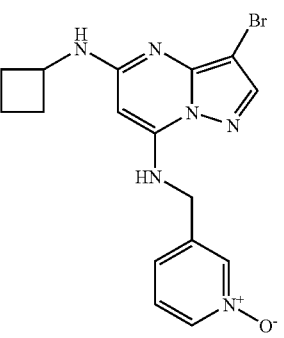 [SMILES: [O-][n+]1cccc(CNc2cc(NC3CCC3)nc3c(Br)cnn23)c1]
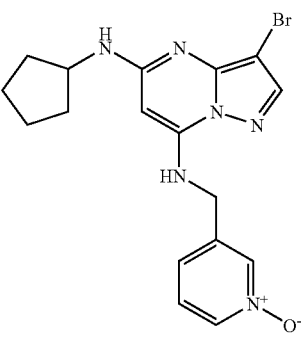 [SMILES: [O-][n+]1cccc(CNc2cc(NC3CCCC3)nc3c(Br)cnn23)c1]

TABLE 1-continued
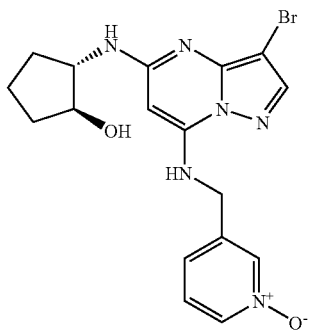 [SMILES: [O-][n+]1cccc(CNc2cc(N[C@H]3CCC[C@@H]3O)nc3c(Br)cnn23)c1]
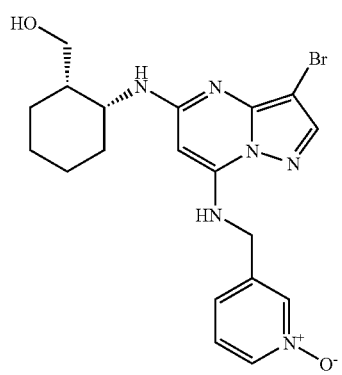 [SMILES: [O-][n+]1cccc(CNc2cc(N[C@@H]3CCCC[C@@H]3CO)nc3c(Br)cnn23)c1]
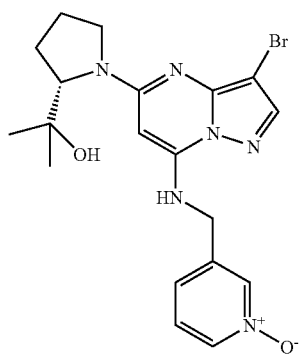 [SMILES: CC(C)(O)[C@@H]1CCCN1c1cc(NCc2ccc[n+]([O-])c2)n2ncc(Br)c2n1]
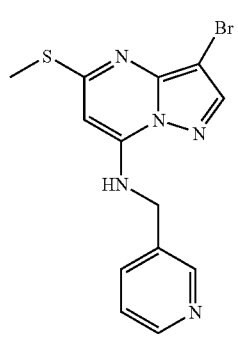 [SMILES: CSc1cc(NCc2cccnc2)n2ncc(Br)c2n1]
TABLE 1-continued
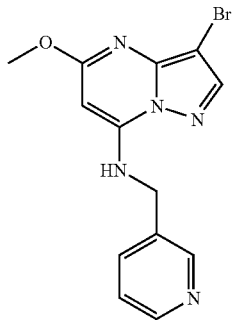 [SMILES: COc1cc(NCc2cccnc2)n2ncc(Br)c2n1]
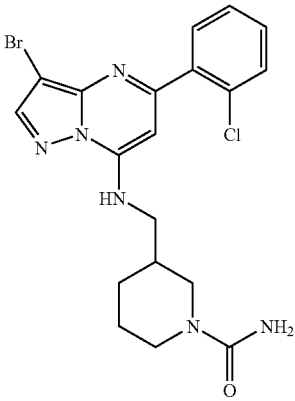 [SMILES: NC(=O)N1CCCC(CNc2cc(-c3ccccc3Cl)nc3c(Br)cnn23)C1]
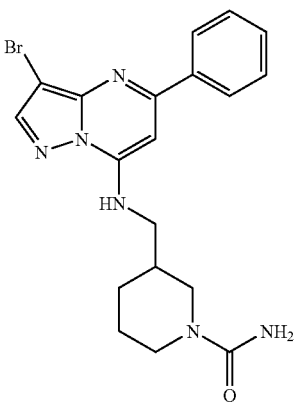 [SMILES: NC(=O)N1CCCC(CNc2cc(-c3ccccc3)nc3c(Br)cnn23)C1]
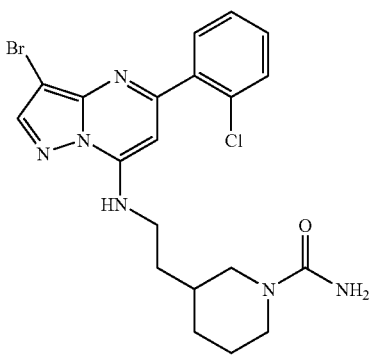

TABLE 1-continued
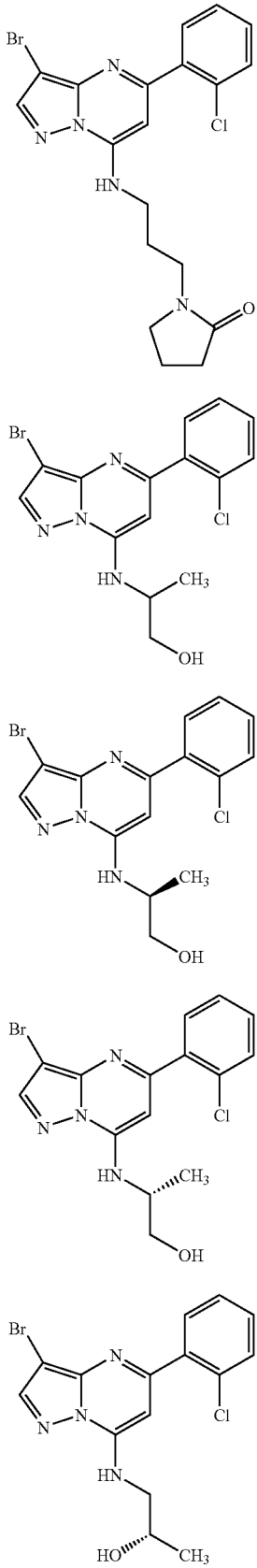
TABLE 1-continued
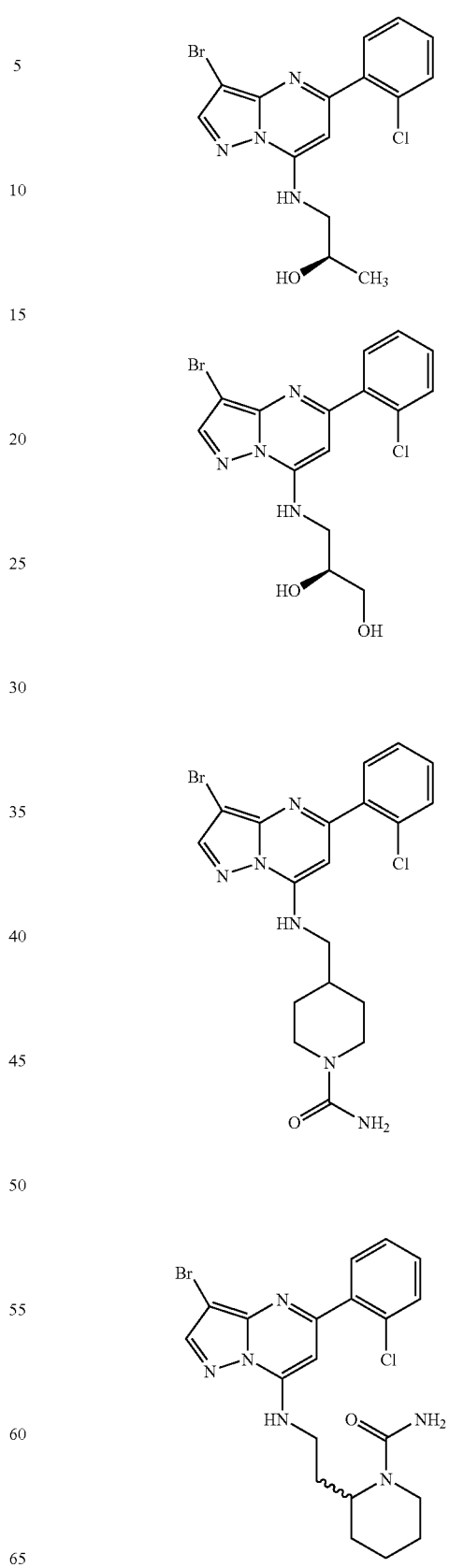

TABLE 1-continued
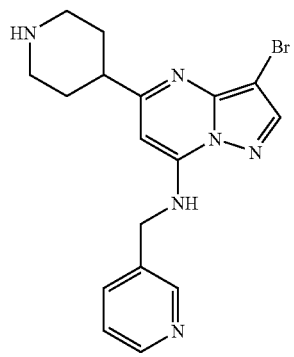 [SMILES: Brc1cnn2c(NCc3cccnc3)cc(C3CCNCC3)nc12]
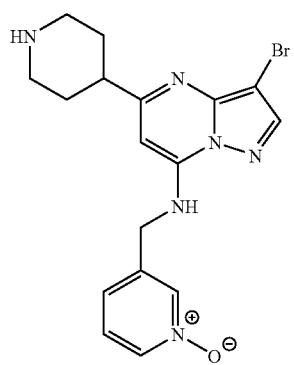 [SMILES: [O-][n+]1cccc(CNc2cc(C3CCNCC3)nc3c(Br)cnn23)c1]
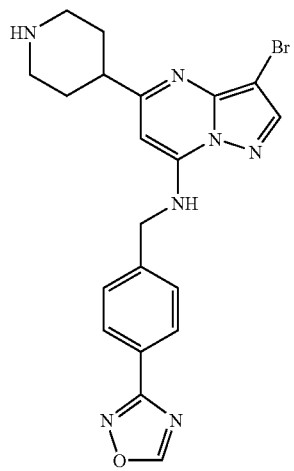 [SMILES: Brc1cnn2c(NCc3ccc(-c4ncon4)cc3)cc(C3CCNCC3)nc12]
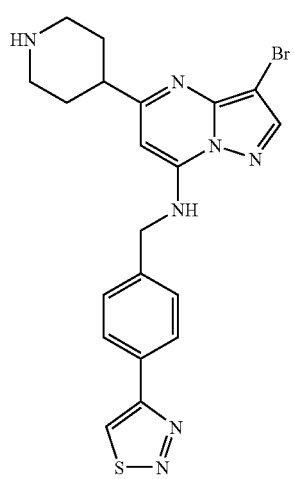 [SMILES: Brc1cnn2c(NCc3ccc(-c4csnn4)cc3)cc(C3CCNCC3)nc12]
TABLE 1-continued
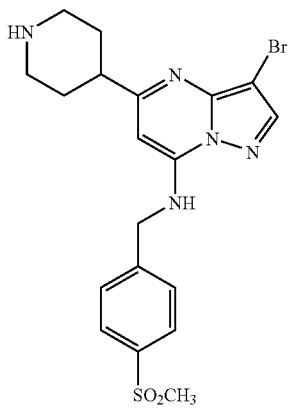
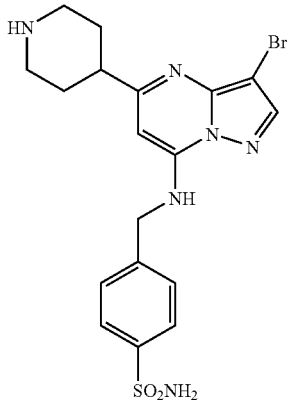
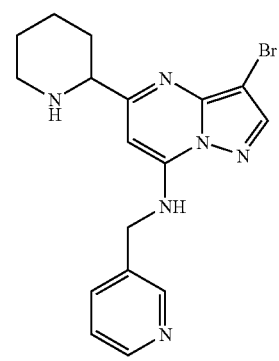 [SMILES: Brc1cnn2c(NCc3cccnc3)cc(C3CCCCN3)nc12]
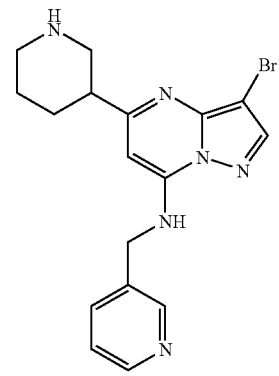 [SMILES: Brc1cnn2c(NCc3cccnc3)cc(C3CCCNC3)nc12]

TABLE 1-continued
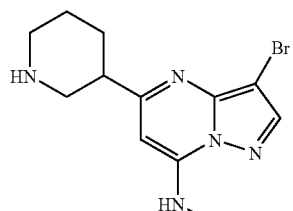
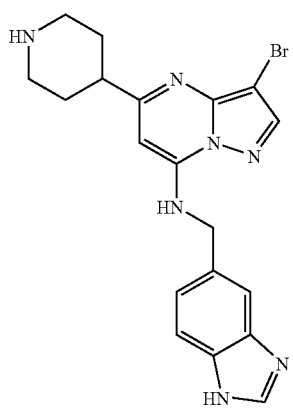 [SMILES: Brc1cnn2c(NCc3ccc4[nH]cnc4c3)cc(C3CCNCC3)nc12]
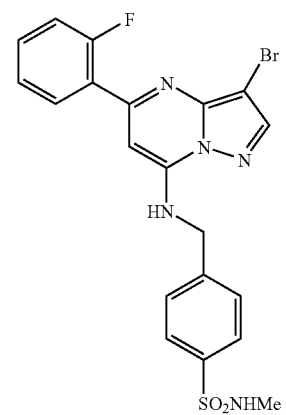
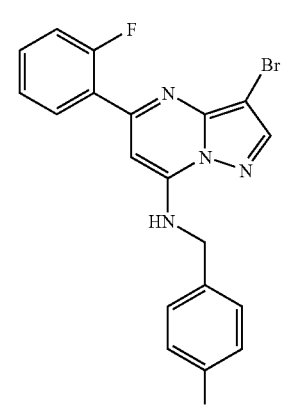
TABLE 1-continued
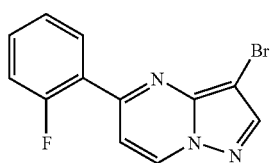
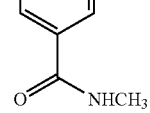
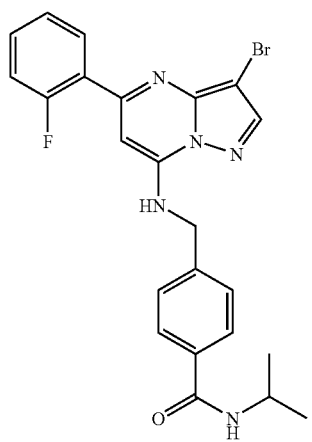 [SMILES: CC(C)NC(=O)c1ccc(CNc2cc(-c3ccccc3F)nc3c(Br)cnn23)cc1]
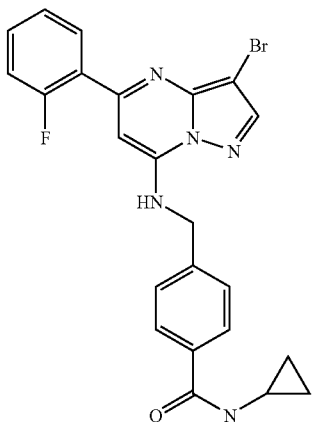

TABLE 1-continued
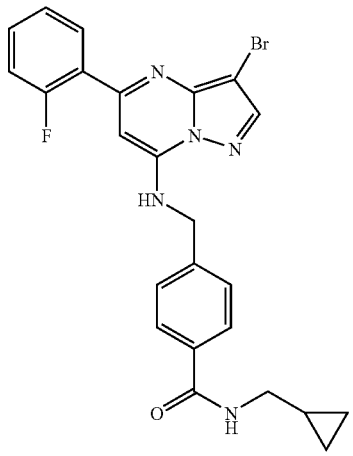 [SMILES: O=C(NCC1CC1)c1ccc(CNc2cc(-c3ccccc3F)nc3c(Br)cnn23)cc1]
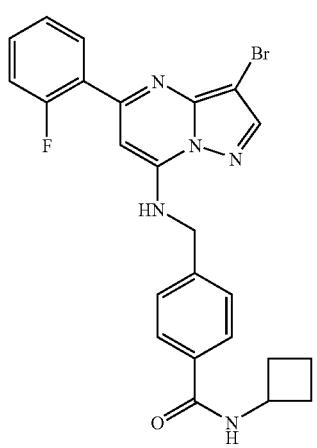 [SMILES: O=C(NC1CCC1)c1ccc(CNc2cc(-c3ccccc3F)nc3c(Br)cnn23)cc1]
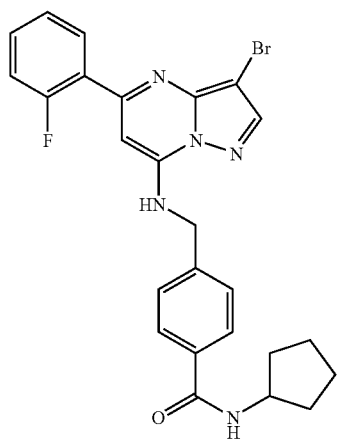 [SMILES: O=C(NC1CCCC1)c1ccc(CNc2cc(-c3ccccc3F)nc3c(Br)cnn23)cc1]
TABLE 1-continued
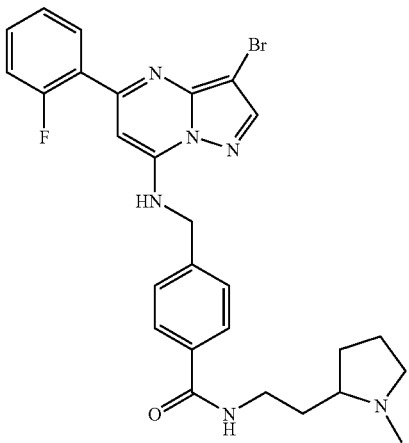 [SMILES: CN1CCCC1CCNC(=O)c1ccc(CNc2cc(-c3ccccc3F)nc3c(Br)cnn23)cc1]
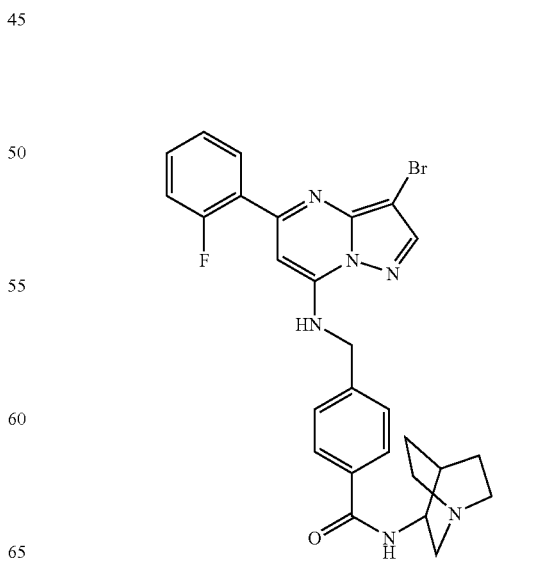

TABLE 1-continued
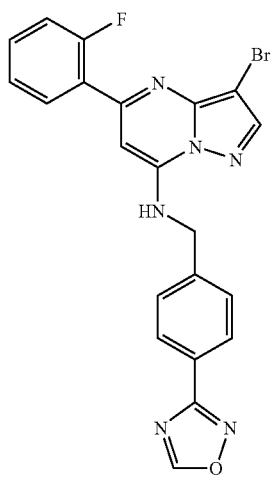 [SMILES: Fc1ccccc1-c1cc(NCc2ccc(-c3ncon3)cc2)n2ncc(Br)c2n1]
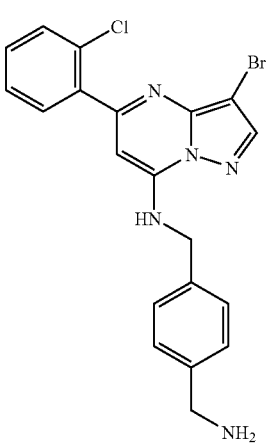 [SMILES: NCc1ccc(CNc2cc(-c3ccccc3Cl)nc3c(Br)cnn23)cc1]
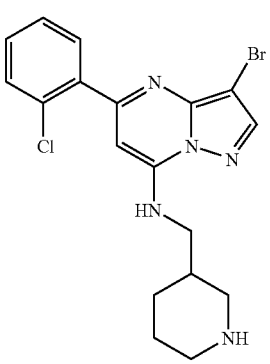 [SMILES: Clc1ccccc1-c1cc(NCC2CCCNC2)n2ncc(Br)c2n1]
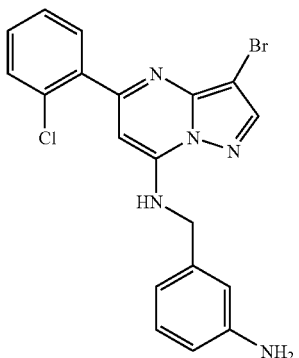
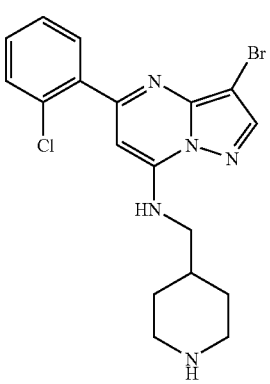 [SMILES: Clc1ccccc1-c1cc(NCC2CCNCC2)n2ncc(Br)c2n1]

TABLE 1-continued
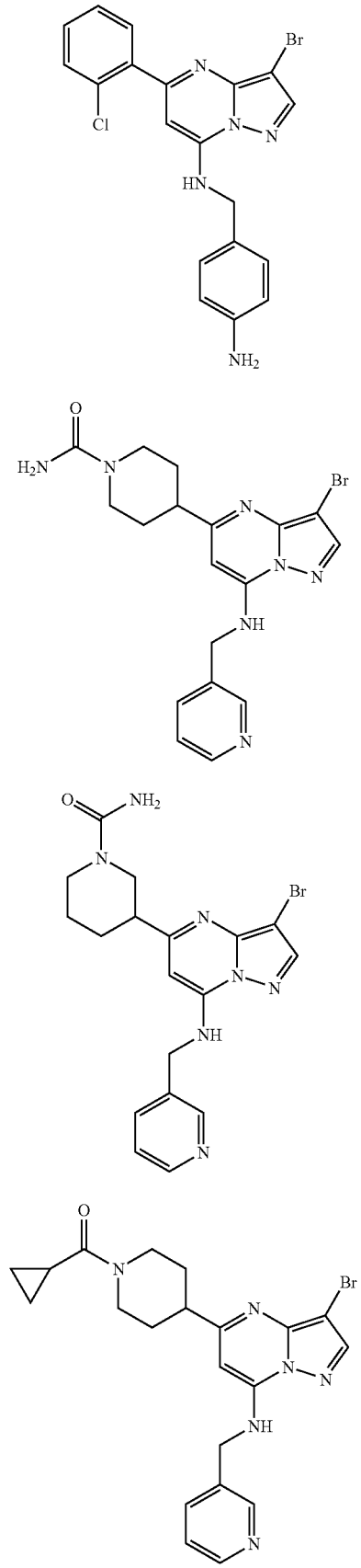
TABLE 1-continued
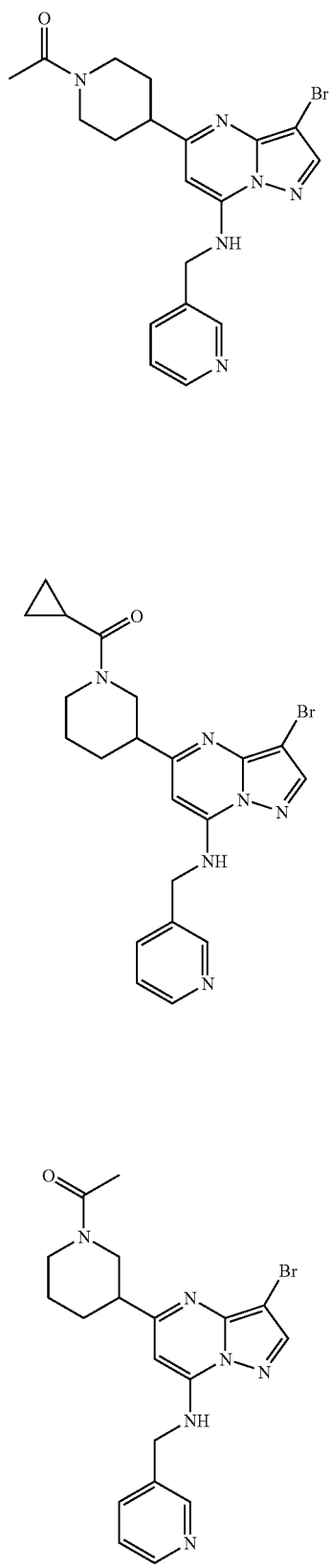

TABLE 1-continued
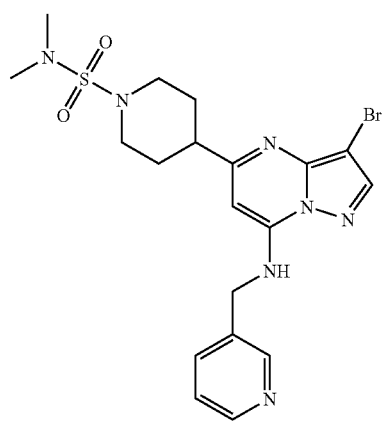 [SMILES: CC(C)S(=O)(=O)N1CCC(c2cc(NCc3cccnc3)n3ncc(Br)c3n2)CC1]
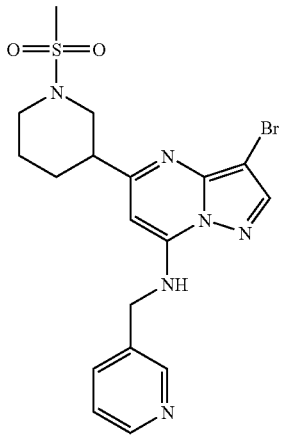 [SMILES: CS(=O)(=O)N1CCCC(c2cc(NCc3cccnc3)n3ncc(Br)c3n2)C1]

TABLE 1-continued
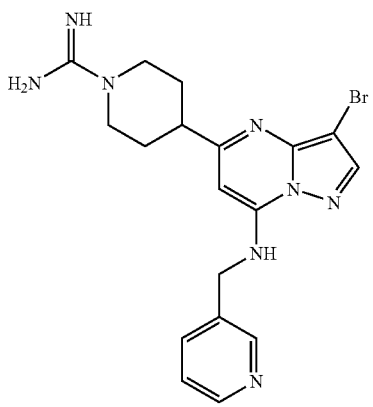 [SMILES: N=C(N)N1CCC(c2cc(NCc3cccnc3)n3ncc(Br)c3n2)CC1]
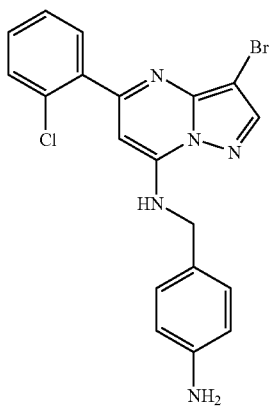 [SMILES: Nc1ccc(CNc2cc(-c3ccccc3Cl)nc3c(Br)cnn23)cc1]
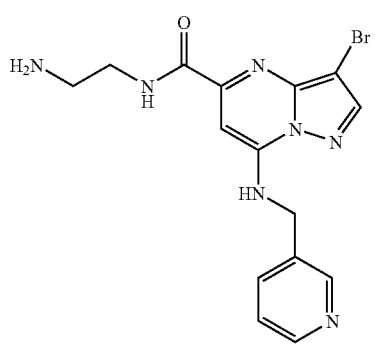 [SMILES: NCCNC(=O)c1cc(NCc2cccnc2)n2ncc(Br)c2n1]
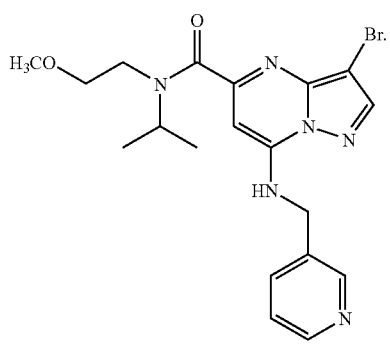 [SMILES: COCCN(C(=O)c1cc(NCc2cccnc2)n2ncc(Br)c2n1)C(C)C]
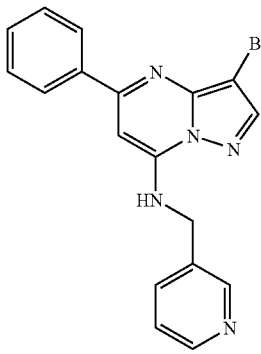
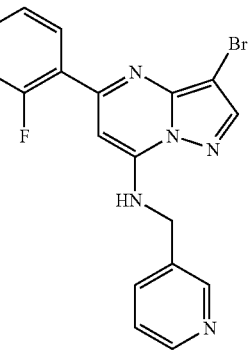
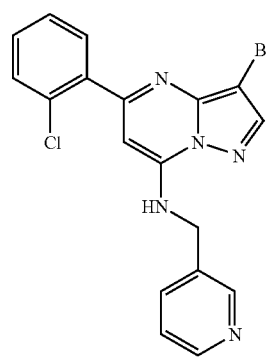
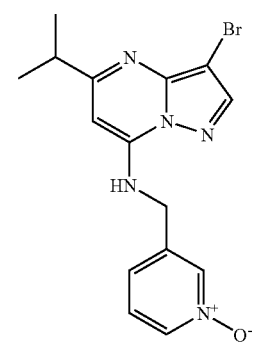
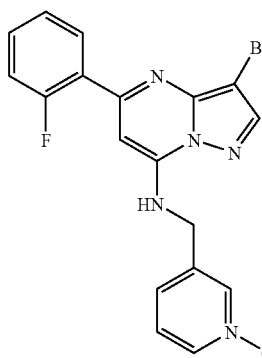
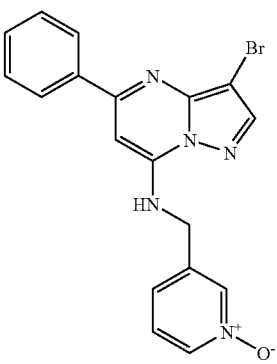
Another embodiment of the invention discloses the following compounds, which exhibited CDK2 inhibitory activity of about 0.0001 μM to about 0.5 μM:

69
-continued
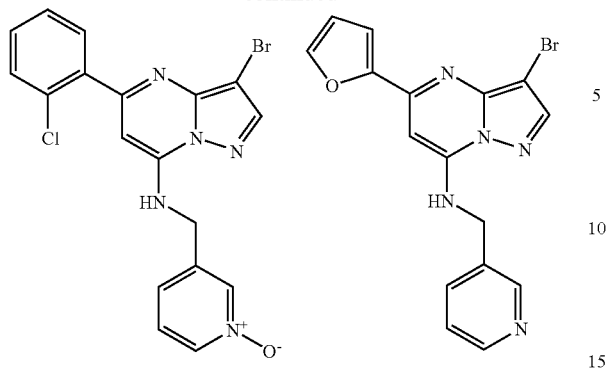
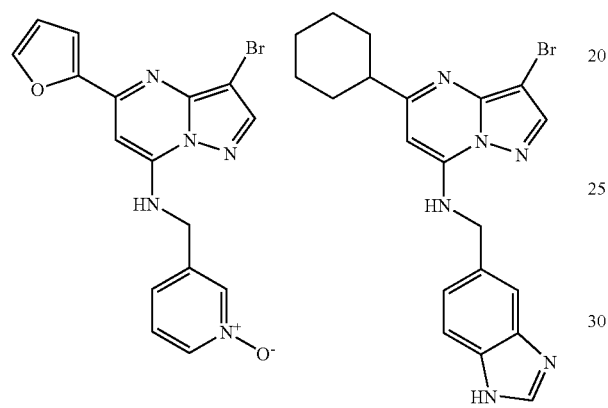
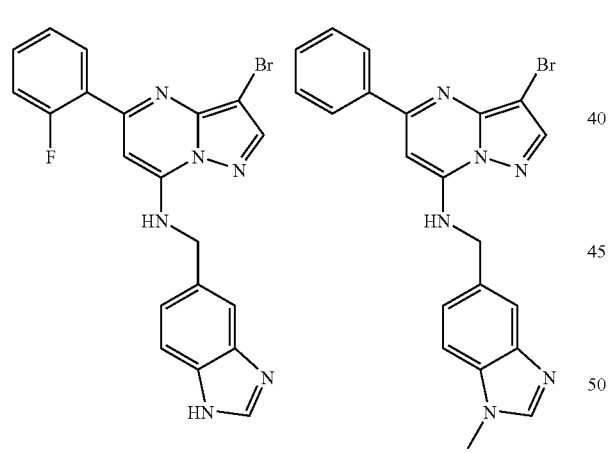
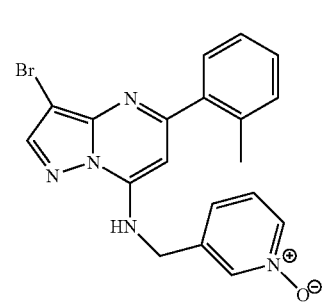
70
-continued
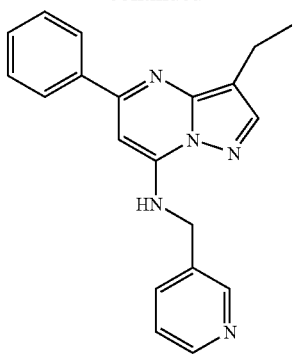
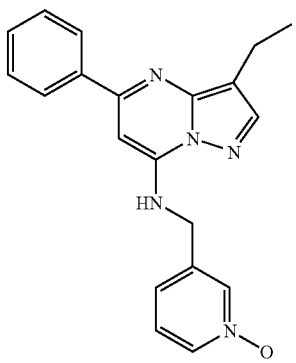
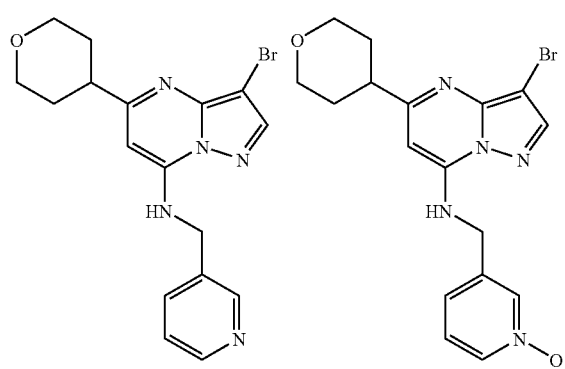
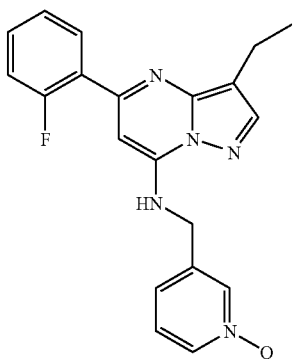

71
-continued
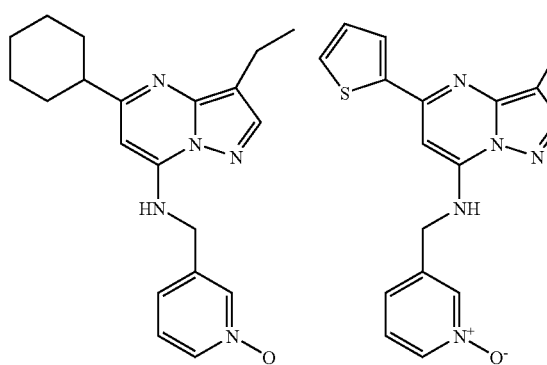
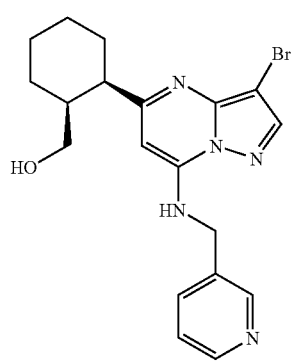
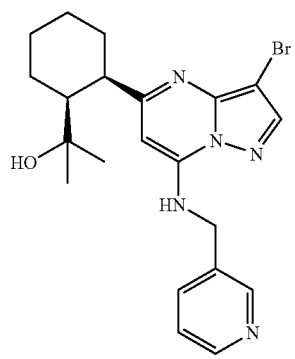
72
-continued
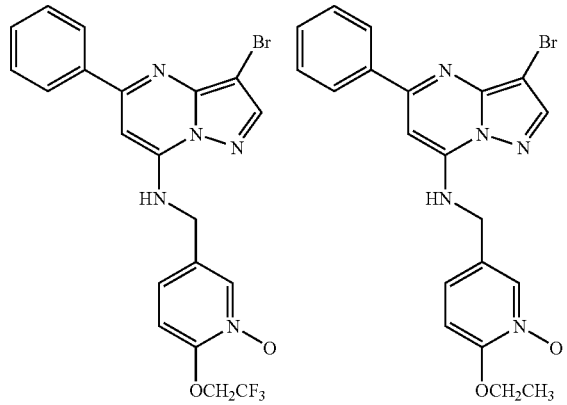
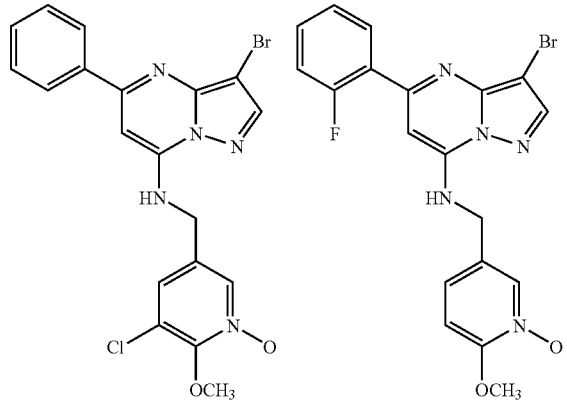
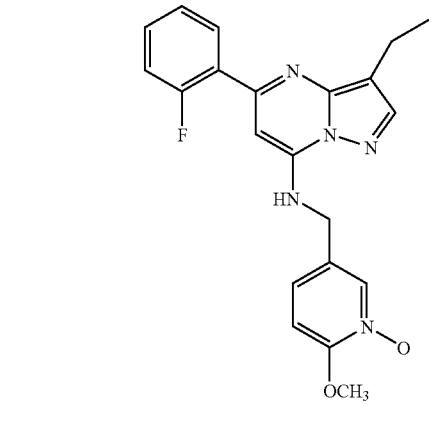

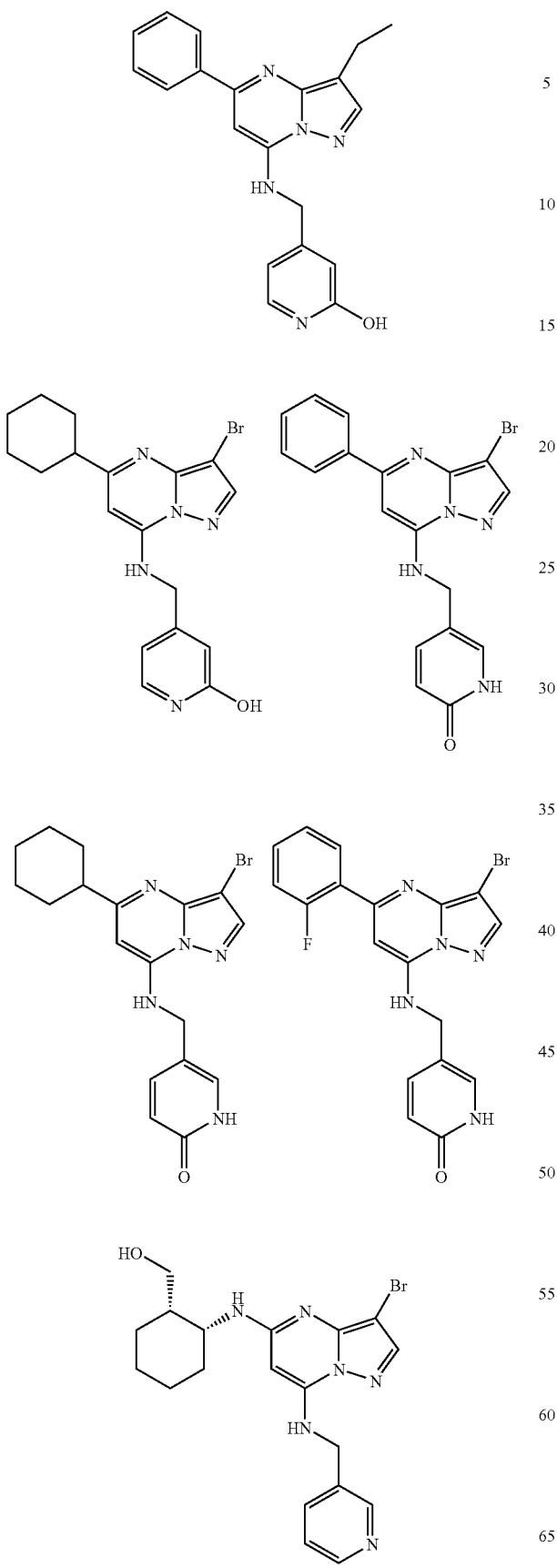
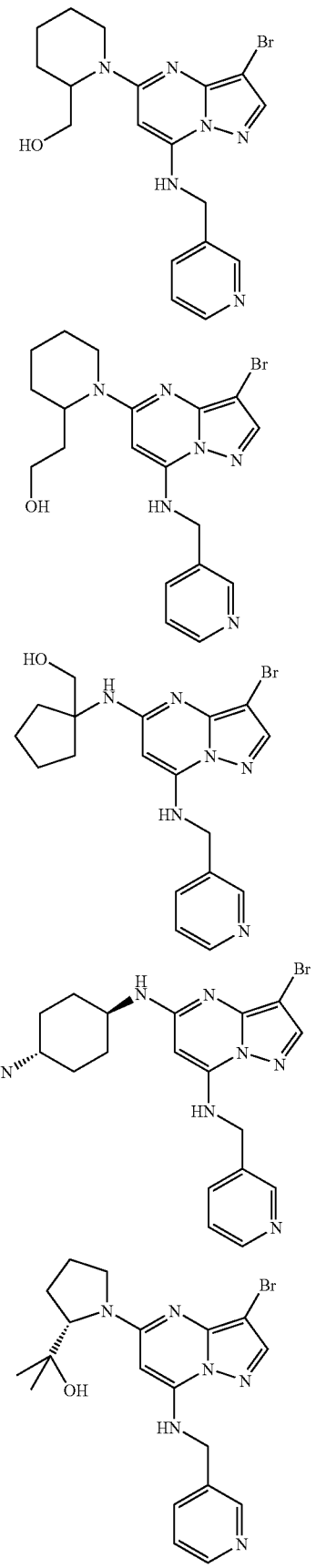

75
-continued
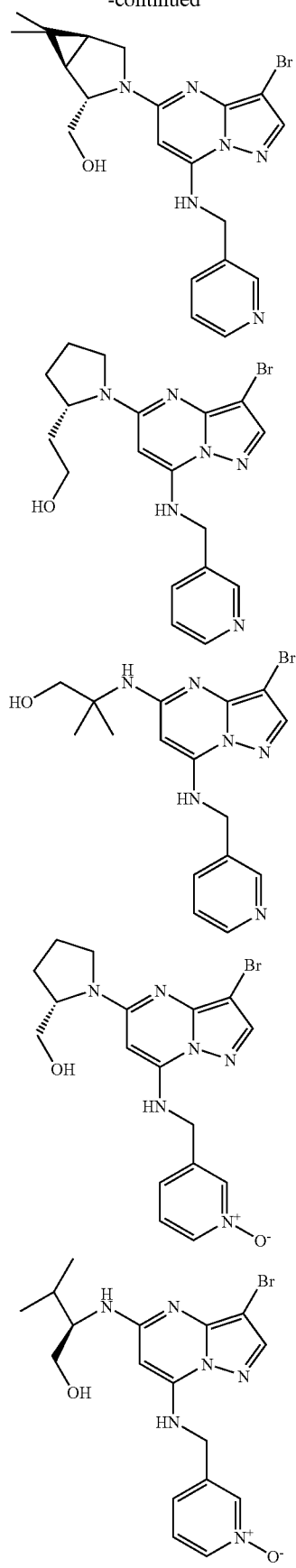
76
-continued
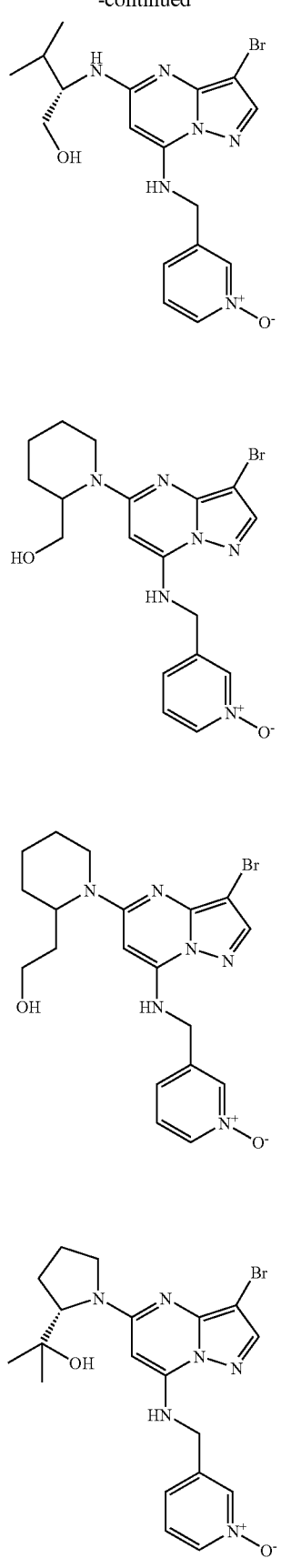

77
-continued
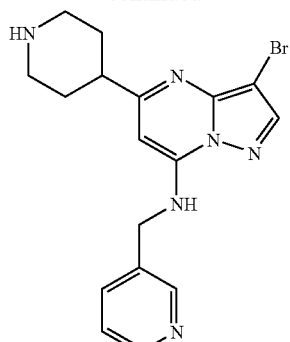
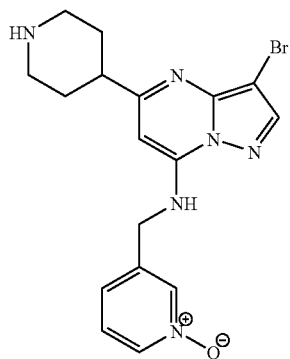
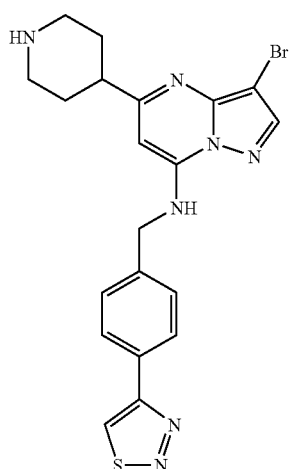
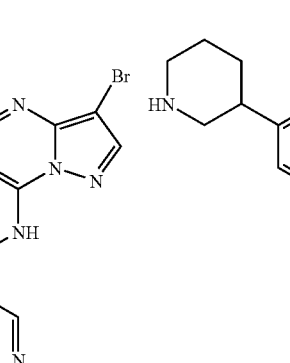
78
-continued
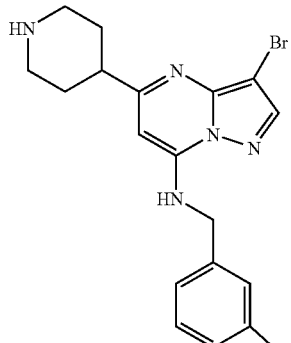
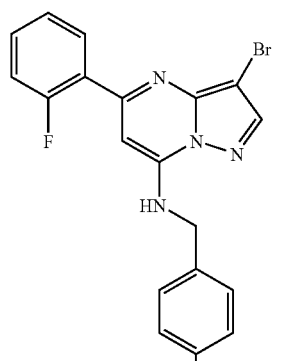
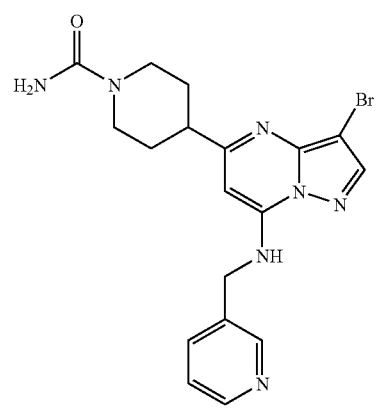
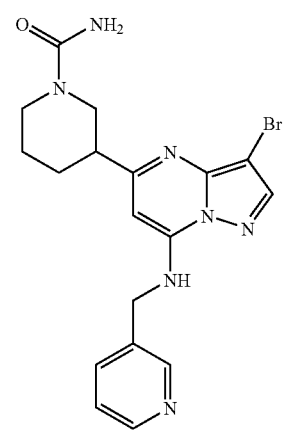

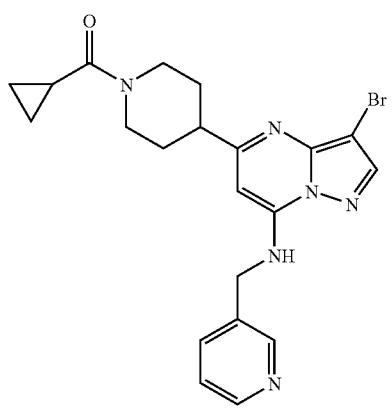
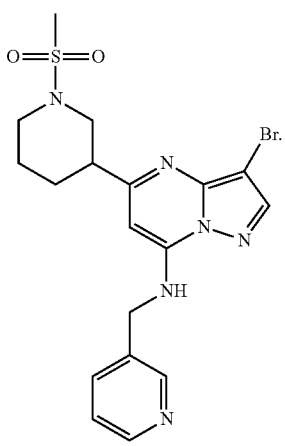
Another embodiment of the invention discloses the following compounds, which exhibited CDK2 inhibitory activity of about 0.0001 µM to about 0.1 µM:
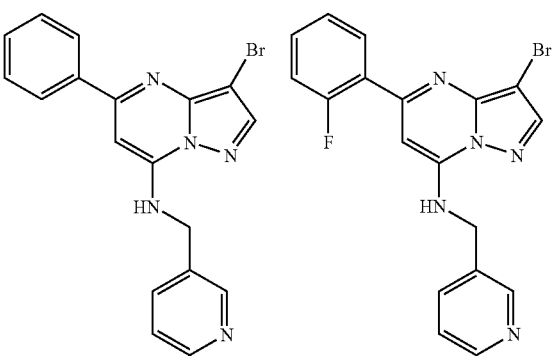
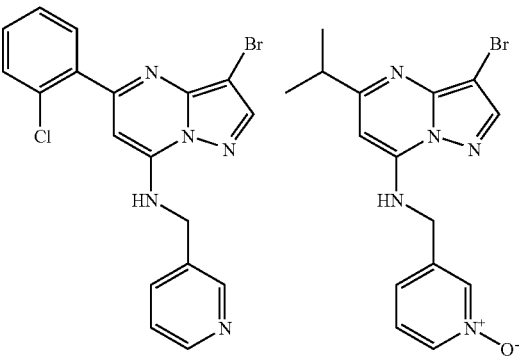
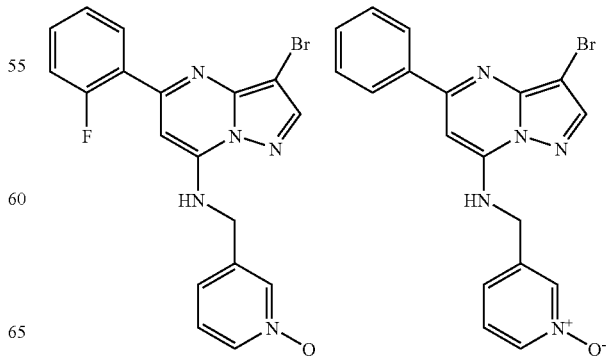

81
-continued
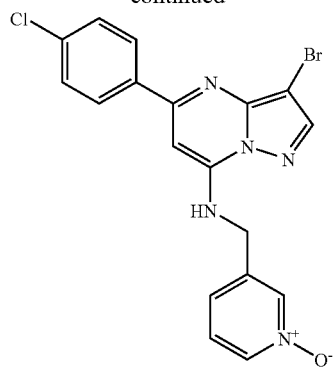
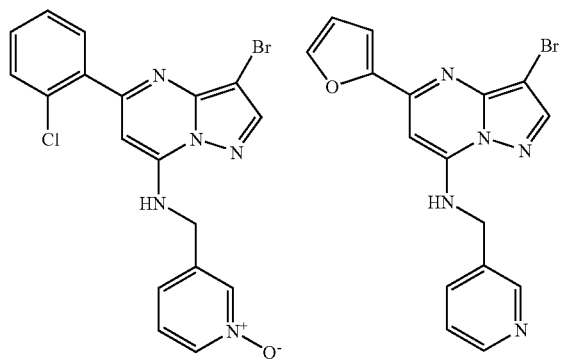
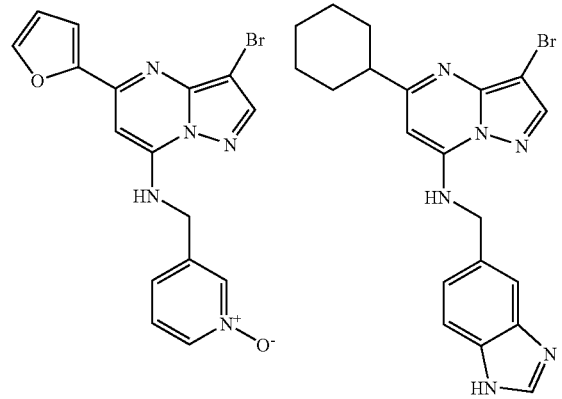
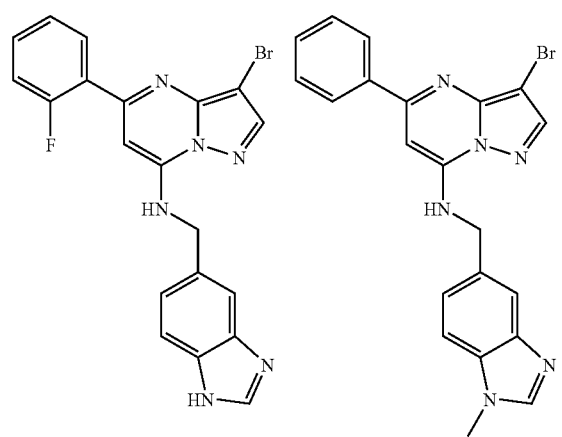
82
-continued
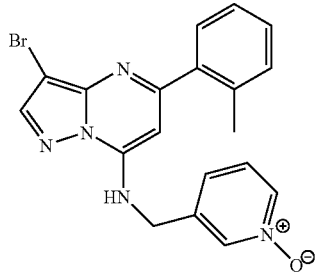
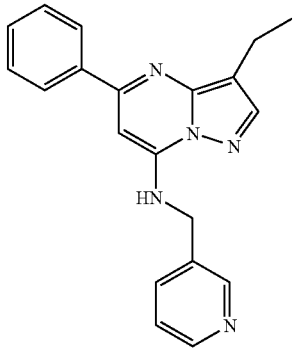
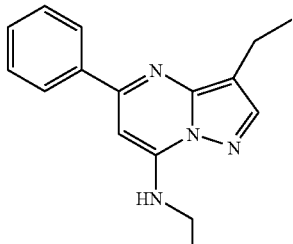
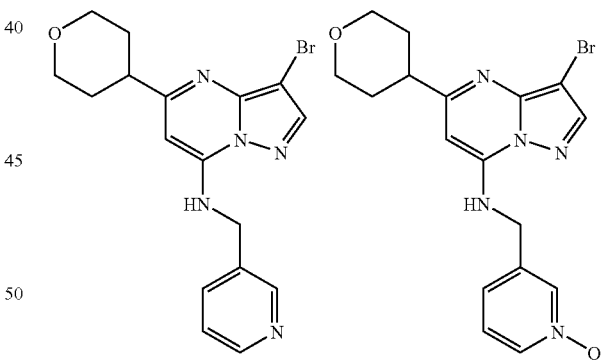
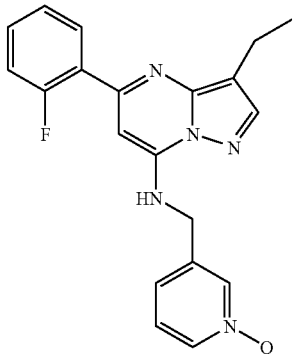

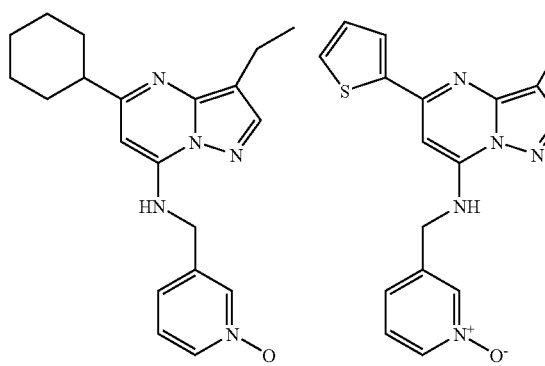
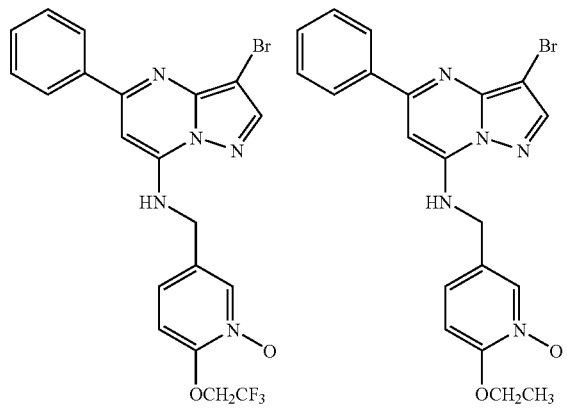
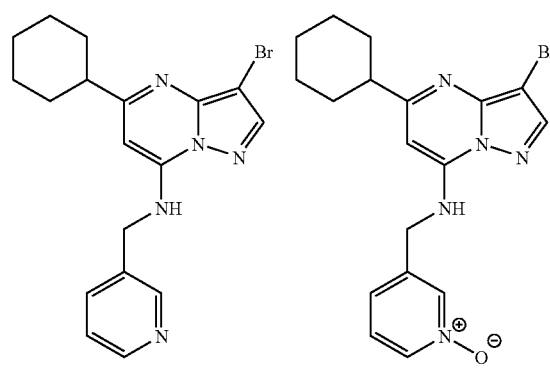
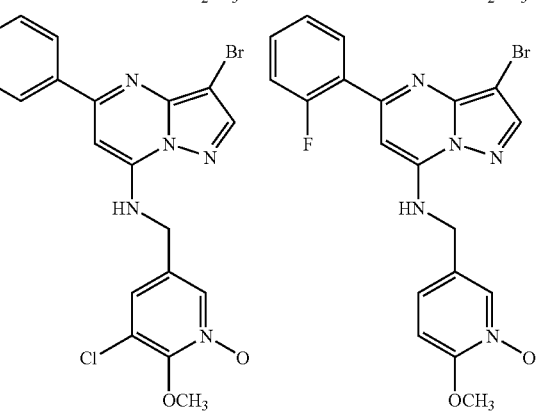
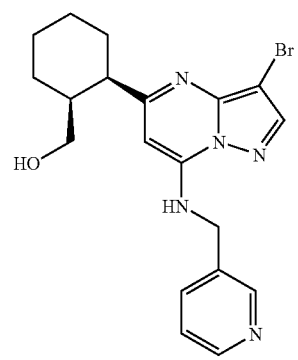
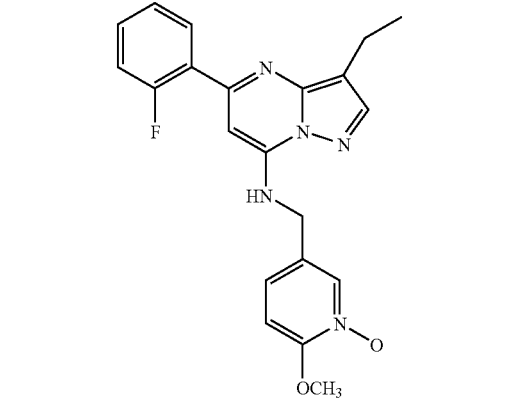
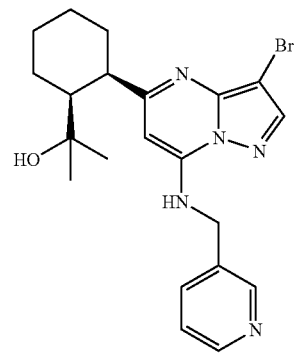
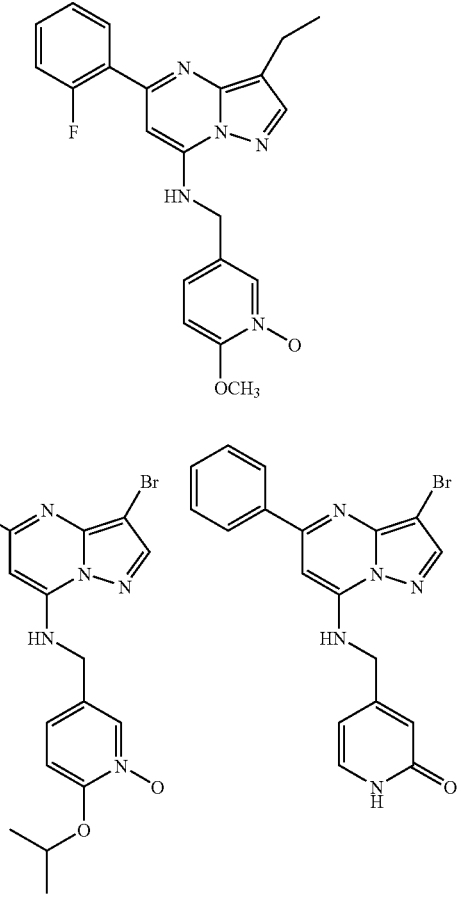

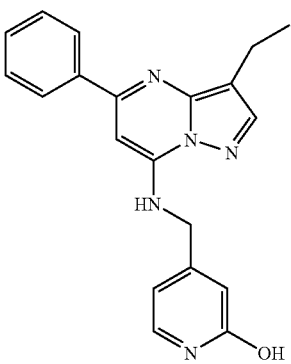
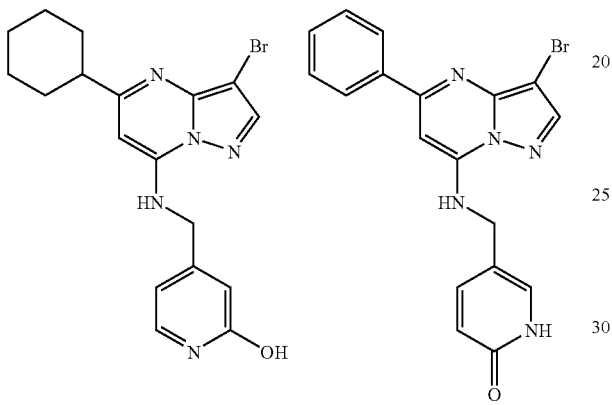
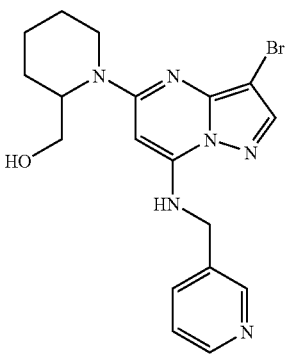
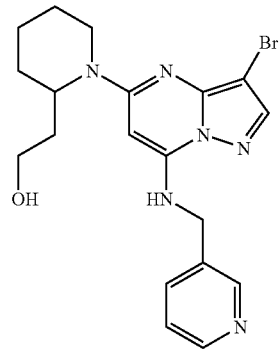
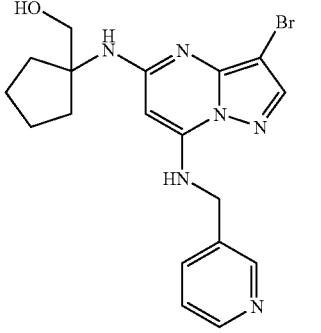
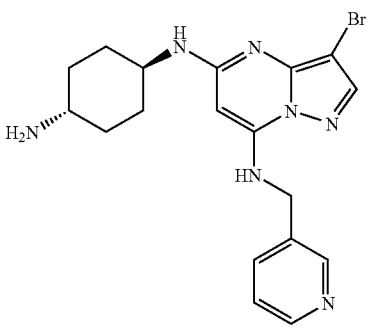
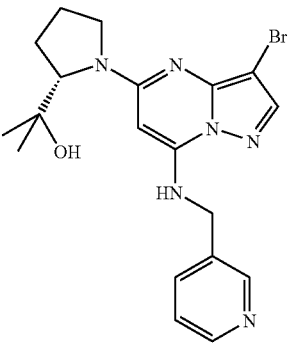

87
-continued
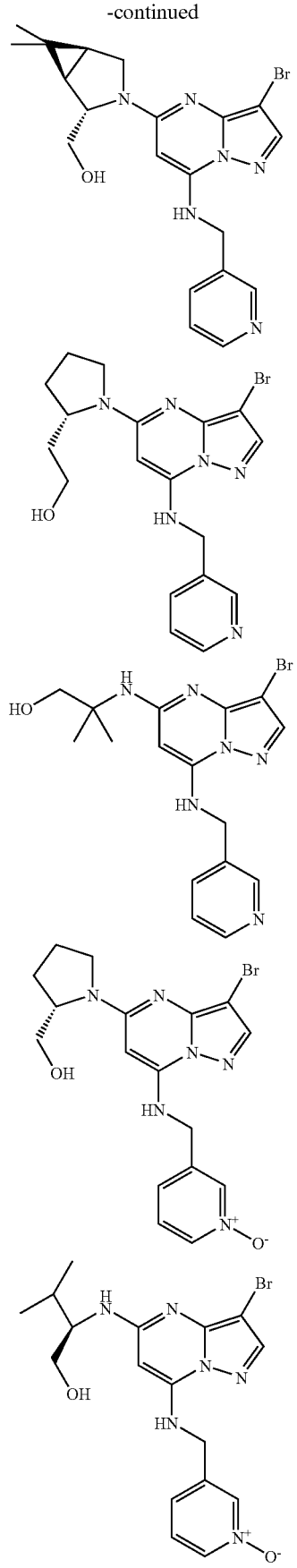
88
-continued
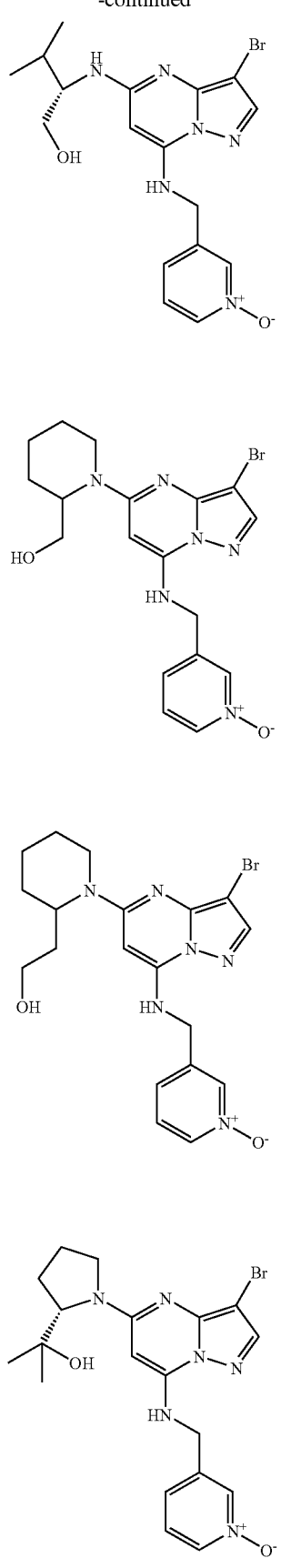

89
-continued
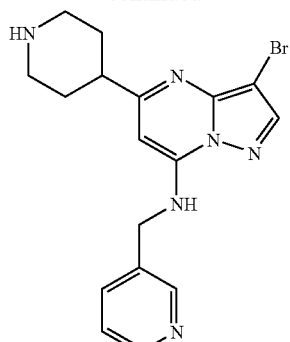
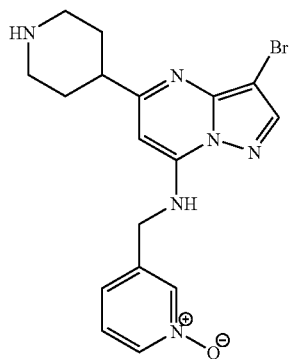
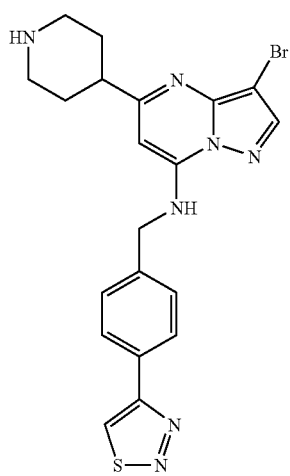
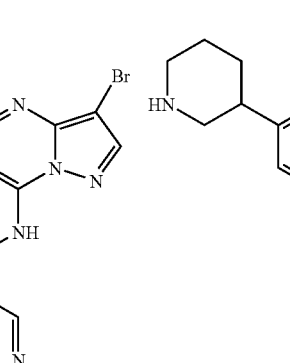
90
-continued
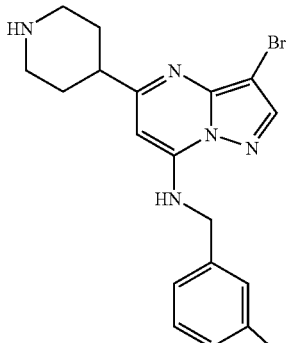
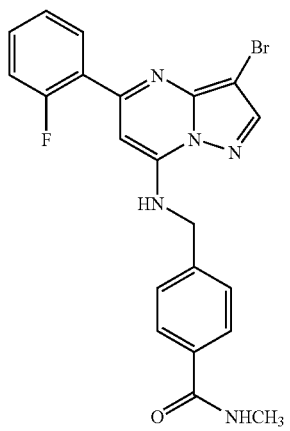
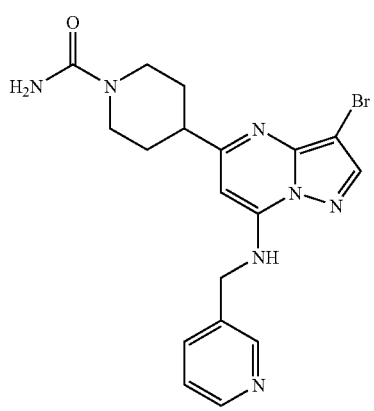

-continued

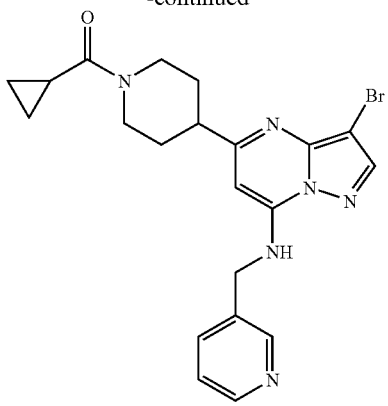

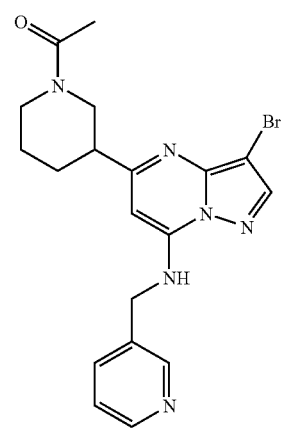

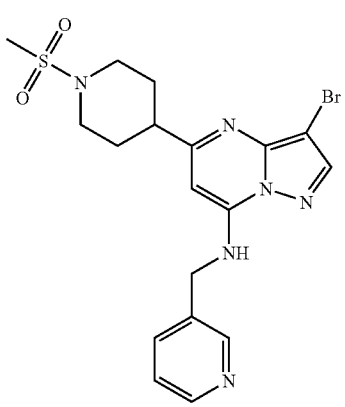

-continued

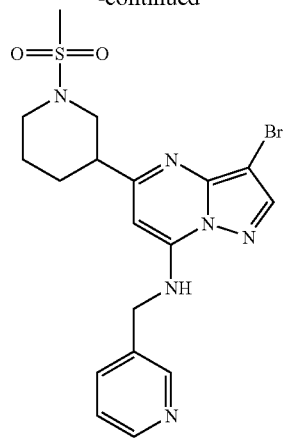

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

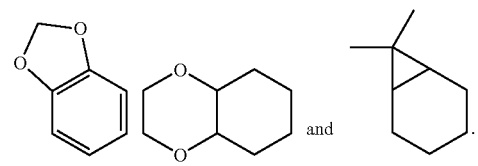

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

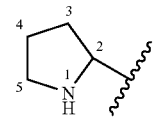

there is no —OH attached directly to carbons marked 2 and 5.

It should also be noted that tautomeric forms such as, for example, the moieties:

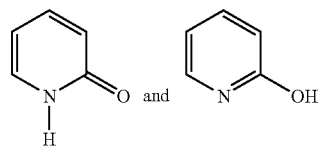 [SMILES: O=c1cccc[nH]1 ; Oc1ccccn1]

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any heteroatom with unsatisfied valences in the text, schemes, examples and Tables herein is assumed to have the hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula II, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula III or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid.

"Solvate" encompasses both solution-phase and isolatable solvates. Non-limiting examples of suitable solvates include ethanolates, methanolates, and the like.

"Hydrate" is a solvate wherein the solvent molecule is $H_2O$.

"Effective amount" or "therapeutically effective amount" is meant to describe an amount of compound or a composition of the present invention effective in inhibiting the CDK(s) and thus producing the desired therapeutic, ameliorative, inhibitory or preventative effect.

The compounds of Formula III can form salts which are also within the scope of this invention. Reference to a compound of Formula III herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula III contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula III may be formed, for example, by reacting a compound of Formula III with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula II, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

The compounds according to the invention have pharmacological properties; in particular, the compounds of Formula III can be inhibitors of protein kinases such as, for example, the inhibitors of the cyclin-dependent kinases, mitogen-activated protein kinase (MAPK/ERK), glycogen synthase kinase 3(GSK3beta) and the like. The cyclin dependent kinases (CDKS) include, for example, CDC2 (CDK1), CDK2, CDK4, CDK5, CDK6, CDK7 and CDK8. The novel compounds of Formula III are expected to be useful in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease. Many of these diseases and disorders are listed in U.S. Pat. No. 6,413,974 cited earlier, the disclosure of which is incorporated herein.

More specifically, the compounds of Formula III can be useful in the treatment of a variety of cancers, including (but not limited to) the following: carcinoma, including that of the bladder, breast, colon, kidney, liver, lung, including small cell lung cancer, non-small cell lung cancer, head and neck, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Non-limiting examples of some specific diseases that can be treated using the compounds and/or pharmaceutical compositions comprising such compounds, and/or with combination anti-cancer agents include the following:

tumor of the bladder, breast (including BRCA-mutated breast cancer), colorectal, colon, kidney, liver, lung, small cell lung cancer, non-small cell lung cancer, head and neck, esophagus, bladder, gall bladder, ovary, pancreas, stomach, cervix, thyroid, prostate, and skin, including squamous cell carcinoma;

leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma and Burkett's lymphoma;

chronic lymphocytic leukemia ("CLL"), acute and chronic myelogenous leukemia, myelodysplastic syndrome and promyelocytic leukemia;

fibrosarcoma, rhabdomyosarcoma;

head and neck, mantle cell lymphoma, myeloma;

astrocytoma, neuroblastoma, glioma, glioblastoma, malignant glial tumors, astrocytoma, hepatocellular carcinoma, gastrointestinal stromal tumors ("GIST") and schwannomas;

melanoma, multiple myeloma, seminoma, teratocarcinoma, osteosarcoma, xenoderoma pigmentosum, keratoctanthoma, thyroid follicular cancer and Kaposi's sarcoma.

Due to the key role of CDKs in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of Formula III may also be useful in the treatment of Alzheimer's disease, as suggested by the recent finding that CDK5 is involved in the phosphorylation of tau protein (*J. Biochem*, (1995) 117, 741-749).

Compounds of Formula III may induce or inhibit apoptosis. The apoptotic response is aberrant in a variety of human diseases. Compounds of Formula III, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of Formula II, as inhibitors of the CDKs, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of Formula III may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formula III may also be useful in inhibiting tumor angiogenesis and metastasis.

Compounds of Formula III may also act as inhibitors of other protein kinases, e.g., protein kinase C, her2, raf 1, MEK1, MAP kinase, EGF receptor, PDGF receptor, IGF receptor, PI3 kinase, weel kinase, Src, Abl and thus be effective in the treatment of diseases associated with other protein kinases.

Another aspect of this invention is a method of treating a mammal (e.g., human) having a disease or condition associated with the CDKs by administering a therapeutically effective amount of at least one compound of Formula III, or a pharmaceutically acceptable salt or solvate of said compound to the mammal.

A preferred dosage is about 0.001 to 500 mg/kg of body weight/day of the compound of Formula II. An especially preferred dosage is about 0.01 to 25 mg/kg of body weight/day of a compound of Formula III, or a pharmaceutically acceptable salt or solvate of said compound.

The compounds of this invention may also be useful in combination (administered together or sequentially) with one or more of anti-cancer treatments such as radiation therapy, and/or one or more anti-cancer agents selected from the group consisting of cytostatic agents, cytotoxic agents (such as for example, but not limited to, DNA interactive agents (such as cisplatin or doxorubicin)); taxanes (e.g. docetaxel (TAXOTERE®, paclitaxel (TAXOL®)); topoisomerase II inhibitors (such as etoposide); topoisomerase I inhibitors (such as irinotecan (CAMPTOSTAR®) (or CPT-11), or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™ (4-[2-[4-[(11R)-3,10-dibromo-8-chloro-6,11-dihydro-5H-benzo[5,6]cyclohepta[1,2-b]pyridin-11-yl-1-1-piperidinyl]-2-oxoethyl]-1-piperidinecarboxamide, or SCH 66336 from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, gefitinib (IRESSA®) (from Astra Zeneca Pharmaceuticals, England)), erlotinib (TARCEVA®) (EGFR kinase inhibitors), antibodies to EGFR (e.g., C225), imatinib (GLEEVEC™) (C-abl kinase inhibitor from Novartis Pharmaceuticals, East Hanover, N.J.); interferons such as, for example, intron (from Schering-Plough Corporation), Peg-interferon alfa-2b (PEG-INTRON™) (from Schering-Plough Corporation); hormonal therapy combinations; aromatase combinations; ara-C, doxorubicin (ADRIAMYCIN®), cyclophospamide (CYTOXAN®), and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaeuticals, France), Pentostatine, Vinblastine, Vincristine, Vindesine, Bleomycin, Dactinomycin, Daunorubicin, Doxorubicin, liposomal doxorubicin (e.g., CAELYX®, MYOCET®, DOXIL®), Epirubicin, Idarubicin, Mithramycin, Deoxycoformycin, Mitomycin-C, L-Asparaginase, Teniposide, 17α-Ethinylestradiol, Diethylstilbestrol, Testosterone, Prednisone, Fluoxymesterone., Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, bevacizumab (AVASTIN®), trastuzumab (HERCEPTIN®) tositumomab (BEXXAR®), bortezomib (VELCADE®), ibritumomab (ZEVALIN™), Arsenic trioxide (TRISENOX®), capecitabine (XELOD®), Vinorelbine, Porfimer, cetuximab (ERBITUX®), Liposomal, Thiotepa, Altretamine, Melphalan, Trastuzumab, Lerozole, Fulvestrant, Exemestane, Ifosfomide, Rituximab, C225 (or Cetuximab from Merck KGaA, Darmstadt, Germany), and alemtuzumab (CAMPATH®).

The compounds of this invention may specifically be useful in combination (administered together, concurrently or sequentially) with at least one compound selected from the group consisting of a cytostatic agent, cisplatin, doxorubicin, (TAXOTERE®), paclitaxel (TAXOL®), etoposide, irinotecan, irinotecan (CAMPTOSTAR®), topotecan, paclitaxel, docetaxel, epothilones, tamoxifen, 5-fluorouracil, methoxtrexate, temozolomide, cyclophosphamide, SCH 66336, R115777®, L778,123®, BMS 214662®, qefitinib (IRESSA®), erlotinib (TARCEVA®), antibodies to EGFR, antibodies to IGFR (including, for example, those published in US 2005/0136063 published Jun. 23, 2005), KSP inhibitors (such as, for example, those published in WO 2006/098962 and WO 2006/098961; ispinesib, SB-743921 from Cytokinetics), centrosome associated protein E ("CENP-E") inhibitors (e.g., GSK-923295), imatinib (GLEEVEC®), intron, ara-C, doxorubicin (ADRIAMYCIN®), cyclophosphamide (CYTOXAN®), gemcitabine, Uracil mustard, Chlormethine, Ifosfamide, Melphalan, Chlorambucil, Pipobroman, Triethylenemelamine. Triethylenethiophosphoramine, Busulfan, Carmustine, Lomustine, Streptozocin, Dacarbazine, Floxuridine, Cytarabine, 6-Mercaptopurine, 6-Thioguanine. Fludarabine phosphate, oxaliplatin. leucovirin oxaliplatin (ELOXATIN™), Pentostatine, Vinblastine, Vincristine, Vindesine, Bleomycin, Dactinomycin, Daunorubicin, Doxorubicin, Epirubicin, Idarubicin, Mithrarnycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, bevacizumab (AVASTIN®), trastuzumab (HERCEPTIN®), tositumomab (BEXXAR®), bortezomib (VELCADE®), ibritumomab (ZEVALIN®), arsenic trioxide (TRISENOX®), capecitabine (XELODA®), Vinorelbine, Porfimer, cetuximab (ERBITUX®)), Liposomal, Thiotepa, Altretamine, Melphalan, Trastuzumab, Lerozole, Fulvestrant, Exemestane, Fulvestrant, Ifosfomide, Rituximab, C225®, satriplatin, ALIMTA® (pemetrexed), MYLOTARG® (Gemtuzumab ozogamicin); AVASTIN® (bevacizumab), panitubimab, SUTENT® (sunitinib), sorafenib, SPRYCEL® (dastinib), nilotinib, TYKERB® (lapatinib) and alemtuzumab (CAMPATH®). This may optionally be combined with radiation therapy.

If formulated as a fixed dose, such combination products employ the compounds of this invention within the dosage range described herein and the other pharmaceutically active agent or treatment within its dosage range. For example, the CDC2 inhibitor olomucine has been found to act synergistically with known cytotoxic agents in inducing apoptosis (*J. Cell Sci.*, (1995) 108, 2897. Compounds of Formula III may also be administered sequentially with known anticancer or cytotoxic agents when a combination formulation is inappropriate. The invention is not limited in the sequence of administration; compounds of Formula III may be administered either prior to or after administration of the known anticancer or cytotoxic agent. For example, the cytotoxic activity of the cyclin-dependent kinase inhibitor flavopiridol is affected by the sequence of administration with anticancer agents. *Cancer Research*, (1997) 57, 3375. Such techniques are within the skills of persons skilled in the art as well as attending physicians.

Accordingly, in an aspect, this invention includes combinations comprising an amount of at least one compound of Formula III, or a pharmaceutically acceptable salt or solvate thereof, and an amount of one or more anti-cancer treatments and anti-cancer agents listed above wherein the amounts of the compounds/treatments result in desired therapeutic effect.

The pharmacological properties of the compounds of this invention may be confirmed by a number of pharmacological assays. The exemplified pharmacological assays which are described later have been carried out with the compounds according to the invention and their salts.

This invention is also directed to pharmaceutical compositions which comprise at least one compound of Formula II, or a pharmaceutically acceptable salt or solvate of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient.

Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula III, or a pharmaceutically acceptable salt or solvate of said compound and a pharmaceutically acceptable carrier, vehicle or diluent.

Yet another aspect of this invention is a kit comprising an amount of at least one compound of Formula II, or a pharmaceutically acceptable salt or solvate of said compound and an amount of at least one anticancer therapy and/or anti-cancer agent listed above, wherein the amounts of the two or more ingredients result in desired therapeutic effect.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The retention time and observed parent ion are given.

The following solvents and reagents may be referred to by their abbreviations in parenthesis:
Thin layer chromatography: TLC
dichloromethane: CH$_2$Cl$_2$
ethyl acetate: AcOEt or EtOAc
methanol: MeOH
trifluoroacetate: TFA
triethylamine: Et$_3$N or TEA
butoxycarbonyl: n-Boc or Boc
nuclear magnetic resonance spectroscopy: NMR
liquid chromatography mass spectrometry: LCMS
high resolution mass spectrometry: HRMS
milliliters: mL
millimoles: mmol
microliters: μl
grams: g
milligrams: mg
room temperature or rt (ambient): about 25° C.
dimethoxyethane: DME

EXAMPLES

In general, the compounds described in this invention can be prepared through the general routes described below in Scheme 1. Treatment of the

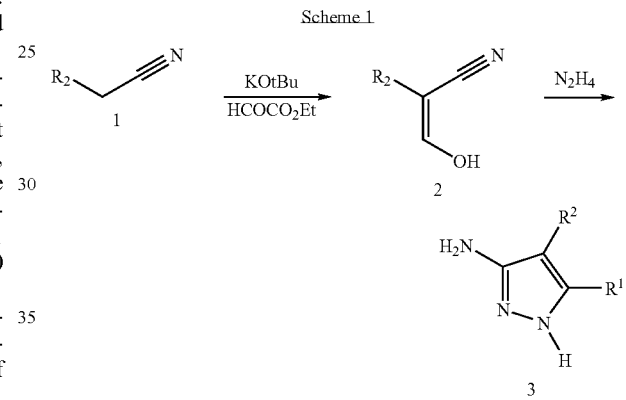

starting nitrile with potassium t-butoxide and ethyl formate gives rise to the intermediate enol 2 which upon treatment with hydrazine gives the desired substituted 3-aminopyrazole. Condensation of compounds of type 3 with the appropriately functionalized keto ester of type 5 gives rise to the pyridones 6 as shown in Scheme 3. The keto esters used in this general route are either commercially available or can be made as illustrated in Scheme 2.

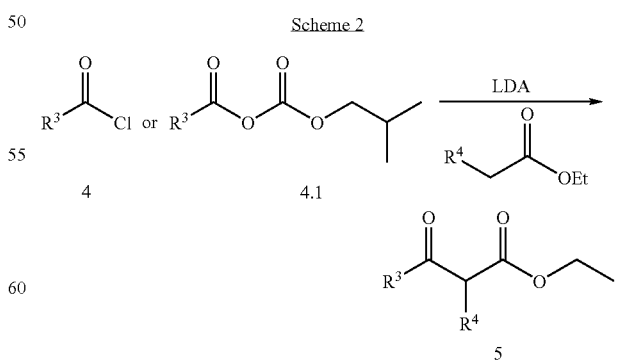

The chlorides of type 9 can be prepared by treatment of the pyridones 8 with POCl$_3$. When R$^2$ is equal to H, substitution in this position is possible on the compounds of type 9 by electrophilic halogenation, acylation, and various other electrophilic aromatic substitutions.

Introduction of the N7-amino functionality can be accomplished through displacement of the chloride of compounds of type 9 by reaction with the appropriate amine as shown in Scheme 3.

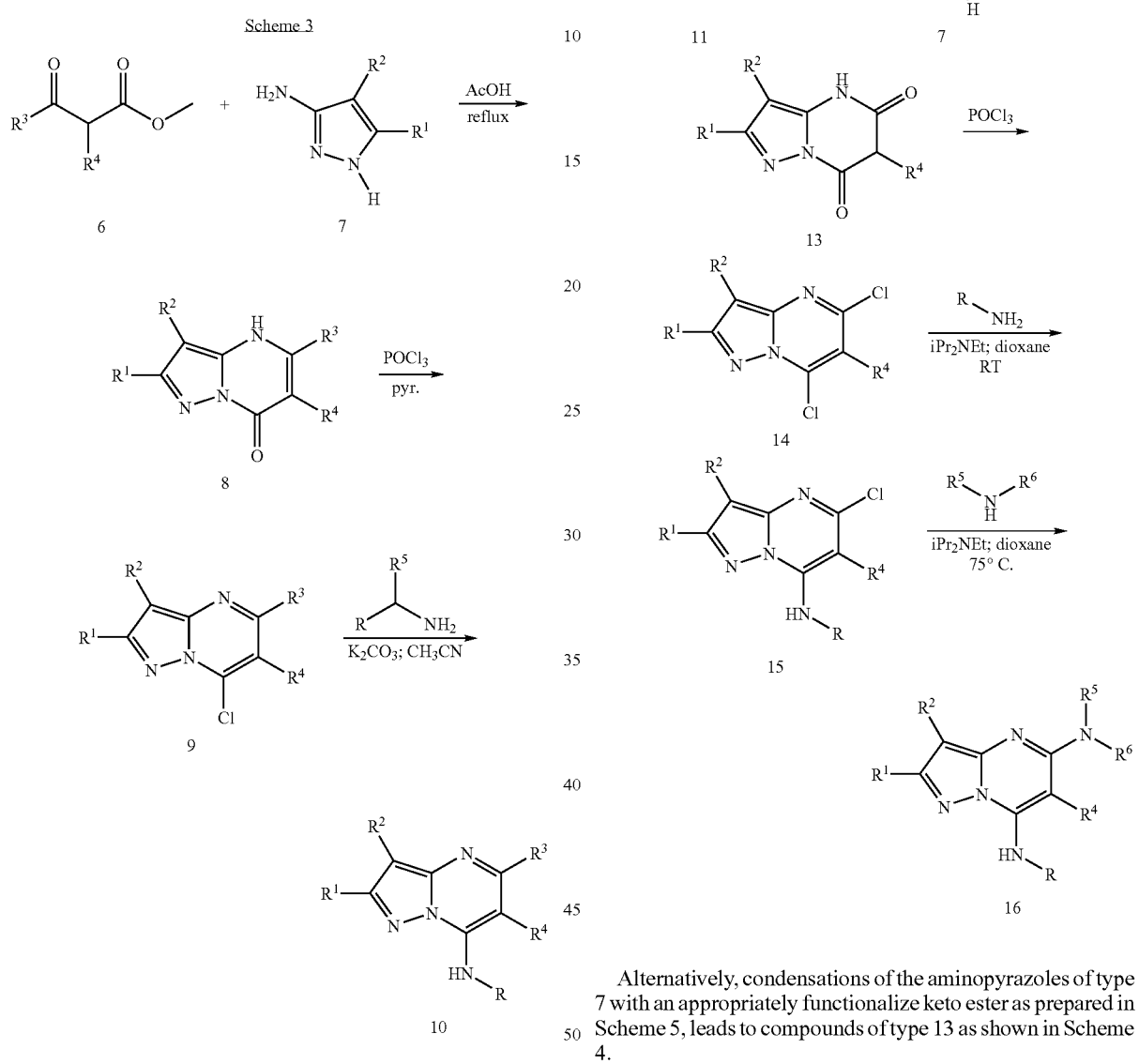

Condensation of compounds of type 7 with the appropriately functionalized malonate ester of type 11 gives rise to the pyridones 13 as shown in Scheme 4.

The chlorides of type 14 can be prepared by treatment of the pyridones 13 with $POCl_3$. When $R^2$ is H, substitution in this position is possible on compounds of type 9 by electrophilic halogenation, acylation, and various other electrophilic aromatic substitutions.

Incorporation of the N7-amino functionality can be accomplished through regioselective displacement of the chloride of compounds of type 14. Incorporation of the N5-amino functionality by addition of an appropriate amine at higher temperature.

Alternatively, condensations of the aminopyrazoles of type 7 with an appropriately functionalize keto ester as prepared in Scheme 5, leads to compounds of type 13 as shown in Scheme 4.

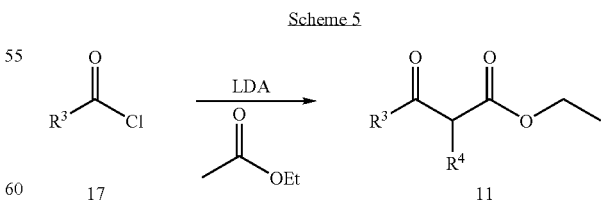

The chlorides of type 14 can be prepared by treatment of the pyridones 13 with $POCl_3$. When $R^2$ is equal to H, substitution in this position is possible on compounds of type 14 by electrophilic halogenation, acylation, and various other electrophilic aromatic substitutions.

107

Incorporation of the N7-amino functionality can be accomplished through displacement of the chloride of compounds of type 15.

Preparative Examples

Preparative Example 1

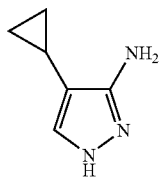

Step A:

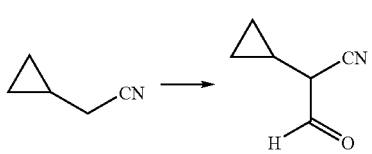

A procedure in German patent DE 19834047 A1, p 19 was followed. To a solution of KOtBu (6.17 g, 0.055 mol) in anhydrous THF (40 mL) was added, dropwise, a solution of cyclopropylacetonitrile (2.0 g, 0.025 mol) and ethyl formate (4.07 g, 0.055 mol) in anhydrous THF (4 mL). A precipitate formed immediately. This mixture was stirred for 12 hr. It was concentrated under vacuum and the residue stirred with Et$_2$O (50 mL). The resulting residue was decanted and washed with Et$_2$O (2×50 mL) and Et$_2$O removed from the residue under vacuum. The residue was dissolved in cold H$_2$O (20 mL) and pH adjusted to 4-5 with 12 N HCl. The mixture was extracted with CH$_2$Cl$_2$ (2×50 mL). The organic layers were combined, dried over MgSO$_4$ and concentrated under vacuum to give the aldehyde as a tan liquid.

Step B:

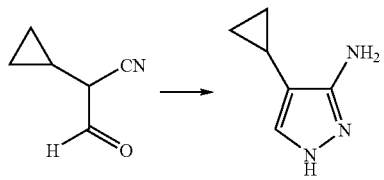 [SMILES: N#CC(C=O)C1CC1 ; Nc1n[nH]cc1C1CC1]

The product from Preparative Example 1, Step A (2.12 g, 0.0195 mol), NH$_2$NH$_2$.H$_2$O (1.95 g, 0.039 mol) and 1.8 g (0.029 mole) of glacial CH$_3$CO$_2$H (1.8 g, 0.029 mol) were dissolved in EtOH (10 mL). It was refluxed for 6 hr and concentrated under vacuum. The residue was slurried in CH$_2$Cl$_2$ (150 mL) and the pH adjusted to 9 with 1N NaOH. The organic layer was washed with brine, dried over MgSO$_4$ and concentrated under vacuum to give the product as a waxy orange solid.

Preparative Examples 2-4

By essentially the same procedure set forth in Preparative Example 1, only substituting the nitrile shown in Column 2 of Table 2, the compounds in Column 3 of Table 2 were prepared:

108

TABLE 2

| Prep. Ex. | Column 2 | Column 3 |
|---|---|---|
| 2 | 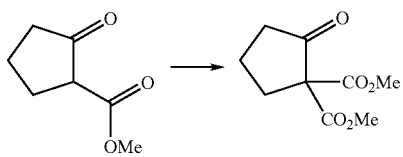 [SMILES: COC(=O)C1CCCC1=O ; COC(=O)C1(C(=O)OC)CCCC1=O] | |
| 3 | | |
| 3.10 | | |

Preparative Example 4

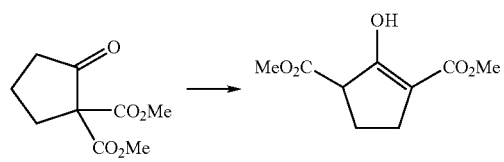 [SMILES: COC(=O)C1(C(=O)OC)CCCC1=O ; COC(=O)C1=C(O)C(C(=O)OC)CC1]

2-Carbomethoxycyclopentanone (6.6 ml, 0.05 mol) in THF (15 ml) was added dropwise to a vigorously stirred suspension of NaH (6.0% in mineral oil, 4 g, 0.1 mol) in THF (100 ml) at 0-10° C. When bubbling ceased, the reaction mixture was treated at the same temperature with ClCOOMe (7.8 ml, 0.1 mol) in THF (15 ml). The resulted off-white suspension was stirred for 30 minutes at room temperature and 30 minutes under reflux. The reaction was monitored by TLC for disappearance of starting material. The reaction mixture was quenched with water carefully and partitioned between ethyl acetate and saturated solution of ammonium chloride in a funnel. Shaken and separated, the organic layer was washed with brine and dried over anhydrous sodium sulfate. Solvents were removed, and the residue was purified by flash chromatography, eluted with 5% and then 10% ethyl acetate in hexane. 9.4 g colorless oil was obtained with 94% yield. $^1$H NMR (CDCl$_3$) δ 3.90 (s, 3H), 3.73 (s, 3H), 2.65 (m, 4H), 1.98 (m, 2H).

Preparative Example 5

To lithium diisopropylamide solution in THF (2.0; N, 0.04 mol) at −65° C., was added dropwise 2,2-dicarbomethoxycyclopentanone (4 g, 0.02 mol) in THF (60 ml). The resulted reaction mixture was stirred at the same temperature before adding methyl chloroformate (1.54 ml, 0.02 mol). Reaction mixture stirred for an hour and poured into saturated ammonium chloride solution with some ice. This solution was extracted three times with ether, and the combined ethearal layers were dried over sodium sulfate. Solvents were removed in vacuo, and the residue was purified by flash chromatography, eluted with 30% increased to 50% ethyl acetate in hexane. 2.3 g yellowish oil was obtained with 58% yield. $^1$H NMR (CDCl$_3$) δ 3.77 (s, 6H), 3.32 (t, 1H), 3.60-3.10 (m, 4H).

Preparative Example 6

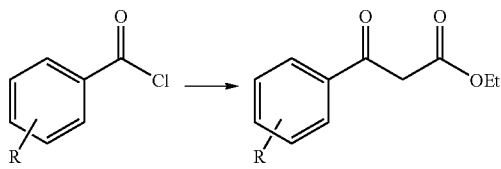

The reactions were done as outlined in (K. O. Olsen, *J. Org. Chem.*, (1987) 52, 4531-4536). Thus, to a stirred solution of lithium diisopropylamide in THF at −65 to −70 C was added freshly distilled ethyl acetate, dropwise. The resulting solution was stirred for 30 min and the acid chloride was added as a solution in THF. The reaction mixture was stirred at −65 to −70° C. for 30 min and then terminated by the addition of 1N HCl solution. The resulting two-phased mixture was allowed to warm to ambient temperature. The resulting mixture was diluted with EtOAc (100 mL) the organic layer was collected. The aqueous layer was extracted with EtOAc (100 mL). The organic layers were combined, washed with brine, dried (Na$_2$SO$_4$), and concentrated in vacuo to give the crude β-keto esters, which were used in the subsequent condensations.

Preparative Examples 7-19

By essentially the same procedure set forth in Preparative Example 6 only substituting the acid chlorides shown in Column 2 of Table 3, the β-keto esters shown in Column 3 of Table 3 were prepared:

TABLE 3

| Prep. Ex. | Column 2 | Column 3 | DATA |
|---|---|---|---|
| 7 |  |  | LCMS: MH$^+$ = 223 |
| 8 |  |  | LCMS: MH$^+$ = 253 |
| 9 |  |  | LCMS: MH$^+$ = 261 |
| 10 |  |  | MH$^+$ = 199 |
| 11 |  |  |  |

TABLE 3-continued

| Prep. Ex. | Column 2 | Column 3 | DATA |
|---|---|---|---|
| 12 | 2-methylbenzoyl chloride | ethyl 3-(2-methylphenyl)-3-oxopropanoate | |
| 13 | 2-bromobenzoyl chloride | ethyl 3-(2-bromophenyl)-3-oxopropanoate | LCMS: MH$^+$ = 271 |
| 14 | 4-tert-butylbenzoyl chloride | ethyl 3-(4-tert-butylphenyl)-3-oxopropanoate | Yield = quant<br>MH$^+$ = 249 |
| 15 | 1,3-benzodioxole-5-carbonyl chloride | ethyl 3-(1,3-benzodioxol-5-yl)-3-oxopropanoate | Yield = quant<br>MH$^+$ = 237 |
| 16 | 2,4-dichlorobenzoyl chloride | ethyl 3-(2,4-dichlorophenyl)-3-oxopropanoate | Yield = quant<br>MH$^+$ = 262 |
| 17 | pyrazine-2-carbonyl chloride | ethyl 3-oxo-3-(pyrazin-2-yl)propanoate | Yield = 48<br>MH$^+$ = 195 |
| 18 | cyclohexanecarbonyl chloride | ethyl 3-cyclohexyl-3-oxopropanoate | Yield = 99<br>MH$^+$ = 199 |
| 19 | 2,6-dimethoxybenzoyl chloride | ethyl 3-(2,6-dimethoxyphenyl)-3-oxopropanoate | Yield = 77%<br>$^1$H NMR (CDCl$_3$)<br>δ 7.42 (t, 1H),<br>6.68 (d, 2H),<br>4.29 (q, 2H),<br>3.97 (d, 2H),<br>3.95 (s, 3H),<br>1.38 (t, 3H). |

Preparative Example 20

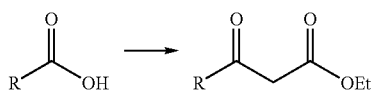

To a solution of the acid in THF was added Et₃N, followed by isobutyl chloroformate at −20 to −30° C. After the mixture was stirred for 30 min at −20 to −30° C., triethylamine hydrochloride was filtered off under argon, and the filtrate was added to the LDA-EtOAc reaction mixture (prepared as outlined in Method A) at −65 to −70° C. After addition of 1N HCl, followed by routine workup of the reaction mixture and evaporation of the solvents, the crude β-keto esters were isolated. The crude material was used in the subsequent condensations.

Preparative Examples 21-28

By essentially the same conditions set forth in Preparative Example 20 only substituting the carboxylic acid shown in Column 2 of Table 4, the compounds shown in Column 3 of Table 4 were prepared:

TABLE 4

| Prep. Ex. | Column 2 | Column 3 | CMPD |
|---|---|---|---|
| 21 | cyclohexyl-CH₂-COOH | cyclohexyl-CH₂-C(O)-CH₂-C(O)OEt | Yield = 99%<br>MH⁺ = 213 |
| 22 | 2,6-dichlorophenyl-CH₂-COOH | 2,6-dichlorophenyl-CH₂-C(O)-CH₂-C(O)OEt | Yield = 70%<br>MH⁺ = 275 |
| 23 | 2-methylcyclohexyl-COOH | 2-methylcyclohexyl-C(O)-CH₂-C(O)OEt | Yield = quant<br>MH⁺ = 213 |
| 24 | norbornyl-CH₂-COOH | norbornyl-CH₂-C(O)-CH₂-C(O)OEt | Yield = quant<br>MH⁺ = 211 |
| 25 | N-Cbz-piperidine-4-COOH | N-Cbz-piperidine-4-C(O)-CH₂-C(O)OEt | Yield = 99<br>MH⁺ = 334 |
| 26 | N-Cbz-piperidine-3-COOH | N-Cbz-piperidine-3-C(O)-CH₂-C(O)OEt | Yield = 99<br>MH⁺ = 334 |
| 27 | N-Cbz-piperidine-2-COOH | N-Cbz-piperidine-2-C(O)-CH₂-C(O)OEt | Yield = 99<br>MH⁺ = 334 |
| 28 | tetrahydrofuran-3-COOH | tetrahydrofuran-3-C(O)-CH₂-C(O)OEt | Yield = 77%<br>¹H NMR (CDCl₃) δ 4.21 (q, 2H), 3.95 (d, 2H), 3.93-3.79 (m, 4H), 3.52 (s, 2H), 2.65 (m, 1H), 1.25 (t, 3H), 1.23-1.2 (m, 2H). |

Preparative Example 29

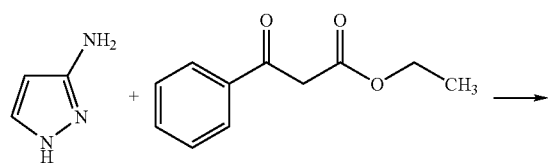

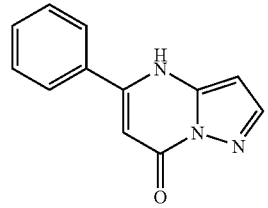 [SMILES: Cc1ccccc1-c1cc(=O)n2nccc2[nH]1]

A solution of 3-aminopyrazole (2.0 g, 24.07 mmol) and ethyl benzoylacetate (4.58 mL, 1.1 eq.) in ACOH (15 mL) was heated at reflux for 3 hours. The reaction mixture was cooled to room temperature and concentrated in vacuo. The resulting solid was diluted with EtOAc and filtered to give a white solid (2.04 g, 40% yield).

Preparative Examples 30-73

By essentially the same procedure set forth in Preparative Example 29 only substituting the aminopyrazole shown in Column 2 of Table 5 and the ester shown in Column 3 of Table 5, the compounds shown in Column 4 of Table 5 were prepared:

TABLE 5

| Prep. Ex. | Column 2 | Column 3 | Column 4 | Column 5 |
|---|---|---|---|---|
| 30 | | | | |
| 31 | | | | |
| 32 | | | | |
| 33 | | | | |
| 34 | | | | |

TABLE 5-continued

| Prep. Ex. | Column 2 | Column 3 | Column 4 | Column 5 |
|---|---|---|---|---|
| 35 | | | | |
| 36 | | | | |
| 37 | | | | |
| 37.10 | | | | |
| 38 | | | | |
| 39 | | | | |
| 40 | | | | |

TABLE 5-continued

| Prep. Ex. | Column 2 | Column 3 | Column 4 | Column 5 |
|---|---|---|---|---|
| 41 | 3-amino-1H-pyrazole | ethyl 3-(2,3-dichlorophenyl)-3-oxopropanoate | 5-(2,3-dichlorophenyl)pyrazolo[1,5-a]pyrimidin-7(4H)-one | |
| 42 | 3-amino-1H-pyrazole | ethyl 3-oxo-3-(thiophen-2-yl)propanoate | 5-(thiophen-2-yl)pyrazolo[1,5-a]pyrimidin-7(4H)-one | |
| 43 | 3-amino-1H-pyrazole | ethyl 4-cyclohexyl-3-oxobutanoate | 5-(cyclohexylmethyl)pyrazolo[1,5-a]pyrimidin-7(4H)-one | |
| 44 | 3-amino-1H-pyrazole | ethyl 4-(2,6-dichlorophenyl)-3-oxobutanoate | 5-(2,6-dichlorobenzyl)pyrazolo[1,5-a]pyrimidin-7(4H)-one | |
| 45 | 3-amino-1H-pyrazole | ethyl 5,5-dimethyl-3-oxohexanoate | 5-neopentylpyrazolo[1,5-a]pyrimidin-7(4H)-one | |
| 46 | ethyl 3-amino-1H-pyrazole-4-carboxylate | ethyl 5,5-dimethyl-3-oxohexanoate | ethyl 5-neopentyl-7-oxo-4,7-dihydropyrazolo[1,5-a]pyrimidine-3-carboxylate | |
| 47 | 3-amino-1H-pyrazole | ethyl 3-oxo-3-(o-tolyl)propanoate | 5-(o-tolyl)pyrazolo[1,5-a]pyrimidin-7(4H)-one | |

TABLE 5-continued

| Prep. Ex. | Column 2 | Column 3 | Column 4 | Column 5 |
|---|---|---|---|---|
| 48 | | | | |
| 49 | | | | |
| 50 | | | | |
| 51 | | | | |
| 52 | | | | |
| 53 | | | | |
| 54 | | | | |
| 55 | | | | |

TABLE 5-continued

| Prep. Ex. | Column 2 | Column 3 | Column 4 | Column 5 |
|---|---|---|---|---|
| 56 | 3-aminopyrazole | EtO₂C—≡—CO₂Et | ethyl 7-oxo-4,7-dihydropyrazolo[1,5-a]pyrimidine-5-carboxylate | |
| 57 | 3-aminopyrazole | 1-(2-bromophenyl)-3-ethoxy-3-oxopropan-1-one | 5-(2-bromophenyl)pyrazolo[1,5-a]pyrimidin-7(4H)-one | |
| 58 | 3-aminopyrazole | diethyl malonate | pyrazolo[1,5-a]pyrimidine-5,7-diol | Yield = 68<br>MH⁺ = 152 |
| 59 | 3-aminopyrazole | ethyl 3-(4-tert-butylphenyl)-3-oxopropanoate | 5-(4-tert-butylphenyl)pyrazolo[1,5-a]pyrimidin-7-ol | Yield = 46<br>MH⁺ = 268 |
| 60 | 3-aminopyrazole | ethyl 3-(benzo[d][1,3]dioxol-5-yl)-3-oxopropanoate | 5-(benzo[d][1,3]dioxol-5-yl)pyrazolo[1,5-a]pyrimidin-7-ol | Yield = 63<br>MH⁺ = 255 |
| 61 | 3-aminopyrazole | ethyl 3-(2,4-dichlorophenyl)-3-oxopropanoate | 5-(2,4-dichlorophenyl)pyrazolo[1,5-a]pyrimidin-7-ol | Yield = 80<br>MH⁺ = 280 |
| 62 | 3-aminopyrazole | ethyl 3-oxo-3-(pyrazin-2-yl)propanoate | 5-(pyrazin-2-yl)pyrazolo[1,5-a]pyrimidin-7-ol | Yield = 72<br>MH⁺ = 214 |

TABLE 5-continued

| Prep. Ex. | Column 2 | Column 3 | Column 4 | Column 5 |
|---|---|---|---|---|
| 63 | 3-aminopyrazole | ethyl 3-oxo-3-(thiophen-2-yl)propanoate | 5-(thiophen-2-yl)pyrazolo[1,5-a]pyrimidin-7-ol | Yield = 51<br>MH⁺ = 218 |
| 64 | 3-aminopyrazole | ethyl 3-cyclohexyl-3-oxopropanoate | 5-cyclohexylpyrazolo[1,5-a]pyrimidin-7-ol | Yield = 82<br>MH⁺ = 218 |
| 65 | 3-aminopyrazole | ethyl 3-(2-methylcyclohexyl)-3-oxopropanoate | 5-(2-methylcyclohexyl)pyrazolo[1,5-a]pyrimidin-7-ol | Yield = 39<br>MH⁺ = 232 |
| 66 | 3-aminopyrazole | ethyl 3-(norbornan-2-yl)-3-oxopropanoate | 5-(norbornan-2-ylmethyl)pyrazolo[1,5-a]pyrimidin-7-ol | Yield = 30<br>MH⁺ = 230 |
| 67 | 3-aminopyrazole | ethyl 3-(1-Cbz-piperidin-4-yl)-3-oxopropanoate | 5-(1-Cbz-piperidin-4-yl)pyrazolo[1,5-a]pyrimidin-7-ol | Yield = 80<br>MH⁺ = 353 |
| 68 | 3-aminopyrazole | ethyl 3-(1-Cbz-piperidin-3-yl)-3-oxopropanoate | 5-(1-Cbz-piperidin-3-yl)pyrazolo[1,5-a]pyrimidin-7-ol | Yield = 49<br>MH⁺ = 353 |
| 69 | 3-aminopyrazole | ethyl 3-(1-Cbz-piperidin-2-yl)-3-oxopropanoate | 5-(1-Cbz-piperidin-2-yl)pyrazolo[1,5-a]pyrimidin-7-ol | Yield = 42<br>MH⁺ = 353 |

TABLE 5-continued

| Prep. Ex. | Column 2 | Column 3 | Column 4 | Column 5 |
|---|---|---|---|---|
| 70 | | | | |
| 71 | | | | |
| 72 | | | | |
| 73 | | | | |

Preparative Example 74

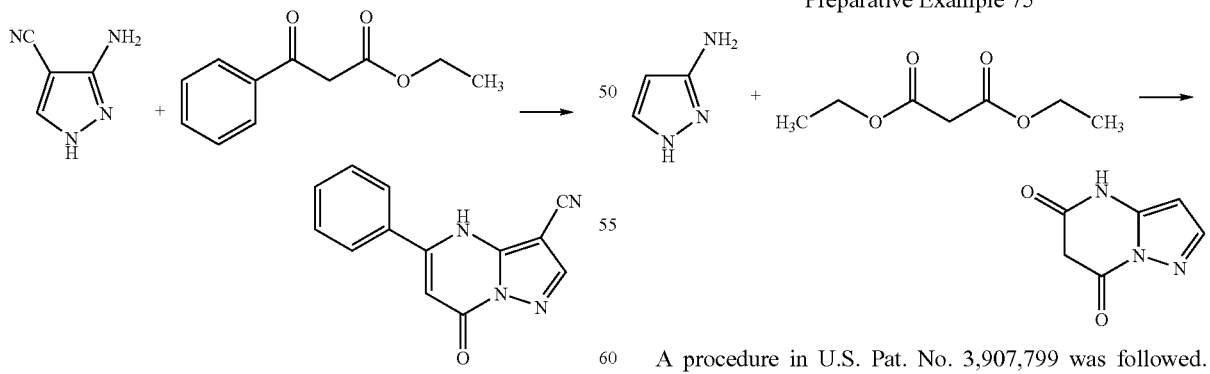

Ethyl benzoylacetate (1.76 mL, 1.1 eq.) and 3-amino-4-cyanopyrazole (1.0 g, 9.25 mmol) in ACOH (5.0 mL) and $H_2O$ (10 mL) was heated at reflux 72 hours. The resulting solution was cooled to room temperature, concentrated in vacuo, and diluted with EtOAc. The resulting precipitate was filtered, washed with EtOAc, and dried in vacuo (0.47 g, 21% yield).

Preparative Example 75

A procedure in U.S. Pat. No. 3,907,799 was followed. Sodium (2.3 g, 2 eq.) was added to EtOH (150 mL) portionwise. When the sodium was completely dissolved, 3-aminopyrazole (4.2 g, 0.05 mol) and diethyl malonate (8.7 g, 1.1 eq.) were added and the resulting solution heated to reflux for 3 hours. The resulting suspension was cooled to room temperature and filtered. The filter cake was washed with EtOH (100 mL) and dissolved in water (250 mL). The resulting solution was cooled in an ice bath and the pH adjusted to 1-2 with concentrated HCl. The resulting suspension was filtered, washed with water (100 mL) and dried under vacuum to give a white solid (4.75 g, 63% yield).

Preparative Examples 76-78

By essentially the same procedure set forth in Preparative Example 75 only substituting the compound shown in Column 2 of Table 6, the compounds shown in Column 3 of Table 6 are prepared:

TABLE 6

| Prep. Ex. | Column 2 | Column 3 |
|---|---|---|
| 76 | H₂N-pyrazole-cyclopropyl | pyrazolo-pyrimidinone-cyclopropyl |
| 77 | H₂N-pyrazole-isopropyl | pyrazolo-pyrimidinone-isopropyl |
| 78 | H₂N-pyrazole-CH₂CH₃ | pyrazolo-pyrimidinone-CH₂CH₃ |

Preparative Example 79

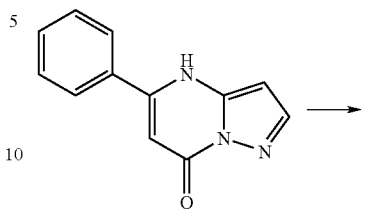

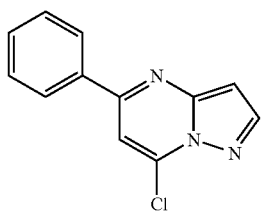

A solution of the compound prepared in Preparative Example 29 (1.0 g, 4.73 mmol) in POCl₃ (5 mL) and pyridine (0.25 mL) was stirred at room temperature 3 days. The resulting slurry was diluted with Et₂O, filtered, and the solid residue washed with Et₂O. The combined Et₂O washings were cooled to 0° C. and treated with ice. When the vigorous reaction ceased, the resulting mixture was diluted with H₂O, separated, and the aqueous layer extracted with Et₂O. The combined organics were washed with H₂O and saturated NaCl, dried over Na₂SO₄, filtered, and concentrated to give a pale yellow solid (0.86 g, 79% yield). LCMS: MH⁺=230.

Preparative Example 80-122

By essentially the same procedure set forth in Preparative Example 79, only substituting the compound shown in Column 2 of Table 7, the compounds shown in Column 3 of Table 7 were prepared:

TABLE 7

| Prep. Ex. | Column 2 | Column 3 | CMPD |
|---|---|---|---|
| 80 | 2-F-phenyl-pyrazolopyrimidinone | 2-F-phenyl-Cl-pyrazolopyrimidine | MS: MH⁺ = 248 |
| 81 | 2-Cl-phenyl-pyrazolopyrimidinone | 2-Cl-phenyl-Cl-pyrazolopyrimidine | |

TABLE 7-continued
| Prep. Ex. | Column 2 | Column 3 | CMPD |
|---|---|---|---|
| 82 | 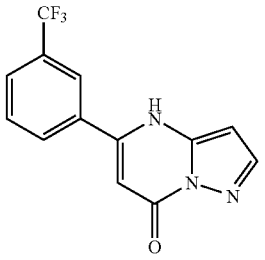 [SMILES: O=c1cc(-c2cccc(C(F)(F)F)c2)[nH]c2ccnn12] |  | MS: MH⁺ = 298 |
| 83 |  | 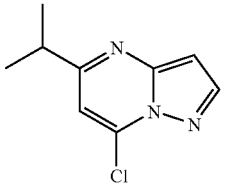 | MS: MH⁺ = 196 |
| 84 | 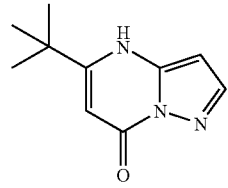 | 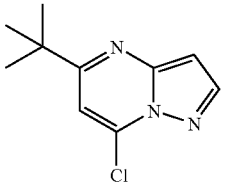 | MS: MH⁺ = 210 |
| 85 | 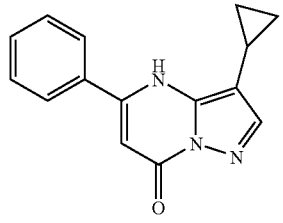 [SMILES: O=c1cc(-c2ccccc2)[nH]c2c(C3CC3)cnn12] | 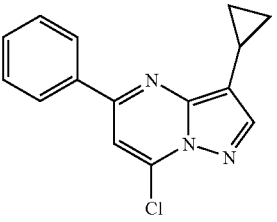 [SMILES: Clc1cc(-c2ccccc2)nc2c(C3CC3)cnn12] | |
| 86 | 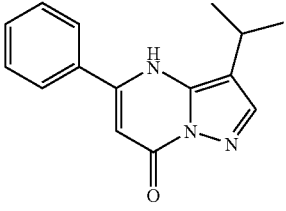 | 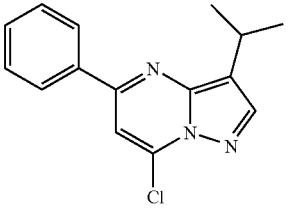 [SMILES: CC(C)c1cnn2c(Cl)cc(-c3ccccc3)nc12] | MS: MH⁺ = 272 |
| 87 | 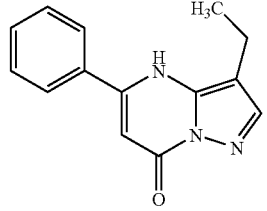 [SMILES: CCc1cnn2c(=O)cc(-c3ccccc3)[nH]c12] | 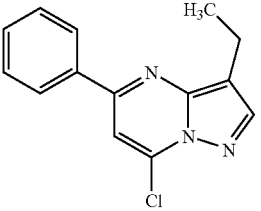 | |
| 87.10 | 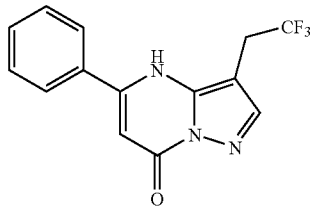 [SMILES: O=c1cc(-c2ccccc2)[nH]c2c(CC(F)(F)F)cnn12] | 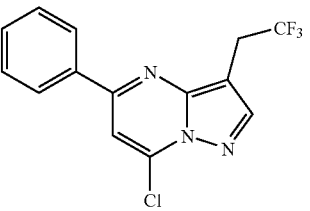 [SMILES: FC(F)(F)Cc1cnn2c(Cl)cc(-c3ccccc3)nc12] | |

TABLE 7-continued

| Prep. Ex. | Column 2 | Column 3 | CMPD |
|---|---|---|---|
| 88 | | | MS: MH⁺ = 255 |
| 89 | | | |
| 90 | | | Yield = 65%<br>MS: MH⁺ = 260 |
| 91 | | | Yield = 35%<br>MS: MH⁺ = 290 |
| 92 | | | Yield = 32%<br>MS: MH⁺ = 298 |
| 93 | | | Yield = 45%<br>MS: MH⁺ = 236 |
| 94 | | | Yield = 100%<br>LCMS: MH⁺ = 250 |

TABLE 7-continued

| Prep. Ex. | Column 2 | Column 3 | CMPD |
|---|---|---|---|
| 95 | | | Yield = 88%<br>MS: MH$^+$ = 314 |
| 96 | | | Yield = 43%<br>MS: MH$^+$ = 223 |
| 97 | | | Yield = 30%<br>MS: MH$^+$ = 295 |
| 98 | | | Yield = 98%<br>MS: MH$^+$ = 244 |
| 99 | | | |
| 100 | | | |
| 101 | | | |

TABLE 7-continued

| Prep. Ex. | Column 2 | Column 3 | CMPD |
|---|---|---|---|
| 102 | F₃C-pyrazolopyrimidinone | F₃C-pyrazolopyrimidine-Cl | |
| 103 | H₃C-pyrazolopyrimidinone | H₃C-pyrazolopyrimidine-Cl | |
| 104 | Et-pyrazolopyrimidinone | Et-pyrazolopyrimidine-Cl | |
| 105 | Pr-pyrazolopyrimidinone | Pr-pyrazolopyrimidine-Cl | |
| 106 | sec-Bu-pyrazolopyrimidinone | sec-Bu-pyrazolopyrimidine-Cl | |
| 107 | EtO₂C-pyrazolopyrimidinone | EtO₂C-pyrazolopyrimidine-Cl | 45% yield; MS: MH⁺ = 226 |
| 108 | (2-Br-phenyl)-pyrazolopyrimidinone | (2-Br-phenyl)-pyrazolopyrimidine-Cl | MS: MH⁺ = 308 |
| 109 | (4-tBu-phenyl)-pyrazolopyrimidine-OH | (4-tBu-phenyl)-pyrazolopyrimidine-Cl | Yield = quant MH⁺ = 286 |

TABLE 7-continued

| Prep. Ex. | Column 2 | Column 3 | CMPD |
|---|---|---|---|
| 110 | | | Yield = 50<br>MH+ = 272 |
| 111 | | | Yield = 85<br>MH+ = 299 |
| 112 | | | Yield = 97<br>MH+ = 231 |
| 113 | | | Yield = 45<br>MH+ = 236 |
| 114 | | | Yield = quant.<br>MH+ = 236 |
| 115 | | | Yield = 57<br>MH+ = 250 |
| 116 | | | Yield = 89<br>MH+ = 248 |

TABLE 7-continued

| Prep. Ex. | Column 2 | Column 3 | CMPD |
|---|---|---|---|
| 117 | 4-(Cbz-piperidinyl)-pyrazolo[1,5-a]pyrimidin-7-ol | 7-chloro-5-(Cbz-piperidin-4-yl)pyrazolo[1,5-a]pyrimidine | Yield = 96 MH$^+$ = 371 |
| 118 | 3-(Cbz-piperidinyl)-pyrazolo[1,5-a]pyrimidin-7-ol | 7-chloro-5-(Cbz-piperidin-3-yl)pyrazolo[1,5-a]pyrimidine | Yield = 99 MH$^+$ = 371 |
| 119 | 2-(Cbz-piperidinyl)-pyrazolo[1,5-a]pyrimidin-7-ol | 7-chloro-5-(Cbz-piperidin-2-yl)pyrazolo[1,5-a]pyrimidine | Yield = 50 MH$^+$ = 371 |
| 120 | 5-(tetrahydrofuran-3-yl)-pyrazolo[1,5-a]pyrimidin-7(4H)-one | 7-chloro-5-(tetrahydrofuran-3-yl)pyrazolo[1,5-a]pyrimidine | Yield = 57% LCMS: MH$^+$ = 224 |
| 121 | ethyl 7-oxo-4,7-dihydropyrazolo[1,5-a]pyrimidine-5-carboxylate | ethyl 7-chloropyrazolo[1,5-a]pyrimidine-5-carboxylate | Yield = 34% LCMS: MH$^+$ = 226 |
| 122 | 5-(2,6-dimethoxyphenyl)pyrazolo[1,5-a]pyrimidin-7(4H)-one | 7-chloro-5-(2,6-dimethoxyphenyl)pyrazolo[1,5-a]pyrimidine | Yield = 100% $^1$H NMR (CDCl$_3$) δ 8.53 (d, 1H), 7.66 (t, 1H), 7.51 (s, 1H), 7.45 (d, 1H), 6.84 (d, 2H). |

Preparative Example 123

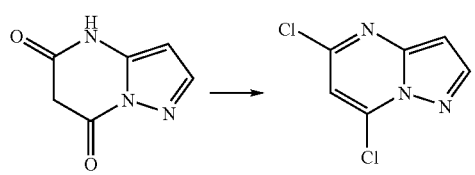

POCl$_3$ (62 mL) was cooled to 5° C. under nitrogen and dimethylaniline (11.4 g, 2.8 eq.) and the compound prepared in Preparative Example 75 (4.75 g, 0.032 mol). The reaction mixture was warmed to 60° C. and stirred overnight. The reaction mixture was cooled to 30° C. and the POCl$_3$ was distilled off under reduced pressure. The residue was dissolved in CH$_2$Cl$_2$ (300 mL) and poured onto ice. After stirring 15 minutes, the pH of the mixture was adjusted to 7-8 with solid NaHCO$_3$. The layers were separated and the organic layer was washed with H$_2$O (3×200 mL), dried over MgSO$_4$, filtered, and concentrated. The crude product was purified by flash chromatography using a 50:50 CH$_2$Cl$_2$: hexanes solution as eluent to elute the dimethyl aniline. The eluent was then changed to 75:25 CH$_2$Cl$_2$: hexanes to elute the desired product (4.58 g, 77% yield). MS: MH$^+$=188.

Preparative Examples 124-126

By essentially the same procedure set forth in Preparative Example 123 only substituting the compound in Column 2 of Table 8, the compounds shown in Column 3 of Table 8 are prepared:

TABLE 8

| Prep. Ex. | Column 2 | Column 3 |
|---|---|---|
| 124 | (structure) | (structure) |
| 125 | (structure) | (structure) |
| 126 | (structure) | (structure) |

Preparative Example 127

A solution of the compound prepared in Preparative Example 79 (0.10 g, 0.435 mmol) in CH$_3$CN (3 mL) was treated with NBS (0.085 g, 1.1 eq.). The reaction mixture was stirred at room temperature 1 hour and concentrated under reduced pressure. The crude product was purified by flash chromatography using a 20% EtOAc-in-hexanes solution as eluent (0.13 g, 100% yield). LCMS: MH$^+$=308.

Preparative Examples 128-164

By essentially the same procedure set forth in Preparative Example 127 only substituting the compounds shown in Column 2 of Table 9, the compounds shown in Column 3 of Table 9 were prepared:

TABLE 9

| Prep. Ex. | Column 2 | Column 3 | CMPD |
|---|---|---|---|
| 128 | (structure) | (structure) | MS: MH$^+$ = 326 |

TABLE 9-continued

| Prep. Ex. | Column 2 | Column 3 | CMPD |
|---|---|---|---|
| 129 | 5-(2-chlorophenyl)-7-chloropyrazolo[1,5-a]pyrimidine | 3-bromo-5-(2-chlorophenyl)-7-chloropyrazolo[1,5-a]pyrimidine | MS: MH$^+$ = 342 |
| 130 | 5-(3-trifluoromethylphenyl)-7-chloropyrazolo[1,5-a]pyrimidine | 3-bromo-5-(3-trifluoromethylphenyl)-7-chloropyrazolo[1,5-a]pyrimidine | MS: MH$^+$ = 376 |
| 131 | 5-isopropyl-7-chloropyrazolo[1,5-a]pyrimidine | 3-bromo-5-isopropyl-7-chloropyrazolo[1,5-a]pyrimidine | MS: MH$^+$ = 274 |
| 132 | 5-tert-butyl-7-chloropyrazolo[1,5-a]pyrimidine | 3-bromo-5-tert-butyl-7-chloropyrazolo[1,5-a]pyrimidine | MS: MH$^+$ = 288 |
| 133 | 5-(4-chlorophenyl)-7-chloropyrazolo[1,5-a]pyrimidine | 3-bromo-5-(4-chlorophenyl)-7-chloropyrazolo[1,5-a]pyrimidine | |
| 134 | 5-(2-methoxyphenyl)-7-chloropyrazolo[1,5-a]pyrimidine | 3-bromo-5-(2-methoxyphenyl)-7-chloropyrazolo[1,5-a]pyrimidine | Yield = 75%<br>MS: MH$^+$ = 338 |
| 135 | 5-(3,4-dimethoxyphenyl)-7-chloropyrazolo[1,5-a]pyrimidine | 3-bromo-5-(3,4-dimethoxyphenyl)-7-chloropyrazolo[1,5-a]pyrimidine | Yield = 52%<br>MS: MH$^+$ = 368 |

TABLE 9-continued

| Prep. Ex. | Column 2 | Column 3 | CMPD |
|---|---|---|---|
| 136 | 2,3-dichlorophenyl-pyrazolo[1,5-a]pyrimidine-Cl | 3-Br analog | Yield = 87%<br>MS: MH⁺ = 376 |
| 137 | 2-thienyl-pyrazolo[1,5-a]pyrimidine-Cl | 3-Br analog | Yield = 100%<br>MS: MH⁺ = 316 |
| 138 | cyclohexylmethyl-pyrazolo[1,5-a]pyrimidine-Cl | 3-Br analog | Yield = 92%<br>MS: MH⁺ = 330 |
| 139 | 2,6-dichlorobenzyl-pyrazolo[1,5-a]pyrimidine-Cl | 3-Br analog | Yield = 82%<br>MS: MH⁺ = 395 |
| 140 | phenyl-pyrazolo[1,5-a]pyrimidine-Cl | 3-Br analog | Yield = 88%<br>MS: MH⁺ = 308 |
| 141 | 2-methylphenyl-pyrazolo[1,5-a]pyrimidine-Cl | 3-Br analog | Yield = 100%<br>MS: MH⁺ = 322 |
| 142 | 5,7-dichloropyrazolo[1,5-a]pyrimidine | 3-Br analog | MH⁺ = 226 |

TABLE 9-continued
| Prep. Ex. | Column 2 | Column 3 | CMPD |
|---|---|---|---|
| 143 | 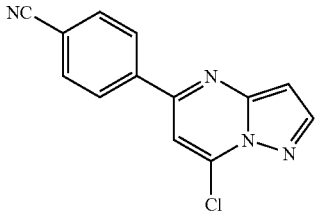 | 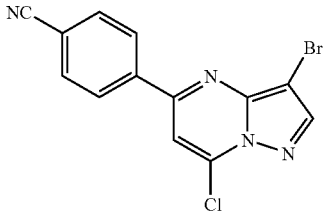 | |
| 144 | 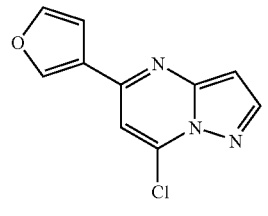 [SMILES: Clc1cc(-c2ccoc2)nc2ccnn12] | 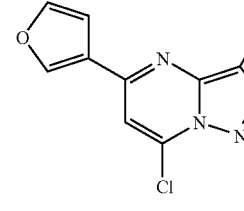 | |
| 145 | 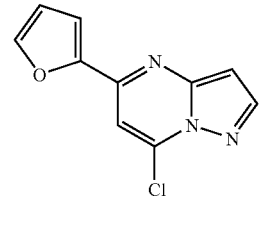 [SMILES: Clc1cc(-c2ccco2)nc2ccnn12] | 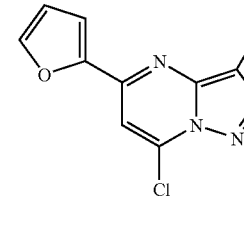 | |
| 146 | 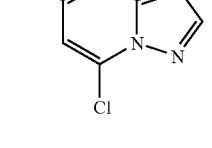 | 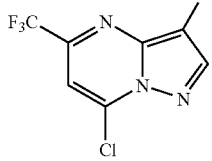 | |
| 147 | 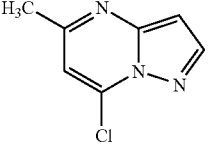 | 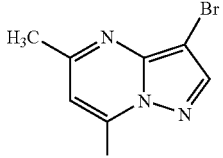 | |
| 148 |  | 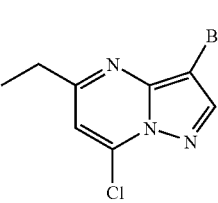 | |
| 149 | 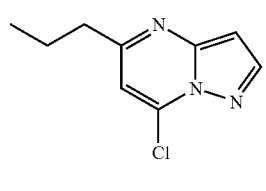 | 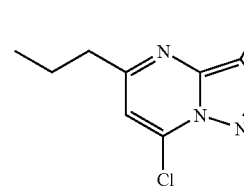 | |

TABLE 9-continued

| Prep. Ex. | Column 2 | Column 3 | CMPD |
|---|---|---|---|
| 150 | | | |
| 151 | | | LCMS: MH⁺ = 386 |
| 152 | | | Yield = quant<br>MH⁺ = 364 |
| 153 | | | Yield = quant<br>MH⁺ = 353 |
| 154 | | | Yield = 95<br>MH⁺ = 378 |
| 155 | | | Yield = 77<br>MH⁺ = 311 |

TABLE 9-continued

| Prep. Ex. | Column 2 | Column 3 | CMPD |
|---|---|---|---|
| 156 | 5-cyclohexyl-7-chloropyrazolo[1,5-a]pyrimidine | 3-bromo-5-cyclohexyl-7-chloropyrazolo[1,5-a]pyrimidine | Yield = quant.<br>$MH^+ = 314$ |
| 157 | 5-(2-methylcyclohexyl)-7-chloropyrazolo[1,5-a]pyrimidine | 3-bromo-5-(2-methylcyclohexyl)-7-chloropyrazolo[1,5-a]pyrimidine | Yield = 99<br>$MH^+ = 328$ |
| 158 | 5-(bicyclo[2.1.1] methyl)-7-chloropyrazolo[1,5-a]pyrimidine | 3-bromo-5-(bicyclo[2.1.1] methyl)-7-chloropyrazolo[1,5-a]pyrimidine | Yield = 98<br>$MH^+ = 326$ |
| 159 | 5-(1-Cbz-piperidin-4-yl)-7-chloropyrazolo[1,5-a]pyrimidine | 3-bromo-5-(1-Cbz-piperidin-4-yl)-7-chloropyrazolo[1,5-a]pyrimidine | Yield = 99<br>$MH^+ = 449$ |
| 160 | 5-(1-Cbz-piperidin-3-yl)-7-chloropyrazolo[1,5-a]pyrimidine | 3-bromo-5-(1-Cbz-piperidin-3-yl)-7-chloropyrazolo[1,5-a]pyrimidine | Yield = 95<br>$MH^+ = 449$ |
| 161 | 5-(1-Cbz-piperidin-2-yl)-7-chloropyrazolo[1,5-a]pyrimidine | 3-bromo-5-(1-Cbz-piperidin-2-yl)-7-chloropyrazolo[1,5-a]pyrimidine | Yield = 72<br>$MH^+ = 449$ |
| 162 | 5-(tetrahydrofuran-3-yl)-7-chloropyrazolo[1,5-a]pyrimidine | 3-bromo-5-(tetrahydrofuran-3-yl)-7-chloropyrazolo[1,5-a]pyrimidine | Yield = 98%<br>LCMS: $MH^+ = 302$ |

TABLE 9-continued

| Prep. Ex. | Column 2 | Column 3 | CMPD |
|---|---|---|---|
| 163 | [pyrazolopyrimidine with OEt, C(=O), Cl] | [3-Br pyrazolopyrimidine with OEt, C(=O), Cl] | Yield = 95%<br>LCMS: MH$^+$ = 305 |
| 164 | [5-(2,6-dimethoxyphenyl)-7-chloropyrazolopyrimidine] | [3-bromo-5-(3-bromo-2,6-dimethoxyphenyl)-7-chloropyrazolopyrimidine] | Yield = 50%<br>$^1$H NMR (CDCl$_3$)<br>δ 8.36 (s,1H),<br>7.72 (d, 1H),<br>7.20 (s, 1H),<br>6.82 (d, 1H),<br>3.99 (s, 3H),<br>3.90 (s, 3H); |

Preparative Example 165

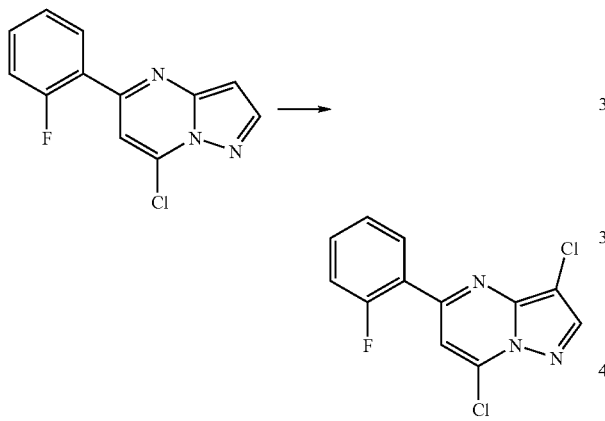

A solution of the compound prepared in Preparative Example 80 (0.3 g, 1.2 mmol) in CH$_3$CN (15 mL) was treated with NCS (0.18 g, 1.1 eq.) and the resulting solution heated to reflux 4 hours. Additional NCS (0.032 g, 0.2 eq.) added and the resulting solution was stirred at reflux overnight. The reaction mixture was cooled to room temperature, concentrated in vacuo and the residue purified by flash chromatography using a 20% EtOAc in hexanes solution as eluent (0.28 g, 83% yield). LCMS: MH$^+$=282.

Preparative Example 166-167

By essentially the same procedure set forth in Preparative Example 165 only substituting the compound shown in Column 2 of Table 10, the compound shown in Column 3 of Table 10 was prepared:

TABLE 10

| Prep. Ex. | Column 2 | Column 3 | CMPD |
|---|---|---|---|
| 166 | [5-(cyclohexylmethyl)-7-chloropyrazolopyrimidine] | [3-chloro-5-(cyclohexylmethyl)-7-chloropyrazolopyrimidine] | Yield = 82%<br>LCMS: MH$^+$ 286 |
| 167 | [5,7-dichloropyrazolopyrimidine] | [3,5,7-trichloropyrazolopyrimidine] | |

Preparative Example 167

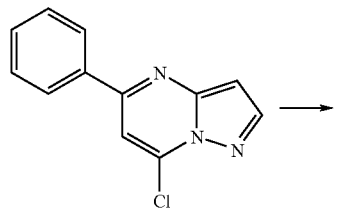

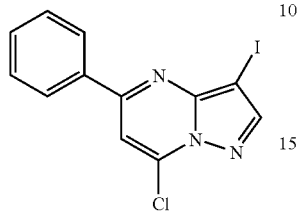

By essentially the same procedure set forth in Preparative Example 165 only substituting N-iodosuccinimide, the above compound was prepared.

Preparative Example 168

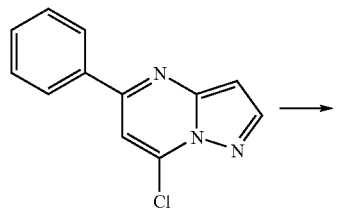

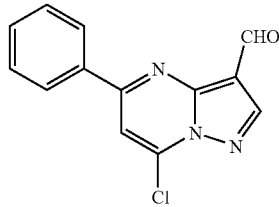

To a solution of the compound from Preparative Example 79 (1.0 g, 4.35 mmol) in DMF (6 mL) was added $POCl_3$ (1.24 mL, 3.05 eq.) and the resulting mixture was stirred at room temperature overnight. The reaction mixture was cooled to 0° C. and the excess $POCl_3$ was quenched by the addition of ice. The resulting solution was neutralized with 1N NaOH, diluted with $H_2O$, and extracted with $CH_2Cl_2$. The combined organics were dried over $Na_2SO_4$, filtered and concentrated in vacuo. The crude product was purified by flash chromatography using a 5% MeOH in $CH_2Cl_2$ solution as eluent (0.95 g, 85% yield). LCMS: $MH^+$=258.

Preparative Example 169

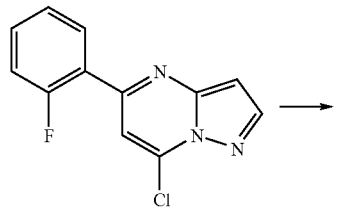

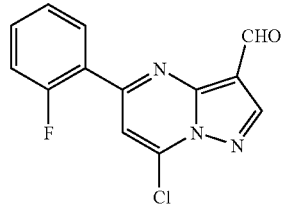

By essentially the same procedure set forth in Preparative Example 168 only substituting the compound prepared in Preparative Example 80, the above compound was prepared (0.45 g, 40% yield).

Preparative Example 170

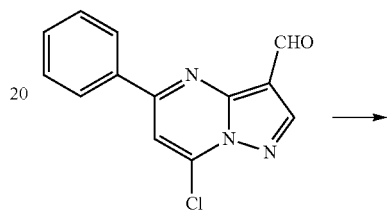

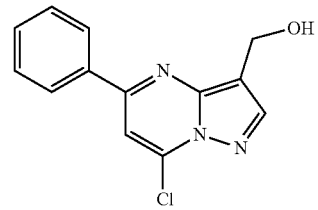

To a solution of the product of Preparative Example 169 (0.25 g, 0.97 mmol) in THF was added $NaBH_4$ (0.041 g, 1.1 eq.) and the resulting solution was stirred at room temperature overnight. The reaction mixture was quenched by the addition of $H_2O$ and extracted with $CH_2Cl_2$. The combined organics were dried over $Na_2SO_4$, filtered, and concentrated under reduced pressure. The crude product was purified by flash chromatography using a 60:40 hexanes: EtOAc mix as eluent (0.17 g, 69% yield). MS: $MH^+$=260.

Preparative Example 171

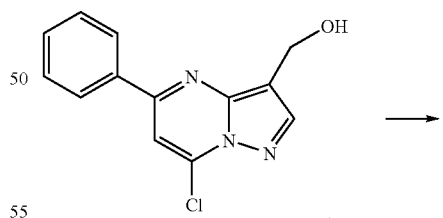

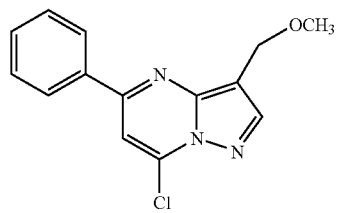

A solution of the compound prepared in Preparative Example 170 (0.12 g, 0.462 mmol), dimethyl sulfate (0.088 mL, 2.0 eq), 50% NaOH (0.26 mL) and catalytic $Bu_4NBr$ in CH$_2$Cl$_2$ (4 mL) was stirred at room temperature overnight. The reaction mixture was diluted with H$_2$O and extracted with CH$_2$Cl$_2$. The combined organics were dried over Na$_2$SO$_4$, filtered, and concentrated under reduced pressure. The crude product was purified by flash chromatography using a 30% EtOAc-in-hexanes solution as eluent (0.062 g, 48% yield).

Preparative Example 172

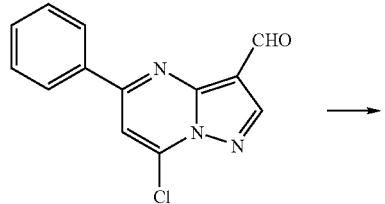

To a solution of PPh$_3$ (4.07 g, 4.0 eq.) and CBr$_4$ (2.57 g, 2.0 eq.) in CH$_2$Cl$_2$ (75 mL) at 0° C. was added the compound prepared in Preparative Example 168 (1.0 g, 3.88 mmol). The resulting solution was stirred at 0° C. for 1 hour and concentrated under reduced pressure. The residue was purified by flash chromatography using a 20% EtOAc in hexanes solution as eluent (1.07 g, 67% yield).

Preparative Example 173

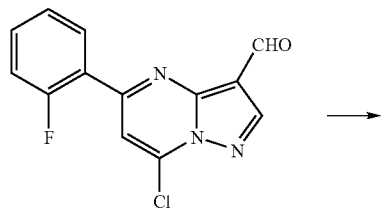

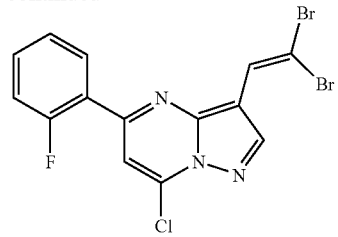

By essentially the same procedure set forth in Preparative Example 172 only substituting the compound prepared in Preparative Example 169 the above compound was prepared (0.5 g, 70% yield).

Preparative Example 174

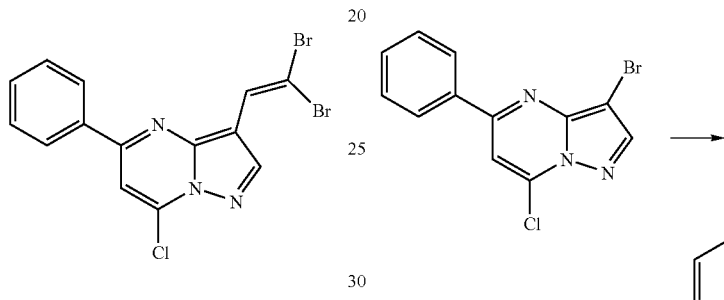

The compound prepared in Preparative Example 127 (3.08 g, 10.0 mmol), 2.0 M NH$_3$ in 2-propanol (50 mL, 100.0 mmol), and 37% aqueous NH$_3$ (10.0 mL) were stirred in a closed pressure vessel at 50° C. for 1 day. The solvent was evaporated and the crude product was purified by flash chromatography using 3:1 CH$_2$Cl$_2$:EtOAc as eluent. Pale yellow solid (2.30 g, 80%) was obtained. LCMS: M$^+$=289.

Preparative Examples 175-180

By essentially the same procedure set forth in Preparative Example 174 only substituting the compound shown in Column 2 of Table 11, the compounds shown in Column 3 of Table 11 were prepared.

TABLE 11

| Prep. Ex. | Column 2 | Column 3 |
|---|---|---|
| 175 | ![structure] | ![structure] |

161
TABLE 11-continued
| Prep. Ex. | Column 2 | Column 3 |
|---|---|---|
| 176 | 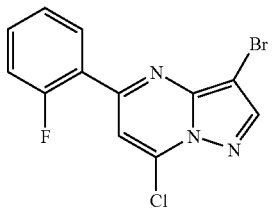 [SMILES: Cc1ccccc1-c1cc(Cl)n2ncc(Br)c2n1] | 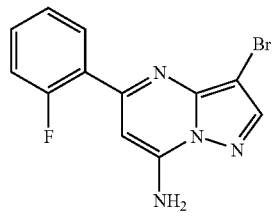 [SMILES: Nc1cc(-c2ccccc2F)nc2c(Br)cnn12] |
| 177 | 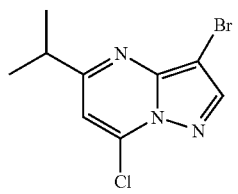 | 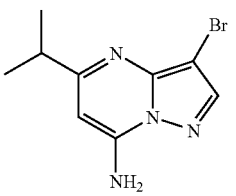 |
| 178 | 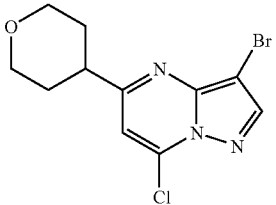 [SMILES: Clc1cc(C2CCOCC2)nc2c(Br)cnn12] | 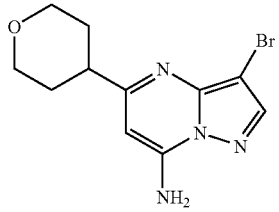 [SMILES: Nc1cc(C2CCOCC2)nc2c(Br)cnn12] |
| 179 | 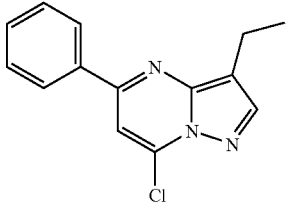 [SMILES: CCc1cnn2c(Cl)cc(-c3ccccc3)nc12] | 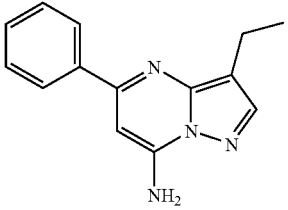 [SMILES: CCc1cnn2c(N)cc(-c3ccccc3)nc12] |
| 180 | 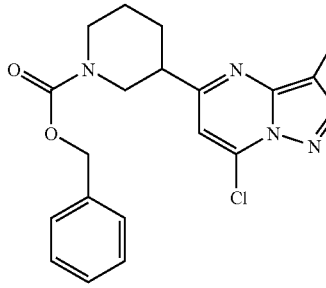 | 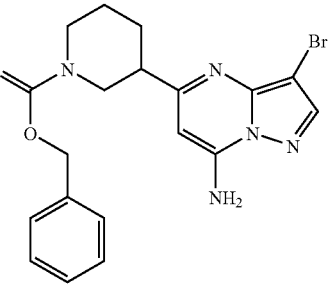 |
Preparative Example 181
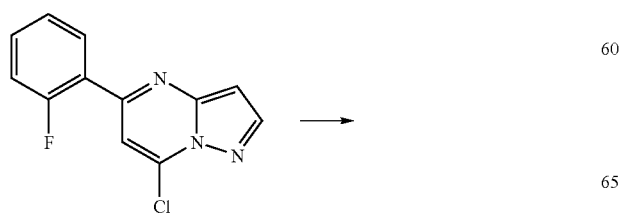
-continued
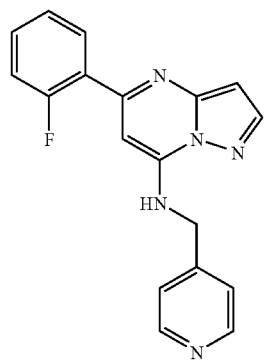

The compound prepared in Preparative Example 80 (0.3 g, 1.2 mmol), K$_2$CO$_3$ (0.33 g, 2 eq.), and 4-aminomethylpyridine (0.13 mL, 1.1 eq.) was heated to reflux overnight. The reaction mixture was cooled to room temperature and concentrated under reduced pressure. The residue was diluted with H$_2$O and extracted with CH$_2$Cl$_2$. The combined organics were dried over Na$_2$SO$_4$, filtered and, concentrated. The crude product was purified by flash chromatography using a 5% (10% NH$_4$OH in MeOH) solution in CH$_2$Cl$_2$ as eluent (0.051 g, 40% yield). LCMS: MH$^+$=320.

Preparative Example 182

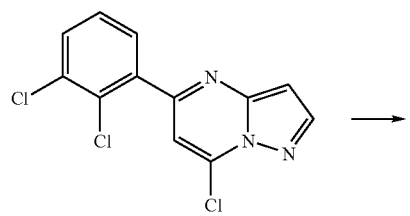

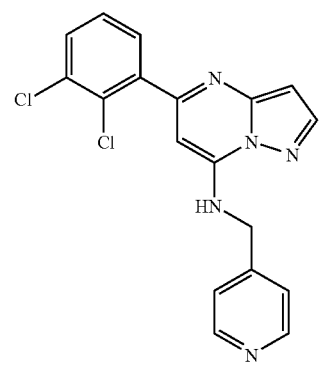

By essentially the same procedure set forth in Preparative Example 181 only substituting the compound described in Preparative Example 92, the above compound was prepared. LCMS: MH$^+$=370.

Preparative Example 183

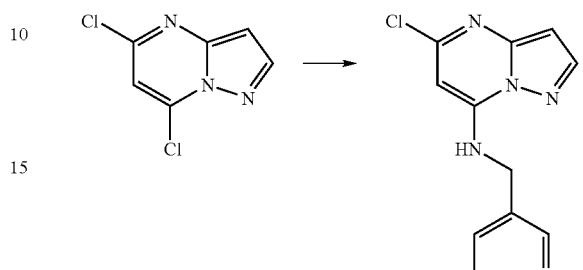

To a solution of the compound prepared in Preparative Example 123 (0.25 g, 1.3 mmol) in dioxane (5 mL) was added iPr$_2$NEt (0.47 mL, 2.0 eq.) and 3-aminomethylpyridine (0.15 ml, 1.1 eq.). The resulting solution was stirred at room temperature 72 hours. The reaction mixture was diluted with H$_2$O and extracted with EtOAc. The combined organics were washed with H$_2$O and saturated NaCl, dried over Na$_2$SO$_4$, filtered, and concentrated in vacuo. The crude product was purified by flash chromatography using a 5% MeOH in CH$_2$Cl$_2$ solution as eluent (0.29 g, 83% yield). MS: MH$^+$=260.

Preparative Examples 184-187

By essentially the same procedure set forth in Preparative Example 183 only substituting the compound shown in Column 2 of Table 12, the compounds shown in Column 3 of Table 12 are prepared.

TABLE 12

| Prep. Ex. | Column 2 | Column 3 |
|---|---|---|
| 184 | ![structure] | ![structure] |

TABLE 12-continued
| Prep. Ex. | Column 2 | Column 3 |
|---|---|---|
| 184.1 | 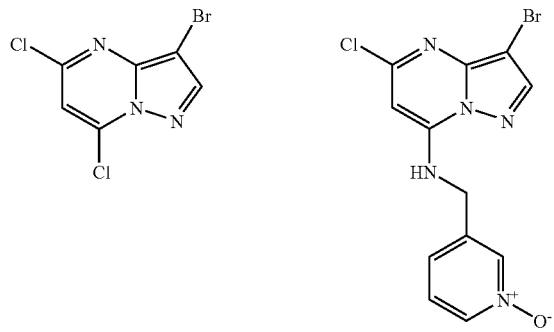 | |
| 185 | 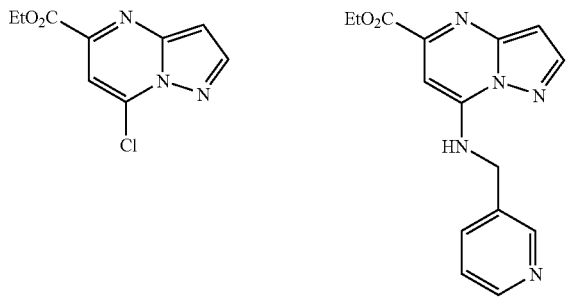 | |
| 186 | 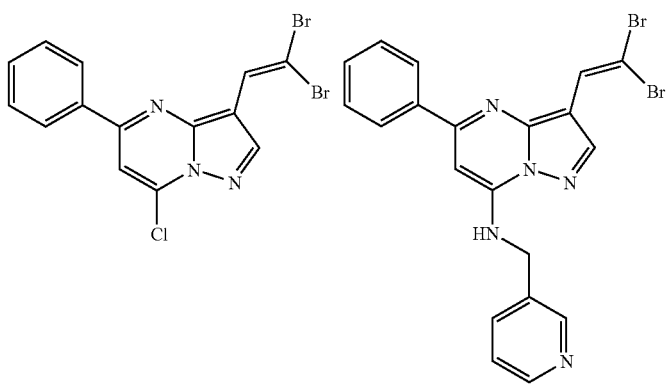 | |
| 187 | 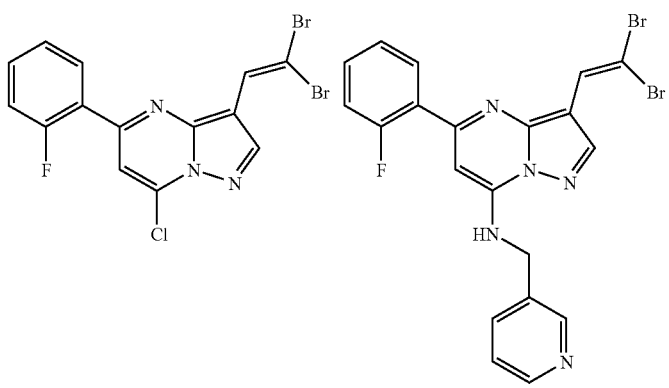 | |

TABLE 12-continued

| Prep. Ex. | Column 2 | Column 3 |
|---|---|---|
| 187.1 | ![structure] | ![structure] |
| 187.11 | ![structure] | ![structure] |

Preparative Example 188 and Preparative Example 189

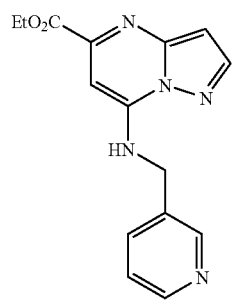 [SMILES: CCOC(=O)c1cc(NCc2cccnc2)n2nccc2n1]

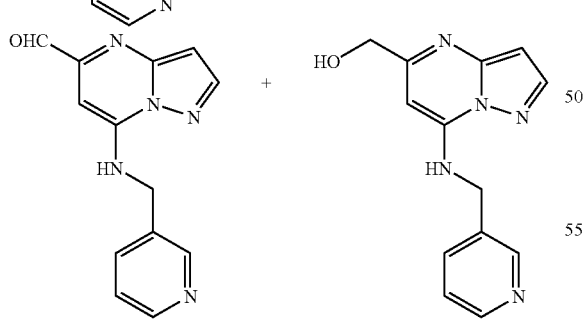

To a solution of the compound prepared in Preparative Example 185 (1.18 g, 3.98 mmol) in THF (35 mL) at −78° C. was added LAH (4.78 mL, 1M in Et$_2$O, 1.0 eq.) dropwise. The reaction mixture was stirred at −78° C. for 3 hours at which time additional LAH (2.0 mL, 1M in Et$_2$O, 0.42 eq.) was added dropwise. The reaction mixture was stirred an additional 1.25 hours and quenched by the addition of saturated Na$_2$SO$_4$ (8.5 mL). The reaction mixture was diluted with EtOAC (23 mL), H$_2$O (2 mL), and CH$_3$OH (50 mL). The resulting slurry was filtered through a plug of Celite. The Celite was washed with CH$_3$OH and the filtrate dried with Na$_2$SO$_4$, filtered, and concentrated. The product was purified by flash chromatography using a CH$_2$Cl$_2$: CH$_3$OH (93:7) solution as eluent to yield aldehyde as the first eluting product and alcohol as the second eluting product.

Preparative Example 188

(aldehyde): 0.4 g, 39% yield. MS: MH$^+$=254.

Preparative Example 189

(alcohol): 0.25 g, 24% yield. MS: MH$^+$=256.

Preparative Example 190

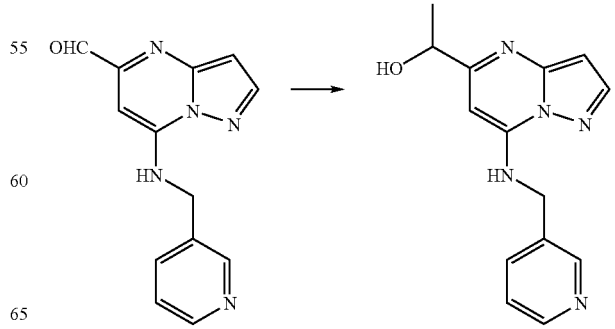

To a solution of the compound prepared in Preparative Example 188 (0.075 g, 0.30 mmol) in THF (2.0 mL) at 0° C. was added CH₃MgBr (0.3 mL, 3.0M solution in Et₂O, 3.0 eq.) dropwise. The resulting solution was stirred at 0° C. an additional 1.5 hours, warmed to room temperature, and stirred overnight. Additional CH₃MgBr (0.15 mL, 3.0M in Et₂O, 1. eq.) was added and the resulting solution stirred an additional 1.5 hours. The reaction mixture was cooled to 0° C. and quenched by the addition of saturated NH₄Cl. The resulting solution was diluted with CH₂Cl₂ and H₂O and extracted with CH₂Cl₂. The combined organics were washed with saturated NaCl and dried over Na₂SO₄, filtered, and concentrated. The crude product was purified by flash chromatography using a CH₂Cl₂: CH₃OH (90:10) solution as eluent (0.048 g, 60% yield). MS: MH⁺=270.

Preparative Example 191

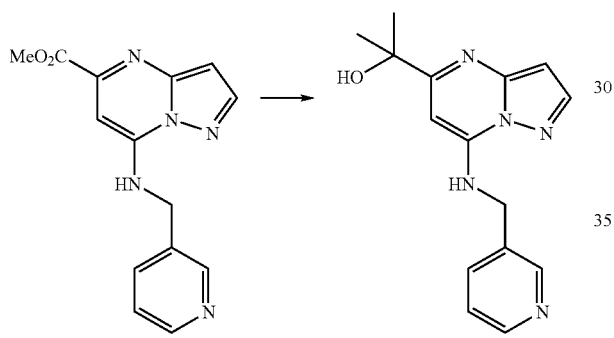

By essentially the same procedure set forth in Preparative Example 190 only substituting the compound prepared in Preparative Example 185 and using excess MeMgBr (5 eq.), the above compound was prepared.

Preparative Example 192

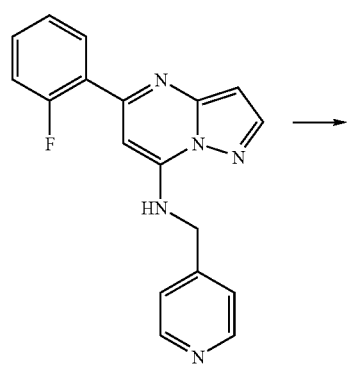

-continued

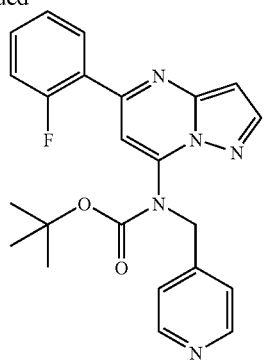

The compound prepared in Preparative Example 181 (0.29 g, 0.91 mmol), BOC₂O (0.22 g, 1.1 eq), and DMAP (0.13 g, 1.1 eq.) in dioxane (10 mL) was stirred at room temperature 3 days. Additional BOC₂O (0.109, 0.5 eq.) was added and the reaction mixture was stirred 4 hours. The reaction mixture was concentrated in vacuo, diluted with saturated NaHCO₃ (15 mL), and extracted with CH₂Cl₂ (2×100 mL). The combined organics were dried over Na₂SO₄, filtered, and concentrated under reduce pressure. The crude product was purified by flash chromatography using a 5% (10% NH₄OH in MeOH) solution in CH₂Cl₂ as eluent (0.35 g, 91% yield). LCMS: MH⁺=420.

Preparative Example 193

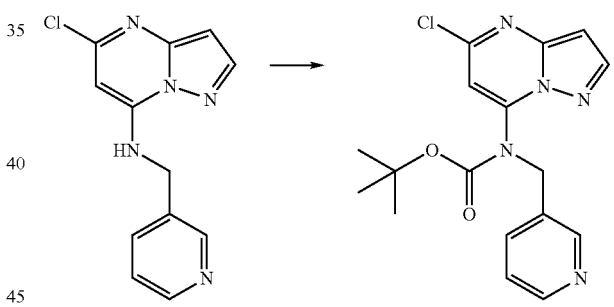

By essentially the same procedure set forth in Preparative Example 192 only substituting the compound prepared in Preparative Example 183, the above compound was prepared. MS: MH⁺=360.

Preparative Example 193.10

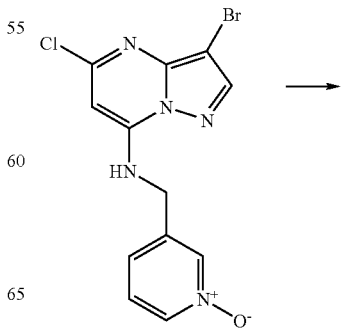

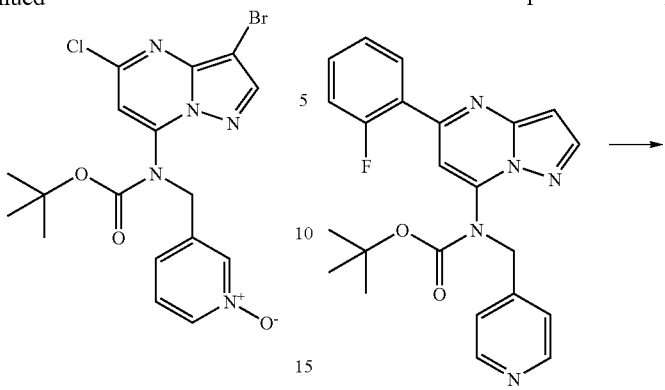

By essentially the same procedure set forth in Preparative Example 192 only substituting the compound prepared in Preparative Example 184.1, the above compound was prepared. MS: MH$^+$=454.

Preparative Example 194

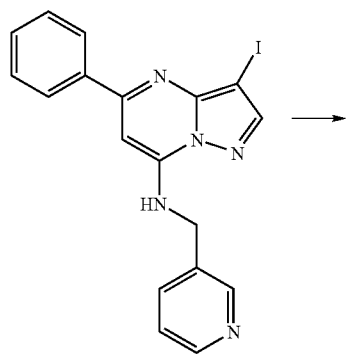

By essentially the same procedure set forth in Preparative Example 192 only substituting the above compound prepared in Preparative Example 187.11, the above compound was prepared (0.223 g, 88% yield). MS: MH$^+$=528.

Preparative Example 195

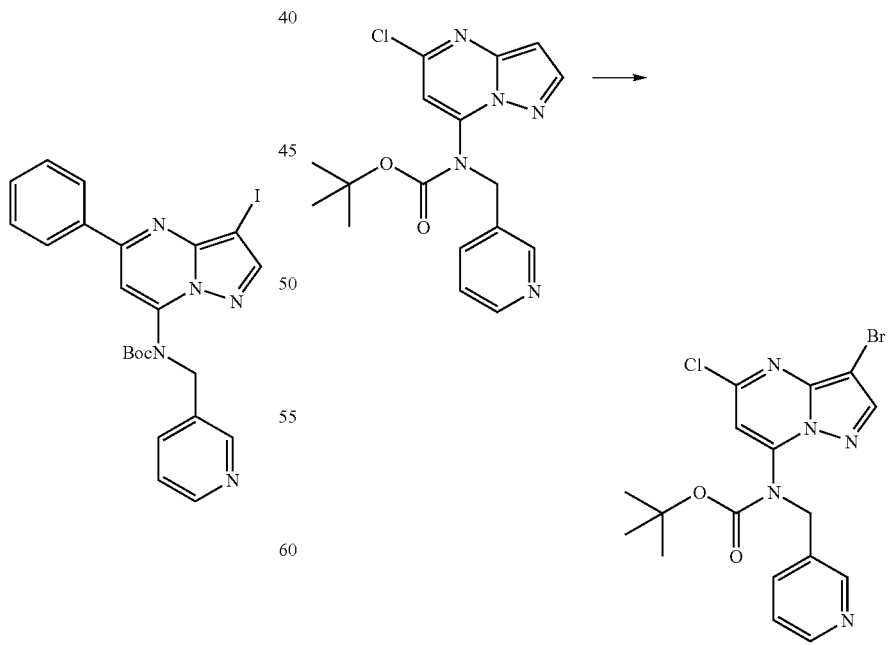

By essentially the same procedure set forth in Preparative Example 127 only substituting the compound prepared in Preparative Example 192, the above compound was prepared (0.38 g, 95% yield). LCMS: MH$^+$=498.

Preparative Example 196

By essentially the same procedure set forth in Preparative Example 195, only substituting the compound prepared in Preparative Example 193, the above compound was prepared (0.3 g, 83% yield). MS: MH+=438.

Preparative Example 197

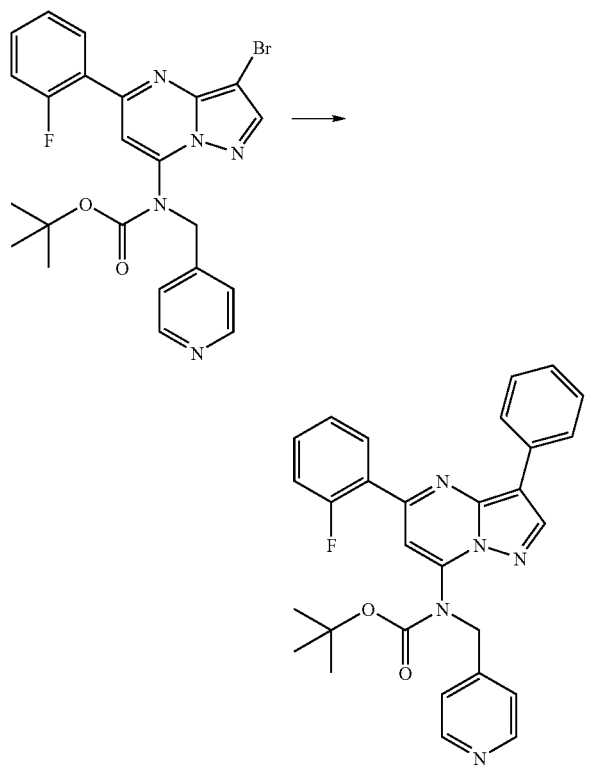 [SMILES: CC(C)(C)OC(=O)N(Cc1ccncc1)c1cc(-c2ccccc2F)nc2c(Br)cnn12 ; CC(C)(C)OC(=O)N(Cc1ccncc1)c1cc(-c2ccccc2F)nc2c(-c3ccccc3)cnn12]

A solution of the compound prepared in Preparative Example 195 (0.15 g, 0.3 mmol), phenylboronic acid (0.073 g, 2.0 eq.), K$_3$PO$_4$ (0.19 g, 3.0 eq.), and Pd(PPh$_3$)$_4$ (0.017 g, 5 mol %) was heated at reflux in DME (16 mL) and H$_2$O (4 mL) 7 hours. The resulting solution was cooled to room temperature, diluted with H$_2$O (10 mL), and extracted with CH$_2$Cl$_2$ (3×50 mL). The combined organics were dried over Na$_2$SO$_4$, filtered, and concentrated. The crude product was purified by flash chromatography using a 2.5% (10% NH$_4$OH in MeOH) in CH$_2$Cl$_2$ solution as eluent (0.16 g, 100% yield).

Preparative Example 198

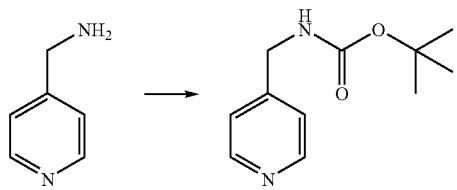

To a solution of 4-aminomethylpyridine (1.41 mL, 13.87 mmol) in CH$_2$Cl$_2$ (50 mL) was added BOC$_2$O (3.3 g, 1.1 eq.) and TEA and the resulting solution was stirred a room temperature 2 hours. The reaction mixture was diluted with H$_2$O (50 mL) and extracted with CH$_2$Cl$_2$. The combined organics were dried over Na$_2$SO$_4$, filtered and concentrated under reduced pressure. The crude product was purified by flash chromatography using a 5% (10% NH$_4$OH in MeOH) solution in CH$_2$Cl$_2$ as eluent to give a yellow solid (2.62 g, 91% yield). LCMS: MH+=209.

Preparative Example 199

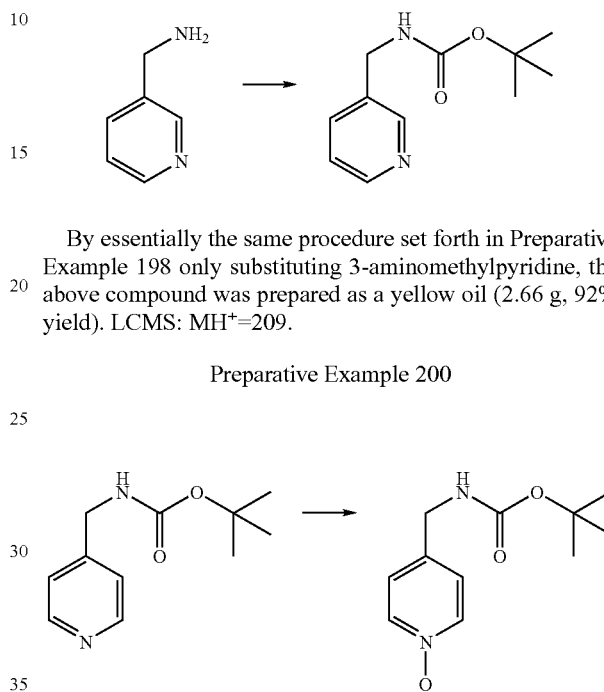

By essentially the same procedure set forth in Preparative Example 198 only substituting 3-aminomethylpyridine, the above compound was prepared as a yellow oil (2.66 g, 92% yield). LCMS: MH+=209.

Preparative Example 200

To a solution of the compound prepared in Preparative Example 198 (0.20 g, 0.96 mmol) in CH$_2$Cl$_2$ (5 mL) at 0° C. was added m-CPBA (0.17 g, 1.0 eq) and the resulting solution stirred at 0° C. 2 hours and stored at 4° C. overnight at which time the reaction mixture was warmed to room temperature and stirred 3 hours. The reaction mixture was diluted with H$_2$O and extracted with CH$_2$Cl$_2$. The combined organics were dried over Na$_2$SO$_4$, filtered, and concentrated. The crude product was purified by flash chromatography using a 10% (10% NH$_4$OH in MeOH) solution as eluent: LCMS: MH+=255.

Preparative Example 201

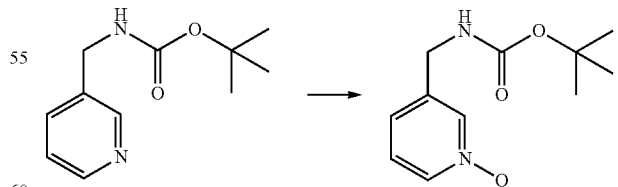

A solution of oxone (58.6 g) in H$_2$O (250 mL) was added dropwise to the compound prepared in Preparative Example 199 (27 g, 0.13 mol) and NaHCO$_3$ (21.8 g, 2.0 eq.) in MeOH (200 mL) and H$_2$O (250 mL). The resulting solution was stirred at room temperature overnight. The reaction mixture was diluted with CH$_2$Cl$_2$ (500 mL) and filtered. The layers were separated and the aqueous layer extracted with $CH_2Cl_2$. The combined organics were dried over $Na_2SO_4$, filtered, and concentrated under reduced pressure to give a white solid (21.0 g, 72% yield). MS: $MH^+$=255.

Preparative Example 202

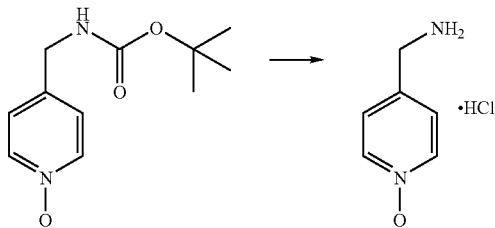

The compound prepared in Preparative Example 200 (0.29 g, 1.29 mmol) was stirred at room temperature in 4M HCl in dioxane (0.97 mL) 2 hours. The reaction mixture was concentrated in vacuo and used without further purification. LCMS: $MH^+$=125.

Preparative Example 203

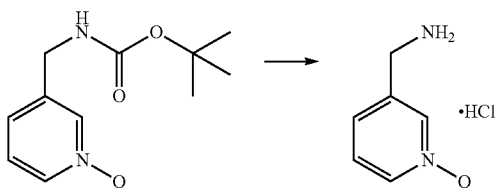

By essentially the same procedure set forth in Preparative Example 202 only substituting the compound prepared in Preparative Example 201, the compound shown above was prepared. LCMS: $MH^+$=125.

Preparative Example 204

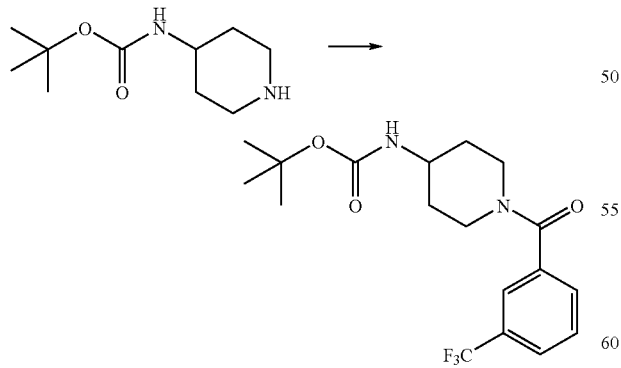

To 4-N-t-Butoxycarbonylaminopiperidine (0.8 g, 4.0 mmol) in $CH_2Cl_2$ (10 mL) at 0° C. was added TEA (1.40 mL, 2.5 eq.) and 3-trifluoromethyl benzoyl chloride (1.05 g, 1.25 eq.). The resulting solution was stirred 15 minutes and warmed to room temperature and stirred 3 hours. The reaction mixture was diluted with $CH_2Cl_2$ and washed with 5% $Na_2CO_3$ (2×100 mL). The organic layer was dried over $Na_2SO_4$, filtered and concentrated to yield a pale yellow solid (quantitative crude yield).

Preparative Example 205

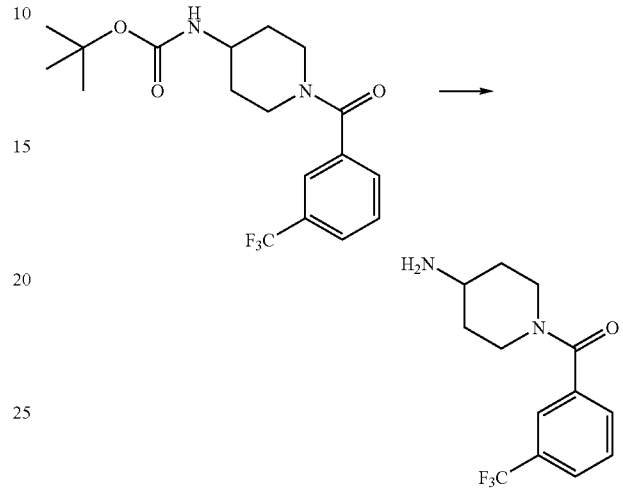

To a solution of the compound prepared in Preparative Example 204 (1.0 g, 2.76 mmol) in $CH_2Cl_2$ (15 mL) at 0° C. was added TFA (8 mL) and the resulting solution was stirred at 0° C. for 30 minutes and room temperature 1 hour. The reaction mixture was poured onto $Na_2CO_3$ (40 g) and $H_2O$ (400 mL) added and the resulting mixture was extracted with $CH_2Cl_2$. The combined organics were dried over $Na_2SO_4$, filtered, and concentrated under reduced pressure. The crude product was purified by flash chromatography using a 20% (7N $NH_3$ in MeOH) solution in $CH_2Cl_2$ as eluent (0.6 g, 82% yield).

Preparative Examples 206

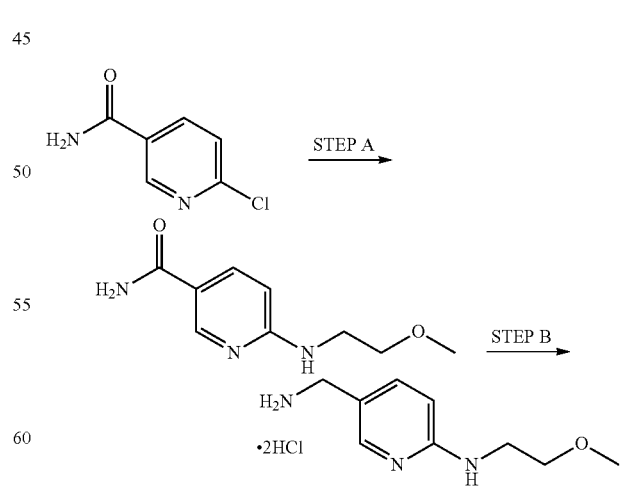

Step A:

To a solution of 6-chloronicotinamide (1 g, 6.39 mmol) in isoamyl alcohol (15 mL) at rt was added $Na_2CO_3$ (0.81 g, 7.67 mmol) followed by methoxyethylamine (0.67 mL, 7.67 mmol). The mixture was heat at 130° C. for 16 h, cooled to rt, and was filtered thru a medium glass-fritted filter. The resulting filtrate was concentrated under reduced pressure and the resultant solid was triturated with Et$_2$O (2×10 mL). The crude solid was placed under high vacuum to afford 1.2 g (96%) of a light yellow solid. M+H=196.

Step B:

To a solution of amide (1.2 g, 6.12 mmol) from Preparative Example 206, Step A in THF (5 mL) at 0° C. was added a solution of BH$_3$-THF (43 mL; 43 mmol) dropwise over 10 min. The resultant solution was warmed to rt and stirred for 14 h. The mixture was cooled to 0° C. and was sequentially treated with 6M HCL (35 mL), water (30 mL), and MeOH (150 mL). The mixture was stirred for 8 h and was concentrated under reduced pressure. The crude residue was triturated with MeOH, concentrated under reduced pressure, and placed under high vacuum to afford 1.6 g (82%) of a white solid as the dihydrochloride salt. M+H (free base)=182.0. This material was used crude in the coupling with 7-Cl adducts.

Preparative Examples 207-211

By essentially the same known procedure set forth in Preparative Example 206 only by utilizing the amines shown in Column 2 of Table 13 and the amines shown in Column 3 of Table 13 were prepared:

Preparative Example 212

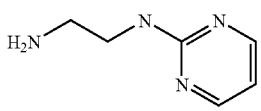

The above compound was prepared accordingly to the methods described in WO 91/18904.

Preparative Example 213

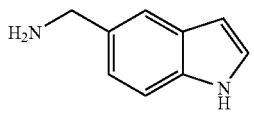

The above compound was prepared accordingly to the methods described in U.S. Pat. No. 6,180,627 B1.

Preparative Example 214

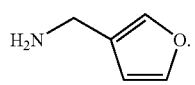

The known amine was prepared as described in *J. Med. Chem.* (2001), 44, 4505-4508.

TABLE 13

| Prep. Ex. | Column 2 (Amine) | Column 3 (Amine) | CMPD M + H (free base) |
|---|---|---|---|
| 207 | H$_2$N–\ | H$_2$N–CH$_2$–(pyridine)–NHMe ·2HCl | M + H = 138 |
| 208 | HN(Me)– | H$_2$N–CH$_2$–(pyridine)–N(Me)$_2$ ·2HCl | M + H = 152 |
| 209 | HN–(pyrrolidine) | H$_2$N–CH$_2$–(pyridine)–N(pyrrolidine) ·2HCl | M + H = 178 |
| 210 | H$_2$N–CH$_2$CH$_2$–N(Me)$_2$ | H$_2$N–CH$_2$–(pyridine)–NH–CH$_2$CH$_2$–N(Me)$_2$ ·3HCl | M + H = 195 |
| 211 | HN(piperazine)N–Me | H$_2$N–CH$_2$–(pyridine)–N(piperazine)N–Me ·3HCl | M + H = 207 |

Preparative Example 215

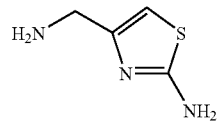

The known amine was prepared as described in *J. Med. Chem.* (1997), 40, 3726-3733.

Preparative Example 216

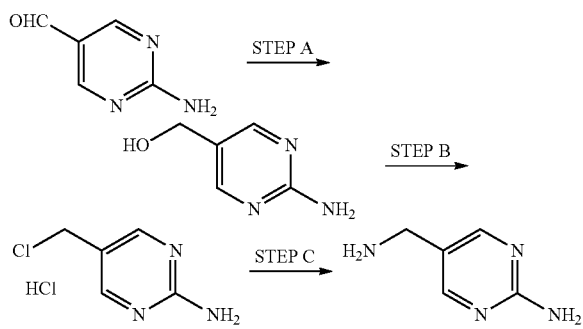

Step A:
A solution of aldehyde (50 g, 0.41 mol) [WO 0232893] in MeOH (300 mL) was cooled to 0° C. and carefully treated with NaBH$_4$ (20 g, 0.53 mol in 6 batches) over 20 minutes. The reaction was then allowed to warm to 20° C. and was stirred for 4 hours. The mixture was again cooled to 0° C., carefully quenched with saturated aqueous NH$_4$Cl, and concentrated. Flash chromatography (5-10% 7N NH$_3$-MeOH/CH$_2$Cl$_2$) provided the primary alcohol (31 g, 62%) as a light yellow solid.

Step B:
A slurry of alcohol (31 g, 0.25 mol) from Preparative Example 216, Step A in CH$_2$Cl$_2$ (500 mL) was cooled to 0° C. and slowly treated with SOCl$_2$ (55 mL, 0.74 mol over 30 minutes). The reaction was then stirred overnight at 20° C. The material was concentrated, slurried in acetone, and then filtered. The resulting beige solid was dried overnight in vacuo (38.4 g, 52%, HCl salt).

Step C:
To a 15 mL pressure tube charged with a stir bar was added chloride (150 mg, 0.83 mmol) from Preparative Example 216, Step B followed by 7 M NH$_3$/MeOH (10 mL). The resulting solution was stirred for 48 h at rt where upon the mixture was concentrated under reduced pressure to afford a light yellow solid (0.146 g, 83%). M+H (free base)=140.

Preparative Example 217

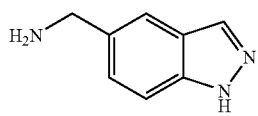

The above compound was prepared accordingly to methods described in WO 00/26210.

Preparative Example 218

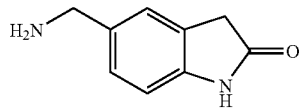

The above compound was prepared accordingly to methods described in WO 99/10325.

Preparative Example 219

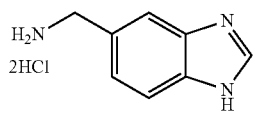

The known amine dihydrochloride was prepared according to methods described in WO 02/64211.

Preparative Example 220

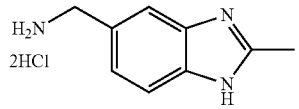

The above compound was prepared according to methods described in WO 02/64211.

Preparative Example 221

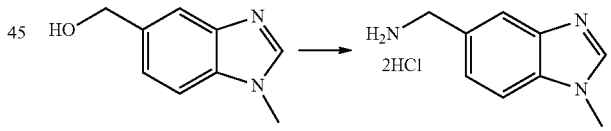

The known primary alcohol was prepared according to WO 00/37473 and was converted to the desired amine dihydrochloride in analogous fashion as Preparative Example 220 according to WO 02/064211.

Preparative Example 222

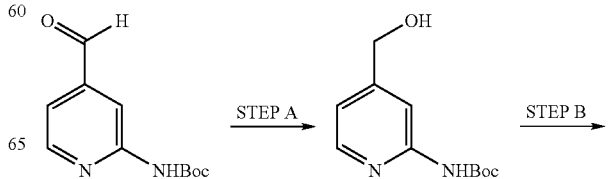

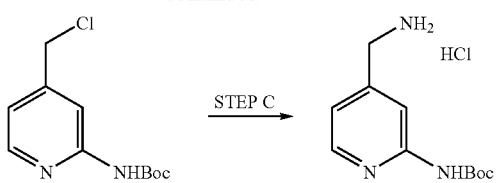

Step A:

To a solution of aldehyde (WO 02/32893) (0.46 g, 2.07 mmol) in MeOH/THF (2 mU2 mL) at 0° C. was added NaBH₄ (94 mg, 2.48 mmol) in one portion. The resulting mixture was stirred for 12 h at rt and was diluted with sat. aq. NH₄Cl (3 mL). The mixture was concentrated under reduced pressure and the resultant aqueous layer was extracted with CH₂Cl₂ (3×5 mL). The organic layers were combined, washed with brine (1×5 mL), dried (Na₂SO₄), and filtered. The organic layer was concentrated under reduced pressure to afford 417 mg (90% yield) of a white solid. M+H=225.

Step B:

The crude alcohol from Preparative Example 222, step A (0.4 g, 1.78 mmol) in CH₂Cl₂ (4 mL) was added SOCl₂ (0.65 mL, 8.91 mmol) and the mixture was stirred for 2 h at rt. The mixture was concentrated under reduced pressure to afford 407 mg (94%) of a light yellow solid. M+H=243. The crude product was taken on without further purification.

Step C:

To a solution of crude chloride from Preparative Example 222, Step B (0.33 g, 1.36 mmol) in a pressure tube charged with 7M NH₃/MeOH (35 mL) and the mixture was stirred for 72 h. The mixture was concentrated under reduced pressure to afford 257 mg (85%) of a yellow semisolid. M+H (free base)=224.

Preparative Example 223

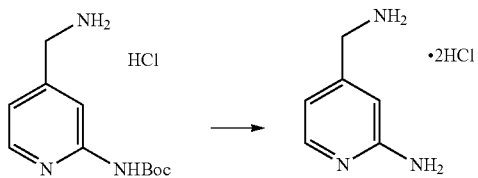 [SMILES: CC(C)(C)OC(=O)Nc1cc(CN)ccn1 ; Cl ; NCc1ccnc(N)c1 ; "·2HCl"]

To a round bottom flask charged with amine hydrochloride (0.24 g, 1.1 mmol) from Preparative Example 222 and a stir bar was added 4N HCl/dioxane (10 mL). The resulting solution was stirred for 12 h at rt, concentrated under reduced pressure, and triturated with CH₂Cl₂ (3×5 mL). The crude product was filtered, washed with Et₂O (2×5 mL), and dried under high vacuum to afford 0.19 g (91%) as the dihydrochloride salt. M+H (free base)=124.

Preparative Example 224

Pd(PPh₃)₄ (0.404 gm, 0.35 mmol) was added to a degassed solution of 4-cyanobenzene boronic acid (1.029 g, 7 mmol) and 2-bromopyridine (1.11 g, 7 mmol) in 75 mL acetonitrile. 0.4 M sodium carbonate solution (35 mL) was added to the reaction mixture and the resulting solution was refluxed at 90° C. under Ar for 24 hours (progress of reaction was monitored by TLC). The reaction mixture was cooled and aqueous layer was separated. The organic layer containing the product and spent catalyst was mixed with silica gel (15 g) and concentrated to dryness. The 4-(2-pyridyl)-benzonitrile was isolated by column chromatography (0.850 g, 68%). LCMS: MH⁺=181; ¹H NMR (CDCl₃) δ 8.85 (d, 1H), 8.7 (dd, 1H), 7.9 (dd, 1H), 7.75 (d, 2H), 7.7 (d, 2H), 7.4 (dd, 1H).

Preparative Examples 225-228

By following essentially same procedure described in Preparative Example 224, only substituting the bromides in column 2 of Table 14, compounds in column 3 of Table 14 were prepared.

TABLE 14

| Prep. Ex. | Column 2 | Column 3 | Column 4 |
|---|---|---|---|
| 225 | ![Br-thiazole] | ![4-CN-phenyl-thiazole] | Yield = 70%<br>LCMS: MH⁺ = 187 |
| 226 | ![Br-thiazole] | ![3-CN-phenyl-thiazole] | Yield = 60%<br>LCMS: MH⁺ = 187 |

TABLE 14-continued

| Prep. Ex. | Column 2 | Column 3 | Column 4 |
|---|---|---|---|
| 227 | 2-bromothiophene | 4-cyanophenyl-thiophene | Yield = 70% LCMS: $MH^+$ = 186 |
| 228 | 3-bromo-4-methylthiophene | 4-cyano-phenyl-(4-methylthiophene) | Yield = 70% LCMS: $MH^+$ = 200 |

Preparative Example 229

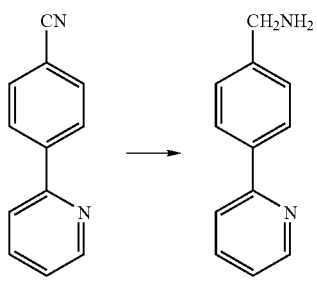

BH$_3$-THF solution (1M, 24 mL, 5 eq) was added slowly to a stirring solution of 4-(2-pyridyl)-benzonitrile (0.85 g, 4.72 mmol) in anhydrous THF (25 mL) under Ar, and the resulting solution was refluxed for about 12 hr. The solution was cooled to 0° C. using ice-water. Methanol (15 mL) was added dropwise to the cold reaction mixture and stirred for 1 h to destroy excess BH$_3$. Added HCl-methanol (1M, 10 mL) slowly to the reaction mixture and refluxed for 5 h. Concentrated the solution to dryness and the residue was dissolved in 25 mL water and extracted with ether to remove any un-reacted material. The aqueous solution was neutralized with solid potassium carbonate to pH 10-11. The free amine, thus formed was extracted with ether, dried over potassium carbonate (0.45 g, 50%). LCMS: $MH^+$=185; $^1$H NMR (CDCl$_3$) δ 8.85 (d, 1H), 8.7 (dd, 1H), 7.9 (dd, 1H), 7.75 (d, 2H), 7.7 (d, 2H), 7.4 (dd, 1H), 3.7 (t, 2H), 1.7 (t, 2H).

Preparative Examples 230-233

By following essentially the same procedure set forth in Preparative Example 229, compounds in column 3 of Table 15 were prepared.

TABLE 15

| Prep. Ex. | Column 2 | Column 3 | Column 4 |
|---|---|---|---|
| 230 | 4-(thiazol-2-yl)benzonitrile | 4-(thiazol-2-yl)benzylamine | Yield = 60% LCMS: $MH^+$ = 191 |
| 231 | 3-(thiazol-2-yl)benzonitrile | 3-(thiazol-2-yl)benzylamine | Yield = 60% LCMS: $MH^+$ = 191 |
| 232 | 4-(thiophen-2-yl)benzonitrile | 4-(thiophen-2-yl)benzylamine | Yield = 70% LCMS: $MH^+$ = 190 |
| 233 | 4-(4-methylthiophen-3-yl)benzonitrile | 4-(4-methylthiophen-3-yl)benzylamine | Yield = 70% LCMS: $MH^+$ = 204 |

Preparative Example 234

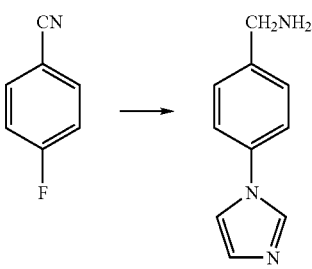

Step A:

A mixture 4-fluorobenzonitrile (3 g, 25 mmol) and imidazolyl sodium (2.48 g, 27.5 mmol) in DMF (50 mL) was stirred at 80° C. under Ar for 12 h. Progress of reaction was monitored by TLC. The reaction mixture was concentrated in vacuo and the residue was diluted with 50 mL water and stirred. The aqueous mixture was extracted with EtOAc (2×50 mL). Combined EtOAc extracts was dried over anhydrous MgSO$_4$, concentrated, and the 4-(1-imidazolyl)-benzonitrile was isolated by column chromatography (3.6 g, 78%). LCMS: MH$^+$=170; $^1$H NMR (CDCl$_3$) δ 8.0 (s, 1H), 7.5 (d, 2H), 7.4 (m, 3H), 7.3 (d, 1H)

Step B:

4-(1-imidazolyl)-benzonitrile (1 g, 5.92 mmol) was dissolved in anhydrous THF (10 mL) and added drop-wise to a stirring solution of LAH-THF (1M in THF, 18 mL) at room temperature. The reaction mixture was refluxed under Ar for 2 h and the progress was monitored by TLC. The mixture was cooled to 0° C. and quenched by drop-wise addition of a saturated Na$_2$SO$_4$—H$_2$O solution. The mixture was stirred for 1 h and filtered to remove lithium salts. The filtrate was dried over anhydrous MgSO$_4$ and concentrated to obtain 4-(1-imidazolyl)-benzylamine (0.8 g, 80%). LCMS: MH$^+$=174.

Preparative Example 235

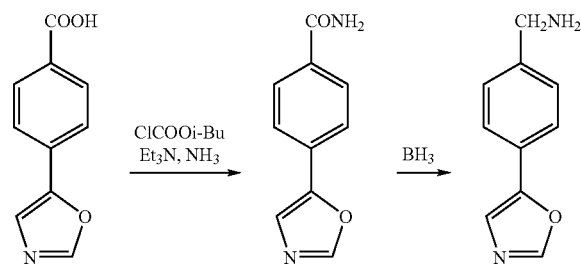

A mixture of 4-(5-oxazolyl)benzoic acid (1.0 g, 5.46 mmol) and Et$_3$N (552 mg, 5.46 mmol) in 25 mL of THF was cooled to 0° C. and ClCOOi-Bu (745 mg, 5.46 mmol) was added dropwise. After the addition was over, the reaction mixture was stirred for additional 5 min and then aq NH$_4$OH (0.63 mL of 28% solution, 10.46 mmol) was added. After overnight stirring, the solvent was evaporated, the residue was taken up in water and basified to pH 9. The precipitated solid was filtered, washed with water and dried over P$_2$O$_5$ in a vacuum desiccator to provide 500 mg (48%) of the 4-(5-oxazolyl)-benzamide: $^1$H NMR (DMSO-d6) δ 8.50 (s, 1H), 8.20-7.80 (m, 5H).

Preparative Example 236

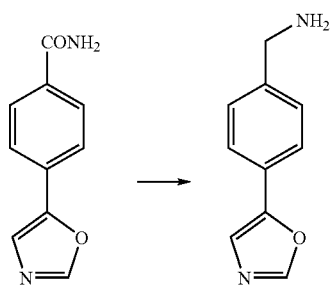 [SMILES: NC(=O)c1ccc(-c2cnco2)cc1 ; NCc1ccc(-c2cnco2)cc1]

A suspension of 4-(5-oxazolyl)benzamide (500 mg, 2.657 mmol) in 10 mL of dry THF was cooled to 0° C. and 10 mL of 1M BH$_3$.THF (10.00 mmol) was added. The contents were refluxed overnight and the excess borane was destroyed by dropwise addition of methanol. The solvent was evaporated and the residue was treated with methanolic HCl to decompose the amine-borane complex. After evaporation of the methanol, the residue was taken in water, basified to pH 10 and the product was extracted in to DCM. The DCM layer was dried (K$_2$CO$_3$) and the solvent was removed to provide 150 mg (32%) of 4-(5-oxazolyl)benzylamine: $^1$H NMR (CDCl$_3$) δ 7.90 (s, 1H), 7.60 (d, 2H), 7.40 (d, 2H), 7.30 (s, 1H), 3.90 (s, 2H).

Preparative Examples 237-239

By essentially the same procedures set forth above, the compounds in Column 2 of Table 16 were reduced using the method indicated in Column 3 of Table 16 to give the amine indicated in Column 4 of Table 16.

TABLE 16

| Prep. Ex. | Column 2 | Column 3 | Column 4 | CMPD |
|---|---|---|---|---|
| 237 | ![CN-benzodioxole-CF2] | BH$_3$ | ![H2N-CH2-benzodioxole-CF2] | $^1$H NMR (CDCl$_3$) δ 7.15-6.90 (m, 3H), 3.85 (s, 2H), 1.45 (s, 2H) |
| 238 | ![CN-pyridine-Me] | H$_2$ | ![H2N-CH2-pyridine-Me] | $^1$H NMR (CDCl$_3$) δ 8.40 (s, 1H), 7.55 (dd, 1H), 7.10 (d, 1H), 3.85 (s, 2H), 2.50 (s, 3H), 1.70 (bs, 2H) |

Preparative Example 240

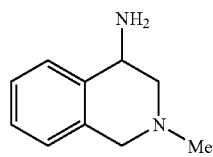 [SMILES: CN1Cc2ccccc2C(N)C1]

Prepared by the literature procedure (PCT Int. Appl, WO 0105783): $^1$H NMR (CDCl$_3$) δ 7.35 (d, 1H), 7.24-7.10 (m, 2H), 7.02 (d, 1H), 3.95 (t, 1H), 3.70 (d, 1H), 3.37 (d, 1H), 2.65 (m, 2H), 2.45 (s, 3H), 1.90 (bs, 2H)

Preparative Example 241

3-(aminomethyl)piperidine-1-carboxamide

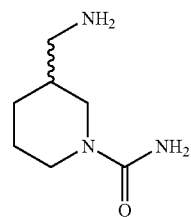 [SMILES: NCC1CCCN(C(N)=O)C1]

A. 3-(tert-butoxycarbonylaminomethyl)piperidine-1-carboxamide

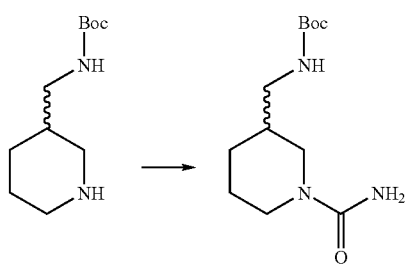 [SMILES: CC(C)(C)OC(=O)NCC1CCCNC1 ; CC(C)(C)OC(=O)NCC1CCCN(C(N)=O)C1]

3(R/S)-(tert-Butoxycarbonylaminomethyl)piperidine (3 g, 14.0 mmoles) was dissolved in anhydrous dichloromethane (50 mL) and trimethylsilylisocyanate (9.68 g, 11.4 mL, 84.0 mmoles) was added. The mixture was stirred under argon at 25° C. for 68 h. Additional trimethylsilylisocyanate (4.84 g, 5.7 mL, 42.0 mmoles) was added and the mixture was stirred at 25° C. for a total of 90 h. The mixture was evaporated to dryness and chromatographed on a silica gel column (30×5 cm) using 2% (10% conc. ammonium hydroxide in methanol)-dichloromethane as the eluant to give 3-(tert-butoxycarbonylaminomethyl)piperidine-1-carboxamide (3.05 g, 85%): FABMS: m/z 258.1 (MH$^+$); HRFABMS: m/z 258.1816 (MH$^+$). Calcd. for C$_{12}$H$_{24}$O$_3$N$_3$: m/z 258.1818; δ$_H$ (CDCl$_3$) 1.22 91H, m, CH$_2$), 1.42 (9H, s, —COOC(CH$_3$)$_3$), 1.48 (1H, m, CH$_2$), 1.67 (2H, m, CH$_2$), 1.78 (1H, m, CH), 2.80 (1H, m, CH$_2$), 2.99, 3H, m, CH$_2$), 3.59 (1H, m, CH$_2$0 3.69 (1H, m, CH$_2$), 4.76 (2H, bm, CONH$_2$) and 4.98 ppm (1H, bm, NH); δ$_C$ (CDCl$_3$) CH$_3$: 28.5, 28.5, 28.5; CH$_2$: 24.0, 28.3, 43.2, 45.1, 47.8; CH: 36.5; C: 79.4, 156.3, 158.5.

B. 3-(aminomethyl)piperidine-1-carboxamide

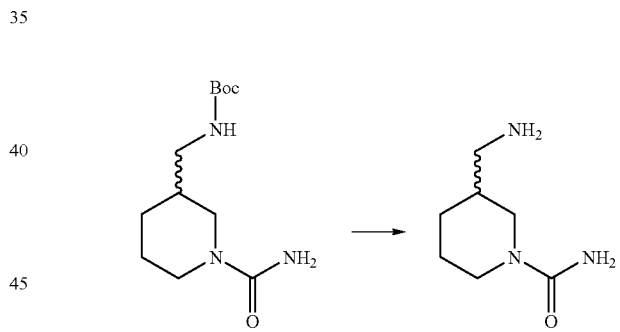

3-(tert-Butoxycarbonylaminomethyl)piperidine-1-carboxamide (150 mg, 0.583 mmoles) (prepared as described in Preparative Example 241, Step A above) was dissolved in methanol (3 mL). 10% conc. sulfuric acid in 1,4-dioxane (7.9 mL) was added and the mixture was stirred at 25° C. for 1 h. The mixture was diluted with methanol and BioRad AG1-X8 resin (OH$^-$ form) was added until the pH was basic. The resin was filtered off, washed with methanol, evaporated to dryness and chromatographed on a silica gel column (15×2 cm) using dichloromethane followed by 15% (10% conc, ammonium hydroxide in methanol)-dichloromethane as the eluant to give the 3-(aminomethyl)piperidine-1-carboxamide (80 mg, 87%): FABMS: m/z 158.1 (MH$^+$); HRFABMS: m/z 158.1294 (MH$^+$). Calcd. for C$_7$H$_{16}$N$_3$O: m/z 158.1293; δ$_H$ (CDCl$_3$+drop CD$_3$OD) 1.20 (1H, m, CH$_2$), 1.48 (1H, m, CH$_2$), 1.60 (1H, m, CH), 1.68 (1H, m, CH$_2$), 1.83 (1H, m, CH$_2$), 2.64 (bm, 2H, —CH$_2$NH$_2$), 2.82 (1H, m, CH$_2$), 3.02 (1H, m, CH$_2$), 2.98 (2H, m, CH$_2$), 3.70 (1H, m, —CH$_2$NH$_2$), 3.78 (1H, m, —CH₂NH₂) and 5.24 ppm (1H, bs, NH); δ$_C$ (CDCl₃+drop CD₃OD) CH₂: 24.1, 28.6, 44.0, 44.8, 47.9; CH: 38.3; C: 159.0.

Preparative Example 242

3-(2-aminoethyl)piperidine-1-carboxamide

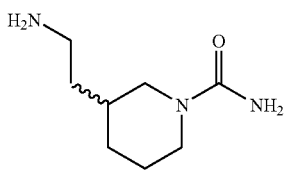

A. 3-(2-tert-butoxycarbonylaminoethyl)piperidine-1-carboxamide

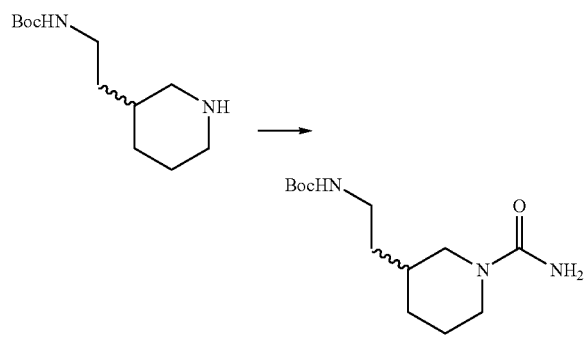

3-(2-tert-Butoxycarbonylaminoethyl)piperidine (500 mg, 2.19 mmoles) was dissolved in anhydrous dichloromethane (10 mL) and trimethylsilylisocyanate (2.96 mL, 21.9 mmoles) was added. The mixture was stirred under argon at 25° C. for 3.35 h. The mixture was diluted with dichloromethane and washed with saturated aqueous sodium bicarbonate. The organic layer was dried (MgSO₄), filtered, evaporated to dryness and chromatographed on a silica gel column (15×5 cm) using 5% (10% conc. ammonium hydroxide in methanol)-dichloromethane as the eluant to give 3-(2-tert-butoxycarbonylaminoethyl)piperidine-1-carboxamide (417.7 mg, 70%): FABMS: m/z 272.0 (MH⁺); HRFABMS: m/z 272.1979 (MH⁺). Calcd. for C₁₃H₂₆O₃: m/z 272.1974; δ$_H$(CDCl₃) 1.16 (1H, m, CH₂), 1-30-1.60 (5H, m, CH/CH₂), 1.46 (9H, s, —COOC(CH₃)₃), 1.68 (1H, m, CH₂), 184 (1H, m, CH₂), 2.54 (1H, dd, CH₂), 2.73 (1H, m, CH₂), 3.08 (1H, m, CH₂), 3.42 (1H, m, CH₂), 4.02 (1H, m, CH₂), 4.10 (1H, m, CH₂), 4.84 (1H, m, NH) and 4.96 ppm (2H, bm, CONH₂); δ$_C$ (CDCl₃) CH₃: 28.5, 28.5, 28.5; CH₂: 25.2, 31.7, 34.9, 37.3, 44.6, 50.3; CH: 32.9; C: 79.5, 156.4, 158.2.

B. 3-(2-aminoethyl)piperidine-1-carboxamide

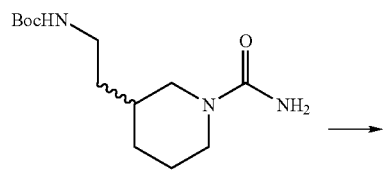

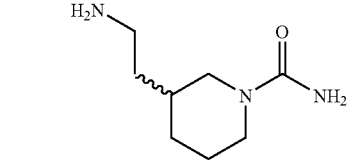 [SMILES: NCCC1CCCN(C(N)=O)C1]

3-(2-tert-Butoxycarbonylaminoethyl)piperidine-1-carboxamide (392.7 mg, 1.45 mmoles) (prepared as described in Preparative Example 242, Step A above) was dissolved in methanol (7.5 mL) and 10% conc. sulfuric acid in 1,4-dioxane (19.5 mL) was added. The mixture was stirred at 25° C. for 1.25 h. The mixture was diluted with methanol and Bio-Rad AG1-X8 resin (OH— form) was added until the pH was basic. The resin was filtered off, washed with methanol, evaporated to dryness and chromatographed on a silica gel column (30×2.5 cm) using 15% (10% conc. ammonium hydroxide in methanol)-dichloromethane as the eluant to give 3-(2-aminoethyl)piperidine-1-carboxamide (233 mg, 94%): FABMS: m/z 172.1 (MH⁺); HRFABMS: m/z 172.1444 (MH⁺). Calcd for C₈H₁₈N₃O requires: m/z 172.1450; δ$_H$ (CDCl₃+3% CD₃OD) 1.14 (1H, m, CH₂), 1.40 (2H, m, CH₂), 1.49 (1H, m, CH), 1.58 (1H, m, CH₂), 1.69 (1H, m, CH₂), 1.85 (1H, m, CH₂), 2.55 (1H, m, CH₂), 2.67 (5H, m, CH₂/NH₂), 2.76 (1H, bm, CH₂), 2.84 (1H, m, CH₂) and 3.82 ppm (2H, m, CONH₂); δ$_C$ (CDCl₃+3% CD₃OD) CH₂: 24.8, 30.9, 36.6, 38.9, 44.9, 50.0; CH: 33.4.

Preparative Example 243

4-(2-aminoethyl)piperidine-1-carboxamide

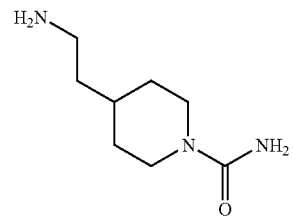 [SMILES: NCCC1CCN(C(N)=O)CC1]

A. 4-(2-Tert-butoxycarbonylaminoethyl)piperidine-1-carboxamide

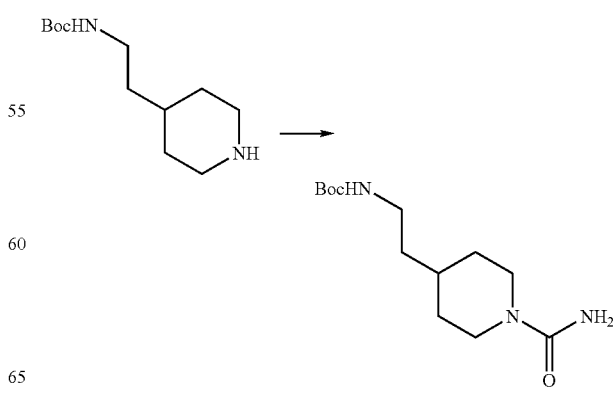

4-(2-tert-Butoxycarbonylaminoethyl)piperidine (500 mg, 2.19 mmoles) was dissolved in anhydrous dichloromethane (10 mL) and trimethylsilylisocyanate (2.96 mL, 21.9 mmoles) was added. The mixture was stirred under argon at 25° C. for 3.25 h. The mixture was diluted with dichloromethane and washed with saturated aqueous sodium bicarbonate. The organic layer was dried ($MgSO_4$), filtered, evaporated to dryness and chromatographed on a silica gel column (15×5 cm) using 5% (10% conc. ammonium hydroxide in methanol)-dichloromethane as the eluant to give 4-(2-tert-butoxycarbonylaminoethyl)piperidine-1-carboxamide (308.2 mg, 52%): FABMS: m/z 272.0 ($MH^+$); HRFABMS: m/z 272.1965 ($MH^+$). Calcd. for $C_{13}H_{26}O_3N_3$: m/z 272.1974; $\delta_H$ ($CDCl_3$) 1.20 (2H, m, $CH_2$), 1.47 (9H, s, —COOC($CH_3$)$_3$), 1.45-1.55 (3H, m, CH/$CH_2$), 1.75 (2H, m, $CH_2$), 2.82 (2H, m, $CH_2$), 3.19 (2H, m, $CH_2$), 3.96 (2H, m, $CH_2$), 4.64 (2H, m, $CH_2$) and 4.70 ppm (1H, bm, NH); $\delta_C$ ($CDCl_3$) $CH_3$: 28.5, 28.5, 28.5; $CH_2$: 31.8, 31.8, 36.7, 38.0, 44.5, 44.5; CH: 33.4; C: 79.2, 156.7, 158.1.

A. 3-(2-aminoethyl)piperidine-1-carboxamide

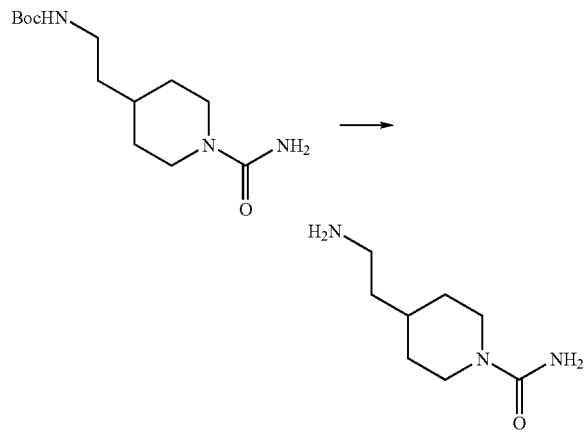

4-(2-tert-Butoxycarbonylaminoethyl)piperidine-1-carboxamide (283.3 mg, 1.04 mmoles) (prepared as described in Preparative Example 243, Step A above) was dissolved in methanol (5.4 mL) and 10% conc. sulfuric acid in 1,4-dioxane (14.2 mL) was added and the mixture was stirred at 25° C. for 1.25 h. The mixture was diluted with methanol and Bio-Rad AG1-X8 resin (OH— form) was added until the pH was basic. The resin was filtered off, washed with methanol, evaporated to dryness and chromatographed on a silica gel column (30×2.5 cm) using 15% (10% conc, ammonium hydroxide in methanol)-dichloromethane as the eluant to give the 3-(2-aminoethyl)piperidine-1-carboxamide (170 mg, 95%): FABMS: m/z 172.1 ($MH^+$); HRFABMS: m/z 172.1442. Calcd for $C_8H_{18}N_3O$ requires: m/z 172.1450; $\delta_H$ ($CDCl_3$+3% $CD_3OD$) 1.16 (2H, m, $CH_2$), 1.43 (2H, m, $CH_2$), 1.52 (1H, m, CH), 1.70 (2H, m, $CH_2$), 2.70-2.85 (8H, m, $CH_2$) and 3.92 ppm (2H, m, $CONH_2$); $\delta_C$ ($CDCl_3$+3% $CD_3OD$) $CH_2$: 31.9, 31.9, 39.0, 39.7, 44.4, 44.4; CH: 33.5; C: 158.7.

Preparative Example 244

3-(aminomethyl)-1-methylpiperidine

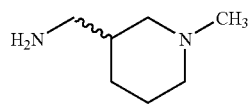

A. 3-(bromomethyl)-1-methylpiperidine

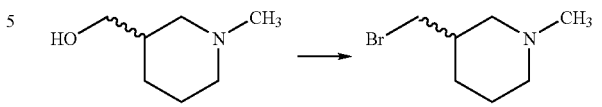

3-(Hydroxymethyl)-1-methylpiperidine (2 g, 15.5 mmoles) was dissolved in anhydrous acetonitrile (32 mL) and anhydrous pyridine (2.02 mL, 24.8 mmoles) was added and the solution was cooled to 0° C. Dibromotriphenylphosphorane (8.49 g, 20.2 mmoles) was added at 0° C. and the mixture was allowed to warm up to 25° C. and was stirred for 94 h. The mixture was evaporated to dryness and the residue was chromatographed on a silica gel column (30×5 cm) using gradient elution with dichloromethane, 35% diethyl ether in dichloromethane and 5-10% methanol in dichloromethane as the eluant to give 3-(bromomethyl)-1-methylpiperidine (3.13 g, 100%): FABMS: m/z 192.1 ($MH^+$); $\delta_H$ ($CDCl_3$) 1.52 (1H, m, $CH_2$), 1.99 (2H, m, $CH_2$), 2.43 (1H, m, $CH_2$), 2.75 (2H, m, $CH_2$), 2.82 (1H, m, CH), 2.86/2.88 (3H, s, $NCH_3$), 3.42/3.49 (2H, dd, —$CH_2Br$) and 3.56 ppm (2H, m, $CH_2$); $\delta_C$ ($CDCl_3$) $CH_3$: 44.3; $CH_2$: 22.1, 26.6, 35.4, 54.8, 58.2; CH: 34.6.

A. 3-(Di-tert-butoxycarbonylaminomethyl)-1-methylpiperidine

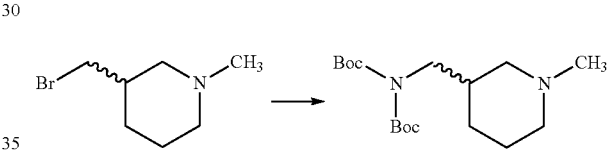

3-(Bromomethyl)-1-methylpiperidine (1.5 g, 7.81 mmoles) (from Preparative Example 244, Step A above) and di-tert-butyliminodicarboxylate (1.697 g, 7.81 mmoles) were dissolved in anhydrous acetonitrile (25 mL). Cesium carbonate (5.1 g, 15.6 mmoles) and lithium iodide (52 mg, 0.391 mmoles) were added and the mixture was stirred at 70° C. for 20 h. The mixture was evaporated to dryness and the residue was partitioned between dichloromethane and saturated aqueous sodium bicarbonate. The organic layer was dried ($MgSO_4$), filtered and evaporated to dryness. the residue was chromatographed on a silica gel column (30×5 cm) using 3% methanol in dichloromethane as the eluant to give 3-(di-tert-butoxycarbonylamino)-1-methylpiperidine (1.331 g, 52%): FABMS: m/z 329.2 ($MH^+$); HRFABMS: m/z 329.2438 ($MH^+$). Calcd. for $C_{17}H_{33}N_2O_4$: m/z 329.2440; $\delta_H$ ($CDCl_3$) 1.10 (1H, m, $CH_2$), 1.54 (18H, s, —COOC($CH_3$)$_3$), 1.86 (2H, m, $CH_2$), 2.01 (1H, m, $CH_2$), 2.19 (1H m, CH), 2.34 (2H, bm, $CH_2$), 2.59 (3H, —$NCH_3$), 3.19 (2H, m, $CH_2$) and 3.52/3.52 ppm (2H, —$CH_2N$—); $\delta_C$ ($CDCl_3$) $CH_3$: 28.5, 28.5, 28.5, 28.5, 28.5, 28.5, 47.2; $CH_2$: 25.4, 28.3, 50.4, 56.8, 60.8; CH: 37.2; C: 83.0, 83.0, 153.5, 153.5.

A. 3-(aminomethyl)-1-methylpiperidine

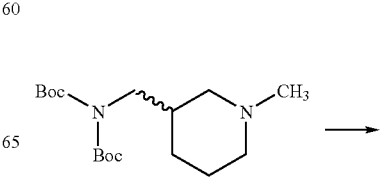

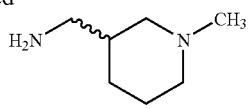

3-(Di-tert-butoxycarbonylamino)-1-methylpiperidine (500 mg, 1.52 mmoles) (from Preparative Example 244, Step B above) was dissolved in methanol (7.5 mL) and 10% (v/v) conc. sulfuric acid in 1,4-dioxane (19.75 mL) was added. The solution was stirred at 25° C. for 0.5 h. Methanol (300 mL) was added, followed by BioRad AG1-X8 resin (OH— form) until the pH was ~10. The resin was filtered off and washed with methanol (2×200 mL). The combined eluates were evaporated to dryness and the residue was chromatographed on a silica gel column (30×2.5 cm) using 10% (10% conc. ammonium hydroxide in methanol)-dichloromethane as the eluant to give 3-(aminomethyl)-1-methylpiperidine (69.2 mg, 35%): FABMS: m/z 129.1 (MH$^+$); HRFABMS: m/z 129.1392 (MH$^+$). Calcd. for $C_7H_{17}N_2$: m/z 129.1392; $\delta_H$ (CDCl$_3$) 0.90 (2H, m, CH$_2$), 1.65 (2H, m, CH$_2$), 1.72 (1H, m, CH), 1.79 (1H, m, CH$_2$), 1.91 (1H, m, CH$_2$), 2.30 (3H, s, —NCH$_3$), 2.64 (2H, m, CH$_2$), 2.82 (1H, m, —CH$_2$NH$_2$) and 2.92 ppm (1H, m, —CH$_2$NH$_2$); $\delta_C$ (CDCl$_3$) CH$_3$: 46.7; CH$_2$: 25.2, 28.0, 46.3, 56.4, 60.3; CH: 39.9.

Preparative Example 245

4-(aminomethyl)-1-methylpiperidine

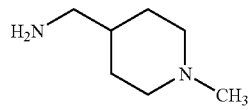

A. 1-methylisonipecotamide

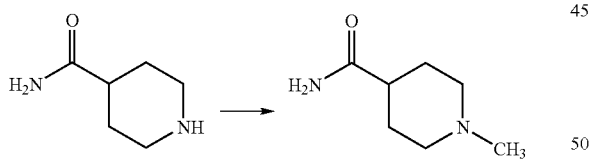

Isonipecotamide (10 g, 78.0 mmoles) was dissolved in distilled water (100 mL) and 37% aqueous formaldehyde (7.6 mL, equivalent to 2.81 g HCHO, 93.6 mmoles) was added. Wet 10% Pd—C (8 spoon spatulas) was added under argon and the mixture was hydrogenated at 25° C. and 50 psi for 43 h. The catalyst was filtered off through Celite and the latter was washed with water and methanol. The combined filtrates were evaporated to dryness and the residue was chromatographed on a silica gel column (60×5 cm) using 8%-10%-20% (10% conc. ammonium hydroxide in methanol)-dichloromethane as the eluant to give 1-methylisonipecotamide (7.15 g, 64%): FABMS: m/z 143.1 (MH$^+$); HRFABMS: m/z 143.1184 (MH$^+$). Calcd. for $C_7H_{15}N_2O$: m/z 143.1184; $\delta_H$ (d$_6$-DMSO) 1.50/1.57 (4H, m, CH$_2$), 1.76/1.94 (4H, m, CH$_2$), 2.10 (3H, s, —NCH$_3$), 2.72 (1H, m, CH) and 6.68/7.18 ppm (2H, m, CONH$_2$); $\delta_C$ (d$_6$-DMSO)CH$_3$: 41.2; CH$_2$: 28.5, 28.5, 54.9, 54.9; CH: 46.2; C: 176.7.

B. 4-(aminomethyl)-1-methylpiperidine

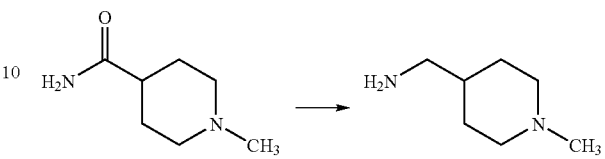

1-Methylisonipecotamide (6.75 g, 47.5 mmoles) (prepared as described in Preparative Example 245, Step A above) was dissolved in anhydrous THF (350 mL) and the resulting mixture was added in portions to a stirred slurry of lithium aluminum hydride (1.8 g, 47.5 mmoles) in anhydrous THF (100 mL) at 0° C. under nitrogen. The mixture was stirred at 0° C. for 30 min and then heated at 66° C. for 25 h under nitrogen. Distilled water (1.88 mL) was added dropwise to the stirred mixture at 0° C., followed by 20% aqueous sodium hydroxide (1.42 mL) and then distilled water (6.75 mL) and the mixture was stirred for 15 min. The mixture was filtered and the solids were washed with THF and dichloromethane. The combined filtrates were evaporated to dryness and chromatographed on a silica gel column (30×5 cm) using 15%-20% (10% conc. ammonium hydroxide in methanol)-dichloromethane as the eluant to give 4-(aminomethyl)-1-methylpiperidine (0.678 g, 11%): FABMS: m/z 129.1 (MH$^+$); HRFABMS: m/z 129.1389 (MH$^+$). Calcd. for $C_7H_{17}N_2$: m/z 129.1392; $\delta_H$ (d$_6$-DMSO): 2.08 ppm (3H, s, —NCH$_3$); $\delta_C$ (d$_6$-DMSO): CH$_3$: under DMSO peaks; CH$_2$: 29.6, 29.6, 46.7, 55.2, 55.2; CH: 46.2.

Preparative Example 246

3-(aminomethyl)benzonitrile

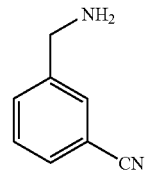

A. 3-(Di-tert-butoxycarbonylamino)benzonitrile

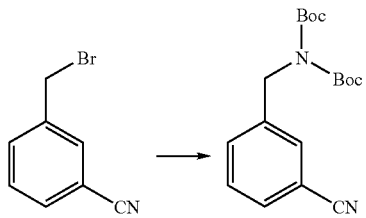 [SMILES: N#Cc1cccc(CBr)c1 ; CC(C)(C)OC(=O)N(Cc1cccc(C#N)c1)C(=O)OC(C)(C)C]

3-(Bromomethyl)benzonitrile (5 g, 25.5 mmoles) and di-tert-butyliminodicarboxylate (5.54 g, 25.5 mmoles) were dissolved in anhydrous THF (50 mL) and cesium carbonate (16.62 g, 25.5 mmoles) and lithium iodide (170.5 mg, 1.275 mmoles) were added. The mixture was stirred at 70° C. for 22 h and the reaction was worked up as described in Preparative Example 89, Step B above. The residue was chromatographed on a silica gel column (60×5 cm) using 5% ethyl acetate in hexane as the eluant to give 3-(di-tert-butoxycarbonylamino)benzonitrile (7.39 g, 87%): FABMS: m/z 333.2 (MH+); HRFABMS: m/z 333.1815 (MH+); Calcd. for $C_{18}H_{25}N_2O_4$: m/z 333.1814; $\delta_H$ (CDCl$_3$) 1.52 (1H, s, —COOC(CH$_3$)$_3$), 4.84 (2H, s, CH$_2$), 7.48 (1H, m, Ar—H), 7.60 (2H, m, Ar—H) and 7.65 ppm (1H, m, Ar—H); $\delta_C$ (CDCl$_3$) CH$_3$: 28.1, 28.1, 28.1, 28.1, 28.1, 28.1; CH$_2$: 48.4; CH: 129.2, 131.0, 131.0, 131.9; C: 83.2, 83.2, 112.5, 118.8, 140.1, 152.5, 152.5.

B. 3-(aminomethyl)benzonitrile

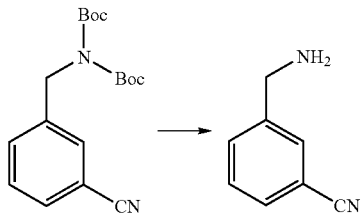 [SMILES: CC(C)(C)OC(=O)N(Cc1cccc(C#N)c1)C(=O)OC(C)(C)C ; N#Cc1cccc(CN)c1]

3-(Di-tert-butoxycarbonylamino)benzonitrile (2 g, 6.0 mmoles) (prepared as described in Preparative Example 246, Step A above) was dissolved in methanol (30 mL) and 10% (v/v) (10% conc. sulfuric acid in 1,4-dioxane) (79 mL) was added. The solution was stirred at 25° C. for 0.25 h and worked up as described in Preparative Example 89, Step C above). The residue was chromatographed on a silica gel column (15×5 cm) using 3% (10% conc. ammonium hydroxide in methanol)-dichloromethane as the eluant to give the title compound (651.4 mg, 82%): FABMS: m/z 133.1 (MH+); HRFABMS: m/z 133.0762 (MH+). Calcd. for C$_8$H$_9$N$_2$: m/z 133.0766; $\delta_H$ (CDCl$_3$) 2.57 (2H, s, —CH$_2$NH$_2$), 3.92 (2H, s, —CH$_2$NH$_2$), 7.46 (1H, m, Ar—H), 7.57 (2H, m, Ar—H) and 7.64 ppm (1H, m, Ar—H); $\delta_C$ (CDCl$_3$) CH$_2$: 45.2; CH: 129.4, 130.7, 130.7, 131.8; C: 112.4, 118.8, 143.8.

Preparative Example 247

4-(aminomethyl)benzonitrile

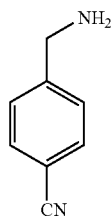

A.
3-(di-tert-butoxycarbonylaminomethyl)benzonitrile

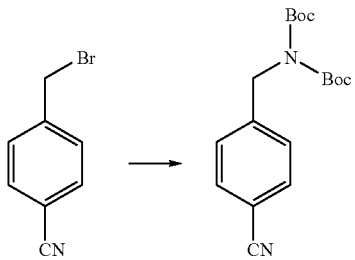 [SMILES: N#Cc1ccc(CBr)cc1 ; CC(C)(C)OC(=O)N(Cc1ccc(C#N)cc1)C(=O)OC(C)(C)C]

4-(Bromomethyl)benzonitrile (5 g, 25.5 mmoles) and di-tert-butyliminodicarboxylate (5.54 g, 25.5 mmoles) were dissolved in anhydrous THF (50 mL) and cesium carbonate (16.62 g, 25.5 mmoles) and lithium iodide (170.5 mg, 1.275 mmoles) were added. The mixture was stirred at 70° C. for 23 h and the reaction was worked up as described in Preparative Example 244, Step B above. The residue was chromatographed on a silica gel column (50×5 cm) using 5% ethyl acetate in hexane as the eluant to give 4-(di-tert-butoxycarbonylaminomethyl)benzonitrile (7.07 g, 83%): FABMS: m/z 333.2 (MH+); HRFABMS: m/z 333.1816 (MH+). Calcd. for $C_{18}H_{25}N_2O_4$: m/z 333.1814; $\delta_H$ (CDCl$_3$) 1.45 (1H, s, —COOC(CH$_3$)$_3$), 4.81 (2H, s, CH$_2$), 7.37 (2H, d, Ar—H) and 7.62 ppm (2H, d, Ar—H); $\delta_C$ (CDCl$_3$) CH$_3$: 28.1, 28.1, 28.1, 28.1, 28.1, 28.1; CH$_2$: 49.2; CH: 127.8, 127.8, 132.3, 132.3; C: 83.2, 83.2, 111.1, 118.9, 144.1, 152.4, 152.4.

B. 4-(aminomethyl)benzonitrile

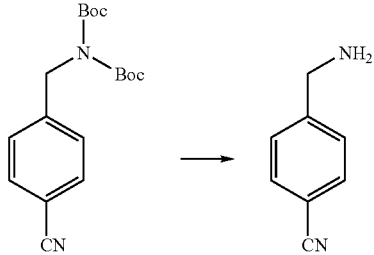 [SMILES: CC(C)(C)OC(=O)N(Cc1ccc(C#N)cc1)C(=O)OC(C)(C)C ; N#Cc1ccc(CN)cc1]

4-(Di-tert-butoxycarbonylaminomethyl)benzonitrile (2 g, 6.0 mmoles) (prepared as described in Preparative Example 247, Step A above) was dissolved in TFA (4 mL) and the solution was stirred at 25° C. for 0.25 h. The reaction mixture was diluted with dichloromethane and extracted with 1N sodium hydroxide. The organic layer was dried (MgSO$_4$), filtered and evaporated to dryness. The residue was chromatographed on a silica gel column (15×5 cm) using 3% (10% conc. ammonium hydroxide in methanol)-dichloromethane as the eluant to give 4-(aminomethyl)benzonitrile (108 mg, 68%): FABMS: m/z 133.1 (MH+); HRFABMS: m/z 133.0764 (MH+). Calcd. for C$_8$H$_9$N$_2$: m/z 133.0766; $\delta_H$ (CDCl$_3$) 2.04 (2H, s, —CH$_2$NH$_2$), 3.89 (2H, s, —CH$_2$NH$_2$), 7.40 (2H, d, Ar—H) and 7.59 ppm (2H, d, Ar—H); δ$_C$ (CDCl$_3$)CH$_2$: 45.7; CH: 127.8, 127.8, 132.4, 132.4; C: 110.6, 118.9, 148.0.

Preparative Example 248

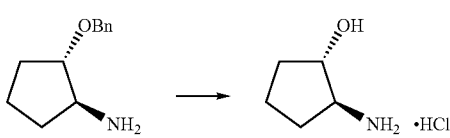 [SMILES: N[C@H]1CCC[C@@H]1OCc1ccccc1 ; N[C@H]1CCC[C@@H]1O ; Cl]

To a solution of (1S,2S)-2-benzyloxycyclopentyl amine (1.5 g, 7.84 mmol) in MeOH (50 mL) at rt was added 10% Pd/C (50% wet, 1.0 g) followed by dropwise addition of conc. HCl (0.7 mL). The mixture was stirred under a balloon of H$_2$ for 14 h and the catalyst was filtered off thru a pad of Celite. The pad of Celite was washed with MeOH (2×10 mL) and the resulting filtrate was concentrated under reduced pressure to afford 0.97 g (90%) of a yellow semisolid; M+H (free base)=102

Preparative Examples 249-251

In an analogous fashion to Preparative Example 248, the benzyl protected cycloalkyl amines (Column 2) were converted to the desired aminocycloalkanol hydrochloride derivatives (Column 3) as listed in Table 17.

TABLE 17

| Ex. | Column 2 (Amine) | Column 3 (Cleavage method) | CMPD M + H |
|---|---|---|---|
| 249 | ![OBn, NH2 cyclopentyl] | ![NH2, OH cyclopentyl] | M + H = 102 (free base) |
| 250 | ![OBn, NH2 cyclohexyl] | ![OH, NH2·HCl cyclohexyl] | M + H = 116 (free base) |
| 251 | ![OBn, NH2 cyclohexyl] | ![OH, NH2·HCl cyclohexyl] | M + H = 116 (free base) |

Preparative Example 252

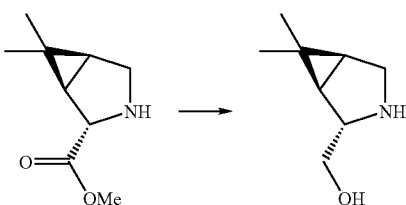

To a solution of ester (prepared according to *J. Org. Chem.* (1999), 64, 330) (0.5 g, 2.43 mmol) in THF (8 mL) at 0° C. was added LiAlH$_4$ (0.37 g, 9.74 mmol) in one portion. The resulting mixture was heated at reflux for 12 h and was cooled to 0° C. The mixture was treated sequentially with H$_2$O (1 mL), 1M NaOH (1 mL), and H$_2$O (3 mL). CH$_2$Cl$_2$ (10 ml) was added to the mixture which was stirred vigorously for 30 min. The mixture was filtered thru a pad of Celite which was washed generously with CH$_2$Cl$_2$ (3×5 mL). The resulting filtrate was concentrated under reduced pressure to afford 0.41 g (85%) of a yellow/orange solid. M+H=142.

Preparative Example 253

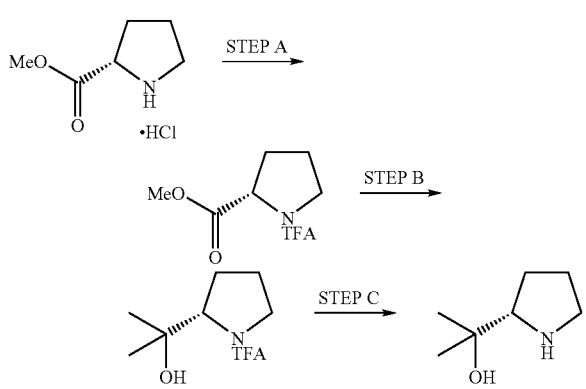

Step A:

To a solution of L-proline methyl ester hydrochloride (0.50 g, 3.0 mmol) in CH$_2$Cl$_2$ (15 mL) at 0° C. was added Et$_3$N (1.1 mL, 7.55 mmol) followed by TFAA (0.56 mL, 3.92 mmol). The mixture was stirred for 12 h at rt and 1N HCl (25 mL) was added. The layers were separated and the organic layer was washed sequentially with sat. aq. NaHCO$_3$ (1×25 mL), and brine (1×25 mL). The organic layer was dried (Na$_2$SO$_4$), filtered, and concentrated under reduced pressure to afford 0.72 g (100%) of a yellow oil. M+H=226. The crude material was taken onto Step B without further purification.

Step B:

To a solution of the compound prepared in Preparative Example 253, Step A (0.68 g, 3.0 mmol) in THF (20 mL) at 0° C. was added MeMgI (5.1 mL, 3.0M in Et$_2$O) dropwise over 10 min. The resulting solution was stirred for 16 h at rt whereupon the mixture was quenched by addition of sat. aq. NH$_4$Cl. The mixture was concentrated to dryness and the resultant residue was stirred with EtOAc (100 mL) for 45 min and filtered. The filtrate was concentrated under reduced pressure to afford 0.68 g (100%) of a yellow/orange oil. M+H=226. The crude material was taken onto Step C without further purification.

Step C:

To a solution of the compound prepared in Preparative Example 253, Step B (0.68 g, 3.0 mmol) in MeOH (5 mL) was added a solution of KOH (0.68 g, 12.1 mmol) in MeOH (5 mL). The mixture was stirred at reflux for 12 h and rt for 72 h whereupon the mixture was concentrated to dryness. The crude residue was suspended in EtOAc (50 mL) and was stirred vigorously for 30 min and was filtered. This procedure was repeated 2× more and the resultant filtrate was concentrated under reduced pressure to afford 128 mg (33%) of a maroon/orange oil. M+H=130. This material was used without purification in the subsequent coupling step.

Preparative Example 254

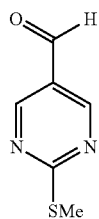

The aldehyde was prepared according to the procedure of Gupton (*J. Heterocyclic Chem.* (1991), 28, 1281).

Preparative Example 255

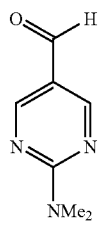 [SMILES: CN(C)c1ncc(C=O)cn1]

Using the aldehyde from Preparative Example 254, the procedure of Gupton (*J. Heterocyclic Chem.* (1991), 28, 1281) was employed to prepare the title aldehyde.

Preparative Example 256

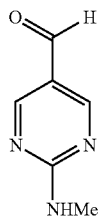

The title aldehyde was prepared according to the procedure of Ragan et. al *Synlett* (2000), 8, 1172-1174.

Preparative Example 257

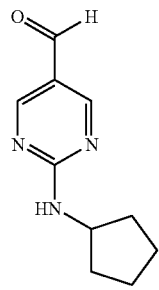 [SMILES: O=Cc1cnc(NC2CCCC2)nc1]

The reaction of known cyclopentyl guanidine hydrochloride (*Org. Lett.* (2003), 5, 1369-1372) under the conditions of Ragan (*Synlett* (2000), 8, 1172-1174) afforded the title aldehyde.

Preparative Example 258

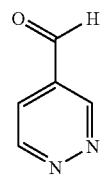

The title compound was prepared according to known literature *Monatshefte fur Chemie* (1973), 104, 1372-1382.

EXAMPLES

Example 1

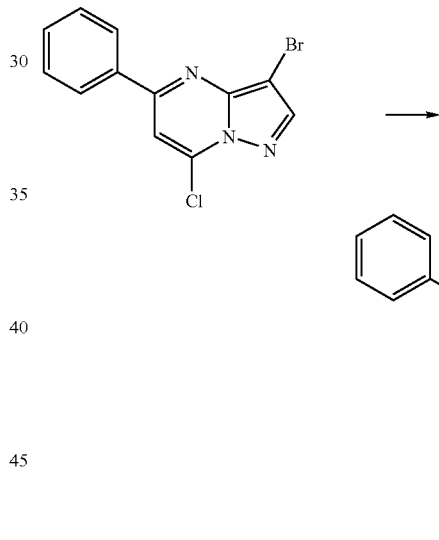

A solution of the product from Preparative Example 127 (0.27 g, 0.875 mmol), 4-aminomethylpyridine (0.12 g, 1.3 eq.), and $K_2CO_3$ (0.24 g, 2 eq.) in $CH_3CN$ (5 mL) was stirred at room temperature 48 hours. The reaction mixture was diluted with $H_2O$ and extracted with $CH_2Cl_2$. The combined organics were dried over $Na_2SO_4$, filtered and concentrated. The crude product was purified by flash chromatography using a 4% MeOH in $CH_2Cl_2$ solution as eluent (0.28 g, 93% yield). LCMS: $MH^+=380$; mp=>205° C. (dec).

Examples 2-210

By following essentially the same procedure set forth in Example 1 only substituting the chlorides shown in Column 2 of Table 18 and the amines shown in Column 3 of Table 18, the compounds in Column 4 of Table 18 were prepared:

TABLE 18

| Ex. | Column 2 | Column 3 | Column 4 | Data |
|---|---|---|---|---|
| 2 | 3-bromo-5-phenyl-7-chloro-pyrazolo[1,5-a]pyrimidine | 3-(aminomethyl)pyridine | 3-bromo-N-(pyridin-3-ylmethyl)-5-phenylpyrazolo[1,5-a]pyrimidin-7-amine | LCMS: MH+ = 380; mp = 175-176° C. |
| 3 | 3-bromo-5-(2-fluorophenyl)-7-chloro-pyrazolo[1,5-a]pyrimidine | 4-(aminomethyl)pyridine | 3-bromo-5-(2-fluorophenyl)-N-(pyridin-4-ylmethyl)pyrazolo[1,5-a]pyrimidin-7-amine | LCMS: MH+ = 398; mp = 156-157° C. |
| 4 | 3-bromo-5-(2-fluorophenyl)-7-chloro-pyrazolo[1,5-a]pyrimidine | 3-(aminomethyl)pyridine | 3-bromo-5-(2-fluorophenyl)-N-(pyridin-3-ylmethyl)pyrazolo[1,5-a]pyrimidin-7-amine | LCMS: MH+ = 398; mp = 45-49° C. |
| 5 | 3,7-dichloro-5-(2-fluorophenyl)-pyrazolo[1,5-a]pyrimidine | 3-(aminomethyl)pyridine | 3-chloro-5-(2-fluorophenyl)-N-(pyridin-3-ylmethyl)pyrazolo[1,5-a]pyrimidin-7-amine | LCMS: MH+ = 354; mp = 43-46° C. |

TABLE 18-continued

| Ex. | Column 2 | Column 3 | Column 4 | Data |
| --- | --- | --- | --- | --- |
| 6 | | | | LCMS: MH+ = 354; mp = 149-150° C. |
| 7 | | | | LCMS: MH+ = 414; mp = 86-92° C. |
| 8 | | | | LCMS: MH+ = 414; mp = 185-186° C. |
| 9 | | | | LCMS: MH+ = 448; mp = 167-168° C. |

TABLE 18-continued

| Ex. | Column 2 | Column 3 | Column 4 | Data |
|---|---|---|---|---|
| 10 | 3-bromo-5-isopropyl-7-chloropyrazolo[1,5-a]pyrimidine | pyridin-4-ylmethanamine | 3-bromo-5-isopropyl-N-(pyridin-4-ylmethyl)pyrazolo[1,5-a]pyrimidin-7-amine | LCMS: MH$^+$ = 346; mp = 57-58° C. |
| 11 | 3-bromo-5-isopropyl-7-chloropyrazolo[1,5-a]pyrimidine | pyridin-3-ylmethanamine | 3-bromo-5-isopropyl-N-(pyridin-3-ylmethyl)pyrazolo[1,5-a]pyrimidin-7-amine | LCMS: MH$^+$ = 347; mp = 122.9-125.3° C. |
| 12 | 3-bromo-5-tert-butyl-7-chloropyrazolo[1,5-a]pyrimidine | pyridin-4-ylmethanamine | 3-bromo-5-tert-butyl-N-(pyridin-4-ylmethyl)pyrazolo[1,5-a]pyrimidin-7-amine | LCMS: MH$^+$ = 360; mp = 127-128° C. |
| 13 | 3-cyclopropyl-5-phenyl-7-chloropyrazolo[1,5-a]pyrimidine | pyridin-3-ylmethanamine | 3-cyclopropyl-5-phenyl-N-(pyridin-3-ylmethyl)pyrazolo[1,5-a]pyrimidin-7-amine | LCMS: MH$^+$ = 342; mp = 133-135° C. |

TABLE 18-continued

| Ex. | Column 2 | Column 3 | Column 4 | Data |
|---|---|---|---|---|
| 14 | 5-phenyl-3-isopropyl-7-chloropyrazolo[1,5-a]pyrimidine | pyridin-3-ylmethanamine | 5-phenyl-3-isopropyl-7-((pyridin-3-ylmethyl)amino)pyrazolo[1,5-a]pyrimidine | LCMS: $MH^+$ = 344; mp = 152–155° C. |
| 15 | 3-bromo-5-isopropyl-7-chloropyrazolo[1,5-a]pyrimidine | (pyridin-3-ylmethyl)amine N-oxide | 3-bromo-5-isopropyl-7-((pyridin-3-ylmethyl)amino)pyrazolo[1,5-a]pyrimidine N-oxide | LCMS: $MH^+$ = 362; mp = 164–167° C. |
| 16 | 5-phenyl-7-chloropyrazolo[1,5-a]pyrimidine-3-carbonitrile | pyridin-4-ylmethanamine | 5-phenyl-7-((pyridin-4-ylmethyl)amino)pyrazolo[1,5-a]pyrimidine-3-carbonitrile | LCMS: $MH^+$ = 327; mp = 146–155° C. |
| 17 | (5-phenyl-7-chloropyrazolo[1,5-a]pyrimidin-3-yl)methanol | pyridin-4-ylmethanamine | (5-phenyl-7-((pyridin-4-ylmethyl)amino)pyrazolo[1,5-a]pyrimidin-3-yl)methanol | LCMS: $MH^+$ = 332; mp = 71–82° C. |

TABLE 18-continued

| Ex. | Column 2 | Column 3 | Column 4 | Data |
|---|---|---|---|---|
| 17.1 | | | | MS: MH⁺ = 332. |
| 18 | | | | LCMS: MH⁺ = 346; mp = 58-65° C. |
| 19 | | | | LCMS: MH = 414; mp = 211-213° C. |
| 20 | | | | LCMS: MH⁺ = 414; mp = 194-197° C. |

TABLE 18-continued

| Ex. | Column 2 | Column 3 | Column 4 | Data |
|---|---|---|---|---|
| 21 | | | | MS: MH⁺ = 414 m.p. 211-216° C. |
| 22 | | | | LCMS: MH⁺ = 544; mp = 104-107° C. |
| 23 | | | | Yield = 83% LCMS: MH⁺ = 410. |
| 24 | | | | Yield = 84% LCMS: MH⁺ = 410. |

TABLE 18-continued

| Ex. | Column 2 | Column 3 | Column 4 | Data |
| --- | --- | --- | --- | --- |
| 25 | 5-(3,4-dimethoxyphenyl)-3-bromo-7-chloropyrazolo[1,5-a]pyrimidine | 4-(aminomethyl)pyridine | 5-(3,4-dimethoxyphenyl)-3-bromo-N-(pyridin-4-ylmethyl)pyrazolo[1,5-a]pyrimidin-7-amine | Yield = 96% LCMS: MH$^+$ = 440. |
| 26 | 5-(3,4-dimethoxyphenyl)-3-bromo-7-chloropyrazolo[1,5-a]pyrimidine | 3-(aminomethyl)pyridine | 5-(3,4-dimethoxyphenyl)-3-bromo-N-(pyridin-3-ylmethyl)pyrazolo[1,5-a]pyrimidin-7-amine | Yield = 99% LCMS: MH$^+$ = 440. |
| 27 | 5-(2,3-dichlorophenyl)-3-bromo-7-chloropyrazolo[1,5-a]pyrimidine | 4-(aminomethyl)pyridine | 5-(2,3-dichlorophenyl)-3-bromo-N-(pyridin-4-ylmethyl)pyrazolo[1,5-a]pyrimidin-7-amine | Yield = 89% LCMS: MH$^+$ = 448. |
| 28 | 5-(2,3-dichlorophenyl)-3-bromo-7-chloropyrazolo[1,5-a]pyrimidine | 3-(aminomethyl)pyridine | 5-(2,3-dichlorophenyl)-3-bromo-N-(pyridin-3-ylmethyl)pyrazolo[1,5-a]pyrimidin-7-amine | Yield = 78% LCMS: MH$^+$ = 448. |

TABLE 18-continued
| Ex. | Column 2 | Column 3 | Column 4 | Data |
|---|---|---|---|---|
| 30 | 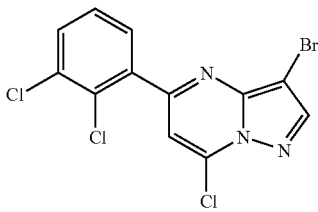 [SMILES: Clc1cccc(-c2cc(Cl)n3ncc(Br)c3n2)c1Cl] | 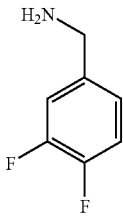 | 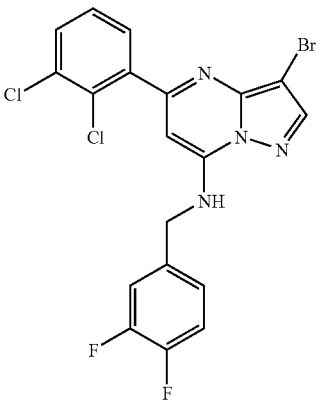 [SMILES: Fc1ccc(CNc2cc(-c3cccc(Cl)c3Cl)nc3c(Br)cnn23)cc1F] | Yield = 96% LCMS: MH$^+$ = 483. |
| 31 | 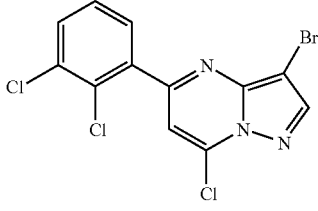 [SMILES: Clc1cccc(-c2cc(Cl)n3ncc(Br)c3n2)c1Cl] | 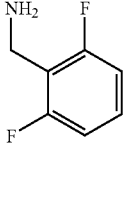 | 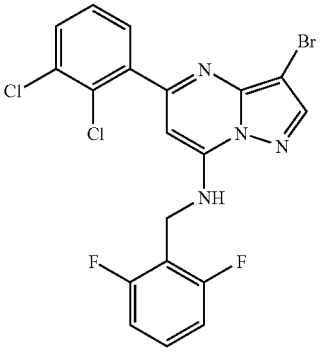 [SMILES: Fc1cccc(F)c1CNc1cc(-c2cccc(Cl)c2Cl)nc2c(Br)cnn12] | Yield = 35% LCMS: MH$^+$ = 483. |
| 32 | 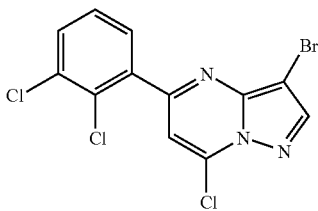 [SMILES: Clc1cccc(-c2cc(Cl)n3ncc(Br)c3n2)c1Cl] | 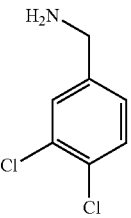 | 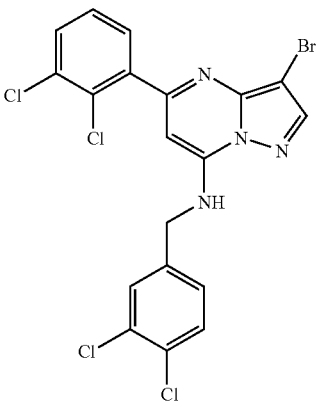 [SMILES: Clc1ccc(CNc2cc(-c3cccc(Cl)c3Cl)nc3c(Br)cnn23)cc1Cl] | Yield = 77% LCMS: MH$^+$ = 515. |
| 33 | 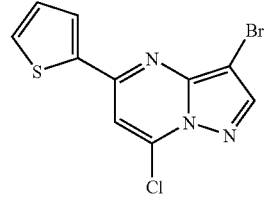 [SMILES: Clc1cc(-c2cccs2)nc2c(Br)cnn12] | 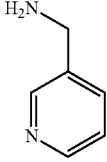 | 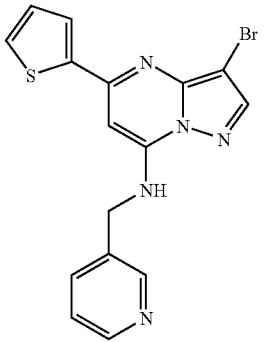 [SMILES: Brc1cnn2c(NCc3cccnc3)cc(-c3cccs3)nc12] | Yield = 100% m.p. 179° C. LCMS: MH$^+$ = 388. |

TABLE 18-continued

| Ex. | Column 2 | Column 3 | Column 4 | Data |
|---|---|---|---|---|
| 34 | | | | Yield = 99% m.p. 186° C. LCMS: MH+ = 456 |
| 35 | | | | Yield = 98% m.p. 181° C. LCMS: MH+ = 401 |
| 36 | | | | Yield = 63% m.p. 192° C. LCMS: MH+ = 480 |
| 37 | | | | Yield = 75% m.p. 126-127° C. LCMS: MH+ = 400 |

TABLE 18-continued

| Ex. | Column 2 | Column 3 | Column 4 | Data |
|---|---|---|---|---|
| 38 | cyclohexylmethyl-3-bromo-7-chloropyrazolo[1,5-a]pyrimidine | 3-(aminomethyl)pyridine | 5-(cyclohexylmethyl)-3-bromo-N-(pyridin-3-ylmethyl)pyrazolo[1,5-a]pyrimidin-7-amine | Yield = 94% m.p. 132-133° C. LCMS: MH$^+$ = 400 |
| 39 | cyclohexylmethyl-3-bromo-7-chloropyrazolo[1,5-a]pyrimidine | 4-(aminomethyl)pyridine | 5-(cyclohexylmethyl)-3-bromo-N-(pyridin-4-ylmethyl)pyrazolo[1,5-a]pyrimidin-7-amine | Yield = 95% m.p. 121-122° C. LCMS: MH$^+$ = 400 |
| 40 | cyclohexylmethyl-3-bromo-7-chloropyrazolo[1,5-a]pyrimidine | 2,4-dimethoxybenzylamine | 5-(cyclohexylmethyl)-3-bromo-N-(2,4-dimethoxybenzyl)pyrazolo[1,5-a]pyrimidin-7-amine | Yield = 98% LCMS: MH$^+$ = 460 |
| 41 | 5-(2,6-dichlorobenzyl)-3-bromo-7-chloropyrazolo[1,5-a]pyrimidine | 2-(aminomethyl)pyridine | 5-(2,6-dichlorobenzyl)-3-bromo-N-(pyridin-2-ylmethyl)pyrazolo[1,5-a]pyrimidin-7-amine | Yield = 87% m.p. 170-171° C. LCMS: MH$^+$ = 464 |

TABLE 18-continued

| Ex. | Column 2 | Column 3 | Column 4 | Data |
|---|---|---|---|---|
| 42 | 5-(2,6-dichlorobenzyl)-3-bromo-7-chloropyrazolo[1,5-a]pyrimidine | 3-(aminomethyl)pyridine | 5-(2,6-dichlorobenzyl)-3-bromo-7-[(pyridin-3-ylmethyl)amino]pyrazolo[1,5-a]pyrimidine | Yield = 84% m.p. 216-217° C. LCMS: MH⁺ = 464 |
| 43 | 5-(cyclohexylmethyl)-3-bromo-7-chloropyrazolo[1,5-a]pyrimidine | 4-(aminomethyl)pyridine | 5-(cyclohexylmethyl)-3-bromo-7-[(pyridin-4-ylmethyl)amino]pyrazolo[1,5-a]pyrimidine | Yield = 96% m.p. 214° C. LCMS: MH⁺ = 464 |
| 44 | 5-(2,6-dichlorobenzyl)-3-bromo-7-chloropyrazolo[1,5-a]pyrimidine | 2,4-dimethoxybenzylamine | 5-(2,6-dichlorobenzyl)-3-bromo-7-[(2,4-dimethoxybenzyl)amino]pyrazolo[1,5-a]pyrimidine | Yield = 95% m.p. 158° C. LCMS: MH⁺ = 522 |
| 45 | ethyl 5-neopentyl-7-chloropyrazolo[1,5-a]pyrimidine-3-carboxylate | 4-(aminomethyl)pyridine | ethyl 5-neopentyl-7-[(pyridin-4-ylmethyl)amino]pyrazolo[1,5-a]pyrimidine-3-carboxylate | Yield = 90% LCMS: MH⁺ = 278 |

US 8,673,924 B2
TABLE 18-continued
| Ex. | Column 2 | Column 3 | Column 4 | Data |
|---|---|---|---|---|
| 46 | 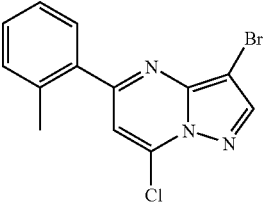 | 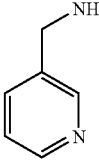 | 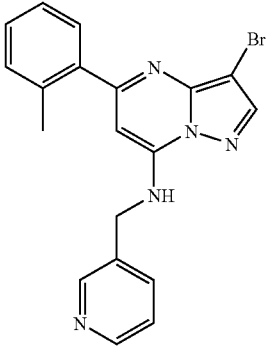 [SMILES: Cc1ccccc1-c1cc(NCc2cccnc2)n2ncc(Br)c2n1] | Yield = 100%; LCMS: MH$^+$ = 394 |
| 47 | 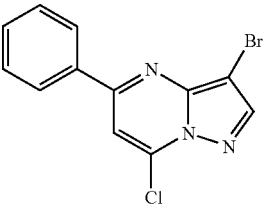 [SMILES: Clc1cc(-c2ccccc2)nc2c(Br)cnn12] | 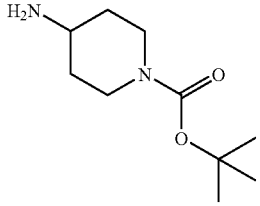 | 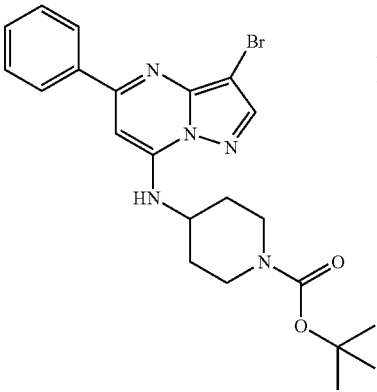 [SMILES: CC(C)(C)OC(=O)N1CCC(Nc2cc(-c3ccccc3)nc3c(Br)cnn23)CC1] | LCMS: MH$^+$ = 473 m.p. 84-87° C. |
| 48 | 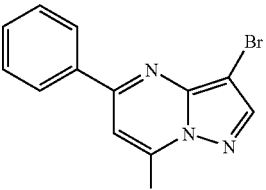 | 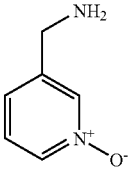 | 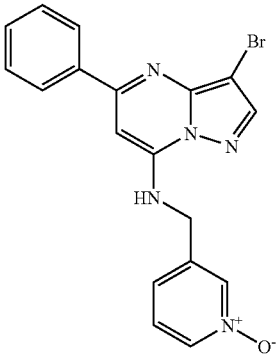 [SMILES: [O-][n+]1cccc(CNc2cc(-c3ccccc3)nc3c(Br)cnn23)c1] | MS: MH$^+$ = 396 m.p. 91.5-93.3° C. |
| 49 | 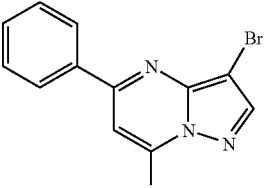 | 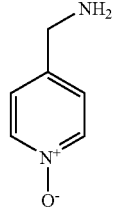 | 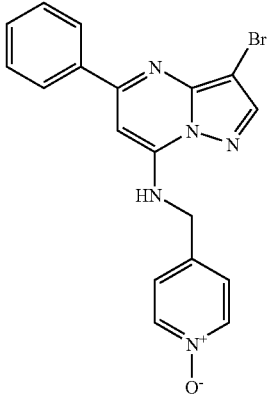 [SMILES: [O-][n+]1ccc(CNc2cc(-c3ccccc3)nc3c(Br)cnn23)cc1] | MS: MH$^+$ = 396 m.p. 196-199° C. |

TABLE 18-continued
| Ex. | Column 2 | Column 3 | Column 4 | Data |
|---|---|---|---|---|
| 50 | 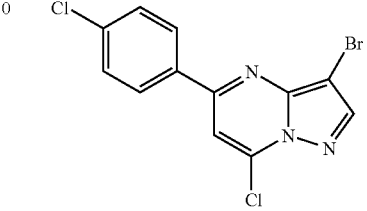 | 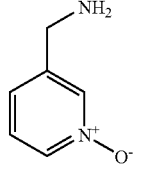 | 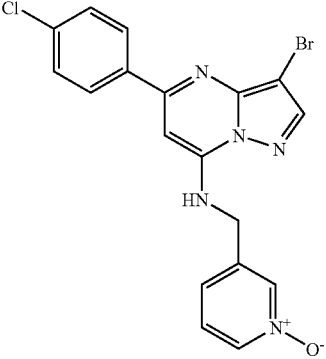 [SMILES: [O-][n+]1cccc(CNc2cc(-c3ccc(Cl)cc3)nc3c(Br)cnn23)c1] | MS: MH+ = 430 m.p. 242-244° C. |
| 51 | 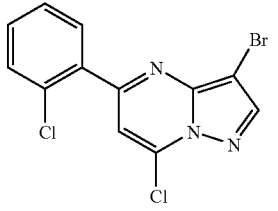 | 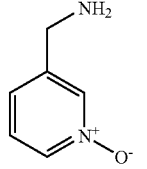 | 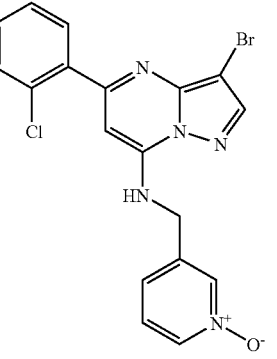 | MS: MH+ = 430 m.p. 218° C. |
| 52 | 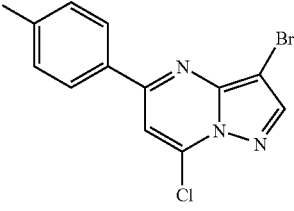 | 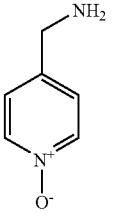 | 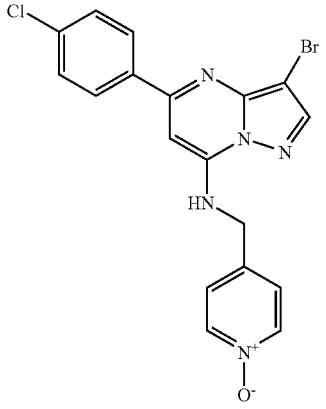 [SMILES: [O-][n+]1ccc(CNc2cc(-c3ccc(Cl)cc3)nc3c(Br)cnn23)cc1] | MS: MH+ = 430 m.p. 230-233° C. |
| 54 | 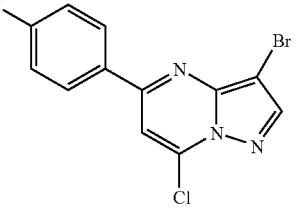 | 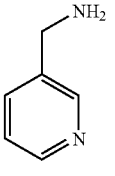 | 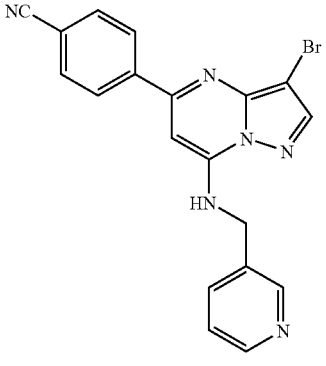 | MS: MH+ = 405 m.p. 185-188° C. |

TABLE 18-continued
| Ex. | Column 2 | Column 3 | Column 4 | Data |
|---|---|---|---|---|
| 55 | 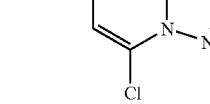 | 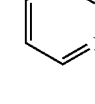 | 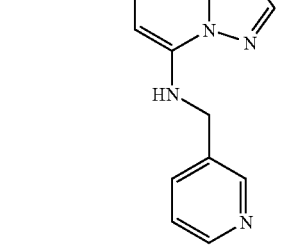 | MS: MH⁺ = 370 m.p. 229-232° C. |
| 56 | 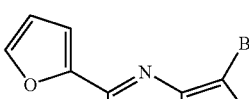 |  | 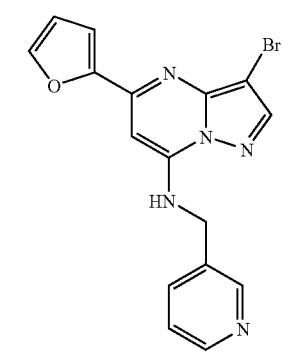 [SMILES: Brc1cnn2c(NCc3cccnc3)cc(-c3ccco3)nc12] | MS: MH⁺ = 370 m.p. 85-90° C. |
| 57 | 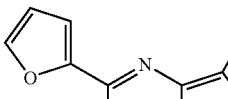 | 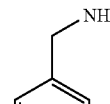 | 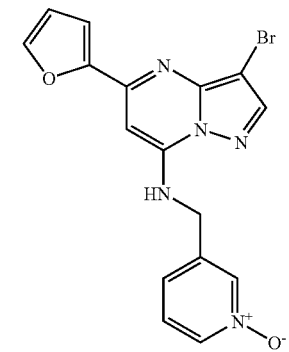 [SMILES: [O-][n+]1cccc(CNc2cc(-c3ccco3)nc3c(Br)cnn23)c1] | MS: MH⁺ = 386 m.p. 227-230° C. |
| 58 | 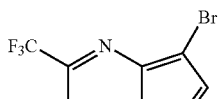 |  | 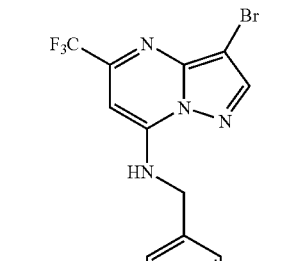 | MS: MH⁺ = 372 m.p. 212-215° C. |

TABLE 18-continued

| Ex. | Column 2 | Column 3 | Column 4 | Data |
|---|---|---|---|---|
| 59 | | | | MS: MH+ = 318 m.p. 169-171° C. |
| 60 | | | | MS: MH+ = 332 m.p. 170-173° C. |
| 61 | | | | MS: MH+ = 346 m.p. 156-159° C. |
| 62 | | | | MS: MH+ = 360 m.p. 114-116° C. |

TABLE 18-continued

| Ex. | Column 2 | Column 3 | Column 4 | Data |
|---|---|---|---|---|
| 63 | 3-bromo-5-ethyl-7-chloropyrazolo[1,5-a]pyrimidine | (pyridin-3-yl)methanamine N-oxide | 3-bromo-5-ethyl-N-((1-oxidopyridin-3-yl)methyl)pyrazolo[1,5-a]pyrimidin-7-amine | MS: MH$^+$ = 348<br>m.p. 197-200° C. |
| 64 | 3-bromo-5-phenyl-7-chloropyrazolo[1,5-a]pyrimidine | 5-(aminomethyl)pyridin-2-amine ·2HCl | 3-bromo-5-phenyl-N-((6-aminopyridin-3-yl)methyl)pyrazolo[1,5-a]pyrimidin-7-amine | 1. mp = 230-232<br>2. M + H = 396 |
| 65 | 3-bromo-5-cyclohexyl-7-chloropyrazolo[1,5-a]pyrimidine | 5-(aminomethyl)pyridin-2-amine ·2HCl | 3-bromo-5-cyclohexyl-N-((6-aminopyridin-3-yl)methyl)pyrazolo[1,5-a]pyrimidin-7-amine | 1. mp = 205-207<br>2. M + H = 402 |
| 66 | 3-bromo-5-(2-fluorophenyl)-7-chloropyrazolo[1,5-a]pyrimidine | 5-(aminomethyl)pyridin-2-amine ·2HCl | 3-bromo-5-(2-fluorophenyl)-N-((6-aminopyridin-3-yl)methyl)pyrazolo[1,5-a]pyrimidin-7-amine | 1. mp = 230-233<br>2. M + H = 414 |

TABLE 18-continued

| Ex. | Column 2 | Column 3 | Column 4 | Data |
|---|---|---|---|---|
| 67 | | •2HCl | | 1. mp = 191-193<br>2. M + H = 431 |
| 68 | | HCl• | | 1. mp = 235-237<br>2. M + H = 397 |
| 69 | | HCl• | | 1. mp = >250<br>2. M + H = 403 |

TABLE 18-continued

| Ex. | Column 2 | Column 3 | Column 4 | Data |
|---|---|---|---|---|
| 70 | | | | 1. mp = 230-232<br>2. M + H = 415 |
| 71 | | | | 1. mp = 235-238<br>2. M + H = 431 |
| 72 | | | | 1. mp = 186-188<br>2. M + H = 410 |

TABLE 18-continued
| Ex. | Column 2 | Column 3 | Column 4 | Data |
|---|---|---|---|---|
| 73 | 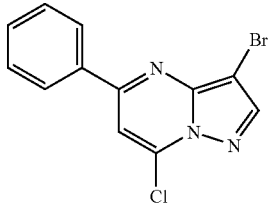 [SMILES: Clc1cc(-c2ccccc2)nc2c(Br)cnn12] | 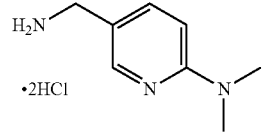 | 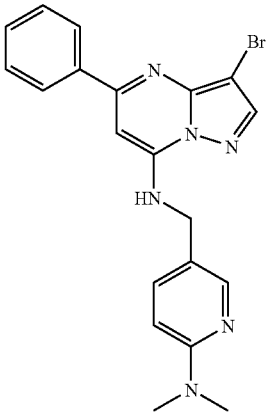 [SMILES: CN(C)c1ccc(CNc2cc(-c3ccccc3)nc3c(Br)cnn23)cn1] | 1. mp = 136-138<br>2. M + H = 424 |
| 74 | 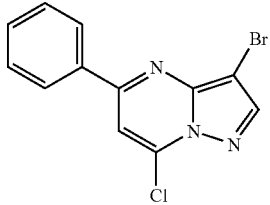 [SMILES: Clc1cc(-c2ccccc2)nc2c(Br)cnn12] | 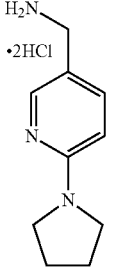 | 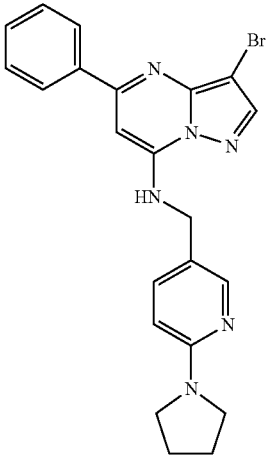 [SMILES: Brc1cnn2c(NCc3ccc(N4CCCC4)nc3)cc(-c3ccccc3)nc12] | 1. mp = 192-195<br>2. M + H = 450 |
| 75 | 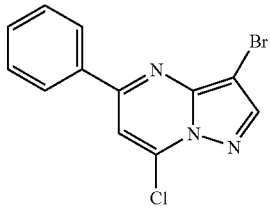 [SMILES: Clc1cc(-c2ccccc2)nc2c(Br)cnn12] | 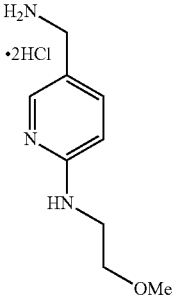 | 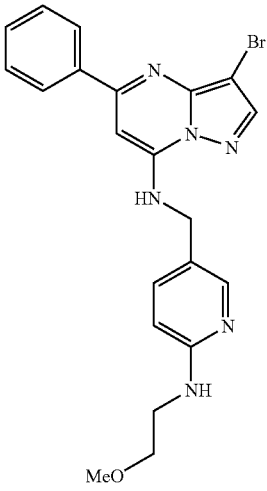 [SMILES: COCCNc1ccc(CNc2cc(-c3ccccc3)nc3c(Br)cnn23)cn1] | 1. mp = 88-90<br>2. M + H = 454 |

TABLE 18-continued

| Ex. | Column 2 | Column 3 | Column 4 | Data |
|---|---|---|---|---|
| 76 | | | | 1. mp = 230-232<br>2. M + H = 467 |
| 77 | | | | 1. mp = 131-133<br>2. M + H = 479 |
| 78 | | | | 1. mp = 85-88<br>2. M + H = 376 |

TABLE 18-continued

| Ex. | Column 2 | Column 3 | Column 4 | Data |
|---|---|---|---|---|
| 79 | 5-(2-fluorophenyl)-3-bromo-7-chloropyrazolo[1,5-a]pyrimidine | furan-3-ylmethanamine | 5-(2-fluorophenyl)-3-bromo-7-(furan-3-ylmethylamino)pyrazolo[1,5-a]pyrimidine | 1. mp = 131-133<br>2. M + H = 388 |
| 80 | 5-cyclohexyl-3-bromo-7-chloropyrazolo[1,5-a]pyrimidine | (2-aminothiazol-4-yl)methanamine ·2HCl | 5-phenyl-3-bromo-7-((2-aminothiazol-4-yl)methylamino)pyrazolo[1,5-a]pyrimidine | 1. mp = 206-208<br>2. M + H = 408 |
| 81 | 5-cyclohexyl-3-bromo-7-chloropyrazolo[1,5-a]pyrimidine | (2-(Boc-amino)pyridin-4-yl)methanamine HCl | 5-cyclohexyl-3-bromo-7-((2-(Boc-amino)pyridin-4-yl)methylamino)pyrazolo[1,5-a]pyrimidine | 1. mp = 108-110<br>2. M + H = 502 |
| 82 | 5-cyclohexyl-3-bromo-7-chloropyrazolo[1,5-a]pyrimidine | (2-aminopyridin-4-yl)methanamine ·2HCl | 5-cyclohexyl-3-bromo-7-((2-aminopyridin-4-yl)methylamino)pyrazolo[1,5-a]pyrimidine | 1. mp = 83-85<br>2. M + H = 402 |

TABLE 18-continued

| Ex. | Column 2 | Column 3 | Column 4 | Data |
| --- | --- | --- | --- | --- |
| 83 | 5-(2-fluorophenyl)-3-bromo-7-chloropyrazolo[1,5-a]pyrimidine | (2-aminopyridin-4-yl)methanamine ·2HCl | product | 1. mp = 220<br>2. M + H = 414 |
| 84 | 5-cyclohexyl-3-bromo-7-chloropyrazolo[1,5-a]pyrimidine | (1H-benzimidazol-5-yl)methanamine ·2HCl | product | 1. mp = 154-156<br>2. M + H = 426 |
| 85 | 5-(2-fluorophenyl)-3-bromo-7-chloropyrazolo[1,5-a]pyrimidine | (1H-benzimidazol-5-yl)methanamine ·2HCl | product | 1. mp = 152-153<br>2. M + H = 438 |
| 86 | 5-phenyl-3-bromo-7-chloropyrazolo[1,5-a]pyrimidine | (1H-benzimidazol-5-yl)methanamine ·2HCl | product | 1. mp = 159-161<br>2. M + H = 420 |

TABLE 18-continued

| Ex. | Column 2 | Column 3 | Column 4 | Data |
|---|---|---|---|---|
| 87 | | ·2HCl | | 1. mp = >220<br>2. M + H = 455 |
| 88 | | | | 1. mp = 223-225<br>2. M + H = 425 |
| 89 | | | | 1. mp = 199-201<br>2. M + H = 419 |

TABLE 18-continued

| Ex. | Column 2 | Column 3 | Column 4 | Data |
|---|---|---|---|---|
| 90 | | | | 1. mp = 184-186<br>2. M + H = 426 |
| 91 | | | | 1. mp = 196-198<br>2. M + H = 420 |
| 92 | | | | 1. mp = 156-159<br>2. M + H = 440 |

TABLE 18-continued

| Ex. | Column 2 | Column 3 | Column 4 | Data |
|---|---|---|---|---|
| 93 | | | | 1. mp = 173-176<br>2. M + H = 434 |
| 94 | | | | 1. mp = 173-175<br>2. M + H = 452 |
| 95 | | | | 1. mp = 174-176<br>2. M + H = 469 |

TABLE 18-continued

| Ex. | Column 2 | Column 3 | Column 4 | Data |
|---|---|---|---|---|
| 96 | | ·2HCl | | 1. mp = 230-234<br>2. M + H = 434 |
| 97 | | | | 1. mp = 191-193<br>2. M + H = 441 |
| 98 | | | | 1. mp = 202-205<br>2. M + H = 434 |

TABLE 18-continued

| Ex. | Column 2 | Column 3 | Column 4 | Data |
|---|---|---|---|---|
| 99 | | | | 1. mp = 209-212<br>2. M + H = 453 |
| 100 | | | | 1. mp = 219-221<br>2. M + H = 469 |
| 101 | | | | 1. mp = 64-66<br>2. M + H = 403 |

TABLE 18-continued

| Ex. | Column 2 | Column 3 | Column 4 | Data |
|---|---|---|---|---|
| 102 | | | | 1. mp = 168-170<br>2. M + H = 420 |
| 103 | | | | 1. mp = 213-216<br>2. M + H = 411 |
| 104 | | | | 1. mp = 98-100<br>2. M + H = 561 |

TABLE 18-continued
| Ex. | Column 2 | Column 3 | Column 4 | Data |
|---|---|---|---|---|
| 105 | 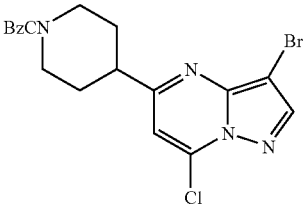 | 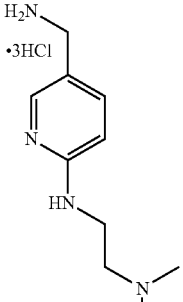 | 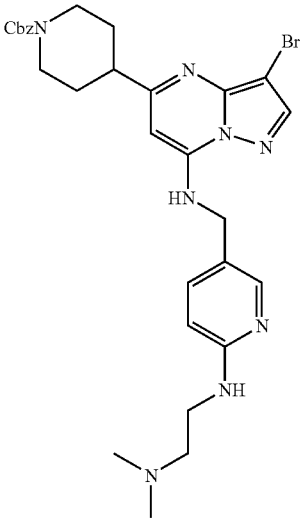 [SMILES: CN(C)CCNc1ccc(CNc2cc(C3CCN(C(=O)OCc4ccccc4)CC3)nc3c(Br)cnn23)cn1] | 1. mp = 70-72<br>2. M + H = 608 |
| 106 | 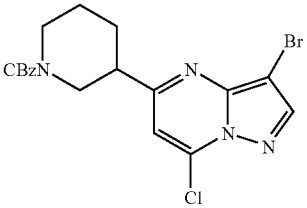 | 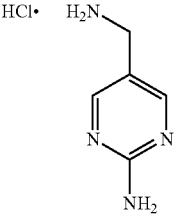 | 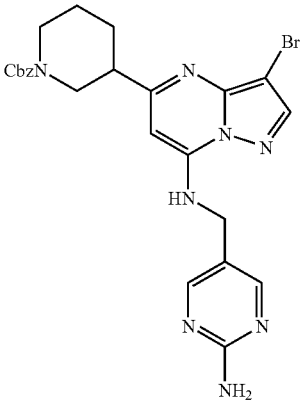 [SMILES: Nc1ncc(CNc2cc(C3CCCN(C(=O)OCc4ccccc4)C3)nc3c(Br)cnn23)cn1] | 1. mp = 168-170<br>2. M + H = 538 |
| 107 | 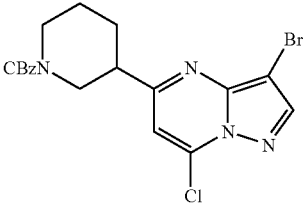 | 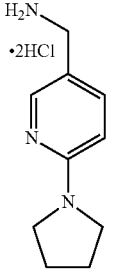 | 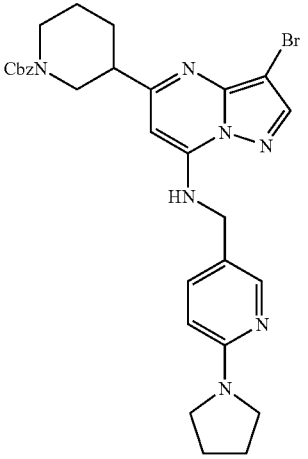 [SMILES: O=C(OCc1ccccc1)N1CCCC(c2cc(NCc3ccc(N4CCCC4)nc3)n3ncc(Br)c3n2)C1] | 1. mp = 189-191<br>2. M + H = 592 |

TABLE 18-continued

| Ex. | Column 2 | Column 3 | Column 4 | Data |
|---|---|---|---|---|
| 108 | | | | LCMS: MH$^+$ = 458; |
| 109 | | | | Yield = 89 LCMS: MH$^+$ = 418 m.p. = 131-132° C. |
| 110 | | | | Yield = 95% LCMS: MH$^+$ = 347 |
| 111 | | | | Yield = 91% 3H); LCMS: MH$^+$ = 484 |

TABLE 18-continued

| Ex. | Column 2 | Column 3 | Column 4 | Data |
|---|---|---|---|---|
| 112 | | | | Yield = 87% LCMS: MH+ = 427 |
| 113 | | | | Yield = 80% LCMS: MH+ = 427 |
| 114 | | | | Yield = 91% LCMS: MH+ = 378 |
| 115 | | | | Yield = 92%, 3H); LCMS: MH+ = 520 |

TABLE 18-continued
| Ex. | Column 2 | Column 3 | Column 4 | Data |
|---|---|---|---|---|
| 116 | 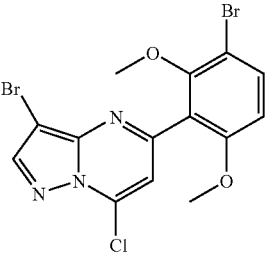 | 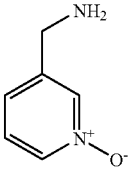 | 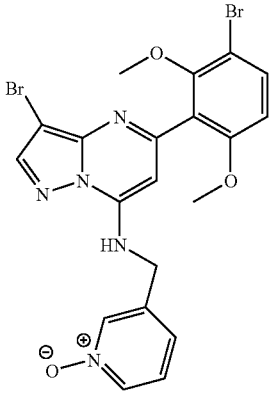 [SMILES: COc1ccc(Br)c(OC)c1-c1cc(NCc2ccc[n+]([O-])c2)n2ncc(Br)c2n1] | Yield = 98% LCMS: MH+ = 536 |
| 117 | 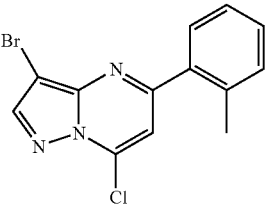 | 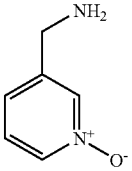 | 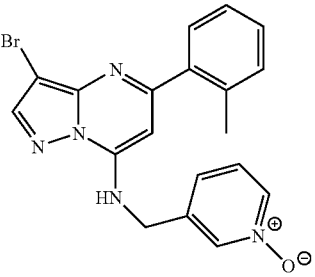 [SMILES: Cc1ccccc1-c1cc(NCc2ccc[n+]([O-])c2)n2ncc(Br)c2n1] | Yield = 82% LCMS: MH+ = 410 |
| 118 | 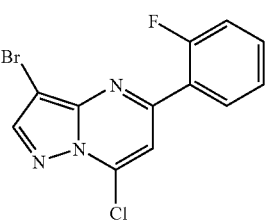 [SMILES: Fc1ccccc1-c1cc(Cl)n2ncc(Br)c2n1] |  | 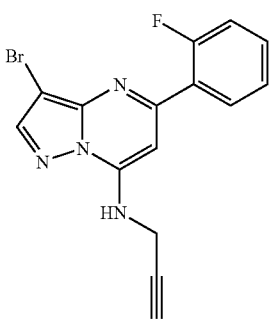 [SMILES: C#CCNc1cc(-c2ccccc2F)nc2c(Br)cnn12] | Yield = 95% LCMS: MH+ = 347 |
| 121 | 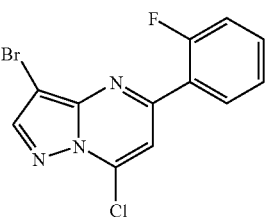 [SMILES: Fc1ccccc1-c1cc(Cl)n2ncc(Br)c2n1] | 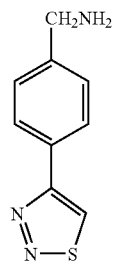 | 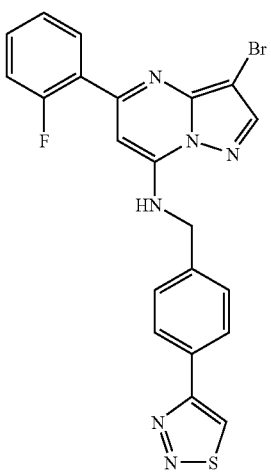 [SMILES: Fc1ccccc1-c1cc(NCc2ccc(-c3csnn3)cc2)n2ncc(Br)c2n1] | Yield = 65% LCMS: MH+ = 481.02 |

TABLE 18-continued

| Ex. | Column 2 | Column 3 | Column 4 | Data |
|---|---|---|---|---|
| 126 | | | | Yield = 71%<br>MH+ = 486 |
| 127 | | | | Yield = 71%<br>LCMS:<br>MH+ = 495.1 |
| 128 | | | | Yield = 55%<br>MH+ = 463 |

TABLE 18-continued

| Ex. | Column 2 | Column 3 | Column 4 | Data |
|---|---|---|---|---|
| 129 | 3-Br, 5-(2-F-phenyl), 7-Cl pyrazolo[1,5-a]pyrimidine | 4-(methoxycarbonyl)benzylamine·HCl | 5-(2-F-phenyl)-3-Br-7-[(4-COOMe-benzyl)amino]pyrazolo[1,5-a]pyrimidine | Yield = 77% LCMS: MH$^+$ = 455 |
| 130 | 3-Br, 5-(2-F-phenyl), 7-Cl pyrazolo[1,5-a]pyrimidine | glycine methyl ester·HCl | 5-(2-F-phenyl)-3-Br-7-[(CH$_2$COOMe)amino]pyrazolo[1,5-a]pyrimidine | $^1$H NMR (Yield = 75% LCMS: MH$^+$ = 379 |
| 131 | 3-Br, 5-(2-F-phenyl), 7-Cl pyrazolo[1,5-a]pyrimidine | β-alanine ethyl ester·HCl | 5-(2-F-phenyl)-3-Br-7-[(CH$_2$CH$_2$COOEt)amino]pyrazolo[1,5-a]pyrimidine | Yield = 75% LCMS: MH$^+$ = 407 |
| 132 | 3-Br, 5-(2-F-phenyl), 7-Cl pyrazolo[1,5-a]pyrimidine | 4-amino-butyric acid ethyl ester·HCl | 5-(2-F-phenyl)-3-Br-7-[(CH$_2$CH$_2$CH$_2$COOEt)amino]pyrazolo[1,5-a]pyrimidine | Yield = 75% LCMS: MH$^+$ = 421 |
| 133 | 3-Br, 5-(2-F-phenyl), 7-Cl pyrazolo[1,5-a]pyrimidine | 5-amino-valeric acid methyl ester·HCl | 5-(2-F-phenyl)-3-Br-7-[(CH$_2$CH$_2$CH$_2$CH$_2$COOMe)amino]pyrazolo[1,5-a]pyrimidine | Yield = 70% LCMS: MH$^+$ = 421 |

TABLE 18-continued

| Ex. | Column 2 | Column 3 | Column 4 | Data |
|---|---|---|---|---|
| 134 | 3-Br, 5-(2-F-phenyl), 7-Cl pyrazolopyrimidine | 4-(methylsulfonyl)benzylamine·HCl | 3-Br-5-(2-F-phenyl)-7-[(4-methylsulfonylbenzyl)amino]pyrazolopyrimidine | Yield = 78%<br>LCMS: MH$^+$ = 475 |
| 135 | 3-Br, 5-(2-F-phenyl), 7-Cl pyrazolopyrimidine | 4-sulfamoylbenzylamine·HCl | 3-Br-5-(2-F-phenyl)-7-[(4-sulfamoylbenzyl)amino]pyrazolopyrimidine | Yield = 75%<br>LCMS: MH$^+$ = 476 |
| 136 | 3-Br, 5-(2-F-phenyl), 7-Cl pyrazolopyrimidine | (2,3-dihydro-1,4-benzodioxin-6-yl)methanamine·HCl | 3-Br-5-(2-F-phenyl)-7-[((2,3-dihydrobenzodioxin-6-yl)methyl)amino]pyrazolopyrimidine | Yield = 65%<br>LCMS: MH$^+$ = 455 |
| 137 | 3-Br, 5-(2-F-phenyl), 7-Cl pyrazolopyrimidine | (6-fluoro-4H-benzo[d][1,3]dioxin-8-yl)methanamine | 3-Br-5-(2-F-phenyl)-7-[((6-fluoro-4H-benzo[d][1,3]dioxin-8-yl)methyl)amino]pyrazolopyrimidine | Yield = 55%<br>LCMS: MH$^+$ = 473) |

TABLE 18-continued

| Ex. | Column 2 | Column 3 | Column 4 | Data |
|---|---|---|---|---|
| 138 | | | | Yield = 60%<br>LCMS: MH+ = 439 |
| 139 | | | | Yield = 65%<br>LCMS: MH+ = 441 |
| 140 | | | | Yield = 80%<br>LCMS: MH+ = 432 |
| 141 | | | | Yield = 60%<br>LCMS: MH+ = 429 |

TABLE 18-continued

| Ex. | Column 2 | Column 3 | Column 4 | Data |
| --- | --- | --- | --- | --- |
| 142 | | | | LCMS: MH⁺ = 330; mp = 109-111° C. |
| 143 | | | | LCMS: MH⁺ = 346; mp = 186-188° C. |
| 144 | | | | LCMS: MH⁺ = 384; mp = 148-150° C. |
| 145 | | | | LCMS: MH⁺ = 400; mp = 186-188° C. |

TABLE 18-continued

| Ex. | Column 2 | Column 3 | Column 4 | Data |
|---|---|---|---|---|
| 146 | | | | LCMS: M2H⁺ = 390; mp = 192-194° C. |
| 147 | | | | LCMS: M⁺ = 404; mp = 220-222° C. |
| 148 | | | | LCMS: MH⁺ = 369; mp > 230° C. |
| 149 | | | | LCMS: MH⁺ = 364; mp = 186-188° C. |

TABLE 18-continued

| Ex. | Column 2 | Column 3 | Column 4 | Data |
|---|---|---|---|---|
| 150 | 5-isopropyl-7-chloro-3-ethyl-pyrazolo[1,5-a]pyrimidine | (pyridin-3-yl N-oxide)methanamine | 5-isopropyl-3-ethyl-N-((pyridin-3-yl N-oxide)methyl)pyrazolo[1,5-a]pyrimidin-7-amine | LCMS: MH$^+$ = 312; mp = 138-140° C. |
| 151 | 5-(2-chlorophenyl)-7-chloro-3-ethyl-pyrazolo[1,5-a]pyrimidine | (pyridin-3-yl N-oxide)methanamine | 5-(2-chlorophenyl)-3-ethyl-N-((pyridin-3-yl N-oxide)methyl)pyrazolo[1,5-a]pyrimidin-7-amine | LCMS: M$^+$ = 380; mp = 172-174° C. |
| 152 | 5-cyclohexyl-7-chloro-3-ethyl-pyrazolo[1,5-a]pyrimidine | (pyridin-3-yl N-oxide)methanamine | 5-cyclohexyl-3-ethyl-N-((pyridin-3-yl N-oxide)methyl)pyrazolo[1,5-a]pyrimidin-7-amine | LCMS: MH$^+$ = 352; mp = 201-203° C. |
| 153 | 5-phenyl-7-chloro-3-methoxy-pyrazolo[1,5-a]pyrimidine | (pyridin-3-yl N-oxide)methanamine | 5-phenyl-3-methoxy-N-((pyridin-3-yl N-oxide)methyl)pyrazolo[1,5-a]pyrimidin-7-amine | LCMS: MH$^+$ = 348; mp = 166-168° C. |

TABLE 18-continued

| Ex. | Column 2 | Column 3 | Column 4 | Data |
|---|---|---|---|---|
| 154 | | | | LCMS: M2H+ = 531; mp = 78-80° C. |
| 155 | | | | LCMS: M2H+ = 474; mp = 161-163° C. |
| 156 | | | | LCMS: M+ = 444; mp = 48-51° C. |

TABLE 18-continued

| Ex. | Column 2 | Column 3 | Column 4 | Data |
|---|---|---|---|---|
| 157 | | | | MH+ = 542.1 |
| 158 | | | | MH+ = 520.1 |
| 159 | | | | MH+ = 542.1 |
| 160 | | | | MH+ = 480.1 |

TABLE 18-continued
| Ex. | Column 2 | Column 3 | Column 4 | Data |
|---|---|---|---|---|
| 161 | 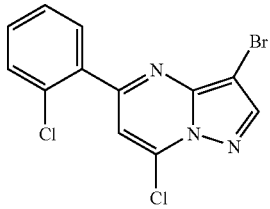 | 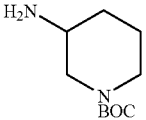 | 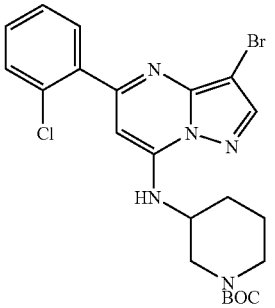 | MH$^+$ = 506.1 |
| 162 | 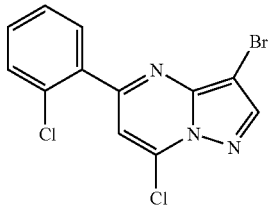 | 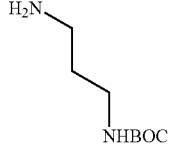 | 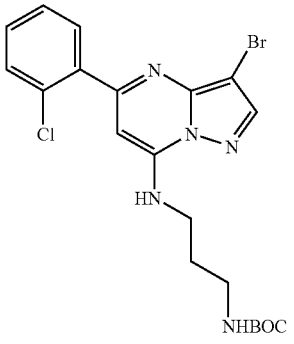 | MH$^+$ = 480.1 |
| 163 | 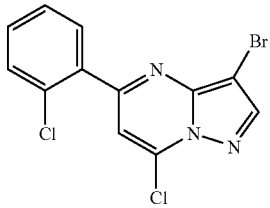 | 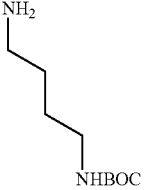 | 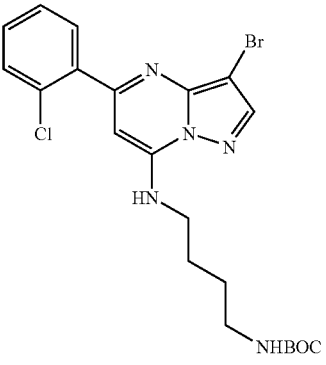 | MH$^+$ = 494.1 |
| 164 | 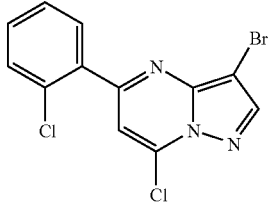 | 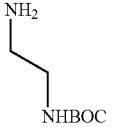 | 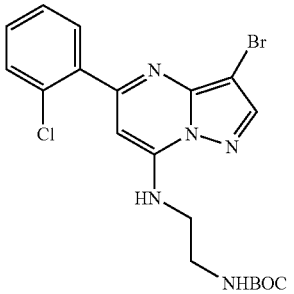 | MH$^+$ = 466.1 |

TABLE 18-continued

| Ex. | Column 2 | Column 3 | Column 4 | Data |
|---|---|---|---|---|
| 165 | | | | MH+ = 494.1 |
| 166 | | | | MH+ = 508.1 |
| 167 | | | | MH+ = 520.1 |
| 168 | | | | MH+ = 528.1 |

TABLE 18-continued

| Ex. | Column 2 | Column 3 | Column 4 | Data |
|---|---|---|---|---|
| 169 | | | | MH+ = 520.1 |
| 170 | | | | MH+ = 528.1 |
| 171 | | | | LCMS: MH+ = 474; |
| 172 | | | | LCMS: MH+ = 437; |

TABLE 18-continued
| Ex. | Column 2 | Column 3 | Column 4 | Data |
|---|---|---|---|---|
| 173 | 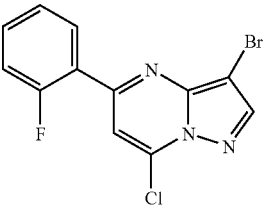 | 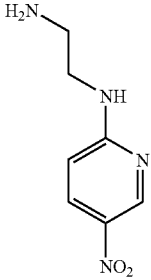 | 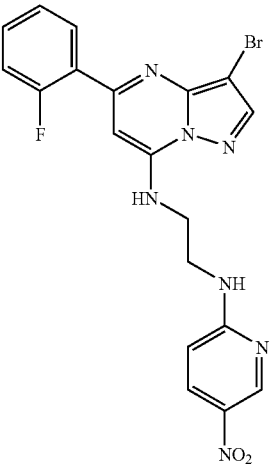 | LCMS: MH+ = 472; |
| 174 | 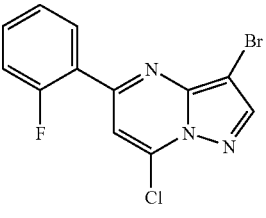 | 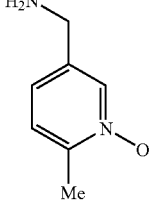 | 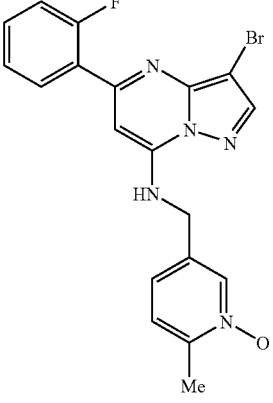 | LCMS: MH+ = 428.1 |
| 175 | 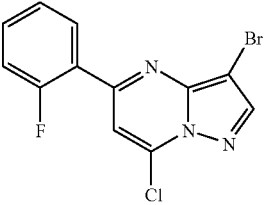 | 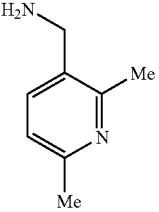 | 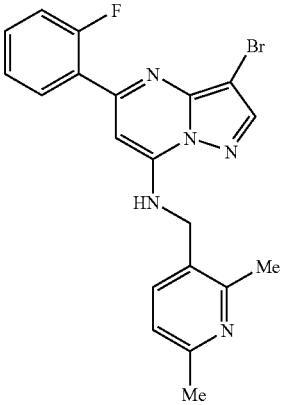 [SMILES: Cc1ccc(CNc2cc(-c3ccccc3F)nc3c(Br)cnn23)c(C)n1] | LCMS: MH+ = 426.2 |

TABLE 18-continued
| Ex. | Column 2 | Column 3 | Column 4 | Data |
|---|---|---|---|---|
| 176 | 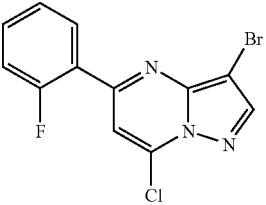 | 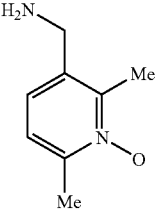 | 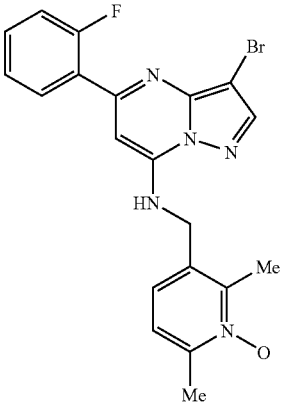 | LCMS: MH$^+$ = 442.0 |
| 177 | 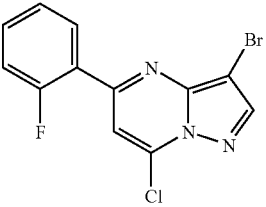 | 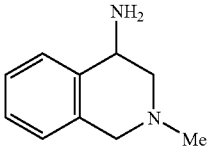 [SMILES: CN1Cc2ccccc2C(N)C1] | 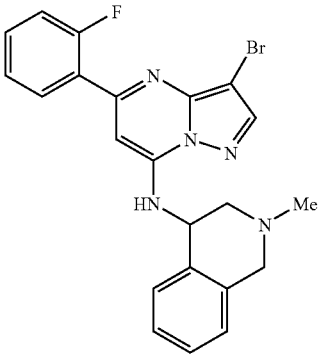 [SMILES: CN1Cc2ccccc2C(Nc2cc(-c3ccccc3F)nc3c(Br)cnn23)C1] | LCMS: MH$^+$ = 452.0 |
| 178 | 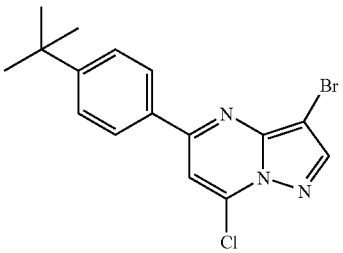 [SMILES: CC(C)(C)c1ccc(-c2cc(Cl)n3ncc(Br)c3n2)cc1] | 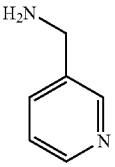 | 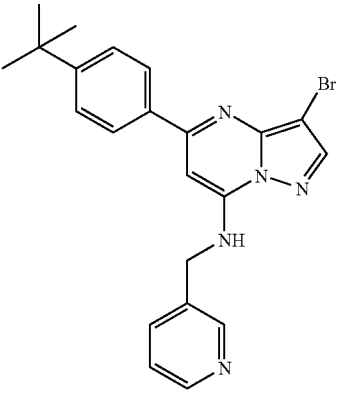 [SMILES: CC(C)(C)c1ccc(-c2cc(NCc3cccnc3)n3ncc(Br)c3n2)cc1] | Yield = 90 MH$^+$ = 436 m. pt. = 89.1° C. |
| 179 | 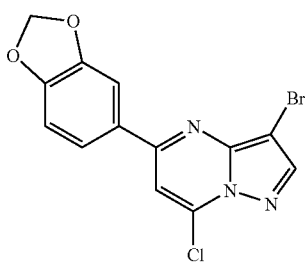 [SMILES: Clc1cc(-c2ccc3c(c2)OCO3)nc2c(Br)cnn12] | 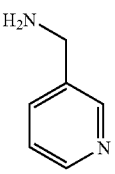 | 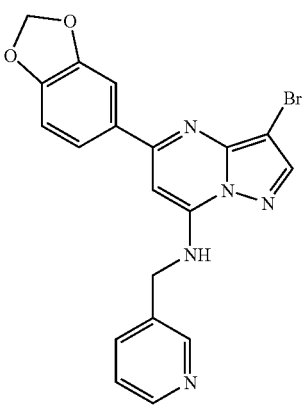 [SMILES: Brc1cnn2c(NCc3cccnc3)cc(-c3ccc4c(c3)OCO4)nc12] | MH$^+$ = 424 m. pt. = 188.2° C. |

TABLE 18-continued

| Ex. | Column 2 | Column 3 | Column 4 | Data |
|---|---|---|---|---|
| 180 | 5-(2,4-dichlorophenyl)-3-bromo-7-chloro-pyrazolo[1,5-a]pyrimidine | 3-(aminomethyl)pyridine | 5-(2,4-dichlorophenyl)-3-bromo-7-[(pyridin-3-ylmethyl)amino]pyrazolo[1,5-a]pyrimidine | MH$^+$ = 448<br>m. pt. = 211.3° C. |
| 181 | 5-(2,4-dichlorophenyl)-3-bromo-7-chloro-pyrazolo[1,5-a]pyrimidine | 3-(aminomethyl)pyridine N-oxide | 5-(2,4-dichlorophenyl)-3-bromo-7-[(pyridin-3-ylmethyl)amino]pyrazolo[1,5-a]pyrimidine N-oxide | Yield = quant.<br>MH$^+$ = 464 |
| 182 | 5-(pyrazin-2-yl)-3-bromo-7-chloro-pyrazolo[1,5-a]pyrimidine | 3-(aminomethyl)pyridine | 5-(pyrazin-2-yl)-3-bromo-7-[(pyridin-3-ylmethyl)amino]pyrazolo[1,5-a]pyrimidine | MH$^+$ = 382<br>m. pt. = 185.8° C. |
| 183 | 5-(thiophen-2-yl)-3-bromo-7-chloro-pyrazolo[1,5-a]pyrimidine | | 5-(thiophen-2-yl)-3-bromo-7-[(pyridin-3-ylmethyl)amino]pyrazolo[1,5-a]pyrimidine | MH$^+$ = 387<br>m. pt. = 181-182° C. |

TABLE 18-continued

| Ex. | Column 2 | Column 3 | Column 4 | Data |
| --- | --- | --- | --- | --- |
| 184 | | | | MH$^+$ = 453 |
| 185 | | | | MH$^+$ = 401<br>m. pt. = 178.3° C. |
| 186 | | | | MH$^+$ = 402 |
| 187 | | | | Yield = 91<br>MH$^+$ = 386<br>m. pt. = 148.3° C. |

TABLE 18-continued

| Ex. | Column 2 | Column 3 | Column 4 | Data |
|---|---|---|---|---|
| 188 | | | | Yield = 65<br>MH⁺ = 402<br>m. pt. = 174.5° C. |
| 189 | | | | MH⁺ = 379<br>m. pt. = 82-83° C. |
| 190 | | | | MH⁺ = 379<br>m. pt. = 50.7° C. |
| 191 | | | | Yield = 89<br>MH⁺ = 469<br>m. pt. = 186.7° C. |

TABLE 18-continued

| Ex. | Column 2 | Column 3 | Column 4 | Data |
| --- | --- | --- | --- | --- |
| 192 | | | | Yield = 93<br>MH+ = 410<br>m. pt. = 86.7° C. |
| 193 | | | | Yield = 76<br>MH+ = 333<br>m. pt. = 120.3° C. |
| 194 | | | | Yield = 86<br>MH+ = 353<br>m. pt. = 188.9° C. |
| 195 | | | | Yield = 11%<br>LCMS: 374<br>MH+ = 390 |

TABLE 18-continued

| Ex. | Column 2 | Column 3 | Column 4 | Data |
|---|---|---|---|---|
| 196 | | | | Yield = 88%<br>LCMS: 374<br>MH+ = 346 |
| 197 | | | | Yield = 88%<br>LCMS: 374<br>MH+ = 346 |
| 198 | | | | Yield =<br>MH+ = 400<br>m. pt. = 111.5-112.2° C. |
| 199 | | | | MH+ = 416 |

TABLE 18-continued

| Ex. | Column 2 | Column 3 | Column 4 | Data |
|---|---|---|---|---|
| 200 | | | | MH$^+$ = 415 |
| 201 | | | | MH$^+$ = 398 m.p. = 156.5° C. |
| 202 | | | | MH$^+$ = 414 m.p. = 89.5° C. |
| 203 | | | | MH$^+$ = 413 |

TABLE 18-continued

| Ex. | Column 2 | Column 3 | Column 4 | Data |
|---|---|---|---|---|
| 204 | | | | Yield = 86<br>MH+ = 521<br>m.p. = 79.9° C. |
| 204.10 | | | | |
| 204.11 | | | | Yield = 87<br>MH+ = 521<br>m.p. = 128.6° C. |
| 205 | | | | Yield = 99<br>MH+ = 537<br>m.p. = 83.5° C. |

TABLE 18-continued

| Ex. | Column 2 | Column 3 | Column 4 | Data |
|---|---|---|---|---|
| 206 | Cbz-piperidine-pyrazolopyrimidine (Br, Cl) | 4-(methylsulfonyl)benzylamine | Coupled product | Yield = 94<br>MH$^+$ = 598<br>m.p. = 110.8° C. |
| 207 | Cbz-piperidine-pyrazolopyrimidine (Br, Cl) | 4-cyanobenzylamine | Coupled product | Yield = quant.<br>MH$^+$ = 545 |
| 208 | Cbz-piperidine-pyrazolopyrimidine (Br, Cl) | propargylamine | Coupled product | Yield = 96<br>MH$^+$ = 468<br>m.p. = 69.2° C. |
| 209 | Cbz-piperidine-pyrazolopyrimidine (Br, Cl) | 4-sulfamoylbenzylamine | Coupled product | MH$^+$ = 498<br>m.p. = 226.5° C. |

TABLE 18-continued

| Ex. | Column 2 | Column 3 | Column 4 | Data |
|---|---|---|---|---|
| 210 | Cbz-piperidine-pyrazolopyrimidine with Br and Cl | 4-aminomethylbenzoic acid (NH$_2$-CH$_2$-C$_6$H$_4$-CO$_2$H) | Cbz-piperidine-pyrazolopyrimidine with Br and NH-CH$_2$-C$_6$H$_4$-CO$_2$H | MH$^+$ = 564<br>m.p. = 174.2° C. |

Additional data for select examples given below.

Example 23

$^1$H NMR (CD$_3$OD) δ 8.63 (d, J=5.7 Hz, 2H), 8.18 (s, 1H), 7.81 (dd, J=8.1 Hz, 2.1 Hz, 1H), 7.58 (d, J=6.0 Hz, 2H), 7.48 (m, 1H), 7.15-7.10 (m, 2H), 6.50 (s, 1H), 4.86 (s, 2H), 3.70 (s, 3H)

Example 24

$^1$H NMR (CDCl$_3$) δ 8.82 (s, 1H), 8.73 (d, J=4.2 Hz, 1H), 8.11 (s, 1H), 8.06 (dd, J=7.8 Hz, 1.8 Hz, 1H), 7.91 (d, J=8.1 Hz, 1H), 7.53-7.47 (m, 2H), 7.20 (m, 1H), 7.08 (d, J=8.1 Hz, 1H), 6.75 (s, 1H), 4.81 (d, J=4.5 Hz, 2H), 3.86 (s, 3H)

Example 25

$^1$H NMR (CDCl$_3$) δ 8.75 (d, J=5.7 Hz, 2H), 8.12 (s, 1H), 7.81 (d, J=2.1 Hz, 1H), 7.53 (dd, J=8.4, 2.1 Hz, 1H), 7.45 (d, J=6.0 Hz, 2H), 6.96 (t, J=6.0 Hz, 2H), 6.33 (s, 1H), 4.85 (d, J=6.0 Hz, 2H), 4.09 (s, 3H), 4.03 (s, 3H)

Example 26

$^1$H NMR (CDCl$_3$) δ 8.82 (s, 1H), 8.72 (s, 1H), 8.09 (m, 1H), 7.87-7.83 (m, 2H), 7.60 (m, 1H), 7.45 (m, 1H), 7.03 (d, J=8.4 Hz, 1H), 6.87 (s, 1H), 6.43 (s, 1H), 4.83 (d, J=4.5 Hz, 2H), 4.11 (s, 3H), 4.04 (s, 3H)

Example 27

$^1$H NMR (CDCl$_3$) δ 8.75 (d, J=4.5 Hz, 2H), 8.19 (s, 1H), 7.63 (d, J=7.8 Hz, 2H), 7.44-7.40 (m, 3H), 7.07 (m, 1H), 6.26 (s, 1H), 4.83 (d, J=5.1 Hz, 2H)

Example 28

$^1$H NMR (CDCl$_3$) δ 8.86 (s, 1H), 8.74 (m, 1H), 8.17 (s, 1H), 7.97 (m, 1H), 7.66-7.63 (m, 2H), 7.62 (m, 1H), 7.41 (m, 1H), 7.07 (m, 1H), 6.35 (s, 1H), 4.87 (d, J=6.0 Hz, 2H)

Example 30

$^1$H NMR (CDCl$_3$) δ 8.16 (s, 1H), 7.66-7.62 (m, 2H), 7.41 (m, 1H), 7.33-7.22 (m, 3H), 6.96 (t, J=6.0 Hz, 1H), 6.33 (s, 1H), 4.73 (d, J=6.0 Hz, 2H)

Example 31

$^1$H NMR (CDCl$_3$) δ 8.13 (s, 1H), 7.66 (d, J=7.8 Hz, 2H), 7.45-7.40 (m, 2H), 7.10-7.04 (m, 2H), 6.93 (t, J=6.6 Hz, 1H), 6.60 (s, 1H), 4.84 (d, J=6.6 Hz, 2H)

Example 32

$^1$H NMR (CDCl$_3$) δ 8.16 (s, 1H), 7.66-7.62 (m, 2H), 7.57-7.55 (m, 2H), 7.41 (t, J=7.8 Hz, 1H), 7.31 (dd, J=7.8, 1.8 Hz, 1H), 6.99 (t, J=6.0 Hz, 1H), 6.32 (s, 1H), 4.73 (d, J=6.0 Hz, 2H)

Example 40

$^1$H NMR (CDCl$_3$) δ 8.01 (s, 1H), 7.31-7.24 (d, J=8.2 Hz, 1H), 6.72-6.64 (br t, J=5.4 Hz, 1H), 6.62-6.52 (m, 2H), 6.05-6.01 (s, 1H), 5.56-4.64 (d, J=6.0 Hz, 2H), 4.03-3.93 (s, 3H), 3.94-3.86 (s, 3H), 2.79-2.70 (d, J=8.1 Hz, 2H), 2.02-1.66 (m, 6H), 1.43-1.22 (m, 3H), 1.20-1.02 (m, 2H)

Example 45

$^1$H NMR (CDCl$_3$) δ 8.73 (d, 2H), 8.54 (s, 1H), 7.41 (d, 2H), 7.02 (br, 1H), 5.90 (s, 1H), 4.80 (s, 2H), 4.48 (q, 2H), 2.75 (s, 2H), 1.50 (t, 2H), 1.06 (s, 9H);

Example 46

$^1$H NMR (CDCl$_3$) δ 8.79 (s, 1H), 8.72 (d, 1H), 8.14 (s, 1H), 7.84 (d, 1H), 7.54-7.33 (m, 4H), 6.97 (t, 1H), 6.18 (s, 1H), 4.79 (d, 2H), 2.47 (s, 3H)

Example 108

$^1$H NMR (CDCl$_3$) δ 8.79 (s, 1H), 8.72 (d, J=3.0 Hz, 1H), 8.16 (s, 1H), 7.84 (d, J=7.8 Hz, 1H), 7.74 (d, J=7.5 Hz, 2H), 7.55-7.35 (m, 3H), 6.92 (t, J=6.3 Hz, 1H), 6.42 (s, 1H), 4.81 (d, J=6.3 Hz, 2H)

Example 110

¹H NMR (CDCl₃) δ 8.18 (t, 1H), 8.03 (s, 1H), 7.44 (m, 1H), 7.30 (t, 1H), 7.17 (q, 1H), 6.66 (s, 1H), 6.56 (br, 1H), 4.28 (d, 2H), 2.38 (s, 1H)

Example 111

¹H NMR (CDCl₃) δ 8.72 (br, 1H), 8.59 (d, 1H), 8.11 (t, 1H), 8.06 (s, 1H), 7.73 (d, 1H), 7.44 (d, 1H), 7.42-7.21 (m, 3H), 7.07 (q, 1H), 6.39 (d, 1H), 5.21 (q, 1H), 4.16 (q, 2H), 3.08 (d, 2H), 1.22 (t, 3H)

Example 112

¹H NMR (CDCl₃) δ 8.22 (t, 1H), 8.15 (s, 1H), 7.51-7.33 (m, 7H), 7.21 (q, 1H), 6.82 (d, 1H), 6.51 (s, 1H), 4.68 (q, 1H), 2.18 (m, 2H), 1.17 (t, 3H)

Example 113

¹H NMR (CDCl₃) δ 8.22 (t, 1H), 8.14 (s, 1H), 7.51-7.33 (m, 7H), 7.21 (q, 1H), 6.82 (d, 1H), 6.51 (s, 1H), 4.68 (q, 1H), 2.18 (m, 2H), 1.17 (t, 3H)

Example 114

¹H NMR (CDCl₃) δ 8.81 (s, 1H), 8.75 (d, 1H), 8.21 (s, 1H), 7.84 (d, 1H), 7.47 (q, 1H), 6.96 (s, 1H), 6.94 (t, 1H), 4.85 (d, 2H), 4.60 (q, 2H), 1.58 (t, 3H)

Example 115

¹H NMR (CDCl₃) δ 8.77 (s, 1H), 8.72 (d, 1H), 8.14 (s, 1H), 7.83 (d, 1H), 7.65 (d, 1H), 7.44 (q, 1H), 7.80 (t, 1H), 7.6 (d, 1H), 6.18 (s, 1H), 4.75 (d, 2H), 3.91 (s, 3H), 3.81 (s, 3H)

Example 116

¹H NMR (CDCl₃) δ 8.67 (s, 1H), 8.55 (d, 1H), 8.50 (s, 1H), 7.92 (d, 1H), 7.90 (d, 1H), 7.78 (t, 1H), 7.10 (d, 1H), 6.97 (s, 1H), 5.11 (s, 2H), 3.77 (s, 6H)

Example 117

¹H NMR (CDCl₃) δ 8.38 (s, 1H), 8.30 (d, 1H), 8.17 (s, 1H), 7.52-7.37 (m, 6H), 6.97 (t, 1H), 6.13 (s, 1H), 4.77 (d, 2H), 2.50 (s, 3H)

Example 118

¹H NMR (CDCl₃) δ 8.18 (t, 1H), 8.03 (s, 1H), 7.44 (m, 1H), 7.30 (t, 1H), 7.17 (q, 1H), 6.66 (s, 1H), 6.56 (br, 1H), 4.28 (d, 2H), 2.38 (s, 1H);

Example 121

¹H NMR (CDCl₃) δ 8.6 (S, 1H), 8.15 (dt, 1H), 8.1 (s, 1H), 8.0 (d, 2H), 7.5 (d, 2H), 7.4 (dd, 1H), 7.2 (d, 1H), 7.15 (dd, 1H), 6.8 (t, 1H), 6.6 (s, 1H), 4.75 (d, 2H).

Example 126

¹H NMR (CDCl₃) δ 8.15 (dt, 1H), 8.0 (s, 1H), 7.5 (d, 1H), 7.42-7.35 (m, 2H), 7.3-7.2 (m, 2H), 7.15 (dd, 1H), 7.1 (dd, 1H), 7.0 (t, 1H), 6.6 (s, 1H), 4.8 (d, 2H).

Example 127

¹H NMR (CDCl₃) δ 8.2 (dt, 1H), 8.0 (s, 1H), 7.4 (dd, 1H), 7.3-7.25 (m, 3H), 7.1 (dd, 1H), 6.9-6.85 (m, 2H), 6.7 (t, 1H), 6.6 (s, 1H), 4.6 (d, 2H), 3.2 (m, 4H), 2.6 (m, 4H), 2.3 (s, 3H)

Example 128

¹H NMR (CDCl₃) δ 8.15 (dt, 1H), 8.1 (s, 1H), 8.0 (d, 2H), 7.5 (d, 2H), 7.4 (m, 2H), 7.25 (d, 1H), 7.2 (s, 1H), 7.15 (dd, 1H), 7.0 (s, 1H), 6.8 (t, 1H), 6.6 (s, 1H), 4.75 (d, 2H).

Example 129

¹H NMR (CDCl₃) δ 8.15 (dt, 1H), 8.05 (s, 1H), 8.0 (d, 2H), 7.5 (d, 2H), 7.4 (m, 1H), 7.3 (dd, 1H), 7.15 (dd, 1H), 6.9 (t, 1H), 6.5 (s, 1H), 4.75 (d, 2H), 3.85 (s, 3H)

Example 130

¹H NMR (CDCl₃) δ 8.2 (dt, 1H), 8.0 (s, 1H), 7.4 (dd, 1H), 7.3 (dd, 1H), 7.15 (dd, 1H), 6.8 (t, 1H), 6.4 (s, 1H), 4.2 (d, 2H), 3.8 (s, 3H).

Example 131

¹H NMR (CDCl₃) δ 8.2 (dt, 1H), 8.0 (s, 1H), 7.4-7.15 (m, 3H), 6.7 (t, 1H), 4.2 (q, 2H), 3.8 (dt, 2H), 2.8 (t, 2H), 1.2 (t, 3H)

Example 132

¹H NMR (CDCl₃) δ 8.2 (dt, 1H), 8.0 (s, 1H), 7.4-7.15 (m, 3H), 6.7 (t, 1H), 4.2 (q, 2H), 3.8 (dt, 2H), 2.8 (t, 2H), 2.05 (m, 2H) 1.2 (t, 3H)

Example 133

¹H NMR (CDCl₃) δ 8.15 (dt, 1H), 8.0 (s, 1H), 7.4 (m, 1H), 7.3 (dd 1H), 7.2 (dd, 1H), 6.5 (s, 1H), 6.4 (t, 1H), 3.7 (s, 3H), 3.5 (dd, 2H), 2.4 (t, 2H), 1.8 (m, 4H)

Example 134

¹H NMR (CDCl₃) δ 8.15 (dt, 1H), 8.0 (s, 1H), 7.95 (d, 2H), 7.6 (d, 2H), 7.4 (m, 1H), 7.25 (dd, 1H), 7.1 (dd, 1H), 6.9 (t, 1H), 6.5 (s, 1H), 4.8 (d, 2H), 3.0 (s, 3H)

Example 135

¹H NMR (DMSO d6) δ 9.1 (bs, 2H), 8.4 (s, 1H), 8.0 (t, 1H), 7.85 (d, 2H), 7.7 (d, 2H), 7.6 (m, 1H), 7.4 (m, 2H), 6.6 (s, 1H), 4.8 (bs, 2H)

Example 136

¹H NMR (CDCl₃) δ 8.2 (dt, 1H), 8.0 (s, 1H), 7.4 (m, 1H), 7.25 (dd, 1H), 7.15 (dd, 1H), 6.9 (m, 3H), 6.7 (t, 1H), 6.5 (s, 1H), 4.5 (d, 2H), 4.2 (s, 4H)

Example 137

¹H NMR (CDCl₃) δ 8.2 (dt, 1H), 8.0 (s, 1H), 7.4 (m, 1H), 7.3 (dd, 1H), 7.2 (dd, 1H), 6.9 (dd, 1H), 6.8 (t, 1H), 6.7 (m, 1H), 6.6 (s, 1H), 5.3 (s, 2H), 4.85 (s, 2H), 4.6 (d, 2H).

Example 138

¹H NMR (CDCl₃) δ 8.2 (dt, 1H), 8.0 (s, 1H), 7.9 (d, 1H), 7.8 (d, 1H), 7.4 (m, 2H), 7.3 (dd, 1H), 7.1 (dd, 1H), 6.9 (t, 1H), 6.6 (s, 1H), 4.8 (d, 2H)

Example 139

¹H NMR (CDCl₃) δ 8.2 (dt, 1H), 8.0 (s, 1H), 7.4 (m, 1H), 7.3 (m, 2H), 7.2 (dd, 1H), 7.1 (dd, 1H), 6.8 (d, 1H), 6.7 (t, 1H), 6.6 (s, 1H), 4.6 (m, 4H), 3.2 (t, 2H)

Example 140

¹H NMR (CDCl₃) δ 8.45 (s, 1H), 8.2 (dt, 1H), 8.0 (s, 1H), 7.7 (dd, 1H), 7.4-7.3 (m, 3H), 7.15 (dd, 1H), 6.8 (t, 1H), 6.6 (s, 1H), 4.7 (d, 2H)

Example 141

¹H NMR (CDCl₃) δ 8.2 (dt, 1H), 8.0 (s, 1H), 7.45-7.1 (m, 7H), 6.6 (s, 1H), 4.4 (dt, 2H), 2.6 (t, 2H), 1.8 (m, 2H), 1.4 (m, 2H)

Example 171

¹H NMR (CD₃OD) δ 8.41 (s, 1H), 8.25 (d, J=6.3 Hz, 1H), 8.15 (s, 1H), 7.67 (d, J=7.8 Hz, 2H), 7.55-7.48 (m, 2H), 7.45 (dd, J=7.5, 1.2 Hz, 1H), 7.34 (dd, J=7.5, 1.8 Hz, 1H), 6.28 (s, 1H), 4.79 (s, 2H).

Example 172

¹H NMR (CDCl₃) δ 8.64 (s, 1H), 7.68-7.64 (m, 2H), 7.52 (m, 1H), 7.43 (t, J=7.8 Hz, 1H), 6.89 (t, J=6.0 Hz, 1H), 6.51 (s, 1H), 6.48 (m, 2H), 4.74 (d, J=6.0 Hz, 2H).

Example 173

¹H NMR (DMSO-d₆) δ 8.86 (s, 1H), 8.46 (s, 1H), 8.32-8.28 (m, 2H), 7.97 (m, 1H), 7.87 (m, 1H), 7.52 (m, 1H), 7.35-7.24 (m, 2H), 6.57 (s, 1H), 6.46 (m, 1H), 3.65 (m, 4H).

Example 174

¹H NMR (CDCl₃) δ 8.37 (s, 1H), 8.16 (t, J=7.5 Hz, 1H), 7.45-7.35 (m, 1H), 7.32-7.20 (m, 3H), 7.17-7.07 (m, 1H), 6.92 (t, J=6 Hz, 1H), 6.48 (s, 1H), 4.65 (d, 2H), 2.50 (s, 3H).

Example 175

¹H NMR (CDCl₃) δ 8.16 (t, J=9 Hz, 1H), 8.00 (s, 1H), 7.49 (d, J=9 Hz, 1H), 7.46-7.36 (m, 1H), 7.18-7.08 (m, 1H), 7.00 (d, J=9 Hz, 1H), 6.62-6.50 (m, 2H), 2.60 (s, 3H), 2.55 (s, 3H).

Example 176

¹H NMR (CDCl₃) δ 8.15 (t, J=9 Hz, 1H), 8.00 (s, 1H), 7.45-7.35 (m, 1H), 7.32-7.20 (m, 1H), 7.20-7.05 (m, 3H), 6.80 (t, 1H), 6.50 (s, 1H), 4.65 (d, 2H), 2.65 (s, 3H), 2.50 (s, 3H):

Example 177

¹H NMR (CDCl₃) δ 8.20 (t, 1H), 7.90 (s, 1H), 7.50-7.05 (m, 8H), 6.80 (s, 1H), 5.05-4.90 (m, 2H), 3.80 (d, 1H), 3.45 (d, 1H), 3.00 (dd, 1H), 2.90 (dd, 1H), 2.50 (s, 3H).

Example 181

¹H NMR (300 MHz, CDCl₃) 8.41 (s, 1H), 8.28-8.23 (d, 1H), 8.15 (s, 1H), 7.69-7.60 (d, 1H), 7.62-7.50 (m, 3H), 7.50-7.47 (dd, 1H), 6.35 (s, 1H), 5.36 (s, 1H), 4.80 (s, 2H).

Example 184

¹H NMR (300 MHz, CDCl₃) 8.96-8.90 (s, 1H), 8.08 (s, 1H), 8.04 (d, 1H), 7.72 (d, 1H), 7.70-7.61 (dd, 1H), 7.24-7.20 (dd, 1H), 6.92-6.84 (t, 1H), 6.36 (s, 1H), 4.96-4.89 (d, 2H).

Example 186

¹H NMR (300 MHz, CDCl₃) 8.96-8.90 (s, 1H), 8.08 (s, 1H), 8.44 (s, 1H), 8.27-8.24 (d, 1H), 8.02 (s, 1H), 7.78-7.76 (d, 1H), 7.73-7.70 (d, 1H), 7.58-7.51 (m, 2H), 7.13-7.08 (dd, 1H), 5.51 (s, 2H).

Example 195

¹H NMR (CD₃OD) δ 8.40 (s, 1H), 8.27 (d, 1H), 8.03 (s, 1H), 7.75-7.50 (m, 2H), 6.10 (s, 1H), 4.76 (s, 2H), 4.05 (m, 2H), 3.88 (m, 2H), 3.52 (m, 1H), 2.33 (m, 1H), 2.20 (m, 1H).

Example 196

¹H NMR (CD₃OD) δ 8.73 (d, 1H), 8.58 (q, 1H), 8.12 (s, 1H), 8.00 (d, 1H), 7.54 (q, 1H), 6.19 (s, 1H), 4.86 (s, 2H), 4.22-4.08 (m, 2H), 4.03-3.93 (m, 2H), 3.63 (m, 1H), 2.50-2.39 (m, 1H), 2.32-2.21 (m, 1H).

Example 197

¹H NMR (CD₃OD) δ 8.73 (d, 1H), 8.58 (q, 1H), 8.12 (s, 1H), 8.00 (d, 1H), 7.54 (q, 1H), 6.19 (s, 1H), 4.86 (s, 2H), 4.22-4.08 (m, 2H), 4.03-3.93 (m, 2H), 3.63 (m, 1H), 2.50-2.39 (m, 1H), 2.32-2.21 (m, 1H).

Example 199

¹H NMR (300 MHz, CDCl₃) 8.29 (s, 1H), 8.15 (brs, 1H), 7.95 (s, 1H), 7.28 (d, 1H), 7.05-6.95 (appt t, 1H), 5.70 (s, 1H), 4.62 (d, 2H), 2.90 (m, 1H), 2.30 (m, 1H), 1.9-1.2 (m, 1H), 0.65 (d, 3H).

Example 200

¹H NMR (300 MHz, CDCl₃) 8.71 (s, 2H), 8.00 (s, 1H), 6.13 (s, 1H), 3.59 (s, 2H), 3.01-2.58 (m, 1H), 2.51-2.45 (m, 1H), 2.44-2.30 (m, 1H), 2.20 (s, 3H), 2.09-1.95 (m, 2H), 1.85-1.70 (m, 2H), 0.80-0.76 (d, 3H).

Example 203

¹H NMR (300 MHz, CDCl₃) 8.10 (s, 1H), 8.08 (s, 1H), 6.27 (s, 2H), 4.95 (s, 2H), 3.00-2.90 (dd, 2H), 2.60 (m, 2H), 2.48 (br s, 1H), 2.39 (s, 3 h), 2.25 m, 1H), 1.95-1.70 (m, 3H).

Example 211

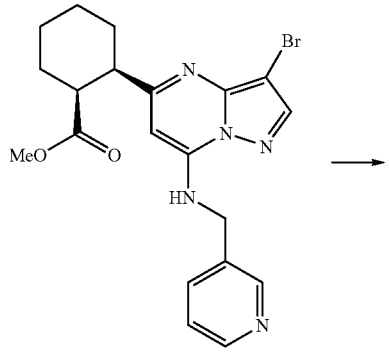

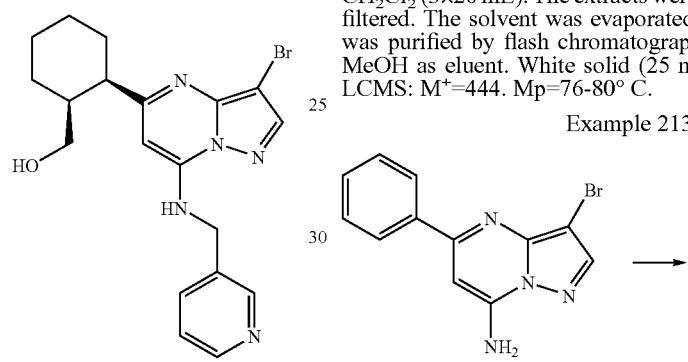

To a solution of the compound prepared in Example 156 (100 mg, 0.23 mmol) in dry THF (4 mL) was added LiAlH₄ (1.0 M in THF, 0.110 mL, 0.110 mmol) at 0° C. under N₂. The mixture was stirred at 0° C. for 1 hr, warmed to 25° C., then additional LiAlH₄ (1.0 M in THF, 0.400 mL) was added, the mixture was stirred for 20 min and then quenched with MeOH (2.0 mL). The solvent was evaporated and the crude product was purified by flash chromatography using 10:1 CH₂Cl₂:MeOH as eluent. White solid (46 mg, 49%) was obtained. LCMS: M⁺=416. Mp=71-72° C.

Example 212

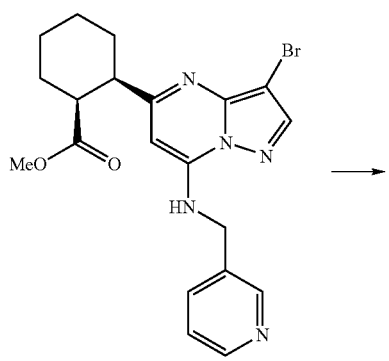

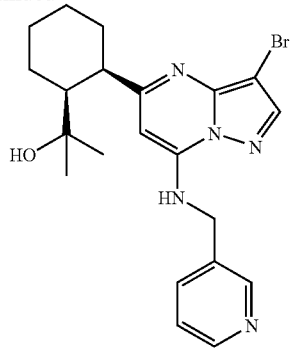

To a solution of the compound prepared in Example 156 (70 mg, 0.16 mmol) in dry THF (3 mL) was added MeMgBr (3.0 M in Et₂O, 1.10 mL, 3.20 mmol) under N₂. The mixture was stirred at 25° C. for 45 min and then quenched with saturated aqueous NH₄Cl (5.0 mL). The mixture was poured into saturated aqueous NH₄Cl (30 mL) and extracted with CH₂Cl₂ (3×20 mL). The extracts were dried over Na₂SO₄ and filtered. The solvent was evaporated and the crude product was purified by flash chromatography using 20:1 CH₂Cl₂:MeOH as eluent. White solid (25 mg, 36%) was obtained. LCMS: M⁺=444. Mp=76-80° C.

Example 213

Anhydrous DMF (40 mL) was added under N₂ to the compound prepared in Preparative Example 174 (2.50 g, 8.65 mmol) and 60% NaH in mineral oil (346 mg, 8.65 mmol). The mixture was stirred at 25° C. for 1 hr, then 2-chloro-5-chloromethylpyridine N-oxide (1.54 g, 8.65 mmol) in anhydrous DMF (20 mL) was added slowly. The mixture was stirred at 25° C. for 18 hr, the solvent was evaporated and the crude product was purified by flash chromatography using 30:1 CH₂Cl₂:MeOH as eluent. So obtained solid was triturated by 50 mL of 1:1 EtOAc:hexane. Pale yellow solid (1.25 g, 34%) was obtained. LCMS: MH⁺=432. Mp=224-226° C.

Examples 214-217

By essentially the same procedure set forth in Example 213 combining the compounds shown in Column 2 of Table 19 with compounds in Column 3 of Table 19, the compounds shown in Column 3 of Table 19 were prepared.

TABLE 19
| Ex. | Column 2 | Column 3 | Column 4 | CMPD |
|---|---|---|---|---|
| 214 | 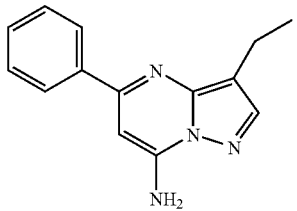 | 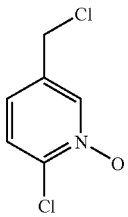 | 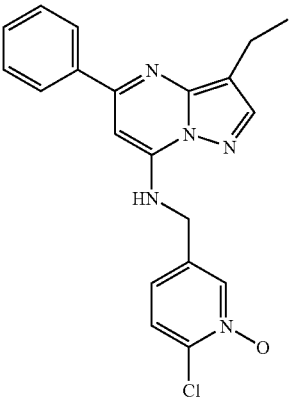 | LCMS: MH+ = 380; mp = ° C. |
| 215 | 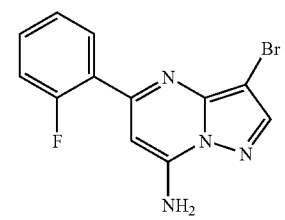 [SMILES: Nc1cc(-c2ccccc2F)nc2c(Br)cnn12] | 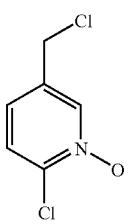 | 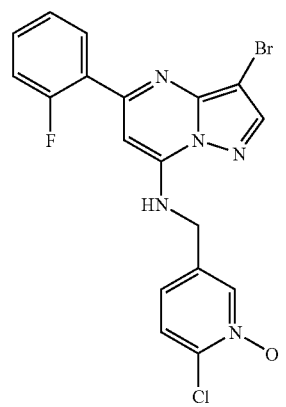 | LCMS: MH+ = 450; mp = 218-222° C. |
| 216 | 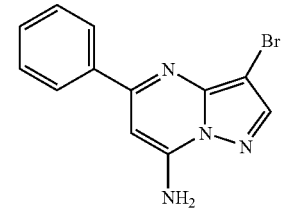 [SMILES: Nc1cc(-c2ccccc2)nc2c(Br)cnn12] | 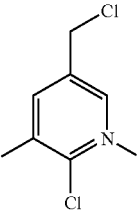 | 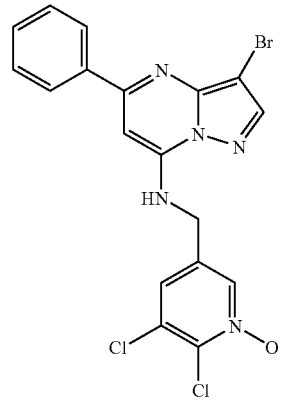 | LCMS: MH+ = 466; mp = 126-128° C. |
| 217 | 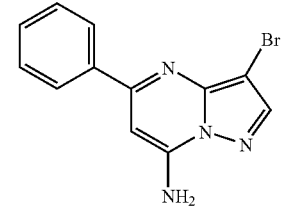 [SMILES: Nc1cc(-c2ccccc2)nc2c(Br)cnn12] | 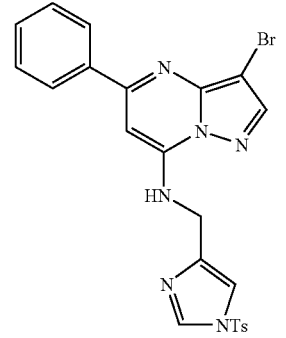 [SMILES: Cc1ccc(S(=O)(=O)n2cnc(CNc3cc(-c4ccccc4)nc4c(Br)cnn34)c2)cc1] | 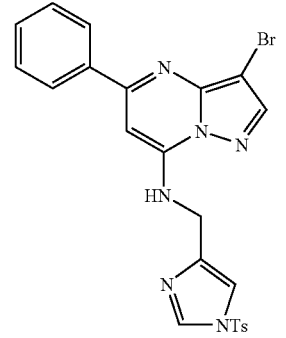 [SMILES: Cc1ccc(S(=O)(=O)n2cnc(CNc3cc(-c4ccccc4)nc4c(Br)cnn34)c2)cc1] | LCMS: M+ = 523 |

Example 218

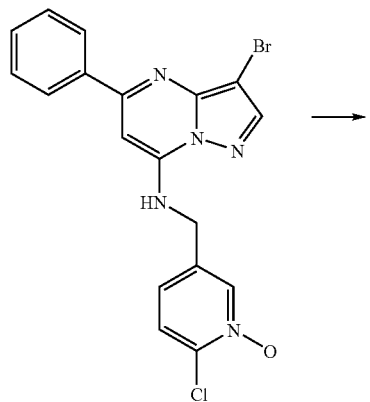

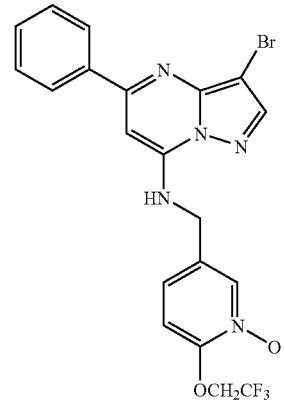

CF₃CH₂OH (3.0 mL) was added under N₂ to 60% NaH in mineral oil (40 mg, 1.0 mmol), the mixture was stirred for 20 min, then the product prepared in Example 213 (50 mg, 0.12 mmol) was added. The mixture was refluxed for 20 hr, the solvent was evaporated, and the residue was purified by flash chromatography using 20:1 CH₂Cl₂:MeOH as eluent to yield pale yellow solid (35 mg, 61%). LCMS: M2H+=496. Mp=208-210° C.

Examples 219-225

By essentially the same procedure set forth in Example 218 combining the compounds shown in Column 1 of Table 20 with the appropriate alcohol, the compounds shown in Column 2 of Table 20 were prepared.

TABLE 20

| Ex. | Column 1 | Column 2 | Data |
|---|---|---|---|
| 219 | | | LCMS: M⁺ = 426; mp = 126-128° C. |
| 220 | | | LCMS: M⁺ = 483; mp = 89-91° C. |

TABLE 20-continued
| Ex. | Column 1 | Column 2 | Data |
|---|---|---|---|
| 221 | 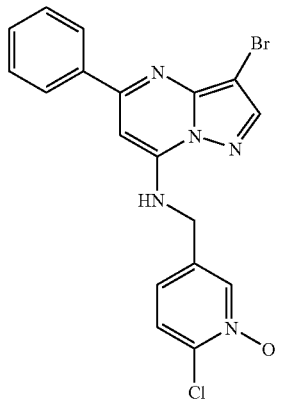 | 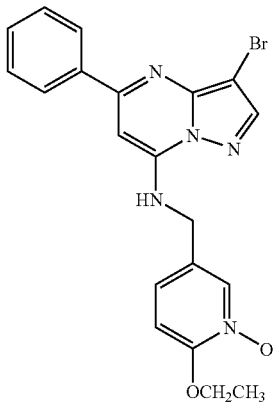 | LCMS: M2H+ = 442; mp = 112-114° C. |
| 222 | 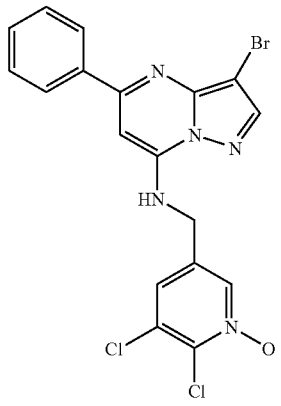 | 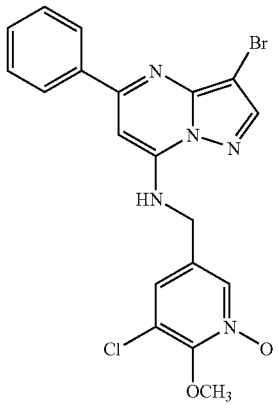 | LCMS: MH+ = 462; mp = 121-123° C. |
| 223 | 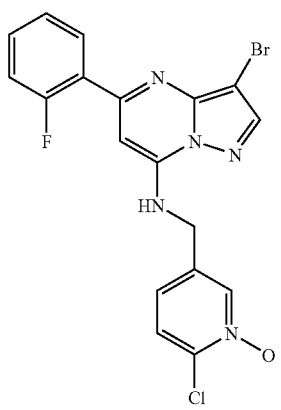 | 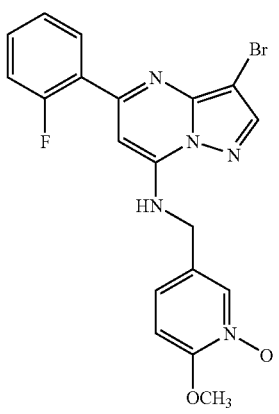 | LCMS: MH+ = 444; mp = 112-114° C. |

TABLE 20-continued

| Ex. | Column 1 | Column 2 | Data |
|---|---|---|---|
| 224 | | | LCMS: M+ = 376; mp = ° C. |
| 225 | | | LCMS: MH+ = ; mp = ° C. |

Example 226

-continued

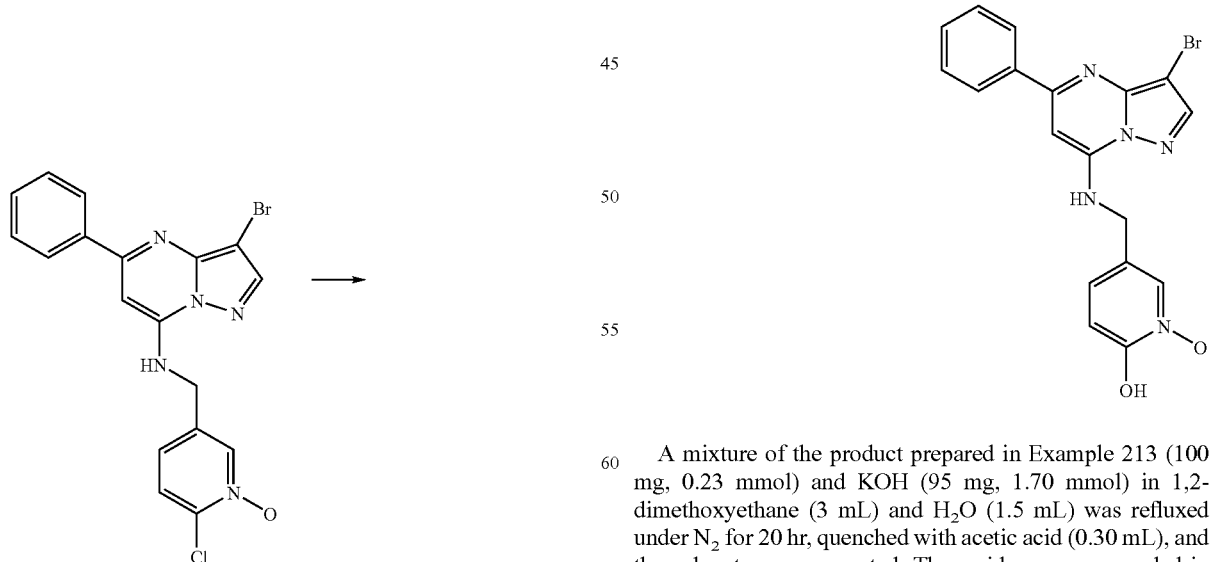

A mixture of the product prepared in Example 213 (100 mg, 0.23 mmol) and KOH (95 mg, 1.70 mmol) in 1,2-dimethoxyethane (3 mL) and H$_2$O (1.5 mL) was refluxed under N$_2$ for 20 hr, quenched with acetic acid (0.30 mL), and the solvent was evaporated. The residue was suspended in H$_2$O (15 mL), filtered and the solid was washed with H$_2$O (15 mL) and Et$_2$O (10 mL). Then it was mixed with CH$_2$Cl$_2$ (2 mL) and Et$_2$O (2 mL) and filtered. Et$_2$O (5 mL) was added to

Example 227

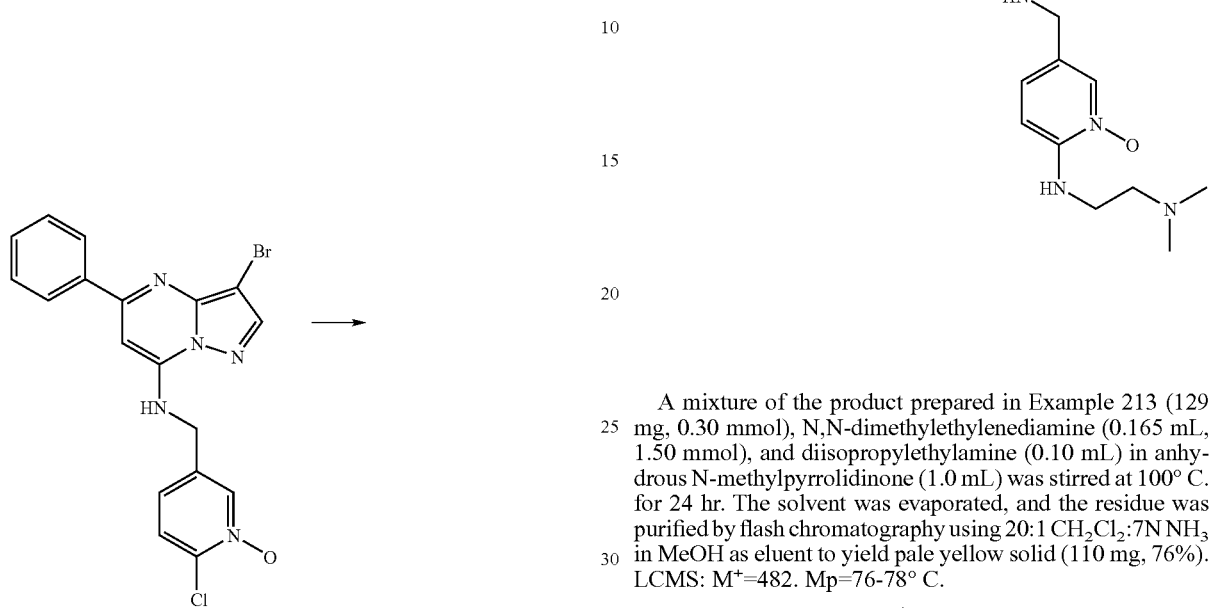

A mixture of the product prepared in Example 213 (129 mg, 0.30 mmol), N,N-dimethylethylenediamine (0.165 mL, 1.50 mmol), and diisopropylethylamine (0.10 mL) in anhydrous N-methylpyrrolidinone (1.0 mL) was stirred at 100° C. for 24 hr. The solvent was evaporated, and the residue was purified by flash chromatography using 20:1 $CH_2Cl_2$:7N $NH_3$ in MeOH as eluent to yield pale yellow solid (110 mg, 76%). LCMS: $M^+$=482. Mp=76-78° C.

Examples 228-233

By essentially the same procedure set forth in Example 227 combining the compounds shown in Column 1 of Table 21 with the appropriate amine, the compounds shown in Column 2 of Table 21 were prepared.

TABLE 21

| Ex. | Column 1 | Column 2 | Data |
|---|---|---|---|
| 228 | 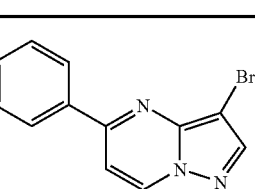 | 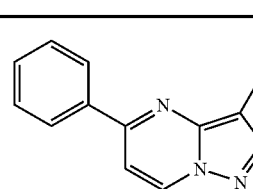 | LCMS: $M2H^+$ = 467; mp 126-128 = ° C. |

TABLE 21-continued

| Ex. | Column 1 | Column 2 | Data |
|---|---|---|---|
| 229 | | | LCMS: M+ = 481; mp = 128-130° C. |
| 230 | | | LCMS: M+ = 494; mp = 108-110° C. |
| 231 | | | LCMS: M2H+ = 482; mp = 129-133° C. |

TABLE 21-continued
| Ex. | Column 1 | Column 2 | Data |
|---|---|---|---|
| 232 | | | LCMS: M2H⁺ = 482; mp = 124-126° C. |
| 233 | | | LCMS: M2H⁺ = 471; mp = 88-90° C. |
Example 234
A mixture of the product prepared in Example 213 (80 mg, 0.19 mmol) and 2.0 M methylamine in THF was stirred in a closed pressure vessel at 50° C. for 72 hr. The solvent was evaporated, and the residue was purified by flash chromatography using 10:1 CH$_2$Cl$_2$: MeOH as eluent to yield pale yellow solid (40 mg, 51%). LCMS: M2H$^+$=427. Mp=217-219° C.

Example 235

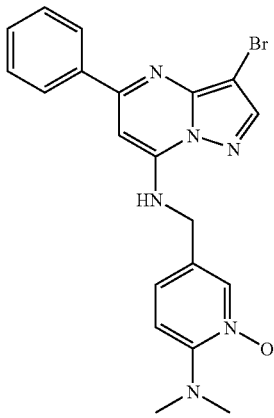

By essentially the same procedure set forth in Example 234, the compound shown above was prepared. LCMS: M2H$^+$=441. Mp=98-101° C.

Example 236

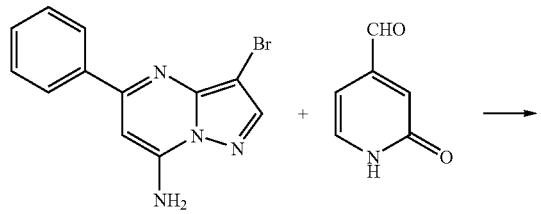

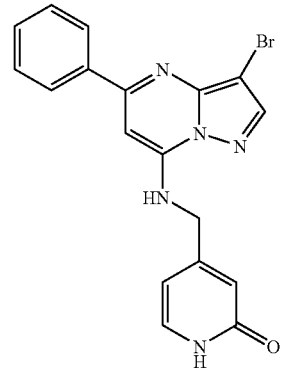

The compound prepared in Preparative Example 174 (140 mg, 0.48 mmol) and the aldehyde (71 mg, 0.58 mmol) were stirred in anhydrous THF (4 mL) at 50° C. under N$_2$. Ti(O-iPr)$_4$ (0.574 mL, 1.92 mmol) was added, the mixture was stirred at 50° C. 3 hr, and cooled to 25° C. NaBH$_3$CN (181 mg, 2.88 mmol) was added, the mixture was stirred for 2 more hr, then poured into 10% aqueous Na$_2$CO$_3$ (100 mL), and extracted with CH$_2$Cl$_2$ (3×50 mL). Combined extracts were dried over Na$_2$SO$_4$, filtered, and the solvent was evaporated. The residue was purified by flash chromatography using 15:1 CH$_2$Cl$_2$:MeOH as eluent to yield pale yellow solid (40 mg, 21%). LCMS: MH$^+$=398. Mp>230° C.

Examples 237-256

By essentially the same procedure set forth in Example 236 combining the compounds shown in Column 2 and 3 of Table 22, the compounds shown in Column 4 of Table 22 were prepared.

TABLE 22

| Ex. | Column 2 | Column 3 | Column 4 | Data |
|---|---|---|---|---|
| 237 | ![structure] | CHO-pyrimidine | ![structure] | LCMS: M$^+$ = 381; mp > 200° C. |

TABLE 22-continued

| Ex. | Column 2 | Column 3 | Column 4 | Data |
| --- | --- | --- | --- | --- |
| 238 | | | | LCMS: M+ = 387; mp = ° C. |
| 239 | | | | LCMS: MH+ = 413; mp = 157-159° C. |
| 240 | | | | LCMS: M2H+ = 419; mp = 77-79° C. |
| 241 | | | | LCMS: M2H+ = 385; mp = 214-216° C. |

TABLE 22-continued

| Ex. | Column 2 | Column 3 | Column 4 | Data |
|---|---|---|---|---|
| 242 | | | | LCMS: MH+ = ; mp = ° C. |
| 243 | | | | LCMS: M+ = 416; mp = 80-82° C. |
| 244 | | | | |
| 245 | | | | |

TABLE 22-continued

| Ex. | Column 2 | Column 3 | Column 4 | Data |
|---|---|---|---|---|
| 246 | | | | LCMS: M⁺ = 452; mp = 54-56° C. |
| 247 | | | | LCMS: MH⁺ = 401; mp > 200° C. |
| 248 | | | | LCMS: M2H⁺ = 474; mp > 200.0.° C. dec. |

TABLE 22-continued

| Ex. | Column 2 | Column 3 | Column 4 | Data |
|---|---|---|---|---|
| 249 | | | | LCMS: MH$^+$ = 377; mp = 65-67° C. |
| 250 | | | | LCMS: M2H$^+$ = 421; mp = 87-93° C. |
| 251 | | | | LCMS: MH$^+$ = 361; mp >225° C. |
| 252 | | | | LCMS: MH$^+$ = 346; mp = 270-271° C. |

TABLE 22-continued

| Ex. | Column 2 | Column 3 | Column 4 | Data |
|---|---|---|---|---|
| 253 | (5-cyclohexyl-3-bromo-pyrazolo[1,5-a]pyrimidin-7-amine) | 2-hydroxypyridine-4-carbaldehyde | corresponding coupled product | LCMS: MH$^+$ = 402; mp = 250-255° C. |
| 254 | (5-(2-fluorophenyl)-3-bromo-pyrazolo[1,5-a]pyrimidin-7-amine) | 2-hydroxypyridine-4-carbaldehyde | corresponding coupled product | LCMS: MH$^+$ = 416; mp = 210-215° C. |
| 255 | (5-(2-fluorophenyl)-3-bromo-pyrazolo[1,5-a]pyrimidin-7-amine) | 6-methoxypyridine-3-carbaldehyde | corresponding coupled product | LCMS: MH$^+$ = 428; mp = 145° C. |
| 256 | (benzyl 3-(7-amino-3-bromo-pyrazolo[1,5-a]pyrimidin-5-yl)piperidine-1-carboxylate) | 2-methoxypyrimidine-5-carbaldehyde | corresponding coupled product | LCMS: MH$^+$ = ; mp = ° C. |

Example 257

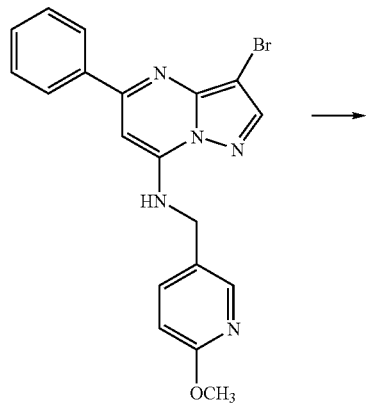

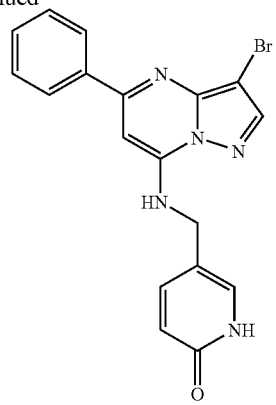

A mixture of the compound prepared in Example 242 (100 mg, 0.24 mmol), conc. aqueous HCl (1.0 mL) and acetic acid (2.0 mL) were stirred at 100° C. under $N_2$ for 2 hr, then poured onto $Na_2CO_3$ (15 g), and extracted with 1:1 acetone:$CH_2Cl_2$ (3×30 mL). Combined extracts were filtered, and the solvent was evaporated. The residue was purified by flash chromatography using 10:1 $CH_2Cl_2$:MeOH as eluent to yield pale yellow solid (36 mg, 37%). LCMS: M2H$^+$=398.

Examples 258-260

By essentially the same procedure set forth in Example 257 starting from the compounds shown in Column 1 of Table 23, the compounds shown in Column 2 of Table 23 were prepared.

TABLE 23

| Ex. | Column 1 | Column 2 | Data |
|---|---|---|---|
| 258 | | | LCMS: M$^+$ = 402; mp = 229-231° C. |
| 259 | | | LCMS: MH$^+$ = 416; mp = 215-218° C. |

TABLE 23-continued

| Ex. | Column 1 | Column 2 | Data |
|-----|----------|----------|------|
| 260 | 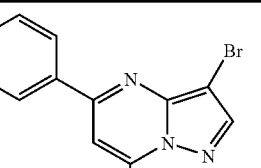 | 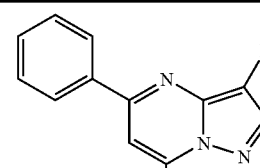 | LCMS: M2H+ = 398; mp >230° C. |

Example 261

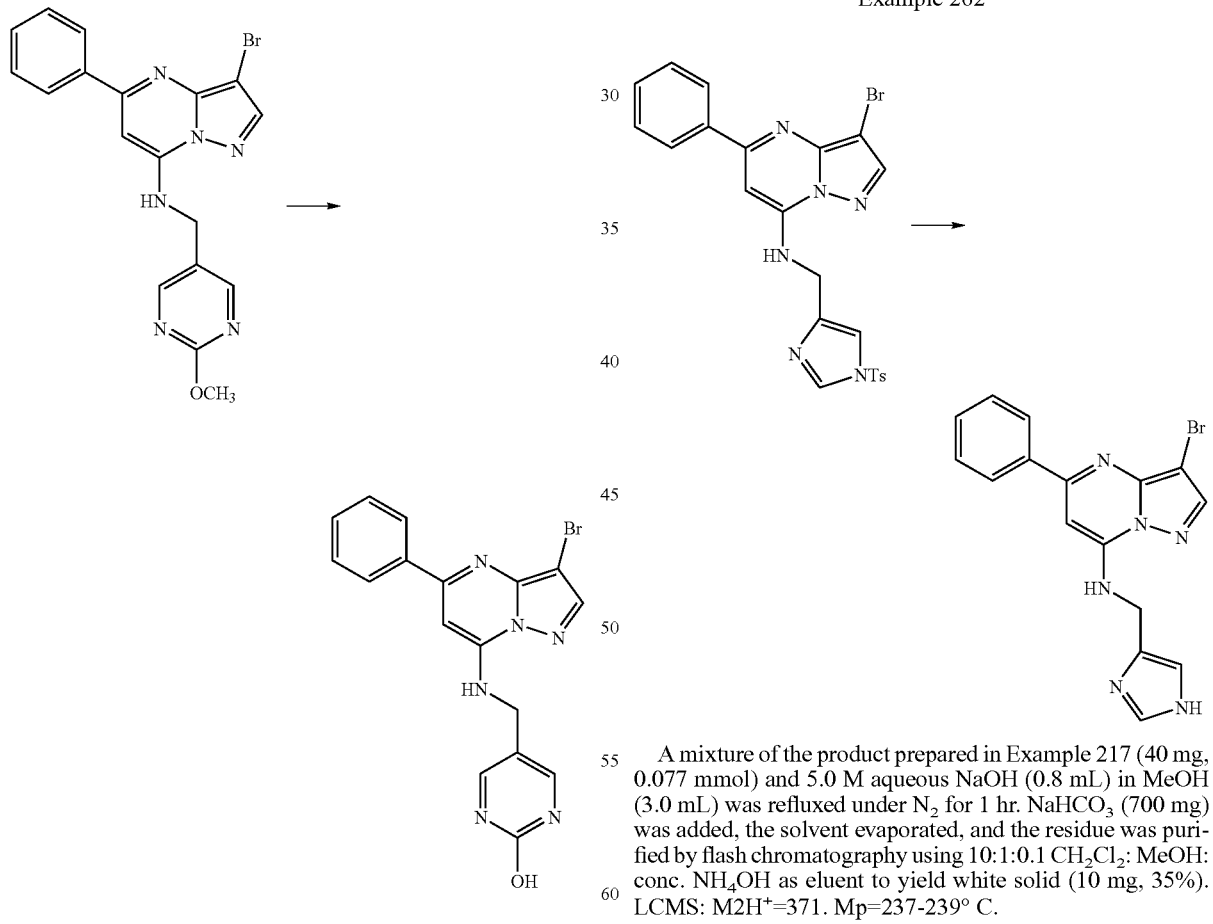

To a stirred solution of the compound prepared in Example 239 (41 mg, 0.10 mmol) in CH$_2$Cl$_2$ was added 1.0 M BBr$_3$ (0.30 mL, 0.30 mmol) in CH$_2$Cl$_2$ at −78° C. The mixture was stirred at −78° C. for 5 min, then at 24° C. for 3 hr, then MeOH (2.0 mL) was added and the mixture was stirred for 10 min. The solvent was evaporated and the residue was purified by flash chromatography using 5:1:0.1 CH$_2$Cl$_2$:MeOH:conc. NH$_4$OH as eluent to yield white solid (39 mg, 99%). LCMS: M+=397. Mp>230° C.

Example 262

A mixture of the product prepared in Example 217 (40 mg, 0.077 mmol) and 5.0 M aqueous NaOH (0.8 mL) in MeOH (3.0 mL) was refluxed under N$_2$ for 1 hr. NaHCO$_3$ (700 mg) was added, the solvent evaporated, and the residue was purified by flash chromatography using 10:1:0.1 CH$_2$Cl$_2$: MeOH: conc. NH$_4$OH as eluent to yield white solid (10 mg, 35%). LCMS: M2H+=371. Mp=237-239° C.

Examples 263-264

By essentially the same procedure set forth in Example 262 starting from the compounds shown in Column 1 of Table 24, the compounds shown in Column 2 of Table 24 were prepared.

TABLE 24

| Ex. | Column 1 | Column 2 | Data |
|---|---|---|---|
| 263 | 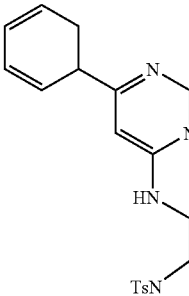 | 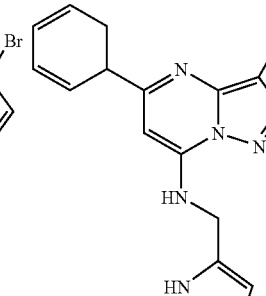 | LCMS: M2H⁺ = 370; mp = 166-168° C. |
| 264 | 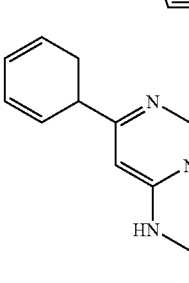 | 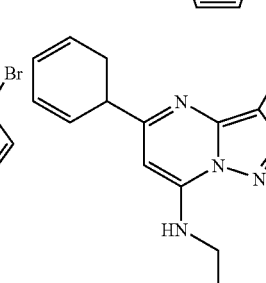 | LCMS: M2H⁺ = 371; mp = 180-182° C. |

Example 265

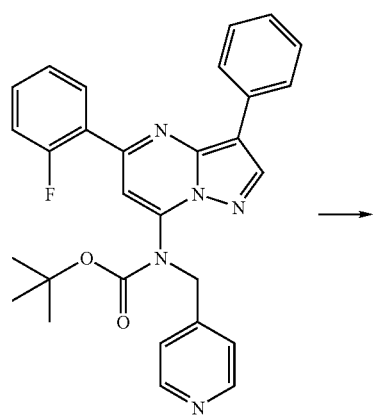

TFA (0.5 mL) was added to a solution of the compound prepared in Preparative Example 197 (0.08 g, 0.16 mmol) in CH$_2$Cl$_2$ (2.0 mL) at 0° C. and the resulting solution stirred 2.5 hours and stored at 4° C. overnight at which time additional TFA (0.5 mL) was added. The resulting solution was stirred 4 hours and concentrated in vacuo. The residue was neutralized with 1N NaOH and extracted with CH$_2$Cl$_2$. The combined organics were dried over Na$_2$SO$_4$, filtered, and concentrated under reduced pressure. The crude product was purified by flash chromatography using a 2.5% (10% NH$_4$OH in MeOH) in CH$_2$Cl$_2$ solution as eluent (0.009 g, 15% yield). LCMS: MH⁺=396; mp=53-54° C.

Example 266

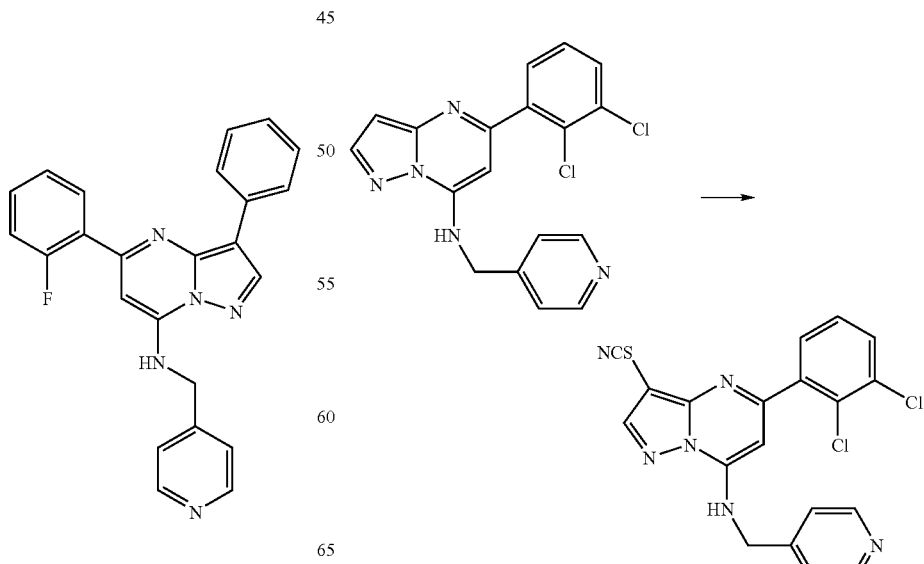

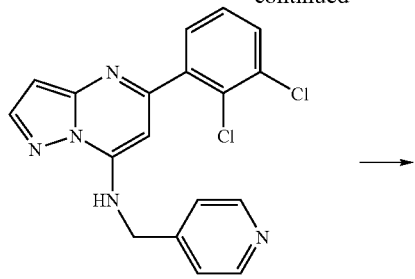

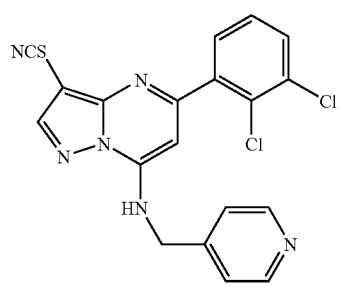

A solution of the compound prepared in Preparative Example 182 (26 mg, 0.070 mmol) and potassium thiocyanate (13 mg, 0.14 mmol) in MeOH (1 mL) was cooled in a cold water bath. To it was added a solution of bromine (22 mg, 0.14 mmol) in MeOH (0.7 mL) dropwise. The resulting reaction mixture was stirred for 4 h at room temperature and the volatiles were removed under reduced pressure. The residue obtained was suspended in a small amount of $CH_2Cl_2$. The potassium bromide was filtered off and pH of the filtrate was adjusted to about 7 by the addition of aqueous ammonia. It was concentrated under reduced pressure and the residual oil was purified by preparative thin-layer chromatography using 15% MeOH in $CH_2Cl_2$ as eluent (26 mg, 87% yield). $^1$H NMR ($CDCl_3$) δ 8.75 (d, J=4.2 Hz, 2H), 8.38 (s, 1H), 7.68-7.64 (m, 2H), 7.46-7.39 (m, 3H), 7.22 (t, J=6.3 Hz, 1H), 6.43 (s, 1H), 4.84 (d, J=6.3 Hz, 2H); LCMS: $MH^+$=427.

Example 267

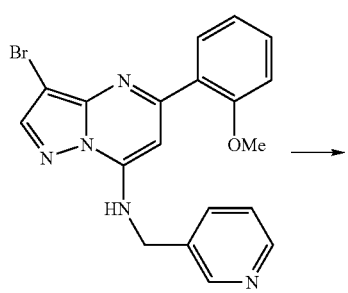

Boron tribromide (1M in $CH_2Cl_2$, 0.60 mL, 0.60 mmol) was added dropwise to an ice-cold stirred solution of the compound prepared in Example 24 (50 mg, 0.12 mmol) in $CH_2Cl_2$ (1.5 mL) under an argon atmosphere. The resulting reaction mixture was stirred at 0° C. for 30 minutes, allowed to warm up to room temperature, and stirred overnight. The mixture was quenched by the addition of a small amount of water and extracted with $CH_2Cl_2$. The organic layer was dried over magnesium sulfate and concentrated in vacuo (45 mg, 94% yield). $^1$H NMR ($CD_3OD$) δ 9.16 (s, 1H), 8.95 (s, 1H), 8.88 (d, J=8.1 Hz, 1H), 8.24 (t, J=6.9 Hz, 1H), 8.18 (s, 1H), 7.95 (d, J=7.8 Hz, 1H), 7.40 (t, J=7.8 Hz, 1H), 7.00-6.96 (m, 2H), 6.86 (s, 1H), 5.28 (s, 2H); LCMS: $MH^+$=396.

Example 268

A solution of the compound from Preparative Example 184 (0.05 g, 0.15 mmol), N-methylpiperazine (20 μL, 1.2 eq.) and $iPr_2Et$ (52 μL, 2.0 eq.) in dioxane (1 mL) was heated to 70° C. overnight. The reaction mixture was cooled to room temperature and diluted with $H_2O$ and saturated $NaHCO_3$. The resulting mixture was extracted with $CH_2Cl_2$, the combined organics dried over $Na_2SO_4$, filtered, and concentrated under reduced pressure. The crude product was purified by Preparative TLC using a 5% (10% $NH_4OH$ in MeOH) in $CH_2Cl_2$ solution as eluent (0.028 g, 47% yield). MS: $MH^+$=402. mp=210° C. (dec.)

Examples 269-275

By essentially the same procedure set forth in Example 268 only substituting the amine in Column 2 of Table 25 and the chlorides in Column 3 of Table 25, the compounds shown in Column 4 of Table 25 are prepared:

TABLE 25
| Ex. | Column 2 | Column 3 | Column 4 | CMPD |
|---|---|---|---|---|
| 269 |  | 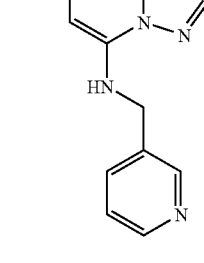 | 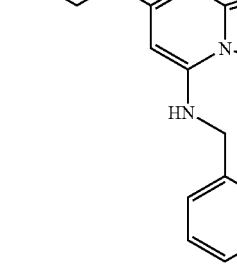 | MS: MH⁺ = 387<br>m.p. 182-183° C. |
| 270 |  | 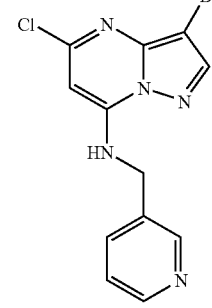 | 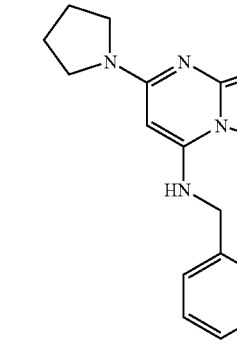 | MS: MH⁺ = 373<br>m.p. 190-191° C. |
| 271 | 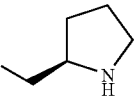 | 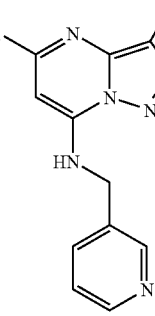 | 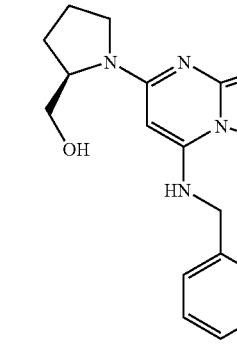 | MS: MH⁺ = 403<br>m.p. 227-230° C. |
| 272 |  | 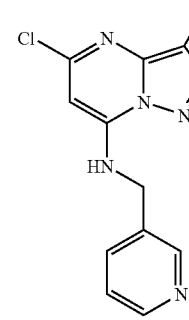 | 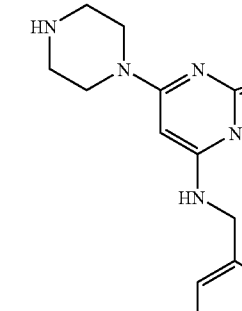 | MS: MH⁺ = 388<br>m.p. 198-201° C. |

TABLE 25-continued
| Ex. | Column 2 | Column 3 | Column 4 | CMPD |
|---|---|---|---|---|
| 273 | | | | MS: MH+ = 430<br>m.p. 100-103° C. |
| 274 | | | | MS: MH+ = 456<br>m.p. 175-178° C. |
| 275 | | | | MS: MH+ = 403<br>m.p. 218° C. |
Examples 279
Step A
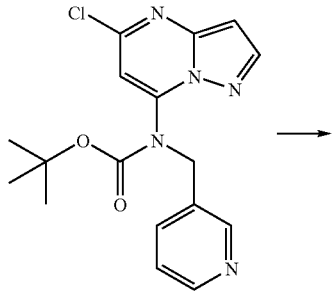
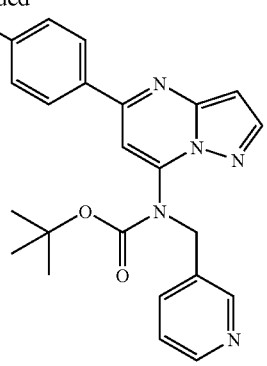
-continued
4-Fluorophenyl magnesium bromide (0.68 mL, 1.2 eq.) was added to the compound prepared in Preparative Example 193 (0.20 g, 0.55 mmol) and PdCl$_2$(dppf)$_2$ (0.037 g, 10 mol %) in THF and the resulting solution was stirred at room temperature 72 hours. The reaction mixture was dilute with saturated NH$_4$Cl and extracted with EtOAc. The combined organics were washed with saturated NaCl, dried over Na$_2$SO$_4$, filtered and concentrated. The crude product was purified by flash chromatography using neat EtOAc as eluent (0.15 g, 65% yield). MS: MH$^+$=420.

Step B

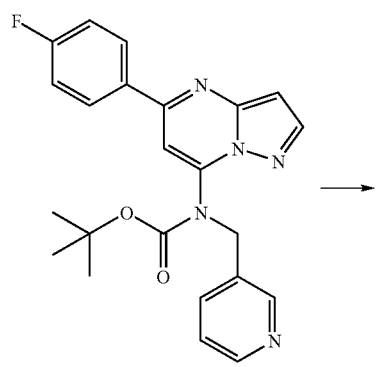

By essentially the same procedure set forth in Preparative Example 127 only substituting the compound prepared in Example 276, Step A, the above compound was prepared (0.17 g, 94% yield).

Step C

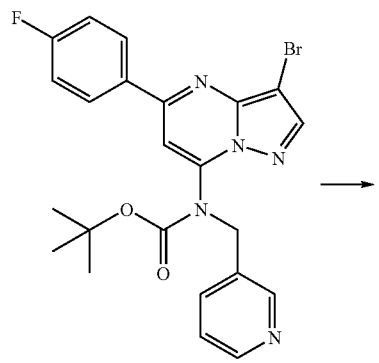

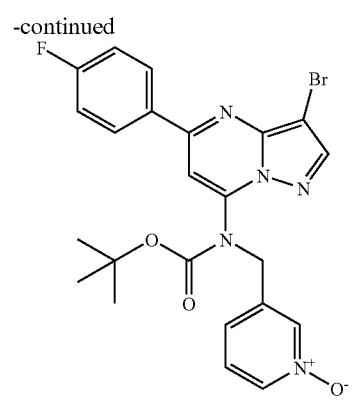

By essentially the same procedure set forth in Preparative Example 200 only substituting the compound prepared in Example 276, Step B, the above compound was prepared (0.1 g, 100% yield).

Step D

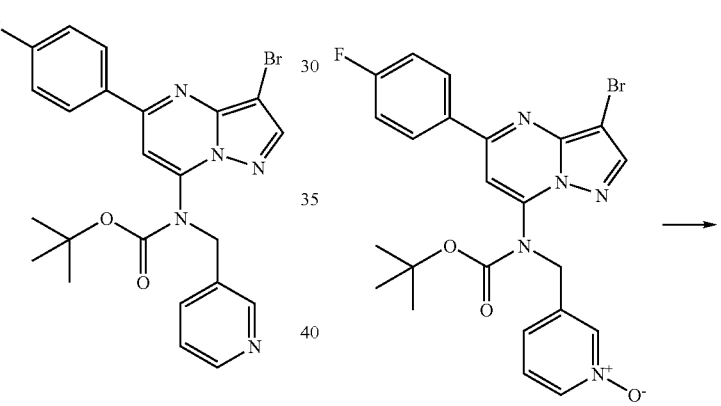

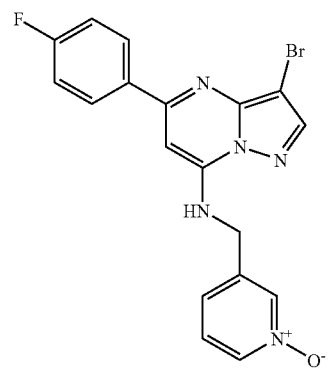

By essentially the same procedure set forth in Example 265 only substituting the compound prepared in Example 276, Step C, the above compound was prepared (0.049 g, 62% yield). MS: MH⁺=414; mp=110-115° C.

Example 277

Step A

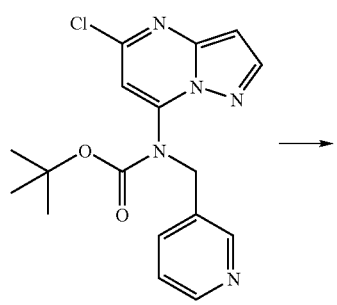

→

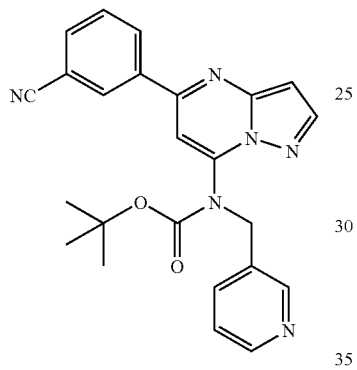

Pd(PPh₃)₄ (0.065 g, 10 mol %) was added to 3-cyanophenyl zinc iodide (2.2 mL, 0.5 M solution in THF, 2 eq.) and the compound prepared in Preparative Example 193 (0.2 g, 0.56 mmol) in DMF (2.0 mL) and the resulting solution heated to 80° C. g for 144 hours. The reaction mixture was cooled to room temperature, diluted with saturated NH₄Cl and extracted with EtOAc. The combined organics were washed with H₂O and brine, dried over Na₂SO₄, filtered, and concentrated under reduced pressure. The crude product was purified by flash chromatography using a neat EtOAC solution as eluent (0.07 g, 29% yield). MS: MH⁺=427.

Step B through Step D

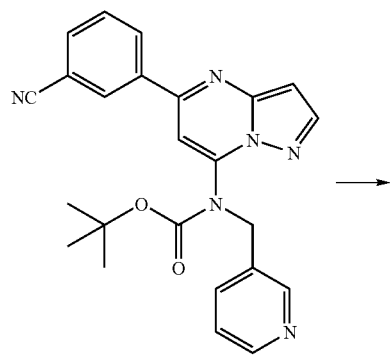

→

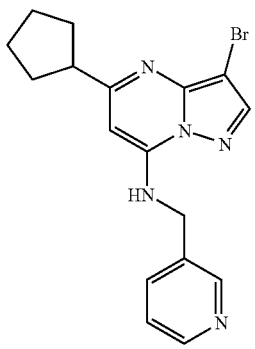 [SMILES: Brc1cnn2c(NCc3cccnc3)cc(C3CCCC3)nc12]

By essentially the same procedures set forth in Example 276, Step B through Step D, the above compound was prepared (0.023 g, 53% yield). MS: MH⁺421; mp=230° C. (dec.)

Example 278

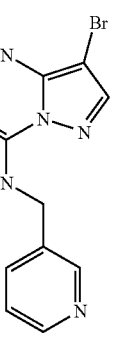

By essentially the same procedure set forth in Example 276 only substituting the appropriate cyclopropylmagnesium bromide in Step A, the compound was prepared. MS: MH⁺=372; m.p.=96-98° C.

Example 279

→

-continued

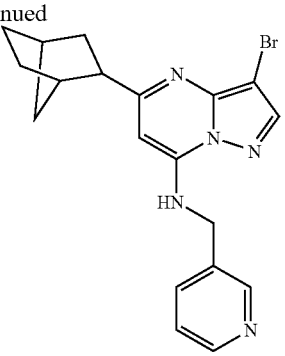

The palladium-catalyzed zinc cross-coupling reaction was carried out in a manner similar to the procedure described in *J. Org. Chem.* (1999), 453. A solution of the chloropyrazolopyrimidine (200 mg, 0.458 mmol), Pd(PPh$_3$)$_4$ (53 mg, 0.046 mmol), and exo-2-norbornylzinc bromide (0.5 M in THF, 0.95 mL, 0.47 mmol) in DMF (2 mL) was refluxed at 100° C. (oil bath temp.) overnight. The reaction mixture was quenched with half-saturated NH$_4$Cl and extracted with CH$_2$Cl$_2$. The organic phase was dried over MgSO$_4$ and concentrated under reduced pressure. The residue was purified by flash chromatography using a 50% EtOAc in hexanes solution as eluent. A solution of the obtained N-Boc-protected product (121 mg, 53% yield, LCMS: MH$^+$=498) and TFA (1 mL) in CH$_2$Cl$_2$ (2 mL) was stirred at room temperature for 2 hr. The volatiles were removed under reduced pressure. The residue was dissolved in CH$_2$Cl$_2$, neutralized with saturated NaHCO$_3$, and extracted with CH$_2$Cl$_2$. The organic phase was dried over MgSO$_4$ and concentrated in vacuo (96 mg, 99% yield). LCMS: MH$^+$=398; $^1$H NMR (CDCl$_3$) δ 8.78 (s, 1H), 8.71 (d, J=4.2 Hz, 1H), 8.04 (d, J=3.9 Hz, 1H), 7.80 (d, J=7.8 Hz, 1H), 7.44 (m, 1H), 6.73 (m, 1H), 5.98 (d, J=7.5 Hz, 1H), 4.74 (d, J=5.4 Hz, 2H), 3.40-1.00 (m, 11H).

Examples 280-294

By following essentially the same procedure set forth in Example 279 only substituting the chlorides shown in Column 2 of Table 26 and the organozinc reagents shown in Column 3 of Table 26, the compounds in Column 4 of Table 26 were prepared:

TABLE 26

| Ex. | Column 2 | Column 3 | Column 4 | Data |
|---|---|---|---|---|
| 280 | [structure] | [structure] | [structure] | LCMS: MH$^+$ = 395 |
| 281 | [structure] | [structure] | [structure] | LCMS: MH$^+$ = 400 |

TABLE 26-continued

| Ex. | Column 2 | Column 3 | Column 4 | Data |
|---|---|---|---|---|
| 282 | | | | LCMS: MH⁺ = 412 |
| 283 | | | | LCMS: MH⁺ = 452 |
| 284 | | | | LCMS: MH⁺ = 422 |
| 285 | | | | LCMS: MH⁺ = 408 |

TABLE 26-continued
| Ex. | Column 2 | Column 3 | Column 4 | Data |
|---|---|---|---|---|
| 286 | 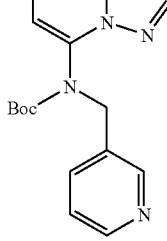 | 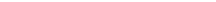 | 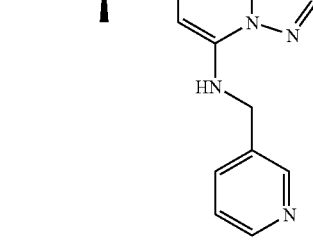 | LCMS: MH$^+$ = 404 |
| 287 | 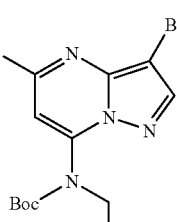 | 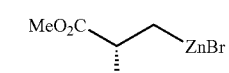 | 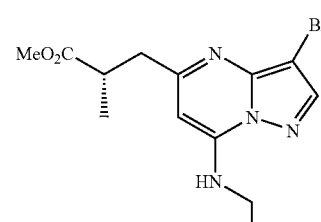 | LCMS: MH$^+$ = 404 |
| 288 | 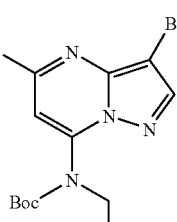 | 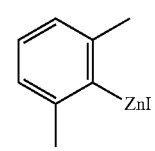 | 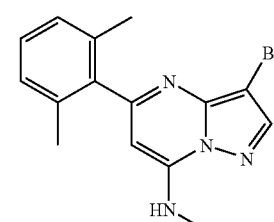 | LCMS: MH$^+$ = 408 |
| 289 |  | 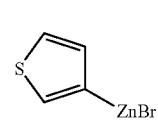 | 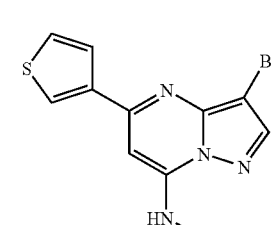 | LCMS: MH$^+$ = 386 |

TABLE 26-continued
| Ex. | Column 2 | Column 3 | Column 4 | Data |
|---|---|---|---|---|
| 290 | 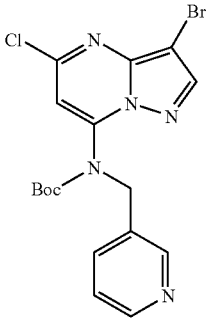 [SMILES: CC(C)(C)OC(=O)N(Cc1cccnc1)c1cc(Cl)nc2c(Br)cnn12] | 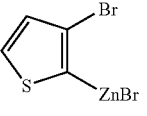 | 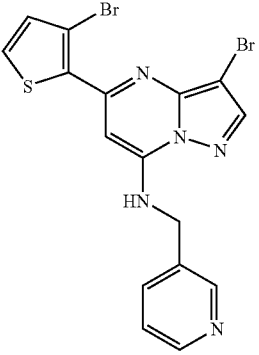 [SMILES: Brc1ccsc1-c1cc(NCc2cccnc2)n2ncc(Br)c2n1] | LCMS: MH⁺ = 464 |
| 291 | 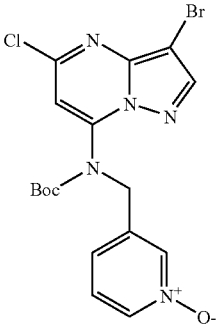 [SMILES: CC(C)(C)OC(=O)N(Cc1ccc[n+]([O-])c1)c1cc(Cl)nc2c(Br)cnn12] | 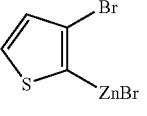 | 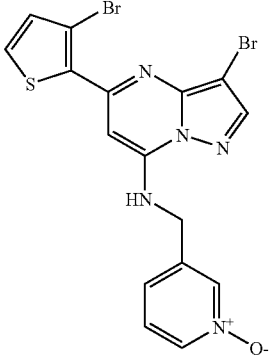 [SMILES: [O-][n+]1cccc(CNc2cc(-c3sccc3Br)nc3c(Br)cnn23)c1] | LCMS: MH⁺ = 480 |
| 292 | 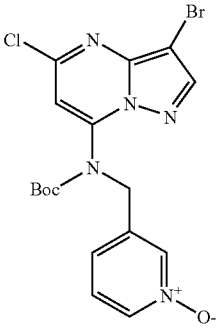 [SMILES: CC(C)(C)OC(=O)N(Cc1ccc[n+]([O-])c1)c1cc(Cl)nc2c(Br)cnn12] | 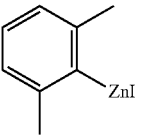 | 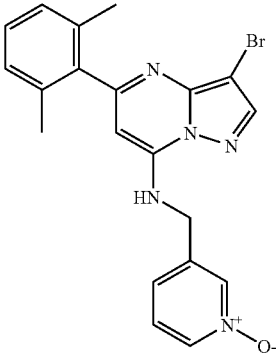 [SMILES: Cc1cccc(C)c1-c1cc(NCc2ccc[n+]([O-])c2)n2ncc(Br)c2n1] | LCMS: MH⁺ = 424 |
| 293 | 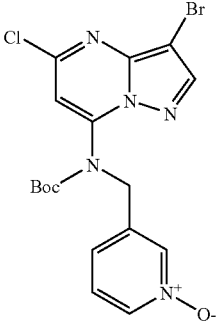 [SMILES: CC(C)(C)OC(=O)N(Cc1ccc[n+]([O-])c1)c1cc(Cl)nc2c(Br)cnn12] | 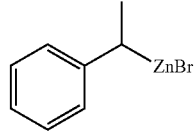 | 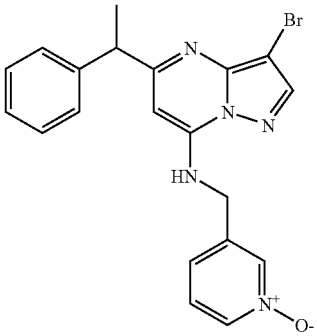 [SMILES: CC(c1ccccc1)c1cc(NCc2ccc[n+]([O-])c2)n2ncc(Br)c2n1] | LCMS: MH⁺ = 424 |

TABLE 26-continued

| Ex. | Column 2 | Column 3 | Column 4 | Data |
|---|---|---|---|---|
| 294 | (5-chloro-3-bromo-pyrazolo[1,5-a]pyrimidin-7-yl)(pyridin-3-ylmethyl)carbamic acid tert-butyl ester | 2-(methylthio)phenylzinc iodide | 3-bromo-5-(2-(methylthio)phenyl)-N-(pyridin-3-ylmethyl)pyrazolo[1,5-a]pyrimidin-7-amine | LCMS: MH⁺ = 426 |

Additional data for select compounds is shown below.

Example 280

¹H NMR (CDCl₃) δ 8.65 (s, 1H), 8.57 (d, J=4.2 Hz, 1H), 8.50 (d, J=4.5 Hz, 1H), 8.01 (s, 1H), 7.69 (d, J=7.5 Hz, 1H), 7.61 (d, J=7.8 Hz, 1H), 7.31-7.22 (m, 2H), 6.77 (m, 2H), 4.71 (d, J=5.4 Hz, 2H), 2.68 (s, 3H).

Example 281

¹H NMR (CDCl₃) δ 8.80 (s, 1H), 8.72 (d, J=4.8 Hz, 1H), 8.08 (s, 1H), 7.85-7.40 (m, 3H), 7.02 (d, J=5.1 Hz, 1H), 6.90 (t, J=6.0 Hz, 1H), 6.29 (s, 1H), 4.79 (d, J=6.0 Hz, 2H), 2.61 (s, 3H).

Example 282

¹H NMR (CDCl₃) δ 8.67 (s, 1H), 8.61 (d, J=3.9 Hz, 1H), 8.03 (s, 1H), 7.72-7.31 (m, 3H), 7.22-7.00 (m, 2H), 6.81 (t, J=6.0 Hz, 1H), 6.03 (s, 1H), 4.68 (d, J=6.0 Hz, 2H), 2.28 (s, 3H).

Example 283

¹H NMR (CDCl₃) δ 8.68 (s, 1H), 8.63 (d, J=4.0 Hz, 1H), 8.00 (s, 1H), 7.80-7.72 (m, 2H), 7.54-7.47 (m, 3H), 7.35 (m, 1H), 6.74 (t, J=6.0 Hz, 1H), 6.19 (s, 1H), 4.67 (d, J=6.0 Hz, 2H), 4.21 (q, J=7.2 Hz, 2H), 1.13 (t, J=7.2 Hz, 3H).

Example 284

¹H NMR (CDCl₃) δ 7.97 (s, 1H), 7.65 (d, J=7.2 Hz, 1H), 7.33-7.15 (m, 5H), 6.73 (t, J=5.4 Hz, 1H), 5.99 (s, 1H), 4.61 (d, J=5.4 Hz, 2H), 3.09 (sept, J=6.9 Hz, 1H), 1.11 (d, J=6.9 Hz, 6H).

Example 285

¹H NMR (CDCl₃) δ 8.56-8.55 (m, 2H), 7.94 (s, 1H), 7.54 (m, 1H), 7.30-7.22 (m, 6H), 6.59 (t, J=5.7 Hz, 1H), 5.66 (s, 1H), 4.47 (d, J=5.7 Hz, 2H), 4.26 (q, J=7.2 Hz, 2H), 1.68 (d, J=7.2 Hz, 3H).

Example 286

¹H NMR (CDCl₃) δ 8.67 (m, 2H), 7.94 (s, 1H), 7.69 (d, J=7.8 Hz, 1H), 7.34 (m, 1H), 6.63 (t, J=5.7 Hz, 1H), 5.87 (s, 1H), 4.62 (d, J=5.7 Hz, 2H), 3.64 (s, 3H), 3.13 (m, 2H), 2.82 (m, 1H), 1.22 (m, 3H).

Example 287

¹H NMR (CDCl₃) δ 8.66 (m, 2H), 7.94 (s, 1H), 7.68 (d, J=7.8 Hz, 1H), 7.34 (m, 1H), 6.62 (t, J=6.0 Hz, 1H), 5.87 (s, 1H), 4.62 (d, J=6.0 Hz, 2H), 3.64 (s, 3H), 3.13 (m, 2H), 2.81 (m, 1H), 1.22 (m, 3H).

Example 288

¹H NMR (CDCl₃) δ 8.64 (s, 1H), 8.60 (d, J=3.6 Hz, 1H), 8.04 (s, 1H), 7.68 (m, 1H), 7.31 (m, 1H), 7.16 (m, 1H), 7.07-7.05 (m, 2H), 6.80 (t, J=6.3 Hz, 1H), 5.93 (s, 1H), 4.64 (d, J=6.3 Hz, 2H), 2.08 (s, 6H).

Example 289

¹H NMR (CDCl₃) δ 8.72 (s, 1H), 8.62 (d, J=4.8 Hz, 1H), 7.99-7.97 (m, 2H), 7.73-7.69 (m, 2H), 7.40-7.33 (m, 2H), 6.67 (t, J=6.0 Hz, 1H), 6.29 (s, 1H), 4.71 (d, J=6.0 Hz, 2H).

Example 290

¹H NMR (CDCl₃) δ 8.73 (s, 1H), 8.62 (d, J=4.5 Hz, 1H), 8.01 (s, 1H), 7.76 (m, 1H), 7.41 (d, J=5.1 Hz, 1H), 7.34 (dd, J=8.1, 5.1 Hz, 1H), 7.05 (d, J=5.1 Hz, 1H), 7.01 (s, 1H), 6.79 (t, J=6.0 Hz, 1H), 4.74 (d, J=6.0 Hz, 2H).

Example 291

¹H NMR (DMSO-d₆) δ 9.12 (s, 1H), 8.40 (s, 1H), 8.33 (s, 1H), 8.13 (m, 1H), 7.82 (d, J=5.1 Hz, 1H), 7.40-7.39 (m, 2H), 7.22 (d, J=5.1 Hz, 1H), 6.86 (s, 1H), 4.86 (s, 2H).

Example 292

¹H NMR (CDCl₃) δ 8.23 (s, 1H), 8.16 (d, J=6.0 Hz, 1H), 8.06 (s, 1H), 7.31-7.05 (m, 5H), 6.86 (m, 1H), 5.87 (s, 1H), 4.62 (d, J=6.3 Hz, 2H), 2.09 (s, 6H).

Example 293

¹H NMR (CDCl₃) δ 8.14 (s, 1H), 8.12 (d, J=6.3 Hz, 1H), 7.94 (s, 1H), 7.29-7.16 (m, 6H), 7.07 (m, 1H), 6.78 (t, J=6.0 Hz, 1H), 5.54 (s, 1H), 4.44 (d, J=6.0 Hz, 2H), 4.24 (t, J=7.2 Hz, 1H), 1.68 (d, J=7.2 Hz, 3H).

Example 294

¹H NMR (CDCl₃) δ 8.67 (s, 1H), 8.59 (d, J=4.8 Hz, 1H), 8.01 (s, 1H), 7.71 (m, 1H), 7.52 (dd, J=7.8, 1.8 Hz, 1H), 7.40-7.19 (m, 4H), 6.78 (t, J=6.0 Hz, 1H), 6.32 (s, 1H), 4.67 (d, J=6.0 Hz, 2H), 2.38 (s, 3H).

Example 295

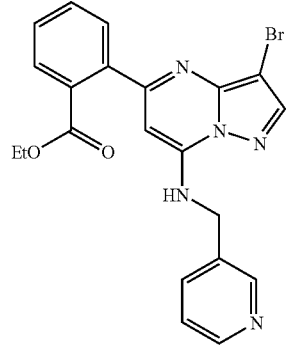
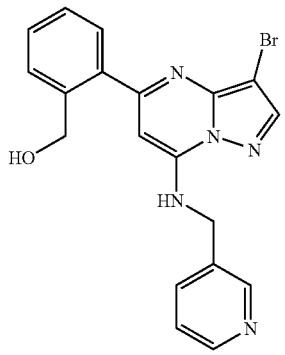

To a suspension of lithium aluminum hydride (10 mg, 0.26 mmol) in anhydrous THF (2 mL) at 0° C. was added dropwise a solution of the compound prepared in Example 283 (20 mg, 0.044 mmol) in anhydrous THF (2 mL). The resulting mixture was refluxed for 1 hr and stirred at room temperature overnight, neutralized with dilute sulfuric acid, and extracted with EtOAc. The organic phase was dried over MgSO$_4$ and concentrated under reduced pressure. The crude product was purified by preparative thin-layer chromatography using a 5% MeOH in EtOAc solution as eluent (15 mg, 83% yield). LCMS: MH$^+$=410; $^1$H NMR (CDCl$_3$) δ 8.69 (s, 1H), 8.61 (d, J=3.9 Hz, 1H), 8.05 (d, J=2.1 Hz, 1H), 7.74 (d, J=7.8 Hz, 1H), 7.52-7.31 (m, 5H), 6.97 (t, J=6.3 Hz, 1H), 6.55 (d, J=2.7 Hz, 1H), 6.20 (s, 1H), 4.71 (d, J=6.3 Hz, 2H), 4.52 (s, 2H).

Example 296

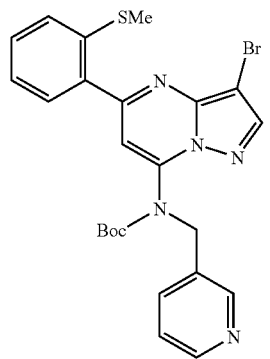

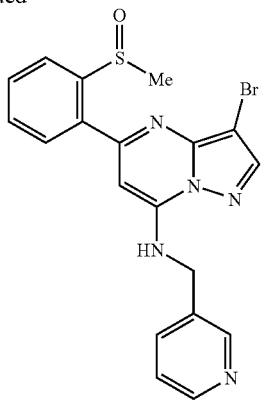

To a solution of the N-Boc-protected compound prepared in Example 294 (45 mg, 0.085 mmol) in CH$_2$Cl$_2$ (4 mL) at −50° C. was added m-CPBA (18 mg, 0.10 mmol). After stirring for 1 hr at −50° C. more m-CPBA (4 mg, 0.02 mmol) was added. The mixture was stirred for a further 2 hr, diluted with CH$_2$Cl$_2$ (20 mL), and washed with saturated NaHCO$_3$ (20 mL). The organic phase was dried over MgSO$_4$ and concentrated under reduced pressure. The residue was purified by preparative thin-layer chromatography using a 2.5% MeOH in CH$_2$Cl$_2$ solution as eluent. A solution of the obtained N-Boc-protected product (37 mg, 80% yield, LCMS: MH$^+$=542) and TFA (1 mL) in CH$_2$Cl$_2$ (2 mL) was stirred at room temperature for 2 hr. The volatiles were removed under reduced pressure. The residue was dissolved in CH$_2$Cl$_2$, neutralized with saturated NaHCO$_3$, and extracted with CH$_2$Cl$_2$. The organic phase was dried over MgSO$_4$ and concentrated under reduced pressure. The crude product was purified by preparative thin-layer chromatography using a 5% MeOH in EtOAc solution as eluent (26 mg, 89% yield). LCMS: MH$^+$=442; $^1$H NMR (CDCl$_3$) δ 8.71 (s, 1H), 8.64 (d, J=3.9 Hz, 1H), 8.41 (m, 1H), 8.03 (s, 1H), 7.75-7.54 (m, 4H), 7.36 (dd, J=8.1, 5.1 Hz, 1H), 6.81 (t, J=6.0 Hz, 1H), 6.34 (s, 1H), 4.74 (d, J=6.0 Hz, 2H), 3.25 (s, 3H).

Example 297

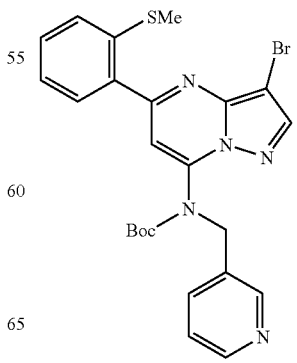
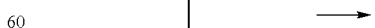

371
-continued

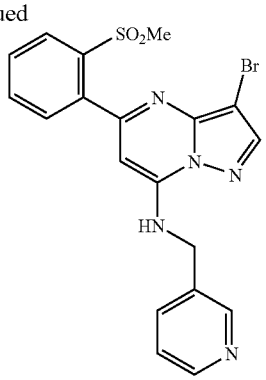

To a solution of the N-Boc-protected compound prepared in Example 294 (56 mg, 0.11 mmol) in CH$_2$Cl$_2$ (4 mL) at 0° C. was added m-CPBA (42 mg, 0.24 mmol). After stirring for 2 hr at room temperature more m-CPBA (13 mg, 0.075 mmol) was added. The mixture was stirred at room temperature overnight, diluted with CH$_2$Cl$_2$ (20 mL), and washed with saturated NaHCO$_3$ (20 mL). The organic phase was dried over MgSO$_4$ and concentrated under reduced pressure. The residue was purified by preparative thin-layer chromatography using a 2.5% MeOH in EtOAc solution as eluent. A solution of the obtained N-Boc-protected product (29 mg, 49% yield, LCMS: MH$^+$=558) and TFA (1 mL) in CH$_2$Cl$_2$ (2 mL) was stirred at room temperature for 2 hr. The volatiles were removed under reduced pressure. The residue was dissolved in CH$_2$Cl$_2$, neutralized with saturated NaHCO$_3$, and extracted with CH$_2$Cl$_2$. The organic phase was dried over MgSO$_4$ and concentrated under reduced pressure. The crude product was purified by preparative thin-layer chromatography using a 2.5% MeOH in EtOAc solution as eluent (21 mg,

372
90% yield). LCMS: MH$^+$=458; $^1$H NMR (CDCl$_3$) δ 8.64 (s, 2H), 8.20 (m, 1H), 8.01 (s, 1H), 7.73-7.60 (m, 3H), 7.46 (m, 1H), 7.35 (s, 1H), 6.82 (t, J=5.9 Hz, 1H), 6.17 (s, 1H), 4.65 (d, J=5.7 Hz, 2H), 3.60 (s, 3H).

Example 298

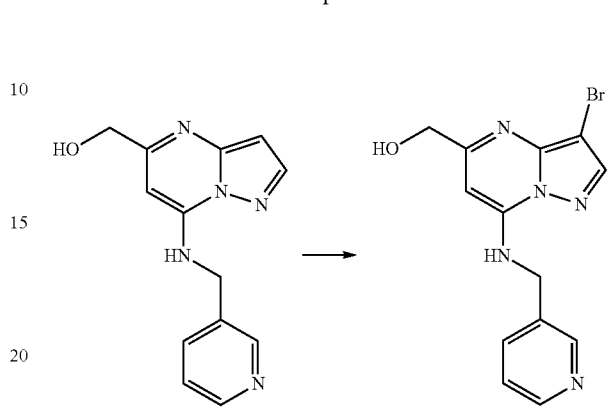

By essentially the same procedure set forth in Preparative Example 127 only substituting the compound prepared in Preparative Example 189, the above compound was prepared. MS: MH$^+$=334; mp=170-173° C.

Examples 299-300

By essentially the same procedure set forth in Example 298 only substituting the compound shown in Table 27, Column 2, the compounds shown in Table 27, Column 3 were prepared:

TABLE 27

| Ex. | Column 2 | Column 3 | CMPD |
|---|---|---|---|
| 299 | | | MS: MH$^+$ = 348<br>m.p. = 73-83° C. |
| 300 | | | MS: MH$^+$ = 362<br>m.p. = 165-175° C. |

Example 301

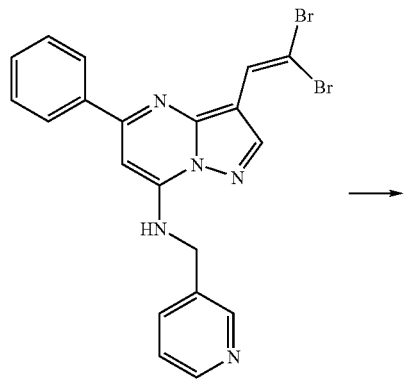

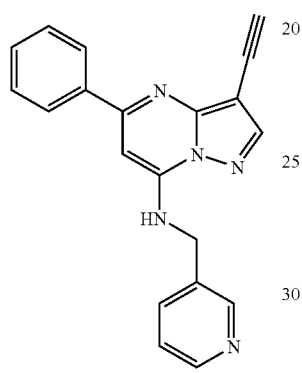

To a solution of the compound prepared in Preparative Example 186 (0.1 g, 0.21 mmol) in THF (4.0 mL) at −78° C. was added nBuLi (0.57 mL, 2.16M in hexanes, 5.0 eq.) at −78° C. The reaction mixture was stirred 2 hours at −78° C., quenched with $H_2O$, warmed to room temperature, and extracted with EtOAc. The combined organics were dried over $Na_2SO_4$, filtered, and concentrated under reduced pressure. The crude product was purified by Preparative TLC using a 2.5% (10% $NH_4OH$ in $CH_3OH$) solution in $CH_2Cl_2$ as eluent (0.013 g, 20% yield). MS: $MH^+$=326; mp=71-72° C.

Example 302

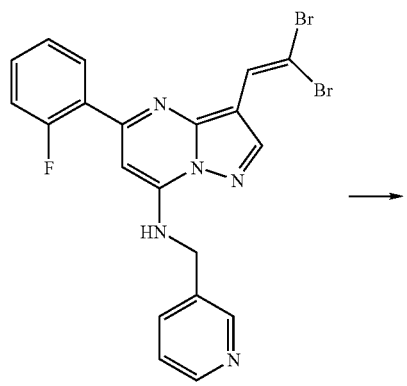

By essentially the same procedure set forth in Example 301 only substituting the compound from Preparative Example 187, the above compound was prepared (0.049 g, 68% yield). MS: $MH^+$=344; mp=69-71° C.

Example 303

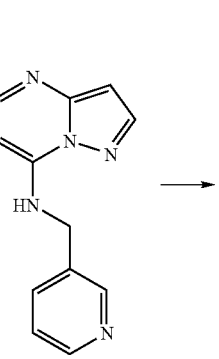

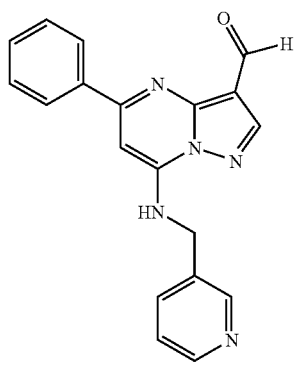

To a solution of 3-H adduct from Preparative Example 187.1 (0.70 g, 2.32 mmol) in DMF (4.2 mL) at 0° C. was added $POCl_3$ (0.67 mL, 7.2 mmol) dropwise. The mixture was stirred for 14 h at rt, cooled to 0° C., and was quenched by addition of ice. 1N NaOH was carefully added to adjust pH to 8 and the mixture was extracted with $CH_2Cl_2$ (3×25 mL). The organic layers were combined, dried ($Na_2SO_4$), filtered, and concentrated under reduced pressure. The crude product was recrystallized from EtOAc to afford 0.43 g (56%) of a yellow solid. mp 181-183° C.; M+H=330.

Example 304

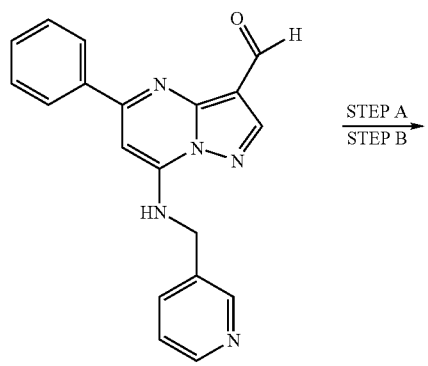

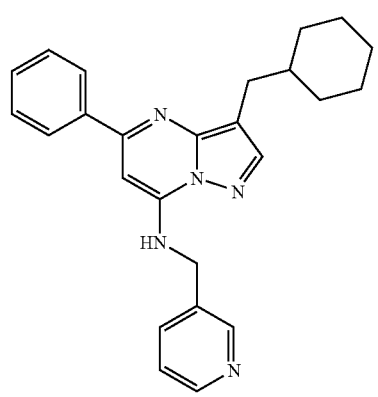 [SMILES: c1ccc(Cc2cnn3c(NCc4cccnc4)cc(-c4ccccc4)nc23)cc1]

Step A:

To a solution of aldehyde (100 mg, 0.30 mmol) from Example 303 in THF (1 mL) at 0° C. was added cyclohexyl magnesium bromide (0.46 mL, 2.0M in $Et_2O$) dropwise over 5 min. The resulting mixture was stirred at 0° C. for 2 h and at rt for 12 h. The mixture was cooled to 0° C. and was treated with sat. aq. $NH_4Cl$ (3 mL) and $CH_2Cl_2$ (5 mL). The layers were separated and the aqueous layer was extracted with $CH_2Cl_2$ (2×5 mL). The organic layers were combined, washed with brine (1×5 mL), dried ($Na_2SO_4$), filtered and concentrated under reduced pressure to afford 110 mg (89%) of a light yellow semisolid. M+H=414. This material was carried on crude to Step B without further purification.

Step B:

To a solution of alcohol (53 mg, 0.13 mmol) in $CH_2Cl_2$ (0.5 mL) at 0° C. was added $Et_3SiH$ (24 µL, 0.15 mmol) followed by TFA (24 µL, 0.30 mmol). The mixture was stirred for 2 h at 0° C. and rt for 2 h whereupon additional portions of $Et_3SiH$ (24 µL, 0.15 mmol) and TFA (24 µL, 0.30 mmol) were added and the mixture was stirred for 3 h at rt (until complete by TLC). The mixture was concentrated under reduced pressure and the crude residue was partitioned between $CH_2Cl_2$ (5 mL) and sat. aq. $NaHCO_3$ (2.5 mL). The layers were separated and the aqueous layer was extracted with $CH_2Cl_2$ (2×5 mL). The organic layers were combined, washed with brine (1×5 mL), dried ($Na_2SO_4$), filtered and concentrated under reduced pressure. The crude product was purified by prep TLC (8×1000 mM) eluting with $CH_2Cl_2$/MeOH (22:1) to afford 29 mg (56%) of a yellow semisolid. M+H=398.

Examples 305-312

By essentially the same procedure set forth in Example 304, utilizing the aldehyde from Example 303 and substituting the Grignard or organolithium reagents shown in Column 2 of Table 28, the compounds in Column 3 of Table 28 were prepared:

TABLE 28

| Ex. | Column 2 (Organometallic) | Column 3 (Final Structure) | CMPD 1. mp (° C.) 2. M + H |
|---|---|---|---|
| 305 | ⟨Ph⟩—MgBr | [structure] | 1. yellow oil 2. M + H = 392 |

TABLE 28-continued

| Ex. | Column 2 (Organometallic) | Column 3 (Final Structure) | CMPD 1. mp (° C.) 2. M + H |
|---|---|---|---|
| 306 | ≡—MgBr | [structure] | 1. red oil 2. M + H = 353 |
| 307 | 2-thienyl-Li | [structure] | 1. red oil 2. M + H = 398 |
| 308 | benzyl-MgCl | [structure] | 1. yellow oil 2. M + H = 406 |
| 309 | cyclopentyl-MgBr | [structure] | 1. yellow semisolid 2. M + H = 384 |

TABLE 28-continued

| Ex. | Column 2 (Organometallic) | Column 3 (Final Structure) | CMPD 1. mp (° C.) 2. M + H |
|---|---|---|---|
| 310 | ≡—MgBr | | 1. semisolid 2. M + H = 340 |
| 311 | iBu-MgCl | | 1. mp = 141-143 2. M + H = 358 |
| 312 | tBu-MgCl | | 1. mp = 148-150 2. M + H = 372 |

Example 313

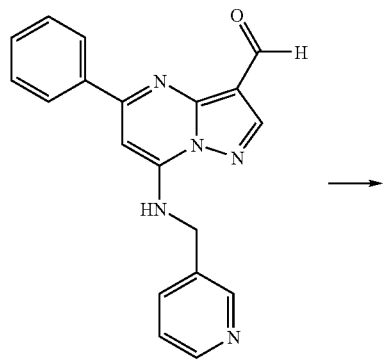

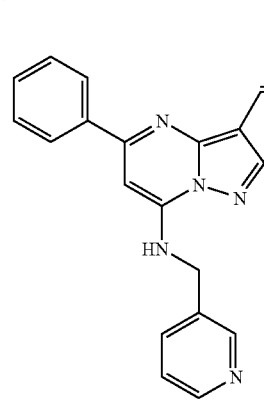

To solution of aldehyde (81 mg, 0.25 mmol) from Example 303 in benzene (2.5 mL) was added carboethoxymethylene triphenyl phosphorane (0.12 g, 0.33 mmol) in one portion. The mixture was heated at reflux for 24 h, cooled to rt, and concentrated under reduced pressure. The mixture was diluted CH$_2$Cl$_2$ (5 mL), brine (2 mL) was added, and the layers were separated. The aqueous layer was extracted with CH$_2$Cl$_2$ (2×4 mL). The organic layers were combined, dried (Na$_2$SO$_4$), filtered, and concentrated under reduced pressure. The crude product was purified by preparative TLC (8×1000 μM) eluting with CH$_2$Cl$_2$/MeOH (20:1) to afford 98 mg (100%) of white solid. mp 151-153° C.; M+H=400.

Example 314

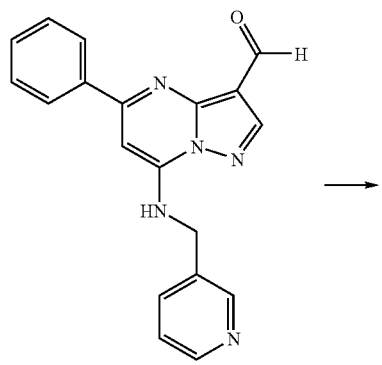

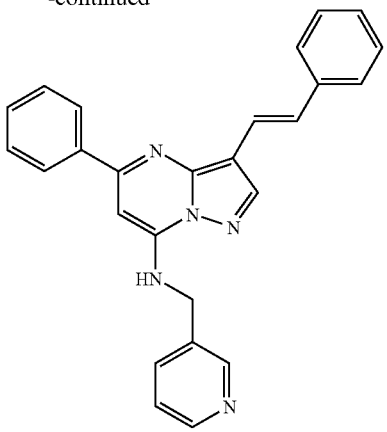

To a mixture of benzyltriphenylphosphonium bromide (0.59 g, 1.37 mmol) in THF (3 mL) was added NaH (55 mg, 1.37 mmol) and the mixture was stirred for 30 min. The aldehyde (0.15 g, 0.46 mmol) from Example 303 was added in a single portion and the mixture was heated at reflux for 36 h. The mixture was cooled to rt and was concentrated under reduced pressure. The mixture was diluted CH$_2$Cl$_2$ (5 mL), brine (2 mL) was added, and the layers were separated. The aqueous layer was extracted with CH$_2$Cl$_2$ (2×4 mL). The organic layers were combined, dried (Na$_2$SO$_4$), filtered, and concentrated under reduced pressure. The crude product was purified by preparative TLC (8×1000 μM) eluting with CH$_2$Cl$_2$/MeOH (20:1) to afford 58 mg (32%) of yellow solid. mp 138-141° C.; M+H=404.

Example 315

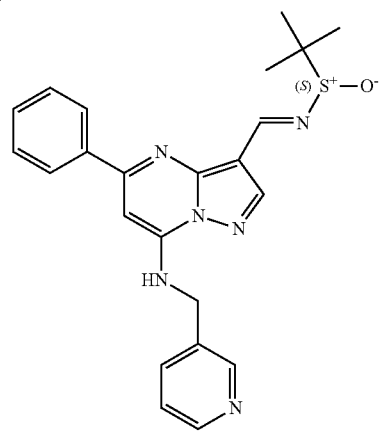

To a solution of aldehyde (0.20 g, 0.60 mmol) from Example 303 in THF (3 mL) was added Ti (i-OPr)$_4$ (0.36 mL, 1.21 mmol) dropwise followed by addition of (S)-(–)-2-methyl-2-propanesulfinamide (74 mg, 0.61 mmol). The resulting mixture was stirred for 18 h at reflux, cooled to rt, and quenched with brine (2 mL). The mixture was filtered thru a pad of Celite which was washed with EtOAc (2×2 mL). The layers were separated and the aqueous layer was extracted with EtOAc (2×4 mL). The organic layers were combined, dried (Na$_2$SO$_4$), filtered, and concentrated under reduced pressure. The crude product was purified by preparative TLC (8×1000 μM) eluting with CH$_2$Cl$_2$/MeOH (20:1) to afford 0.21 g (80%) of yellow solid. mp 108-110° C.; M+H=433.

Example 316

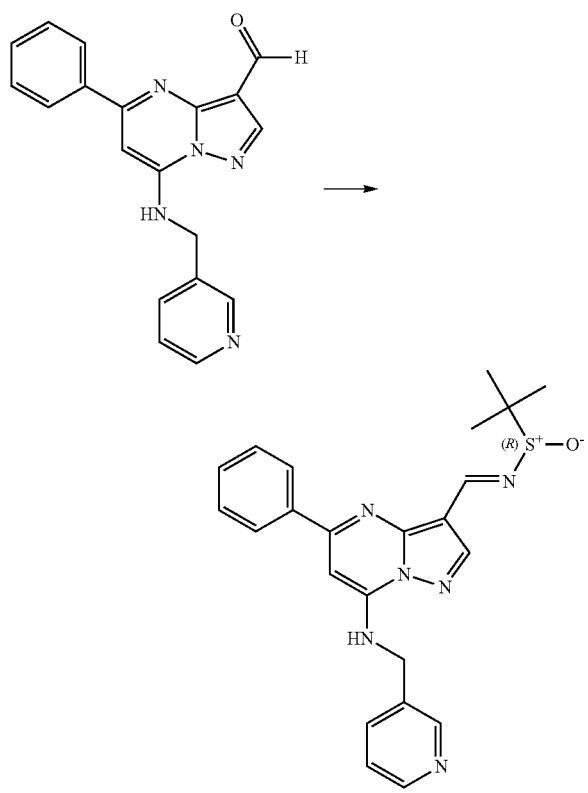

Prepared in the same fashion as Example 315 except substituting (R)-(–)-2-methyl-2-propanesulfinamide to afford 0.25 g (94%) as a yellow solid. mp 107-109° C.; M+H=433.

Example 317

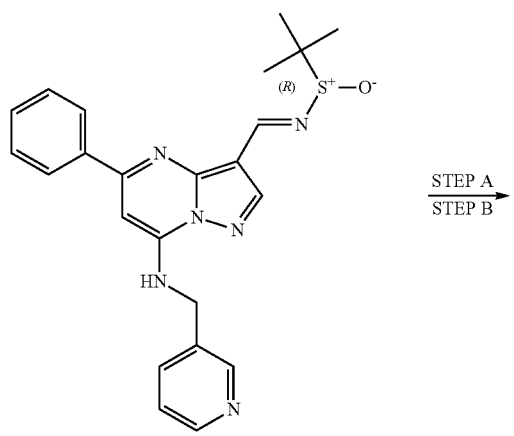

STEP A
STEP B

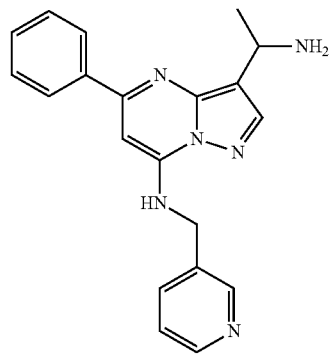

Step A:

To a solution of sulfinimine (50 mg, 0.12 mmol) from Example 316 in CH$_2$Cl$_2$ (2.5 mL) at –40° C. was added MeMgBr (96 mL, 0.29 mmol) dropwise. The mixture was stirred for 5 h at –40° C. and was stirred at rt for 12 h. An additional portion of MeMgBr (96 mL, 0.29 mmol) and the mixture was stirred for 12 h. Sat. aq. NH$_4$Cl (2 mL) was added and the mixture was extracted with EtOAc (3×4 mL). The organic layers were combined, dried (Na$_2$SO$_4$), filtered, and concentrated under reduced pressure to afford 30 mg (58%) of crude residue. This material was taken onto the next step without purification.

Step B:

The crude material from Step A (30 mg, 0.067 mmol) in MeOH (2 mL) was added conc. HCl (2 mL). The mixture was stirred at rt for 12 h and the mixture was concentrated to dryness. The crude material was partitioned between CH$_2$Cl$_2$ (3 mL) and sat. aq. NaHCO$_3$ (2 mL) and the layers were separated. The aqueous layer was extracted with CH$_2$Cl$_2$ (2×3 mL) and the organic layers were combined. The organic layer was dried (Na$_2$SO$_4$), filtered, and concentrated under reduced pressure to afford 6 mg (24%) of the title compound as a light yellow solid. mp 100-102° C.; M+H=345.

Example 318

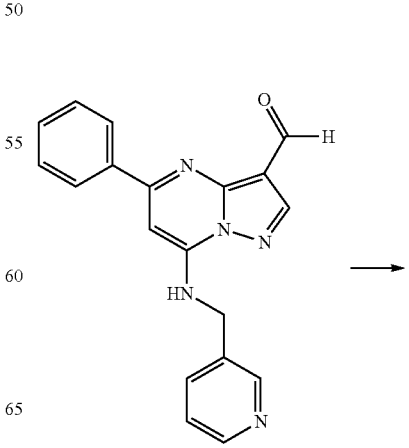

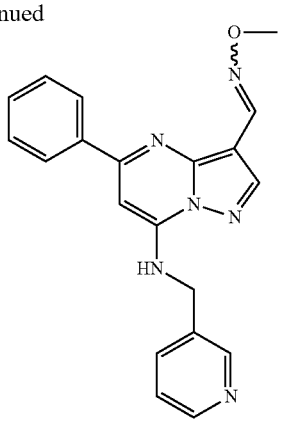

To a solution of aldehyde (75 mg, 0.23 mmol) from Example 300 in THF/CH$_2$Cl$_2$ (5 mL/1 mL) at rt was added MeONH$_2$·HCl (38 mg, 0.46 mmol) followed by dropwise addition of pyridine (46 µL, 0.57 mmol). The mixture was stirred for 72 h at rt whereupon the mixture was concentrated to dryness. The crude material was partitioned between CH$_2$Cl$_2$ (3 mL) and sat. aq. NaHCO$_3$ (2 mL) and the layers were separated. The aqueous layer was extracted with CH$_2$Cl$_2$ (2×3 mL) and the organic layers were combined. The organic layer was dried (Na$_2$SO$_4$), filtered, and concentrated under reduced pressure. The crude product was purified by preparative TLC (3×1000 µM) eluting with CH$_2$Cl$_2$/MeOH (22:1) to afford 90 mg (100%) of light yellow solid. mp 173-175° C.; M+H=359.

Example 319

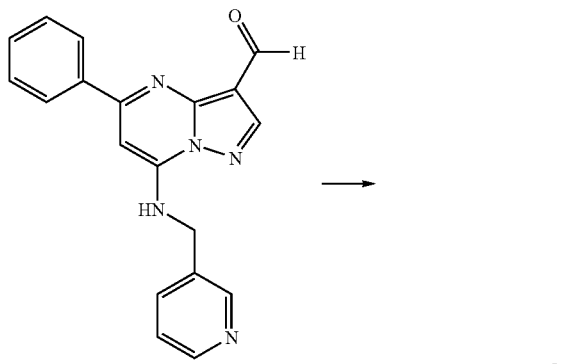

To solution of aldehyde (60 mg, 0.18 mmol) from Example 303 at EtOH (2.5 mL) was added oxindole (48 mg, 0.37

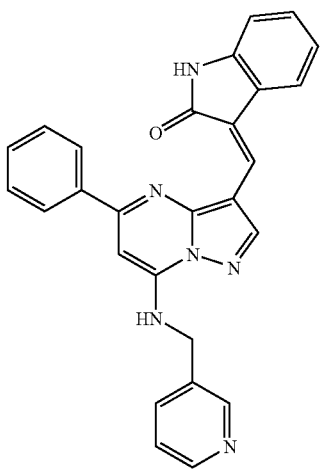

mmol) followed by piperidine (3 drops). The mixture was heated at reflux for 14 h and the mixture was cooled to rt. The resultant precipitate was filtered and washed with cold EtOH (2×2 mL). The product was dried under high vacuum to afford 81 mg (100%) of the title compound as an orange/brown solid. mp 182-185° C.; M+H=445.

Example 320

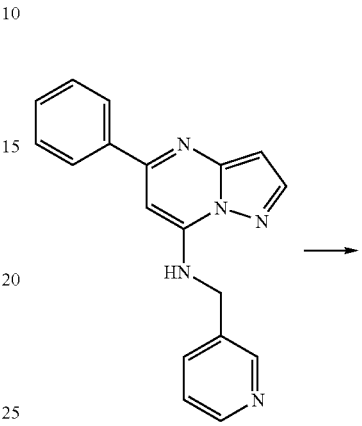

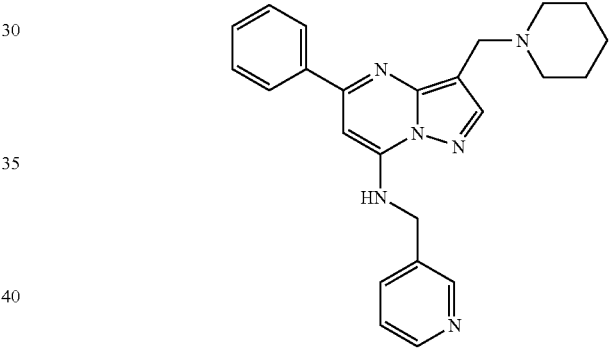

To a solution of 3-H analog (106 mg, 0.35 mmol) from Preparative Example 187.10 in AcOH (2 mL) was added 37% aqueous formaldehyde (1.5 ml; 1.40 mmol) followed by piperidine (100 µL; 0.37 mmol). The resulting mixture was stirred at rt for 24 h and the AcOH was removed under reduced pressure. The mixture was diluted with water (2 mL) and neutralized with 2M NaOH until pH=8. The aqueous layer was extracted with CH$_2$Cl$_2$ (3×7 mL) and the organic layers were combined. The organic layer was washed with brine (1×4 mL), dried (Na$_2$SO$_4$), filtered, and concentrated under reduced pressure to afford 96 mg (69%) of an off-white solid. mp 88-90° C.; M+H 399.

Examples 321-322

By essentially the same procedure set forth in Example 320 only substituting the amines in Column 2 of Table 29 and employing the 3-H adduct from Preparative Example 187.10, the compounds in Column 3 of Table 29 were prepared:

TABLE 29

| Ex. | Column 2 (Amine) | Column 3 (Final Structure) | CMPD 1. mp (° C.) 2. M + H |
|---|---|---|---|
| 321 | | | 1. mp = 178-180 2. M + H = 401 |
| 322 | | | 1. mp = 102-104 2. M + H = 414 |

Example 323

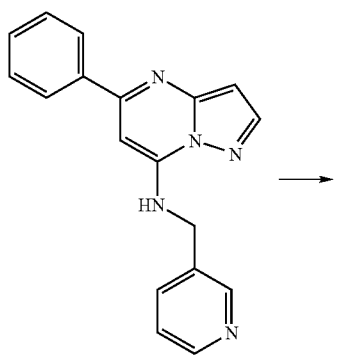

To a solution of 3-H analog (113 mg, 0.38 mmol) from Preparative Example 187.10 in CH$_2$Cl$_2$ (5 mL) at rt was added AlCl$_3$ (215 mg, 1.61 mmol) followed by AcCl (100 mL, 1.40 mmol). The mixture was heated at reflux for 12 h and was cooled to rt. The mixture was treated sequentially with 3M HCl (3 mL) followed by sat. aq. NaHCO$_3$ (until pH=8). The layers were separated and the aqueous layer was extracted with CH$_2$Cl$_2$ (2×5 mL). The organic layers were combined, dried (Na$_2$SO$_4$), filtered, and concentrated under reduced pressure. The crude product was purified by preparative TLC (8×1000 mM) eluting with CH$_2$Cl$_2$/MeOH (20:1) to afford 68 mg (52%) of white solid. mp 220-221° C.; M+H=344.

Example 324

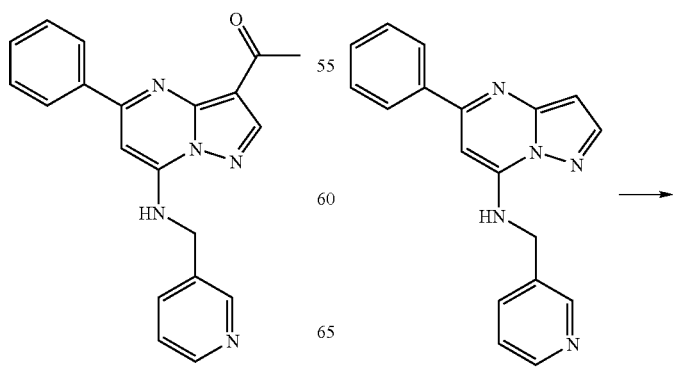

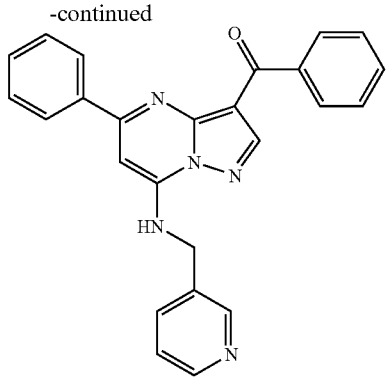

Utilizing the method described in Example 323, except employing benzoyl chloride, the title compound was prepared in 61% yield as a white solid. mp 172-175° C.; M+H=406.

Example 325

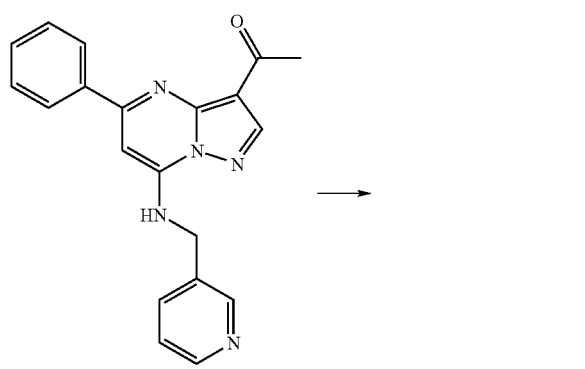

To a solution of ketone (100 mg, 0.29 mmol) from Example 323 in CH$_2$Cl$_2$ (2.5 mL) at 0° C. was added MeMgBr (0.35 mL, 3.0M in Et$_2$O) dropwise. The resulting mixture was stirred for 18 h at rt and was carefully quenched by addition of sat. aq. NH$_4$Cl (2 mL) and CH$_2$Cl$_2$ (2 mL) were added. The layers were separated and the aqueous layer was extracted with CH$_2$Cl$_2$ (2×4 mL). The organic layers were combined, dried (Na$_2$SO$_4$), filtered, and concentrated under reduced pressure. The crude product was purified by preparative TLC (8×1000 μM) eluting with CH$_2$Cl$_2$/MeOH (10:1) to afford 68 mg (52%) of a yellow solid. mp 160-162° C.; M+H=360.

Example 326

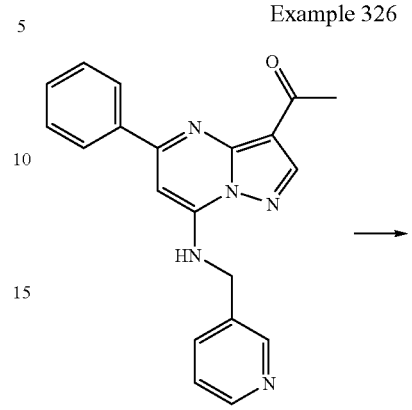

To a solution of ketone (84 mg, 0.24 mmol) from Example 323 in MeOH/THF (1:1; 2 mL total) at 0° C. was added NaBH$_4$ (12 mg, 0.30 mmol) in one portion. The resulting mixture was stirred for 18 h at rt whereupon and additional portion of NaBH$_4$ (12 mg, 0.30 mmol) was added. The mixture was stirred for 12 h whereupon the mixture was quenched with ice followed by addition of 1M NaOH to adjust the pH=9. The mixture was diluted with CH$_2$Cl$_2$ (5 mL). The layers were separated and the aqueous layer was extracted with CH$_2$Cl$_2$ (2×4 mL). The organic layers were combined, dried (Na$_2$SO$_4$), filtered, and concentrated under reduced pressure. The crude product was purified by preparative TLC (8×1000 μM) eluting with CH$_2$Cl$_2$/MeOH (10:1) to afford 25 mg (30%) of a yellow solid. mp 148-150° C.; M+H=346.

Example 327

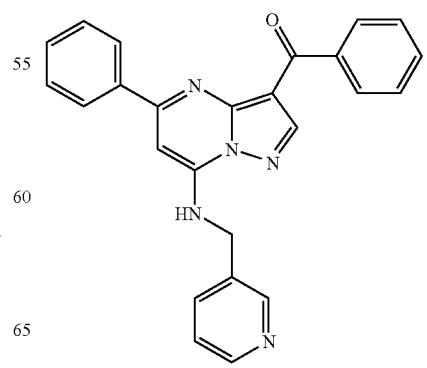

-continued

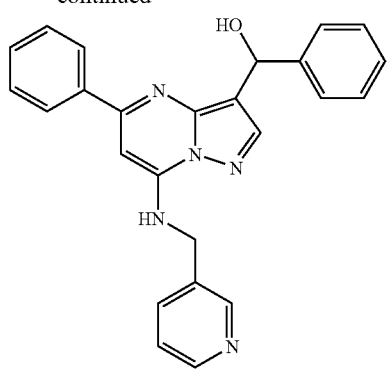

Using the same procedure as outlined in Example 326, the ketone (84 mg, 0.21 mmol) was converted to 53 mg (62%) as a light yellow solid. mp 78-80° C.; M+H=408.

Example 328

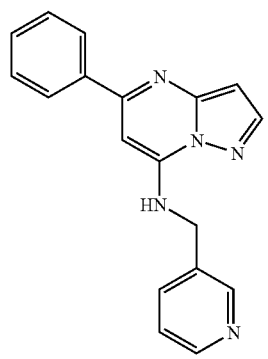

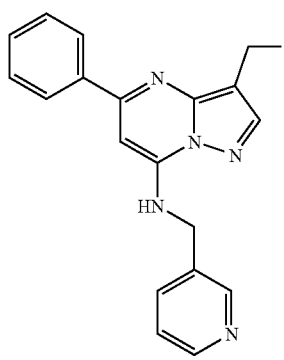

To a solution of 3-H adduct (1.3 g, 4.31 mmol) from Preparative Example 187.10 in $CH_2Cl_2$ (50 mL) was added Eschenmoser's salt (0.79 g, 4.31 mmol) followed by dropwise addition of TFA (0.56 mL, 7.33 mmol). The mixture was stirred at rt for 48 h and was diluted with $CH_2Cl_2$ (250 mL).

The organic layer was washed with sat. aq. $NaHCO_3$ (2×125 mL) to afford 1.41 h (92%) of a yellow solid. mp 231-233° C.; M+H=359.

Example 329

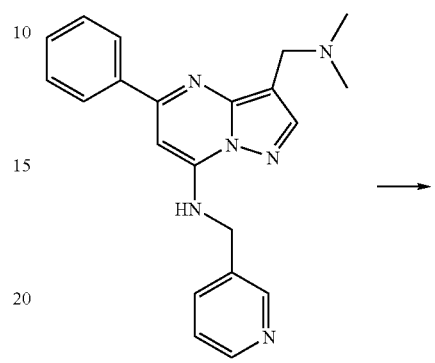

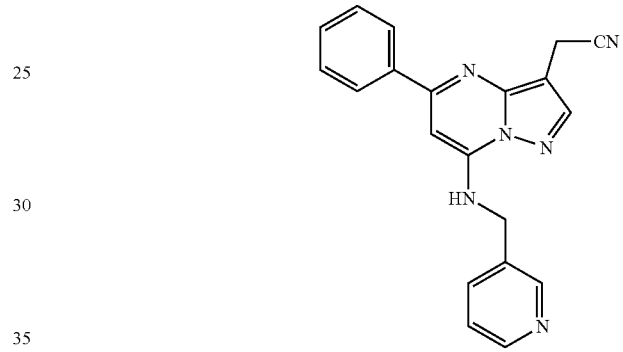

To a solution of tertiary amine adduct (100 mg, 0.28 mmol) from Example 328 in 50% aq. DMF (5 mL) in a pressure tube was added KCN (0.15 g, 2.32 mmol). The tube was capped and heated at 100° C. for 96 h. The mixture was cooled to rt and was diluted with EtOAc (25 mL). The organic layer was washed with brine (1×5 mL) and water (1×5 mL). The organic layers was dried ($Na_2SO_4$), filtered, and concentrated under reduced pressure. The crude product was purified by preparative TLC (4×1000 μM) eluting with EtOAc to afford 21 mg (30%) of brown solid. mp 152-155° C.; M+H=341.

Example 330

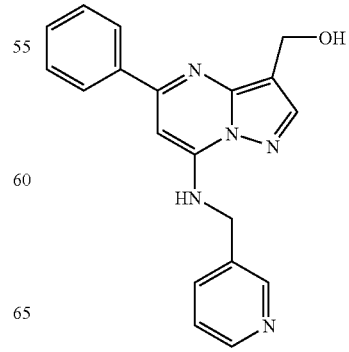

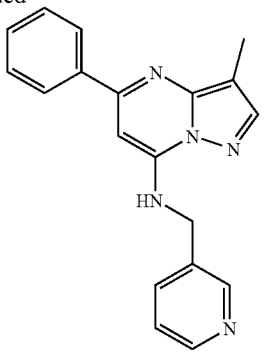

To a solution of alcohol (45 mg, 0.14 mmol) from Example 17.10 in CH$_2$Cl$_2$ (0.7 mL) at 0° C. was added Et$_3$SiH (26 µL, 0.16 mmol) followed by TFA (25 µL, 0.33 mmol). The mixture was stirred for 2 h at 0° C. and rt for 2 h whereupon additional portions of Et$_3$SiH (26 mL, 0.16 mmol) and TFA (25 µL, 0.33 mmol) were added and the mixture was stirred for 4 h at rt (until complete by TLC). The mixture was concentrated under reduced pressure and the crude residue was partitioned between CH$_2$Cl$_2$ (3 mL) and sat. aq. NaHCO$_3$ (1.5 mL). The layers were separated and the aqueous layer was extracted with CH$_2$Cl$_2$ (2×4 mL). The organic layers were combined, washed with brine (1×5 mL), dried (Na$_2$SO$_4$), filtered and concentrated under reduced pressure. The crude product was purified by prep TLC (4×1000 mM) eluting with CH$_2$Cl$_2$/MeOH (20:1) to afford 21 mg (48%) of a yellow solid. mp 146-148° C.; M+H=316.

Example 331

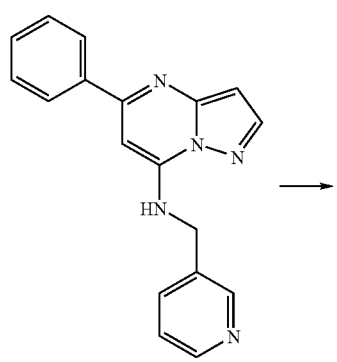

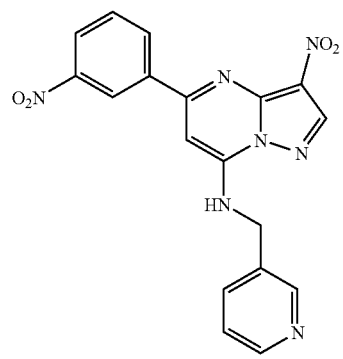

To a solution of 3-H adduct (90 mg, 0.30 mmol) from Preparative Example 187.10 in conc. H$_2$SO$_4$ (2 mL) at 0° C. was added fuming HNO$_3$ (30 µL, 0.72 mmol) dropwise. The resulting mixture was stirred for 1 h at 0° C. whereupon ice (~1 g) was added to the mixture. The resulting precipitate was collected and was washed with water (2×2 mL) and CH$_2$Cl$_2$ (2×2 mL). The crude product was dried under high vacuum to afford 67 mg (60%) of the monosulfate salt as a yellow/orange solid. mp 250° C.; M+H (free base)=392.

Example 332

Step A

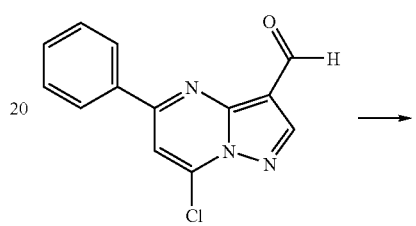

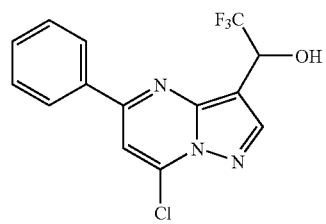

To a solution of aldehyde (0.10 g, 0.39 mmol) from Preparative Example 168 in THF (2.5 mL) at 0° C. was added CF$_3$TMS (64 mL, 0.43 mmol) followed by CsF (10 mg). The resulting mixture was stirred for 2 h at 0° C. and 2 h at rt. 1M HCl (5 mL) was added and the mixture was diluted with CH$_2$Cl$_2$ (10 mL). The layers were separated, the aqueous layer was extracted with CH$_2$Cl$_2$ (2×10 mL), and the organic layers were combined. The organic layer was washed with brine (1×10 mL), dried (Na$_2$SO$_4$), filtered, and concentrated under reduced pressure to afford 127 mg (99%) of a yellow semisolid. M+H=328. The crude product was carried on without further purification.

Step B

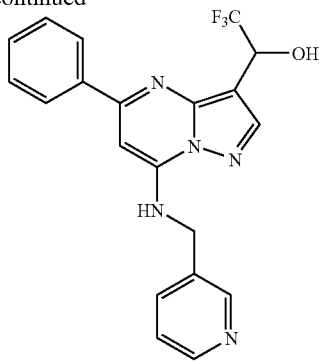

By utilizing the general procedure set forth in Example 1, the 7-Cl adduct (127 mg, 0.39 mmol) from Example 332, Step A was reacted with 3-(aminomethyl)pyridine (73 mL, 0.43 mmol) to afford 80 mg (51%) of the title compound as a light yellow solid. mp 68-72° C.; M+H=400.

Example 333

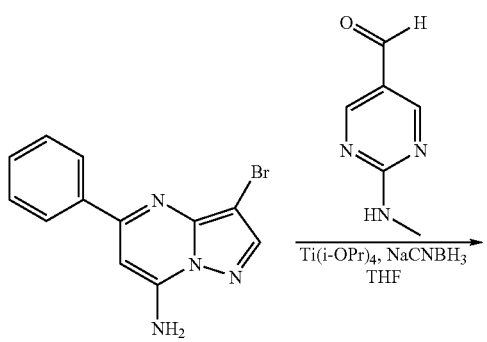

To a solution of aniline (200 mg, 0.69 mmol) from Preparative Example 174 in THF (6 mL) at rt was added aldehyde (114 mg, 0.83 mmol) from Preparative Example 256 followed by dropwise addition of Ti(i-OPr)$_4$ (0.82 mL, 2.77 mmol). The mixture was stirred at reflux for 4 h and was cooled to rt. NaCNBH$_3$ (347 mg, 5.53 mmol) was added and the mixture was stirred for 2 h at rt. The mixture was cooled to 0° C., treated with 1M NaOH (4 mL) and brine (1 mL) and stirred for 30 min. The mixture was extracted with CH$_2$Cl$_2$ (3×10 mL) and the organic layers were combined. The organic layer was washed with brine (1×7 mL), dried (Na$_2$SO$_4$), filtered, and concentrated under reduced pressure. The crude product was purified by preparative thin-layer chromatography (8×1000 uM plates) eluting with CH$_2$Cl$_2$/MeOH (25:1) to afford 89 mg (31%) of the title compound as a yellow solid. mp 210-213° C. M+H=411.

Examples 334-337

By essentially the same procedure set forth in Example 333 only by utilizing the anilines shown in Column 2 of Table 30 and the aldehydes shown in Column 3 of Table 30, the compounds in Column 4 of Table 30 were prepared:

TABLE 30

| Ex. | Column 2 (Aniline) | Column 3 (Aldehyde) | Column 4 (Final Structure) | CMPD 1. mp (° C.) 2. M + H |
|---|---|---|---|---|
| 334 | 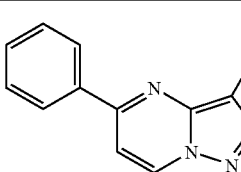 | 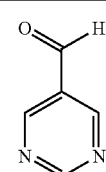 | 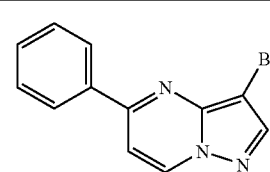 | 1. mp = 85-87 2. M + H = 425 |

TABLE 30-continued
| Ex. | Column 2 (Aniline) | Column 3 (Aldehyde) | Column 4 (Final Structure) | CMPD 1. mp (° C.) 2. M + H |
|---|---|---|---|---|
| 335 |  | 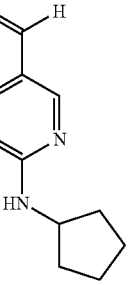 | 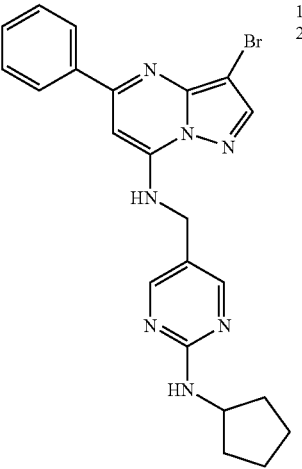 | 1. mp = 160-162 2. M + H = 451 |
| 336 |  | 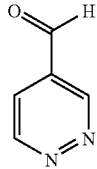 | 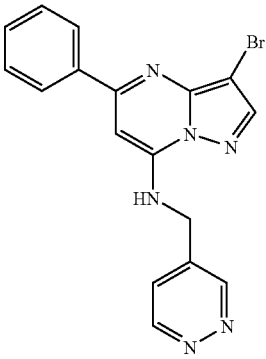 [SMILES: Brc1cnn2c(NCc3ccnnc3)cc(-c3ccccc3)nc12] | 1. mp = 117-119 2. M + H = 382 |
| 337 | 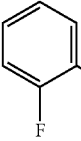 | 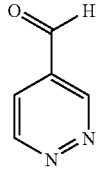 | 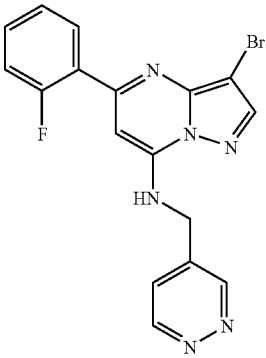 [SMILES: Fc1ccccc1-c1cc(NCc2ccnnc2)n2ncc(Br)c2n1] | 1. mp = 171-175 2. M + H = 400 |

Example 338

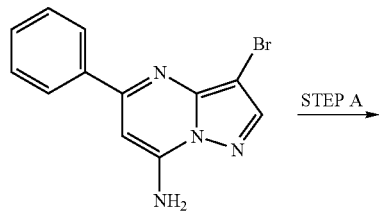

STEP A →

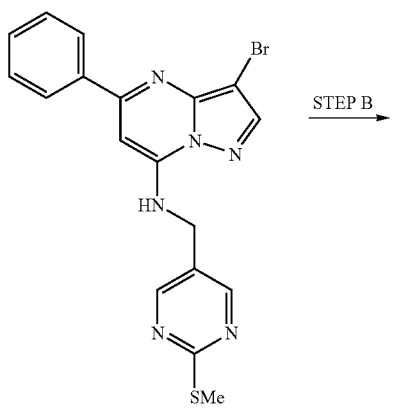

STEP B →

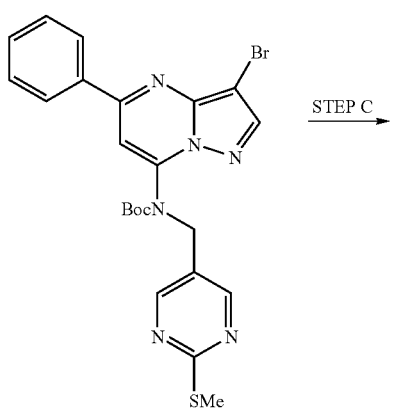

STEP C →

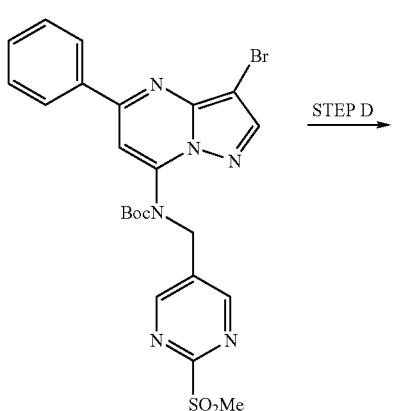

STEP D →

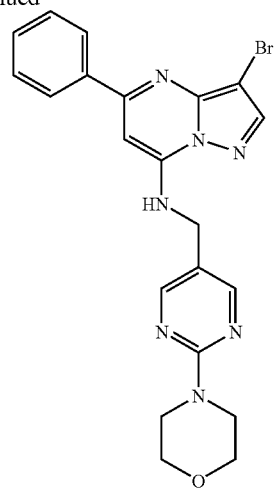

Step A:

Reaction of aniline (0.20 g, 0.69 mmol) with aldehyde (0.13 g, 0.83 mmol) under the reaction conditions described in Example 333 afforded 70 mg (23%) of thiomethyl derivative as a yellow solid. M+H=428.

Step B:

To a solution of thiomethyl derivative (60 mg, 0.14 mmol) from Example 338, Step A in dioxane (2 mL) was added Boc$_2$O (61 mg, 0.28 mmol) followed by DMAP (21 mg, 0.17 mmol). The mixture was stirred for 14 h at rt and was concentrated under reduced pressure. The crude product was purified by preparative thin-layer chromatography (6×1000 µM plates) eluting with hexanes/EtOAc (4:1) to afford 61 mg (83%) of the title compound as a yellow solid. M+H=528.

Step C:

To a solution of thiomethyl derivative from Example 338, Step B (41 mg, 0.078 mmol) in CH$_2$Cl$_2$ (2 mL) was added MCPBA (33 mg, 0.19 mmol) in one portion. The resulting mixture was stirred for 3 h at rt and the mixture was diluted with CH$_2$Cl$_2$ (5 mL) and sat. aq. NaHCO$_3$ (2.5 mL). The layers were separated, the aqueous layer was extracted with CH$_2$Cl$_2$ (2×5 mL), and the organic layers were combined. The organic layer was dried (Na$_2$SO$_4$), filtered, and concentrated under reduced pressure to afford 40 mg (92%) of the sulfone adduct as a light yellow solid. M+H=560.

Step D:

To a flask charged with sulfone from Example 338, Step C (75 mg, 0.13 mmol) and a stir bar was added morpholine (2 ml; 22 mmol). The mixture was heated at reflux for 12 h, cooled to rt, and concentrated to dryness under high vacuum. The crude product was purified by preparative thin-layer chromatography (6×1000 µM plates) eluting with CH$_2$Cl$_2$/

MeOH (40:1) to afford 41 mg (68%) of the title compound as a yellow solid. mp 209-210° C.; M+H=466.

Example 339

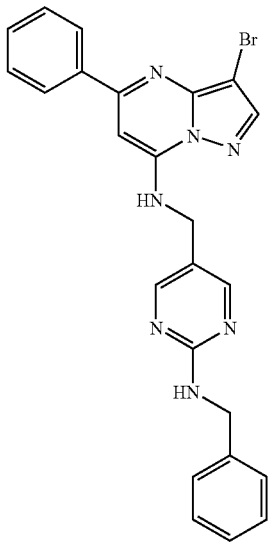 [SMILES: Brc1cnn2c(NCc3cnc(NCc4ccccc4)nc3)cc(-c3ccccc3)nc12]

The title compound was prepared according to the procedure outlined in Example 338 except using benzyl amine to afford 12 mg (70%) of a white solid. mp 194-196; M+H=487.

Example 340

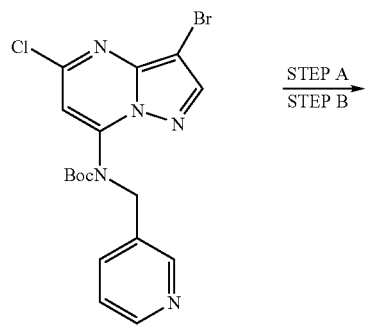

STEP A
STEP B

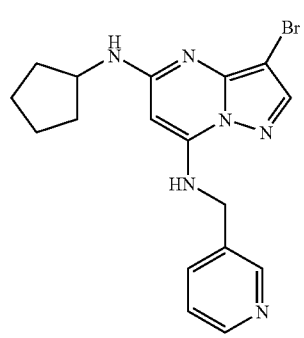

Step A:

To a solution of 5-chloro adduct (0.15 g, 0.34 mmol) in dioxane/DIPEA (2.5 mL/1.0 mL) at rt was added cyclopentylamine (0.041 μL, 0.41 mmol) dropwise. The resulting solution was stirred at reflux for 16 h, cooled to rt, and concentrated under reduced pressure. The crude material was purified by preparative thin-layer chromatography (8×1000 μM) eluting with $CH_2Cl_2$/MeOH (25:1) to afford 148 mg (89%) of a yellow oil. M+H=489.

Step B: Removal of the t-butoxycarbonyl Protecting Group with TFA

To a solution of the compound prepared in Example 340, Step A (135 mg, 0.28 mmol) in $CH_2Cl_2$ (2 mL) at rt was added TFA (0.54 mL, 7.0 mmol) dropwise. The resulting solution was stirred for 18 h at rt and was concentrated under reduced pressure. The crude material was redissolved in $CH_2Cl_2$ (5 mL) and the organic layer was sequentially washed with sat. aq. $NaHCO_3$ (2×2 mL) and brine (1×2 mL). The organic layer was dried ($Na_2SO_4$), filtered, and concentrated under reduced pressure. The crude material was purified by preparative thin-layer chromatography (8×1000 μM) eluting with $CH_2Cl_2$/MeOH (20:1) to afford 105 mg (97%) of white solid. mp 120-122° C.; M+H=389.

Example 341

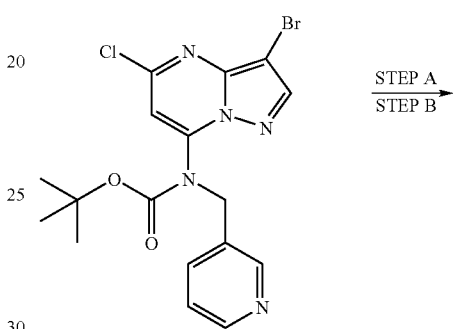

STEP A
STEP B

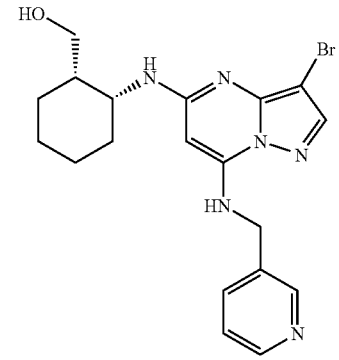

Step A:
By essentially the same procedure set forth in Example 340 only substituting the appropriate amine, the above compound was prepared. MS: $MH^+$=431.

Step B: Removal to t-butoxycarbonyl Protecting Group with KOH.

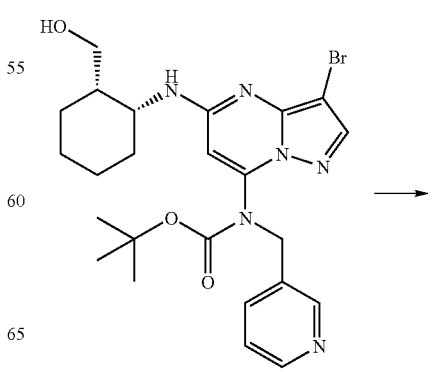

-continued

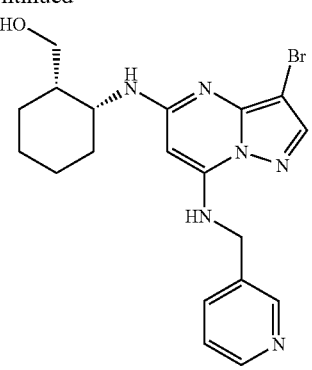

To a mixture of the compound prepared in Example 341, Step A (0.14 g, 0.26 mmol) in EtOH:H$_2$O (3 mL, 2:1) was added KOH (0.29 g, 20 eq.) in one portion. The resulting solution was stirred at reflux 14 hours, cooled to room temperature, and concentrated under reduced pressure. The residue was taken up in CH$_2$Cl$_2$ (5 mL) and diluted with saturated NaHCO$_3$ (2 mL). The layers were separated and the aqueous layer extracted with CH$_2$Cl$_2$ (2×4 mL). The combined organics were washed with brine, dried over Na$_2$SO$_4$, filtered, and concentrated under reduced pressure. The crude product was purified by preparative TLC (8×1000 µM) eluting with 5% MeOH in CH$_2$Cl$_2$ solution (0.066 g, 59% yield). MS: MH$^+$=432; mp=219-221° C.

Examples 342-397

By essentially the same procedure set forth in Example 340 only substituting the chlorides in Column 2 of Table 31 and removing the t-butoxycarbonyl protecting group by the method shown in Column 3 of Table 31, the compounds shown in Column 4 of Table 31 were prepared.

TABLE 31

| Ex. | Column 2 | Column 3 | Column 4 | CMPD |
|---|---|---|---|---|
| 342 | (structure) | HCl | (structure) | MS: MH$^+$ = 403  m.p. 151-157° C. |
| 343 | (structure) | HCl | (structure) | MS: MH$^+$ = 466  m.p. 212-217° C. |
| 344 | (structure) | HCl | (structure) | MS: MH$^+$ = 405  m.p. 53-58° C. |

TABLE 31-continued
| Ex. | Column 2 | Column 3 | Column 4 | CMPD |
|---|---|---|---|---|
| 345 | 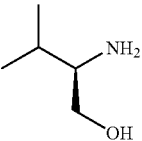 | HCl | 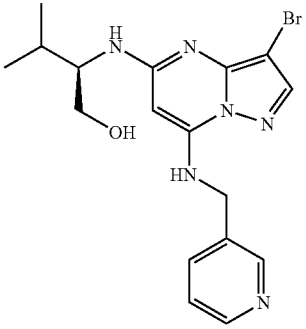 [SMILES: CC(C)[C@@H](CO)Nc1cc(NCc2cccnc2)n2ncc(Br)c2n1] | MS: MH⁺ = 405<br>m.p. 63-69° C. |
| 346 | 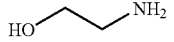 | HCl | 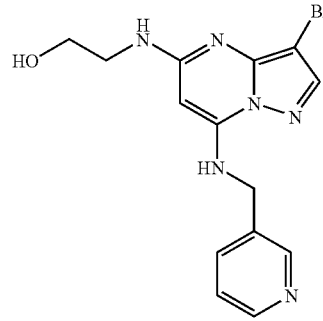 | MS: MH⁺ = 363<br>m.p. 170-171° C. |
| 347 | 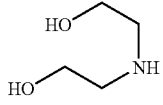 | HCl | 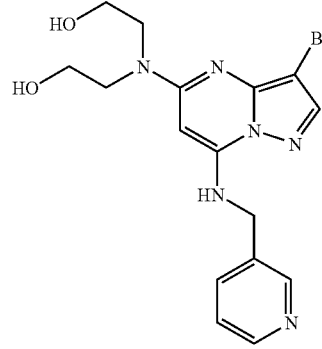 | MS: MH⁺ = 407<br>m.p. 148-151° C. |
| 348 | 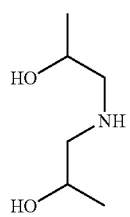 | HCl | 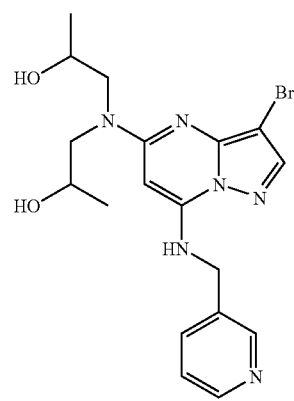 [SMILES: CC(O)CN(CC(C)O)c1cc(NCc2cccnc2)n2ncc(Br)c2n1] | MS: MH⁺ = 435<br>m.p. 56-59° C. |

TABLE 31-continued

| Ex. | Column 2 | Column 3 | Column 4 | CMPD |
|---|---|---|---|---|
| 349 | | HCl | | MS: MH$^+$ = 445<br>m.p. 66-68° C. |
| 350 | | KOH | | MS: MH$^+$ = 417<br>m.p. 149-151° C. |
| 351 | | KOH | | MS: MH$^+$ = 431<br>m.p. 111-114° C. |
| 352 | | KOH | | MS: MH$^+$ = 417<br>m.p. 53-58° C. |

TABLE 31-continued

| Ex. | Column 2 | Column 3 | Column 4 | CMPD |
|---|---|---|---|---|
| 353 | (S)-1-(pyrrolidin-1-ylmethyl)pyrrolidine | KOH | 3-bromo-5-[(S)-2-(pyrrolidin-1-ylmethyl)pyrrolidin-1-yl]-N-(pyridin-3-ylmethyl)pyrazolo[1,5-a]pyrimidin-7-amine | MS: MH$^+$ = 456<br>m.p. 186-189° C. |
| 354 | (S)-pyrrolidine-2-carboxamide | KOH | (S)-1-(3-bromo-7-((pyridin-3-ylmethyl)amino)pyrazolo[1,5-a]pyrimidin-5-yl)pyrrolidine-2-carboxamide | MS: MH$^+$ = 416<br>m.p. 210-213° C. |
| 355 | (1R,2S)-2-(benzyloxy)cyclopentanamine | TFA | 3-bromo-N5-((1R,2S)-2-(benzyloxy)cyclopentyl)-N7-(pyridin-3-ylmethyl)pyrazolo[1,5-a]pyrimidine-5,7-diamine | 1. mp = 68-70<br>2. M + H = 494 |
| 356 | (1R,2S)-2-aminocyclopentanol | KOH | (1S,2R)-2-((3-bromo-7-((pyridin-3-ylmethyl)amino)pyrazolo[1,5-a]pyrimidin-5-yl)amino)cyclopentanol | 1. mp = 181-183<br>2. M + H = 404 |

TABLE 31-continued

| Ex. | Column 2 | Column 3 | Column 4 | CMPD |
|---|---|---|---|---|
| 357 | cyclopentyl with NH₂ and OBn (trans) | TFA | pyrazolopyrimidine with Br, NH-cyclopentyl-OBn, and NH-CH₂-pyridin-3-yl | 1. mp = 69-71<br>2. M + H = 494 |
| 358 | cyclopentyl with NH₂ and OH (trans) | KOH | pyrazolopyrimidine with Br, NH-cyclopentyl-OH, and NH-CH₂-pyridin-3-yl | 1. mp = 182-184<br>2. M + H = 404 |
| 359 | 1-(aminomethyl)cyclopentanol | KOH | pyrazolopyrimidine with Br, NH-C(cyclopentyl)(CH₂OH), and NH-CH₂-pyridin-3-yl | 1. mp = 202-204<br>2. M + H = 418 |
| 360 | cyclohexylamine | TFA | pyrazolopyrimidine with Br, NH-cyclohexyl, and NH-CH₂-pyridin-3-yl | 1. mp = 160-162<br>2. M + H = 402 |

TABLE 31-continued

| Ex. | Column 2 | Column 3 | Column 4 | CMPD |
|-----|----------|----------|----------|------|
| 361 | cyclohexyl-N(Me)H | TFA | (structure) | 1. mp = 151-153<br>2. M + H = 416 |
| 362 | trans-2-aminocyclohexanol | KOH | (structure) | 1. mp = 140-143<br>2. M + H = 418 |
| 363 | trans-2-aminocyclohexanol | KOH | (structure) | 1. mp = 139-142<br>2. M + H = 418 |
| 364 | cis-2-aminocyclohexanol (+/-) | KOH | (structure) | 1. mp = 115-117<br>2. M + H = 418 |

TABLE 31-continued
| Ex. | Column 2 | Column 3 | Column 4 | CMPD |
|---|---|---|---|---|
| 366 | 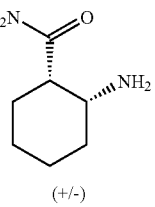 (+/-) | TFA | 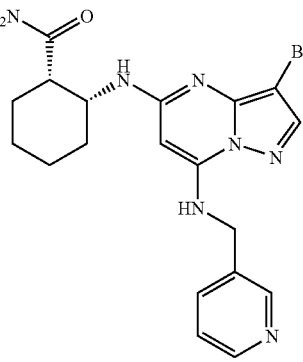 | 1. mp = 102-104<br>2. M + H = 445 |
| 367 | 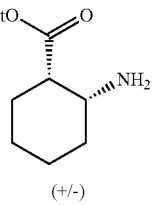 (+/-) | TFA | 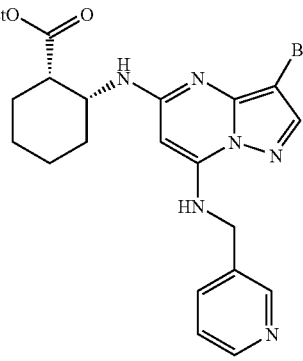 | 1. mp = 118-120<br>2. M + H = 474 |
| 368 | 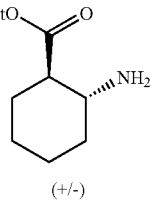 (+/-) | TFA | 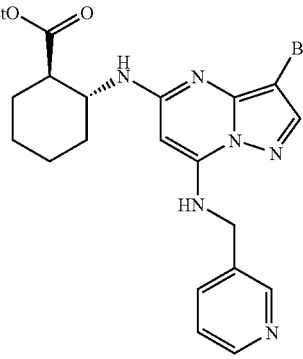 | 1. mp = 106-108<br>2. M + H = 474 |
| 369 | 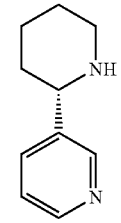 [SMILES: c1cncc([C@@H]2CCCCN2)c1] | TFA | 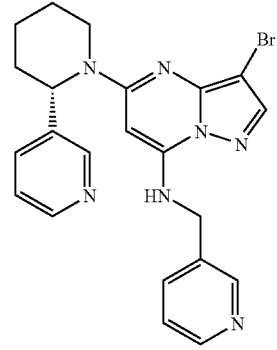 [SMILES: Brc1cnn2c(NCc3cccnc3)cc(N3CCCC[C@H]3c3cccnc3)nc12] | 1. mp = 160-161<br>2. M + H = 464 |

TABLE 31-continued

| Ex. | Column 2 | Column 3 | Column 4 | CMPD |
|---|---|---|---|---|
| 370 | cyclohexane with OH and CH₂NH₂ (+/−) | TFA | pyrazolopyrimidine with Br, cyclohexyl-OH-CH₂-NH, and pyridylmethyl-HN substituents | 1. mp = 93-95<br>2. M + H = 432 |
| 371 | cyclohexane with NH₂ and CH₂OH (+/−) | KOH | pyrazolopyrimidine with Br, cyclohexyl-NH (with CH₂OH), and pyridylmethyl-HN substituents | 1. mp = 108-110<br>2. M + H = 432 |
| 372 | 4-aminocyclohexanol | KOH | pyrazolopyrimidine with Br, 4-hydroxycyclohexyl-NH, and pyridylmethyl-HN substituents | 1. mp = 180-182<br>2. M + H = 418 |
| 373 | trans-4-BocHN-cyclohexylamine | TFA | pyrazolopyrimidine with Br, 4-aminocyclohexyl-NH, and pyridylmethyl-HN substituents | 1. mp = 169-170<br>2. M + H = 417 |

TABLE 31-continued
| Ex. | Column 2 | Column 3 | Column 4 | CMPD |
|---|---|---|---|---|
| 374 | 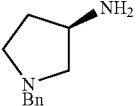 | TFA | 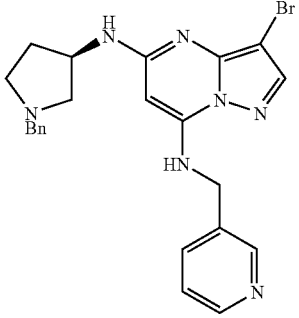 [SMILES: Brc1cnn2c(NCc3cccnc3)cc(N[C@@H]3CCN(Cc4ccccc4)C3)nc12] | 1. mp = 77-79<br>2. M + H = 479 |
| 375 | 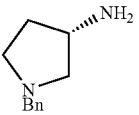 | TFA | 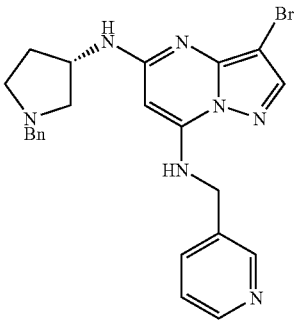 [SMILES: Brc1cnn2c(NCc3cccnc3)cc(N[C@H]3CCN(Cc4ccccc4)C3)nc12] | 1. mp = 76-79<br>2. M + H = 479 |
| 376 | 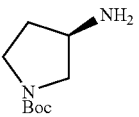 | TFA | 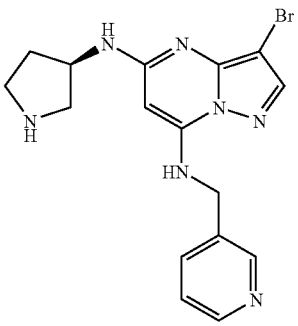 [SMILES: Brc1cnn2c(NCc3cccnc3)cc(N[C@@H]3CCNC3)nc12] | 1. mp = 105-107<br>2. M + H = 389 |
| 377 | 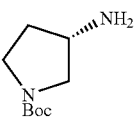 | TFA | 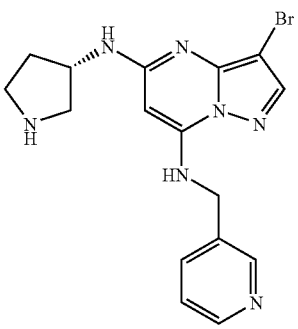 [SMILES: Brc1cnn2c(NCc3cccnc3)cc(N[C@H]3CCNC3)nc12] | 1. mp = 105-107<br>2. M + H = 389 |

TABLE 31-continued
| Ex. | Column 2 | Column 3 | Column 4 | CMPD |
|---|---|---|---|---|
| 378 | 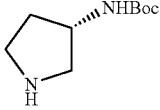 | TFA | 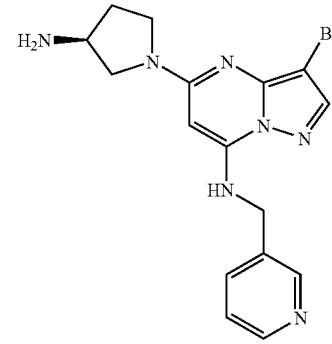 | 1. mp = 130-133<br>2. M + H = 389 |
| 379 | 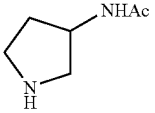 | TFA | 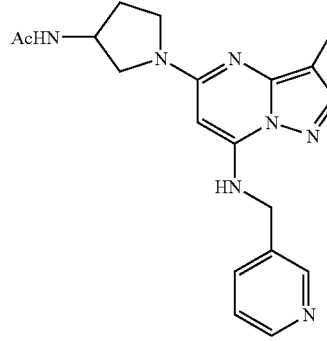 | 1. mp = 132-135<br>2. M + H = 431 |
| 380 | 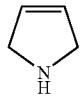 | TFA | 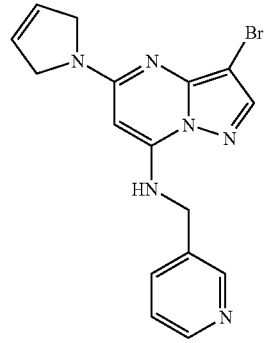 [SMILES: Brc1cnn2c(NCc3cccnc3)cc(N3CC=CC3)nc12] | 1. mp = 135-137<br>2. M + H = 372 |
| 381 | 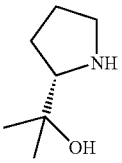 | KOH | 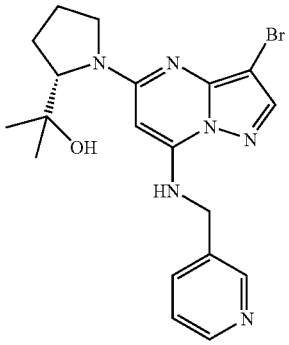 [SMILES: CC(C)(O)[C@@H]1CCCN1c1cc(NCc2cccnc2)n2ncc(Br)c2n1] | 1. mp = 78-82<br>2. M + H = 432 |

TABLE 31-continued

| Ex. | Column 2 | Column 3 | Column 4 | CMPD |
|---|---|---|---|---|
| 382 | (structure) | TFA | (structure) | 1. mp = 101-103<br>2. M + H = 432 |
| 383 | (structure) | TFA | (structure) | 1. mp = 92-95<br>2. M + H = 472 |
| 384 | (structure) | TFA | (structure) | 1. mp = 107-111<br>2. M + H = 444 |
| 384.10 | (structure) | TFA | (structure) | 1. mp =<br>2. M + H = 417 |

TABLE 31-continued
| Ex. | Column 2 | Column 3 | Column 4 | CMPD |
|---|---|---|---|---|
| 384.11 | 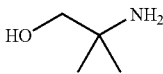 | TFA | 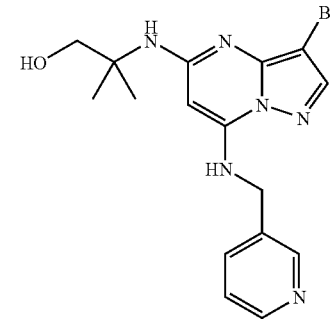 | 1. mp = 210-212<br>2. M + H = 391 |
| 385 | 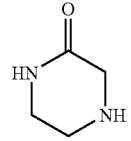 | TFA | 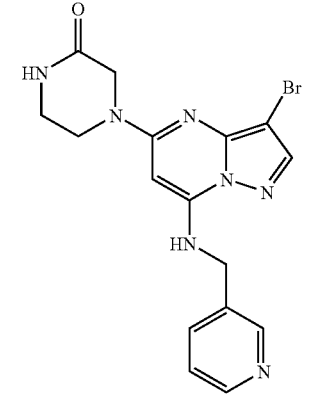 [SMILES: O=C1CN(c2cc(NCc3cccnc3)n3ncc(Br)c3n2)CCN1] | 1. mp = 122-124<br>2. M + H = 403 |
| 386 | 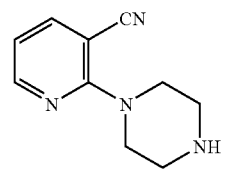 [SMILES: N#Cc1cccnc1N1CCNCC1] | TFA | 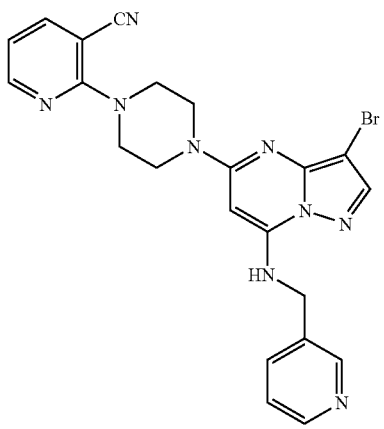 [SMILES: N#Cc1cccnc1N1CCN(c2cc(NCc3cccnc3)n3ncc(Br)c3n2)CC1] | 1. mp = 186-188<br>2. M + H = 491 |
| 387 | 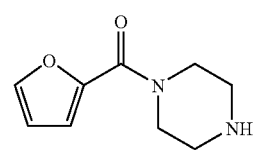 [SMILES: O=C(c1ccco1)N1CCNCC1] | TFA | 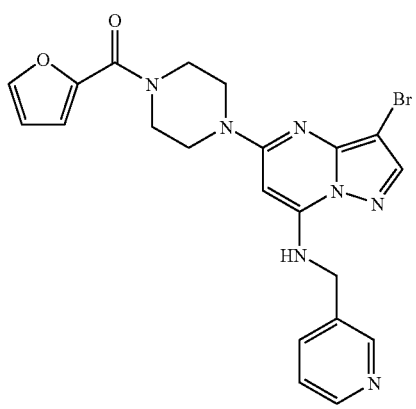 [SMILES: O=C(c1ccco1)N1CCN(c2cc(NCc3cccnc3)n3ncc(Br)c3n2)CC1] | 1. mp = 173-175<br>2. M + H = 483 |

TABLE 31-continued
| Ex. | Column 2 | Column 3 | Column 4 | CMPD |
|---|---|---|---|---|
| 388 | 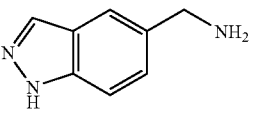 [SMILES: NCc1ccc2[nH]ncc2c1] | TFA | 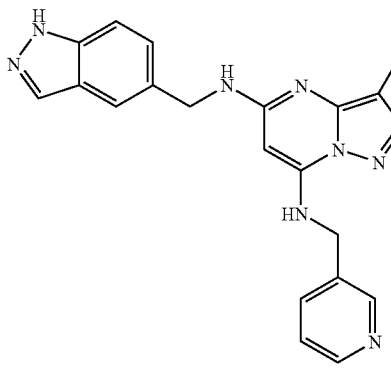 | 1. mp = 167-169<br>2. M + H = 450 |
| 389 | 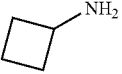 | TFA | 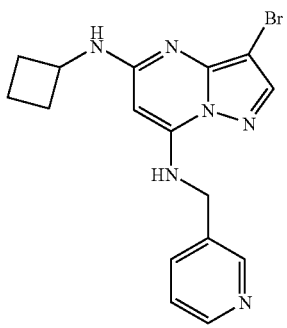 [SMILES: Brc1cnn2c(NCc3cccnc3)cc(NC3CCC3)nc12] | 1. mp = 90-92<br>2. M + H = 374 |
| 390 | 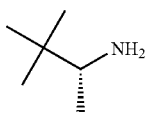 | TFA | 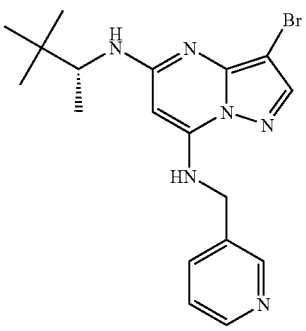 [SMILES: C[C@@H](Nc1cc(NCc2cccnc2)n2ncc(Br)c2n1)C(C)(C)C] | 1. mp = 113-115<br>2. M + H = 404 |
| 391 | 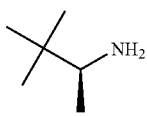 | TFA | 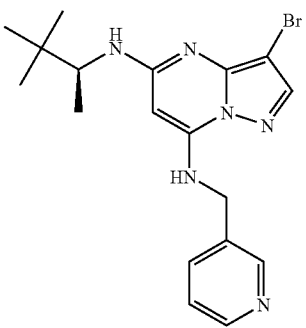 | 1. mp = 114-116<br>2. M + H = 404 |

TABLE 31-continued

| Ex. | Column 2 | Column 3 | Column 4 | CMPD |
|---|---|---|---|---|
| 392 | HNMe₂ | TFA | (Me₂N/Br pyrazolopyrimidine with HN-CH₂-pyridin-3-yl) | LCMS: MH⁺ = 347; |
| 393 | H₂NMe | TFA | (MeHN/Br pyrazolopyrimidine with HN-CH₂-pyridin-3-yl) | LCMS: MH⁺ = 333; |
| 394 | cyclopropyl-NH₂ | TFA | (cyclopropyl-NH/Br pyrazolopyrimidine with HN-CH₂-pyridin-3-yl) | LCMS: MH⁺ = 359; |
| 395 | (S)-2-aminopentan-1-ol | TFA | (2-(1-hydroxymethyl)butylamino/Br pyrazolopyrimidine with HN-CH₂-pyridin-3-yl) | LCMS: MH⁺ = 405; |

TABLE 31-continued

| Ex. | Column 2 | Column 3 | Column 4 | CMPD |
|---|---|---|---|---|
| 396 | 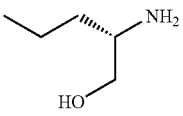 | TFA | 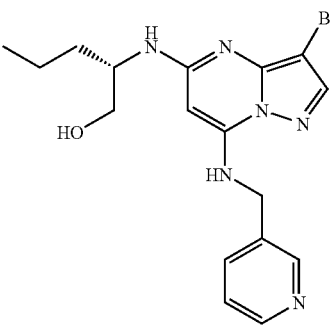 | LCMS: MH+ = 405; |
| 397 | 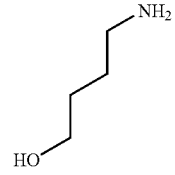 | TFA | 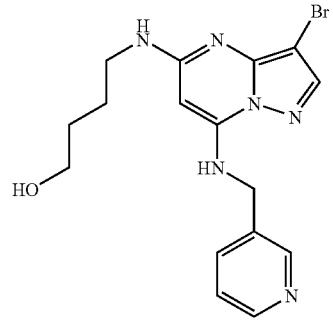 [SMILES: OCCCCNc1cc(NCc2cccnc2)n2ncc(Br)c2n1] | LCMS: MH+ = 391; |

Additional data for select example shown below:

Example 392

¹H NMR (DMSO-d₆) δ 8.65 (s, 1H), 8.46 (d, J=3.3 Hz, 1H), 8.21 (t, J=6.6 Hz, 1H), 7.90 (s, 1H), 7.80 (d, J=7.8 Hz, 1H), 7.35 (dd, J=7.8, 4.8 Hz, 1H), 5.46 (s, 1H), 4.61 (d, J=6.9 Hz, 2H), 3.01 (s, 6H).

Example 393

¹H NMR (CDCl₃) δ 8.65 (s, 1H), 8.60 (d, J=4.8 Hz, 1H), 7.76 (s, 1H), 7.70 (m, 1H), 7.32 (dd, J=8.1, 4.8 Hz, 1H), 6.43 (t, J=6.0 Hz, 1H), 5.08 (s, 1H), 4.80 (m, 1H), 4.56 (d, J=6.0 Hz, 2H), 2.96 (d, J=5.1 Hz, 3H).

Example 394

¹H NMR (CDCl₃) δ 8.68 (s, 1H), 8.60 (d, J=4.8 Hz, 1H), 7.76 (s, 1H), 7.72 (m, 1H), 7.32 (dd, J=7.8, 5.4 Hz, 1H), 6.55 (t, J=5.7 Hz, 1H), 5.53 (s, 1H), 5.35 (s, 1H), 4.62 (d, J=5.7 Hz, 2H), 2.49 (m, 1H), 0.75 (m, 2H), 0.51 (m, 2H).

Example 395

¹H NMR (CDCl₃) δ 8.65 (s, 1H), 8.60 (d, J=4.0 Hz, 1H), 7.75 (s, 1H), 7.69 (m, 1H), 7.33 (dd, J=8.1, 5.1 Hz, 1H), 6.45 (t, J=6.0 Hz, 1H), 5.07 (s, 1H), 4.69 (m, 1H), 4.54 (d, J=6.0 Hz, 2H), 3.98 (m, 1H), 3.79 (dd, J=10.8, 2.4 Hz, 1H), 3.59 (dd, J=11.1, 7.2 Hz, 1H), 1.59-1.36 (m, 4H), 0.94 (t, J=6.9 Hz, 3H).

Example 396

¹H NMR (CDCl₃) δ 8.60 (s, 1H), 8.56 (d, J=4.2 Hz, 1H), 7.73 (s, 1H), 7.66 (m, 1H), 7.31 (dd, J=7.8, 4.8 Hz, 1H), 6.51 (t, J=6.0 Hz, 1H), 5.05 (s, 1H), 4.86 (d, J=6.6 Hz, 1H), 4.50 (d, J=6.0 Hz, 2H), 3.94 (m, 1H), 3.78 (dd, J=11.1, 2.4 Hz, 1H), 3.57 (dd, J=11.1, 7.2 Hz, 1H), 1.57-1.34 (m, 4H), 0.91 (t, J=7.2 Hz, 3H).

Example 397

¹H NMR (CDCl₃) δ 8.65 (s, 1H), 8.59 (d, J=4.5 Hz, 1H), 7.75 (s, 1H), 7.69 (m, 1H), 7.31 (m, 1H), 6.43 (t, J=6.0 Hz, 1H), 5.06 (s, 1H), 4.88 (m, 1H), 4.55 (d, J=6.0 Hz, 2H), 3.70 (m, 2H), 3.38 (m, 2H), 1.79-1.61 (m, 4H).

Examples 398-416

By essentially the same conditions set forth in Example 341, Steps A and B only substituting the compound prepared in Preparative Example 193.10, the compounds in Column 4 of Table 32 were prepared.

TABLE 32

| Ex. | Column 2 | Column 3 | Column 4 | CMPD |
|---|---|---|---|---|
| 398 | (S)-pyrrolidin-2-ylmethanol | | pyrazolo[1,5-a]pyrimidine derivative | MS: MH⁺ = 419<br>m.p. 102-105° C. |
| 399 | (S)-2-amino-3-methylbutan-1-ol | | pyrazolo[1,5-a]pyrimidine derivative | MS: MH⁺ = 421<br>m.p. 79-81° C. |
| 400 | (R)-2-amino-3-methylbutan-1-ol | | pyrazolo[1,5-a]pyrimidine derivative | MS: MH⁺ = 421<br>m.p. 78-79° C. |
| 401 | piperidin-2-ylmethanol | | pyrazolo[1,5-a]pyrimidine derivative | MS: MH⁺ = 433<br>m.p. 228-231° C. |

TABLE 32-continued

| Ex. | Column 2 | Column 3 | Column 4 | CMPD |
|-----|----------|----------|----------|------|
| 402 | | | | MS: MH⁺ = 447<br>m.p. 97-102° C. |
| 403 | | | | MS: MH⁺ = 421<br>m.p. ° C. |
| 404 | | | | MS: MH⁺ = 421<br>m.p. ° C. |
| 405 | | | | MS: MH⁺ = 386<br>m.p. ° C. |

TABLE 32-continued

| Ex. | Column 2 | Column 3 | Column 4 | CMPD |
|---|---|---|---|---|
| 407 | cyclobutylamine | KOH | (structure) | 1. mp = 98-100<br>2. M + H = 390 |
| 408 | cyclopentylamine | TFA | (structure) | 1. mp = 170-173<br>2. M + H = 404 |
| 409 | (1S,2R)-2-aminocyclopentanol | KOH | (structure) | 1. mp = 219-221<br>2. M + H = 420 |
| 410 | (±) (1R,2S)-2-amino-1-(hydroxymethyl)cyclohexane | KOH | (structure) | 1. mp = 110-112<br>2. M + H = 448 |

TABLE 32-continued

| Ex. | Column 2 | Column 3 | Column 4 | CMPD |
|---|---|---|---|---|
| 411 | (structure: 2-(pyrrolidin-2-yl)propan-2-ol) | TFA | (structure: 3-bromo-5-[2-(2-hydroxypropan-2-yl)pyrrolidin-1-yl]-N-[(1-oxidopyridin-3-yl)methyl]pyrazolo[1,5-a]pyrimidin-7-amine) | 1. mp = 81-83<br>2. M + H = 448 |
| 412 | (structure: methyl prolinate) | TFA | (structure: methyl 1-{3-bromo-7-[(1-oxidopyridin-3-yl)methylamino]pyrazolo[1,5-a]pyrimidin-5-yl}pyrrolidine-2-carboxylate) | 1. mp = 136-138<br>2. M + H = 448 |
| 413 | NaOMe | KOH | (structure: 3-bromo-5-methoxy-N-[(1-oxidopyridin-3-yl)methyl]pyrazolo[1,5-a]pyrimidin-7-amine) | 1. mp = 107-110<br>2. M + H = 351 |
| 414 | cyclopropylamine | | (structure: 3-bromo-N5-cyclopropyl-N7-[(1-oxidopyridin-3-yl)methyl]pyrazolo[1,5-a]pyrimidine-5,7-diamine) | LCMS: MH⁺ = 375; |

Additional data for select examples shown below:

Example 414

$^1$H NMR (DMSO-d$_6$) δ 8.26 (s, 1H), 8.23 (m, 1H), 8.13 (m, 1H), 7.90 (s, 1H), 7.40-7.27 (m, 3H), 5.34 (s, 1H), 4.49 (d, J=6.3 Hz, 2H), 2.56 (m, 1H), 0.67 (m, 2H), 0.35 (m, 2H).

Example 403

$^1$H NMR (DMSO-d$_6$+CDCl$_3$) δ 8.08 (s, 1H), 7.90 (d, J=6.3 Hz, 1H), 7.49 (s, 1H), 7.34 (t, J=6.3 Hz, 1H), 7.16-7.09 (m, 2H), 5.65 (d, J=6.6 Hz, 1H), 4.97 (s, 1H), 4.90 (s, 1H), 4.29 (d, J=6.3 Hz, 2H), 3.70 (m, 1H), 3.46 (m, 1H), 3.34 (m, 1H), 1.35-1.17 (m, 4H), 0.71 (t, J=7.2 Hz, 3H).

Example 404

¹H NMR (DMSO-d₆) δ 8.21 (s, 1H), 8.12 (d, J=6.6 Hz, 1H), 8.06 (m, 1H), 7.86 (s, 1H), 7.38 (t, J=7.8 Hz, 1H), 7.30 (d, J=7.5 Hz, 1H), 6.73 (d, J=8.7 Hz, 1H), 5.28 (s, 1H), 4.70 (t, J=5.1 Hz, 1H), 4.41 (d, J=6.6 Hz, 2H), 4.00 (s, 1H), 3.39 (m, 1H), 1.53 (m, 1H), 1.36-1.25 (m, 3H), 0.86 (t, J=7.0 Hz, 3H).

Examples 417-421

By the procedure set forth in *Chem. Pharm. Bull.* 1999, 47, 928-938. utilizing the oxygen or sulfur nucleophiles shown in Column 2 as described of Table 33 and by employing the cleavage method listed in Column 3 of Table 33, the compounds in Column 4 of Table 33 were prepared:

TABLE 33

| Ex. | Column 2 (Nucleophile) | Column 3 (Cleavage method) | Column 4 (Final Structure) | CMPD 1. mp. 2. M + H |
|---|---|---|---|---|
| 417 | NaSMe | TFA | | 1. mp = 172-175  2. M + H = 351 |
| 418 | NaSt-Bu | TFA | | 1. mp = 165-168  2. M + H = 392 |
| 419 | NaSPh | TFA | | 1. mp = 154-156  2. M + H = 412 |
| 420 | NaOMe | TFA | | 1. mp = 161-163  2. M + H = 335 |

TABLE 33-continued

| Ex. | Column 2 (Nucleophile) | Column 3 (Cleavage method) | Column 4 (Final Structure) | CMPD 1. mp. 2. M + H |
|---|---|---|---|---|
| 421 | NaOPh | TFA | | 1. mp = 64-66 2. M + H = 397 |

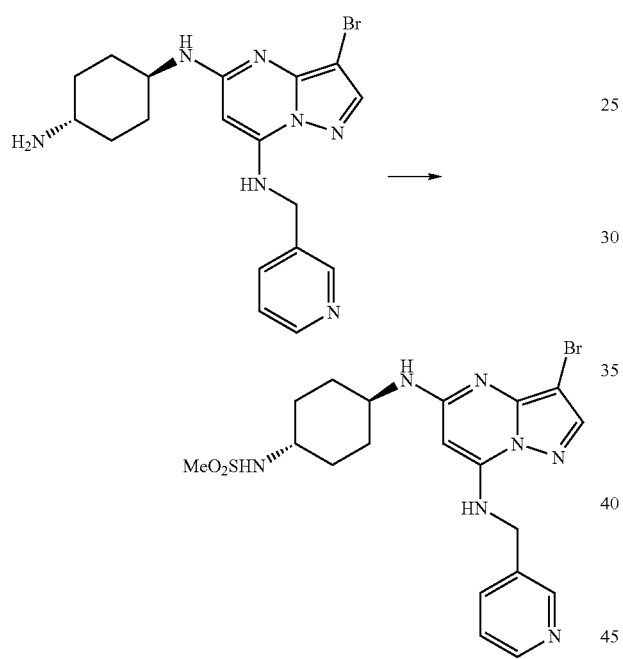

Example 422

To a solution of amino compound (18 mg, 0.043 mmol) from Example 373 in $CH_2Cl_2$ (1 mL) at rt was added DIPEA (10 µL, 0.056 mmol) followed by $MeSO_2Cl$ (4 mL, 0.052 mmol). The mixture was stirred at rt for 12 h and was diluted with $CH_2Cl_2$ (2 mL) and sat. aq. $NaHCO_3$ (2 mL). The layers were separated and the organic layer was extracted with brine (1×2 mL). The organic layer was dried ($Na_2SO_4$), filtered, and concentrated under reduced pressure. The crude material was purified by preparative thin-layer chromatography (4×1000 µM) eluting with $CH_2Cl_2$/MeOH (20:1) to afford 16 mg (75%) of white solid. mp 152-154° C.; M+H=495.

Examples 423-424

Utilizing the procedure outlined in Example 422, the amino compounds (Column 2) were converted to the corresponding methylsulfonamides (Column 3) in Table 34.

TABLE 34

| Ex. | Column 2 (Amine) | Column 3 (Final Structure) | CMPD 1. mp. 2. M + H |
|---|---|---|---|
| 423 | | | 1. mp = 166-168 2. M + H = 467 |

TABLE 34-continued

| Ex. | Column 2 (Amine) | Column 3 (Final Structure) | CMPD 1. mp. 2. M + H |
|---|---|---|---|
| 424 |  |  | 1. mp = 165-168 2. M + H = 467 |

Example 425

Step A

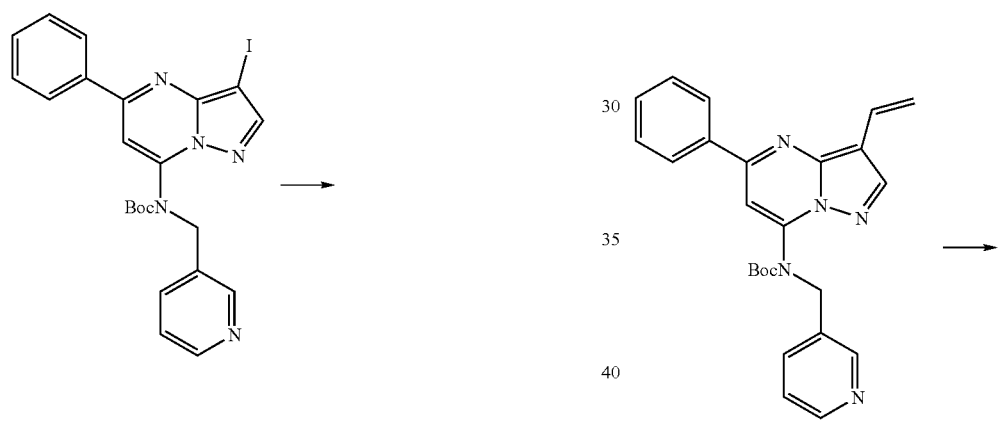

A mixture of the compound prepared in Preparative Example 194 (132 mg, 0.25 mmol), tributylvinyltin (95 mg, 0.30 mmol) and tetrakis(triphenylphospine) palladium (29 mg, 0.025 mmol) in anhydrous dioxane (5 mL) was refluxed under N₂ for 24 hr. The solvent was evaporated and the residue was purified by flash chromatography using 2:1 CH₂Cl₂:EtOAc as eluent to yield yellow waxy solid (53 mg, 50%). LCMS: MH⁺=428.

Step B

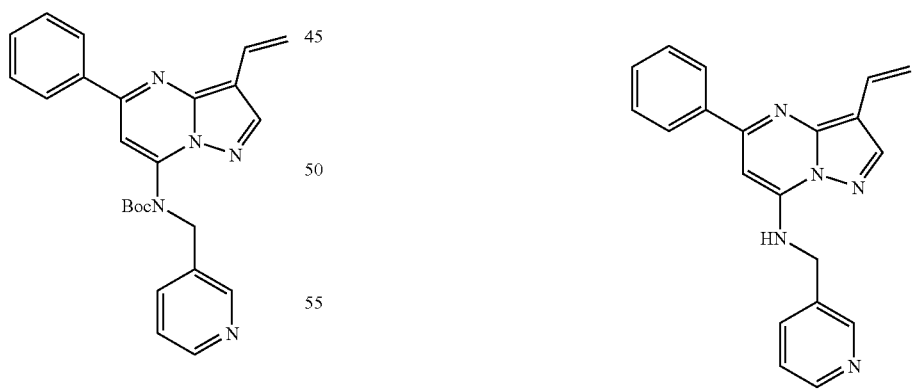

A mixture of the compound prepared in Example 425, Step A (50 mg, 0.12 mmol) and KOH (100 mg, 1.80 mmol) in ethanol (3 mL) and H₂O (0.6 mL) was stirred at 70° C. under N₂ for 24 hr. NaHCO₃ (1.0 g), Na₂SO₄ (2.0 g), and CH₂Cl₂ (20 mL) were added, the mixture was shaken and then filtered. The solvent was evaporated and the residue was purified by flash chromatography using 20:1:0.1 CH₂Cl₂:MeOH:

conc.NH₄OH as eluent to yield yellow waxy solid (17 mg, 45%). LCMS: MH⁺=328. Mp=48-51° C.

Example 426

Step A

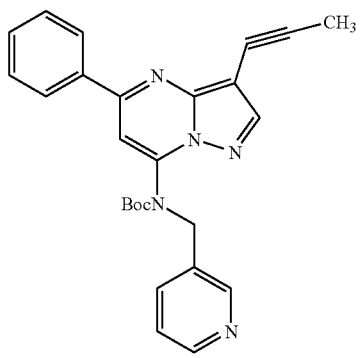 [SMILES: CC#Cc1cnn2c(N(Cc3cccnc3)C(=O)OC(C)(C)C)cc(-c3ccccc3)nc12]

By essentially the same procedure set forth in Example 425, Step A only using tributylmethylethynyltin, the compound shown above was prepared.

Step B

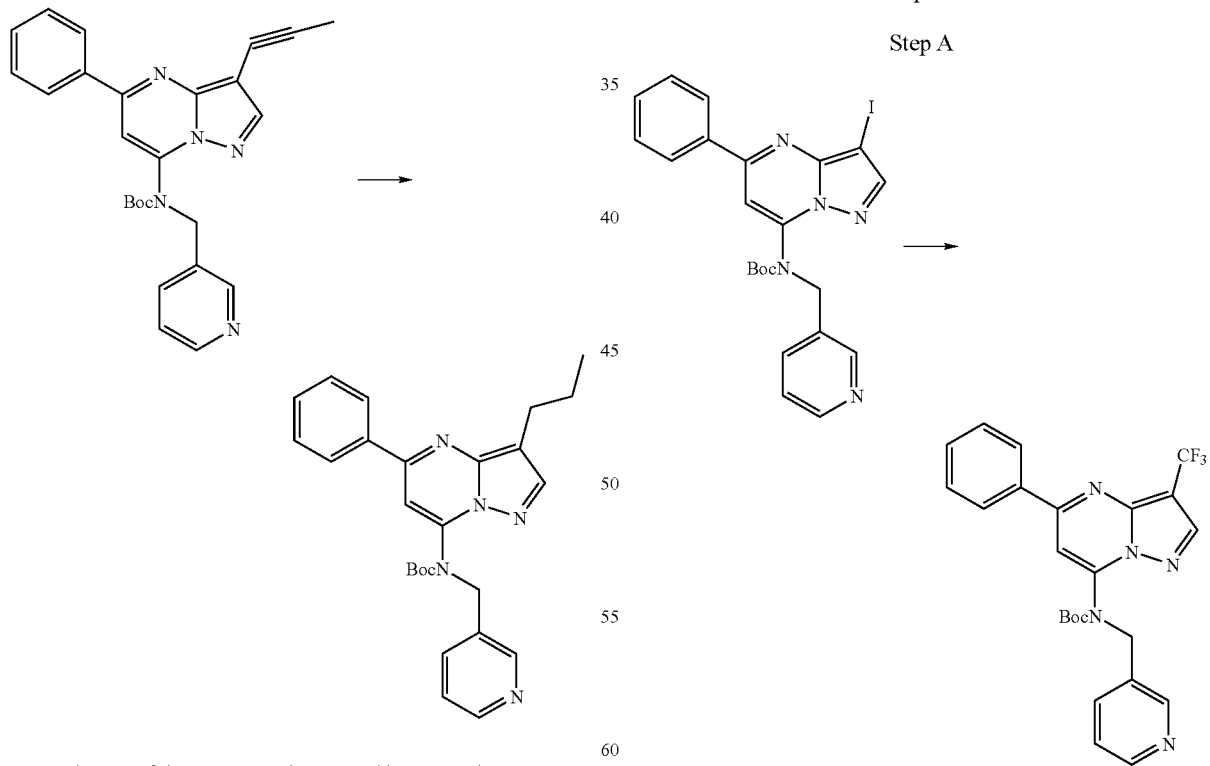

A mixture of the compound prepared in Example 426, Step A (150 mg, 0.34 mmol) and PtO2 (30 mg, 0.13 mmol) in glacial acetic acid (5 mL) was stirred under 1 atmosphere of H₂ for 20 hr. The mixture was filtered, fresh PtO2 (30 mg, 0.13 mmol) was added and the mixture was stirred under 1 atmosphere of H₂ for 2.5 hr. The mixture was poured onto Na₂CO₃ (20 g) and H₂O (200 mL) and it was extracted with CH₂Cl₂ (4×20 mL). The combined extracts were dried over Na₂SO₄ and filtered. The solvent was evaporated and the residue was purified by flash chromatography using 1:1 CH₂Cl₂:EtOAc as eluent to yield yellow waxy solid (68 mg, 45%).

Step C

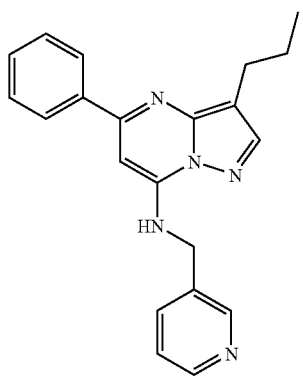 [SMILES: CCCc1cnn2c(NCc3cccnc3)cc(-c3ccccc3)nc12]

By essentially the same procedure set forth in Example 425, Step B only substituting the compound prepared in Example 426, Step B, the compound shown above was prepared, MS: MH⁺=344. Mp=110-112° C.

Example 427

Step A

A mixture of the compound prepared in Preparative Example 194 (527 mg, 1.00 mmol), triethyl(trifluoromethyl)silane (666 mg, 3.60 mmol), potassium fluoride (210 mg, 3.60 mmol), and CuI (850 mg, 4.46 mmol) in anhydrous DMF (4 mL) was stirred in a closed pressure vessel at 80° C. for 72 hr. CH2Cl2 (80 mL) was added and the mixture was filtered through Celite. The solvent was evaporated and the residue was purified by flash chromatography using 2:1 CH$_2$Cl$_2$:EtOAc as eluent to yield pale orange waxy solid (70 mg, 15%). LCMS: M$^+$=470.

Step B

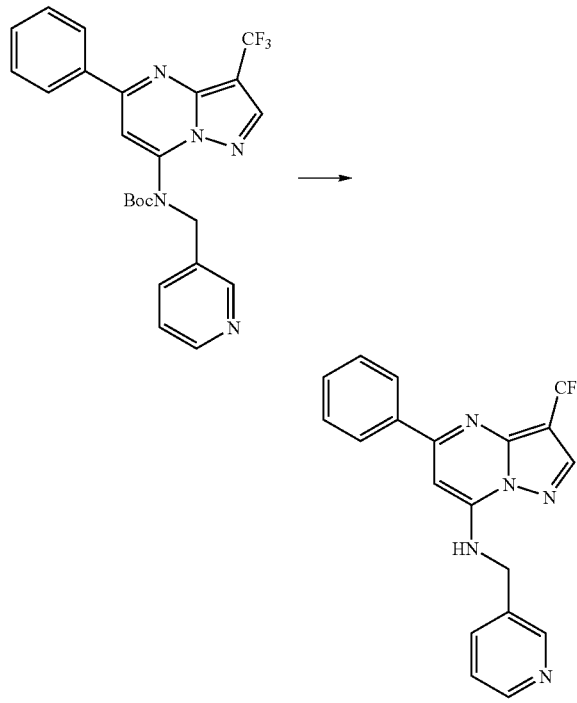

TFA (0.70 mL) was added at 0° C. under N$_2$ to a stirred solution of the compound prepared in Example 427, Step A (70 mg, 0.15 mmol), in anhydrous CH$_2$Cl$_2$ (3 mL). The mixture was stirred at 0° C. for 10 min, then at 25° C. for 2 hr. It was poured into 10% aqueous Na$_2$CO$_3$ (50 mL), extracted with CH$_2$Cl$_2$ (3×15 mL), dried over Na$_2$SO$_4$, and filtered. The solvent was evaporated and the residue was purified by flash chromatography using EtOAc as eluent to yield off-white solid (40 mg, 73%). LCMS: M$^+$=370. Mp=156-158° C.

Example 428

Step A

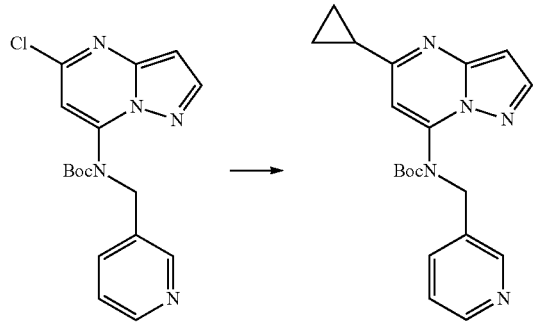 [SMILES: CC(C)(C)OC(=O)N(Cc1cccnc1)c1cc(Cl)nc2ccnn12 ; CC(C)(C)OC(=O)N(Cc1cccnc1)c1cc(C2CC2)nc2ccnn12]

A mixture of the compound prepared in Preparative Example 193 (100 mg, 0.28 mmol), tetracyclopropyltin (91 mg, 0.32 mmol), Pd$_2$dba$_3$ (8.0 mg, 0.009 mmol) and Pd(P-t-Bu$_3$)$_2$ (9.0 mg, 0.017 mmol) in anhydrous dioxane (3 mL) was refluxed under N$_2$ for 27 hr. The solvent was evaporated and the residue was purified by flash chromatography using 1:1 CH$_2$Cl$_2$:EtOAc as eluent to yield colorless waxy solid (38 mg, 38%). LCMS: MH$^+$=366.

Step B

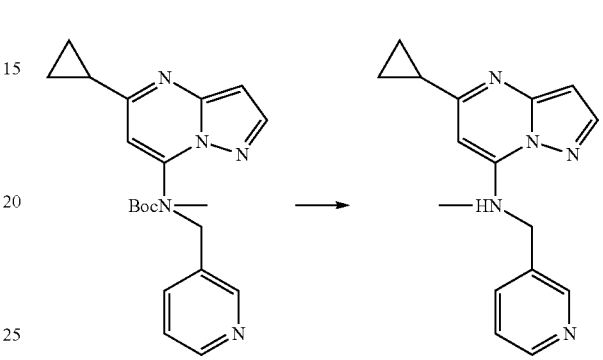

A mixture of the compound prepared in Example 428, Step A (36 mg, 0.10 mmol) and KOH (300 mg, 5.40 mmol) in ethanol (3 mL), 1,2-dimethoxyethane (3.0 mL0 and H$_2$O (0.8 mL) was refluxed under N$_2$ for 4 hr. It was poured into saturated aqueous NaHCO$_3$ (100 mL), extracted with CH$_2$Cl$_2$ (5×10 mL), dried over Na$_2$SO$_4$, and filtered. The solvent was evaporated and the residue was purified by flash chromatography using 30:1 EtOAc:MeOH as eluent to yield colorless waxy (18 mg, 69%). LCMS: MH$^+$=266.

Step C:

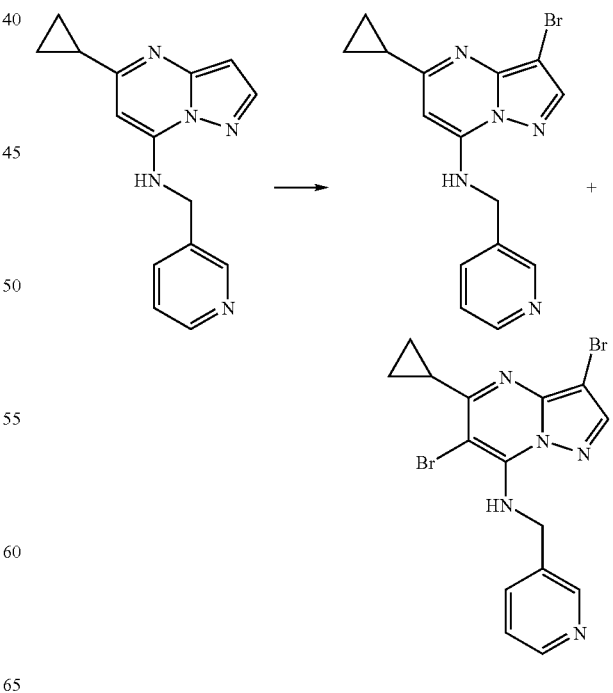

N-bromosuccinimide (12 mg, 0.068 mmol) in anhydrous CH$_3$CN (2 mL) was added under N$_2$ to a stirred solution of the compound prepared in Example 428, Step B (18 mg, 0.068 mmol), in anhydrous CH$_3$CN (2 mL). The mixture was stirred at 25° C. for 2 hr. The solvent was evaporated and the residue was purified by flash chromatography using EtOAc as eluent to yield 5 mg (17%) of the dibromo compound (white solid, LCMS: MH$^+$=370, mp=150-152° C.) and 8 mg (34%) of the monobromo compound (colorless solid, LCMS: M$^+$=344, mp=196-198° C.).

Example 429

Step A

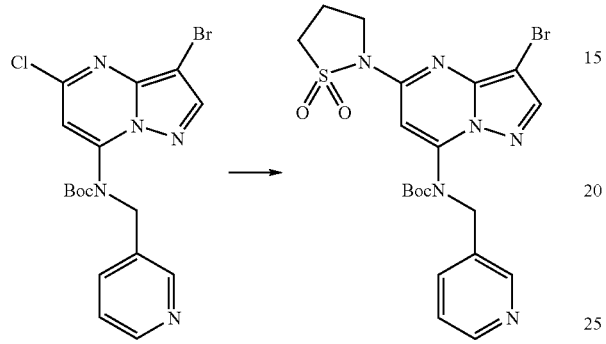

1,3-propanesultam (72 mg, 0.60 mmol) in anhydrous DMF (3 mL) was added under N$_2$ to 60% NaH in mineral oil (36 mg, 0.90 mmol). The mixture was stirred for 20 min, then the compound prepared in Preparative Example 196 (200 mg, 0.46 mmol) was added. The mixture was stirred at 100° C. for 30 min, the solvent was evaporated and the residue was purified by flash chromatography using EtOAc as eluent to yield colorless solid (150 mg, 63%). LCMS: M$^+$=523.

Step B

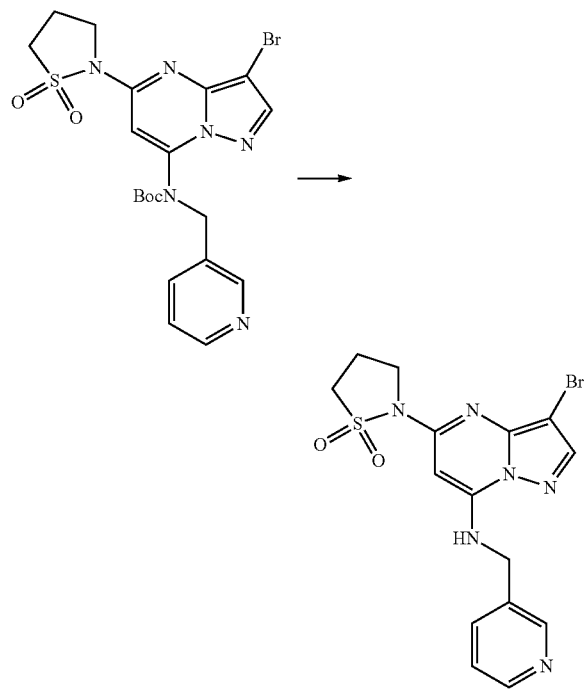

TFA (1.5 mL) was added at 0° C. under N$_2$ to a stirred solution of the compound prepared in Preparative Example 196 (140 mg, 0.27 mmol), in anhydrous CH$_2$Cl$_2$ (5 mL). The mixture was stirred at 0° C. for 10 min, then at 25° C. for 2 hr. It was poured onto Na$_2$CO$_3$ (10 g), extracted with CH$_2$Cl$_2$ (3×50 mL), and filtered. The solvent was evaporated and the residue was purified by flash chromatography using 40:1 EtOAc:MeOH as eluent to yield white solid (32 mg, 28%). LCMS: M$^+$=423. Mp=218-220° C.

Example 430

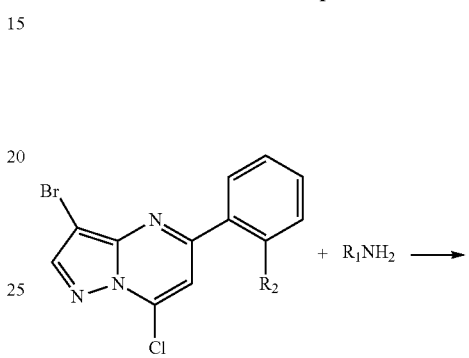

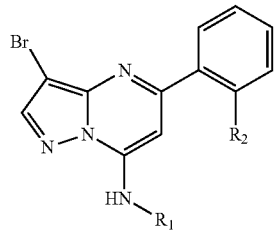

Where: R$_2$ = H, or Cl

3-Bromo-7-chloro-5-(2-chlorophenyl)pyrazolo[1,5-a]pyrimidine (1 equivalent) (prepared as described in Preparative Example 129), or 3-Bromo-7-chloro-5-phenylpyrazolo[1,5-a]pyrimidine (1 equivalent) (prepared as described in Preparative Example 127), R$_1$NH$_2$ (1.2 equivalents) and diisopropyl ethylamine (2 equivalents) were dissolved in anhydrous 1,4-dioxane and the mixture was heated at 75° C. for the time given in Table 97. The solution was evaporated to dryness and the residue was chromatographed on a silica gel column as described in Table 97, to give the title compound.

Using the appropriate reactants and essentially the same procedure as described above, the products of Examples 431 to 438 were prepared. Variations in the reaction conditions are noted in Table 35.

TABLE 35

| Ex. | Structure | MW | FABMS MH+ | Reaction Conditions | Yield | Chromatographic Data |
|---|---|---|---|---|---|---|
| 431 | 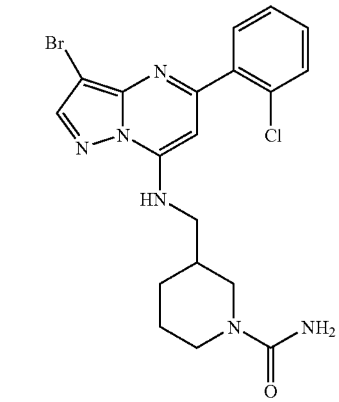 [SMILES: NC(=O)N1CCCC(CNc2cc(-c3ccccc3Cl)nc3c(Br)cnn23)C1] | 463.8 | 463.0 | 75° C./ 26 h | 52% | 15 × 2.5 cm 0.5-2% (10% Conc. ammonium hydroxide in methanol)-dichloromethane |
| 432 | 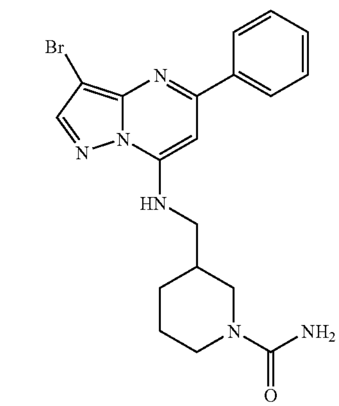 [SMILES: NC(=O)N1CCCC(CNc2cc(-c3ccccc3)nc3c(Br)cnn23)C1] | 429.3 | 429.2 | 75° C./ 26 h 25° C./ 39 h | 53% | 15 × 5 cm Dichloromethane; 1.5% (10% conc. ammonium hydroxide in methanol)-dichloromethane |
| 433 | 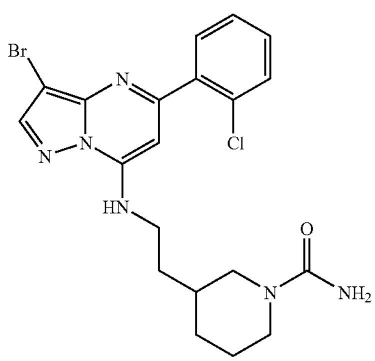 [SMILES: NC(=O)N1CCCC(CCNc2cc(-c3ccccc3Cl)nc3c(Br)cnn23)C1] | 477.8 | 477.1 | 75° C./ 26 h | 48% | 15 × 5 cm Dichloromethane; 3.5-15% (10% Conc. ammonium hydroxide in methanol)-dichloromethane |
| 434 | 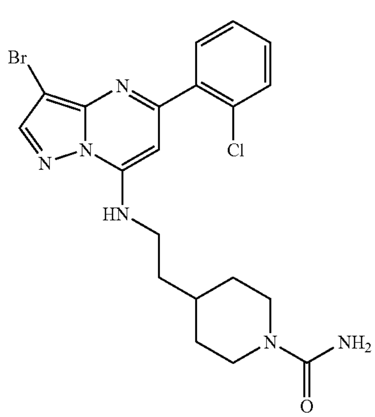 [SMILES: NC(=O)N1CCC(CCNc2cc(-c3ccccc3Cl)nc3c(Br)cnn23)CC1] | 477.8 | 477.0 | 75° C./ 26 h | 50% | 15 × 5 cm Dichloromethane; 3.5-15% (10% Conc. ammonium hydroxide in methanol)-dichloromethane |

TABLE 35-continued
| 435 | 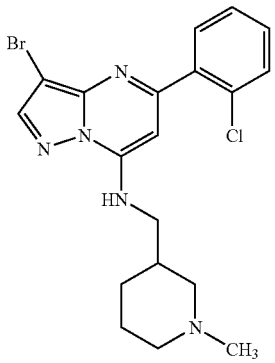 [SMILES: CN1CCCC(CNc2cc(-c3ccccc3Cl)nc3c(Br)cnn23)C1] | 434.8 | 434.1 | 75° C./ 26 h 25° C./ 65 h | 53% | 15 × 2.5 cm 3% (10% Conc. ammonium hydroxide in methanol)- dichloromethane |
| 436 | 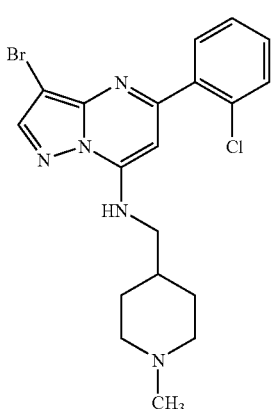 [SMILES: CN1CCC(CNc2cc(-c3ccccc3Cl)nc3c(Br)cnn23)CC1] | 434.8 | 434.2 | 75° C./ 27 h | 31% | 15 × 2.5 cm 3% (10% Conc. ammonium hydroxide in methanol)- dichloromethane |
| 437 | 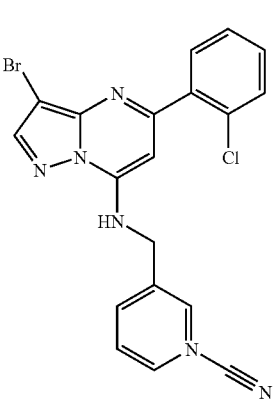 | 438.7 | 438.1 | 75° C./ 21 h 25° C./ 46 h | 97% | 15 × 2.5 cm 0.25% (10% Conc. ammonium hydroxide in methanol)- dichloromethane |
| 438 | 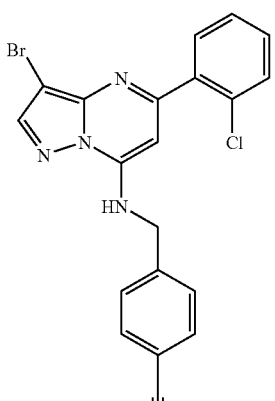 | 438.7 | 438.1 | 75° C./ 28 h −20° C./ 72 h | 95% | 60 × 2.5 cm 20% Ethyl acetate in hexane |

Additional physical data for the compounds are given below:

Example 431

Reactants: 3-Bromo-7-chloro-5-(2-chlorophenyl)pyrazolo[1,5-a]pyrimidine (110 mg, 0.318 mmoles) (prepared as described in Preparative Example 129); 3-(aminomethyl)piperidine-1-carboxamide (60 mg, 0.382 mmoles) (prepared as described in Preparative Example 241 above); diisopropyl ethylamine (0.111 mL, 0.636 mmoles); anhydrous 1,4-dioxane (2.5 mL). Physical properties: HRFABMS: m/z 463.0628 (MH$^+$). Calcd. for $C_{19}H_{21}N_6OBrCl$: m/z 463.0649: $\delta_H$ (CDCl$_3$) 1.38 (1H, m, CH$_2$), 1.52 (1H, m, CH$_2$), 1.73 (1H, m, CH), 1.93 (1H, m, CH$_2$), 2.02 (1H, m, CH$_2$), 2.98 (1H, m, CH$_2$), 3.06 (1H, m, CH$_2$), 3.37 (2H, m, CH$_2$), 3.58 (1H, m, CH$_2$), 3.82 (1H, m, CH$_2$), 4.87 (2H, bm, CONH$_2$), 6.28 (1H, s, H$_6$), 7.02 (1H, m, NH), 7.36 (2H, m, Ar—H), 7.45 (1H, m, Ar—H), 7.68 (1H, m, Ar—H) and 8.00 ppm (1H, s, H$_2$); $\delta_C$ (CDCl$_3$) CH$_2$: 23.7, 28.1, 44.6, 45.5, 47.2; CH: 35.2, 87.4, 127.2, 130.1, 130.3, 131.6, 143.9: C: 83.1, 132.1, 138.6, 145.5, 146.5, 158.0, 158.4.

Example 432

Reactants: 3-Bromo-7-chloro-5-phenylpyrazolo[1,5-a]pyrimidine (500 mg, 1.62 mmoles) (prepared as described in Preparative Example 127); 3-(aminomethyl)piperidine-1-carboxamide (306 mg, 1.944 mmoles) (prepared as described in Preparative Example 241 above); diisopropyl ethylamine (0.566 mL, 3.24 mmoles); anhydrous 1,4-dioxane (13 mL). Physical properties: HRFABMS: m/z 429.1031 (MH$^+$). Calcd. for $C_{19}H_{22}N_6OBr$: m/z 429.1038; $\delta_H$ (CDCl$_3$) 1.44 (1H, m, CH$_2$), 1.59 (1H, m, CH$_2$), 1.79 (1H, m, CH), 2.01 (1H, m, CH$_2$), 2.08 (1H, m, CH$_2$), 3.03 (1H, m, CH$_2$), 3.13 (1H, m, CH$_2$), 3.39 (1H, m, CH$_2$), 3.47 (1H, m, CH$_2$), 3.63 (1H, m, CH$_2$), 3.90 (1H, m, CH$_2$), 4.88 (2H, bm, CONH$_2$), 6.40 (1H, s, H$_6$), 6.90 (1H, m, NH), 7.53 (2H, m, Ar—H), 8.02 (1H, s, H$_2$) and 8.12 (1H, m, Ar—H); $\delta_C$ (CDCl$_3$) CH$_2$: 23.7, 28.2, 44.7, 45.5, 47.3; CH: 35.2, 82.9, 127.5, 127.5, 128.7, 128.7, 130.0, 143.9; C: 83.0, 138.5, 145.8, 147.1, 158.3, 158.5.

Example 433

Reactants: 3-Bromo-7-chloro-5-(2-chlorophenyl)pyrazolo[1,5-a]pyrimidine (347 mg, 1.01 mmoles) (prepared as described in Preparative Example 129); 3-(aminoethyl)piperidine-1-carboxamide (208 mg, 1.21 mmoles) (prepared as described in Preparative Example 242 above); diisopropyl ethylamine (0.393 mL, 2.02 mmoles); anhydrous 1,4-dioxane (9 mL). Physical properties: $\delta_H$ (CDCl$_3$) 1.24 (1H, m, CH$_2$), 1.55 (1H, m, CH), 1.72 (4H, m, CH$_2$), 1.93 (1H, m, CH$_2$), 2.69 (1H, m, CH$_2$), 2.94 (1H, m, CH$_2$), 3.55 (2H, m, CH$_2$), 3.73 (1H, m, CH$_2$), 3.98 (1H, m, CH$_2$), 4.83 (2H, bm, CONH$_2$), 6.55 (1H, s, H$_6$), 6.78 (1H, m, NH), 7.41 (2H, m, Ar—H), 7.50 (1H, m, Ar—H), 7.75 (1H, m, Ar—H) and 8.04 ppm (1H, s, H$_2$); $\delta_C$ (CDCl$_3$) CH$_2$: 24.6, 30.7, 32.6, 39.9, 45.3, 49.3; CH: 33.3, 87.5, 127.4, 130.1, 130.2, 131.6, 143.8; C: 83.2, 132.1, 138.8, 145.7, 146.2, 158.1, 158.1.

Example 434

Reactants: 3-Bromo-7-chloro-5-(2-chlorophenyl)pyrazolo[1,5-a]pyrimidine (275 mg, 0.803 mmoles) (prepared as described in Preparative Example 129); 4-(aminoethyl)piperidine-1-carboxamide (165 mg, 0.963 mmoles) (prepared as described in Preparative Example 243 above); diisopropyl ethylamine (0.311 mL, 0.963 mmoles); anhydrous 1,4-dioxane (7.2 mL). Physical properties: $\delta_H$ (d$_6$-DMSO) 1.00 (2H, m, CH$_2$), 1.50 (1H, m, CH), 1.59 (2H, m, CH$_2$), 1.67 (2H, m, CH$_2$), 2.60 (2H, m, CH$_2$), 3.48 (2H, m, CH$_2$), 3.70 (2H, m, CH$_2$), 5.84 (2H, bs, CONH$_2$), 6.43 (1H, s, H$_6$), 7.50 (2H, m, Ar—H), 7.62 (2H, m, Ar—H), 8.30 (1H, s, H$_2$) and 8.36 ppm (1H, m, NH); $\delta_C$ (d$_6$-DMSO)CH$_2$: 31.5, 31.5, 34.8, 43.5, 43.5, 43.5; CH: 32.8, 86.8, 127.1, 129.7, 130.3, 131.0, 143.3; CH: 81.3, 131.0, 138.7, 145.1, 146.4, 157.3, 157.8.

Example 435

Reactants: 3-Bromo-7-chloro-5-phenylpyrazolo[1,5-a]pyrimidine (174 mg, 0.507 mmoles) (prepared as described in Preparative Example 129) and 3-(aminomethyl)-1-methylpiperidine (65 mg, 0.507 mmoles) (prepared as described in Preparative Example 244 above); diisopropyl ethylamine (0.178 mL, 1.014 mmoles); anhydrous 1,4-dioxane (2.5 mL). Physical properties: HRFABMS: m/z 434.0742 (MH$^+$). Calcd. for $C_{19}H_{22}N_5BrCl$: m/z 434.0747; $\delta_H$ (CDCl$_3$) 1.18 (1H, m, CH$_2$), 1.68 (1H, m, CH$_2$), 1.80 (1H, m, CH$_2$), 1.87 (1H, m, CH$_2$), 1.96 (1H, m, CH), 2.14 (2H, m, CH$_2$), 2.32 (3H, s, NCH$_3$), 2.75 (1H, m, CH$_2$), 2.29 (1H, m, CH$_2$), 3.42 (2H, m, —NHCH$_2$CH), 6.36 (1H, s, H$_6$), 6.64 (1H, bm, NH), 7.41 (2H, m, Ar—H), 7.51 (1H, m, Ar—H), 7.74 (1H, m, Ar—H) and 8.06 ppm (1H, s, H$_2$); $\delta_C$ (CDCl$_3$) CH$_3$: 46.6; CH$_2$: 24.4, 27.9, 46.1, 56.1, 59.6; CH: 36.0, 87.4, 127.1, 130.1, 130.2, 131.6, 143.8; C: 83.2, 132.1, 138.9, 145.6, 146.4, 158.2.

Example 436

Reactants: 3-Bromo-7-chloro-5-phenylpyrazolo[1,5-a]pyrimidine (111.4 mg, 0.325 mmoles) (prepared as described in Preparative Example 129); 4-(aminomethyl)-1-methylpiperidine (50 mg, 0.39 mmoles) (prepared as described in Preparative Example 245 above); diisopropyl ethylamine (0.1135 mL, 0.65 mmoles); anhydrous 1,4-dioxane (1.5 mL). Physical data: HRFABMS: m/z 434.0735 (MH$^+$). Calcd. for $C_{19}H_{22}N_5BrCl$: m/z 434.0747; $\delta_H$ (CDCl$_3$) 1.42 (2H, m, CH$_2$), 1.72 (1H, m, CH), 1.82 (2H, m, CH$_2$), 1.93 (2H, m, CH$_2$), 2.20 (3H, s, NCH$_3$), 2.89 (2H, m, CH$_2$), 3.34 (2H, m, —NHCH$_2$CH), 6.31 (1H, s, H$_6$), 6.46 (1H, m, NH), 7.36 (2H, m, Ar—H), 7.46 (1H, m, Ar—H), 7.70 (1H, m, Ar—H) and 8.00 ppm (1H, s, H$_2$); $\delta_C$ (CDCl$_3$) CH$_3$: 46.4; CH$_2$: 30.2, 30.2, 48.0, 55.3, 55.3; CH: 35.4, 87.5, 127.2, 130.2, 130.2, 131.6, 143.8; C: 83.3, 132.2, 138.9, 145.7, 146.4, 158.1.

Example 437

Reactants: 3-Bromo-7-chloro-5-phenylpyrazolo[1,5-a]pyrimidine (191 mg, 0.557 mmoles) (prepared as described in Preparative Example 129); 3-(aminomethyl)benzonitrile (88.3 mg, 0.668 mmoles) (prepared as described in Preparative Example 246 above); diisopropyl ethylamine (0.192 mL, 1.114 mmoles); anhydrous 1,4-dioxane (4.5 mL). Physical data: HRFABMS: m/z 438.0125 (MH$^+$). Calcd. for $C_{19}H_{12}N_5BrCl$: m/z 438.0121; $\delta_H$ (CDCl$_3$) 4.76 (2H, d, —CH$_2$NH—), 6.32 (1H, s, H$_6$), 7.00 (1H, m, —CH$_2$NH—), 7.40 (2H, m, Ar—H), 7.46 (1H, m, Ar—H), 7.55 (1H, m, Ar—H), 7.67 (2H, m, Ar—H), 7.71 (1H, m, Ar—H), 7.75 (1H, m Ar—H) and 8.10 ppm (1H, s, H$_2$); $\delta_C$ (CDCl$_3$) CH$_2$: 45.5; CH: 88.2, 127.2, 130.0, 130.2, 130.4, 130.6, 131.4, 131.6, 131.9, 144.1; C: 83.8, 113.4, 118.3, 132.0, 137.8, 138.3, 145.6, 145.9, 158.0.

Example 438

Reactants: 3-Bromo-7-chloro-5-phenylpyrazolo[1,5-a]pyrimidine (233.5 mg, 0.681 mmoles) (prepared as described in Preparative Example 129); 4-(aminomethyl)benzonitrile (108 mg, 0.817 mmoles) (prepared as described in Preparative Example 247 above); diisopropyl ethylamine (0.235 mL, 1.362 mmoles); anhydrous 1,4-dioxane (5.3 mL). Physical data: HRFABMS: m/z 438.0117 (MH$^+$) Calcd. for $C_{20}H_{14}N_5BrCl$: m/z 438.0121; $\delta_H$ (CDCl$_3$) 4.80 (2H, d, CH$_2$), 6.30 (1H, s, H$_6$), 7.01 (1H, m, NH), 7.40 (2H, m, Ar—H), 7.47 (1H, m, Ar—H), 7.70 (2H, m, Ar—H), 7.72 (2H, m, Ar—H), 7.80 (1H, m, Ar—H) and 8.10 ppm (1H, s, H$_2$); $\delta_C$ (CDCl$_3$) CH$_2$: 45.8; CH: 88.2, 127.2, 127.7, 127.7, 130.2, 130.4, 131.6, 132.9, 132.9, 144.1; C: 83.8, 112.2, 118.4, 132.0, 138.2, 141.5, 145.5, 146.0, 158.0.

Example 439

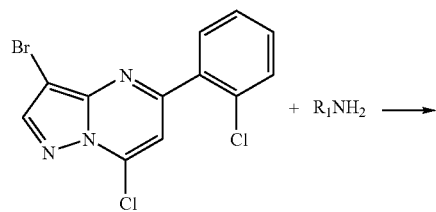

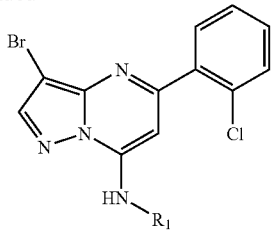

3-Bromo-7-chloro-5-(2-chlorophenyl)pyrazolo[1,5-a]pyrimidine (50 mg, 0.146 mmoles) (prepared as described in Preparative Example 129) was dissolved in anhydrous 1,4-dioxane (5 mL) in a GeneVac Technologies carousel reaction tube. PS-diisopropyl ethylamine resin (161 mg, 0.5828 mmoles) was added to each tube. A freshly prepared 1M solution of the appropriate amine R$_1$ NH$_2$ in anhydrous 1,4-dioxane (0.2185 mL, 0.2185 mmoles) was added to each tube and the tubes were sealed and heated at 70° C. for 78 h with magnetic stirring in the reaction block. Each tube was filtered and the resin was washed with anhydrous 1,4-dioxane and then dichloromethane. The combined individual filtrates from each tube were evaporated to dryness and the residues were each re-dissolved in anhydrous 1,4-dioxane (5 mL) and placed in GeneVac reaction tubes. To each tube was added PS-isocyanate resin (594 mg, 0.8742 mmoles) and PS-trisamine resin (129 mg, 0.4371 mmoles) and the tubes were stirred at 25° C. for 20 h in the reaction block. The resins were filtered off and washed with anhydrous 1,4-dioxane and dichloromethane. The filtrates from each tube were evaporated to dryness and the residues were each chromatographed on a silica gel column using the column size and the eluant shown in Table 36, to give the title compounds.

TABLE 36

| Ex. | Structure | MW | FABMS MH$^+$ | Yield | Chromatographic Data |
|---|---|---|---|---|---|
| 440 | 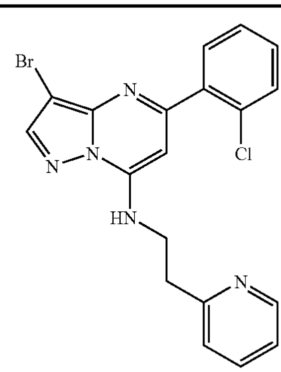 | 428.7 | 428.0 | 81% | 15 × 2.5 cm Dichloromethane; 0.5% Methanol in dichloromethane |
| 441 | 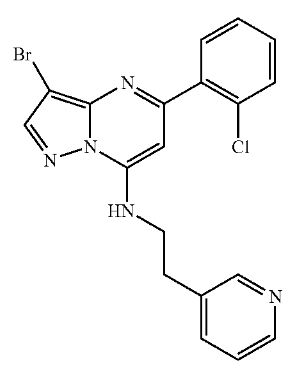 [SMILES: Clc1ccccc1-c1cc(NCCc2cccnc2)n2ncc(Br)c2n1] | 428.7 | 428.0 | 48% | 20 × 2 cm Dichloromethane; 1.5% Methanol in dichloromethane |

TABLE 36-continued

| Ex. | Structure | MW | FABMS MH+ | Yield | Chromatographic Data |
|---|---|---|---|---|---|
| 442 | 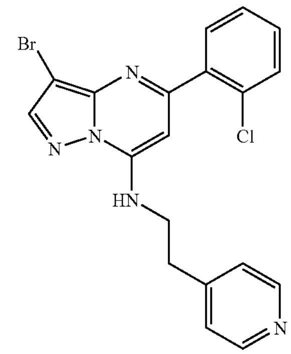 [SMILES: Clc1ccccc1-c1cc(NCCc2ccncc2)n2ncc(Br)c2n1] | 428.7 | 428.0 | 24% | 15 × 2.5 cm Dichloromethane; 1.5% Methanol in dichloromethane |
| 443 | 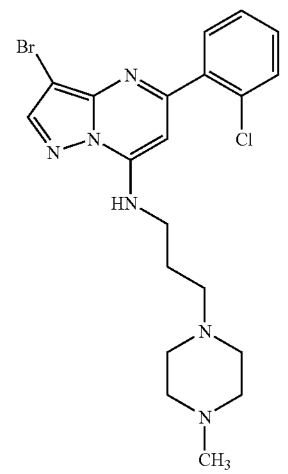 [SMILES: CN1CCN(CCCNc2cc(-c3ccccc3Cl)nc3c(Br)cnn23)CC1] | 463.8 | 463.0 | 44% | 15 × 2.5 cm Dichloromethane; 1.5% Methanol in dichloromethane |
| 444 | 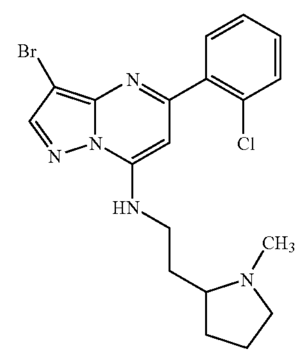 [SMILES: CN1CCCC1CCNc1cc(-c2ccccc2Cl)nc2c(Br)cnn12] | 434.8 | 434.1 | 63% | 15 × 2.5 cm 5% Methanol in dichloromethane |
| 445 | 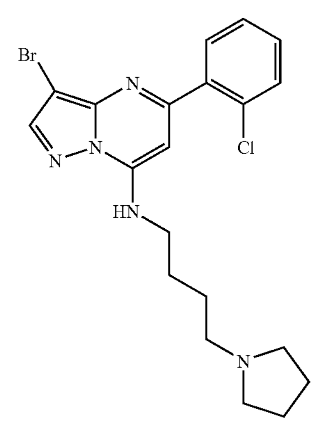 [SMILES: Clc1ccccc1-c1cc(NCCCCN2CCCC2)n2ncc(Br)c2n1] | 448.8 | 448.2 | 65% | 15 × 2.5 cm 5% Methanol in dichloromethane |

TABLE 36-continued

| Ex. | Structure | MW | FABMS MH+ | Yield | Chromatographic Data |
|---|---|---|---|---|---|
| 446 | 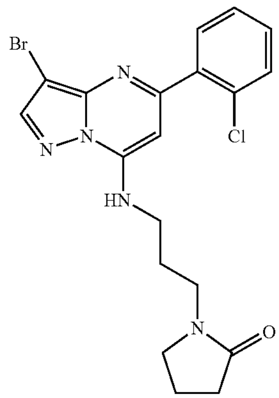 [SMILES: O=C1CCCN1CCCNc1cc(-c2ccccc2Cl)nc2c(Br)cnn12] | 448.8 | 448.1 | 40% | 15 × 2.5 cm Dichloromethane; 0.5% Methanol in dichloromethane |
| 447 | 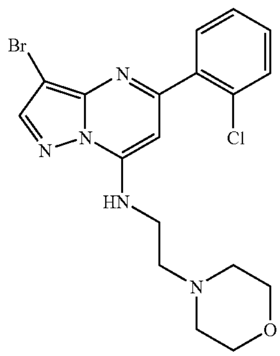 [SMILES: Clc1ccccc1-c1cc(NCCN2CCOCC2)n2ncc(Br)c2n1] | 436.7 | 436.1 | 72% | 15 × 2.5 cm 0.5% Methanol in dichloromethane |
| 448 | 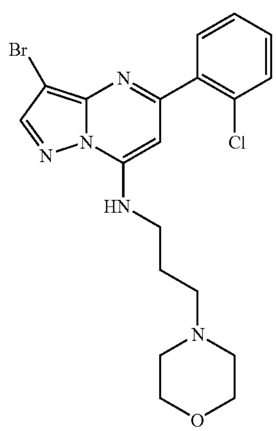 [SMILES: Clc1ccccc1-c1cc(NCCCN2CCOCC2)n2ncc(Br)c2n1] | 450.8 | 450.0 | 53% | 20 × 2 cm Dichloromethane; 0.5% Methanol in dichloromethane |
| 449 | 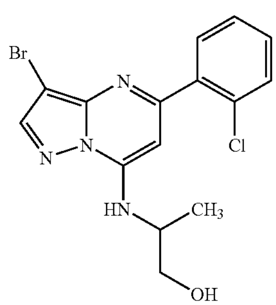 [SMILES: CC(CO)Nc1cc(-c2ccccc2Cl)nc2c(Br)cnn12] | 381.7 | 381.0 | 44% | 20 × 2 cm 1.5% Methanol in dichloromethane |

Additional physical data for the compounds are given below:

Example 440

Physical properties: HRFABMS: m/z 428.0272 (MH$^+$). Calcd. for $C_{19}H_{16}N_5BrCl$: m/z 428.0278; $\delta_H$ (CDCl$_3$) 3.28 (2H, dd, C$_5$H$_4$NCH$_2$CH$_2$NH—), 3.94 (2H, ddd, C$_5$H$_4$NCH$_2$CH$_2$NH—), 6.40 (1H, s, H$_6$), 7.22-7.29 (3H, m, Ar—H), 7.38-7.44 (2H, m, Ar—H), 7.51 (1H, m, Ar—H), 7.68 (1H, ddd, Ar—H), 7.73 (1H, Ar—H), 8.18 (1H, s, H$_2$) and 8.68 ppm (1H, NH); $\delta_C$ (CDCl$_3$) CH$_2$: 36.4, 41.5; CH: 87.3, 122.1, 123.6, 127.1, 130.1, 130.1, 131.6, 137.0, 143.8, 149.5; C: 83.1, 132.1, 138.9, 145.7, 146.3, 158.0, 158.1.

Example 441

Physical properties: HRFABMS: m/z 428.0272 (MH$^+$). Calcd. for $C_{19}H_{16}N_5BrCl$: m/z 428.0278; $\delta_H$ (CDCl$_3$) 3.12 (2H, dd, C$_5$H$_4$NCH$_2$CH$_2$NH—), 3.77 (2H, ddd, C$_5$H$_4$NCH$_2$CH$_2$NH—), 6.40 (1H, s, H$_6$), 6.59 (1H, m, Ar—H), 7.34 (1H, bm, Ar—H), 7.39-7.45 (2H, m, Ar—H), 7.52 (1H, m, Ar—H), 7.62 (1H, m, Ar—H), 7.75 (1H, m, Ar—H), 8.05 (1H, s, H$_2$) and 8.63 ppm (1H, m, NH); $\delta_C$ (CDCl$_3$) CH$_2$: 32.7, 43.1; CH: 87.5, 127.2, 130.2, 130.3, 131.6, 136.4, 142.9, 148.3, 149.8; C: 83.5, 132.0, 138.6, 145.6, 145.9, 158.1.

Example 442

Physical properties: HRFABMS: m/z 428.0275 (MH$^+$). Calcd. for $C_{19}H_{16}N_5BrCl$: m/z 428.0278; $\delta_H$ (CDCl$_3$) 3.13 (2H, dd, C$_5$H$_4$NCH$_2$CH$_2$NH—), 3.80 (2H, ddd, C$_5$H$_4$NCH$_2$CH$_2$NH—), 6.42 (1H, s, H$_6$), 6.53 (1H, m, Ar—H), 7.23 (2H, m, Ar—H), 7.40-7.46 (2H, m, Ar—H), 7.62 (1H, m, Ar—H), 7.76 (1H, m, Ar—H), 8.07 (1H, s, H$_2$) and 8.63 ppm (1H, m, NH); $\delta_C$ (CDCl$_3$) CH$_2$: 34.7, 42.5; CH: 87.4, 124.5, 124.5, 127.2, 130.2, 130.3, 131.6, 144.0, 150.2, 150.2; C: 83.5, 132.0, 138.6, 145.6, 145.9, 146.6, 158.1.

Example 443

Physical properties: HRFABMS: m/z 463.1003 (MH$^+$). Calcd. for $C_{20}H_{25}N_6BrCl$: m/z 463.1013; $\delta_H$ (CDCl$_3$) 1.98 (2H, m, =NCH$_2$CH$_2$CH$_2$NH—), 2.43 (3H, s, NCH$_3$), 2.67 (2H, m, =NCH$_2$CH$_2$CH$_2$NH—), 2.70 (8H, piperazine CH$_2$), 3.58 (2H, m, =NCH$_2$CH$_2$CH$_2$NH—), 6.32 (1H, s, H$_6$), 7.37-7.43 (2H, m, Ar—H), 7.50 (1H, m, Ar—H), 7.73 (1H, m, Ar—H), 8.06 (1H, s, H$_2$) and 8.60 ppm (1H, m, NH); $\delta_C$ (CDCl$_3$) CH$_3$: 46.1; CH$_2$: 24.1, 42.8, 53.3, 54.6, 54.6, 57.5, 57.5; CH: 87.1, 127.0, 130.0, 130.1, 131.5, 143.4; C: 82.7, 132.1, 139.2, 145.7, 146.7, 158.0.

Example 444

Physical properties: HRFABMS: m/z 434.0742 (MH$^+$). Calcd. for $C_{19}H_{22}N_5BrCl$: m/z 434.0747; $\delta_H$ (CDCl$_3$) 1.72 (1H, m, CH/CH$_2$), 1.78-1.90 (2H, m, CH/CH$_2$), 2.02 (3H, m, CH/CH$_2$), 2.50 (1H, m, CH/CH$_2$), 2.45 (3H, s, NCH$_3$), 2.51 (1H, m, CH/CH$_2$), 3.23 (1H, m, CH/CH$_2$), 3.54 (1H, m, CH/CH$_2$), 3.60 (1H, m, CH/CH$_2$), 6.32 (1H, s, H$_6$), 7.38-7.44 (2H, m, Ar—H), 7.51 (1H, m, Ar—H), 7.75 (1H, m, Ar—H), 7.96 (1H, bm, NH) and 8.05 ppm (1H, s, H$_2$); $\delta_C$ (CDCl$_3$) CH$_3$: 40.7; CH$_2$: 22.7, 29.3, 30.1, 39.4, 57.0; CH: 64.2, 87.1, 127.1, 130.0, 130.1, 131.6, 143.8; C: 82.8, 132.1, 139.1, 145.7, 146.4, 158.0.

Example 445

Physical properties: HRFABMS: m/z 448.0910 (MH$^+$). Calcd. for $C_{20}H_{24}N_5BrCl$: m/z 448.0904; $\delta_H$ (CDCl$_3$) 1.90 (4H, m, CH$_2$), 2.00 (4H, m, CH$_2$), 2.84 (2H, m, CH$_2$), 2.95 (4H, m, CH$_2$), 3.51 (2H, m, CH$_2$), 6.32 (1H, s, H$_6$), 7.05 (1H, bm, NH), 7.37-7.43 (2H, m, Ar—H), 7.50 (1H, m, Ar—H), 7.73 (1H, m, Ar—H) and 8.04 ppm (1H, s, H$_2$); $\delta_C$ (CDCl$_3$) CH$_2$: 23.4, 23.4, 24.8, 26.4, 41.8, 53.9, 53.9, 55.2; CH: 87.3, 127.1, 130.1, 130.2, 131.6, 143.7; C: 83.0, 132.0, 138.9, 145.7, 146.3, 158.1.

Example 446

Physical properties: HRFABMS: m/z 448.0548 (MH$^+$). Calcd. for $C_{19}H_{20}N_5OBrCl$: m/z 448.0540; $\delta_H$ (CDCl$_3$) 1.94 (2H, m, CH$_2$), 2.09 (2H, m, CH$_2$), 2.49 (2H, m, CH$_2$), 3.45 (2H, m, CH$_2$), 3.51 (4H, m, CH$_2$), 6.32 (1H, s, H$_6$), 7.37-7.44 (3H, m, Ar—H/NH), 7.51 (1H, m, Ar—H), 7.75 (1H, m, Ar—H) and 8.10 ppm (1H, s, H$_2$); $\delta_C$ (CDCl$_3$) CH$_2$: 18.0, 26.3, 30.8, 39.2, 39.9, 47.5; CH: 87.0, 127.1, 130.1, 130.1, 131.6, 144.1; C: 82.9, 132.1, 138.9, 145.6, 146.2, 157.9, 176.2.

Example 447

Physical properties: HRFABMS: m/z 436.0532 (MH$^+$). Calcd. for $C_{18}H_{20}N_5OBrCl$: m/z 436.0540; $\delta_H$ (CDCl$_3$) 2.60 (4H, bm, —N(CH$_2$CH$_2$)$_2$O), 2.83 (2H, m, =NCH$_2$CH$_2$NH—), 3.57 (2H, m, =NCH$_2$CH$_2$NH—), 3.83 (4H, m, —N(CH$_2$CH$_2$)$_2$O), 6.37 (1H, s, H$_6$), 6.99 (1H, bm, NH), 7.38-7.45 (2H, m, Ar—H), 7.51 (1H, m, Ar—H), 7.75 (1H, m, Ar—H) and 8.09 ppm (1H, s, H$_2$); $\delta_C$ (CDCl$_3$) CH$_2$: 38.2, 53.3, 53.3, 56.2, 66.9, 66.9; CH: 87.6, 127.1, 130.1, 130.2, 131.6, 143.9; C, 83.1, 132.1, 138.9, 145.7, 146.2, 158.1.

Example 448

Physical properties: HRFABMS: m/z 450.0688 (MH$^+$). Calcd. for $C_{19}H_{22}N_5OBrCl$: m/z 450.0696; $\delta_H$ (CDCl$_3$) 1.98 (2H, m, =NCH$_2$CH$_2$CH$_2$NH—), 2.58 (4H, m, —N(CH$_2$CH$_2$)$_2$O), 2.67 (2H, m, =NCH$_2$CH$_2$CH$_2$NH—), 3.59 (2H, m, =NCH$_2$CH$_2$CH$_2$NH—), 3.94 (4H, m, —N(CH$_2$CH$_2$)$_2$O), 6.31 (1H, s, H$_6$), 7.37-7.44 (2H, Ar—H), 7.51 (1H, m, Ar—H), 7.78 (1H, m, Ar—H), 8.08 (1H, s, H$_2$) and 8.60 ppm (1H, bm, NH); $\delta_C$ (CDCl$_3$) CH$_2$: 23.7, 42.7, 52.9, 52.9, 58.0, 66.6, 66.6; CH: 87.0, 127.0, 130.1, 131.5, 143.6; C: 82.8, 132.1, 139.1, 145.7, 146.7, 158.0.

Example 449

Physical properties: HRFABMS: m/z 381.0114 (MH$^+$). Calcd. for $C_{15}H_{15}N_4OBrCl$: m/z 381.0118; $\delta_H$ (CDCl$_3$) 1.39 (3H, d, CHCH$_3$), 2.76 (1H, bm, —OH), 3.71 (1H, m, =CHCH$_2$OH), 3.81 (1H, m, =CHCH$_2$OH), 3.88 (1H, m, =CHCH$_2$OH), 6.38 (1H, s, H$_6$), 7.38 (2H, m, Ar—H), 7.48 (1H, m, Ar—H), 7.68 (1H, m, Ar—H) and 8.02 ppm (1H, s, H$_2$); $\delta_C$ (CDCl$_3$) CH$_3$: 16.9; CH$_2$: 65.0; CH: 50.0, 88.0, 127.1, 130.1, 130.3, 131.4, 143.8; C: 83.0, 132.0, 138.5, 145.6, 146.0, 158.2.

Example 450

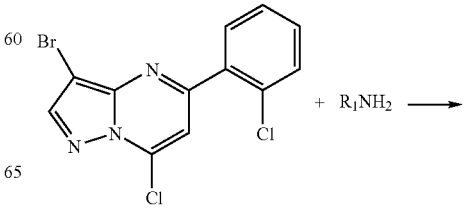

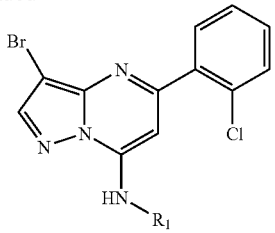

3-Bromo-7-chloro-5-(2-chlorophenyl)pyrazolo[1,5-a]pyrimidine (50 mg, 0.146 mmoles) (prepared as described in Preparative Example 129) was dissolved in anhydrous 1,4-dioxane (5 mL) in a GeneVac Technologies carousel reaction tube. PS-diisopropyl ethylamine resin (161 mg, 0.5828 mmoles) was added to each tube. A freshly prepared solution of the appropriate amine $R_1NH_2$ (0.219 mmoles) in anhydrous 1,4-dioxane (0.3 mL) was added to each tube, with the exception of Example 99-5 in which the amine was dissolved in 10% MeOH in 1,4-dioxane (0.3 mL), and the tubes were sealed and heated at 70° C. for 74 h with magnetic stirring in the reaction block. Each tube was filtered and the resin was washed with anhydrous 1,4-dioxane and then dichloromethane. The combined individual filtrates from each tube were evaporated to dryness and the residues were each re-dissolved in anhydrous 1,4-dioxane (5 mL) and placed in GeneVac reaction tubes. To each tube was added PS-isocyanate resin (594 mg, 0.8742 mmoles) and PS-trisamine resin (129 mg, 0.4371 mmoles) and the tubes were stirred at 25° C. for 20 h in the reaction block. The resins were filtered off and washed with anhydrous 1,4-dioxane and dichloromethane. The filtrates from each tube were evaporated to dryness and the residues were each chromatographed on a silica gel column using the column size and the eluant shown in Table 37, to give the title compounds.

TABLE 37

| Ex. | Structure | MW | FABMS MH+ | Yield | Chromatographic Data |
|---|---|---|---|---|---|
| 451 | 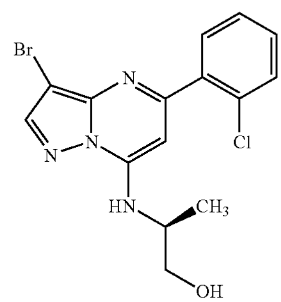 [SMILES: C[C@@H](CO)Nc1cc(-c2ccccc2Cl)nc2c(Br)cnn12] | 381.7 | 380.9 | 66% | 15 × 2.5 cm; 0.5% Methanol in dichloromethane |
| 452 | 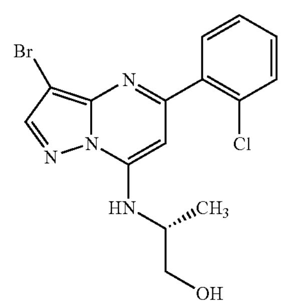 | 381.7 | 380.9 | 60% | 20 × 2 cm; 0.5% Methanol in dichloromethane |
| 453 | 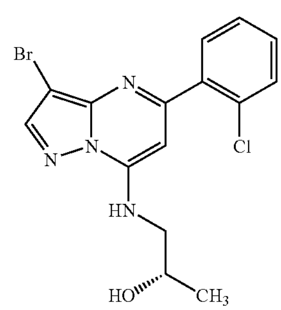 [SMILES: C[C@H](O)CNc1cc(-c2ccccc2Cl)nc2c(Br)cnn12] | 381.7 | 380.9 | 69% | 15 × 2.5 cm; 0.35% Methanol in dichloromethane |

TABLE 37-continued

| Ex. | Structure | MW | FABMS MH+ | Yield | Chromatographic Data |
|---|---|---|---|---|---|
| 454 | 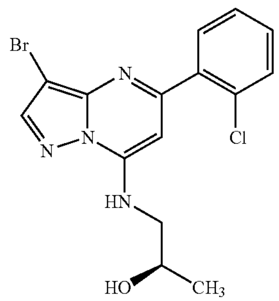 [SMILES: C[C@@H](O)CNc1cc(-c2ccccc2Cl)nc2c(Br)cnn12] | 381.7 | 380.9 | 75% | 15 × 2.5 cm; 0.35% Methanol in dichloromethane |
| 455 | 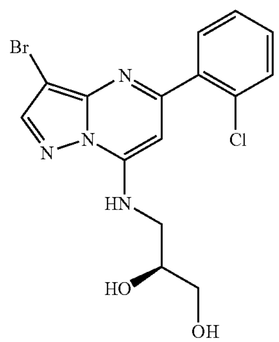 [SMILES: OC[C@@H](O)CNc1cc(-c2ccccc2Cl)nc2c(Br)cnn12] | 397.7 | 397.2 | 84% | 15 × 2.5 cm; 1.5% Methanol in dichloromethane |
| 456 | 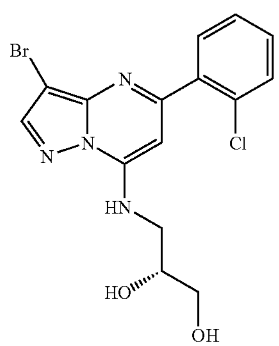 [SMILES: OC[C@H](O)CNc1cc(-c2ccccc2Cl)nc2c(Br)cnn12] | 397.7 | | | |
| 457 | 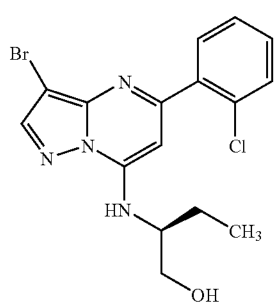 [SMILES: CC[C@@H](CO)Nc1cc(-c2ccccc2Cl)nc2c(Br)cnn12] | 395.7 | 395.0 | 60 | 15 × 2.5 cm; 0.35% Methanol in dichloromethane |
| 458 | 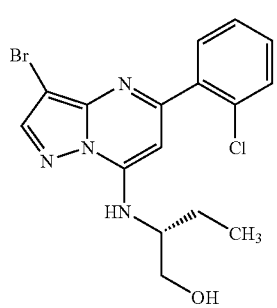 [SMILES: CC[C@H](CO)Nc1cc(-c2ccccc2Cl)nc2c(Br)cnn12] | 395.7 | 396.3 | 50% | 15 × 2.5 cm; 0.35% Methanol in dichloromethane |

TABLE 37-continued

| Ex. | Structure | MW | FABMS MH+ | Yield | Chromatographic Data |
|---|---|---|---|---|---|
| 459 | [structure: 3-bromo-5-(2-chlorophenyl)-7-[(4-hydroxybutyl)amino]pyrazolo[1,5-a]pyrimidine] | 395.7 | 396.0 | 76% | 15 × 2.5 cm; 0.35% Methanol in dichloromethane |

Additional physical data for the compounds are given below:

Example 451

Physical properties: HRFABMS: m/z 381.0115 (MH+). Calcd. for $C_{15}H_{15}N_4OBrCl$: m/z 381.0118; $[\alpha]_D^{25\ °C}$ +1.4° (c=0.25, MeOH); $\delta_H$ (CDCl$_3$) 1.44 (3H, d, —CHCH$_3$), 3.77 3.89 (1H, dd, CHCH$_2$OH), (1H, dd, CHCH$_2$OH), 3.94 (1H, m, CHCH$_2$OH), 6.41 (1H, s, H$_6$), 6.58 (1H, d, NH), 7.41 (2H, m, Ar—H), 7.51 (1H, m, Ar—H), 7.74 (1H, m, Ar—H) and 8.04 ppm (1H, s, H$_2$); $\delta_C$ (CDCl$_3$) CH$_3$: 17.1; CH$_2$: 65.5; CH: 49.9, 88.0, 127.1, 130.1, 130.2, 131.6, 143.8; C: 83.2, 132.1, 138.7, 145.6, 145.8, 158.1.

Example 452

Physical properties: HRFABMS: m/z 381.0115 (MH+). Calcd. for $C_{15}H_{15}N_4OBrCl$: m/z 381.0118; $[\alpha]_D^{25\ °C}$ +6.5° (c=0.32, MeOH); $\delta_H$ (CDCl$_3$) 1.44 (3H, d, —CHCH$_3$), 3.78 (1H, dd, CHCH$_2$OH), 3.89 (1H, dd, CHCH$_2$OH), 3.96 (1H, m, CHCH$_2$OH), 6.41 (1H, s, H$_6$), 6.58 (1H, d, NH), 7.41 (2H, m, Ar—H), 7.51 (1H, m, Ar—H), 7.75 (1H, m, Ar—H) and 8.04 ppm (1H, s, H$_2$); $\delta_C$ (CDCl$_3$) CH$_3$: 17.1; CH$_2$: 65.5; CH: 49.9, 88.0, 127.1, 130.1, 130.3, 131.6, 143.8; C: 83.2, 132.1, 138.6, 145.6, 145.8, 158.1.

Example 453

Physical properties: HRFABMS: m/z 381.0115 (MH+). Calcd. for $C_{15}H_{15}N_4OBrCl$: m/z 381.0118; $[\alpha]_D^{25\ °C}$ +9.4° (c=0.27, MeOH); $\delta_H$ (CDCl$_3$) 1.33 (3H, d, CH$_3$), 2.25 (1H, bs, OH), 3.37 (1H, dd, CH$_2$), 3.51 (1H, m, CH$_2$), 4.16 (1H, m, C HOH), 6.35 (1H, s, H$_6$), 6.93 (1H, m, NH), 7.40 (2H, m, Ar—H), 7.50 (1H, m, Ar—H), 7.70 (1H, m, Ar—H) and 8.04 ppm (1H, s, H$_2$); $\delta_C$ (CDCl$_3$) CH$_3$: 20.8; CH$_2$: 49.2; CH: 65.7, 87.8, 127.1, 130.1, 130.2, 131.2, 143.9; C: 83.1, 132.1, 138.5, 145.6, 146.6, 158.3.

Example 454

Physical properties: HRFABMS: m/z 381.0112 (MH+). Calcd. for $C_{15}H_{15}N_4OBrCl$: m/z 381.0118; $[\alpha]_D^{25\ °C}$ -3.2° (c=0.29, MeOH); $\delta_H$ (CDCl$_3$) 1.32 (3H, d, CH$_3$), 2.48 (1H, bs, OH), 3.35 (1H, dd, CH$_2$), 3.49 (1H, m, CH$_2$), 4.15 (1H, m, C HOH), 6.34 (1H, s, H$_6$), 6.93 (1H, m, NH), 7.39 (2H, m, Ar—H), 7.49 (1H, m, Ar—H), 7.68 (1H, m, Ar—H) and 8.03 ppm (1H, s, H$_2$); $\delta_C$ (CDCl$_3$) CH$_3$: 20.8; CH$_2$: 49.2; CH: 65.7, 87.7, 127.1, 130.1, 130.3, 131.4, 143.9; C: 83.0, 132.0, 138.6, 145.6, 146.6, 158.3.

Example 455

Physical properties: HRFABMS: m/z 397.0054 (MH+). Calcd. for $C_{15}H_{15}N_4O_2BrCl$: m/z 397.0067; $[\alpha]_D^{25\ °C}$ -9.5° (c=0.28, MeOH); $\delta_H$ (CDCl$_3$) 3.18 (2H, bs, OH), 3.47 (1H, dd, CH$_2$), 3.58 (1H, dd, CH$_2$), 3.63 (1H, dd, CH$_2$OH), 3.70 (1H, dd, CH$_2$OH), 3.98 (1H, m, CH), 6.35 (1H, s, H$_6$), 7.10 (1H, m, NH), 7.37 (2H, m, Ar—H), 7.46 (1H, m, Ar—H), 7.64 (1H, m, Ar—H) and 8.01 ppm (1H, s, H$_2$); $\delta_C$ (CDCl$_3$) CH$_2$: 44.7, 64.0; CH: 69.7, 87.7, 127.0, 130.1, 130.3, 131.3, 143.9; C: 82.9, 132.0, 138.4, 145.4, 146.7, 158.3.

Example 456

This enantiomer may be prepared by essentially the same manner as described above.

Example 457

Physical properties: HRFABMS: m/z 395.0260 (MH+). Calcd. for $C_{16}H_{17}N_4OBrCl$: m/z 395.0274; $[\alpha]_D^{25\ °C}$ -34.3° (c=0.28, MeOH); $\delta_H$ (CDCl$_3$) 1.08 (3H, dd, CH$_3$), 1.78 (1H, m, CH$_2$), 1.86 (1H, m, CH$_2$), 2.35 (1H, bs, CH$_2$OH), 3.71 (1H, m, CHNH), 3.81 (1H, dd, CH$_2$OH), 3.90 (1H, dd, C H$_2$OH), 6.42 (1H, s, H$_6$), 6.53 (1H, m, NH), 7.41 (2H, m, Ar—H), 7.51 (1H, Ar—H), 7.75 (1H, m, Ar—H) and 8.04 ppm (1H, s, H$_2$); $\delta_C$ (CDCl$_3$) CH$_3$: 10.5; CH$_2$: 24.5, 63.7; CH: 55.9, 88.0, 127.1, 130.1, 130.2, 131.6, 143.8; C: 83.2, 132.1, 138.6, 145.6, 146.3, 158.1.

Example 458

Physical properties: HRFABMS: m/z 395.0274 (MH+). Calcd. for $C_{16}H_{17}N_4OBrCl$: m/z 395.0274; $[\alpha]_D^{25\ °C}$ +27.5° (c=0.25, MeOH); $\delta_H$ (CDCl$_3$) 1.05 (3H, dd, CH$_3$), 1.76 (1H, m, CH$_2$), 1.85 (1H, m, CH$_2$), 2.28 (1H, bs, CH$_2$OH), 3.67 (1H, m, CHNH), 3.77 (1H, dd, CH$_2$OH), 3.84 (1H, dd, C H$_2$OH), 6.49 (1H, s, H$_6$), 6.66 (1H, m, NH), 7.39 (2H, m, Ar—H), 7.49 (1H, Ar—H), 7.71 (1H, m, Ar—H) and 8.04 ppm (1H, s, H$_2$); $\delta_C$ (CDCl$_3$) CH$_3$: 10.5; CH$_2$: 24.3, 63.3; CH: 56.1, 88.0, 127.1, 130.1, 130.3, 131.5, 143.8; C: 83.0, 132.1, 138.6, 145.6, 146.3, 158.2.

Example 459

Physical properties: HRFABMS: m/z 395.0264 (MH$^+$). Calcd. for $C_{16}H_{17}N_4OBrCl$: m/z 395.0274; $\delta_H$ (CDCl$_3$) 1.77 (2H, m, —NHCH$_2$CH$_2$CH$_2$CH$_2$OH), 1.90 (1H, bm, —NHCH$_2$CH$_2$CH$_2$CH$_2$OH), 1.93 (2H, m, —NHCH$_2$CH$_2$CH$_2$CH$_2$OH), 3.54 (2H, m, —NHCH$_2$CH$_2$CH$_2$CH$_2$OH), 3.77 (2H, m, —NHCH$_2$CH$_2$CH$_2$CH$_2$OH), 6.37 (1H, s, H$_6$), 6.72 (1H, m, —NHCH$_2$CH$_2$CH$_2$CH$_2$OH), 7.41 (2H, m, Ar—H), 7.51 (1H, m, Ar—H), 7.75 (1H, m, Ar—H) and 8.06 ppm (1H, s, H$_2$); $\delta_C$ (CDCl$_3$) CH$_2$: 25.7, 29.7, 42.2, 62.2; CH: 87.4, 127.1, 130.1, 130.2, 131.6, 143.8; C: 83.1, 132.1, 138.8, 145.6, 146.3, 158.1.

Example 460

4-{[3-bromo-5-(2-chlorophenyl)pyrazolo[1,5-a]pyrimidin-7-ylamino]methyl}piperidine-1-carboxylic acid amide

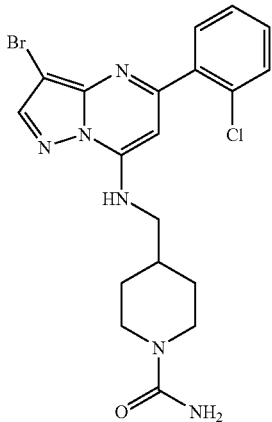 [SMILES: NC(=O)N1CCC(CNc2cc(-c3ccccc3Cl)nc3c(Br)cnn23)CC1]

A. 4-{[3-BROMO-5-(2-chlorophenyl)pyrazolo[1,5-a]pyrimidin-7-ylamino]methyl}piperidine-1-carboxylic acid tert-butyl ester

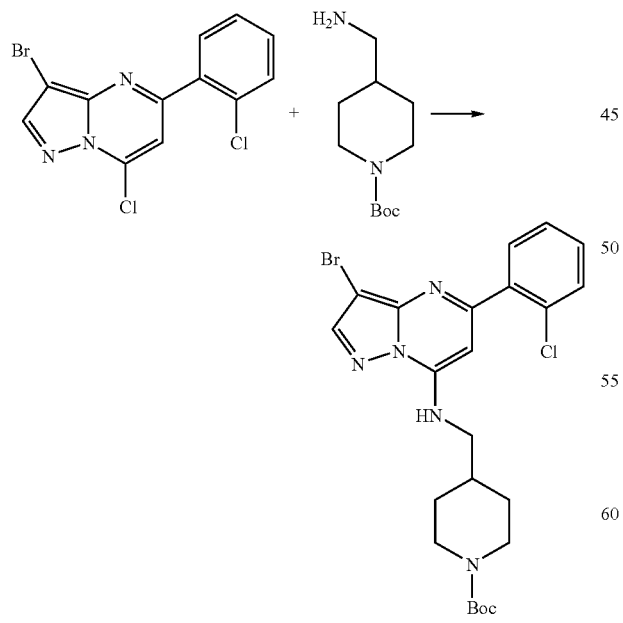

3-Bromo-7-chloro-5-(2-chlorophenyl)pyrazolo[1,5-a]pyrimidine (300 mg, 0.875 mmoles) (prepared as described in Preparative Example 129) was dissolved in anhydrous 1,4-dioxane (6.8 mL). 4-(aminomethyl)piperidine-1-carboxylic acid tert-butyl ester (225 mg, 1.05 mmoles) and diisopropyl ethylamine (0.3055 mL, 1.75 mmoles) were added and the mixture was heated at 75° C. for 24 h. The solution was evaporated to dryness and the residue was chromatographed on a silica gel column (15×5 cm) using dichloromethane as the eluant to give 4-{[3-bromo-5-(2-chlorophenyl)pyrazolo[1,5-a]pyrimidin-7-ylamino]methyl}piperidine-1-carboxylic acid tert-butyl ester (461.2 mg, 100%): FABMS: m/z 520.1 (MH$^+$); HRFABMS: m/z 520.1111 (MH$^+$). Calcd. for $C_{23}H_{28}N_5O_2BrCl$: m/z 520.1115; $\delta_H$ (CDCl$_3$) 1.30 (2H, m, CH$_2$), 1.51 (9H, s, —COOC(CH$_3$)$_3$), 1.85 (2H, d, CH$_2$), 1.95 (1H, m, CH), 2.76 (2H, m, CH$_2$), 3.40 (2H, m, CH$_2$), 6.37 (1H, s, H$_6$), 6.55 (1H, m, NH), 7.42 (2H, m, Ar—H), 7.52 (1H, m, Ar—H), 7.76 (1H, m, Ar—H) and 8.07 ppm (1H, s, H$_2$); $\delta_C$ (CDCl$_3$) CH$_3$: 28.5, 28.5, 28.5; CH$_2$: 29.1, 29.1, 43.5, 43.5, 47.9; CH: 36.3, 87.5, 127.2, 130.2, 130.3, 131.6, 143.9; C: 79.7, 83.3, 132.1, 138.6, 145.4, 146.3, 154.7, 158.1.

B. [3-bromo-5-(2-chlorophenyl)pyrazolo[1,5-a]pyrimidin-7-yl]piperidin-4-ylmethylamine

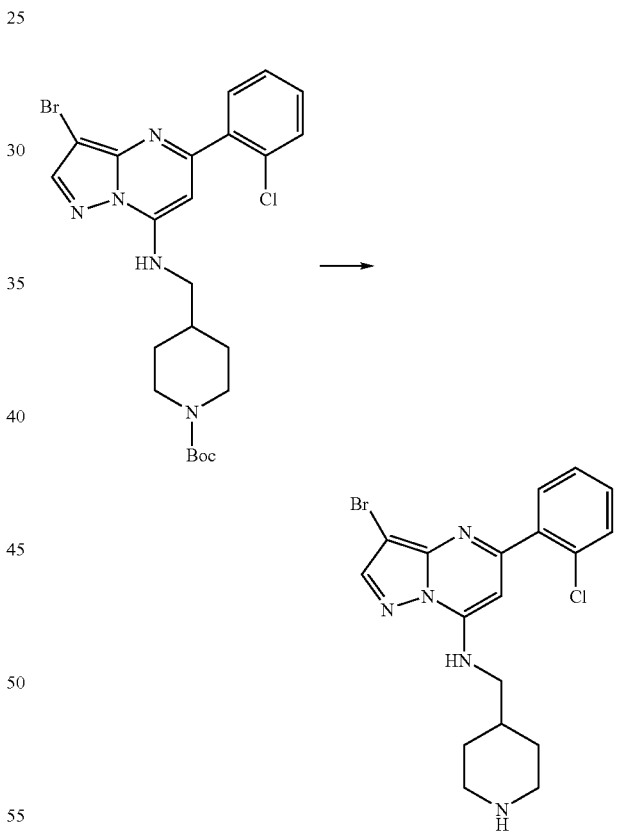

4-{[3-Bromo-5-(2-chlorophenyl)pyrazolo[1,5-a]pyrimidin-7-ylamino]methyl}piperidine-1-carboxylic acid tert-butyl ester (441 mg, 0.847 mmoles) (prepared as described in Example 460, Step A above) was dissolved in methanol (4.5 mL) and 10% (v/v) conc. sulfuric acid in 1,4-dioxane (11.46 mL) was added. The mixture was stirred at 25° C. for 0.5 h. The product was worked up as described in Preparative Example 241, step B and chromatographed on a silica gel column (15×5 cm) using 8% (10% conc. ammonium hydroxide in methanol)-dichloromethane as the eluant to give

[3-bromo-5-(2-chlorophenyl)pyrazolo[1,5-a]pyrimidin-7-yl]piperidin-4-ylmethylamine (314.4 mg, 88%): FABMS: m/z 420.0 (MH+); HRFABMS: m/z 420.0585 (MH+). Calcd. for $C_{18}H_{20}N_5BrCl$: m/z 420.0591; $\delta_H$ (CDCl$_3$) 1.34 (2H, m, CH$_2$), 1.86 (2H, m, CH$_2$), 1.91 (1H, m, CH), 2.10 (1H, bm, piperidine-NH), 2.67 (2H, m, CH$_2$), 3.18 (2H, m, CH$_2$), 3.38 (2H, m, CH$_2$), 6.37 (1H, s, H$_6$), 6.53 (1H, m, NH), 7.42 (2H, m, Ar—H), 7.52 (1H, m, Ar—H), 7.76 (1H, m, Ar—H) and 8.06 ppm (1H, s Ar—H); $\delta_C$ (CDCl$_3$) CH$_2$: 31.2, 31.2, 46.2, 46.2, 48.4; CH: 36.4, 89.5, 127.1, 130.1, 130.5, 131.6, 143.8; C: 83.2, 132.1, 138.9, 145.6, 146.4, 158.1.

C. 4-{[3-bromo-5-(2-chlorophenyl)pyrazolo[1,5-a]pyrimidin-7-ylamino]methyl}piperidine-1-carboxylic acid amide

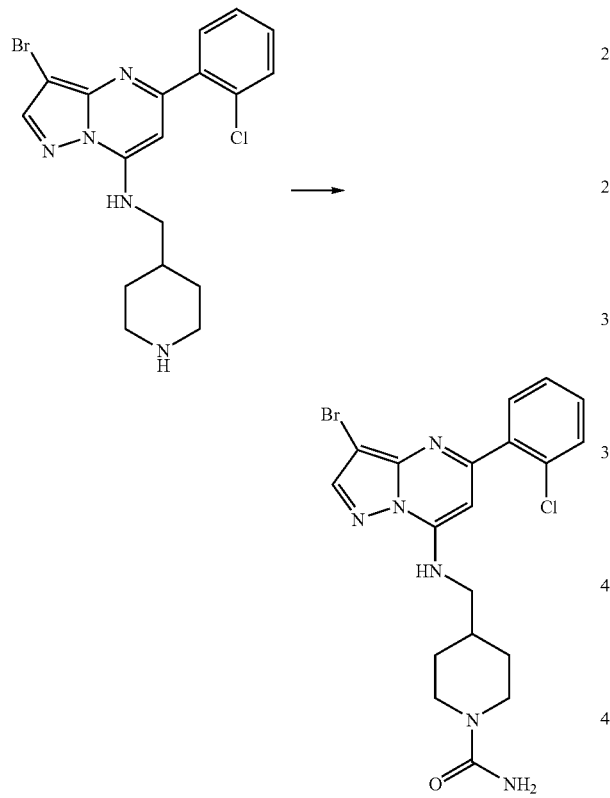

[3-Bromo-5-(2-chlorophenyl)pyrazolo[1,5-a]pyrimidin-7-yl]piperidin-4-ylmethylamine (57 mg, 0.136 mmoles) (prepared as described in Example 460, Step B above) was dissolved in anhydrous dichloromethane (1.2 mL) and trimethylsilylisocyanate (0.091 mL, 0.679 mmoles) was added. The mixture was stirred at 25° C. for 2.5 h. The mixture was diluted with dichloromethane and washed with saturated aqueous sodium bicarbonate. The organic layer was dried (MgSO$_4$), filtered and evaporated to dryness. The residue was chromatographed on a silica gel column (30×2.5 cm) using 3% (10% conc. ammonium hydroxide in methanol)-dichloromethane as the eluant to give 4-{[3-bromo-5-(2-chlorophenyl)pyrazolo[1,5-a]pyrimidin-7-ylamino]methyl}piperidine-1-carboxylic acid amide (53.7 mg, 86%): FABMS: m/z 463.1 (MH+); HRFABMS: m/z 463.0647 (MH+). Calcd. for $C_{19}H_{21}N_6OBrCl$: m/z 463.0649; $\delta_H$ (d$_6$-DMSO) 1.09 (2H, m, CH$_2$), 1.63 (2H, m, CH$_2$), 1.87 (1H, m, CH), 2.60 (2H, m, CH$_2$), 3.53 (2H, bm, CONH$_2$), 3.91 (2H, d, CH$_2$), 6.52 (1H, s, H$_6$), 7.50 (2H, m, Ar—H), 7.62 (2H, m, Ar—H), 8.33 (1H, s, H$_2$) and 8.52 ppm (1H, m, NH); $\delta_C$ (d$_6$-DMSO)CH$_2$: 30.1, 30.1, 44.2, 44.2, 47.7; CH: 36.4, 88.2, 128.1, 130.7, 131.4, 132.1, 147.9; C: 82.1, 132.1, 139.4, 145.7, 147.9, 158.1, 158.8.

Example 461

2-{2-[3-bromo-5-(2-chlorophenyl)pyrazolo[1,5-a]pyrimidin-7-ylamino]ethyl}piperidine-1-carboxylic acid amide

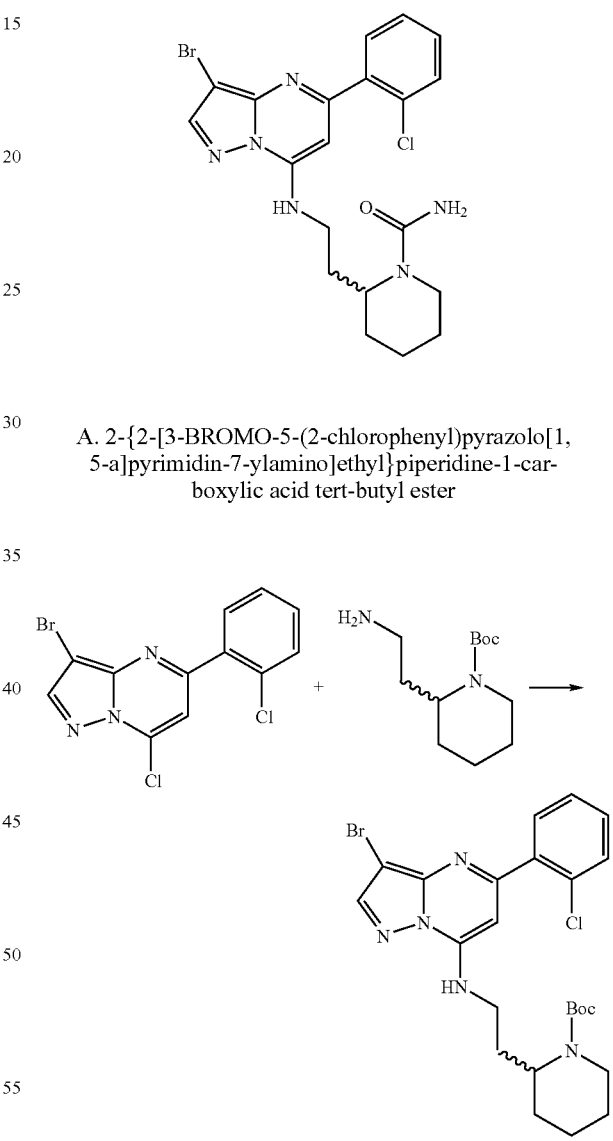

A. 2-{2-[3-BROMO-5-(2-chlorophenyl)pyrazolo[1,5-a]pyrimidin-7-ylamino]ethyl}piperidine-1-carboxylic acid tert-butyl ester 3-Bromo-7-chloro-5-(2-chlorophenyl)pyrazolo[1,5-a]pyrimidine (400 mg, 1.166 mmoles) (prepared as described in Preparative Example 129) was dissolved in anhydrous 1,4-dioxane (5.7 mL). 2-Aminoethylpiperidine-1-carboxylic acid tert-butyl ester (266 mg, 1.166 mmoles) and diisopropyl ethylamine (0.409 mL, 2.33 mmoles) were added and the mixture was heated at 75° C. for 48 h. Additional diisopropyl ethylamine (0.204 mL, 1.166 mmoles) was added and the heating was continued for a total of 58 h. The solution was evaporated to dryness and the residue was chromatographed on a silica gel column (15×5 cm) using dichloromethane followed by 0.3% (10% conc. ammonium hydroxide in methanol)-dichloromethane as the eluant to give 2-{[3-bromo-5-(2-chlorophenyl)pyrazolo[1,5-a]pyrimidin-7-ylamino]ethyl}piperidine-1-carboxylic acid tert-butyl ester (491.1 mg, 79%): FABMS: m/z 534.1 (MH$^+$); HRESIMS: m/z 534.12797 (MH$^+$). Calcd. for $C_{24}H_{30}N_5O_2BrCl$: m/z 534.12714; $\delta_H$ (CDCl$_3$) 1.50 (1H, m, CH$_2$), 1.51 (9H, s, COOC(CH$_3$)$_3$), 1.57 (2H, m, CH$_2$), 1.68 (2H, m, CH$_2$), 1.76 (2H, m, CH$_2$), 2.24 (1H, bm, CH$_2$), 2.82/3.4013.54/4.0814.51 (5H, m, CH/CH$_2$), 6.34 (1H, s, H$_6$), 7.41 (2H, m, Ar—H), 7.51 (1H, m, Ar—H), 7.76 (1H, m, Ar—H) and 8.08 ppm (1H, s, H$_2$); $\delta_C$ (CDCl$_3$) CH$_3$: 28.5, 28.5, 28.5; CH$_2$: 19.2, 25.5, 29.2, 29.2, 39.2, 67.1; CH: ~47.4, 87.1, 127.1, 130.1, 130.1, 131.6, 143.9; C: 80.0, 83.0, 132.1, 138.9, 145.7, 146.2, 158.0.

B. [3-bromo-5-(2-chlorophenyl)pyrazolo[1,5-a]pyrimidin-7-yl]-(2-piperidin-2-ylethyl)amine

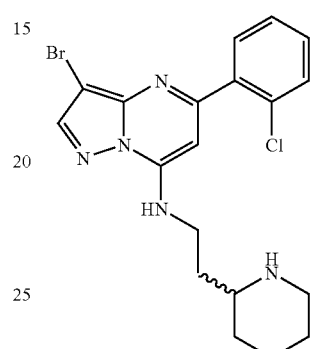

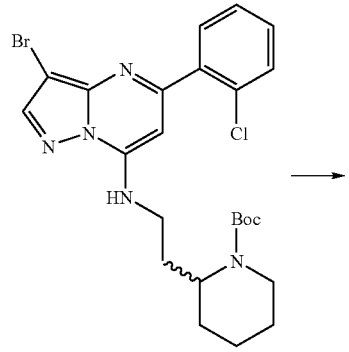

2-{[3-Bromo-5-(2-chlorophenyl)pyrazolo[1,5-a]pyrimidin-7-ylamino]ethyl}piperidine-1-carboxylic acid tert-butyl ester (465 mg, 0.869 mmoles) (prepared as described in Example 461, Step A above) was dissolved in methanol (4.5 mL) and 10% (v/v) conc. sulfuric acid in 1,4-dioxane (11.76 mL) was added. The mixture was stirred at 25° C. for 1.5 h. The product was worked up as described in Preparative Example 241, step B and chromatographed on a silica gel column (15×5 cm) using 3.5% (10% conc. ammonium hydroxide in methanol)-dichloromethane as the eluant to give [3-bromo-5-(2-chlorophenyl)pyrazolo[1,5-a]pyrimidin-7-yl]piperidin-2-ylethyl)amine (365.6 mg, 97%): FABMS: m/z 434.1 (MH$^+$); HRFABMS: m/z 434.0726 (MH$^+$). Calcd. for $C_{19}H_{22}N_5BrCl$: m/z 434.0747; $\delta_H$ (CDCl$_3$) 1.24 (1H, m, CH$_2$), 1.41 (1H, m, CH$_2$), 1.49 (1H, m, CH$_2$), 1.66 (1H, m, CH$_2$), 1.73 (1H, m, CH$_2$), 1.81 (1H, m, CH$_2$), 1.88 (2H, m, CH$_2$), 2.68 (1H, m, CH$_2$), 2.78 (1H, m, CH$_2$), 3.20 (1H, m, CH), 3.55 (1H, m, CH$_2$), 3.60 (1H, m, CH$_2$), 6.32 (1H, s, H$_6$), 7.41 (2H, m, Ar—H), 7.51 (1H, m, Ar—H), 7.74 (1H, m, Ar—H), 7.78 (1H, m, NH) and 8.05 ppm (1H, s, H$_2$); $\delta_C$ (CDCl$_3$) CH$_2$: 24.7, 26.8, 33.1, 35.2, 40.3, 47.0; CH: 55.7, 87.2, 127.1, 130.0, 130.1, 131.5, 143.8; C: 82.9, 132.1, 139.0, 145.7, 146.5, 158.1.

C. 2-{2-[3-bromo-5-(2-chlorophenyl)pyrazolo[1,5-a]pyrimidin-7-ylamino]ethyl}piperidine-1-carboxylic acid amide

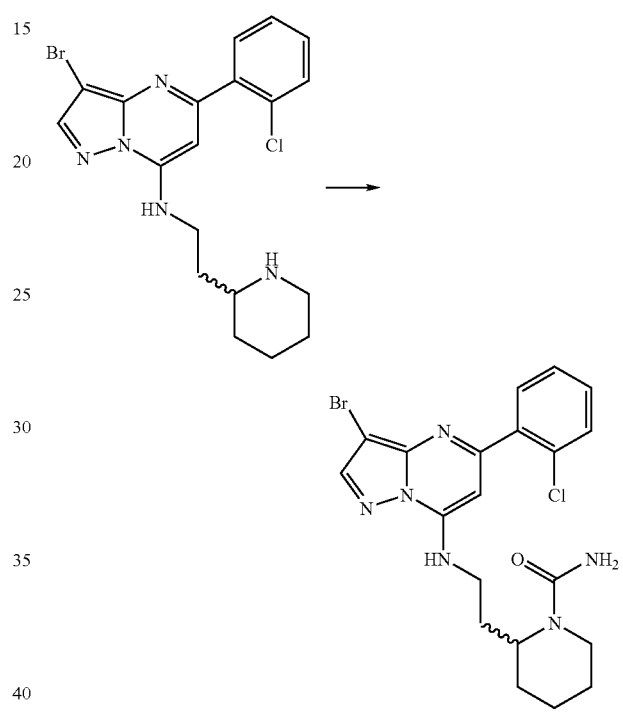

[3-Bromo-5-(2-chlorophenyl)pyrazolo[1,5-a]pyrimidin-7-yl]piperidin-2-ylethyl)amine (200 mg, 0.46 mmoles) (prepared as described in Example 461, Step B above) was dissolved in anhydrous dichloromethane (2 mL) and trimethylsilylisocyanate (0.31 mL, 2.3 mmoles) was added. The mixture was stirred at 25° C. for 1.25 h. Additional trimethylsilylisocyanate (0.155 mL, 1.15 mmoles) was added and the stirring was continued for a total of 3 h. The mixture was diluted with dichloromethane and washed with saturated aqueous sodium bicarbonate. The organic layer was dried (MgSO$_4$), filtered and evaporated to dryness. The residue was chromatographed on a silica gel column (30×2.5 cm) using 2% (10% conc. ammonium hydroxide in methanol)-dichloromethane as the eluant to give 2-{2-[3-bromo-5-(2-chlorophenyl)pyrazolo[1,5-a]pyrimidin-7-ylamino]ethyl}piperidine-1-carboxylic acid amide (106.3 mg, 48%): FABMS: m/z 477.0 (MH$^+$); HRFABMS: m/z 477.0804 (MH$^+$). Calcd. for $C_{20}H_{23}N_6OBrCl$: m/z 477.0805; $\delta_H$ (d$_6$-DMSO) 1.29 (1H, m, CH$_2$), 1.52 (5H, m, CH$_2$), 1.72 (1H, m, CH$_2$), 2.05 (1H, m, CH$_2$), 2.51 (2H, s, CONH$_2$), 2.79 (1H, dd, CH), 3.31 (1H, m, CH$_2$), 3.34 (1H, m, CH$_2$), 3.76 (1H, m, CH$_2$), 4.30 (1H, bm, CH$_2$), 6.42 (1H, s, H$_6$), 7.50 (2H, m, Ar—H), 7.60 (1H, m, Ar—H), 7.63 (1H, m, Ar—H), 8.29 (1H, s, H$_2$) and 8.38 ppm (1H, dd, NH); $\delta_C$ (d$_6$-DMSO)CH$_2$:

18.6, 25.2, 28.2, 38.4, 38.6, 54.8; CH: 46.7, 86.6, 127.1, 129.7, 130.3, 131.0, 143.4; C: 81.2, 131.0, 138.7, 145.1, 146.4, 158.2.

Example 462

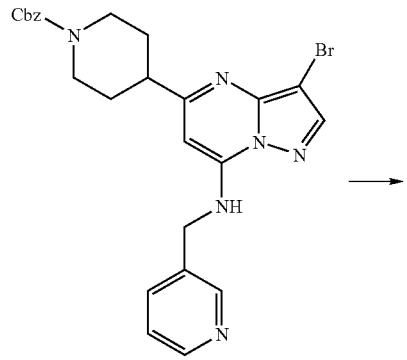

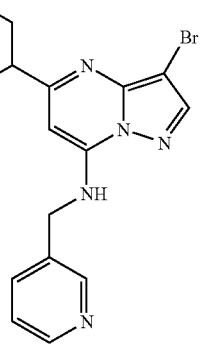

To a solution of the compound prepared in Example 204 (1.11 g, 2.12 mmol) in anhydrous acetonitrile (20 mL) was added TMSI (1.70 g, 8.52 mmol), dropwise at ambient temperature. After 10 minutes the acetonitrile was removed in vacuo. The resulting yellow foam was treated with 2 N HCl solution (7 mL) and then washed immediately with Et$_2$O (5×). The pH of the aqueous was adjusted to 10 with 50% NaOH (aq) and the product was isolated by saturation of the solution with NaCl (s) followed by extraction with CH$_2$Cl$_2$ (5×) to give the crystalline product (733 mg, 89% yield). MH$^+$=387; m.p.=207.5° C.

Examples 463-472

By essentially the same procedure set forth in Example 462 only substituting the compounds shown in Column 2 of Table 38, the compounds shown in Column 3 of Table 38 were prepared.

TABLE 38

| Ex. | Column 2 | Column 3 | CMPD |
|---|---|---|---|
| 463 | [Cbz-piperidine-pyrazolopyrimidine-Br with NH-CH$_2$-pyridine N-oxide] | [HN-piperidine-pyrazolopyrimidine-Br with NH-CH$_2$-pyridine N-oxide] | MH$^+$ = 403<br>$^1$H NMR (300 MHz, CDCl$_3$) δ 8.52 (s, 1H), 8.38 (d, 1H), 8.04 (s, 1H), 7.78 (d, 1H), 7.65 (t, 1H), 6.18 (s, 1H), 4.89 (s, 2H), 2.96-2.70 (m, 3H), 2.05-1.78 (m, 4H). |
| 464 | [Cbz-piperidine-pyrazolopyrimidine-Br with NH-CH$_2$-phenyl-oxadiazole] | [HN-piperidine-pyrazolopyrimidine-Br with NH-CH$_2$-phenyl-oxadiazole] | MH$^+$ = 454<br>m. p. = 175.4° C. |

TABLE 38-continued

| Ex. | Column 2 | Column 3 | CMPD |
|---|---|---|---|
| 465 | Cbz-piperidine-pyrazolopyrimidine-Br with NH-benzyl-thiadiazole | HN-piperidine-pyrazolopyrimidine-Br with NH-benzyl-thiadiazole | Yield = 87<br>MH⁺ = 470<br>m. p. = 220° C.<br>m. pt (hydrochloride salt) = 164.3° C. |
| 466 | Cbz-piperidine-pyrazolopyrimidine-Br with NH-benzyl-SO₂CH₃ | HN-piperidine-pyrazolopyrimidine-Br with NH-benzyl-SO₂CH₃ | MH⁺ = 464<br>m. p. = 206° C. |
| 467 | Cbz-piperidine-pyrazolopyrimidine-Br with NH-benzyl-CN | HN-piperidine-pyrazolopyrimidine-Br with NH-benzyl-CN | MH⁺ = 411<br>m. p. = 169.5° C. |

TABLE 38-continued

| Ex. | Column 2 | Column 3 | CMPD |
|---|---|---|---|
| 468 | Cbz-piperidinyl-pyrazolopyrimidine-Br with NH-propargyl | piperidinyl-pyrazolopyrimidine-Br with NH-propargyl | MH+ = 334<br>m. p. = 176.2° C. |
| 469 | Cbz-piperidinyl-pyrazolopyrimidine-Br with NH-CH2-C6H4-SO2NH2 | piperidinyl-pyrazolopyrimidine-Br with NH-CH2-C6H4-SO2NH2 | MH+ = 465<br>m. p. = 250.4° C. |
| 470 | N-Cbz-2-piperidinyl-pyrazolopyrimidine-Br with NH-CH2-(3-pyridyl) | 2-piperidinyl-pyrazolopyrimidine-Br with NH-CH2-(3-pyridyl) | MH+ = 387<br>m. p. = 68.5° C. |
| 471 | N-Cbz-3-piperidinyl-pyrazolopyrimidine-Br with NH-CH2-(3-pyridyl) | 3-piperidinyl-pyrazolopyrimidine-Br with NH-CH2-(3-pyridyl) | MH+ = 387<br>m. p. = 59.4° C. |

TABLE 38-continued

| Ex. | Column 2 | Column 3 | CMPD |
|---|---|---|---|
| 472 | | | 1. mp = 230-232<br>2. M + H = 396 |
| 472.10 | | | 1. mp = 157-160<br>2. M + H = 427 |

Example 473

Step A

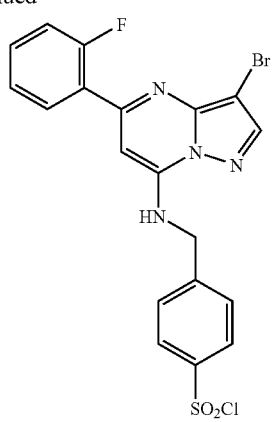

A solution of the sulfonic acid (560 mg, 1.17 mmol) in 5 mL of dry DMF was cooled to 0° C. and SOCl$_2$ (278 mg, 2.34 mmol) was added. The reaction mixture was brought to RT and stirred overnight. The next day the contents were poured on ice and the pH was carefully adjusted to 8. The product was extracted in to EtOAc and the solvent was removed after drying (Na$_2$SO$_4$) to provide 240 mg (41%) of the crude sulfonyl chloride which was used for the next step without further purification. $^1$H NMR (CDCl$_3$) δ 8.20-8.10 (m, 1H), 8.10-7.95 (m, 3H), 7.65 (d, 2H), 7.45-7.35 (m, 1H), 7.35-7.20 (m, 1H), 7.15-7.05 (m, 1H), 6.95 (t, 1H), 4.85 (d, 2H).

Step B

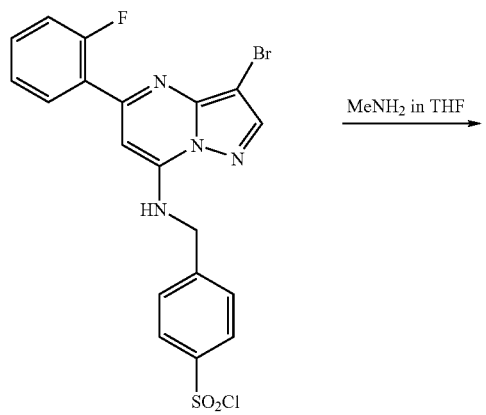

A solution of compound prepared in Example 473, Step A (120 mg, 0.24 mmol) in 10 mL of THF was treated with 2 mL of 1M MeNH$_2$ (2.00 mmol) in THF at RT overnight. The solvent was removed and the residue was purified by chromatography (silica, hexane:EtOAc (4:1→1:1)) to provide 56 mg (48%) of the sulfonamide. $^1$H NMR (DMSO-d6) δ 9.05 (t, J=9 Hz, 1H), 8.35 (s, 1H), 7.90 (t, J=7.5 Hz, 1H), 7.75 (d, J=9 Hz, 2H), 7.62 (d, J=9 Hz, 2H), 7.55-7.46 (m, 1H), 7.45-7.38 (m, 1H), 7.38-7.25 (m, 1H), 6.50 (s, 1H), 4.80 (d, 2H), 3.30 (s, 3H) LCMS: MH$^+$=492.1

Example 474

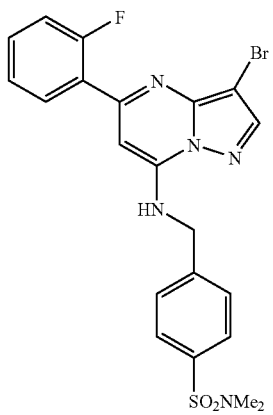

By essentially the same procedure set forth in Example 473, only substituting dimethylamine, the above compound was prepared. $^1$H NMR (CDCl$_3$) δ 8.14 (t, J=9 Hz, 1H), 8.00 (s, 1H), 7.76 (d, J=9 Hz, 2H), 7.54 (d, J=9 Hz, 2H), 7.34-7.44 (m, 1H), 7.26 (t, J=9 Hz, 1H), 7.14-7.04 (m, 1H), 6.93 (t, J=6 Hz, 1H), 6.45 (s, 1H), 4.75 (d, 2H), 2.70 (s, 6H) LCMS: MH$^+$=504.2

Example 475

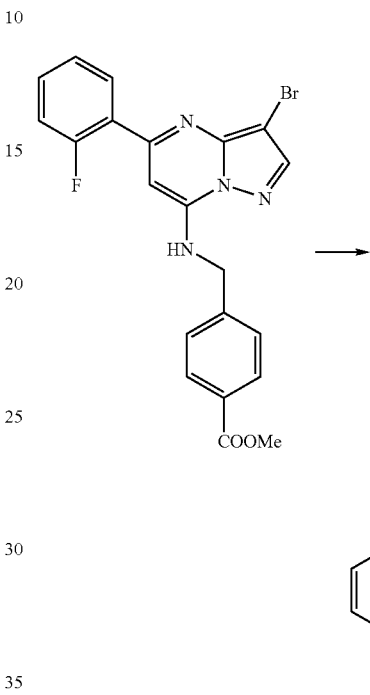

A mixture of the compound prepared in Example 129 (300 mg, 0.66 mmol), NaOH (5 g), CH$_3$OH —H$_2$O (100 mL, 90:10) was stirred at 25 C for about 15 h. Progress of hydrolysis was checked by TLC. Reaction mixture was concentrated to remove methanol. The concentrate was diluted with 50 mL water, and extracted with ether to remove any un-reacted ester. Aqueous solution, thus obtained, was neutralized with 3 N HCl to pH 4 to obtain free acid, filtered and washed repeatedly with water. The acid was dried under vacuum (270 mg, 93%) and used without further purification.

Example 476-479

By essentially the same procedure set forth in Example 475 only substituting the compounds in Column 2 of Table 39, the compounds in Column 3 of Table 39 were prepared.

TABLE 39
| Ex. | Column 2 | Column 3 | CMPD |
|---|---|---|---|
| 476 | 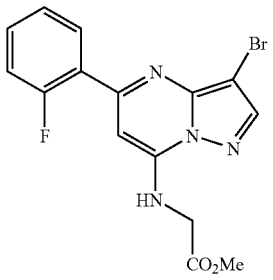 [SMILES: COC(=O)CNc1cc(-c2ccccc2F)nc2c(Br)cnn12] | 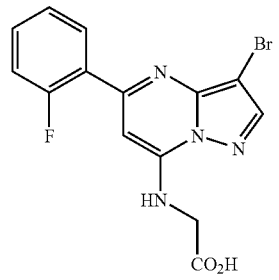 [SMILES: O=C(O)CNc1cc(-c2ccccc2F)nc2c(Br)cnn12] | Yield = 82%<br>LCMS: MH⁺ = 365 |
| 477 | 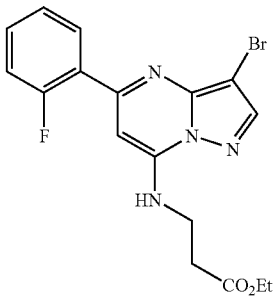 [SMILES: CCOC(=O)CCNc1cc(-c2ccccc2F)nc2c(Br)cnn12] | 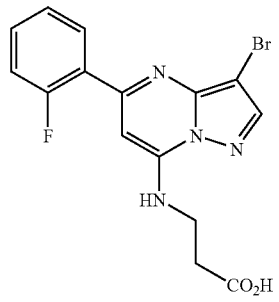 [SMILES: O=C(O)CCNc1cc(-c2ccccc2F)nc2c(Br)cnn12] | Yield = 82%<br>LCMS: MH⁺ = 379 |
| 478 | 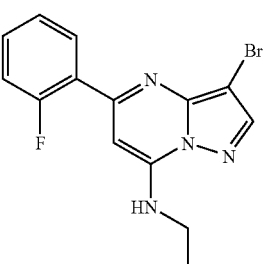 | 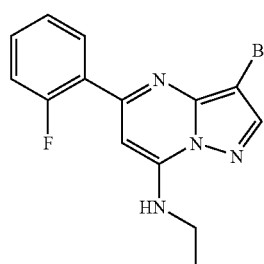 | Yield = 72%<br>LCMS: MH⁺ = 393 |
| 479 | 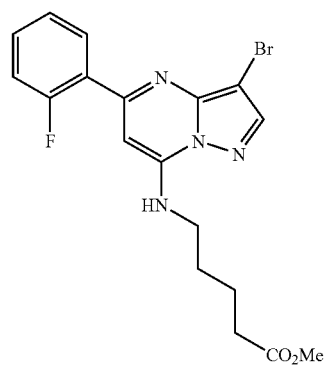 [SMILES: COC(=O)CCCCNc1cc(-c2ccccc2F)nc2c(Br)cnn12] | 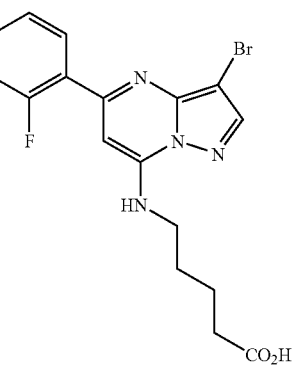 | Yield = 70%<br>LCMS: MH⁺ = 407 |

Additional data for select examples shown below:

Example 476

$^1$H NMR (CDCl$_3$) δ 8.15 (m, 2H), 8.0 (m, 1H), 7.6 (m, 1H), 7.3 (m, 2H), 6.6 (s, 1H), 4.2 (d, 2H).

Example 477

$^1$H NMR (CDCl$_3$) δ 8.15 (dt, 1H), 8.0 (s, 1H), 7.4 (m, 1H), 7.25 (dd, 1H), 7.15 (dd, 1H), 7.0 (t, 1H), 6.5 (s, 1H), 3.8 (dt, 2H), 2.6 (t, 2H).

Example 479

$^1$H NMR (CDCl$_3$) δ 8.15 (dt, 1H), 8.0 (s, 1H), 7.4 (m, 1H), 7.25 (dd, 1H), 7.15 (dd, 1H), 6.8 (t, 1H), 3.5 (dt, 2H), 2.4 (t, 2H), 1.8 (m, 4H).

Example 480

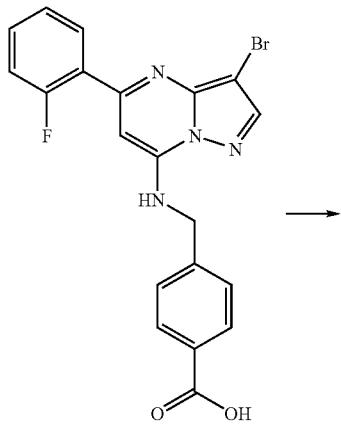

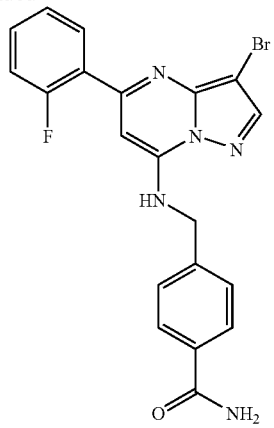 [SMILES: O=C(O)c1ccc(CNc2cc(-c3ccccc3F)nc3c(Br)cnn23)cc1]

A mixture of the acid from Example 475 (85 mg, 0.193 mmol) and Et$_3$N (20 mg, 0.193 mmol) in THF (20 mL) was stirred at 25 C for 15 min. Isobutyryl chloroformate (28 mg, 0.205 mmol) was added to the reaction mixture and stirred for 10 min followed by addition of NH4OH solution (0.5 mL). The reaction mixture was stirred for 1 hr and concentrated to dryness. The dry mass was purified by column chromatography.

Examples 481-509

By essentially the same procedure set forth in Example 480 only substituting the carboxylic acid shown in Column 2 of Table 40 and the amine shown in Column 3 of Table 40, the compounds shown in Column 4 of Table 40 were prepared.

TABLE 40

| Ex. | Column 2 | Column 3 | Column 4 | CMPD |
|---|---|---|---|---|
| 481 | (structure) | CH$_3$NH$_2$ | (structure) | Yield = 88%<br>LCMS<br>MH = 454 |

TABLE 40-continued

| Ex. | Column 2 | Column 3 | Column 4 | CMPD |
|---|---|---|---|---|
| 482 | | (CH₃)₂NH | | Yield = 80%<br>LCMS:<br>MH⁺ = 468 |
| 483 | | CH₃NH₂ | | Yield = 70%<br>LCMS<br>MH⁺ = 454. |
| 484 | | | | Yield = 75%<br>LCMS<br>MH⁺ = 482.1 |

TABLE 40-continued

| Ex. | Column 2 | Column 3 | Column 4 | CMPD |
|---|---|---|---|---|
| 485 | | | | Yield = 71%<br>LCMS<br>MH⁺ = 480.1 |
| 486 | | | | Yield = 75%<br>LCMS<br>MH⁺ = 494.1 |
| 487 | | | | Yield = 75%<br>MH⁺ = 494.1 |

TABLE 40-continued

| Ex. | Column 2 | Column 3 | Column 4 | CMPD |
|---|---|---|---|---|
| 488 | | | | Yield = 75%<br>MH+ = =<br>496.1 |
| 489 | | | | Yield = 75%<br>LCMS<br>MH+ =<br>508.1 |
| 490 | | | | Yield = 78%<br>LCMS<br>MH+ =<br>524.1 |

TABLE 40-continued

| Ex. | Column 2 | Column 3 | Column 4 | CMPD |
|---|---|---|---|---|
| 491 | | piperidine | | Yield = 73%<br>LCMS<br>MH⁺ = 508.1 |
| 492 | | morpholine | | Yield = 73%<br>LCMS<br>MH⁺ = 510.1 |
| 493 | | thiomorpholine | | Yield = 76%<br>LCMS<br>MH⁺ = 526.1 |

TABLE 40-continued

| Ex. | Column 2 | Column 3 | Column 4 | CMPD |
|---|---|---|---|---|
| 494 | | | | Yield = 76%<br>MH+ = 523.1 |
| 495 | | | | Yield = 76%<br>MH+ = 523.1 |
| 496 | | | | Yield = 51%<br>LCMS<br>MH+ = 484.1 |

TABLE 40-continued

| Ex. | Column 2 | Column 3 | Column 4 | CMPD |
|---|---|---|---|---|
| 497 | | | | Yield = 66%<br>MH+ = 537.1 |
| 498 | | | | Yield = 76%<br>LCMS<br>MH+ = 551.2 |
| 499 | | | | Yield = 79%<br>LCMS<br>MH+ = 552.1 |

TABLE 40-continued

| Ex. | Column 2 | Column 3 | Column 4 | CMPD |
|---|---|---|---|---|
| 500 | | | | Yield = 80%<br>MH+ = 549.1 |
| 501 | | | | Yield = 80%<br>LCMS MH+ = 478.1 |
| 502 | | | | Yield = 80%<br>LCMH+ = 468.1 |

TABLE 40-continued

| Ex. | Column 2 | Column 3 | Column 4 | CMPD |
|---|---|---|---|---|
| 503 | (structure) | H₂N-CH₂-CF₃ | (structure) | Yield = 80%<br>MH⁺ = 522.1 |
| 504 | (structure) | H₂N-CH₂-CH₂-S-Et | (structure) | Yield = 82%<br>LCMS MH⁺ = 528.1 |
| 505 | (structure) | CH₃NH₂ | (structure) | Yield = 60%<br>MH⁺ = 392 |
| 506 | (structure) | morpholine | (structure) | Yield = 60%<br>LCMH⁺ = 448.1 |

TABLE 40-continued

| Ex. | Column 2 | Column 3 | Column 4 | CMPD |
|---|---|---|---|---|
| 507 | | | | Yield = 70%<br>MH+ = 464.1 |
| 508 | | | | Yield = 50%<br>LCMS MH+ = 436.1 |
| 508.10 | | | | Yield = 92<br>MH+ = 577 |

Additional data for select examples given below:

Example 481

$^1$H NMR (CDCl$_3$) δ 8.15 (dt, 1H), 8.0 (s, 1H), 7.7 (d, 2H), 7.4 (s, 1H), 7.35 (d, 2H), 7.25 (dd, 1H), 7.1 (dd, 1H), 6.95 (t, 1H), 6.5 (s, 1H), 6.25 (bs, 1H), 4.7 (d, 2H), 3.0 (d, 3H).

Example 482

$^1$H NMR (CDCl$_3$) δ 8.15 (dt, 1H), 8.0 (s, 1H), 7.45-7.35 (m, 4H), 7.25 (d, 2H), 7.15 (dd, 1H), 6.7 (t, 1H), 6.5 (s, 1H), 4.7 (d, 2H), 3.1 (s, 3H), 3.0 (s, 3H).

Example 483

$^1$H NMR (CDCl$_3$) δ 8.15 (dt, 1H), 8.0 (s, 1H), 7.8 (bs, 1H), 7.7 (d, 1H), 7.5-7.3 (m, 3H), 7.25 (d, 1H), 7.15 (dd, 1H), 6.75 (t, 1H), 6.5 (s, 1H), 6.2 (bs, 1H), 4.7 (d, 2H), 3.0 (d, 3H).

Example 484

$^1$H NMR (CDCl$_3$) δ 8.15 (dt, 1H), 8.0 (s, 1H), 7.7 (d, 2H), 7.4 (d, 2H), 7.35 (m, 1H), 7.25 (dd, 1H), 7.15 (dd, 1H), 6.8 (t, 1H), 6.5 (s, 1H), 6.0 bs, 1H), 4.7 (d, 2H), 4.25 (m, 1H), 1.2 (d, 6H).

Example 485

$^1$H NMR (CDCl$_3$) δ 8.15 (dt, 1H), 8.0 (s, 1H), 7.7 (d, 2H), 7.4 (d, 2H), 7.35 (s, 1H), 7.25 (dd, 1H), 7.1 (dd, 1H), 6.9 (t, 1H), 6.5 (s, 1H), 6.3 (t, 1H), 4.7 (d, 2H), 2.9 (m, 1H), 0.8 (bt, 2H), 0.6 (bt, 2H).

Example 486

$^1$H NMR (CDCl$_3$) δ 8.15 (dt, 1H), 8.0 (s, 1H), 7.8 (d, 2H), 7.4 (d, 2H), 7.35 (d, 1H), 7.25 (dd, 1H), 7.1 (dd, 1H), 6.9 (t, 1H), 6.5 (s, 1H), 6.2 (t, 1H), 4.7 (d, 2H), 3.3 (dd, 2H), 1.05 (m, 1H), 0.5 (m, 2H), 0.25 (m, 2H).

Example 487

$^1$H NMR (CDCl$_3$) δ 8.15 (dt, 1H), 8.0 (s, 1H), 7.7 (d, 2H), 7.4 (d, 2H), 7.35 (m, 1H), 7.25 (dd, 1H), 7.15 (dd, 1H), 6.85 (t, 1H), 6.5 (s, 1H), 6.2 (bs, 1H), 4.7 (d, 2H), 4.6 (m, 1H), 2.4 (m, 2H), 1.95 (m, 1H), 1.75 (m, 2H).

Example 488

$^1$H NMR (CDCl$_3$) δ 8.5 (t, 1H), 8.15 (dt, 1H), 8.0 (s, 1H), 7.7 (d, 2H), 7.4 (d, 2H), 7.35 (m, 1H), 7.25 (dd, 1H), 7.15 (dd, 1H), 6.8 (t, 1H), 6.5 (s, 1H), 5.9 (bs, 1H), 4.7 (d, 2H), 1.4 (s, 9H).

Example 489

$^1$H NMR (CDCl$_3$) δ 8.15 (dt, 1H), 8.0 (s, 1H), 7.7 (d, 2H), 7.4 (d, 2H), 7.35 (m, 1H), 7.25 (dd, 1H), 7.15 (dd, 1H), 6.8 (t, 1H), 6.5 (s, 1H), 6.0 bs, 1H), 4.7 (d, 2H), 4.4 (m, 1H), 2.05 (m, 2H), 1.7 (m, 4H), 1.4 (m, 2H).

Example 490

$^1$H NMR (CDCl$_3$) δ 8.15 (dt, 1H), 8.0 (s, 1H), 7.7 (d, 2H), 7.4 (d, 2H), 7.35 (m, 1H), 7.25 (dd, 1H), 7.15 (dd, 1H), 6.8 (t, 1H), 6.5 (s, 1H), 6.5 (bs, 2H), 4.7 (d, 2H), 4.1 (m, 1H), 3.9-3.7 (m, 3H), 3.3 (m, 1H), 2.0-1.9 (m, 4H).

Example 491

$^1$H NMR (CDCl$_3$) δ 8.15 (dt, 1H), 8.0 (s, 1H), 7.45-7.35 (m, 5H), 7.25 (dd, 1H), 7.1 (dd, 1H), 6.8 (t, 1H), 6.5 (s, 1H), 4.7 (d, 2H), 3.7 (bs, 2H), 3.3 bs, 2H), 1.7 (bs, 4H), 1.5 (bs, 2H).

Example 492

$^1$H NMR (CDCl$_3$) δ 8.15 (dt, 1H), 8.0 (s, 1H), 7.45-7.35 (m, 5H), 7.25 (dd, 1H), 7.1 (dd, 1H), 6.85 (t, 1H), 6.5 (s, 1H), 4.7 (d, 2H), 3.8-3.4 (bm, 8H).

Example 493

$^1$H NMR (CDCl$_3$) δ 8.15 (dt, 1H), 8.0 (s, 1H), 7.45-7.35 (m, 5H), 7.25 (dd, 1H), 7.1 (dd, 1H), 6.80 (t, 1H), 6.5 (s, 1H), 4.7 (d, 2H), 4.0 (m, 2H), 3.6 (m, 2H), 2.8-2.45 (m, 4H).

Example 494

$^1$H NMR (CH3OD) δ 8.15 (s, 1H), 8.0 (dt, 1H), 7.45-7.35 (m, 5H), 7.25 (dd, 1H), 7.1 (dd, 1H), 6.80 (t, 1H), 6.5 (s, 1H), 4.7 (d, 2H), 3.7 (bs, 2H), 3.4 (bs, 2H), 2.5-2.4 (m, 4H), 2.2 (s, 3H).

Example 495

$^1$H NMR (CDCl$_3$) δ 8.15 (dt, 1H), 8.0 (s, 1H), 7.45-7.35 (m, 5H), 7.25 (dd, 1H), 7.1 (dd, 1H), 6.80 (t, 1H), 6.5 (s, 1H), 4.7 (d, 2H), 3.75 (bs, 2H), 3.35 (bs, 2H), 2.4 (bs, 2H), 2.3 (s, 3H), 2.2 (bs, 2H).

Example 496

$^1$H NMR (CDCl$_3$) δ 7.95 (s, 1H), 7.9 (dt, 1H), 7.8 (t, 1H), 7.7 (d, 2H), 7.15 (m, 4H), 7.05 (dd, 1H), 6.9 (dd, 1H), 6.2 (s, 1H), 4.5 (d, 2H), 3.6 (t, 2H), 3.3 (dt, 2H).

Example 497

$^1$H NMR (CH3OD) δ 8.1 (s, 1H), 7.9 (dt, 1H), 7.8 (d, 2H), 7.5 (d, 2H), 7.4 (m, 1H), 7.3 (dd, 1H), 7.2 (dd, 1H), 6.4 (s, 1H), 4.7 (d, 2H), 3.5 (t, 2H), 2.7 (m, 2H), 2.6 (bs, 4H), 1.8 (bs, 4H).

Example 498

$^1$H NMR (CDCl$_3$) δ 8.5 (t, 1H), 8.15 (dt, 1H), 8.0 (s, 1H), 7.8 (d, 2H), 7.4 (d, 2H), 7.35 (m, 1H), 7.25 (dd, 1H), 7.15 (dd, 1H), 6.8 (t, 1H), 6.5 (s, 1H), 4.7 (d, 2H), 3.7-2.5 (m, 4H), 2.35 (s, 3H), 2.2 (m, 1H), 1.9-1.6 (m, 6H).

Example 499

$^1$H NMR (CDCl$_3$) δ 8.15 (dt, 1H), 8.0 (s, 1H), 7.8 (d, 2H), 7.4 (d, 2H), 7.35 (m, 1H), 7.25 (dd, 1H), 7.15 (dd, 1H), 6.8 (t, 1H), 6.5 (s, 1H), 4.7 (d, 2H), 3.7 (m, 4H), 3.5 (dt, 2H), 2.6 (t, 2H), 2.5 (m, 4H).

Example 500

$^1$H NMR (CH3OD) δ 8.15 (s, 1H), 7.9 (dt, 1H), 7.8 (d, 2H), 7.45 (d, 2H), 7.4 (m, 1H), 7.25 (dd, 1H), 7.15 (dd, 1H), 6.4 (s, 1H), 4.75 (d, 2H), 4.2 (m, 1H), 3.4-2.8 (m, 7H), 1.9-1.6 (m, 4H).

Example 501

$^1$H NMR (CDCl$_3$) δ 8.05 (dt, 1H), 8.0 (s, 1H), 7.6 (d, 2H), 7.4 (s, 1H), 7.35 (d, 2H), 7.25 (dd, 1H), 7.1 (dd, 1H), 6.9 (t, 1H), 6.5 (s, 1H), 6.4 (t, 1H), 4.7 (d, 2H), 4.2 (d, 2H), 2.3 (bs, 1H).

Example 502

$^1$H NMR (CDCl$_3$) δ 8.15 (dt, 1H), 8.0 (s, 1H), 7.75 (d, 2H), 7.45 (s, 1H), 7.4 (d, 2H), 7.3 (dd, 1H), 7.1 (dd, 1H), 6.8 (t, 1H), 6.5 (s, 1H), 6.1 (bs, 1H), 4.7 (d, 2H), 3.5 (dq, 2H), 1.2 (t, 3H).

Example 503

$^1$H NMR (CDCl$_3$) δ 8.15 (dt, 1H), 8.0 (s, 1H), 7.8 (d, 2H), 7.4 (d, 2H), 7.35 (m, 1H), 7.25 (dd, 1H), 7.15 (dd, 1H), 6.9 (t, 1H), 6.5 (s, 1H), 6.4 (t, 1H), 4.75 (d, 2H), 4.1 (m, 2H).

Example 504

$^1$H NMR (CDCl$_3$) δ 8.15 (dt, 1H), 8.0 (s, 1H), 7.8 (d, 2H), 7.45 (d, 2H), 7.4 (m, 1H), 7.25 (dd, 1H), 7.1 (dd, 1H), 6.8 (t, 1H), 6.6 (t, 1H), 6.5 (s, 1H), 4.7 (d, 1H), 3.6 (m, 2H), 2.8 (t, 2H), 2.6 (q, 2H), 1.3 (t, 3H).

Example 505

$^1$H NMR (CDCl$_3$) δ 8.15 (dt, 1H), 8.0 (s, 1H), 7.4 (m, 1H), 7.25 (dd, 1H), 7.15 (dd, 1H), 7.0 (t, 1H), 6.5 (s, 1H), 3.8 (m, 2H), 2.7 (t, 2H), 3.0 (d, 3H).

Example 506

$^1$H NMR (CDCl$_3$) δ 8.15 (dt, 1H), 8.0 (s, 1H), 7.4 (m, 1H), 7.25 (dd, 1H), 7.15 (dd, 1H), 7.0 (t, 1H), 6.5 (s, 1H), 3.8 (m, 2H), 3.6 (m, 6H), 3.4 (m, 2H), 2.7 (t, 2H).

Example 507

$^1$H NMR (CDCl$_3$) δ 8.15 (dt, 1H), 8.0 (s, 1H), 7.4 (m, 1H), 7.25 (dd, 1H), 7.15 (dd, 1H), 7.0 (t, 1H), 6.5 (s, 1H), 3.9 (t, 2H), 3.8 (dt, 2H), 3.7 (t, 2H), 2.7 (t, 2H), 2.6 (m, 4H).

Example 508

$^1$H NMR (CH$_3$OD) δ 8.1 (s, 1H), 7.95 (dt, 1H), 7.5 (m, 1H), 7.35-7.2 (m, 2H), 6.5 (s, 1H), 3.6 (m, 4H), 3.25 (m, 4H), 2.4 (t, 2H), 2.05 (dt, 2H).

Example 509

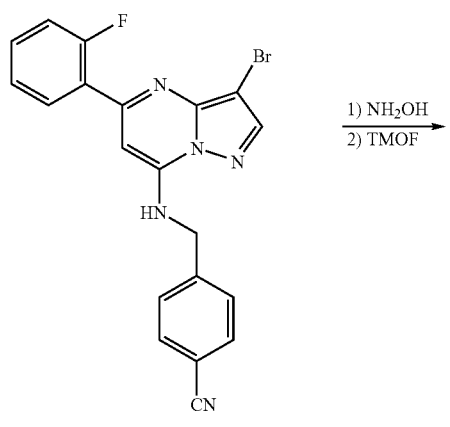

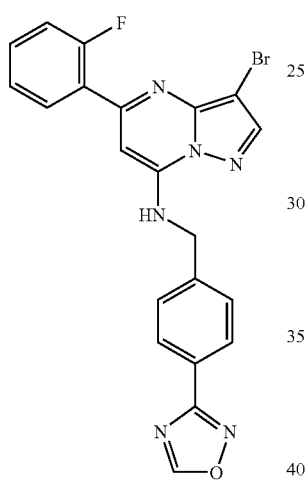

A solution of NaOH (59 mg, 1.47 mmol) in 1 mL of water was added to a suspension of NH₂OH.HCl (102 mg, 1.47 mmol) in 10 mL of methanol at 0° C. After 5 min, the compound prepared in Example 210.10 (208 mg, 0.49 mmol) was added and the reaction mixture was refluxed overnight. The solvent was removed in vacuo and the residue was partitioned between water and EtOAc. The EtOAc layer was dried (Na₂SO₄) and the solvent was evaporated. The resulting crude amidoxime was suspended in trimethyl orthoformate containing catalytic amount of PTS acid and refluxed overnight. The solvent was removed and the residue was taken up in EtOAc. The EtOAc layer was washed with aq NaHCO₃ followed by water and brine. The solvent was evaporated and the residue was purified by chromatography (silica, hexane:EtOAc (1:1)) to provide 80 mg (35%) of the oxadiazole. $^1$H NMR (CDCl₃) δ 8.75 (s, 1H), 8.20-8.10 (m, 3H), 8.03 (s, 1H), 7.53 (d, J=9 Hz, 2H), 7.45-7.36 (m, 1H), 7.30-7.22 (m, 2H), 7.16-7.08 (m, 1H), 6.80 (t, J=5 Hz, 1H), 6.56 (s, 1H). LCMS: MH⁺=465.2

Example 510

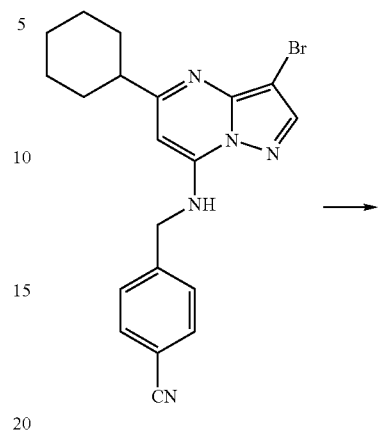

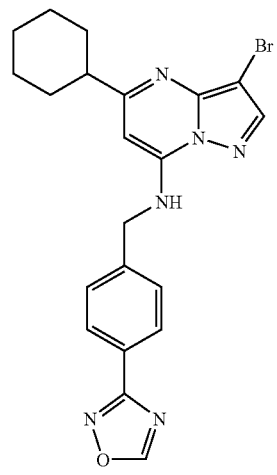

By essentially the same procedure set forth in Example 509 only substituting the compound prepared in Preparative Example 192, the above compound was prepared. yield=75; MH⁺=453; m.p.=79.3° C.

Example 511

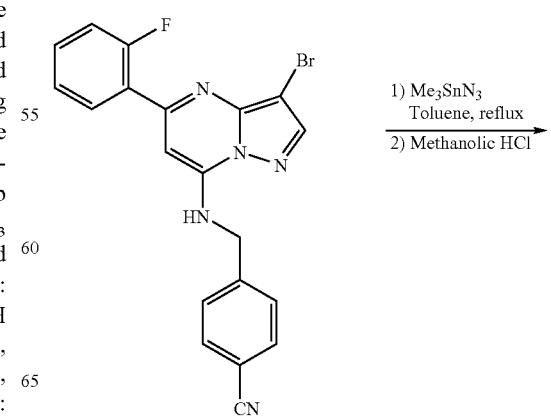

515
-continued

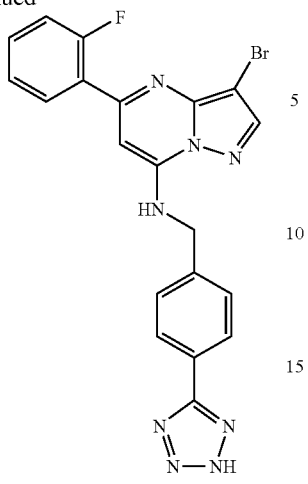

A mixture of the nitrile (235 mg, 0.56 mmol) and Me₃SnN₃ (343 mg, 1.67 mmol) in 20 mL of dry toluene was refluxed for 2 days under Ar. The solvent was removed in vacuo and the residue was dissolved in dry methanol. HCl gas was bubbled through the solution for 15 min and the reaction mixture allowed to stand at overnight at RT. The next day, the solvent was removed, the residue was taken in water and the pH was adjusted to 5. The precipitated product was extracted into EtOAc. Evaporation of the EtOAc layer after drying (Na₂SO₄) provided the residue which was purified by chromatography (silica, DCM:MeOH (98:2→95:5)) to yield 50 mg (19%) of the pure tetrazole. ¹H NMR (CD₃OD) δ 8.10 (s, 1H), 8.00 (d, J=9 Hz, 2H), 7.90 (t, J=7 Hz, 1H), 7.65 (d, J=9 Hz, 2H), 7.50-7.40 (m, 1H), 7.30-7.10 (m, 2H), 6.45 (s, 1H), 4.80 (s, 2H); LCMS: MH⁺=465.0

Example 512

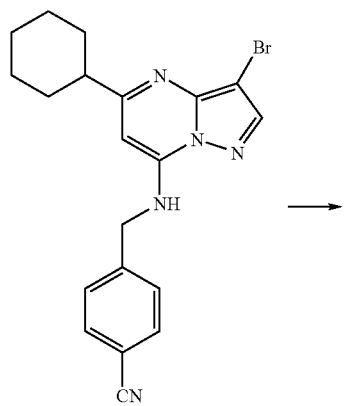

516
-continued

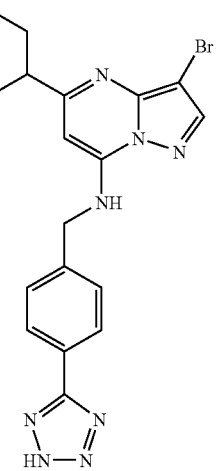

By essentially the same procedure set forth in Example 511 only substituting the compound prepared in Example 192, the above compound was prepared. Yield=64; MH⁺=453; m.p.=238.9° C.

Example 513

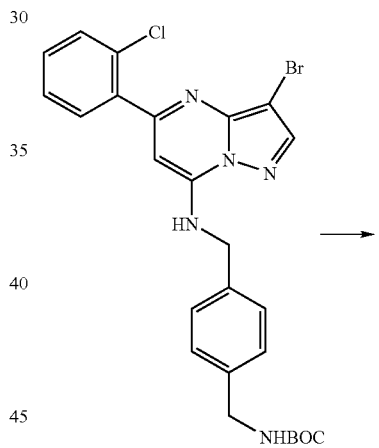

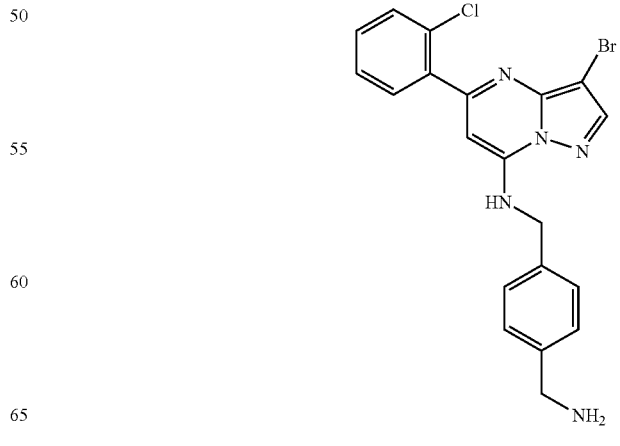

The compound prepared in Example 157 was dissolved in dioxane (30 mL) and a HCl-dioxane solution (4 M, 30 mL) was added. The reaction mixture was stirred at room temperature for 4 h. The reaction mixture was evaporated under reduced pressure and ethyl acetate (200 mL) was added. The organic solution was washed with 1N sodium hydroxide followed by saturated brine. The organic layer was dried over anhydrous sodium sulfate and evaporated under reduced pressure. MH$^+$=442.1

Example 514-526

By essentially the same procedure set forth in Example 513, only substituting the compounds shown in Column 2 of Table 41, the compounds shown in Column 3 of Table 41 were prepared.

TABLE 41

| Ex. | Column 2 | Column 3 | CMPD |
|---|---|---|---|
| 514 | 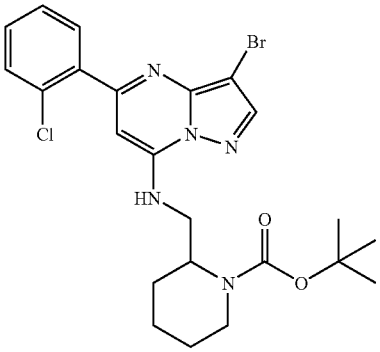 [SMILES: CC(C)(C)OC(=O)N1CCCCC1CNc1cc(-c2ccccc2Cl)nc2c(Br)cnn12] | 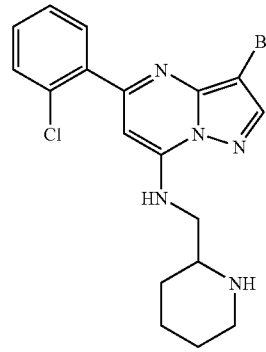 | MH$^+$ = 420.1 |
| 515 | 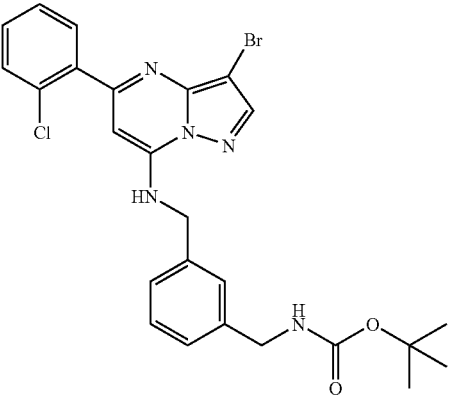 [SMILES: CC(C)(C)OC(=O)NCc1cccc(CNc2cc(-c3ccccc3Cl)nc3c(Br)cnn23)c1] | 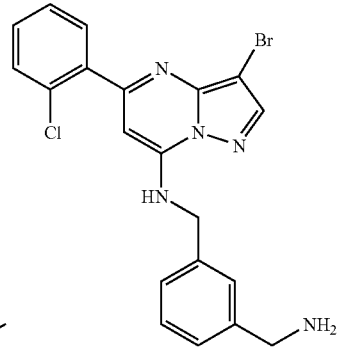 | MH$^+$ = 442.1 |
| 516 | 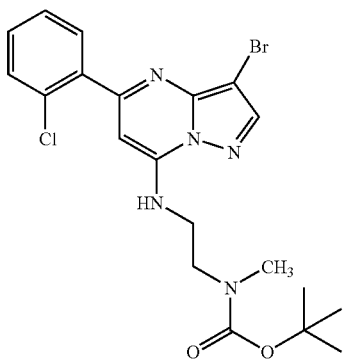 [SMILES: CN(CCNc1cc(-c2ccccc2Cl)nc2c(Br)cnn12)C(=O)OC(C)(C)C] | 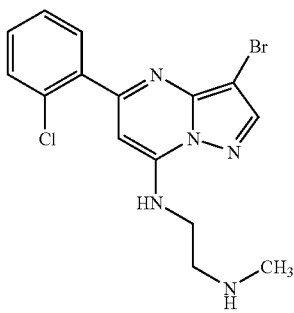 [SMILES: CNCCNc1cc(-c2ccccc2Cl)nc2c(Br)cnn12] | MH$^+$ = 380.1 |

TABLE 41-continued

| Ex. | Column 2 | Column 3 | CMPD |
|---|---|---|---|
| 517 | | | MH+ = 406.1 |
| 518 | | | MH+ = 380.1 |
| 519 | | | MH+ = 394.1 |
| 520 | | | MH+ = 366 |

TABLE 41-continued
| Ex. | Column 2 | Column 3 | CMPD |
|-----|----------|----------|------|
| 521 | 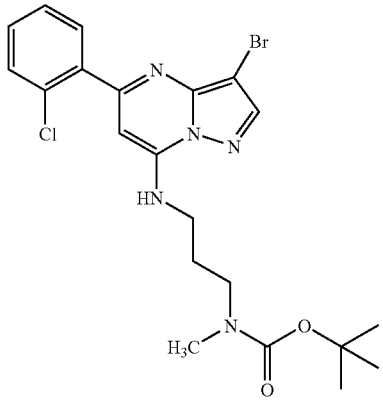 [SMILES: CN(CCCNc1cc(-c2ccccc2Cl)nc2c(Br)cnn12)C(=O)OC(C)(C)C] | 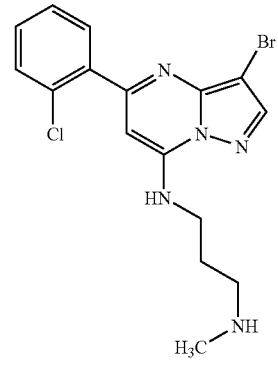 [SMILES: CNCCCNc1cc(-c2ccccc2Cl)nc2c(Br)cnn12] | MH+ = 394 |
| 522 | 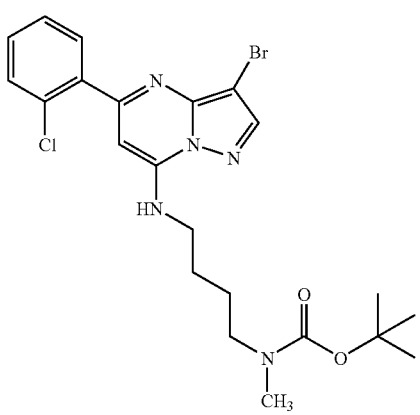 [SMILES: CN(CCCCNc1cc(-c2ccccc2Cl)nc2c(Br)cnn12)C(=O)OC(C)(C)C] | 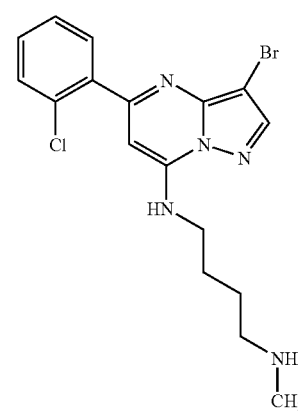 | MH+ = 408.1 |
| 523 | 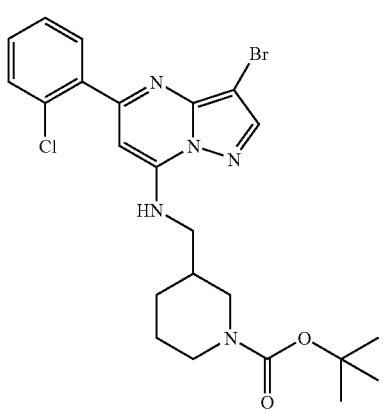 [SMILES: CC(C)(C)OC(=O)N1CCCC(CNc2cc(-c3ccccc3Cl)nc3c(Br)cnn23)C1] | 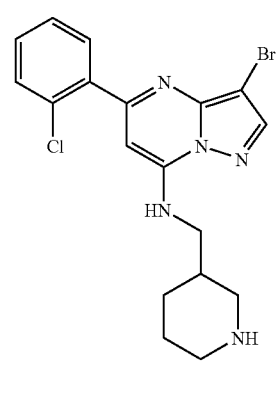 [SMILES: Clc1ccccc1-c1cc(NCC2CCCNC2)n2ncc(Br)c2n1] | MH+ = 420.1 |

TABLE 41-continued
| Ex. | Column 2 | Column 3 | CMPD |
|---|---|---|---|
| 524 | 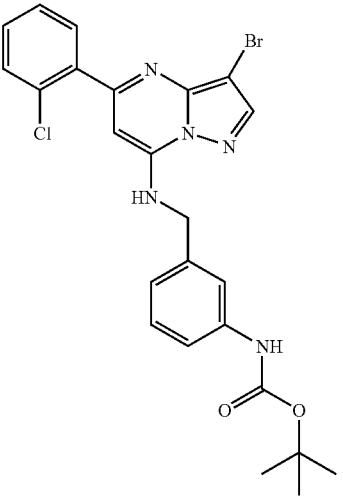 [SMILES: CC(C)(C)OC(=O)Nc1cccc(CNc2cc(-c3ccccc3Cl)nc3c(Br)cnn23)c1] | 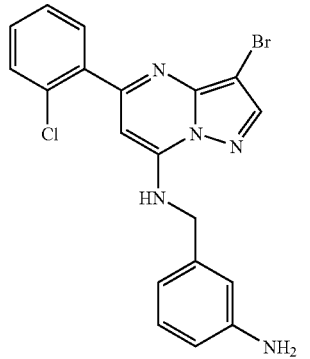 [SMILES: Nc1cccc(CNc2cc(-c3ccccc3Cl)nc3c(Br)cnn23)c1] | |
| 525 | 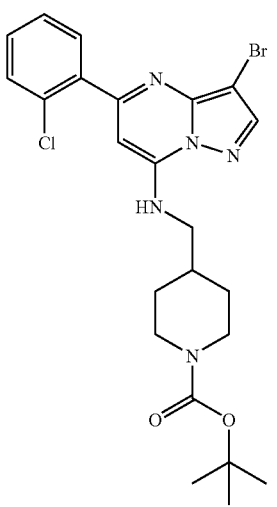 [SMILES: CC(C)(C)OC(=O)N1CCC(CNc2cc(-c3ccccc3Cl)nc3c(Br)cnn23)CC1] | 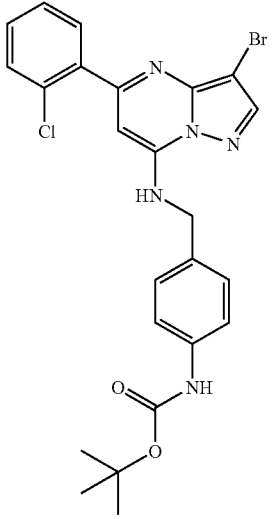 | MH+ = 420.1 |
| 526 | | | MH+ = 428.1 |

TABLE 41-continued

| Ex. | Column 2 | Column 3 | CMPD |
|---|---|---|---|
| 526.10 | 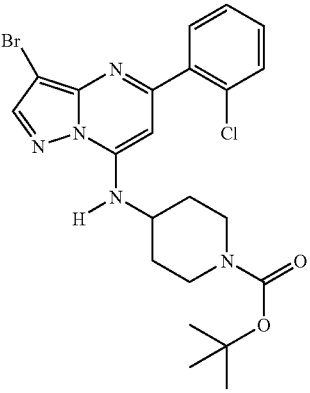 [SMILES: CC(C)(C)OC(=O)N1CCC(Nc2cc(-c3ccccc3Cl)nc3c(Br)cnn23)CC1] | 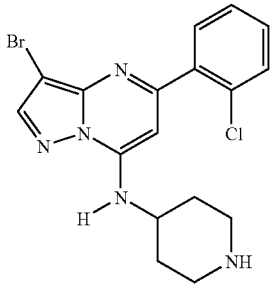 [SMILES: Clc1ccccc1-c1cc(NC2CCNCC2)n2ncc(Br)c2n1] | |

Examples 528-564

General Procedure for 5-piperidinyl Parallel Library Formation

To a mixture of the starting material (80 mg, 0.21 mmol) shown in Column 2 of Table 42 in anhydrous $CH_2Cl_2$ (1.5 mL) was added DIPEA (75 µL, 0.42 mmol) and the appropriate capping reagent (1.1 equiv., 0.23 mmol). After 1 to 2 h, the reaction mixture was applied to 1000 micron preparatory TLC plate and was subsequently developed using a 8-10% EtOH—$CH_2Cl_2$ as eluent to afford the compounds shown in Column 3 of Table 42.

TABLE 42

| Ex. | Column 2 | Column 3 | CMPD |
|---|---|---|---|
| 528 | 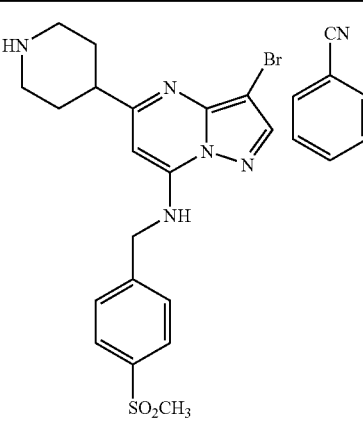 | 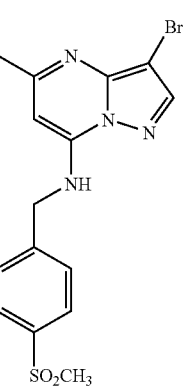 | $MH^+$ = 608<br>m. p. = 230.1° C. |

TABLE 42-continued
| Ex. | Column 2 | Column 3 | CMPD |
|---|---|---|---|
| 529 | 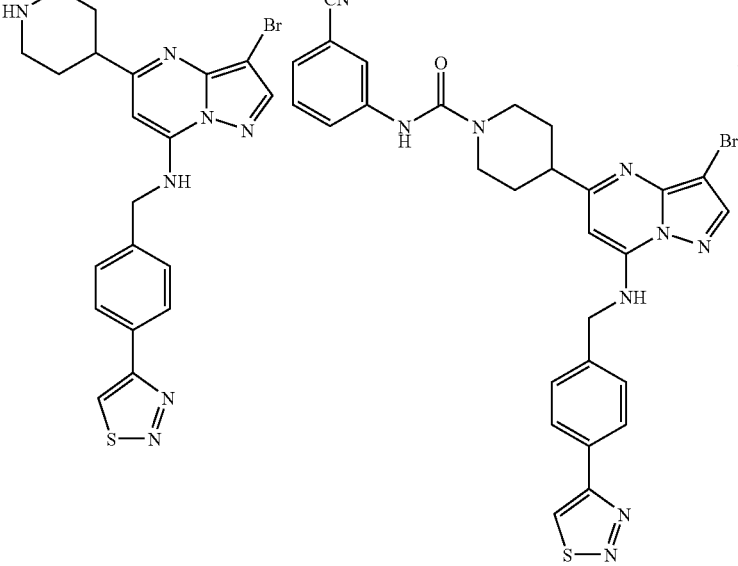 | 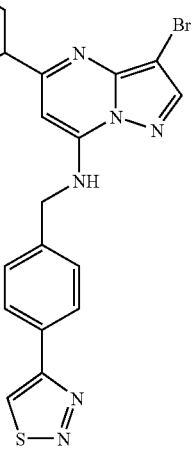 | Yield = 82<br>$MH^+$ =614<br>m. p. = 235.4° C. |
| 530 | 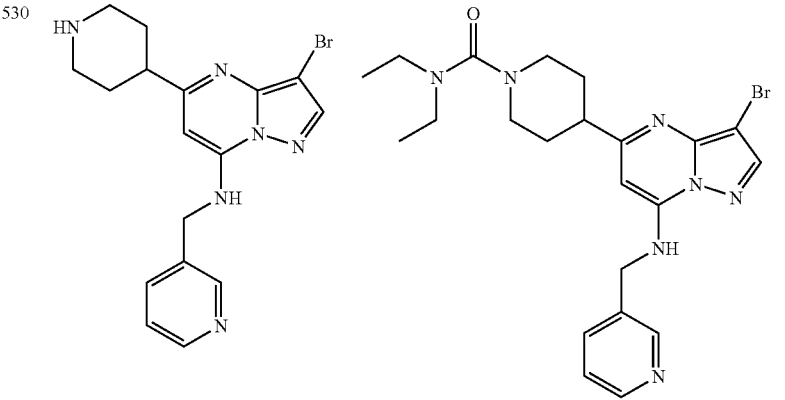 | 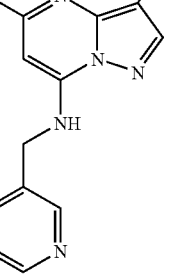 | $MH^+$ = 486<br>m. p. = 60.5° C. |
| 531 | 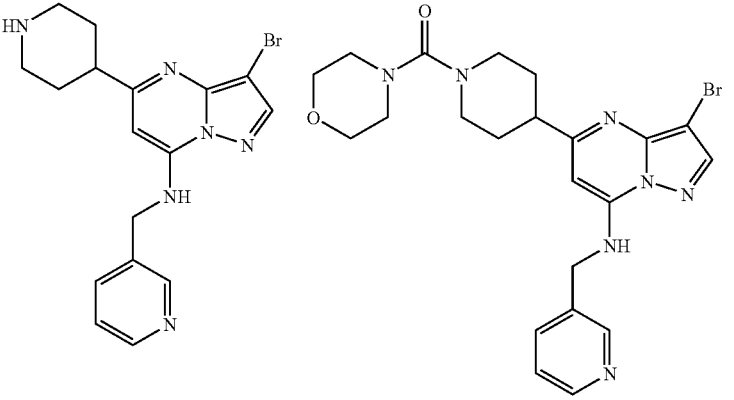 | 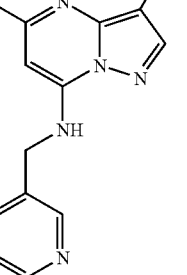 | $MH^+$ = 500<br>m. p. = 113.6° C. |

TABLE 42-continued

| Ex. | Column 2 | Column 3 | CMPD |
|---|---|---|---|
| 532 | | | MH+ = 430<br>m. p. = 158.3–159.2° C. |
| 533 | | | MH+ = 531<br>m. p. = 105.9° C. |
| 534 | | | MH+ = 486 |

TABLE 42-continued

| Ex. | Column 2 | Column 3 | CMPD |
|---|---|---|---|
| 535 | | | MH+ = 500 |
| 536 | | | MH+ = 430 |
| 537 | | | MH+ = 531 |

TABLE 42-continued

| Ex. | Column 2 | Column 3 | CMPD |
|---|---|---|---|
| 538 | | | MH⁺ = 486<br>m. p. = 69.6° C. |
| 539 | | | MH⁺ = 500<br>m. p. = 82.3° C. |
| 540 | | | MH⁺ = 430<br>m. p. = 223.6° C. |
| 541 | | | MH⁺ = 531<br>m. p. = 118.1° C. |

TABLE 42-continued

| Ex. | Column 2 | Column 3 | CMPD |
|---|---|---|---|
| 542 | | | MH+ = 455<br>m. p. = 109-110° C. |
| 543 | | | MH+ = 429<br>m. p. = 111.5° C. |
| 544 | | | MH+ = 455 |

TABLE 42-continued

| Ex. | Column 2 | Column 3 | CMPD |
|---|---|---|---|
| 545 | | | MH+ = 429 |
| 546 | | | MH+ = 455<br>m. p. = 80.1° C. |
| 547 | | | MH+ = 429<br>m. p. = 64.7° C. |
| 548 | | | MH+ = 494<br>m. p. = 76.5° C. |

TABLE 42-continued

| Ex. | Column 2 | Column 3 | CMPD |
|---|---|---|---|
| 549 | | | MH+ = 493<br>m. p. = 83.6° C. |
| 550 | | | MH+ = 465<br>m. p. = 207.5° C. |
| 551 | | | MH+ = 494 |

TABLE 42-continued

| Ex. | Column 2 | Column 3 | CMPD |
|---|---|---|---|
| 552 | | | MH+ = 493 |
| 553 | | | MH+ = 465 |
| 554 | | | MH+ = 481<br>m. p. = 102.7° C. |

TABLE 42-continued

| Ex. | Column 2 | Column 3 | CMPD |
|---|---|---|---|
| 555 | | | MH⁺ = 494<br>m. p. = 85.3° C. |
| 556 | | | MH⁺ = 493<br>m. p. = 89.1° C. |
| 557 | | | MH⁺ = 465<br>m. p. = 83.8° C. |
| 558 | | | Yield = quant.<br>MH⁺ = 443<br>m. p. = 98.3° C.<br>(HCl salt) |

TABLE 42-continued

| Ex. | Column 2 | Column 3 | CMPD |
|---|---|---|---|
| 559 | | | MH+ = 454 |
| 560 | | | Yield = quant. MH+ = 429 m. p. = 111.5-112.6° C. |
| 561 | | | MH+ = 460 m. p. = 122.7° C. |
| 562 | | | MH+ = 460 m. p. = 95.4° C. |

TABLE 42-continued

| Ex. | Column 2 | Column 3 | CMPD |
|---|---|---|---|
| 563 | | | MH+ = 460 |
| 564 | | | MH+ = 460 m. p. = 95.4° C. |

Additional data for select examples given below.

Example 534

$^1$H NMR (300 MHz, CDCl$_3$) δ 8.66-8.62 (s, 1H), 8.62-8.58 (d, 1H), 7.95 (s, 1H), 7.72-7.68 (d, 1H), 7.36-7.31 (dd, 1H), 6.66-6.62 (t, 1H), 5.93 (s, 1H), 4.65-4.62 (d, 2H), 3.86-3.82 (d, 1H), 3.65-3.58 (m, 1H), 3.26-3.12 (dd, 4H), 3.02-2.80 (m, 3H), 2.10-2.00 (m, 1H), 1.67-1.57 (m, 3H).

Example 535

$^1$H NMR (300 MHz, CDCl$_3$) δ 8.66-8.62 (s, 1H), 8.62-8.58 (d, 1H), 7.95 (s, 1H), 7.72-7.67 (d, 1H), 7.36-7.30 (dd, 1H), 6.70-6.64 (t, 1H), 5.90 (s, 1H), 4.63-4.61 (d, 2H), 3.93-3.86 (m, 1H), 3.69-3.61 (m, 4H), 3.27-3.23 (m, 4H), 3.10-3.01 (dd, 1H), 2.93-2.84 (m, 2H), 2.08-2.03 (m, 1H), 1.90-1.57 (m, 4H).

Example 536

$^1$H NMR (300 MHz, CDCl$_3$) δ 8.67 (s, 1H), 8.62-8.58 (d, 1H), 7.96 (s, 1H), 7.72-7.68 (d, 1H), 7.36-7.30 (dd, 1H), 6.79-6.72 (t, 1H), 5.96 (s, 1H), 4.86 (br s, 2H), 4.66-4.63 (d, 2H), 3.89-3.73 (m, 2H), 3.55-3.32 (m, 2H), 3.00-2.89 (m, 1H), 2.10-1.97 (m, 2H), 1.70-1.53 (m, 2H).

Example 537

$^1$H NMR (300 MHz, CDCl$_3$) δ 8.66 (s, 1H), 8.62-8.58 (d, 1H), 7.98 (s, 1H), 7.77-7.76 (t, 1H), 7.72-7.69 (d, 1H), 7.63-7.59 (m, 1H), 7.56 (s, 1H), 7.36-7.29 (dd, 1H), 6.83-6.79 (t, 1H), 5.96 (s, 1H), 4.67-4.64 (d, 2H), 3.98-3.93 (dd, 1H), 3.79-3.68 (m, 2H), 3.37-3.28 (m, 1H), 3.03-2.94 (m, 1H), 2.12-1.99 (m, 1H), 1.76-1.56 (m, 3H).

Example 544

$^1$H NMR (300 MHz, CDCl$_3$) δ 8.66-8.62 (d, 1H), 8.61-8.58 (dd, 1H), 7.95 (s, 1H), 7.72-7.67 (d, 1H), 7.36-7.30 (dd, 1H), 6.80-6.62 (br s, 1H), 5.88 (s, 1H), 4.63 (s, 2H), 3.08-2.95 (m, 2H), 2.87-2.80 (m, 2H), 2.04 (m, 1H), 1.85-1.78 (m, 4H), 1.52-1.44 (m, 1H), 0.87-0.82 (m, 2H), 0.72-0.66 (m, 2H).

Example 545

$^1$H NMR (300 MHz, CDCl$_3$) δ 8.66 (s, 1H), 8.62-8.58 (br t, 1H), 7.97 (s, 1H), 7.73-7.68 (d, 1H), 7.36-7.30 (br t, 1H), 6.79-6.72 (br t, 1H), 5.96 (s, 1H), 4.64 (br s, 2H), 4.59-4.46 (br d, 1H), 3.95-3.74 (br m, 1H), 3.57-3.49 (dd, 1H), 3.10-3.01 (dd, 1H), 2.86-2.70 (m, 2H), 2.13 (s, 3H), 2.06-2.00 (m, 2H), 1.65-1.48 (m, 2H).

Example 551

$^1$H NMR (300 MHz, CDCl$_3$) δ 8.67 (s, 1H), 8.63-8.59 (d, 1H), 7.96 (s, 1H), 7.74-7.69 (d, 1H), 7.36-7.30 (dd, 1H), 6.69-6.64 (t, 1H), 5.95 (s, 1H), 4.67-4.63 (d, 2H), 3.85 3.65 (m, 1H), 3.75-3.65 (m, 1H), 3.25-3.18 (dd, 1H), 3.03-2.90 (m, 2H), 2.81 (s, 6H), 2.03-1.95 (m, 1H), 1.89-1.68 (m, 3H).

Example 552

¹H NMR (300 MHz, CDCl₃) δ 8.67 (s, 1H), 8.62-8.59 (d, 1H), 7.95 (s, 1H), 7.74-7.69 (d, 1H), 7.36-7.31 (dd, 1H), 6.67-6.60 (t, 1H), 5.98 (s, 1H), 4.67-4.63 (d, 2H), 3.92-3.86 (m, 1H), 3.85-3.75 (m, 1H), 3.40-3.30 (dd, 1H), 3.27-3.16 (m, 1H), 3.10-2.86 (m, 2H), 2.10-1.78 (m, 3H), 1.40-1.30 (d, 6H).

Example 553

¹H NMR (300 MHz, CDCl₃) δ 8.67 (s, 1H), 8.62 (br s, 1H), 7.96 (s, 1H), 7.74-7.69 (d, 1H), 7.36-7.31 (dd, 1H), 6.70-6.66 (t, 1H), 5.98 (s, 1H), 4.67-4.63 (d, 2H), 3.88-3.81 (m, 1H), 3.71-3.65 (m, 1H), 3.20-3.11 (dd, 1H), 3.02-2.91 (m, 1H), 2.90-2.80 (m, 4H), 2.01-1.80 (m, 3H).

Example 559

¹H NMR (300 MHz, CDCl₃) δ 8.66-8.60 (d, 1H), 8.50-8.44 (dd, 1H), 8.01 (s, 1H), 7.93 (m, 1H), 7.48-7.40 (dd, 1H), 6.08 (s, 1H), 4.80-7.74 (s, 2H), 4.32-4.19 (br d, 2H), 3.10-2.86 (m, 2H), 1.95-1.68 (m, 4H).

Example 563

¹H NMR (300 MHz, CDCl₃) δ 8.66 (s, 1H), 8.62-8.58 (d, 1H), 7.96 (s, 1H), 7.73-7.68 (d, 1H), 7.36-7.30 (dd, 1H), 6.96-6.86 (br s, 1H), 6.79-6.74 (t, 1H), 6.00 (s, 1H), 4.67-4.64 (d, 2H), 4.37-4.30 (dd, 1H), 4.22-4.13 (m, 1H), 3.97-3.86 (dd, 1H), 3.73-3.64 (m, 1H), 3.17-3.14 (d, 3H), 3.07-2.99 (m, 1H), 2.20-1.97 (m, 2H), 1.68-1.48 (m, 2H).

General Procedure 1

Procedure for the Amide Formation Parallel Synthesis

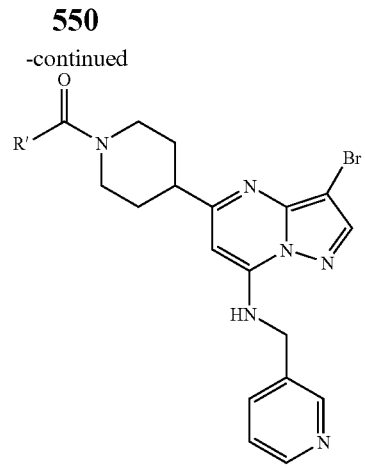

Parallel synthesis was conducted in polypropylene 96-well reaction blocks with removable top seal and fixed bottom seal. Each reaction well was fitted with a 20 micron polypropylene bottom frit and the maximum volume was 3 mL. Collection block was not fitted with bottom frit. To each reaction well was added a solution of an amine (0.021 mmol) dissolved in a DMF-THF-MeCN mixture (4:3:3 v/v, 0.95 mL), EDC resin (P-EDC, Polymer Laboratories Ltd., 43 mg, 0.063 mmol), 1-hydroxybenzotriazole (HOBt, 5.67 mg, 0.042 mmol) and a solution of a carboxylic acid in dimethylformamide (1M, 0.0315 mL, 0.0315 mmol). The reaction mixture was agitated at room temperature for 16 h. The crude product solution was filtered into a reaction well loaded with trisamine resin (P—NH2, Argonaut Tech. Inc., 30 mg, 0.126 mmol) and isocyanate resin (P—NCO, Argonaut Tech. Inc., 35 mg, 0.063 mmol). The reaction mixture was agitated at room temperature for 16 h and filtered into the collection block. The product solution was evaporated under reduced pressure to afford the desired amide product.

General Procedure 2

Procedure for the Sulfonamide Formation Parallel Synthesis

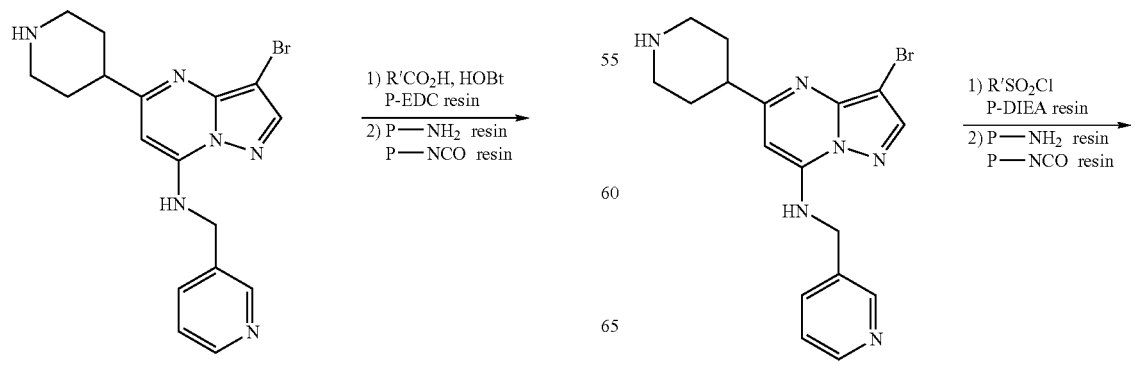

-continued

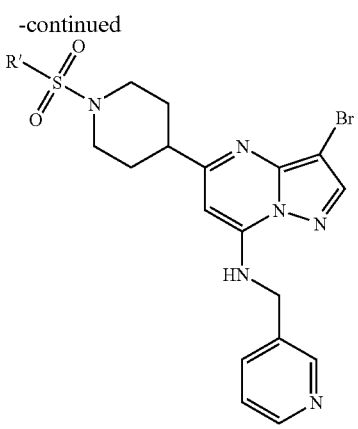

Parallel synthesis was conducted in polypropylene 96-well reaction blocks with removable top seal and fixed bottom seal. Each reaction well was fitted with a 20 micron polypropylene bottom frit and the maximum volume was 3 mL. Collection block was not fitted with bottom frit. To each reaction well was added a solution of an amine (0.021 mmol) dissolved in a DMF-THF-MeCN mixture (3:2:2 v/v, 0.95 mL), DIEA resin (P-DIEA, Argonaut Tech. Inc., 18 mg, 0.063 mmol) and a solution of a sulfonyl chloride in dimethylformamide (1M, 0.0315 mL, 0.0315 mmol). The reaction mixture was agitated at room temperature for 16 h. The crude product solution was filtered into a reaction well loaded with trisamine resin (P—NH2, Argonaut Tech. Inc., 30 mg, 0.126 mmol) and isocyanate resin (P—NCO, Argonaut Tech. Inc., 35 mg, 0.063 mmol). The reaction mixture was agitated at room temperature for 16 h and filtered into the collection block. The product solution was evaporated under reduced pressure to afford the desired sulfonamide product.

General Procedure 3

Procedure for the Urea Formation Parallel Synthesis

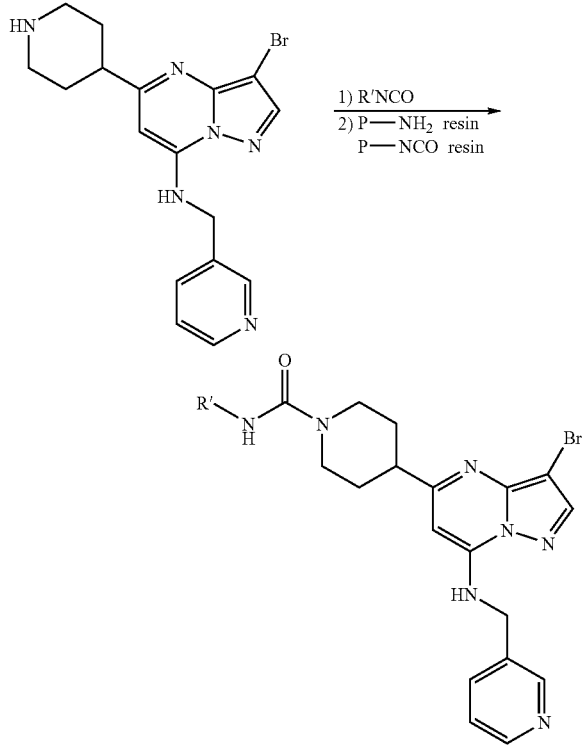

Parallel synthesis was conducted in polypropylene 96-well reaction blocks with removable top seal and fixed bottom seal. Each reaction well was fitted with a 20 micron polypropylene bottom frit and the maximum volume was 3 mL. Collection block was not fitted with bottom frit. To each reaction well was added a solution of an amine (0.021 mmol) dissolved in a DMF-MeCN mixture (1:1 v/v, 0.95 mL) and a solution of an isocyanate in dichloromethane (0.33 M, 0.126 mL, 0.042 mmol). The reaction mixture was agitated at room temperature for 16 h. The crude product solution was filtered into a reaction well loaded with trisamine resin (P—NH2, Argonaut Tech. Inc., 30 mg, 0.126 mmol) and isocyanate resin (P—NCO, Argonaut Tech. Inc., 35 mg, 0.063 mmol). The reaction mixture was agitated at room temperature for 16 h and filtered into the collection block. The product solution was evaporated under reduced pressure to afford the desired urea product.

General Procedure 4: Procedure for the Reductive Alkylation Parallel Synthesis

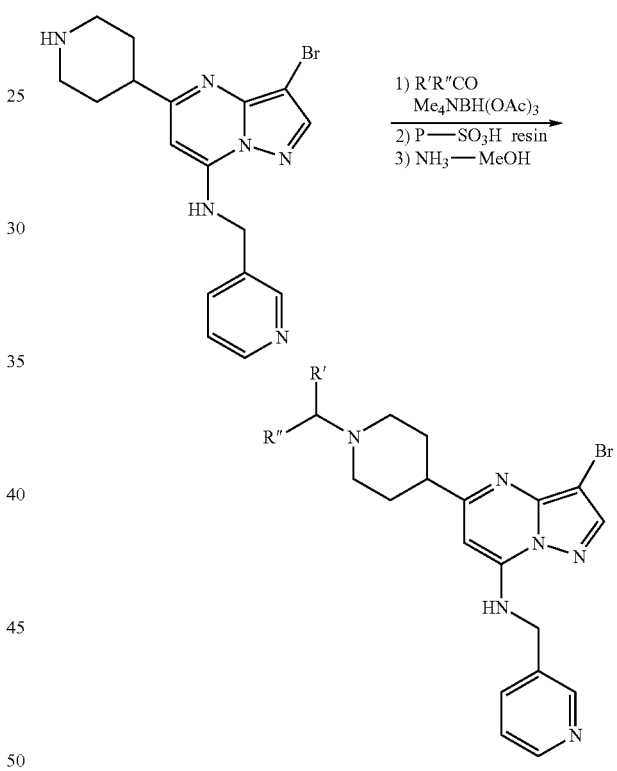

Parallel synthesis was conducted in polypropylene 96-well reaction blocks with removable top seal and fixed bottom seal. Each reaction well was fitted with a 20 micron polypropylene bottom frit and the maximum volume was 3 mL. Collection block was not fitted with bottom frit. To each reaction well was added a solution of an amine (0.021 mmol) dissolved in AcOH-DCE mixture (1:99 v/v, 0.5 mL), a solution of an aldehyde or ketone in dichloroethane (1M, 0.147 mL, 0.147 mmol), and a solution of tetramethylammonium triacetoxyborohydride (11 mg, 0.042 mmol) dissolved in AcOH-DCE mixture 1:99 v/v, 0.5 mL). The reaction mixture was agitated at room temperature for 3 days. The crude product solution was filtered into a reaction well loaded with sulfonic acid resin Lanterns (P—SO$_3$H, MimotopesPty Ltd., 0.3 mmol). The reaction mixture was agitated at room temperature for 2 h and decanted. The product resin Lanterns were washed with methanol (1 mL) for three times. A solution of ammonia in methanol (2 M, 1.2 mL) was added. The reaction mixture was agitated at room temperature for 30 min. and filtered into the collection block. The product solution was evaporated under reduced pressure to afford the desired tertiary amine product.

General Procedure 5

Procedure for the Parallel Synthesis of 7,N-substituted pyrazolo[1,5a]pyrimidines

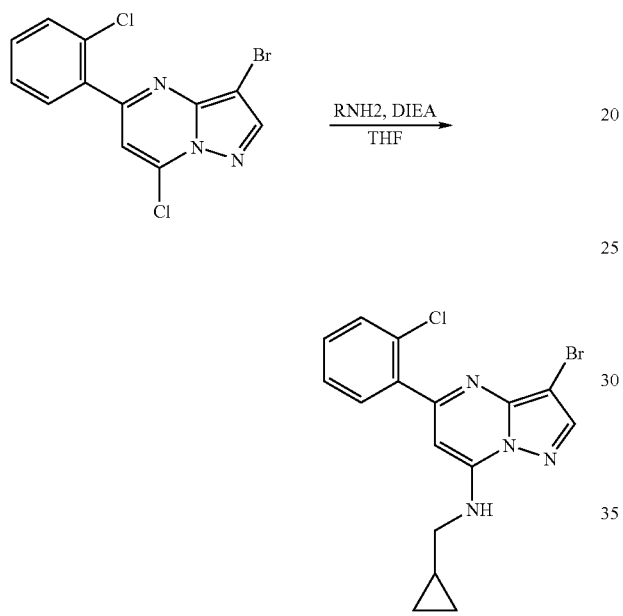

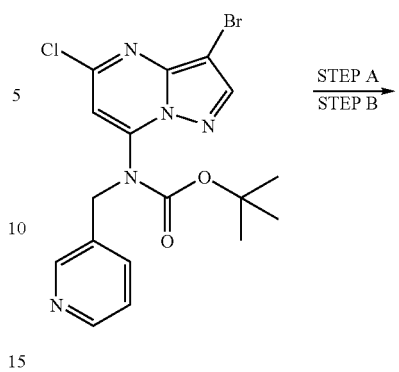

To 3-bromo-7-chloro-5-(2-chloro-phenyl)-pyrazolo[1,5-a]pyrimidine (9.0 mg, 0.03 mmol) in tetrahydrofuran were added di-iso-propylethylamine (12 μL, 0.07), followed by cyclopropylmethylamine (70 μL, 0.07 mmol; 1M solution in DMF). The reaction mixture was heated to 70° C. for 36 h and then cooled to rt. The mixture was treated with (P—NCO, Argonaut Tech. Inc 70 mg, 0.12 mmol), and P—CO$_3^-$ (Argonaut Tech. Inc 70 mg, 0.24 mmol) and shaken at rt for 12-18 h. The solution was filtered and evaporated to dryness to provide the product. observed m/z 375.21.

General Procedure 6

Procedure for the Parallel Synthesis of 5,N-substituted pyrazolo[1,5a]pyrimidines General Protocols:

Parallel synthesis was performed in a 96 well polypropylene blocks as described elsewhere. In the instance that heating was required, reactions were conducted in 2.5 mL glass tubes individually sealed with a polypropylene mat and heating achieved by a 96 well heat transfer block.

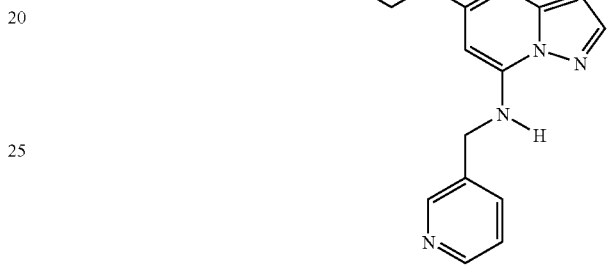

Step A:

To the 3-bromo-5-chloro-7-N-Boc-alkylamino-pyrazolo[1,5-a]pyrimidine (17 mg, 0.04 mmol) in p-dioxane were added DIEA (9 μL, 0.05), followed by cyclopropyl-methylamine (80 μL, 0.08 mmol; 1M solution in isopropanol). The reaction mixture was heated to 90° C. for 36 h and then cooled to rt. The mixture was treated with P—NCO (Argonaut Tech. Inc. 70 mg, 0.12 mmol) and P—CO$_3^-$ (Argonaut Tech. Inc. 70 mg, 0.24 mmol) and shaken at rt for 12-18 h. The solution was filtered and evaporated to dryness to provide the product.

Step B (acidic):

The product from STEP A was taken up in 35% TFA/DCM and agitated for 4 h followed by concentration under high vacuum. The residue was treated with 10% HCl(aq) in MeOH agitated for 2 h and then concentrated to give the desired product. observed m/z 375.21.

Step B (basic):

The product from step A was taken up in EtOH and treated with Ambersepe 900-OH ion exchange resin (Acros, 100 mg), heated at reflux for 48 h with gently stirring. The reaction mixture was cooled to rt, filtered and concentrated to provide the desired product.

Example 565

By utilizing the procedure set forth in General Procedure 1 and the compound from Example 462 shown below, the compounds with the observed m/z shown in Table 43 were prepared.

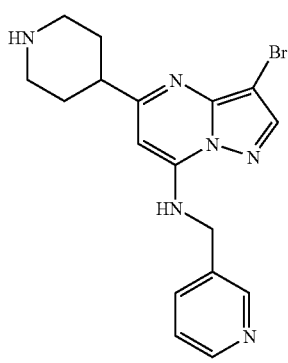

Example 566

By utilizing the procedure set forth in General Procedure 1 and the compound from Example 471 shown below, the compounds shown in Table 44 with the observed m/z were prepared.

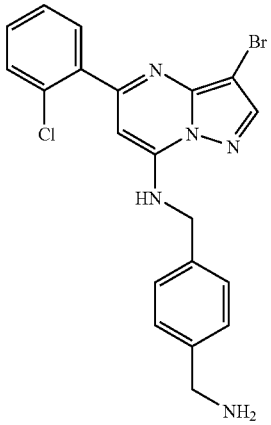 [SMILES: NCc1ccc(CNc2cc(-c3ccccc3Cl)nc3c(Br)cnn23)cc1]

Example 568

By utilizing the procedure set forth in General Procedure 1 and the compound from Example 513 shown below, the compounds shown in Table 46 with the observed m/z were prepared.

Example 569

By utilizing the procedure set forth in General Procedure 1 and the compound from Example 526 shown below, the compounds shown in Table 47 with the observed m/z were prepared.

Example 567

By utilizing the procedure set forth in General Procedure 1 and the compound from Example 515 shown below, the compounds shown in Table 45 with the observed m/z were prepared.

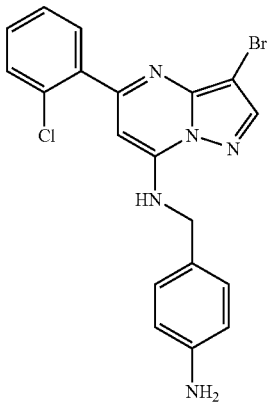 [SMILES: Nc1ccc(CNc2cc(-c3ccccc3Cl)nc3c(Br)cnn23)cc1]

Example 570

By utilizing the procedure set forth in General Procedure 1 and the compound from Example 524 shown below, the compounds shown in Table 48 with the observed m/z were prepared.

557

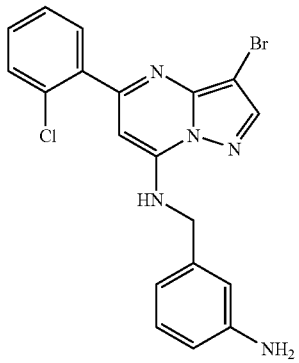 [SMILES: Nc1cccc(CNc2cc(-c3ccccc3Cl)nc3c(Br)cnn23)c1]

Example 571

By utilizing the procedure set forth in General Procedure 1 and the compound from Example 525 shown below, the compounds shown in Table 49 with the observed m/z were prepared.

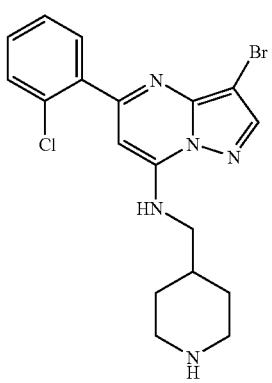 [SMILES: Clc1ccccc1-c1cc(NCC2CCNCC2)n2ncc(Br)c2n1]

Example 572

By utilizing the procedure set forth in General Procedure 1 and the compound from Example 526.10 shown below, the compounds shown in Table 50 with the observed m/z were prepared.

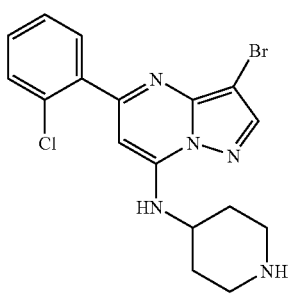 [SMILES: Clc1ccccc1-c1cc(NC2CCNCC2)n2ncc(Br)c2n1]

Example 573

By utilizing the procedure set forth in General Procedure 1 and the compound from Example 518 shown below, the compounds shown in Table 51 with the observed m/z were prepared.

558

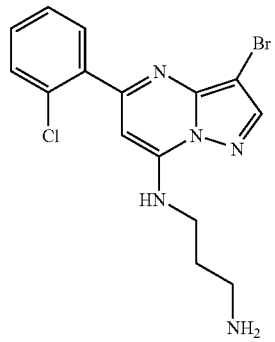 [SMILES: NCCCNc1cc(-c2ccccc2Cl)nc2c(Br)cnn12]

Example 574

By utilizing the procedure set forth in General Procedure 1 and the compound from Example 519 shown below, the compounds shown in Table 52 with the observed m/z were prepared.

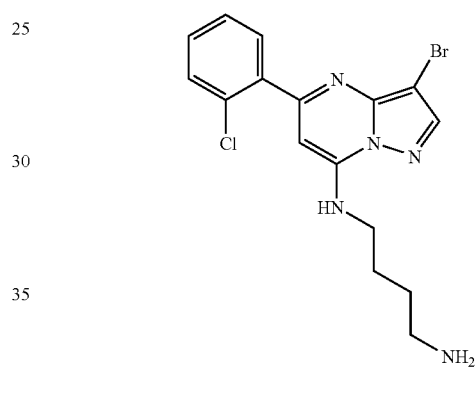

Example 575

By utilizing the procedure set forth in General Procedure 1 and the compound from Example 520 shown below, the compounds shown in Table 53 with the observed m/z were prepared.

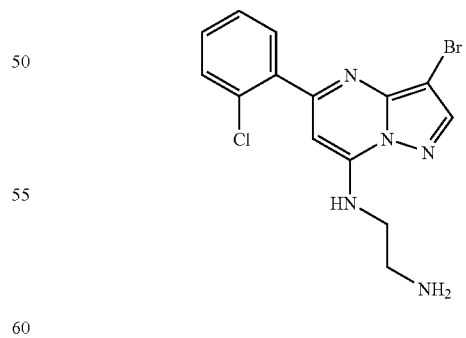

Example 576

By utilizing the procedure set forth in General Procedure 1 and the compound from Example 522 shown below, the compounds shown in Table 54 with the observed m/z were prepared.

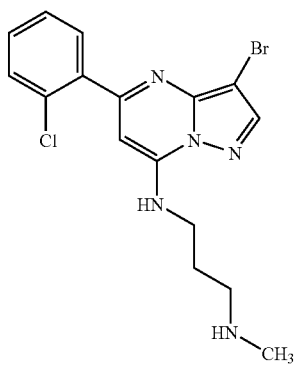 [SMILES: CNCCCNc1cc(-c2ccccc2Cl)nc2c(Br)cnn12]

Example 577

By utilizing the procedure set forth in General Procedure 1 and the compound from Example 523 shown below, the compounds shown in Table 55 with the observed m/z were prepared.

Example 578

By utilizing the procedure set forth in General Procedure 2 and the compound from Example 462 shown below, the compounds shown in Table 56 with the observed m/z were prepared.

Example 579

By utilizing the procedure set forth in General Procedure 2 and the compound from Example 471 shown below, the compounds shown in Table 57 with the observed m/z were prepared.

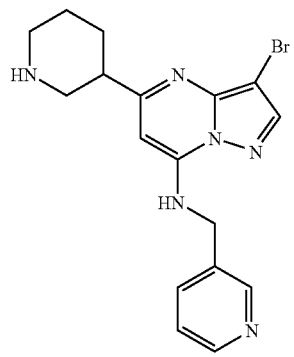 [SMILES: Brc1cnn2c(NCc3cccnc3)cc(C3CCCNC3)nc12]

Example 580

By utilizing the procedure set forth in General Procedure 2 and the compound from Example 515 shown below, the compounds shown in Table 58 with the observed m/z were prepared.

Example 581

By utilizing the procedure set forth in General Procedure 2 and the compound from Example 513 shown below, the compounds shown in Table 59 with the observed m/z were prepared.

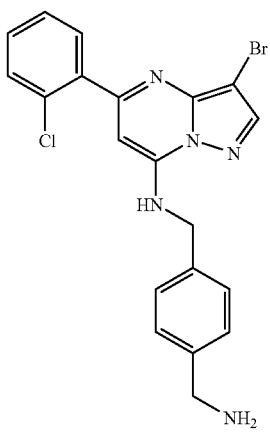 [SMILES: NCc1ccc(CNc2cc(-c3ccccc3Cl)nc3c(Br)cnn23)cc1]

Example 582

By utilizing the procedure set forth in General Procedure 2 and the compound from Example 513 shown below, the compounds shown in Table 60 with the observed m/z were prepared.

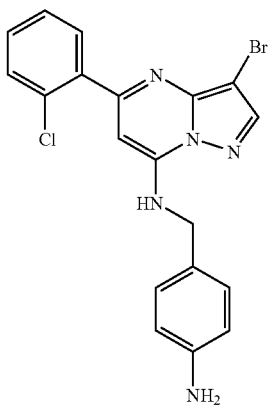 [SMILES: Nc1ccc(CNc2cc(-c3ccccc3Cl)nc3c(Br)cnn23)cc1]

Example 583

By utilizing the procedure set forth in General Procedure 2 and the compound from Example 524 shown below, the compounds shown in Table 61 with the observed m/z were prepared.

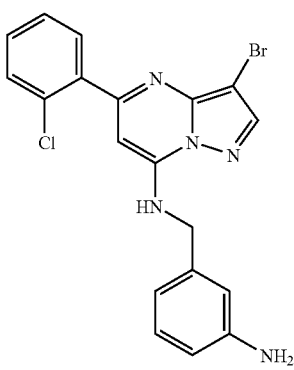 [SMILES: Nc1cccc(CNc2cc(-c3ccccc3Cl)nc3c(Br)cnn23)c1]

Example 584

By utilizing the procedure set forth in General Procedure 2 and the compound from Example 525 shown below, the compounds shown in Table 62 with the observed m/z were prepared.

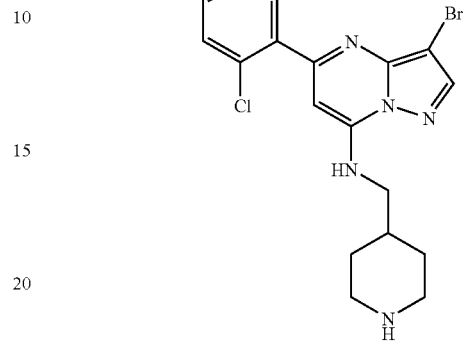

Example 585

By utilizing the procedure set forth in General Procedure 2 and the compound from Example 526.10 shown below, the compounds shown in Table 63 with the observed m/z were prepared.

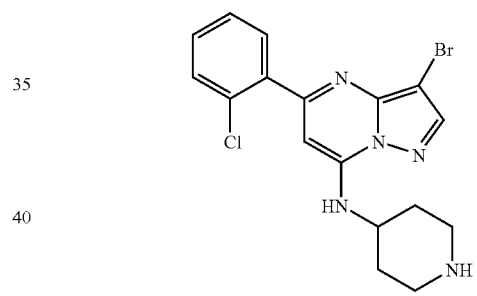

Example 586

By utilizing the procedure set forth in General Procedure 2 and the compound from Example 518 shown below, the compounds shown in Table 64 with the observed m/z were prepared.

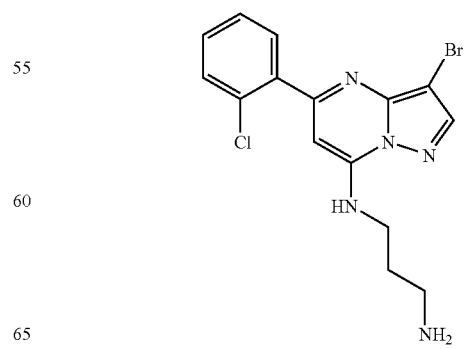

Example 587

By utilizing the procedure set forth in General Procedure 2 and the compound from Example 519 shown below, the compounds shown in Table 65 with the observed m/z were prepared.

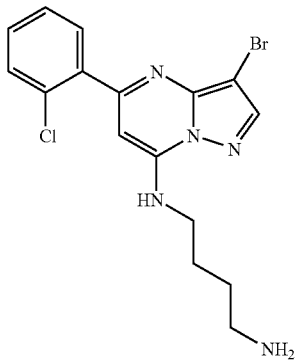 [SMILES: NCCCCNc1cc(-c2ccccc2Cl)nc2c(Br)cnn12]

Example 588

By utilizing the procedure set forth in General Procedure 2 and the compound from Example 520 shown below, the compounds shown in Table 67 with the observed m/z were prepared.

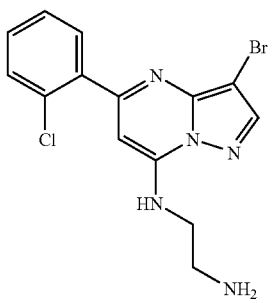 [SMILES: NCCNc1cc(-c2ccccc2Cl)nc2c(Br)cnn12]

Example 589

By utilizing the procedure set forth in General Procedure 2 and the compound from Example 521 shown below, the compounds shown in Table 68 with the observed m/z were prepared.

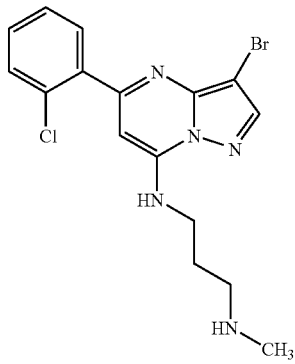 [SMILES: CNCCCNc1cc(-c2ccccc2Cl)nc2c(Br)cnn12]

Example 590

By utilizing the procedure set forth in General Procedure 2 and the compound from Example 523 shown below, the compounds shown in Table 69 with the observed m/z were prepared.

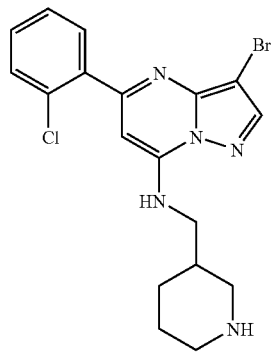 [SMILES: Clc1ccccc1-c1cc(NCC2CCCNC2)n2ncc(Br)c2n1]

Example 591

By utilizing the procedure set forth in General Procedure 3 and the compound from Example 462 shown below, the compounds shown in Table 70 with the observed m/z were prepared.

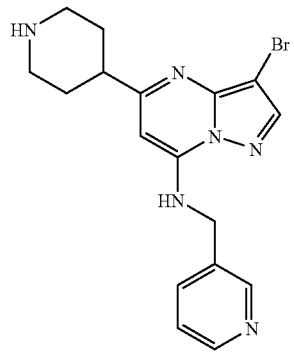

Example 592

By utilizing the procedure set forth in General Procedure 3 and the compound from Example 471 shown below, the compounds shown in Table 71 with the observed m/z were prepared.

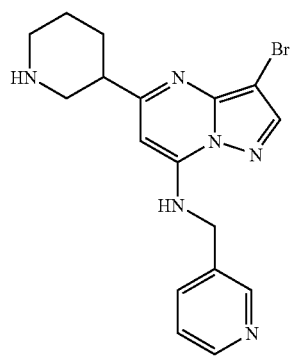 [SMILES: Brc1cnn2c(NCc3cccnc3)cc(C3CCCNC3)nc12]

Example 593

By utilizing the procedure set forth in General Procedure 3 and the compound from Example 513 shown below, the compounds shown in Table 72 with the observed m/z were prepared.

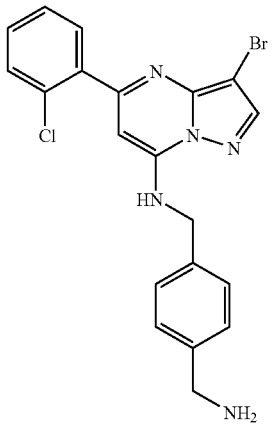 [SMILES: NCc1ccc(CNc2cc(-c3ccccc3Cl)nc3c(Br)cnn23)cc1]

Example 594

By utilizing the procedure set forth in General Procedure 3 and the compound from Example 524 shown below, the compounds shown in Table 73 with the observed m/z were prepared.

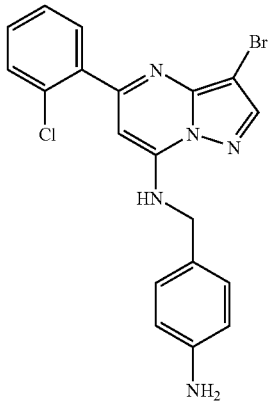 [SMILES: Nc1ccc(CNc2cc(-c3ccccc3Cl)nc3c(Br)cnn23)cc1]

Example 595

By utilizing the procedure set forth in General Procedure 3 and the compound from Example 524 shown below, the compounds shown in Table 74 with the observed m/z were prepared.

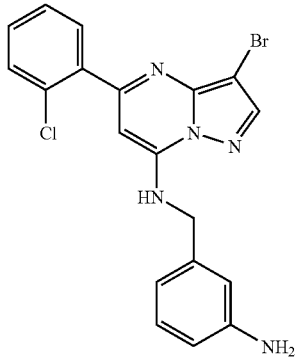 [SMILES: Nc1cccc(CNc2cc(-c3ccccc3Cl)nc3c(Br)cnn23)c1]

Example 596

By utilizing the procedure set forth in General Procedure 3 and the compound from Example 519 shown below, the compounds shown in Table 75 with the observed m/z were prepared.

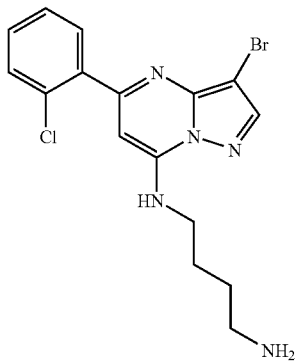 [SMILES: NCCCCNc1cc(-c2ccccc2Cl)nc2c(Br)cnn12]

Example 597

By utilizing the procedure set forth in General Procedure 3 and the compound from Example 520 shown below, the compounds shown in Table 76 with the observed m/z were prepared.

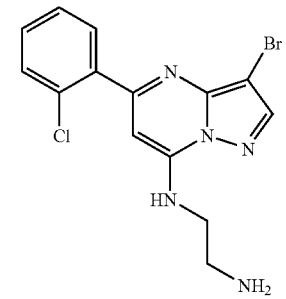 [SMILES: NCCNc1cc(-c2ccccc2Cl)nc2c(Br)cnn12]

Example 598

By utilizing the procedure set forth in General Procedure 3 and the compound from Example 521 shown below, the compounds shown in Table 77 with the observed m/z were prepared.

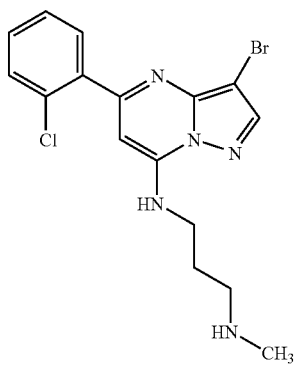 [SMILES: CNCCCNc1cc(-c2ccccc2Cl)nc2c(Br)cnn12]

Example 599

By utilizing the procedure set forth in General Procedure 3 and the compound from Example 523 shown below, the compounds shown in Table 78 with the observed m/z were prepared.

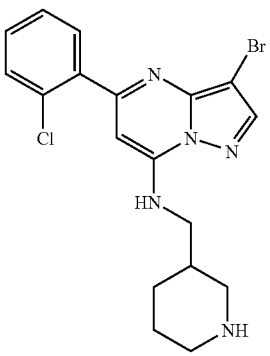 [SMILES: Clc1ccccc1-c1cc(NCC2CCCNC2)n2ncc(Br)c2n1]

Example 600

By utilizing the procedure set forth in General Procedure 4 and the compound from Example 462 shown below, the compounds shown in Table 79 with the observed m/z were prepared.

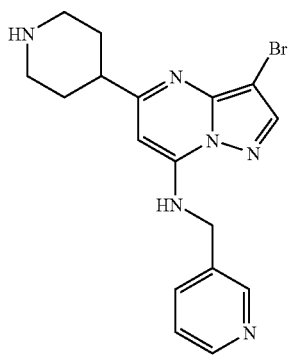 [SMILES: Brc1cnn2c(NCc3cccnc3)cc(C3CCNCC3)nc12]

Example 601

By utilizing the procedure set forth in General Procedure 4 and the compound from Example 471 shown below, the compounds shown in Table 80 with the observed m/z were prepared.

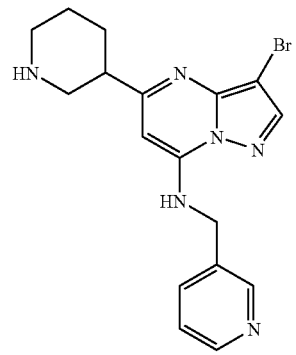 [SMILES: Brc1cnn2c(NCc3cccnc3)cc(C3CCCNC3)nc12]

Example 602

By utilizing the procedure set forth in General Procedure 4 and the compound from Example 525 shown below, the compounds shown in Table 81 with the observed m/z were prepared.

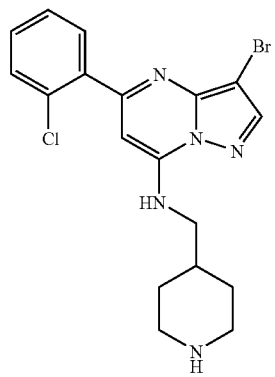 [SMILES: Clc1ccccc1-c1cc(NCC2CCNCC2)n2ncc(Br)c2n1]

Example 603

By utilizing the procedure set forth in General Procedure 4 and the compound from Example 526.10 shown below, the compounds shown in Table 82 with the observed m/z were prepared.

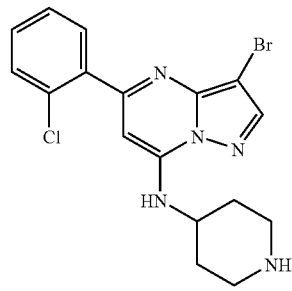 [SMILES: Clc1ccccc1-c1cc(NC2CCNCC2)n2ncc(Br)c2n1]

Example 604

By utilizing the procedure set forth in General Procedure 4 and the compound from Example 521 shown below, the compounds shown in Table 83 with the observed m/z were prepared.

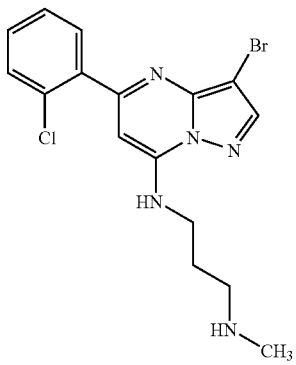 [SMILES: CNCCCNc1cc(-c2ccccc2Cl)nc2c(Br)cnn12]

Example 605

By utilizing the procedure set forth in General Procedure 4 and the compound from Example 523 shown below, the compounds shown in Table 84 with the observed m/z were prepared.

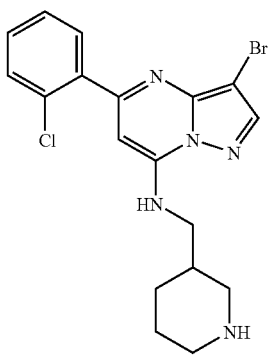 [SMILES: Clc1ccccc1-c1cc(NCC2CCCNC2)n2ncc(Br)c2n1]

Example 606

By utilizing the procedure set forth in General Procedure 5 and the compound from Preparative Example 81 shown below, the compounds shown in Table 85 with the observed m/z were prepared.

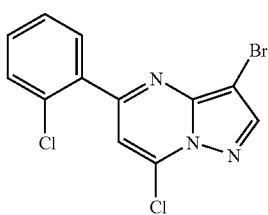 [SMILES: Clc1ccccc1-c1cc(Cl)n2ncc(Br)c2n1]

Example 607

By utilizing the procedure set forth in General Procedure 6 and the compound from Preparative Example 196, the compounds shown in Table 86 with the observed m/z were prepared.

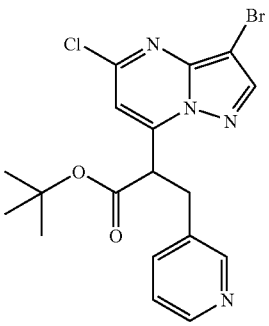 [SMILES: CC(C)(C)OC(=O)C(Cc1cccnc1)c1cc(Cl)nc2c(Br)cnn12]

Preparative Example 500

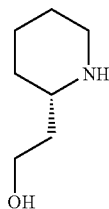

Piperidine-2-ethanol (127 g, 980 mmol) in 95% EtOH (260 mL) was added to (S)-(+)-camphorsulfonic acid (228.7 g, 1.0 eq.) in 95% EtOH (150 mL) and the resulting solution was warmed to reflux. To the warm solution was added Et$_2$O (600 mL) and the solution cooled to room temperature and let stand 3 days. The resulting crystals were filtered and dried in vacuo (25 g): mp 173-1730° C. (lit. 168° C.). The salt was then dissolved in NaOH (3M, 100 mL) and stirred 2 hours and the resulting solution was extracted with CH$_2$Cl$_2$ (5×100 mL). The combined organics were dried over Na$_2$SO$_4$, filtered, filtered and concentrated under reduced pressure to give (S)-piperidine-2-ethanol (7.8 g) a portion of which was recrystallized from Et$_2$O: mp=69-70° C. (lit. 68-69° C.); [α]$_D$=14.09° (CHCl$_3$, c=0.2).

Preparative Example 501

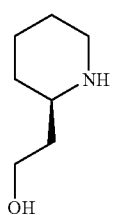

Bye essentially the same procedure set forth in Preparative Example 500 only substituting (R)-(−)-camphorsulfonic acid, (R)-piperidine-2-ethanol was prepared. (1.27 g): $[\alpha]_D=11.3°$ (CHCl$_3$, c=0.2).

Preparative Example 502

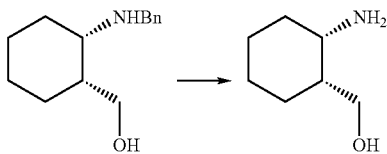

To pressure bottle charged with a solution of cis-(1R,2S)-(+)-2-(Benzylamino) cyclohexanemethanol (1 g, 4.57 mmol) in MeOH (35 mL) was added 20% wt Pd(OH)$_2$ (0.3 g, >50% wet) in one portion. The mixture was shaken under 50 psi of H$_2$ in a Parr hydrogenation apparatus for 12 h. The mixture was purged to N$_2$ and was filtered through a pad of Celite. The pad was generously washed with MeOH (2×25 mL) and the resulting filtrate was concentrated under reduces pressure to afford 0.57 g (97%) of a white solid. M+H=130.

Preparative Example 503

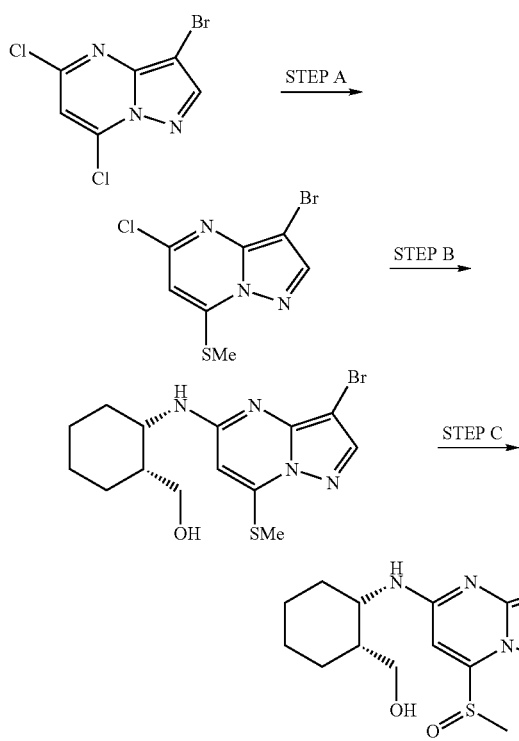

Step A:
To a solution of 3-Br adduct (1.1 g, 4.1 mmol) from Preparative Example 142 in THF (40 mL) at 0° C. was added CH$_3$SNa (0.32 g, 4.53 mmol) in one portion. The heterogenous mixture was stirred for 72 h at rt and the mixture was concentrated under reduced pressure. The crude product was partitioned between water (10 mL) and EtOAc (30 mL) and the layers were separated. The organic layer was washed with brine (1×10 mL) and dried (Na$_2$SO$_4$). The organic layer was filtered and concentrated under reduced pressure to afford 1.0 g (88%) of a yellow solid. mp 150-152° C.; M+H=280. This material was taken onto Step B without further purification.

Step B:
To a solution of thiomethyl derivative (1.5 g, 5.37 mmol) from Step A in dioxane/DIPEA (15 mU4 mL) at rt was added amino alcohol (1.3 g, 8.06 mmol) from Preparative Example 10. The mixture was heated at reflux for 48 h, cooled to rt, and concentrated under reduced pressure. The crude product was purified by flash chromatography using CH$_2$Cl$_2$/MeOH (30:1) as eluent to afford 1.8 g of product (90%) as a yellow crystalline solid. mp 167-169° C.; M+H=373.

Step C:
To a solution of thiomethyl derivative (2.2 g, 5.92 mmol) from Step B in CH$_2$Cl$_2$ (20 mL) at 0° C. was added MCPBA (1.53 g, 8.9 mmol) in one portion. The resulting mixture was stirred for 2 h at 0° C. whereupon the mixture was diluted with CH$_2$Cl$_2$ (20 mL) and sat. aq. NaHCO$_3$ (15 mL). The layers were separated and the organic layer was washed with sat. aq. NaHCO$_3$ (15 mL) and brine (1×15 mL). The organic layer was dried (Na$_2$SO$_4$), filtered, and concentrated under reduced pressure to afford 2.0 g of a brown solid (87%). mp 181-183° C.; M+H=388.

Preparative Example 504

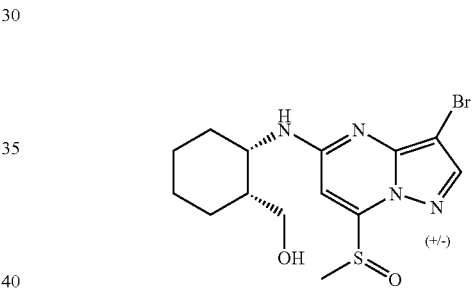

The title compound (racemic) was prepared according to the procedure set forth in Preparative Example 503 except substituting the commercially available cis-hydroxymethyl-1-cyclohexylamine hydrochloride in Step B.

Preparative Example 505

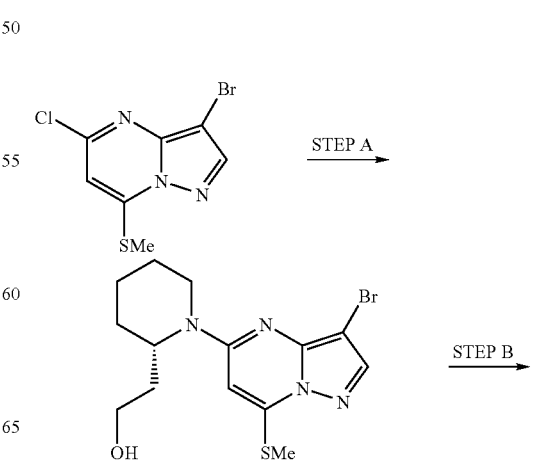

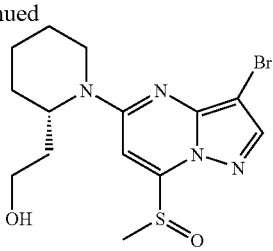

Step A:

Treatment of thiomethyl derivative (2.0 g, 7.2 mmol) from Step A of Preparative Example 503 with (S)-piperidine-2-ethanol (1.2 g, 9.3 mmol) from Preparative Example 500 under the identical conditions as described in Step B of Preparative Example 503, 0.90 g (34%) of the title compound was prepared semisolid. mp 173-175° C. M+H=372.

Step B:

Following the procedure from Step C in Preparative Example 503, the thiomethyl derivative (0.30 g, 0.81 mmol) was treated with MCPBA (0.21 g, 1.2 mmol) to afford 0.31 g (99%) the title compound as a yellow viscous oil. M+H=388.

Preparative Example 506

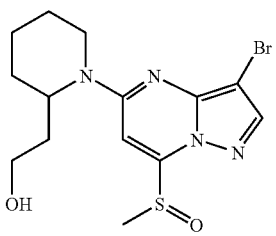 [SMILES: CS(=O)c1cc(N2CCCCC2CCO)nc2c(Br)cnn12]

The title compound (racemic) was prepared according to the procedure set forth in Preparative Example 505 except substituting the commercially available piperidine-2-ethanol. M+H=388.

Preparative Example 507

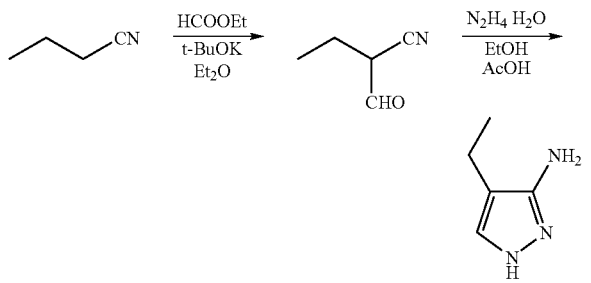

t-BuOK (112.0 g, 1.00 mol) was stirred under $N_2$ in dry $Et_2O$ (3.0 L) in a 5 L flask equipped with an addition funnel. A mixture of butyronitrile (69.0 g, 1.00 mol) and ethylformate (77.7 g, 1.05 mol) was added dropwise during 3 hrs, the reaction mixture was then stirred overnight at room temperature. The mixture was cooled to 0° C., AcOH (57 mL) was added, the mixture was filtered, and the solid was washed with $Et_2O$ (500 mL). The combined filtrates were evaporated at room temperature on a rotovap to give pale yellow oil (95.1 g). The oil was dissolved in dry EtOH (100 mL), 99% hydrazine monohydrate (48 mL) was added, then AcOH (14 mL) was added, and the mixture was refluxed under $N_2$ overnight. The solvents were evaporated and the resulting oil was chromatographed on silicagel with $CH_2Cl_2$:7N $NH_3$ in MeOH. 22.4 g (20%) of 3-amino-4-ethylpyrazole was obtained as clear oil that solidified upon standing.

Preparative Example 508

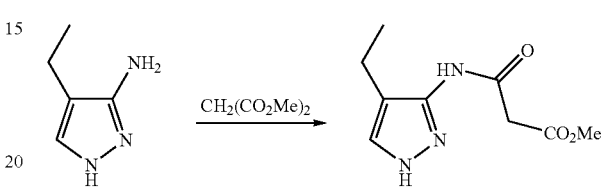

Step A:

The pyrazole from Preparative Example 507 (9.80 g) and dimethylmalonate (45 mL) were stirred and refluxed under $N_2$ for 3 hrs. The excess of dimethylmalonate was evaporated in a vacuum and the residue was chromatographed with 15:1 $CH_2Cl_2$:MeOH to yield pale yellow solid (10.6 g, 57%). LCMS: $MH^+$=212.

Step B:

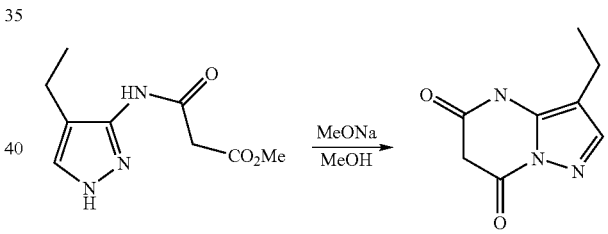

Dry MeOH (200 mL) was added under $N_2$ to a mixture of the amide from Step A (11.9 g, 56.4 mmol) and sodium methoxide (4.57 g, 84.6 mmol). The mixture was stirred and refluxed under $N_2$ for 5 hrs, cooled to rt, and conc. HCl (20 mL) was added. The solvents were evaporated and the residue was suspended in $H_2O$ (300 mL). The solid was filtered off, washed on filter with 2×300 mL of $H_2O$, and dried in a vacuum at 100° C. 7.40 g (73%) of cream-colored solid was obtained. LCMS: $MH^+$=180.

Step C:

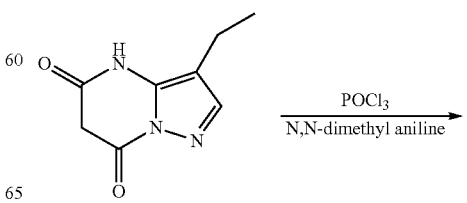

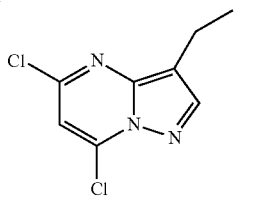

POCl$_3$ (100 mL) and N,N-dimethylaniline (20 mL) were added under N$_2$ to the diketone from Step B (7.70 g), and the mixture was stirred and refluxed for 20 hrs under N$_2$. Then it was cooled to rt, carefully poured onto 1 L of crushed ice, and extracted with EtOAc (2×500 mL). The extracts were washed with H$_2$O (500 mL), dried over Na$_2$SO$_4$, filtered, and the solvent was evaporated. The residue was chromatographed with CH$_2$Cl$_2$ to yield pale yellow solid (8.20 g, 90%). LCMS: MH$^+$=216.

Preparative Example 508.10

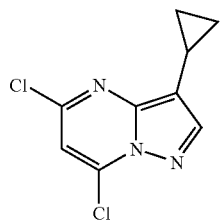 [SMILES: Clc1cc(Cl)n2ncc(C3CC3)c2n1]

By essentially the same procedure set forth in Preparative Example 508, only substituting the compound from Preparative Example 1, the above compound was prepared. LCMS: MH$^+$=228.

Preparative Example 509

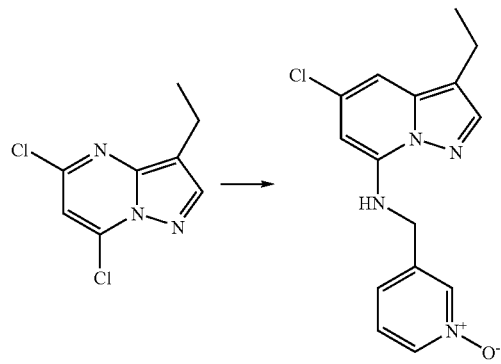 [SMILES: CCc1cnn2c(Cl)cc(Cl)nc12 ; CCc1cnn2c(NCc3ccc[n+]([O-])c3)cc(Cl)cc12]

A mixture of the dichloride from Preparative Example 508 (3.13 g, 14.5 mmol), the amine.HCl from Preparative Example (3.00 g, 18.9 mmol), DIPEA (7.5 mL), and dry NMP (40 mL) plus dry dioxane (40 mL) was stirred at 60° C. for 4 days under N$_2$. The solvents were then distilled off in a vacuum and the residue was chromatographed with 6:1 EtOAc:MeOH and then rechromatographed with 12:1 CH$_2$Cl$_2$:MeOH. So obtained solid was suspended in H$_2$O (100 mL), filtered, washed on filter with H$_2$O (2×100 mL), and dried in a vacuum. Pale rose solid (2.37 g, 54%) was obtained. M+H=304.

Preparative Examples 510-516

By essentially the same procedure set forth in Preparative Example 509 only substituting the amines in Column 2 of Table 500 and the chlorides shown in Column 3 of Table 500, the compounds shown in Column 4 of Table 500 were prepared.

TABLE 500

| Prep. Ex. | Column 2 | Column 3 | Column 4 | CMPD |
|---|---|---|---|---|
| 510 | ![NH3Cl pyridine N-oxide] | ![cyclopropyl dichloropyrazolopyrimidine] | ![product] | M + H = 316 |

TABLE 500-continued
| Prep. Ex. | Column 2 | Column 3 | Column 4 | CMPD |
|---|---|---|---|---|
| 512 | | | | M + H = 318 |
| 513 | | | | M + H = 318 |
| 514 | | | | |
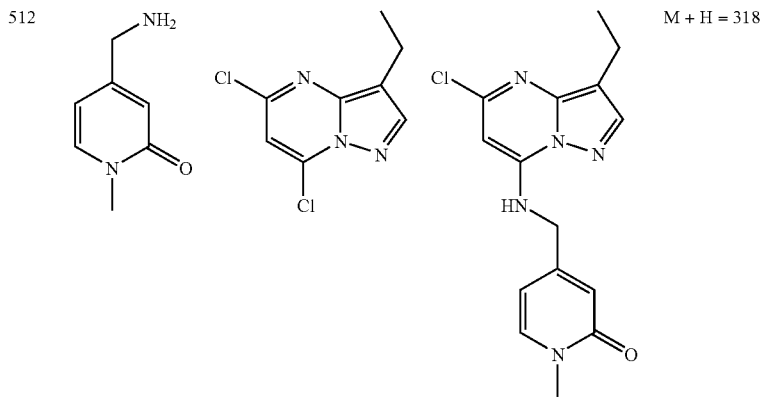
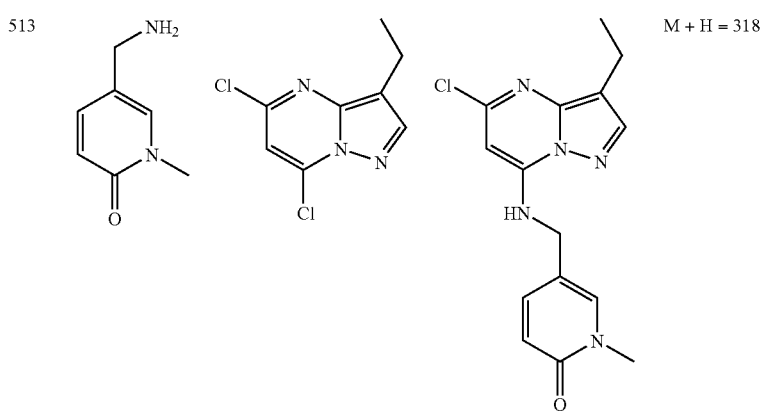
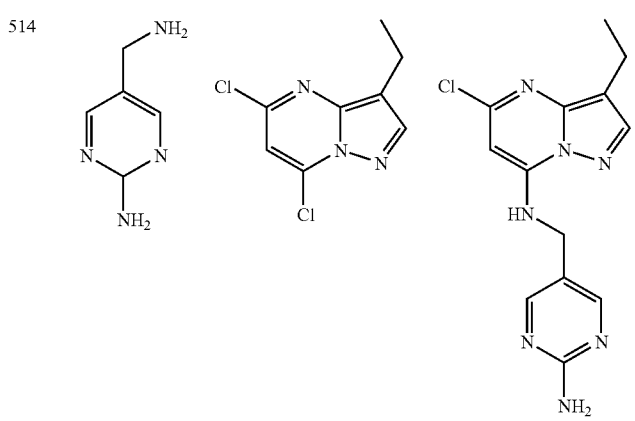

TABLE 500-continued

| Prep. Ex. | Column 2 | Column 3 | Column 4 | CMPD |
|---|---|---|---|---|
| 515 | (structure) | (structure) | (structure) | M + H = 332 |
| 516 | (structure) | (structure) | (structure) | |

Preparative Example 517

By essentially the same procedure set forth in Preparative Example 184 only substituting the amines in Column 2 of Table 501, the compounds shown in Column 3 of Table 501 were prepared.

TABLE 501

| Prep. Ex. | Column 2 | Column 3 | CMPD |
|---|---|---|---|
| 518 | (structure) | (structure) | M + H = 422.1 |

TABLE 501-continued

| Prep. Ex. | Column 2 | Column 3 | CMPD |
|---|---|---|---|
| 519 | [structure: 4-aminomethyl-phenyl-NH-C(O)-CH2-N(CH3)2] | [structure: 5-chloro-3-bromo-pyrazolo[1,5-a]pyrimidin-7-yl-NH-CH2-phenyl-NH-C(O)-CH2-N(CH3)2] | |

Preparative Example 520-521

By essentially the same procedure set forth in Preparative Example 192 only substituting the compounds in Column 2 of Table 502, the compounds shown in Column 3 of Table 502 were prepared.

TABLE 502

| Prep. Ex. | Column 2 | Column 3 | CMPD |
|---|---|---|---|
| 520 | [structure with cyclopropyl amide] | [structure with Boc-protected N and cyclopropyl amide] | M + H = 522.1 |
| 521 | [structure with dimethylaminoacetamide] | [structure with Boc-protected N and dimethylaminoacetamide] | M + H = 539.1 |

Example 1000

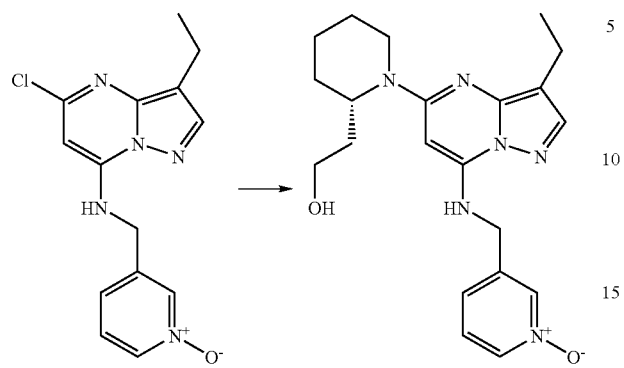

A mixture of the compound prepared in Preparative Example 509 (1.50 g, 4.94 mmol) with the aminoalcohol from Preparative Example 500 (1.91 g, 14.8 mmol) in dry NMP (3 mL) was stirred under N₂ at 160° C. for 48 hr. The NMP was distilled off in a vacuum and the residue was chromatographed first with 5:1 EtOAc:MeOH, then the crude product was rechromatographed with 10:1 CH$_2$Cl$_2$:MeOH. White solid (460 mg, 24%) was obtained. LCSM: MH$^+$=397; mp=113-115° C.

Example 1001

Major side product isolated (540 mg, 29%) was deoxygenated product (LCMS: MH$^+$=381; mp=49-52° C.:

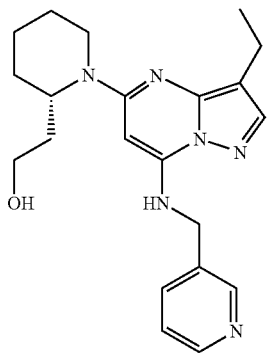 [SMILES: CCc1cnn2c(NCc3cccnc3)cc(N3CCCC[C@H]3CCO)nc12]

Examples 1002-1014

By essentially the same procedure set forth in Example 1000 only substituting the amines in Column 2 of Table 1000 and the chlorides in Column 3 of Table 1000 the compounds in column 4 of Table 1000 were prepared.

TABLE 1000

| Ex. | Column 2 | Column 3 | Column 4 | CMPD |
|---|---|---|---|---|
| 1002 |  |  | 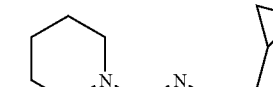 | MH$^+$ = 409; mp = 165-171° C. |
| 1003 |  |  |  | MH$^+$ = 397; mp = 219-221° C. |

TABLE 1000-continued
| Ex. | Column 2 | Column 3 | Column 4 | CMPD |
|---|---|---|---|---|
| 1004 |  | 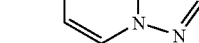 |  | $MH^+$ = 409; mp = 138-142° C. |
| 1005 |  |  |  | $MH^+$ = 411; mp = 194-196° C. |
| 1006 |  |  | 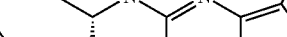 | $MH^+$ = 411; mp = 118-120° C. |
| 1007 |  | 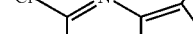 |  | $MH^+$ = 411; mp = 85-87° C. |

TABLE 1000-continued
| Ex. | Column 2 | Column 3 | Column 4 | CMPD |
|---|---|---|---|---|
| 1008 | 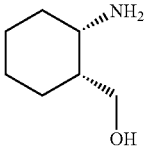 | 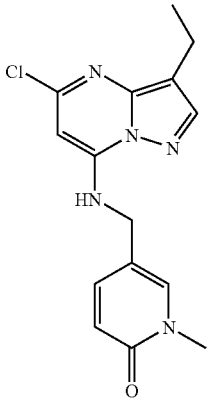 | 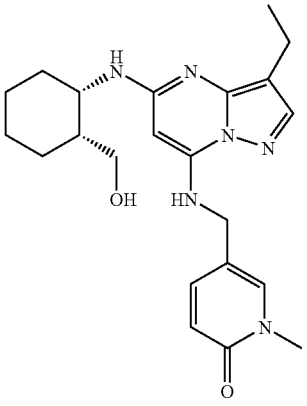 [SMILES: CCc1cnn2c(NCc3ccc(=O)n(C)c3)cc(N[C@H]3CCCC[C@H]3CO)nc12] | MH+ = 411; mp = 105-108° C. |
| 1009 | 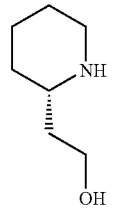 | 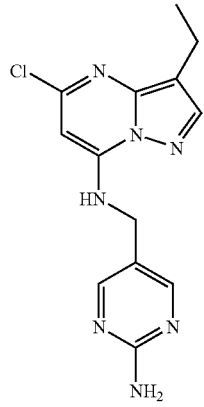 | 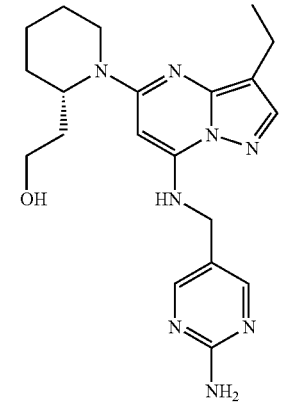 [SMILES: CCc1cnn2c(NCc3cnc(N)nc3)cc(N3CCCC[C@H]3CCO)nc12] | MH+ = 397; mp = 173-177° C. |
| 1010 | 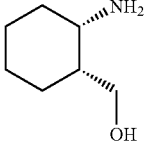 | 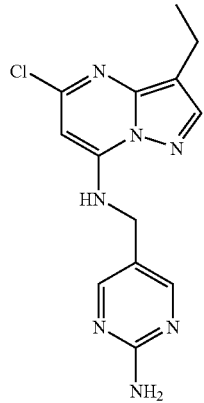 | 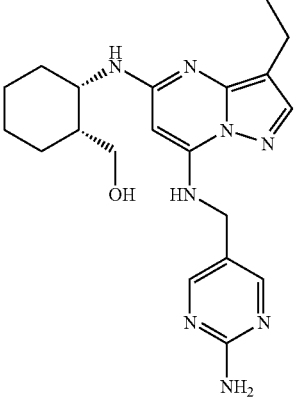 [SMILES: CCc1cnn2c(NCc3cnc(N)nc3)cc(N[C@H]3CCCC[C@H]3CO)nc12] | MH+ = 397; mp = 169-173° C. |

TABLE 1000-continued
| Ex. | Column 2 | Column 3 | Column 4 | CMPD |
|---|---|---|---|---|
| 1011 | 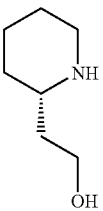 | 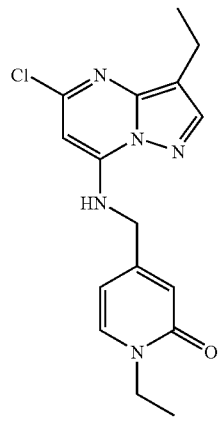 | 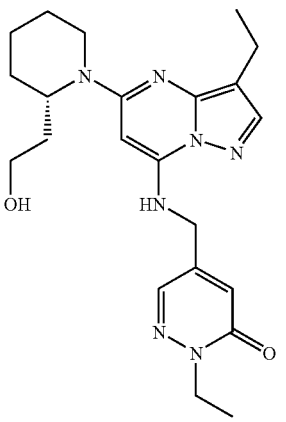 [SMILES: CCc1cnn2c(NCc3cnn(CC)c(=O)c3)cc(N3CCCC[C@H]3CCO)nc12] | MH+ = 425 |
| 1012 | 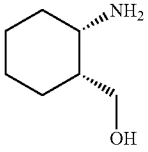 | 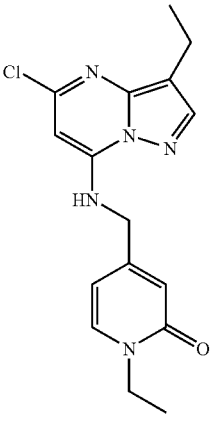 [SMILES: CCc1cnn2c(NCc3ccn(CC)c(=O)c3)cc(Cl)nc12] | 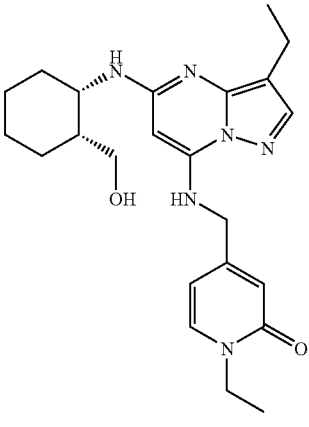 [SMILES: CCc1cnn2c(NCc3ccn(CC)c(=O)c3)cc(N[C@H]3CCCC[C@H]3CO)nc12] | MH+ = 425; mp = 232-234° C. |
| 1013 | 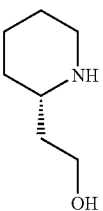 | 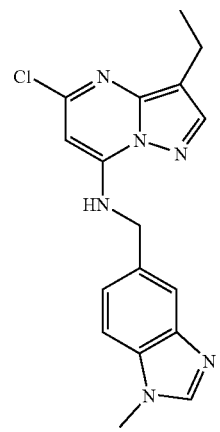 [SMILES: CCc1cnn2c(NCc3ccc4c(c3)ncn4C)cc(Cl)nc12] | 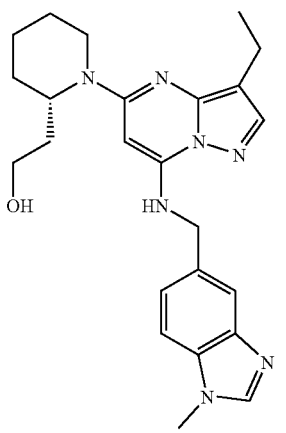 [SMILES: CCc1cnn2c(NCc3ccc4c(c3)ncn4C)cc(N3CCCC[C@H]3CCO)nc12] | |

591 592

TABLE 1000-continued

| Ex. | Column 2 | Column 3 | Column 4 | CMPD |
|---|---|---|---|---|
| 1014 |  | 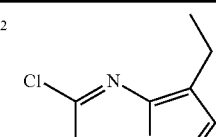 | 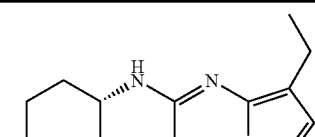 | |

Example 1015

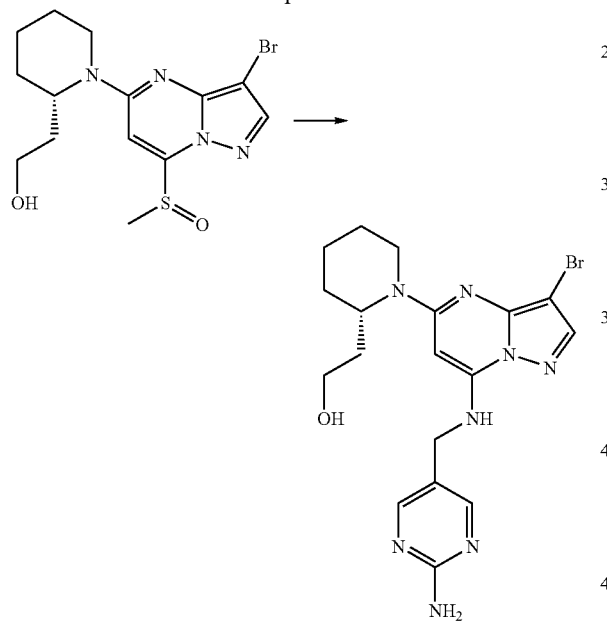

To a solution of sulfoxide from Preparative Example 505 (0.10 g, 0.28 mmol) in n-BuOH in a sealed tube was added Et$_3$N (0.13 mL, 1.0 mmol) followed by the amine dihydrochloride (0.13 g, 0.65 mmol) from Preparative Example 216. The tube was sealed and was heated to 100° C., cooled to room temperature, and was concentrated under reduced pressure. The crude residue was purified by preparative TLC (6×1000 μM) eluting with CH$_2$Cl$_2$/MeOH (20:1) to afford 50 mg (40%) of a pale white solid. mp 182-185° C.; M+H=446.

Examples 1016-1026

By essentially the same procedure set forth in Example 1015 only substituting the sulfoxide shown in Column 2 of Table 1001 and the amine in Column 3 of Table 1001, the compounds shown in Column 4 of Table 1001 were prepared.

TABLE 1001

| Ex. | Column 2 | Column 3 | Column 4 | CMPD |
|---|---|---|---|---|
| 1016 |  | | | mp = 182-185° C.; M + H = 448 |

TABLE 1001-continued

| Ex. | Column 2 | Column 3 | Column 4 | CMPD |
|---|---|---|---|---|
| 1017 | | | | mp = 187-189° C.; M + H = 445 |
| 1018 | | | | mp = 139-143° C.; M + H = 453 |
| 1020 | | | | mp = 186-189° C.; M + H = 485 |
| 1021 | | | | mp = 154-157° C.; M + H = 448 |

TABLE 1001-continued

| Ex. | Column 2 | Column 3 | Column 4 | CMPD |
|-----|----------|----------|----------|------|
| 1022 | | | | mp = 103-105° C.; M + H = 485 |
| 1023 | | | | mp = 203-205° C.; M + H = 432 |
| 1024 | | | | mp = 210-212° C.; M + H = 395 |
| 1025 | | | | mp = 82-84° C.; M + H = 446 |

TABLE 1001-continued

| Ex. | Column 2 | Column 3 | Column 4 | CMPD |
|---|---|---|---|---|
| 1026 | | | | mp = 86-90°C.; M + H = 462 |

Examples 1027-1038

By essentially the same procedure set forth in Example 341, Steps A and B only substituting the amines in Column 2 of Table 1002 and the compound prepared in Preparative Example 193.10, the compounds in Column 4 of Table 1002 were prepared.

TABLE 1002

| Ex. | Column 2 | Column 4 | CMPD |
|---|---|---|---|
| 1027 | | | mp = 160-163° C.; M + H = 434 |
| 1028 | | | mp = 122-124° C.; M + H = 434 |

TABLE 1002-continued
| Ex. | Column 2 | Column 4 | CMPD |
|---|---|---|---|
| 1029 | 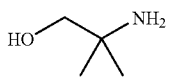 | 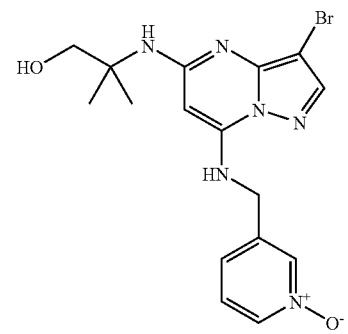 [SMILES: CC(C)(CO)Nc1cc(NCc2ccc[n+]([O-])c2)n2ncc(Br)c2n1] | mp = 153-156° C.; M + H = 408 |
| 1030 | 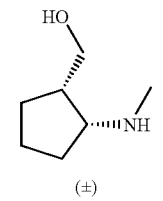 (±) | 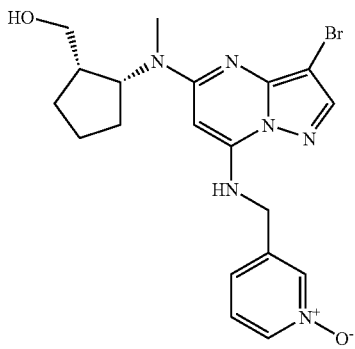 (±) | mp = 170-174° C.; M + H = 448 |
| 1031 | 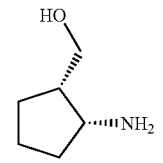 | 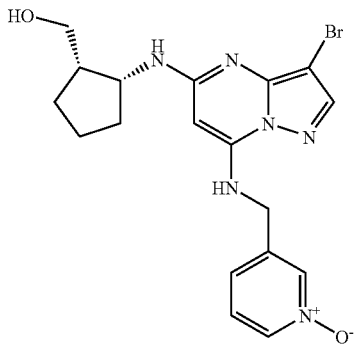 [SMILES: [O-][n+]1cccc(CNc2cc(N[C@@H]3CCC[C@@H]3CO)nc3c(Br)cnn23)c1] | mp = 166-169° C.; M + H = 434 |
| 1032 | 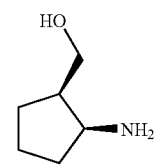 | 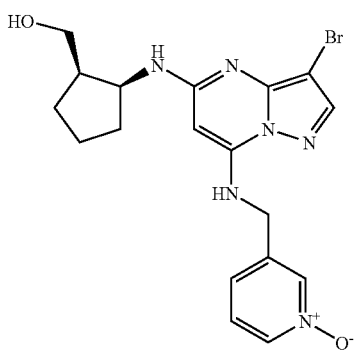 [SMILES: [O-][n+]1cccc(CNc2cc(N[C@H]3CCC[C@H]3CO)nc3c(Br)cnn23)c1] | mp = 167-168° C.; M + H = 434 |

TABLE 1002-continued

| Ex. | Column 2 | Column 4 | CMPD |
|---|---|---|---|
| 1033 | HO-CH2CH2CH2-NH2 | (structure) | MH+ = 393 |
| 1034 | (2-(piperidin-2-yl)ethanol) | (structure) | mp = 157-160° C.; M + H = 447 |
| 1035 | ((1,2-trans-aminocyclohexyl)methanol) | (structure) | mp = 164-168° C.; M + H = 448 |
| 1036 | ((1,2-trans-aminocyclohexyl)methanol) | (structure) | mp = 165-168° C.; M + H = 448 |

TABLE 1002-continued

| Ex. | Column 2 | Column 4 | CMPD |
|---|---|---|---|
| 1037 | (2-piperidinyl)ethanol | 2-[1-(3-bromo-7-{[(1-oxidopyridin-3-yl)methyl]amino}pyrazolo[1,5-a]pyrimidin-5-yl)piperidin-2-yl]ethanol | mp = 131-135° C.; M + H = 447 |
| 1038 | (1H-imidazol-4-yl)methanol | {1-[3-bromo-7-({[(1-oxidopyridin-3-yl)methyl]amino})pyrazolo[1,5-a]pyrimidin-5-yl]-1H-imidazol-4-yl}methanol | |

Examples 1039-1041

By essentially the same procedure set forth in Example 340 only substituting the amines in Column 2 of Table 1003, the compounds shown in Column 4 of Table 1003 were prepared.

TABLE 1003

| Ex. | Column 2 | Column 4 | CMPD |
|---|---|---|---|
| 1039 | 2-amino-2-methylpropan-1-ol | 2-[(3-bromo-7-{[(pyridin-3-yl)methyl]amino}pyrazolo[1,5-a]pyrimidin-5-yl)amino]-2-methylpropan-1-ol | mp = 210-212° C.; M + H = 392 |

TABLE 1003-continued

| Ex. | Column 2 | Column 4 | CMPD |
|---|---|---|---|
| 1040 | [structure: HO-CH2-cyclopentyl-NH-CH3 (±)] | [structure: pyrazolopyrimidine with Br, N(CH3)-cyclopentyl-CH2OH, and HN-CH2-pyridin-3-yl (±)] | mp = 128-130°0 C.; M + H = 432 |
| 1041 | [structure: HO-CH2-cyclopentyl-NH2] | [structure: pyrazolopyrimidine with Br, NH-cyclopentyl-CH2OH, and HN-CH2-pyridin-3-yl] | mp = 148-151° C.; M + H = 18 |

Examples 1042-1057

By essentially the same procedure set forth in Example 340 only using the appropriate 5-chloroderivative and substituting the amines in Column 2 of Table 1004, the compounds shown in Column 4 of Table 1004 were prepared.

TABLE 1004

| Ex. | Column 2 | Column 4 | CMPD |
|---|---|---|---|
| 1042 | [structure: 1-aminocyclopentyl-CH2OH] | [structure: pyrazolopyrimidine with Br, NH-(1-(hydroxymethyl)cyclopentyl), and HN-CH2-phenyl-NHC(O)-cyclopropyl] | M + H = 500.3 |

TABLE 1004-continued

| Ex. | Column 2 | Column 4 | CMPD |
|---|---|---|---|
| 1043 | | | M + H = 514.1 |
| 1044 | | | M + H = 460.3 |
| 1045 | | | M + H = 477.1 |

TABLE 1004-continued
| Ex. | Column 2 | Column 4 | CMPD |
|---|---|---|---|
| 1046 | 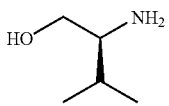 | 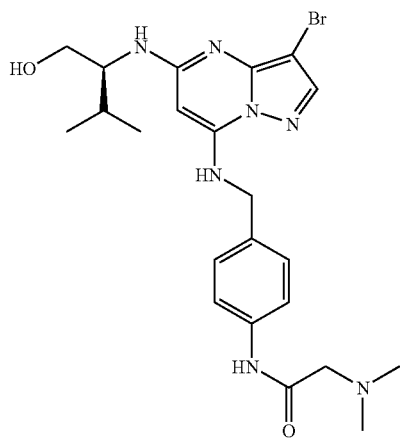 [SMILES: CC(C)[C@@H](CO)Nc1cc(NCc2ccc(NC(=O)CN(C)C)cc2)n2ncc(Br)c2n1] | M + H = 505.1 |
| 1047 | 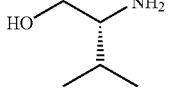 | 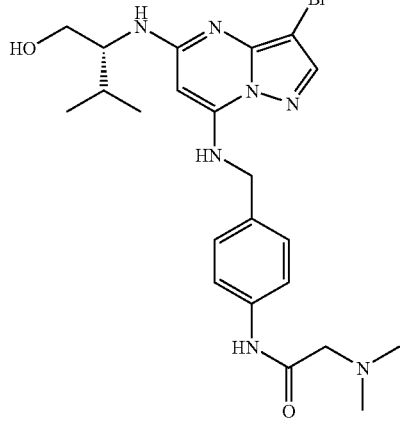 | M + H = 505.1 |
| 1048 | 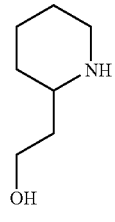 | 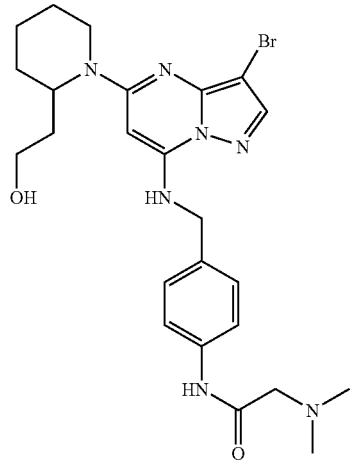 [SMILES: CN(C)CC(=O)Nc1ccc(CNc2cc(N3CCCCC3CCO)nc3c(Br)cnn23)cc1] | M + H = 531.1 |

TABLE 1004-continued

| Ex. | Column 2 | Column 4 | CMPD |
|---|---|---|---|
| 1049 | | | M + H = 477.1 |
| 1050 | | | M + H = 505.1 |
| 1051 | | | M + H = 505.1 |

TABLE 1004-continued
| Ex. | Column 2 | Column 4 | CMPD |
|---|---|---|---|
| 1052 | 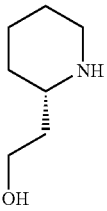 | 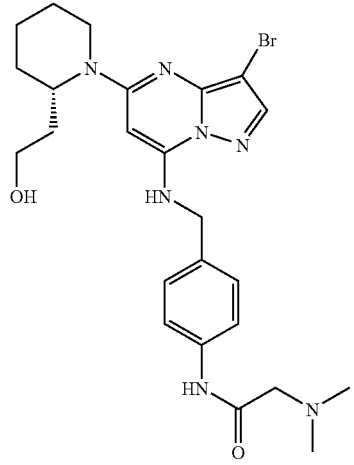 [SMILES: CN(C)CC(=O)Nc1ccc(CNc2cc(N3CCCC[C@H]3CCO)nc3c(Br)cnn23)cc1] | M + H = 531.1 |
| 1053 | 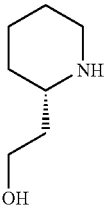 | 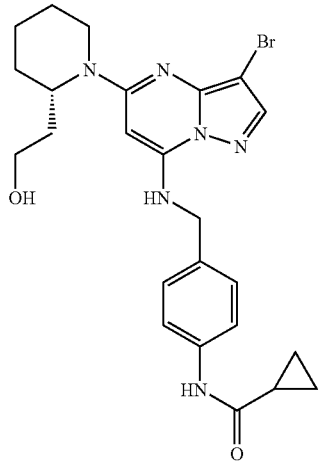 [SMILES: O=C(Nc1ccc(CNc2cc(N3CCCC[C@H]3CCO)nc3c(Br)cnn23)cc1)C1CC1] | M + H = 514.1 |
| 1054 | 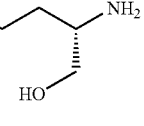 | 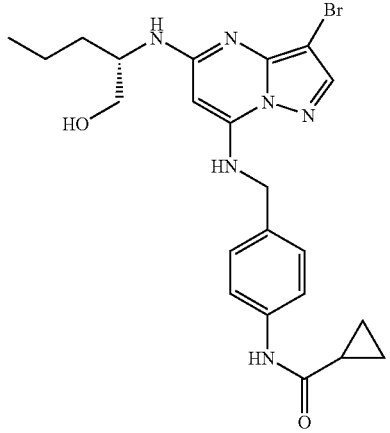 [SMILES: CCC[C@@H](CO)Nc1cc(NCc2ccc(NC(=O)C3CC3)cc2)n2ncc(Br)c2n1] | M + H = 488.3 |

TABLE 1004-continued

| Ex. | Column 2 | Column 4 | CMPD |
|---|---|---|---|
| 1055 | (S)-2-aminopentan-1-ol | 3-bromo-N5-(1-hydroxypentan-2-yl)-N7-(4-cyclopropanecarboxamidobenzyl)pyrazolo[1,5-a]pyrimidine-5,7-diamine | M + H = 488.3 |
| 1056 | (R)-2-amino-3-methylbutan-1-ol | 3-bromo-N5-(1-hydroxy-3-methylbutan-2-yl)-N7-(4-cyclopropanecarboxamidobenzyl)pyrazolo[1,5-a]pyrimidine-5,7-diamine | M + H = 488.1 |
| 1057 | (S)-2-amino-3-methylbutan-1-ol | 3-bromo-N5-(1-hydroxy-3-methylbutan-2-yl)-N7-(4-cyclopropanecarboxamidobenzyl)pyrazolo[1,5-a]pyrimidine-5,7-diamine | M + H = 488.1 |

Assay:

BACULOVIRUS CONSTRUCTIONS: Cyclins A and E were cloned into pFASTBAC (Invitrogen) by PCR, with the addition of a GluTAG sequence (EYMPME) at the amino-terminal end to allow purification on anti-GluTAG affinity columns. The expressed proteins were approximately 46 kDa (cyclin E) and 50 kDa (cyclin A) in size. CDK2 was also cloned into pFASTBAC by PCR, with the addition of a haemaglutinin epitope tag at the carboxy-terminal end (YD-VPDYAS). The expressed protein was approximately 34 kDa in size.

ENZYME PRODUCTION: Recombinant baculoviruses expressing cyclins A, E and CDK2 were infected into SF9 cells at a multiplicity of infection (MOI) of 5, for 48 hrs. Cells were harvested by centrifugation at 1000 RPM for 10 minutes. Cyclin-containing (E or A) pellets were combined with CDK2 containing cell pellets and lysed on ice for 30 minutes in five times the pellet volume of lysis buffer containing 50 mM Tris pH 8.0, 0.5% NP40, 1 mM DTT and protease/phosphatase inhibitors (Roche Diagnostics GmbH, Mannheim, Germany). Mixtures were stirred for 30-60 minutes to promote cyclin-CDK2 complex formation. Mixed lysates were then spun down at 15000 RPM for 10 minutes and the supernatant retained. 5 ml of anti-GluTAG beads (for one liter of SF9 cells) were then used to capture cyclin-CDK2 complexes. Bound beads were washed three times in lysis buffer. Proteins were competitively eluted with lysis buffer containing 100-200 ug/mL of the GluTAG peptide. Eluate was dialyzed overnight in 2 liters of kinase buffer containing 50 mM Tris pH 8.0, 1 mM DTT, 10 mM MgCl2, 100 uM sodium orthovanadate and 20% glycerol. Enzyme was stored in aliquots at −70° C.

IN VITRO KINASE ASSAY: CDK2 kinase assays (either cyclin A or E-dependent) were performed in low protein binding 96-well plates (Corning Inc, Corning, N.Y.). Enzyme was diluted to a final concentration of 50 µg/ml in kinase buffer containing 50 mM Tris pH 8.0, 10 mM MgCl$_2$, 1 mM DTT, and 0.1 mM sodium orthovanadate. The substrate used in these reactions was a biotinylated peptide derived from Histone H1 (from Amersham, UK). The substrate was thawed on ice and diluted to 2 µM in kinase buffer. Compounds were diluted in 10% DMSO to desirable concentrations. For each kinase reaction, 20 µl of the 50 µg/ml enzyme solution (1 µg of enzyme) and 20 µl of the 1 µM substrate solution were mixed, then combined with 10 µl of diluted compound in each well for testing. The kinase reaction was started by addition of 50 µl of 4 µM ATP and 1 µCi of 33P-ATP (from Amersham, UK). The reaction was allowed to run for 1 hour at room temperature. The reaction was stopped by adding 200 µl of stop buffer containing 0.1% Triton X-100, 1 mM ATP, 5 mM EDTA, and 5 mg/ml streptavidine coated SPA beads (from Amersham, UK) for 15 minutes. The SPA beads were then captured onto a 96-well GF/B filter plate (Packard/Perkin Elmer Life Sciences) using a Filtermate universal harvester (Packard/Perkin Elmer Life Sciences.). Non-specific signals were eliminated by washing the beads twice with 2M NaCl then twice with 2 M NaCl with 1% phosphoric acid. The radioactive signal was then measured using a TopCount 96 well liquid scintillation counter (from Packard/Perkin Elmer Life Sciences).

IC$_{50}$ DETERMINATION: Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate IC$_{50}$ values, the dose-response curves were then fitted to a standard sigmoidal curve and IC$_{50}$ values were derived by nonlinear regression analysis. The thus-obtained IC$_{50}$ values for the compounds of the invention are shown in Table 87. These kinase activities were generated by using cyclin A or cyclin E using the above-described assay.

TABLE 87

| CMPD | Example | IC$_{50}$ (µM) |
|---|---|---|
| [structure: 5-phenyl-3-bromo-pyrazolo[1,5-a]pyrimidin-7-yl with HN-CH2-4-pyridyl] | 1 | 0.020 0.029 |
| [structure: 5-(2-fluorophenyl)-3-bromo-pyrazolo[1,5-a]pyrimidin-7-yl with HN-CH2-4-pyridyl] | 3 | 0.032 0.024 |
| [structure: 5-(2-fluorophenyl)-3-bromo-pyrazolo[1,5-a]pyrimidin-7-yl with HN-CH2-3-pyridyl] | 4 | 0.011 |
| [structure: 5-(2-fluorophenyl)-3-chloro-pyrazolo[1,5-a]pyrimidin-7-yl with HN-CH2-3-pyridyl] | 5 | 0.021 |
| [structure: 5-(2-chlorophenyl)-3-bromo-pyrazolo[1,5-a]pyrimidin-7-yl with HN-CH2-3-pyridyl] | 8 | 0.003 |

TABLE 87-continued

| CMPD | Example | IC$_{50}$ (µM) |
|---|---|---|
| 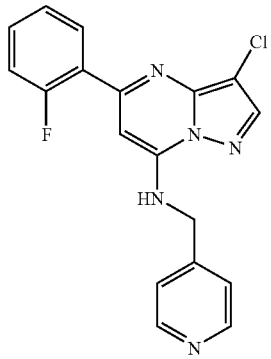 | 6 | 0.064<br>0.029 |
| 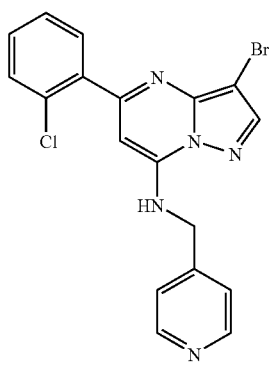 | 7 | 0.01<br>0.006 |
| 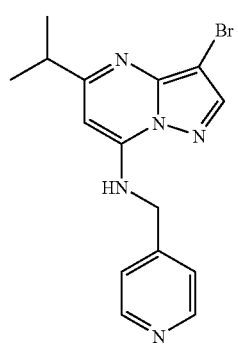 | 10 | 0.042 |
| 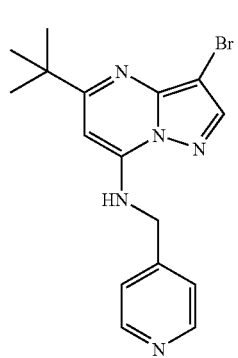 | 12 | 0.17 |

TABLE 87-continued

| CMPD | Example | IC$_{50}$ (µM) |
|---|---|---|
| 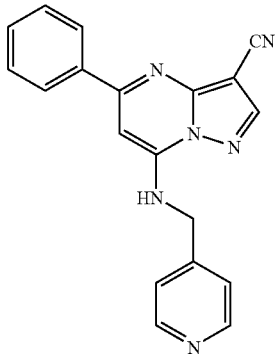 | 16 | 0.62 |
| 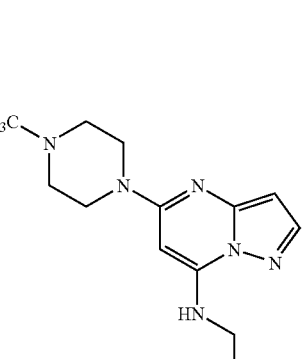 | 1 | 5.6 |
|  | 3 | 0.14 |

As demonstrated above by the assay values, the compounds of the present invention exhibit excellent CDK inhibitory properties.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

TABLE 43
| Ex. | Compound | m/z |
|---|---|---|
| 4301 | 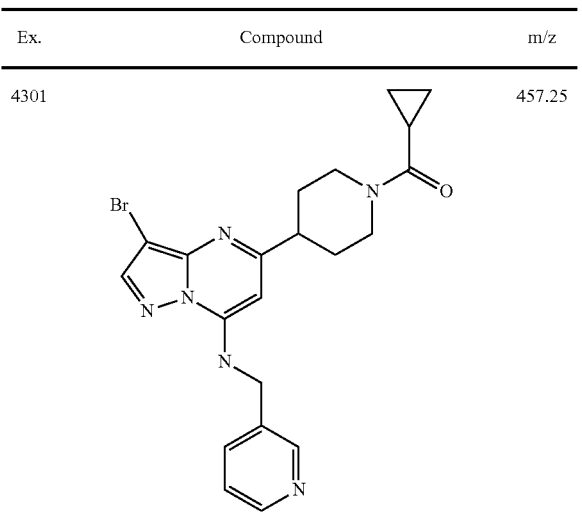 | 457.25 |
| 4302 | 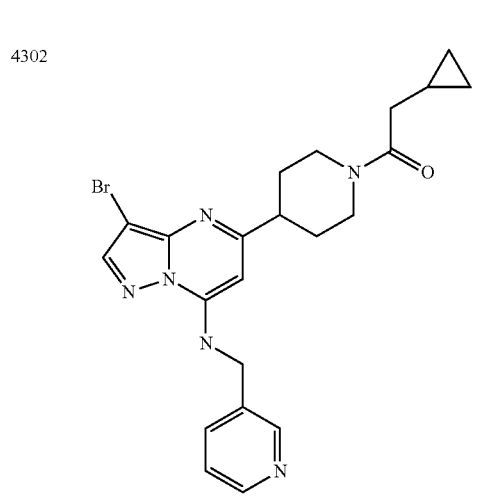 | 471.26 |
| 4303 | 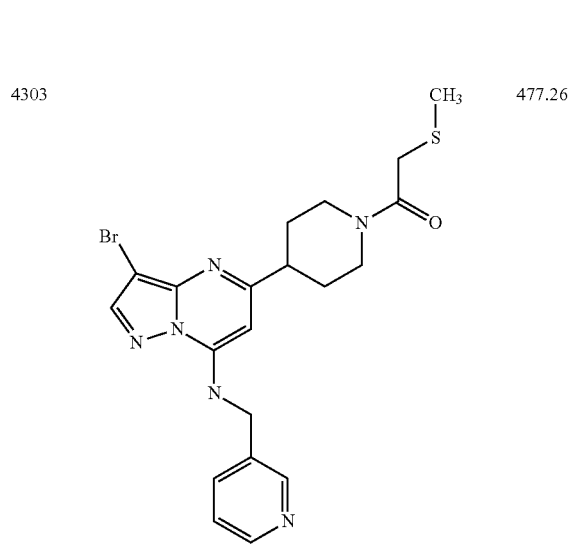 | 477.26 |
TABLE 43-continued
| Ex. | Compound | m/z |
|---|---|---|
| 4304 | 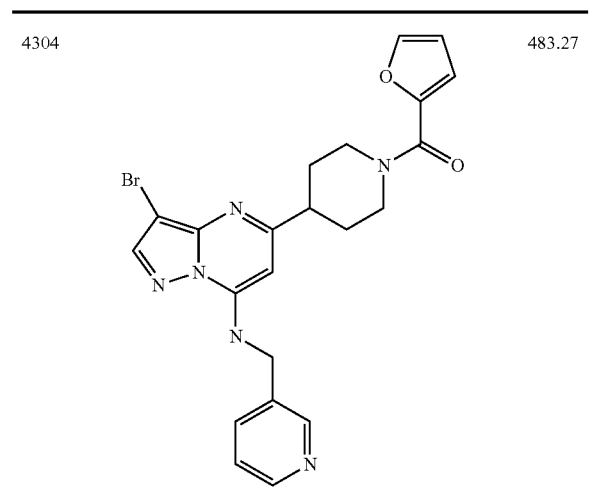 | 483.27 |
| 4305 | 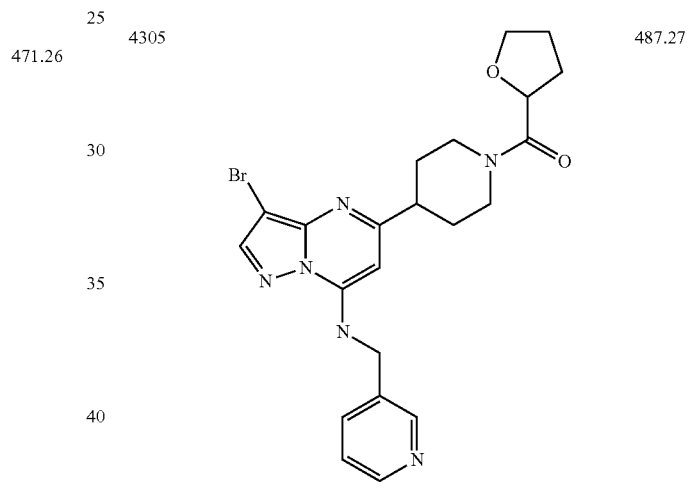 | 487.27 |
| 4306 | 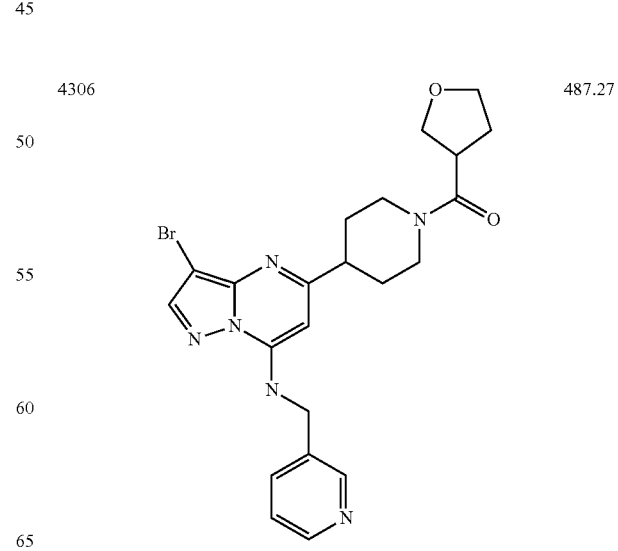 | 487.27 |

TABLE 43-continued
| 4307 | 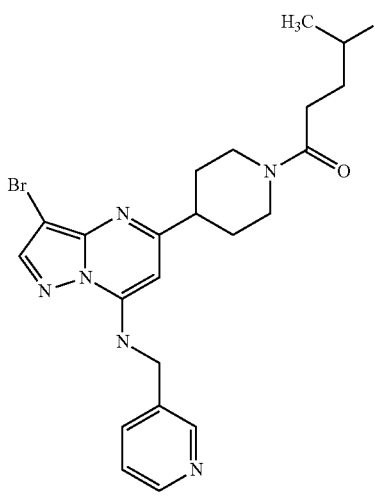 | 487.27 |
| 4308 | 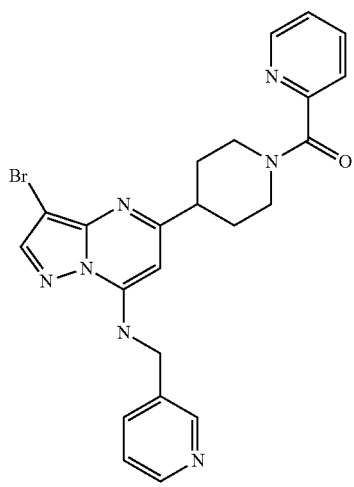 [SMILES: O=C(c1ccccn1)N1CCC(c2cc(NCc3cccnc3)n3ncc(Br)c3n2)CC1] | 494.27 |
| 4309 | 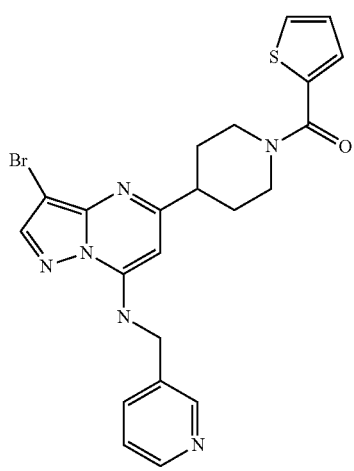 [SMILES: O=C(c1cccs1)N1CCC(c2cc(NCc3cccnc3)n3ncc(Br)c3n2)CC1] | 499.27 |
| 4310 | 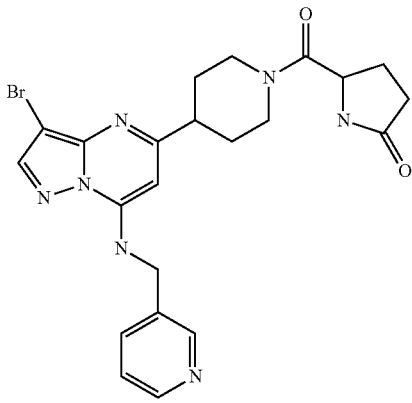 [SMILES: O=C1CCC(C(=O)N2CCC(c3cc(NCc4cccnc4)n4ncc(Br)c4n3)CC2)N1] | 500.27 |
| 4311 | 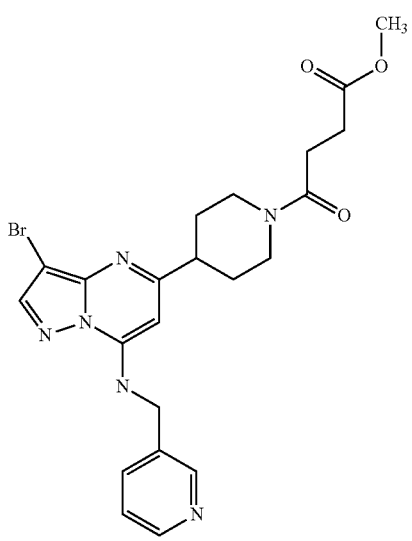 [SMILES: COC(=O)CCC(=O)N1CCC(c2cc(NCc3cccnc3)n3ncc(Br)c3n2)CC1] | 503.28 |
| 4312 | 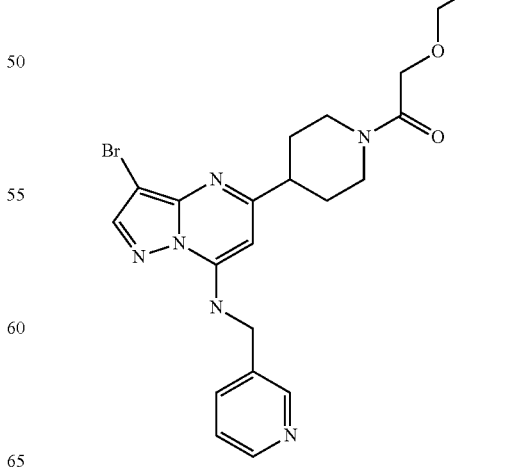 | 505.28 |

TABLE 43-continued
4313 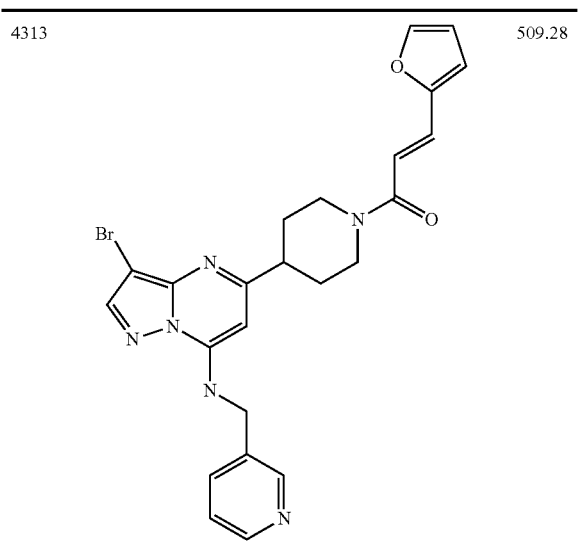 509.28
4314 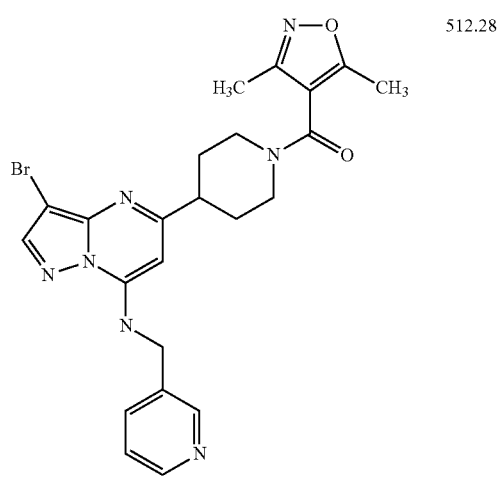 512.28
4315 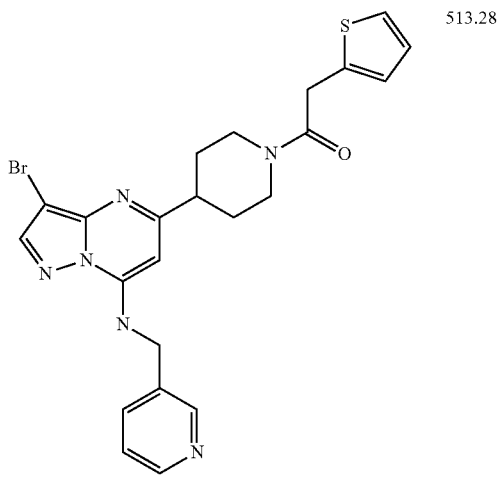 513.28
TABLE 43-continued
4316 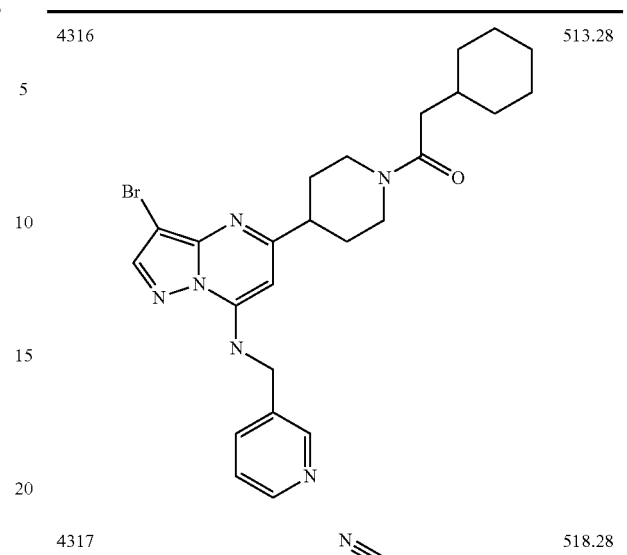 513.28
4317 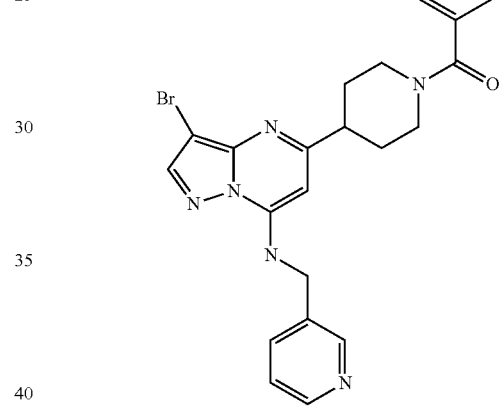 518.28
4318 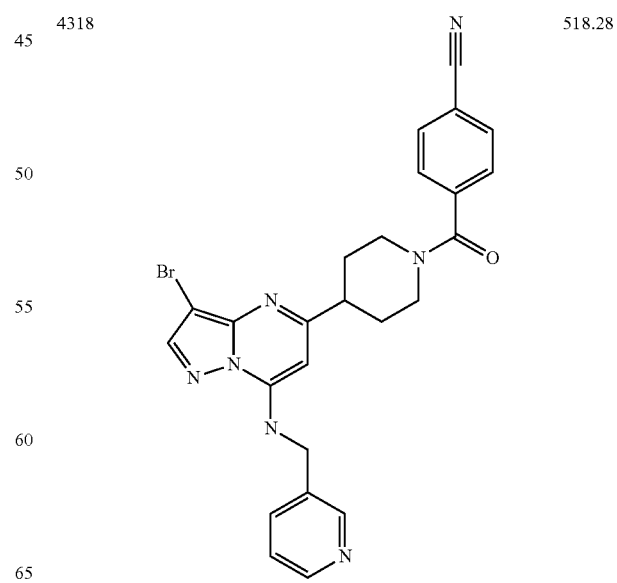 518.28

TABLE 43-continued
| 4319 | 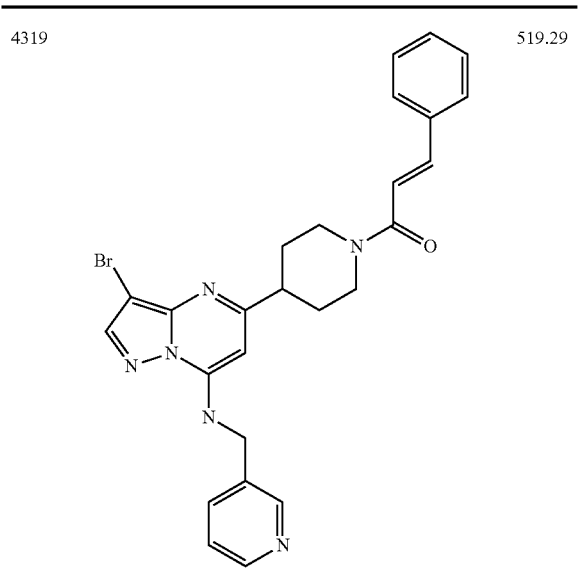 | 519.29 |
| 4320 | 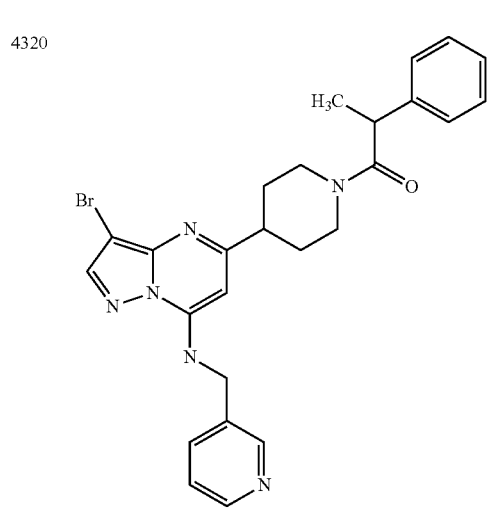 | 521.29 |
| 4321 | 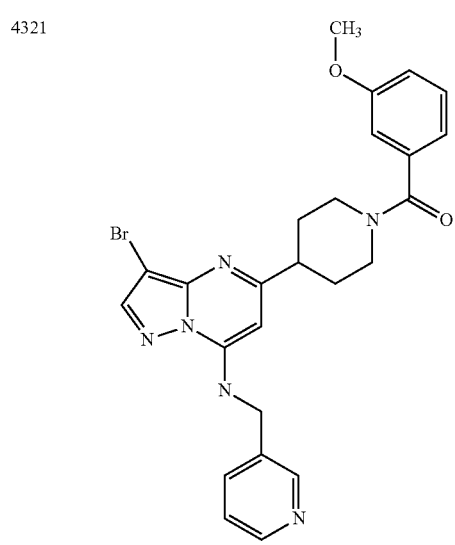 | 523.29 |
TABLE 43-continued
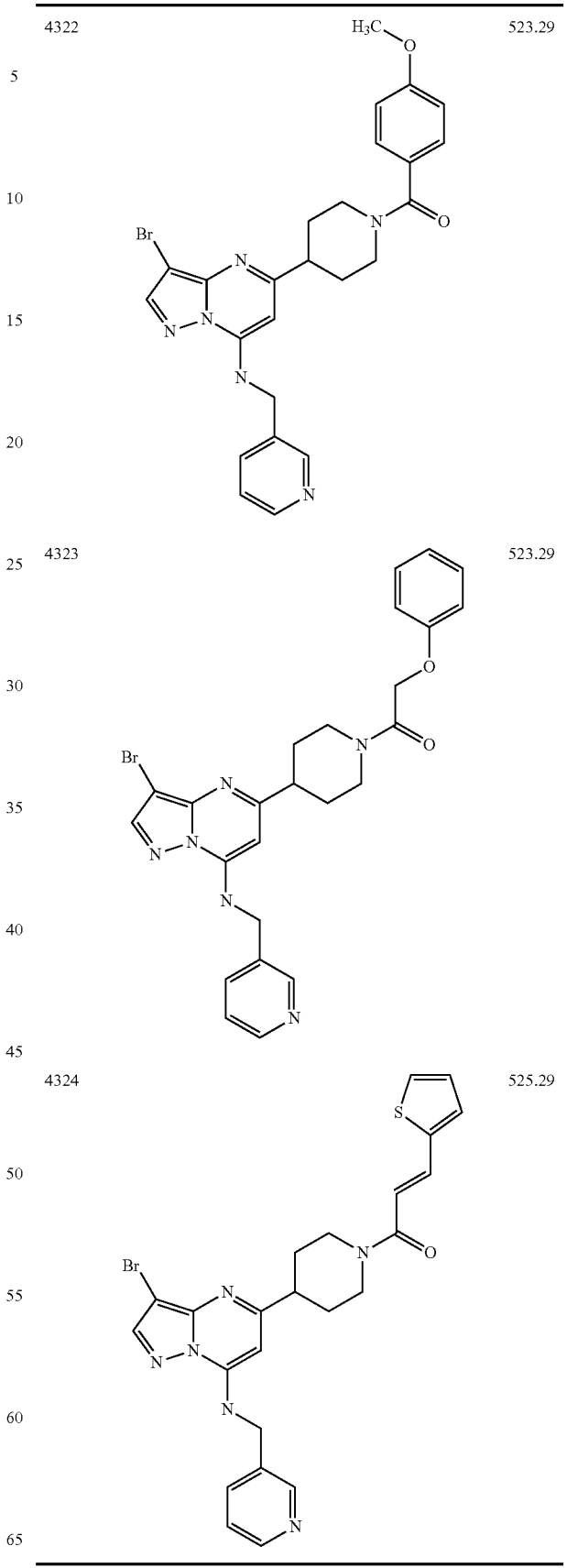
4322  523.29
4323  523.29
4324  525.29

TABLE 43-continued
| Product | 1. Ex.<br>2. m/z |
|---|---|
| 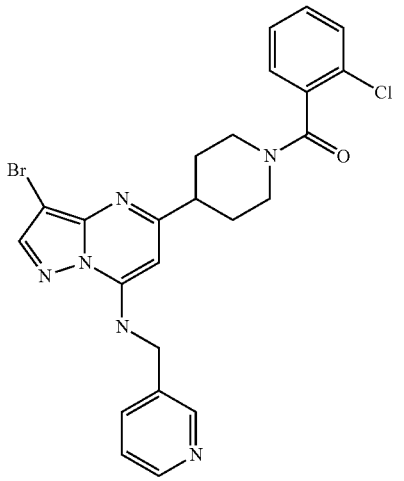 [SMILES: O=C(c1ccccc1Cl)N1CCC(c2cc(NCc3cccnc3)n3ncc(Br)c3n2)CC1] | 1. 4325<br>2. 527.29 |
| 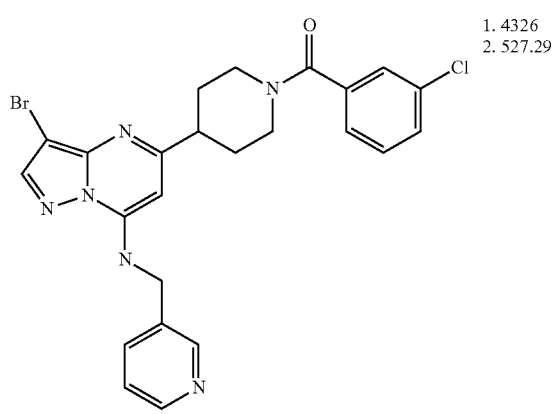 | 1. 4326<br>2. 527.29 |
| 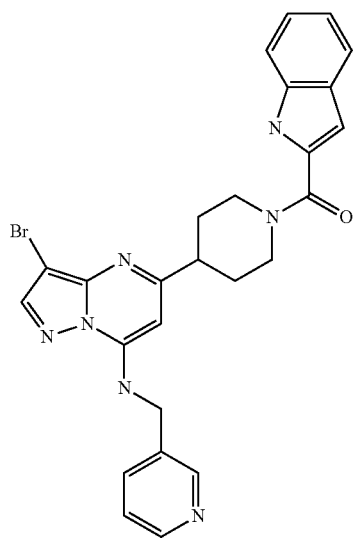 [SMILES: O=C(c1cc2ccccc2o1)N1CCC(c2cc(NCc3cccnc3)n3ncc(Br)c3n2)CC1] | 1. 4327<br>2. 532.29 |
TABLE 43-continued
| Product | 1. Ex.<br>2. m/z |
|---|---|
| 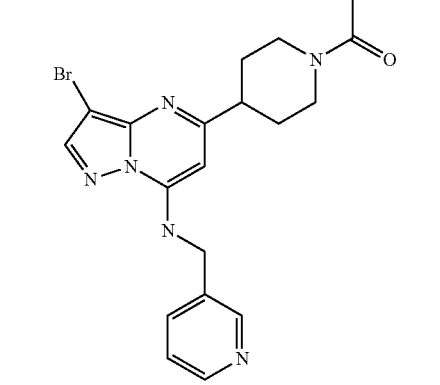 | 1. 4328<br>2. 532.29 |
| 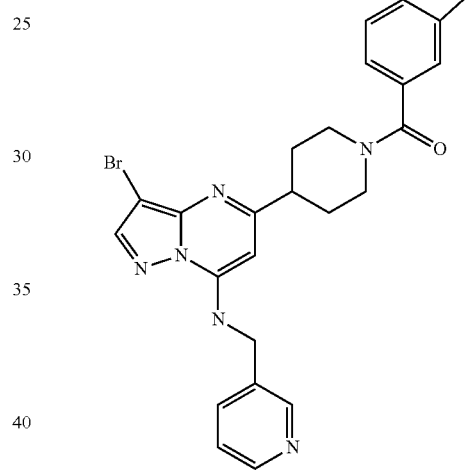 | 1. 4329<br>2. 532.29 |
| 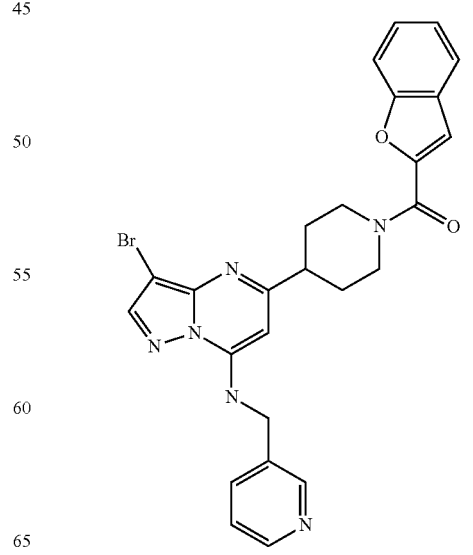 | 1. 4330<br>2. 533.29 |

TABLE 43-continued
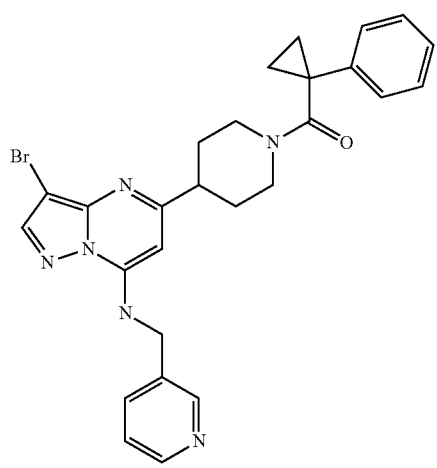 [SMILES: O=C(N1CCC(c2cc(NCc3cccnc3)n3ncc(Br)c3n2)CC1)C1(c2ccccc2)CC1]
4331
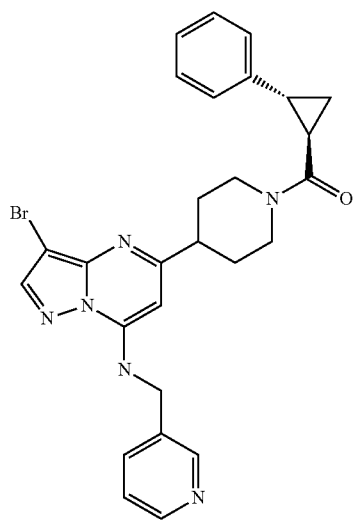 [SMILES: O=C([C@@H]1C[C@H]1c1ccccc1)N1CCC(c2cc(NCc3cccnc3)n3ncc(Br)c3n2)CC1]
1. 4332
2. 533.29
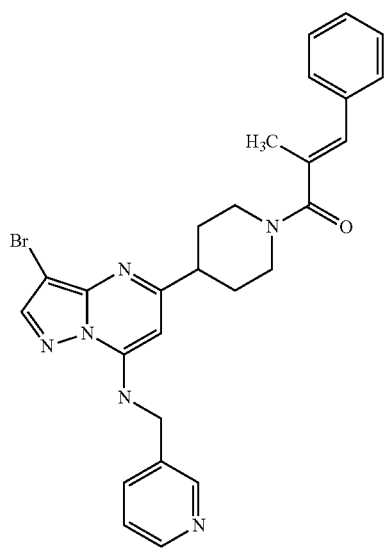 [SMILES: C/C(=C\c1ccccc1)C(=O)N1CCC(c2cc(NCc3cccnc3)n3ncc(Br)c3n2)CC1]
1. 4333
2. 533.29
TABLE 43-continued
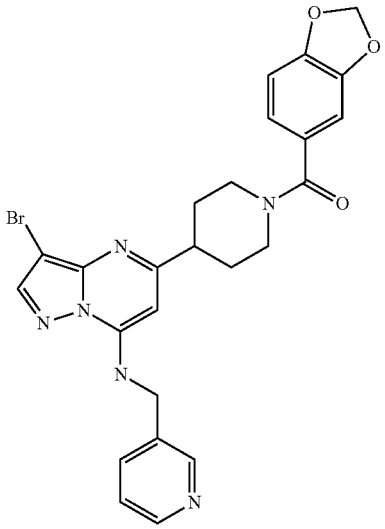 [SMILES: O=C(c1ccc2c(c1)OCO2)N1CCC(c2cc(NCc3cccnc3)n3ncc(Br)c3n2)CC1]
1. 4334
2. 537.3
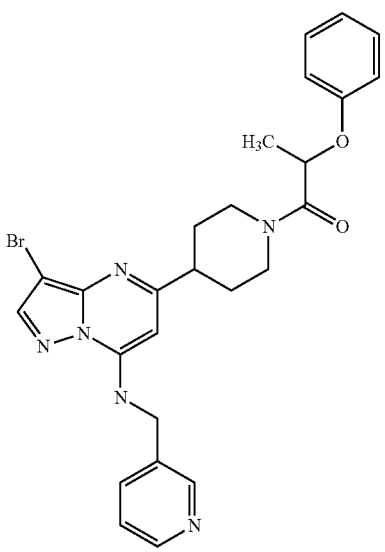 [SMILES: CC(Oc1ccccc1)C(=O)N1CCC(c2cc(NCc3cccnc3)n3ncc(Br)c3n2)CC1]
1. 4335
2. 537.3
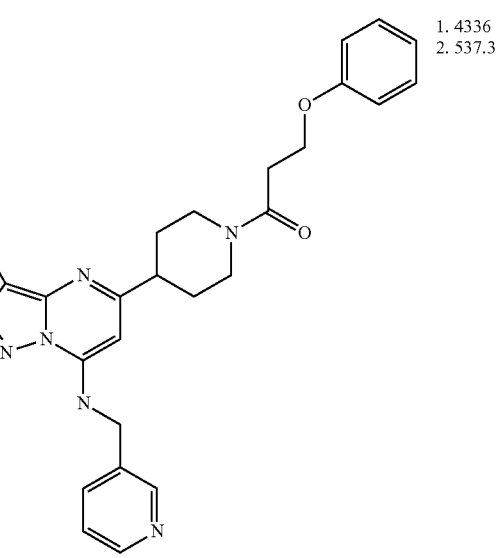
1. 4336
2. 537.3

TABLE 43-continued
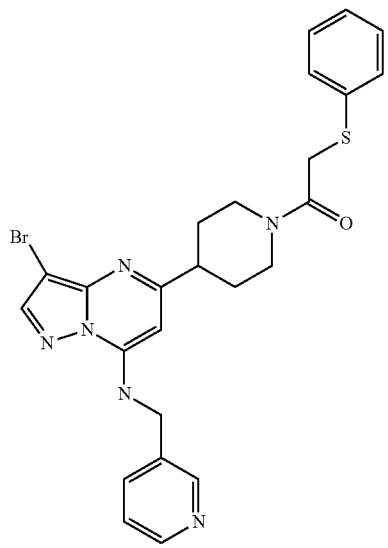
1. 4337
2. 539.3
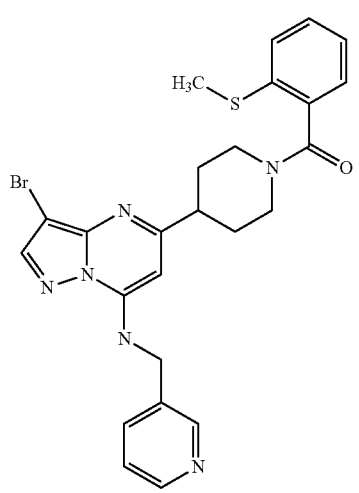 [SMILES: CSc1ccccc1C(=O)N1CCC(c2cc(NCc3cccnc3)n3ncc(Br)c3n2)CC1]
1. 4338
2. 539.3
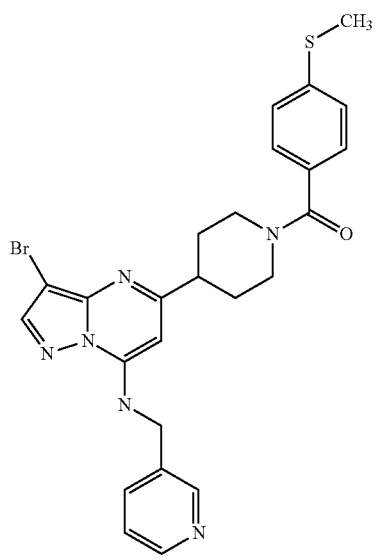 [SMILES: CSc1ccc(C(=O)N2CCC(c3cc(NCc4cccnc4)n4ncc(Br)c4n3)CC2)cc1]
1. 4339
2. 539.3
TABLE 43-continued
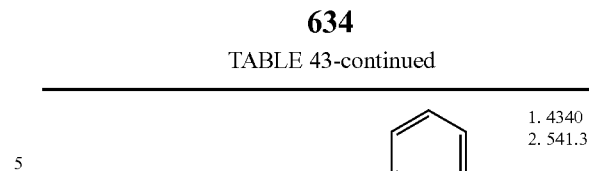
1. 4340
2. 541.3
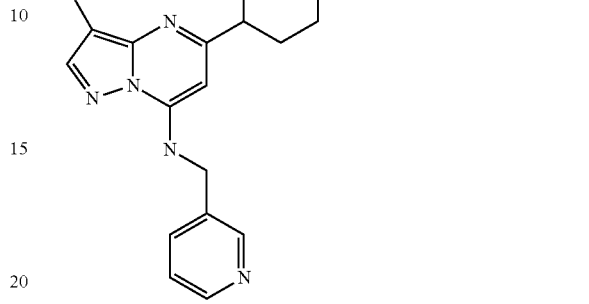
1. 4341
2. 543.3
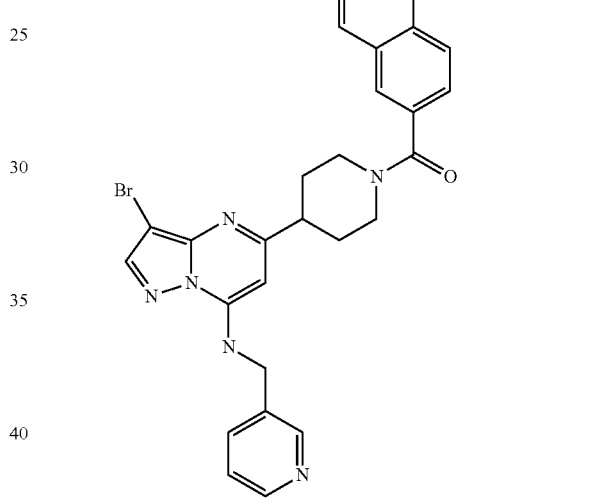
1. 4342
2. 546.3
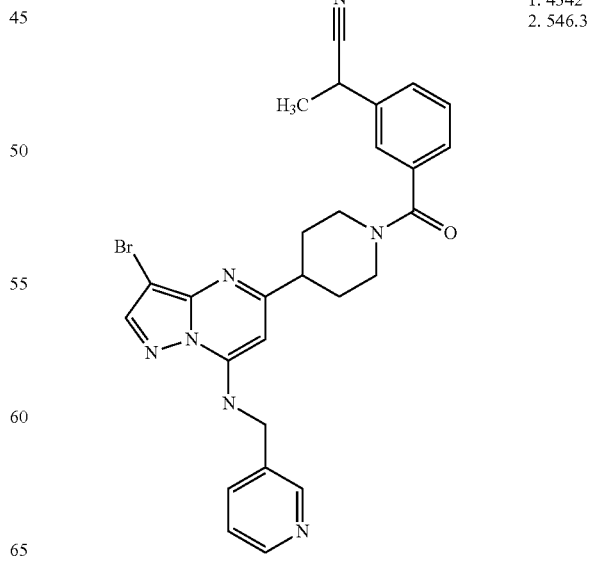

TABLE 43-continued
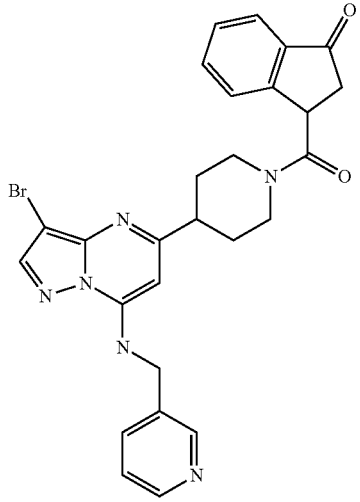 [SMILES: O=C1CC(C(=O)N2CCC(c3cc(NCc4cccnc4)n4ncc(Br)c4n3)CC2)c2ccccc21]
1. 4343
2. 547.3
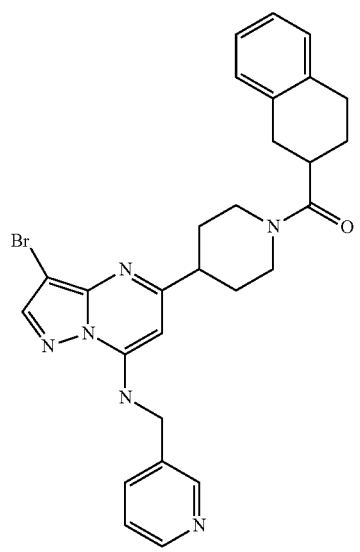 [SMILES: O=C(C1CCc2ccccc2C1)N1CCC(c2cc(NCc3cccnc3)n3ncc(Br)c3n2)CC1]
1. 4344
2. 547.3
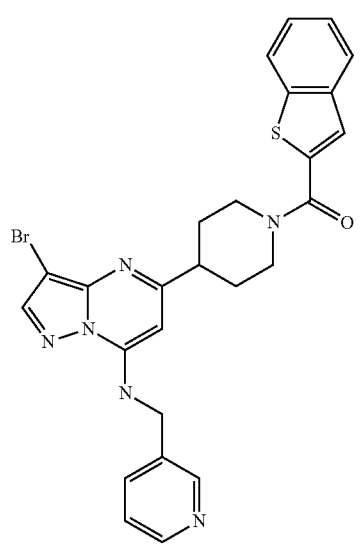
1. 4345
2. 549.3
TABLE 43-continued
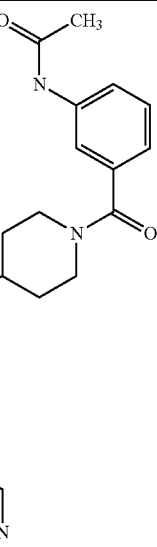
1. 4346
2. 550.3
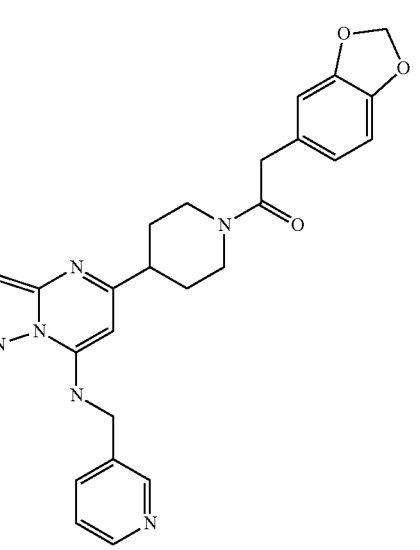
1. 4347
2. 551.3
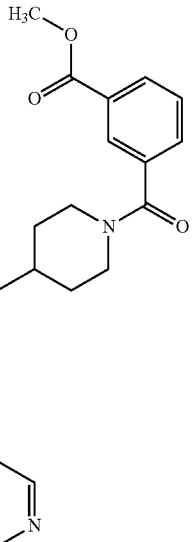
1. 4348
2. 551.3

TABLE 43-continued
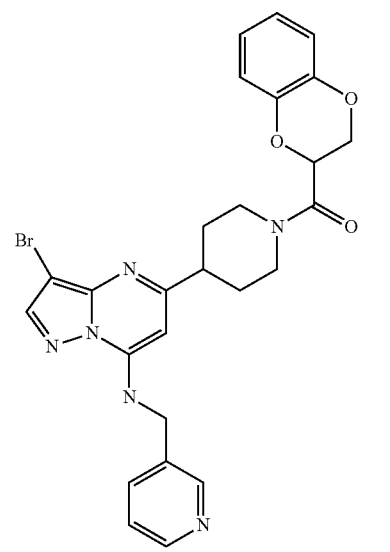 [SMILES: O=C(C1COc2ccccc2O1)N1CCC(c2cc(NCc3cccnc3)n3ncc(Br)c3n2)CC1]
1. 4349
2. 551.3
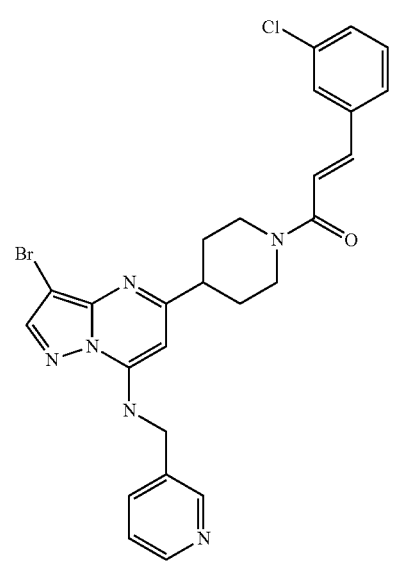 [SMILES: O=C(/C=C/c1cccc(Cl)c1)N1CCC(c2cc(NCc3cccnc3)n3ncc(Br)c3n2)CC1]
1. 4350
2. 553.3
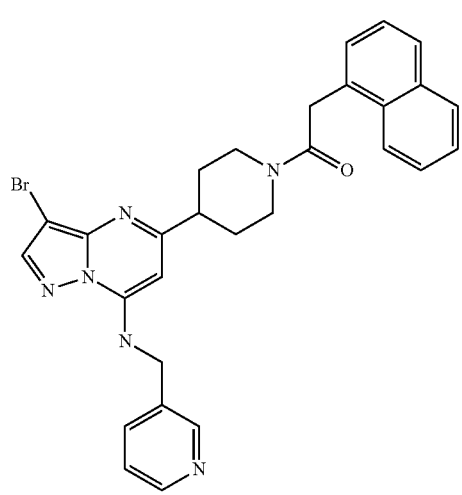 [SMILES: O=C(Cc1cccc2ccccc12)N1CCC(c2cc(NCc3cccnc3)n3ncc(Br)c3n2)CC1]
1. 4351
2. 557.31
TABLE 43-continued
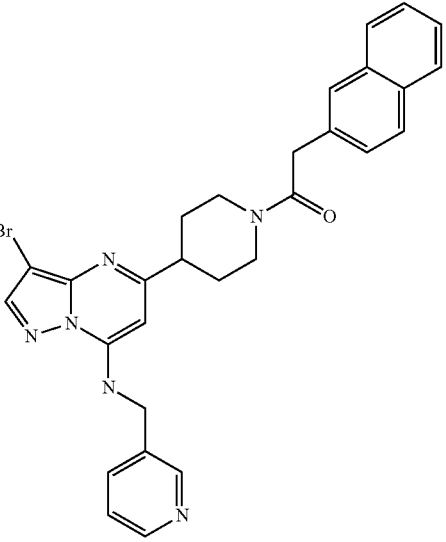
1. 4352
2. 557.31
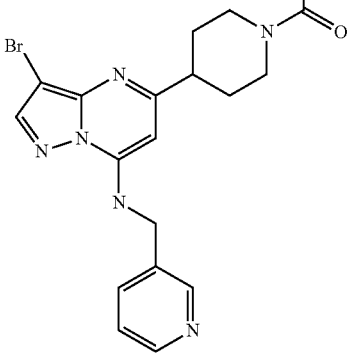
1. 4353
2. 558.31
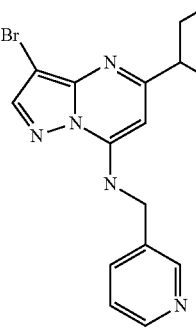
1. 4354
2. 561.31

TABLE 43-continued
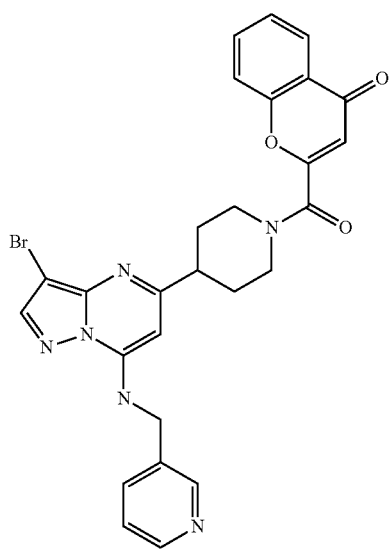 [SMILES: O=C(c1cc(=O)c2ccccc2o1)N1CCC(c2cc(NCc3cccnc3)n3ncc(Br)c3n2)CC1]
1. 4355
2. 561.31
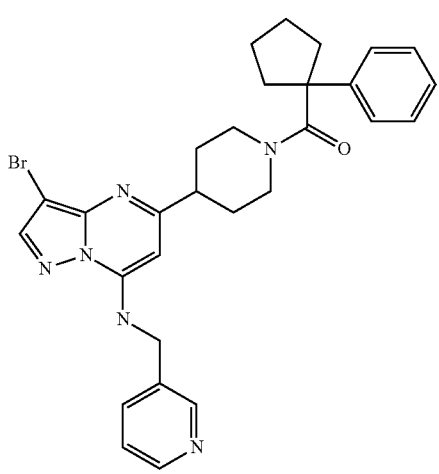 [SMILES: O=C(N1CCC(c2cc(NCc3cccnc3)n3ncc(Br)c3n2)CC1)C1(c2ccccc2)CCCC1]
1. 4356
2. 561.31
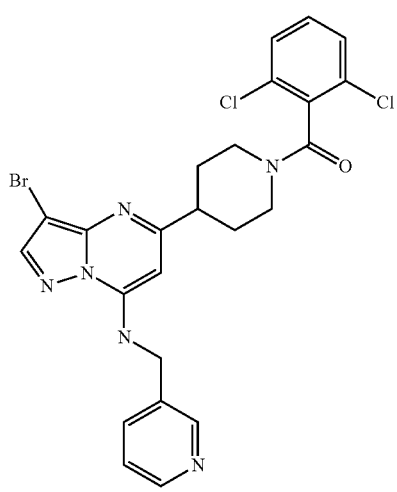 [SMILES: O=C(c1c(Cl)cccc1Cl)N1CCC(c2cc(NCc3cccnc3)n3ncc(Br)c3n2)CC1]
1. 4357
2. 561.31
TABLE 43-continued
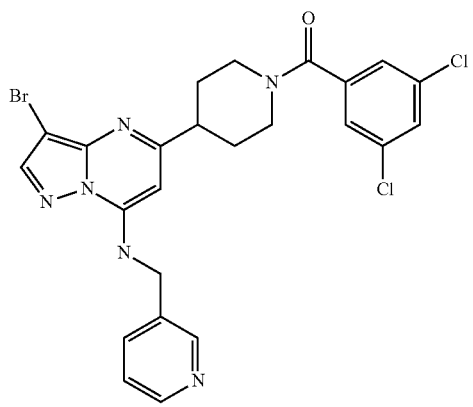 [SMILES: O=C(c1cc(Cl)cc(Cl)c1)N1CCC(c2cc(NCc3cccnc3)n3ncc(Br)c3n2)CC1]
1. 4358
2. 561.31
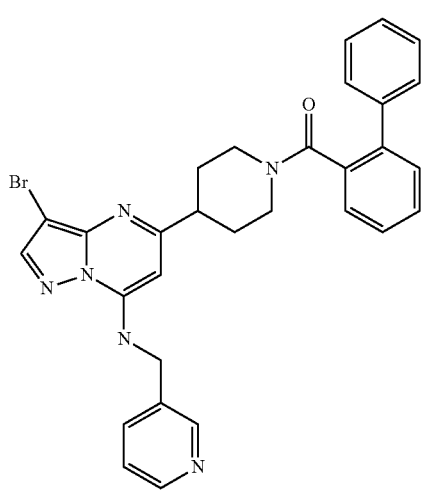 [SMILES: O=C(c1ccccc1-c1ccccc1)N1CCC(c2cc(NCc3cccnc3)n3ncc(Br)c3n2)CC1]
1. 4359
2. 569.31
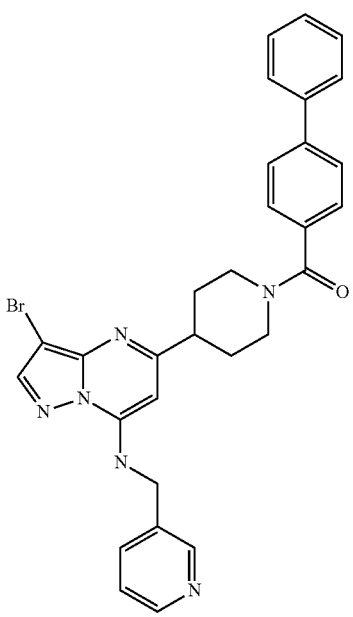 [SMILES: O=C(c1ccc(-c2ccccc2)cc1)N1CCC(c2cc(NCc3cccnc3)n3ncc(Br)c3n2)CC1]
1. 4360
2. 569.31

TABLE 43-continued
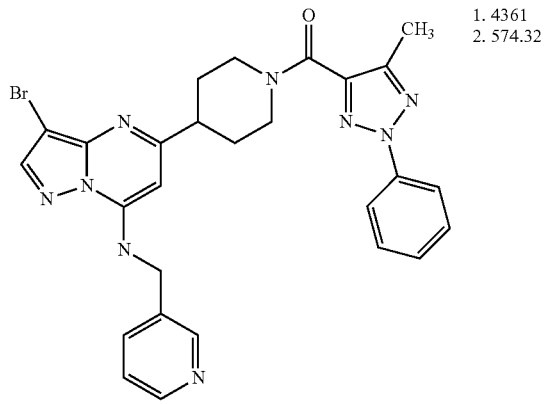
1. 4361
2. 574.32
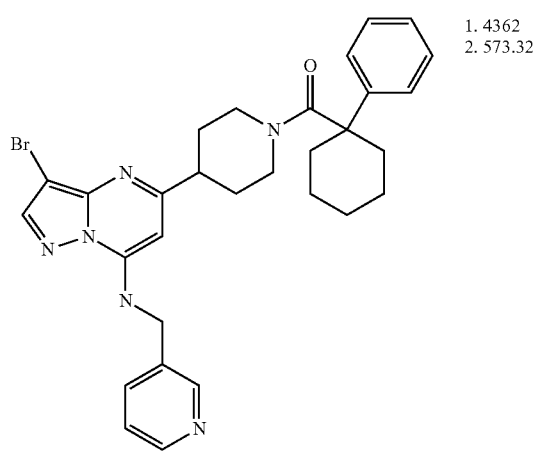
1. 4362
2. 573.32
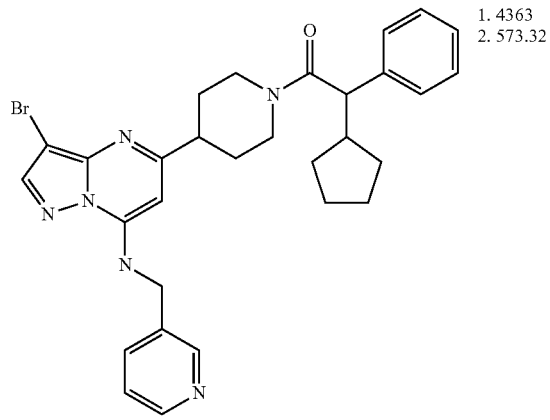
1. 4363
2. 573.32
TABLE 43-continued
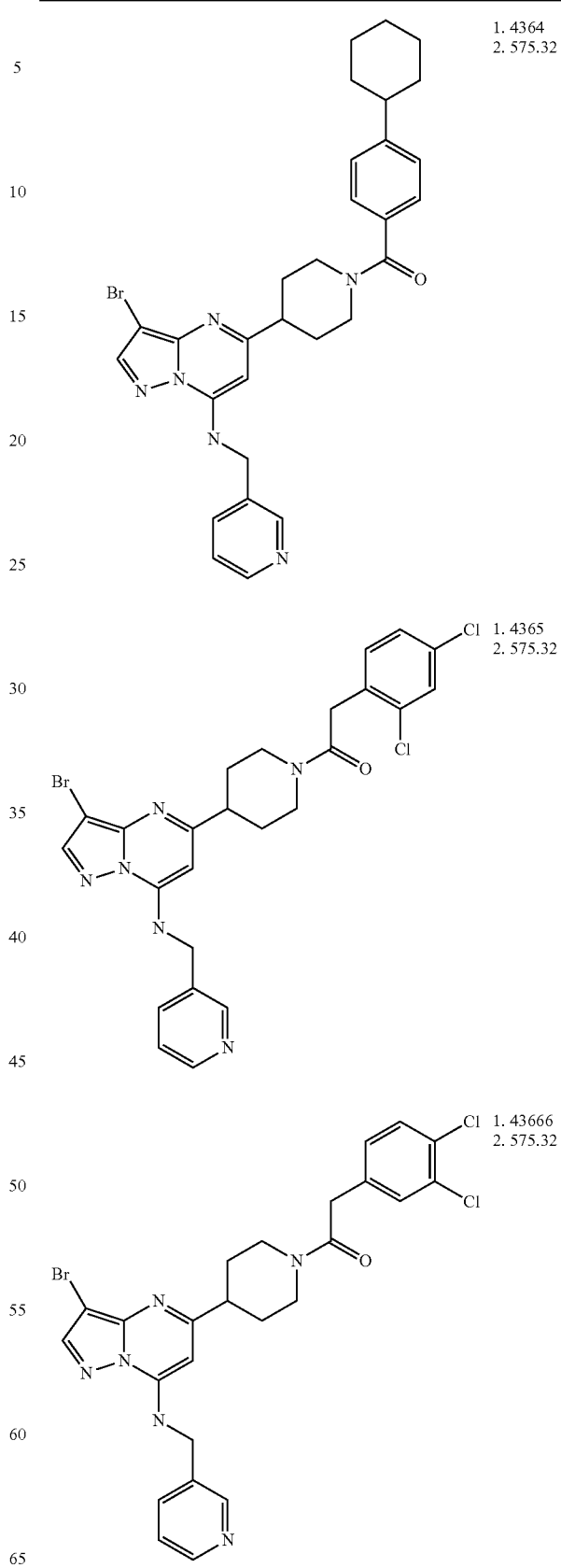
1. 4364
2. 575.32
1. 4365
2. 575.32
1. 43666
2. 575.32

TABLE 43-continued
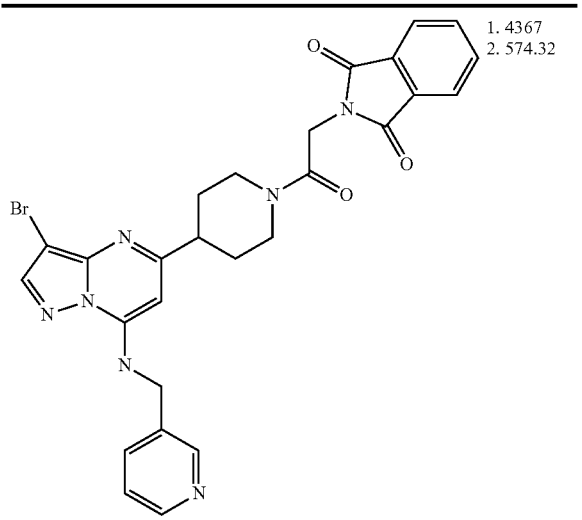
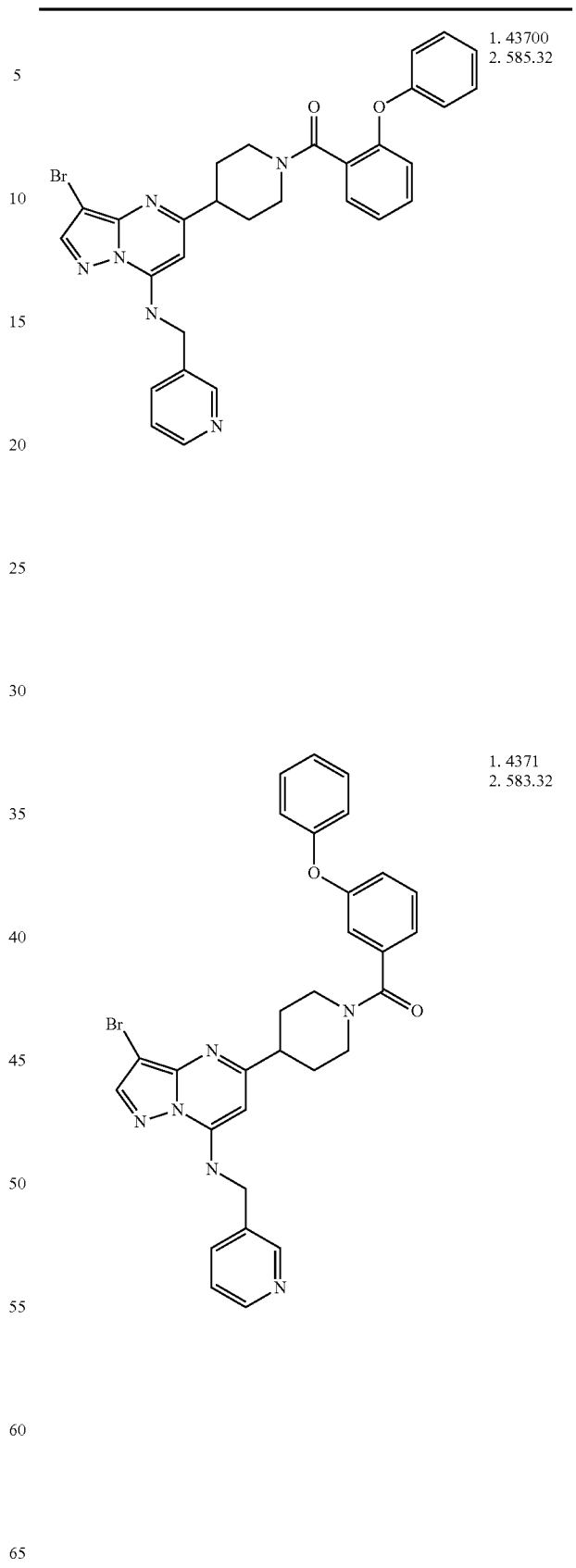

TABLE 43-continued
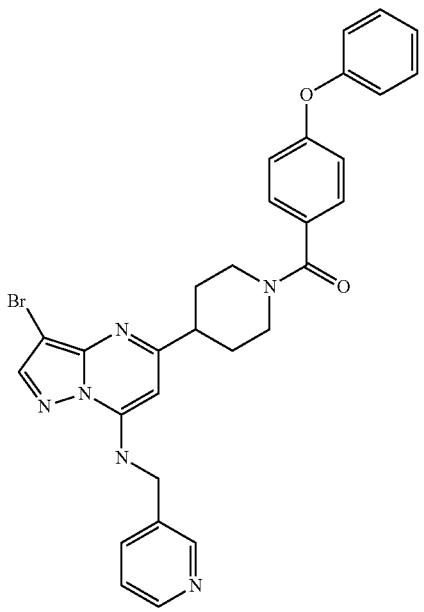 [SMILES: O=C(c1ccc(Oc2ccccc2)cc1)N1CCC(c2cc(NCc3cccnc3)n3ncc(Br)c3n2)CC1]
1. 4372
2. 585.32
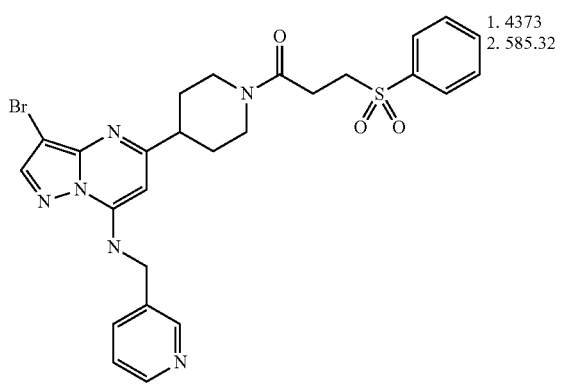
1. 4373
2. 585.32
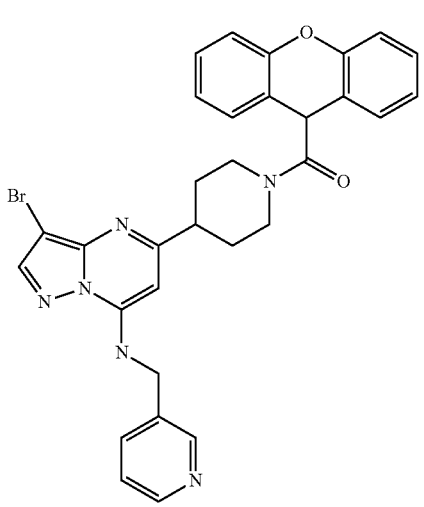 [SMILES: O=C(C1c2ccccc2Oc2ccccc21)N1CCC(c2cc(NCc3cccnc3)n3ncc(Br)c3n2)CC1]
1. 4374
2. 597.33
TABLE 43-continued
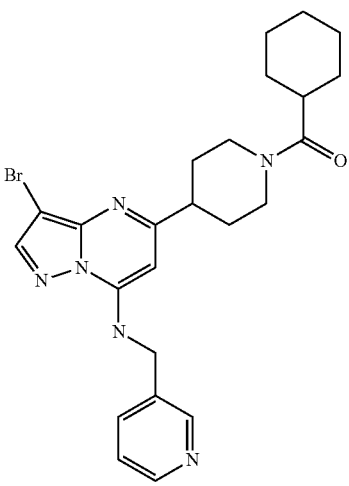 [SMILES: O=C(C1CCCCC1)N1CCC(c2cc(NCc3cccnc3)n3ncc(Br)c3n2)CC1]
1. 4375
2. 499.27
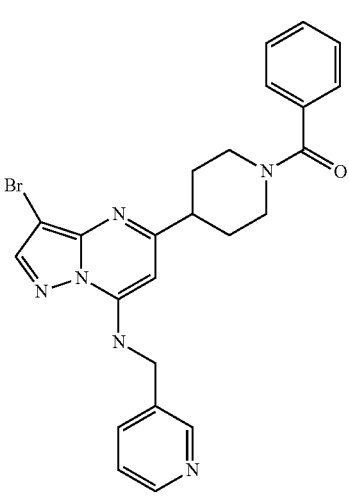 [SMILES: O=C(c1ccccc1)N1CCC(c2cc(NCc3cccnc3)n3ncc(Br)c3n2)CC1]
1. 4376
2. 493.27
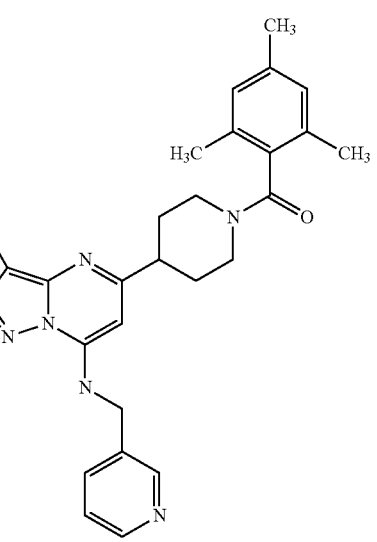
1. 4377
2. 535.29

TABLE 44

| Product | 1. Ex.<br>2. m/z |
|---|---|
| (structure) | 1. 4401<br>2. 471.3 |
| (structure) | 1. 4402<br>2. 475.26 |
| (structure) | 1. 4403<br>2. 483.27 |
| (structure) | 1. 4404<br>2. 481.26 |

TABLE 44-continued

| Product | 1. Ex.<br>2. m/z |
|---|---|
| (structure) | 1. 4405<br>2. 485.27 |
| (structure) | 1. 4406<br>2. 487.27 |
| (structure) | 1. 4407<br>2. 487.27 |
| (structure) | 1. 4408<br>2. 487.27 |

TABLE 44-continued

| Product | 1. Ex. 2. m/z |
|---|---|
| (structure) | 1. 4409  2. 494.3 |
| (structure) | 1. 4410  2. 496.27 |
| (structure) | 1. 4411  2. 499.27 |
| (structure) | 2. 4412  2. 499.27 |

TABLE 44-continued

| Product | 1. Ex. 2. m/z |
|---|---|
| (structure) | 1. 4413  2. 500.27 |
| (structure) | 1. 4414  2. 503.28 |
| (structure) | 1. 4415  2. 505.28 |
| (structure) | 1. 4416  2. 507.28 |

TABLE 44-continued

| Product | 1. Ex. 2. m/z |
|---|---|
| (structure with furan-acrylamide) | 1. 4417 2. 509.3 |
| (structure with 3,5-dimethylisoxazole carbonyl) | 1. 4418 2. 512.28 |
| (structure with 2-thienyl acetyl) | 1. 4419 2. 513.28 |
| (structure with 3-thienyl acetyl) | 1. 4420 2. 513.28 |
| (structure with cyclohexylacetyl) | 1. 4421 2. 513.28 |
| (structure with cycloheptanecarbonyl) | 1. 4422 2. 513.28 |
| (structure with 3-cyanobenzoyl) | 1. 4423 2. 518.28 |
| (structure with 4-cyanobenzoyl) | 1. 4424 2. 518.28 |

TABLE 44-continued
| Product | 1. Ex. 2. m/z |
|---|---|
| 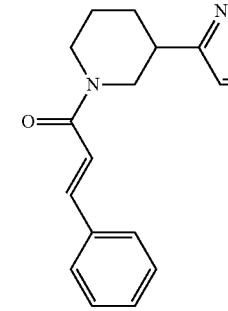 | 1. 4425  2. 519.3 |
| | 1. 4426  2. 521.29 |
| | 1. 4428  2. 521.29 |
| | 1. 4428  2. 523.29 |
TABLE 44-continued
| Product | 1. Ex. 2. m/z |
|---|---|
| 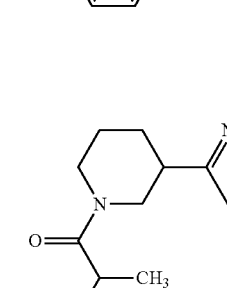 | 1. 4429  2. 523.29 |
| | 1. 4430  2. 523.29 |
| | 1. 4431  2. 523.29 |
| | 1. 4432  2. 525.29 |

TABLE 44-continued
| Product | 1. Ex.<br>2. m/z |
|---|---|
| 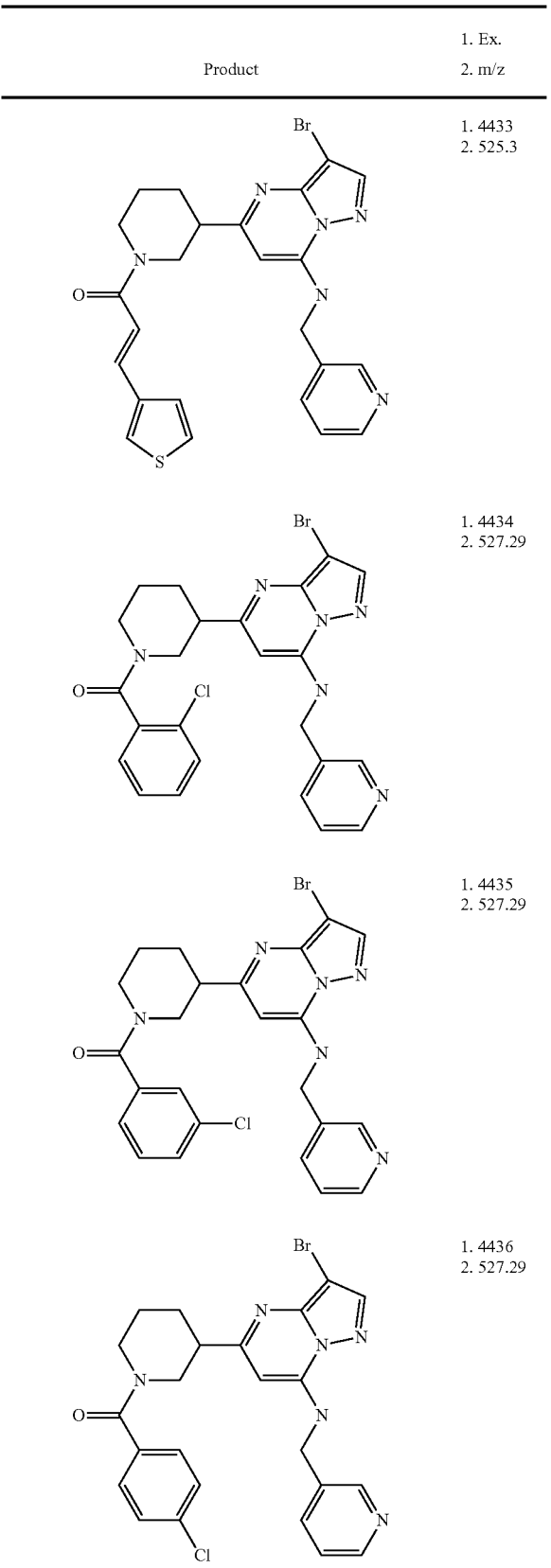 | 1. 4433<br>2. 525.3 |
| | 1. 4434<br>2. 527.29 |
| | 1. 4435<br>2. 527.29 |
| | 1. 4436<br>2. 527.29 |
TABLE 44-continued
| Product | 1. Ex.<br>2. m/z |
|---|---|
| 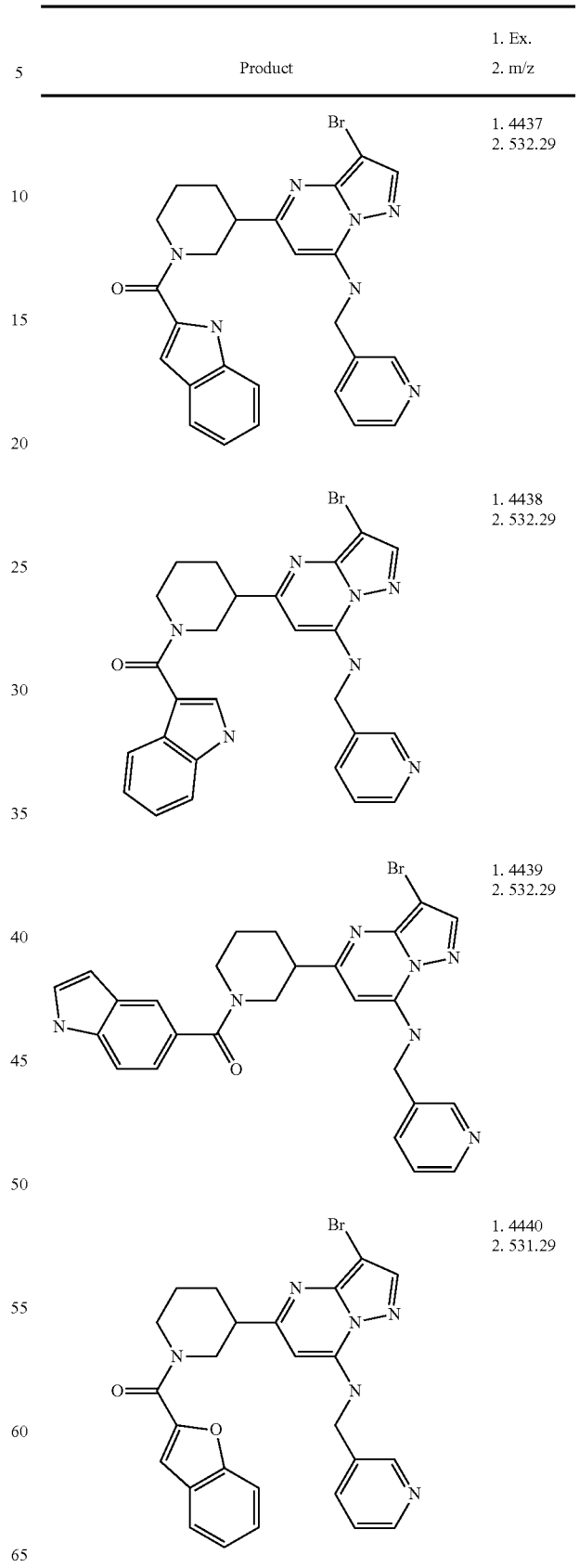 | 1. 4437<br>2. 532.29 |
| | 1. 4438<br>2. 532.29 |
| | 1. 4439<br>2. 532.29 |
| | 1. 4440<br>2. 531.29 |

TABLE 44-continued
| Product | 1. Ex. 2. m/z |
|---|---|
| 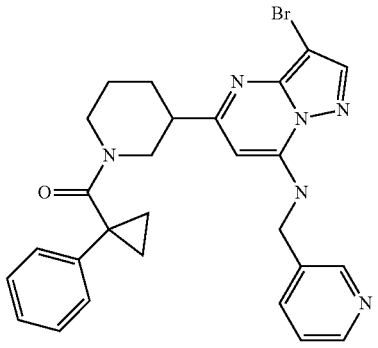 [SMILES: O=C(N1CCCC(c2cc(NCc3cccnc3)n3ncc(Br)c3n2)C1)C1(c2ccccc2)CC1] | 1. 4441 2. 533.3 |
| 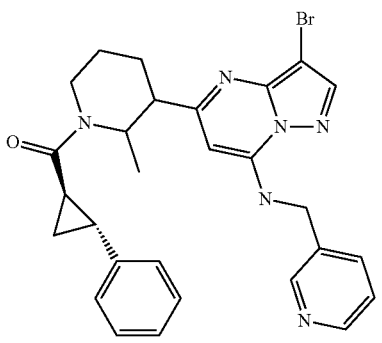 [SMILES: CC1C(c2cc(NCc3cccnc3)n3ncc(Br)c3n2)CCCN1C(=O)[C@@H]1C[C@H]1c1ccccc1] | 1. 4442 2. 531.29 |
| 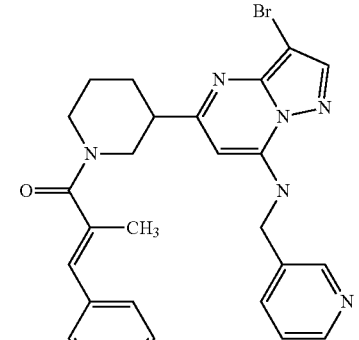 | 1. 4443 2. 533.29 |
| 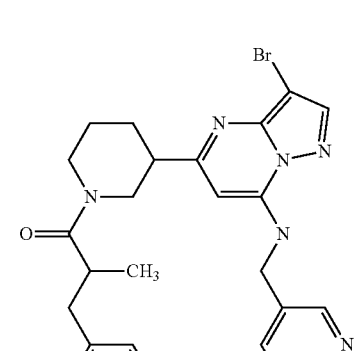 | 1. 4444 2. 535.29 |
TABLE 44-continued
| Product | 1. Ex. 2. m/z |
|---|---|
| 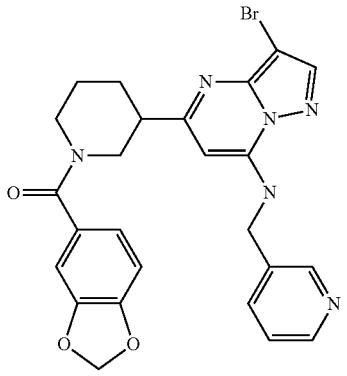 | 1. 4445 2. 537.3 |
| 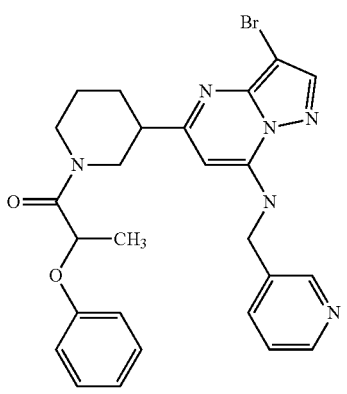 [SMILES: C/C(=C\c1ccccc1)C(=O)N1CCCC(c2cc(NCc3cccnc3)n3ncc(Br)c3n2)C1] | 1. 4446 2. 537.3 |
| 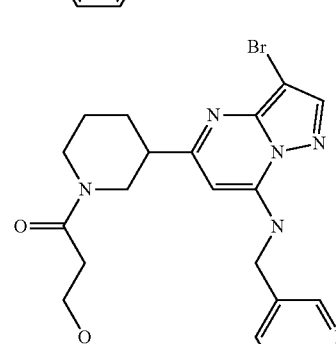 | 1. 4447 2. 537.3 |
| 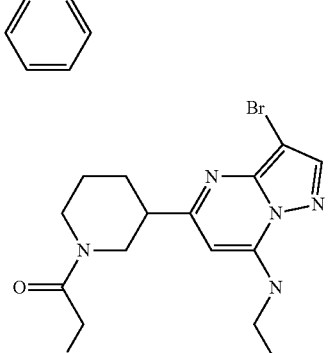 | 1. 4448 2. 539.3 |

TABLE 44-continued
| Product | 1. Ex.<br>2. m/z |
|---|---|
| 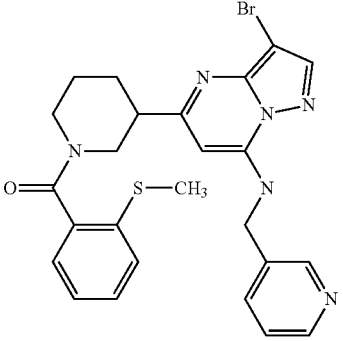 | 1. 4449<br>2. 539.3 |
| 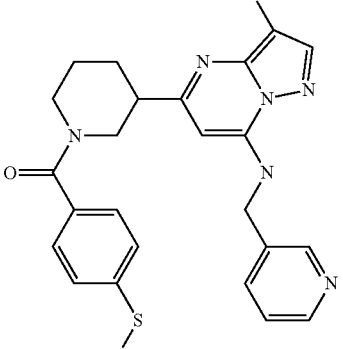 | 1. 4450<br>2. 539.3 |
| 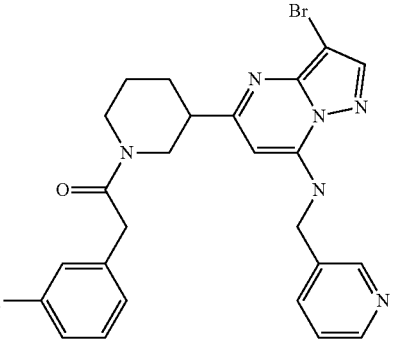 | 1. 4451<br>2. 541.3 |
| 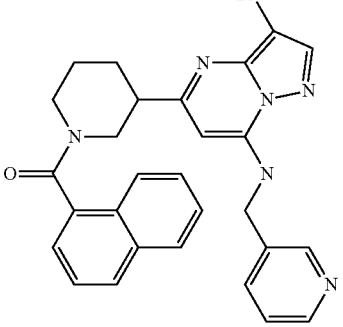 | 1. 4451<br>2. 543.3 |
TABLE 44-continued
| Product | 1. Ex.<br>2. m/z |
|---|---|
| 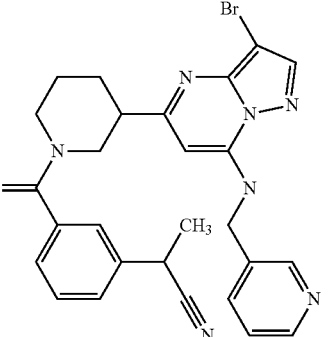 | 1. 4453<br>2. 546.3 |
| 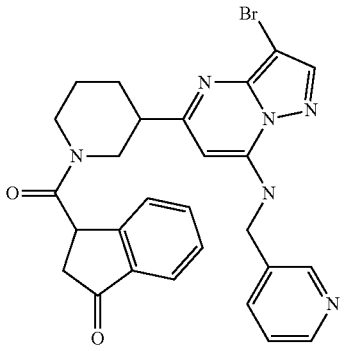 [SMILES: O=C1CC(C(=O)N2CCCC(c3cc(NCc4cccnc4)n4ncc(Br)c4n3)C2)c2ccccc21] | 1. 4454<br>2. 547.3 |
| 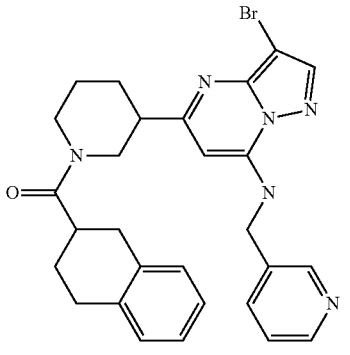 [SMILES: O=C(C1CCc2ccccc2C1)N1CCCC(c2cc(NCc3cccnc3)n3ncc(Br)c3n2)C1] | 1. 4455<br>2. 547.3 |
| 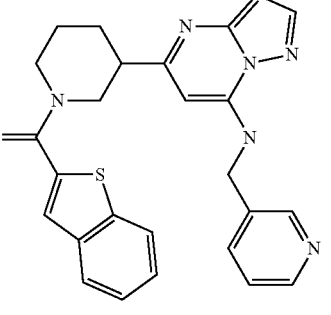 | 1. 4456<br>2. 549.3 |

TABLE 44-continued

| Product | 1. Ex.<br>2. m/z |
|---|---|
| (structure) | 1. 4457<br>2. 550.3 |
| (structure) | 1. 4458<br>2. 550.3 |
| (structure) | 1. 4459<br>2. 551.3 |
| (structure) | 1. 4460<br>2. 551.3 |

TABLE 44-continued

| Product | 1. Ex.<br>2. m/z |
|---|---|
| (structure) | 1. 4461<br>2. 549.3 |
| (structure) | 1. 4462<br>2. 553.3 |
| (structure) | 1. 4463<br>2. 557.3 |
| (structure) | 1. 4464<br>2. 557.31 |

TABLE 44-continued
| Product | 1. Ex. 2. m/z |
|---|---|
| 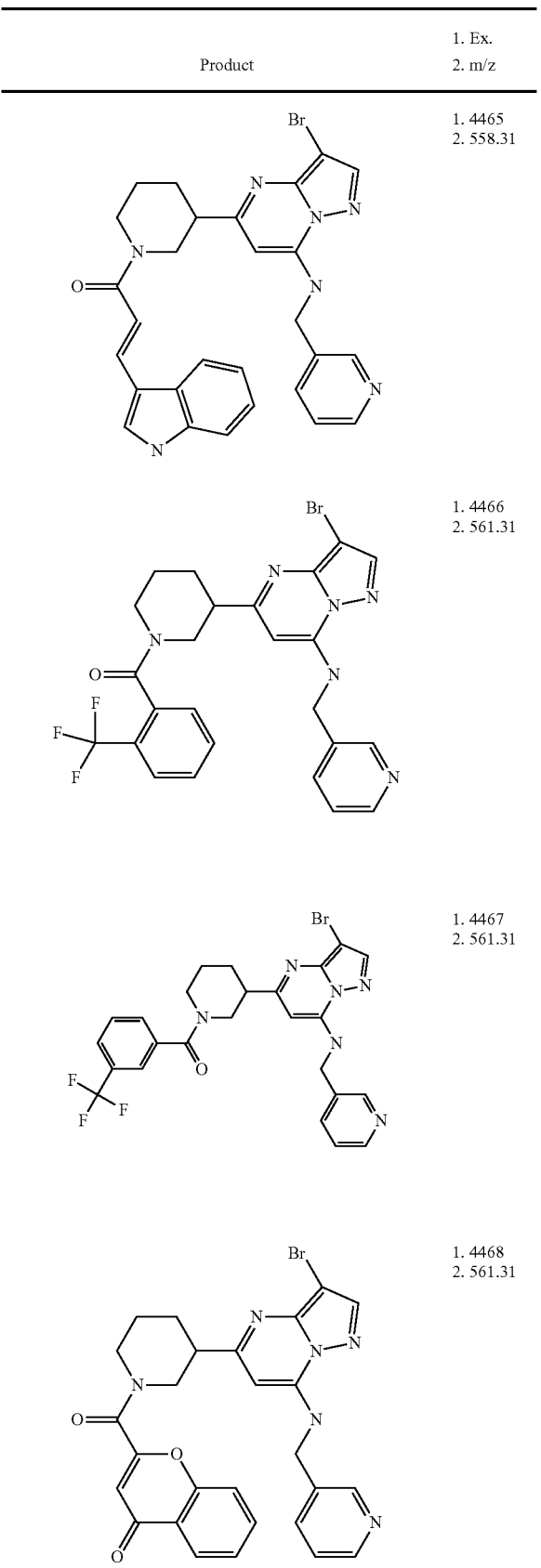 | 1. 4465  2. 558.31 |
| | 1. 4466  2. 561.31 |
| | 1. 4467  2. 561.31 |
| | 1. 4468  2. 561.31 |
TABLE 44-continued
| Product | 1. Ex. 2. m/z |
|---|---|
| 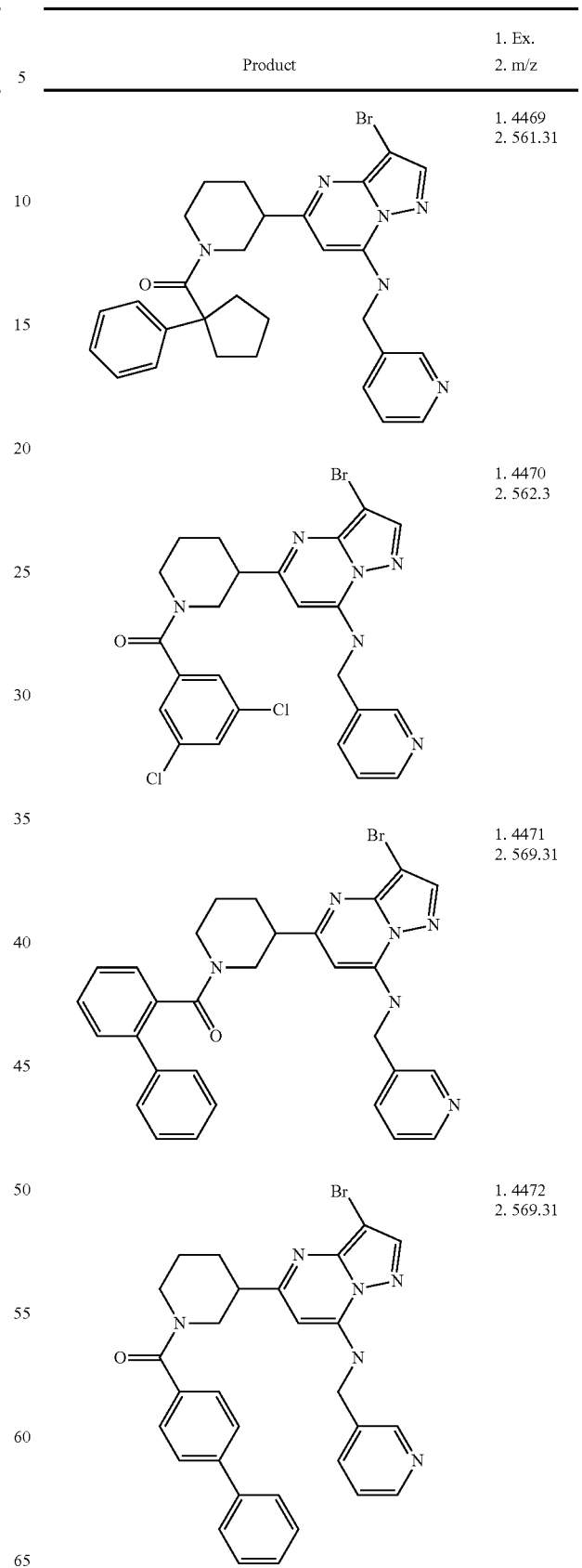 | 1. 4469  2. 561.31 |
| | 1. 4470  2. 562.3 |
| | 1. 4471  2. 569.31 |
| | 1. 4472  2. 569.31 |

TABLE 44-continued

| Product | 1. Ex. 2. m/z |
|---|---|
| (structure) | 1. 4473 2. 572.31 |
| (structure) | 1. 4474 2. 572.31 |
| (structure) | 1. 4475 2. 575.32 |
| (structure) | 1. 4476 2. 572.31 |
| (structure) | 1. 4477 2. 573.32 |
| (structure) | 1. 4478 2. 574.32 |
| (structure) | 1. 4479 2. 576.32 |
| (structure) | 1. 4480 2. 583.32 |

TABLE 44-continued
| Product | 1. Ex. 2. m/z |
|---|---|
| 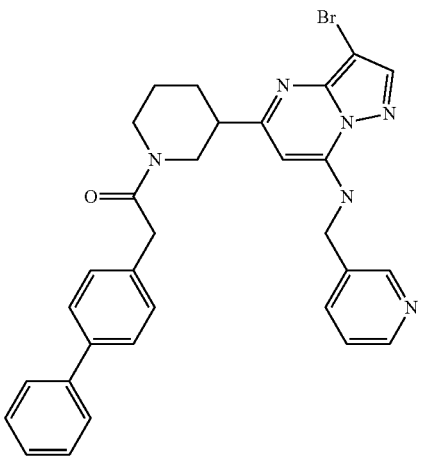 [SMILES: O=C(Cc1ccc(-c2ccccc2)cc1)N1CCCC(c2cc(NCc3cccnc3)n3ncc(Br)c3n2)C1] | 1. 4481 2. 583.32 |
| 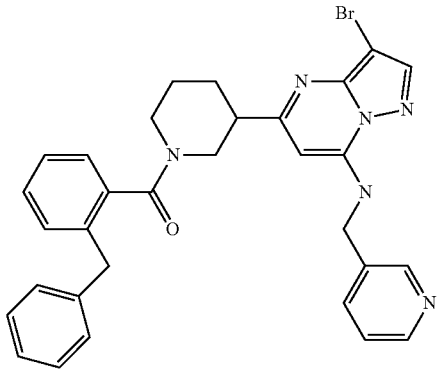 [SMILES: O=C(c1ccccc1Oc1ccccc1)N1CCCC(c2cc(NCc3cccnc3)n3ncc(Br)c3n2)C1] | 1. 4482 2. 583.32 |
| 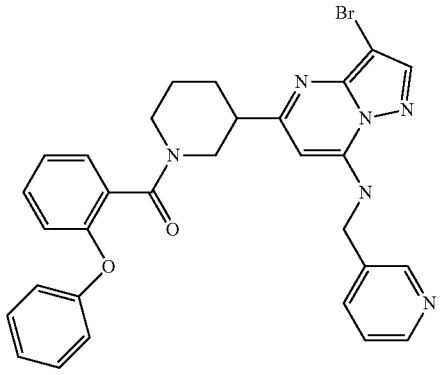 | 1. 4483 2. 585.32 |
| 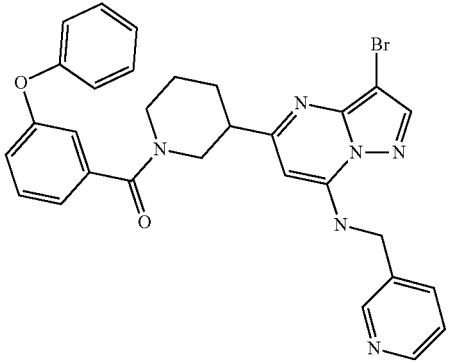 [SMILES: O=C(c1cccc(Oc2ccccc2)c1)N1CCCC(c2cc(NCc3cccnc3)n3ncc(Br)c3n2)C1] | 1. 4484 2. 585.32 |
TABLE 44-continued
| Product | 1. Ex. 2. m/z |
|---|---|
| 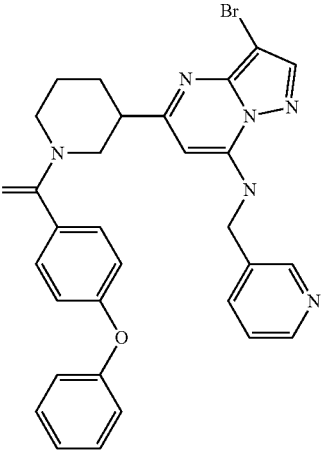 | 1. 4485 2. 585.3 |
| 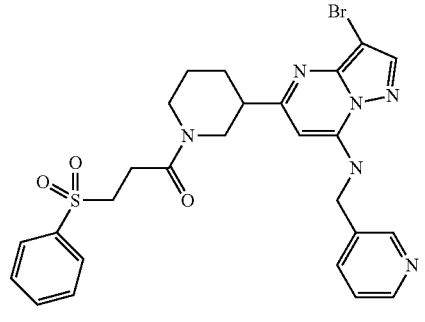 [SMILES: O=C(CCS(=O)(=O)c1ccccc1)N1CCCC(c2cc(NCc3cccnc3)n3ncc(Br)c3n2)C1] | 1. 4486 2. 585.32 |
| 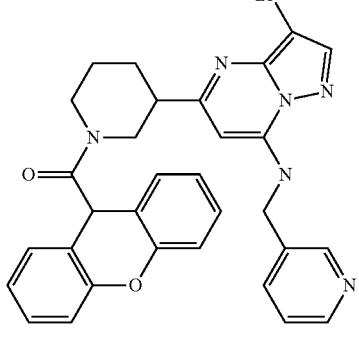 | 1. 4487 2. 597.33 |
| 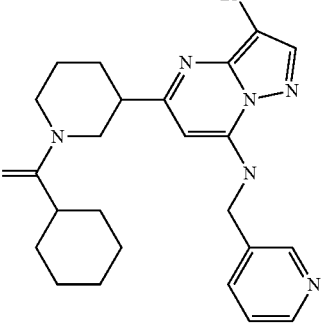 | 1. 4488 2. 499.27 |

TABLE 45
| Product | 1. Ex.<br>2. m/z |
|---|---|
| 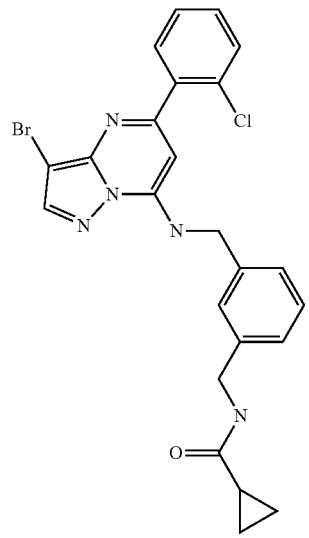 [SMILES: O=C(NCc1cccc(CNc2cc(-c3ccccc3Cl)nc3c(Br)cnn23)c1)C1CC1] | 1. 4501<br>2. 512.28 |
| 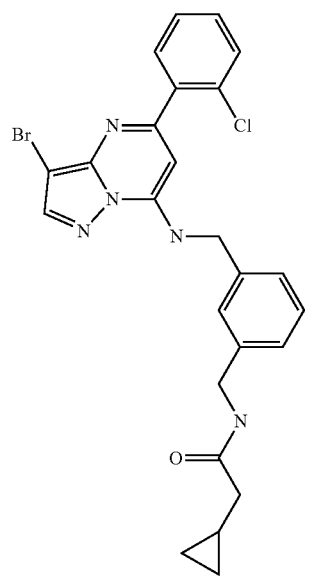 [SMILES: O=C(CC1CC1)NCc1cccc(CNc2cc(-c3ccccc3Cl)nc3c(Br)cnn23)c1] | 1. 4502<br>2. 526.29 |
TABLE 45-continued
| Product | 1. Ex.<br>2. m/z |
|---|---|
| 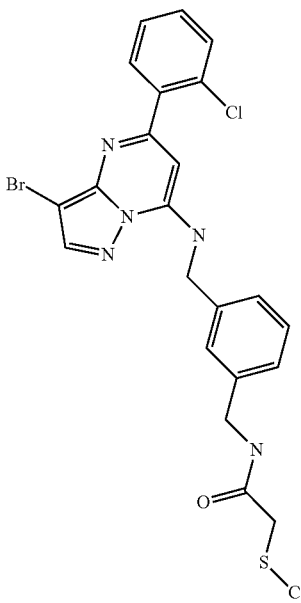 | 1. 4503<br>2. 532.29 |
| 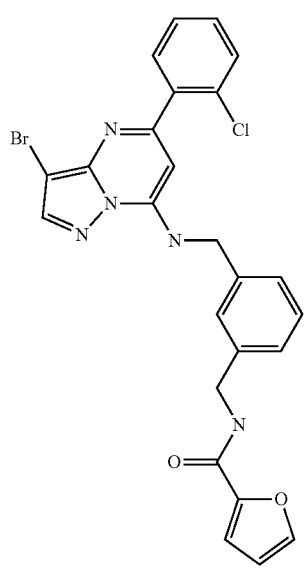 [SMILES: O=C(NCc1cccc(CNc2cc(-c3ccccc3Cl)nc3c(Br)cnn23)c1)c1ccco1] | 1. 4504<br>2. 538.3 |

TABLE 45-continued
| Product | 1. Ex.<br>2. m/z |
|---|---|
| 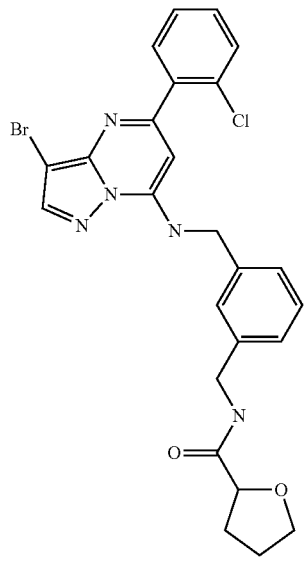 [SMILES: O=C(NCc1cccc(CNc2cc(-c3ccccc3Cl)nc3c(Br)cnn23)c1)C1CCCO1] | 1. 4505<br>2. 538.3 |
| (structure) | 1. 4506<br>2. 540.3 |
TABLE 45-continued
| Product | 1. Ex.<br>2. m/z |
|---|---|
| 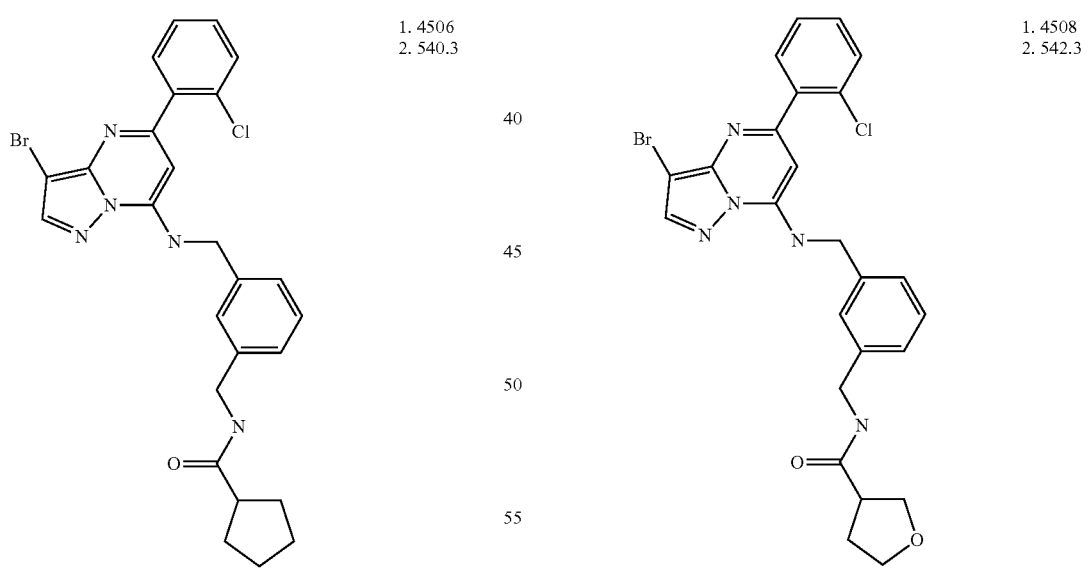 | 1. 4507<br>2. 542.3 |
| (structure) | 1. 4508<br>2. 542.3 |

TABLE 45-continued

| Product | 1. Ex. 2. m/z |
|---|---|
| (structure) | 1. 4509 2. 542.3 |
| (structure) | 1. 4510 2. 549.3 |
| (structure) | 1. 4511 2. 551.3 |
| (structure) | 1. 4512 2. 554.3 |

TABLE 45-continued

| Product | 1. Ex.<br>2. m/z |
|---|---|
| (structure) | 1. 4513<br>2. 554.3 |
| (structure) | 1. 4514.<br>2. 555.31 |

TABLE 45-continued

| Product | 1. Ex.<br>2. m/z |
|---|---|
| (structure) | 1. 4515<br>2. 558.31 |
| (structure) | 1. 4516<br>2. 560.31 |

TABLE 45-continued

| Product | 1. Ex. 2. m/z |
|---|---|
| (structure 677) | 1. 4517 2. 562.31 |
| (structure 4518) | 1. 4518 2. 564.31 |

TABLE 45-continued

| Product | 1. Ex. 2. m/z |
|---|---|
| (structure 678) | 1. 4519 2. 567.31 |
| (structure 4520) | 1. 4520 2. 568.31 |

TABLE 45-continued
| Product | 1. Ex. 2. m/z |
|---|---|
| 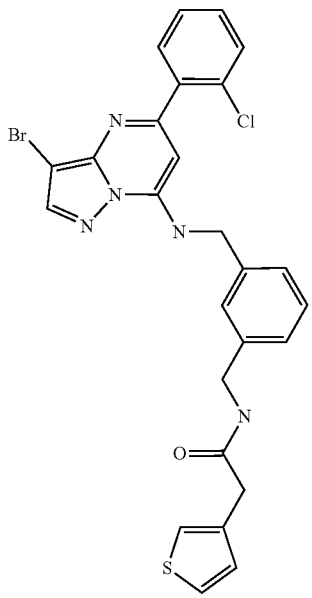 [SMILES: O=C(Cc1ccsc1)NCc1cccc(CNc2cc(-c3ccccc3Cl)nc3c(Br)cnn23)c1] | 1. 4521 2. 568.31 |
| | 1. 4522 2. 568.31 |
TABLE 45-continued
| Product | 1. Ex. 2. m/z |
|---|---|
| 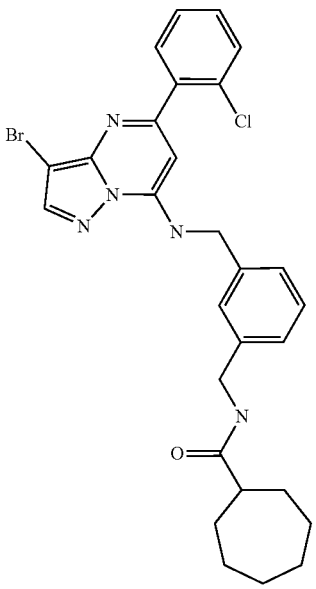 [SMILES: O=C(NCc1cccc(CNc2cc(-c3ccccc3Cl)nc3c(Br)cnn23)c1)C1CCCCCC1] | 1. 4523 2. 568.31 |
| | 1. 4524 2. 573.32 |

TABLE 45-continued
| Product | 1. Ex.<br>2. m/z |
|---|---|
| 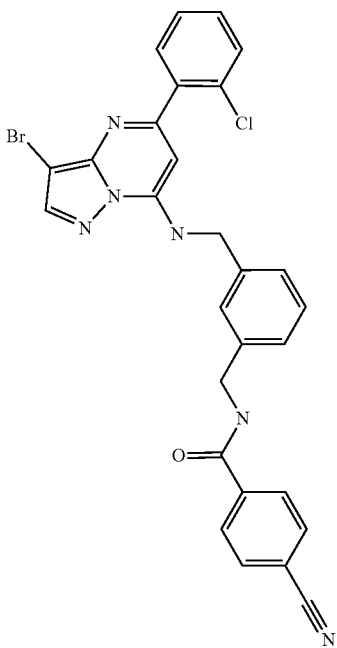 [SMILES: N#Cc1ccc(C(=O)NCc2cccc(CNc3cc(-c4ccccc4Cl)nc4c(Br)cnn34)c2)cc1] | 1. 4525<br>2. 573.32 |
| | 1. 4526<br>2. 574.32 |
TABLE 45-continued
| Product | 1. Ex.<br>2. m/z |
|---|---|
| | 1. 4527<br>2. 576.32 |
| | 1. 4528<br>2. 576.32 |

TABLE 45-continued

| Product | 1. Ex.<br>2. m/z |
|---|---|
| (structure: 3-bromo-5-(2-chlorophenyl)-N-(3-((2-methoxybenzamido)methyl)benzyl)pyrazolo[1,5-a]pyrimidin-7-amine — 2-methoxybenzamide) | 1. 4529<br>2. 578.32 |
| (structure: 3-bromo-5-(2-chlorophenyl)-N-(3-((3-methoxybenzamido)methyl)benzyl)pyrazolo[1,5-a]pyrimidin-7-amine — 3-methoxybenzamide) | 1. 4530<br>2. 578.32 |
| (structure: 3-bromo-5-(2-chlorophenyl)-N-(3-((4-methoxybenzamido)methyl)benzyl)pyrazolo[1,5-a]pyrimidin-7-amine — 4-methoxybenzamide) | 1. 4531<br>2. 578.32 |
| (structure: 3-bromo-5-(2-chlorophenyl)-N-(3-((2-phenoxyacetamido)methyl)benzyl)pyrazolo[1,5-a]pyrimidin-7-amine — 2-phenoxyacetamide) | 1. 4532<br>2. 578.32 |

TABLE 45-continued
| Product | 1. Ex. 2. m/z |
|---|---|
| 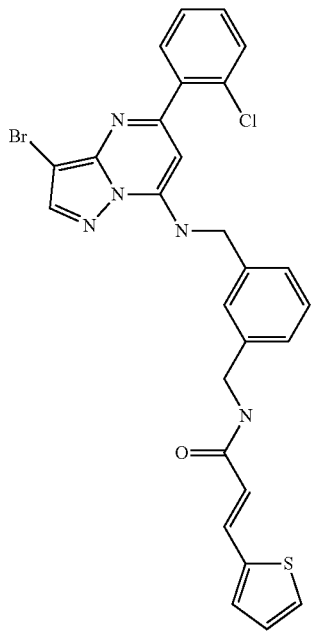 [SMILES: O=C(/C=C/c1cccs1)NCc1cccc(CNc2cc(-c3ccccc3Cl)nc3c(Br)cnn23)c1] | 1. 4533 2. 580.32 |
| | 1. 4534 2. 580.32 |
TABLE 45-continued
| Product | 1. Ex. 2. m/z |
|---|---|
| 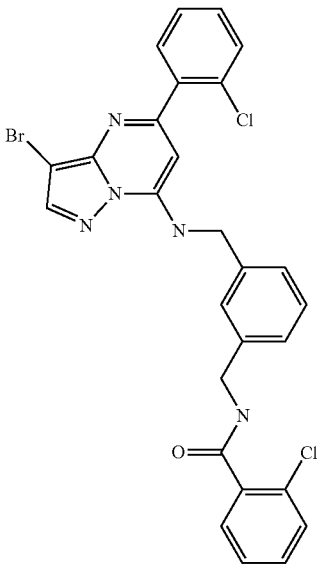 [SMILES: O=C(NCc1cccc(CNc2cc(-c3ccccc3Cl)nc3c(Br)cnn23)c1)c1ccccc1Cl] | 1. 4535 2. 582.32 |
| | 1. 4536 2. 582.32 |

TABLE 45-continued
| Product | 1. Ex.<br>2. m/z |
|---|---|
| 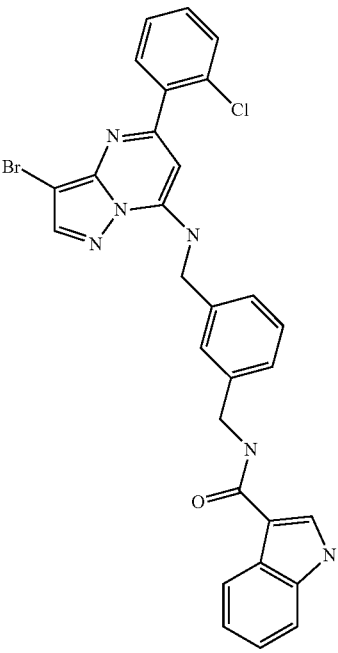 [SMILES: O=C(NCc1cccc(CNc2cc(-c3ccccc3Cl)nc3c(Br)cnn23)c1)c1c[nH]c2ccccc12] | 1. 4537<br>2. 582.32 |
| 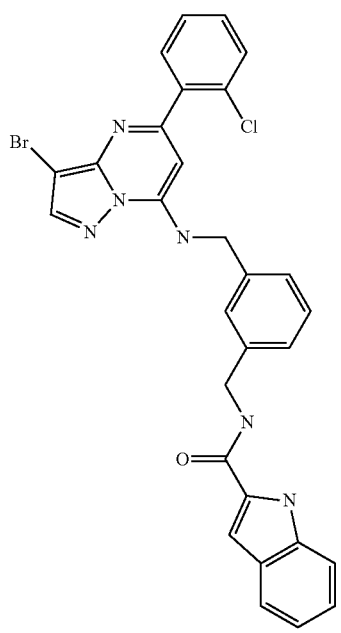 | 1. 4538<br>2. 587.32 |
TABLE 45-continued
| Product | 1. Ex.<br>2. m/z |
|---|---|
| (structure) | 1. 4539<br>2. 587.32 |
| 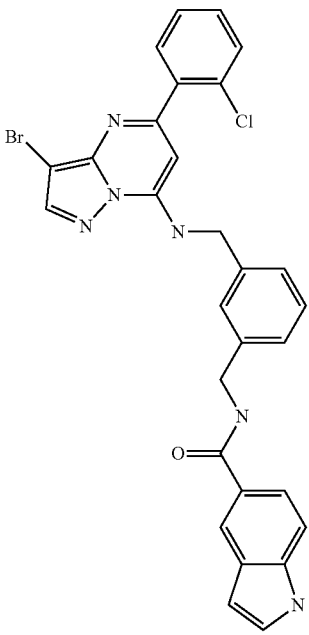 [SMILES: O=C(NCc1cccc(CNc2cc(-c3ccccc3Cl)nc3c(Br)cnn23)c1)c1ccc2[nH]ccc2c1] | 1. 4540<br>2. 587.32 |

TABLE 45-continued
| Product | 1. Ex.<br>2. m/z |
|---|---|
| 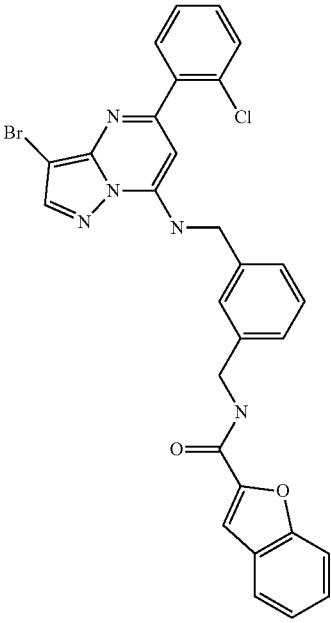 [SMILES: O=C(NCc1cccc(CNc2cc(-c3ccccc3Cl)nc3c(Br)cnn23)c1)c1cc2ccccc2o1] | 1. 4541<br>2. 588.32 |
| 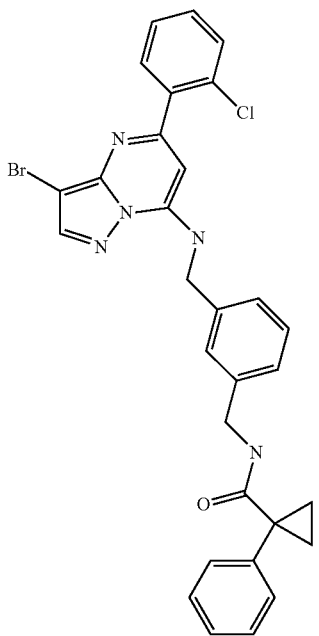 [SMILES: O=C(NCc1cccc(CNc2cc(-c3ccccc3Cl)nc3c(Br)cnn23)c1)C1(c2ccccc2)CC1] | 1. 4542<br>2. 588.32 |
TABLE 45-continued
| Product | 1. Ex.<br>2. m/z |
|---|---|
| 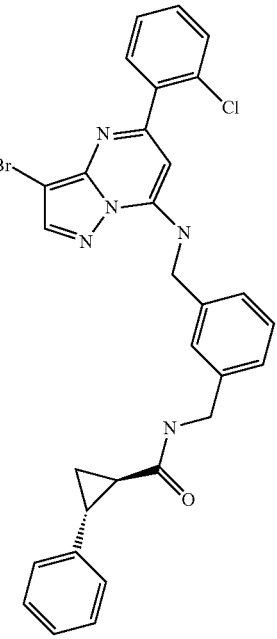 | 1. 4543<br>2. 588.32 |
| 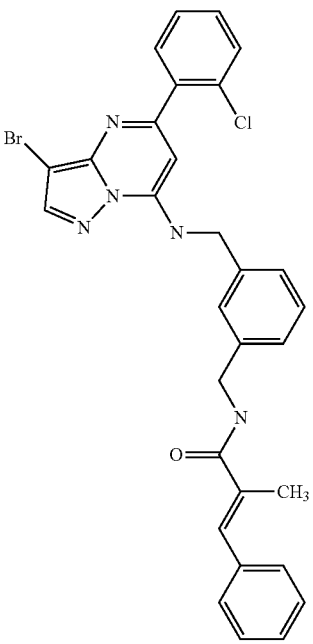 [SMILES: C/C(=C\c1ccccc1)C(=O)NCc1cccc(CNc2cc(-c3ccccc3Cl)nc3c(Br)cnn23)c1] | 1. 4544<br>2. 588.32 |

TABLE 45-continued

| Product | 1. Ex. 2. m/z |
|---|---|
| (structure) | 1. 4545  2. 590.32 |
| (structure) | 1. 4546  2. 588.32 |
| (structure) | 1. 4547  2. 588.32 |
| (structure) | 1. 4548  2. 588.32 |

TABLE 45-continued

| Product | 1. Ex. 2. m/z |
|---|---|
| (structure) | 1. 4549  2. 588.32 |
| (structure) | 1. 4550  2. 590.32 |
| (structure) | 1. 4551  2. 592.33 |
| (structure) | 1. 4552  2. 592.33 |

TABLE 45-continued
| Product | 1. Ex. 2. m/z |
|---|---|
| 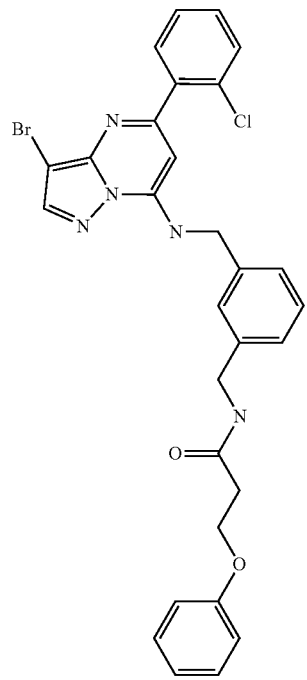 [SMILES: O=C(CCOc1ccccc1)NCc1cccc(CNc2cc(-c3ccccc3Cl)nc3c(Br)cnn23)c1] | 1. 4553 2. 592.33 |
|  | 1. 4554 2. 594.33 |
TABLE 45-continued
| Product | 1. Ex. 2. m/z |
|---|---|
|  | 1. 4555 2. 594.33 |
| 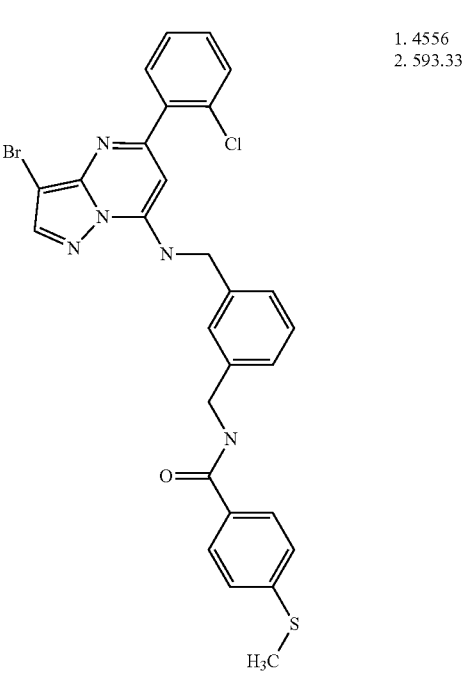 | 1. 4556 2. 593.33 |

TABLE 45-continued

| Product | 1. Ex. 2. m/z |
|---|---|
| (structure: 3-bromo-5-(2-chlorophenyl)-pyrazolo[1,5-a]pyrimidin-7-yl amine linked via N-CH2-(3-phenyl)-CH2-NH-C(O)-CH2-(3-chlorophenyl)) | 1. 4557 2. 596.33 |
| (structure: 3-bromo-5-(2-chlorophenyl)-pyrazolo[1,5-a]pyrimidin-7-yl amine linked via N-CH2-(3-phenyl)-CH2-NH-C(O)-naphthalen-2-yl) | 1. 4559 2. 598.33 |
| (structure: 3-bromo-5-(2-chlorophenyl)-pyrazolo[1,5-a]pyrimidin-7-yl amine linked via N-CH2-(3-phenyl)-CH2-NH-C(O)-naphthalen-1-yl) | 1. 4558 2. 596.33 |
| (structure: 3-bromo-5-(2-chlorophenyl)-pyrazolo[1,5-a]pyrimidin-7-yl amine linked via N-CH2-(3-phenyl)-CH2-NH-C(O)-(3-(1-cyanoethyl)phenyl)) | 1. 4560 2. 601.33 |

TABLE 45-continued

| Product | 1. Ex.<br>2. m/z |
|---|---|
| (structure) | 1. 4561<br>2. 602.33 |
| (structure) | 1. 4562<br>2. 602.33 |

TABLE 45-continued

| Product | 1. Ex.<br>2. m/z |
|---|---|
| (structure) | 1. 4563<br>2. 604.33 |
| (structure) | 1. 4564<br>2. 603.3 |

TABLE 45-continued
| Product | 1. Ex.<br>2. m/z |
|---|---|
| 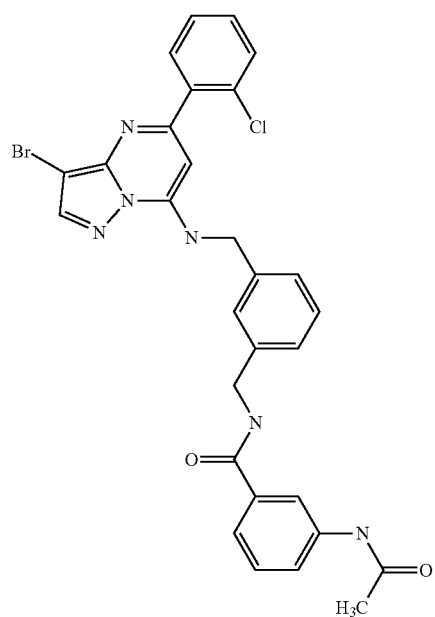 [SMILES: CC(=O)Nc1cccc(C(=O)NCc2cccc(CNc3cc(-c4ccccc4Cl)nc4c(Br)cnn34)c2)c1] | 1. 4565<br>2. 605.33 |
| 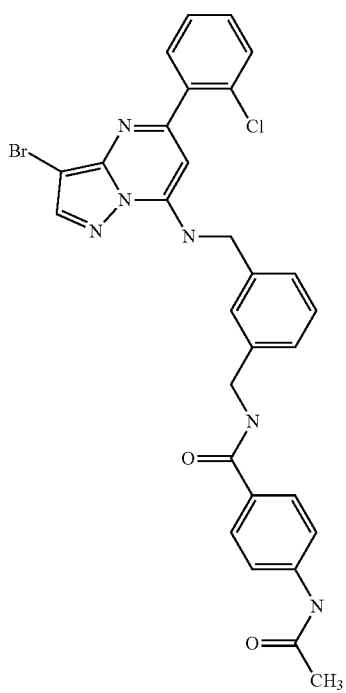 [SMILES: CC(=O)Nc1ccc(C(=O)NCc2cccc(CNc3cc(-c4ccccc4Cl)nc4c(Br)cnn34)c2)cc1] | 1. 4665<br>2. 605.33 |
TABLE 45-continued
| Product | 1. Ex.<br>2. m/z |
|---|---|
| 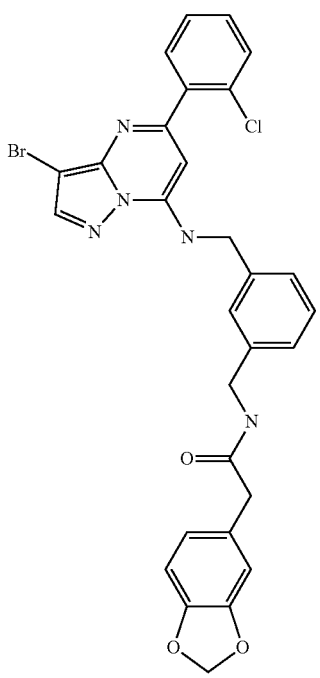 [SMILES: O=C(Cc1ccc2c(c1)OCO2)NCc1cccc(CNc2cc(-c3ccccc3Cl)nc3c(Br)cnn23)c1] | 1. 4567<br>2. 606.33 |
| 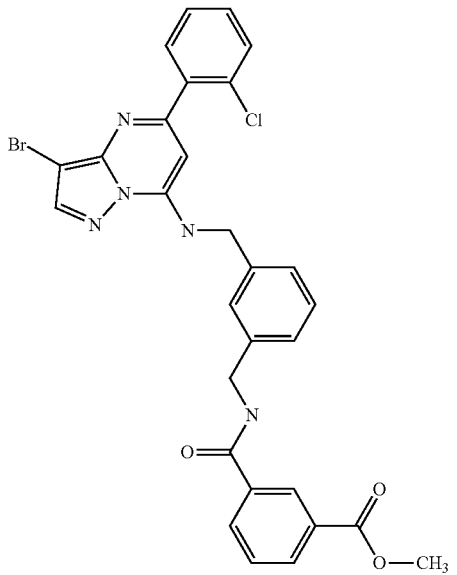 [SMILES: COC(=O)c1cccc(C(=O)NCc2cccc(CNc3cc(-c4ccccc4Cl)nc4c(Br)cnn34)c2)c1] | 1. 4568<br>2. 606.33 |

TABLE 45-continued
| Product | 1. Ex.<br>2. m/z |
|---|---|
| 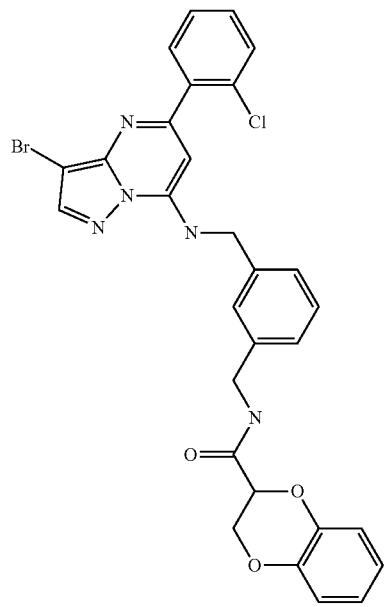 [SMILES: O=C(NCc1cccc(CNc2cc(-c3ccccc3Cl)nc3c(Br)cnn23)c1)C1COc2ccccc2O1] | 1. 4569<br>2. 606.33 |
| | 1. 4570<br>2. 608.33 |
TABLE 45-continued
| Product | 1. Ex.<br>2. m/z |
|---|---|
| 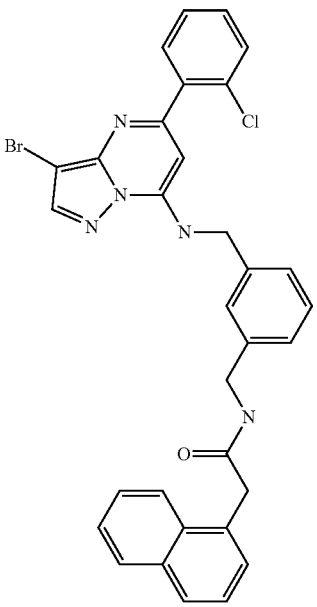 [SMILES: O=C(Cc1cccc2ccccc12)NCc1cccc(CNc2cc(-c3ccccc3Cl)nc3c(Br)cnn23)c1] | 1. 4571<br>2. 612.34 |
| | 1. 4572<br>2. 612.34 |

TABLE 45-continued
| Product | 1. Ex. 2. m/z |
|---|---|
| 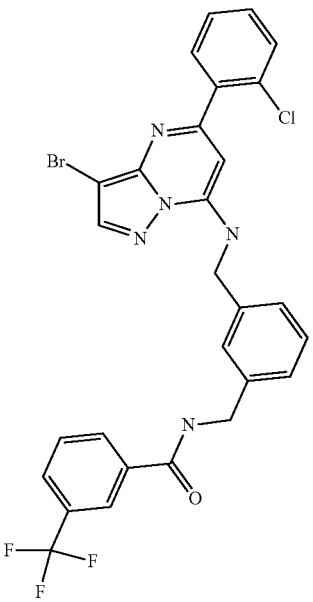 | 1. 4573 2. 613.34 |
| | 1. 4574 2. 616.34 |
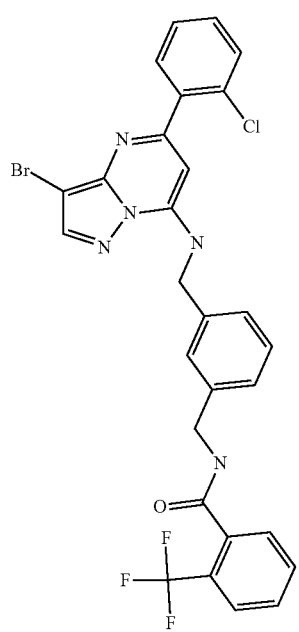 [SMILES: O=C(NCc1cccc(CNc2cc(-c3ccccc3Cl)nc3c(Br)cnn23)c1)c1ccccc1C(F)(F)F]
TABLE 45-continued
| Product | 1. Ex. 2. m/z |
|---|---|
| | 1. 4575 2. 616.34 |
| | 1. 4576 2. 616.34 |

TABLE 45-continued

| Product | 1. Ex. 2. m/z |
|---|---|
| (structure 707) | 1. 4577 2. 616.34 |
| (structure 708) | 1. 4579 2. 616.34 |
| (structure, Ex. 4578) | 1. 4578 2. 616.34 |
| (structure, Ex. 4580) | 1. 4580 2. 624.34 |

TABLE 45-continued
| Product | 1. Ex.<br>2. m/z |
|---|---|
| 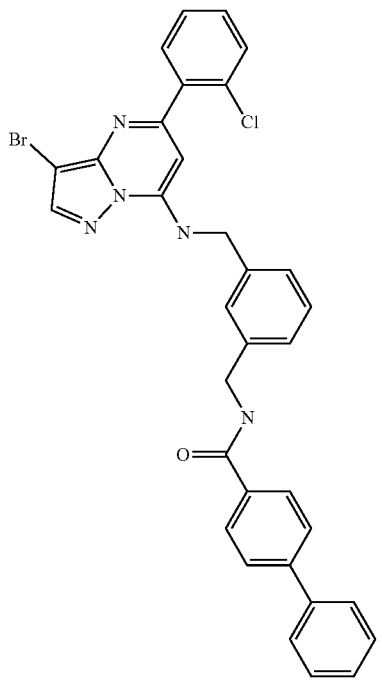 [SMILES: O=C(NCc1cccc(CNc2cc(-c3ccccc3Cl)nc3c(Br)cnn23)c1)c1ccc(-c2ccccc2)cc1] (top-left structure) | 1. 4581<br>2. 624.34 |
| (bottom-left structure in img_3) | 1. 4582<br>2. 629.35 |
TABLE 45-continued
| Product | 1. Ex.<br>2. m/z |
|---|---|
| 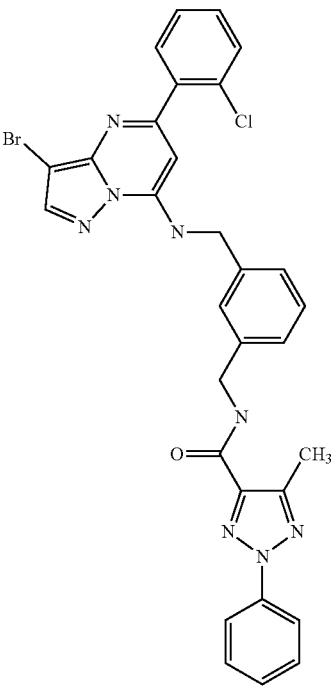 [SMILES: Cc1nn(-c2ccccc2)nc1C(=O)NCc1cccc(CNc2cc(-c3ccccc3Cl)nc3c(Br)cnn23)c1] (top-right structure) | 1. 4583<br>2. 629.35 |
| (bottom-right structure in img_3) | 1. 4584<br>2. 630.35 |
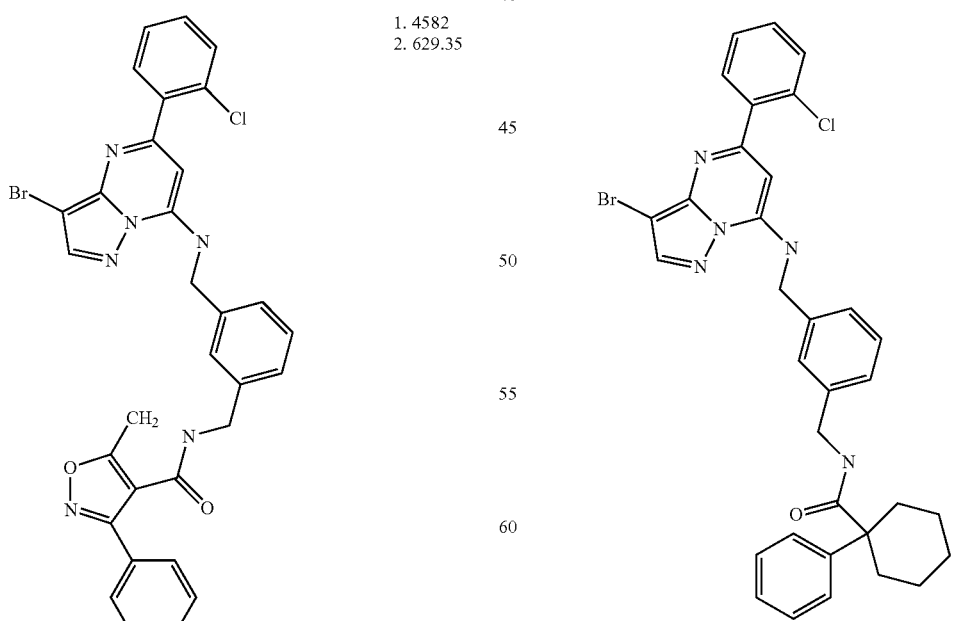

TABLE 45-continued

| Product | 1. Ex.<br>2. m/z |
|---|---|
| (structure 4585) | 1. 4585<br>2. 630.35 |
| (structure 4586) | 1. 4586<br>2. 630.35 |
| (structure 4587) | 1. 4587<br>2. 630.35 |
| (structure 4588) | 1. 4588<br>2. 630.35 |

TABLE 45-continued
| Product | 1. Ex.<br>2. m/z |
|---|---|
| 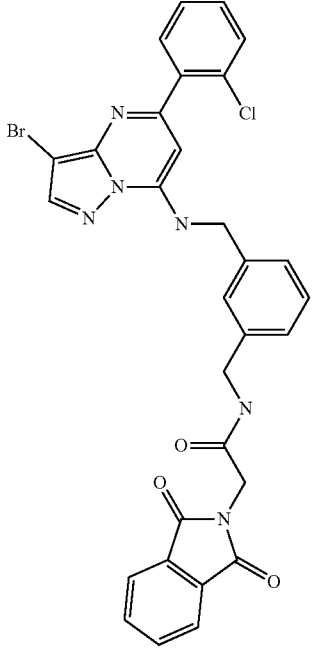 [SMILES: O=C(CN1C(=O)c2ccccc2C1=O)NCc1cccc(CNc2cc(-c3ccccc3Cl)nc3c(Br)cnn23)c1] | 1. 4589<br>2. 631.35 |
| 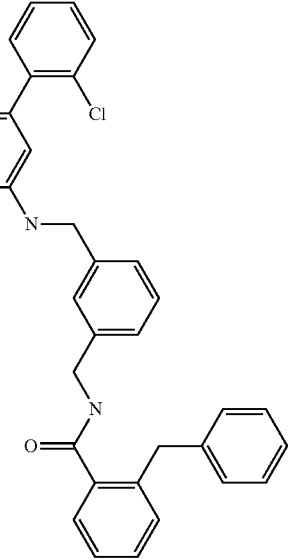 | 1. 4590<br>2. 638.35 |
| 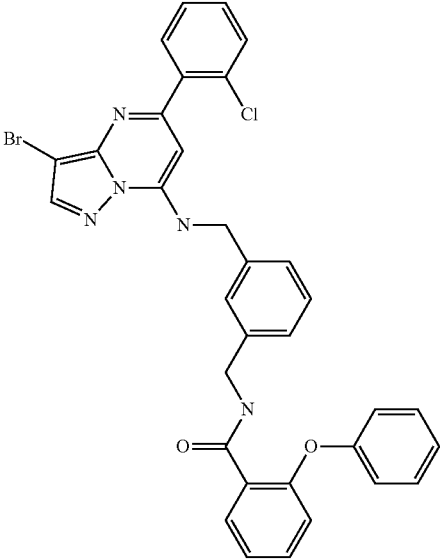 | 1. 4591<br>2. 638.35 |
| 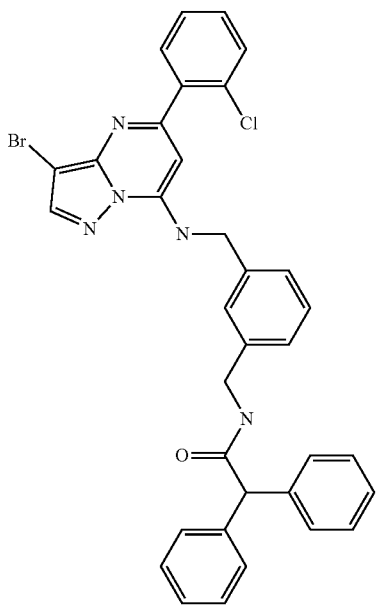 [SMILES: O=C(NCc1cccc(CNc2cc(-c3ccccc3Cl)nc3c(Br)cnn23)c1)C(c1ccccc1)c1ccccc1] | 1. 4592<br>2. 640.35 |

TABLE 45-continued
| Product | 1. Ex. 2. m/z |
|---|---|
| 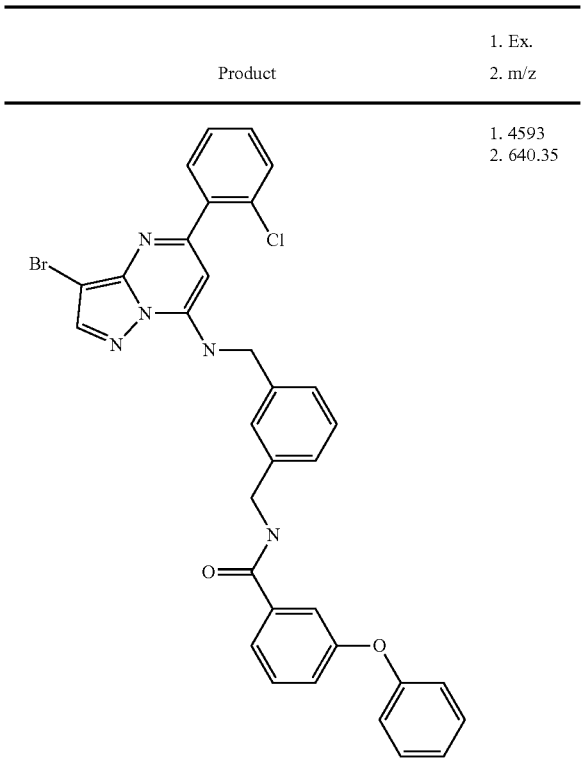 | 1. 4593<br>2. 640.35 |
| 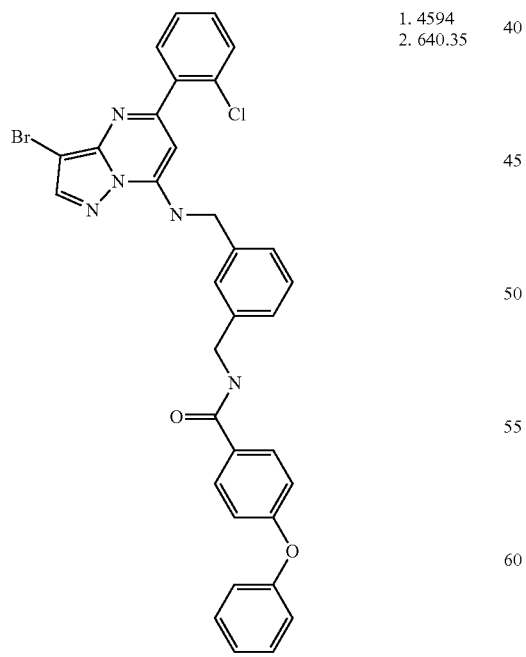 | 1. 4594<br>2. 640.35 |
TABLE 45-continued
| Product | 1. Ex. 2. m/z |
|---|---|
| 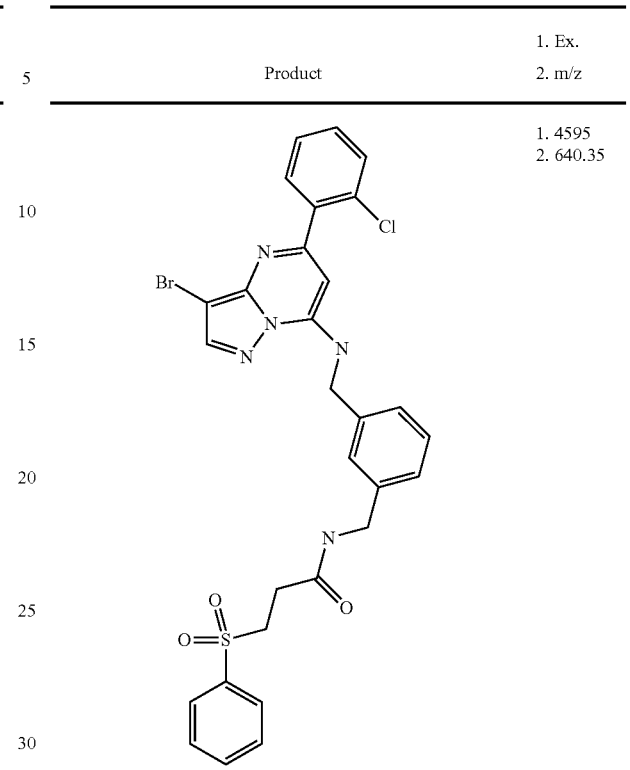 | 1. 4595<br>2. 640.35 |
| 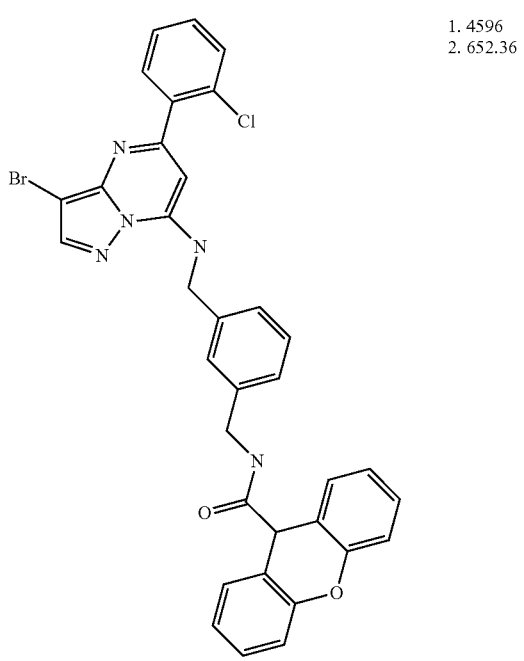 | 1. 4596<br>2. 652.36 |

TABLE 45-continued
| Product | 1. Ex.<br>2. m/z |
|---|---|
| (structure: 5-(2-chlorophenyl)-3-bromo-pyrazolo[1,5-a]pyrimidin-7-yl amine linked via CH2 to 3-(acetamidomethyl)phenyl) | 1. 4597<br>2. 486.27 |
| (structure: same core, N-benzoyl variant) | 1. 4598<br>2. 554.3 |
TABLE 45-continued
| Product | 1. Ex.<br>2. m/z |
|---|---|
| (structure: 5-(2-chlorophenyl)-3-bromo-pyrazolo[1,5-a]pyrimidin-7-yl amine linked via CH2 to 3-(benzamidomethyl)phenyl) | 1. 4599<br>2. 548.3 |
| 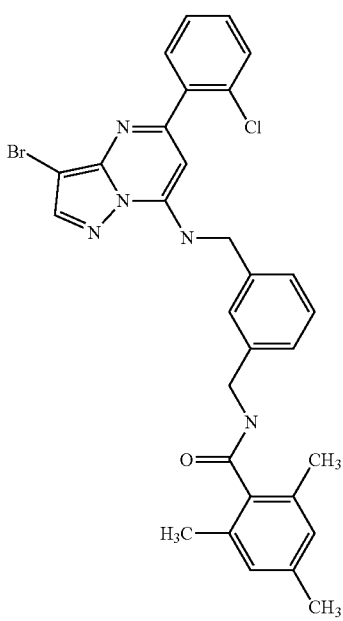 [SMILES: Cc1cc(C)c(C(=O)NCc2cccc(CNc3cc(-c4ccccc4Cl)nc4c(Br)cnn34)c2)c(C)c1] | 1. 45100<br>2. |

TABLE 46
| Product | 1. Ex.<br>2. m/z |
|---|---|
| 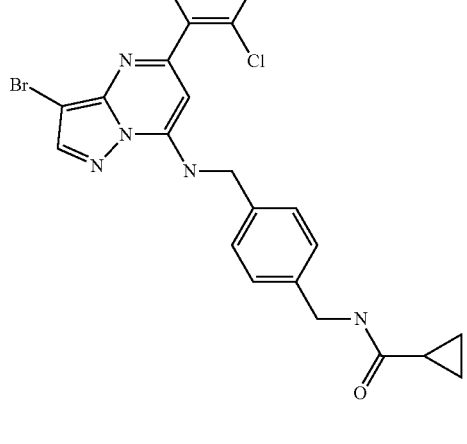 | 1. 4601<br>2. 512.28 |
| 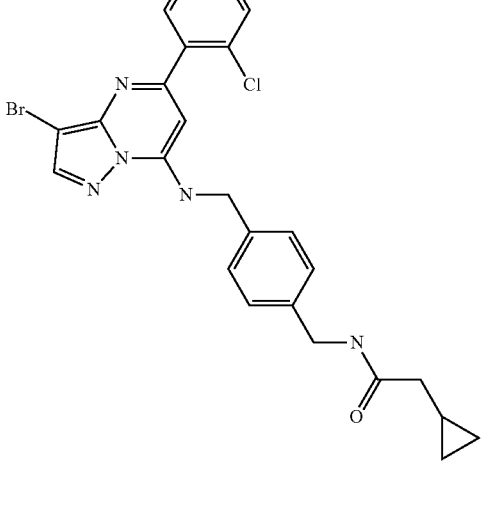 | 1. 4602<br>2. 526.29 |
| 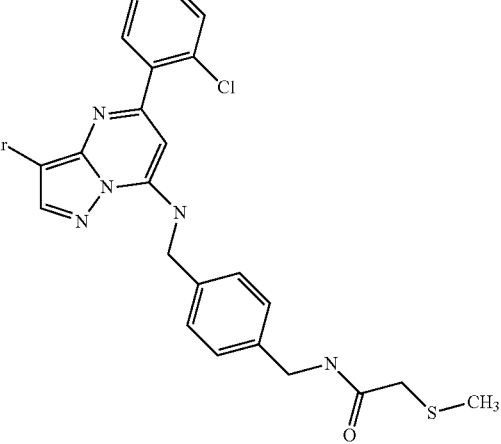 | 1. 4603<br>2. 532.29 |

TABLE 46-continued
| Product | 1. Ex.<br>2. m/z |
|---|---|
| 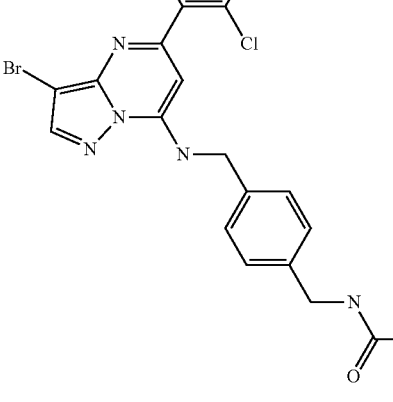 | 1. 4604<br>2. 538.3 |
| 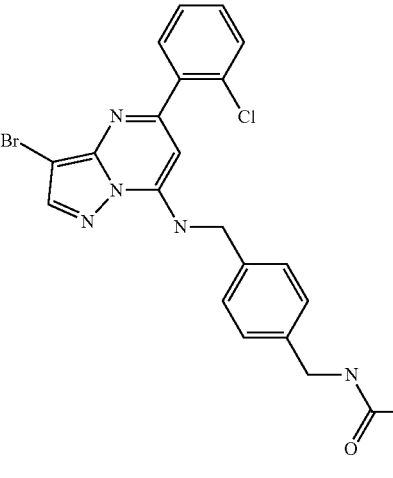 | 1. 4605<br>2. 536.3 |
| 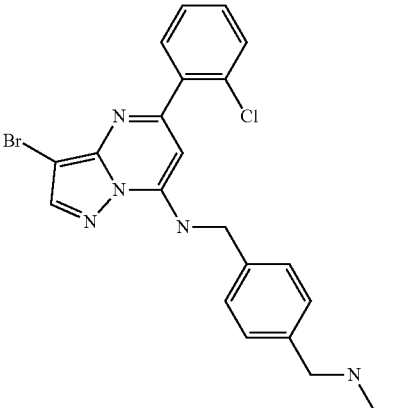 | 1. 4606<br>2. 540.3 |

TABLE 46-continued

| Product | 1. Ex.<br>2. m/z |
|---|---|
| (structure) | 1. 4607<br>2. 542.3 |
| (structure) | 1. 4608<br>2. 542.3 |
| (structure) | 1. 4609<br>2. 542.3 |

TABLE 46-continued

| Product | 1. Ex.<br>2. m/z |
|---|---|
| (structure) | 1. 4610<br>2. 547.3 |
| (structure) | 1. 4611<br>2. 551.3 |
| (structure) | 1. 4612<br>2. 552.3 |

TABLE 46-continued

| Product | 1. Ex.<br>2. m/z |
|---|---|
| (structure: 3-bromo-5-(2-chlorophenyl)pyrazolo[1,5-a]pyrimidin-7-yl amine linked via CH₂-phenyl-CH₂-NH-C(O)-thiophene) | 1. 4613<br>2. 552.3 |
| (structure: 3-bromo-5-(2-chlorophenyl)pyrazolo[1,5-a]pyrimidin-7-yl amine linked via CH₂-phenyl-CH₂-NH-C(O)-5-oxopyrrolidin-2-yl) | 1. 4614<br>2. 555.31 |
| (structure: 3-bromo-5-(2-chlorophenyl)pyrazolo[1,5-a]pyrimidin-7-yl amine linked via CH₂-phenyl-CH₂-NH-C(O)-CH₂CH₂-C(O)-O-CH₃) | 1. 4615<br>2. 558.31 |

TABLE 46-continued

| Product | 1. Ex.<br>2. m/z |
|---|---|
| | 1. 4616<br>2. 560.31 |
| | 1. 4617<br>2. 562.31 |
| | 1. 4618<br>2. 562.3 |

TABLE 46-continued
| Product | 1. Ex.<br>2. m/z |
|---|---|
| 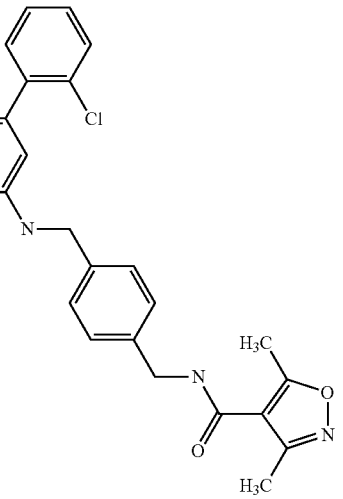 | 1. 4619<br>2. 567.31 |
|  | 1. 4620<br>2. 568.31 |
|  | 1. 4621<br>2. 568.31 |

TABLE 46-continued
| Product | 1. Ex.<br>2. m/z |
|---|---|
| 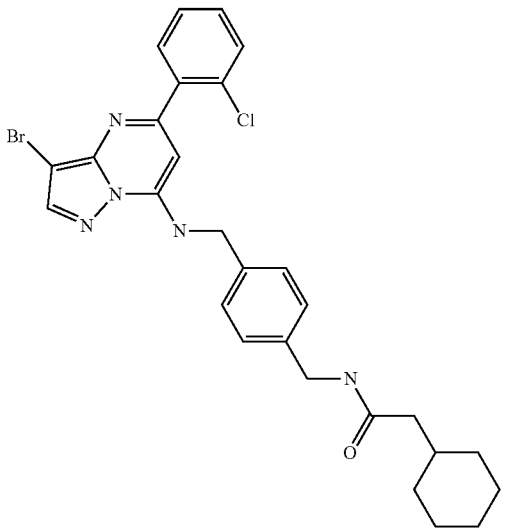 [SMILES: O=C(CC1CCCCC1)NCc1ccc(CNc2cc(-c3ccccc3Cl)nc3c(Br)cnn23)cc1] | 1. 4622<br>2. 568.31 |
| 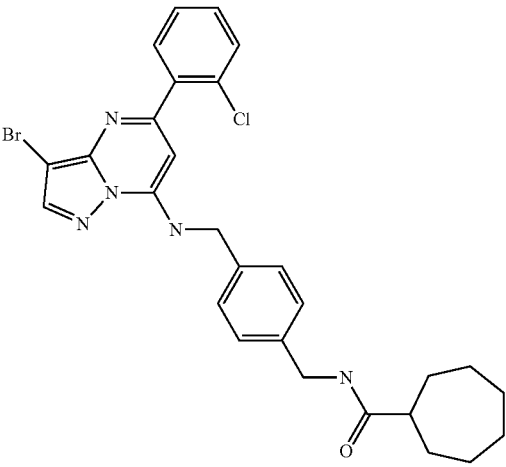 [SMILES: O=C(NCc1ccc(CNc2cc(-c3ccccc3Cl)nc3c(Br)cnn23)cc1)C1CCCCCC1] | 1. 4623<br>2. 568.31 |
| 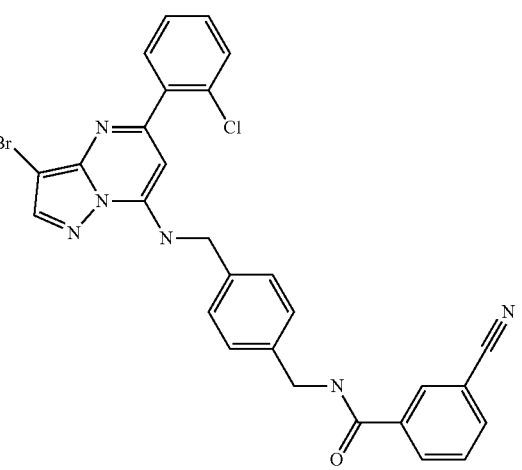 | 1. 4624<br>2. 573.32 |

TABLE 46-continued

| Product | 1. Ex.<br>2. m/z |
|---|---|
| (structure) | 1. 4625<br>2. 573.32 |
| (structure) | 1. 4626<br>2. 574.32 |
| (structure) | 1. 4627<br>2. 576.32 |

TABLE 46-continued

| Product | 1. Ex.<br>2. m/z |
|---|---|
| (structure) | 1. 4628<br>2. 576.32 |
| (structure) | 1. 4629<br>2. 578.32 |
| (structure) | 1. 4630<br>2. 578.32 |

TABLE 46-continued

| Product | 1. Ex.<br>2. m/z |
|---|---|
| *structure* | 1. 4631<br>2. 578.32 |
| *structure* | 1. 4632<br>2. 578.32 |
| *structure* | 1. 4633<br>2. 580.32 |

TABLE 46-continued
| Product | 1. Ex.<br>2. m/z |
|---|---|
| 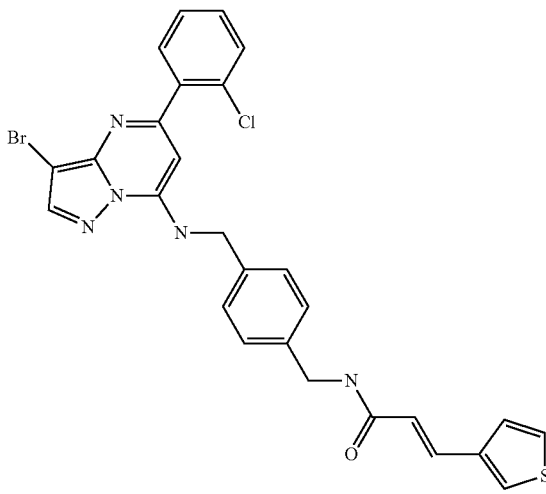 | 1. 4634<br>2. 580.32 |
| 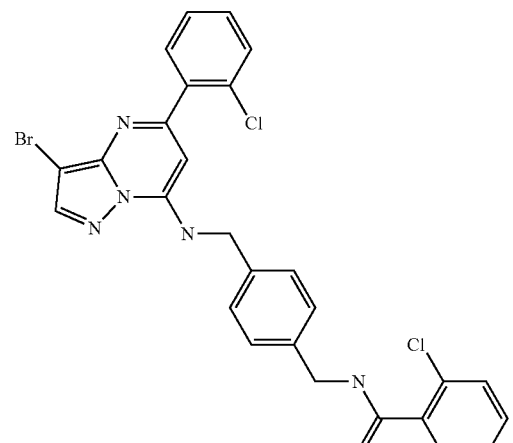 | 1. 4635<br>2. 582.32 |
| 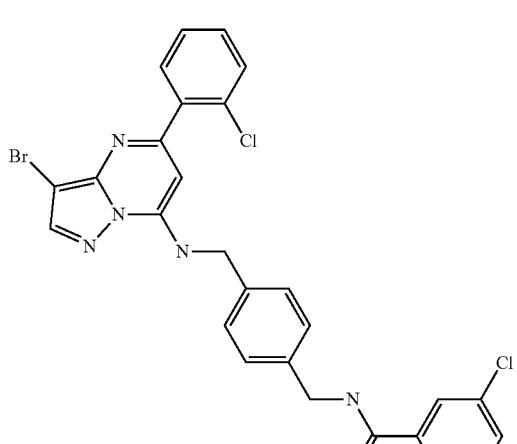 | 1. 4636<br>2. 582.32 |

TABLE 46-continued

| Product | 1. Ex.<br>2. m/z |
|---|---|
| | 1. 4637<br>2. 582.32 |
| | 1. 4638<br>2. 587.32 |
| | 1. 4639<br>2. 585.3 |

TABLE 46-continued
| Product | 1. Ex.<br>2. m/z |
|---|---|
| 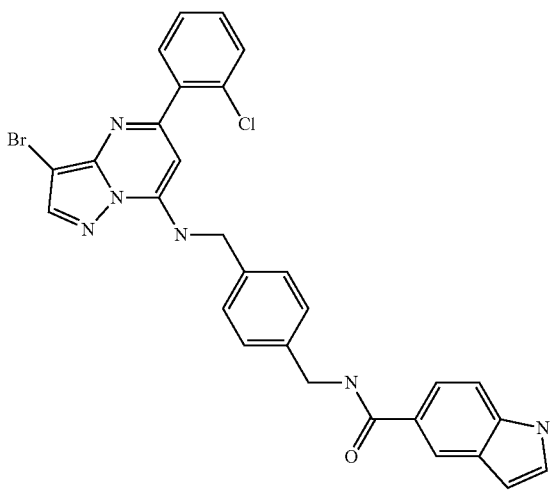 | 1. 4640<br>2. 585.3 |
| 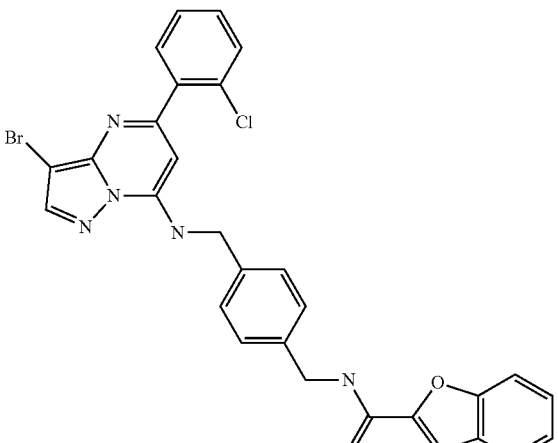 | 1. 4641<br>2. 588.32 |
| 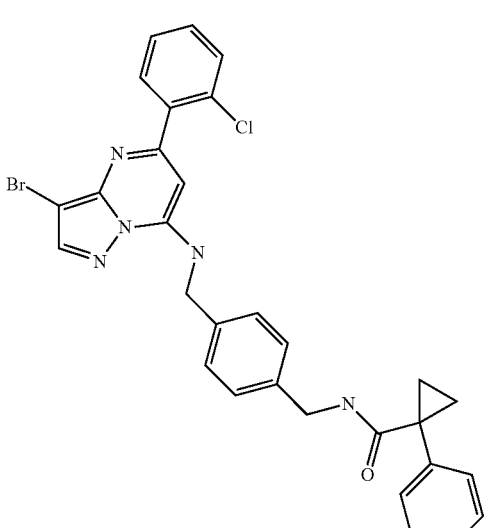 | 1. 4642<br>2. 588.32 |

TABLE 46-continued

| Product | 1. Ex.<br>2. m/z |
|---|---|
| (structure) | 1. 4643<br>2. 588.32 |
| (structure) | 1. 4644<br>2. 588.32 |
| (structure) | 1. 4645<br>2. 590.32 |

TABLE 46-continued
| Product | 1. Ex.<br>2. m/z |
|---|---|
| 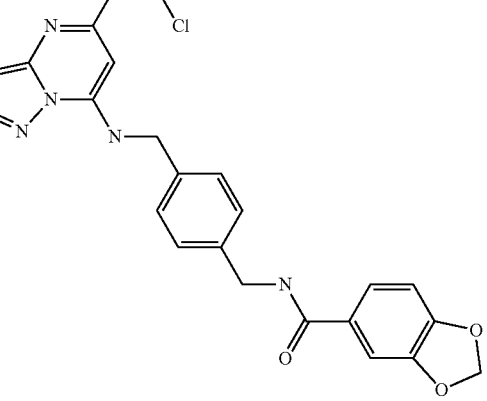 | 1. 4646<br>2. 592.33 |
| 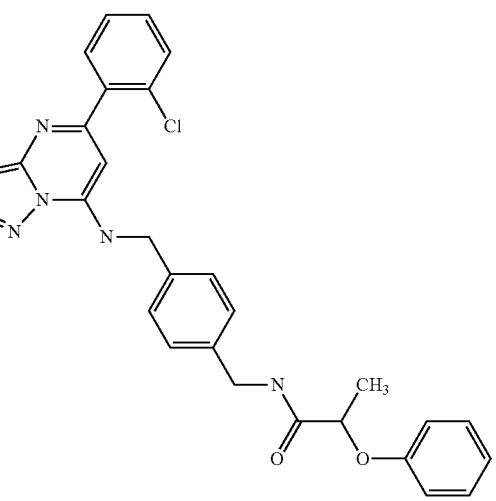 | 1. 4647<br>2. 592.33 |
| 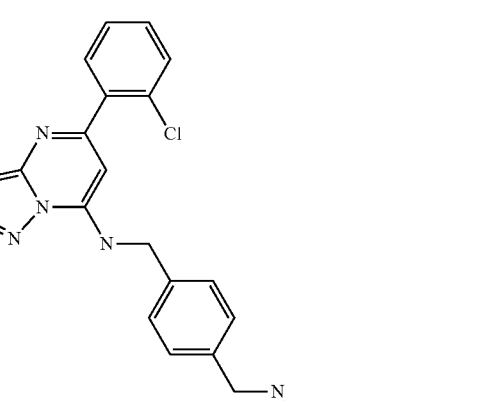 | 1. 4648<br>2. 592.33 |

TABLE 46-continued
| Product | 1. Ex.<br>2. m/z |
|---|---|
| 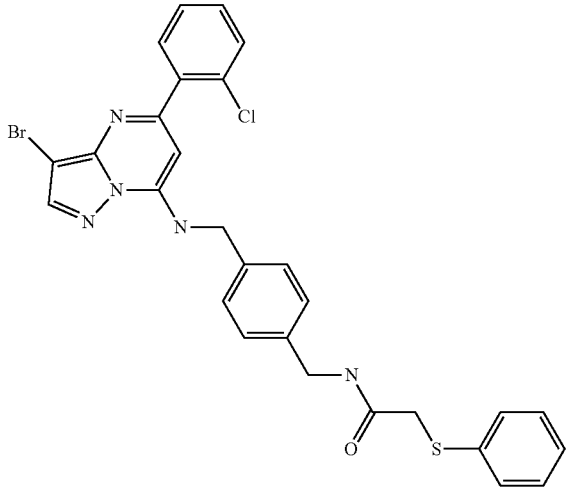 [SMILES: O=C(CCc1ccccc1)NCc1ccc(CNc2cc(-c3ccccc3Cl)nc3c(Br)cnn23)cc1] | 1. 4649<br>2. |
| 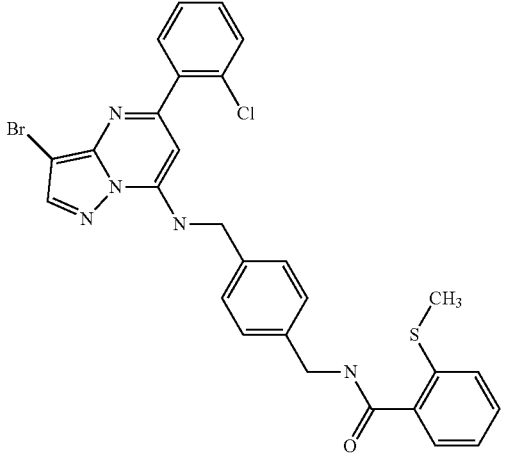 [SMILES: COc1ccccc1C(=O)NCc1ccc(CNc2cc(-c3ccccc3Cl)nc3c(Br)cnn23)cc1] | 1. 4650<br>2. 594.33 |
| 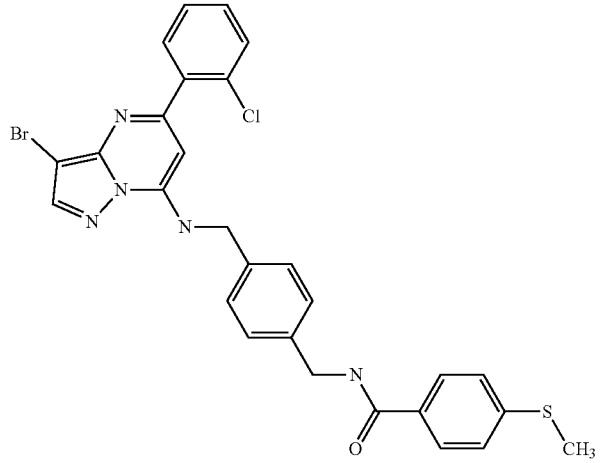 [SMILES: CSc1ccc(C(=O)NCc2ccc(CNc3cc(-c4ccccc4Cl)nc4c(Br)cnn34)cc2)cc1] | 1. 4651<br>2. 594.33 |

TABLE 46-continued

| Product | 1. Ex.<br>2. m/z |
|---|---|
| | 1. 4652<br>2. 596.33 |
| | 1. 4653<br>2. 596.3 |
| | 1. 4654<br>2. 598.33 |

TABLE 46-continued
| Product | 1. Ex. 2. m/z |
|---|---|
| 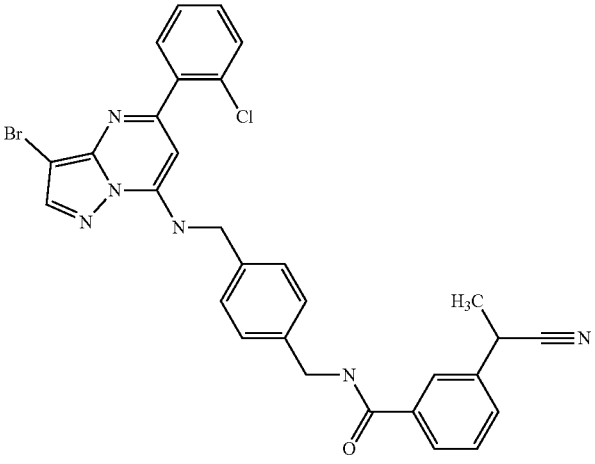 [SMILES: CC(C#N)c1cccc(C(=O)NCc2ccc(CNc3cc(-c4ccccc4Cl)nc4c(Br)cnn34)cc2)c1] | 1. 4655 2. 601.33 |
| 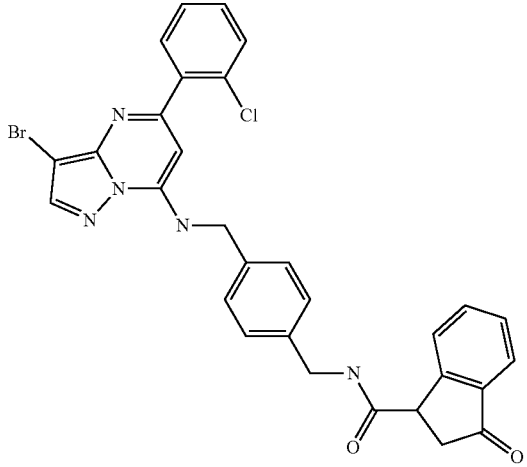 [SMILES: O=C1CC(C(=O)NCc2ccc(CNc3cc(-c4ccccc4Cl)nc4c(Br)cnn34)cc2)c2ccccc21] | 1. 4656 2. 602.33 |
| 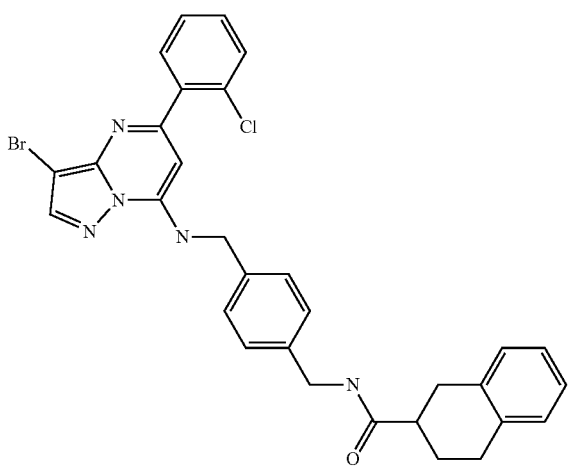 [SMILES: O=C(NCc1ccc(CNc2cc(-c3ccccc3Cl)nc3c(Br)cnn23)cc1)C1CCc2ccccc2C1] | 1. 4657 2. 602.33 |

TABLE 46-continued
| Product | 1. Ex.<br>2. m/z |
|---|---|
| 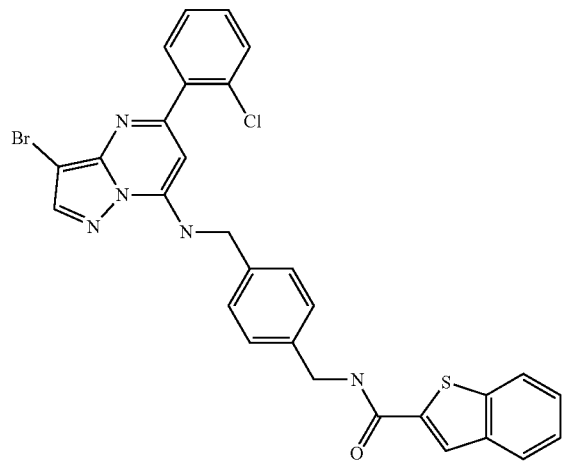 | 1. 4658<br>2. 604.33 |
| 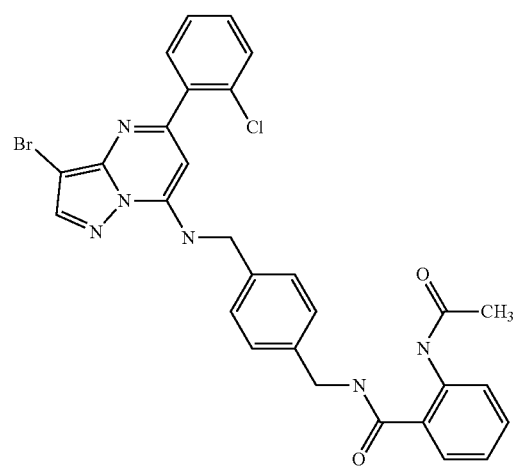 [SMILES: CC(=O)Nc1ccccc1C(=O)NCc1ccc(CNc2cc(-c3ccccc3Cl)nc3c(Br)cnn23)cc1] | 1. 4659<br>2. 603.3 |
| 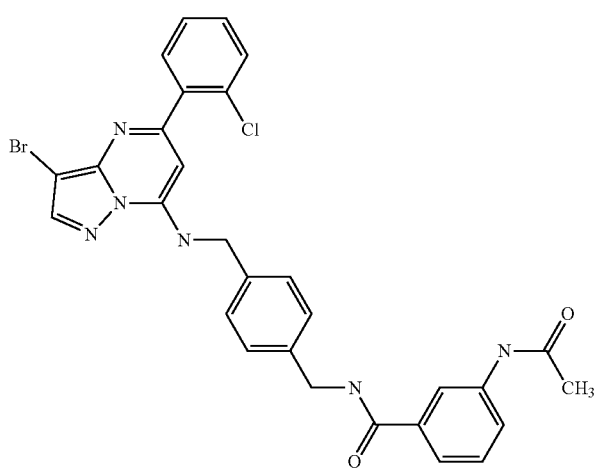 [SMILES: CC(=O)Nc1cccc(C(=O)NCc2ccc(CNc3cc(-c4ccccc4Cl)nc4c(Br)cnn34)cc2)c1] | 1. 4660<br>2. 605.33 |

TABLE 46-continued
| Product | 1. Ex.<br>2. m/z |
|---|---|
| 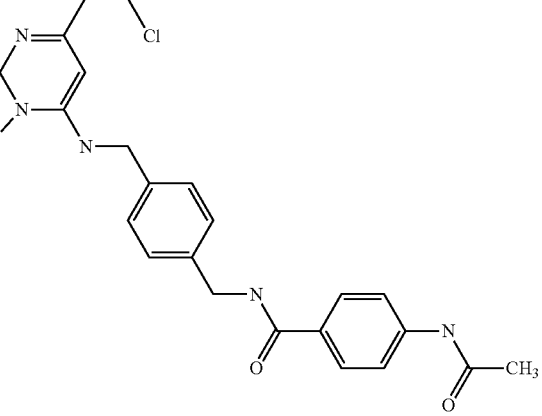 | 1. 4661<br>2. 605.33 |
| 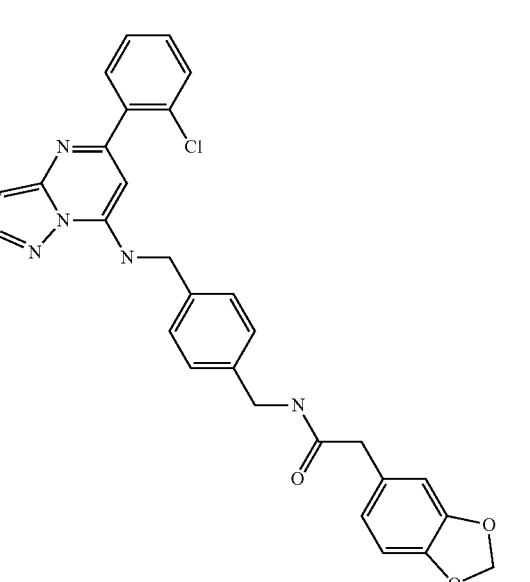 | 1. 4662<br>2. 606.33 |
| 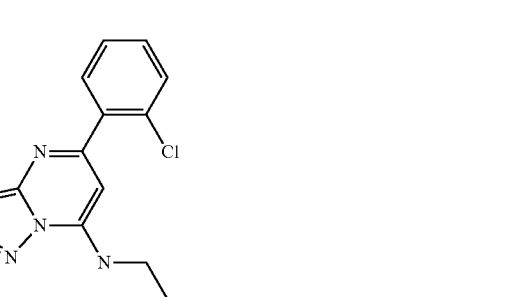 | 1. 4663<br>2. 606.33 |

TABLE 46-continued
| Product | 1. Ex.<br>2. m/z |
|---|---|
| 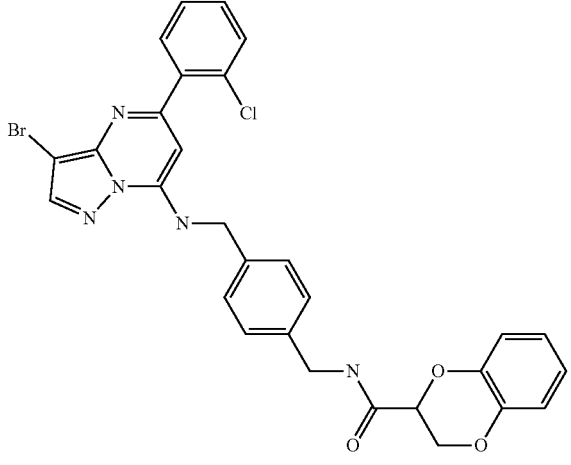 [SMILES: O=C(NCc1ccc(CNc2cc(-c3ccccc3Cl)nc3c(Br)cnn23)cc1)C1COc2ccccc2O1] | 1. 4664<br>2. 606.33 |
| 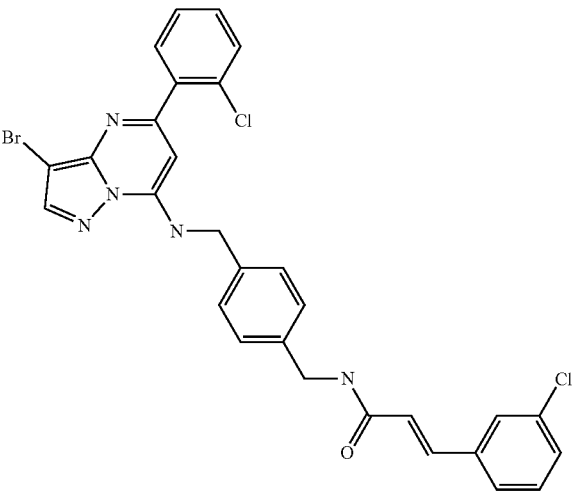 [SMILES: O=C(/C=C/c1cccc(Cl)c1)NCc1ccc(CNc2cc(-c3ccccc3Cl)nc3c(Br)cnn23)cc1] | 1. 4665<br>2. 608.33 |
| 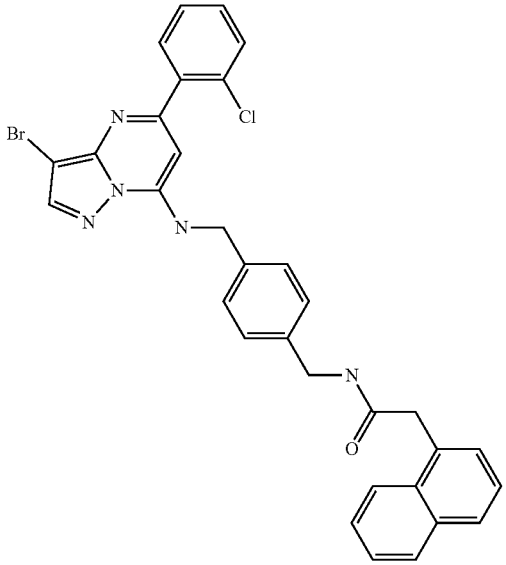 [SMILES: O=C(Cc1cccc2ccccc12)NCc1ccc(CNc2cc(-c3ccccc3Cl)nc3c(Br)cnn23)cc1] | 1. 4666<br>2. 612.34 |

TABLE 46-continued
| Product | 1. Ex.<br>2. m/z |
|---|---|
| 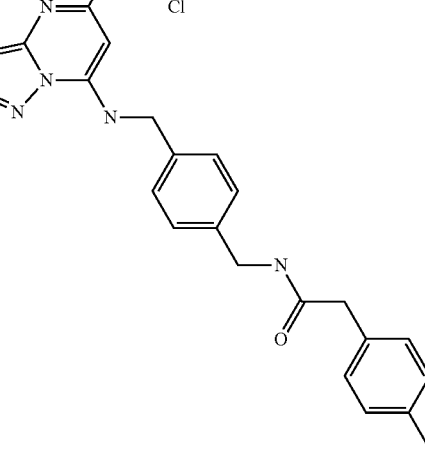 | 1. 4667<br>2. 612.34 |
| 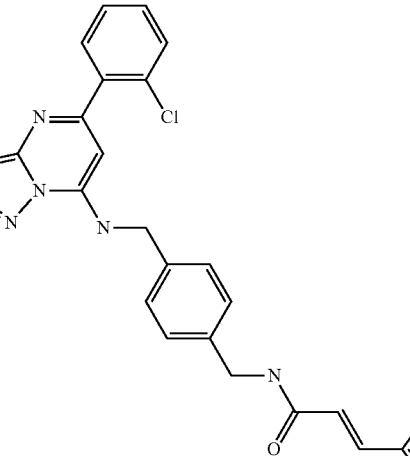 | 1. 4668<br>2. 613.34 |
| 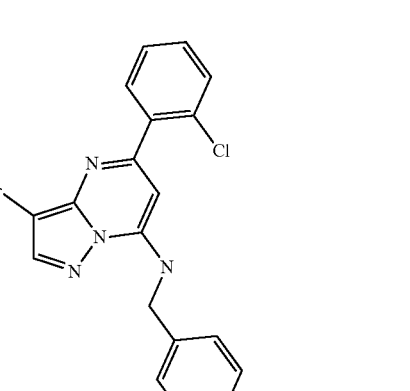 | 1. 4669<br>2. 616.34 |

TABLE 46-continued
| Product | 1. Ex.<br>2. m/z |
|---|---|
| 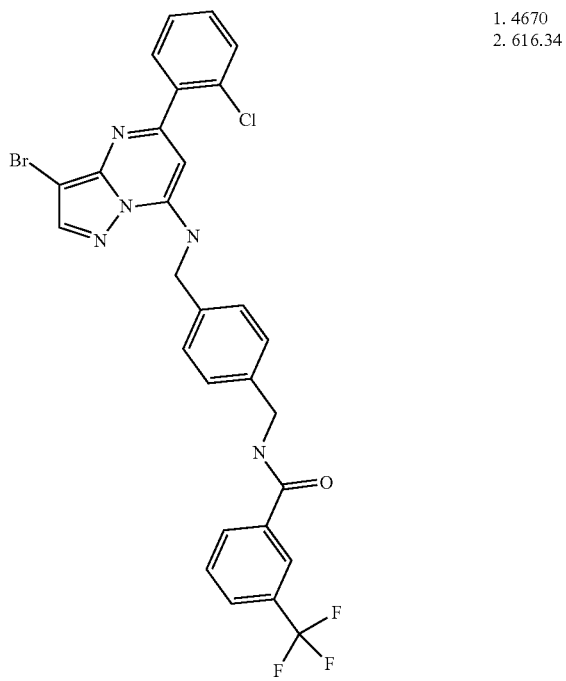 | 1. 4670<br>2. 616.34 |
| 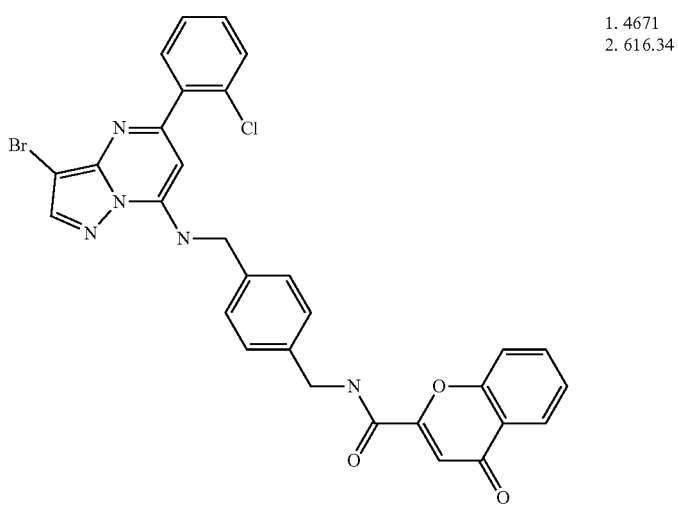 | 1. 4671<br>2. 616.34 |

TABLE 46-continued
| Product | 1. Ex.<br>2. m/z |
|---|---|
| 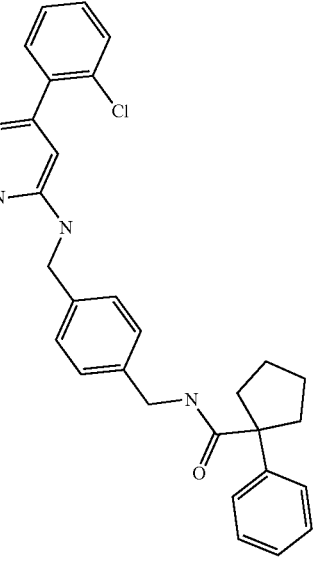 | 1. 4672<br>2. 616.34 |
| 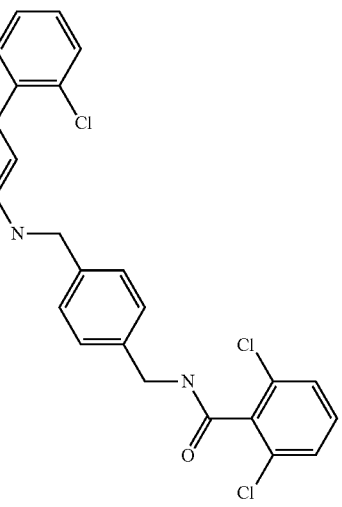 | 1. 4673<br>2. 616.34 |
| 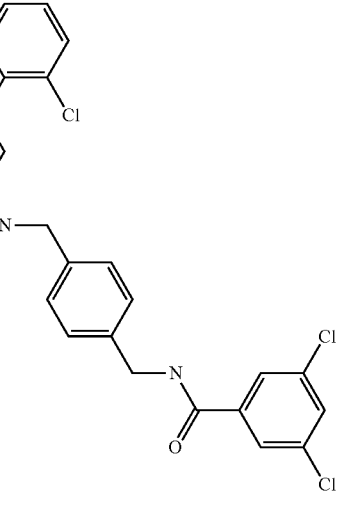 | 1. 4674<br>2. 616.34 |

TABLE 46-continued

| Product | 1. Ex.<br>2. m/z |
|---|---|
| (structure) | 1. 4675<br>2. 624.34 |
| (structure) | 1. 4676<br>2. 624.34 |
| (structure) | 1. 4677<br>2. 629.35 |

TABLE 46-continued

| Product | 1. Ex. 2. m/z |
|---|---|
| | 1. 4678 2. 629.35 |
| | 1. 4679 2. 630.35 |
| | 1. 4680 2. 630.35 |

TABLE 46-continued
| Product | 1. Ex.<br>2. m/z |
|---|---|
| 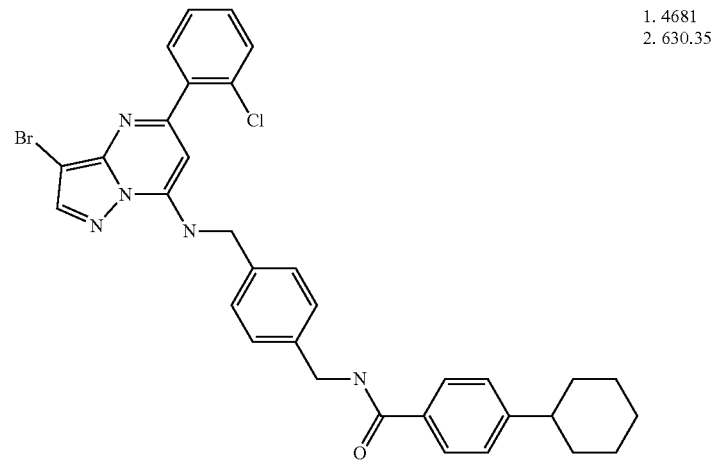 | 1. 4681<br>2. 630.35 |
| 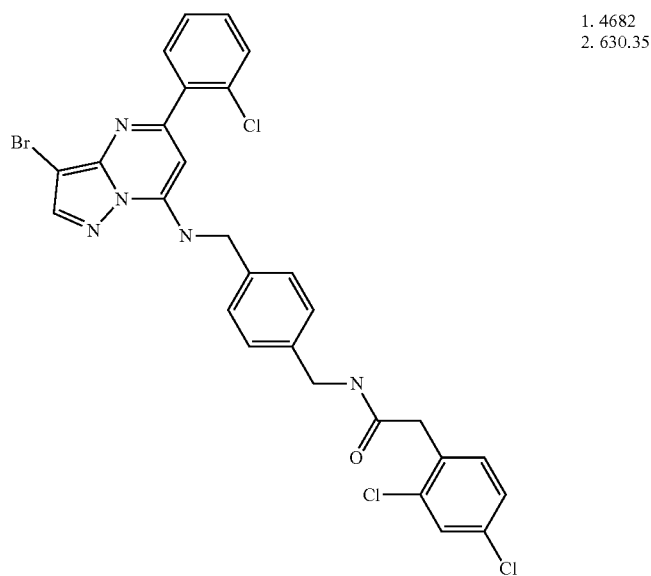 | 1. 4682<br>2. 630.35 |

TABLE 46-continued
| Product | 1. Ex.<br>2. m/z |
|---|---|
| 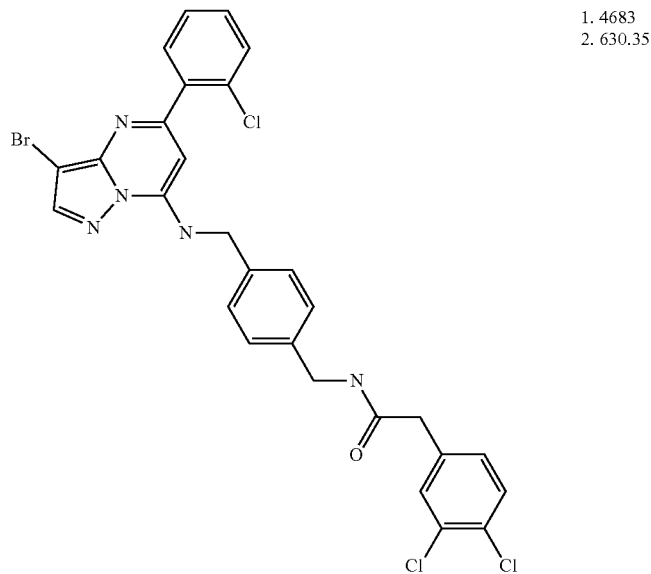 | 1. 4683<br>2. 630.35 |
| 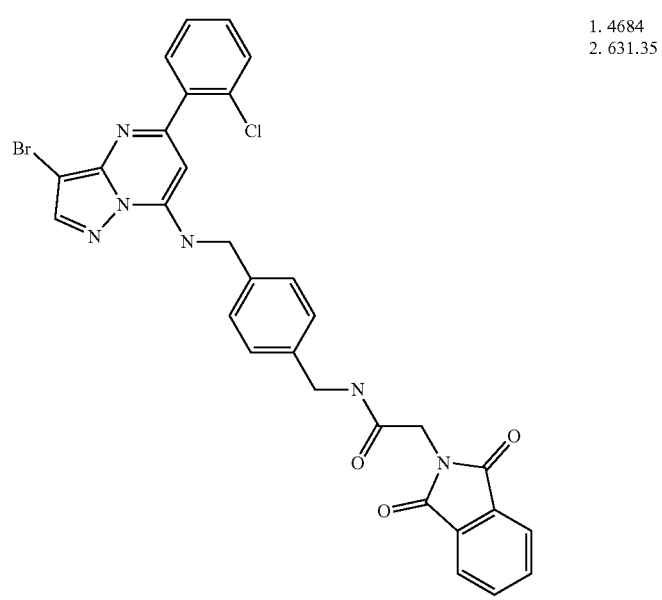 | 1. 4684<br>2. 631.35 |

TABLE 46-continued

| Product | 1. Ex.<br>2. m/z |
|---|---|
| | 1. 4685<br>2. 638.35 |
| | 1. 4686<br>2. 638.35 |
| | 1. 4687<br>2. 640.35 |

TABLE 46-continued
| Product | 1. Ex.<br>2. m/z |
|---|---|
| 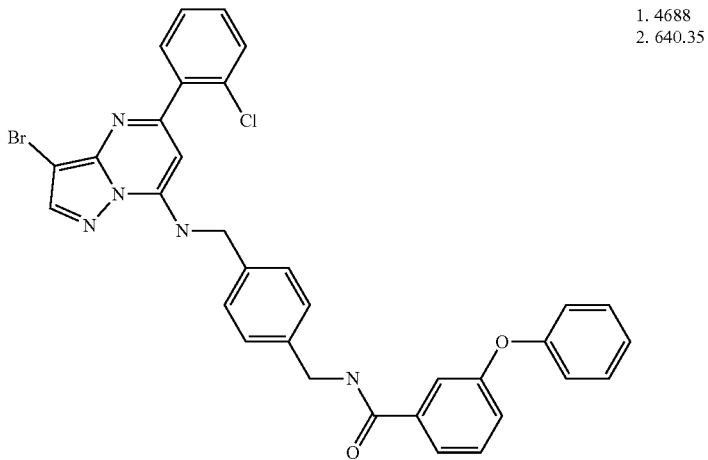 | 1. 4688<br>2. 640.35 |
| | 4689<br>2. |

TABLE 46-continued
| Product | 1. Ex.<br>2. m/z |
|---|---|
| 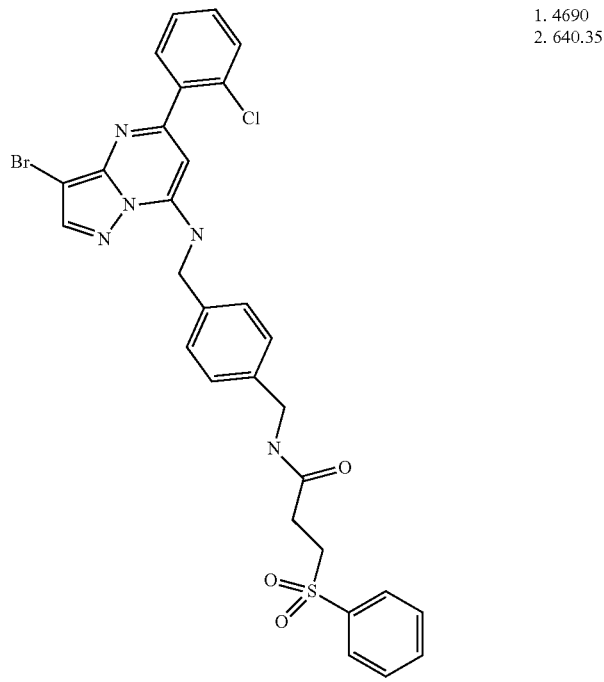 | 1. 4690<br>2. 640.35 |
| 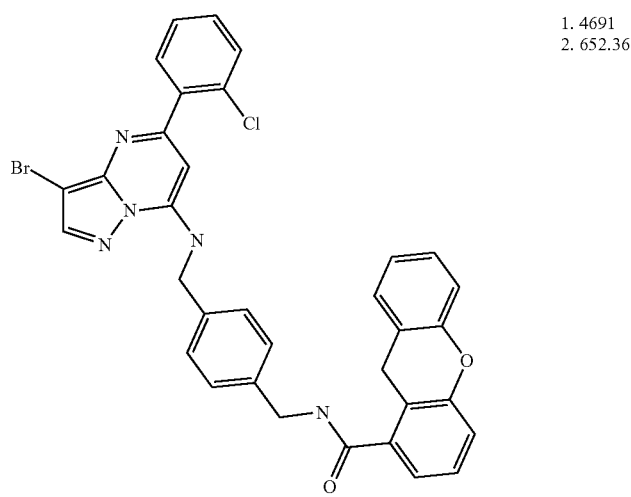 | 1. 4691<br>2. 652.36 |

TABLE 46-continued
| Product | 1. Ex.<br>2. m/z |
|---|---|
| 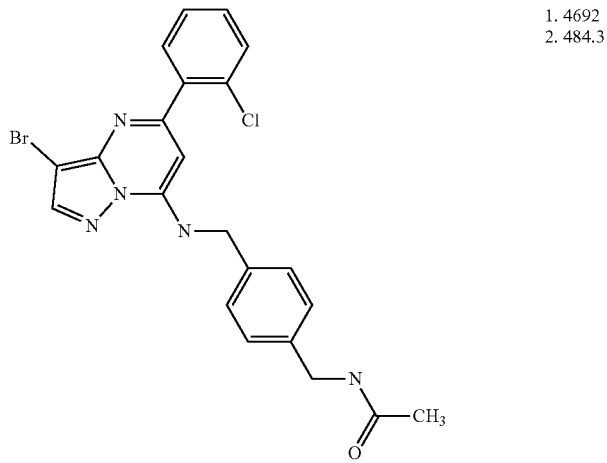 | 1. 4692<br>2. 484.3 |
| 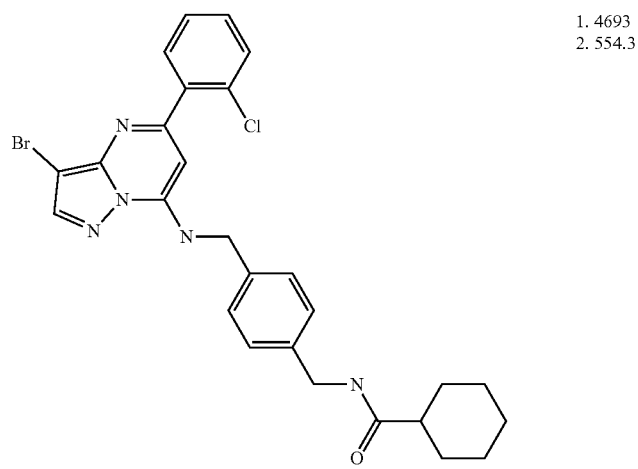 [SMILES: O=C(NCc1ccc(CNc2cc(-c3ccccc3Cl)nc3c(Br)cnn23)cc1)c1ccc(C2CCCCC2)cc1] | 1. 4693<br>2. 554.3 |
| 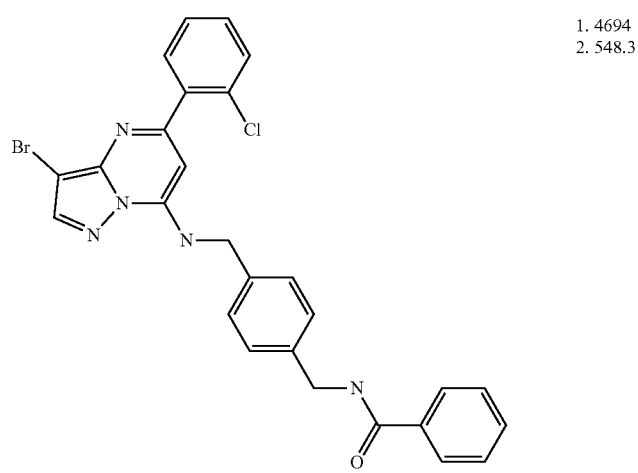 | 1. 4694<br>2. 548.3 |

TABLE 46-continued

| Product | 1. Ex.<br>2. m/z |
|---|---|
| (structure) | 1. 4695<br>2. 590.32 |

TABLE 47

| Product | 1. Ex.<br>2. m/z |
|---|---|
| (structure) | 1. 4701<br>2. 498.27 |

TABLE 47-continued
| Product | 1. Ex. 2. m/z |
|---|---|
| 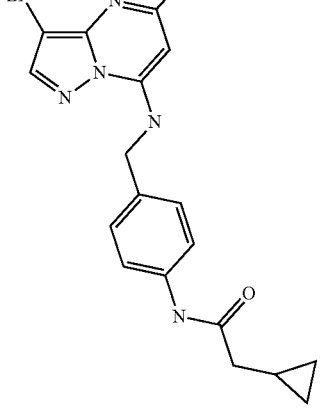 | 1. 4702 2. 512.28 |
| 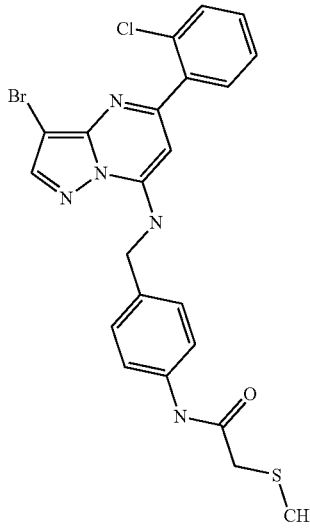 | 1. 4703 2. 518.28 |
| 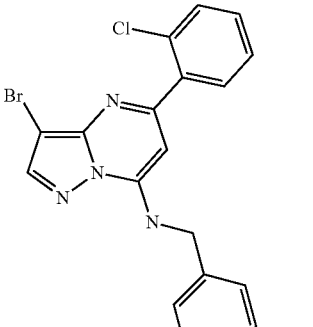 | 1. 4704 2. 524.29 |

TABLE 47-continued
| Product | 1. Ex.<br>2. m/z |
|---|---|
| 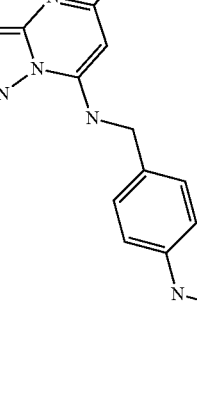 | 1. 4705<br>2. 528.29 |
| 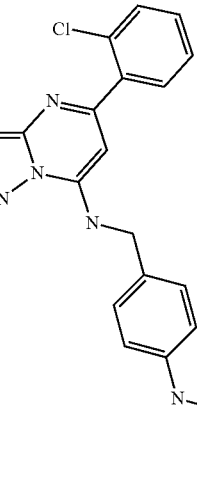 | 1. 4706<br>2. 528.29 |
| 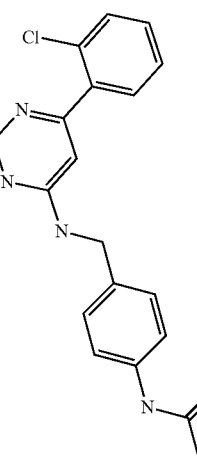 | 1. 4707<br>2. 528.29 |

TABLE 47-continued
| Product | 1. Ex.<br>2. m/z |
|---------|------------------|
| 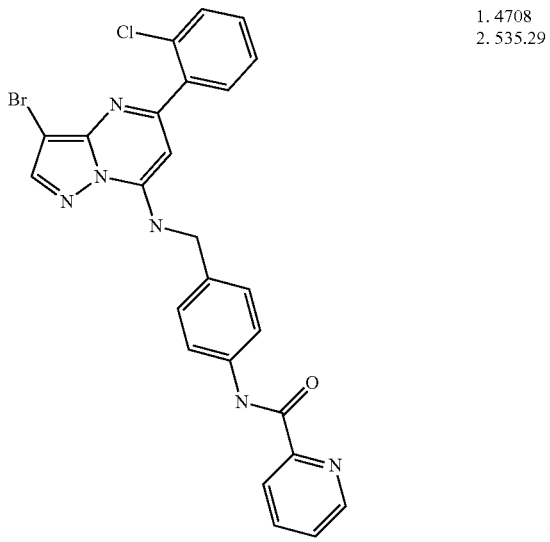 | 1. 4708<br>2. 535.29 |
| 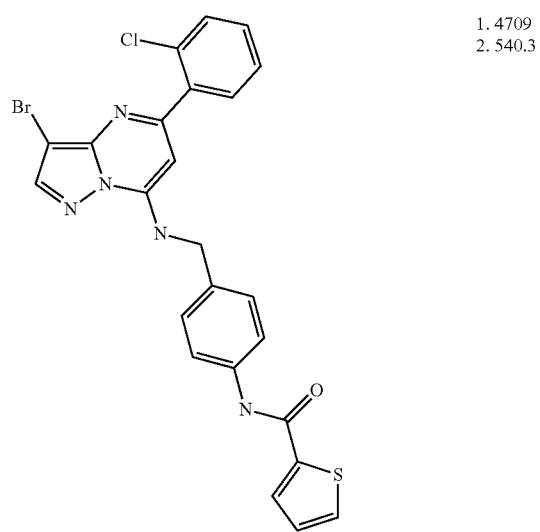 | 1. 4709<br>2. 540.3 |

TABLE 47-continued
| Product | 1. Ex.<br>2. m/z |
|---|---|
| 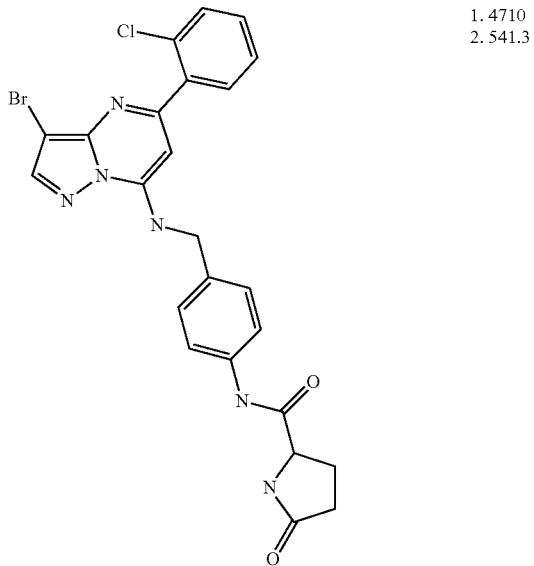 | 1. 4710<br>2. 541.3 |
| 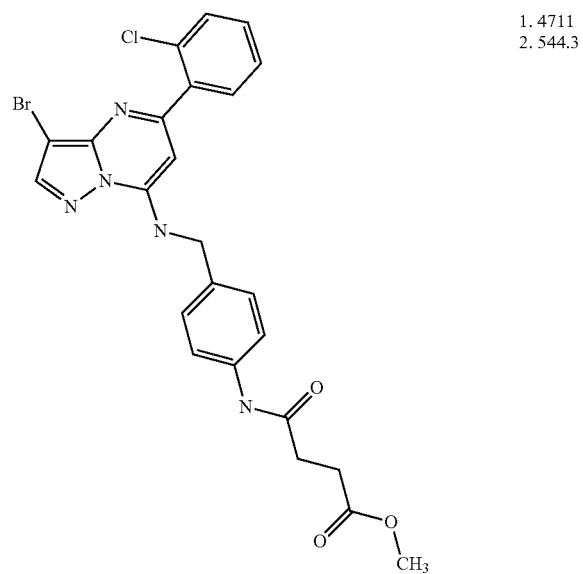 | 1. 4711<br>2. 544.3 |

TABLE 47-continued
| Product | 1. Ex.<br>2. m/z |
|---|---|
| 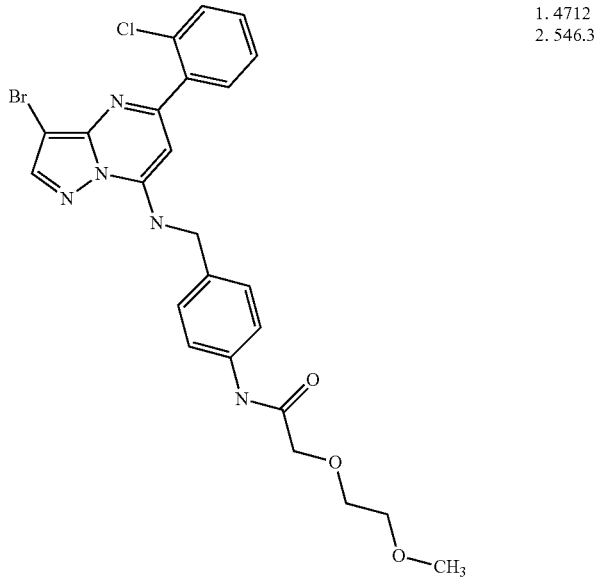 | 1. 4712<br>2. 546.3 |
| 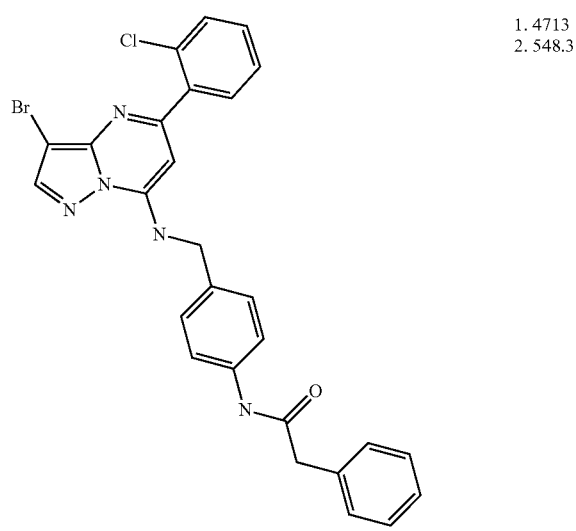 | 1. 4713<br>2. 548.3 |

TABLE 47-continued
| Product | 1. Ex.<br>2. m/z |
|---|---|
| 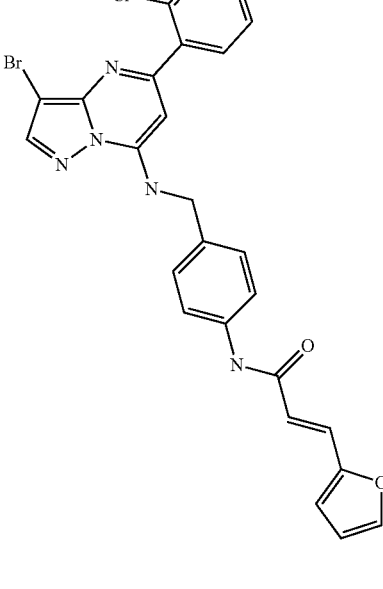 | 1. 4714<br>2. 550.3 |
| 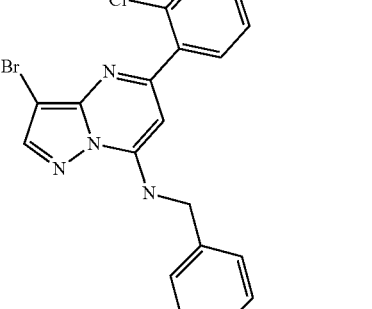 | 1. 4715<br>2. 553.3 |

TABLE 47-continued
| Product | 1. Ex. 2. m/z |
|---|---|
| 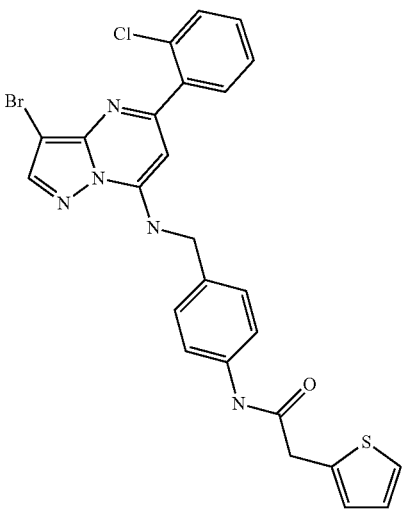 [SMILES: O=C(Cc1cccs1)Nc1ccc(CNc2cc(-c3ccccc3Cl)nc3c(Br)cnn23)cc1] | 1. 4716 2. 554.3 |
| 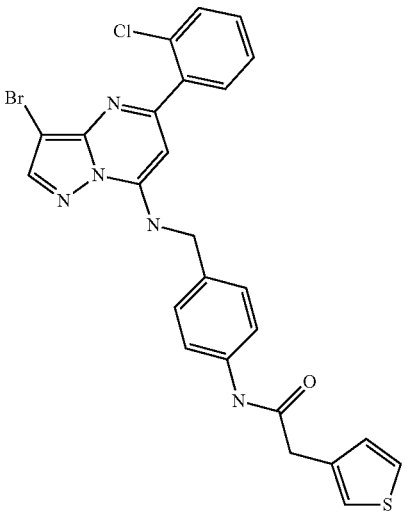 [SMILES: O=C(Cc1ccsc1)Nc1ccc(CNc2cc(-c3ccccc3Cl)nc3c(Br)cnn23)cc1] | 1. 4717 2. 554.3 |
| 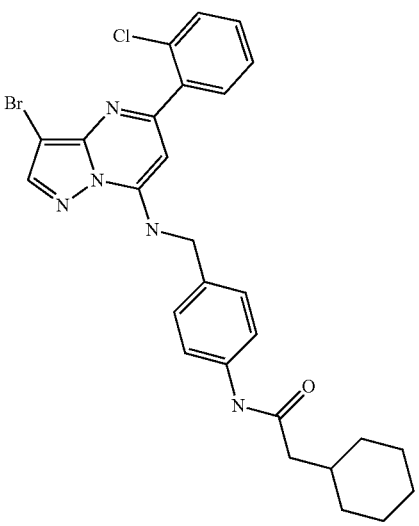 [SMILES: O=C(CC1CCCCC1)Nc1ccc(CNc2cc(-c3ccccc3Cl)nc3c(Br)cnn23)cc1] | 1. 4718 2. 554.3 |

TABLE 47-continued
| Product | 1. Ex.<br>2. m/z |
|---|---|
| 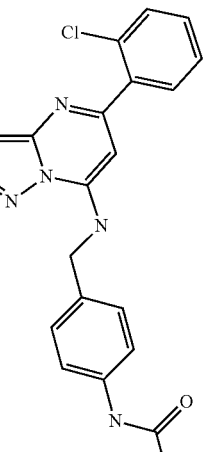 | 1. 4719<br>2. 559.31 |
| | 1. 4720<br>2. 559.31 |

TABLE 47-continued

| Product | 1. Ex.<br>2. m/z |
|---|---|
| (structure) | 1. 4721<br>2. 562.31 |
| (structure) | 1. 4722<br>2. 562.31 |

TABLE 47-continued
| Product | 1. Ex. 2. m/z |
|---|---|
| 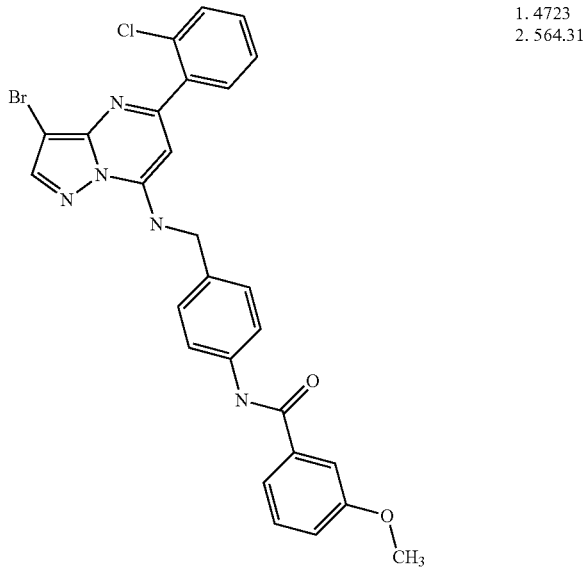 | 1. 4723 2. 564.31 |
| 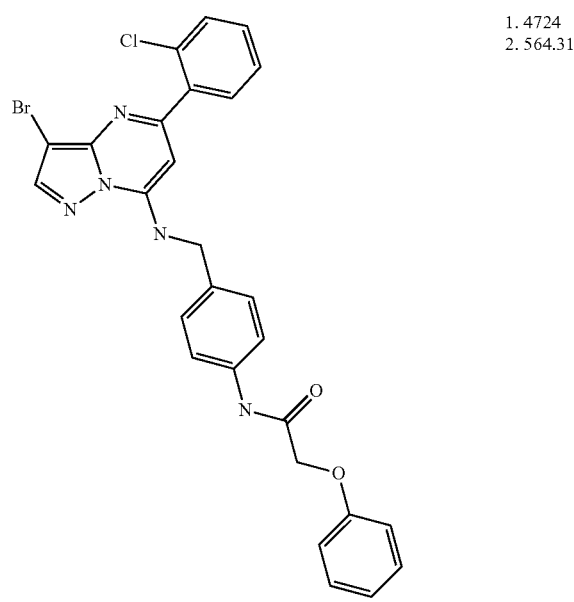 | 1. 4724 2. 564.31 |

TABLE 47-continued
| Product | 1. Ex.<br>2. m/z |
|---|---|
| 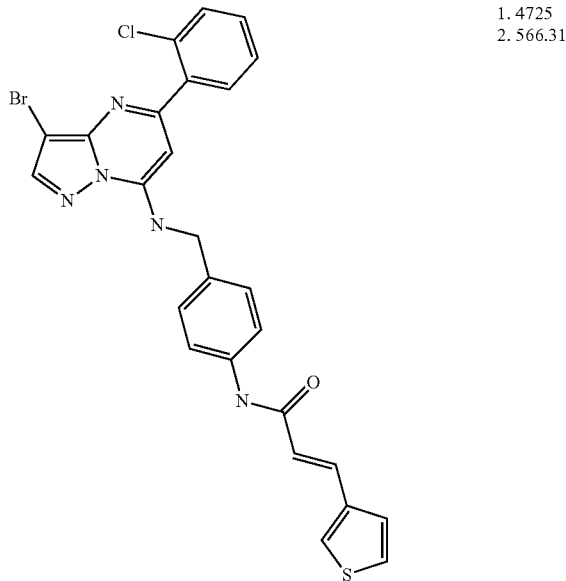 | 1. 4725<br>2. 566.31 |
| 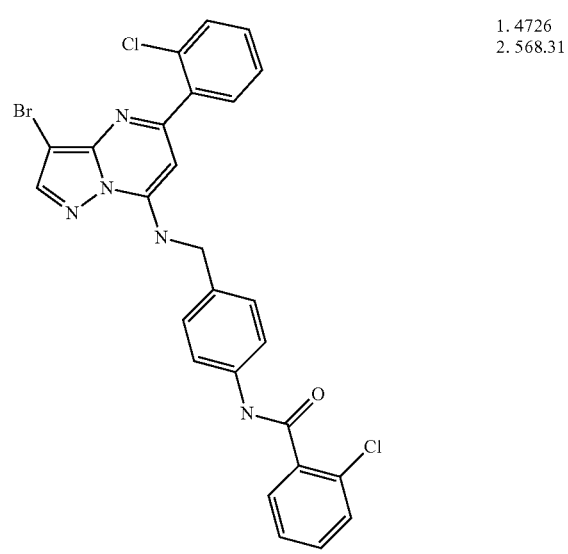 | 1. 4726<br>2. 568.31 |

TABLE 47-continued
| Product | 1. Ex.<br>2. m/z |
|---|---|
| 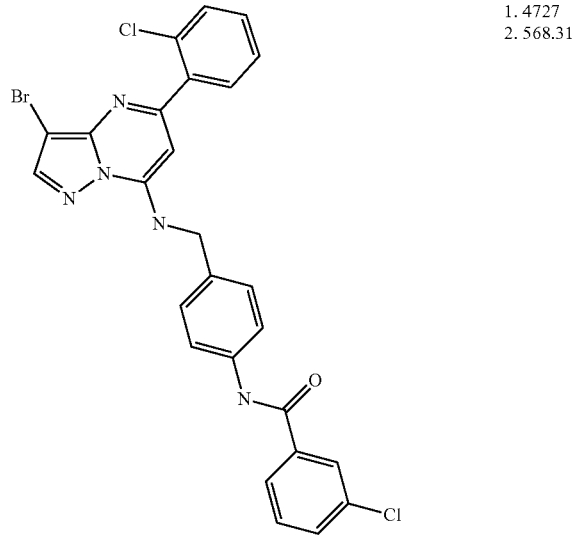 | 1. 4727<br>2. 568.31 |
| 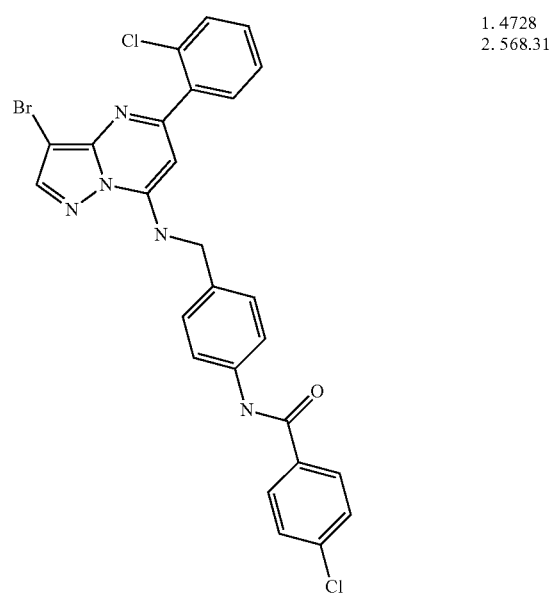 | 1. 4728<br>2. 568.31 |

TABLE 47-continued
| Product | 1. Ex.<br>2. m/z |
|---|---|
| 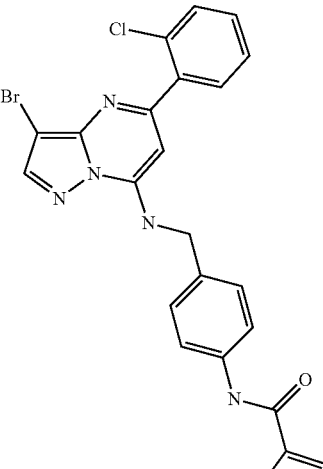 | 1. 4729<br>2. 573.32 |
| | 1. 4730<br>2. 574.32 |

TABLE 47-continued
| Product | 1. Ex.<br>2. m/z |
|---|---|
| 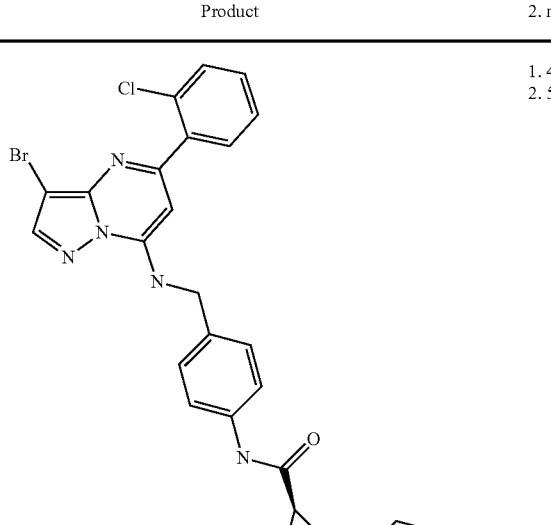 | 1. 4731<br>2. 574.32 |
| | 1. 4732<br>2. 576.32 |

TABLE 47-continued
| Product | 1. Ex.<br>2. m/z |
|---|---|
| 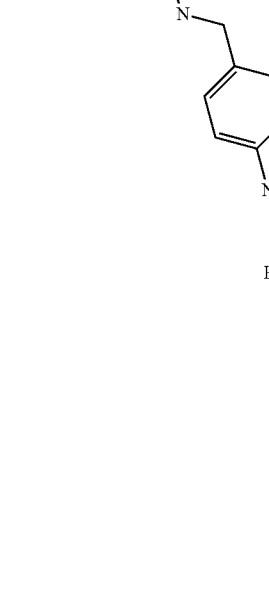 | 1. 4733<br>2. 578.32 |
| 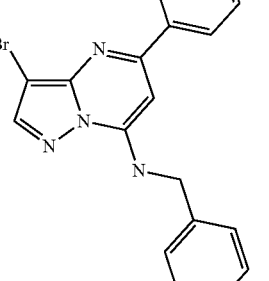 | 1. 4734<br>2. 578.32 |

TABLE 47-continued
| Product | 1. Ex.<br>2. m/z |
|---|---|
| 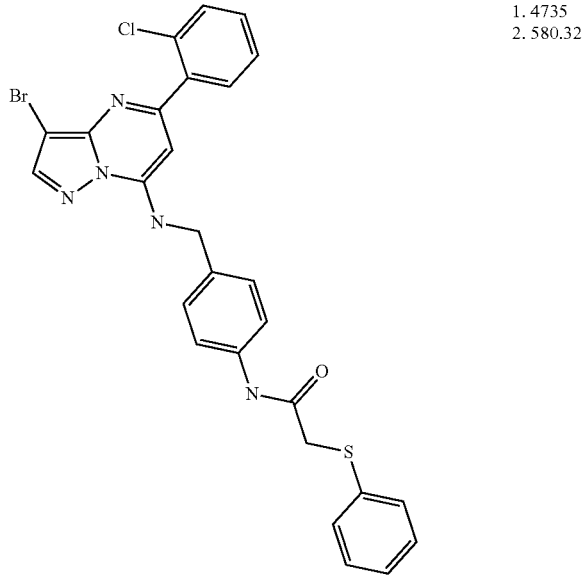 | 1. 4735<br>2. 580.32 |
| 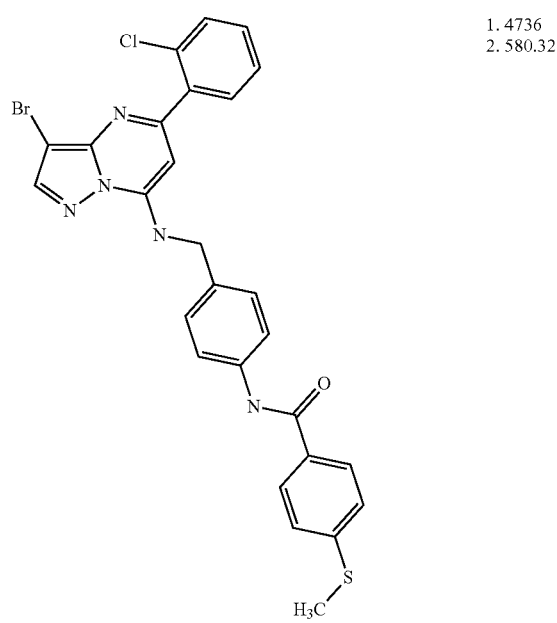 | 1. 4736<br>2. 580.32 |

TABLE 47-continued
| Product | 1. Ex.<br>2. m/z |
|---|---|
| 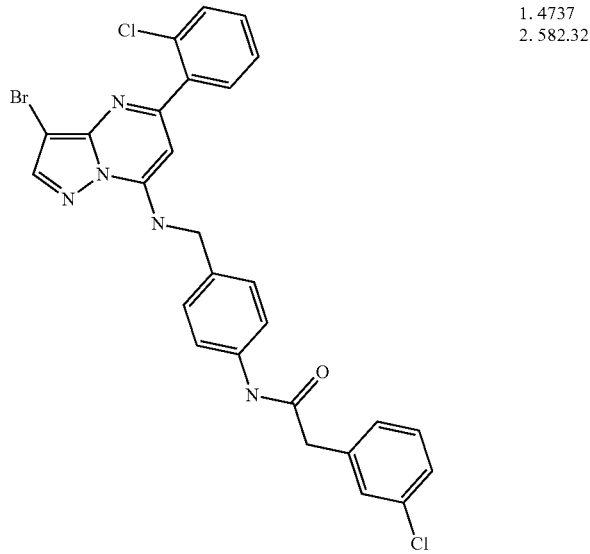 | 1. 4737<br>2. 582.32 |
| 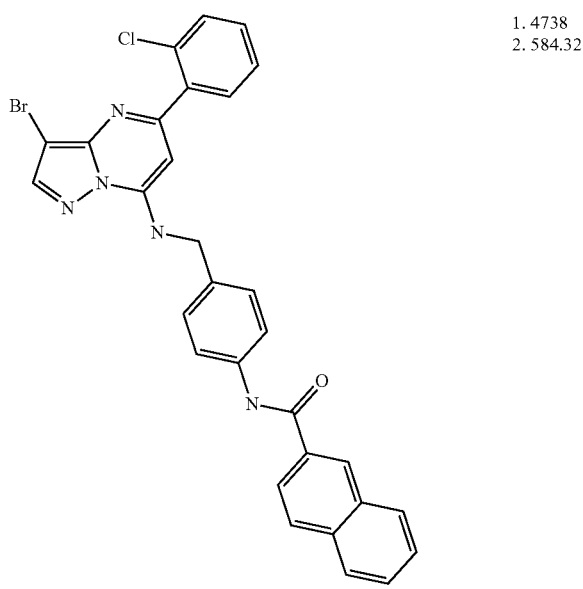 | 1. 4738<br>2. 584.32 |

TABLE 47-continued
| Product | 1. Ex.<br>2. m/z |
|---|---|
| 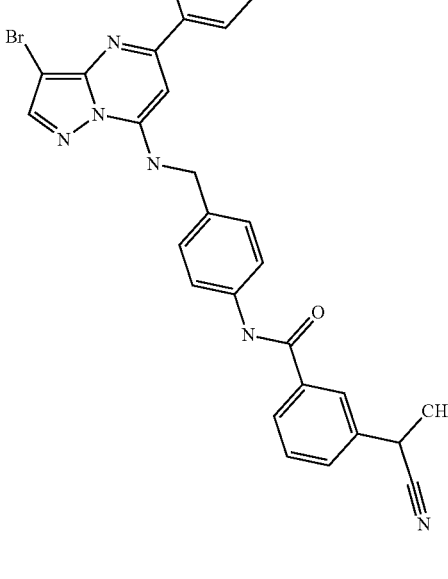 | 1. 4739<br>2. 585.32 |
| 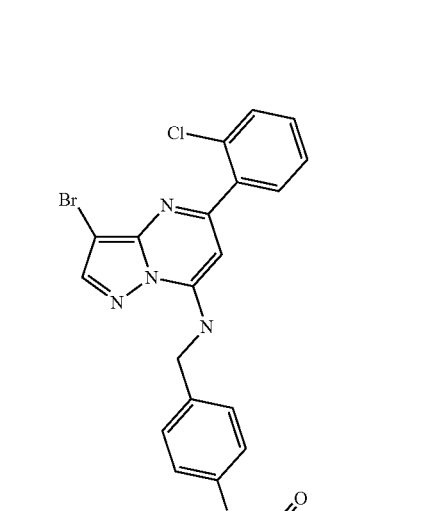 | 1. 4740<br>2. 588.32 |

TABLE 47-continued
| Product | 1. Ex.<br>2. m/z |
|---|---|
| 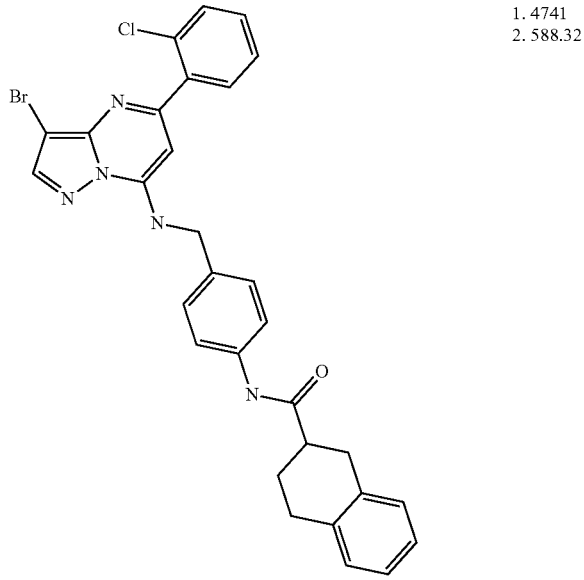 | 1. 4741<br>2. 588.32 |
| 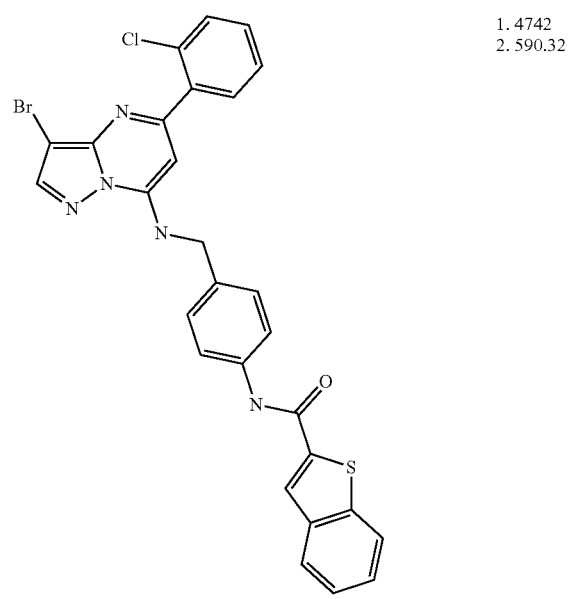 | 1. 4742<br>2. 590.32 |

TABLE 47-continued
| Product | 1. Ex.<br>2. m/z |
|---|---|
| 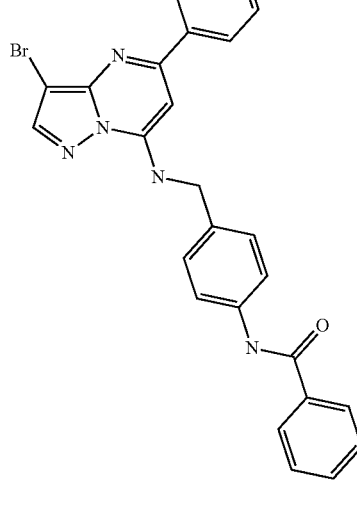 | 1. 4743<br>2. 591.33 |
| 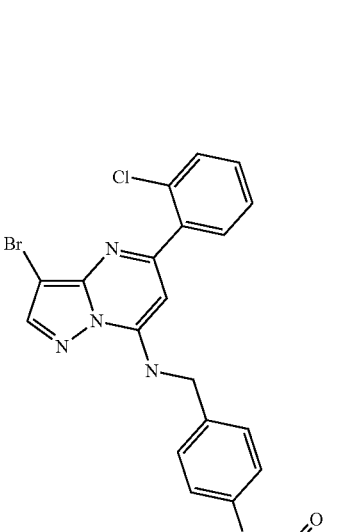 | 1. 4744<br>2. 592.33 |

TABLE 47-continued
| Product | 1. Ex.<br>2. m/z |
|---|---|
| 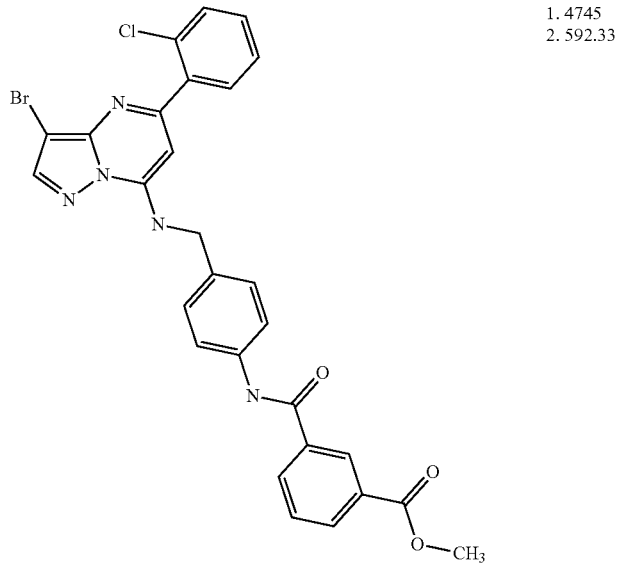 | 1. 4745<br>2. 592.33 |
| 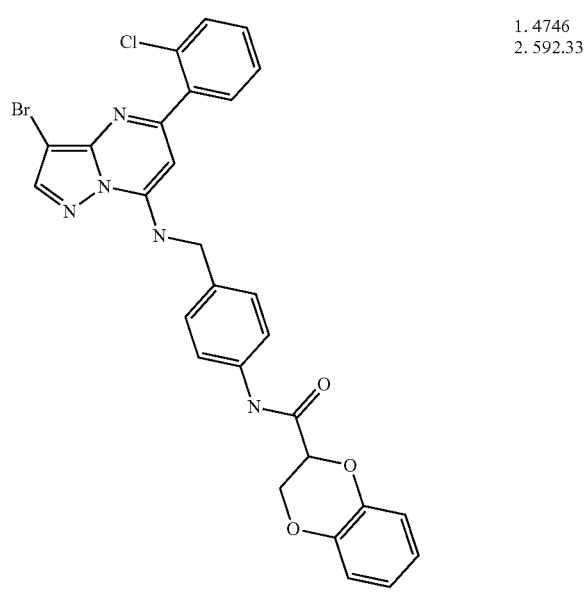 | 1. 4746<br>2. 592.33 |

TABLE 47-continued
| Product | 1. Ex.<br>2. m/z |
|---|---|
| 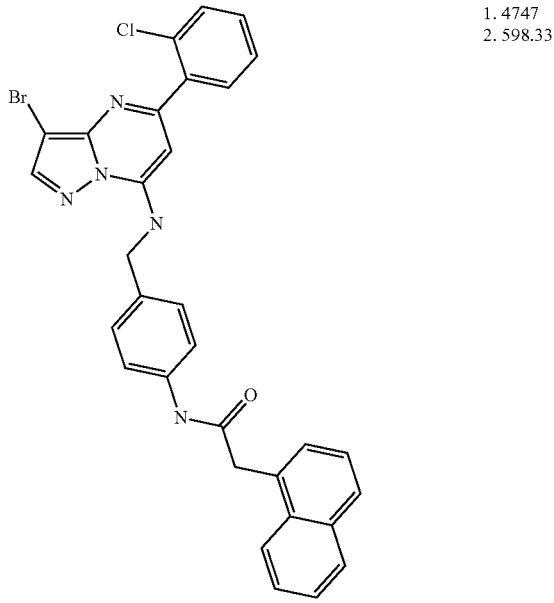 | 1. 4747<br>2. 598.33 |
| 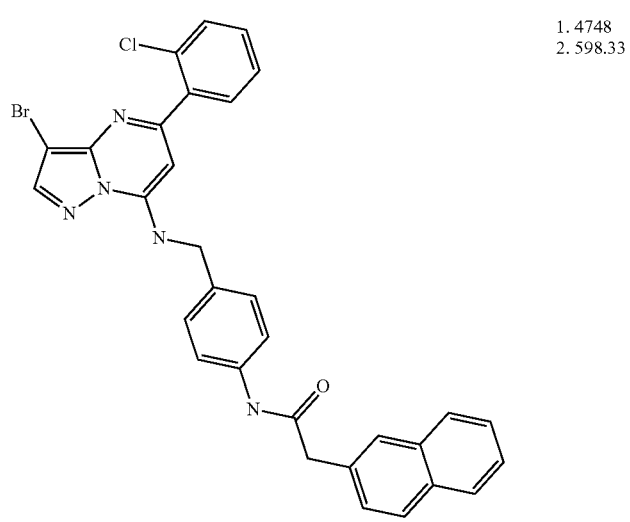 | 1. 4748<br>2. 598.33 |

TABLE 47-continued
| Product | 1. Ex.<br>2. m/z |
|---------|------------------|
| 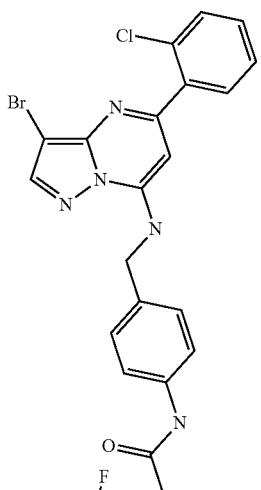 | 1. 4749<br>2. 602.33 |
| | 1. 4750<br>2. 602.33 |

TABLE 47-continued
| Product | 1. Ex.<br>2. m/z |
|---|---|
| 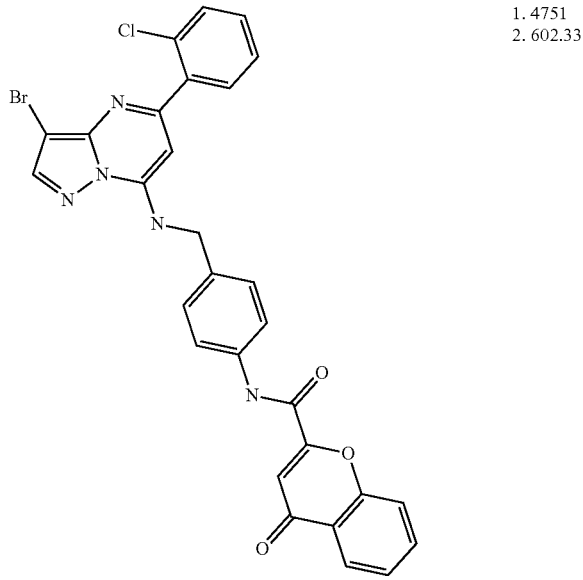 | 1. 4751<br>2. 602.33 |
| 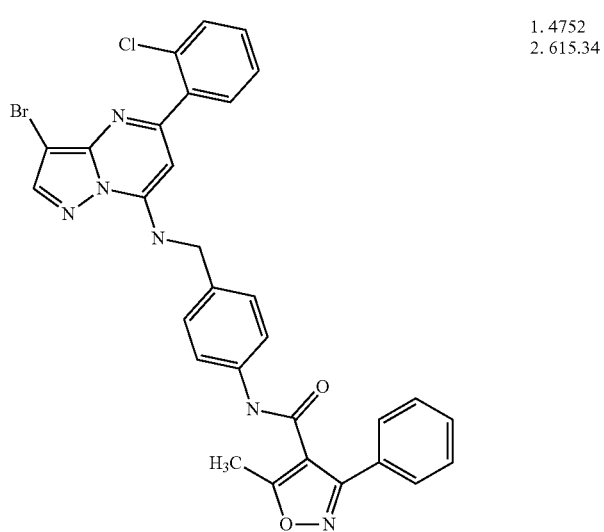 | 1. 4752<br>2. 615.34 |

TABLE 47-continued
| Product | 1. Ex.<br>2. m/z |
|---|---|
| 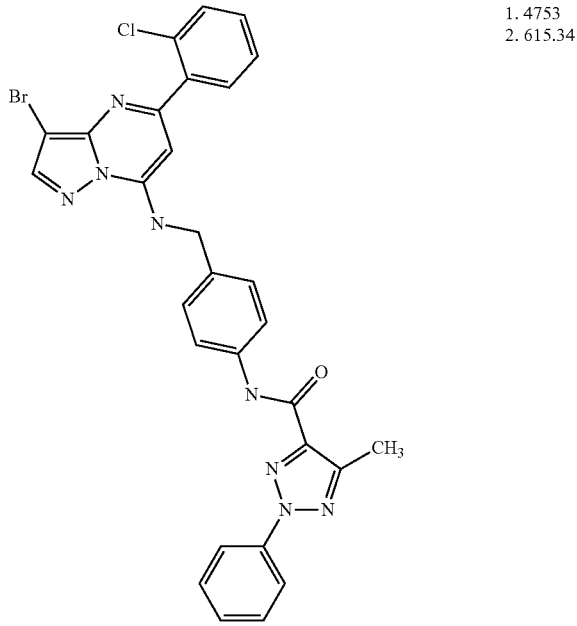 | 1. 4753<br>2. 615.34 |
| 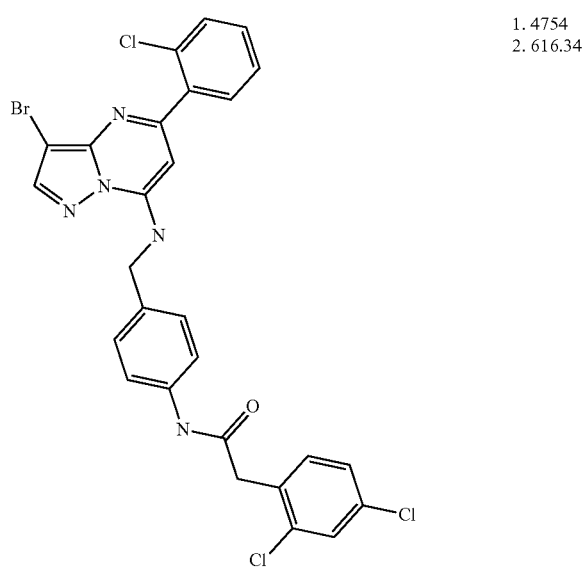 | 1. 4754<br>2. 616.34 |

TABLE 47-continued
| Product | 1. Ex.<br>2. m/z |
|---|---|
| 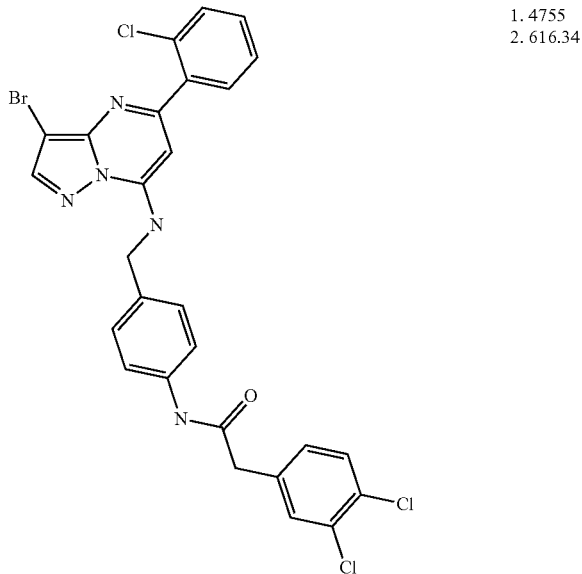 | 1. 4755<br>2. 616.34 |
| 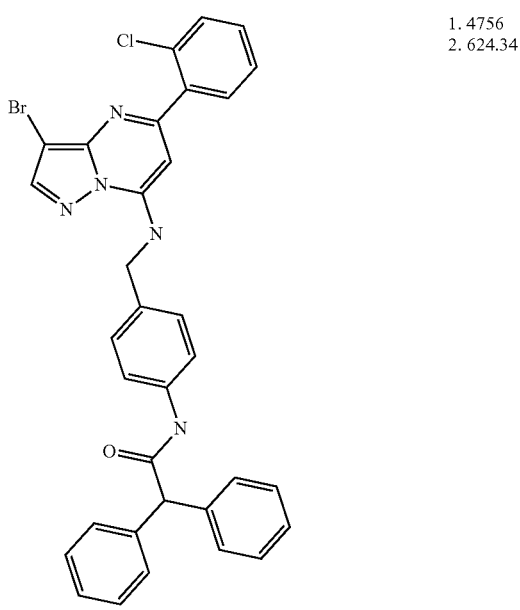 | 1. 4756<br>2. 624.34 |

TABLE 47-continued
| Product | 1. Ex.<br>2. m/z |
|---|---|
| 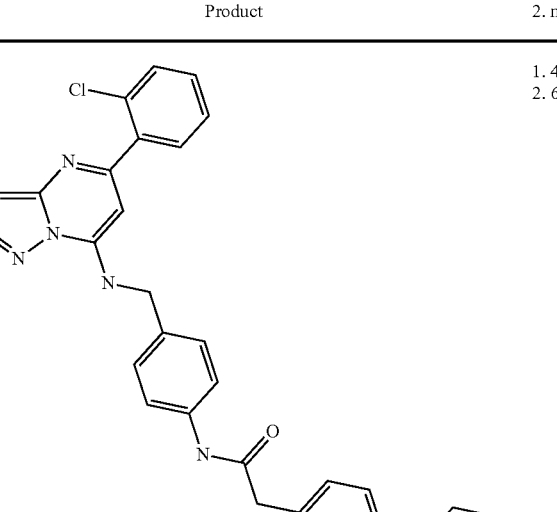 | 1. 4757<br>2. 624.34 |
| 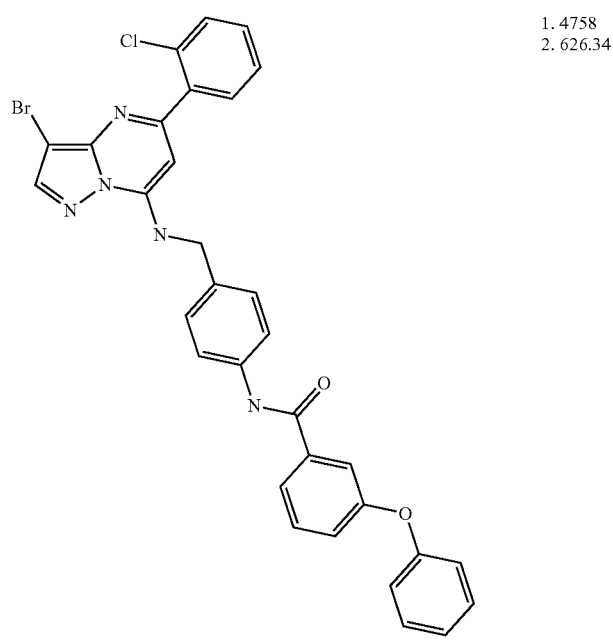 | 1. 4758<br>2. 626.34 |

TABLE 47-continued
| Product | 1. Ex.<br>2. m/z |
|---|---|
| 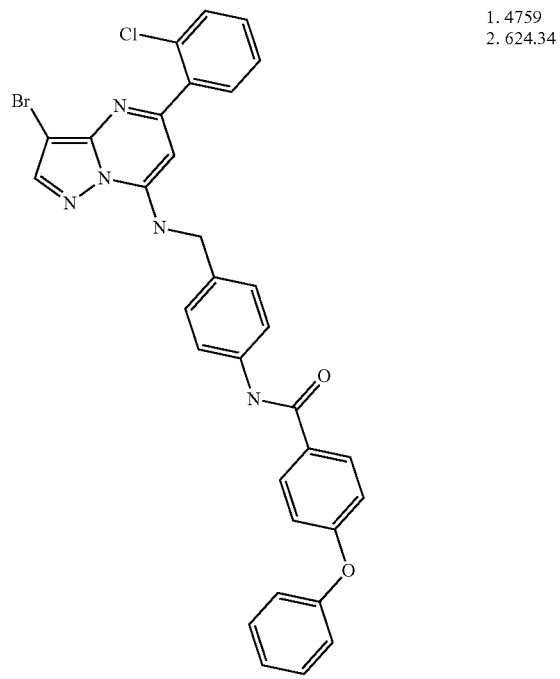 | 1. 4759<br>2. 624.34 |
| | 1. 4760<br>2. 626.34 |

TABLE 47-continued

| Product | 1. Ex. 2. m/z |
|---|---|
| (structure) | 1. 4761 2. 638.35 |
| (structure) | 1. 4762 2. 472.26 |
| (structure) | 1. 4763 2. 534.29 |

TABLE 48
| Product | 1. Ex.<br>2. m/z |
|---|---|
| 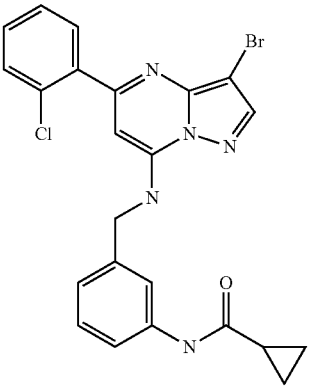 [SMILES: O=C(Nc1cccc(CNc2cc(-c3ccccc3Cl)nc3c(Br)cnn23)c1)C1CC1] | 1. 4801<br>2. 498.27 |
| 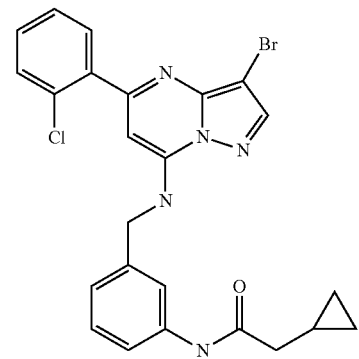 [SMILES: O=C(CC1CC1)Nc1cccc(CNc2cc(-c3ccccc3Cl)nc3c(Br)cnn23)c1] | 1. 4802<br>2. 512.28 |
| 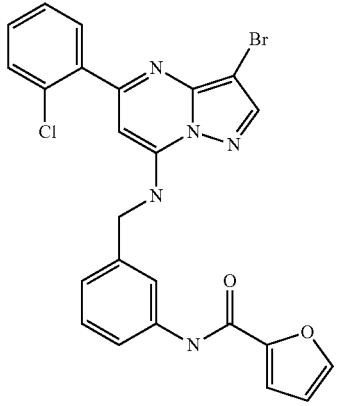 [SMILES: O=C(Nc1cccc(CNc2cc(-c3ccccc3Cl)nc3c(Br)cnn23)c1)c1ccco1] | 1. 4803<br>2. 524.29 |
| 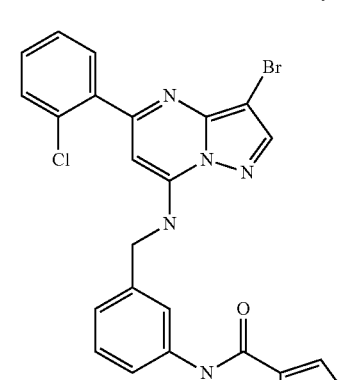 | 1. 4804<br>2. 524.29 |
TABLE 48-continued
| Product | 1. Ex.<br>2. m/z |
|---|---|
|  | 1. 4805<br>2. 526.29 |
| 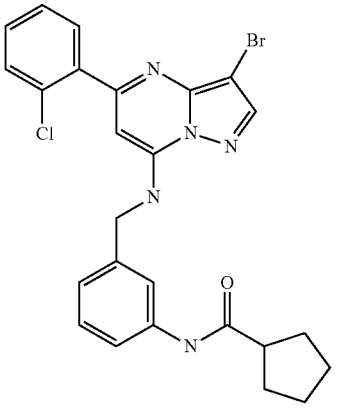 [SMILES: O=C(Nc1cccc(CNc2cc(-c3ccccc3Cl)nc3c(Br)cnn23)c1)C1CCCC1] | 1. 4806<br>2. 528.26 |
| 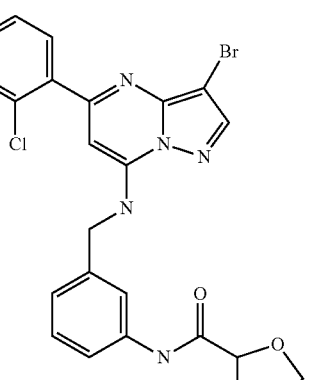 | 1. 4807<br>2. 528.29 |

TABLE 48-continued

| Product | 1. Ex. 2. m/z |
|---|---|
| (structure) | 1. 4808  2. 528.29 |
| (structure) | 1. 4809  2. 540.3 |
| (structure) | 1. 4810  2. 540.3 |

TABLE 48-continued

| Product | 1. Ex. 2. m/z |
|---|---|
| (structure) | 1. 4811  2. 544.3 |
| (structure) | 1. 4812  2. 548.3 |
| (structure) | 1. 4813  2. 553.3 |
| (structure) | 1. 4814  2. 554.3 |

TABLE 48-continued
| Product | 1. Ex. 2. m/z |
|---|---|
| 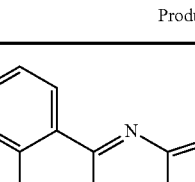 | 1. 4815 2. 560.31 |
| 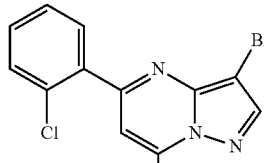 | 1. 4816 2. 562.31 |
| 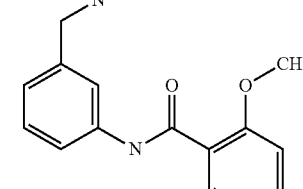 | 1. 4817 2. 562.31 |
TABLE 48-continued
| Product | 1. Ex. 2. m/z |
|---|---|
| 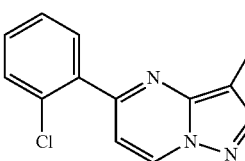 | 1. 4818 2. 564.31 |
| 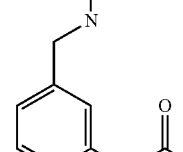 | 1. 4819 2. 564.31 |
| 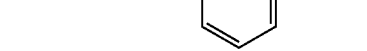 | 1. 4820 2. 568.31 |

TABLE 48-continued
| Product | 1. Ex. 2. m/z |
|---|---|
| 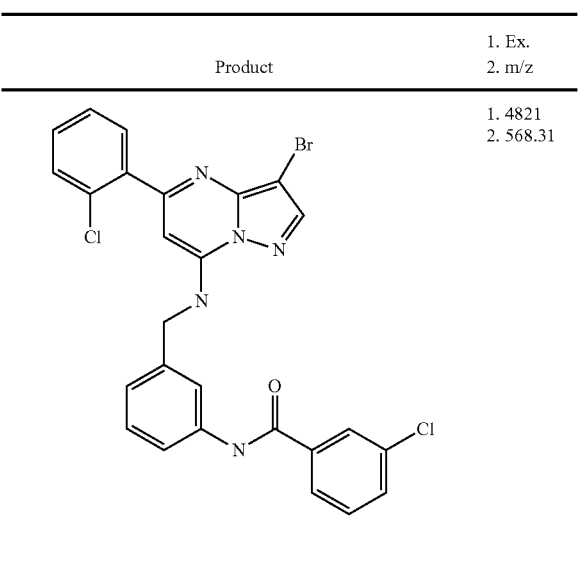 | 1. 4821 2. 568.31 |
| | 1. 4822 2. 573.32 |
| 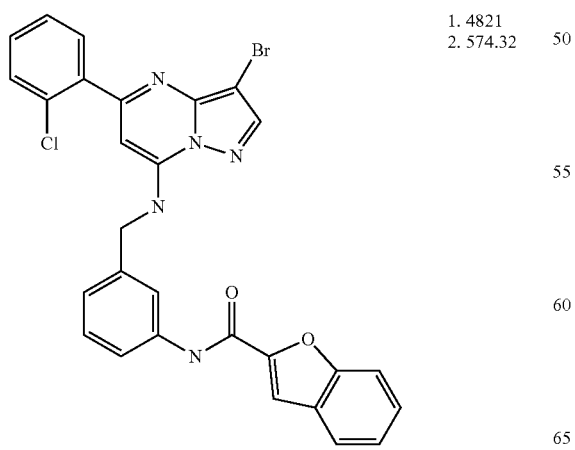 | 1. 4821 2. 574.32 |
TABLE 48-continued
| Product | 1. Ex. 2. m/z |
|---|---|
| 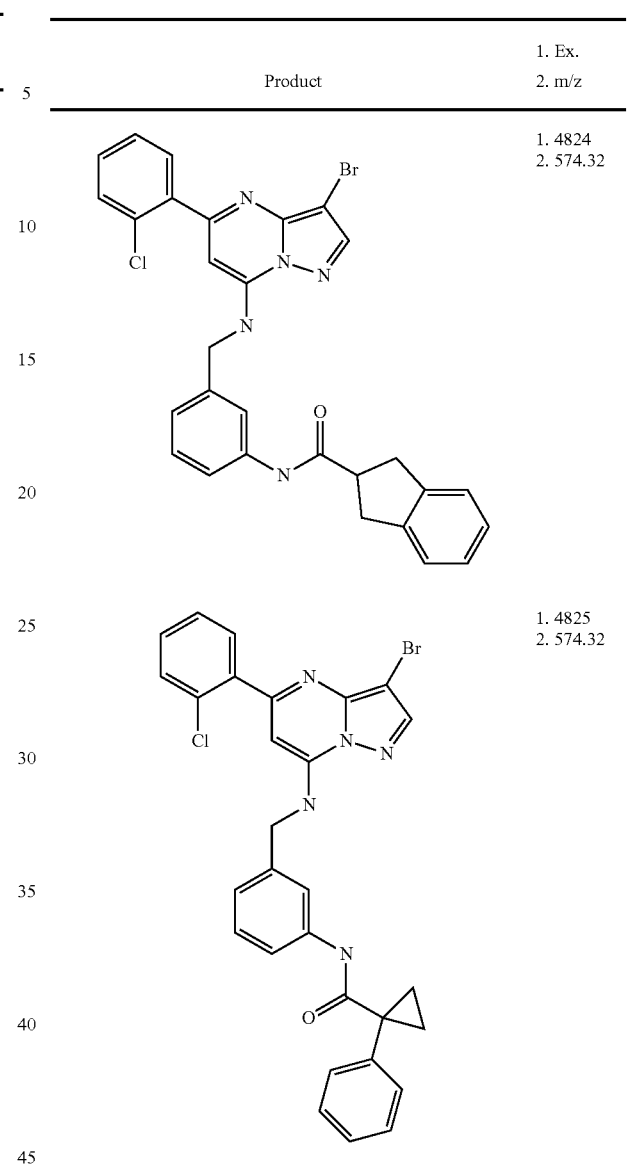 | 1. 4824 2. 574.32 |
| | 1. 4825 2. 574.32 |
| | 1. 4826 2. 574.32 |

TABLE 48-continued
| Product | 1. Ex.<br>2. m/z |
|---|---|
| 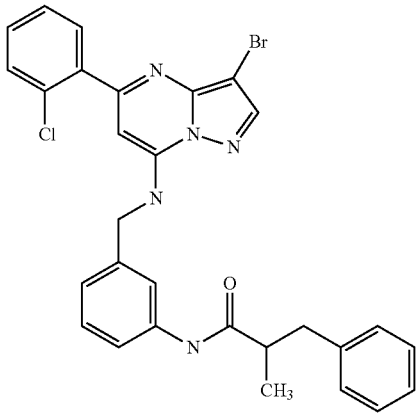 | 1. 4828<br>2. 576.32 |
| 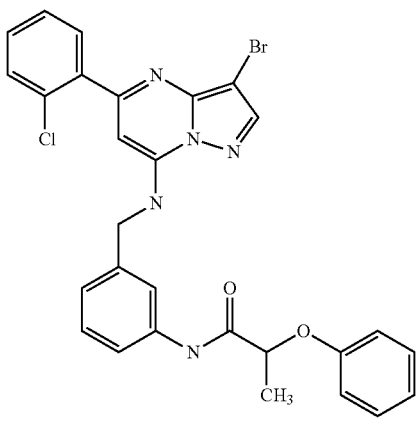 [SMILES: CC(Oc1ccccc1)C(=O)Nc1cccc(CNc2cc(-c3ccccc3Cl)nc3c(Br)cnn23)c1] | 1. 4829<br>2. 578.32 |
| 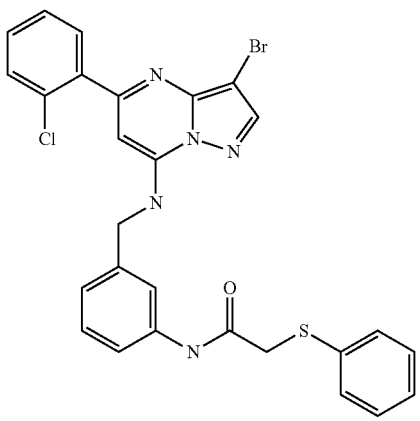 [SMILES: O=C(CSc1ccccc1)Nc1cccc(CNc2cc(-c3ccccc3Cl)nc3c(Br)cnn23)c1] | 1. 4829<br>2. 580.32 |
| 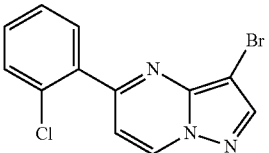 | 1. 4830<br>2. 584.32 |
| 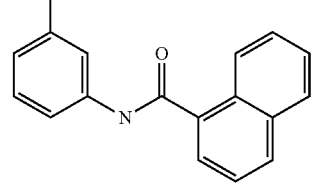 | 1. 4831<br>2. 588.32 |
| 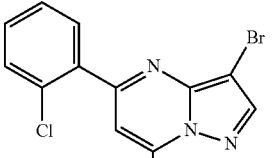 | 1. 4832<br>2. 602.33 |

TABLE 48-continued

| Product | 1. Ex. 2. m/z |
|---|---|
| (structure) | 1. 4833 2. 602.33 |
| (structure) | 1. 4834 2. 602.33 |
| (structure) | 1. 4835 2. 610.34 |
| (structure) | 1. 4836 2. 616.34 |

TABLE 48-continued
| Product | 1. Ex. 2. m/z |
|---|---|
| 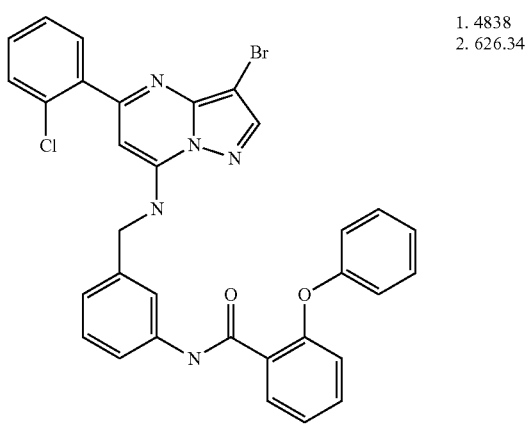 | 1. 4837<br>2. 624.34 |
| | 1. 4838<br>2. 626.34 |
TABLE 48-continued
| Product | 1. Ex. 2. m/z |
|---|---|
| 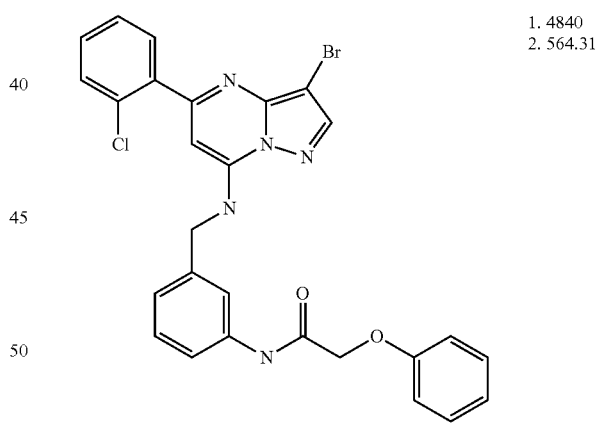 | 1. 4839<br>2. 626.34 |
| | 1. 4840<br>2. 564.31 |

TABLE 48-continued
| Product | 1. Ex.<br>2. m/z |
|---|---|
| 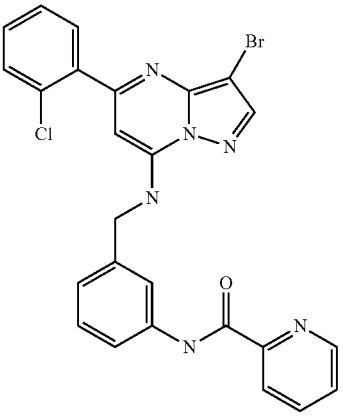 | 1. 4841<br>2. 535.29 |
| 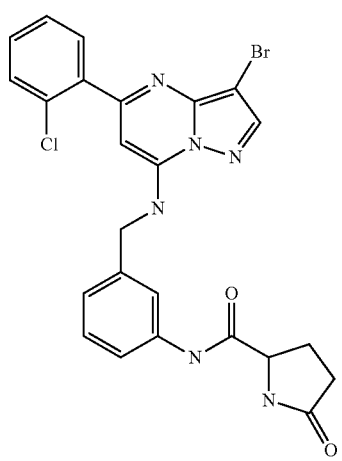 | 1. 4842<br>2. 541.3 |
TABLE 48-continued
| Product | 1. Ex.<br>2. m/z |
|---|---|
| 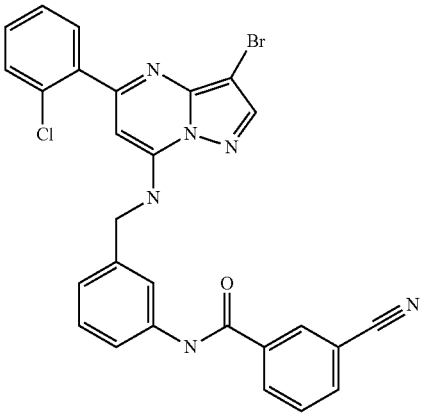 | 1. 4843<br>2. 559.31 |
| 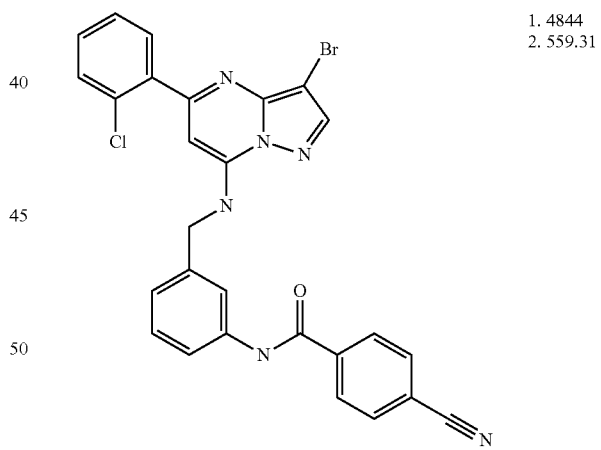 | 1. 4844<br>2. 559.31 |

TABLE 48-continued
| Product | 1. Ex. 2. m/z |
|---|---|
| 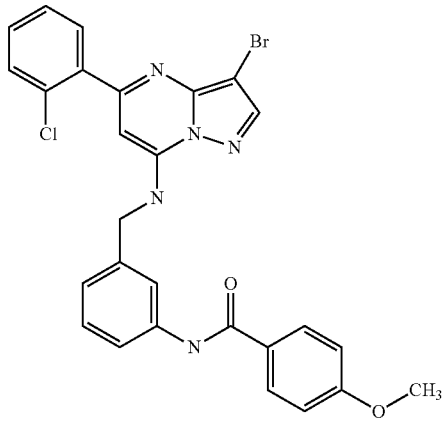 | 1. 4845 2. 564.31 |
| 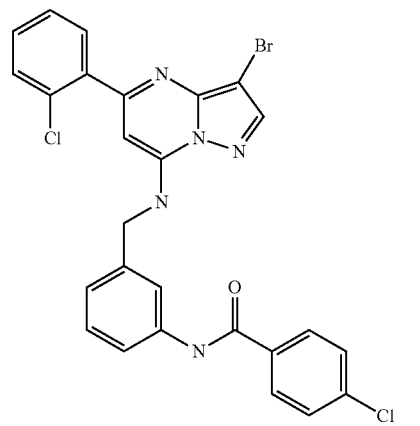 [SMILES: O=C(Nc1cccc(CNc2cc(-c3ccccc3Cl)nc3c(Br)cnn23)c1)c1ccc(Cl)cc1] | 1. 4846 2. 568.31 |
| 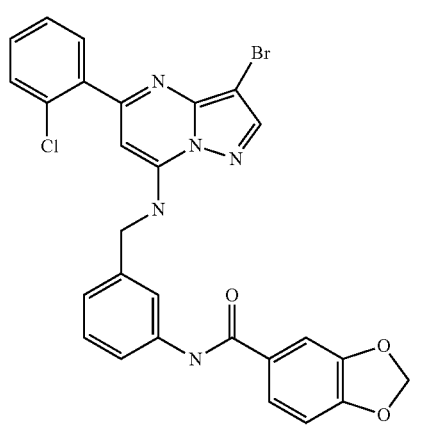 [SMILES: O=C(Nc1cccc(CNc2cc(-c3ccccc3Cl)nc3c(Br)cnn23)c1)c1ccc2c(c1)OCO2] | 1. 4847 2. 578.32 |
TABLE 48-continued
| Product | 1. Ex. 2. m/z |
|---|---|
| 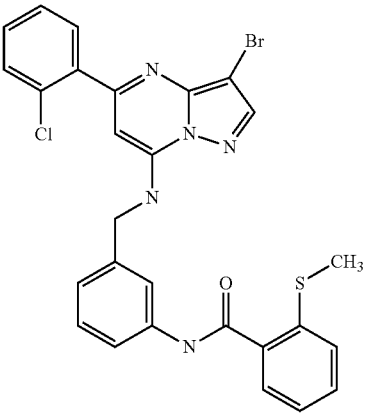 [SMILES: CSc1ccccc1C(=O)Nc1cccc(CNc2cc(-c3ccccc3Cl)nc3c(Br)cnn23)c1] | 1. 4848 2. 580.32 |
| 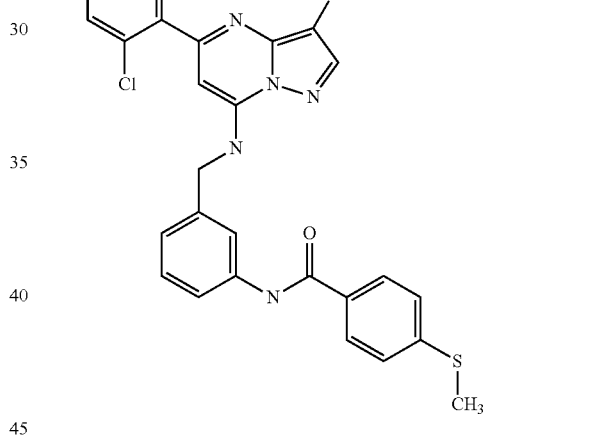 | 1. 4849 2. 580.32 |
| 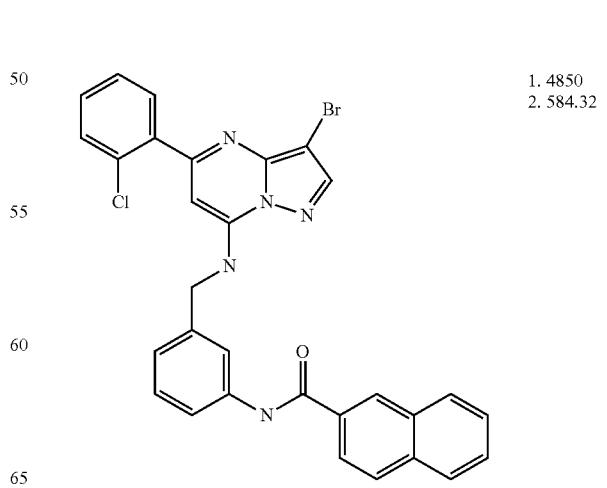 | 1. 4850 2. 584.32 |

TABLE 48-continued

| Product | 1. Ex.<br>2. m/z |
|---|---|
| (structure) | 1. 4851<br>2. 590.32 |
| (structure) | 1. 4852<br>2. 591.33 |
| (structure) | 1. 4853<br>2. 610.34 |
| (structure) | 1. 4854<br>2. 615.34 |
| (structure) | 1. 4855<br>2. 615.34 |
| (structure) | 1. 4856<br>2. 616.34 |

TABLE 48-continued
| Product | 1. Ex. 2. m/z |
|---|---|
| 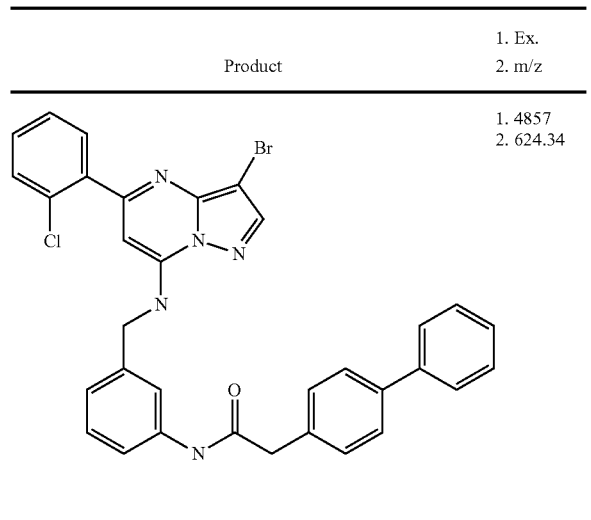 | 1. 4857 2. 624.34 |
| 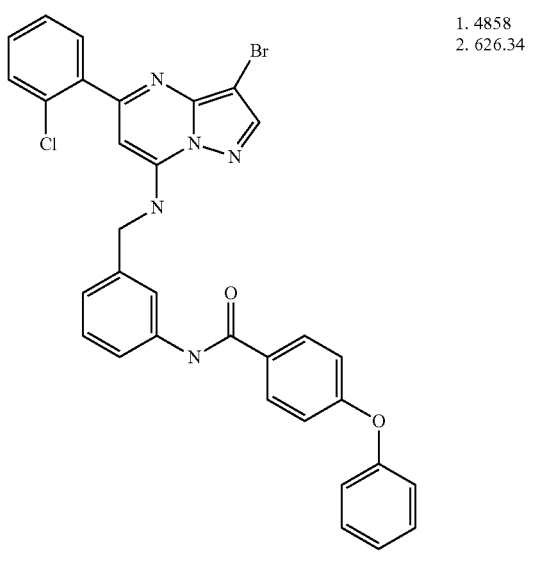 | 1. 4858 2. 626.34 |
| 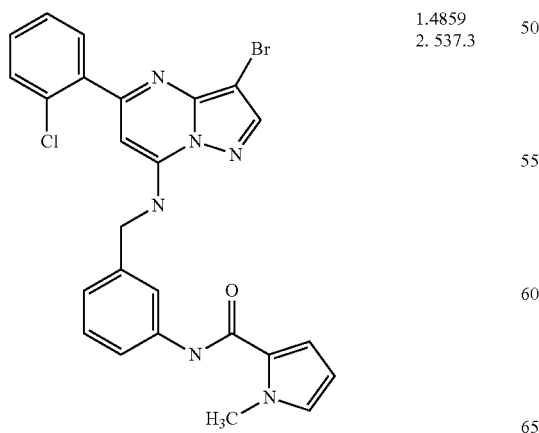 | 1. 4859 2. 537.3 |
TABLE 48-continued
| Product | 1. Ex. 2. m/z |
|---|---|
| 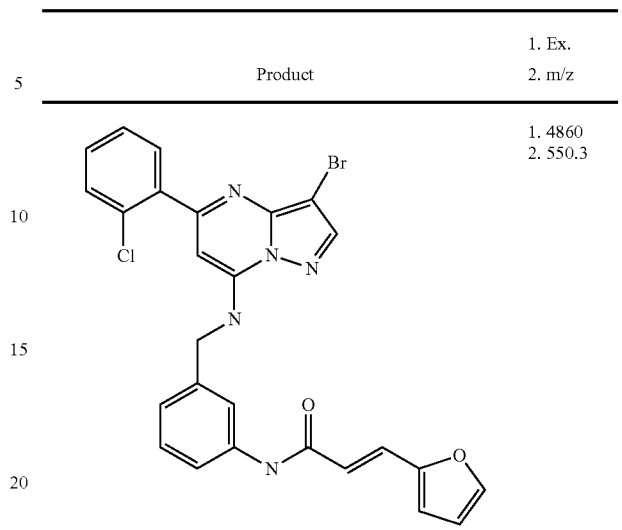 | 1. 4860 2. 550.3 |
| 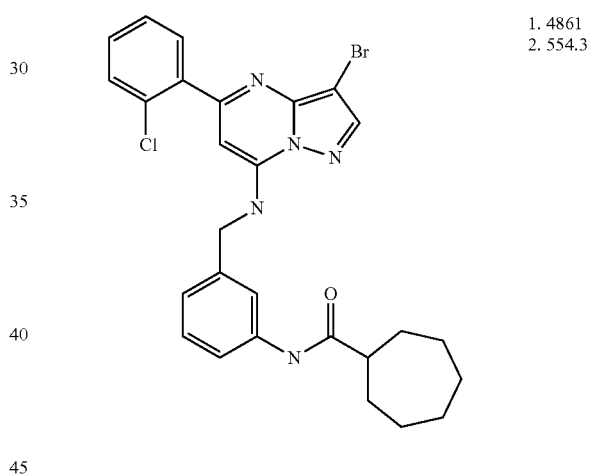 | 1. 4861 2. 554.3 |
| 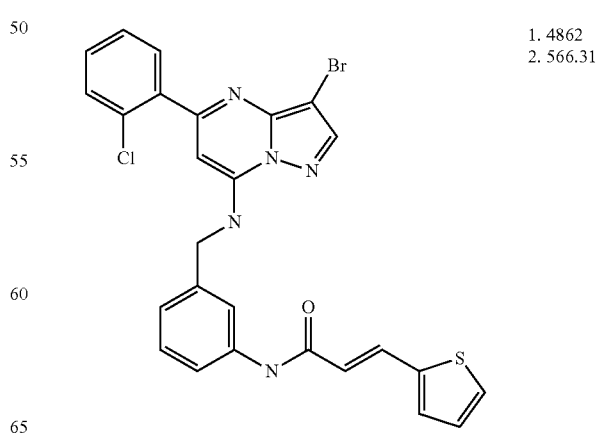 | 1. 4862 2. 566.31 |

TABLE 48-continued

| Product | 1. Ex.<br>2. m/z |
|---|---|
| (structure) | 1. 4863<br>2. 566.31 |
| (structure) | 1. 4864<br>2. 578.32 |
| (structure) | 1. 4865<br>2. 582.32 |
| (structure) | 1. 4866<br>2. 587.32 |
| (structure) | 1. 4867<br>2. 588.32 |
| (structure) | 1. 4868<br>2. 592.33 |
| (structure) | 1. 4869<br>2. 592.33 |

TABLE 48-continued
| Product | 1. Ex.<br>2. m/z |
|---|---|
| 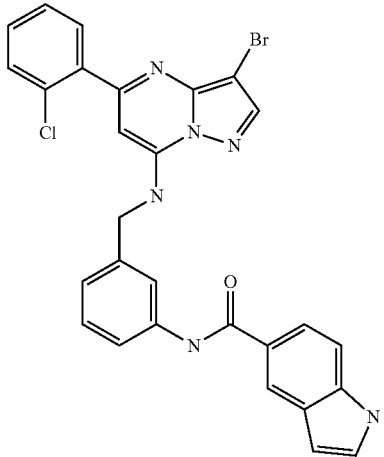 [SMILES: O=C(Nc1cccc(CNc2cc(-c3ccccc3Cl)nc3c(Br)cnn23)c1)c1ccc2[nH]ccc2c1] | 1. 4870<br>2. 573.32 |
| 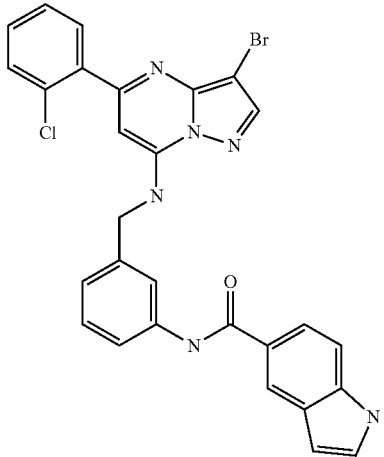 [SMILES: O=C(Nc1cccc(CNc2cc(-c3ccccc3Cl)nc3c(Br)cnn23)c1)c1ccc2[nH]ccc2c1] | 1. 4871<br>2. 616.34 |
| 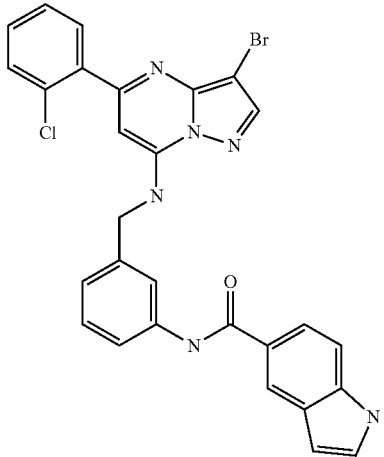 [SMILES: O=C(Nc1cccc(CNc2cc(-c3ccccc3Cl)nc3c(Br)cnn23)c1)c1ccc2[nH]ccc2c1] | 1. 4872<br>2. 616.34 |
TABLE 48-continued
| Product | 1. Ex.<br>2. m/z |
|---|---|
| 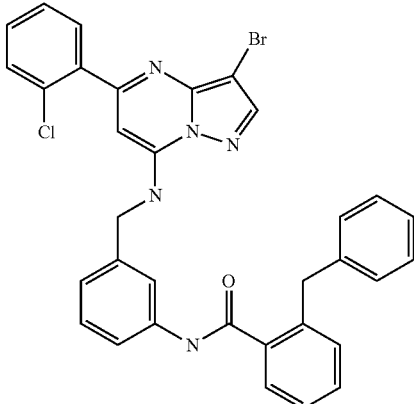 | 1. 4873<br>2. 624.34 |
| 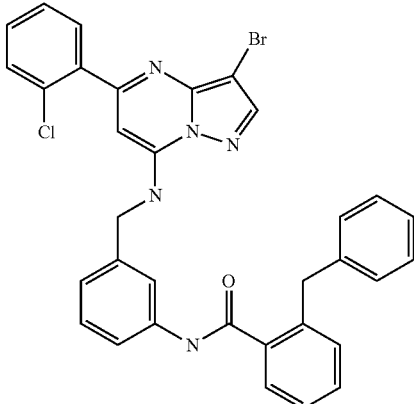 | 1. 4874<br>2. 638.35 |
| 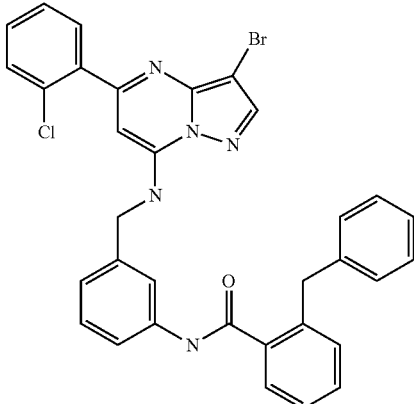 | 1. 4875<br>2. 546.3 |

TABLE 48-continued
| Product | 1. Ex.<br>2. m/z |
|---|---|
| | 1. 4876<br>2. 594.33 |
| 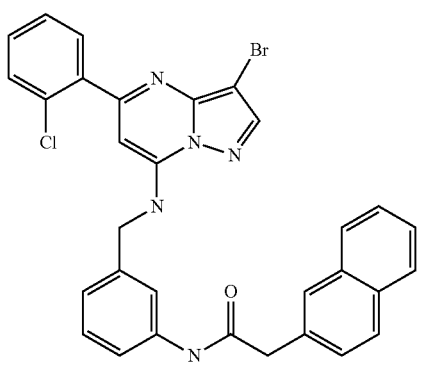 [SMILES: O=C(Cc1ccc2ccccc2c1)Nc1cccc(CNc2cc(-c3ccccc3Cl)nc3c(Br)cnn23)c1] | 1. 4877<br>2. 598.33 |
| | 1. 4878<br>2. 592.33 |
TABLE 48-continued
| Product | 1. Ex.<br>2. m/z |
|---|---|
| | 1. 4879<br>2. 569.31 |
| | 1. 4880<br>2. 583.32 |
TABLE 49
| Product | 1. Ex.<br>2. m/z |
|---|---|
| | 1. 4901<br>2. 490.27 |

TABLE 49-continued
| Product | 1. Ex.<br>2. m/z |
|---|---|
| 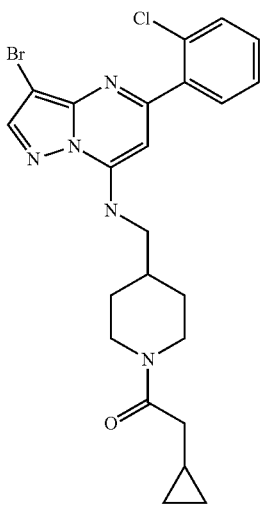 [SMILES: O=C(CC1CC1)N1CCC(CNc2cc(-c3ccccc3Cl)nc3c(Br)cnn23)CC1] | 1. 4902<br>2. 504.28 |
| 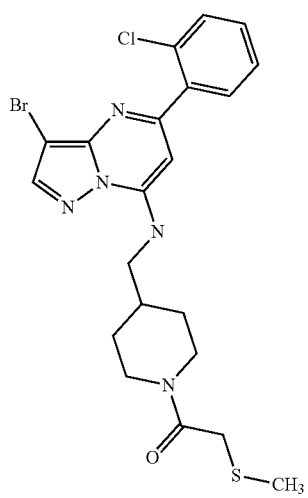 [SMILES: CSCC(=O)N1CCC(CNc2cc(-c3ccccc3Cl)nc3c(Br)cnn23)CC1] | 1. 4903<br>2. 510.28 |
| 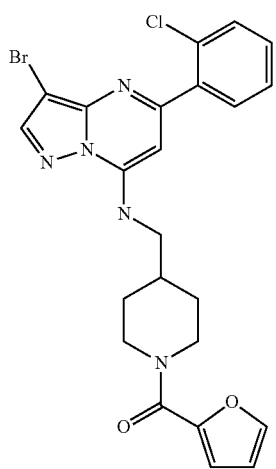 [SMILES: O=C(c1ccco1)N1CCC(CNc2cc(-c3ccccc3Cl)nc3c(Br)cnn23)CC1] | 1. 4904<br>2. 516.28 |
TABLE 49-continued
| Product | 1. Ex.<br>2. m/z |
|---|---|
| 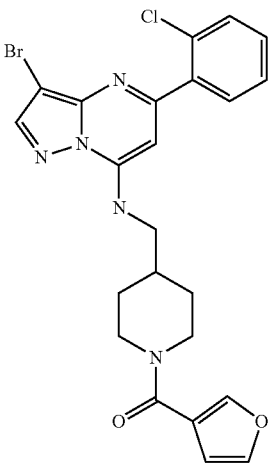 [SMILES: O=C(c1ccoc1)N1CCC(CNc2cc(-c3ccccc3Cl)nc3c(Br)cnn23)CC1] | 1. 4905<br>2. 516.28 |
| 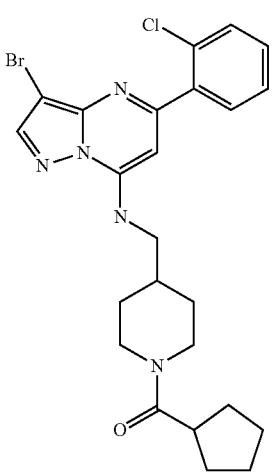 [SMILES: O=C(C1CCCC1)N1CCC(CNc2cc(-c3ccccc3Cl)nc3c(Br)cnn23)CC1] | 1. 4906<br>2. 518.28 |
| 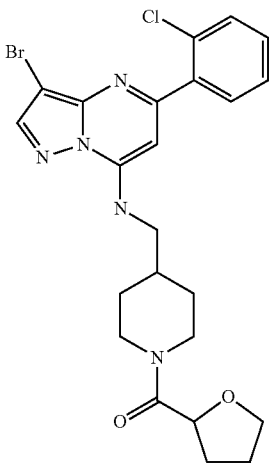 [SMILES: O=C(C1CCCO1)N1CCC(CNc2cc(-c3ccccc3Cl)nc3c(Br)cnn23)CC1] | 1. 4907<br>2. 520.29 |

TABLE 49-continued
| Product | 1. Ex.<br>2. m/z |
|---|---|
| 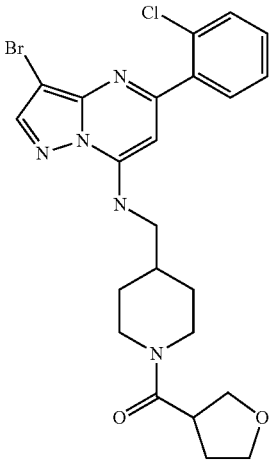 | 1. 4908<br>2. 520.29 |
| 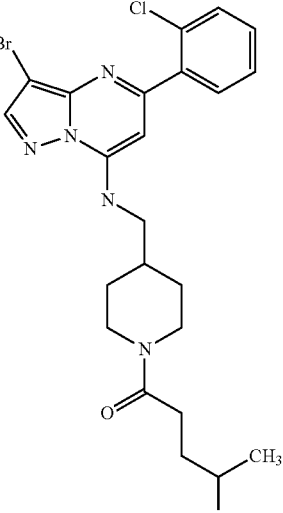 | 1. 4909<br>2. 520.29 |
| 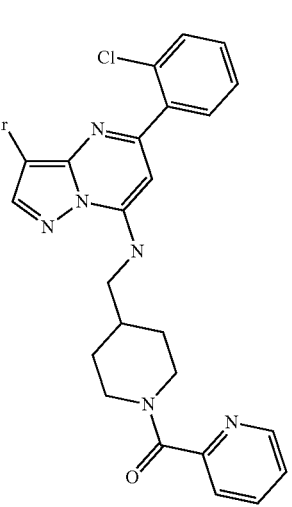 | 1. 4910<br>2. 527.29 |
TABLE 49-continued
| Product | 1. Ex.<br>2. m/z |
|---|---|
| 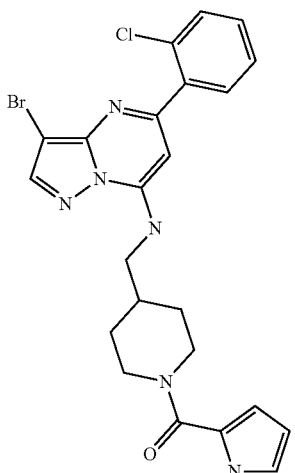 | 1. 4911<br>2. 529.29 |
| 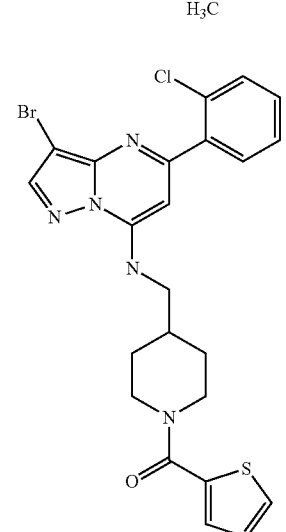 | 1. 4912<br>2. 532.29 |
| 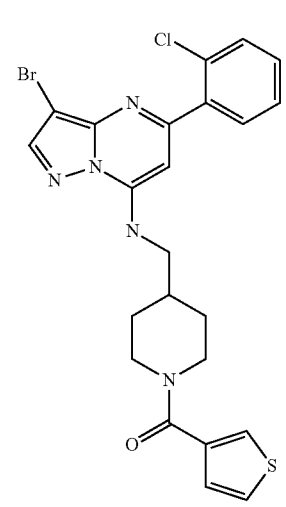 [SMILES: O=C(c1ccsc1)N1CCC(CNc2cc(-c3ccccc3Cl)nc3c(Br)cnn23)CC1] | 1. 4913<br>2. 532.29 |

TABLE 49-continued

| Product | 1. Ex. 2. m/z |
|---|---|
| (structure) | 1. 4914 2. 533.29 |
| (structure) | 1. 4915 2. 536.29 |
| (structure) | 1. 4916 2. 538.3 |
| (structure) | 1. 4917 2. 540.3 |

TABLE 49-continued
| Product | 1. Ex. 2. m/z |
|---|---|
| 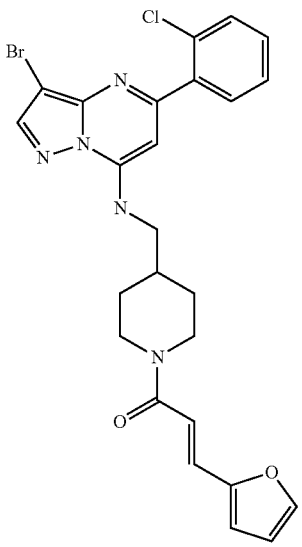 [SMILES: O=C(/C=C/c1ccco1)N1CCC(CNc2cc(-c3ccccc3Cl)nc3c(Br)cnn23)CC1] | 1. 4918 2. 542.3 |
| 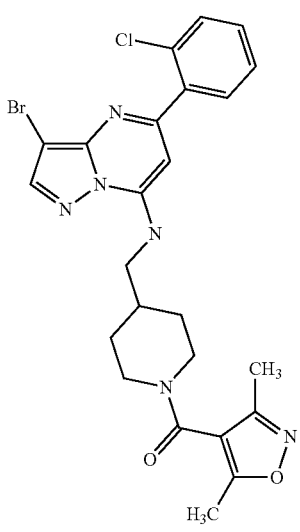 [SMILES: Cc1noc(C)c1C(=O)N1CCC(CNc2cc(-c3ccccc3Cl)nc3c(Br)cnn23)CC1] | 1. 4919 2. 545.3 |
| 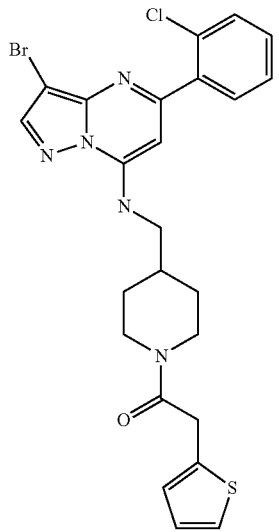 [SMILES: O=C(Cc1cccs1)N1CCC(CNc2cc(-c3ccccc3Cl)nc3c(Br)cnn23)CC1] | 1. 4920 2. 546.3 |
TABLE 49-continued
| Product | 1. Ex. 2. m/z |
|---|---|
| 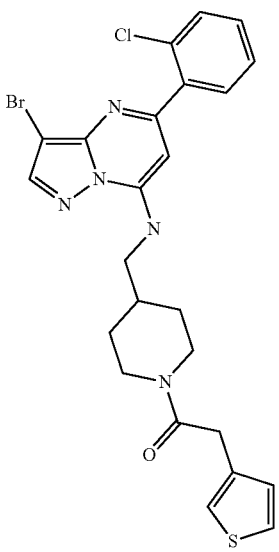 [SMILES: O=C(Cc1ccsc1)N1CCC(CNc2cc(-c3ccccc3Cl)nc3c(Br)cnn23)CC1] | 1. 4921 2. 546.3 |
| 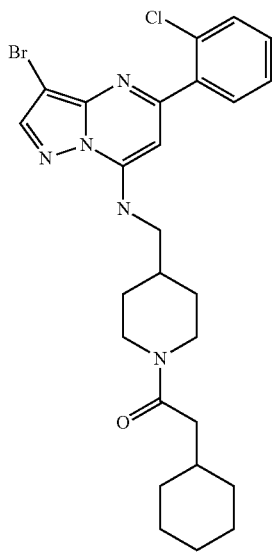 [SMILES: O=C(CC1CCCCC1)N1CCC(CNc2cc(-c3ccccc3Cl)nc3c(Br)cnn23)CC1] | 1. 4922 2. 546.3 |
| 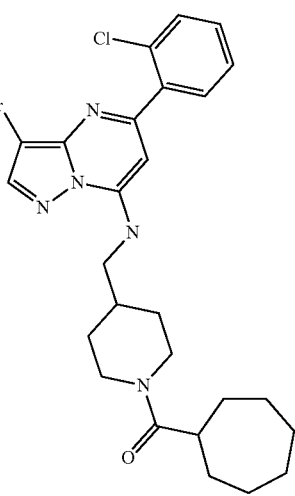 | 1. 4923 2. 546.3 |

TABLE 49-continued

| Product | 1. Ex. 2. m/z |
|---|---|
| 3-bromo-5-(2-chlorophenyl)-N-((1-(3-cyanobenzoyl)piperidin-4-yl)methyl)pyrazolo[1,5-a]pyrimidin-7-amine | 1. 4924<br>2. 551.3 |
| 3-bromo-5-(2-chlorophenyl)-N-((1-(4-cyanobenzoyl)piperidin-4-yl)methyl)pyrazolo[1,5-a]pyrimidin-7-amine | 1. 4925<br>2. 551.3 |

TABLE 49-continued

| Product | 1. Ex. 2. m/z |
|---|---|
| 3-bromo-5-(2-chlorophenyl)-N-((1-cinnamoylpiperidin-4-yl)methyl)pyrazolo[1,5-a]pyrimidin-7-amine | 1. 4926<br>2. 552.3 |
| 3-bromo-5-(2-chlorophenyl)-N-((1-(2-phenylpropanoyl)piperidin-4-yl)methyl)pyrazolo[1,5-a]pyrimidin-7-amine | 1. 4927<br>2. 554.3 |

TABLE 49-continued

| Product | 1. Ex. 2. m/z |
|---|---|
| (structure: 3-bromo-5-(2-chlorophenyl)-N-((1-(3-phenylpropanoyl)piperidin-4-yl)methyl)pyrazolo[1,5-a]pyrimidin-7-amine) | 1. 4928 2. 554.3 |
| (structure: 3-bromo-5-(2-chlorophenyl)-N-((1-(2-methoxybenzoyl)piperidin-4-yl)methyl)pyrazolo[1,5-a]pyrimidin-7-amine) | 1. 4929 2. 556.31 |
| (structure: 3-bromo-5-(2-chlorophenyl)-N-((1-(3-methoxybenzoyl)piperidin-4-yl)methyl)pyrazolo[1,5-a]pyrimidin-7-amine) | 1. 4930 2. 556.31 |
| (structure: 3-bromo-5-(2-chlorophenyl)-N-((1-(4-methoxybenzoyl)piperidin-4-yl)methyl)pyrazolo[1,5-a]pyrimidin-7-amine) | 1. 4931 2. 556.31 |
| (structure: 3-bromo-5-(2-chlorophenyl)-N-((1-(2-phenoxyacetyl)piperidin-4-yl)methyl)pyrazolo[1,5-a]pyrimidin-7-amine) | 1. 4932 2. 556.31 |
| (structure: 3-bromo-5-(2-chlorophenyl)-N-((1-((E)-3-(thiophen-2-yl)acryloyl)piperidin-4-yl)methyl)pyrazolo[1,5-a]pyrimidin-7-amine) | 1. 4933 2. 558.31 |

TABLE 49-continued
| Product | 1. Ex. 2. m/z |
|---|---|
| 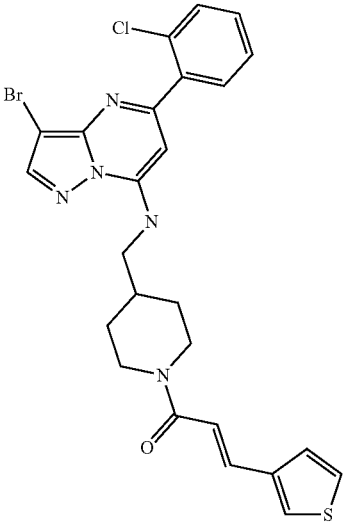 [SMILES: O=C(/C=C/c1ccsc1)N1CCC(CNc2cc(-c3ccccc3Cl)nc3c(Br)cnn23)CC1] | 1. 4934 3. 558.31 |
| 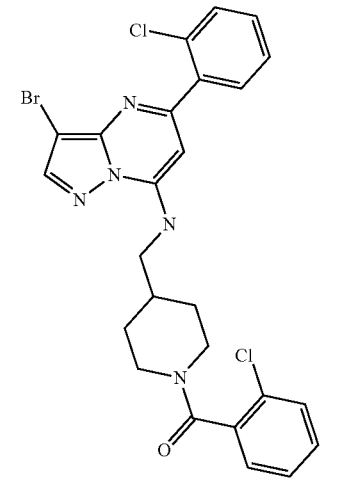 [SMILES: O=C(c1ccccc1Cl)N1CCC(CNc2cc(-c3ccccc3Cl)nc3c(Br)cnn23)CC1] | 1. 4935 2. 560.31 |
| 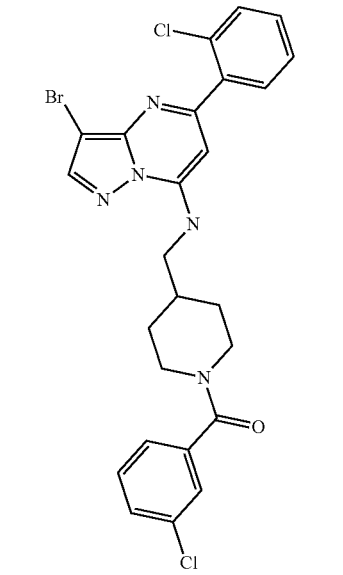 [SMILES: O=C(c1cccc(Cl)c1)N1CCC(CNc2cc(-c3ccccc3Cl)nc3c(Br)cnn23)CC1] | 1. 4936 2. 560.31 |
TABLE 49-continued
| Product | 1. Ex. 2. m/z |
|---|---|
| 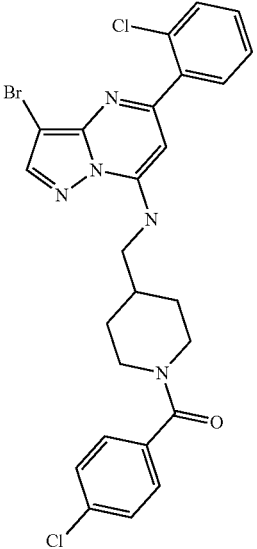 [SMILES: O=C(c1ccc(Cl)cc1)N1CCC(CNc2cc(-c3ccccc3Cl)nc3c(Br)cnn23)CC1] | 1. 4937 2. 560.31 |
| 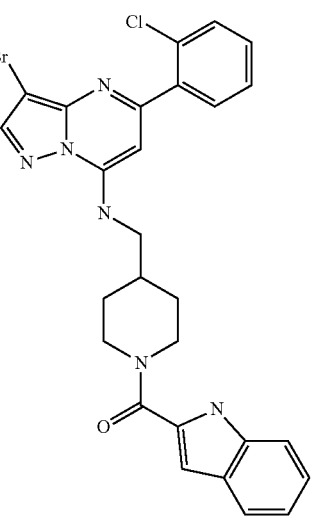 | 4938 2. 565.31 |

TABLE 49-continued
| Product | 1. Ex. 2. m/z |
|---|---|
| 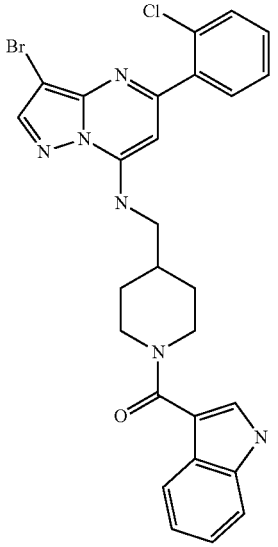 [SMILES: O=C(c1c[nH]c2ccccc12)N1CCC(CNc2cc(-c3ccccc3Cl)nc3c(Br)cnn23)CC1] | 1. 4939<br>2. 565.3 |
| 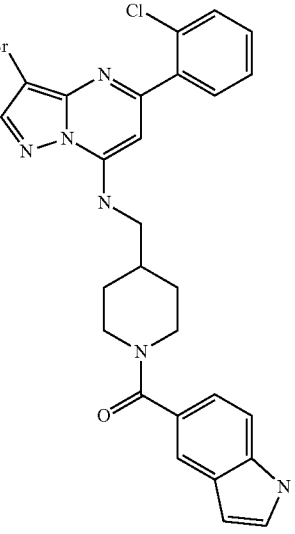 | 1. 4940<br>2. 565.31 |
| 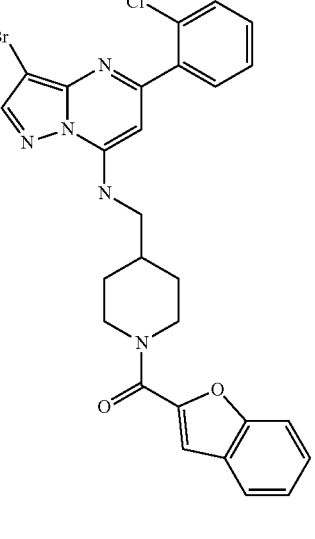 | 1. 4941<br>2. 566.31 |
TABLE 49-continued
| Product | 1. Ex. 2. m/z |
|---|---|
| 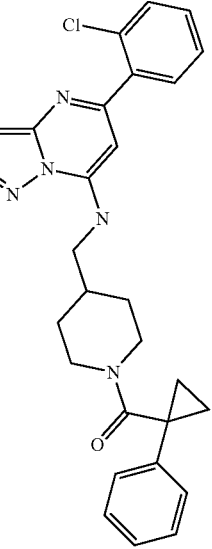 | 1. 4942<br>2. 566.31 |
| 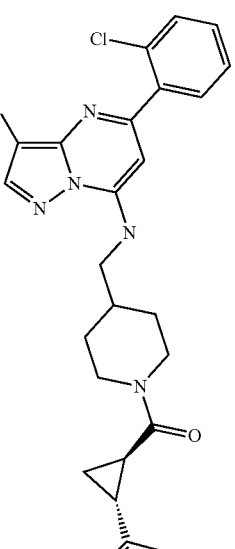 | 1. 4943<br>2. 566.31 |

TABLE 49-continued

| Product | 1. Ex.<br>2. m/z |
|---|---|
| (structure) | 1. 4944<br>2. 566.31 |
| (structure) | 1. 4945<br>2. 568.31 |
| (structure) | 1. 4946<br>2. 570.31 |
| (structure) | 1. 4947<br>2. 570.31 |

TABLE 49-continued

| Product | 1. Ex.<br>2. m/z |
|---|---|
| (structure: 3-bromo-5-(2-chlorophenyl)pyrazolo[1,5-a]pyrimidin-7-yl amine linked via CH2 to piperidine N-acylated with 3-phenoxypropanoyl) | 1. 4948<br>2. 570.31 |
| (structure: 3-bromo-5-(2-chlorophenyl)pyrazolo[1,5-a]pyrimidin-7-yl amine linked via CH2 to piperidine N-acylated with (phenylthio)acetyl) | 1. 4949<br>2. 572.31 |

TABLE 49-continued

| Product | 1. Ex.<br>2. m/z |
|---|---|
| (structure: 3-bromo-5-(2-chlorophenyl)pyrazolo[1,5-a]pyrimidin-7-yl amine linked via CH2 to piperidine N-acylated with 2-(methylthio)benzoyl) | 1. 4950<br>2. 572.31 |
| (structure: 3-bromo-5-(2-chlorophenyl)pyrazolo[1,5-a]pyrimidin-7-yl amine linked via CH2 to piperidine N-acylated with 4-(methylthio)benzoyl) | 1. 4951<br>2. 571.31 |

TABLE 49-continued
| Product | 1. Ex.<br>2. m/z |
|---|---|
| 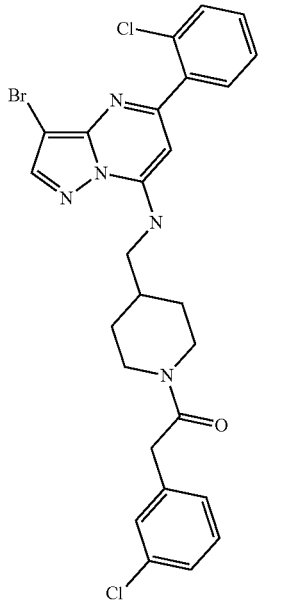 [SMILES: O=C(Cc1cccc(Cl)c1)N1CCC(CNc2cc(-c3ccccc3Cl)nc3c(Br)cnn23)CC1] | 1. 4952<br>2. 574.32 |
| 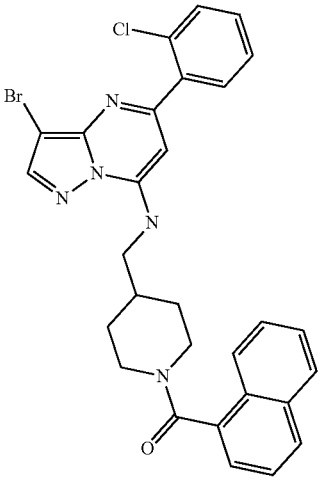 [SMILES: O=C(c1cccc2ccccc12)N1CCC(CNc2cc(-c3ccccc3Cl)nc3c(Br)cnn23)CC1] | 1. 4953<br>2. 576.32 |
| 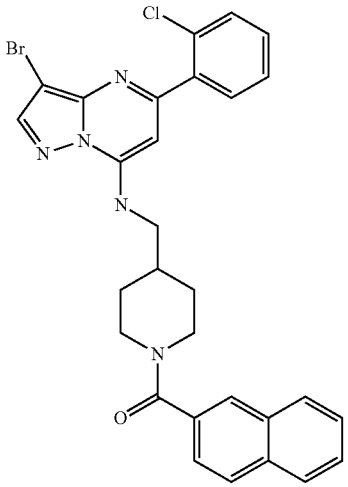 [SMILES: O=C(c1ccc2ccccc2c1)N1CCC(CNc2cc(-c3ccccc3Cl)nc3c(Br)cnn23)CC1] | 1. 4954<br>2. 576.32 |
| 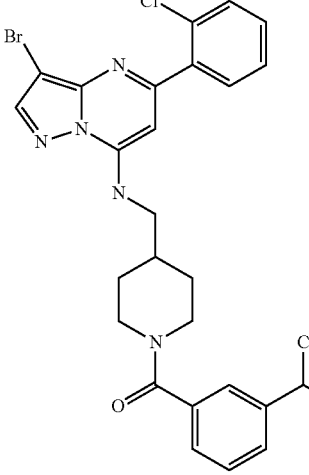 | 1. 4955<br>2. 579.32 |
| 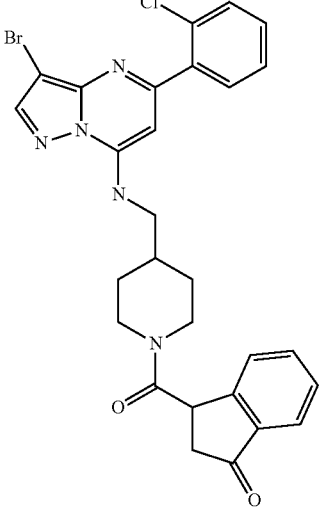 | 1. 4956<br>2. 580.32 |
| 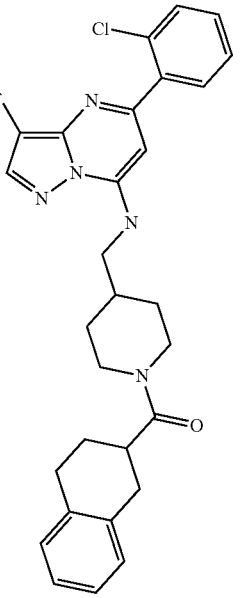 | 1. 4957<br>2. 580.32 |

TABLE 49-continued
| Product | 1. Ex. 2. m/z |
|---|---|
| 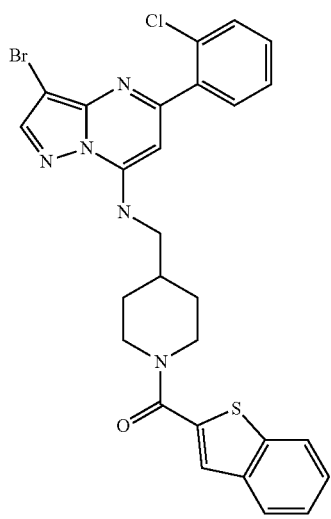 | 1. 4958 2. 582.32 |
| | 1. 4959 2. 583.32 |
TABLE 49-continued
| Product | 1. Ex. 2. m/z |
|---|---|
| 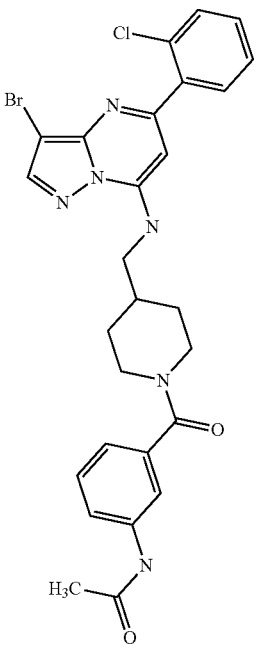 [SMILES: CC(=O)Nc1cccc(C(=O)N2CCC(CNc3cc(-c4ccccc4Cl)nc4c(Br)cnn34)CC2)c1] | 1. 4960 2. 583.32 |
| | 1. 4961 2. 583.32 |

TABLE 49-continued
| Product | 1. Ex. 2. m/z |
|---|---|
| 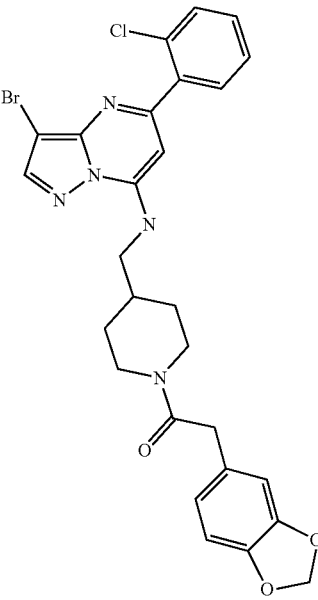 [SMILES: O=C(Cc1ccc2c(c1)OCO2)N1CCC(CNc2cc(-c3ccccc3Cl)nc3c(Br)cnn23)CC1] | 1. 4962<br>2. 584.32 |
| 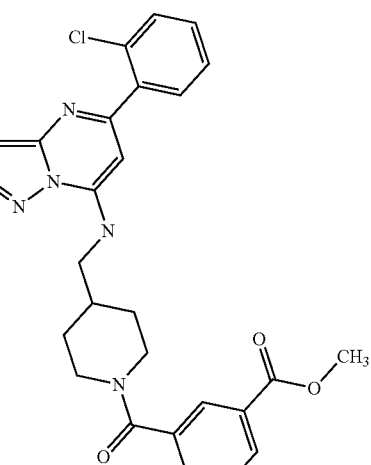 | 1. 4963<br>2. 584.32 |
| 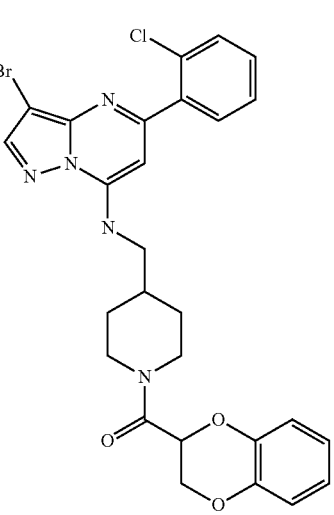 | 1. 4965<br>2. 584.32 |
| 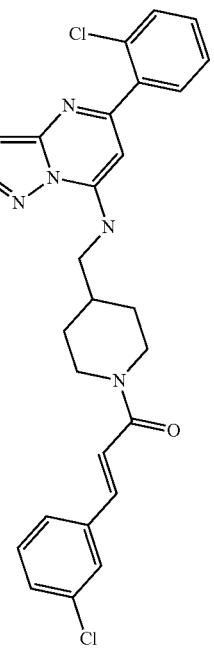 | 1. 4965<br>2. 586.32 |
| 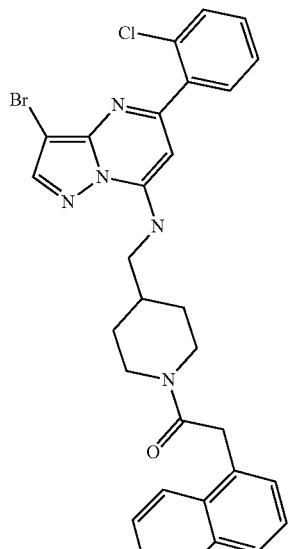 | 1. 4966<br>2. 590.32 |

TABLE 49-continued
| Product | 1. Ex.<br>2. m/z |
|---|---|
| 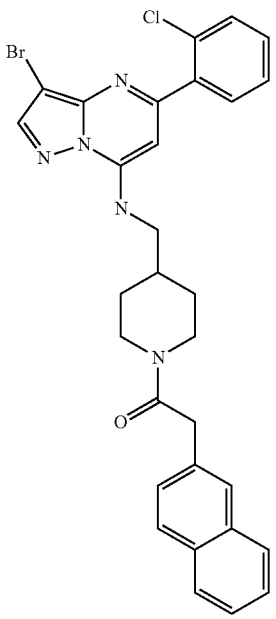 [SMILES: O=C(Cc1ccc2ccccc2c1)N1CCC(CNc2cc(-c3ccccc3Cl)nc3c(Br)cnn23)CC1] | 1. 4967<br>2. 590.32 |
| 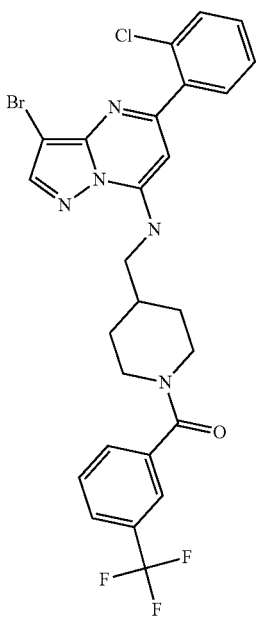 [SMILES: O=C(c1cccc(C(F)(F)F)c1)N1CCC(CNc2cc(-c3ccccc3Cl)nc3c(Br)cnn23)CC1] | 1. 4968<br>2. 591.3 |
TABLE 49-continued
| Product | 1. Ex.<br>2. m/z |
|---|---|
| 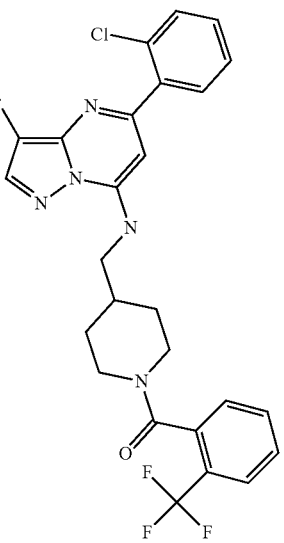 | 1. 4969<br>2. 594.33 |
| | 1. 4970<br>2. 594.33 |

TABLE 49-continued

| Product | 1. Ex. 2. m/z |
|---|---|
| (structure) | 1. 4971 2. 594.33 |
| (structure) | 1. 4972 2. 594.33 |

TABLE 49-continued

| Product | 1. Ex. 2. m/z |
|---|---|
| (structure) | 1. 4973 2. 594.33 |
| (structure) | 1. 4974 2. 594.33 |

TABLE 49-continued
| Product | 1. Ex.<br>2. m/z |
|---|---|
| 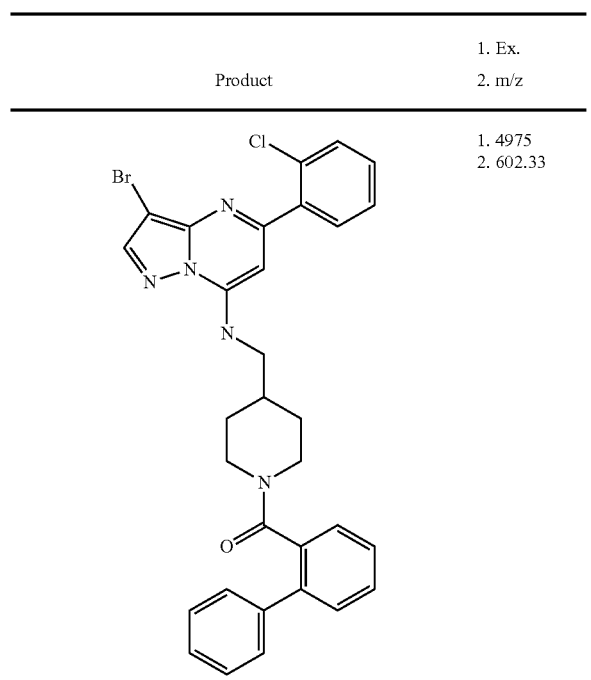 | 1. 4975<br>2. 602.33 |
| 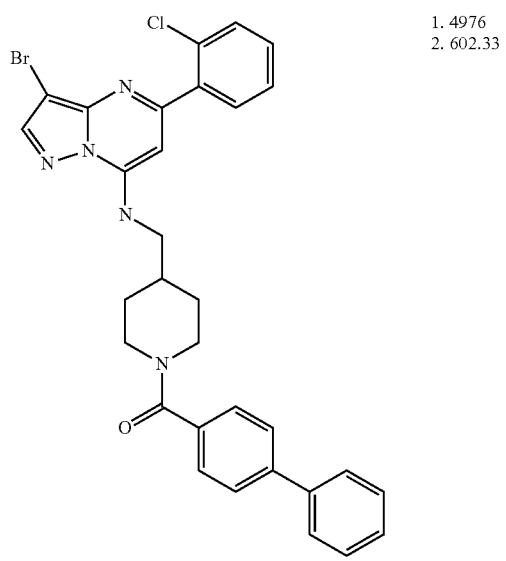 | 1. 4976<br>2. 602.33 |
TABLE 49-continued
| Product | 1. Ex.<br>2. m/z |
|---|---|
| 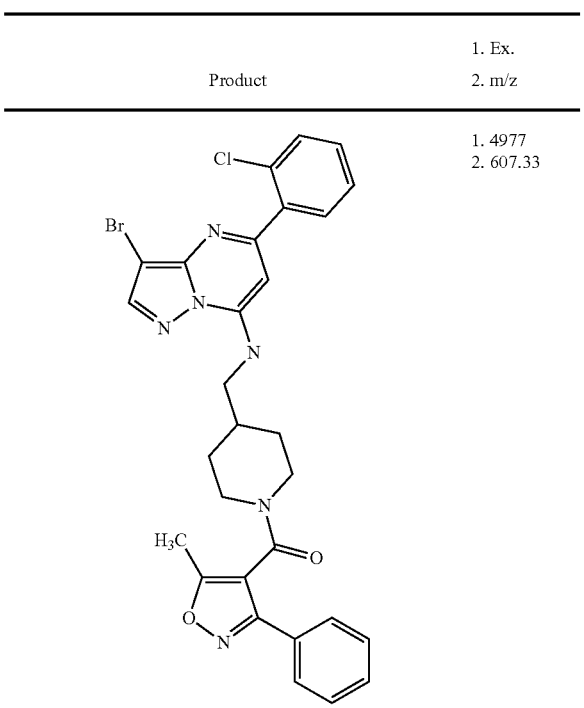 | 1. 4977<br>2. 607.33 |
| 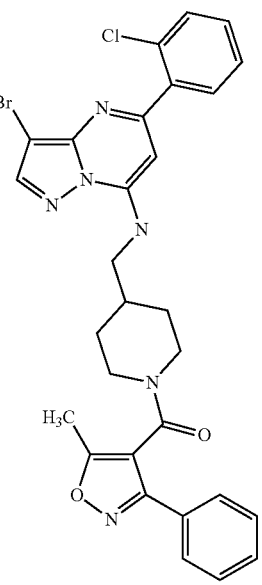 | 1. 4978<br>2. 607.33 |

TABLE 49-continued
| Product | 1. Ex. 2. m/z |
|---|---|
| 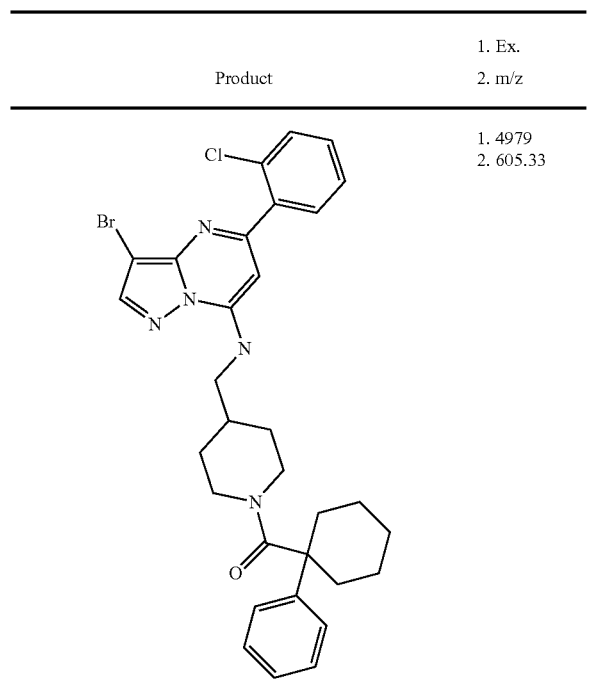 | 1. 4979 2. 605.33 |
| 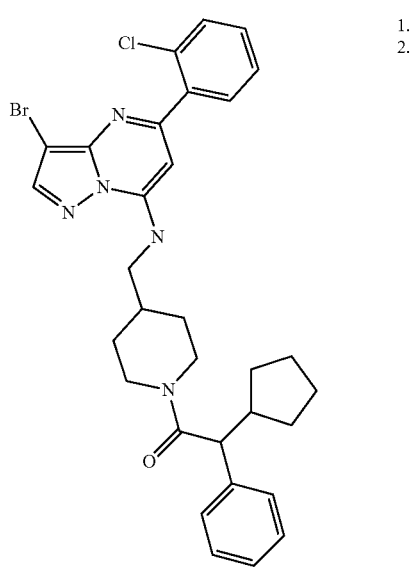 | 1. 4980 2. 608.33 |
| 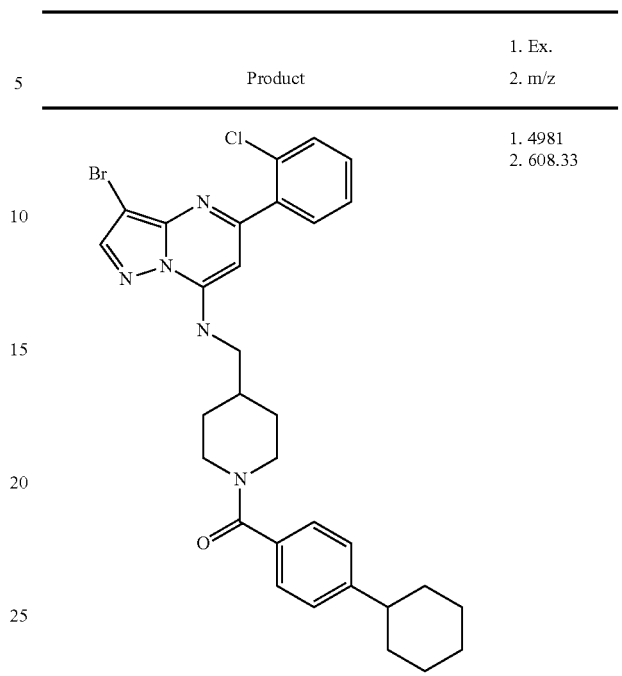 | 1. 4981 2. 608.33 |
| 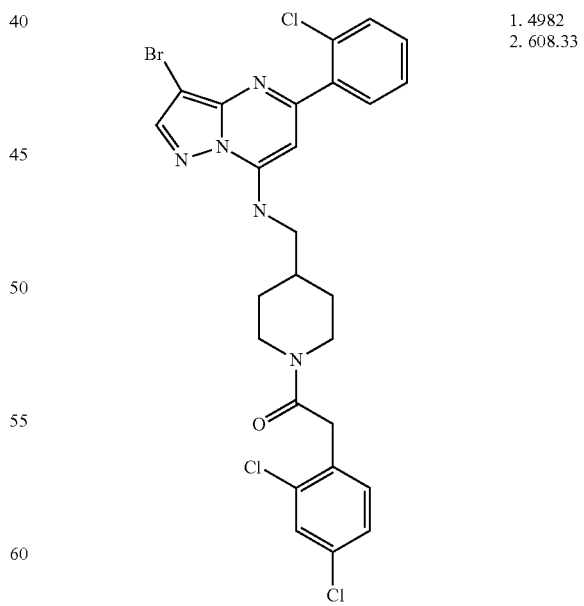 | 1. 4982 2. 608.33 |

TABLE 49-continued

| Product | 1. Ex.<br>2. m/z |
|---|---|
| (structure) | 1. 4983<br>2. 608.33 |
| (structure) | 1. 4984<br>2. 609.33 |
| (structure) | 1. 4985<br>2. 616.34 |
| (structure) | 1. 4986<br>2. 616.34 |
| (structure) | 1. 4987<br>2. 618.34 |

TABLE 49-continued
| Product | 1. Ex.<br>2. m/z |
|---|---|
| 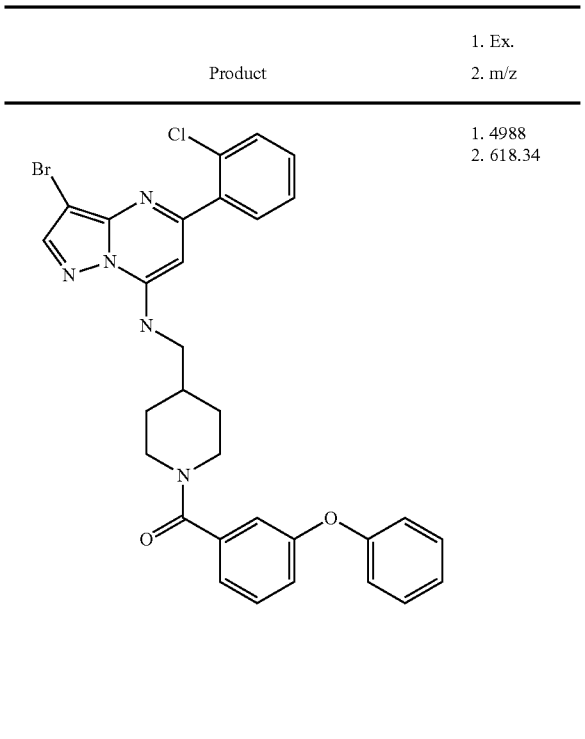 | 1. 4988<br>2. 618.34 |
| 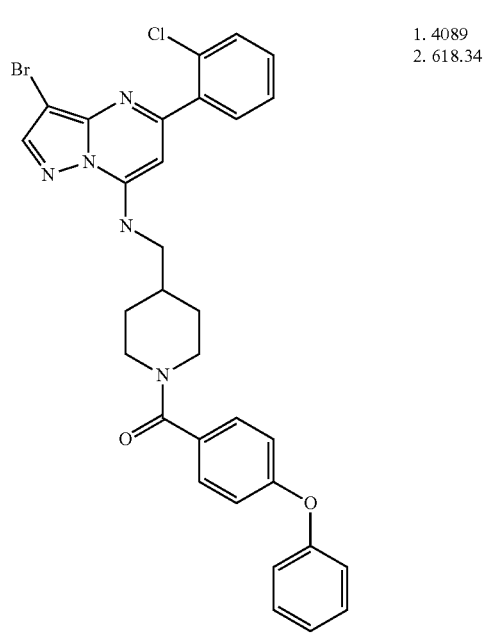 | 1. 4089<br>2. 618.34 |
TABLE 49-continued
| Product | 1. Ex.<br>2. m/z |
|---|---|
| 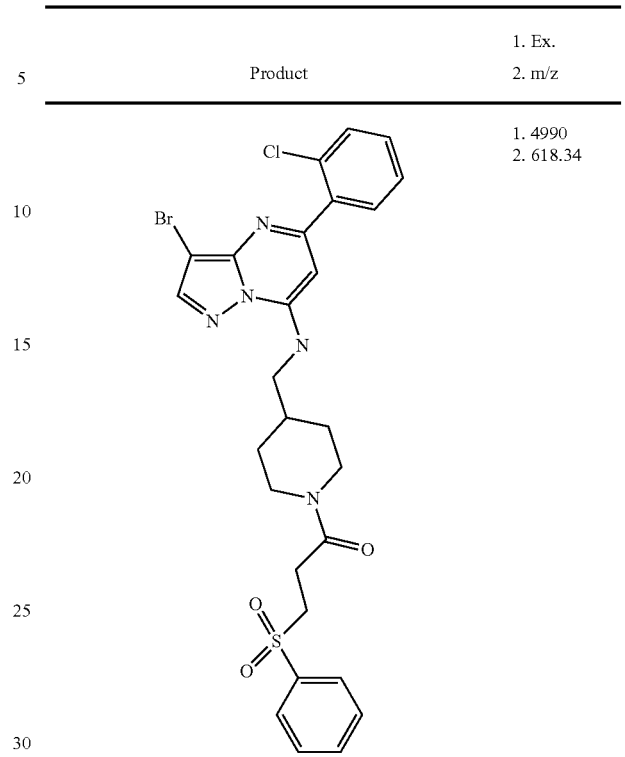 | 1. 4990<br>2. 618.34 |
| 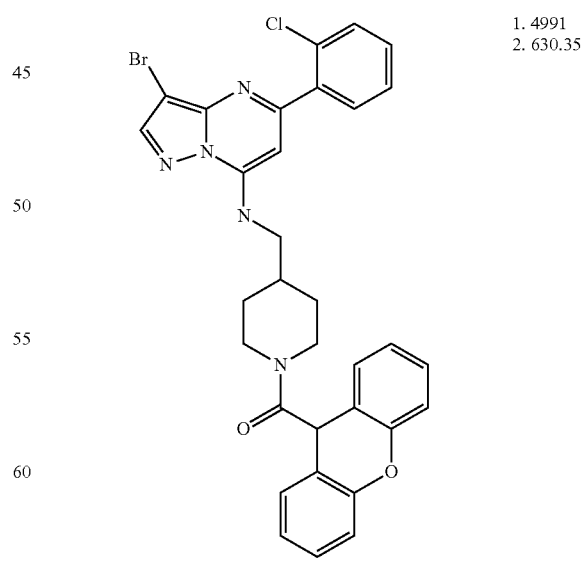 | 1. 4991<br>2. 630.35 |

TABLE 49-continued
| Product | 1. Ex.<br>2. m/z |
|---|---|
| 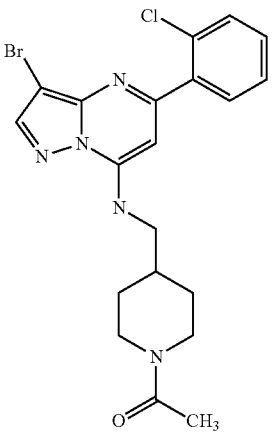 [SMILES: CC(=O)N1CCC(CNc2cc(-c3ccccc3Cl)nc3c(Br)cnn23)CC1] | 1. 4992<br>2. 464.26 |
| 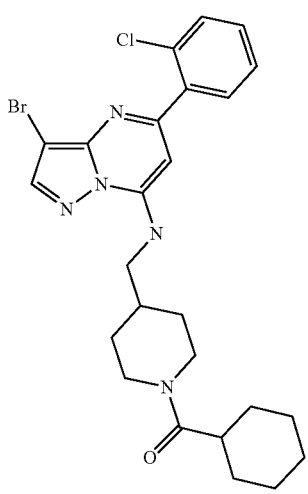 [SMILES: O=C(C1CCCCC1)N1CCC(CNc2cc(-c3ccccc3Cl)nc3c(Br)cnn23)CC1] | 1. 4993<br>2. 532.29 |
| 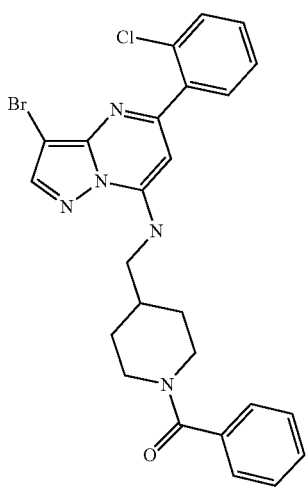 [SMILES: O=C(c1ccccc1)N1CCC(CNc2cc(-c3ccccc3Cl)nc3c(Br)cnn23)CC1] | 1. 4994<br>2. 526.29 |
TABLE 49-continued
| Product | 1. Ex.<br>2. m/z |
|---|---|
| 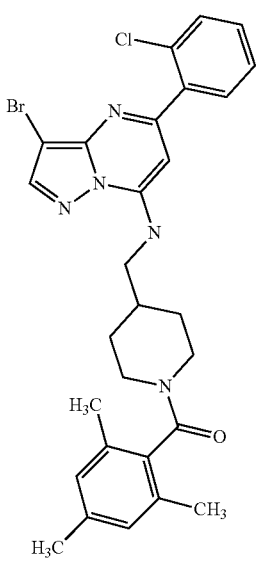 [SMILES: Cc1cc(C)c(C(=O)N2CCC(CNc3cc(-c4ccccc4Cl)nc4c(Br)cnn34)CC2)c(C)c1] | 1. 4995<br>2. 568.31 |
TABLE 50
| Product | 1. Ex.<br>2. m/z |
|---|---|
| 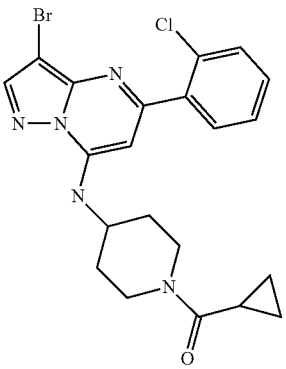 [SMILES: O=C(C1CC1)N1CCC(Nc2cc(-c3ccccc3Cl)nc3c(Br)cnn23)CC1] | 1. 5001<br>2. 476.26 |
| 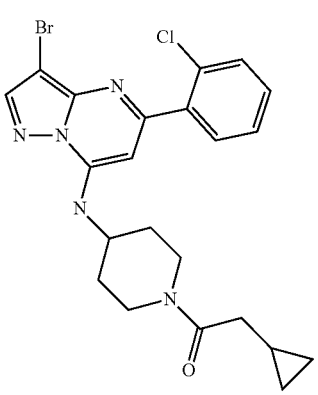 [SMILES: O=C(CC1CC1)N1CCC(Nc2cc(-c3ccccc3Cl)nc3c(Br)cnn23)CC1] | 1. 5002<br>2. 490.27 |

TABLE 50-continued

| Product | 1. Ex.<br>2. m/z |
|---|---|
| (structure) | 1. 5003<br>2. 496.27 |
| (structure) | 1. 5004<br>2. 502.28 |
| (structure) | 1. 5005<br>2. 502.28 |
| (structure) | 1. 5006<br>2. 504.28 |

TABLE 50-continued

| Product | 1. Ex.<br>2. m/z |
|---|---|
| (structure) | 1. 5007<br>2. 506.28 |
| (structure) | 1. 5008<br>2. 506.28 |
| (structure) | 1. 5009<br>2. 506.28 |
| (structure) | 1. 5010<br>2. 513.28 |

TABLE 50-continued

| Product | 1. Ex. 2. m/z |
|---|---|
| (structure) | 1. 5011 2. 515.28 |
| (structure) | 1. 5012 2. 518.28 |
| (structure) | 1. 5013 2. 518.28 |
| (structure) | 1. 5014 2. 519.29 |
| (structure) | 1. 5015 2. 522.29 |
| (structure) | 1. 5016 2. 524.29 |

TABLE 50-continued
| Product | 1. Ex.<br>2. m/z |
|---|---|
| 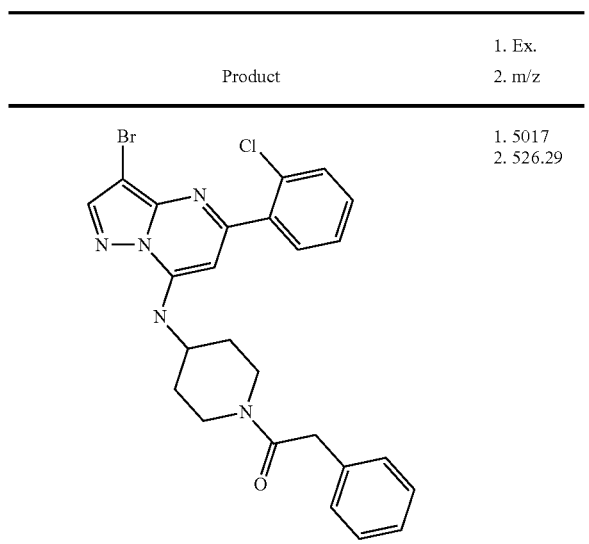 | 1. 5017<br>2. 526.29 |
| 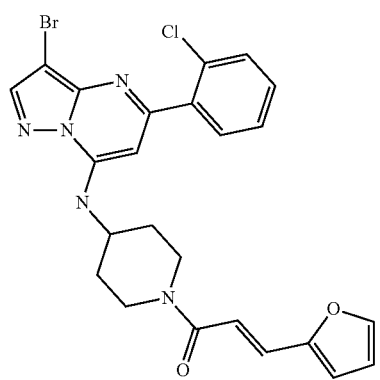 [SMILES: O=C(/C=C/c1ccco1)N1CCC(Nc2cc(-c3ccccc3Cl)nc3c(Br)cnn23)CC1] | 1. 5018<br>2. 528.29 |
| 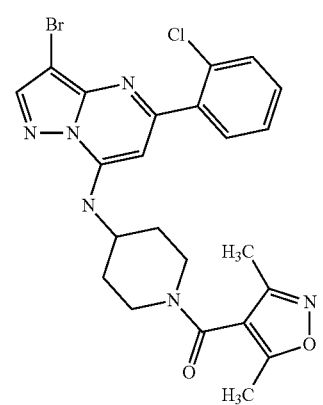 [SMILES: Cc1noc(C)c1C(=O)N1CCC(Nc2cc(-c3ccccc3Cl)nc3c(Br)cnn23)CC1] | 1. 5019<br>2. 531.29 |
TABLE 50-continued
| Product | 1. Ex.<br>2. m/z |
|---|---|
| 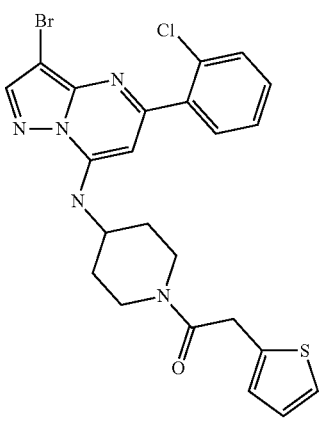 [SMILES: O=C(Cc1cccs1)N1CCC(Nc2cc(-c3ccccc3Cl)nc3c(Br)cnn23)CC1] | 1. 5020<br>2. 532.29 |
| 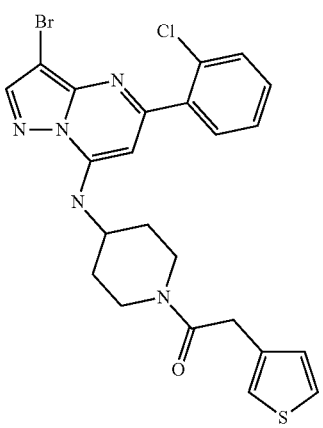 [SMILES: O=C(Cc1ccsc1)N1CCC(Nc2cc(-c3ccccc3Cl)nc3c(Br)cnn23)CC1] | 1. 5021<br>2. 532.29 |
| 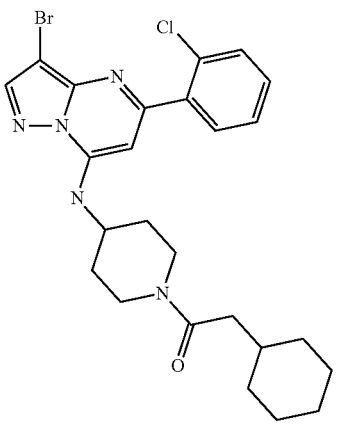 [SMILES: O=C(CC1CCCCC1)N1CCC(Nc2cc(-c3ccccc3Cl)nc3c(Br)cnn23)CC1] | 1. 5022<br>2. 532.29 |

TABLE 50-continued
| Product | 1. Ex. 2. m/z |
|---|---|
| 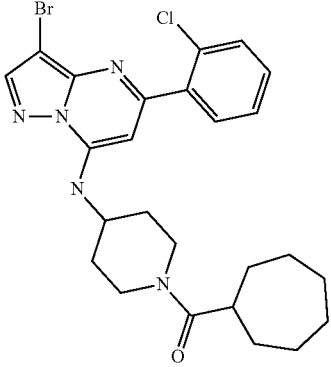 [SMILES: O=C(C1CCCCCC1)N1CCC(Nc2cc(-c3ccccc3Cl)nc3c(Br)cnn23)CC1] | 1. 5023  2. 532.29 |
| 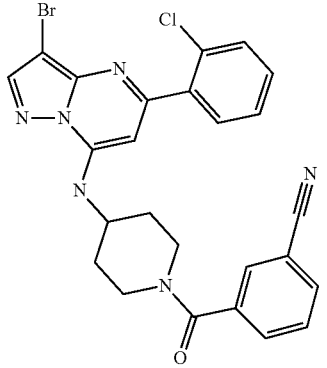 [SMILES: N#Cc1cccc(C(=O)N2CCC(Nc3cc(-c4ccccc4Cl)nc4c(Br)cnn34)CC2)c1] | 1. 5024  2. 537.3 |
| 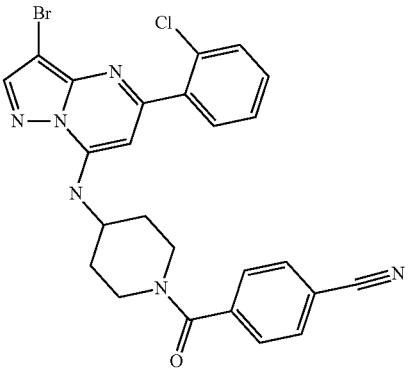 [SMILES: N#Cc1ccc(C(=O)N2CCC(Nc3cc(-c4ccccc4Cl)nc4c(Br)cnn34)CC2)cc1] | 1. 5025  2. 537.3 |
| 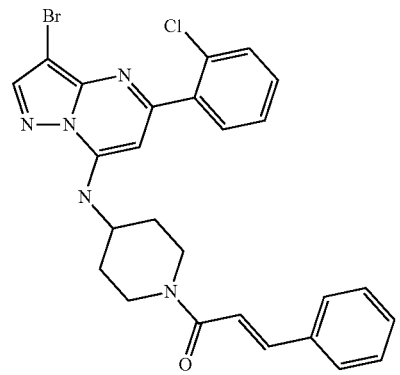 [SMILES: O=C(/C=C/c1ccccc1)N1CCC(Nc2cc(-c3ccccc3Cl)nc3c(Br)cnn23)CC1] | 1. 5026  2. 538.3 |
TABLE 50-continued
| Product | 1. Ex. 2. m/z |
|---|---|
| 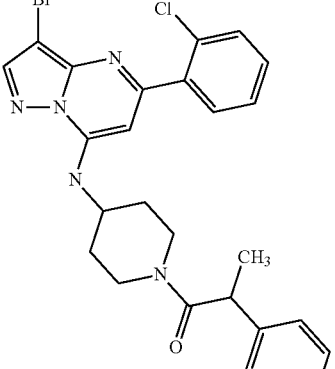 | 1. 5027  2. 540.3 |
| 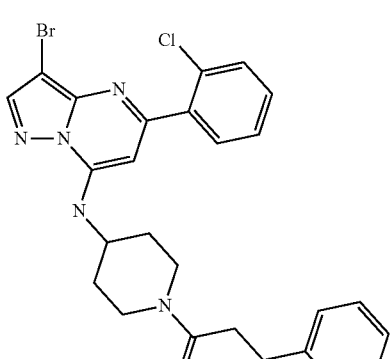 | 1. 5028  2. 540.3 |
| 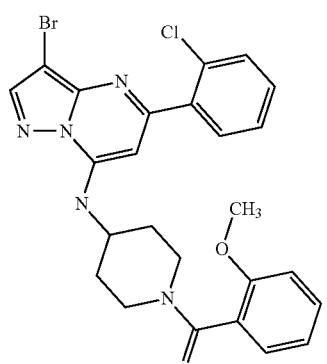 | 1. 5029  2. 542.3 |
| 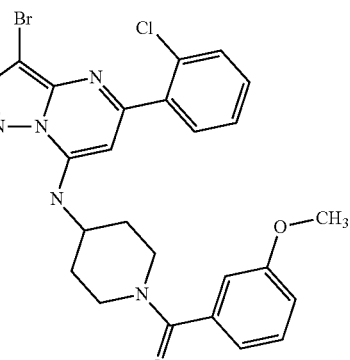 | 1. 5030  2. 542.3 |

TABLE 50-continued

| Product | 1. Ex.<br>2. m/z |
|---|---|
| (structure) | 1. 5031<br>2. 542.3 |
| (structure) | 1. 5032<br>2. 542.3 |
| (structure) | 1. 5033<br>2. 544.3 |
| (structure) | 1. 5034<br>2. 544.3 |

TABLE 50-continued

| Product | 1. Ex.<br>2. m/z |
|---|---|
| (structure) | 1. 5035<br>2. 546.3 |
| (structure) | 1. 5036<br>2. 546.3 |
| (structure) | 1. 5037<br>2. 546.3 |
| (structure) | 1. 5038<br>2. 551.3 |

TABLE 50-continued

| Product | 1. Ex.<br>2. m/z |
|---|---|
| (3-bromo-5-(2-chlorophenyl)pyrazolo[1,5-a]pyrimidin-7-yl)-piperidin-4-yl-amine with 1H-indole-3-carbonyl | 1. 5039<br>2. 551.3 |
| (3-bromo-5-(2-chlorophenyl)pyrazolo[1,5-a]pyrimidin-7-yl)-piperidin-4-yl-amine with 1H-indole-5-carbonyl | 1. 5040 |
| (3-bromo-5-(2-chlorophenyl)pyrazolo[1,5-a]pyrimidin-7-yl)-piperidin-4-yl-amine with benzofuran-2-carbonyl | 1. 5041<br>2. 552.3 |

TABLE 50-continued

| Product | 1. Ex.<br>2. m/z |
|---|---|
| (3-bromo-5-(2-chlorophenyl)pyrazolo[1,5-a]pyrimidin-7-yl)-piperidin-4-yl-amine with 1-phenylcyclopropane-1-carbonyl | 1. 5042<br>2. 552.3 |
| (3-bromo-5-(2-chlorophenyl)pyrazolo[1,5-a]pyrimidin-7-yl)-piperidin-4-yl-amine with 2-methyl-3-phenylacryloyl | 1. 5043<br>2. 552.3 |
| (3-bromo-5-(2-chlorophenyl)pyrazolo[1,5-a]pyrimidin-7-yl)-piperidin-4-yl-amine with 2-methyl-3-phenylacryloyl | 1. 5044<br>2. 552.3 |
| (3-bromo-5-(2-chlorophenyl)pyrazolo[1,5-a]pyrimidin-7-yl)-piperidin-4-yl-amine with 2-methyl-3-phenylpropanoyl | 1. 5045<br>2. 554.3 |

TABLE 50-continued
| Product | 1. Ex. 2. m/z |
|---|---|
| 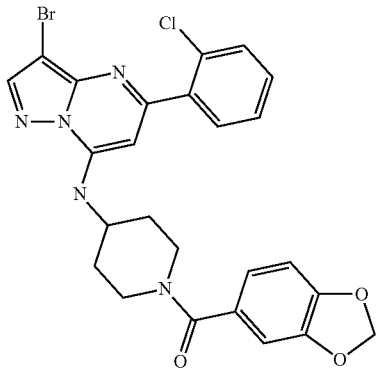 [SMILES: O=C(c1ccc2c(c1)OCO2)N1CCC(Nc2cc(-c3ccccc3Cl)nc3c(Br)cnn23)CC1] | 1. 5046<br>2. 556.31 |
| 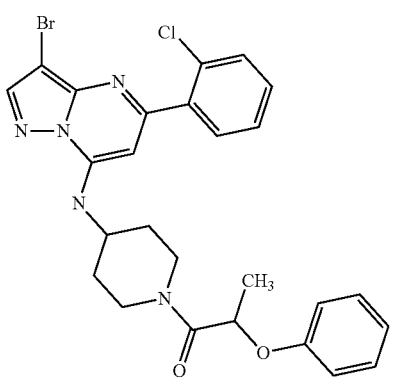 [SMILES: CC(Oc1ccccc1)C(=O)N1CCC(Nc2cc(-c3ccccc3Cl)nc3c(Br)cnn23)CC1] | 1. 5047<br>2. 556.31 |
| 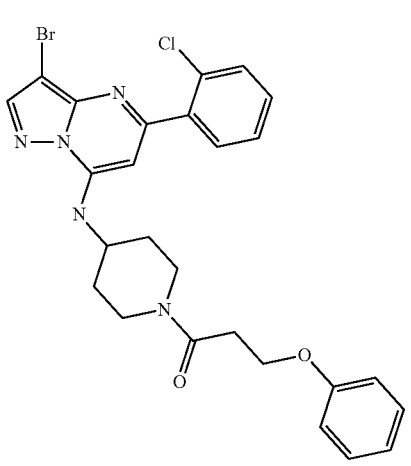 [SMILES: O=C(CCOc1ccccc1)N1CCC(Nc2cc(-c3ccccc3Cl)nc3c(Br)cnn23)CC1] | 1. 5048<br>2. 556.31 |
|  | 1. 5049<br>2. 558.31 |
TABLE 50-continued
| Product | 1. Ex. 2. m/z |
|---|---|
| 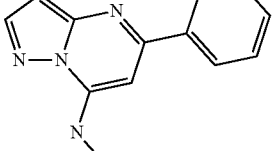 | 1. 5050<br>2. 558.31 |
| 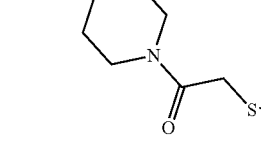 | 1. 5051<br>2. 558.31 |
|  | 1. 5052<br>2. 560.31 |
|  | 1. 5053<br>2. 562.31 |

TABLE 50-continued
| Product | 1. Ex. 2. m/z |
|---|---|
| 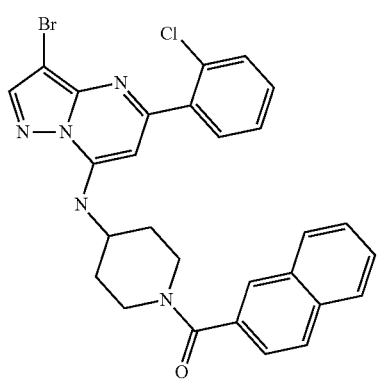 [SMILES: O=C(c1ccc2ccccc2c1)N1CCC(Nc2cc(-c3ccccc3Cl)nc3c(Br)cnn23)CC1] | 1. 5054 2. 562.31 |
| 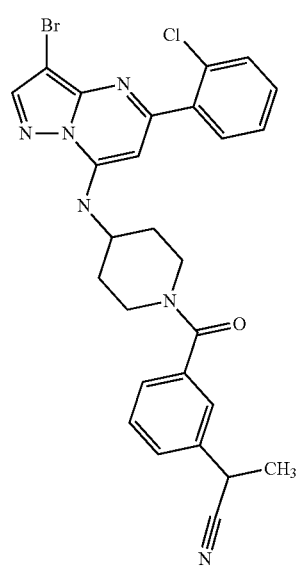 [SMILES: CC(C#N)c1cccc(C(=O)N2CCC(Nc3cc(-c4ccccc4Cl)nc4c(Br)cnn34)CC2)c1] | 1. 5055 2. 565.31 |
| 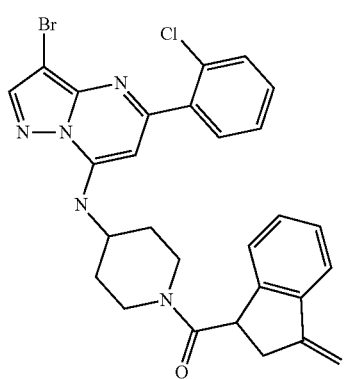 [SMILES: C=C1CC(C(=O)N2CCC(Nc3cc(-c4ccccc4Cl)nc4c(Br)cnn34)CC2)c2ccccc21] | 1. 5056 2. 566.31 |
TABLE 50-continued
| Product | 1. Ex. 2. m/z |
|---|---|
| 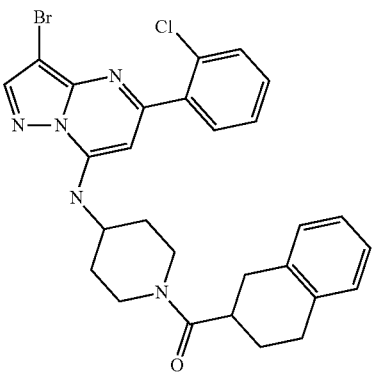 [SMILES: O=C(C1CCc2ccccc2C1)N1CCC(Nc2cc(-c3ccccc3Cl)nc3c(Br)cnn23)CC1] | 1. 5057 2. 566.31 |
| 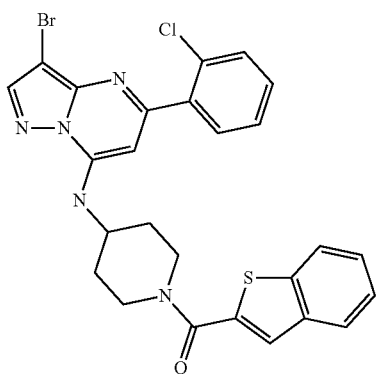 [SMILES: O=C(c1cc2ccccc2s1)N1CCC(Nc2cc(-c3ccccc3Cl)nc3c(Br)cnn23)CC1] | 1. 5058 2. 568.31 |
| 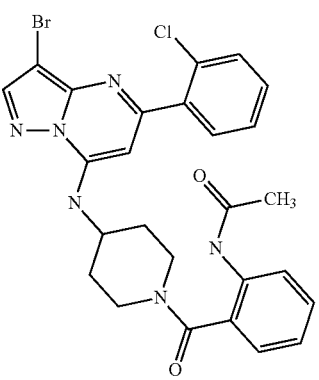 [SMILES: CC(=O)Nc1ccccc1C(=O)N1CCC(Nc2cc(-c3ccccc3Cl)nc3c(Br)cnn23)CC1] | 1. 5059 2. 569.31 |

TABLE 50-continued

| Product | 1. Ex. 2. m/z |
|---|---|
| (structure) | 1. 5060 2. 569.31 |
| (structure) | 1. 5061 |
| (structure) | 1. 5062 2. 570.31 |
| (structure) | 1. 5063 2. 570.31 |
| (structure) | 1. 5064 2. 570.31 |
| (structure) | 1. 5065 572.31 |

TABLE 50-continued
| Product | 1. Ex.<br>2. m/z |
|---|---|
| 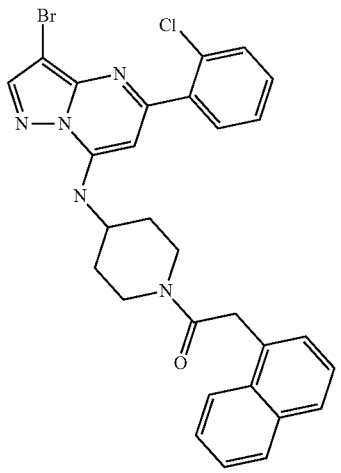 [SMILES: O=C(Cc1cccc2ccccc12)N1CCC(Nc2cc(-c3ccccc3Cl)nc3c(Br)cnn23)CC1] | 1. 5066<br>2. 576.32 |
| 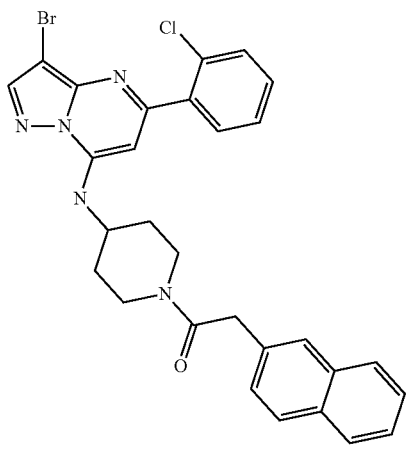 [SMILES: O=C(Cc1ccc2ccccc2c1)N1CCC(Nc2cc(-c3ccccc3Cl)nc3c(Br)cnn23)CC1] | 1. 5067<br>2. 576.32 |
| 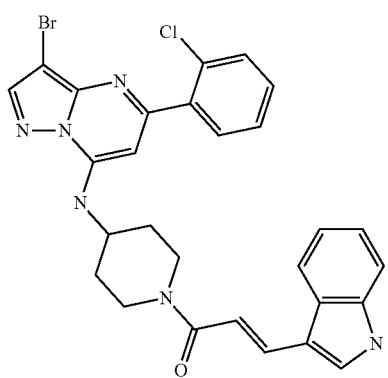 [SMILES: O=C(/C=C/c1c[nH]c2ccccc12)N1CCC(Nc2cc(-c3ccccc3Cl)nc3c(Br)cnn23)CC1] | 1. 5068<br>2. 577.32 |
TABLE 50-continued
| Product | 1. Ex.<br>2. m/z |
|---|---|
| 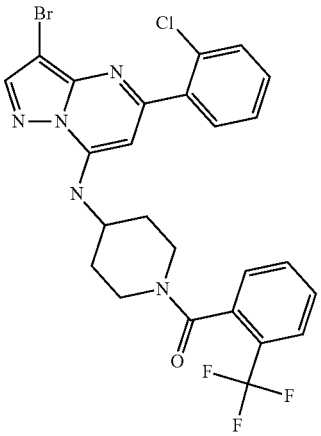 [SMILES: O=C(c1ccccc1C(F)(F)F)N1CCC(Nc2cc(-c3ccccc3Cl)nc3c(Br)cnn23)CC1] | 1. 5069<br>2. 580.32 |
| 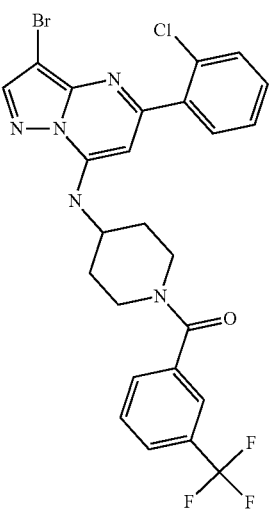 [SMILES: O=C(c1cccc(C(F)(F)F)c1)N1CCC(Nc2cc(-c3ccccc3Cl)nc3c(Br)cnn23)CC1] | 1. 5070<br>2. 580.32 |
| 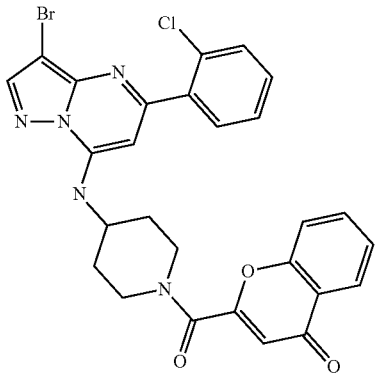 [SMILES: O=C(c1cc(=O)c2ccccc2o1)N1CCC(Nc2cc(-c3ccccc3Cl)nc3c(Br)cnn23)CC1] | 1. 5071<br>2. 580.32 |

TABLE 50-continued
| Product | 1. Ex.<br>2. m/z |
|---|---|
| 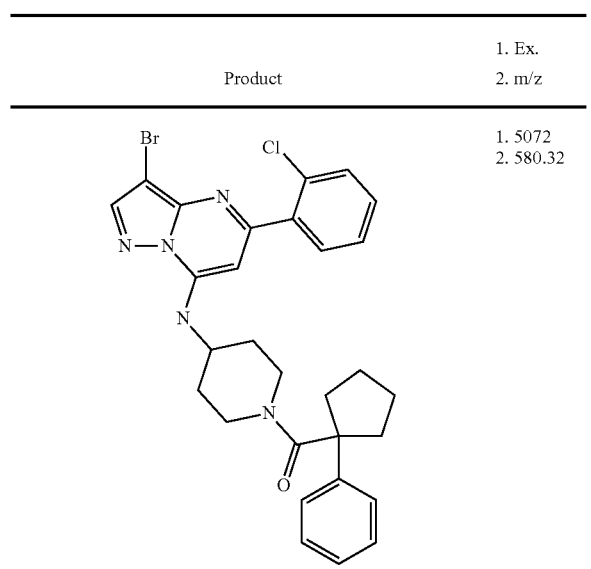 | 1. 5072<br>2. 580.32 |
| 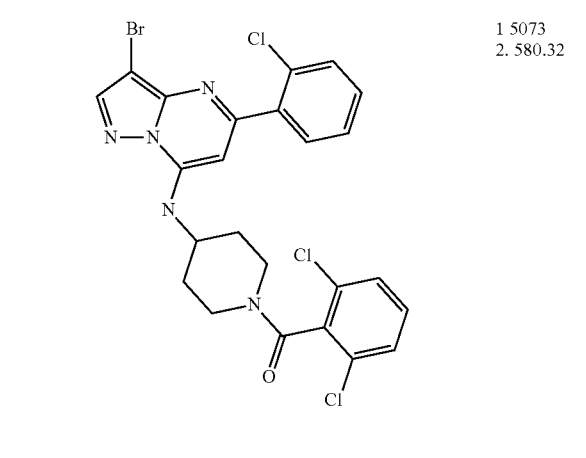 | 1 5073<br>2. 580.32 |
| 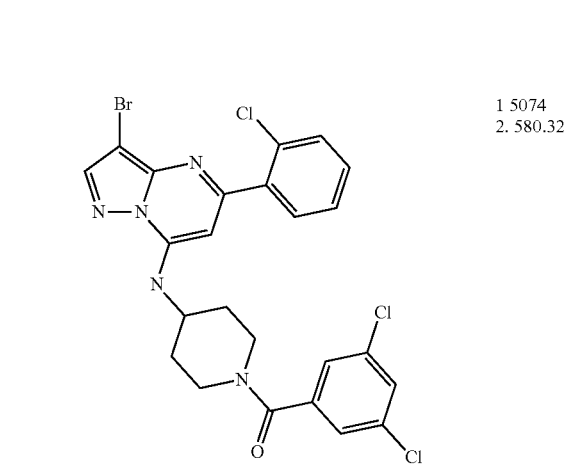 | 1 5074<br>2. 580.32 |
TABLE 50-continued
| Product | 1. Ex.<br>2. m/z |
|---|---|
| 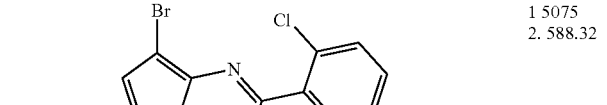 | 1 5075<br>2. 588.32 |
| 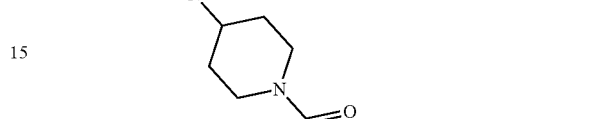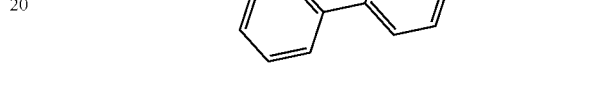 | 1 5076<br>2. 588.32 |
| 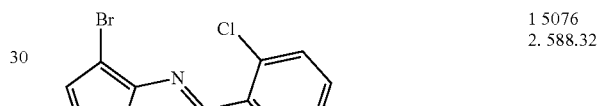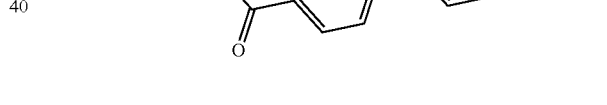 | 1. 5077<br>2. 593.33 |

TABLE 50-continued
| Product | 1. Ex.<br>2. m/z |
|---|---|
| 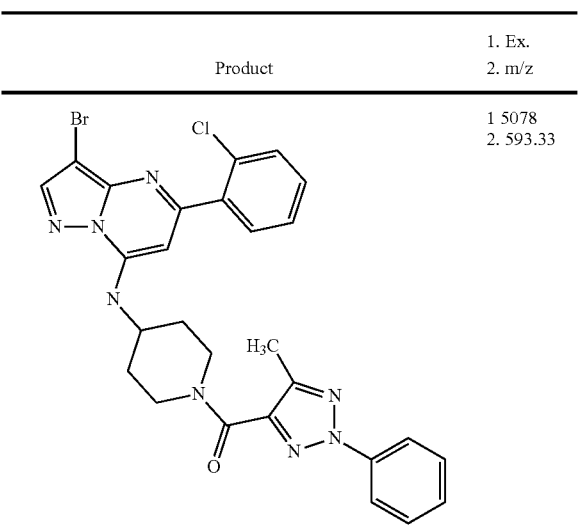 | 1. 5078<br>2. 593.33 |
| | 1. 5079<br>2. 594.33 |
| | 1. 5080<br>2. 594.33 |
TABLE 50-continued
| Product | 1. Ex.<br>2. m/z |
|---|---|
| 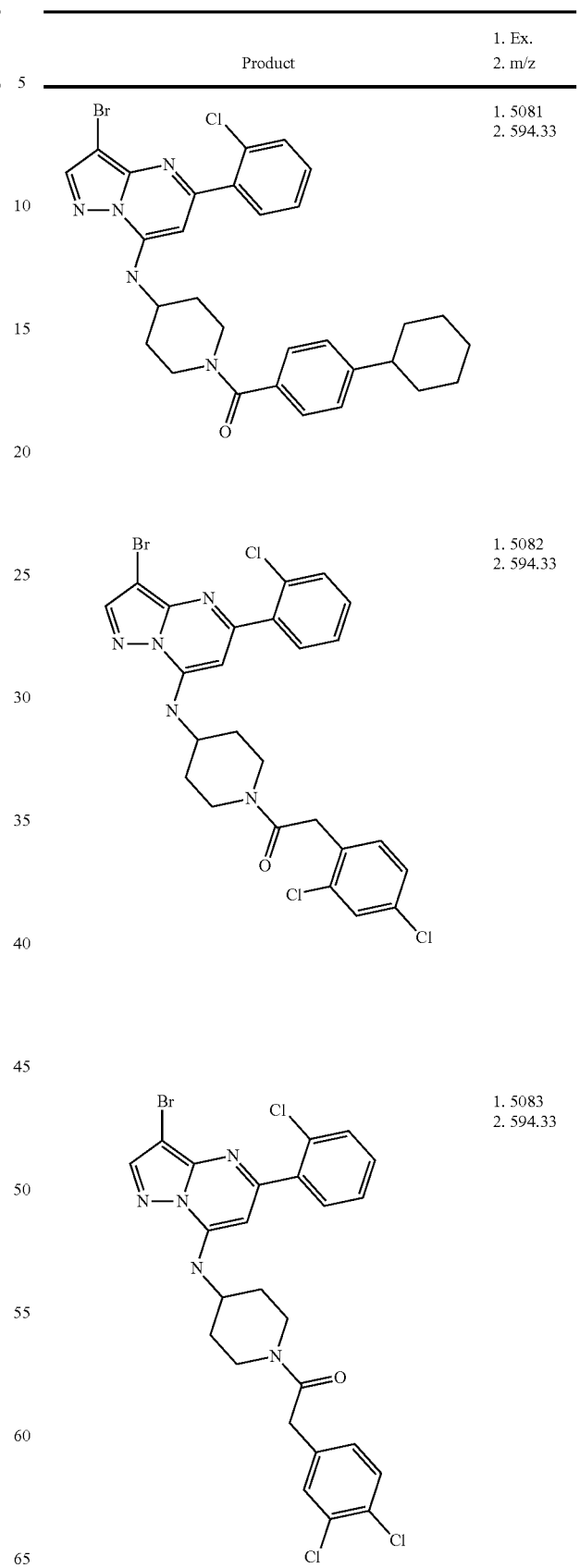 | 1. 5081<br>2. 594.33 |
| | 1. 5082<br>2. 594.33 |
| | 1. 5083<br>2. 594.33 |

TABLE 50-continued

| Product | 1. Ex. 2. m/z |
|---|---|
| (structure) | 1. 5084  2. 595.33 |
| (structure) | 1. 5085  2. 602.33 |
| (structure) | 1. 5086  2. 602.33 |

TABLE 50-continued

| Product | 1. Ex. 2. m/z |
|---|---|
| (structure) | 1. 5087  2. 604.33 |
| (structure) | 1. 5088  2. 604.33 |
| (structure) | 1. 5089  2. 604.33 |

TABLE 50-continued

| Product | 1. Ex. 2. m/z |
|---|---|
| (structure: 3-bromo-5-(2-chlorophenyl)pyrazolo[1,5-a]pyrimidin-7-yl amino piperidine N-C(O)CH2CH2-S(O)2-phenyl) | 1. 5090 2. 604.33 |
| (structure: 3-bromo-5-(2-chlorophenyl)pyrazolo[1,5-a]pyrimidin-7-yl amino piperidine N-C(O)-9H-xanthen-9-yl) | 1. 5091 2. 616.34 |
| (structure: 3-bromo-5-(2-chlorophenyl)pyrazolo[1,5-a]pyrimidin-7-yl amino piperidine N-C(O)CH3) | 1. 5092 2. 450.25 |

TABLE 50-continued

| Product | 1. Ex. 2. m/z |
|---|---|
| (structure: 3-bromo-5-(2-chlorophenyl)pyrazolo[1,5-a]pyrimidin-7-yl amino piperidine N-C(O)-cyclohexyl) | 1. 50903 2. 518.28 |
| (structure: 3-bromo-5-(2-chlorophenyl)pyrazolo[1,5-a]pyrimidin-7-yl amino piperidine N-C(O)-phenyl) | 1. 5094 2. 512.28 |
| (structure: 3-bromo-5-(2-chlorophenyl)pyrazolo[1,5-a]pyrimidin-7-yl amino piperidine N-C(O)-2,4,6-trimethylphenyl) | 1. 5095 2. 554.3 |

TABLE 51
| Product | 1. Ex. 2. m/z |
|---|---|
| 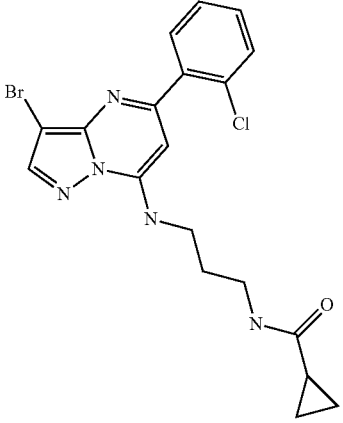 [SMILES: O=C(NCCCNc1cc(-c2ccccc2Cl)nc2c(Br)cnn12)C1CC1] | 1. 5101 2. 448.8 |
| | 1. 5102 2. 462.8 |
| | 1. 5103 2. 468.8 |
TABLE 51-continued
| Product | 1. Ex. 2. m/z |
|---|---|
| | 1. 5104 2. 474.7 |
| | 1. 5105 2. 474.7 |
| | 1. 5106 2. 476.8 |

TABLE 51-continued
| Product | 1. Ex. 2. m/z |
|---|---|
| 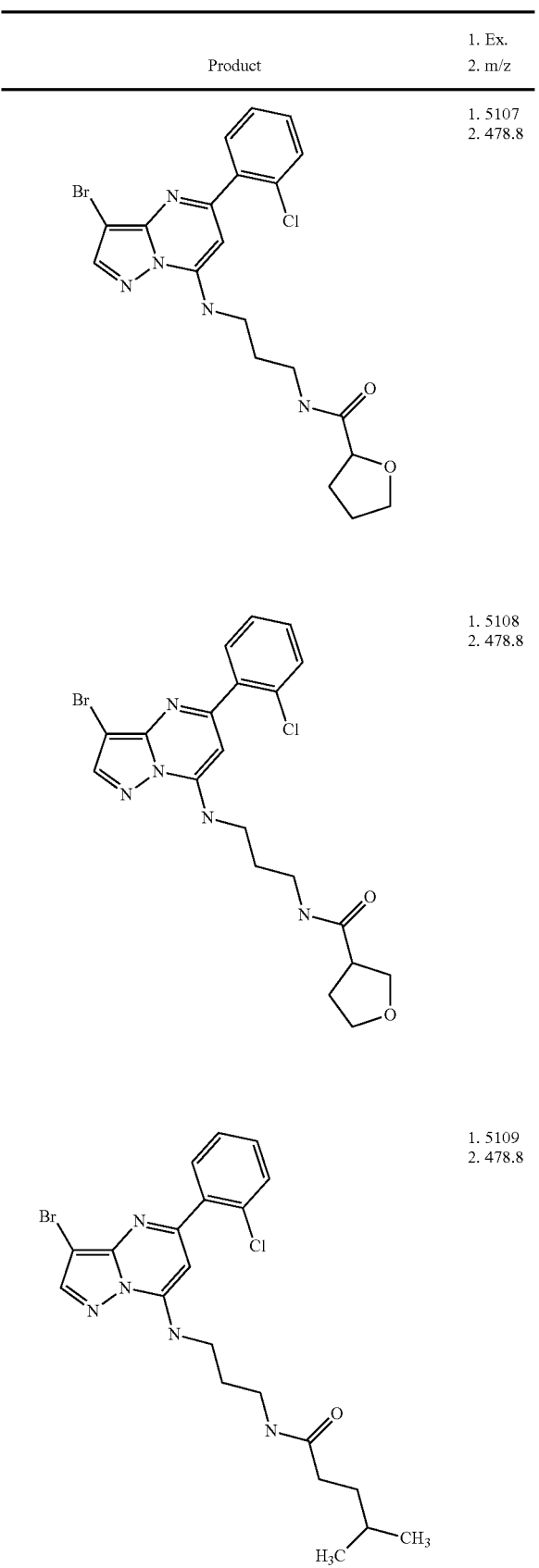 | 1. 5107 2. 478.8 |
| | 1. 5108 2. 478.8 |
| | 1. 5109 2. 478.8 |
TABLE 51-continued
| Product | 1. Ex. 2. m/z |
|---|---|
| 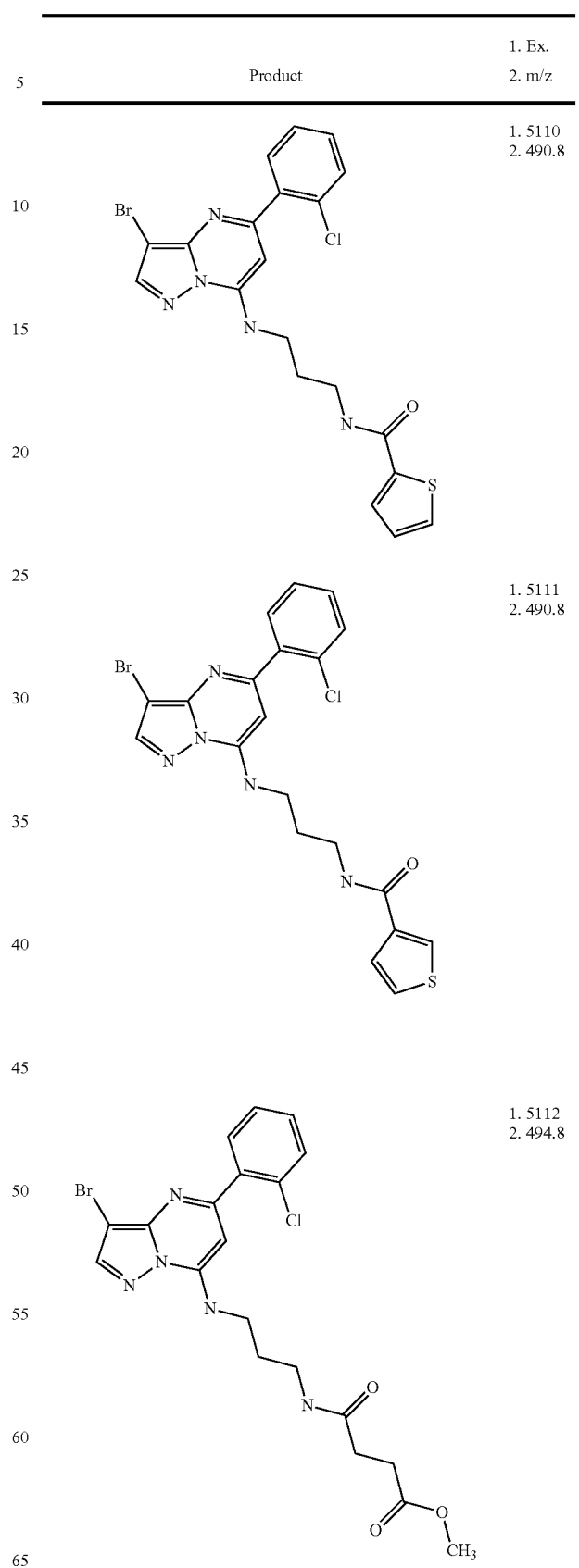 | 1. 5110 2. 490.8 |
| | 1. 5111 2. 490.8 |
| | 1. 5112 2. 494.8 |

TABLE 51-continued
| Product | 1. Ex.<br>2. m/z |
|---|---|
| 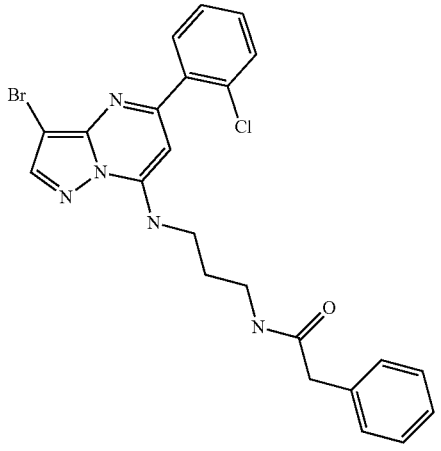 [SMILES: O=C(Cc1ccccc1)NCCCNc1cc(-c2ccccc2Cl)nc2c(Br)cnn12] | 1. 5113<br>2. 498.8 |
| 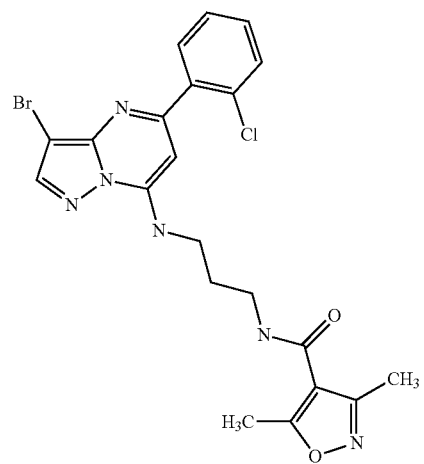 [SMILES: Cc1noc(C)c1C(=O)NCCCNc1cc(-c2ccccc2Cl)nc2c(Br)cnn12] | 1. 5114<br>2. 503.8 |
| 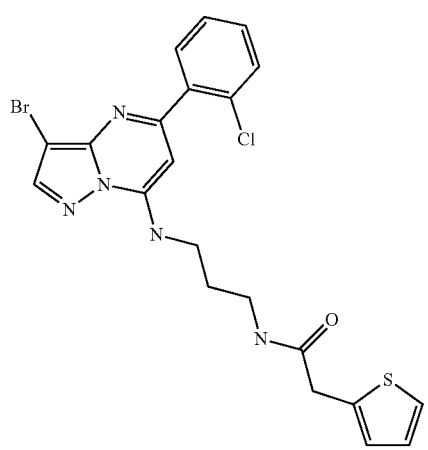 [SMILES: O=C(Cc1cccs1)NCCCNc1cc(-c2ccccc2Cl)nc2c(Br)cnn12] | 1. 5115<br>2. 504.8 |
TABLE 51-continued
| Product | 1. Ex.<br>2. m/z |
|---|---|
| 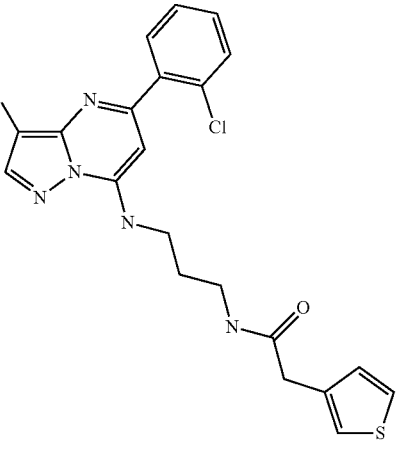 | 1. 5116<br>2. 504.8 |
| 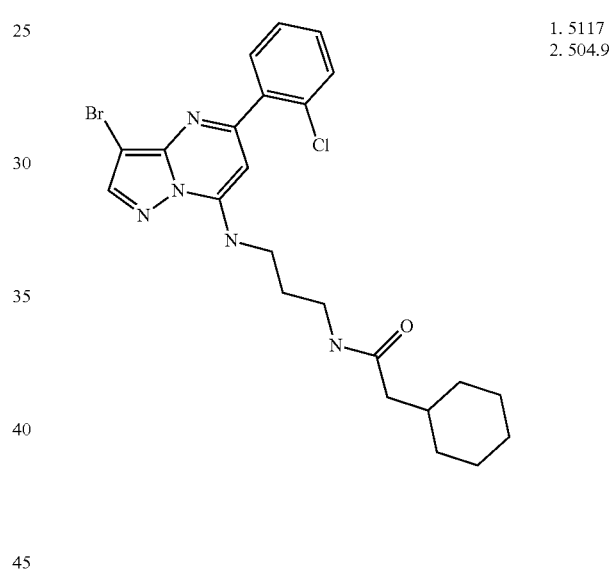 | 1. 5117<br>2. 504.9 |
| 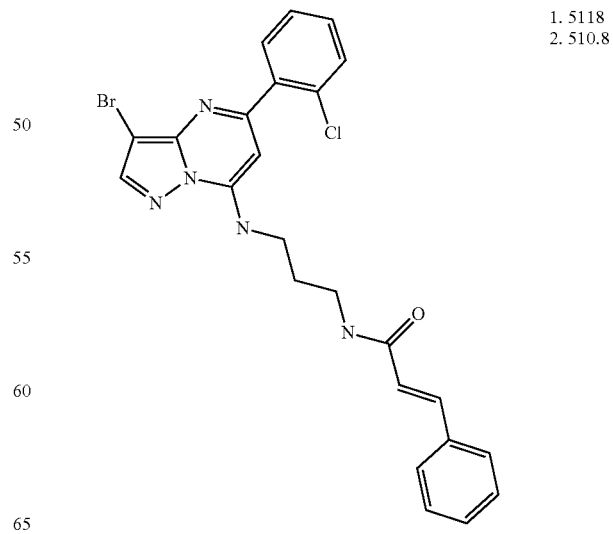 | 1. 5118<br>2. 510.8 |

TABLE 51-continued
| Product | 1. Ex.<br>2. m/z |
|---|---|
| 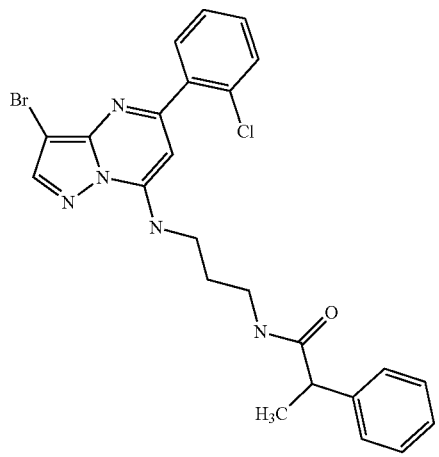 [SMILES: CC(C(=O)NCCCNc1cc(-c2ccccc2Cl)nc2c(Br)cnn12)c1ccccc1] | 1. 5119<br>2. 512.8 |
| 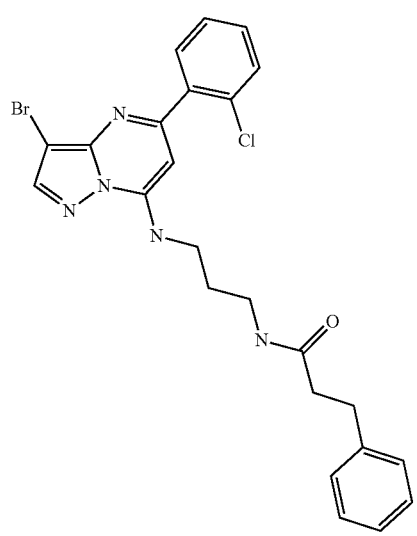 [SMILES: O=C(CCc1ccccc1)NCCCNc1cc(-c2ccccc2Cl)nc2c(Br)cnn12] | 1. 5120<br>2. 512.8 |
| 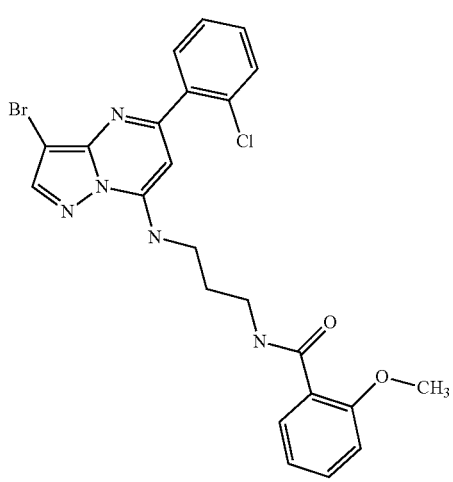 [SMILES: COc1ccccc1C(=O)NCCCNc1cc(-c2ccccc2Cl)nc2c(Br)cnn12] | 1. 5121<br>2. 514.8 |
TABLE 51-continued
| Product | 1. Ex.<br>2. m/z |
|---|---|
| 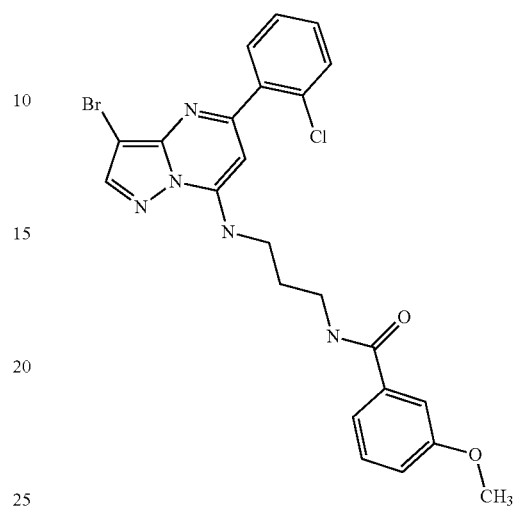 | 1. 5122<br>2. 514.8 |
| 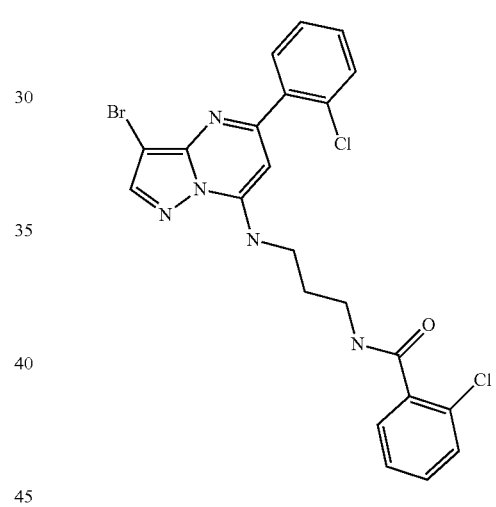 | 1. 5123<br>2. 519.2 |
| 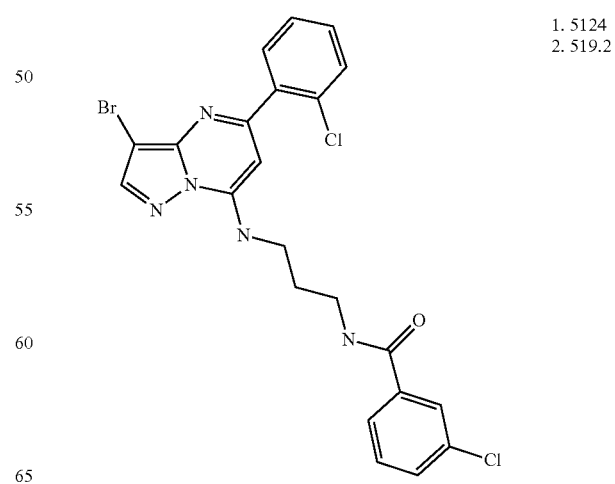 | 1. 5124<br>2. 519.2 |

TABLE 51-continued
| Product | 1. Ex. 2. m/z |
|---|---|
| 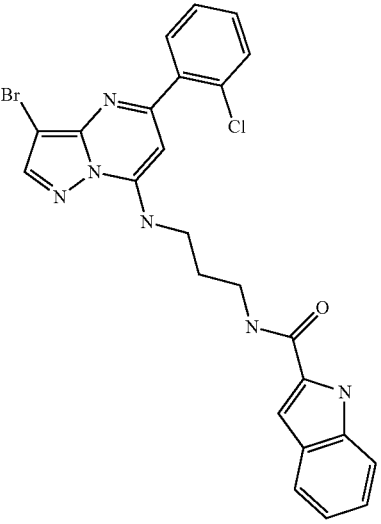 | 1. 5125 2. 523.8 |
| 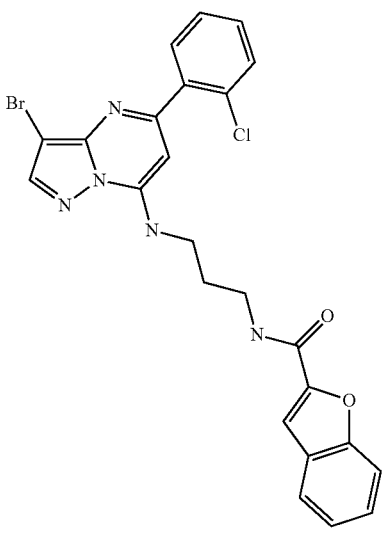 [SMILES: O=C(NCCCNc1cc(-c2ccccc2Cl)nc2c(Br)cnn12)c1cc2ccccc2o1] | 1. 5126 2. 524.8 |
| 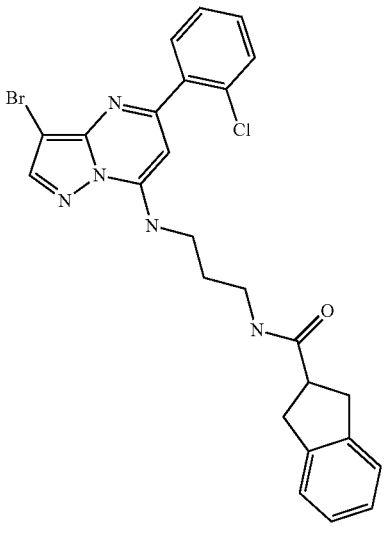 [SMILES: O=C(NCCCNc1cc(-c2ccccc2Cl)nc2c(Br)cnn12)C1Cc2ccccc2C1] | 1. 5127 2. 524.9 |
TABLE 51-continued
| Product | 1. Ex. 2. m/z |
|---|---|
| 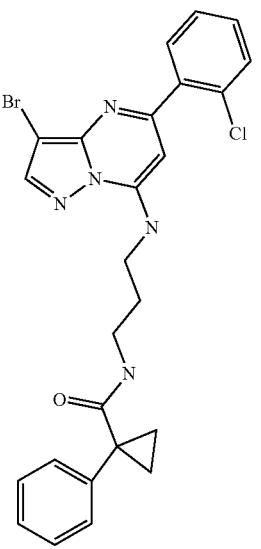 [SMILES: O=C(NCCCNc1cc(-c2ccccc2Cl)nc2c(Br)cnn12)C1(c2ccccc2)CC1] | 1. 5128 2. 524.9 |
| 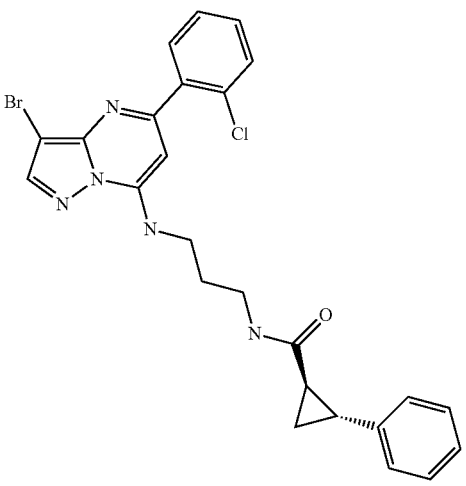 [SMILES: O=C(NCCCNc1cc(-c2ccccc2Cl)nc2c(Br)cnn12)[C@@H]1C[C@H]1c1ccccc1] | 1. 5129 2. 524.9 |
| 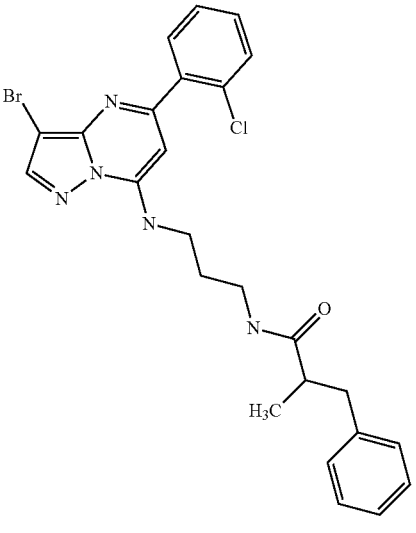 [SMILES: CC(Cc1ccccc1)C(=O)NCCCNc1cc(-c2ccccc2Cl)nc2c(Br)cnn12] | 1. 5130 2. 526.9 |

TABLE 51-continued
| Product | 1. Ex. 2. m/z |
|---|---|
| 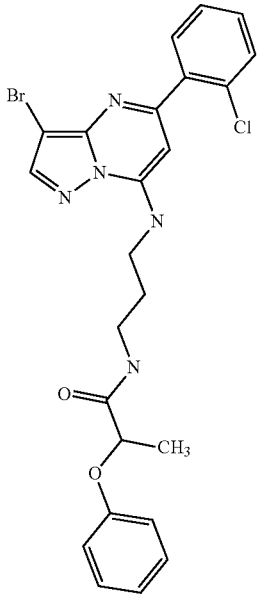 [SMILES: CC(Oc1ccccc1)C(=O)NCCCNc1cc(-c2ccccc2Cl)nc2c(Br)cnn12] | 1. 5131 2. 528.8 |
| 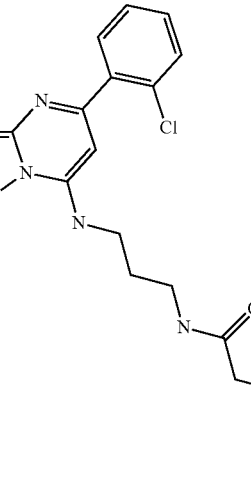 | 1. 5132 2. 530.9 |
| 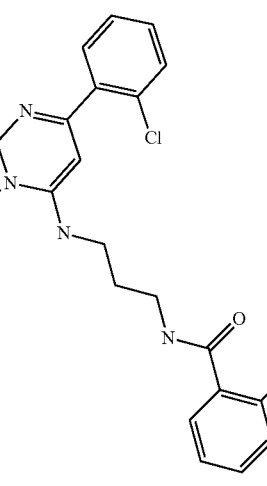 | 1. 5133 2. 534.8 |
TABLE 51-continued
| Product | 1. Ex. 2. m/z |
|---|---|
| 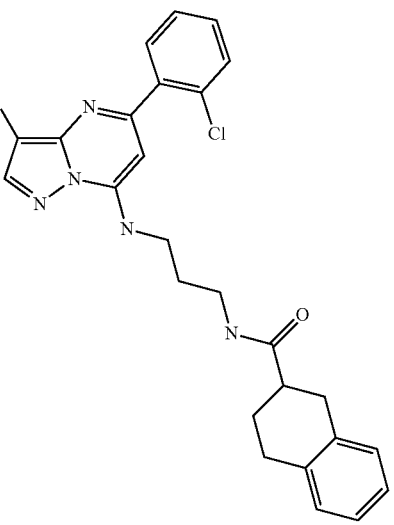 | 1. 5134 2. 538.9 |
| 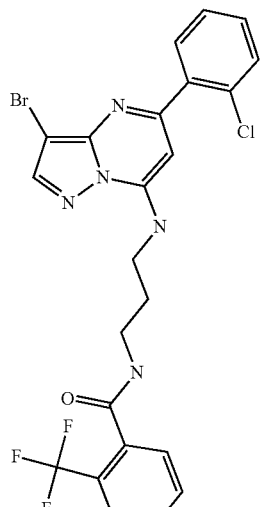 | 1. 5135 2. 552.8 |

TABLE 51-continued
| Product | 1. Ex.<br>2. m/z |
|---|---|
| 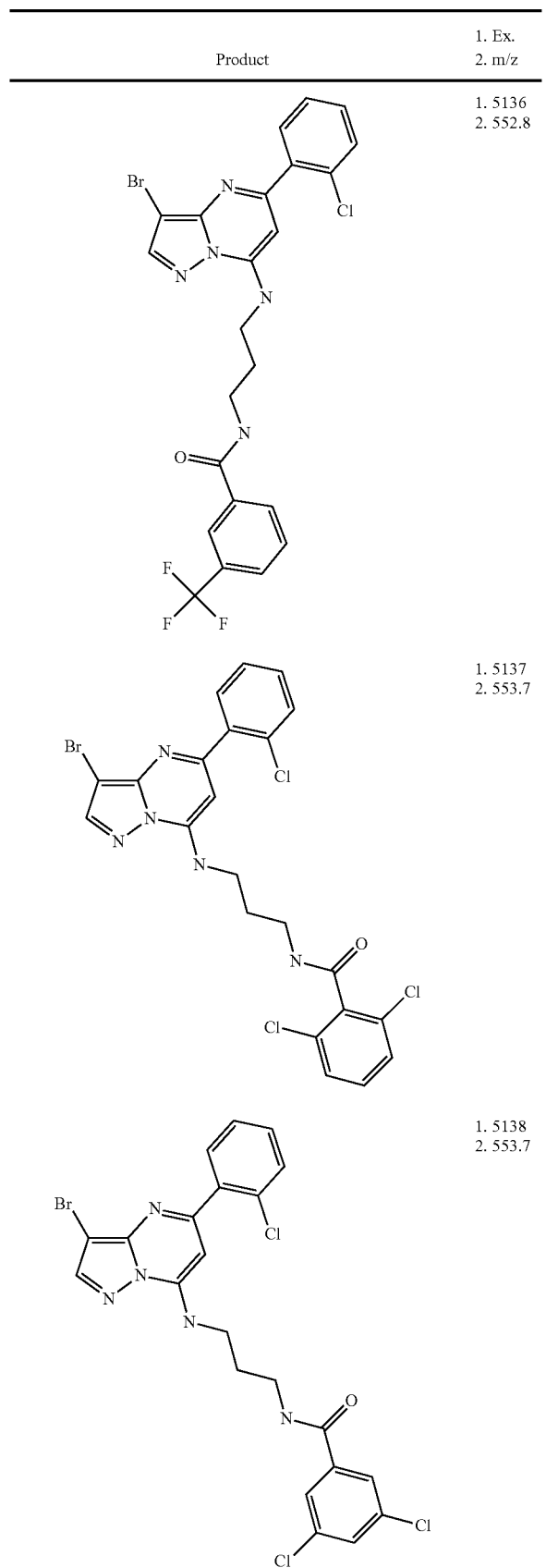 | 1. 5136<br>2. 552.8<br><br>1. 5137<br>2. 553.7<br><br>1. 5138<br>2. 553.7 |
TABLE 51-continued
| Product | 1. Ex.<br>2. m/z |
|---|---|
| 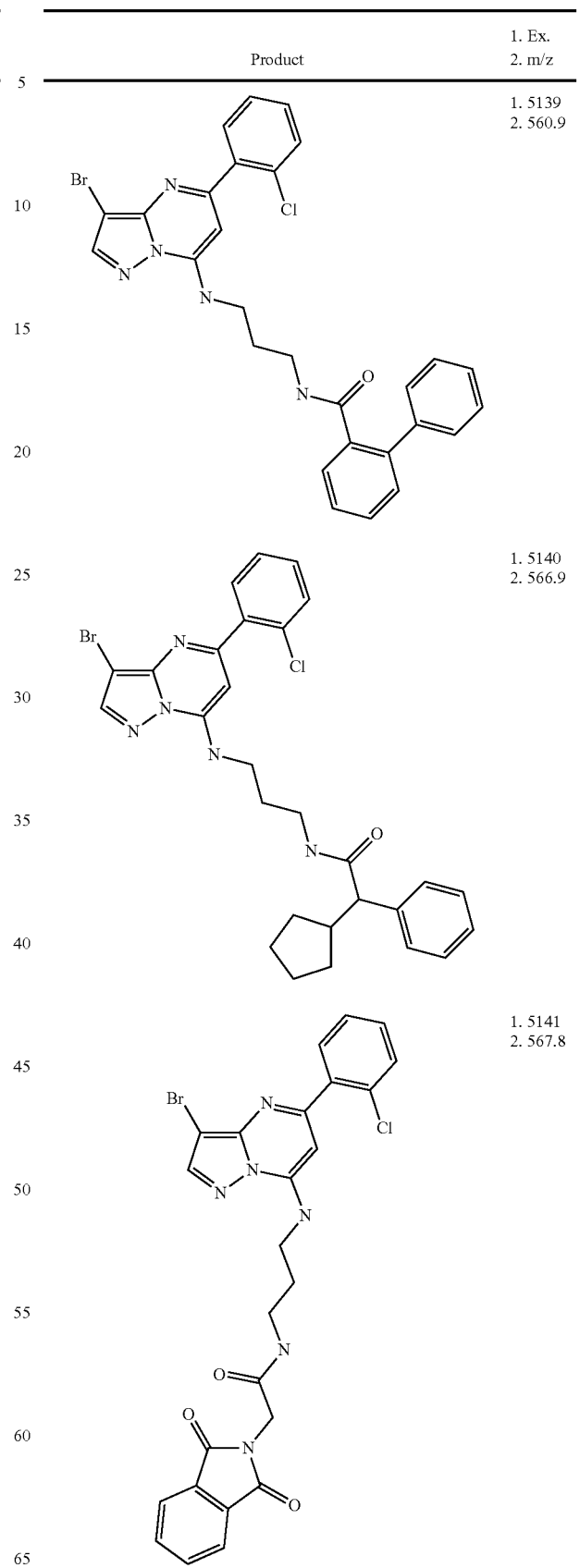 | 1. 5139<br>2. 560.9<br><br>1. 5140<br>2. 566.9<br><br>1. 5141<br>2. 567.8 |

TABLE 51-continued
| Product | 1. Ex. 2. m/z |
|---|---|
| 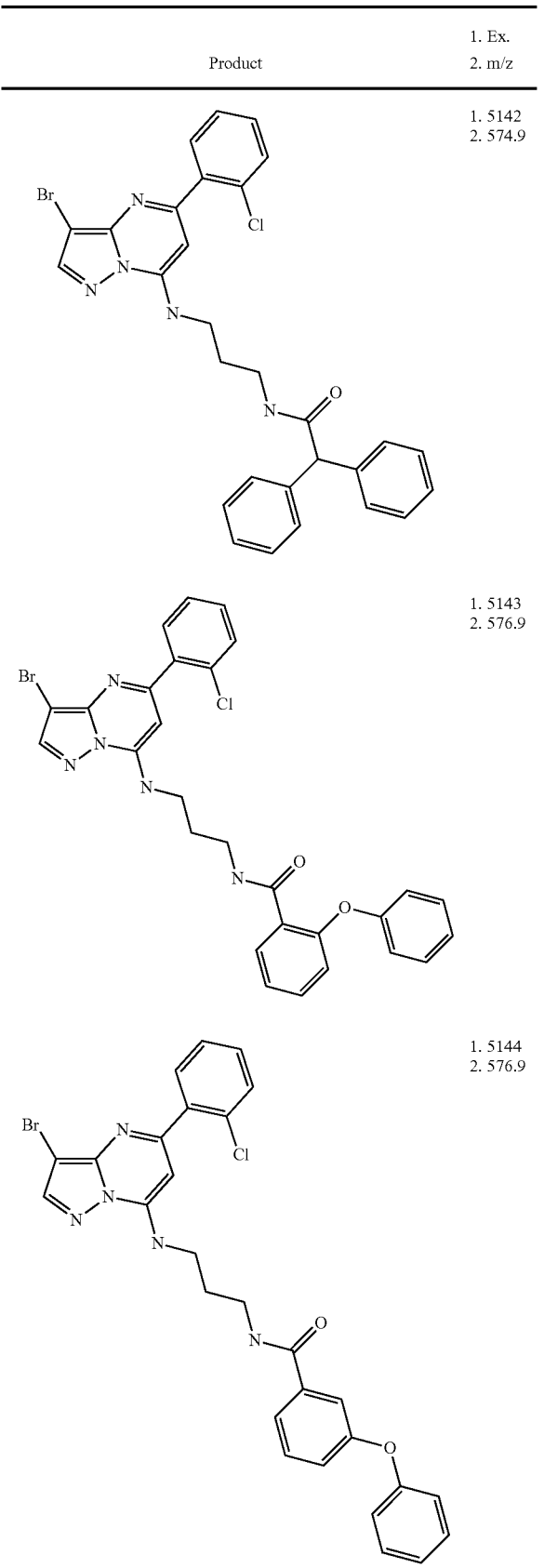 | 1. 5142 2. 574.9 |
| | 1. 5143 2. 576.9 |
| | 1. 5144 2. 576.9 |
TABLE 51-continued
| Product | 1. Ex. 2. m/z |
|---|---|
| 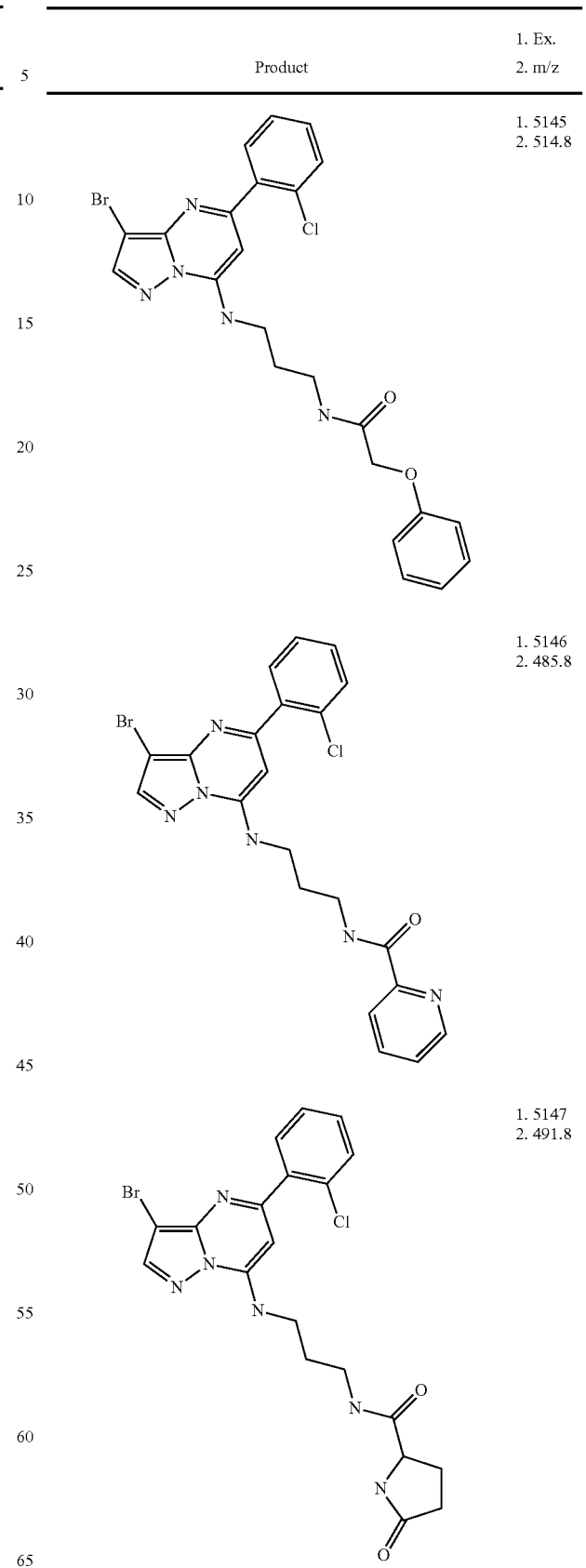 | 1. 5145 2. 514.8 |
| | 1. 5146 2. 485.8 |
| | 1. 5147 2. 491.8 |

TABLE 51-continued
| Product | 1. Ex. 2. m/z |
|---|---|
| 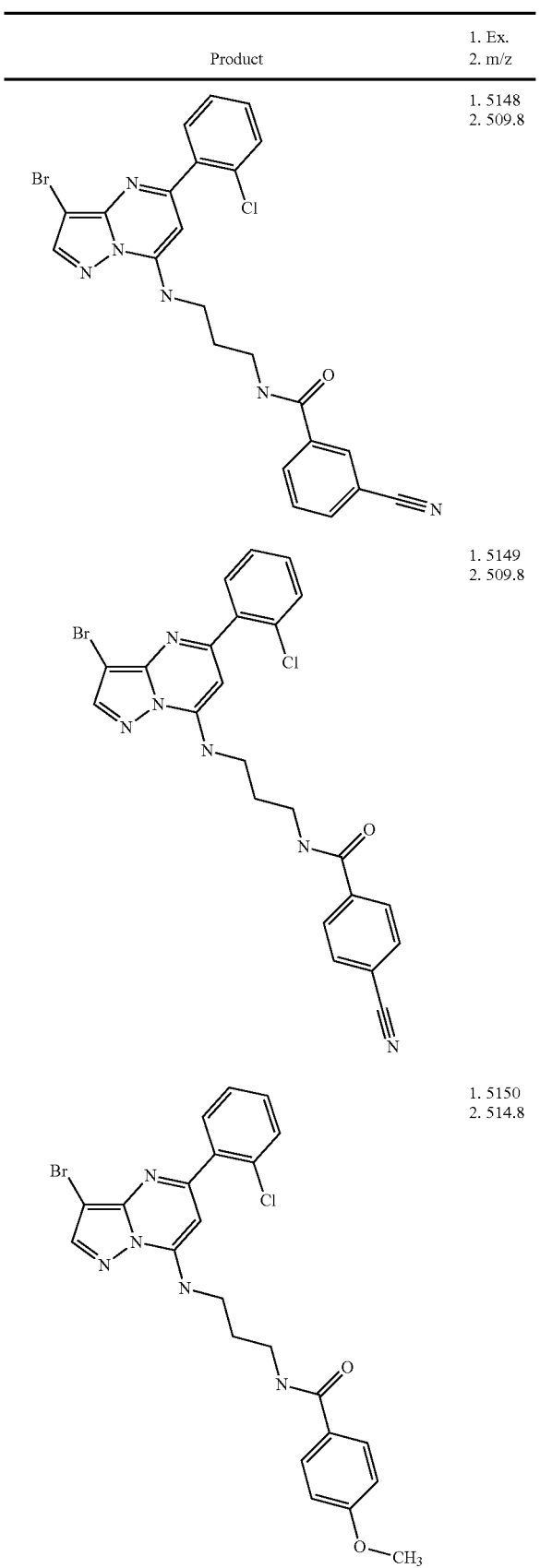 | 1. 5148 2. 509.8 |
| | 1. 5149 2. 509.8 |
| | 1. 5150 2. 514.8 |
TABLE 51-continued
| Product | 1. Ex. 2. m/z |
|---|---|
| 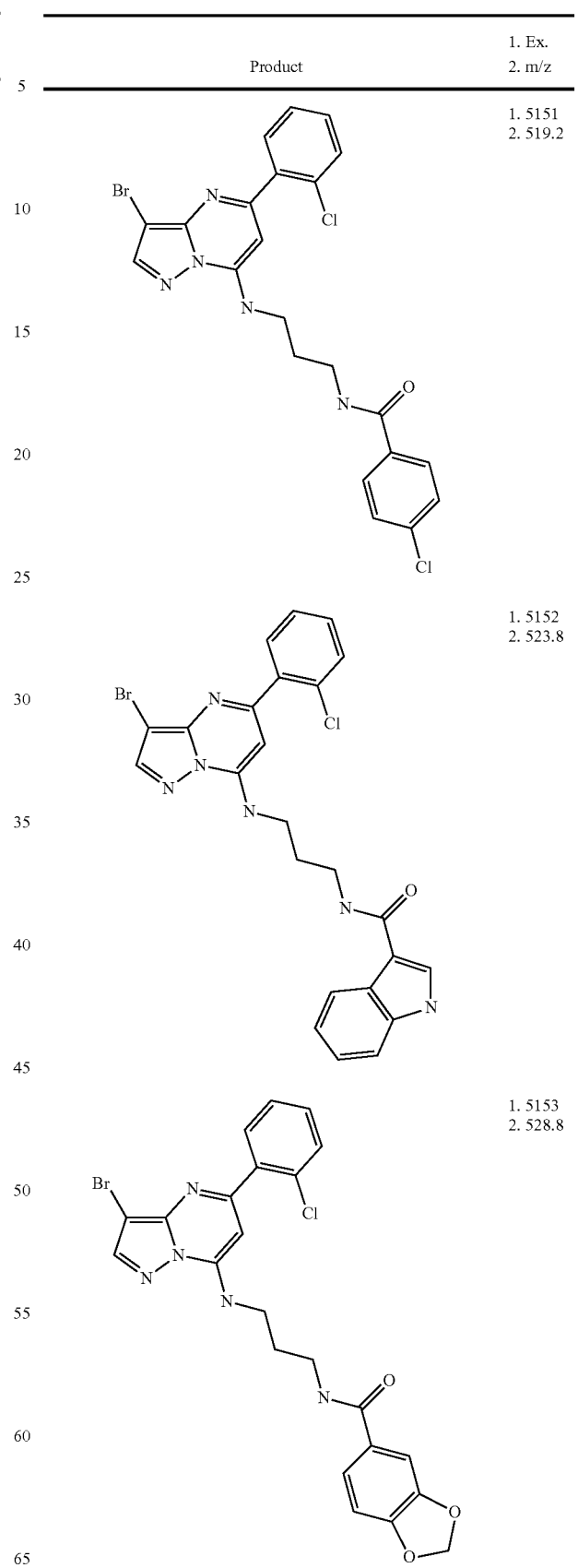 | 1. 5151 2. 519.2 |
| | 1. 5152 2. 523.8 |
| | 1. 5153 2. 528.8 |

TABLE 51-continued
| Product | 1. Ex. 2. m/z |
|---|---|
| 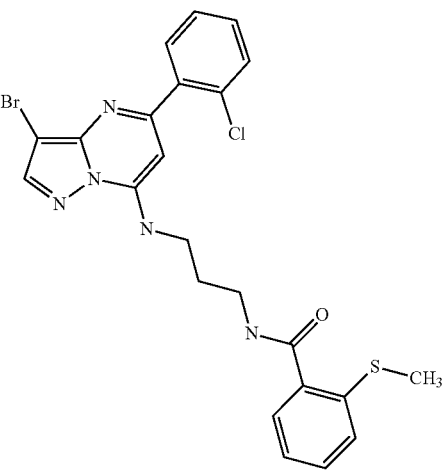 [SMILES: CSc1ccccc1C(=O)NCCCNc1cc(-c2ccccc2Cl)nc2c(Br)cnn12] | 1. 5154<br>2. 530.9 |
| 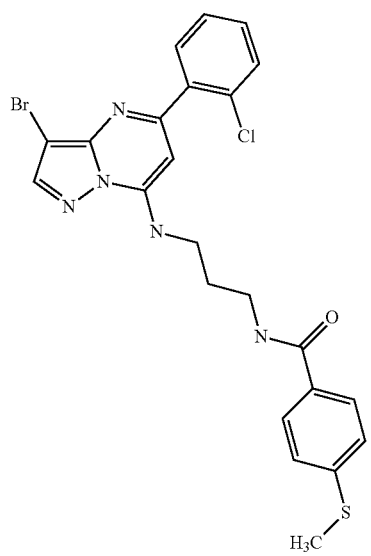 [SMILES: CSc1ccc(C(=O)NCCCNc2cc(-c3ccccc3Cl)nc3c(Br)cnn23)cc1] | 1. 5155<br>2. 530.9 |
| 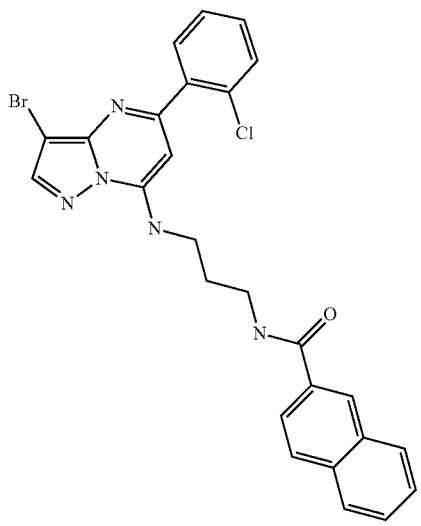 [SMILES: O=C(NCCCNc1cc(-c2ccccc2Cl)nc2c(Br)cnn12)c1ccc2ccccc2c1] | 1. 5156<br>2. 534.8 |
TABLE 51-continued
| Product | 1. Ex. 2. m/z |
|---|---|
| 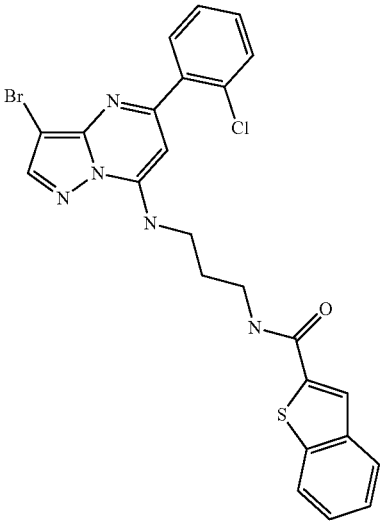 [SMILES: O=C(NCCCNc1cc(-c2ccccc2Cl)nc2c(Br)cnn12)c1cc2ccccc2s1] | 1. 5157<br>2. 540.9 |
| 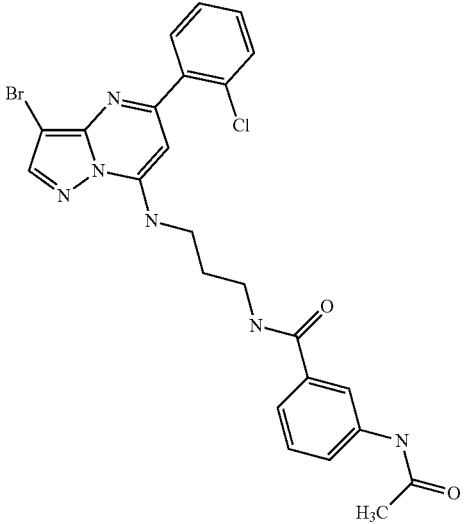 [SMILES: CC(=O)Nc1cccc(C(=O)NCCCNc2cc(-c3ccccc3Cl)nc3c(Br)cnn23)c1] | 1. 5158<br>2. 541.8 |

TABLE 51-continued

| Product | 1. Ex. 2. m/z |
|---|---|
| (structure: 3-bromo-5-(2-chlorophenyl)pyrazolo[1,5-a]pyrimidin-7-yl with NH-(CH2)3-NH-C(=O)-C6H4-NH-C(=O)-CH3) | 1. 5159<br>2. 541.8 |
| (structure: 3-bromo-5-(2-chlorophenyl)pyrazolo[1,5-a]pyrimidin-7-yl with NH-(CH2)3-NH-C(=O)-biphenyl) | 1. 5160<br>2. 560.9 |

TABLE 52

| Product | 1. Ex. 2. m/z |
|---|---|
| (structure: 3-bromo-5-(2-chlorophenyl)pyrazolo[1,5-a]pyrimidin-7-yl with NH-(CH2)4-NH-C(=O)-cyclopropyl) | 1. 5201<br>2. 462.8 |
| (structure: 3-bromo-5-(2-chlorophenyl)pyrazolo[1,5-a]pyrimidin-7-yl with NH-(CH2)4-NH-C(=O)-CH2-cyclopropyl) | 1. 5202<br>2. 476.8 |
| (structure: 3-bromo-5-(2-chlorophenyl)pyrazolo[1,5-a]pyrimidin-7-yl with NH-(CH2)4-NH-C(=O)-CH2-S-CH3) | 1. 5203<br>2. 482.8 |

TABLE 52-continued
| Product | 1. Ex.<br>2. m/z |
|---|---|
| 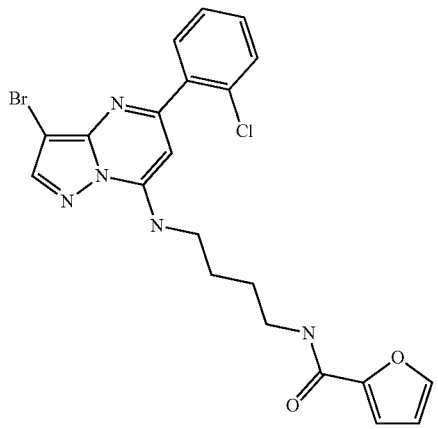 [SMILES: O=C(NCCCCNc1cc(-c2ccccc2Cl)nc2c(Br)cnn12)c1ccco1] | 1. 5204<br>2. 488.8 |
| 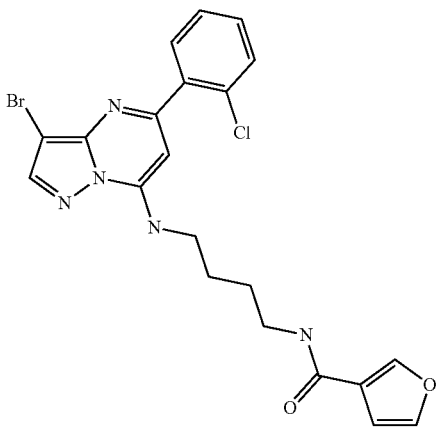 [SMILES: O=C(NCCCCNc1cc(-c2ccccc2Cl)nc2c(Br)cnn12)c1ccoc1] | 1. 5205<br>2. 488.8 |
| 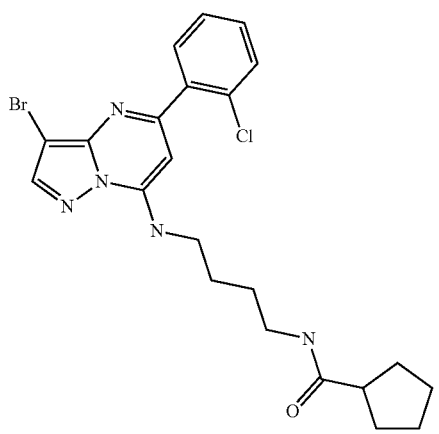 [SMILES: O=C(NCCCCNc1cc(-c2ccccc2Cl)nc2c(Br)cnn12)C1CCCO1] | 1. 5206<br>2. 490.8 |
TABLE 52-continued
| Product | 1. Ex.<br>2. m/z |
|---|---|
| 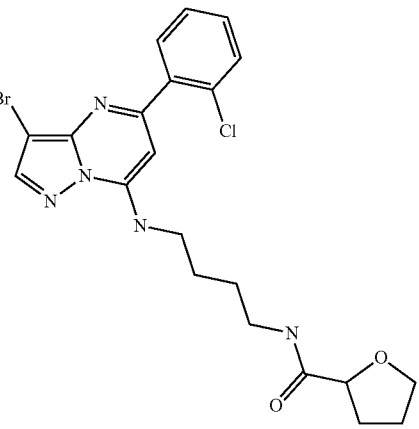 | 1. 5207<br>2. 492.8 |
| 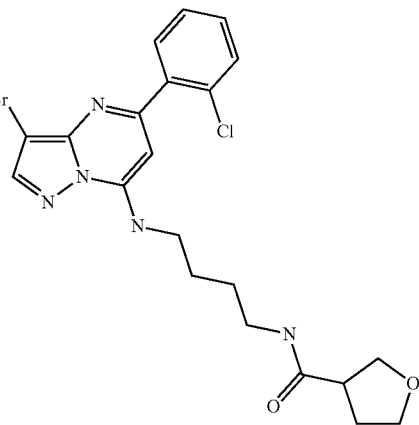 | 1. 5208<br>2. 492.8 |
| 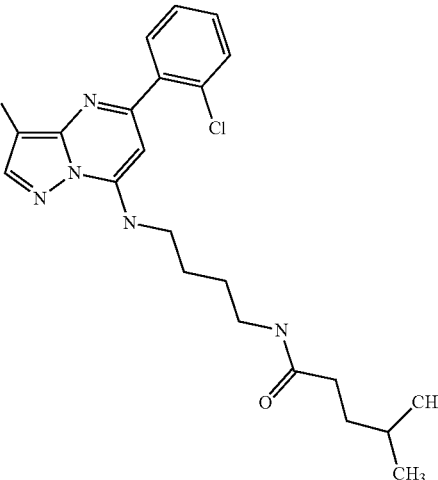 | 1. 52009<br>2. 492.9 |

TABLE 52-continued

| Product | 1. Ex. 2. m/z |
|---|---|
| (structure) | 1. 5210 2. 504.8 |
| (structure) | 1. 5211 2. 504.8 |
| (structure) | 2. 5212 2. 508.8 |
| (structure) | 1. 5213 2. 512.8 |
| (structure) | 1. 5214 2. 517.8 |
| (structure) | 1. 5215 2. 518.9 |

TABLE 52-continued
| Product | 1. Ex. 2. m/z |
|---|---|
| 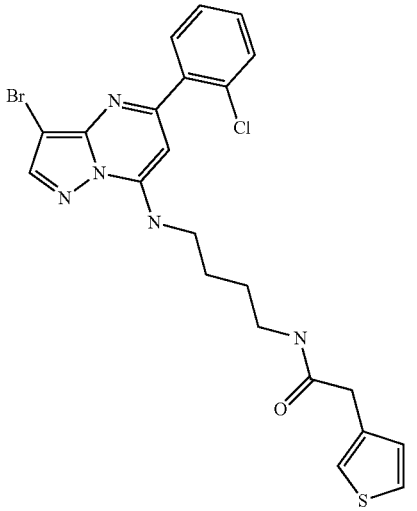 [SMILES: O=C(Cc1ccsc1)NCCCCNc1cc(-c2ccccc2Cl)nc2c(Br)cnn12] | 1. 5216 2. 518.9 |
| 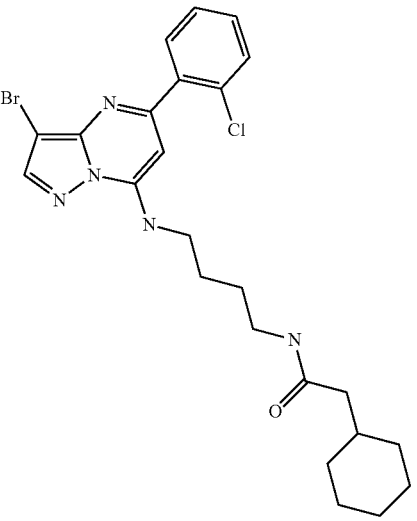 [SMILES: O=C(CC1CCCCC1)NCCCCNc1cc(-c2ccccc2Cl)nc2c(Br)cnn12] | 1. 5217 2. 518.9 |
| 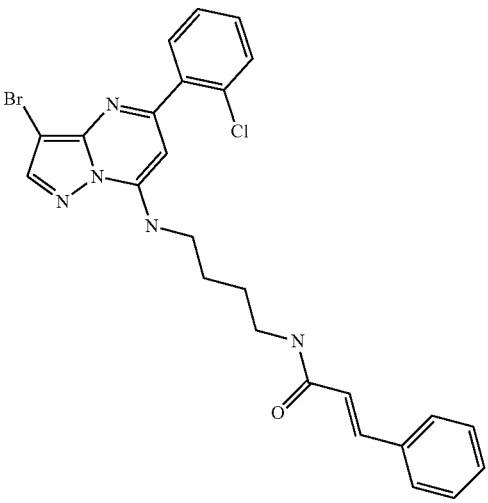 [SMILES: O=C(/C=C/c1ccccc1)NCCCCNc1cc(-c2ccccc2Cl)nc2c(Br)cnn12] | 1. 5218 2. 524.9 |
TABLE 52-continued
| Product | 1. Ex. 2. m/z |
|---|---|
| 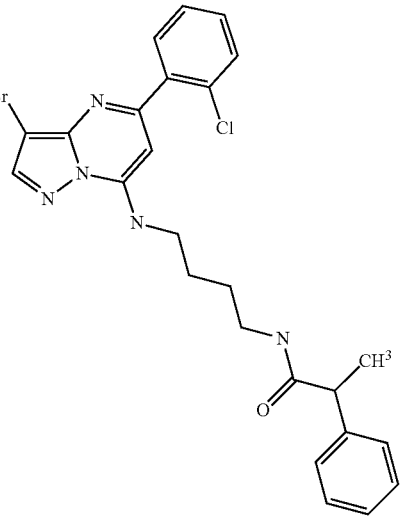 | 1. 5219 2. 526.9 |
| 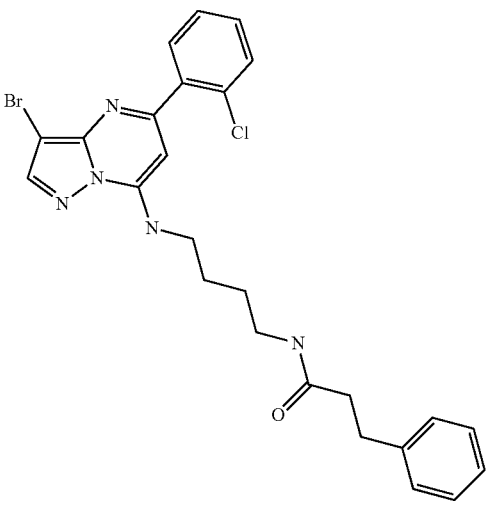 [SMILES: O=C(CCc1ccccc1)NCCCCNc1cc(-c2ccccc2Cl)nc2c(Br)cnn12] | 1. 5220 2. 526.9 |
| 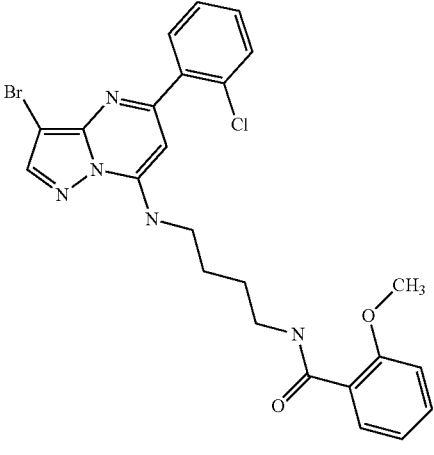 [SMILES: COc1ccccc1C(=O)NCCCCNc1cc(-c2ccccc2Cl)nc2c(Br)cnn12] | 1. 5221 2. 528.8 |

TABLE 52-continued

| Product | 1. Ex. 2. m/z |
|---|---|
| (structure) | 1. 5222  2. 528.8 |
| (structure) | 1. 5223  2. 533.3 |
| (structure) | 1. 5224  2. 533.3 |

TABLE 52-continued

| Product | 1. Ex. 2. m/z |
|---|---|
| (structure) | 1. 5225  2. 537.9 |
| (structure) | 1. 5226  2. 538.8 |
| (structure) | 1. 5227  2. 538.9 |

TABLE 52-continued
| Product | 1. Ex. 2. m/z |
|---|---|
| 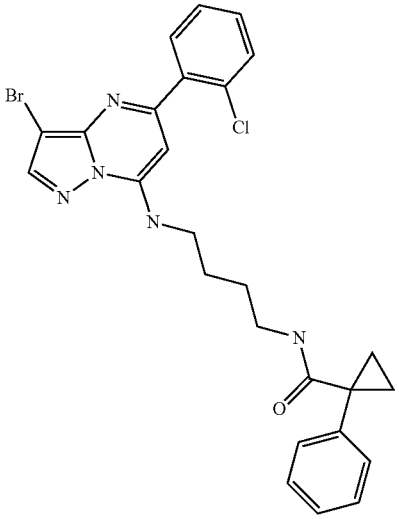 [SMILES: O=C(NCCCCNc1cc(-c2ccccc2Cl)nc2c(Br)cnn12)C1(c2ccccc2)CC1] | 1. 5228  2. 538.9 |
| 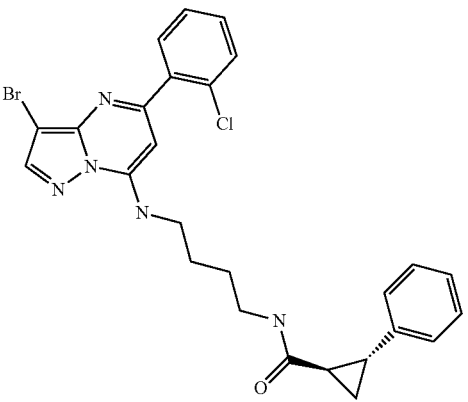 [SMILES: O=C(NCCCCNc1cc(-c2ccccc2Cl)nc2c(Br)cnn12)[C@@H]1C[C@H]1c1ccccc1] | 1. 5229  2. 538.9 |
| 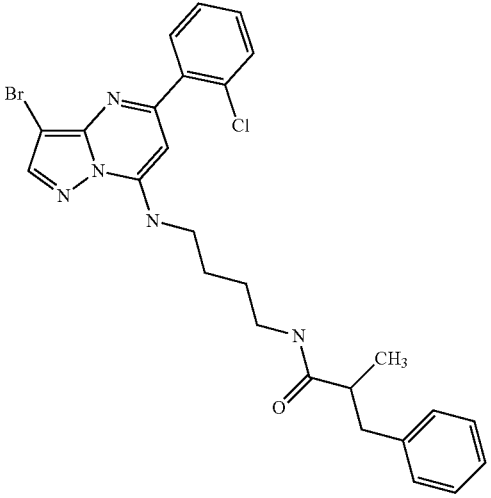 [SMILES: CC(Oc1ccccc1)C(=O)NCCCCNc1cc(-c2ccccc2Cl)nc2c(Br)cnn12] | 1. 5230  2. 540.9 |АН
| 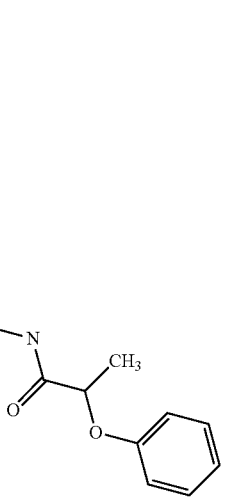 | 1. 5231  2. 542.9 |
| 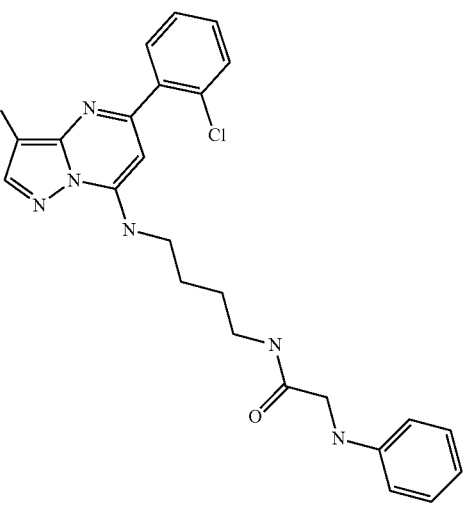 | 1. 5232  2. 544.9 |
| 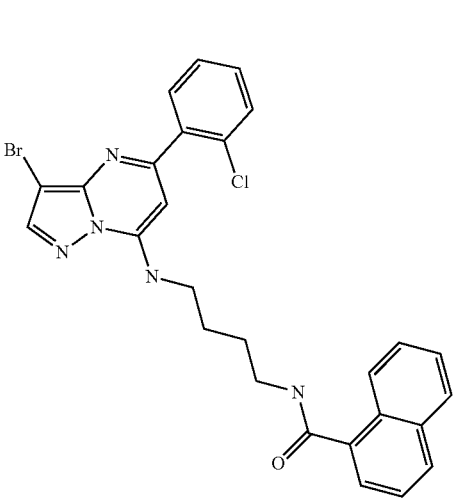 [SMILES: O=C(NCCCCNc1cc(-c2ccccc2Cl)nc2c(Br)cnn12)c1cccc2ccccc12] | 1. 5233  2. 548.9 |

TABLE 52-continued
| Product | 1. Ex.<br>2. m/z |
|---|---|
| 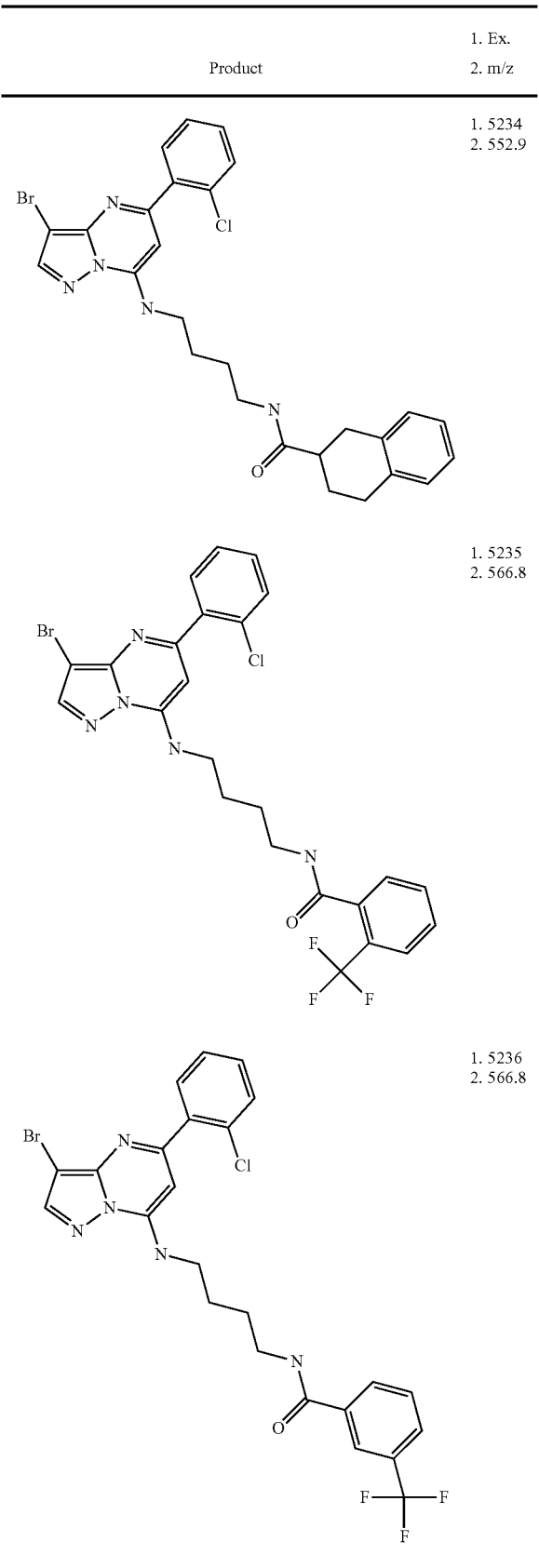 | 1. 5234<br>2. 552.9 |
| | 1. 5235<br>2. 566.8 |
| | 1. 5236<br>2. 566.8 |
TABLE 52-continued
| Product | 1. Ex.<br>2. m/z |
|---|---|
| 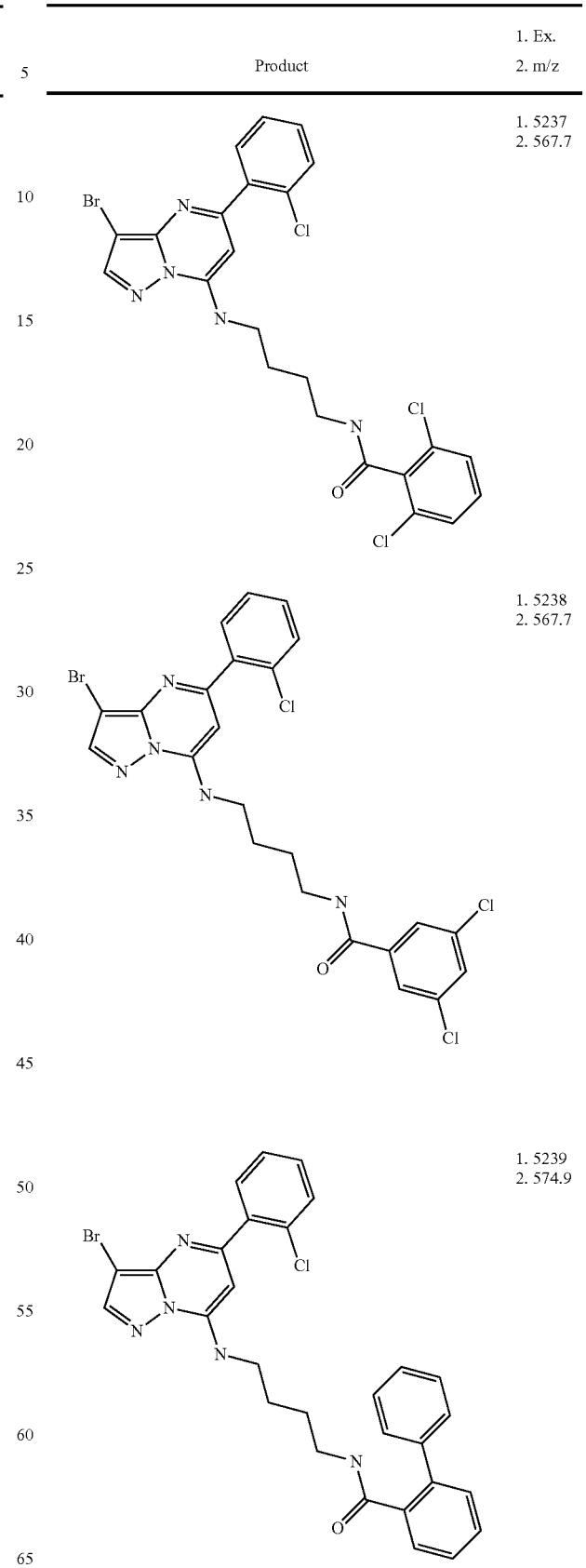 | 1. 5237<br>2. 567.7 |
| | 1. 5238<br>2. 567.7 |
| | 1. 5239<br>2. 574.9 |

TABLE 52-continued
| Product | 1. Ex. 2. m/z |
|---|---|
| 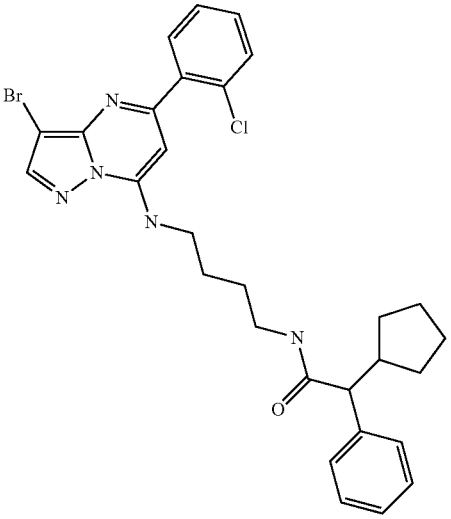 [SMILES: O=C(NCCCCNc1cc(-c2ccccc2Cl)nc2c(Br)cnn12)C(c1ccccc1)C1CCCC1] | 1. 5240 2. 581 |
| 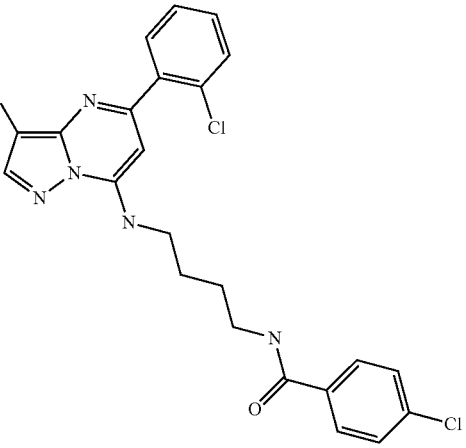 | 1. 5241 2. 533.3 |
| 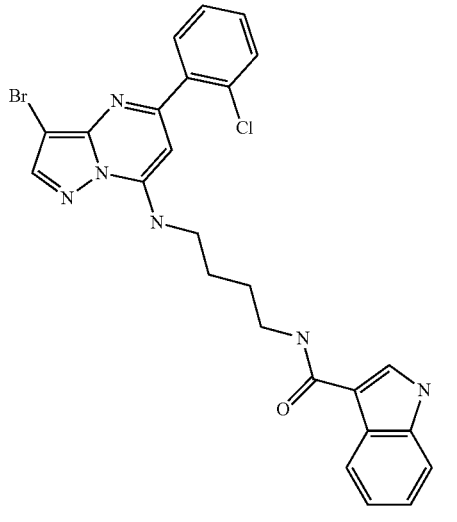 [SMILES: O=C(NCCCCNc1cc(-c2ccccc2Cl)nc2c(Br)cnn12)c1c[nH]c2ccccc12] | 1. 5242 2. 537.9 |
TABLE 52-continued
| Product | 1. Ex. 2. m/z |
|---|---|
| 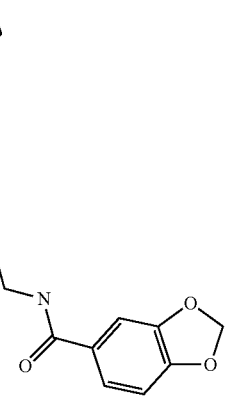 | 1. 5243 2. 542.8 |
| 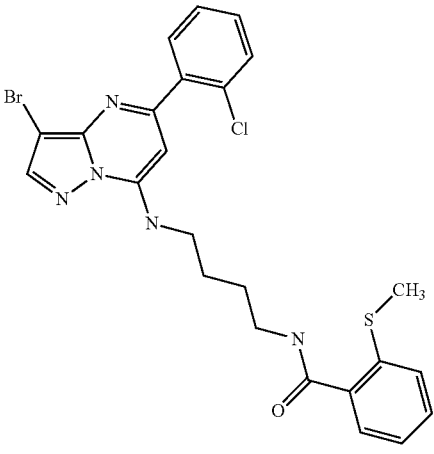 | 1. 5244 2. 544.9 |
| 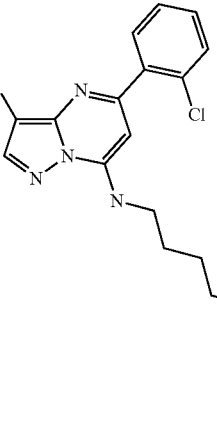 | 1. 5245 2. 544.9 |

TABLE 52-continued
| Product | 1. Ex.<br>2. m/z |
|---|---|
| 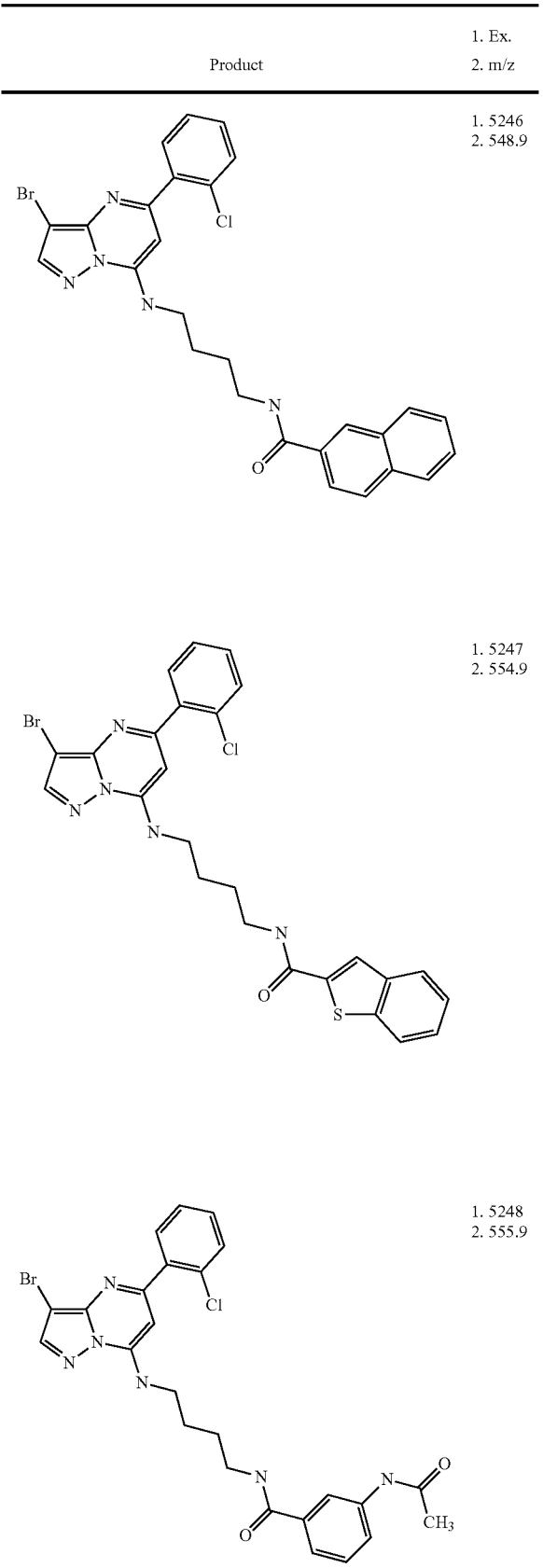 | 1. 5246<br>2. 548.9 |
| | 1. 5247<br>2. 554.9 |
| | 1. 5248<br>2. 555.9 |
TABLE 52-continued
| Product | 1. Ex.<br>2. m/z |
|---|---|
| 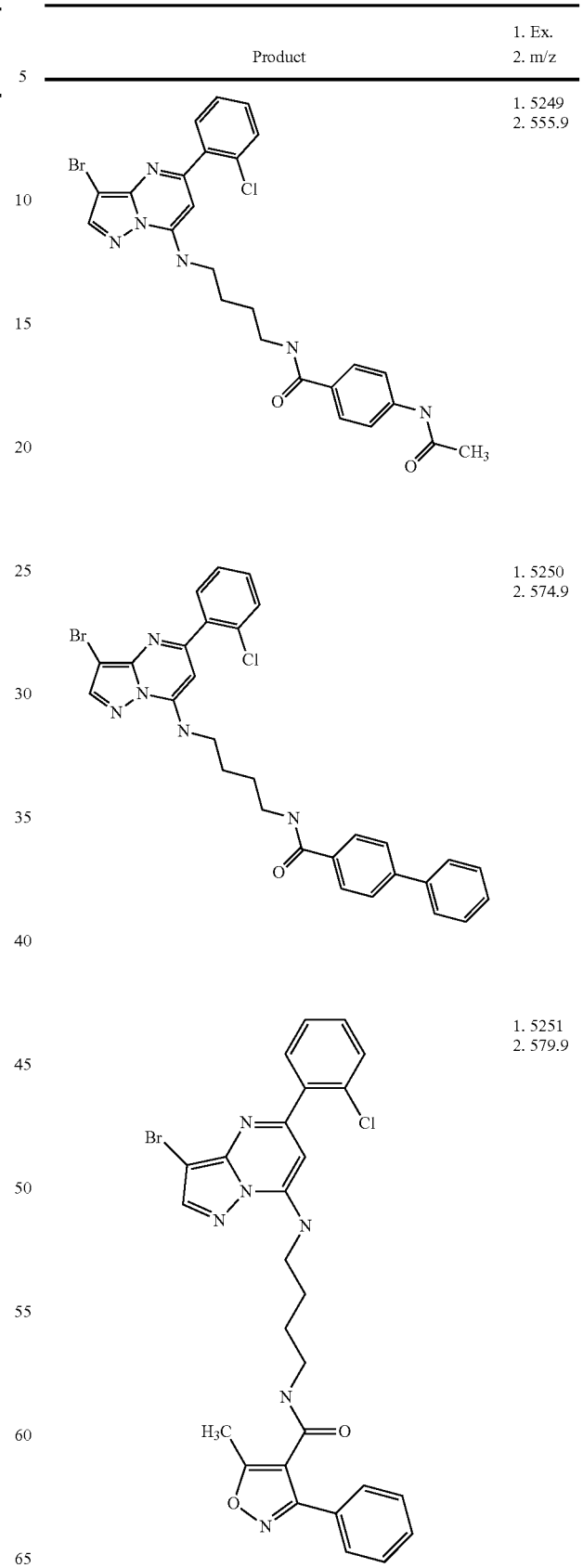 | 1. 5249<br>2. 555.9 |
| | 1. 5250<br>2. 574.9 |
| | 1. 5251<br>2. 579.9 |

TABLE 52-continued
| Product | 1. Ex.<br>2. m/z |
|---|---|
| 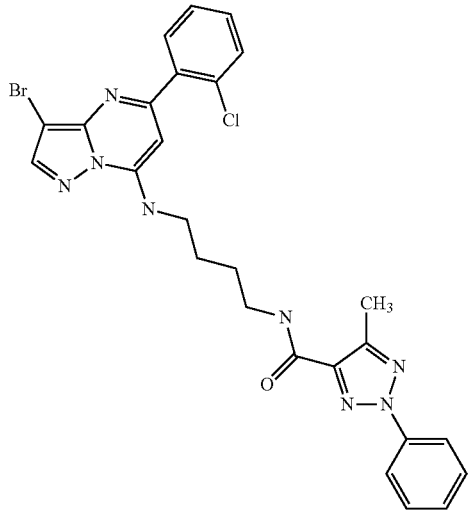 [SMILES: Cc1nn(-c2ccccc2)nc1C(=O)NCCCCNc1cc(-c2ccccc2Cl)nc2c(Br)cnn12] | 1. 5252<br>2. 579.9 |
| 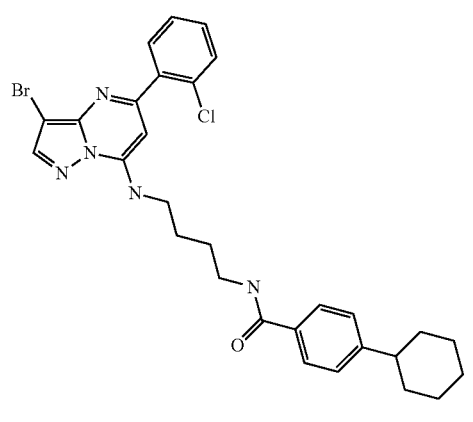 [SMILES: O=C(NCCCCNc1cc(-c2ccccc2Cl)nc2c(Br)cnn12)c1ccc(C2CCCCC2)cc1] | 1. 5253<br>2. 581 |
| 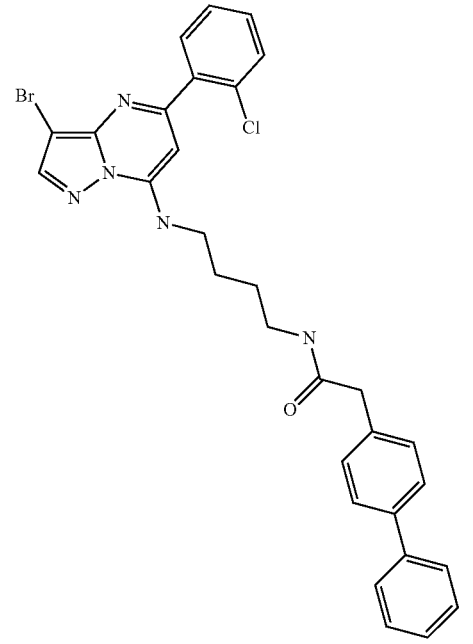 [SMILES: O=C(Cc1ccc(-c2ccccc2)cc1)NCCCCNc1cc(-c2ccccc2Cl)nc2c(Br)cnn12] | 1. 5254<br>2. 588.9 |
TABLE 52-continued
| Product | 1. Ex.<br>2. m/z |
|---|---|
| 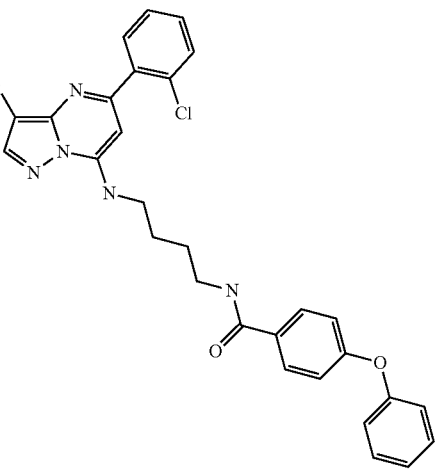 | 1. 5255<br>2. 590.9 |
| 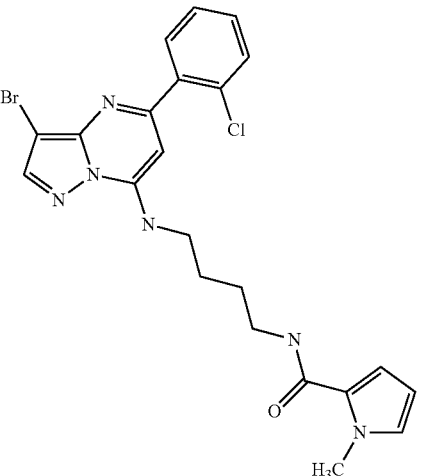 [SMILES: Cn1cccc1C(=O)NCCCCNc1cc(-c2ccccc2Cl)nc2c(Br)cnn12] | 1. 5256<br>2. 501.8 |
| 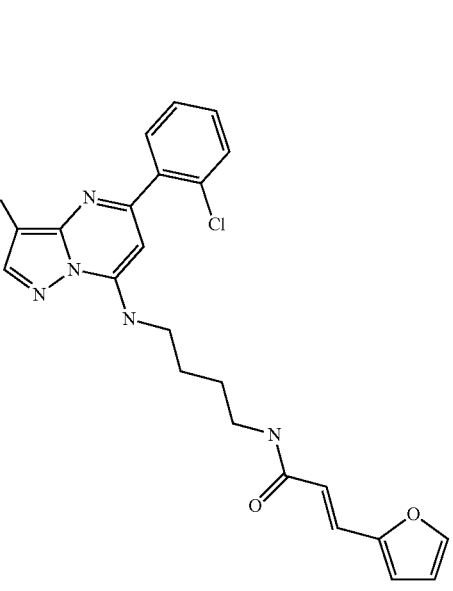 | 1. 5257<br>2. 514.8 |

TABLE 52-continued

| Product | 1. Ex. 2. m/z |
|---|---|
| (3-bromo-5-(2-chlorophenyl)pyrazolo[1,5-a]pyrimidin-7-yl)amino-butyl cycloheptanecarboxamide | 1. 5258 2. 518.9 |
| (3-bromo-5-(2-chlorophenyl)pyrazolo[1,5-a]pyrimidin-7-yl)amino-butyl (E)-3-(thiophen-2-yl)acrylamide | 1. 5259 2. 530.9 |
| (3-bromo-5-(2-chlorophenyl)pyrazolo[1,5-a]pyrimidin-7-yl)amino-butyl (E)-3-(thiophen-3-yl)acrylamide | 1. 5260 2. 530.9 |

TABLE 52-continued

| Product | 1. Ex. 2. m/z |
|---|---|
| (3-bromo-5-(2-chlorophenyl)pyrazolo[1,5-a]pyrimidin-7-yl)amino-butyl 2-methyl-3-phenylacrylamide | 1. 5261 2. 538.9 |
| (3-bromo-5-(2-chlorophenyl)pyrazolo[1,5-a]pyrimidin-7-yl)amino-butyl 3-phenoxypropanamide | 1. 5262 2. 542.9 |
| (3-bromo-5-(2-chlorophenyl)pyrazolo[1,5-a]pyrimidin-7-yl)amino-butyl 2-(3-chlorophenyl)acetamide | 1. 5263 2. 547.3 |

TABLE 52-continued

| Product | 1. Ex. 2. m/z |
|---|---|
| (structure) | 1. 5264 2. 551.9 |
| (structure) | 1. 5265 2. 552.9 |
| (structure) | 1. 5266 2. 556.9 |
| (structure) | 1. 5267 2. 556.9 |
| (structure) | 1. 5268 2. 537.9 |

TABLE 52-continued
| Product | 1. Ex. 2. m/z |
|---|---|
| 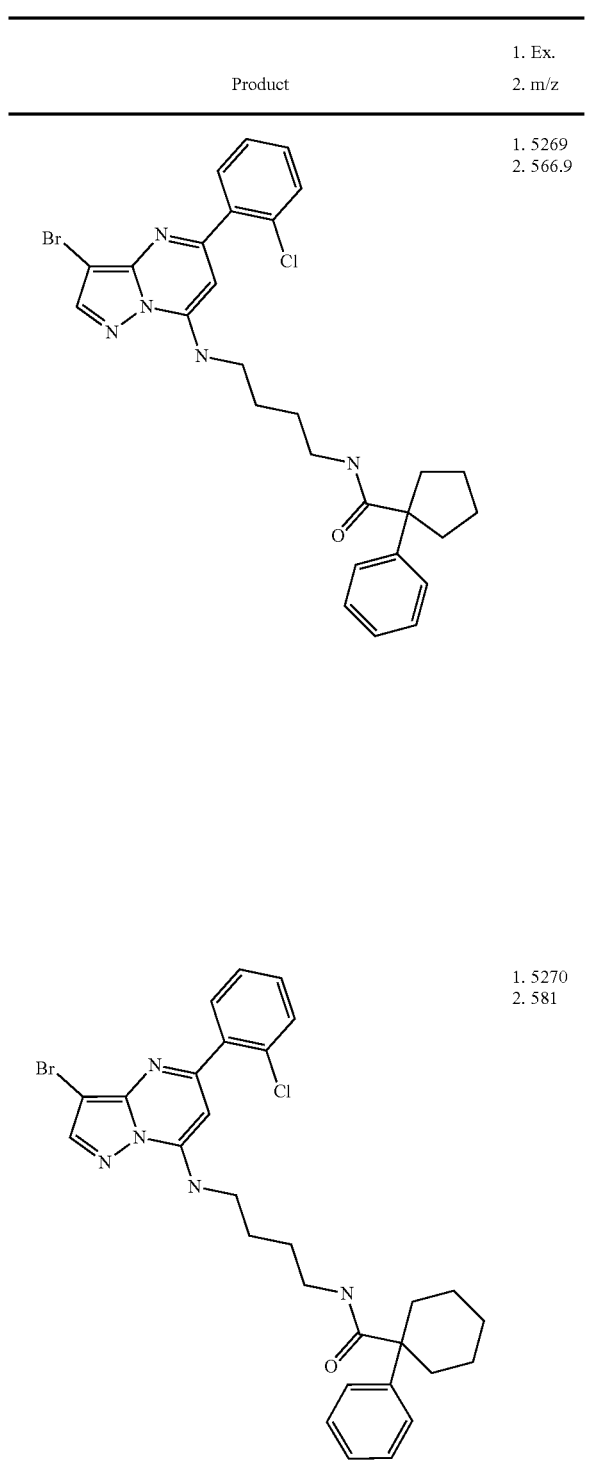 | 1. 5269 2. 566.9 |
| | 1. 5270 2. 581 |
TABLE 52-continued
| Product | 1. Ex. 2. m/z |
|---|---|
| 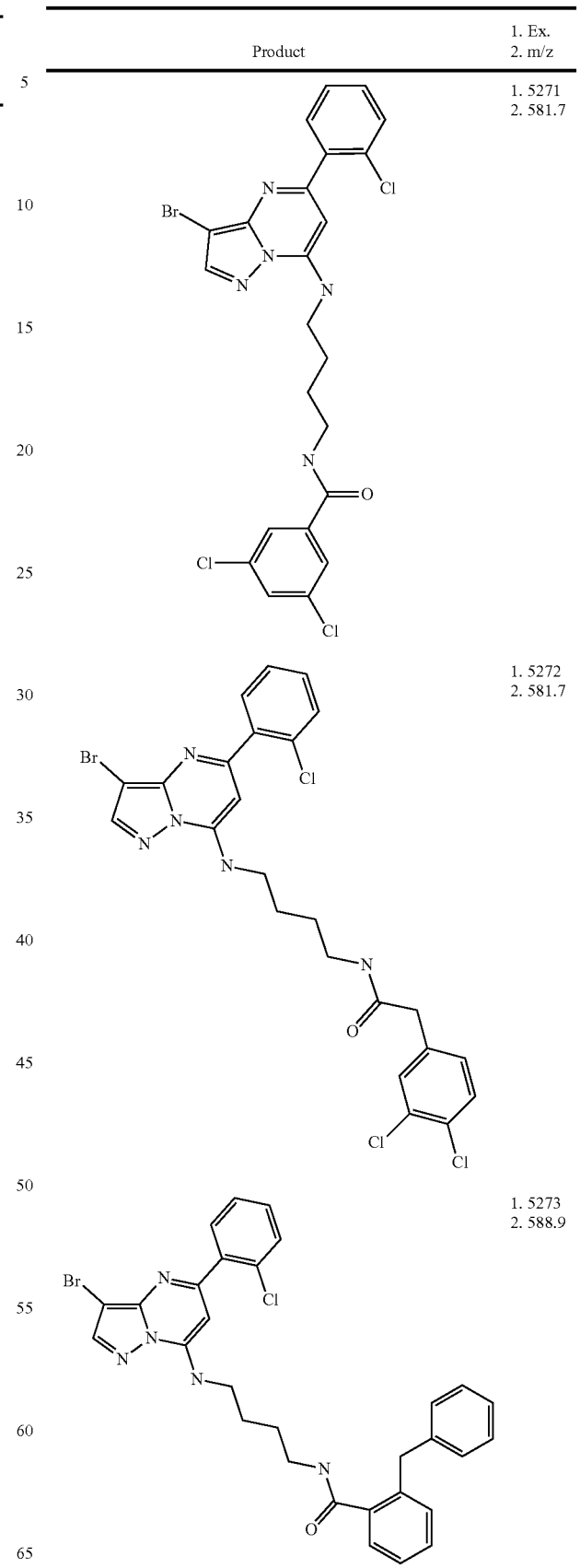 | 1. 5271 2. 581.7 |
| | 1. 5272 2. 581.7 |
| | 1. 5273 2. 588.9 |

TABLE 52-continued
| Product | 1. Ex. 2. m/z |
|---|---|
| 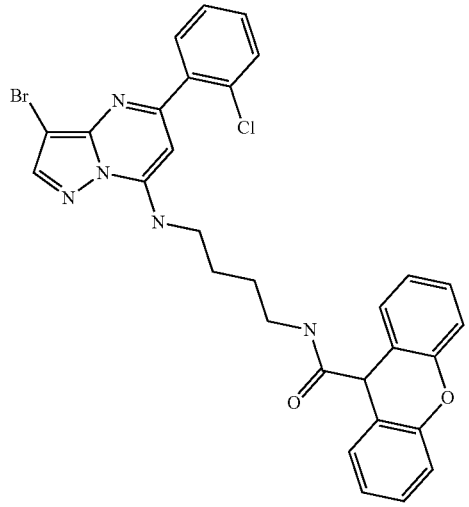 [SMILES: O=C(NCCCCNc1cc(-c2ccccc2Cl)nc2c(Br)cnn12)C1c2ccccc2Oc2ccccc21] | 1. 5274 2. 602.9 |
| 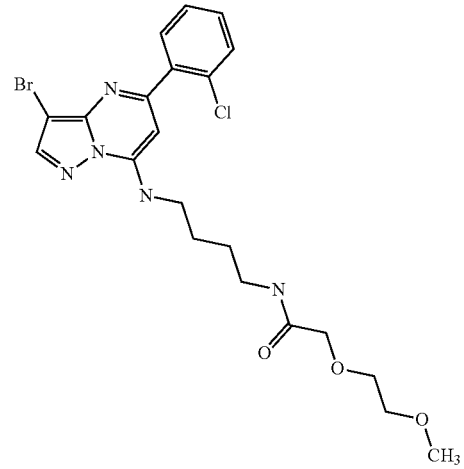 [SMILES: COCCOCC(=O)NCCCCNc1cc(-c2ccccc2Cl)nc2c(Br)cnn12] | 1. 5275 2. 510.8 |
| 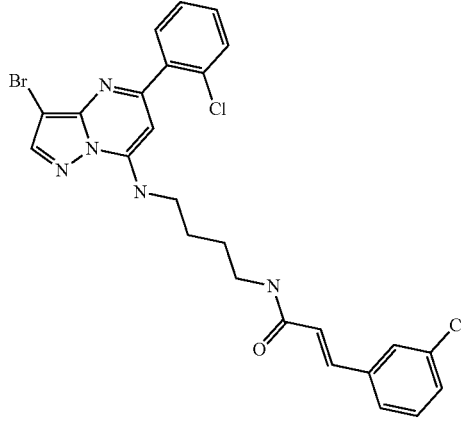 [SMILES: O=C(/C=C/c1cccc(Cl)c1)NCCCCNc1cc(-c2ccccc2Cl)nc2c(Br)cnn12] | 1. 5276 2. 559.3 |
TABLE 52-continued
| Product | 1. Ex. 2. m/z |
|---|---|
| 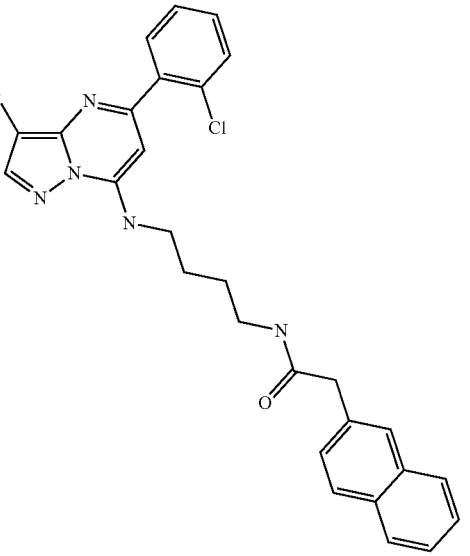 | 1. 5277 2. 562.9 |
| 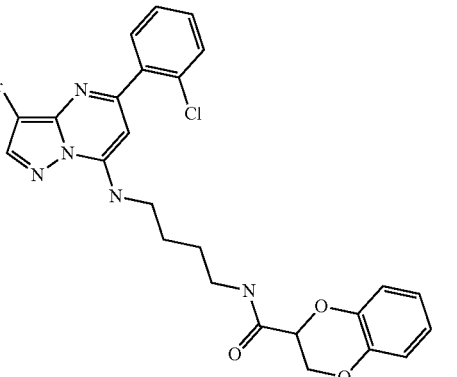 | 1. 5278 2. 556.9 |
| 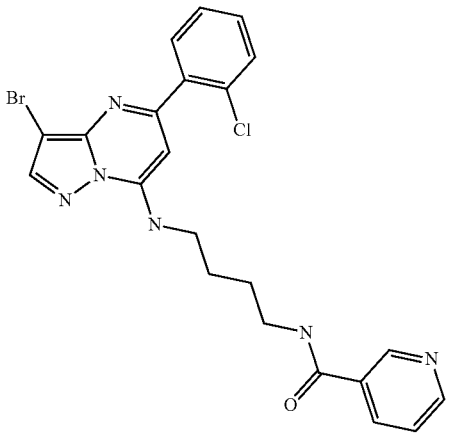 [SMILES: O=C(NCCCCNc1cc(-c2ccccc2Cl)nc2c(Br)cnn12)c1cccnc1] | 1. 5279 2. 499.8 |

TABLE 52-continued
| Product | 1. Ex.<br>2. m/z |
|---|---|
| 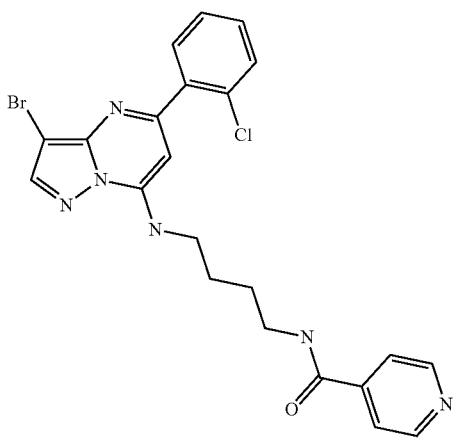 [SMILES: O=C(NCCCCNc1cc(-c2ccccc2Cl)nc2c(Br)cnn12)c1ccncc1] | 1. 5280<br>2. 499.8 |
TABLE 53
| Product | 1. Ex.<br>2. m/z |
|---|---|
| 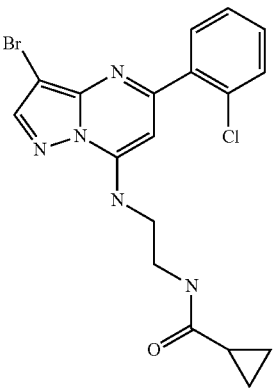 [SMILES: O=C(NCCNc1cc(-c2ccccc2Cl)nc2c(Br)cnn12)C1CC1] | 1. 5301<br>2. 434.7 |
| 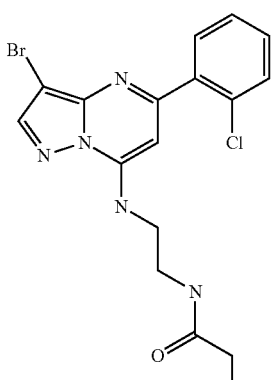 | 1. 5302<br>2. 448.8 |
TABLE 53-continued
| Product | 1. Ex.<br>2. m/z |
|---|---|
| 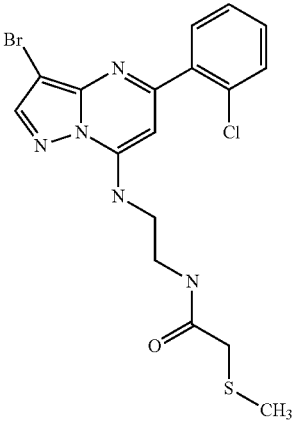 [SMILES: CSCC(=O)NCCNc1cc(-c2ccccc2Cl)nc2c(Br)cnn12] | 1. 5303<br>2. 454.8 |
| 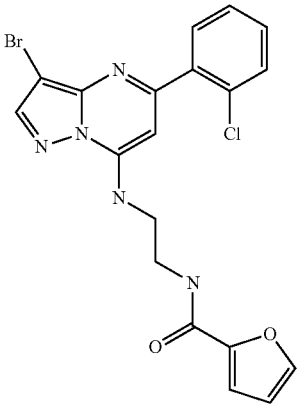 | 1. 5304<br>2. 460.7 |
| 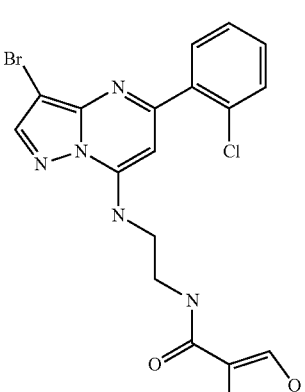 | 1. 5305<br>2. 460.7 |

TABLE 53-continued
| Product | 1. Ex.<br>2. m/z |
|---|---|
| 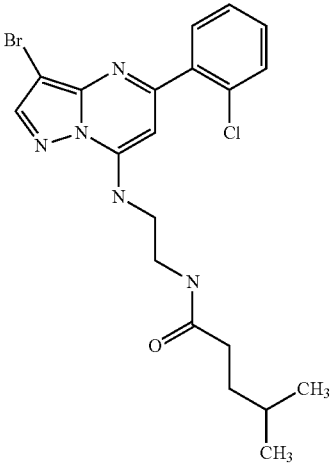 [SMILES: CC(C)CCC(=O)NCCNc1cc(-c2ccccc2Cl)nc2c(Br)cnn12] | 1. 5309<br>2. 464.8 |
| 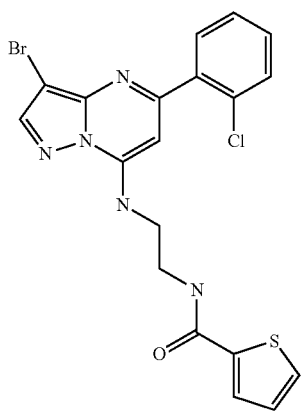 [SMILES: O=C(NCCNc1cc(-c2ccccc2Cl)nc2c(Br)cnn12)c1cccs1] | 1. 5310<br>2. 476.8 |
| 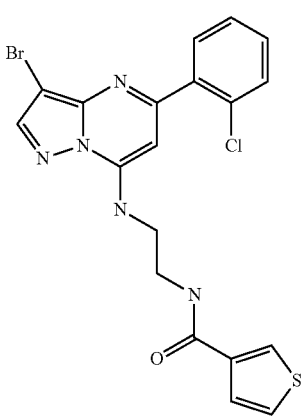 [SMILES: O=C(NCCNc1cc(-c2ccccc2Cl)nc2c(Br)cnn12)c1ccsc1] | 1. 5311<br>2. 476.8 |
TABLE 53-continued
| Product | 1. Ex.<br>2. m/z |
|---|---|
| 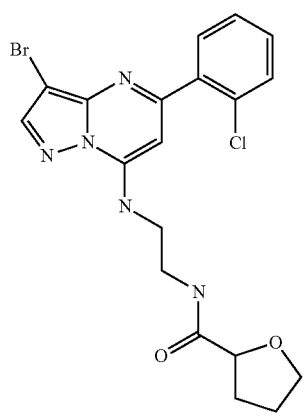 | 1. 5307<br>2. 464.8 |
| 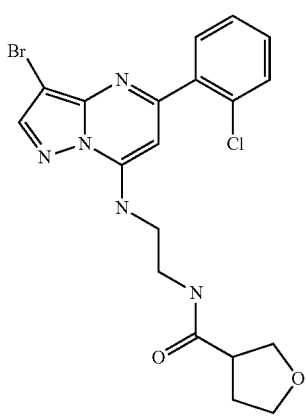 | 1. 5308<br>2. 464.8 |
(Note: The first entry 1. 5306 / 2. 462.8 appears at the top of column 991.)

TABLE 53-continued

| Product | 1. Ex.<br>2. m/z |
|---|---|
| (structure) | 1. 5312<br>2. 480.8 |
| (structure) | 1. 5313<br>2. 484.8 |
| (structure) | 1. 5314<br>2. 489.8 |
| (structure) | 1. 5315<br>2. 490.8 |
| (structure) | 1. 5316<br>2. 490.8 |
| (structure) | 1. 5317<br>2. 490.8 |

TABLE 53-continued
| Product | 1. Ex. 2. m/z |
|---|---|
| 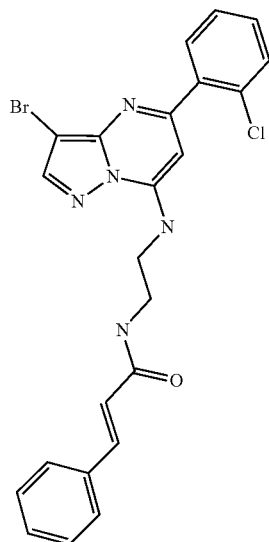 [SMILES: O=C(/C=C/c1ccccc1)NCCNc1cc(-c2ccccc2Cl)nc2c(Br)cnn12] | 1. 5318 2. 496.8 |
| 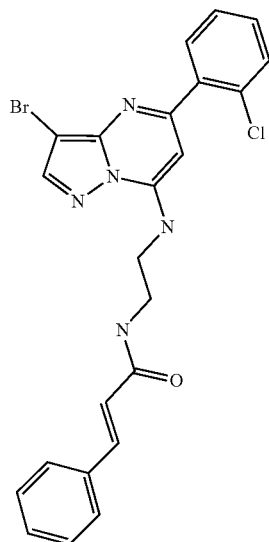 [SMILES: O=C(/C=C/c1ccccc1)NCCNc1cc(-c2ccccc2Cl)nc2c(Br)cnn12] | 1. 5319 2. 498.8 |
TABLE 53-continued
| Product | 1. Ex. 2. m/z |
|---|---|
| 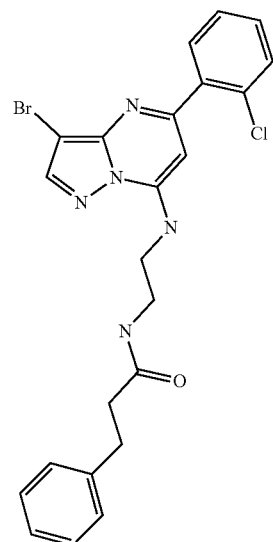 [SMILES: O=C(CCc1ccccc1)NCCNc1cc(-c2ccccc2Cl)nc2c(Br)cnn12] | 1. 5320 2. 498.8 |
| 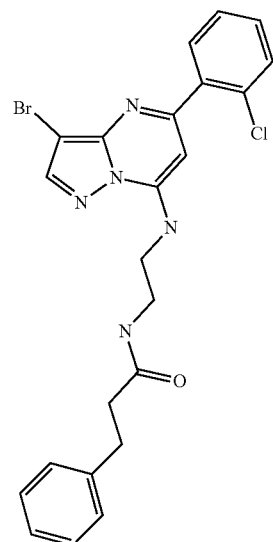 [SMILES: O=C(CCc1ccccc1)NCCNc1cc(-c2ccccc2Cl)nc2c(Br)cnn12] | 1. 5321 2. 500.8 |
| 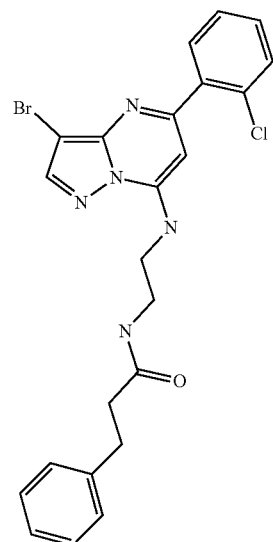 [SMILES: O=C(CCc1ccccc1)NCCNc1cc(-c2ccccc2Cl)nc2c(Br)cnn12] | 1. 5322 2. 500.8 |

TABLE 53-continued
| Product | 1. Ex.<br>2. m/z |
|---|---|
| 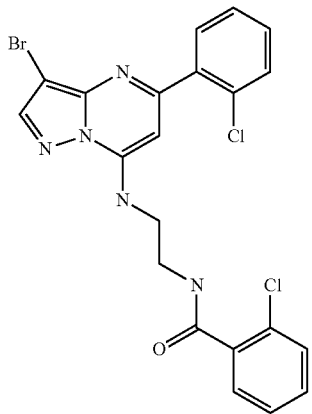 [SMILES: O=C(NCCNc1cc(-c2ccccc2Cl)nc2c(Br)cnn12)c1ccccc1Cl] | 1. 5323<br>2. 505.2 |
| 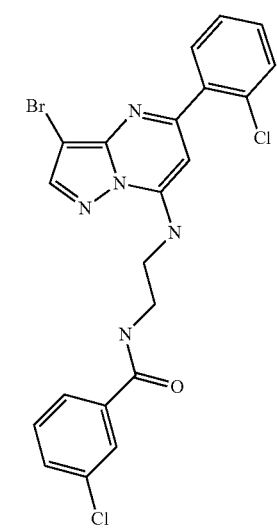 [SMILES: O=C(NCCNc1cc(-c2ccccc2Cl)nc2c(Br)cnn12)c1cccc(Cl)c1] | 1. 5324<br>2. 505.2 |
| 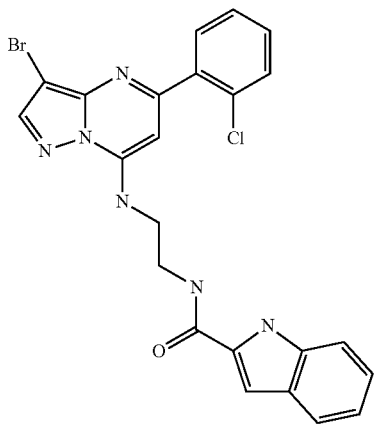 [SMILES: O=C(NCCNc1cc(-c2ccccc2Cl)nc2c(Br)cnn12)c1cc2ccccc2o1] | 1. 5325<br>2. 509.8 |
TABLE 53-continued
| Product | 1. Ex.<br>2. m/z |
|---|---|
| 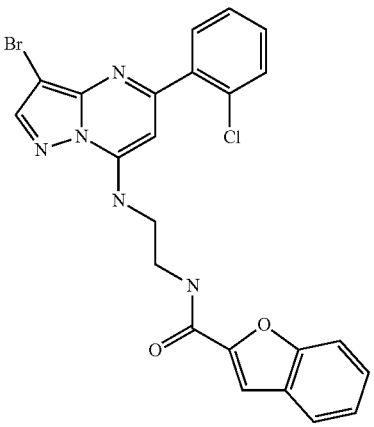 | 1. 5326<br>2. 510.8 |
| 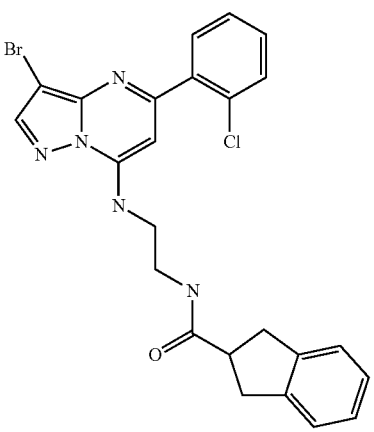 [SMILES: O=C(NCCNc1cc(-c2ccccc2Cl)nc2c(Br)cnn12)C1Cc2ccccc2C1] | 1. 5327<br>2. 510.8 |
| 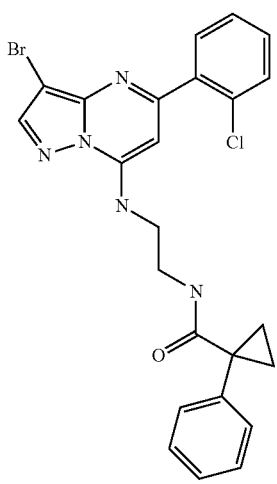 [SMILES: O=C(NCCNc1cc(-c2ccccc2Cl)nc2c(Br)cnn12)C1(c2ccccc2)CC1] | 1. 5328<br>2. 510.8 |

TABLE 53-continued
| Product | 1. Ex.<br>2. m/z |
|---|---|
| 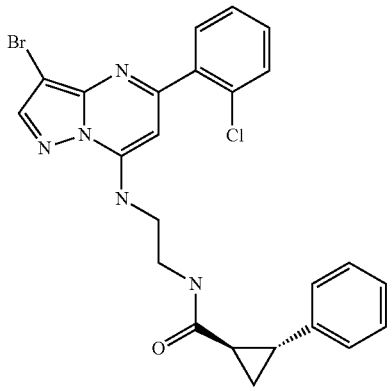 [SMILES: O=C(NCCNc1cc(-c2ccccc2Cl)nc2c(Br)cnn12)[C@@H]1C[C@H]1c1ccccc1] | 1. 5329<br>2. 510.8 |
| 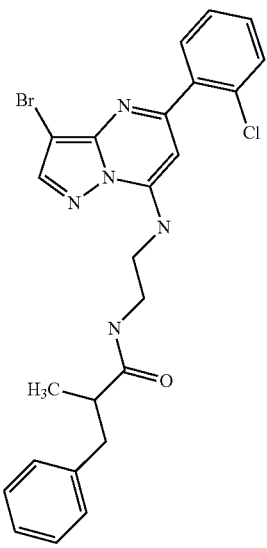 [SMILES: CC(Cc1ccccc1)C(=O)NCCNc1cc(-c2ccccc2Cl)nc2c(Br)cnn12] | 1. 5330<br>2. 512.8 |
| 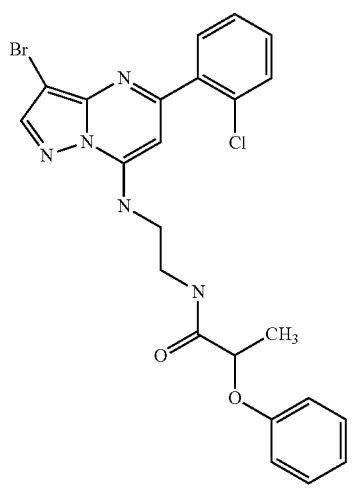 [SMILES: CC(Oc1ccccc1)C(=O)NCCNc1cc(-c2ccccc2Cl)nc2c(Br)cnn12] | 1. 5331<br>2. 514.8 |
TABLE 53-continued
| Product | 1. Ex.<br>2. m/z |
|---|---|
| 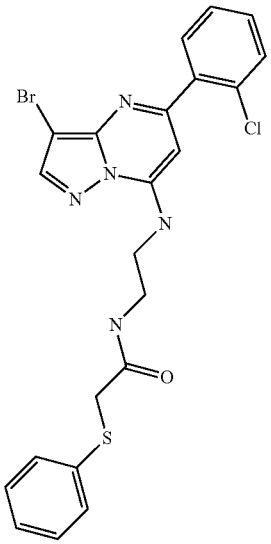 [SMILES: O=C(CSc1ccccc1)NCCNc1cc(-c2ccccc2Cl)nc2c(Br)cnn12] | 1. 5332<br>2. 516.9 |
| 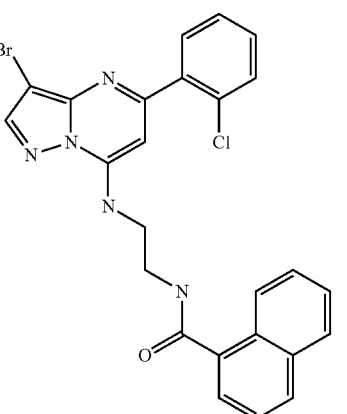 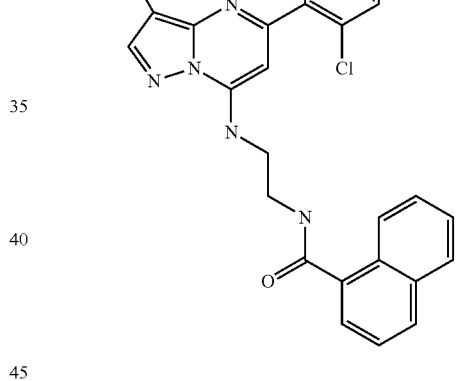 | 1. 5333<br>2. 520.8 |
| 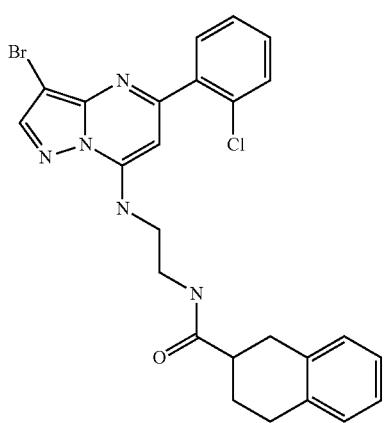 [SMILES: O=C(NCCNc1cc(-c2ccccc2Cl)nc2c(Br)cnn12)C1CCc2ccccc2C1] | 1. 5334<br>2. 524.9 |

TABLE 53-continued
| Product | 1. Ex. 2. m/z |
|---|---|
| 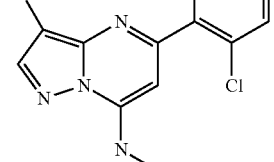 | 1. 5335 2. 538.8 |
| 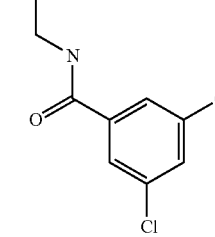 | 1. 5336 2. 538.8 |
| 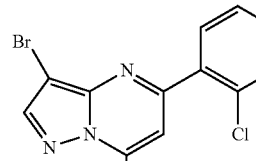 | 1. 5337 2. 539.6 |
TABLE 53-continued
| Product | 1. Ex. 2. m/z |
|---|---|
| 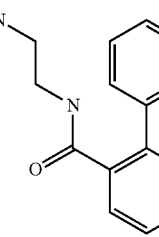 | 1. 5338 2. 539.6 |
| 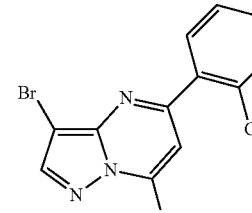 | 1. 5339 2. 546.9 |
| 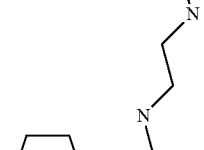 | 1. 5340 2. 552.9 |

TABLE 53-continued
| Product | 1. Ex.<br>2. m/z |
|---|---|
| 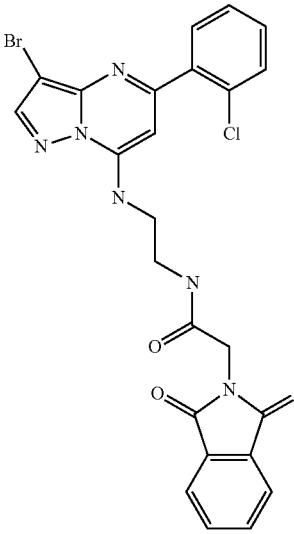 | 1. 5341<br>2. 553.8 |
| 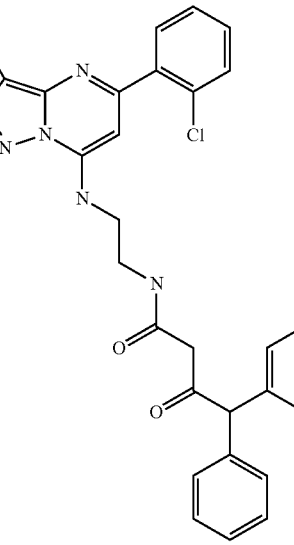 | 1. 5342<br>2. 560.9 |
| 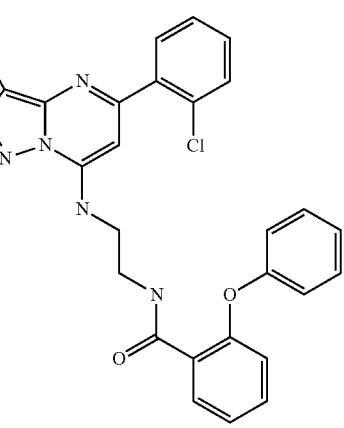 | 1. 5343<br>2. 562.9 |
TABLE 53-continued
| Product | 1. Ex.<br>2. m/z |
|---|---|
| 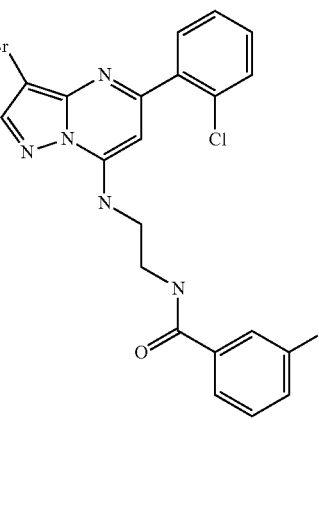 | 1. 5344<br>2. 562.9 |
| 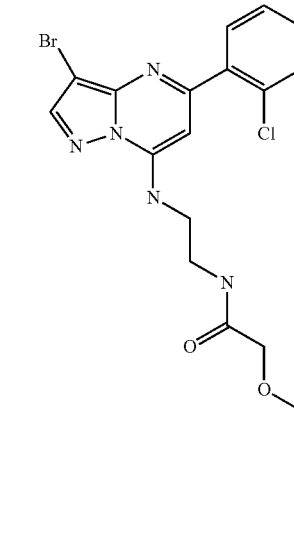 | 1. 5345<br>2. 500.8 |
| 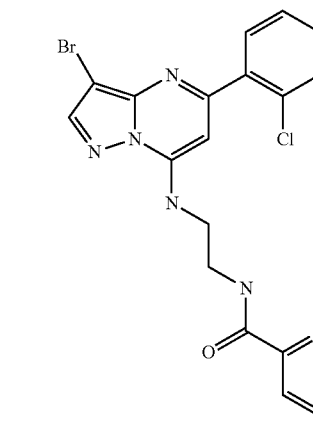 | 1. 5346<br>2. 471.7 |

TABLE 53-continued
| Product | 1. Ex.<br>2. m/z |
|---|---|
| 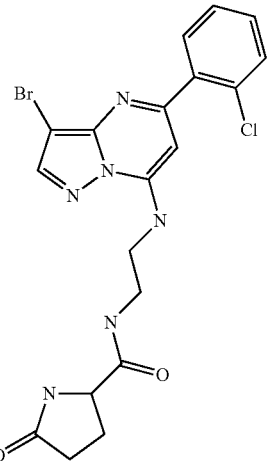 | 1. 5347<br>2. 477.8 |
| 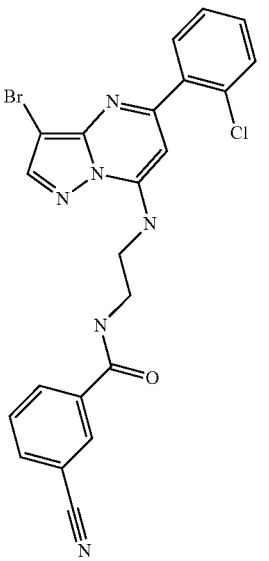 [SMILES: N#Cc1cccc(C(=O)NCCNc2cc(-c3ccccc3Cl)nc3c(Br)cnn23)c1] | 1. 5348<br>2. 495.8 |
| 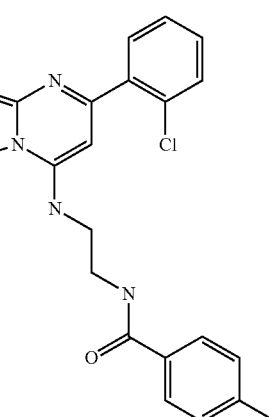 | 1. 5349<br>2. 495.8 |
TABLE 53-continued
| Product | 1. Ex.<br>2. m/z |
|---|---|
| 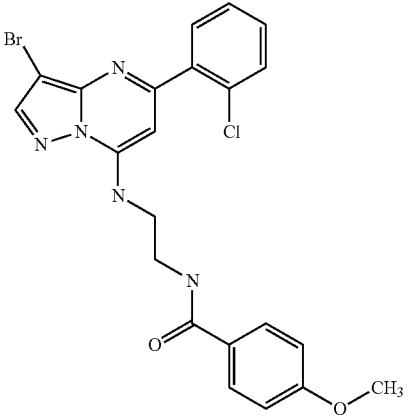 [SMILES: COc1ccc(C(=O)NCCNc2cc(-c3ccccc3Cl)nc3c(Br)cnn23)cc1] | 1. 5350<br>2. 500.8 |
| 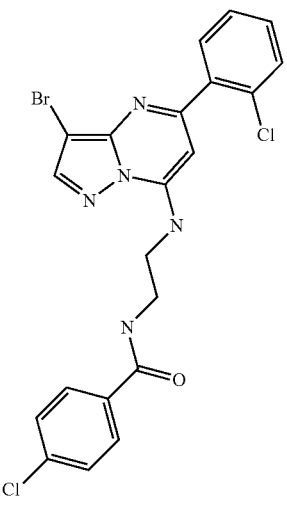 [SMILES: O=C(NCCNc1cc(-c2ccccc2Cl)nc2c(Br)cnn12)c1ccc(Cl)cc1] | 1. 5351<br>2. 505.2 |
| 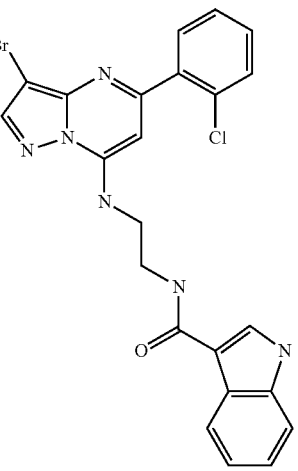 | 1. 5352<br>2. 509.8 |

TABLE 53-continued

| Product | 1. Ex.<br>2. m/z |
|---|---|
| (structure: 3-bromo-5-(2-chlorophenyl)pyrazolo[1,5-a]pyrimidin-7-yl with NH-CH2CH2-NH-C(=O)-benzo[1,3]dioxol-5-yl) | 1. 5353<br>2. 514.8 |
| (structure: 3-bromo-5-(2-chlorophenyl)pyrazolo[1,5-a]pyrimidin-7-yl with NH-CH2CH2-NH-C(=O)-2-(methylthio)phenyl) | 1. 5355<br>2. 516.9 |
| (structure: 3-bromo-5-(2-chlorophenyl)pyrazolo[1,5-a]pyrimidin-7-yl with NH-CH2CH2-NH-C(=O)-4-(methylthio)phenyl) | 1. 5356<br>2. 516.9 |
| (structure: 3-bromo-5-(2-chlorophenyl)pyrazolo[1,5-a]pyrimidin-7-yl with NH-CH2CH2-NH-C(=O)-naphthalen-2-yl) | 1. 5356<br>2. 520.8 |
| (structure: 3-bromo-5-(2-chlorophenyl)pyrazolo[1,5-a]pyrimidin-7-yl with NH-CH2CH2-NH-C(=O)-benzo[b]thiophen-2-yl) | 1. 5357<br>2. 526.8 |
| (structure: 3-bromo-5-(2-chlorophenyl)pyrazolo[1,5-a]pyrimidin-7-yl with NH-CH2CH2-NH-C(=O)-3-(acetylamino)phenyl) | 1. 5358<br>2. 527.8 |

TABLE 53-continued
| Product | 1. Ex.<br>2. m/z |
|---|---|
| 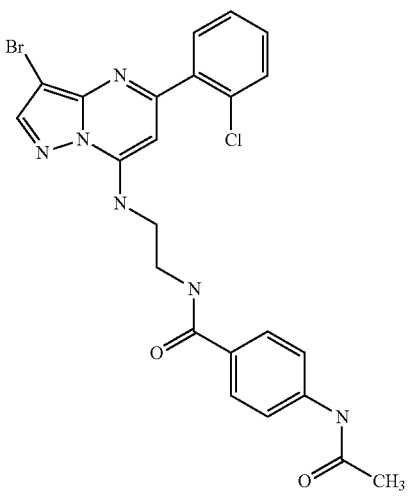 [SMILES: CC(=O)Nc1ccc(C(=O)NCCNc2cc(-c3ccccc3Cl)nc3c(Br)cnn23)cc1] | 1. 5359<br>2. 527.8 |
| 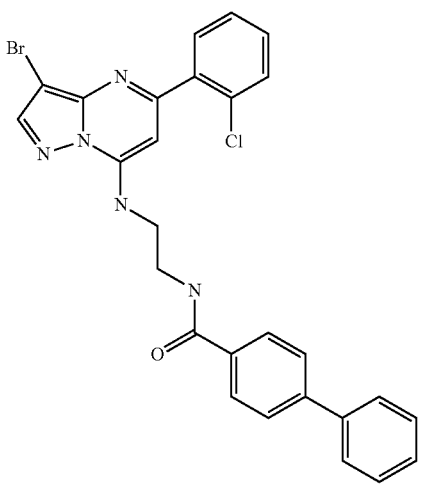 [SMILES: O=C(NCCNc1cc(-c2ccccc2Cl)nc2c(Br)cnn12)c1ccc(-c2ccccc2)cc1] | 1. 5360<br>2. 546.9 |
| 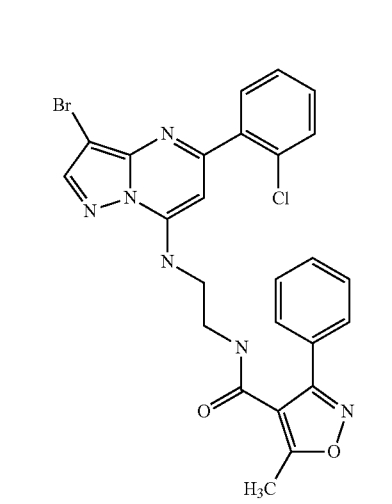 [SMILES: Cc1onc(-c2ccccc2)c1C(=O)NCCNc1cc(-c2ccccc2Cl)nc2c(Br)cnn12] | 1. 5361<br>2. 551.8 |
TABLE 53-continued
| Product | 1. Ex.<br>2. m/z |
|---|---|
| 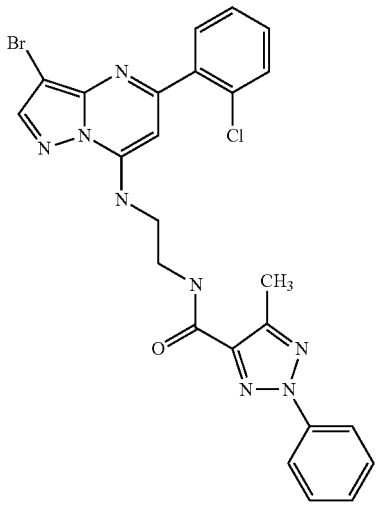 [SMILES: Cc1nn(-c2ccccc2)nc1C(=O)NCCNc1cc(-c2ccccc2Cl)nc2c(Br)cnn12] | 1. 5362<br>2. 551.8 |
| 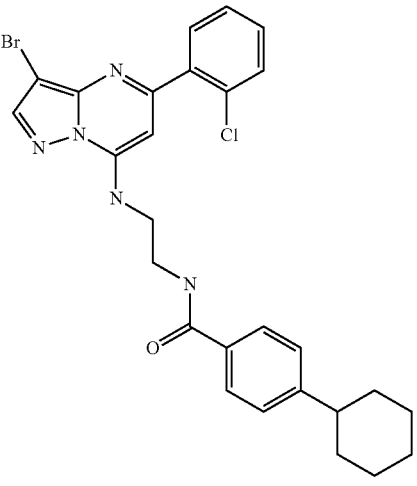 [SMILES: O=C(NCCNc1cc(-c2ccccc2Cl)nc2c(Br)cnn12)c1ccc(C2CCCCC2)cc1] | 1. 5363<br>2. 552.9 |
| 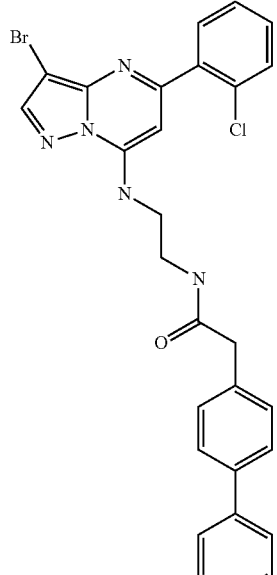 | 1. 5364<br>2. 560.9 |

TABLE 53-continued
| Product | 1. Ex.<br>2. m/z |
|---|---|
| 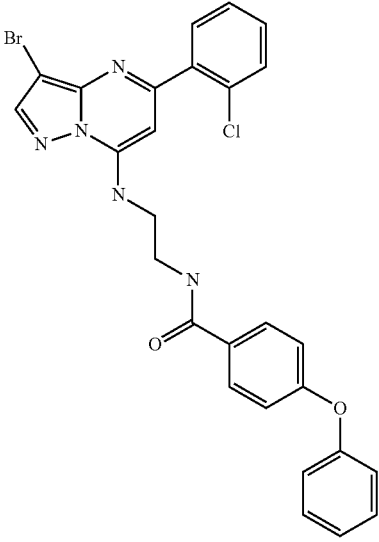 [SMILES: O=C(NCCNc1cc(-c2ccccc2Cl)nc2c(Br)cnn12)c1ccc(Oc2ccccc2)cc1] | 1. 5365<br>2. 562.9 |
| 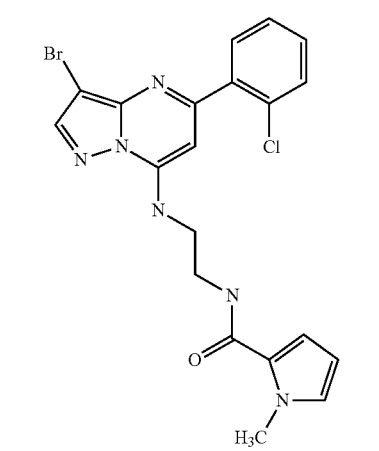 [SMILES: Cn1cccc1C(=O)NCCNc1cc(-c2ccccc2Cl)nc2c(Br)cnn12] | 1. 5366<br>2. 473.8 |
| 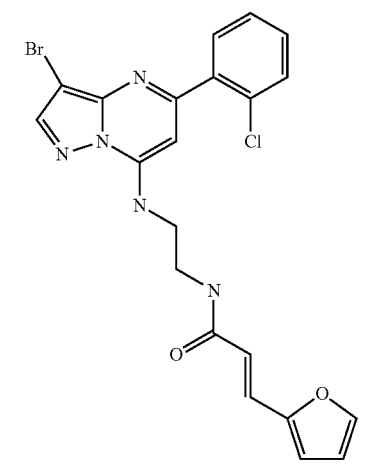 [SMILES: O=C(/C=C/c1ccco1)NCCNc1cc(-c2ccccc2Cl)nc2c(Br)cnn12] | 1. 5367<br>2. 486.8 |
TABLE 53-continued
| Product | 1. Ex.<br>2. m/z |
|---|---|
| 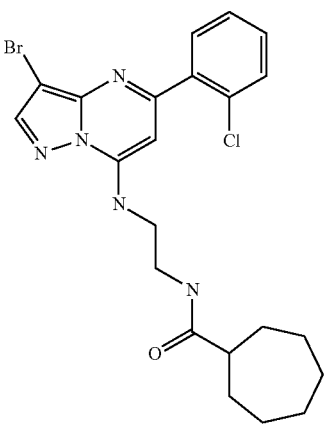 [SMILES: O=C(NCCNc1cc(-c2ccccc2Cl)nc2c(Br)cnn12)C1CCCCCC1] | 1. 5368<br>2. 490.8 |
| 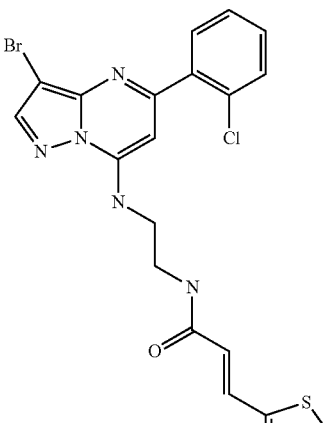 | 1. 5369<br>2. 502.8 |
| 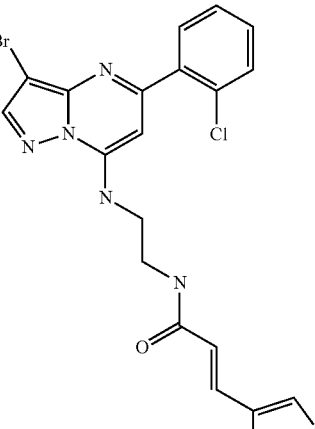 | 1. 5370<br>2. 502.8 |

TABLE 53-continued
| Product | 1. Ex.<br>2. m/z |
|---|---|
| 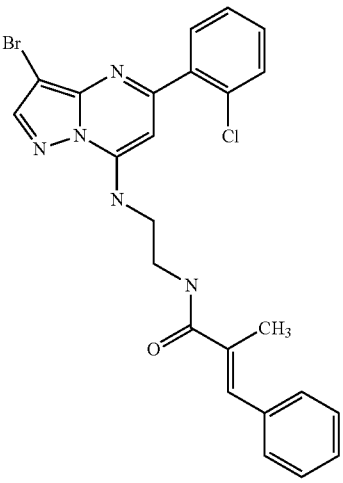 | 1. 5371<br>2. 510.8 |
| 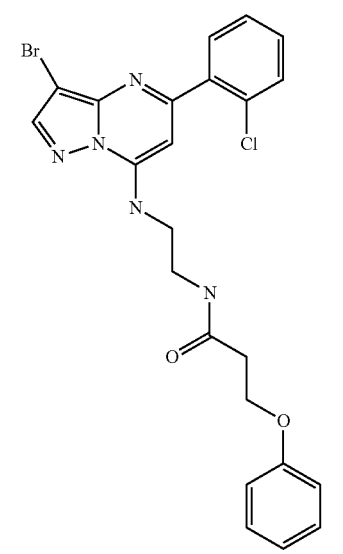 [SMILES: O=C(CCOc1ccccc1)NCCNc1cc(-c2ccccc2Cl)nc2c(Br)cnn12] | 1. 5372<br>2. 514.8 |
| 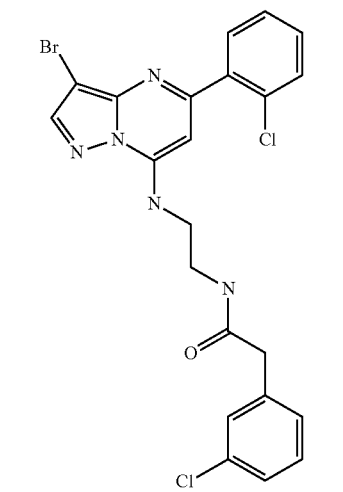 [SMILES: O=C(Cc1cccc(Cl)c1)NCCNc1cc(-c2ccccc2Cl)nc2c(Br)cnn12] | 1. 5373<br>2. 519.2 |
TABLE 53-continued
| Product | 1. Ex.<br>2. m/z |
|---|---|
| 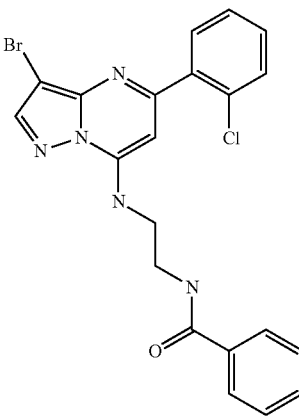 | 1. 5374<br>2. 523.8 |
| 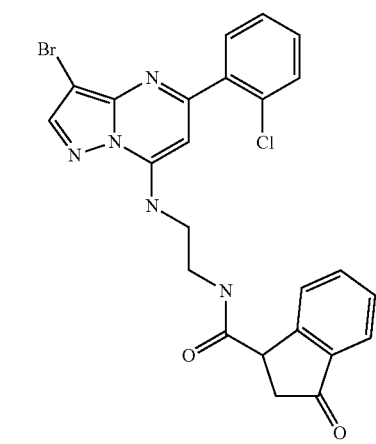 [SMILES: O=C1CC(C(=O)NCCNc2cc(-c3ccccc3Cl)nc3c(Br)cnn23)c2ccccc21] | 1. 5375<br>2. 524.8 |
| 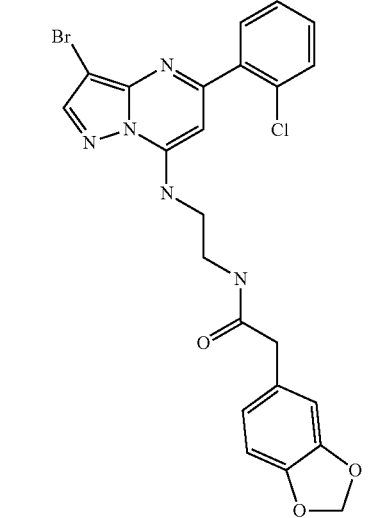 [SMILES: O=C(Cc1ccc2c(c1)OCO2)NCCNc1cc(-c2ccccc2Cl)nc2c(Br)cnn12] | 1. 5376<br>2. 528.8 |

TABLE 53-continued

| Product | 1. Ex. 2. m/z |
|---|---|
| (structure) | 1. 5377  2. 528.8 |
| (structure) | 1. 5378  2. 509.8 |
| (structure) | 1. 5379  2. 538.9 |

TABLE 53-continued

| Product | 1. Ex. 2. m/z |
|---|---|
| (structure) | 1. 5380  2. 552.9 |
| (structure) | 1. 5381  2. 553.7 |
| (structure) | 1. 5382  2. 553.7 |

TABLE 53-continued
| Product | 1. Ex.<br>2. m/z |
|---|---|
| 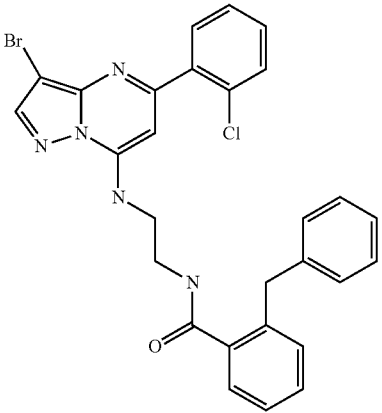 [SMILES: O=C(NCCNc1cc(-c2ccccc2Cl)nc2c(Br)cnn12)c1ccccc1Cc1ccccc1] | 1. 5383<br>2. 560.9 |
| 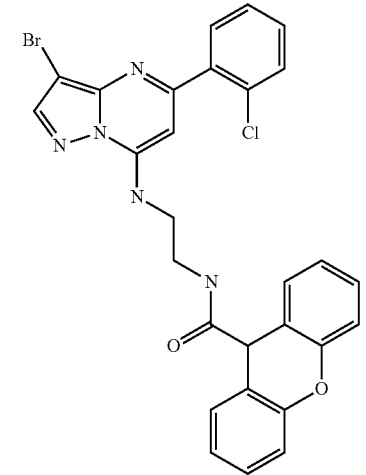 [SMILES: O=C(NCCNc1cc(-c2ccccc2Cl)nc2c(Br)cnn12)C1c2ccccc2Oc2ccccc21] | 1. 5384<br>2. 574.9 |
| 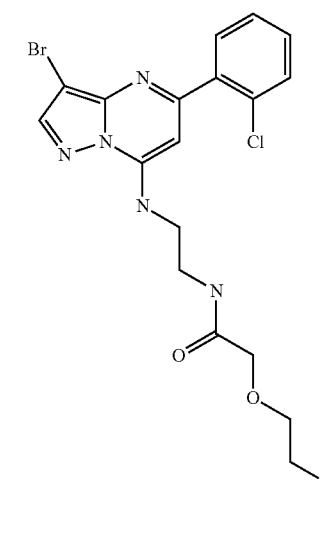 | 1. 5385<br>2. 482.8 |
| 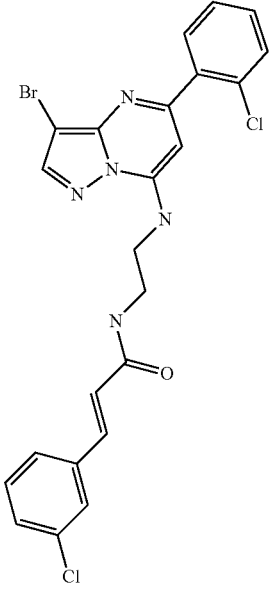 [SMILES: O=C(/C=C/c1cccc(Cl)c1)NCCNc1cc(-c2ccccc2Cl)nc2c(Br)cnn12] | 1. 5386<br>2. 531.2 |
| 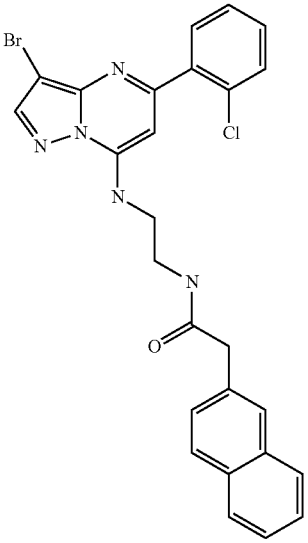 [SMILES: O=C(Cc1ccc2ccccc2c1)NCCNc1cc(-c2ccccc2Cl)nc2c(Br)cnn12] | 1. 5387<br>2. 534.8 |
| 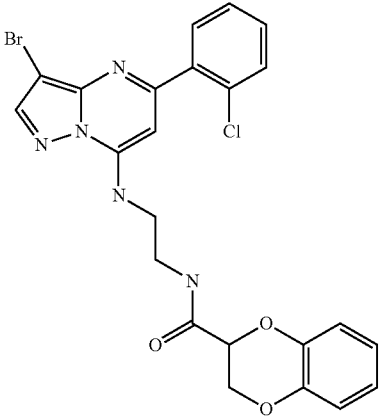 [SMILES: O=C(NCCNc1cc(-c2ccccc2Cl)nc2c(Br)cnn12)C1COc2ccccc2O1] | 1. 5388<br>2. 528.8 |

TABLE 53-continued

| Product | 1. Ex.<br>2. m/z |
|---|---|
| (structure: 3-bromo-5-(2-chlorophenyl)-N-[2-[(4-oxo-4H-chromen-2-yl)carbonylamino]ethyl]pyrazolo[1,5-a]pyrimidin-7-amine) | 1. 5389<br>2. 538.8 |
| (structure: 3-bromo-5-(2-chlorophenyl)-N-[2-(nicotinoylamino)ethyl]pyrazolo[1,5-a]pyrimidin-7-amine) | 1. 5390<br>2. 471.7 |

TABLE 54

| Product | 1. Ex.<br>2. m/z |
|---|---|
| (structure: 3-bromo-5-(2-chlorophenyl)-N-[3-[N-methyl-(cyclopropylacetyl)amino]propyl]pyrazolo[1,5-a]pyrimidin-7-amine) | 1. 5401<br>2. 463.3 |
| (structure: 3-bromo-5-(2-chlorophenyl)-N-[3-[N-methyl-(cyclopropylacetyl)amino]propyl]pyrazolo[1,5-a]pyrimidin-7-amine variant) | 1. 5402<br>2. 477.3 |
| (structure: 3-bromo-5-(2-chlorophenyl)-N-[3-[N-methyl-(methylthioacetyl)amino]propyl]pyrazolo[1,5-a]pyrimidin-7-amine) | 1. 5403<br>2. 483.3 |
| (structure: 3-bromo-5-(2-chlorophenyl)-N-[3-[N-methyl-(2-furoyl)amino]propyl]pyrazolo[1,5-a]pyrimidin-7-amine) | 1. 5404<br>2. 489.3 |

TABLE 54-continued
| Product | 1. Ex.<br>2. m/z |
|---|---|
| 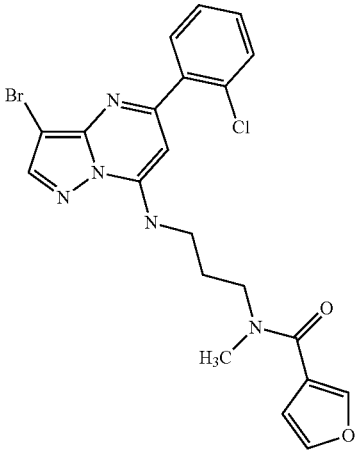 | 1. 5405<br>2. 489.3 |
| 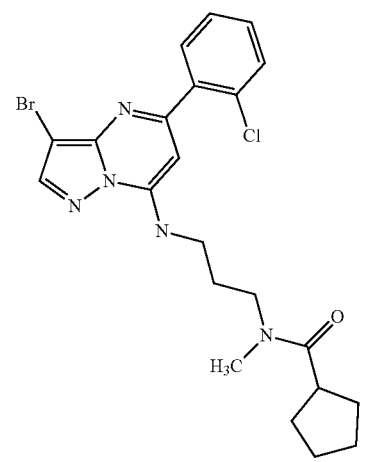 [SMILES: CN(CCCNc1cc(-c2ccccc2Cl)nc2c(Br)cnn12)C(=O)C1CCCC1] | 1. 5406<br>2. 491.3 |
| 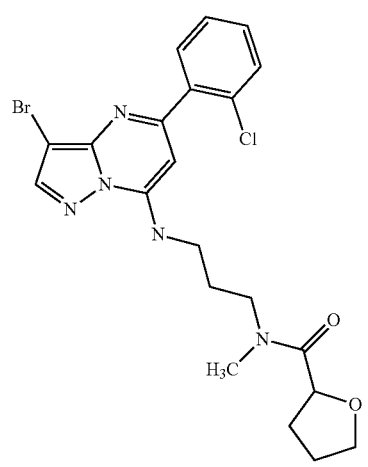 | 1. 5407<br>2. 493.3 |
TABLE 54-continued
| Product | 1. Ex.<br>2. m/z |
|---|---|
| 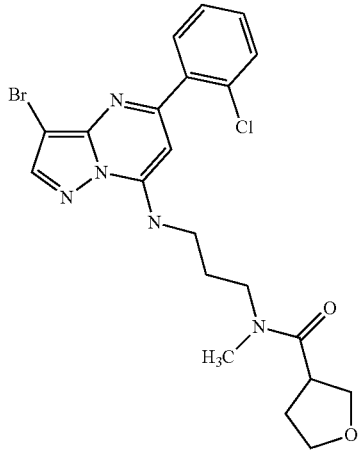 [SMILES: CN(CCCNc1cc(-c2ccccc2Cl)nc2c(Br)cnn12)C(=O)C1CCOC1] | 1. 5408<br>2. 493.3 |
| 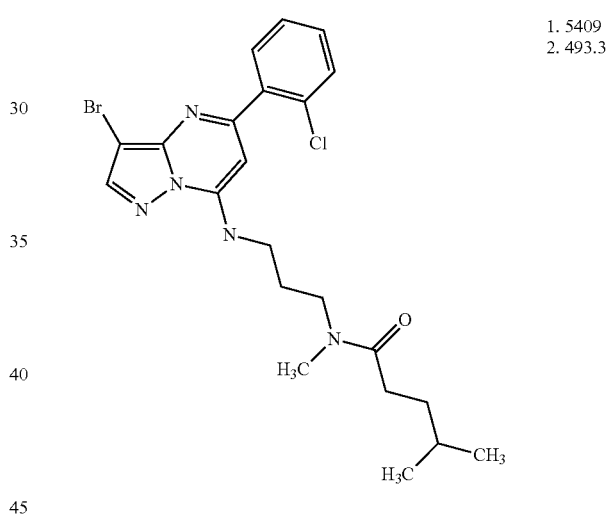 | 1. 5409<br>2. 493.3 |
| 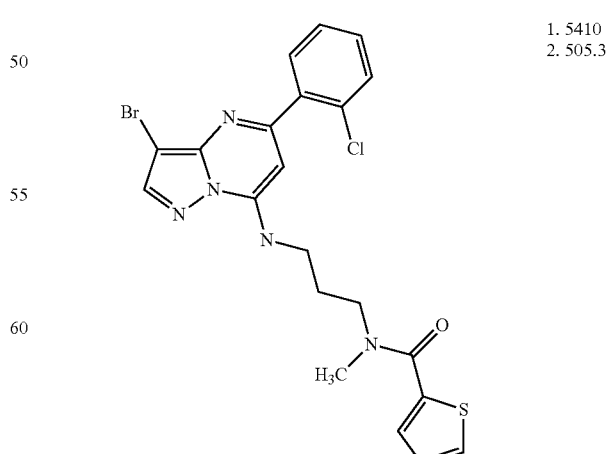 | 1. 5410<br>2. 505.3 |

TABLE 54-continued
| Product | 1. Ex.<br>2. m/z |
|---|---|
| 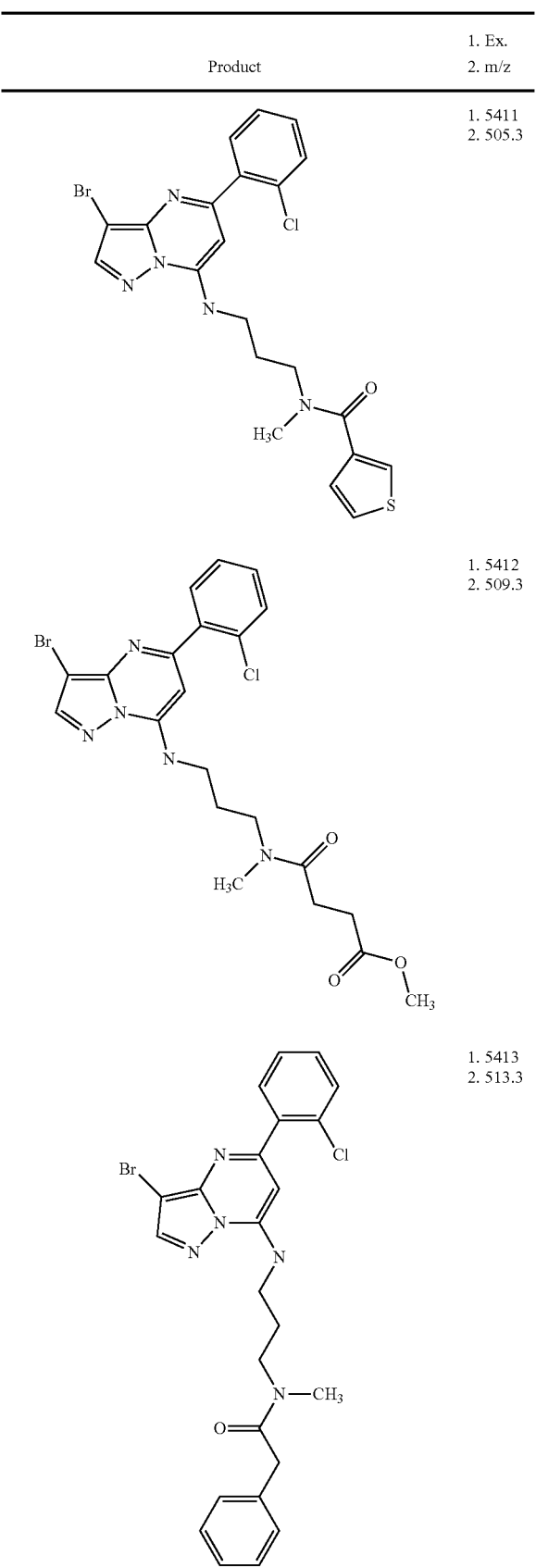 | 1. 5411<br>2. 505.3 |
| | 1. 5412<br>2. 509.3 |
| | 1. 5413<br>2. 513.3 |
TABLE 54-continued
| Product | 1. Ex.<br>2. m/z |
|---|---|
| 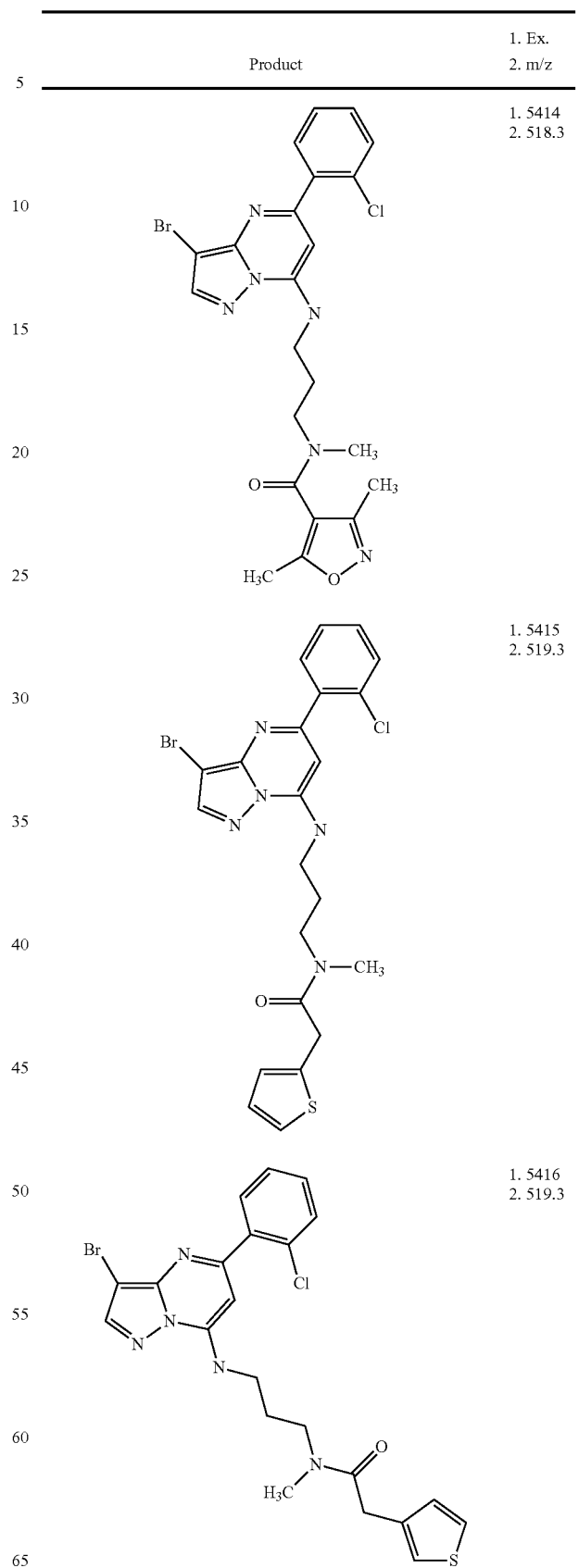 | 1. 5414<br>2. 518.3 |
| | 1. 5415<br>2. 519.3 |
| | 1. 5416<br>2. 519.3 |

TABLE 54-continued
| Product | 1. Ex. 2. m/z |
|---|---|
| 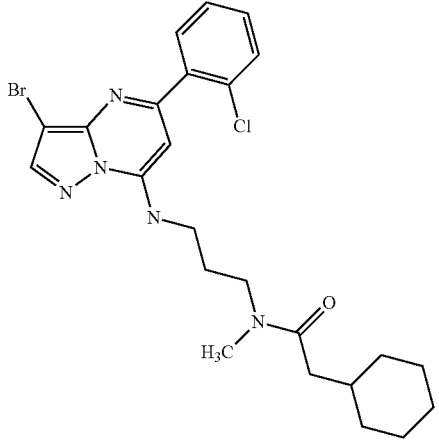 [SMILES: CN(CCCNc1cc(-c2ccccc2Cl)nc2c(Br)cnn12)C(=O)CC1CCCCC1] | 1. 5417 2. 519.3 |
| 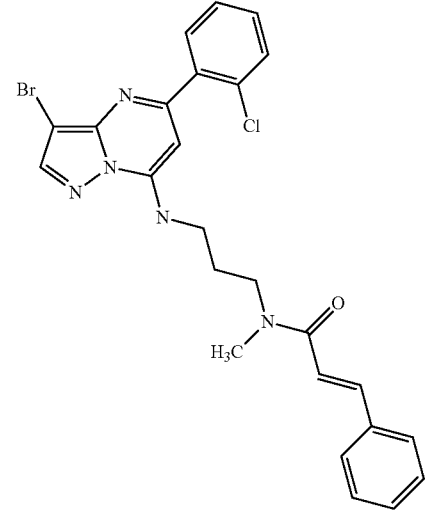 [SMILES: CN(CCCNc1cc(-c2ccccc2Cl)nc2c(Br)cnn12)C(=O)/C=C/c1ccccc1] | 1. 5418 2. 525.3 |
| 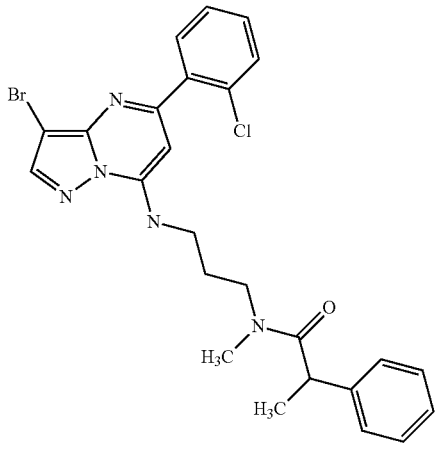 [SMILES: CC(C(=O)N(C)CCCNc1cc(-c2ccccc2Cl)nc2c(Br)cnn12)c1ccccc1] | 1. 5419 2. 527.3 |
TABLE 54-continued
| Product | 1. Ex. 2. m/z |
|---|---|
| 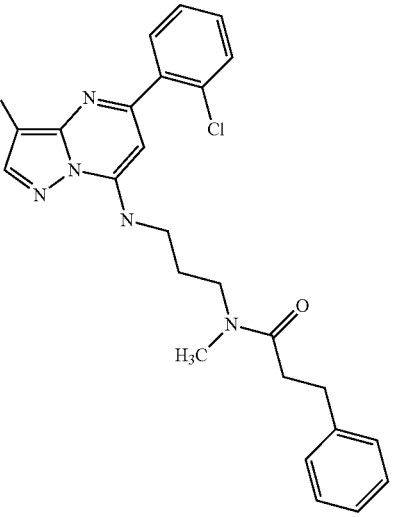 | 1. 5420 2. 527.3 |
| 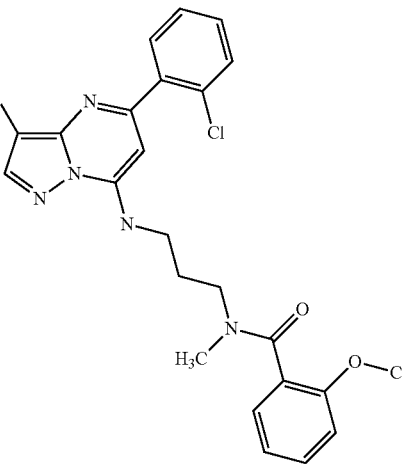 | 1. 5121 2. 529.3 |
| 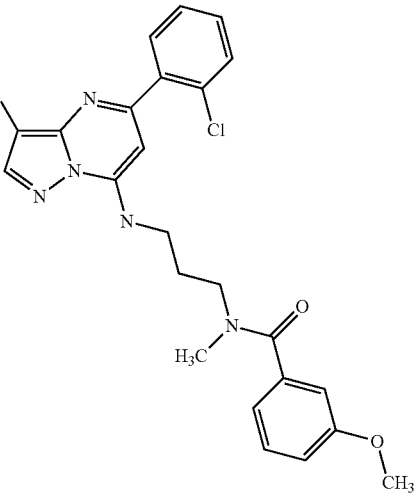 | 1. 5422 2. 529.3 |

TABLE 54-continued

| Product | 1. Ex. 2. m/z |
|---|---|
| (structure) | 1. 5423 2. 533.3 |
| (structure) | 1. 5424 2. 533.3 |
| (structure) | 1. 5425 2. 538.3 |
| (structure) | 1. 5426 2. 539.3 |
| (structure) | 1. 5427 2. 539.3 |
| (structure) | 1. 5428 2. 539.3 |

TABLE 54-continued
| Product | 1. Ex.<br>2. m/z |
|---|---|
| 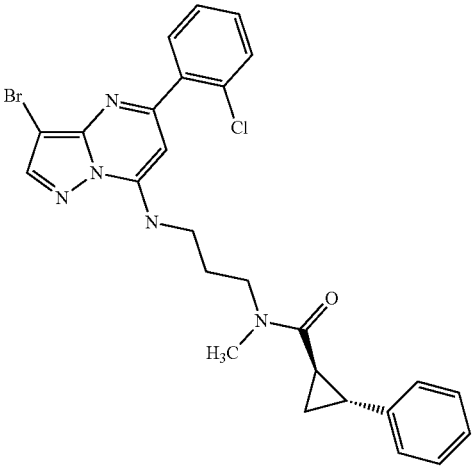 [SMILES: CN(CCCNc1cc(-c2ccccc2Cl)nc2c(Br)cnn12)C(=O)[C@@H]1C[C@H]1c1ccccc1] | 1. 5429<br>2. 539.3 |
| 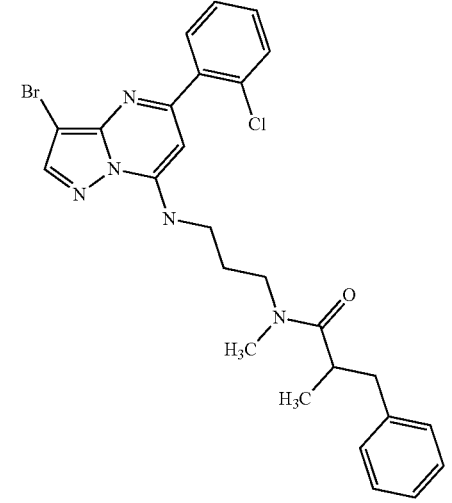 [SMILES: CC(Cc1ccccc1)C(=O)N(C)CCCNc1cc(-c2ccccc2Cl)nc2c(Br)cnn12] | 1. 5430<br>2. 541.3 |
| 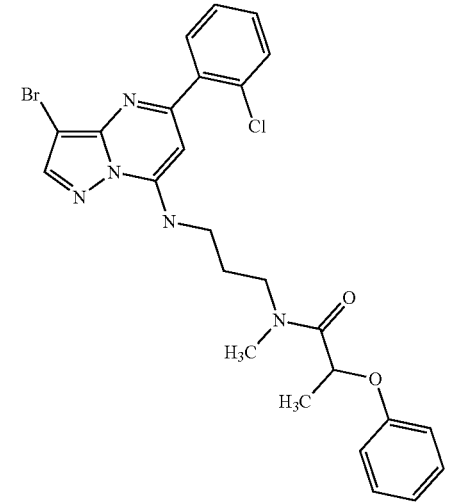 [SMILES: CC(Oc1ccccc1)C(=O)N(C)CCCNc1cc(-c2ccccc2Cl)nc2c(Br)cnn12] | 1. 5431<br>2. 543.3 |
TABLE 54-continued
| Product | 1. Ex.<br>2. m/z |
|---|---|
| 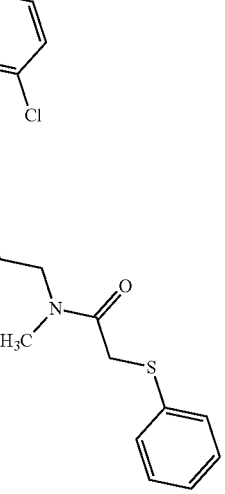 | 1. 5432<br>2. 545.3 |
| 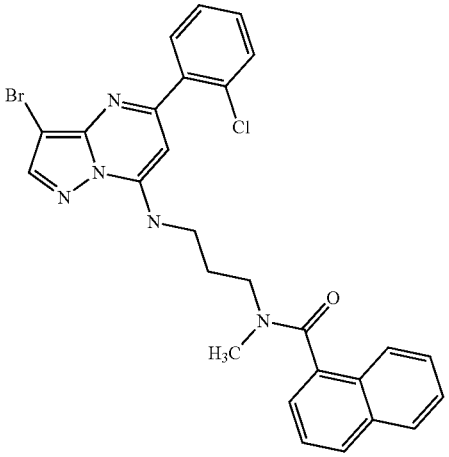 [SMILES: CN(CCCNc1cc(-c2ccccc2Cl)nc2c(Br)cnn12)C(=O)c1cccc2ccccc12] | 1. 5433<br>2. 549.3 |
| 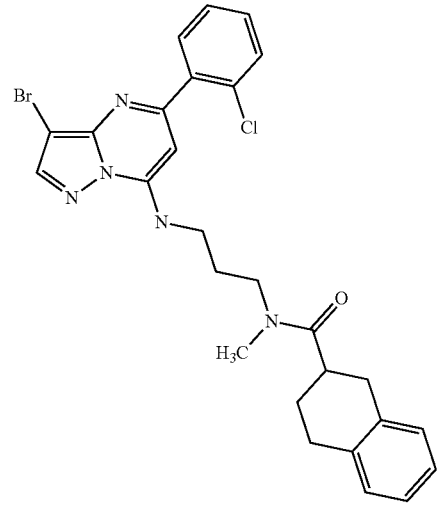 [SMILES: CN(CCCNc1cc(-c2ccccc2Cl)nc2c(Br)cnn12)C(=O)C1CCc2ccccc2C1] | 1. 5434<br>2. 553.3 |

TABLE 54-continued
| Product | 1. Ex. 2. m/z |
|---|---|
| 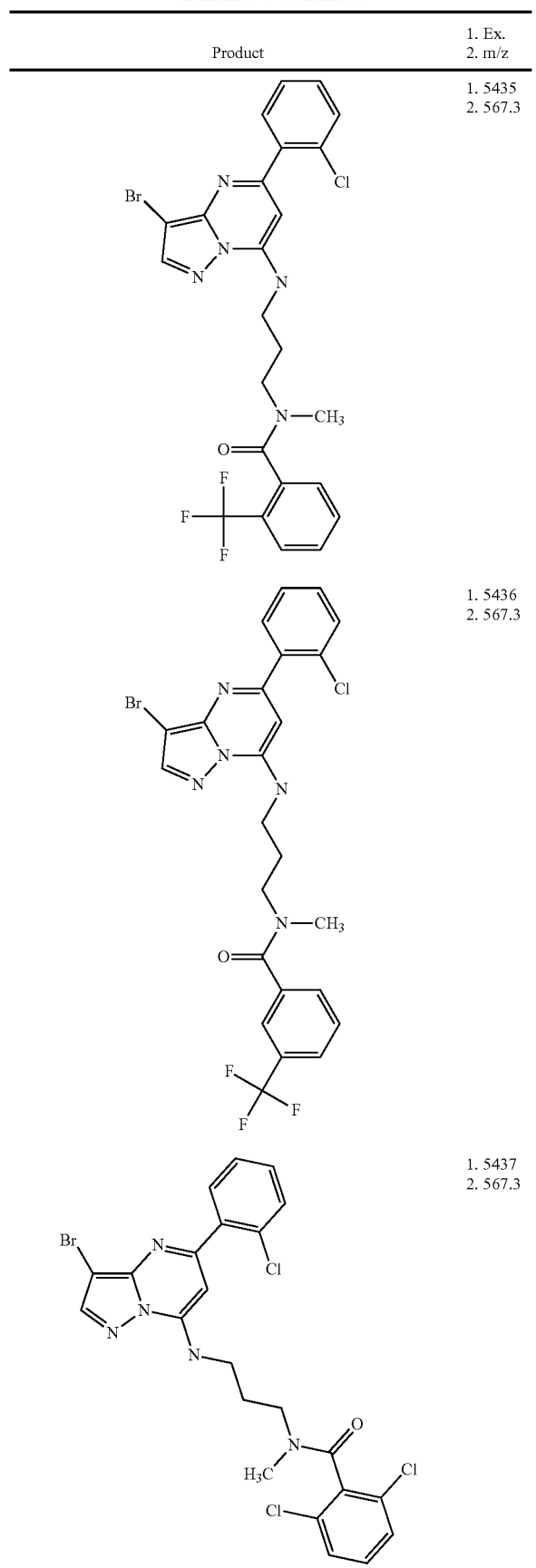 | 1. 5435 2. 567.3 |
| | 1. 5436 2. 567.3 |
| | 1. 5437 2. 567.3 |
TABLE 54-continued
| Product | 1. Ex. 2. m/z |
|---|---|
| 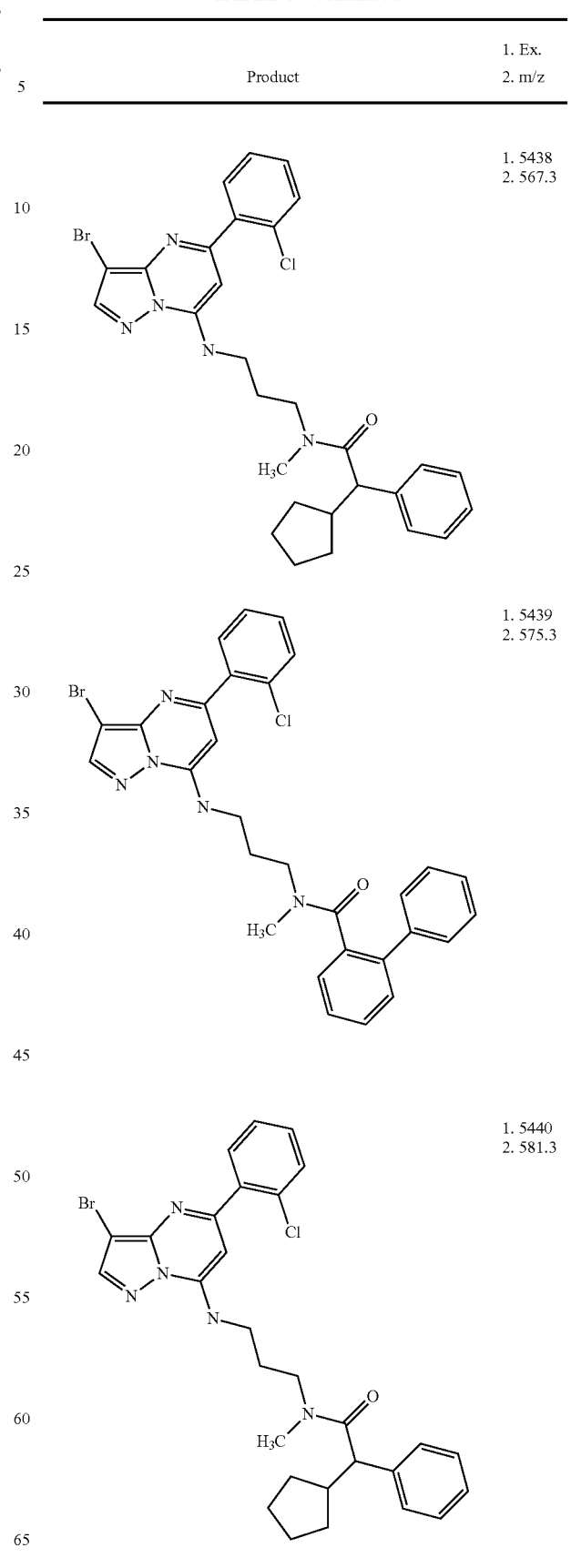 | 1. 5438 2. 567.3 |
| | 1. 5439 2. 575.3 |
| | 1. 5440 2. 581.3 |

TABLE 54-continued

| Product | 1. Ex. 2. m/z |
|---|---|
| (structure) | 1. 5441 2. 582.3 |
| (structure) | 1. 5442 2. 589.3 |
| (structure) | 1. 5443 2. 591.3 |
| (structure) | 1. 5444 2. 591.3 |
| (structure) | 1. 5445 2. 529.3 |
| (structure) | 1. 5446 2. 500.3 |

TABLE 54-continued
| Product | 1. Ex.<br>2. m/z |
|---|---|
| | 1. 5447<br>2. 830.5 |
| | 1. 5448<br>2. 524.3 |
| | 1. 5449<br>2. 524.3 |
| | 1. 5450<br>2. 529.3 |
| | 1. 5451<br>2. 533.3 |
| | 1. 54525<br>2. 719.4 |
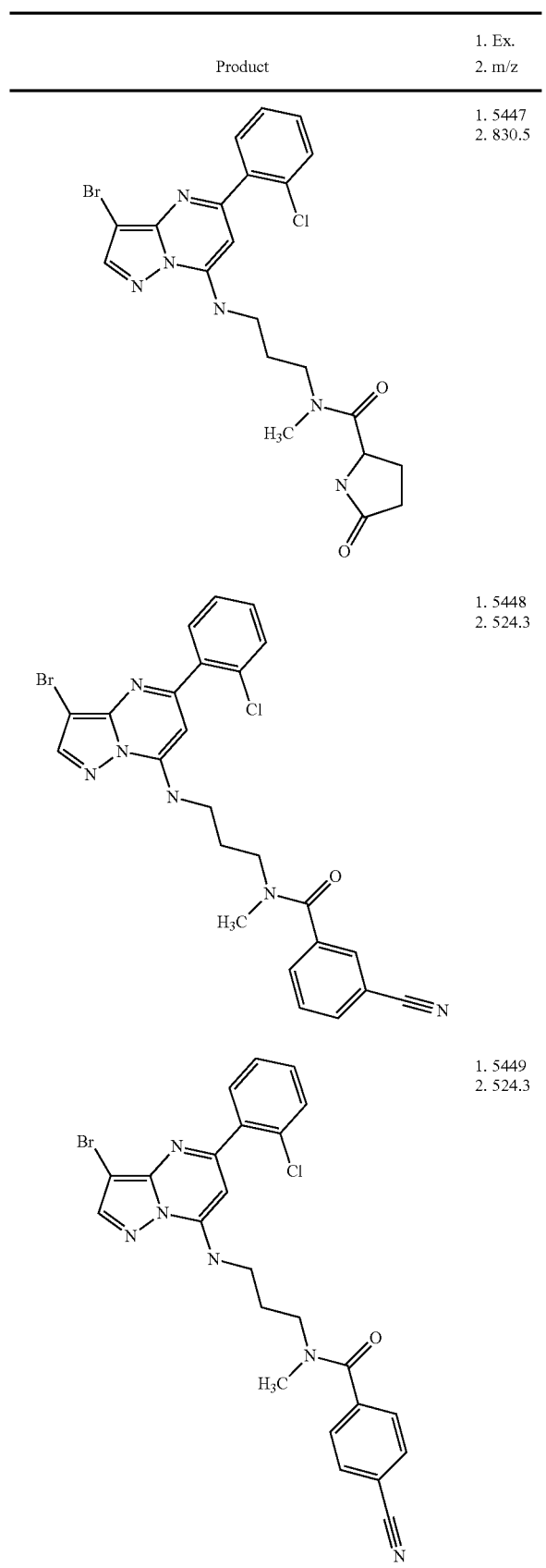
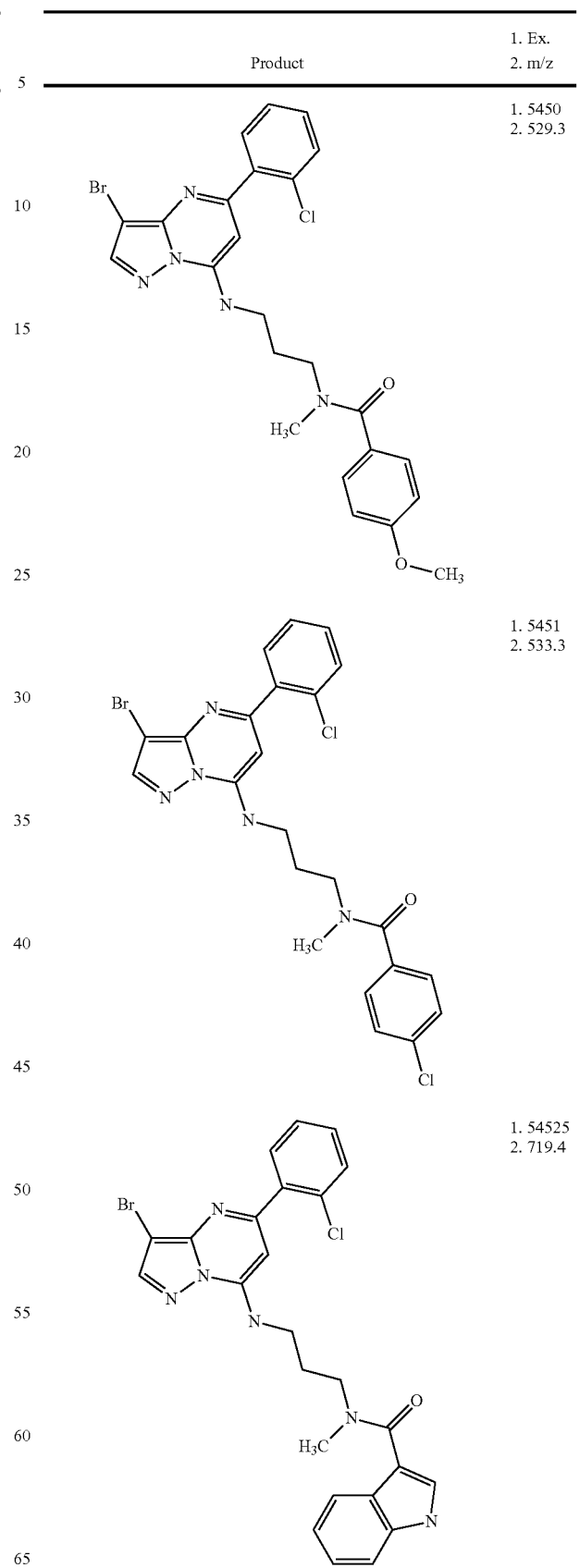

TABLE 54-continued
| Product | 1. Ex. 2. m/z |
|---|---|
| 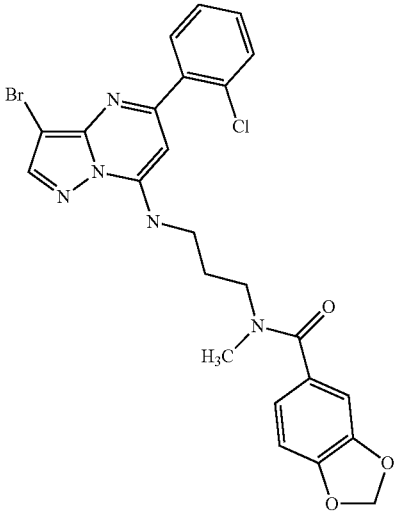 [SMILES: CN(CCCNc1cc(-c2ccccc2Cl)nc2c(Br)cnn12)C(=O)c1ccc2c(c1)OCO2] | 1. 5453 2. 543.3 |
| 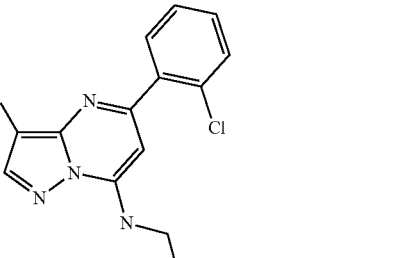 | 1. 5454 2. 545.3 |
| 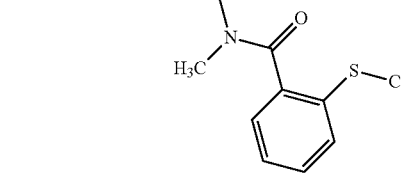 | 1. 5455 2. 545.3 |
TABLE 54-continued
| Product | 1. Ex. 2. m/z |
|---|---|
|  | 1. 5456 2. 549.3 |
| 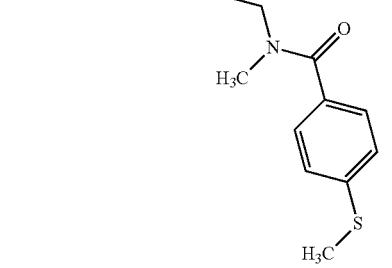 | 1. 5457 2. 555.3 |

TABLE 54-continued
| Product | 1. Ex.<br>2. m/z |
|---|---|
| 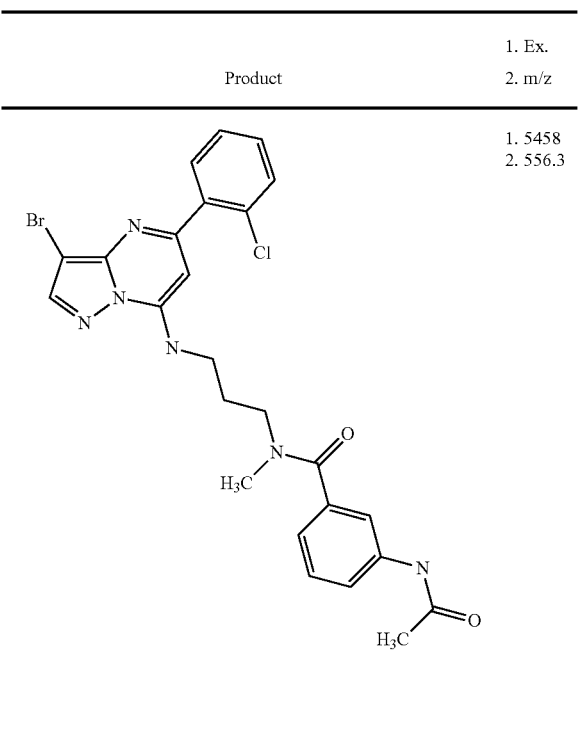 | 1. 5458<br>2. 556.3 |
| 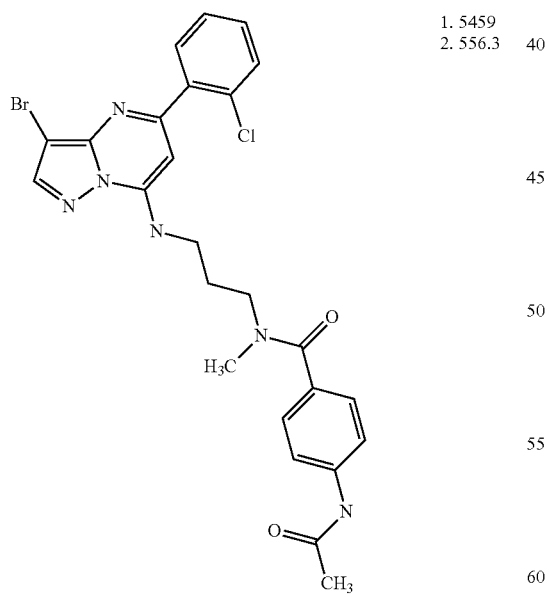 | 1. 5459<br>2. 556.3 |
TABLE 54-continued
| Product | 1. Ex.<br>2. m/z |
|---|---|
| 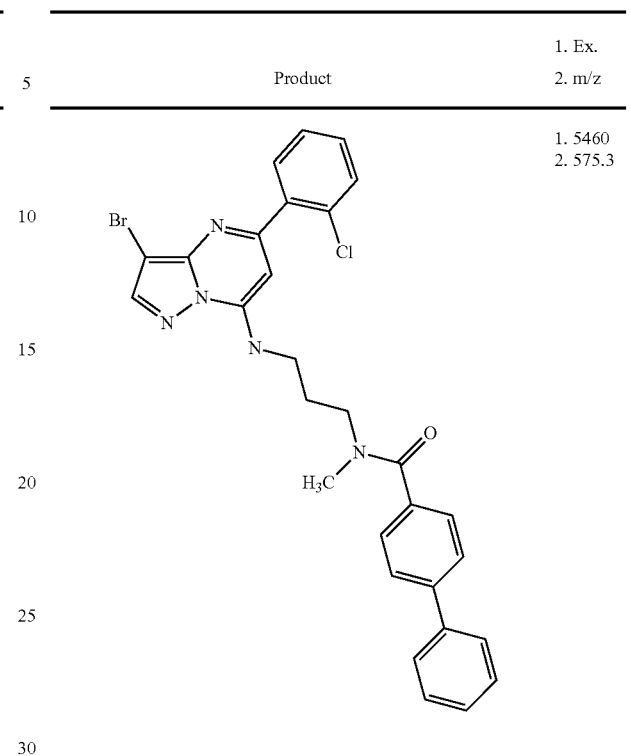 | 1. 5460<br>2. 575.3 |
| 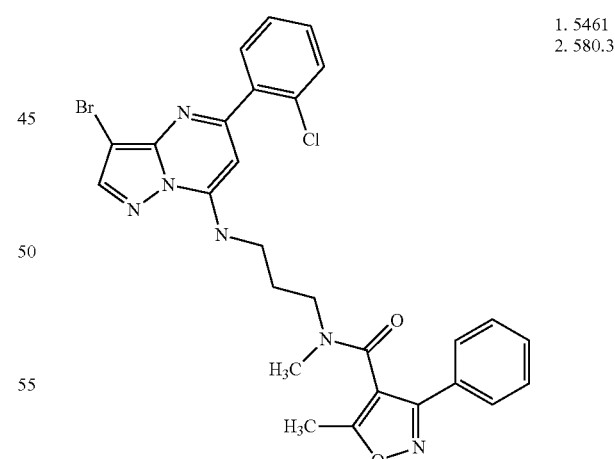 | 1. 5461<br>2. 580.3 |

TABLE 54-continued
| Product | 1. Ex. 2. m/z |
|---|---|
| 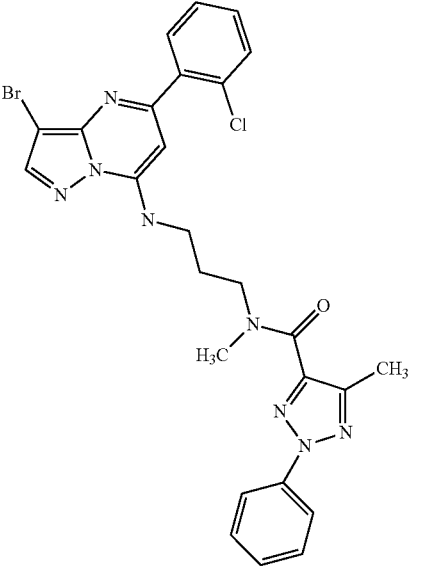 [SMILES: Cc1nn(-c2ccccc2)nc1C(=O)N(C)CCCNc1cc(-c2ccccc2Cl)nc2c(Br)cnn12] | 1. 5462 2. 580.3 |
| 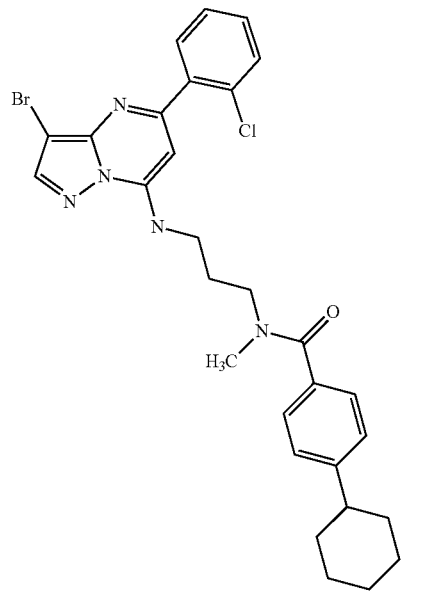 [SMILES: CN(CCCNc1cc(-c2ccccc2Cl)nc2c(Br)cnn12)C(=O)c1ccc(C2CCCCC2)cc1] | 1. 5463 2. 581.3 |
| 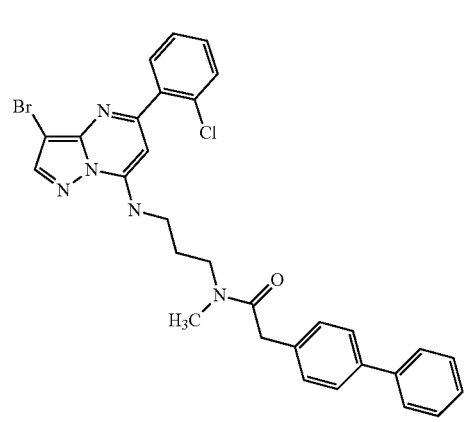 [SMILES: CN(CCCNc1cc(-c2ccccc2Cl)nc2c(Br)cnn12)C(=O)Cc1ccc(-c2ccccc2)cc1] | 1. 5464 2. 589.3 |
TABLE 54-continued
| Product | 1. Ex. 2. m/z |
|---|---|
| 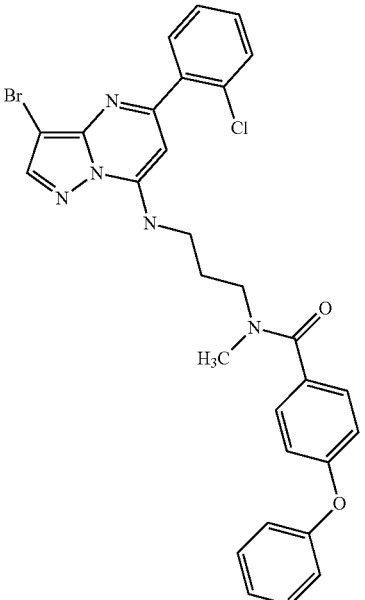 [SMILES: CN(CCCNc1cc(-c2ccccc2Cl)nc2c(Br)cnn12)C(=O)c1ccc(Oc2ccccc2)cc1] | 1. 5465 2. 591.3 |
| 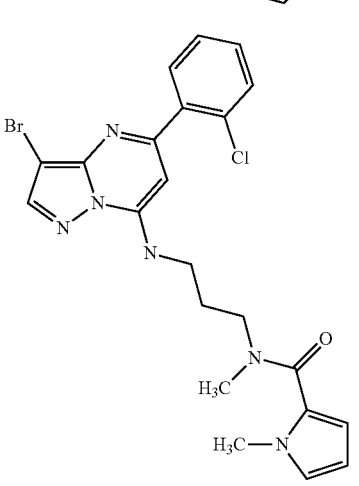 | 1. 5466 2. 502.3 |
| 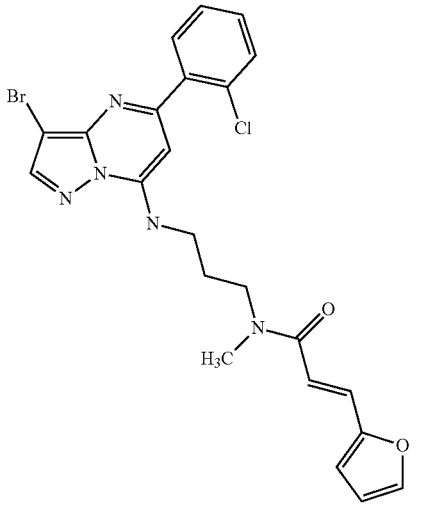 [SMILES: CN(CCCNc1cc(-c2ccccc2Cl)nc2c(Br)cnn12)C(=O)/C=C/c1ccco1] | 1. 5467 2. 515.3 |

TABLE 54-continued
| Product | 1. Ex. 2. m/z |
|---|---|
| 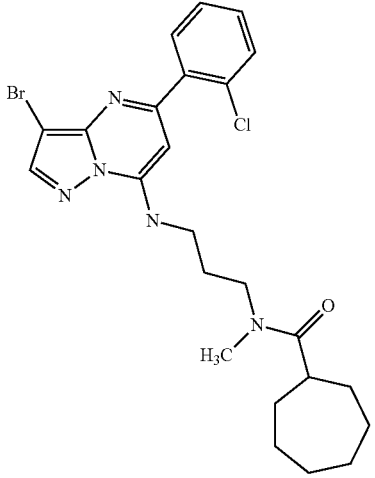 [SMILES: CN(CCCNc1cc(-c2ccccc2Cl)nc2c(Br)cnn12)C(=O)C1CCCCCC1] | 1. 5468 2. 519.3 |
| 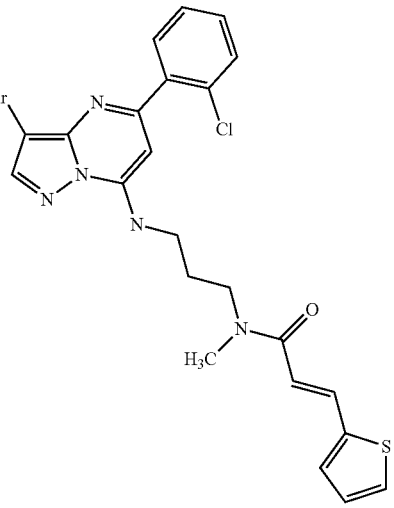 | 1. 5469 2. 531.3 |
| 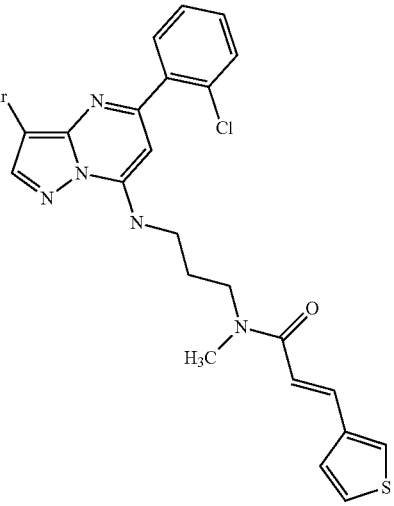 | 1. 5470 2. 531.3 |
TABLE 54-continued
| Product | 1. Ex. 2. m/z |
|---|---|
| 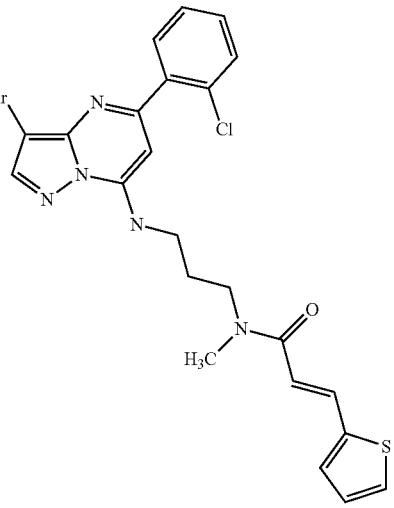 | 1. 5471 2. 539.3 |
| 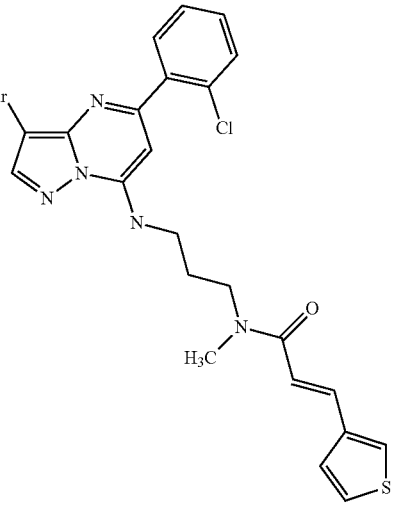 | 1. 5472 2. 543.3 |

TABLE 54-continued
| Product | 1. Ex. 2. m/z |
|---|---|
| 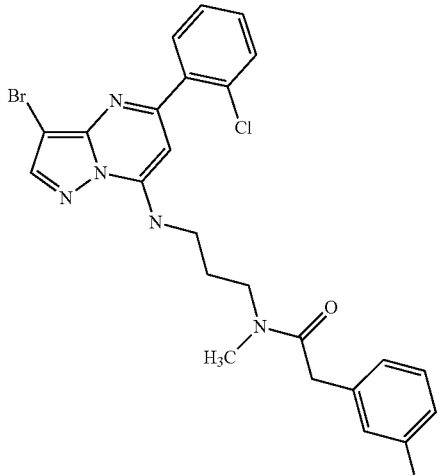 | 1. 5473 2. 547.3 |
| 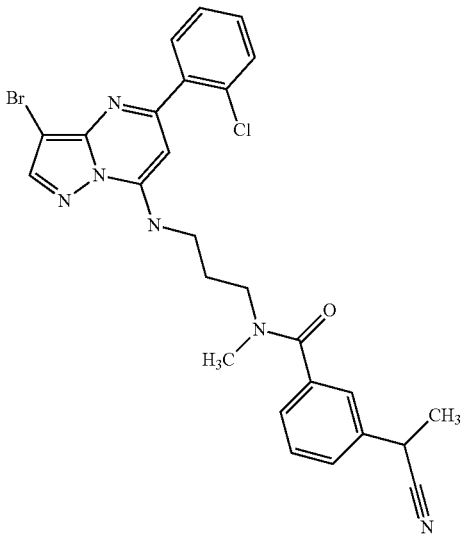 [SMILES: CC(C#N)c1cccc(C(=O)N(C)CCCNc2cc(-c3ccccc3Cl)nc3c(Br)cnn23)c1] | 1. 5474 2. 552.3 |
| 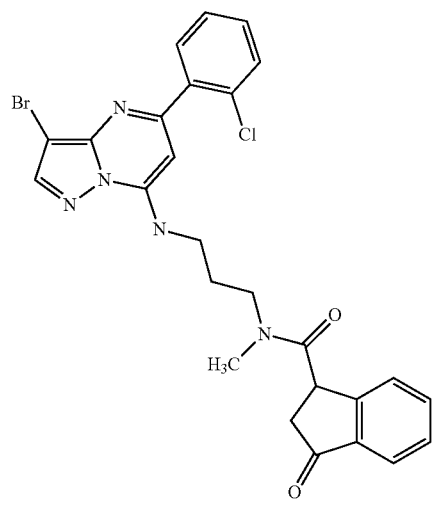 [SMILES: CN(CCCNc1cc(-c2ccccc2Cl)nc2c(Br)cnn12)C(=O)C1CC(=O)c2ccccc21] | 1. 5475 2. 553.3 |
TABLE 54-continued
| Product | 1. Ex. 2. m/z |
|---|---|
| 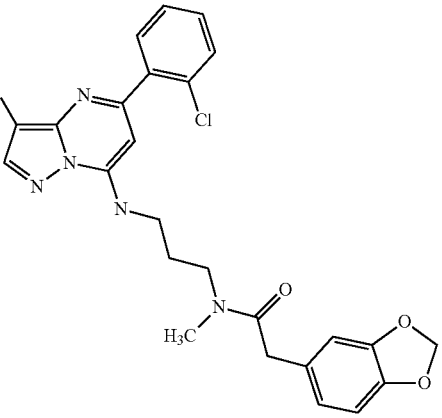 | 1. 5476 2. 557.3 |
| 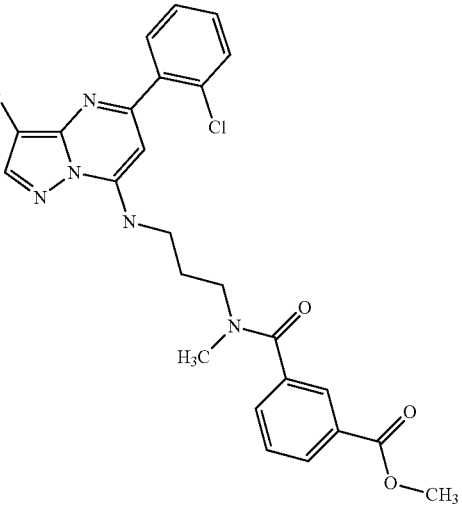 | 1. 5477 2. 557.3 |
| 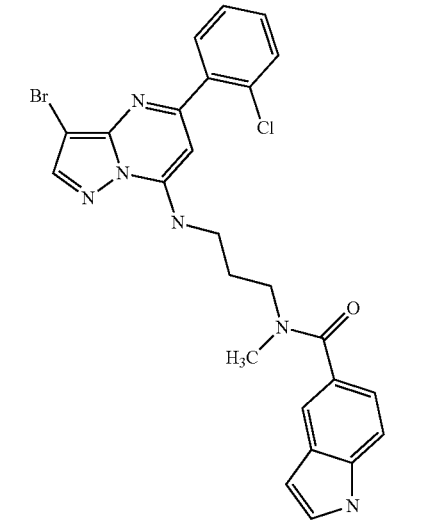 [SMILES: CN(CCCNc1cc(-c2ccccc2Cl)nc2c(Br)cnn12)C(=O)c1ccc2[nH]ccc2c1] | 1. 5478 2. 538.3 |

TABLE 54-continued

| Product | 1. Ex. 2. m/z |
|---|---|
| (structure) | 1. 5479 2. 567.3 |
| (structure) | 1. 5480 2. 581.3 |
| (structure) | 1. 5481 2. 581.3 |
| (structure) | 1. 5482 2. 589.3 |
| (structure) | 1. 5483 2. 511.3 |
| (structure) | 1. 5484 2. 559.3 |

TABLE 54-continued
| Product | 1. Ex.<br>2. m/z |
|---|---|
| 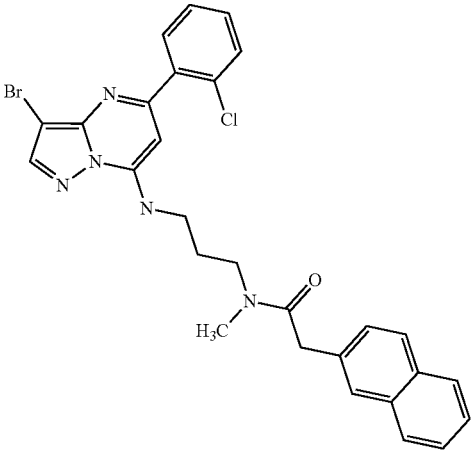 [SMILES: CN(CCCNc1cc(-c2ccccc2Cl)nc2c(Br)cnn12)C(=O)Cc1ccc2ccccc2c1] | 1. 5485<br>2. 563.3 |
| 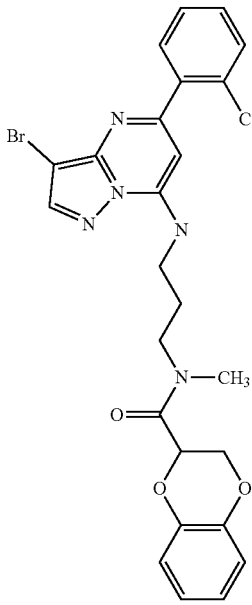 | 1. 5486<br>2. |
| 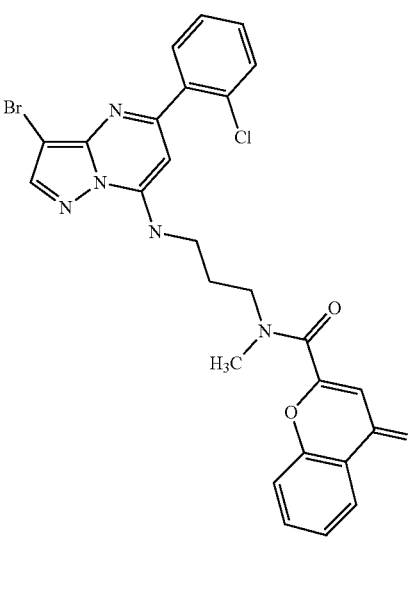 | 1. 5487<br>2. 891.5 |
TABLE 54-continued
| Product | 1. Ex.<br>2. m/z |
|---|---|
| 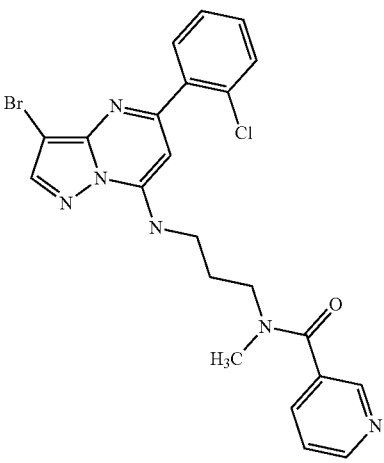 [SMILES: CN(CCCNc1cc(-c2ccccc2Cl)nc2c(Br)cnn12)C(=O)c1cccnc1] | 1. 5488<br>2. 500.3 |
| 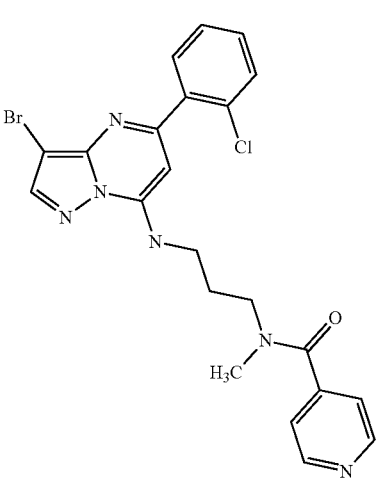 [SMILES: CN(CCCNc1cc(-c2ccccc2Cl)nc2c(Br)cnn12)C(=O)c1ccncc1] | 1. 5489<br>2. 500.3 |
| 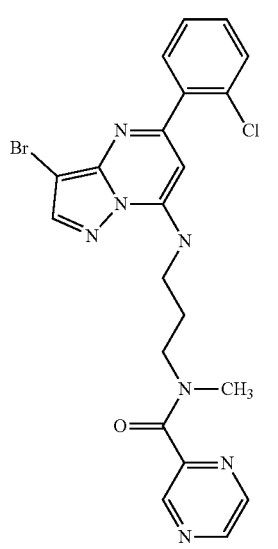 [SMILES: CN(CCCNc1cc(-c2ccccc2Cl)nc2c(Br)cnn12)C(=O)c1cnccn1] | 1. 5490<br>2. 501.3 |

TABLE 55
| Product | 1. Ex.<br>2. m/z |
|---|---|
| 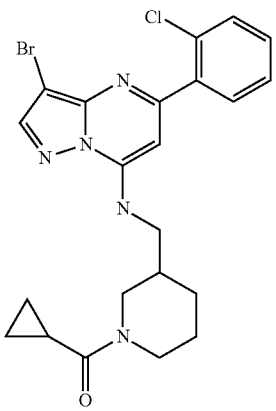 [SMILES: O=C(C1CC1)N1CCCC(CNc2cc(-c3ccccc3Cl)nc3c(Br)cnn23)C1] | 1. 5501<br>2. 488.81 |
| 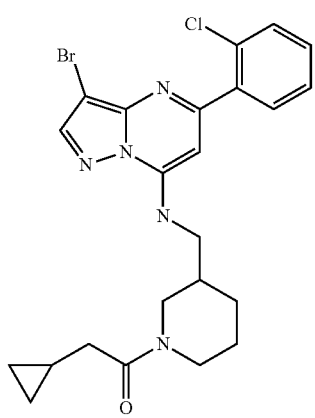 [SMILES: O=C(CC1CC1)N1CCCC(CNc2cc(-c3ccccc3Cl)nc3c(Br)cnn23)C1] | 1. 5502<br>2. 502.84 |
| 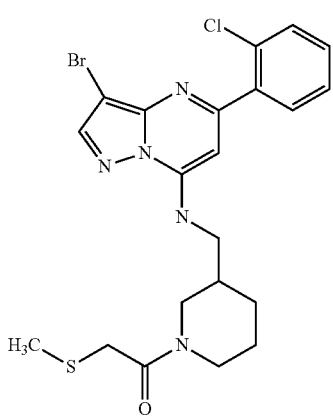 [SMILES: CSCC(=O)N1CCCC(CNc2cc(-c3ccccc3Cl)nc3c(Br)cnn23)C1] | 1. 5503<br>2. 508.87 |
TABLE 55-continued
| Product | 1. Ex.<br>2. m/z |
|---|---|
| 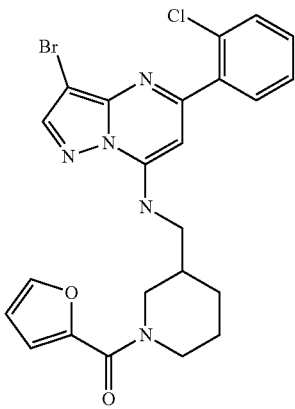 [SMILES: O=C(c1ccco1)N1CCCC(CNc2cc(-c3ccccc3Cl)nc3c(Br)cnn23)C1] | 1. 5504<br>2. 514.81 |
| 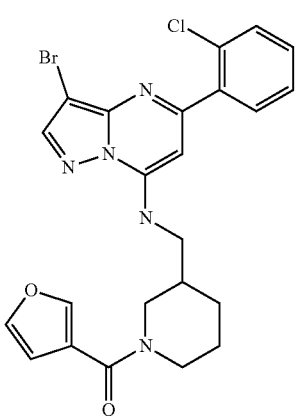 [SMILES: O=C(c1ccoc1)N1CCCC(CNc2cc(-c3ccccc3Cl)nc3c(Br)cnn23)C1] | 1. 5505<br>2. 514.81 |
| 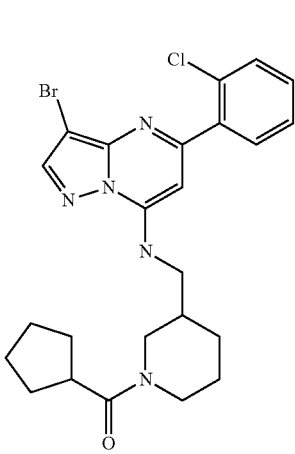 [SMILES: O=C(C1CCOC1)N1CCCC(CNc2cc(-c3ccccc3Cl)nc3c(Br)cnn23)C1] | 1. 5506<br>2. 516.87 |

TABLE 55-continued

| Product | 1. Ex.<br>2. m/z |
|---|---|
| (structure) | 1. 5507<br>2. 518.84 |
| (structure) | 1. 5508<br>2. 518.84 |
| (structure) | 1. 5509<br>2. 518.88 |
| (structure) | 1. 5510<br>2. 530.87 |
| (structure) | 1. 5511<br>2. 530.87 |
| (structure) | 1. 5512<br>2. 534.84 |

TABLE 55-continued
| Product | 1. Ex.<br>2. m/z |
|---|---|
| 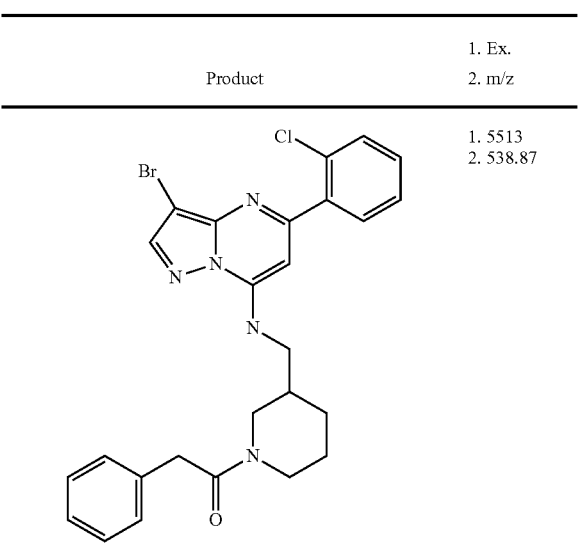 | 1. 5513<br>2. 538.87 |
| | 1. 5514<br>2. 543.85 |
| | 1. 5515<br>2. 544.9 |
TABLE 55-continued
| Product | 1. Ex.<br>2. m/z |
|---|---|
| 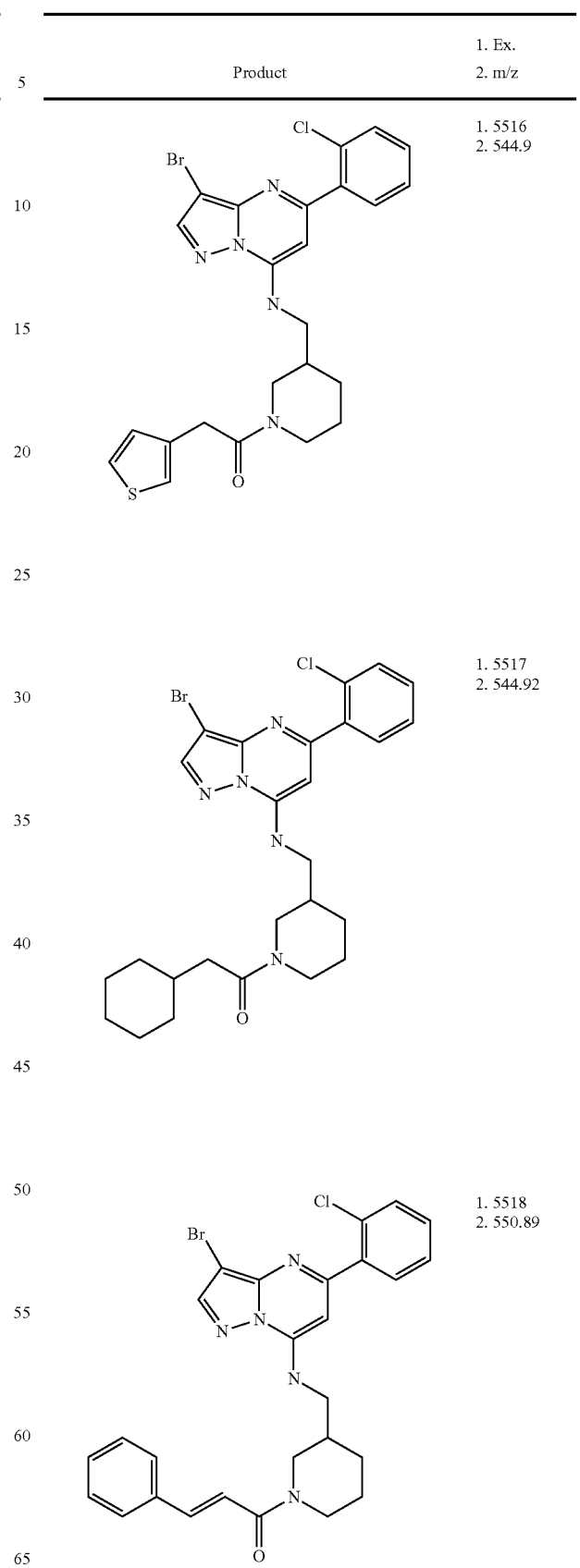 | 1. 5516<br>2. 544.9 |
| | 1. 5517<br>2. 544.92 |
| | 1. 5518<br>2. 550.89 |

TABLE 55-continued
| Product | 1. Ex.<br>2. m/z |
|---|---|
| 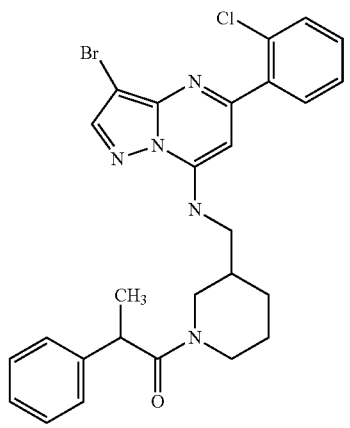 [SMILES: CC(C(=O)N1CCCC(CNc2cc(-c3ccccc3Cl)nc3c(Br)cnn23)C1)c1ccccc1] | 1. 5519<br>2. 552.9 |
| 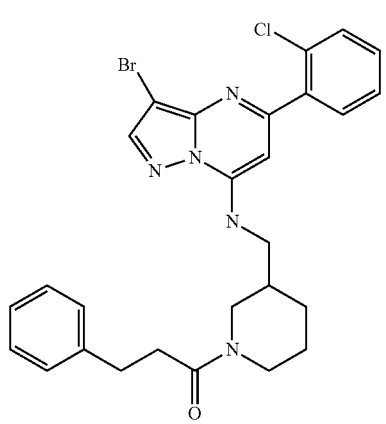 [SMILES: O=C(CCc1ccccc1)N1CCCC(CNc2cc(-c3ccccc3Cl)nc3c(Br)cnn23)C1] | 1. 5520<br>2. 552.9 |
| 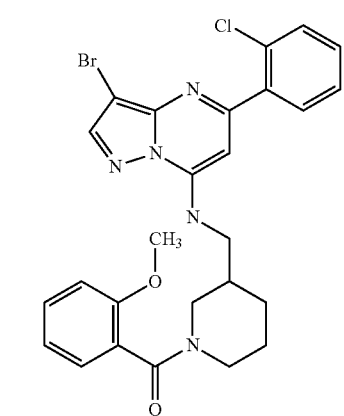 [SMILES: COc1ccccc1C(=O)N1CCCC(CNc2cc(-c3ccccc3Cl)nc3c(Br)cnn23)C1] | 1. 5521<br>2. 554.87 |
TABLE 55-continued
| Product | 1. Ex.<br>2. m/z |
|---|---|
| 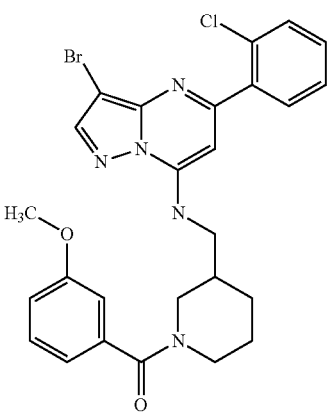 [SMILES: COc1cccc(C(=O)N2CCCC(CNc3cc(-c4ccccc4Cl)nc4c(Br)cnn34)C2)c1] | 1. 5522<br>2. 554.87 |
| 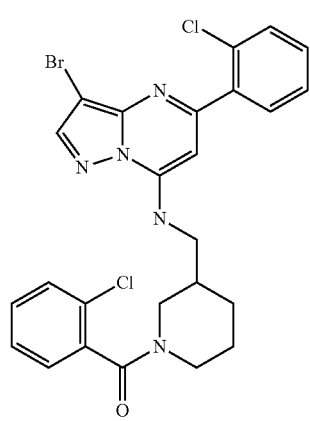 [SMILES: O=C(c1ccccc1Cl)N1CCCC(CNc2cc(-c3ccccc3Cl)nc3c(Br)cnn23)C1] | 1. 5523<br>2. 559.29 |
| 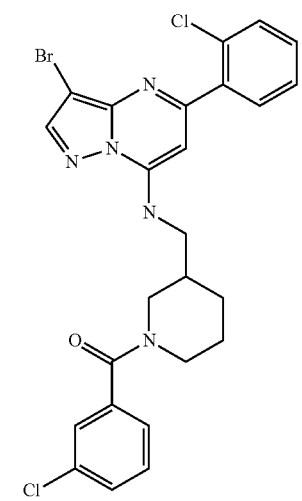 [SMILES: O=C(c1cccc(Cl)c1)N1CCCC(CNc2cc(-c3ccccc3Cl)nc3c(Br)cnn23)C1] | 1. 5524<br>2. 559.29 |

TABLE 55-continued
| Product | 1. Ex. 2. m/z |
|---|---|
| 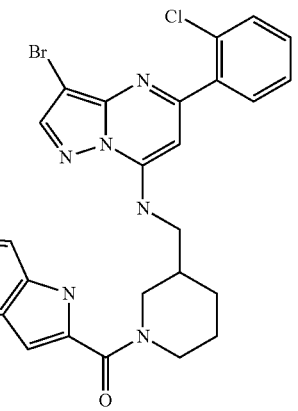 | 1. 5525<br>2. 563.88 |
| 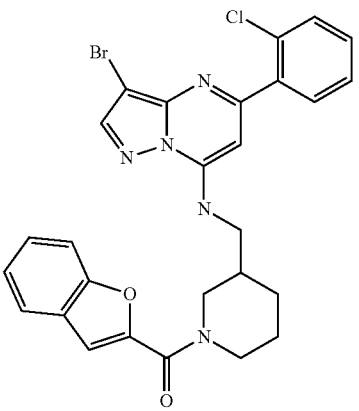 [SMILES: O=C(c1cc2ccccc2o1)N1CCCC(CNc2cc(-c3ccccc3Cl)nc3c(Br)cnn23)C1] | 1. 5526<br>2. 564.87 |
| 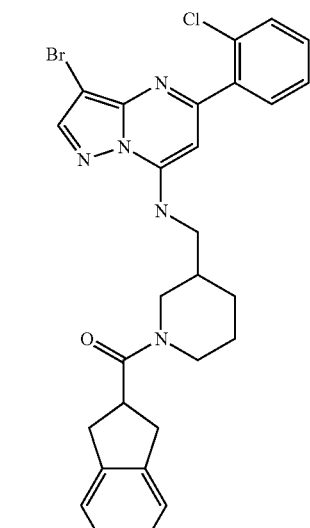 | 1. 5527<br>2. 564.91 |
| 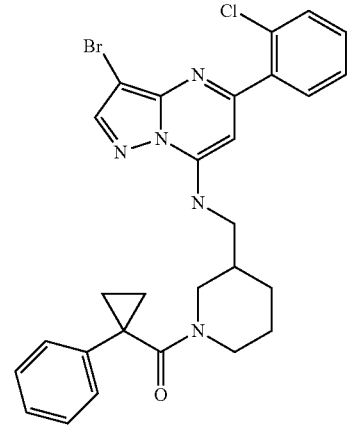 [SMILES: O=C(N1CCCC(CNc2cc(-c3ccccc3Cl)nc3c(Br)cnn23)C1)C1(c2ccccc2)CC1] | 1. 5528<br>2. 564.91 |
| 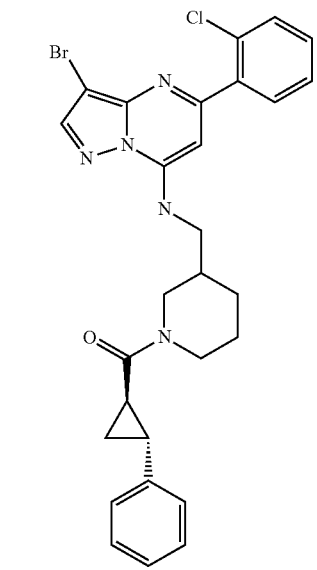 [SMILES: O=C([C@@H]1C[C@H]1c1ccccc1)N1CCCC(CNc2cc(-c3ccccc3Cl)nc3c(Br)cnn23)C1] | 1. 5529<br>2. 564.91 |
| 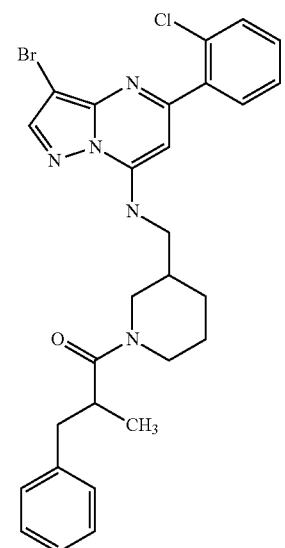 | 1. 5530<br>2. 566.93 |

TABLE 55-continued
| Product | 1. Ex. 2. m/z |
|---|---|
| 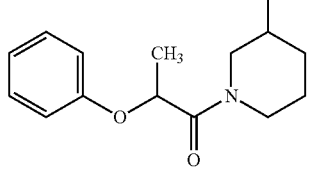 | 1. 5531  2. 568.9 |
| 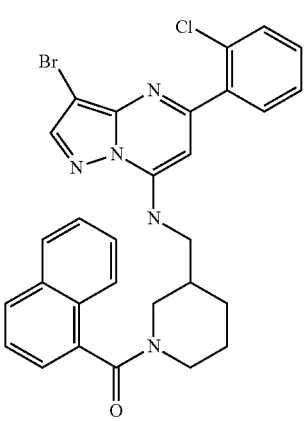 [SMILES: O=C(c1cccc2ccccc12)N1CCCC(CNc2cc(-c3ccccc3Cl)nc3c(Br)cnn23)C1] | 1. 5532  2. 574.91 |
| 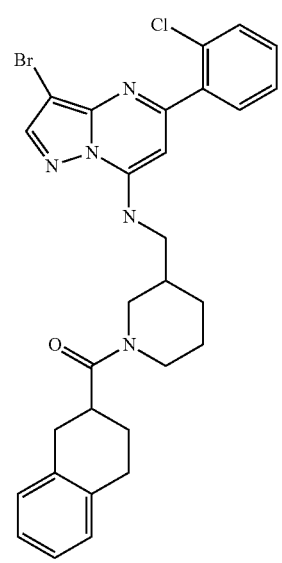 [SMILES: O=C(C1CCc2ccccc2C1)N1CCCC(CNc2cc(-c3ccccc3Cl)nc3c(Br)cnn23)C1] | 1. 5533  2. 578.94 |
TABLE 55-continued
| Product | 1. Ex. 2. m/z |
|---|---|
| 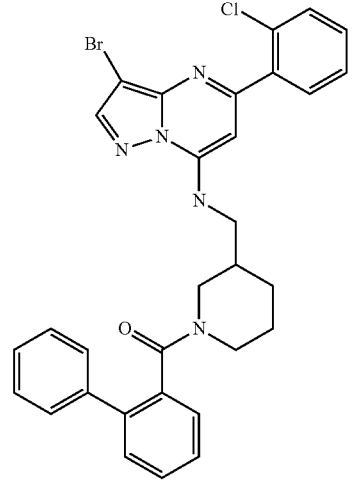 [SMILES: O=C(c1ccccc1-c1ccccc1)N1CCCC(CNc2cc(-c3ccccc3Cl)nc3c(Br)cnn23)C1] | 1. 5534  2. 592.85 |
| | 1. 5535  2. 592.85 |
| | 1. 5536  2. 600.95 |

TABLE 55-continued
| Product | 1. Ex.<br>2. m/z |
|---|---|
| 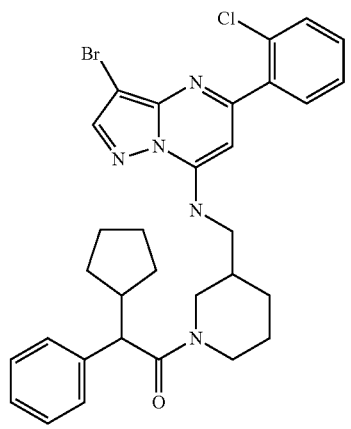 [SMILES: O=C(C(c1ccccc1)C1CCCC1)N1CCCC(CNc2cc(-c3ccccc3Cl)nc3c(Br)cnn23)C1] | 1. 5537<br>2. 606.99 |
| 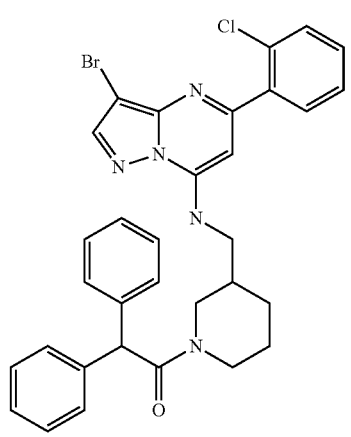 [SMILES: O=C(C(c1ccccc1)c1ccccc1)N1CCCC(CNc2cc(-c3ccccc3Cl)nc3c(Br)cnn23)C1] | 1. 5538<br>2. 614.97 |
| 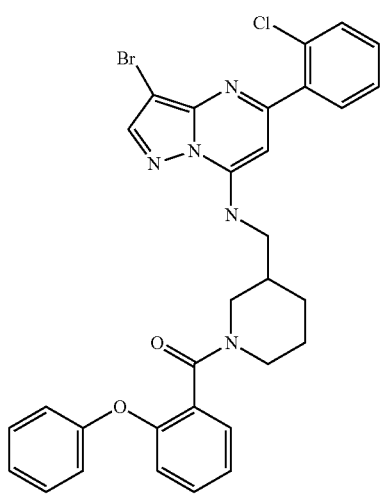 [SMILES: O=C(c1ccccc1Oc1ccccc1)N1CCCC(CNc2cc(-c3ccccc3Cl)nc3c(Br)cnn23)C1] | 1. 5539<br>2. 616.95 |
TABLE 55-continued
| Product | 1. Ex.<br>2. m/z |
|---|---|
| 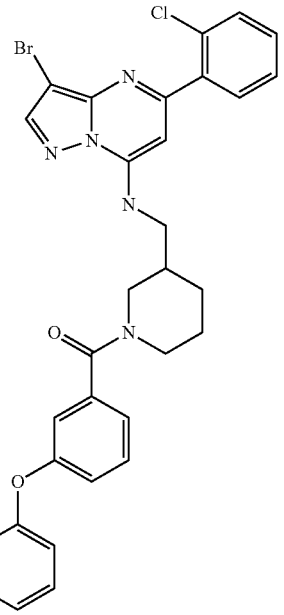 | 1. 5540<br>2. 616.95 |
| 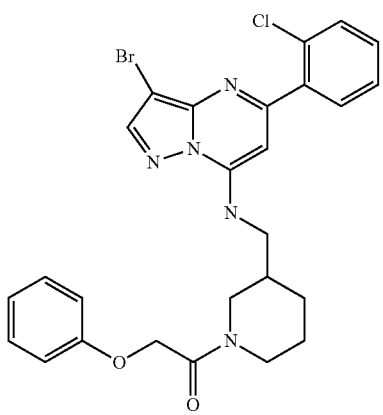 [SMILES: O=C(COc1ccccc1)N1CCCC(CNc2cc(-c3ccccc3Cl)nc3c(Br)cnn23)C1] | 1. 5541 |
| 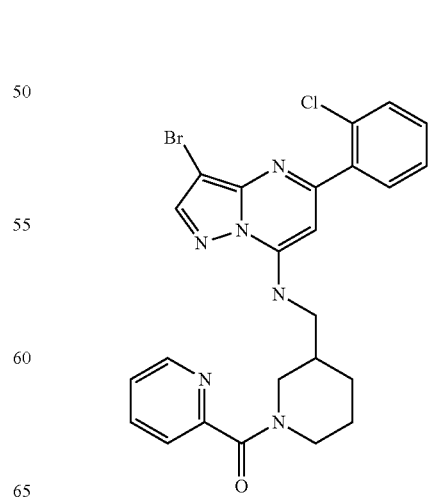 | 1. 5542<br>2. 525.83 |

TABLE 55-continued

| Product | 1. Ex.<br>2. m/z |
|---|---|
| (structure: 3-bromo-5-(2-chlorophenyl)pyrazolo[1,5-a]pyrimidin-7-yl amino-methyl-piperidine-1-carbonyl-3-(acetamido)phenyl) | 1. 5543<br>2. 581.9 |
| (structure: 3-bromo-5-(2-chlorophenyl)pyrazolo[1,5-a]pyrimidin-7-yl amino-methyl-piperidine-1-carbonyl-4-(acetamido)phenyl) | 1. 5544<br>2. 581.9 |
| (structure: 3-bromo-5-(2-chlorophenyl)pyrazolo[1,5-a]pyrimidin-7-yl amino-methyl-piperidine with 4-methyl-2-phenyl-2H-1,2,3-triazole-5-carbonyl) | 1. 5545<br>2. 605.92 |
| (structure: 3-bromo-5-(2-chlorophenyl)pyrazolo[1,5-a]pyrimidin-7-yl amino-methyl-piperidine-1-(3-chlorophenyl)acetyl) | 1. 5546<br>2. 573.32 |
| (structure: 3-bromo-5-(2-chlorophenyl)pyrazolo[1,5-a]pyrimidin-7-yl amino-methyl-piperidine-1-(benzo[d][1,3]dioxol-5-yl)acetyl) | 1. 5547<br>2. 582.88 |
| (structure: 3-bromo-5-(2-chlorophenyl)pyrazolo[1,5-a]pyrimidin-7-yl amino-methyl-piperidine-1-(2,4-dichlorophenyl)acetyl) | 1. 5548<br>2. 607.76 |

TABLE 55-continued
| Product | 1. Ex. 2. m/z |
|---|---|
| 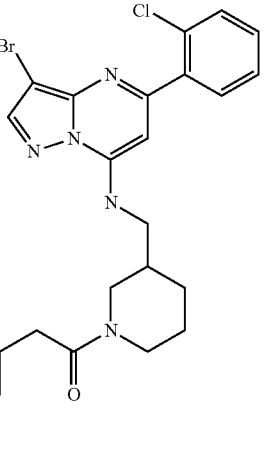 | 1. 5549  2. 607.76 |
| 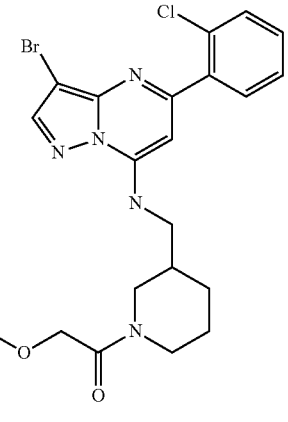 | 1. 5550  2. 536.86 |
| 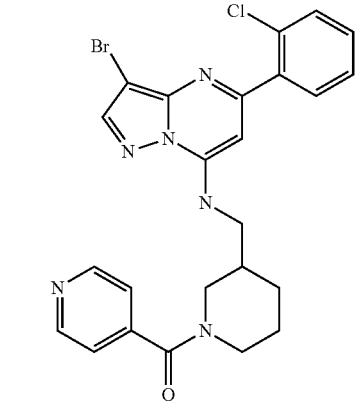 [SMILES: O=C(c1ccncc1)N1CCCC(CNc2cc(-c3ccccc3Cl)nc3c(Br)cnn23)C1] | 1. 5551  2. 525.83 |
TABLE 55-continued
| Product | 1. Ex. 2. m/z |
|---|---|
| 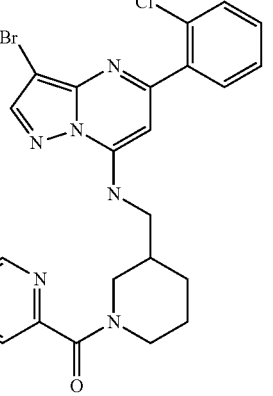 | 1. 5552  2. 526.82 |
| 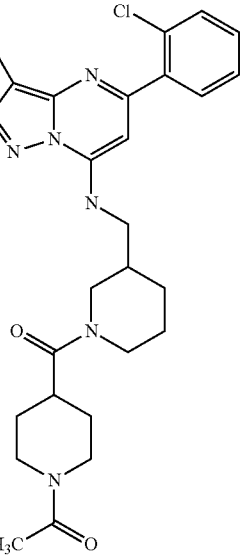 | 1. 5553  2. 573.92 |
TABLE 56
| Product | 1. Ex. 2. m/z |
|---|---|
| 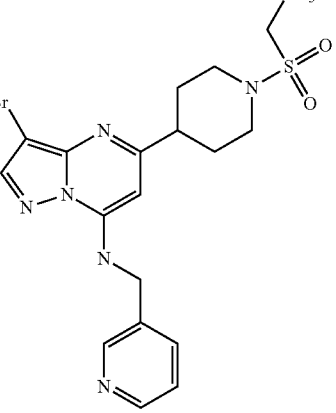 | 1. 5601  2. 481.26 |

TABLE 56-continued
| Product | 1. Ex.<br>2. m/z |
|---|---|
| 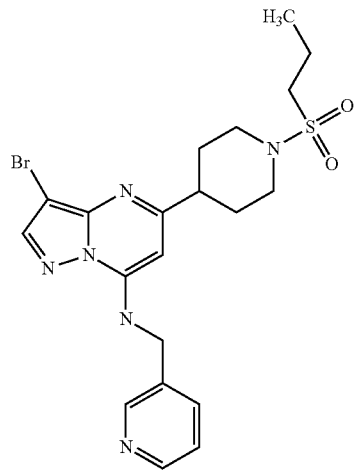 [SMILES: CCCS(=O)(=O)N1CCC(c2cc(NCc3cccnc3)n3ncc(Br)c3n2)CC1] | 1. 5602<br>2. 495.27 |
| 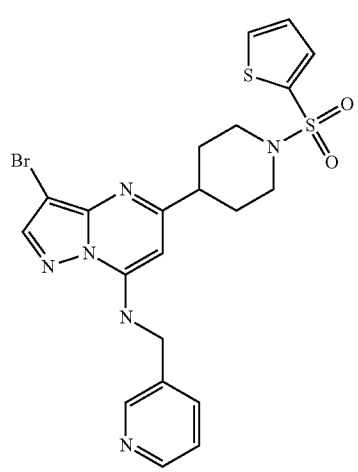 [SMILES: O=S(=O)(c1cccs1)N1CCC(c2cc(NCc3cccnc3)n3ncc(Br)c3n2)CC1] | 1. 5603<br>2. 535.29 |
| 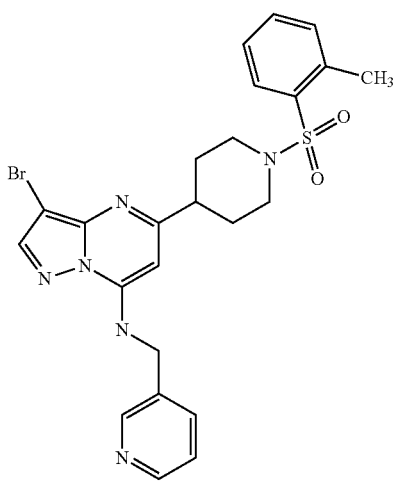 [SMILES: Cc1ccccc1S(=O)(=O)N1CCC(c2cc(NCc3cccnc3)n3ncc(Br)c3n2)CC1] | 1. 5604<br>2. 543.3 |
TABLE 56-continued
| Product | 1. Ex.<br>2. m/z |
|---|---|
| 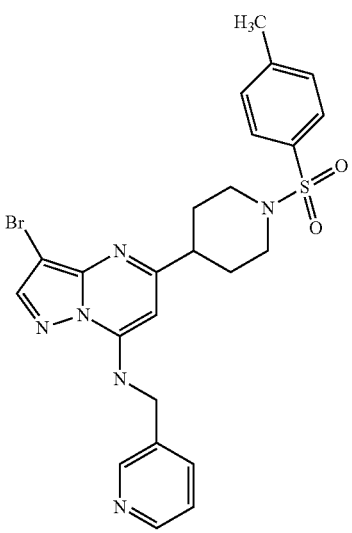 | 1. 5605<br>2. 543.3 |
| 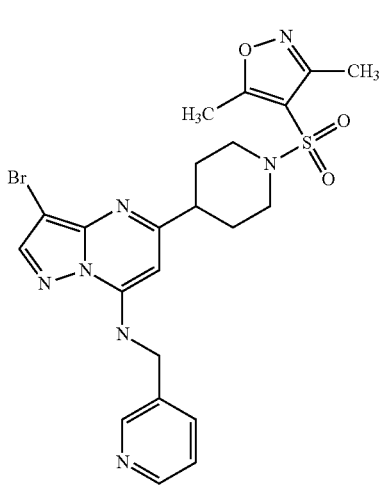 [SMILES: Cc1noc(C)c1S(=O)(=O)N1CCC(c2cc(NCc3cccnc3)n3ncc(Br)c3n2)CC1] | 1. 5606<br>2. 548.3 |
| | 1. 5607<br>2. 554.3 |

TABLE 56-continued
| Product | 1. Ex.<br>2. m/z |
|---|---|
| 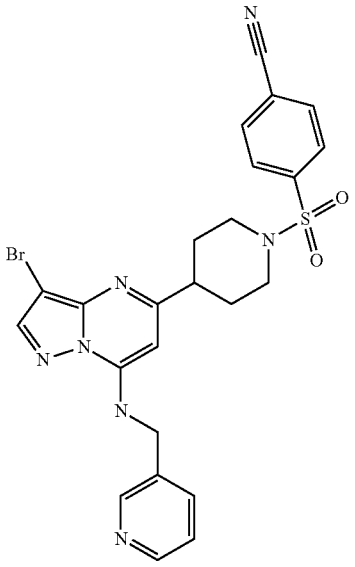 [SMILES: N#Cc1ccc(S(=O)(=O)N2CCC(c3cc(NCc4cccnc4)n4ncc(Br)c4n3)CC2)cc1] | 1. 5608<br>2. 554.3 |
| 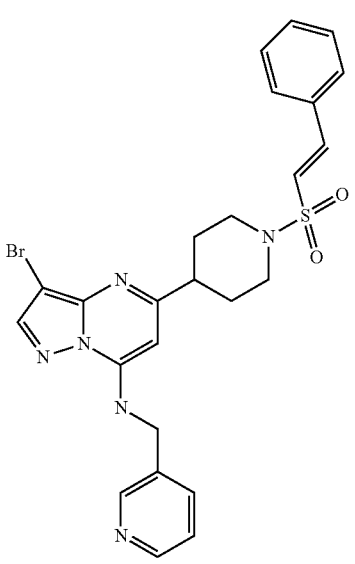 [SMILES: O=S(=O)(/C=C/c1ccccc1)N1CCC(c2cc(NCc3cccnc3)n3ncc(Br)c3n2)CC1] | 1. 5609<br>2. 555.31 |
TABLE 56-continued
| Product | 1. Ex.<br>2. m/z |
|---|---|
| 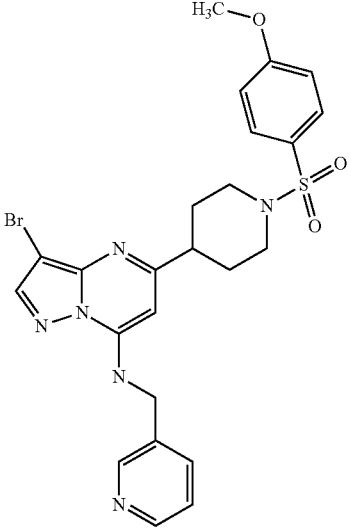 [SMILES: CCc1ccc(S(=O)(=O)N2CCC(c3cc(NCc4cccnc4)n4ncc(Br)c4n3)CC2)cc1] | 1. 5610<br>2. 559.31 |
| 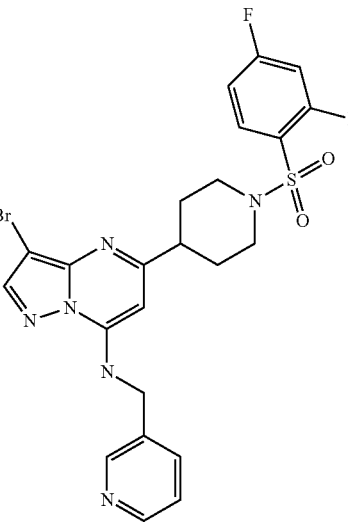 | 1. 5611<br>2. 565.31 |
| 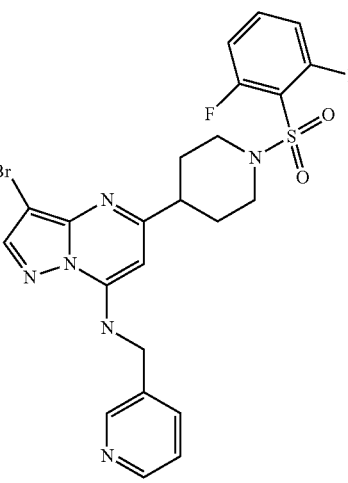 | 1. 5612<br>2. 565.31 |

TABLE 56-continued
| Product | 1. Ex.<br>2. m/z |
|---|---|
| 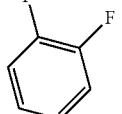 | 1. 5613<br>2. 565.31 |
| 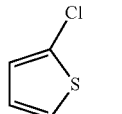 | 1. 5614<br>2. 569.31 |
| 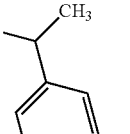 | 1. 5615<br>2. 571.31 |
TABLE 56-continued
| Product | 1. Ex.<br>2. m/z |
|---|---|
| 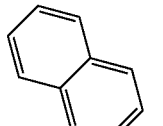 | 1. 5616<br>2. 579.32 |
| 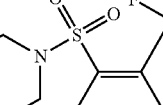 | 1. 5617 |
| 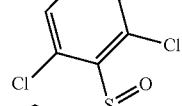 | 1. 5618 |

TABLE 56-continued

| Product | 1. Ex. 2. m/z |
|---|---|
| (structure) | 1. 5619 |
| (structure) | 1. 5620 |
| (structure) | 1. 5621<br>2. 615.34 |
| (structure) | 2. 5622<br>2. 680.37 |
| (structure) | 1. 5623<br>2. 529.29 |
| (structure) | 1. 5624<br>2. 543.3 |

TABLE 56-continued
| Product | 1. Ex. 2. m/z |
|---|---|
| 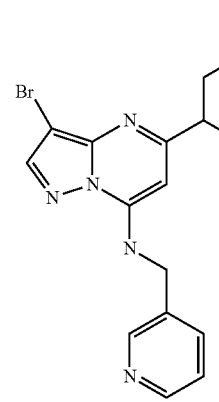 | 1. 5625  2. 547.3 |
| 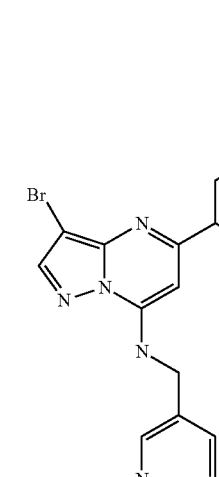 | 1. 5626  2. 547.3 |
| 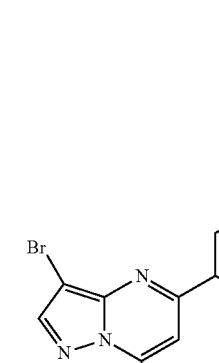 | 1. 5627  2. 547.3 |
TABLE 56-continued
| Product | 1. Ex. 2. m/z |
|---|---|
| 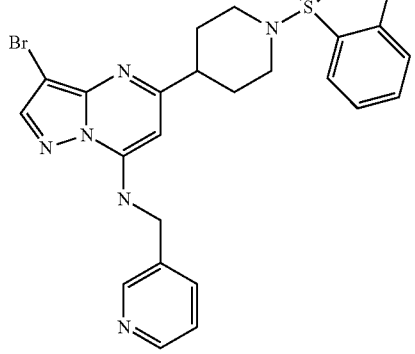 | 1. 5628  2. 554.3 |
| 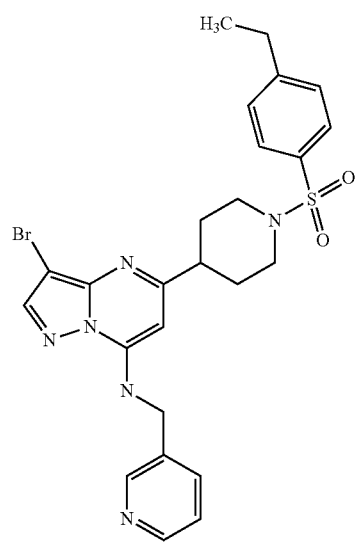 | 1. 5629  2. 555.31 |
| 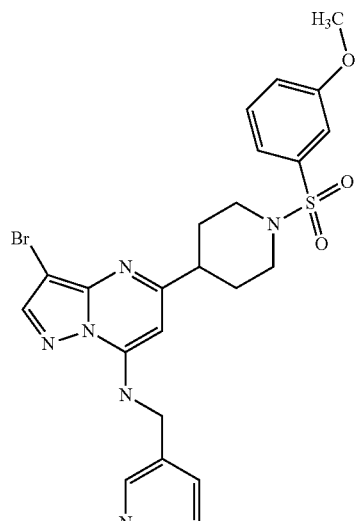 | 1. 5630  2. 559.31 |

TABLE 56-continued
| Product | 1. Ex. 2. m/z |
|---|---|
| 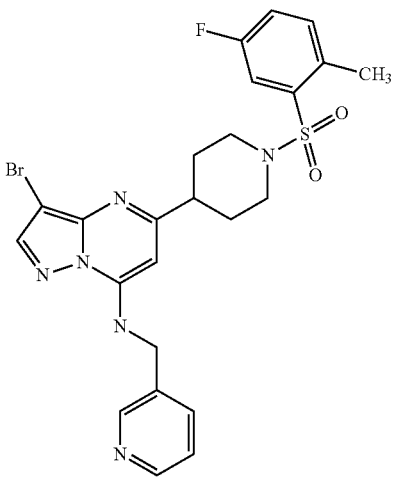 [SMILES: Cc1ccc(F)cc1S(=O)(=O)N1CCC(c2cc(NCc3cccnc3)n3ncc(Br)c3n2)CC1] | 1. 5631 2. 561.31 |
| 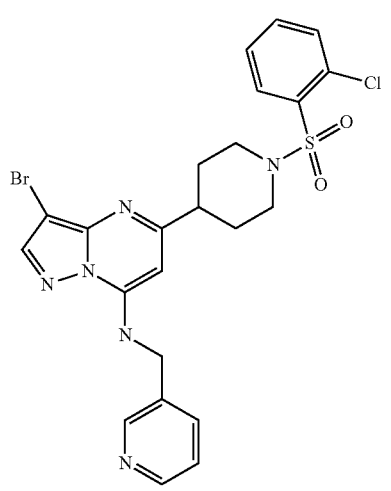 [SMILES: O=S(=O)(c1ccccc1Cl)N1CCC(c2cc(NCc3cccnc3)n3ncc(Br)c3n2)CC1] | 1. 5632 2. 563.31 |
| 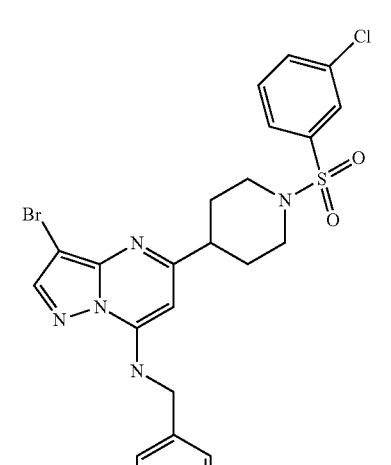 | 1. 5633 2. 563.31 |
TABLE 56-continued
| Product | 1. Ex. 2. m/z |
|---|---|
|  | 1. 5634 2. 563.31 |
|  | 1. 5635 2. 563.31 |
|  | 1. 5636 2. 565.31 |

TABLE 56-continued

| Product | 1. Ex.<br>2. m/z |
|---|---|
| (structure) | 1. 5637<br>2. 579.32 |
| (structure) | 1. 5638<br>2. 581.32 |
| (structure) | 1. 5639<br>2. 581.32 |
| (structure) | 1. 5640<br>2. 585.32 |
| (structure) | 1. 5641<br>2. 587.32 |
| (structure) | 1. 5642<br>2. 589.32 |

TABLE 56-continued
| Product | 1. Ex.<br>2. m/z |
|---|---|
| 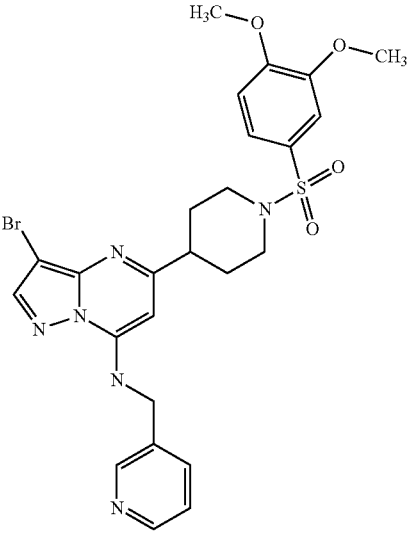 [SMILES: COc1ccc(S(=O)(=O)N2CCC(c3cc(NCc4cccnc4)n4ncc(Br)c4n3)CC2)cc1OC] | 1. 5643<br>2. 589.32 |
| 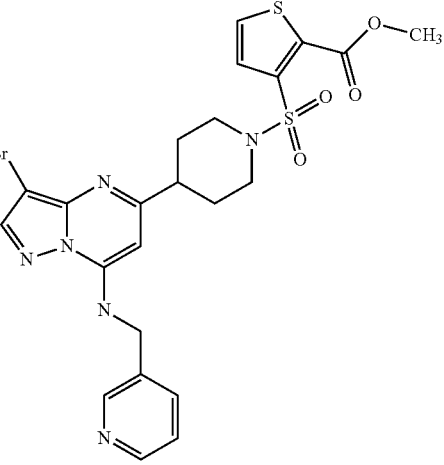 | 1. 5644<br>2. 593.33 |
| 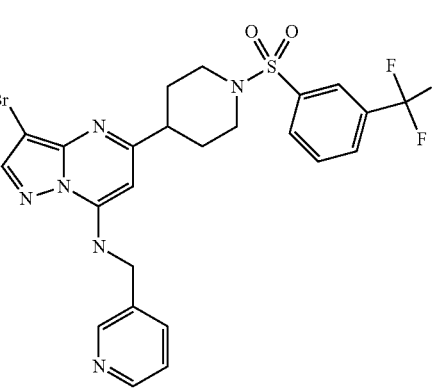 | 1. 5645<br>2. 597.33 |
TABLE 56-continued
| Product | 1. Ex.<br>2. m/z |
|---|---|
| 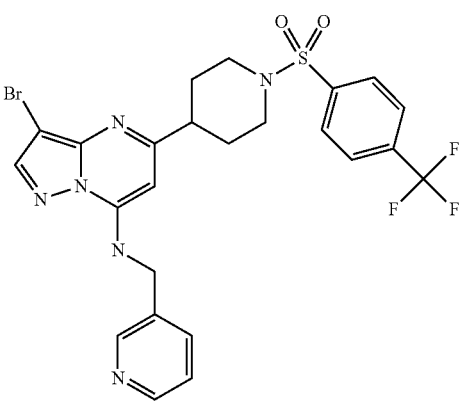 [SMILES: O=S(=O)(c1ccc(C(F)(F)F)cc1)N1CCC(c2cc(NCc3cccnc3)n3ncc(Br)c3n2)CC1] | 1. 5646 |
| 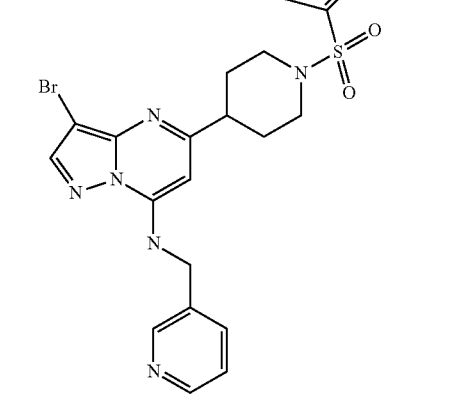 | 1. 5647<br>2. 597.33 |
| 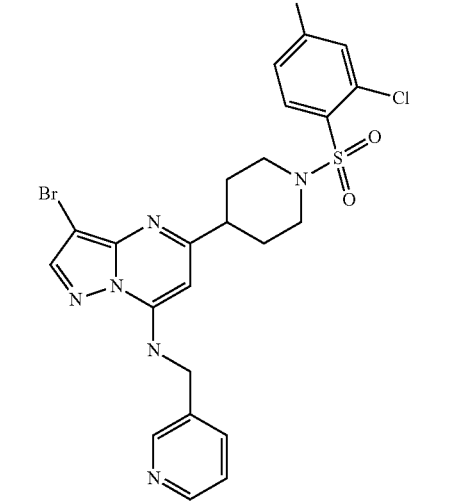 | 1. 5648<br>2. 597.33 |

TABLE 56-continued
| Product | 1. Ex.<br>2. m/z |
|---|---|
| 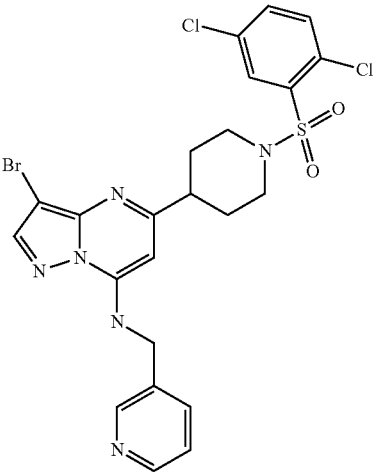 [SMILES: O=S(=O)(c1cc(Cl)ccc1Cl)N1CCC(c2cc(NCc3cccnc3)n3ncc(Br)c3n2)CC1] | 1. 5649<br>2. 597.33 |
| 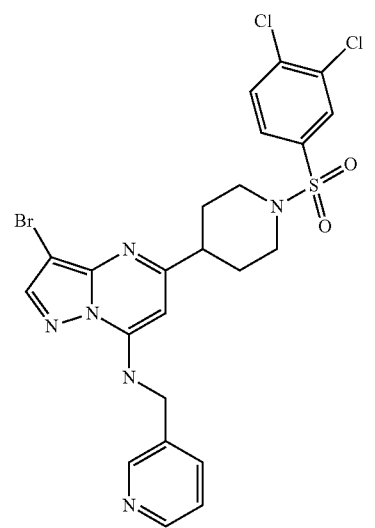 [SMILES: O=S(=O)(c1ccc(Cl)c(Cl)c1)N1CCC(c2cc(NCc3cccnc3)n3ncc(Br)c3n2)CC1] | 1. 5650<br>2. 597.33 |
| 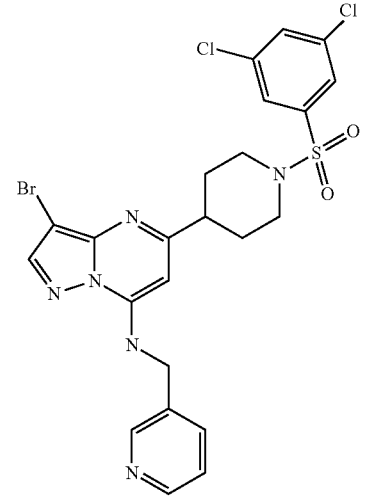 | 1. 5651<br>2. 597.33 |
TABLE 56-continued
| Product | 1. Ex.<br>2. m/z |
|---|---|
| 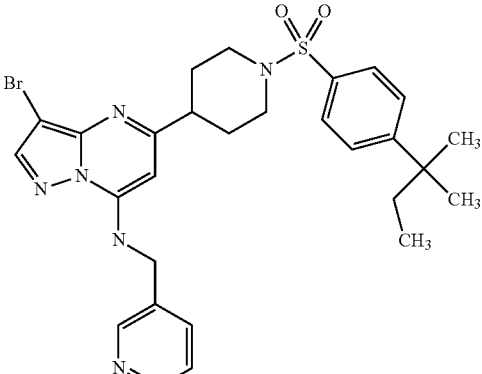 | 1. 5652<br>2. 599.33 |
| 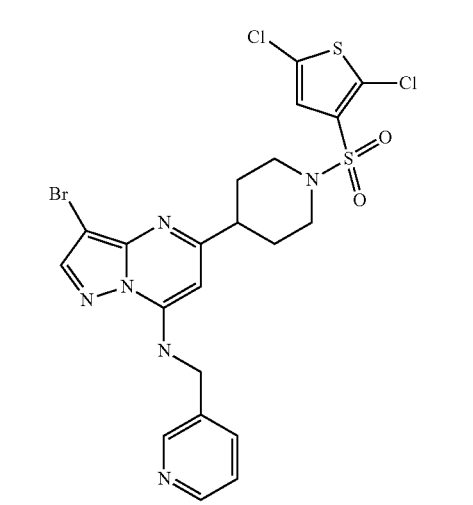 [SMILES: O=S(=O)(c1cc(Cl)sc1Cl)N1CCC(c2cc(NCc3cccnc3)n3ncc(Br)c3n2)CC1] | 1. 5653<br>2. 603.33 |
| 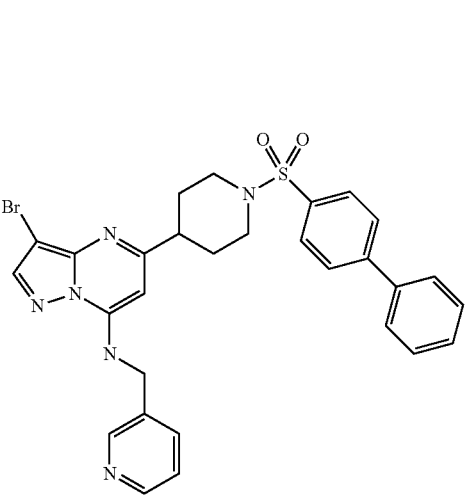 [SMILES: O=S(=O)(c1ccc(-c2ccccc2)cc1)N1CCC(c2cc(NCc3cccnc3)n3ncc(Br)c3n2)CC1] | 1. 5654<br>2. 605.33 |

TABLE 56-continued

| Product | 1. Ex. 2. m/z |
|---|---|
| (structure) | 1. 5655  2. 607.33 |
| (structure) | 1. 5656  2. 607.33 |
| (structure) | 1. 5657  2. 607.33 |
| (structure) | 1. 5658  2. 607.33 |
| (structure) | 1. 5659  2. 621.34 |
| (structure) | 1. 5660  2. 631.35 |

TABLE 56-continued
| Product | 1. Ex. 2. m/z |
|---|---|
| 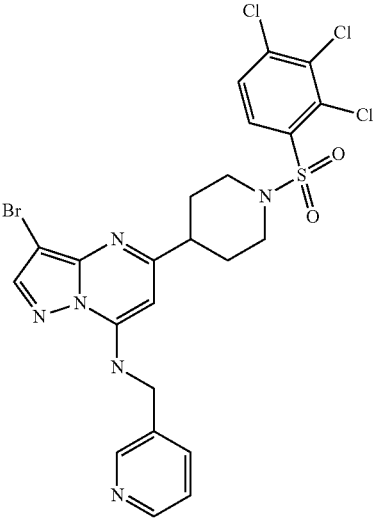 [SMILES: O=S(=O)(c1ccc(Cl)c(Cl)c1Cl)N1CCC(c2cc(NCc3cccnc3)n3ncc(Br)c3n2)CC1] | 1. 5661 2. 631.35 |
| 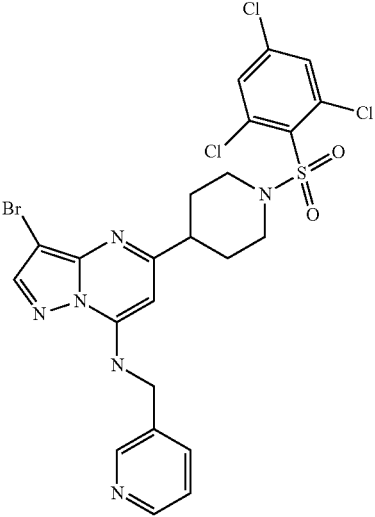 [SMILES: O=S(=O)(c1c(Cl)cc(Cl)cc1Cl)N1CCC(c2cc(NCc3cccnc3)n3ncc(Br)c3n2)CC1] | 1. 5662 2. 631.35 |
| 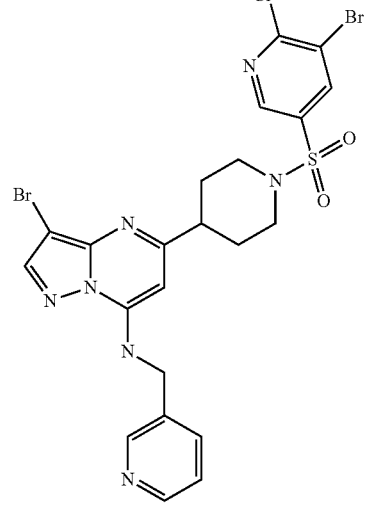 | 1. 5663 2. 642.35 |
TABLE 56-continued
| Product | 1. Ex. 2. m/z |
|---|---|
| 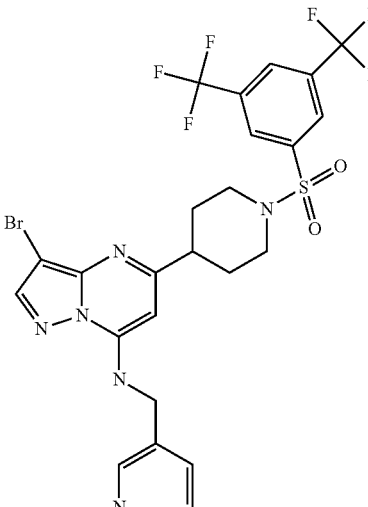 | 1. 5664 2. 665.37 |
| 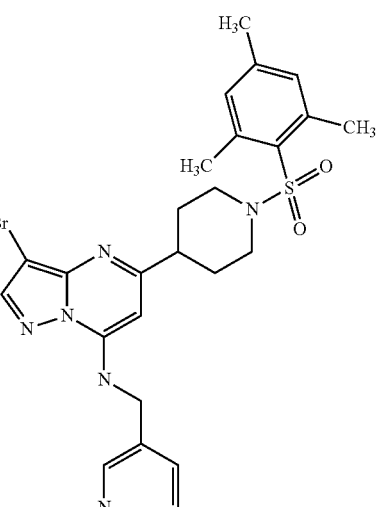 | 1. 5665 2. 571.31 |
TABLE 57
| Product | 1. Ex. 2. m/z |
|---|---|
| 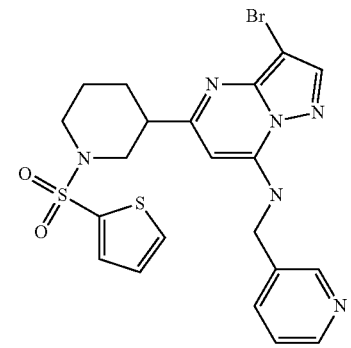 [SMILES: O=S(=O)(c1cccs1)N1CCCC(c2cc(NCc3cccnc3)n3ncc(Br)c3n2)C1] | 1. 5701 2. 535.29 |

TABLE 57-continued

| Product | 1. Ex. 2. m/z |
|---|---|
| (3-bromo-pyrazolo[1,5-a]pyrimidine with 3-(1-(2-methylphenylsulfonyl)piperidin-3-yl) and N-(pyridin-3-ylmethyl)amino substituents) | 1. 5702 2. 540.3 |
| (3-bromo-pyrazolo[1,5-a]pyrimidine with 3-(1-(3-methylphenylsulfonyl)piperidin-3-yl) and N-(pyridin-3-ylmethyl)amino substituents) | 1. 5703 2. 543.3 |
| (3-bromo-pyrazolo[1,5-a]pyrimidine with 3-(1-(4-methylphenylsulfonyl)piperidin-3-yl) and N-(pyridin-3-ylmethyl)amino substituents) | 1. 5704 2. 543.3 |
| (3-bromo-pyrazolo[1,5-a]pyrimidine with 3-(1-(2-fluorophenylsulfonyl)piperidin-3-yl) and N-(pyridin-3-ylmethyl)amino substituents) | 1. 5705 2. 547.3 |

TABLE 57-continued

| Product | 1. Ex. 2. m/z |
|---|---|
| (3-bromo-pyrazolo[1,5-a]pyrimidine with 3-(1-(3-fluorophenylsulfonyl)piperidin-3-yl) and N-(pyridin-3-ylmethyl)amino substituents) | 1. 5706 2. 547.3 |
| (3-bromo-pyrazolo[1,5-a]pyrimidine with 3-(1-(4-fluorophenylsulfonyl)piperidin-3-yl) and N-(pyridin-3-ylmethyl)amino substituents) | 1. 5707 2. 547.3 |
| (3-bromo-pyrazolo[1,5-a]pyrimidine with 3-(1-(4-cyanophenylsulfonyl)piperidin-3-yl) and N-(pyridin-3-ylmethyl)amino substituents) | 1. 5708 2. 554.3 |
| (3-bromo-pyrazolo[1,5-a]pyrimidine with 3-(1-(styrylsulfonyl)piperidin-3-yl) and N-(pyridin-3-ylmethyl)amino substituents) | 1. 5709 2. 555.31 |

TABLE 57-continued
| Product | 1. Ex. 2. m/z |
|---|---|
| 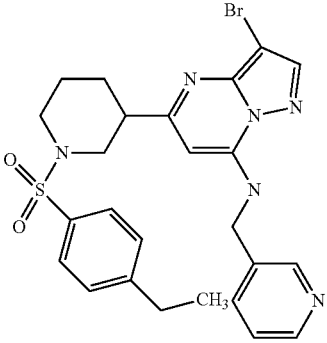 [SMILES: CCc1ccc(S(=O)(=O)N2CCCC(c3cc(NCc4cccnc4)n4ncc(Br)c4n3)C2)cc1] | 1. 5710 2. 555.31 |
| 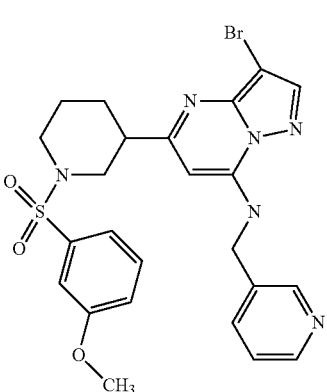 [SMILES: COc1cccc(S(=O)(=O)N2CCCC(c3cc(NCc4cccnc4)n4ncc(Br)c4n3)C2)c1] | 1. 5711 2. 559.31 |
| 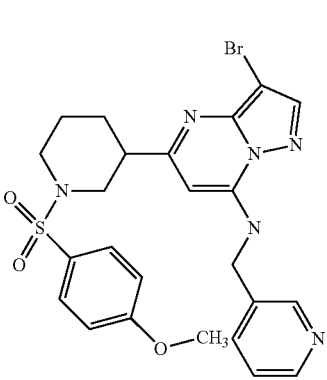 [SMILES: COc1ccc(S(=O)(=O)N2CCCC(c3cc(NCc4cccnc4)n4ncc(Br)c4n3)C2)cc1] | 1. 5712 2. 559.31 |
| 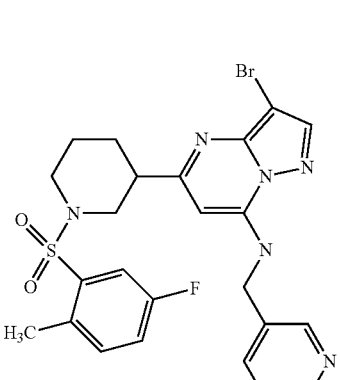 | 1. 5713 2. 561.31 |
TABLE 57-continued
| Product | 1. Ex. 2. m/z |
|---|---|
| 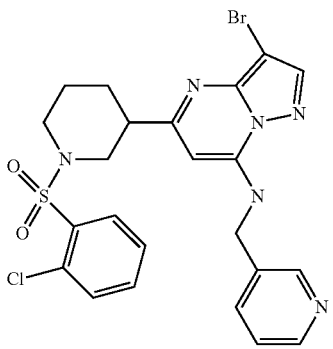 [SMILES: O=S(=O)(c1ccccc1Cl)N1CCCC(c2cc(NCc3cccnc3)n3ncc(Br)c3n2)C1] | 1. 5714 2. 562.31 |
| 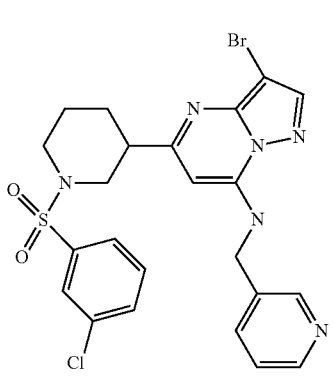 [SMILES: O=S(=O)(c1cccc(Cl)c1)N1CCCC(c2cc(NCc3cccnc3)n3ncc(Br)c3n2)C1] | 1. 5715 2. 563.31 |
| 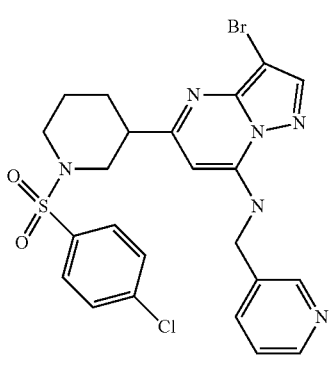 [SMILES: O=S(=O)(c1ccc(Cl)cc1)N1CCCC(c2cc(NCc3cccnc3)n3ncc(Br)c3n2)C1] | 1. 5716 2. 563.31 |
| 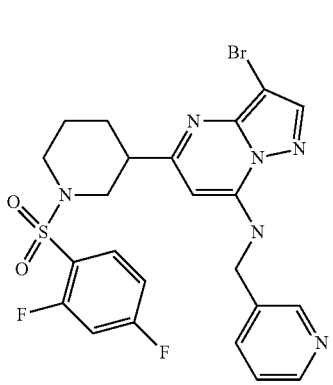 [SMILES: O=S(=O)(c1ccc(F)cc1F)N1CCCC(c2cc(NCc3cccnc3)n3ncc(Br)c3n2)C1] | 1. 5717 2. 565.31 |

TABLE 57-continued

| Product | 1. Ex. 2. m/z |
|---|---|
| (structure) | 1. 5718  2. 565.31 |
| (structure) | 1. 5719  2. 565.31 |
| (structure) | 1. 5720  2. 565.31 |
| (structure) | 1. 5721  2. 569.31 |

TABLE 57-continued

| Product | 1. Ex. 2. m/z |
|---|---|
| (structure) | 1. 5722  2. 571.31 |
| (structure) | 1. 5723  2. 579.32 |
| (structure) | 1. 5724  2. 579.32 |
| (structure) | 1. 5725  2. 581.32 |

TABLE 57-continued
| Product | 1. Ex.<br>2. m/z |
|---|---|
| 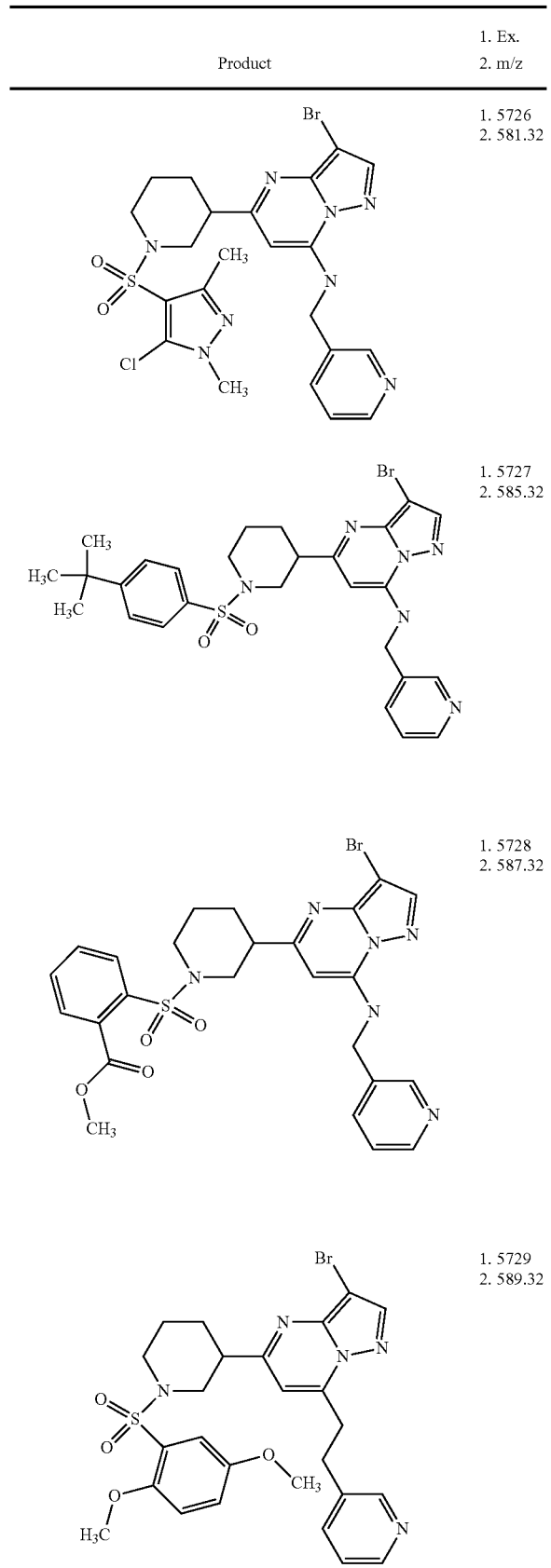 | 1. 5726<br>2. 581.32 |
| | 1. 5727<br>2. 585.32 |
| | 1. 5728<br>2. 587.32 |
| | 1. 5729<br>2. 589.32 |
TABLE 57-continued
| Product | 1. Ex.<br>2. m/z |
|---|---|
| 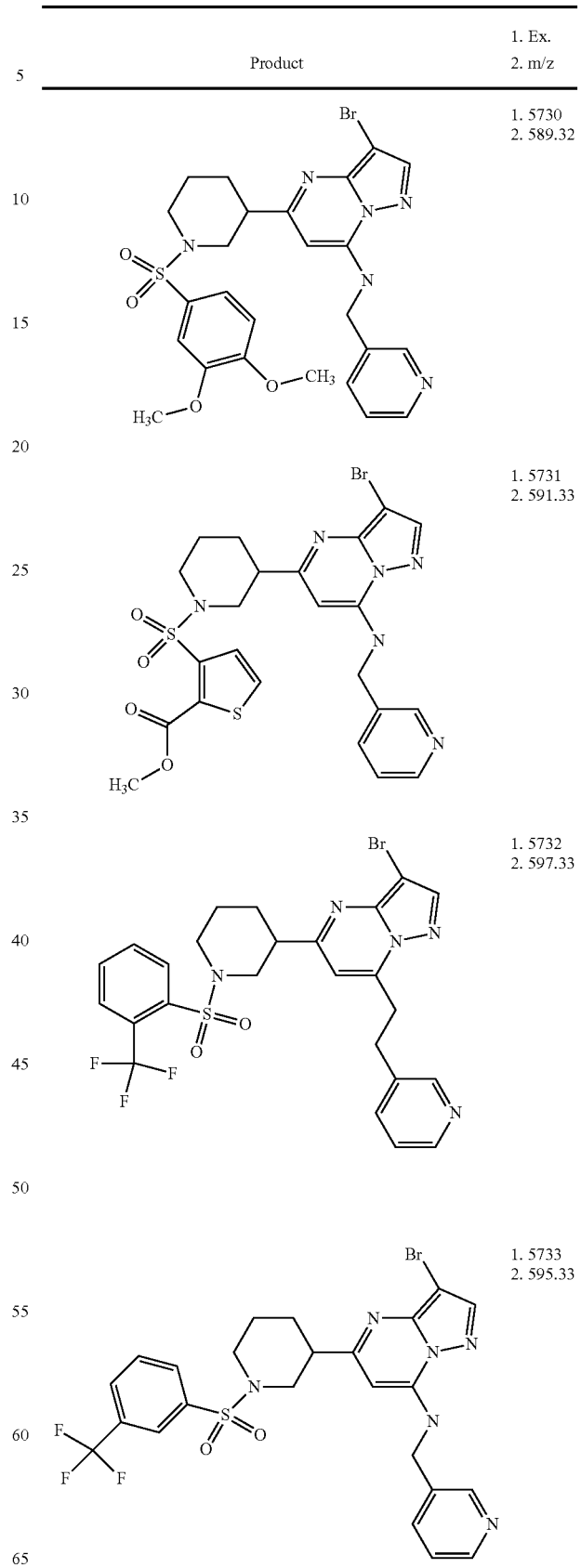 | 1. 5730<br>2. 589.32 |
| | 1. 5731<br>2. 591.33 |
| | 1. 5732<br>2. 597.33 |
| | 1. 5733<br>2. 595.33 |

TABLE 57-continued
| Product | 1. Ex.<br>2. m/z |
|---|---|
| 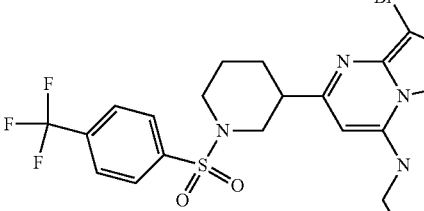 | 1. 5734<br>2. 597.33 |
| 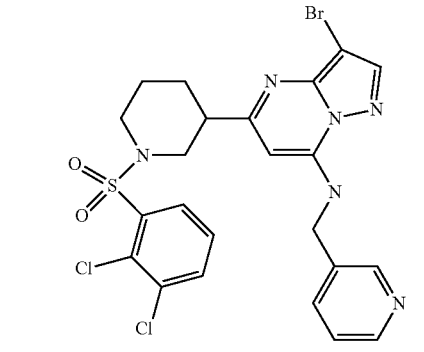 [SMILES: O=S(=O)(c1cccc(Cl)c1Cl)N1CCCC(c2cc(NCc3cccnc3)n3ncc(Br)c3n2)C1] | 1. 5735<br>2. 597.33 |
|  | 1. 5736<br>2. 597.33 |
|  | 1. 5737<br>2. 597.33 |
TABLE 57-continued
| Product | 1. Ex.<br>2. m/z |
|---|---|
| 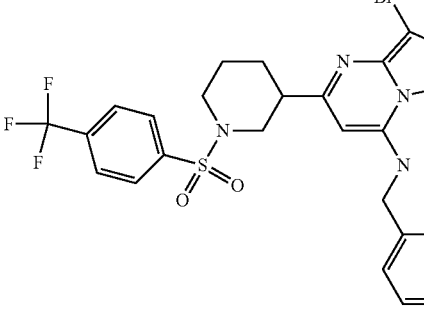 | 1. 5738<br>2. 596.33 |
| 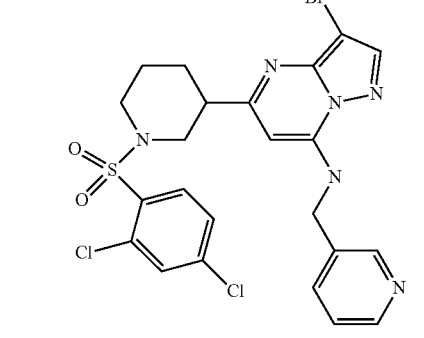 | 1. 5739<br>2. 597.33 |
| 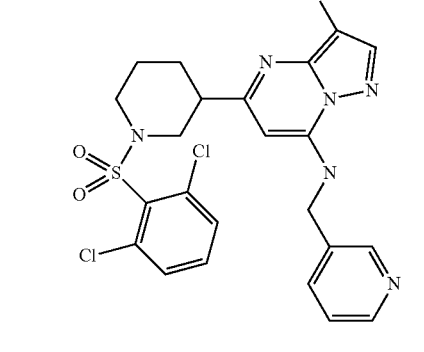 | 1. 5740<br>2. 581.32 |
| 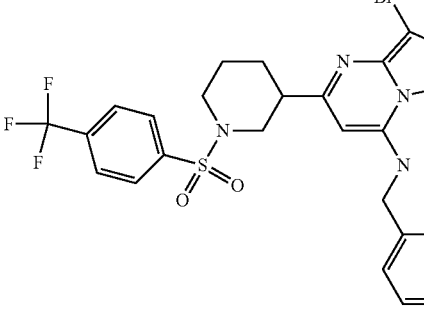 | 1. 5741<br>2. 605.33 |

TABLE 57-continued
| Product | 1. Ex. 2. m/z |
|---|---|
| 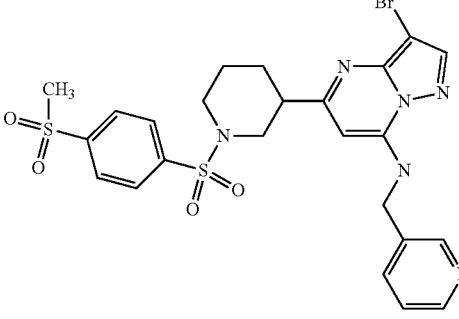 | 1. 5742<br>2. 607.33 |
| 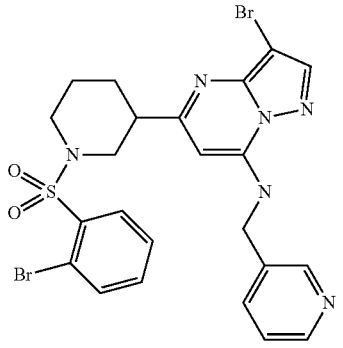 [SMILES: O=S(=O)(c1ccccc1Br)N1CCCC(c2cc(NCc3cccnc3)n3ncc(Br)c3n2)C1] | 1. 5743<br>2. 607.33 |
| 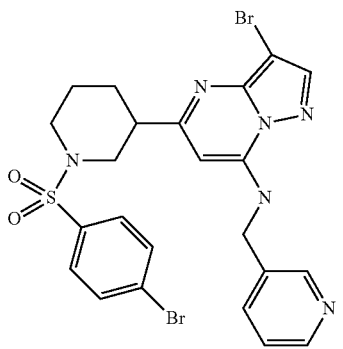 [SMILES: O=S(=O)(c1ccc(Br)cc1)N1CCCC(c2cc(NCc3cccnc3)n3ncc(Br)c3n2)C1] | 1. 5744<br>2. 607.33 |
| 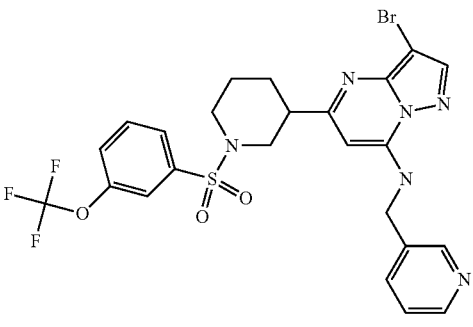 [SMILES: O=S(=O)(c1cccc(OC(F)(F)F)c1)N1CCCC(c2cc(NCc3cccnc3)n3ncc(Br)c3n2)C1] | 1. 57454<br>2. 613.34 |
TABLE 57-continued
| Product | 1. Ex. 2. m/z |
|---|---|
| 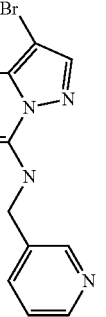 | 1. 5746<br>2. 613.34 |
| 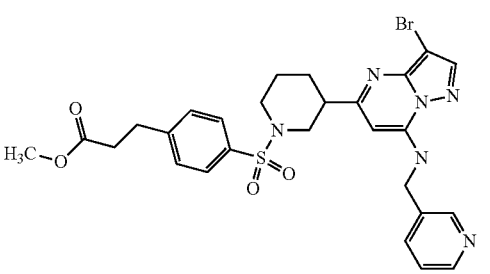 [SMILES: COC(=O)CCc1ccc(S(=O)(=O)N2CCCC(c3cc(NCc4cccnc4)n4ncc(Br)c4n3)C2)cc1] | 1. 5747<br>2. 615.34 |
| 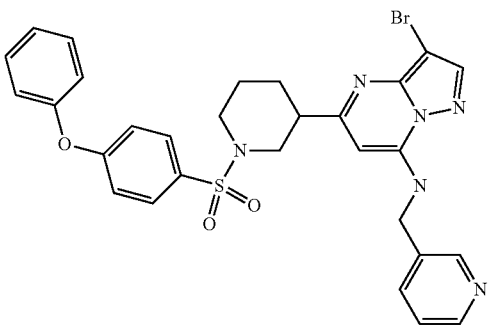 [SMILES: O=S(=O)(c1ccc(Oc2ccccc2)cc1)N1CCCC(c2cc(NCc3cccnc3)n3ncc(Br)c3n2)C1] | 1. 5748<br>2. 621.34 |
| 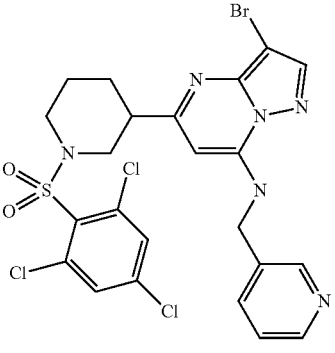 [SMILES: O=S(=O)(c1c(Cl)cc(Cl)cc1Cl)N1CCCC(c2cc(NCc3cccnc3)n3ncc(Br)c3n2)C1] | 1. 5749<br>2. 631.35 |

TABLE 57-continued
| Product | 1. Ex.<br>2. m/z |
|---|---|
| 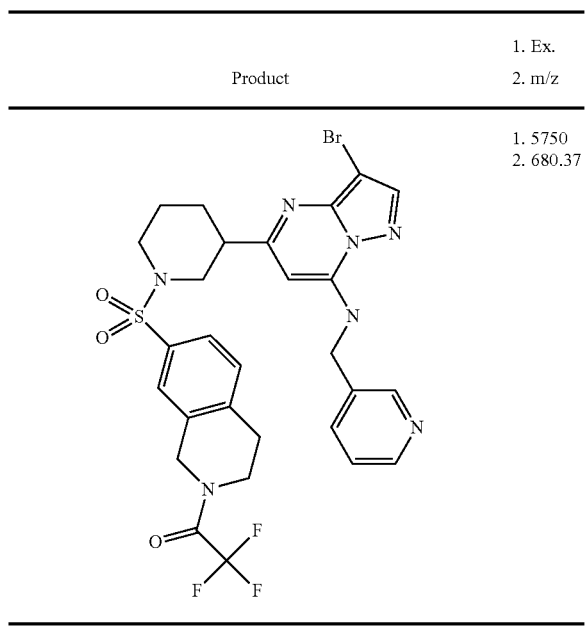 | 1. 5750<br>2. 680.37 |
TABLE 58
| Product | 1. Ex.<br>2. m/z |
|---|---|
| 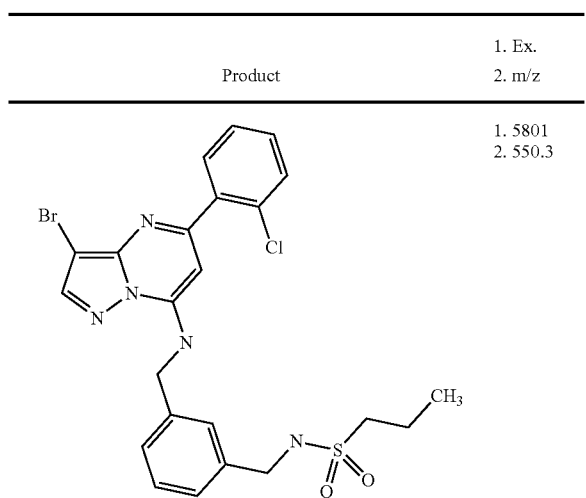 | 1. 5801<br>2. 550.3 |
| 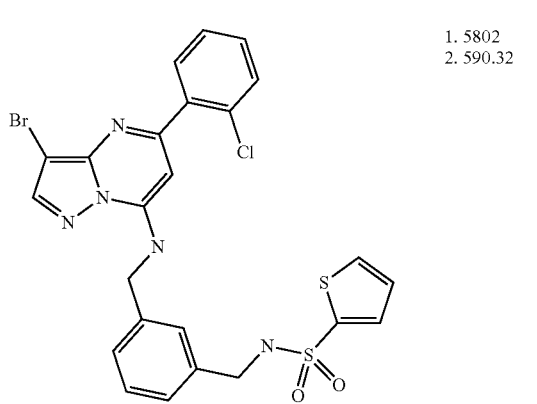 | 1. 5802<br>2. 590.32 |
TABLE 58-continued
| Product | 1. Ex.<br>2. m/z |
|---|---|
| 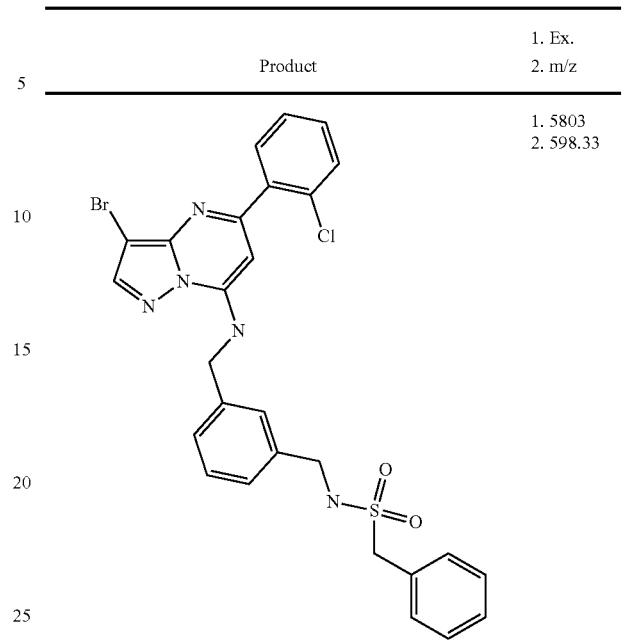 | 1. 5803<br>2. 598.33 |
| 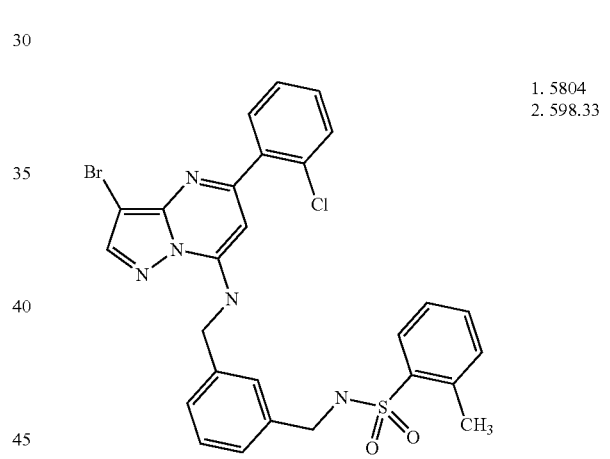 | 1. 5804<br>2. 598.33 |
| 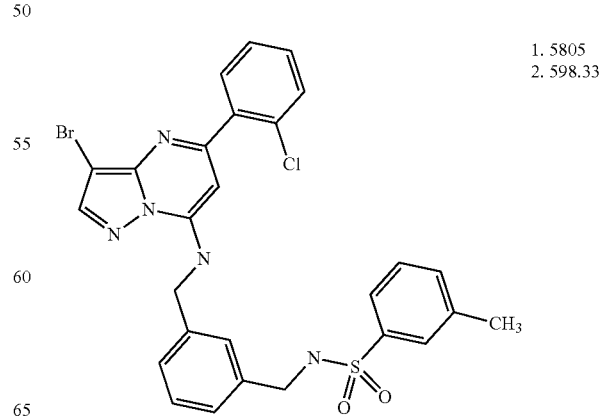 | 1. 5805<br>2. 598.33 |

TABLE 58-continued
| Product | 1. Ex. 2. m/z |
|---|---|
| 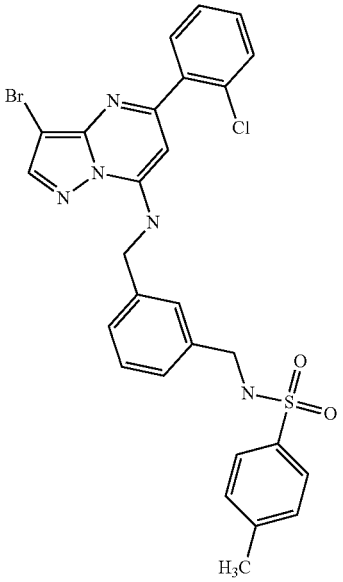 [SMILES: Cc1ccc(S(=O)(=O)NCc2cccc(CNc3cc(-c4ccccc4Cl)nc4c(Br)cnn34)c2)cc1] | 1. 5806 2. 598.33 |
| 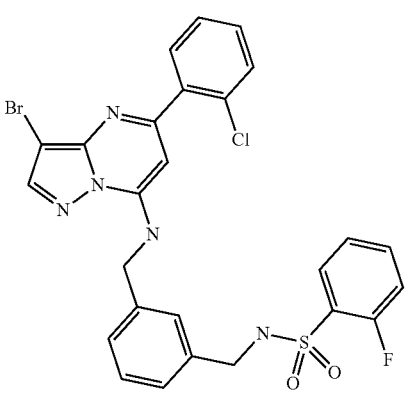 [SMILES: O=S(=O)(NCc1cccc(CNc2cc(-c3ccccc3Cl)nc3c(Br)cnn23)c1)c1ccccc1F] | 1. 5807 2. 602.33 |
| 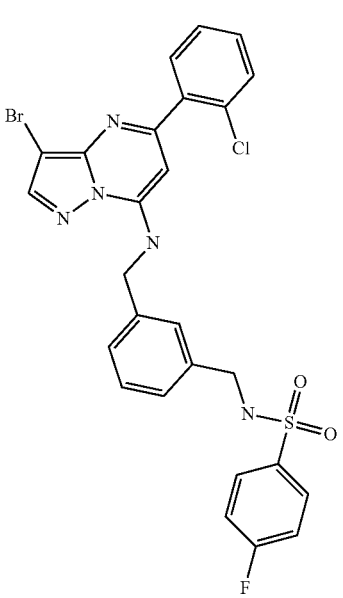 [SMILES: O=S(=O)(NCc1cccc(CNc2cc(-c3ccccc3Cl)nc3c(Br)cnn23)c1)c1ccc(F)cc1] | 1. 5808 2. 602.33 |
TABLE 58-continued
| Product | 1. Ex. 2. m/z |
|---|---|
| 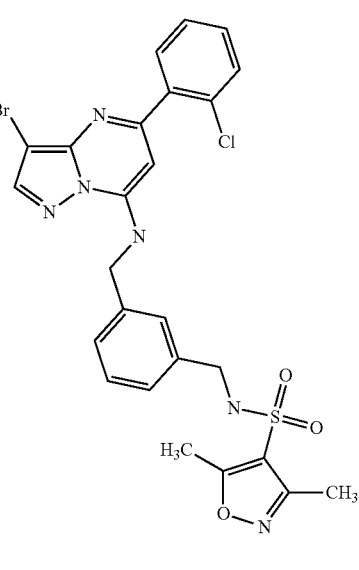 | 1. 5809 2. 603.33 |
| 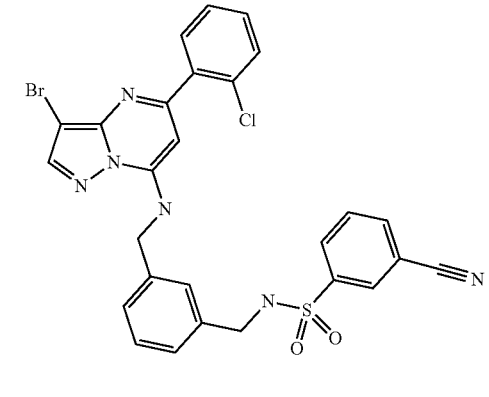 [SMILES: N#Cc1cccc(S(=O)(=O)NCc2cccc(CNc3cc(-c4ccccc4Cl)nc4c(Br)cnn34)c2)c1] | 1. 5810 2. 609.33 |
| 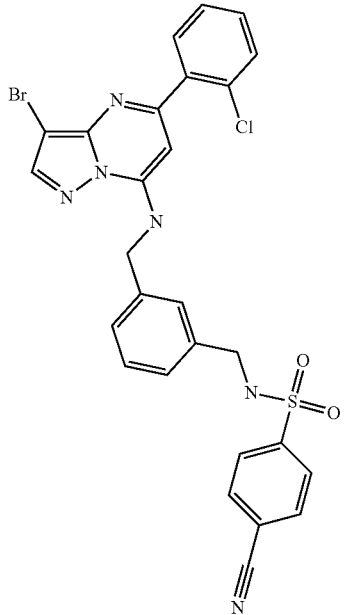 [SMILES: N#Cc1ccc(S(=O)(=O)NCc2cccc(CNc3cc(-c4ccccc4Cl)nc4c(Br)cnn34)c2)cc1] | 1. 5811 2. 609.33 |

TABLE 58-continued
| Product | 1. Ex. 2. m/z |
|---|---|
| 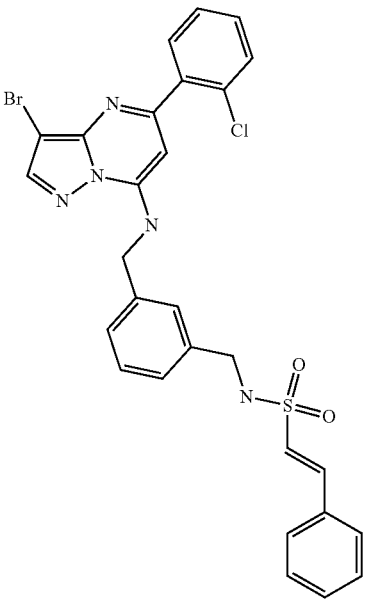 [SMILES: O=S(=O)(/C=C/c1ccccc1)NCc1cccc(CNc2cc(-c3ccccc3Cl)nc3c(Br)cnn23)c1] | 1. 5812 2. 610.34 |
| 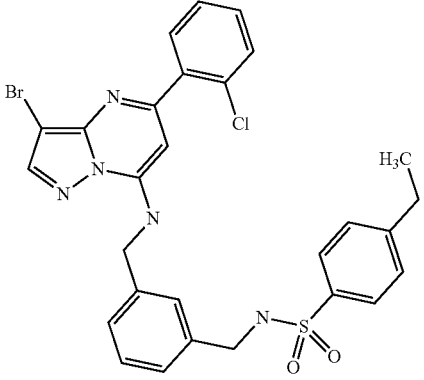 [SMILES: CCc1ccc(S(=O)(=O)NCc2cccc(CNc3cc(-c4ccccc4Cl)nc4c(Br)cnn34)c2)cc1] | 1. 5813 2. 612.34 |
| 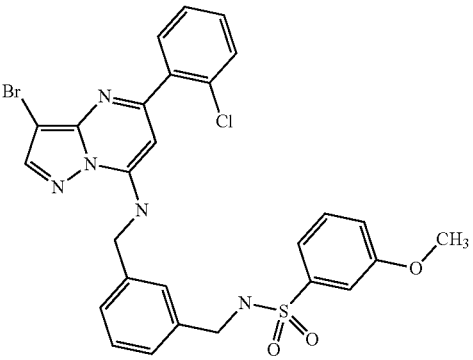 [SMILES: COc1cccc(S(=O)(=O)NCc2cccc(CNc3cc(-c4ccccc4Cl)nc4c(Br)cnn34)c2)c1] | 1. 5814 2. 614.34 |
TABLE 58-continued
| Product | 1. Ex. 2. m/z |
|---|---|
| 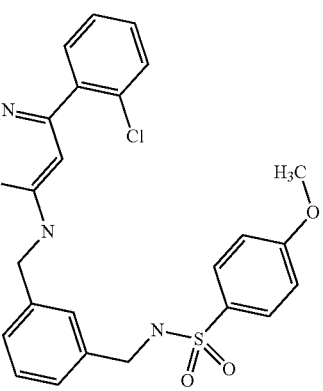 | 1. 5815 2. 614.34 |
| 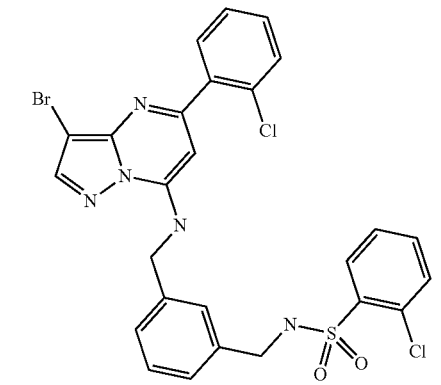 [SMILES: O=S(=O)(NCc1cccc(CNc2cc(-c3ccccc3Cl)nc3c(Br)cnn23)c1)c1ccccc1Cl] | 1. 5816 2. 618.34 |
| 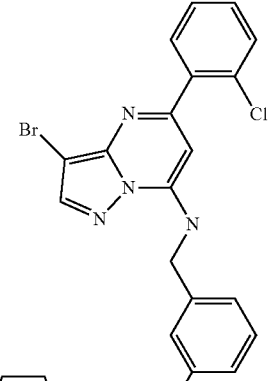 | 1. 5817 2. 624.34 |

TABLE 58-continued
| Product | 1. Ex. 2. m/z |
|---|---|
| 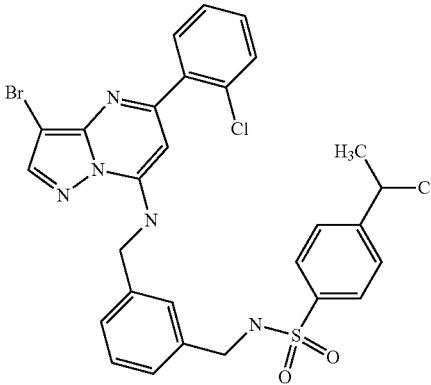 | 1. 5818<br>2. 626.34 |
| 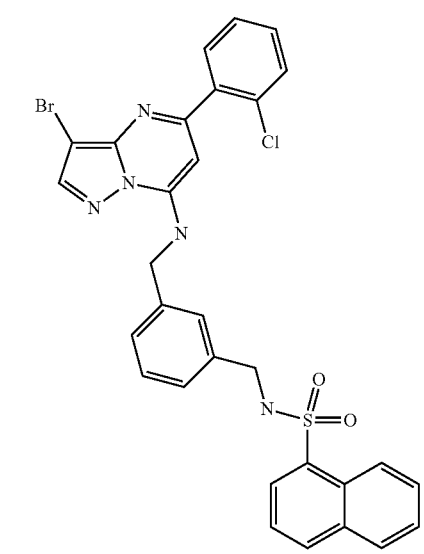 [SMILES: O=S(=O)(NCc1cccc(CNc2cc(-c3ccccc3Cl)nc3c(Br)cnn23)c1)c1cccc2ccccc12] | 1. 5819<br>2. 634.35 |
| 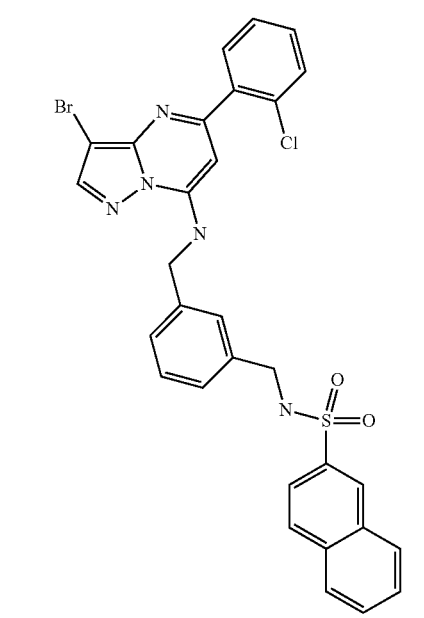 [SMILES: O=S(=O)(NCc1cccc(CNc2cc(-c3ccccc3Cl)nc3c(Br)cnn23)c1)c1ccc2ccccc2c1] | 1. 5820<br>2. 632.35 |
| 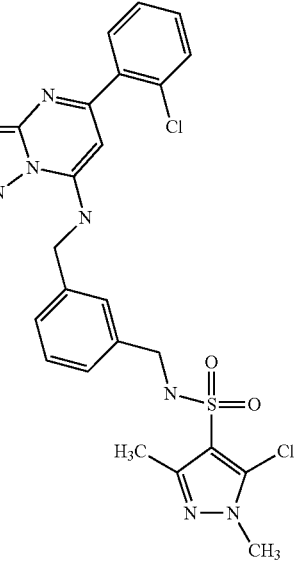 | 1. 5821<br>2. 636.35 |
| 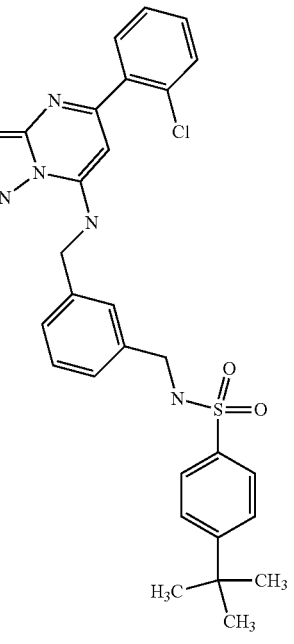 | 1. 5822<br>2. 640.35 |

TABLE 58-continued
| Product | 1. Ex. 2. m/z |
|---|---|
| 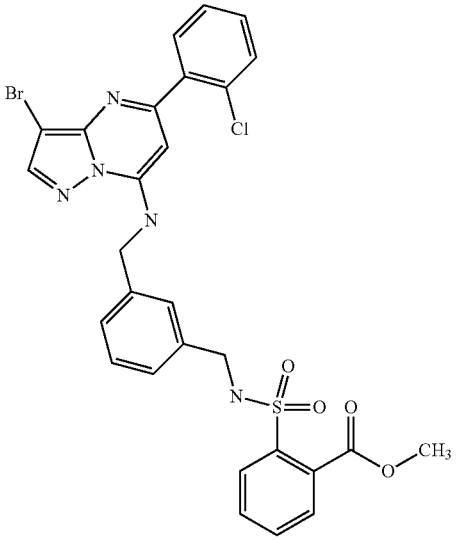 [SMILES: COC(=O)c1ccccc1S(=O)(=O)NCc1cccc(CNc2cc(-c3ccccc3Cl)nc3c(Br)cnn23)c1] | 1. 5823 2. 642.35 |
| | 1. 5824 2. 644.35 |
| | 1. 5825 2. 644.35 |
TABLE 58-continued
| Product | 1. Ex. 2. m/z |
|---|---|
| 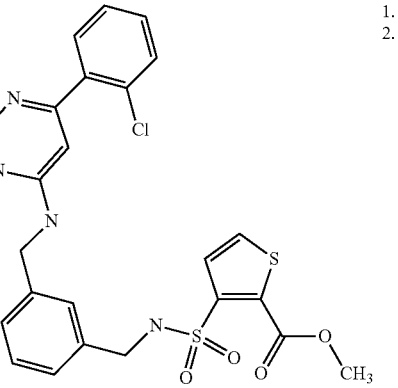 | 1. 5826 2. 648.36 |
| | 1. 5827 2. 654.36 |

TABLE 58-continued

| Product | 1. Ex.<br>2. m/z |
|---|---|
| (structure) | 1. 5828<br>2. 660.36 |
| (structure) | 1. 5829<br>2. 670.37 |
| (structure) | 1. 5830<br>2. 676.37 |
| (structure) | 1. 5831<br>2. 735.4 |
| (structure) | 1. 5832<br>2. 522.29 |

TABLE 58-continued

| Product | 1. Ex. 2. m/z |
|---|---|
| (structure) | 1. 5833 2. 584.32 |

TABLE 59

| Product | 1. Ex 2. m/z |
|---|---|
| (structure) | 1. 5901 2. 536.29 |
| (structure) | 1. 5902 2. 550.3 |

TABLE 59-continued

| Product | 1. Ex 2. m/z |
|---|---|
| (structure) | 1. 5903 2. 590.32 |
| (structure) | 1. 5904 2. 598.33 |

TABLE 59-continued

| Product | 1. Ex 2. m/z |
|---|---|
| (structure) | 1. 5905 2. 598.33 |
| (structure) | 1. 5906 2. 598.33 |

TABLE 59-continued

| Product | 1. Ex 2. m/z |
|---|---|
| (structure) | 1. 5907 2. 598.33 |
| (structure) | 1. 5908 2. 602.33 |

TABLE 59-continued
| Product | 1. Ex<br>2. m/z |
|---|---|
| 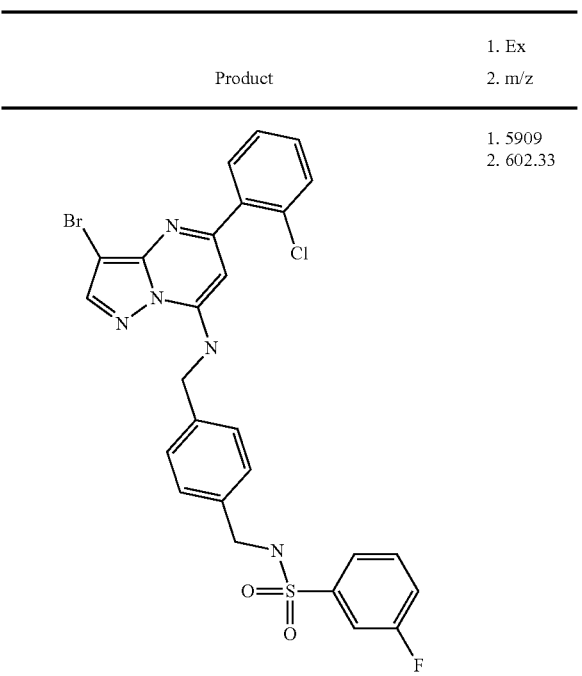 | 1. 5909<br>2. 602.33 |
| | 1. 5910<br>2. 602.33 |
TABLE 59-continued
| Product | 1. Ex<br>2. m/z |
|---|---|
| 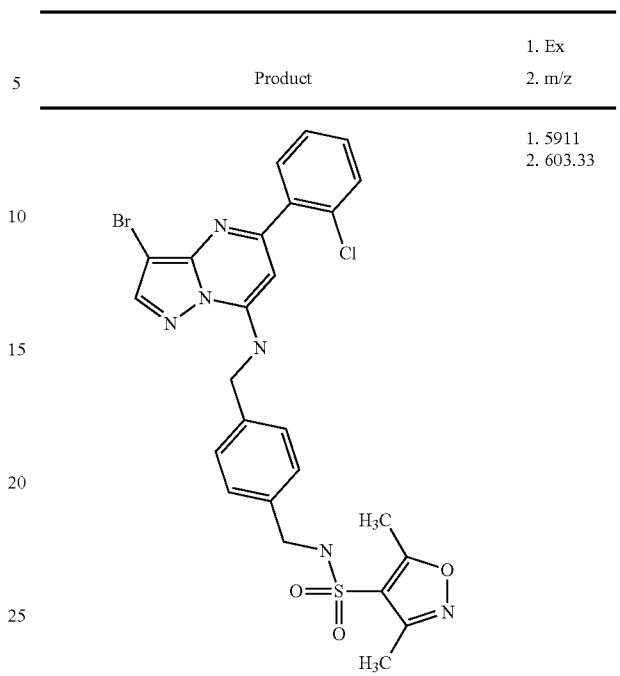 | 1. 5911<br>2. 603.33 |
| | 1. 5912<br>2. 609.33 |

TABLE 59-continued
| Product | 1. Ex 2. m/z |
|---|---|
| 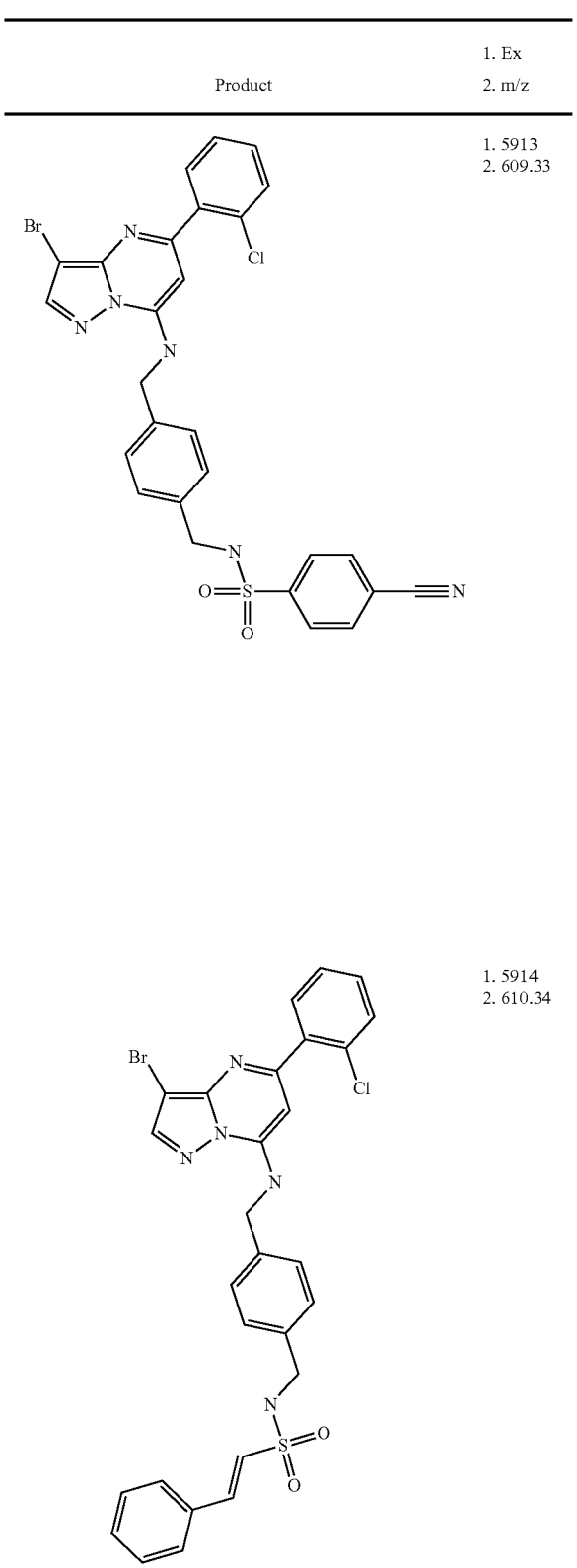 | 1. 5913 2. 609.33 |
| | 1. 5914 2. 610.34 |
TABLE 59-continued
| Product | 1. Ex 2. m/z |
|---|---|
| 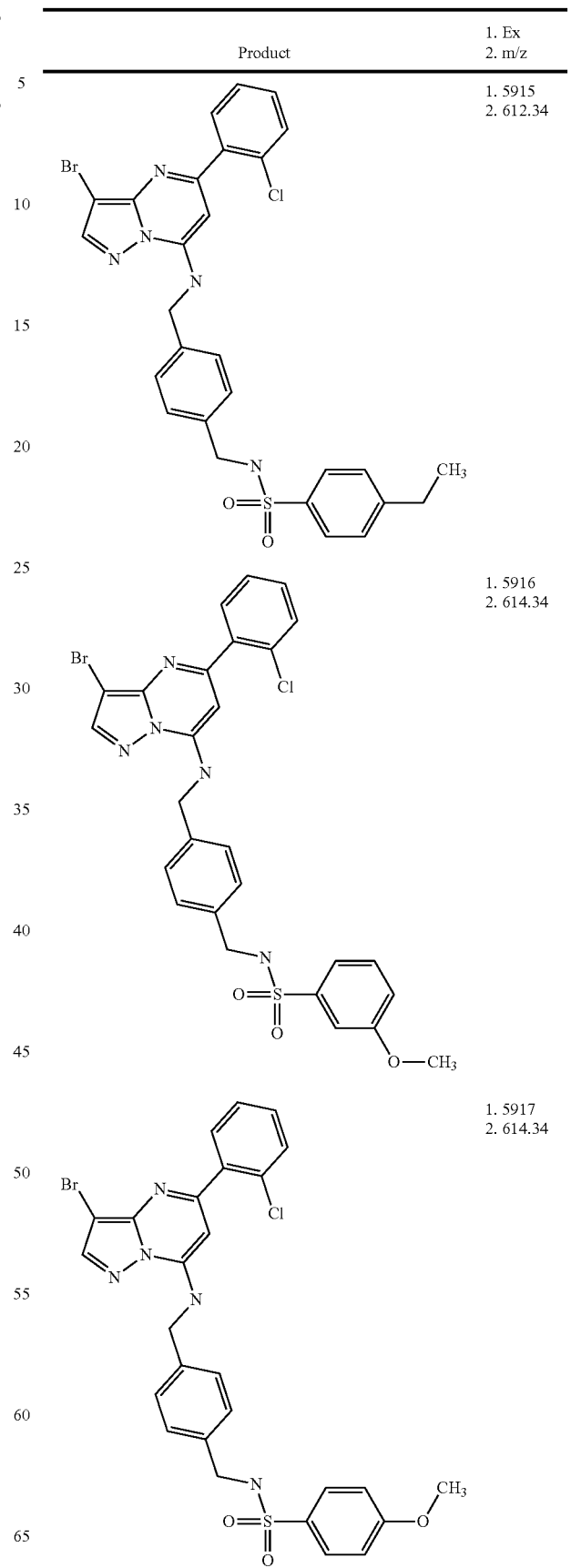 | 1. 5915 2. 612.34 |
| | 1. 5916 2. 614.34 |
| | 1. 5917 2. 614.34 |

TABLE 59-continued
| Product | 1. Ex<br>2. m/z |
|---|---|
| 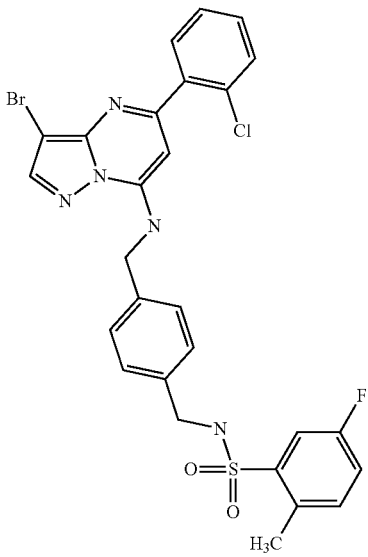 [SMILES: Cc1ccc(F)cc1S(=O)(=O)NCc1ccc(CNc2cc(-c3ccccc3Cl)nc3c(Br)cnn23)cc1] | 1. 5918<br>2. 616.34 |
| 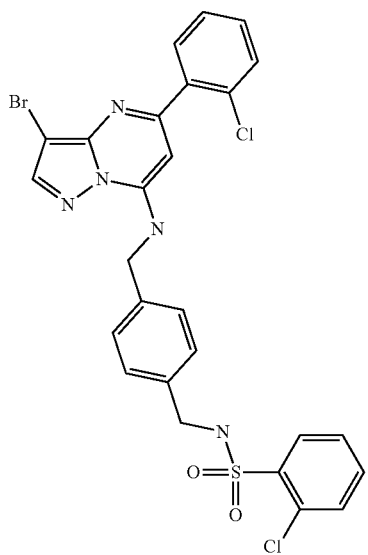 [SMILES: O=S(=O)(NCc1ccc(CNc2cc(-c3ccccc3Cl)nc3c(Br)cnn23)cc1)c1ccccc1Cl] | 1. 5919<br>2. 618.34 |
TABLE 59-continued
| Product | 1. Ex<br>2. m/z |
|---|---|
| 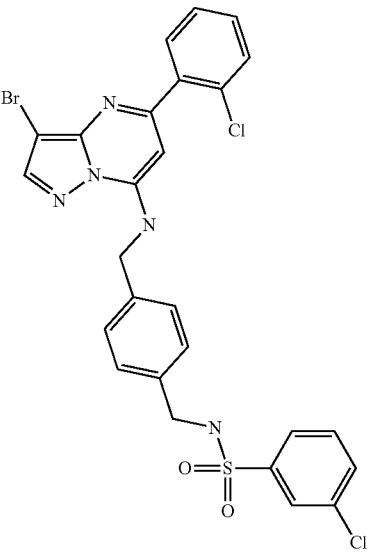 [SMILES: O=S(=O)(NCc1ccc(CNc2cc(-c3ccccc3Cl)nc3c(Br)cnn23)cc1)c1cccc(Cl)c1] | 1. 5920<br>2. 618.34 |
| | 1. 5921<br>2. 618.34 |

TABLE 59-continued

| Product | 1. Ex<br>2. m/z |
|---|---|
| (structure) | 1. 5922<br>2. 620.34 |
| (structure) | 1. 5923<br>2. 620.34 |
| (structure) | 1. 5924<br>2. 620.34 |
| (structure) | 1. 5925<br>2. 620.34 |

TABLE 59-continued

| Product | 1. Ex 2. m/z |
|---|---|
| (structure) | 1. 5926 2. 620.34 |
| (structure) | 1. 5927 2. 624.34 |
| (structure) | 1. 5928 2. 626.34 |
| (structure) | 1. 5929 2. 626.34 |
| (structure) | 1. 5930 2. 632.35 |

TABLE 60

| Product | 1. Ex.<br>2. m/z |
|---|---|
| (structure) | 1. 6001<br>2. 536.29 |
| (structure) | 1. 6002<br>2. 576.32 |
| (structure) | 1. 6003<br>2. 584.32 |

TABLE 60-continued

| Product | 1. Ex.<br>2. m/z |
|---|---|
| (structure) | 1. 6004<br>2. 584.32 |
| (structure) | 1. 6005<br>2. 584.32 |

TABLE 60-continued
| Product | 1. Ex. 2. m/z |
|---|---|
| 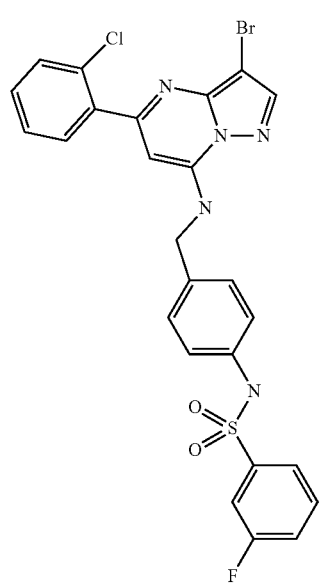 [SMILES: O=S(=O)(Nc1ccc(CNc2cc(-c3ccccc3Cl)nc3c(Br)cnn23)cc1)c1cccc(F)c1] | 1. 6006 2. 588.32 |
|  | 1. 6007 2. 588.32 |
TABLE 60-continued
| Product | 1. Ex. 2. m/z |
|---|---|
|  | 1. 6008 2. 588.32 |
|  | 1. 6009 2. 589.32 |
|  | 1. 6010 2. 595.33 |

TABLE 60-continued

| Product | 1. Ex. 2. m/z |
|---|---|
| (structure: 5-(2-chlorophenyl)-3-bromo-pyrazolo[1,5-a]pyrimidin-7-yl-NH-CH2-C6H4-N(H)-SO2-(3-cyanophenyl)) | 1. 6011<br>2. 595.33 |
| (structure: 5-(2-chlorophenyl)-3-bromo-pyrazolo[1,5-a]pyrimidin-7-yl-NH-CH2-C6H4-N(H)-SO2-(4-cyanophenyl)) | 1. 6012<br>2. 595.33 |
| (structure: 5-(2-chlorophenyl)-3-bromo-pyrazolo[1,5-a]pyrimidin-7-yl-NH-CH2-C6H4-N(H)-SO2-CH=CH-phenyl) | 1. 6013<br>2. 596.33 |
| (structure: 5-(2-chlorophenyl)-3-bromo-pyrazolo[1,5-a]pyrimidin-7-yl-NH-CH2-C6H4-N(H)-SO2-(4-ethylphenyl)) | 1. 6014<br>2. 598.33 |

TABLE 60-continued

| Product | 1. Ex.<br>2. m/z |
|---|---|
| (structure) | 1. 6015<br>2. 600.33 |
| (structure) | 1. 6016<br>2. 600.33 |

TABLE 60-continued

| Product | 1. Ex.<br>2. m/z |
|---|---|
| (structure) | 1. 6017<br>2. 602.33 |
| (structure) | 1. 6018<br>2. 604.33 |

TABLE 60-continued

| Product | 1. Ex.<br>2. m/z |
|---|---|
| (structure) | 1. 6019<br>2. 604.33 |
| (structure) | 1. 6020<br>2. 604.33 |

TABLE 60-continued

| Product | 1. Ex.<br>2. m/z |
|---|---|
| (structure) | 1. 6021<br>2. 606.33 |
| (structure) | 1. 6022<br>2. 606.33 |

TABLE 60-continued

| Product | 1. Ex.<br>2. m/z |
|---------|------------------|
| (structure) | 1. 6023<br>2. 606.33 |
| (structure) | 1. 6024<br>2. 606.33 |

TABLE 60-continued

| Product | 1. Ex.<br>2. m/z |
|---------|------------------|
| (structure) | 1. 6025<br>2. 606.33 |
| (structure) | 1. 6026<br>2. 612.34 |

TABLE 60-continued
| Product | 1. Ex.<br>2. m/z |
|---|---|
| 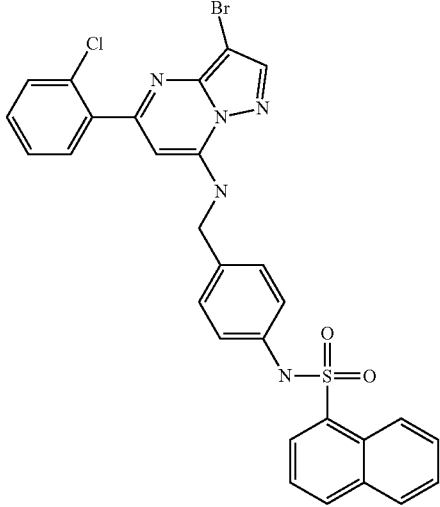 [SMILES: O=S(=O)(Nc1ccc(CNc2cc(-c3ccccc3Cl)nc3c(Br)cnn23)cc1)c1cccc2ccccc12] | 1. 6027<br>2. 620.34 |
| 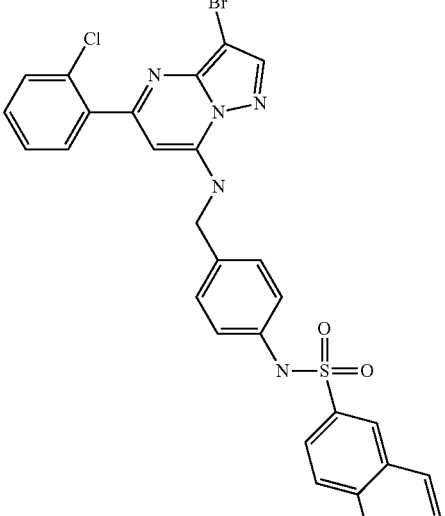 | 1. 6028<br>2. 620.34 |
TABLE 60-continued
| Product | 1. Ex.<br>2. m/z |
|---|---|
| 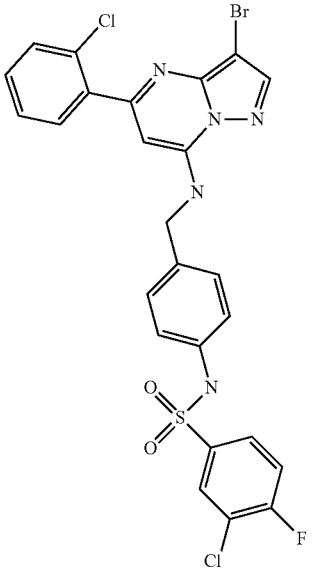 [SMILES: O=S(=O)(Nc1ccc(CNc2cc(-c3ccccc3Cl)nc3c(Br)cnn23)cc1)c1ccc(F)c(Cl)c1] | 1. 6029<br>2. 622.34 |
| 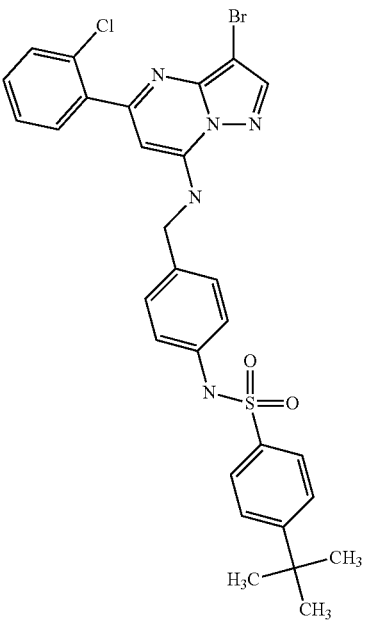 [SMILES: CC(C)(C)c1ccc(S(=O)(=O)Nc2ccc(CNc3cc(-c4ccccc4Cl)nc4c(Br)cnn34)cc2)cc1] | 1. 6030<br>2. 626.34 |

TABLE 60-continued

| Product | 1. Ex.<br>2. m/z |
|---|---|
| (structure) | 1. 6031<br>2. 628.35 |
| (structure) | 1. 6032<br>2. 630.35 |
| (structure) | 1. 6033<br>2. 630.35 |
| (structure) | 1. 6034<br>2. 634.35 |

TABLE 60-continued
| Product | 1. Ex. 2. m/z |
|---|---|
| 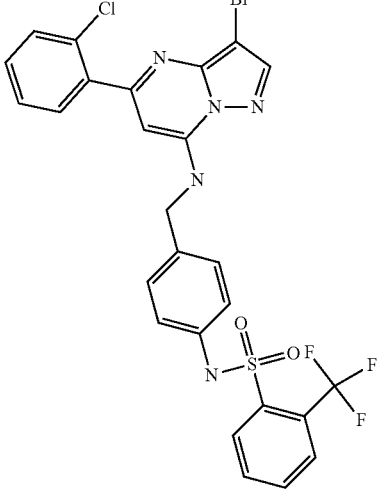 | 1. 6035 2. 638.35 |
| 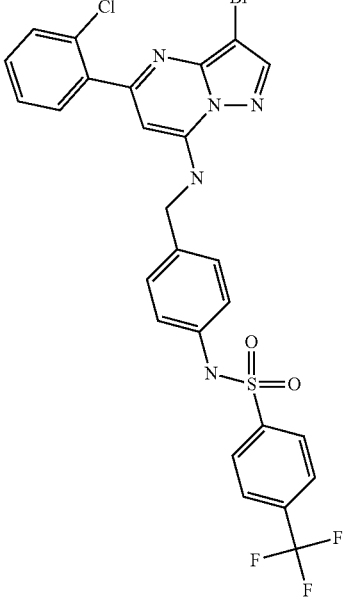 | 1. 6036 2. 638.35 |
| 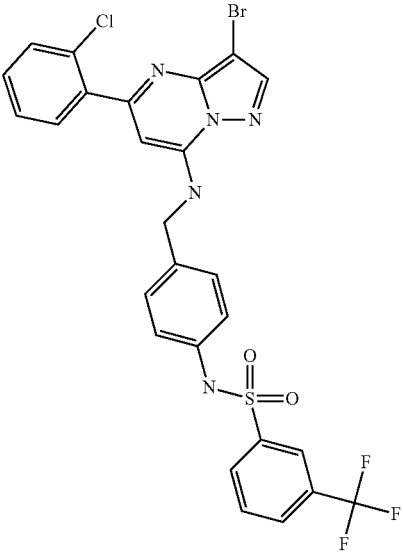 [SMILES: O=S(=O)(Nc1ccc(CNc2cc(-c3ccccc3Cl)nc3c(Br)cnn23)cc1)c1cccc(C(F)(F)F)c1] | 1. 6037 2. 638.35 |
| 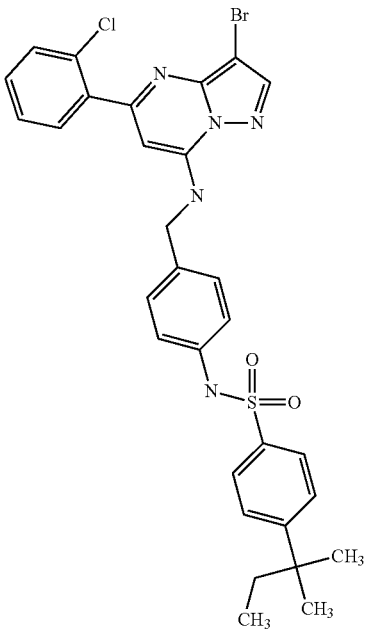 [SMILES: CCC(C)(C)c1ccc(S(=O)(=O)Nc2ccc(CNc3cc(-c4ccccc4Cl)nc4c(Br)cnn34)cc2)cc1] | 1. 6038 2. 638.35 |

TABLE 60-continued
| Product | 1. Ex.<br>2. m/z |
|---|---|
| 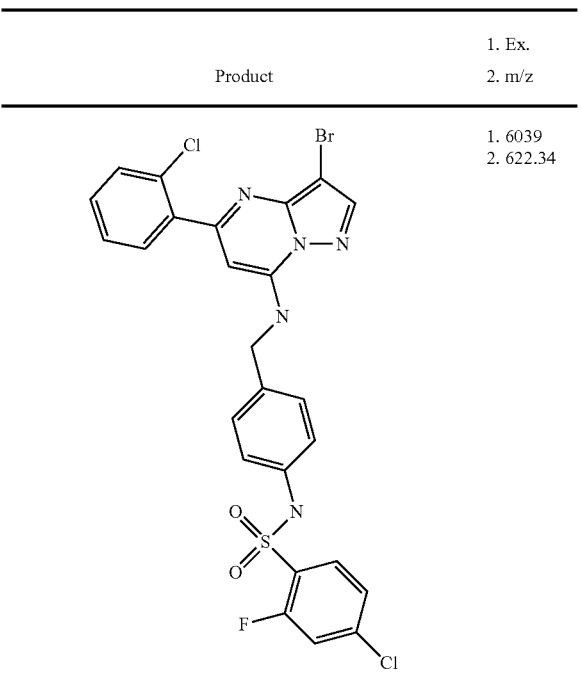 | 1. 6039<br>2. 622.34 |
| | 1. 6040<br>2. 646.36 |
TABLE 60-continued
| Product | 1. Ex.<br>2. m/z |
|---|---|
| 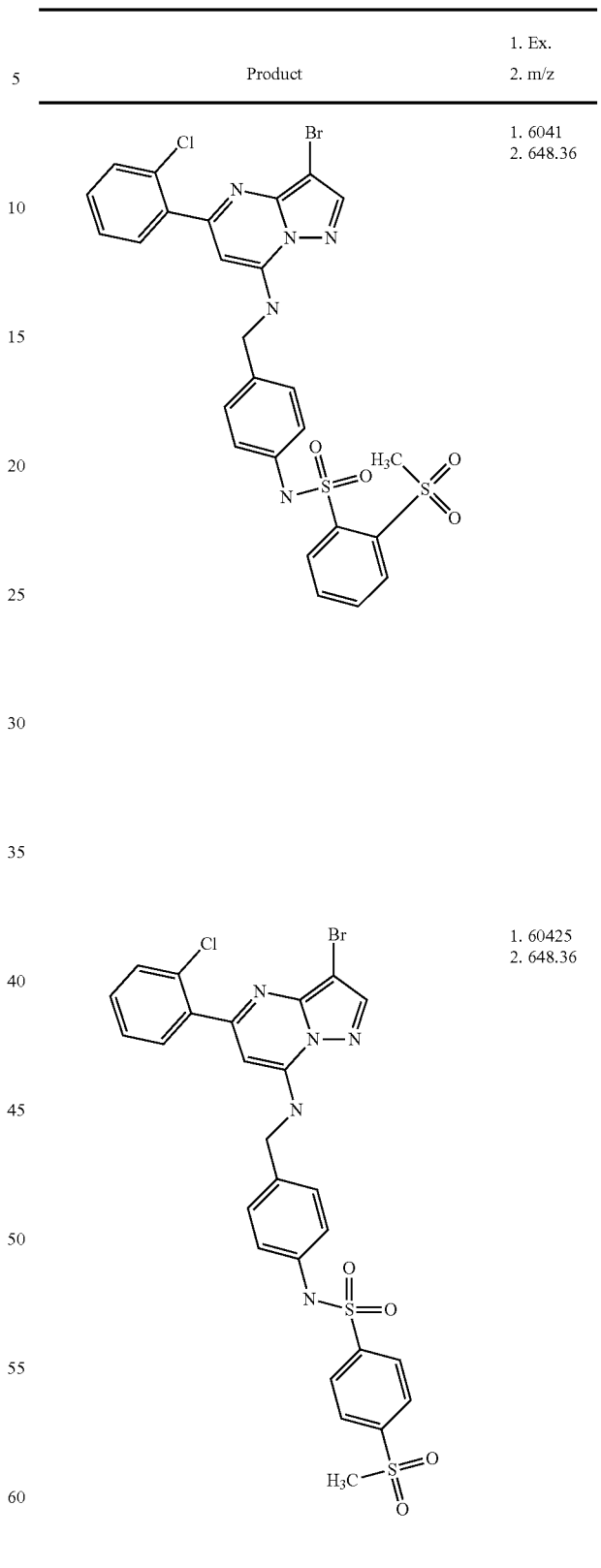 | 1. 6041<br>2. 648.36 |
| | 1. 60425<br>2. 648.36 |

TABLE 60-continued

| Product | 1. Ex. 2. m/z |
|---|---|
| (structure) | 1. 6043 2. 648.36 |
| (structure) | 1. 6044 2. 648.36 |
| (structure) | 1. 6045 2. 654.36 |
| (structure) | 1. 6046 2. 654.36 |

TABLE 60-continued
| Product | 1. Ex. 2. m/z |
|---|---|
| 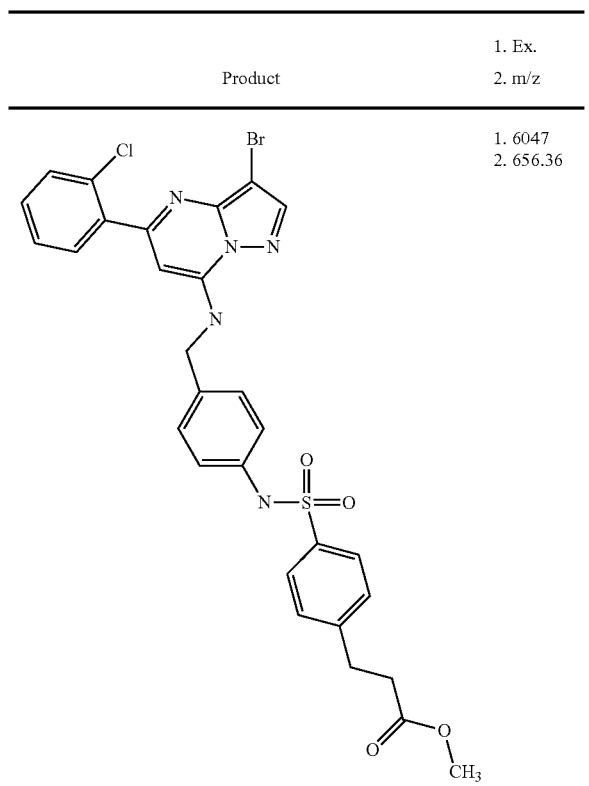 | 1. 6047<br>2. 656.36 |
| 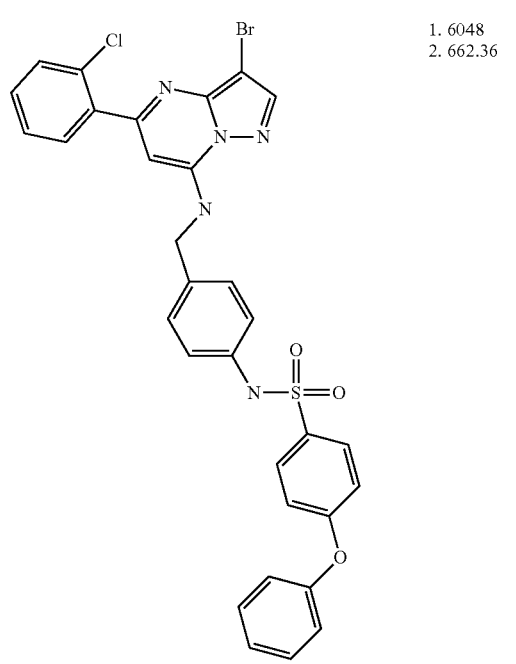 | 1. 6048<br>2. 662.36 |
TABLE 60-continued
| Product | 1. Ex. 2. m/z |
|---|---|
| 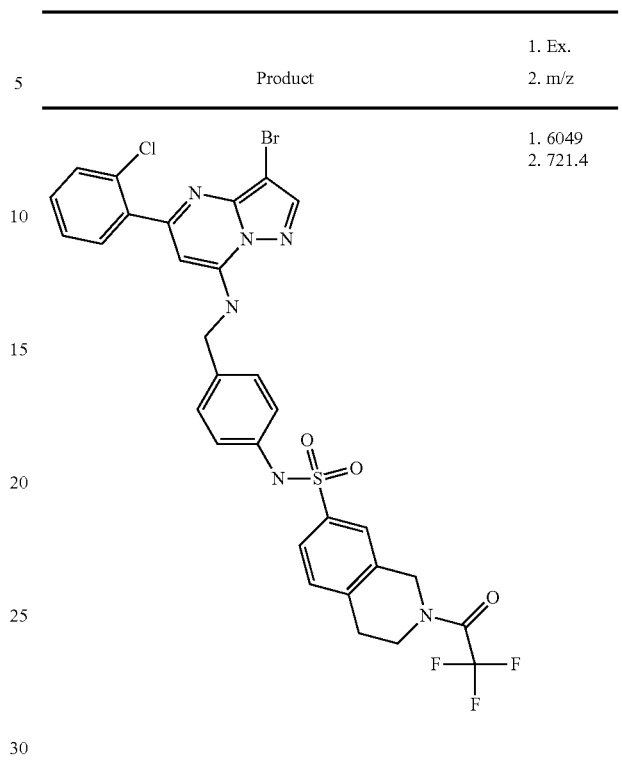 | 1. 6049<br>2. 721.4 |
| 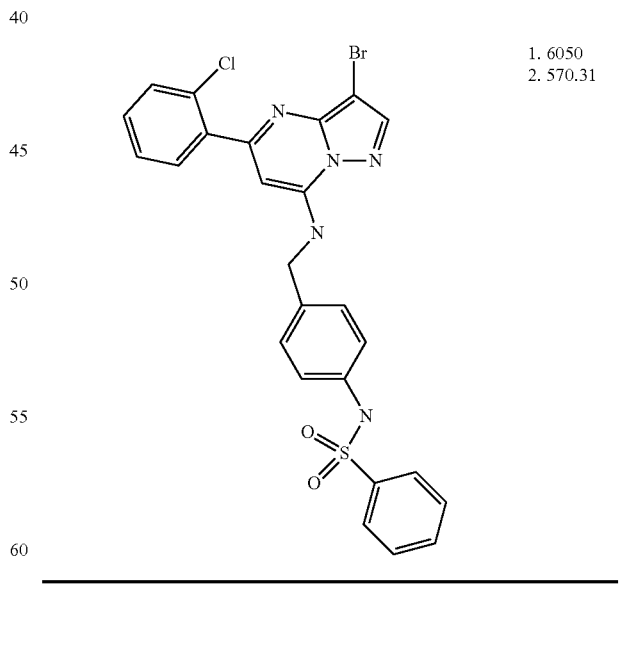 | 1. 6050<br>2. 570.31 |

TABLE 61

| Product | 1. Ex. 2. m/z |
|---|---|
| (structure) | 1. 6101  2. 584.32 |
| (structure) | 1. 6102  2. 584.32 |
| (structure) | 1. 6103  2. 584.32 |

TABLE 61-continued

| Product | 1. Ex. 2. m/z |
|---|---|
| (structure) | 1. 6104  2. 588.32 |
| (structure) | 1. 6105  2. 588.32 |
| (structure) | 1. 6106  2. 588.32 |

TABLE 61-continued
| Product | 1. Ex. 2. m/z |
|---|---|
| 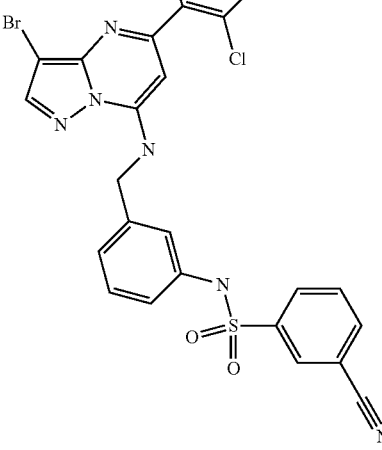 | 1. 6107 2. 595.33 |
| 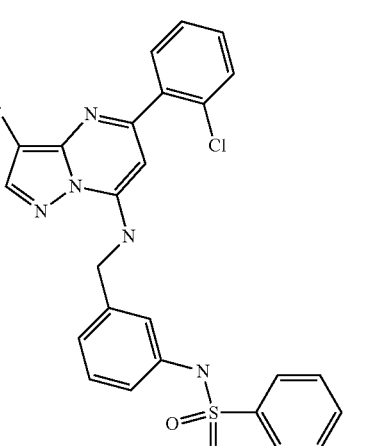 | 1. 6108 2. 600.33 |
| 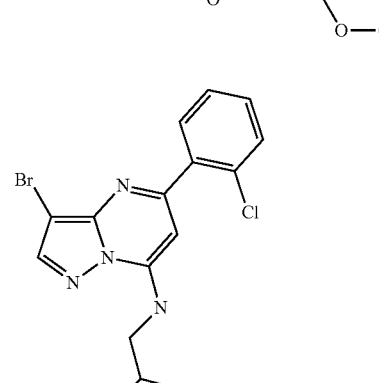 | 1. 6109 2. 602.33 |
TABLE 61-continued
| Product | 1. Ex. 2. m/z |
|---|---|
| 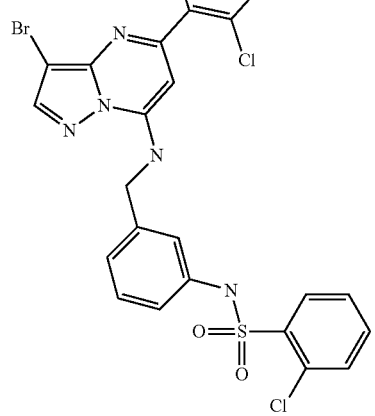 | 1. 6110 2. 604.33 |
| 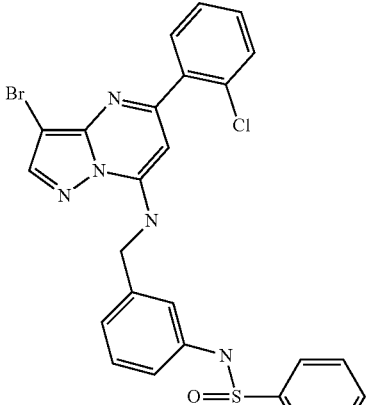 | 1. 6111 2. 604.33 |
| 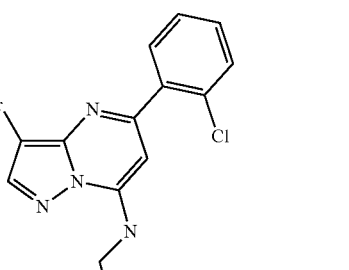 | 1. 6112 2. 604.33 |

TABLE 61-continued
| Product | 1. Ex.<br>2. m/z |
|---|---|
| 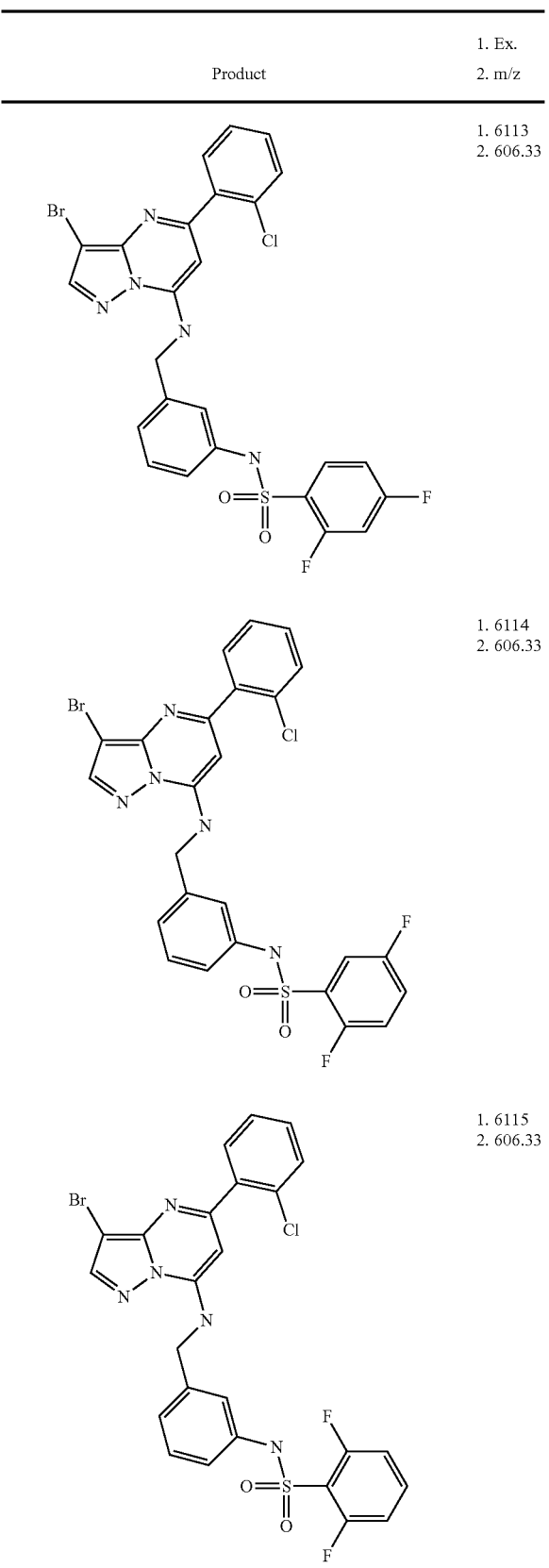 | 1. 6113<br>2. 606.33 |
| | 1. 6114<br>2. 606.33 |
| | 1. 6115<br>2. 606.33 |
TABLE 61-continued
| Product | 1. Ex.<br>2. m/z |
|---|---|
| 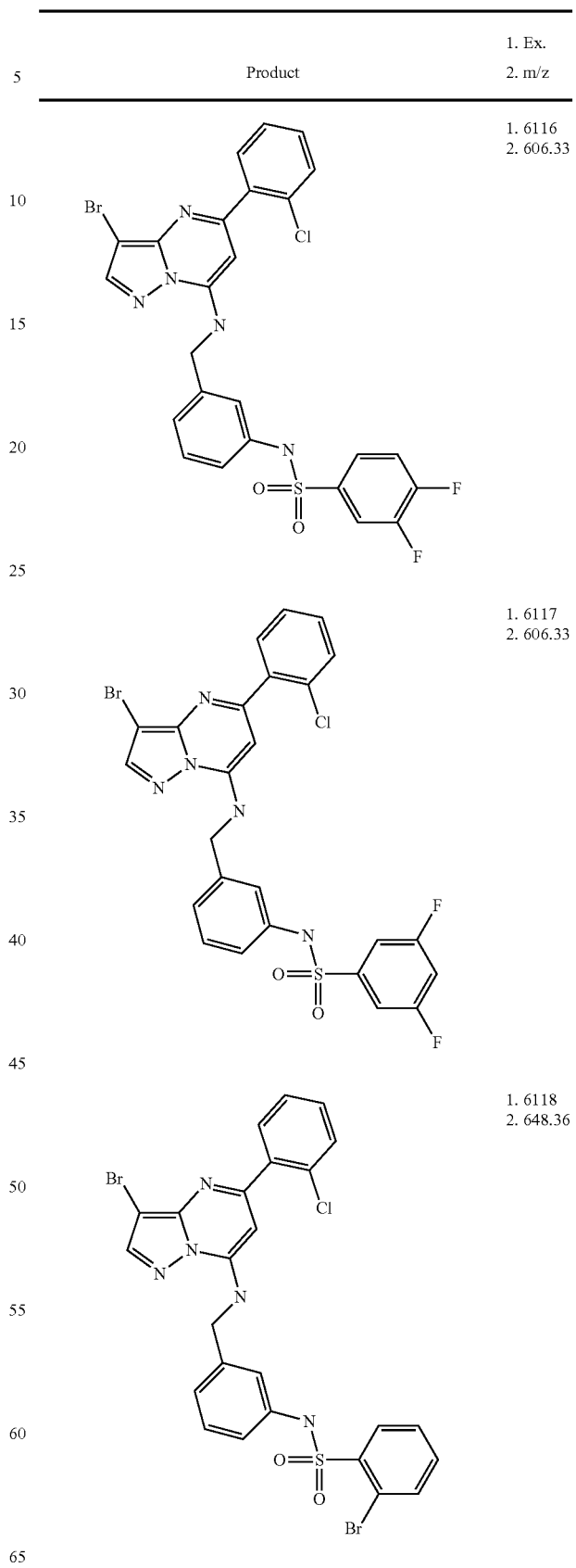 | 1. 6116<br>2. 606.33 |
| | 1. 6117<br>2. 606.33 |
| | 1. 6118<br>2. 648.36 |

TABLE 61-continued
| Product | 1. Ex.<br>2. m/z |
|---|---|
| 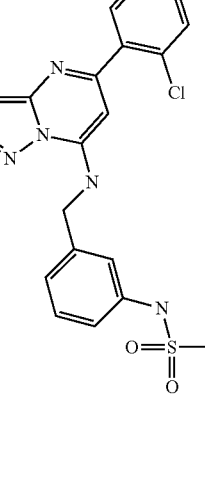 | 1. 6119<br>2. 721.4 |
| 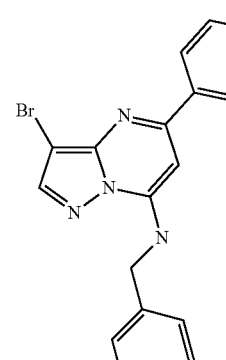 | 1. 6120<br>2. 570.31 |
TABLE 62
| Product | 1. Ex.<br>2. m/z |
|---|---|
| 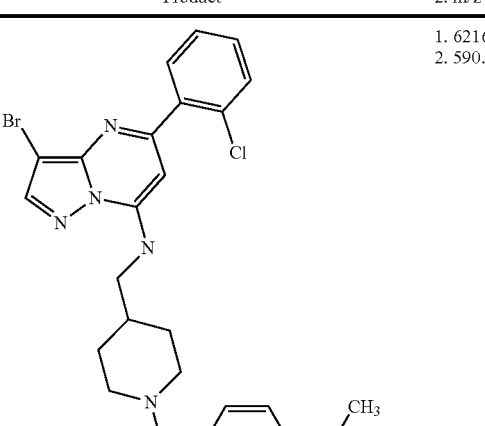 | 1. 6216<br>2. 590.32 |
TABLE 62-continued
| Product | 1. Ex.<br>2. m/z |
|---|---|
| 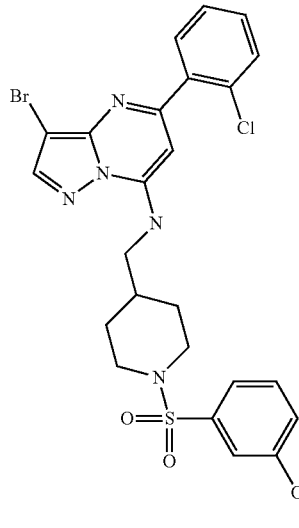 | 1. 6217<br>2. 592.33 |
| 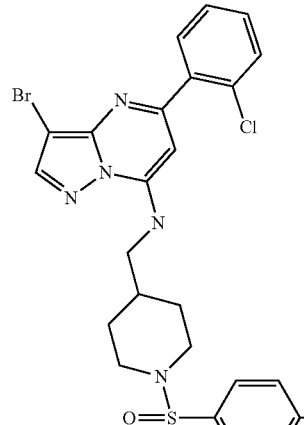 | 1. 6218<br>2. 592.33 |
| | 1. 6219<br>2. 592.33 |

TABLE 62-continued

| Product | 1. Ex.<br>2. m/z |
|---|---|
| (structure) | 1. 6220<br>2. 594.33 |
| (structure) | 1. 6221<br>2. 596.33 |
| (structure) | 1. 6222<br>2. 596.33 |

TABLE 62-continued

| Product | 1. Ex.<br>2. m/z |
|---|---|
| (structure) | 1. 6223<br>2. 598.33 |
| (structure) | 1. 6224<br>2. 596.33 |
| (structure) | 1. 6225<br>2. 598.33 |

TABLE 62-continued
| Product | 1. Ex. 2. m/z |
|---|---|
| 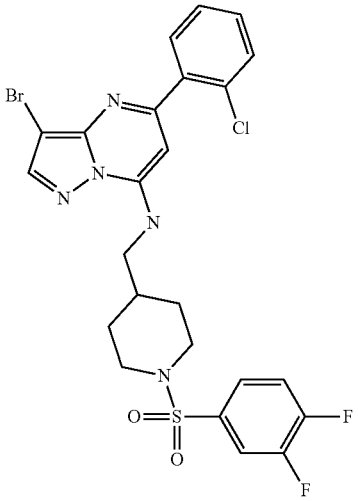 [SMILES: O=S(=O)(c1ccc(F)c(F)c1)N1CCC(CNc2cc(-c3ccccc3Cl)nc3c(Br)cnn23)CC1] | 1. 6226 2. 598.33 |
| 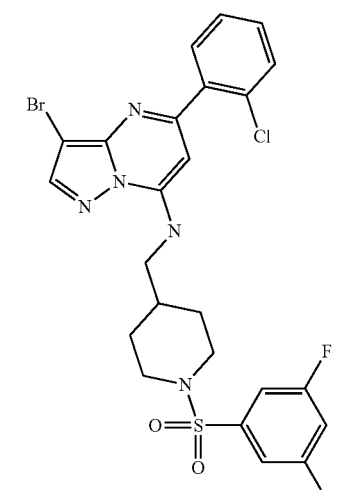 | 1. 6227 2. 596.33 |
| 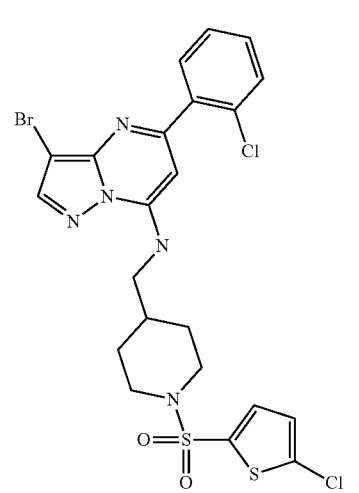 [SMILES: O=S(=O)(c1ccc(Cl)s1)N1CCC(CNc2cc(-c3ccccc3Cl)nc3c(Br)cnn23)CC1] | 1. 6228 2. 602.33 |
TABLE 62-continued
| Product | 1. Ex. 2. m/z |
|---|---|
| 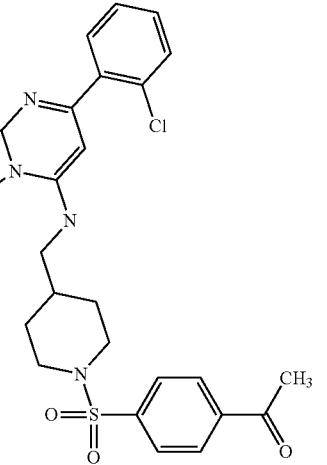 | 1. 6229 2. 604.33 |
| 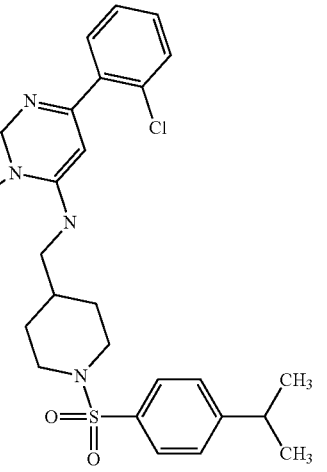 | 1. 6230 2. 604.33 |
| 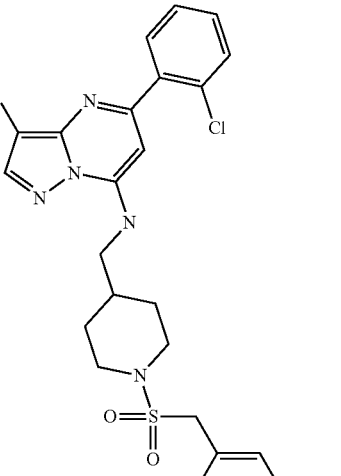 | 1. 6231 2. 610.34 |

TABLE 62-continued
| Product | 1. Ex.<br>2. m/z |
|---|---|
| 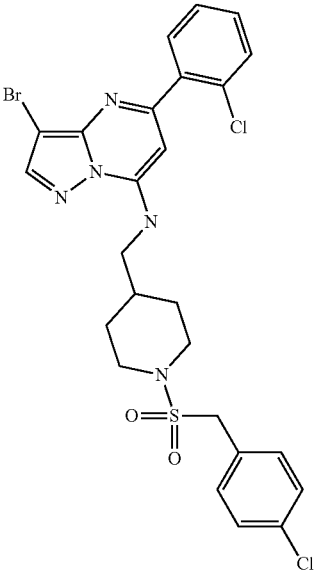 [SMILES: O=S(=O)(Cc1ccc(Cl)cc1)N1CCC(CNc2cc(-c3ccccc3Cl)nc3c(Br)cnn23)CC1] | 1. 6232<br>2. 610.34 |
| 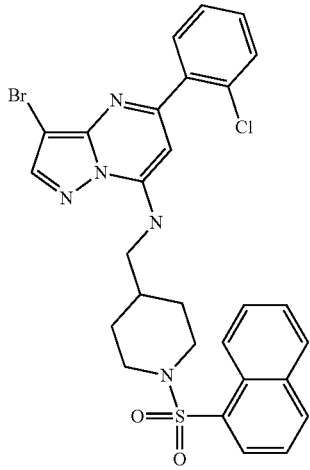 [SMILES: O=S(=O)(c1cccc2ccccc12)N1CCC(CNc2cc(-c3ccccc3Cl)nc3c(Br)cnn23)CC1] | 1. 6233<br>2. 612.34 |
| 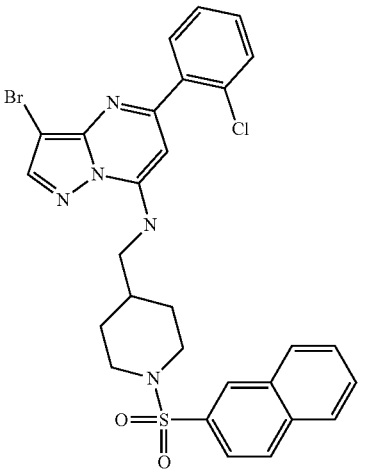 [SMILES: O=S(=O)(c1ccc2ccccc2c1)N1CCC(CNc2cc(-c3ccccc3Cl)nc3c(Br)cnn23)CC1] | 1. 6234<br>2. 612.34 |
TABLE 62-continued
| Product | 1. Ex.<br>2. m/z |
|---|---|
| 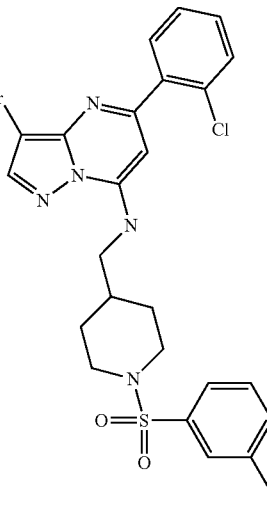 | 1. 6235<br>2. 614.34 |
| 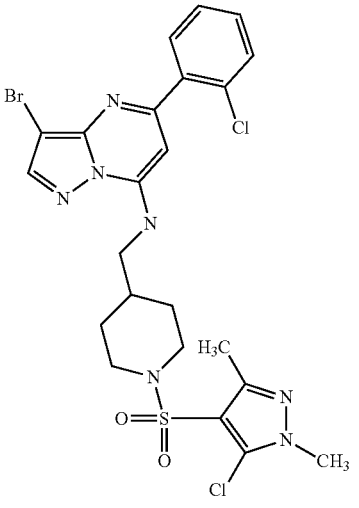 [SMILES: Cc1nn(C)c(Cl)c1S(=O)(=O)N1CCC(CNc2cc(-c3ccccc3Cl)nc3c(Br)cnn23)CC1] | 1. 6236<br>2. 614.34 |
| 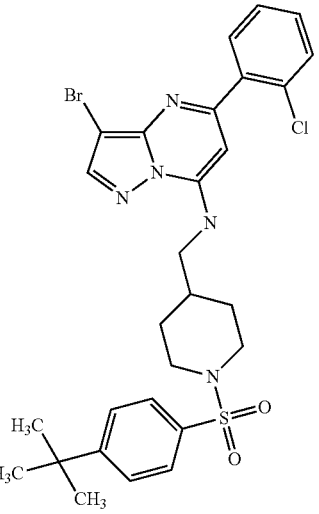 | 1. 6237<br>2. 618.34 |

TABLE 62-continued

| Product | 1. Ex.<br>2. m/z |
|---|---|
| (structure) | 1. 6238<br>2. 622.34 |
| (structure) | 1. 6239<br>2. 622.34 |

TABLE 62-continued

| Product | 1. Ex.<br>2. m/z |
|---|---|
| (structure) | 1. 6240<br>2. 626.34 |
| (structure) | 1. 6241<br>2. 630.35 |

TABLE 62-continued
| Product | 1. Ex.<br>2. m/z |
|---|---|
| 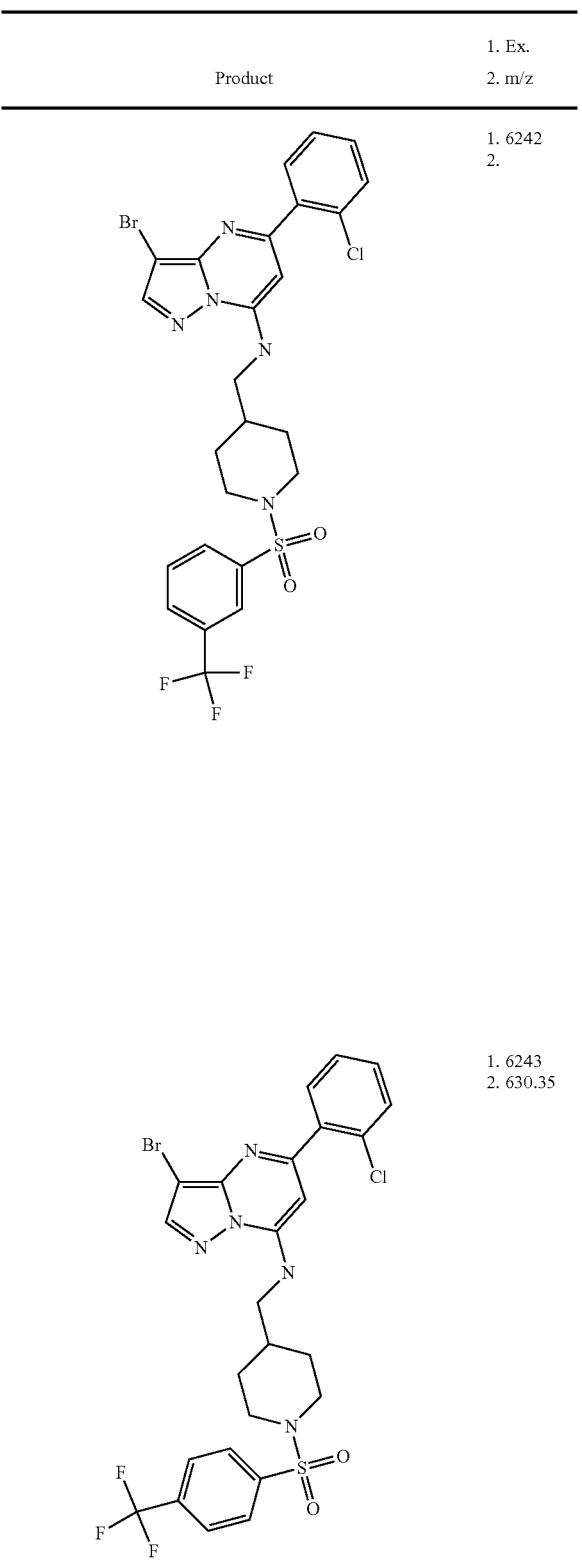 | 1. 6242<br>2. |
| | 1. 6243<br>2. 630.35 |
TABLE 62-continued
| Product | 1. Ex.<br>2. m/z |
|---|---|
| 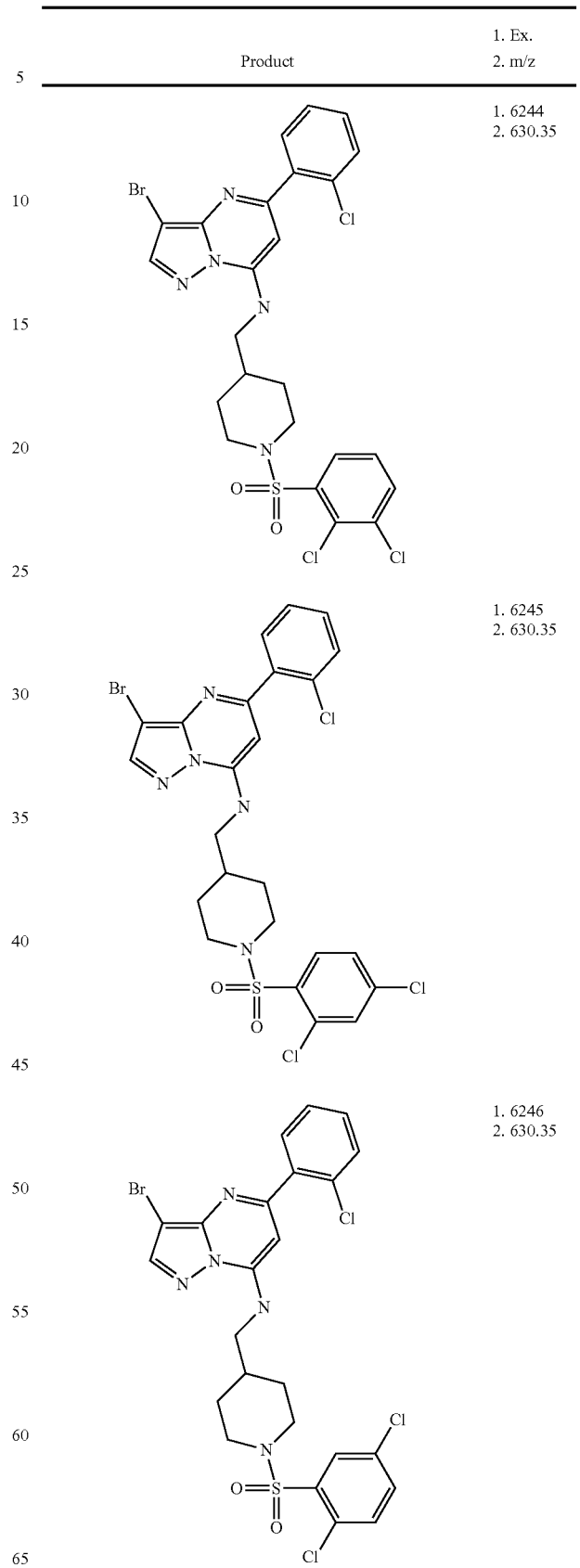 | 1. 6244<br>2. 630.35 |
| | 1. 6245<br>2. 630.35 |
| | 1. 6246<br>2. 630.35 |

TABLE 62-continued
| Product | 1. Ex.<br>2. m/z |
|---|---|
| 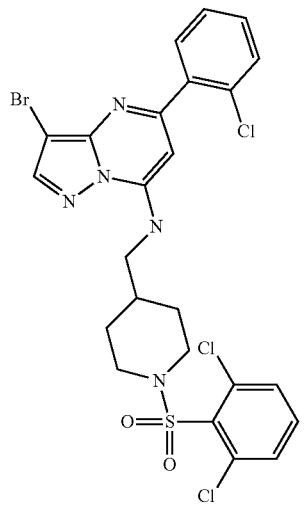 [SMILES: O=S(=O)(c1c(Cl)cccc1Cl)N1CCC(CNc2cc(-c3ccccc3Cl)nc3c(Br)cnn23)CC1] | 1. 6247<br>2. 630.35 |
| 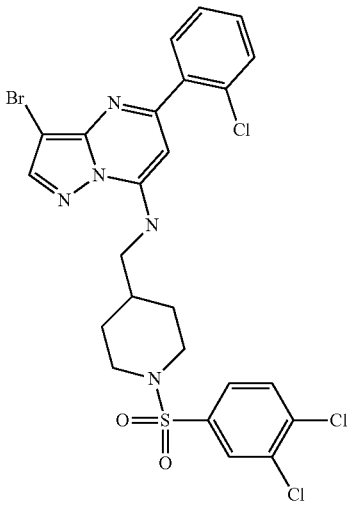 [SMILES: O=S(=O)(c1ccc(Cl)c(Cl)c1)N1CCC(CNc2cc(-c3ccccc3Cl)nc3c(Br)cnn23)CC1] | 1. 6248<br>2. 630.35 |
| 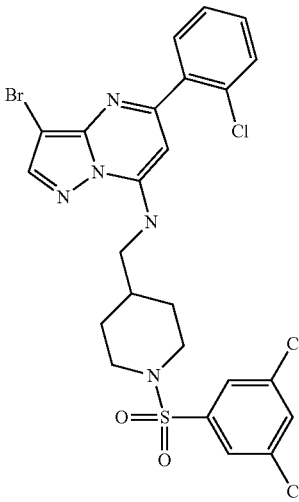 | 1. 6249<br>2. 630.35 |
TABLE 62-continued
| Product | 1. Ex.<br>2. m/z |
|---|---|
| 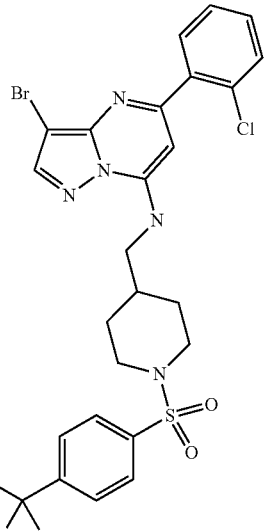 | 1. 6250<br>2. 632.35 |
| 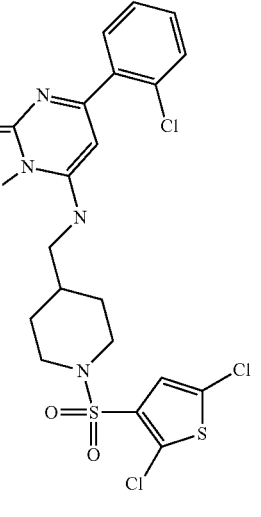 | 1. 6251<br>2. 636.35 |

TABLE 62-continued
| Product | 1. Ex. 2. m/z |
|---|---|
| 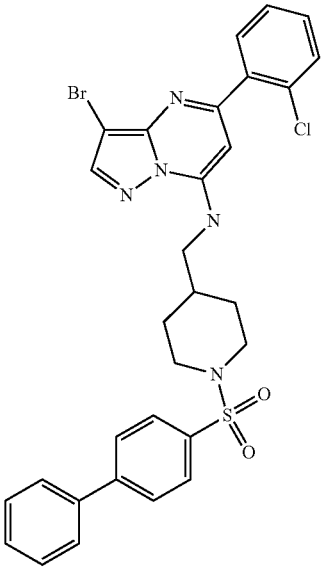 [SMILES: O=S(=O)(c1ccc(-c2ccccc2)cc1)N1CCC(CNc2cc(-c3ccccc3Cl)nc3c(Br)cnn23)CC1] | 1. 6252  2. 638.35 |
| 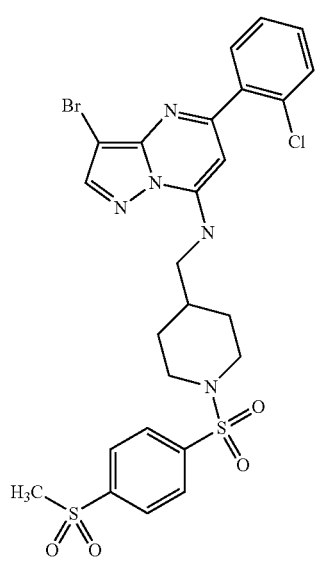 [SMILES: CS(=O)(=O)c1ccc(S(=O)(=O)N2CCC(CNc3cc(-c4ccccc4Cl)nc4c(Br)cnn34)CC2)cc1] | 1. 6253  2. 640.35 |
| 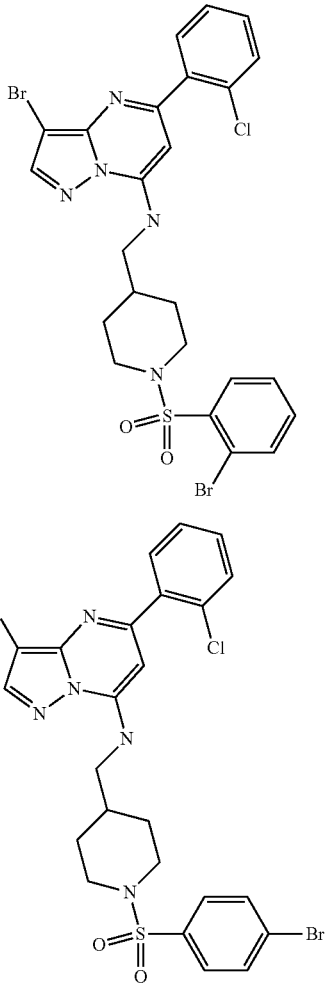 | 1. 6254  2. 640.35 |
| 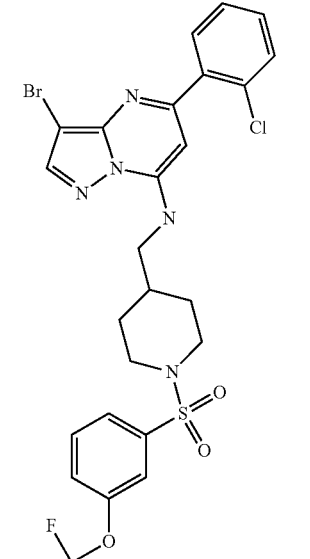 | 1. 6255  2. 638.35 |
| 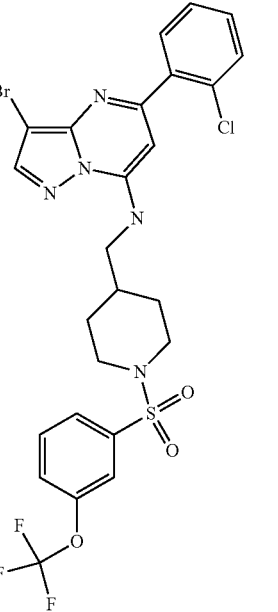 | 1. 6256  2. 646.36 |

TABLE 62-continued
| Product | 1. Ex. 2. m/z |
|---|---|
| 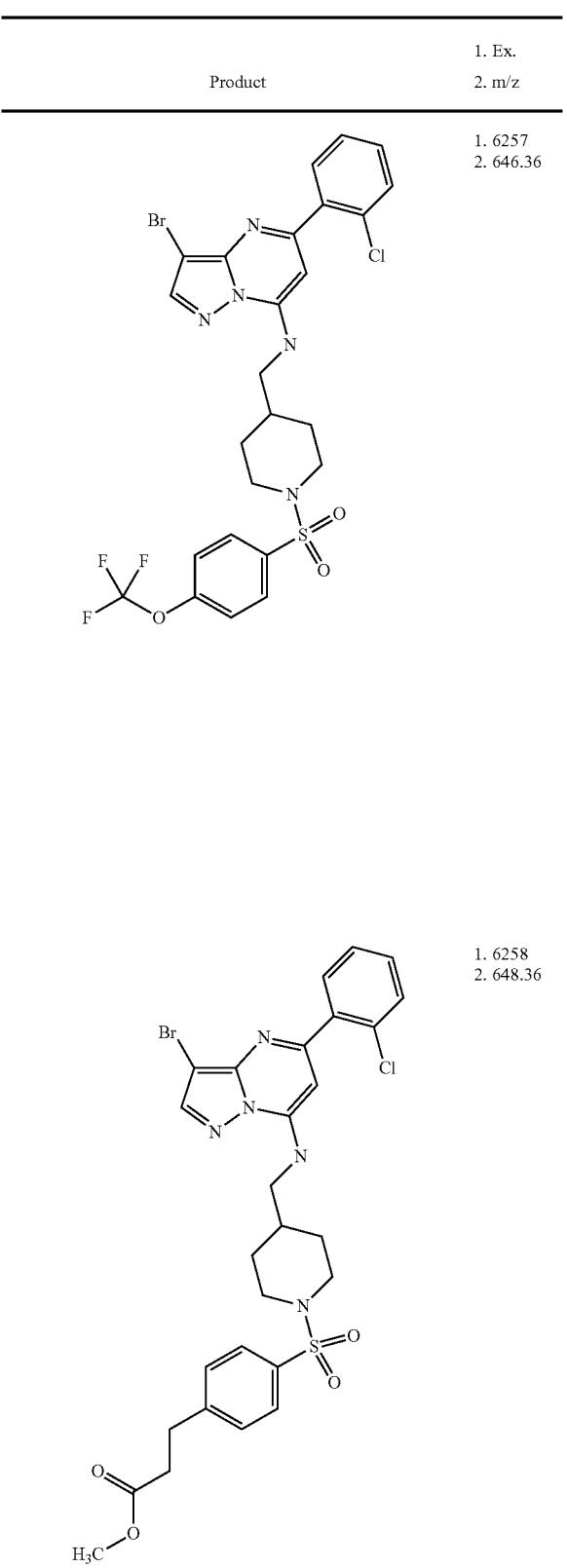 | 1. 6257<br>2. 646.36<br><br>1. 6258<br>2. 648.36 |
TABLE 62-continued
| Product | 1. Ex. 2. m/z |
|---|---|
| 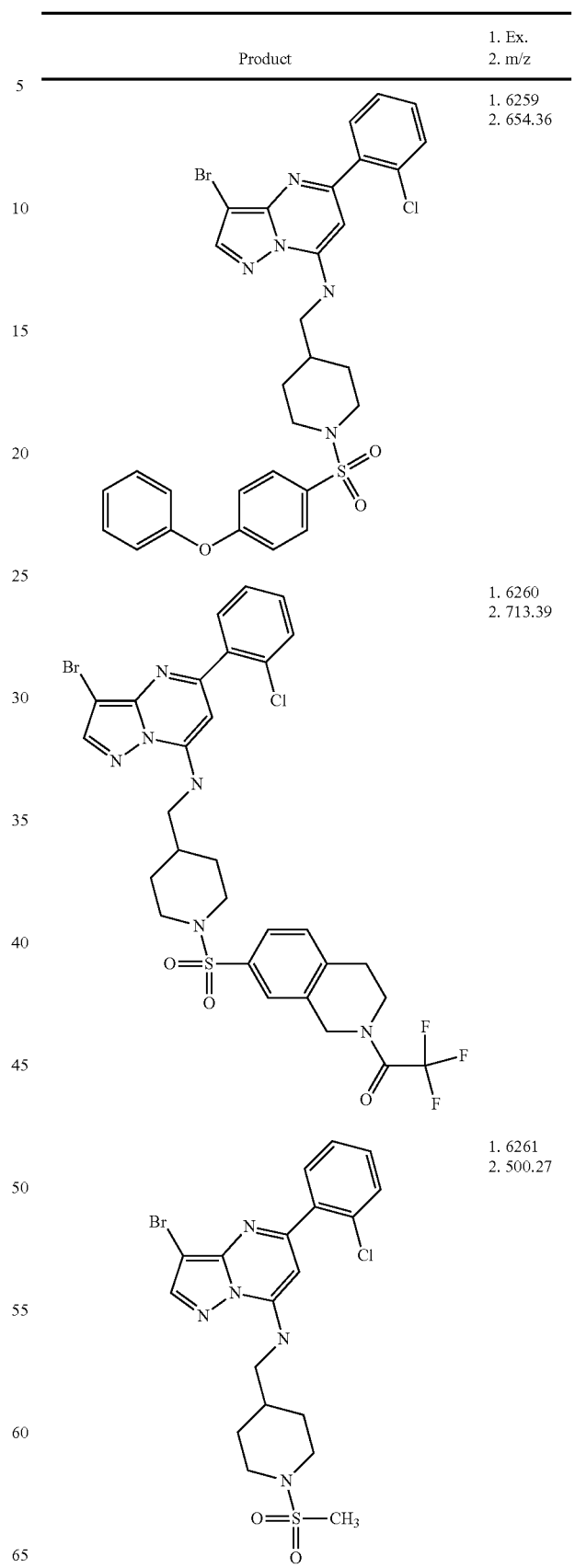 | 1. 6259<br>2. 654.36<br><br>1. 6260<br>2. 713.39<br><br>1. 6261<br>2. 500.27 |

TABLE 62-continued
| Product | 1. Ex.<br>2. m/z |
|---|---|
| 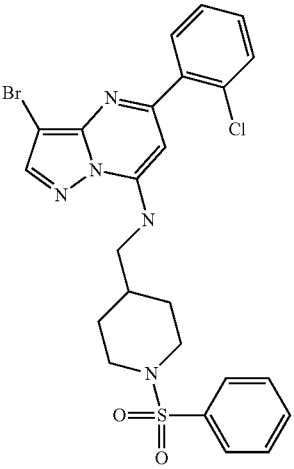 [SMILES: O=S(=O)(c1ccccc1)N1CCC(CNc2cc(-c3ccccc3Cl)nc3c(Br)cnn23)CC1] | 1. 6262<br>2. 562.31 |
| 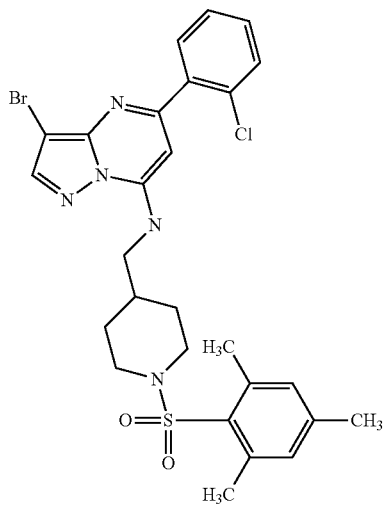 [SMILES: Cc1cc(C)c(S(=O)(=O)N2CCC(CNc3cc(-c4ccccc4Cl)nc4c(Br)cnn34)CC2)c(C)c1] | 1. 6263<br>2. 604.33 |
TABLE 63
| Product | 1. Ex.<br>2. m/z |
|---|---|
| 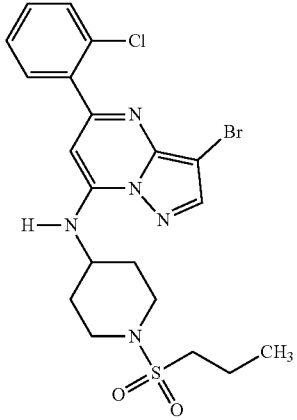 [SMILES: CCCS(=O)(=O)N1CCC(Nc2cc(-c3ccccc3Cl)nc3c(Br)cnn23)CC1] | 1. 6301<br>2. 500.27 |
TABLE 63-continued
| Product | 1. Ex.<br>2. m/z |
|---|---|
| 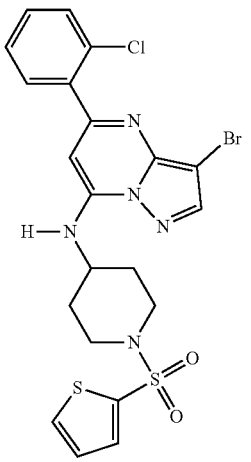 [SMILES: O=S(=O)(c1cccs1)N1CCC(Nc2cc(-c3ccccc3Cl)nc3c(Br)cnn23)CC1] | 1. 6302<br>2. 514.28 |
| 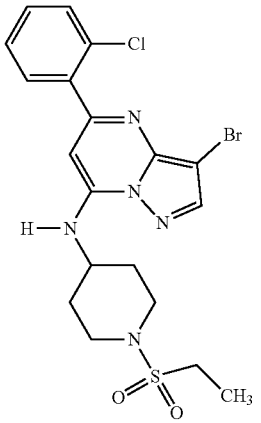 | 1. 6303<br>2. 554.3 |
| 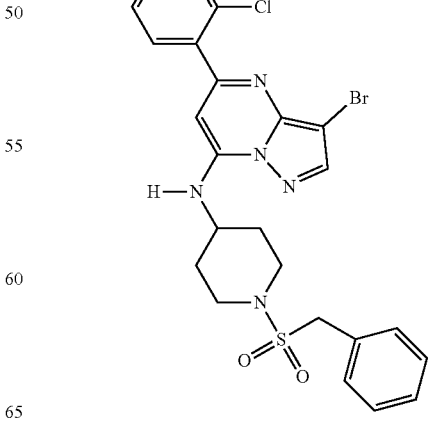 | 1. 6304<br>2. 562.31 |

TABLE 63-continued
| Product | 1. Ex. 2. m/z |
|---|---|
| 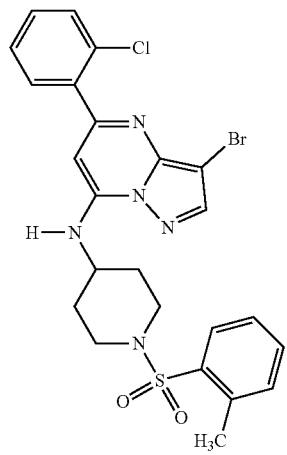 [SMILES: Cc1ccccc1S(=O)(=O)N1CCC(Nc2cc(-c3ccccc3Cl)nc3c(Br)cnn23)CC1] | 1. 6305<br>2. 562.31 |
| 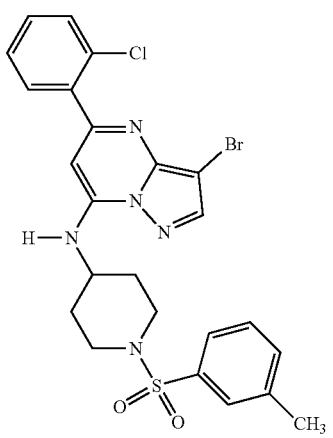 [SMILES: Cc1cccc(S(=O)(=O)N2CCC(Nc3cc(-c4ccccc4Cl)nc4c(Br)cnn34)CC2)c1] | 1. 6306<br>2. 562.31 |
| 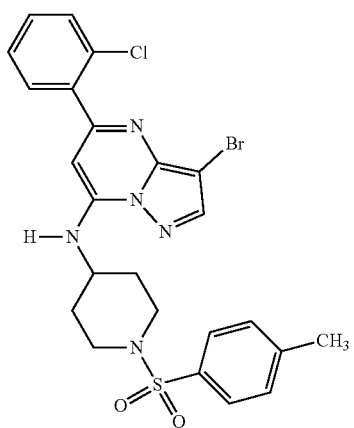 [SMILES: Cc1ccc(S(=O)(=O)N2CCC(Nc3cc(-c4ccccc4Cl)nc4c(Br)cnn34)CC2)cc1] | 1. 6307<br>2. 562.31 |
TABLE 63-continued
| Product | 1. Ex. 2. m/z |
|---|---|
| 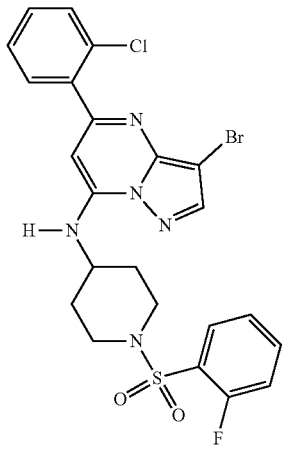 [SMILES: O=S(=O)(c1ccccc1F)N1CCC(Nc2cc(-c3ccccc3Cl)nc3c(Br)cnn23)CC1] | 1. 6308<br>2. 566.31 |
| 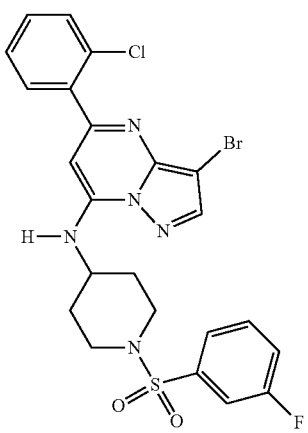 [SMILES: O=S(=O)(c1cccc(F)c1)N1CCC(Nc2cc(-c3ccccc3Cl)nc3c(Br)cnn23)CC1] | 1. 6309<br>2. 566.31 |
| 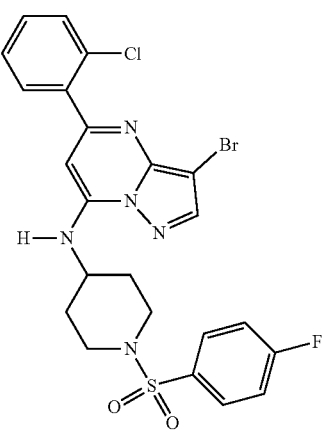 [SMILES: O=S(=O)(c1ccc(F)cc1)N1CCC(Nc2cc(-c3ccccc3Cl)nc3c(Br)cnn23)CC1] | 1. 6310<br>2. 566.31 |

TABLE 63-continued

| Product | 1. Ex. 2. m/z |
|---|---|
| [5-(2-chlorophenyl)-3-bromo-pyrazolo[1,5-a]pyrimidin-7-yl]-[1-(3,5-dimethyl-isoxazol-4-ylsulfonyl)-piperidin-4-yl]-amine | 1. 6311<br>2. 567.31 |
| [5-(2-chlorophenyl)-3-bromo-pyrazolo[1,5-a]pyrimidin-7-yl]-[1-(2-cyanophenylsulfonyl)-piperidin-4-yl]-amine | 1. 6312<br>2. 573.32 |
| [5-(2-chlorophenyl)-3-bromo-pyrazolo[1,5-a]pyrimidin-7-yl]-[1-(3-cyanophenylsulfonyl)-piperidin-4-yl]-amine | 1. 6313<br>2. 573.32 |
| [5-(2-chlorophenyl)-3-bromo-pyrazolo[1,5-a]pyrimidin-7-yl]-[1-(4-cyanophenylsulfonyl)-piperidin-4-yl]-amine | 1. 6314<br>2. 573.32 |
| [5-(2-chlorophenyl)-3-bromo-pyrazolo[1,5-a]pyrimidin-7-yl]-[1-(styrylsulfonyl)-piperidin-4-yl]-amine | 1. 6315<br>2. 574.32 |
| [5-(2-chlorophenyl)-3-bromo-pyrazolo[1,5-a]pyrimidin-7-yl]-[1-(4-ethylphenylsulfonyl)-piperidin-4-yl]-amine | 1. 6316<br>2. 576.32 |

TABLE 63-continued
| Product | 1. Ex.<br>2. m/z |
|---|---|
| 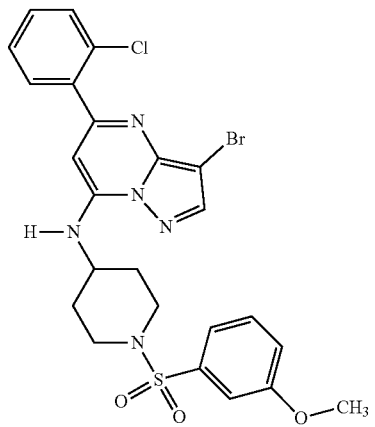 [SMILES: COc1cccc(S(=O)(=O)N2CCC(Nc3cc(-c4ccccc4Cl)nc4c(Br)cnn34)CC2)c1] | 1. 6317<br>2. 578.32 |
| 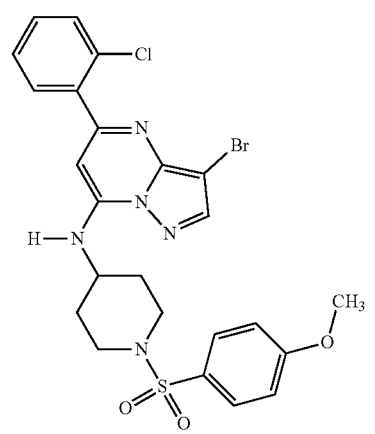 [SMILES: COc1ccc(S(=O)(=O)N2CCC(Nc3cc(-c4ccccc4Cl)nc4c(Br)cnn34)CC2)cc1] | 1. 6318<br>2. 578.32 |
| 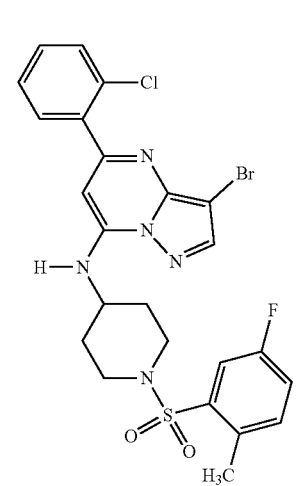 [SMILES: Cc1ccc(F)cc1S(=O)(=O)N1CCC(Nc2cc(-c3ccccc3Cl)nc3c(Br)cnn23)CC1] | 1. 6319<br>2. 580.32 |
TABLE 63-continued
| Product | 1. Ex.<br>2. m/z |
|---|---|
| 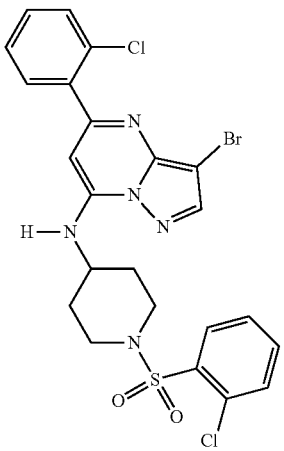 [SMILES: O=S(=O)(c1ccccc1Cl)N1CCC(Nc2cc(-c3ccccc3Cl)nc3c(Br)cnn23)CC1] | 1. 6320<br>2. 582.32 |
| 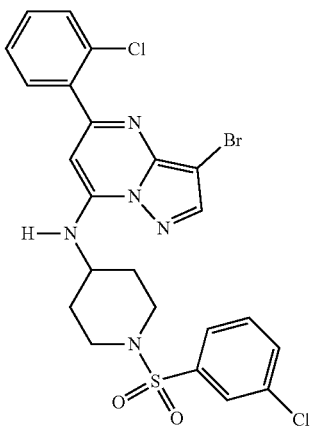 [SMILES: O=S(=O)(c1cccc(Cl)c1)N1CCC(Nc2cc(-c3ccccc3Cl)nc3c(Br)cnn23)CC1] | 1. 6321<br>2. 582.32 |
| 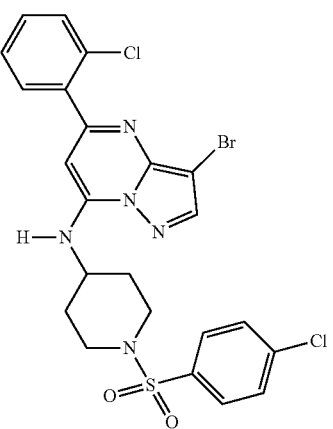 [SMILES: O=S(=O)(c1ccc(Cl)cc1)N1CCC(Nc2cc(-c3ccccc3Cl)nc3c(Br)cnn23)CC1] | 1. 6322<br>2. 582.32 |

TABLE 63-continued
| Product | 1. Ex. 2. m/z |
|---|---|
| 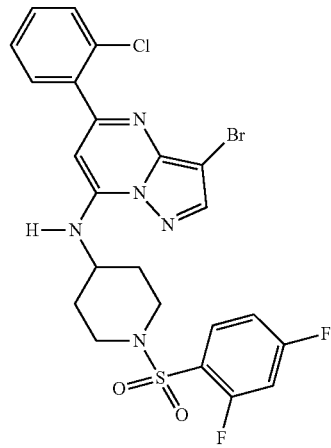 [SMILES: O=S(=O)(c1ccc(F)cc1F)N1CCC(Nc2cc(-c3ccccc3Cl)nc3c(Br)cnn23)CC1] | 1. 6323<br>2. 584.32 |
| 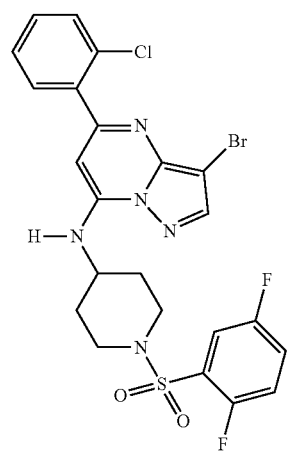 [SMILES: O=S(=O)(c1cc(F)ccc1F)N1CCC(Nc2cc(-c3ccccc3Cl)nc3c(Br)cnn23)CC1] | 1. 6324<br>2. 582.32 |
| 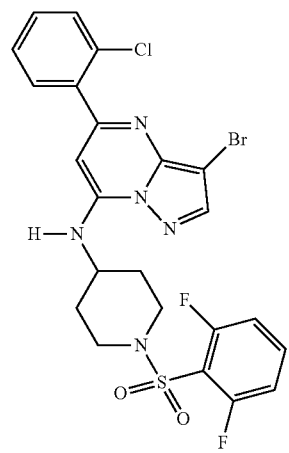 [SMILES: O=S(=O)(c1c(F)cccc1F)N1CCC(Nc2cc(-c3ccccc3Cl)nc3c(Br)cnn23)CC1] | 1. 6325<br>2. 584.32 |
TABLE 63-continued
| Product | 1. Ex. 2. m/z |
|---|---|
| 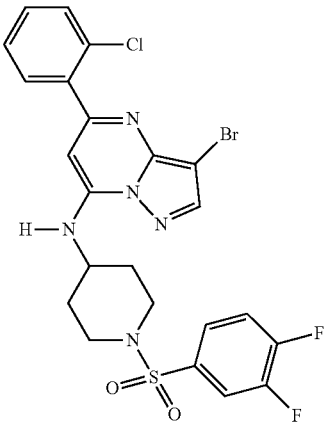 [SMILES: O=S(=O)(c1ccc(F)c(F)c1)N1CCC(Nc2cc(-c3ccccc3Cl)nc3c(Br)cnn23)CC1] | 1. 6326<br>2. 584.32 |
| 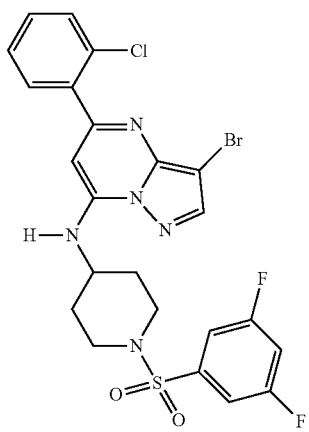 [SMILES: O=S(=O)(c1cc(F)cc(F)c1)N1CCC(Nc2cc(-c3ccccc3Cl)nc3c(Br)cnn23)CC1] | 1. 6327<br>2. 584.32 |
| 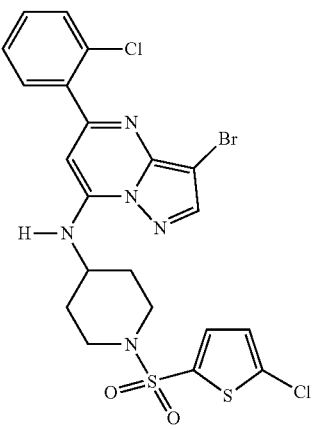 [SMILES: O=S(=O)(c1ccc(Cl)s1)N1CCC(Nc2cc(-c3ccccc3Cl)nc3c(Br)cnn23)CC1] | 1. 6328<br>2. 588.32 |

TABLE 63-continued
| Product | 1. Ex. 2. m/z |
|---|---|
| 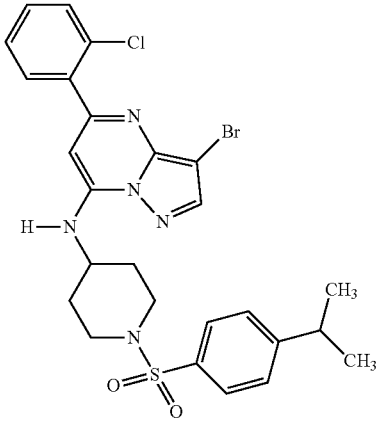 [SMILES: CC(C)c1ccc(S(=O)(=O)N2CCC(Nc3cc(-c4ccccc4Cl)nc4c(Br)cnn34)CC2)cc1] | 1. 6329<br>2. 590.32 |
| 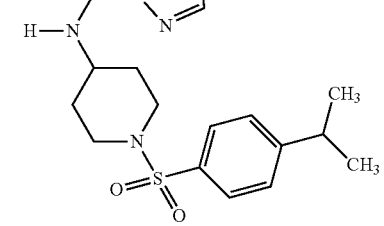 | 1. 6330<br>2. 596.33 |
|  | 1. 6331<br>2. 598.33 |
TABLE 63-continued
| Product | 1. Ex. 2. m/z |
|---|---|
| 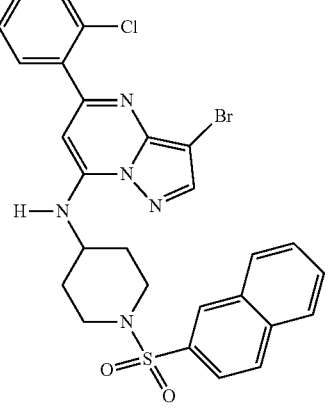 | 1. 6332<br>2. 598.33 |
| 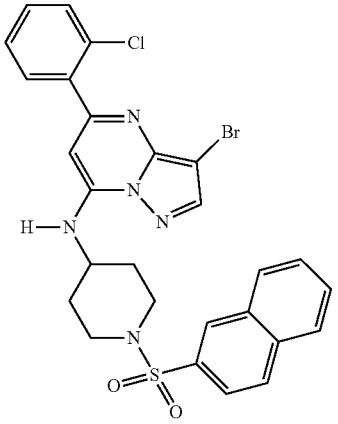 [SMILES: O=S(=O)(c1ccc2ccccc2c1)N1CCC(Nc2cc(-c3ccccc3Cl)nc3c(Br)cnn23)CC1] | 1. 6333<br>2. 600.33 |
| | 1. 6334<br>2. 600.33 |

TABLE 63-continued
| Product | 1. Ex. 2. m/z |
|---|---|
| 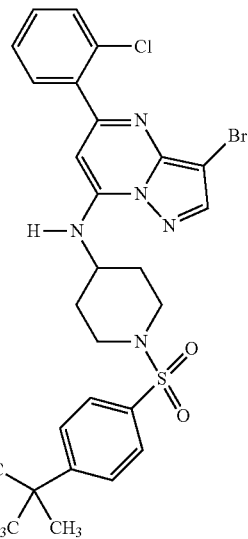 | 1. 6335 2. 604.33 |
| 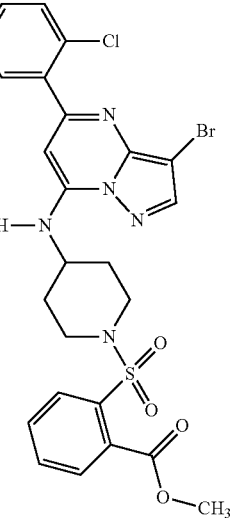 | 1. 6336 2. 606.33 |
| 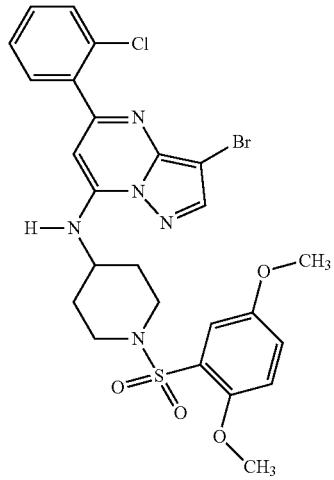 [SMILES: COc1ccc(OC)c(S(=O)(=O)N2CCC(Nc3cc(-c4ccccc4Cl)nc4c(Br)cnn34)CC2)c1] | 1. 6337 2. 608.33 |
TABLE 63-continued
| Product | 1. Ex. 2. m/z |
|---|---|
| 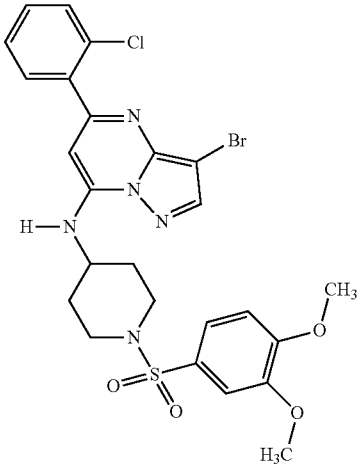 [SMILES: COc1ccc(S(=O)(=O)N2CCC(Nc3cc(-c4ccccc4Cl)nc4c(Br)cnn34)CC2)cc1OC] | 1. 6338 2. 608.33 |
| 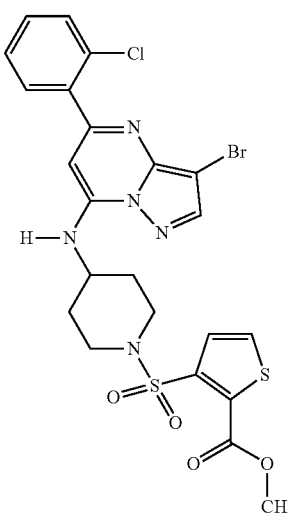 | 1. 6339 2. 612.34 |
| 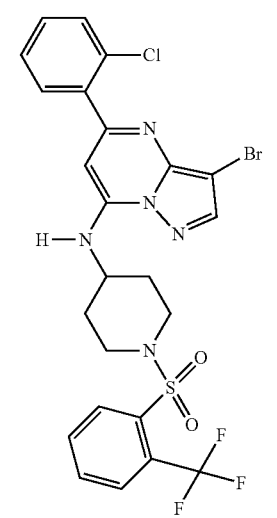 [SMILES: O=S(=O)(c1ccccc1C(F)(F)F)N1CCC(Nc2cc(-c3ccccc3Cl)nc3c(Br)cnn23)CC1] | 1. 6340 2. 616.34 |

TABLE 63-continued

| Product | 1. Ex. 2. m/z |
|---|---|
| (5-(2-chlorophenyl)-3-bromo-pyrazolo[1,5-a]pyrimidin-7-yl)-amino-piperidine-N-(3-trifluoromethylphenyl)sulfonyl | 1. 6341<br>2. 616.34 |
| (5-(2-chlorophenyl)-3-bromo-pyrazolo[1,5-a]pyrimidin-7-yl)-amino-piperidine-N-(4-trifluoromethylphenyl)sulfonyl | 1. 6342<br>2. 616.34 |
| (5-(2-chlorophenyl)-3-bromo-pyrazolo[1,5-a]pyrimidin-7-yl)-amino-piperidine-N-(2,3-dichlorophenyl)sulfonyl | 1. 6343<br>2. 616.34 |
| (5-(2-chlorophenyl)-3-bromo-pyrazolo[1,5-a]pyrimidin-7-yl)-amino-piperidine-N-(2,4-dichlorophenyl)sulfonyl | 1. 6344<br>2. 616.34 |
| (5-(2-chlorophenyl)-3-bromo-pyrazolo[1,5-a]pyrimidin-7-yl)-amino-piperidine-N-(2,5-dichlorophenyl)sulfonyl | 1. 6345<br>2. 616.34 |
| (5-(2-chlorophenyl)-3-bromo-pyrazolo[1,5-a]pyrimidin-7-yl)-amino-piperidine-N-(2,6-dichlorophenyl)sulfonyl | 1. 6346<br>2. 616.34 |

TABLE 63-continued
| Product | 1. Ex. 2. m/z |
|---|---|
| 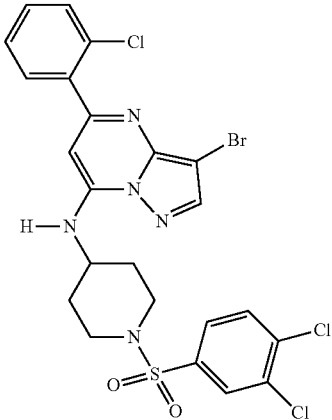 [SMILES: O=S(=O)(c1ccc(Cl)c(Cl)c1)N1CCC(Nc2cc(-c3ccccc3Cl)nc3c(Br)cnn23)CC1] | 1. 6347 2. 616.34 |
| 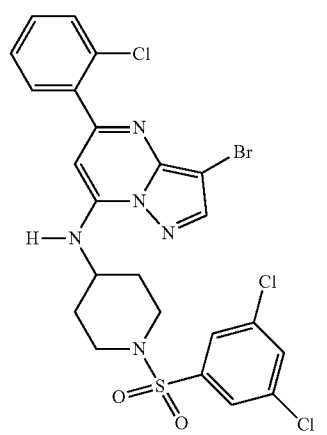 [SMILES: O=S(=O)(c1cc(Cl)cc(Cl)c1)N1CCC(Nc2cc(-c3ccccc3Cl)nc3c(Br)cnn23)CC1] | 1. 6348 2. 616.34 |
| 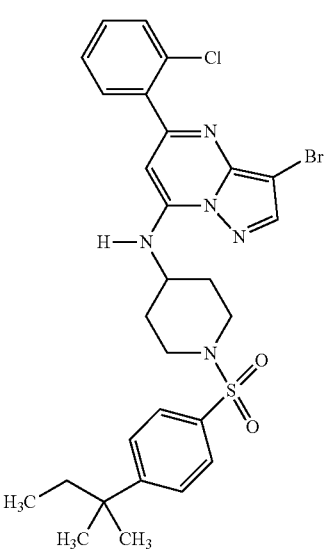 [SMILES: CCC(C)(C)c1ccc(S(=O)(=O)N2CCC(Nc3cc(-c4ccccc4Cl)nc4c(Br)cnn34)CC2)cc1] | 1. 6349 2. 618.34 |
| | 1. 6350 2. 600.33 |
| | 1. 6351 2. 622.34 |
| | 1. 6352 2. 624.34 |

TABLE 63-continued

| Product | 1. Ex. 2. m/z |
|---|---|
| (structure) | 1. 6353  2. 626.34 |
| (structure) | 1. 6354  2. 626.34 |
| (structure) | 1. 6355  2. 626.34 |
| (structure) | 1. 6356  2. 626.34 |
| (structure) | 1. 6357  2. 632.35 |
| (structure) | 1. 6358  2. 632.35 |

TABLE 63-continued
| Product | 1. Ex.<br>2. m/z |
|---|---|
| 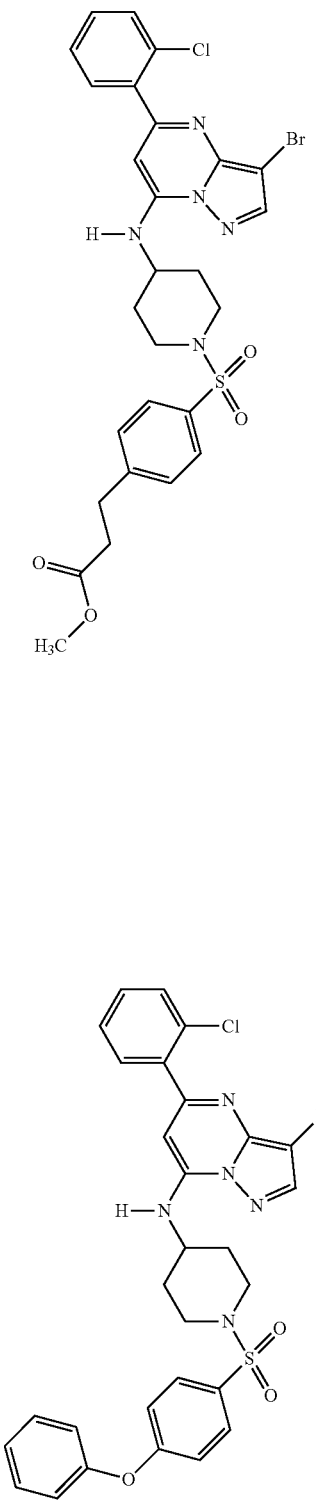 | 1. 6359<br>2. 634.35 |
| | 1. 6360<br>2. 640.35 |
TABLE 63-continued
| Product | 1. Ex.<br>2. m/z |
|---|---|
| 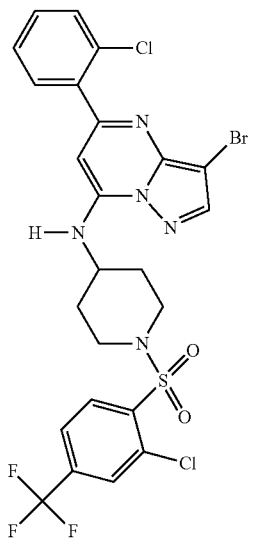 [SMILES: O=S(=O)(c1ccc(C(F)(F)F)cc1Cl)N1CCC(Nc2cc(-c3ccccc3Cl)nc3c(Br)cnn23)CC1] | 1. 6361<br>2. 650.36 |
| 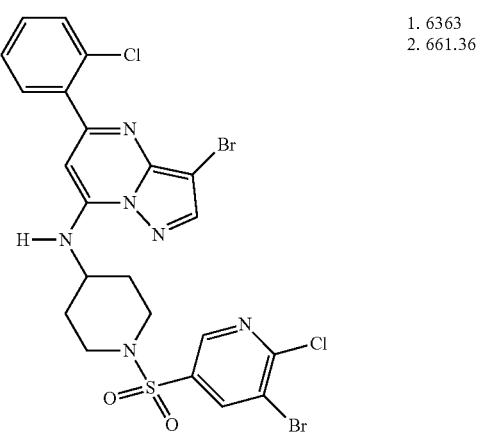 | 1. 6362<br>2. 650.36 |
| | 1. 6363<br>2. 661.36 |

TABLE 63-continued
| Product | 1. Ex.<br>2. m/z |
|---|---|
| 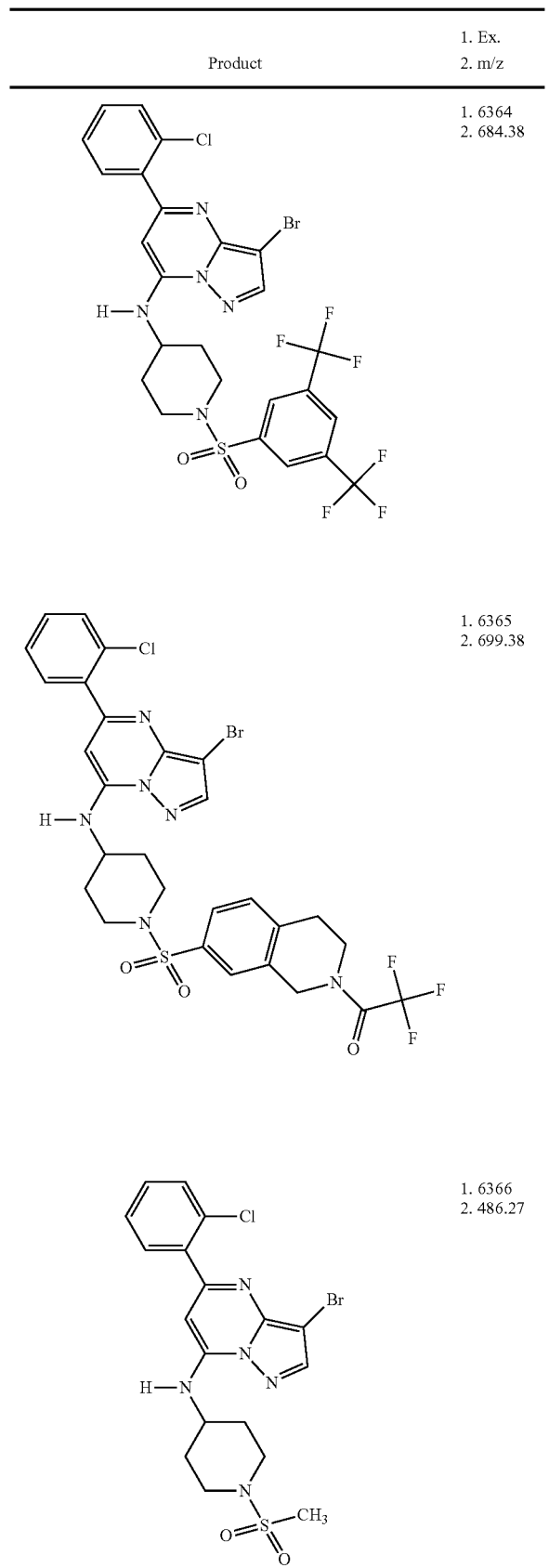 | 1. 6364<br>2. 684.38 |
| | 1. 6365<br>2. 699.38 |
| | 1. 6366<br>2. 486.27 |
TABLE 63-continued
| Product | 1. Ex.<br>2. m/z |
|---|---|
| 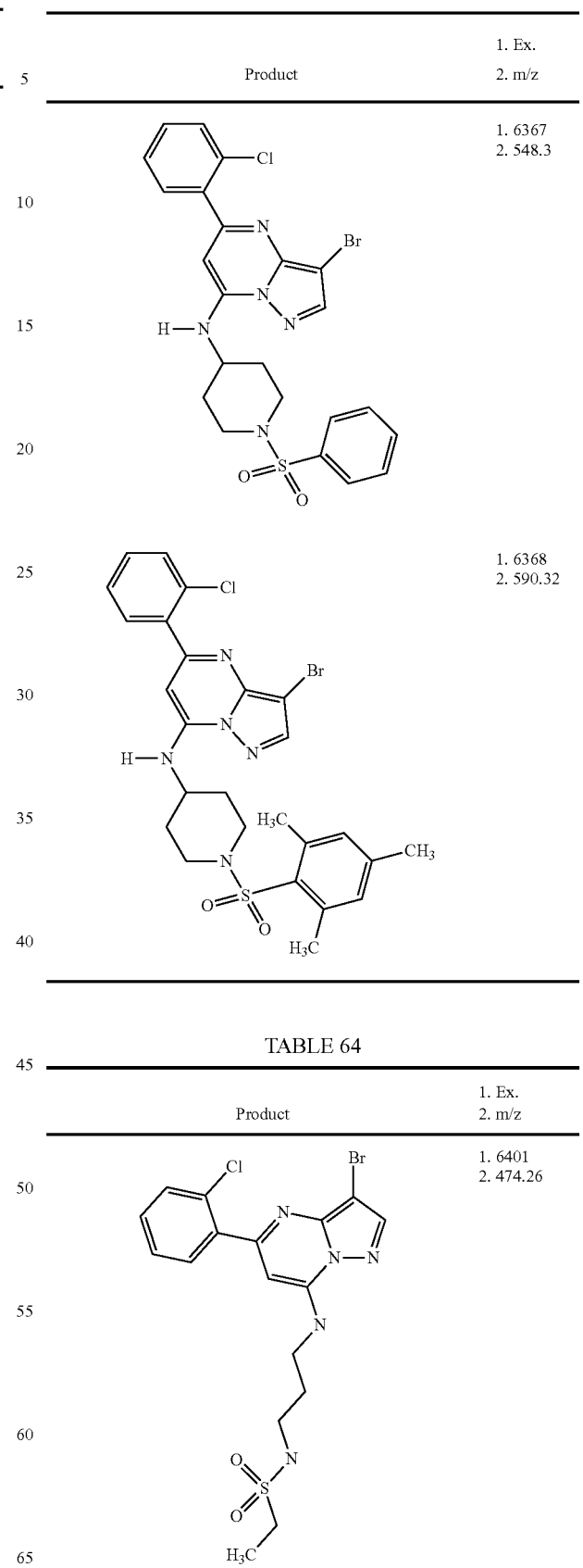 | 1. 6367<br>2. 548.3 |
| | 1. 6368<br>2. 590.32 |
TABLE 64
| Product | 1. Ex.<br>2. m/z |
|---|---|
| | 1. 6401<br>2. 474.26 |

TABLE 64-continued

| Product | 1. Ex. 2. m/z |
|---|---|
| (structure) | 1. 6402  2. 488.27 |
| (structure) | 1. 6403  2. 528.29 |
| (structure) | 1. 6404  2. 536.29 |
| (structure) | 1. 6405  2. 536.29 |
| (structure) | 1. 6406  2. 536.29 |
| (structure) | 1. 6407  2. 536.29 |

TABLE 64-continued

| Product | 1. Ex.<br>2. m/z |
|---|---|
| (structure) | 1. 6408<br>2. 540.3 |
| (structure) | 1. 6409<br>2. 540.3 |
| (structure) | 1. 6410<br>2. 540.3 |

TABLE 64-continued

| Product | 1. Ex.<br>2. m/z |
|---|---|
| (structure) | 1. 6411<br>2. 541.3 |
| (structure) | 1. 6412<br>2. 547.3 |
| (structure) | 1. 6413<br>2. 547.3 |

TABLE 64-continued

| Product | 1. Ex. 2. m/z |
|---|---|
| [5-(2-chlorophenyl)-3-bromo-pyrazolo[1,5-a]pyrimidin-7-yl with NH-propyl-NH-SO2-CH=CH-phenyl (styryl sulfonamide)] | 1. 6414  2. 548.3 |
| [5-(2-chlorophenyl)-3-bromo-pyrazolo[1,5-a]pyrimidin-7-yl with NH-propyl-NH-SO2-(4-ethylphenyl)] | 1. 6415  2. 550.3 |
| [5-(2-chlorophenyl)-3-bromo-pyrazolo[1,5-a]pyrimidin-7-yl with NH-propyl-NH-SO2-(3-methoxyphenyl)] | 1. 6416  2. 552.3 |
| [5-(2-chlorophenyl)-3-bromo-pyrazolo[1,5-a]pyrimidin-7-yl with NH-propyl-NH-SO2-(4-methoxyphenyl)] | 1. 6417  2. 552.3 |
| [5-(2-chlorophenyl)-3-bromo-pyrazolo[1,5-a]pyrimidin-7-yl with NH-propyl-NH-SO2-(5-fluoro-2-methylphenyl)] | 1. 6418  2. 554.3 |

TABLE 64-continued
| Product | 1. Ex. 2. m/z |
|---|---|
| 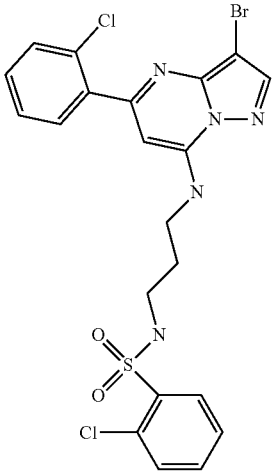 [SMILES: O=S(=O)(NCCCNc1cc(-c2ccccc2Cl)nc2c(Br)cnn12)c1ccccc1Cl] | 1. 6419<br>2. 556.31 |
| 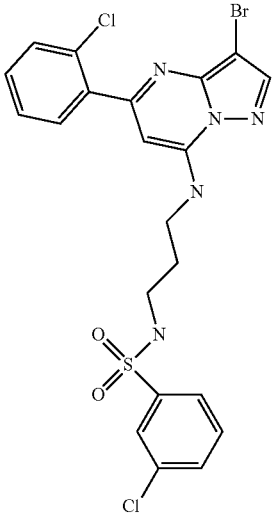 [SMILES: O=S(=O)(NCCCNc1cc(-c2ccccc2Cl)nc2c(Br)cnn12)c1cccc(Cl)c1] | 1. 6420<br>2. 556.31 |
| 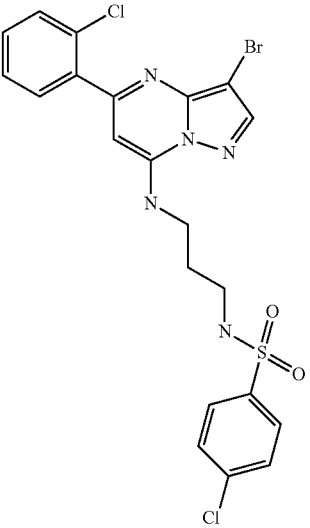 | 1. 6421<br>2. 556.31 |
TABLE 64-continued
| Product | 1. Ex. 2. m/z |
|---|---|
| 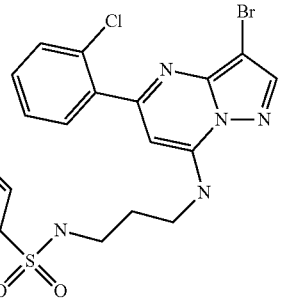 | 1. 6122<br>2. 558.31 |
| 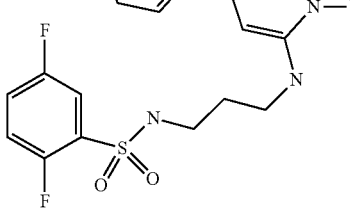 | 1. 6423<br>2. 558.31 |
| 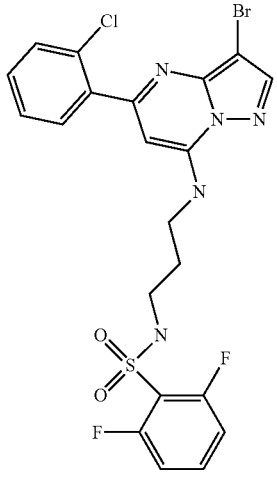 [SMILES: O=S(=O)(NCCCNc1cc(-c2ccccc2Cl)nc2c(Br)cnn12)c1c(F)cccc1F] | 1. 6424<br>2. 558.31 |
| 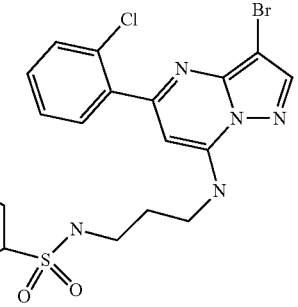 | 1. 6425<br>2. 558.31 |

TABLE 64-continued
| Product | 1. Ex.<br>2. m/z |
|---|---|
| 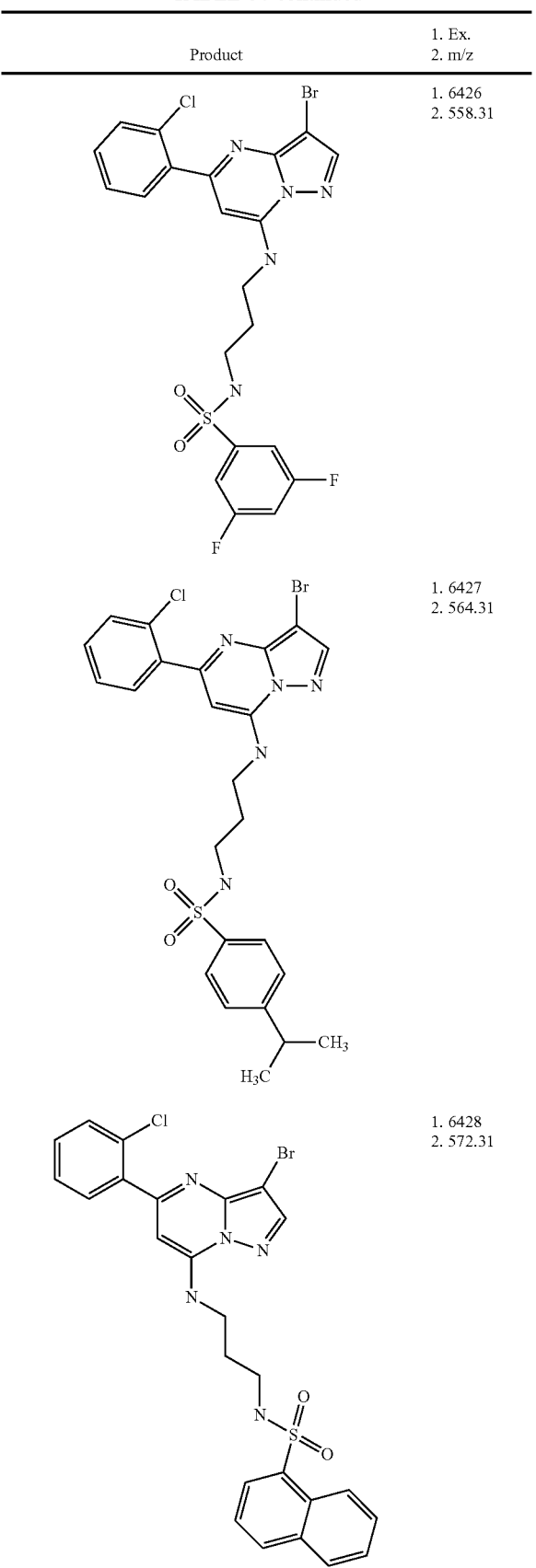 | 1. 6426<br>2. 558.31<br><br>1. 6427<br>2. 564.31<br><br>1. 6428<br>2. 572.31 |
TABLE 64-continued
| Product | 1. Ex.<br>2. m/z |
|---|---|
| 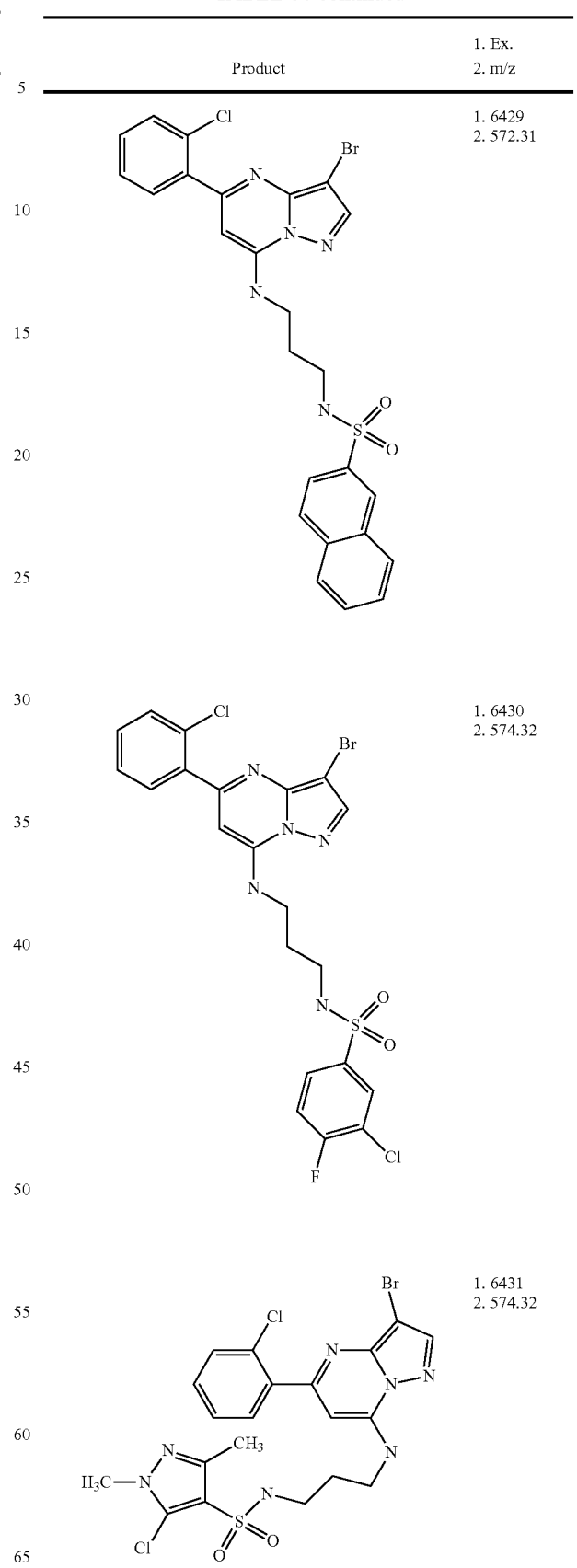 | 1. 6429<br>2. 572.31<br><br>1. 6430<br>2. 574.32<br><br>1. 6431<br>2. 574.32 |

TABLE 64-continued
| Product | 1. Ex.<br>2. m/z |
|---|---|
| 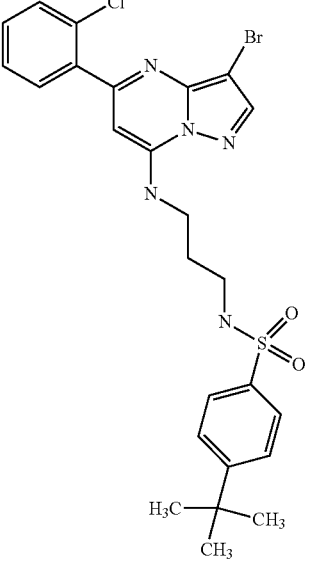 [SMILES: CC(C)(C)c1ccc(S(=O)(=O)NCCCNc2cc(-c3ccccc3Cl)nc3c(Br)cnn23)cc1] | 1. 6432<br>2. 578.32 |
| 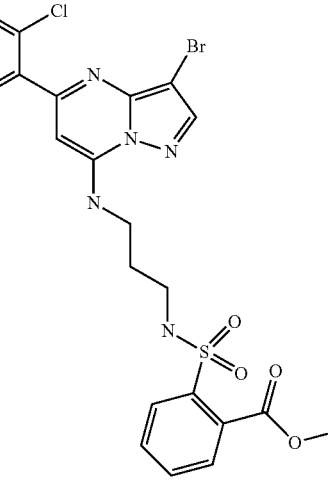 | 1. 6433<br>2. 580.32 |
| 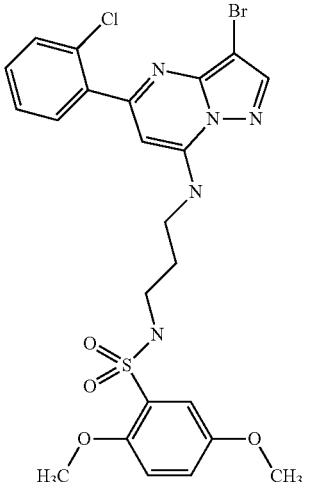 | 1. 6434<br>2. 582.32 |
TABLE 64-continued
| Product | 1. Ex.<br>2. m/z |
|---|---|
| 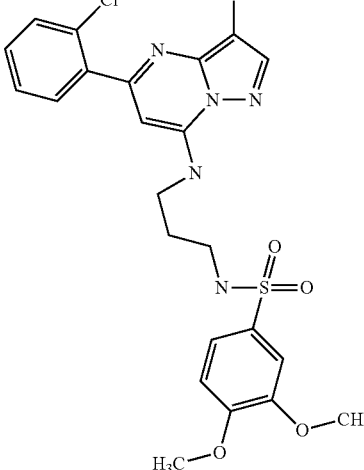 | 1. 6435<br>2. 582.32 |
| 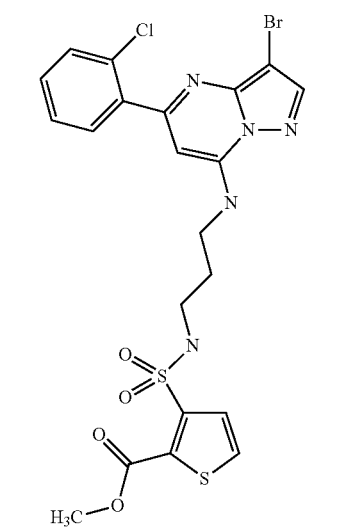 [SMILES: COC(=O)c1sccc1S(=O)(=O)NCCCNc1cc(-c2ccccc2Cl)nc2c(Br)cnn12] | 1. 6436<br>2. 586.32 |
| 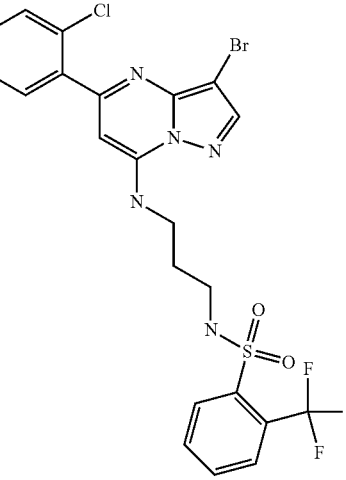 | 1. 6437<br>2. 590.32 |

TABLE 64-continued
| Product | 1. Ex.<br>2. m/z |
|---|---|
| 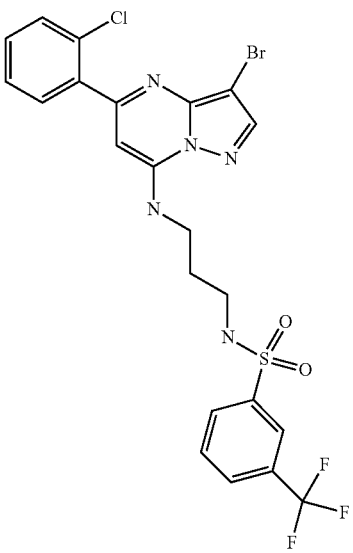 [SMILES: O=S(=O)(NCCCNc1cc(-c2ccccc2Cl)nc2c(Br)cnn12)c1cccc(C(F)(F)F)c1] | 1. 6438<br>2. 590.32 |
| 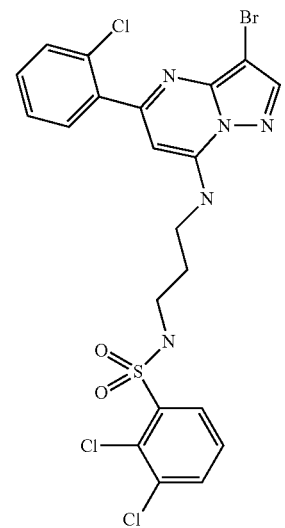 [SMILES: O=S(=O)(NCCCNc1cc(-c2ccccc2Cl)nc2c(Br)cnn12)c1cccc(Cl)c1Cl] | 1. 6439<br>2. 590.32 |
TABLE 64-continued
| Product | 1. Ex.<br>2. m/z |
|---|---|
| 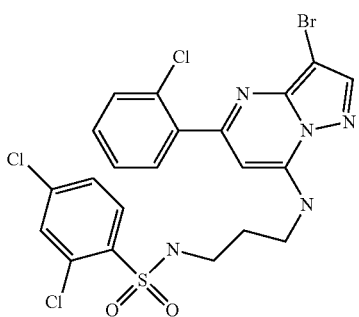 [SMILES: O=S(=O)(NCCCNc1cc(-c2ccccc2Cl)nc2c(Br)cnn12)c1ccc(Cl)cc1Cl] | 1. 6440<br>2. 589.32 |
| 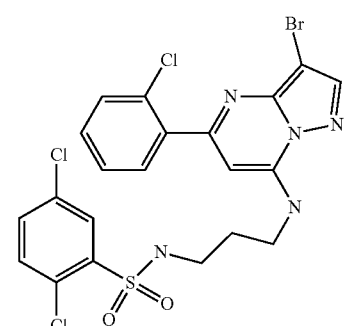 | 1. 6441<br>2. 590.32 |
| | 1. 6442<br>2. 590.32 |

TABLE 64-continued
| Product | 1. Ex. 2. m/z |
|---|---|
| 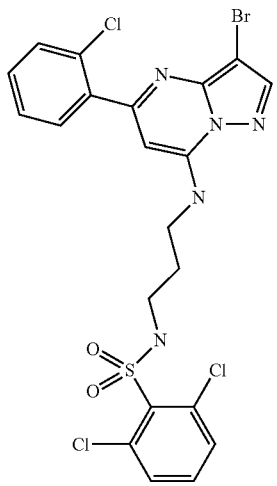 [SMILES: O=S(=O)(NCCCNc1cc(-c2ccccc2Cl)nc2c(Br)cnn12)c1c(Cl)cccc1Cl] | 1. 6443 2. 590.32 |
| 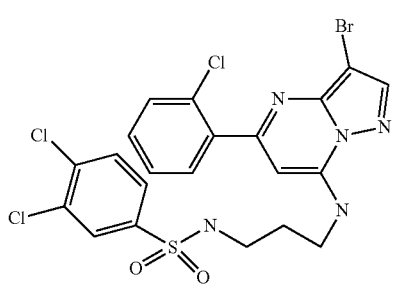 [SMILES: O=S(=O)(NCCCNc1cc(-c2ccccc2Cl)nc2c(Br)cnn12)c1ccc(Cl)c(Cl)c1] | 1. 6444 2. 590.32 |
| 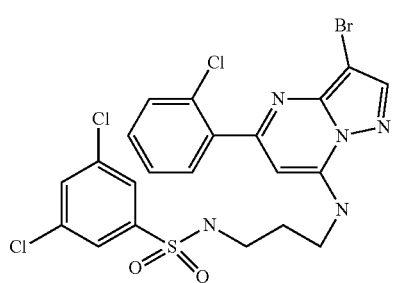 [SMILES: O=S(=O)(NCCCNc1cc(-c2ccccc2Cl)nc2c(Br)cnn12)c1cc(Cl)cc(Cl)c1] | 1. 6445 2. 590.32 |
TABLE 64-continued
| Product | 1. Ex. 2. m/z |
|---|---|
| 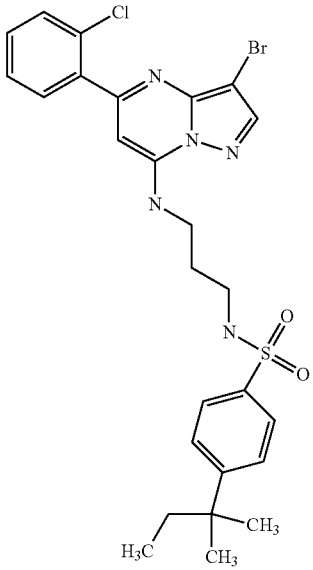 [SMILES: CCC(C)(C)c1ccc(S(=O)(=O)NCCCNc2cc(-c3ccccc3Cl)nc3c(Br)cnn23)cc1] | 1. 6446 2. 592.33 |
| 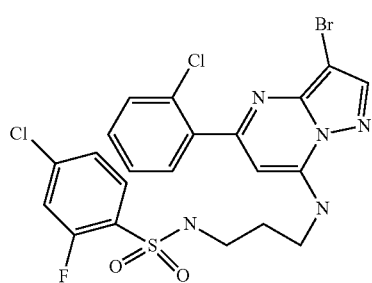 [SMILES: O=S(=O)(NCCCNc1cc(-c2ccccc2Cl)nc2c(Br)cnn12)c1ccc(Cl)cc1F] | 1. 6447 2. 574.32 |
| 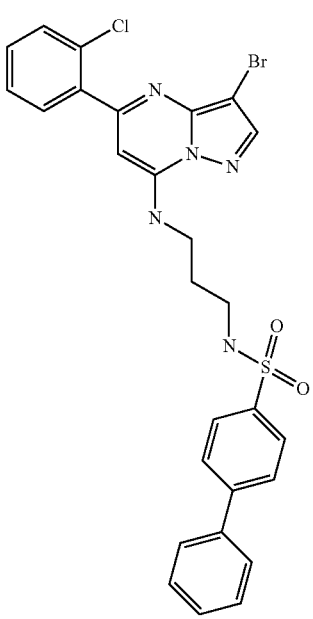 [SMILES: O=S(=O)(NCCCNc1cc(-c2ccccc2Cl)nc2c(Br)cnn12)c1ccc(-c2ccccc2)cc1] | 1. 6448 2. 598.33 |

TABLE 64-continued

| Product | 1. Ex.<br>2. m/z |
|---|---|
| (structure: 5-(2-chlorophenyl)-3-bromo-pyrazolo[1,5-a]pyrimidin-7-yl amine with propyl-NH-SO2-(2-methylsulfonyl)phenyl) | 1. 6449<br>2. 600.33 |
| (structure: 5-(2-chlorophenyl)-3-bromo-pyrazolo[1,5-a]pyrimidin-7-yl amine with propyl-NH-SO2-(4-methylsulfonyl)phenyl) | 1. 6450<br>2. 600.33 |
| (structure: 5-(2-chlorophenyl)-3-bromo-pyrazolo[1,5-a]pyrimidin-7-yl amine with propyl-NH-SO2-(2-bromo)phenyl) | 1. 6451<br>2. 600.33 |
| (structure: 5-(2-chlorophenyl)-3-bromo-pyrazolo[1,5-a]pyrimidin-7-yl amine with propyl-NH-SO2-(4-bromo)phenyl) | 1. 6452<br>2. 600.33 |
| (structure: 5-(2-chlorophenyl)-3-bromo-pyrazolo[1,5-a]pyrimidin-7-yl amine with propyl-NH-SO2-(3-trifluoromethoxy)phenyl) | 1. 6453<br>2. 606.33 |

TABLE 64-continued
| Product | 1. Ex.<br>2. m/z |
|---|---|
| 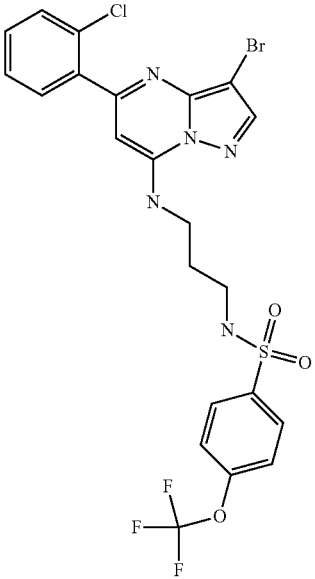 [SMILES: O=S(=O)(NCCCNc1cc(-c2ccccc2Cl)nc2c(Br)cnn12)c1ccc(OC(F)(F)F)cc1] | 1. 5454<br>2. 606.33 |
| 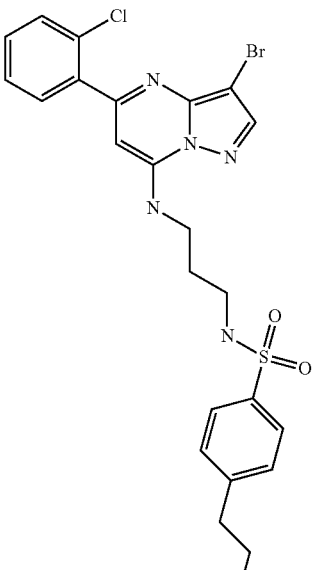 | 1. 6455<br>2. 608.33 |
TABLE 64-continued
| Product | 1. Ex.<br>2. m/z |
|---|---|
| 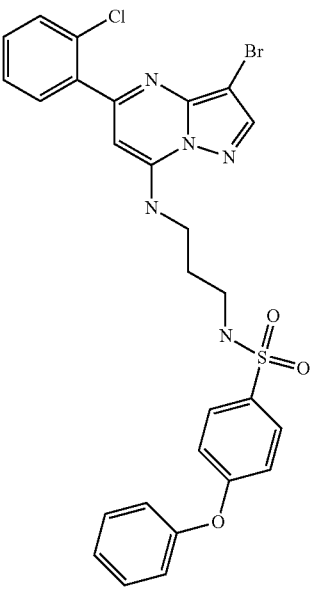 [SMILES: O=S(=O)(NCCCNc1cc(-c2ccccc2Cl)nc2c(Br)cnn12)c1ccc(Oc2ccccc2)cc1] | 1. 6456<br>2. 614.34 |
| 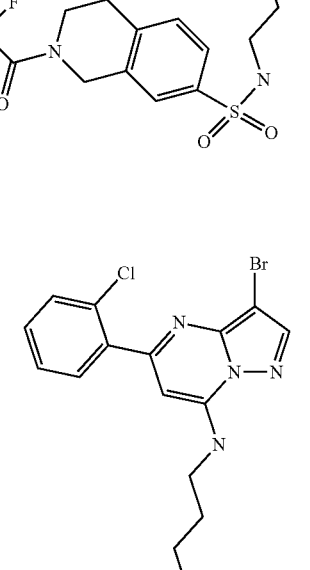 | 1. 6447<br>2. 673.37 |
| 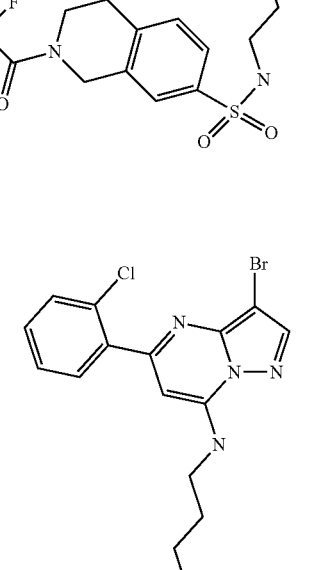 | 1. 6458<br>2. 460.25 |

TABLE 64-continued
| Product | 1. Ex. 2. m/z |
|---|---|
| 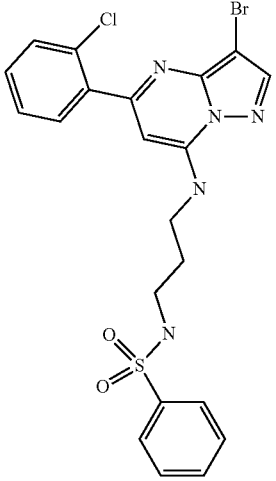 [SMILES: O=S(=O)(NCCCNc1cc(-c2ccccc2Cl)nc2c(Br)cnn12)c1ccccc1] | 6459 2. |
| 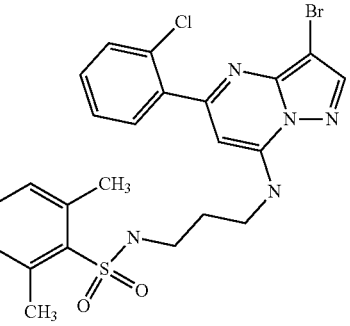 | 1. 6460 2. 564.31 |
TABLE 65
| Product | 1. Ex. 2. m/z |
|---|---|
| 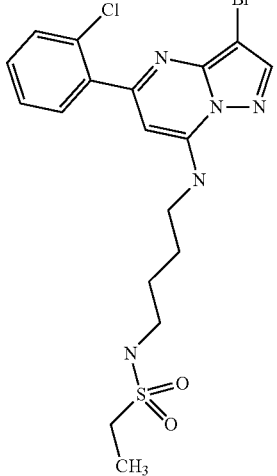 | 1. 6501 2. 488.27 |
TABLE 65-continued
| Product | 1. Ex. 2. m/z |
|---|---|
| 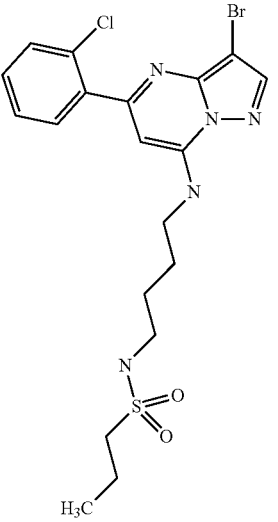 [SMILES: CCCS(=O)(=O)NCCCCNc1cc(-c2ccccc2Cl)nc2c(Br)cnn12] | 1. 6502 2. 502.28 |
| 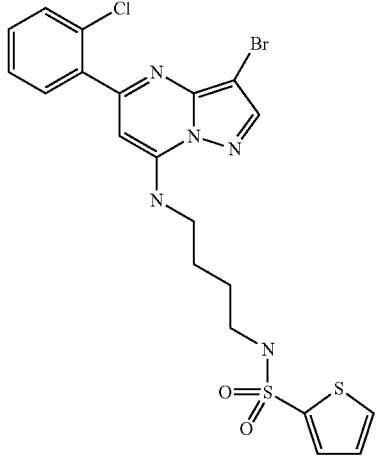 [SMILES: O=S(=O)(NCCCCNc1cc(-c2ccccc2Cl)nc2c(Br)cnn12)c1cccs1] | 1. 6503 2. 542.3 |
| 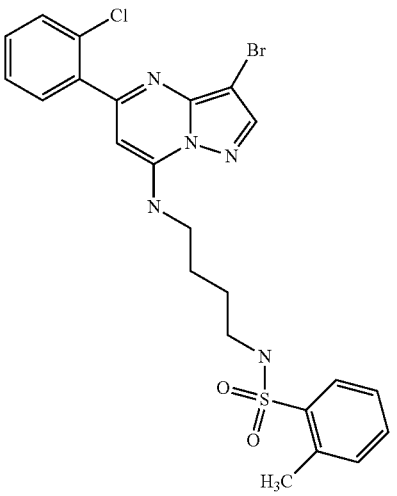 [SMILES: Cc1ccccc1S(=O)(=O)NCCCCNc1cc(-c2ccccc2Cl)nc2c(Br)cnn12] | 1. 6504 2. 550.3 |

TABLE 65-continued
| Product | 1. Ex.<br>2. m/z |
|---|---|
| 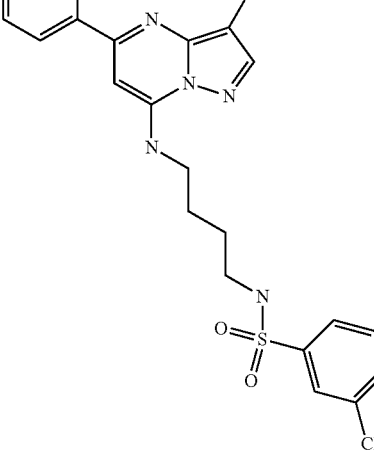 | 1. 6505<br>2. 550.3 |
| 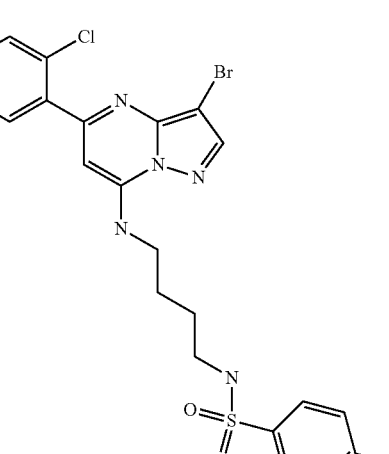 | 1. 6506<br>2. 550.3 |
| 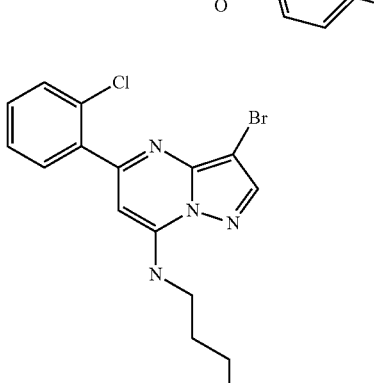 | 1. 6507<br>2. 554.3 |
TABLE 65-continued
| Product | 1. Ex.<br>2. m/z |
|---|---|
| 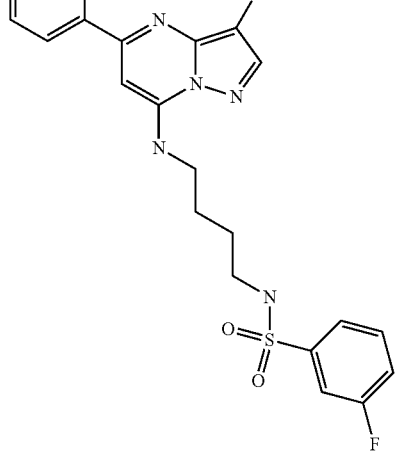 | 1. 6508<br>2. 554.3 |
| 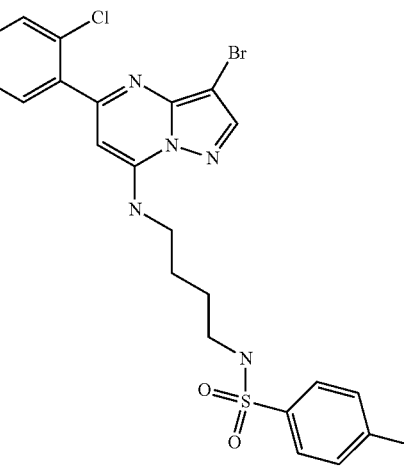 | 1. 6509<br>2. 554.3 |
| 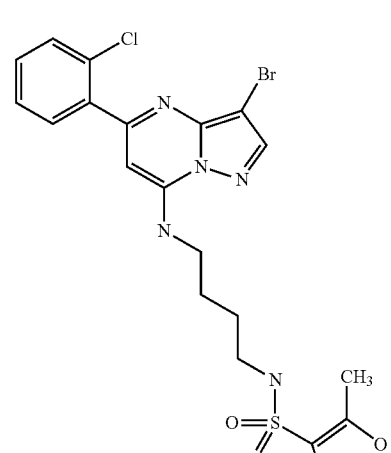 | 1. 6510<br>2. 555.31 |

TABLE 65-continued

| Product | 1. Ex. 2. m/z |
|---|---|
| (structure) | 1. 6511  2. 561.31 |
| (structure) | 1. 6512  2. 561.31 |
| (structure) | 1. 6213  2. 561.31 |
| (structure) | 1. 6514  2. 562.31 |
| (structure) | 1. 6515  2. 564.31 |
| (structure) | 1. 6516  2. 566.31 |

TABLE 65-continued
| Product | 1. Ex.<br>2. m/z |
|---|---|
| 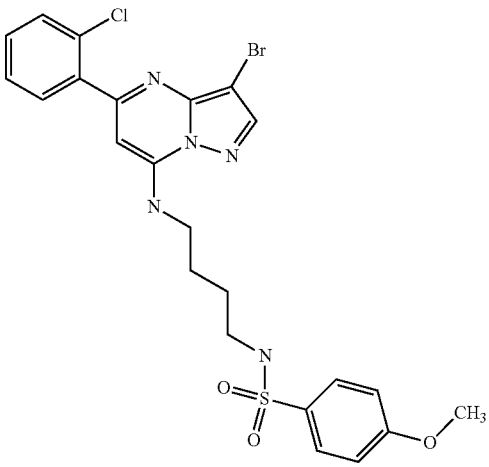 [SMILES: COc1ccc(S(=O)(=O)NCCCCNc2cc(-c3ccccc3Cl)nc3c(Br)cnn23)cc1] | 1. 6517<br>2. 566.31 |
| 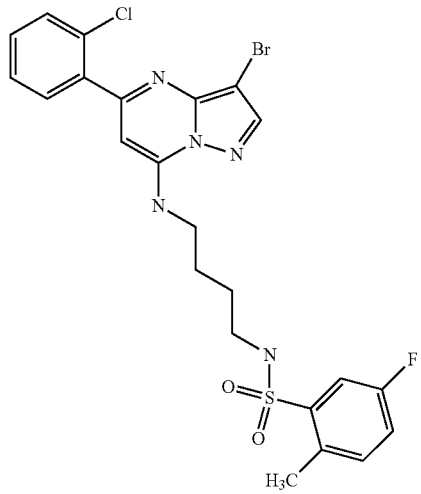 [SMILES: Cc1ccc(F)cc1S(=O)(=O)NCCCCNc1cc(-c2ccccc2Cl)nc2c(Br)cnn12] | 1. 6518<br>2. 568.31 |
| 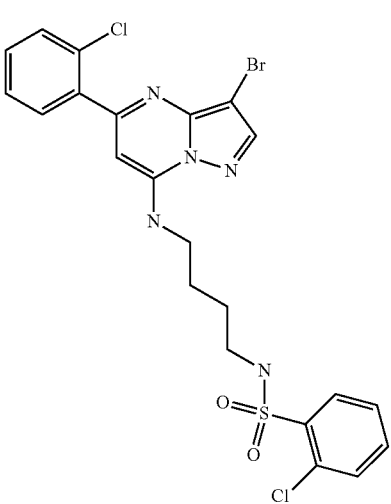 [SMILES: O=S(=O)(NCCCCNc1cc(-c2ccccc2Cl)nc2c(Br)cnn12)c1ccccc1Cl] | 1. 6519<br>2. 570.31 |
TABLE 65-continued
| Product | 1. Ex.<br>2. m/z |
|---|---|
| 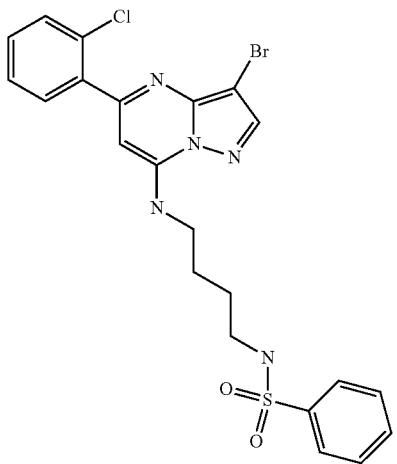 | 1. 6520<br>2. 570.31 |
| 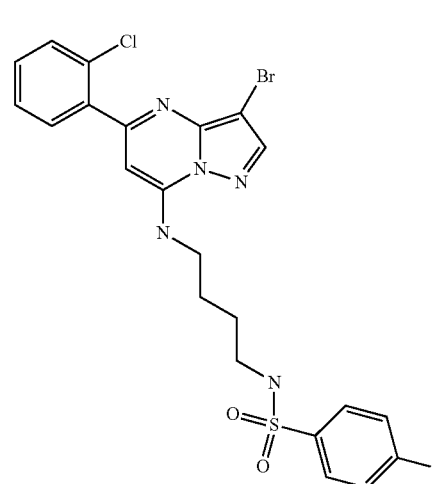 | 1. 6521<br>2. 570.31 |
| 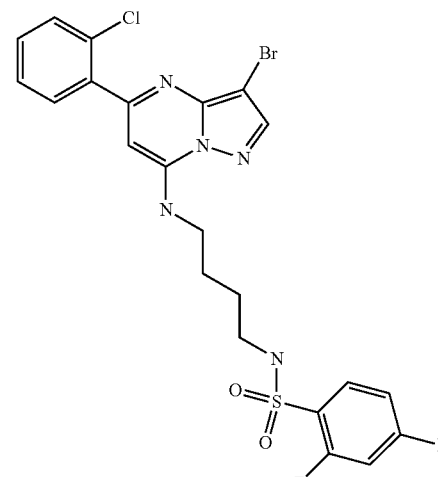 | 1. 6522<br>2. 572.31 |

TABLE 65-continued

| Product | 1. Ex. 2. m/z |
|---|---|
| [5-(2-chlorophenyl)-3-bromopyrazolo[1,5-a]pyrimidin-7-yl]amino-butyl-N-(2,6-difluorophenyl)sulfonamide | 1. 6523<br>2. 572.31 |
| [5-(2-chlorophenyl)-3-bromopyrazolo[1,5-a]pyrimidin-7-yl]amino-butyl-N-(3,4-difluorophenyl)sulfonamide | 1. 6524<br>2. 572.31 |
| [5-(2-chlorophenyl)-3-bromopyrazolo[1,5-a]pyrimidin-7-yl]amino-butyl-N-(3,5-difluorophenyl)sulfonamide | 1. 6525<br>2. 572.31 |
| [5-(2-chlorophenyl)-3-bromopyrazolo[1,5-a]pyrimidin-7-yl]amino-butyl-N-(5-chlorothiophen-2-yl)sulfonamide | 1. 6526<br>2. 576.32 |
| [5-(2-chlorophenyl)-3-bromopyrazolo[1,5-a]pyrimidin-7-yl]amino-butyl-N-(4-isopropylphenyl)sulfonamide | 1. 6527<br>2. 578.32 |
| [5-(2-chlorophenyl)-3-bromopyrazolo[1,5-a]pyrimidin-7-yl]amino-butyl-N-(naphthalen-1-yl)sulfonamide | 1. 6528<br>2. 586.32 |

TABLE 65-continued
| Product | 1. Ex. 2. m/z |
|---|---|
| 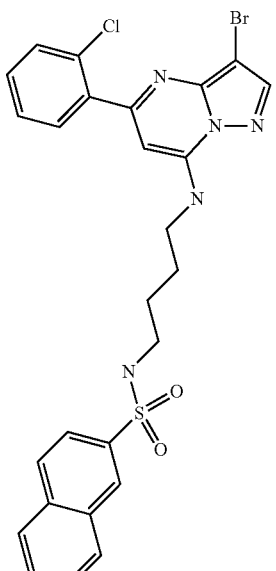 | 1. 6529 2. 586.32 |
| 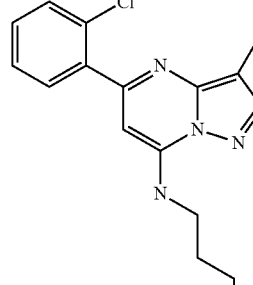 | 1. 6530 2. 588.32 |
| 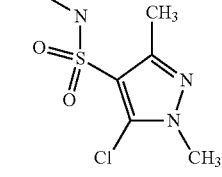 | 1. 6531 2. 588.32 |
| 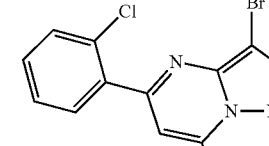 | 1. 6532 2. 592.33 |

TABLE 65-continued
| Product | 1. Ex.<br>2. m/z |
|---|---|
| 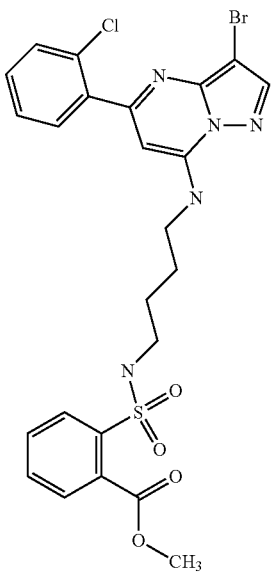 [SMILES: COC(=O)c1ccccc1S(=O)(=O)NCCCCNc1cc(-c2ccccc2Cl)nc2c(Br)cnn12] | 1. 6533<br>2. 594.33 |
| | 1. 6534<br>2. 596.33 |
TABLE 65-continued
| Product | 1. Ex.<br>2. m/z |
|---|---|
| 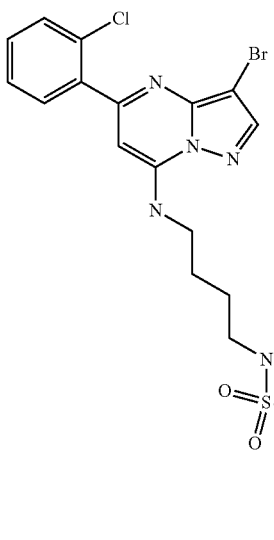 | 1. 6535<br>2. 596.33 |
| | 1. 6536<br>2. 600.33 |

TABLE 65-continued
| Product | 1. Ex.<br>2. m/z |
|---|---|
| 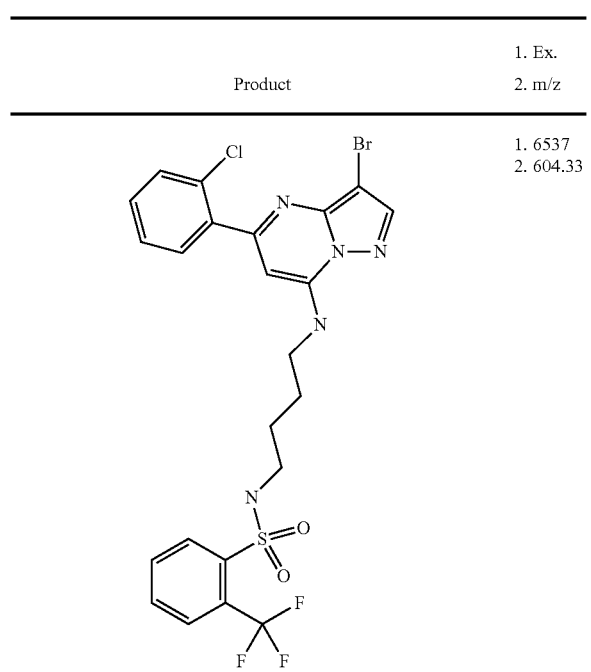 | 1. 6537<br>2. 604.33 |
| 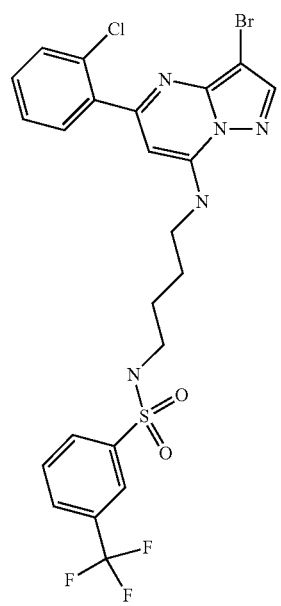 [SMILES: O=S(=O)(NCCCCNc1cc(-c2ccccc2Cl)nc2c(Br)cnn12)c1cccc(C(F)(F)F)c1] | 1. 6538<br>2. 604.33 |
TABLE 65-continued
| Product | 1. Ex.<br>2. m/z |
|---|---|
| 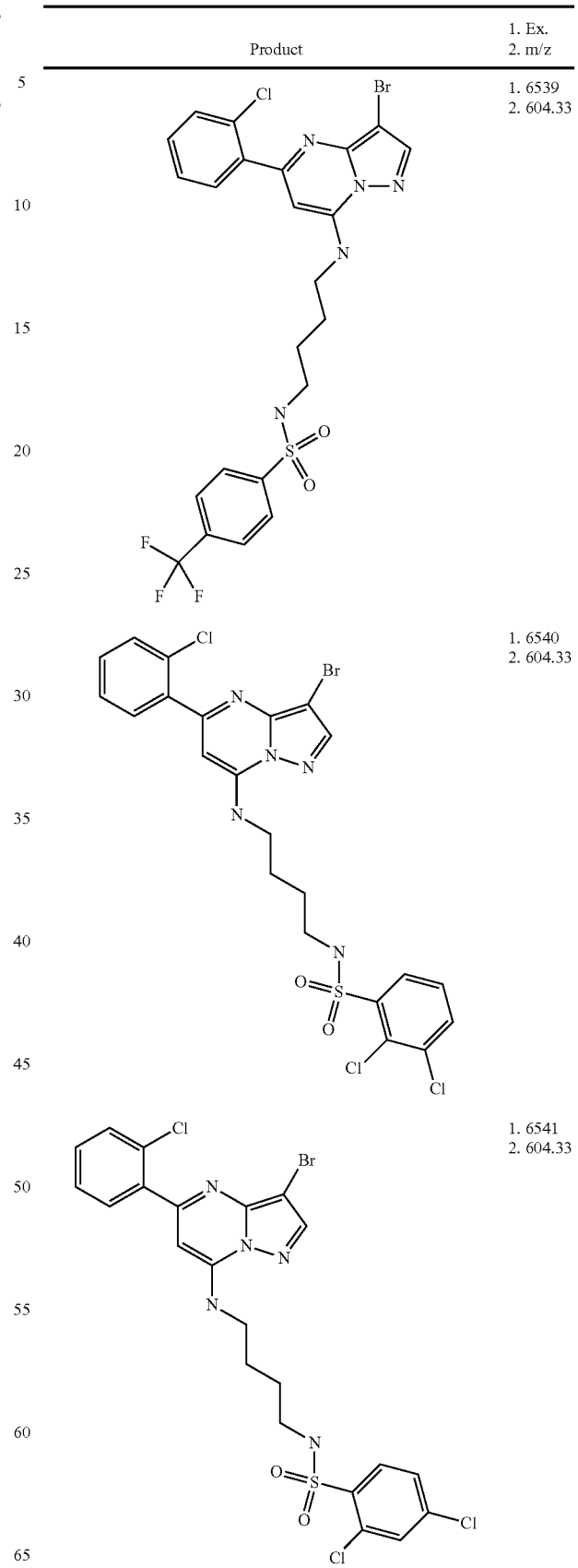 | 1. 6539<br>2. 604.33<br><br>1. 6540<br>2. 604.33<br><br>1. 6541<br>2. 604.33 |

TABLE 65-continued
| Product | 1. Ex.<br>2. m/z |
|---|---|
| 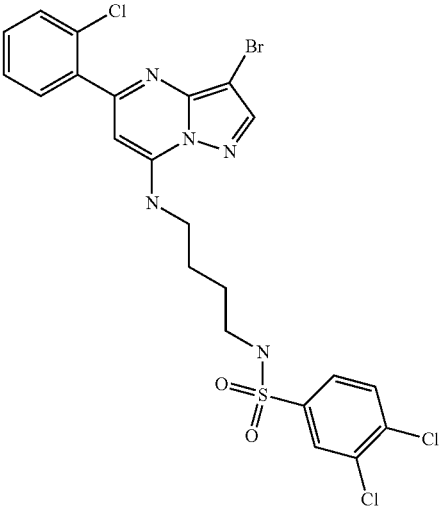 [SMILES: O=S(=O)(NCCCCNc1cc(-c2ccccc2Cl)nc2c(Br)cnn12)c1ccc(Cl)c(Cl)c1] | 1. 6542<br>2. 604.33 |
| 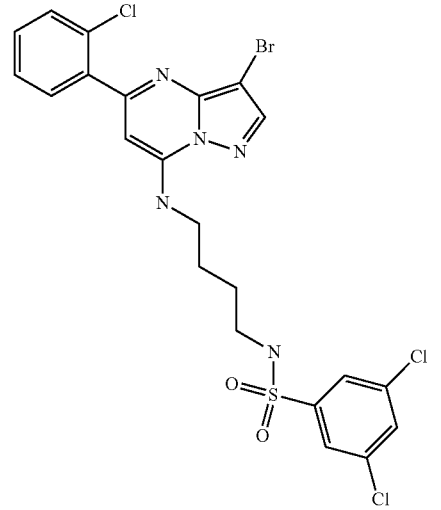 [SMILES: O=S(=O)(NCCCCNc1cc(-c2ccccc2Cl)nc2c(Br)cnn12)c1cc(Cl)cc(Cl)c1] | 1. 6543<br>2. 604.33 |
| 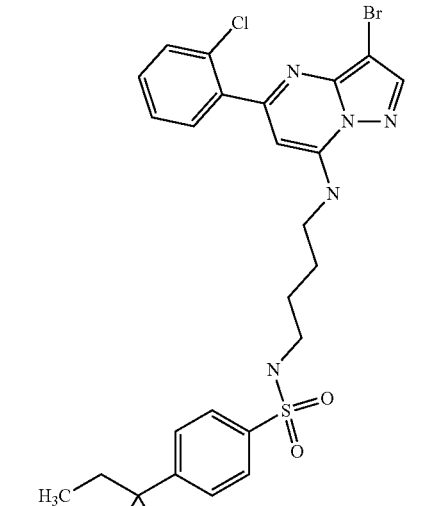 | 1. 6544<br>2. 606.33 |
TABLE 65-continued
| Product | 1. Ex.<br>2. m/z |
|---|---|
|  | 1. 6545<br>2. 588.32 |
| 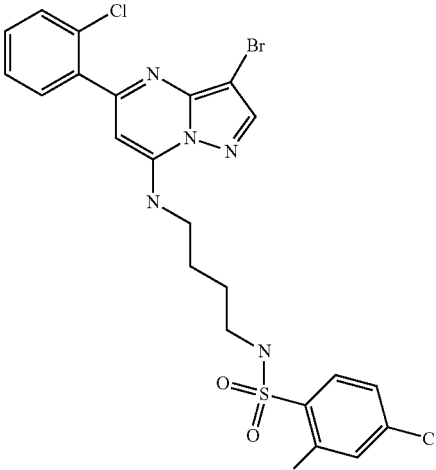 | 1. 6546<br>2. 612.34 |
| 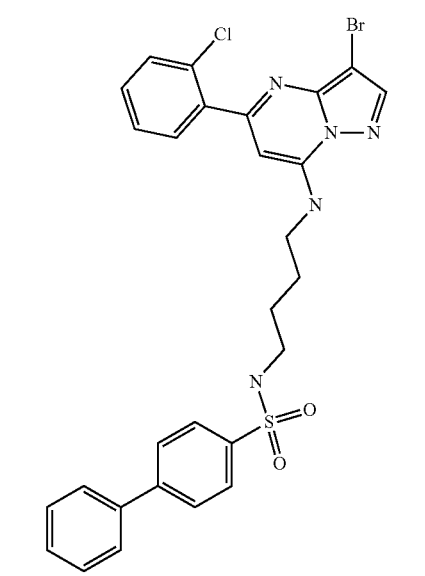 [SMILES: O=S(=O)(NCCCCNc1cc(-c2ccccc2Cl)nc2c(Br)cnn12)c1ccc(-c2ccccc2)cc1] | 1. 6547<br>2. 614.34 |

TABLE 65-continued
| Product | 1. Ex. 2. m/z |
|---|---|
| 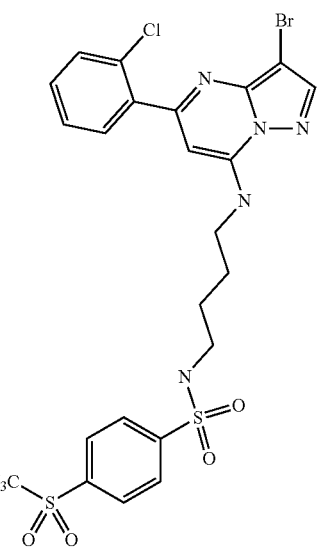 | 1. 6548 2. 614.34 |
| 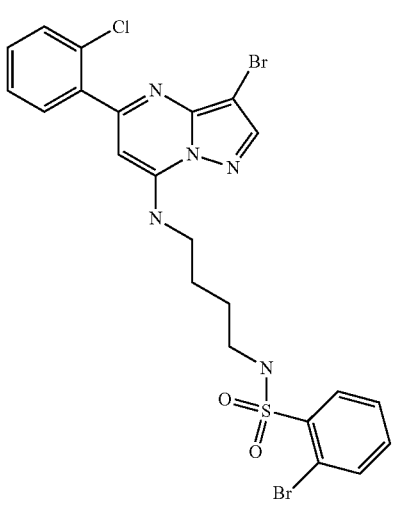 [SMILES: O=S(=O)(NCCCCNc1cc(-c2ccccc2Cl)nc2c(Br)cnn12)c1ccccc1Br] | 1. 6549 2. 614.34 |
|  | 1. 6550 2. 614.34 |
TABLE 65-continued
| Product | 1. Ex. 2. m/z |
|---|---|
| 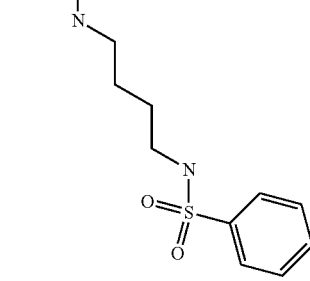 | 1. 6551 2. 620.34 |
| 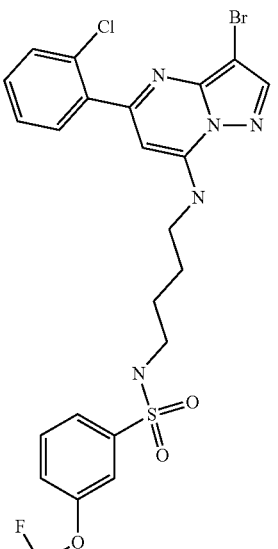 | 1. 6552 2. 620.34 |

TABLE 65-continued

| Product | 1. Ex. 2. m/z |
|---|---|
| (structure) | 1. 6553  2. 622.34 |
| (structure) | 1. 6554  2. 628.35 |
| (structure) | 1. 6555  2. 687.38 |
| (structure) | 1. 6556  2. 474.26 |
| (structure) | 1. 6557  2. 536.29 |

TABLE 65-continued
| Product | 1. Ex.<br>2. m/z |
|---|---|
| 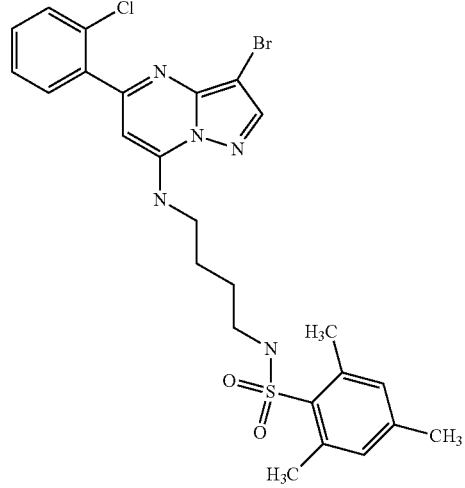 [SMILES: Cc1cc(C)c(S(=O)(=O)NCCCCNc2cc(-c3ccccc3Cl)nc3c(Br)cnn23)c(C)c1] | 1. 6558<br>2. 578.32 |
TABLE 67
| Product | 1. Ex.<br>2. m/z |
|---|---|
| | 1. 6701<br>2. 474.26 |
| | 1. 6702<br>2. 514.28 |
TABLE 67-continued
| Product | 1. Ex.<br>2. m/z |
|---|---|
| 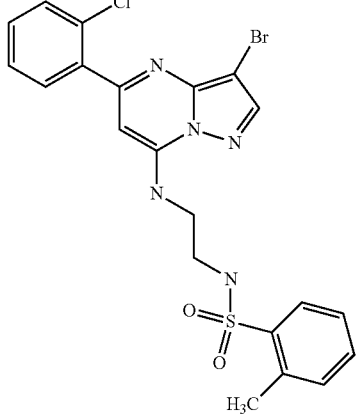 | 1. 6703<br>2. 522.29 |
| | 1. 6704<br>2. 522.29 |
| | 6705<br>2. 22.29 |

TABLE 67-continued
| Product | 1. Ex.<br>2. m/z |
|---|---|
| 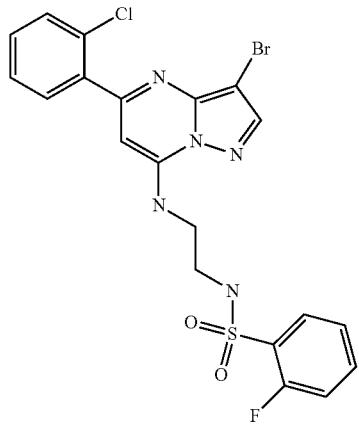 [SMILES: O=S(=O)(NCCNc1cc(-c2ccccc2Cl)nc2c(Br)cnn12)c1ccccc1F] | 1. 6706<br>2. 526.29 |
| 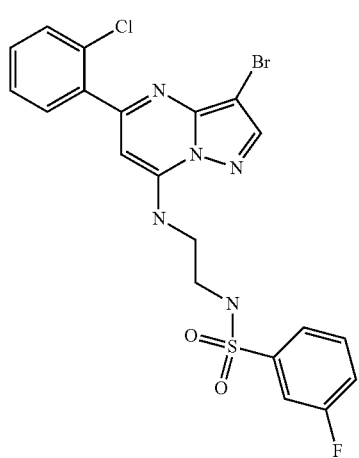 [SMILES: O=S(=O)(NCCNc1cc(-c2ccccc2Cl)nc2c(Br)cnn12)c1cccc(F)c1] | 1. 6707<br>2. 526.29 |
| 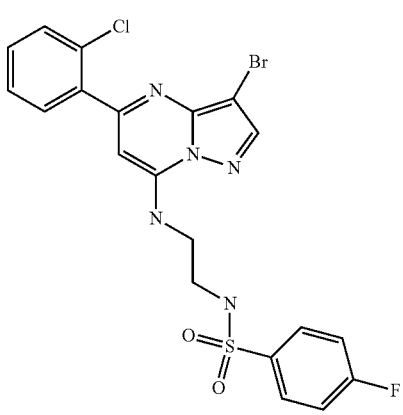 [SMILES: O=S(=O)(NCCNc1cc(-c2ccccc2Cl)nc2c(Br)cnn12)c1ccc(F)cc1] | 1. 6708<br>2. 526.29 |
TABLE 67-continued
| Product | 1. Ex.<br>2. m/z |
|---|---|
| 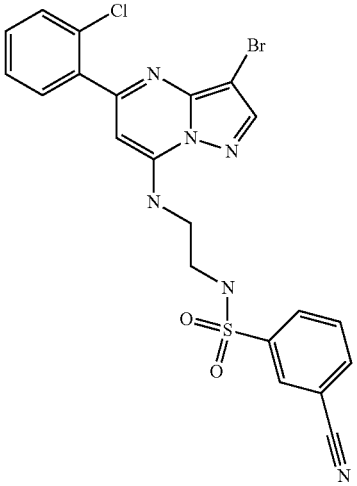 [SMILES: N#Cc1cccc(S(=O)(=O)NCCNc2cc(-c3ccccc3Cl)nc3c(Br)cnn23)c1] | 1. 6709<br>2. 533.29 |
| 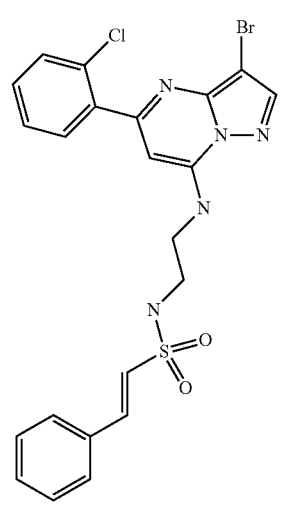 [SMILES: O=S(=O)(/C=C/c1ccccc1)NCCNc1cc(-c2ccccc2Cl)nc2c(Br)cnn12] | 1. 6710<br>2. 534.29 |
| 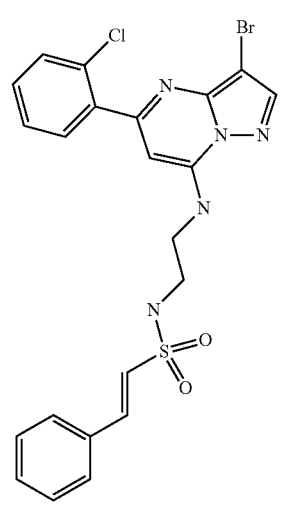 [SMILES: O=S(=O)(/C=C/c1ccccc1)NCCNc1cc(-c2ccccc2Cl)nc2c(Br)cnn12] | 1. 6711<br>2. 536.29 |

TABLE 67-continued
| Product | 1. Ex.<br>2. m/z |
|---|---|
| 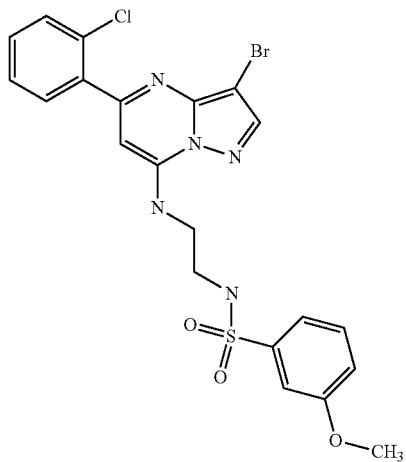 [SMILES: COc1cccc(S(=O)(=O)NCCNc2cc(-c3ccccc3Cl)nc3c(Br)cnn23)c1] | 1. 6712<br>2. 538.3 |
| 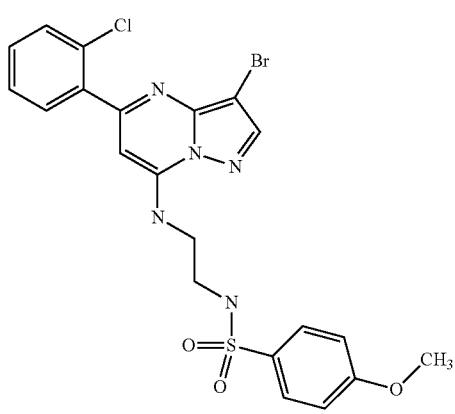 [SMILES: COc1ccc(S(=O)(=O)NCCNc2cc(-c3ccccc3Cl)nc3c(Br)cnn23)cc1] | 1. 6713<br>2. 538.3 |
| 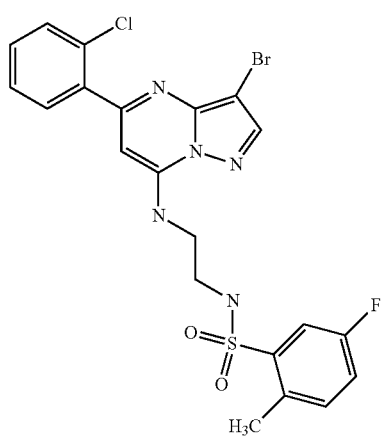 [SMILES: Cc1ccc(F)cc1S(=O)(=O)NCCNc1cc(-c2ccccc2Cl)nc2c(Br)cnn12] | 1. 6714<br>2. |
TABLE 67-continued
| Product | 1. Ex.<br>2. m/z |
|---|---|
| 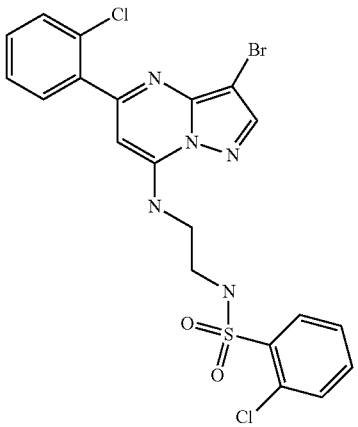 [SMILES: O=S(=O)(NCCNc1cc(-c2ccccc2Cl)nc2c(Br)cnn12)c1ccccc1Cl] | 1. 6715<br>2. 542.3 |
| 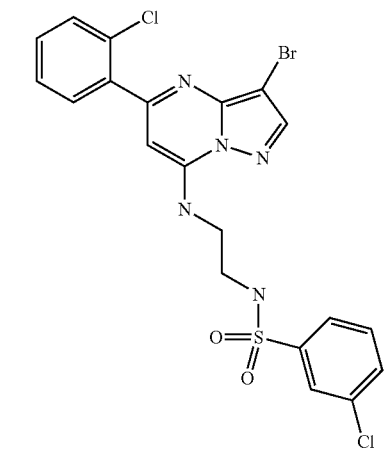 [SMILES: O=S(=O)(NCCNc1cc(-c2ccccc2Cl)nc2c(Br)cnn12)c1cccc(Cl)c1] | 1. 6716<br>2. 542.3 |
| | 1. 6717<br>2. 542.3 |

TABLE 67-continued
| Product | 1. Ex. 2. m/z |
|---|---|
| 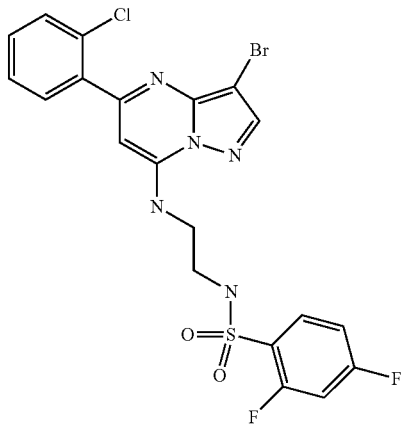 [SMILES: O=S(=O)(NCCNc1cc(-c2ccccc2Cl)nc2c(Br)cnn12)c1ccc(F)cc1F] | 1. 6718 2. 544.3 |
| 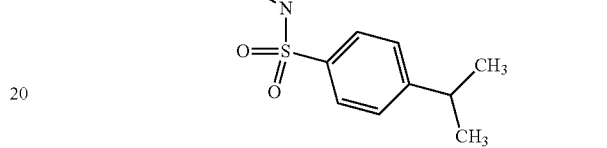 | 1. 6719 2. 544.3 |
| (structure) | 1. 6720 2. 544.3 |
TABLE 67-continued
| Product | 1. Ex. 2. m/z |
|---|---|
| 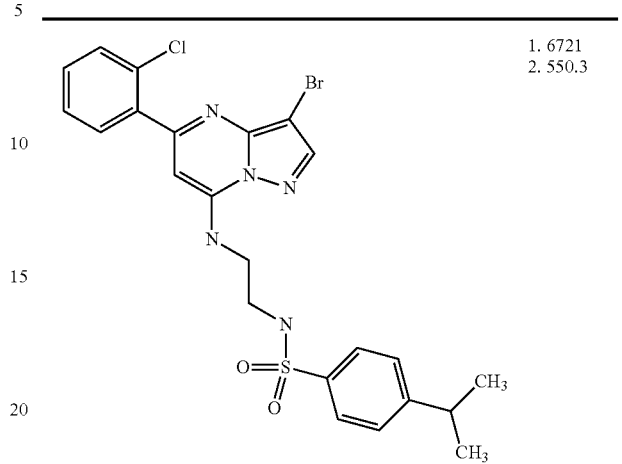 | 1. 6721 2. 550.3 |
| (structure) | 1. 6722 2. 558.31 |
| (structure) | 1. 6723 2. 558.31 |

TABLE 67-continued
| Product | 1. Ex. 2. m/z |
|---|---|
| 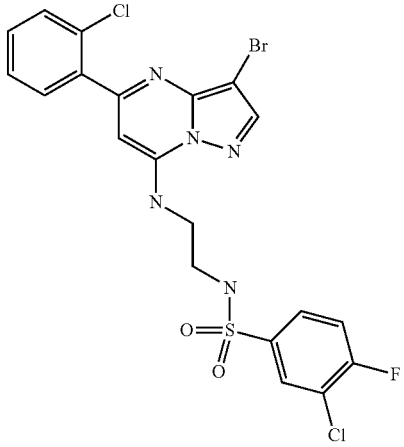 [SMILES: O=S(=O)(NCCNc1cc(-c2ccccc2Cl)nc2c(Br)cnn12)c1ccc(F)c(Cl)c1] | 1. 6724 2. 560.31 |
| 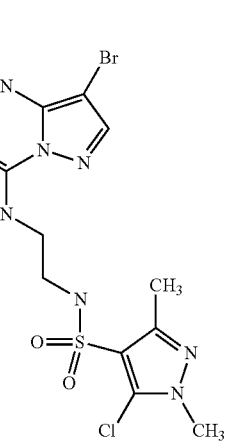 | 1. 6725 2. 560.31 |
| 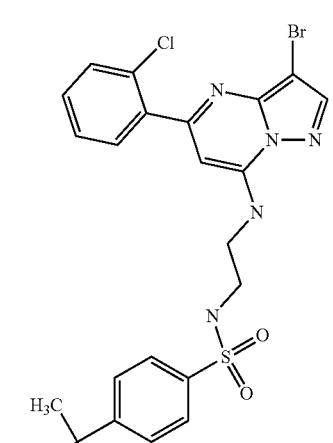 | 1. 6726 2. 564.31 |
| 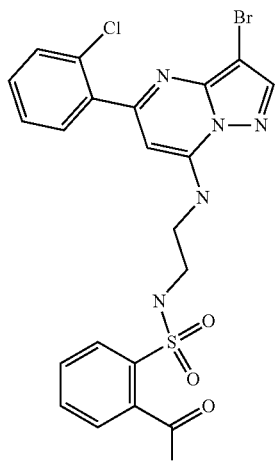 | 1. 6727 2. 566.31 |
| 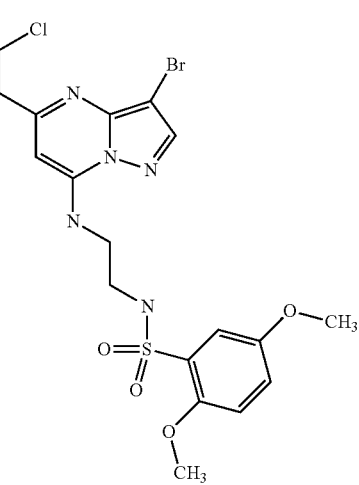 | 1. 6728 2. 568.31 |
| 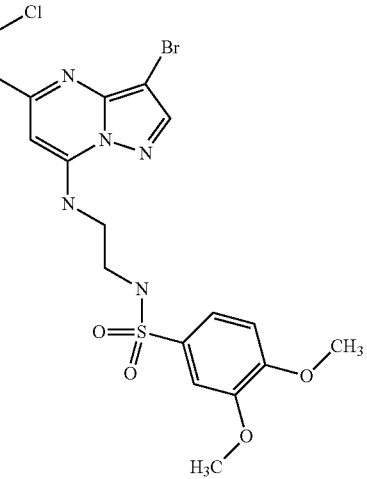 | 1. 6729 2. 568.31 |

TABLE 67-continued

| Product | 1. Ex.<br>2. m/z |
|---|---|
| (structure) | 1. 6730<br>2. 572.31 |
| (structure) | 1. 6731<br>2. 576.32 |
| (structure) | 1. 6732<br>2. 576.32 |
| (structure) | 1. 6733<br>2. 576.32 |
| (structure) | 1. 6734<br>2. 576.32 |
| (structure) | 1. 6735<br>2. 576.32 |

TABLE 67-continued

| Product | 1. Ex.<br>2. m/z |
|---|---|
| [5-(2-chlorophenyl)-3-bromo-pyrazolo[1,5-a]pyrimidin-7-yl]-NH-CH₂CH₂-N(H)-SO₂-(3,4-dichlorophenyl) | 1. 6736<br>2. 576.32 |
| [5-(2-chlorophenyl)-3-bromo-pyrazolo[1,5-a]pyrimidin-7-yl]-NH-CH₂CH₂-N(H)-SO₂-(3,5-dichlorophenyl) | 1. 6737<br>2. 576.32 |
| [5-(2-chlorophenyl)-3-bromo-pyrazolo[1,5-a]pyrimidin-7-yl]-NH-CH₂CH₂-N(H)-SO₂-(4-tert-amylphenyl) | 1. 6738<br>2. 576.32 |
| [5-(2-chlorophenyl)-3-bromo-pyrazolo[1,5-a]pyrimidin-7-yl]-NH-CH₂CH₂-N(H)-SO₂-(biphenyl-4-yl) | 1. 6739<br>2. 584.32 |
| [5-(2-chlorophenyl)-3-bromo-pyrazolo[1,5-a]pyrimidin-7-yl]-NH-CH₂CH₂-N(H)-SO₂-(4-methylsulfonylphenyl) | 1. 6740<br>2. 586.32 |
| [5-(2-chlorophenyl)-3-bromo-pyrazolo[1,5-a]pyrimidin-7-yl]-NH-CH₂CH₂-N(H)-SO₂-(2-bromophenyl) | 1. 6741<br>2. 586.32 |

TABLE 67-continued
| Product | 1. Ex.<br>2. m/z |
|---|---|
| 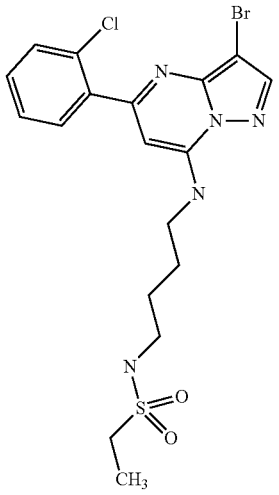 [SMILES: CCS(=O)(=O)NCCCCNc1cc(-c2ccccc2Cl)nc2c(Br)cnn12] | 1. 6742<br>2. 586.32 |
| 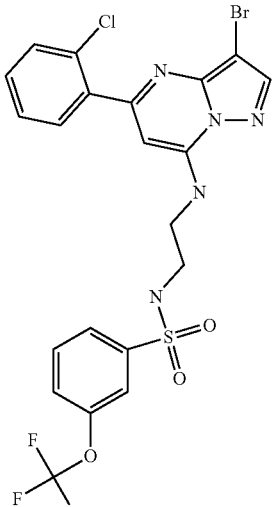 | 1. 6743<br>2. 592.33 |
TABLE 67-continued
| Product | 1. Ex.<br>2. m/z |
|---|---|
| 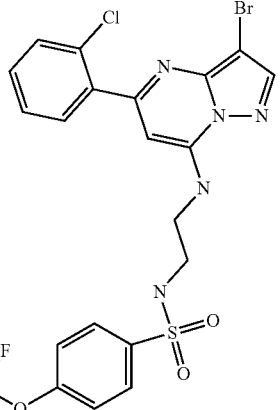 | 1. 6744<br>2. 592.33 |
| 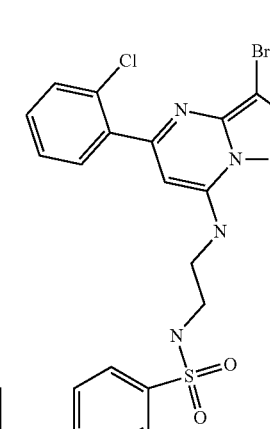 | 1. 6745<br>2. 600.33 |
TABLE 68
| Product | 1. Ex.<br>2. m/z |
|---|---|
| 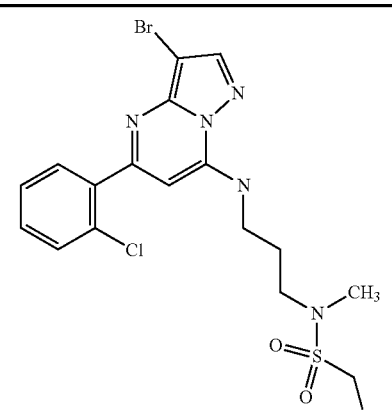 | 1. 6801<br>2. 488.27 |

TABLE 68-continued
| Product | 1. Ex.<br>2. m/z |
|---|---|
| 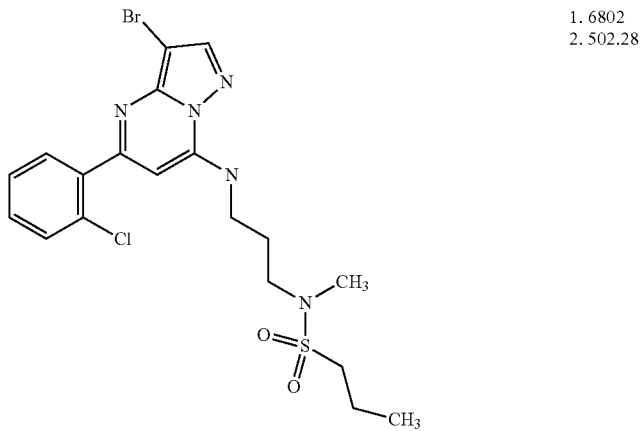 | 1. 6802<br>2. 502.28 |
| 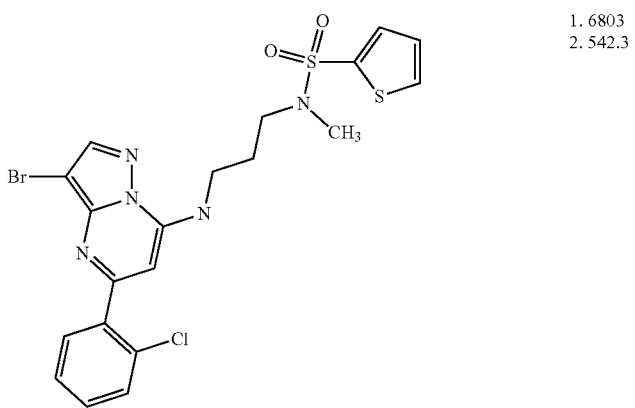 | 1. 6803<br>2. 542.3 |
| 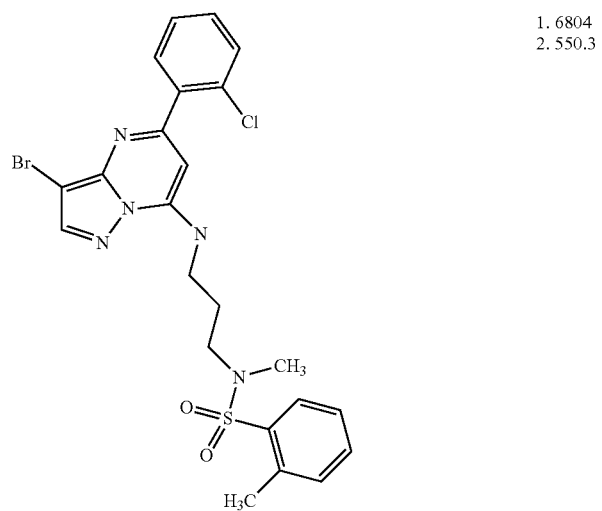 | 1. 6804<br>2. 550.3 |

TABLE 68-continued

| Product | 1. Ex.<br>2. m/z |
|---|---|
| (structure) | 1. 68058<br>2. 550.3 |
| (structure) | 1. 6806<br>2. 550.3 |
| (structure) | 1. 6807<br>2. 554.3 |

TABLE 68-continued
| Product | 1. Ex.<br>2. m/z |
|---|---|
| 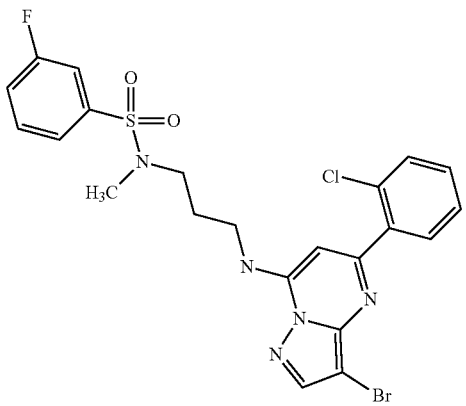 [SMILES: CN(CCCNc1cc(-c2ccccc2Cl)nc2c(Br)cnn12)S(=O)(=O)c1cccc(F)c1] | 1. 6808<br>2. 554.3 |
| 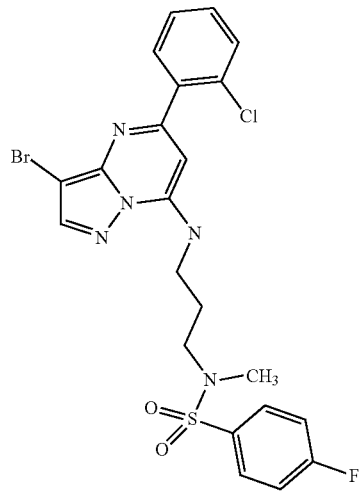 [SMILES: CN(CCCNc1cc(-c2ccccc2Cl)nc2c(Br)cnn12)S(=O)(=O)c1ccc(F)cc1] | 1. 6809<br>2. 554.3 |
| 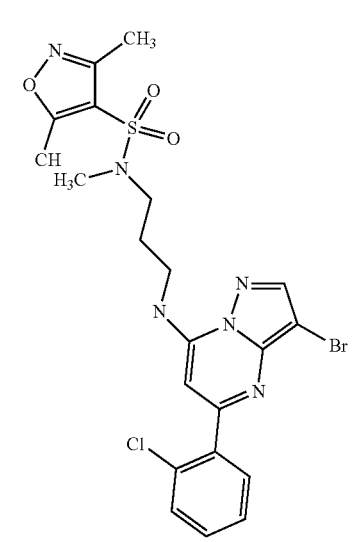 [SMILES: Cc1noc(C)c1S(=O)(=O)N(C)CCCNc1cc(-c2ccccc2Cl)nc2c(Br)cnn12] | 1. 6810<br>2. 555.31 |

TABLE 68-continued
| Product | 1. Ex.<br>2. m/z |
|---|---|
| 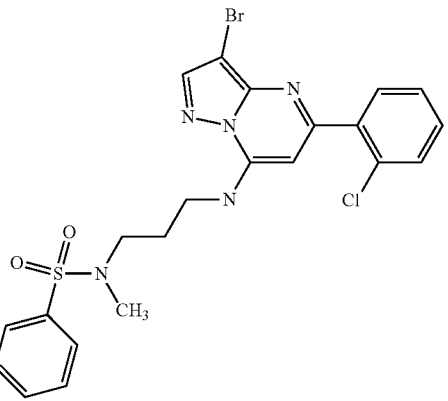 | 1. 6811<br>2. 561.31 |
| 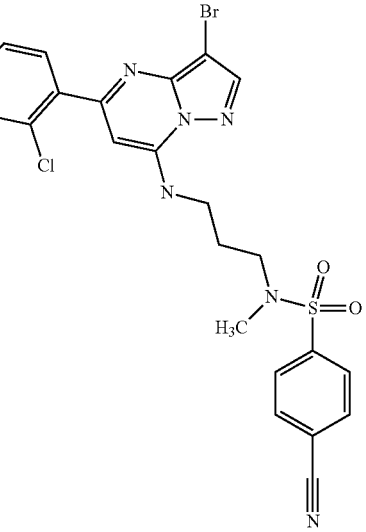 | 1. 6812<br>2. 561.31 |
| 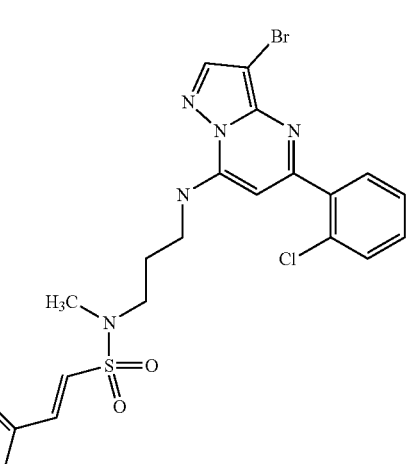 | 1. 6813<br>2. 562.31 |

TABLE 68-continued
| Product | 1. Ex.<br>2. m/z |
|---|---|
| 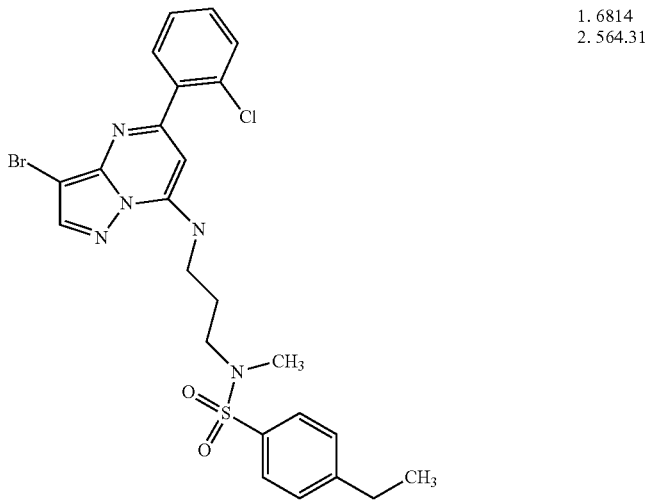 | 1. 6814<br>2. 564.31 |
| 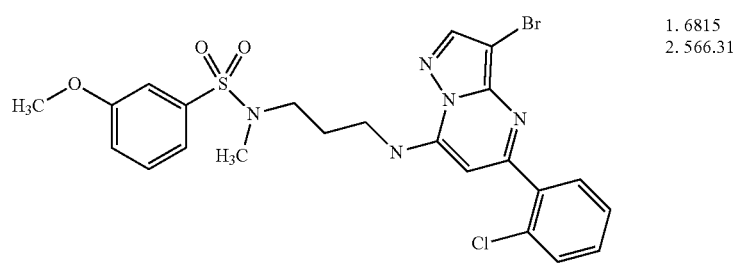 | 1. 6815<br>2. 566.31 |
| 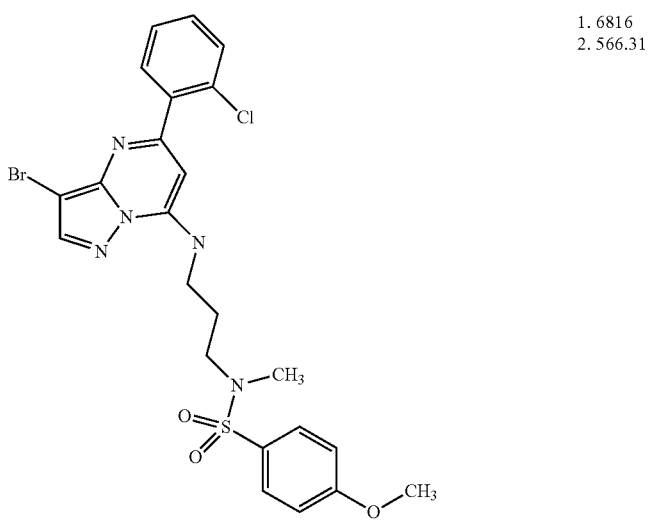 | 1. 6816<br>2. 566.31 |

TABLE 68-continued
| Product | 1. Ex.<br>2. m/z |
|---|---|
| 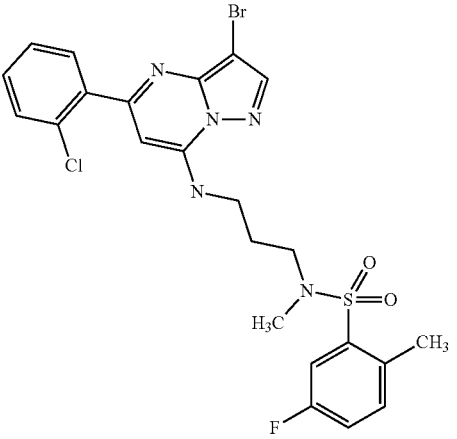 [SMILES: Cc1ccc(F)cc1S(=O)(=O)N(C)CCCNc1cc(-c2ccccc2Cl)nc2c(Br)cnn12] | 1. 6817<br>2. 568.31 |
| 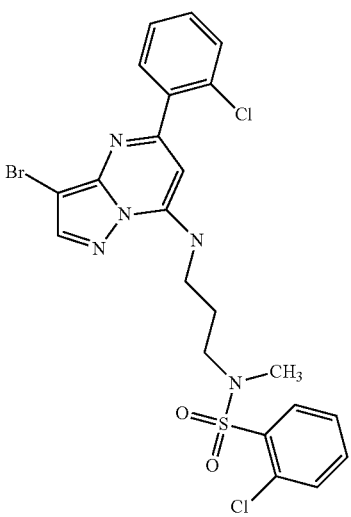 [SMILES: CN(CCCNc1cc(-c2ccccc2Cl)nc2c(Br)cnn12)S(=O)(=O)c1ccccc1Cl] | 1. 6818<br>2. 570.31 |
| 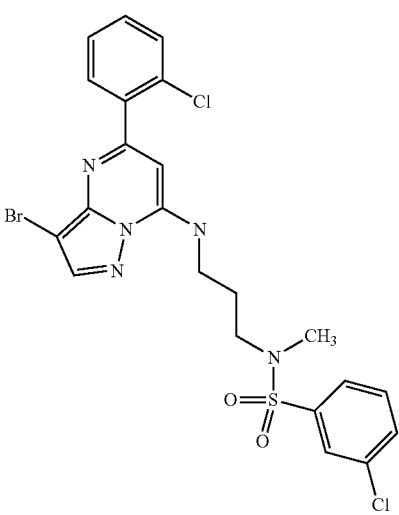 [SMILES: CN(CCCNc1cc(-c2ccccc2Cl)nc2c(Br)cnn12)S(=O)(=O)c1cccc(Cl)c1] | 1. 6819<br>2. 570.31 |

TABLE 68-continued

| Product | 1. Ex.<br>2. m/z |
|---|---|
| (structure) | 1. 6820<br>2. 570.31 |
| (structure) | 1. 6821<br>2. 571.31 |
| (structure) | 1. 6822<br>2. 572.31 |

TABLE 68-continued
| Product | 1. Ex.<br>2. m/z |
|---|---|
| 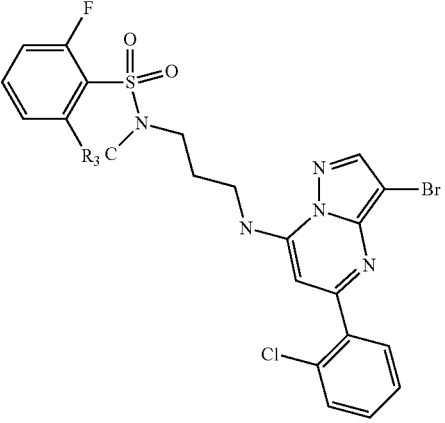 | 1. 6823<br>2. 572.31 |
| 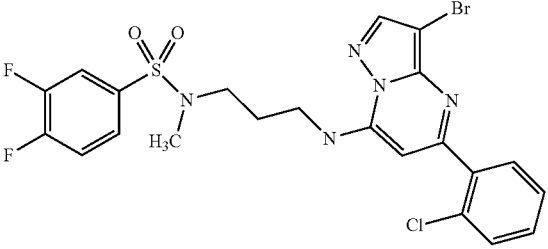 [SMILES: CN(CCCNc1cc(-c2ccccc2Cl)nc2c(Br)cnn12)S(=O)(=O)c1ccc(F)c(F)c1] | 1. 6824<br>2. 572.31 |
| 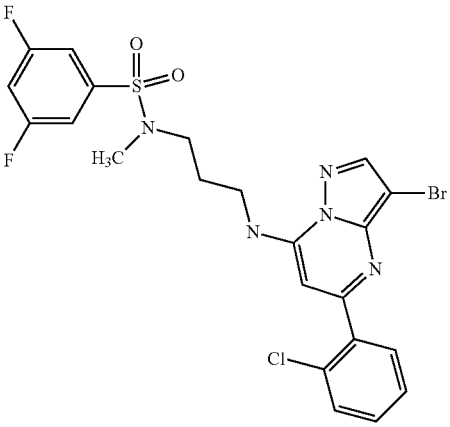 [SMILES: CN(CCCNc1cc(-c2ccccc2Cl)nc2c(Br)cnn12)S(=O)(=O)c1cc(F)cc(F)c1] | 1. 6825<br>2. 572.31 |
| 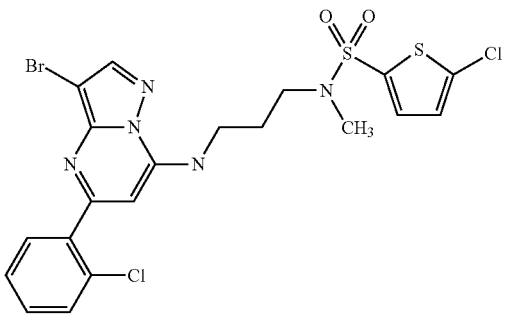 [SMILES: CN(CCCNc1cc(-c2ccccc2Cl)nc2c(Br)cnn12)S(=O)(=O)c1ccc(Cl)s1] | 1. 6826<br>2. 576.32 |

TABLE 68-continued
| Product | 1. Ex.<br>2. m/z |
|---|---|
| 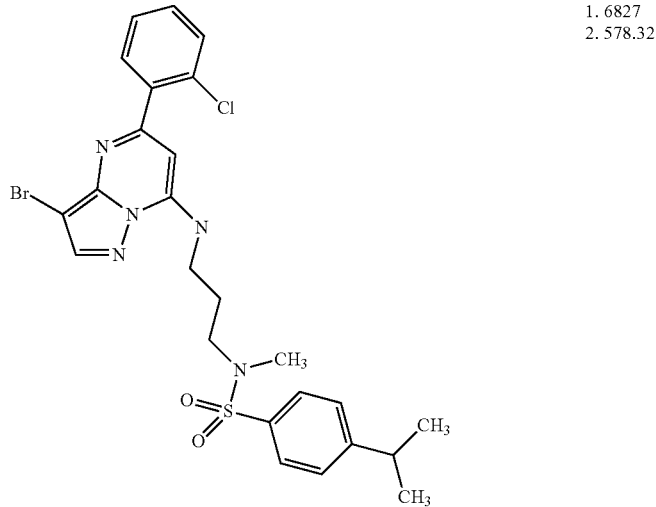 | 1. 6827<br>2. 578.32 |
| 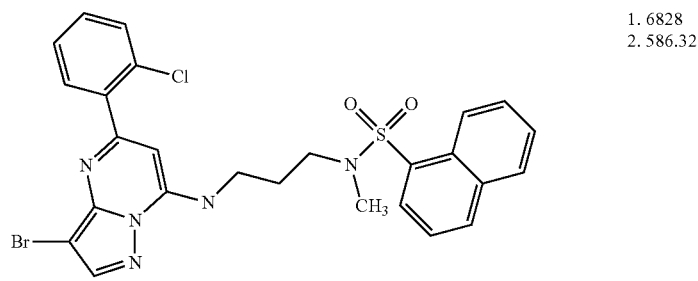 | 1. 6828<br>2. 586.32 |
| 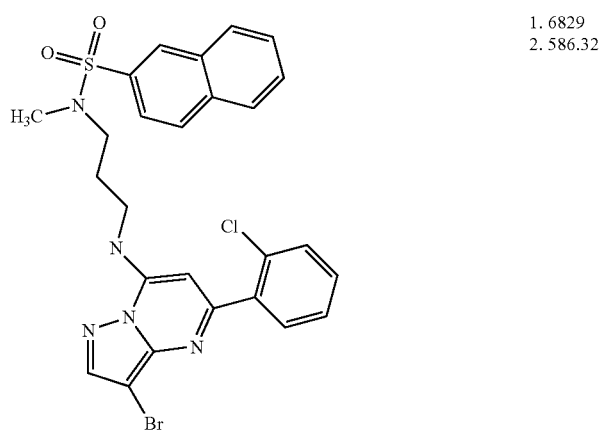 | 1. 6829<br>2. 586.32 |

TABLE 68-continued
| Product | 1. Ex.<br>2. m/z |
|---|---|
| 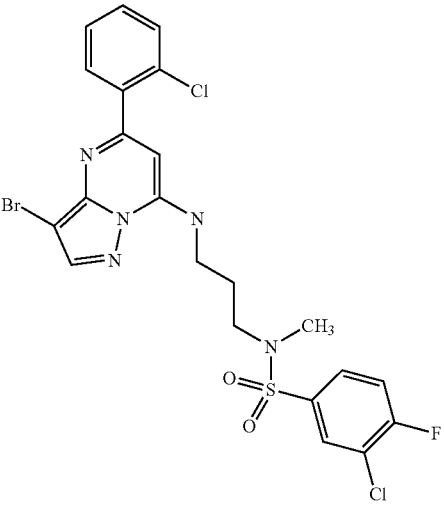 [SMILES: CN(CCCNc1cc(-c2ccccc2Cl)nc2c(Br)cnn12)S(=O)(=O)c1ccc(F)c(Cl)c1] | 1. 6830<br>2. 588.32 |
| 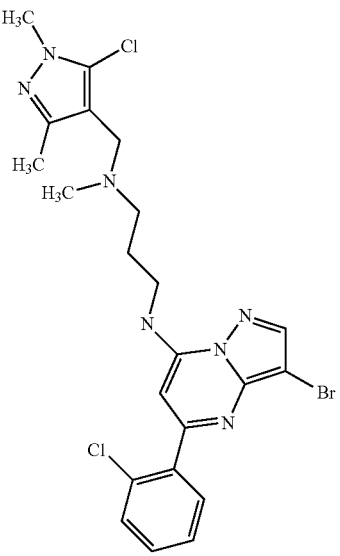 [SMILES: Cc1nn(C)c(Cl)c1CN(C)CCCNc1cc(-c2ccccc2Cl)nc2c(Br)cnn12] | 1. 6831<br>2. 588.32 |
| 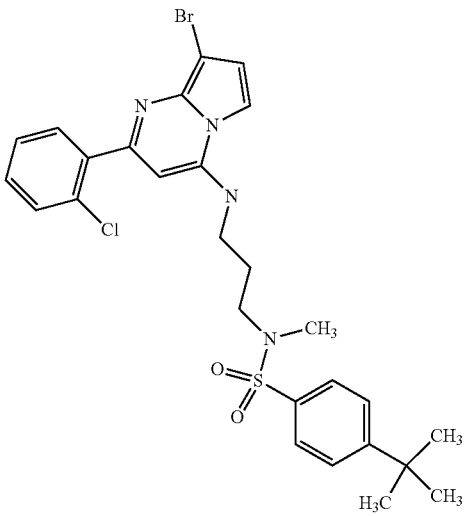 [SMILES: CN(CCCNc1cc(-c2ccccc2Cl)nc2c(Br)ccn12)S(=O)(=O)c1ccc(C(C)(C)C)cc1] | 1. 6832<br>2. 592.33 |

TABLE 68-continued
| Product | 1. Ex.<br>2. m/z |
|---|---|
| 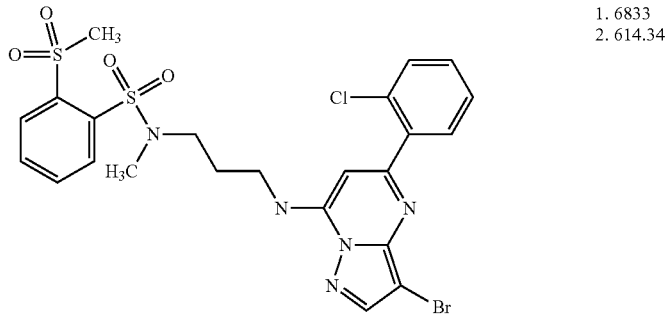 | 1. 6833<br>2. 614.34 |
| 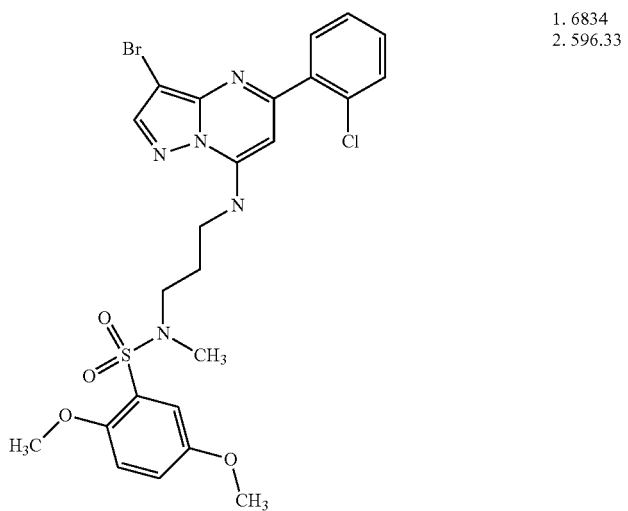 | 1. 6834<br>2. 596.33 |
| 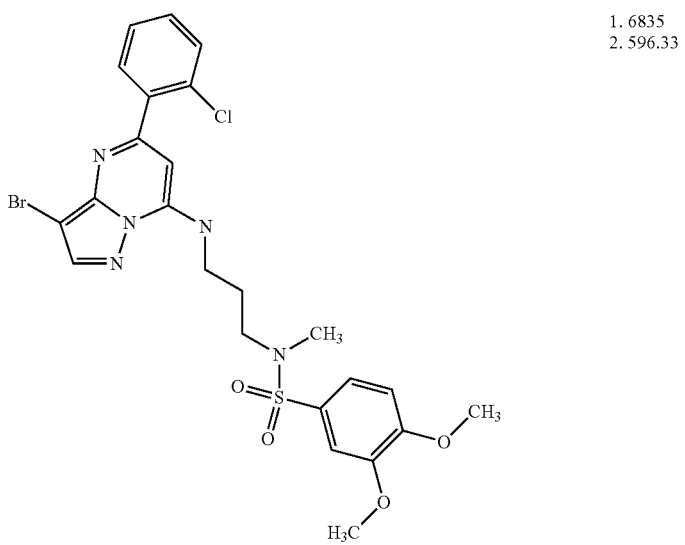 | 1. 6835<br>2. 596.33 |

TABLE 68-continued

| Product | 1. Ex.<br>2. m/z |
|---|---|
| (structure) | 1. 6836<br>2. 600.33 |
| (structure) | 1. 6837<br>2. 602.33 |
| (structure) | 1. 6838<br>2. 604.33 |

TABLE 68-continued
| Product | 1. Ex.<br>2. m/z |
|---|---|
| 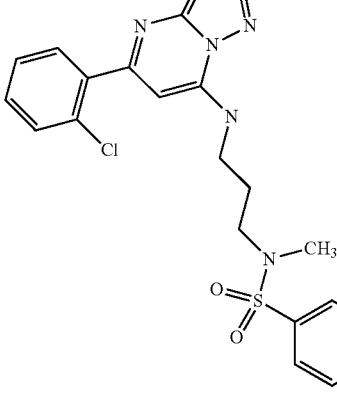 | 1. 6839<br>2. 604.33 |
| 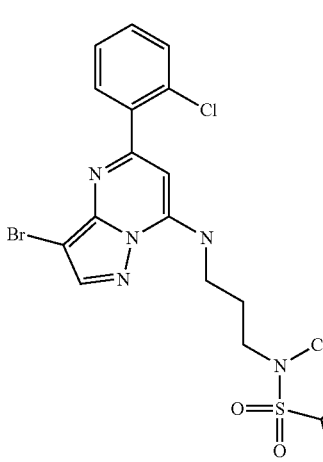 | 1. 6840<br>2. 604.33 |
| 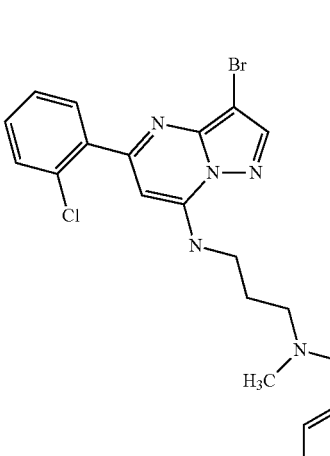 | 1. 6841<br>2. 604.33 |

TABLE 68-continued

| Product | 1. Ex.<br>2. m/z |
|---|---|
| [structure] | 1. 6842<br>2. 604.33 |
| [structure] | 1. 6843<br>2. 605.33 |
| [structure] | 1. 6844<br>2. 604.33 |

TABLE 68-continued

| Product | 1. Ex.<br>2. m/z |
|---------|------------------|
| | 1. 6845<br>2. 604.33 |
| | 1. 6846<br>2. 606.33 |
| | 1. 6847<br>2. 588.32 |

TABLE 68-continued
| Product | 1. Ex.<br>2. m/z |
|---|---|
| 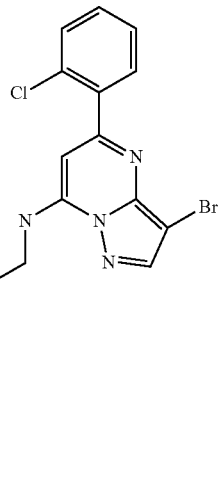 | 1. 6848<br>2. 610.34 |
| 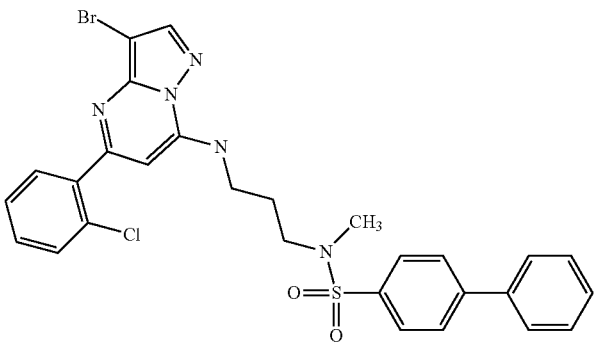 [SMILES: CN(CCCNc1cc(-c2ccccc2Cl)nc2c(Br)cnn12)S(=O)(=O)c1ccc(-c2ccccc2)cc1] | 1. 6849<br>2. 612.34 |
| 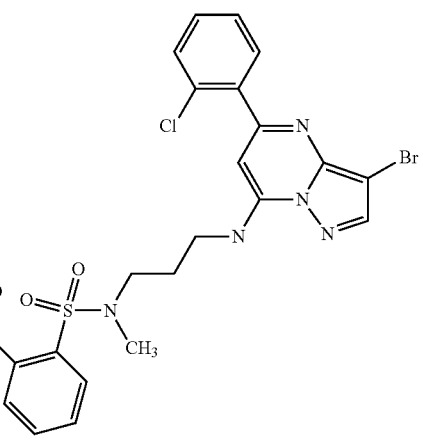 | 1. 6850<br>2. 594.33 |
| 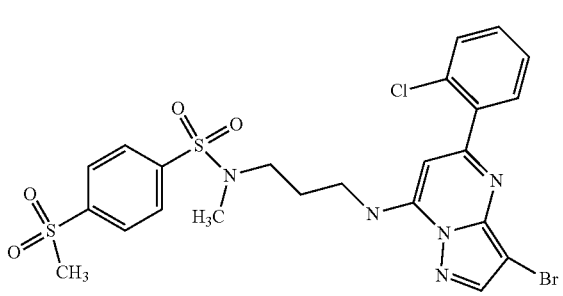 [SMILES: CN(CCCNc1cc(-c2ccccc2Cl)nc2c(Br)cnn12)S(=O)(=O)c1ccc(S(C)(=O)=O)cc1] | 1. 6851<br>2. 614.34 |

TABLE 68-continued
| Product | 1. Ex.<br>2. m/z |
|---|---|
| 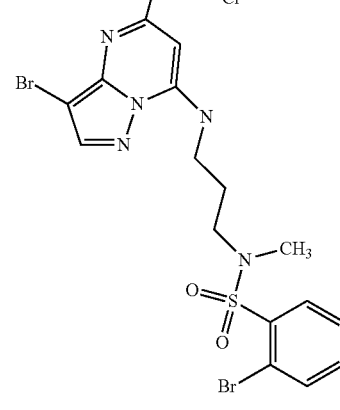 | 1. 6852<br>2. 614.34 |
| 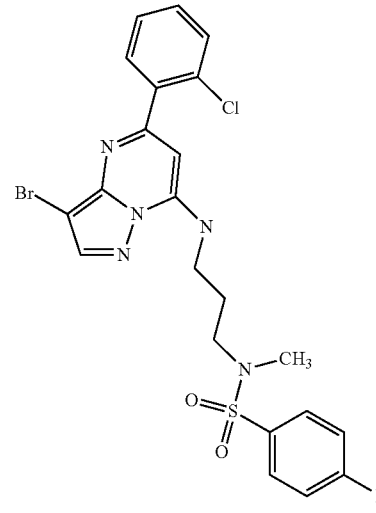 | 1. 6853<br>2. 614.34 |
| 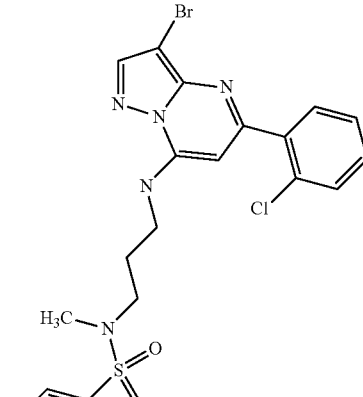 | 1. 6854<br>2. 620.34 |

TABLE 68-continued
| Product | 1. Ex.<br>2. m/z |
|---|---|
| 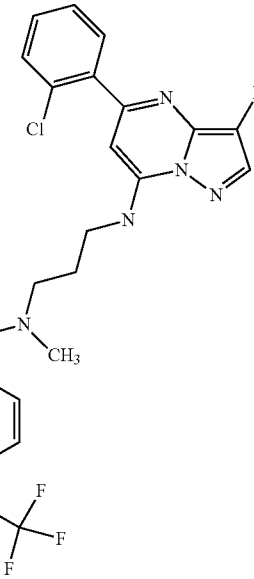 | 1. 6855<br>2. 620.34 |
| 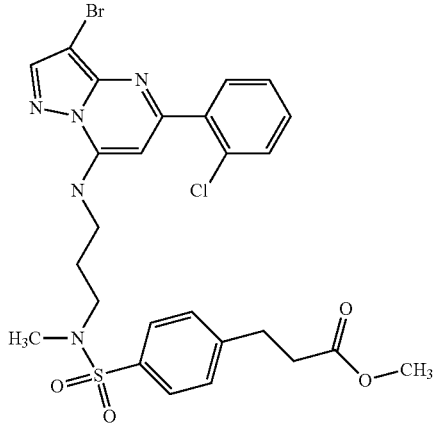 [SMILES: COC(=O)CCc1ccc(S(=O)(=O)N(C)CCCNc2cc(-c3ccccc3Cl)nc3c(Br)cnn23)cc1] | 1. 6856<br>2. 620.34 |
| 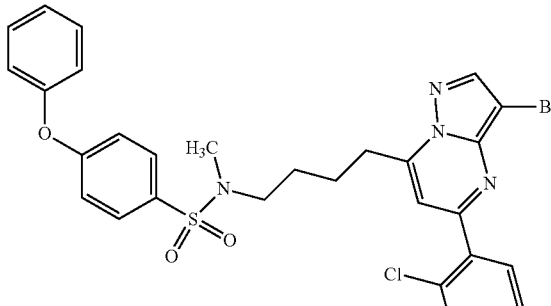 | 1. 6856<br>2. 628.35 |

TABLE 68-continued
| Product | 1. Ex.<br>2. m/z |
|---|---|
| 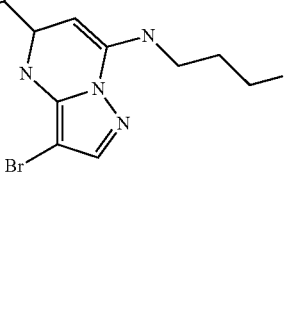 | 1. 6857<br>2. 687.38 |
| 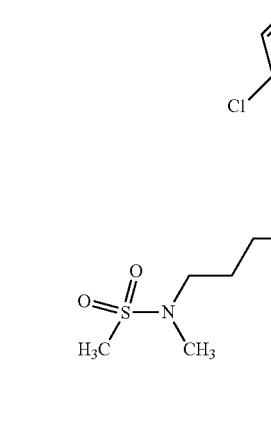 | 1. 6859<br>2. 474.26 |
| 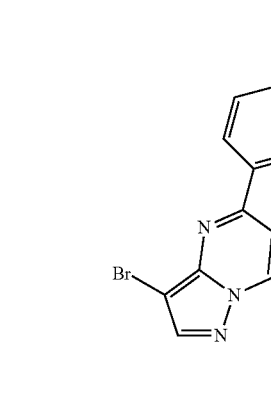 | 1. 6860<br>2. 536.29 |

TABLE 69

| Product | 1. Ex. 2. m/z |
|---|---|
| (structure) | 1. 6901  2. 514.28 |
| (structure) | 1. 6902  2. 568.31 |
| (structure) | 1. 6903  2. 576.32 |
| (structure) | 1. 6904  2. 576.32 |

TABLE 69-continued

| Product | 1. Ex. 2. m/z |
|---|---|
| (structure) | 1. 6905  2. 576.32 |
| (structure) | 1. 6906  2. 580.32 |
| (structure) | 1. 6907  2. 580.32 |

TABLE 69-continued

| Product | 1. Ex. 2. m/z |
|---|---|
| (structure) | 1. 6908 2. 580.32 |
| (structure) | 1. 6909 2. 581.32 |
| (structure) | 1. 6910 2. 587.32 |
| (structure) | 1. 6911 2. 587.32 |
| (structure) | 1. 6912 2. 588.32 |
| (structure) | 1. 6913 2. 590.32 |

TABLE 69-continued

| Product | 1. Ex.<br>2. m/z |
|---|---|
| (structure) | 1. 6914<br>2. 592.33 |
| (structure) | 1. 6915<br>2. 592.33 |
| (structure) | 1. 6916<br>2. 594.33 |
| (structure) | 1. 6917<br>2. 596.33 |
| (structure) | 1. 6918<br>2. 596.33 |
| (structure) | 1. 6919<br>2. 596.33 |
| (structure) | 1. 6920<br>2. 598.33 |

TABLE 69-continued

| Product | 1. Ex. 2. m/z |
|---|---|
| (structure) | 1. 6921  2. 589.33 |
| (structure) | 1. 6922  2. 598.33 |
| (structure) | 1. 6923  2. 598.33 |
| (structure) | 1. 6924  2. 598.33 |
| (structure) | 1. 6925  2. 602.33 |
| (structure) | 1. 6926  2. 604.33 |
| (structure) | 1. 6927  2. 612.34 |

TABLE 69-continued
| Product | 1. Ex.<br>2. m/z |
|---|---|
| 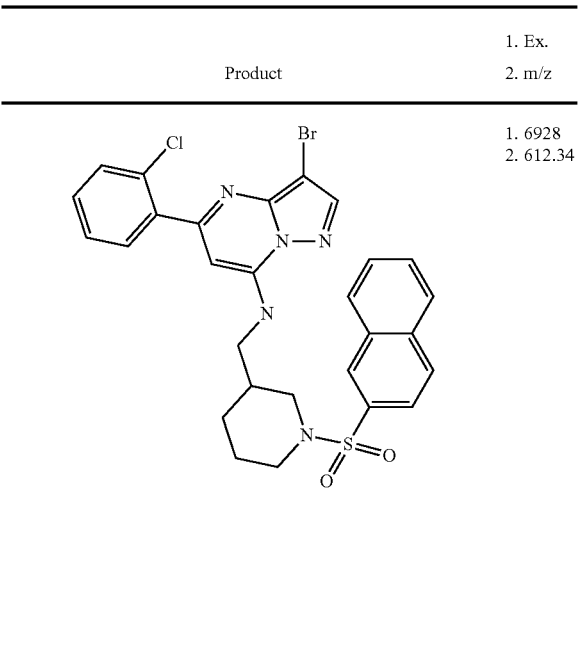 | 1. 6928<br>2. 612.34 |
| 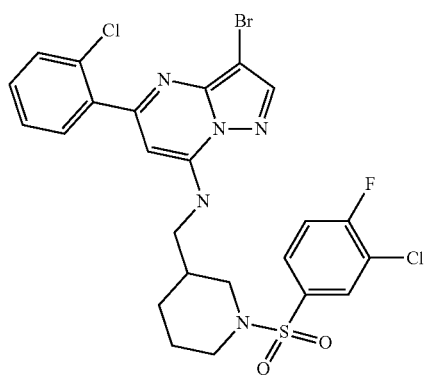 [SMILES: O=S(=O)(c1ccc(F)c(Cl)c1)N1CCCC(CNc2cc(-c3ccccc3Cl)nc3c(Br)cnn23)C1] | 1. 6929<br>2. 614.34 |
| 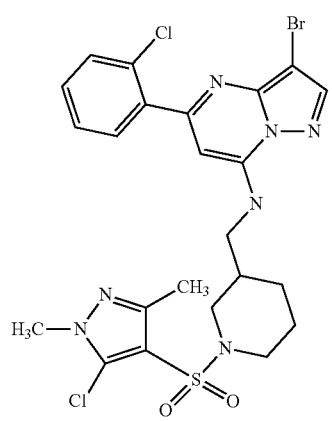 [SMILES: Cc1nn(C)c(Cl)c1S(=O)(=O)N1CCCC(CNc2cc(-c3ccccc3Cl)nc3c(Br)cnn23)C1] | 1. 6930<br>2. 614.34 |
TABLE 69-continued
| Product | 1. Ex.<br>2. m/z |
|---|---|
| 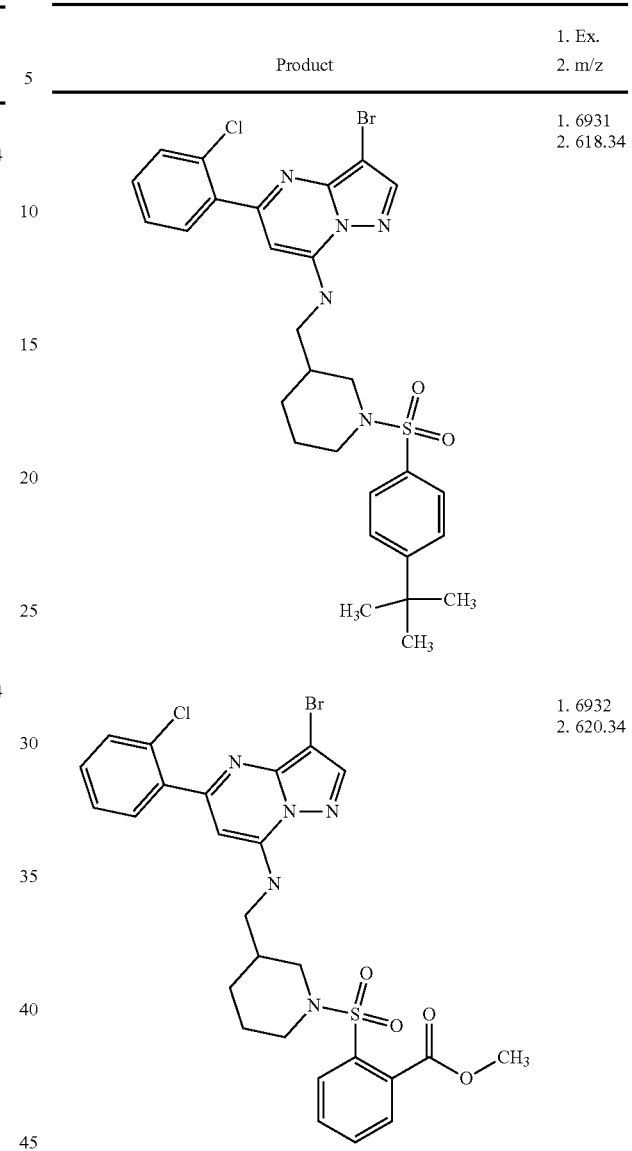 | 1. 6931<br>2. 618.34 |
| | 1. 6932<br>2. 620.34 |
| 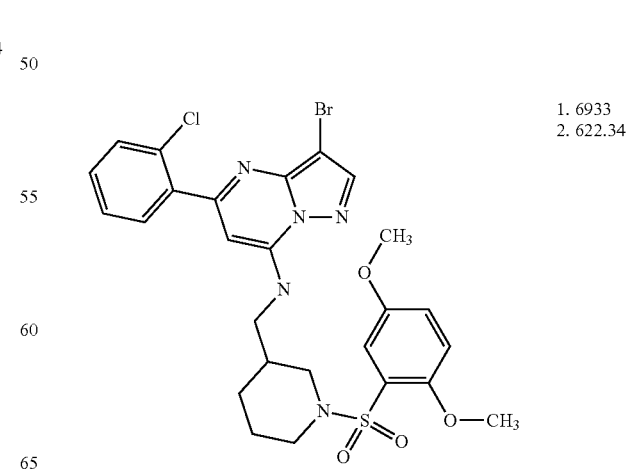 | 1. 6933<br>2. 622.34 |

TABLE 69-continued

| Product | 1. Ex. 2. m/z |
|---|---|
| (structure) | 1. 6934  2. 622.34 |
| (structure) | 1. 6935  2. 626.34 |
| (structure) | 1. 6936  2. 630.35 |
| (structure) | 1. 6937  2. 630.35 |
| (structure) | 1. 6938  2. 630.35 |
| (structure) | 1. 6939  2. 630.35 |

TABLE 69-continued
| Product | 1. Ex.<br>2. m/z |
|---|---|
| 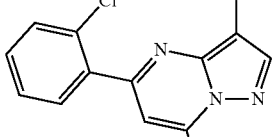 | 1. 6940<br>2. 630.35 |
|  | 1. 6941<br>2. 630.35 |
|  | 1. 6942<br>2. 630.35 |
| 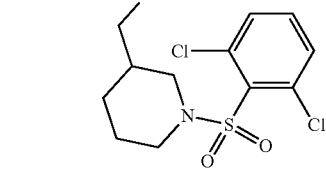 | 1. 6943<br>2. 630.35 |
TABLE 69-continued
| Product | 1. Ex.<br>2. m/z |
|---|---|
| 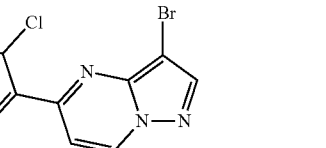 | 1. 6944<br>2. 632.35 |
| 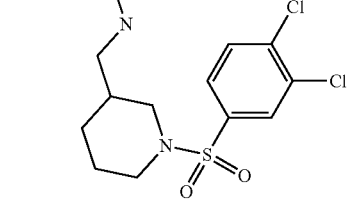 | 1. 6945<br>2. 614.34 |
| 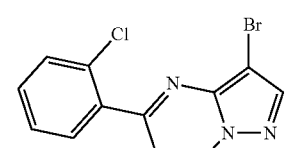 | 1. 6946<br>2. 636.35 |

TABLE 69-continued

| Product | 1. Ex. 2. m/z |
|---|---|
| (structure) | 1. 6947  2. 638.35 |
| (structure) | 1. 6948  2. 640.35 |
| (structure) | 1. 6949  2. 640.35 |
| (structure) | 1. 6950  2. 640.35 |
| (structure) | 1. 6951  2. 640.35 |
| (structure) | 1. 6952  2. 646.36 |

TABLE 69-continued
| Product | 1. Ex.<br>2. m/z |
|---|---|
| 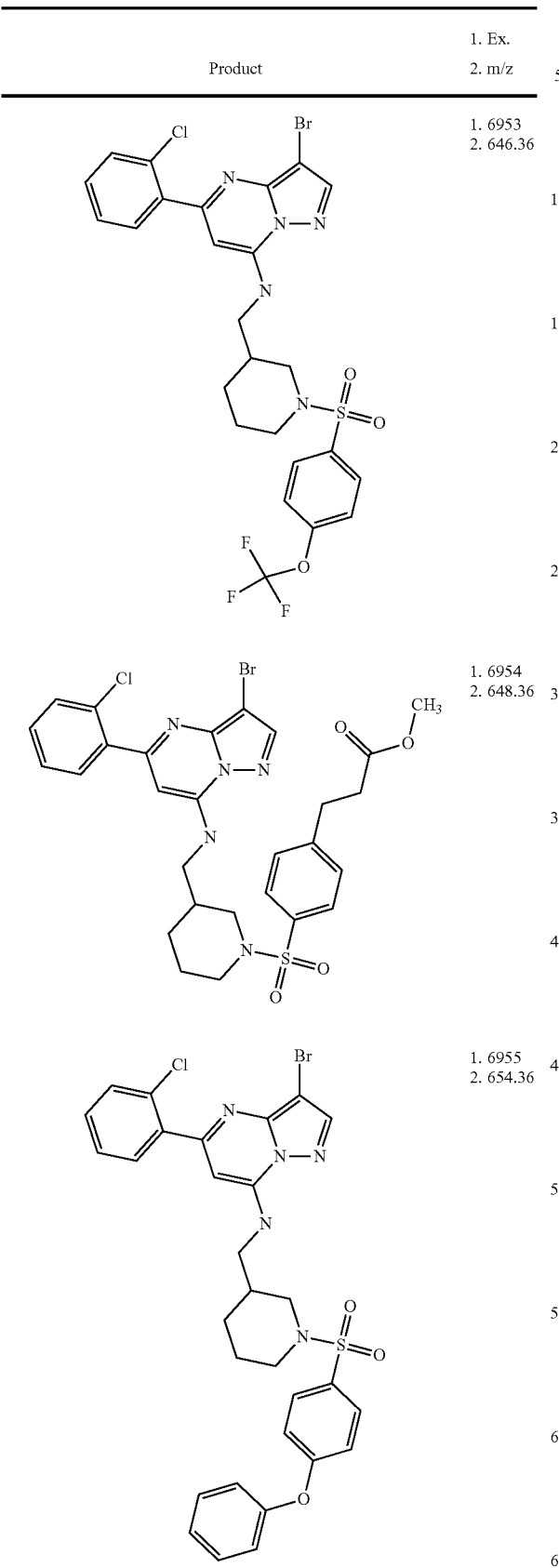 | 1. 6953<br>2. 646.36 |
| | 1. 6954<br>2. 648.36 |
| | 1. 6955<br>2. 654.36 |
TABLE 69-continued
| Product | 1. Ex.<br>2. m/z |
|---|---|
| 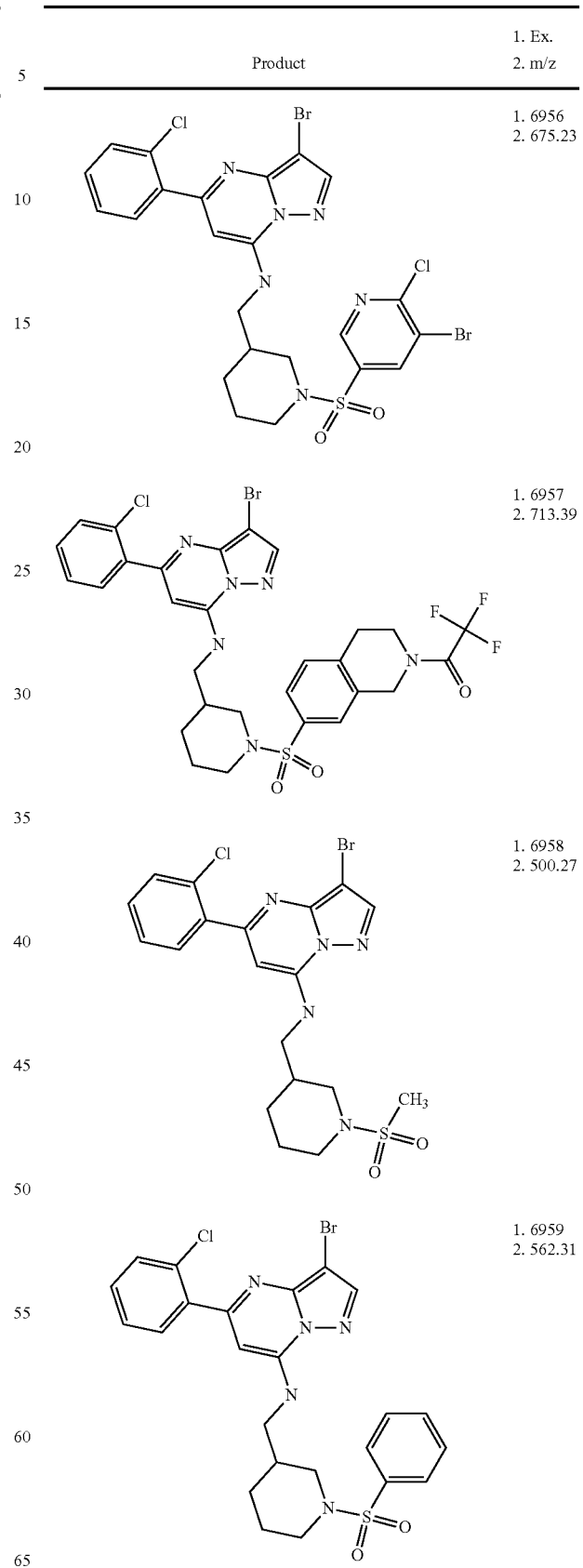 | 1. 6956<br>2. 675.23 |
| | 1. 6957<br>2. 713.39 |
| | 1. 6958<br>2. 500.27 |
| | 1. 6959<br>2. 562.31 |

TABLE 69-continued
| Product | 1. Ex.<br>2. m/z |
|---|---|
| 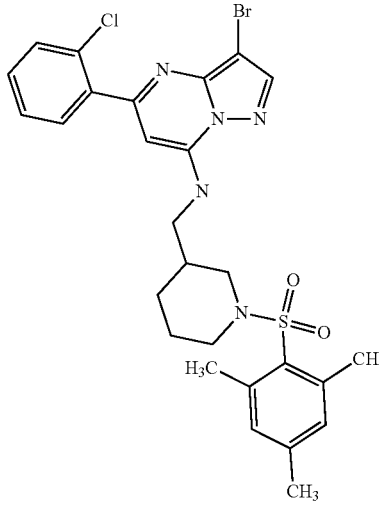 | 1. 6960<br>2. 604.33 |
TABLE 70
| Product | 1. Ex.<br>2. m/z |
|---|---|
| 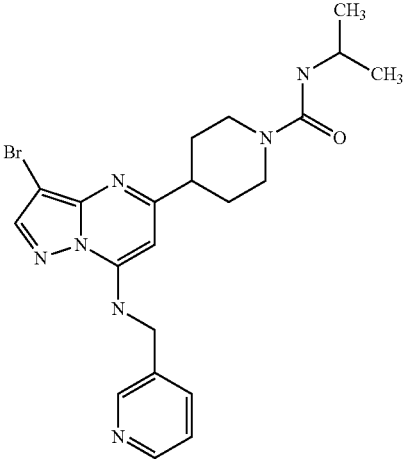 [SMILES: CC(C)NC(=O)N1CCC(c2cc(NCc3cccnc3)n3ncc(Br)c3n2)CC1] | 1. 7001<br>2. 472.26 |
| 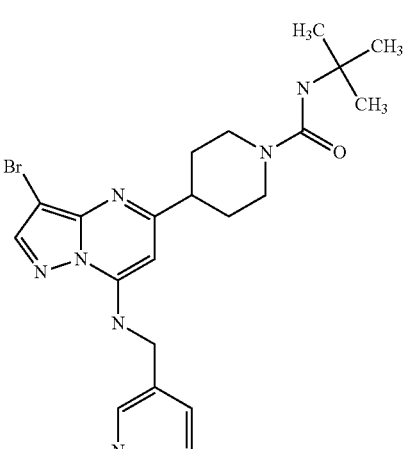 | 1. 7002<br>2. 488.27 |
TABLE 70-continued
| Product | 1. Ex.<br>2. m/z |
|---|---|
| 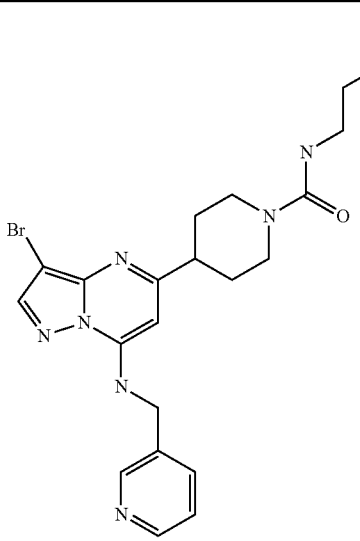 | 1. 7003<br>2. 488.27 |
| 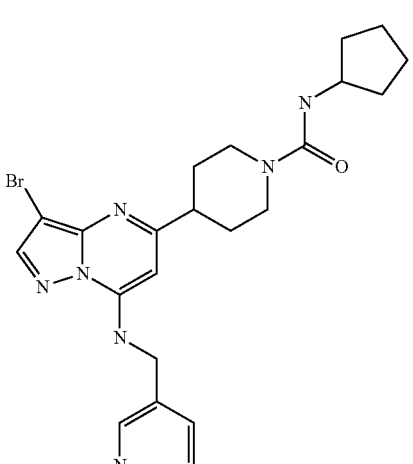 | 1. 7004<br>2. 500.27 |
| 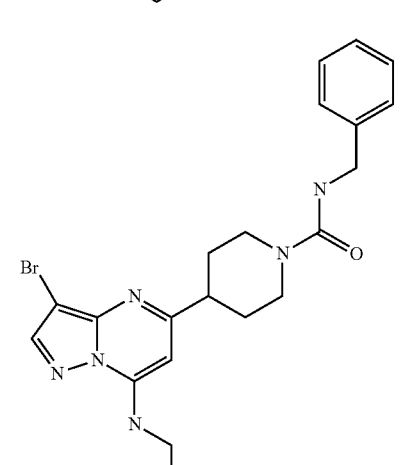 | 1. 7005<br>2. 520.29 |

TABLE 70-continued

| Product | 1. Ex. 2. m/z |
|---|---|
| (structure with 2-methylphenyl) | 1. 7006  2. 522.29 |
| (structure with 3-methylphenyl) | 1. 7007  2. 520.29 |
| (structure with 4-methylphenyl) | 1. 7008  2. 520.29 |
| (structure with 4-fluorophenyl) | 1. 7009  2. 526.29 |
| (structure with 4-cyanophenyl) | 1. 7010  2. 533.29 |
| Chiral (structure with (S)-1-phenylethyl) | 1. 7011  2. 536.29 |

TABLE 70-continued

| Product | 1. Ex.<br>2. m/z |
|---|---|
| (structure) | Chiral 1. 7012<br>2. 536.29 |
| (structure) | 1. 7013<br>2. 536.29 |
| (structure) | 1. 7014<br>2. 536.29 |
| (structure) | 1. 7015<br>2. 536.29 |
| (structure) | 1. 7016<br>2. 538.3 |
| (structure) | 1. 7017<br>2. 540.3 |

TABLE 70-continued

| Product | 1. Ex.<br>2. m/z |
|---|---|
| (structure with 4-chlorophenyl carboxamide) | 1. 7018<br>2. 542.3 |
| (structure with 3,4-difluorophenyl carboxamide) | 1. 7019<br>2. 544.3 |
| (structure with 3,5-difluorophenyl carboxamide) | 1. 7020<br>2. 544.3 |
| (structure with trans-2-phenylcyclopropyl carboxamide) | 1. 7021<br>2. 548.3 |
| (structure with benzo[1,3]dioxol-5-yl carboxamide) | 1. 7022<br>2. 552.3 |

TABLE 70-continued
| Product | 1. Ex.<br>2. m/z |
|---|---|
| 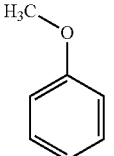 | 1. 7023<br>2. 552.3 |
| 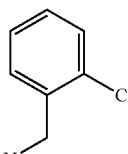 | 1. 7024<br>2. 556.31 |
TABLE 70-continued
| Product | 1. Ex.<br>2. m/z |
|---|---|
| 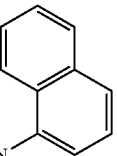 | 1. 7025<br>2. 558.31 |
| 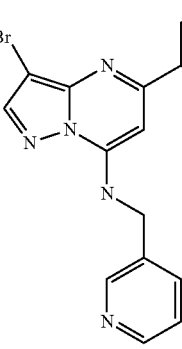 | 1. 7026<br>2. 566.31 |
| 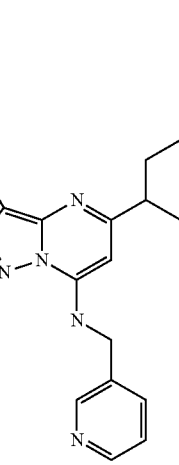 | 1. 7027<br>2. 568.31 |

TABLE 70-continued
| Product | 1. Ex. 2. m/z |
|---|---|
|  | 1. 7028 2. 572.31 |
|  | 1. 7029 2. 576.32 |
|  | 1. 7030 2. 576.32 |
TABLE 70-continued
| Product | 1. Ex. 2. m/z |
|---|---|
|  | 1. 7031 2. 576.32 |
|  | 1. 7032 2. 576.32 |

TABLE 70-continued
| Product | 1. Ex. 2. m/z |
|---|---|
| 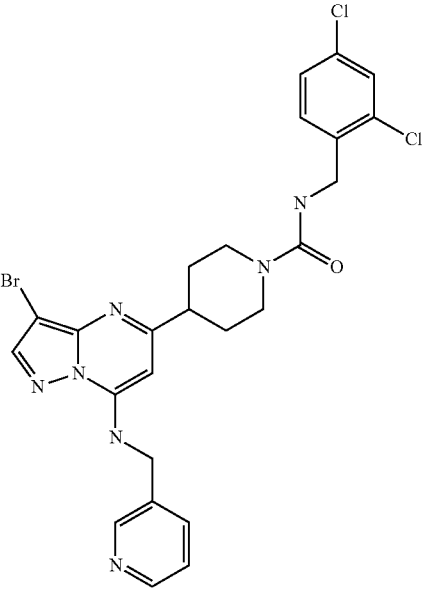 [SMILES: O=C(NCc1ccc(Cl)cc1Cl)N1CCC(c2cc(NCc3cccnc3)n3ncc(Br)c3n2)CC1] | 1. 7033 2. 590.32 |
| 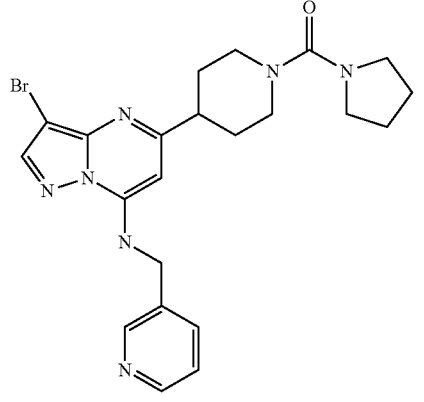 [SMILES: O=C(N1CCCC1)N1CCC(c2cc(NCc3cccnc3)n3ncc(Br)c3n2)CC1] | 1. 7034 2. 486.28 |
| 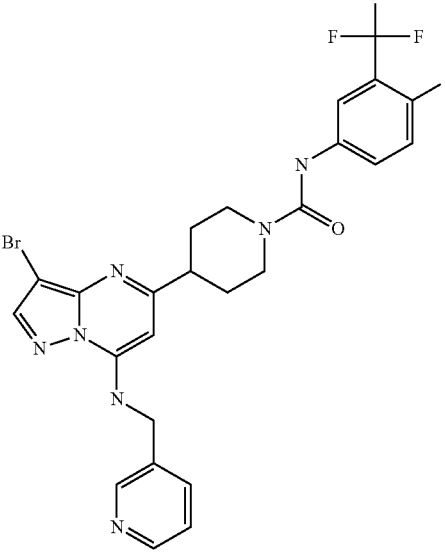 | 1. 7035 2. 594.33 |
TABLE 70-continued
| Product | 1. Ex. 2. m/z |
|---|---|
| 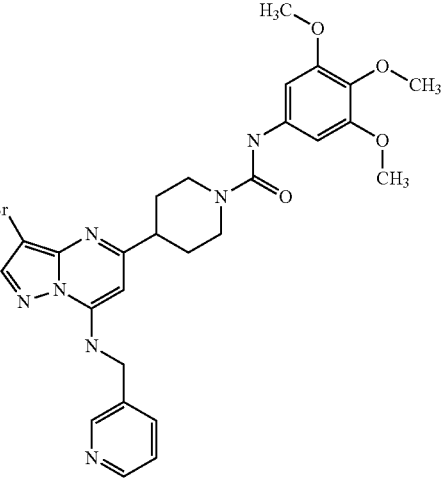 | 1. 7036 2. 598.33 |
| 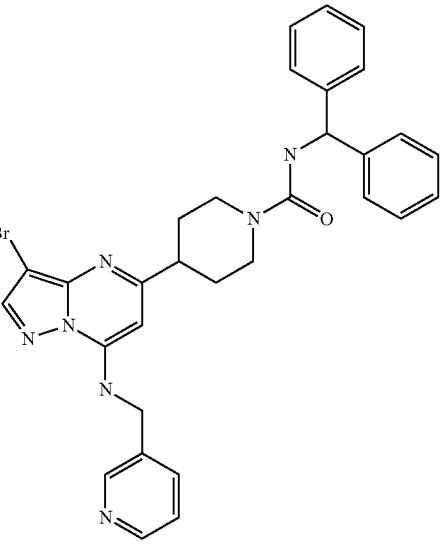 | 1. 7037 2. 598.33 |
| 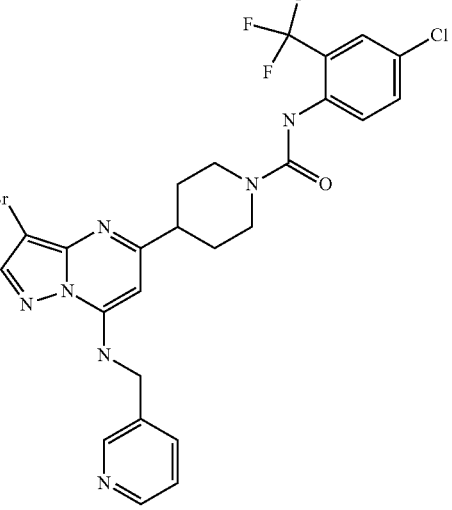 | 1. 7038 2. 610.34 |

TABLE 71

| Product | 1. Ex. 2. m/z |
|---|---|
| (structure) | 1. 7101  2. 474.26 |
| (structure) | 1. 7102  2. 488.27 |
| (structure) | 1. 7103  2. 500.27 |
| (structure) | 1. 7104  2. 522.29 |
| (structure) | 1. 7105  2. 522.29 |
| (structure) | 1. 7106  2. 522.29 |
| (structure) | 1. 7107  2. 522.29 |
| (structure) | 1. 7108  2. 526.3 |

TABLE 71-continued
| Product | 1. Ex. 2. m/z |
|---|---|
| 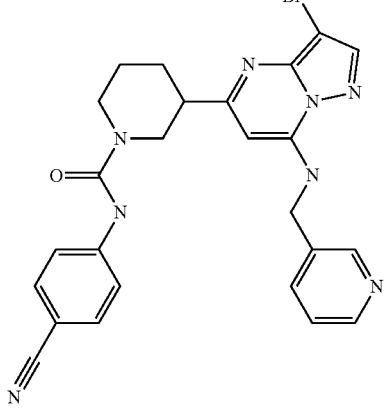 | 1. 7109  2. 533.29 |
| 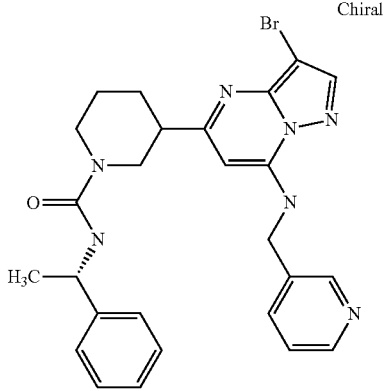 [SMILES: C[C@H](NC(=O)N1CCCC(c2cc(NCc3cccnc3)n3ncc(Br)c3n2)C1)c1ccccc1] Chiral | 1. 7110  2. 536.29 |
| 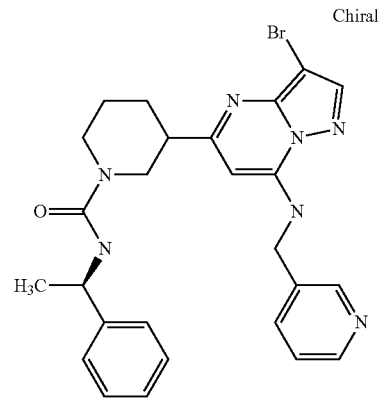 [SMILES: C[C@@H](NC(=O)N1CCCC(c2cc(NCc3cccnc3)n3ncc(Br)c3n2)C1)c1ccccc1] Chiral | 1. 7111  2. 536.29 |
| 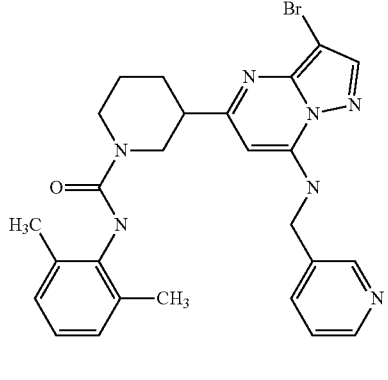 [SMILES: Cc1cccc(C)c1NC(=O)N1CCCC(c2cc(NCc3cccnc3)n3ncc(Br)c3n2)C1] | 1. 7112  2. 536.29 |
TABLE 71-continued
| Product | 1. Ex. 2. m/z |
|---|---|
| 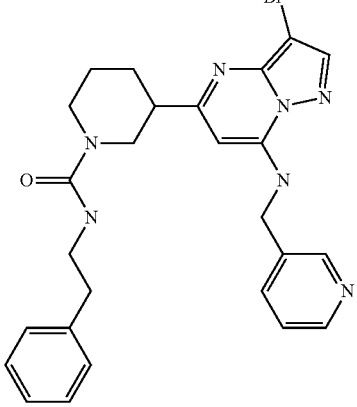 | 1. 7113  2. 536.29 |
| 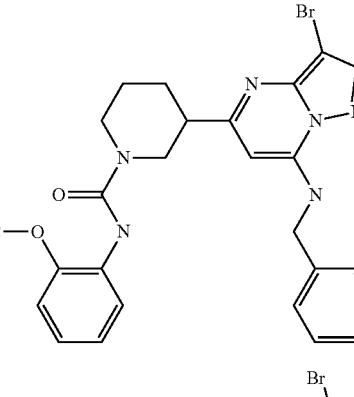 | 1. 7114  2. 536.29 |
| 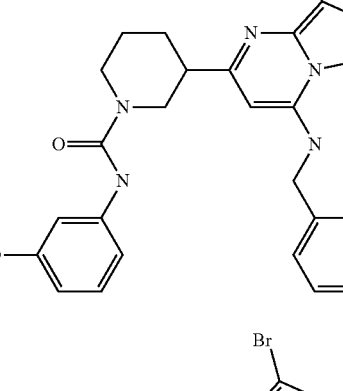 | 1. 7115  2. 536.3 |
| 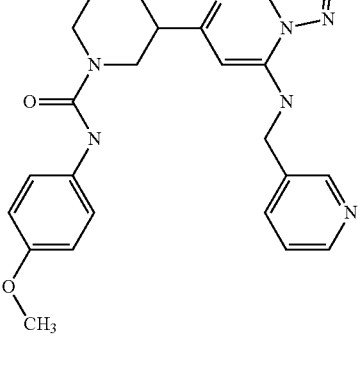 | 1. 7116  2. 538.3 |

TABLE 71-continued
| Product | 1. Ex.<br>2. m/z |
|---|---|
| 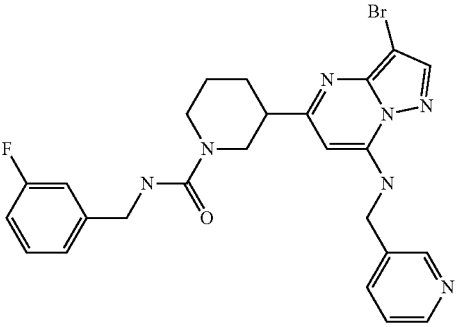 [SMILES: O=C(NCc1cccc(F)c1)N1CCCC(c2cc(NCc3cccnc3)n3ncc(Br)c3n2)C1] | 1. 7117<br>2. 540.3 |
| 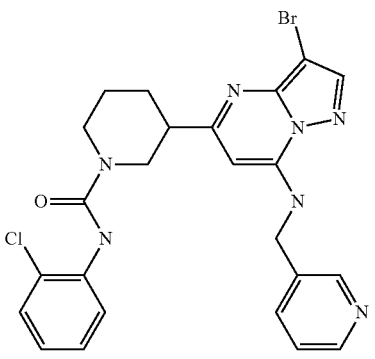 [SMILES: O=C(Nc1ccccc1Cl)N1CCCC(c2cc(NCc3cccnc3)n3ncc(Br)c3n2)C1] | 1. 7118<br>2. 542.3 |
| 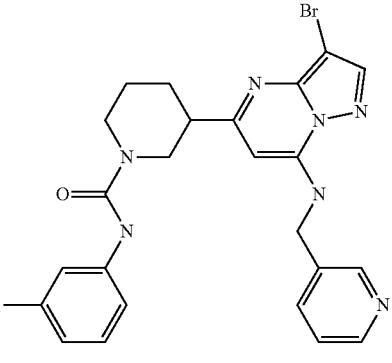 | 1. 7119<br>2. 542.3 |
| 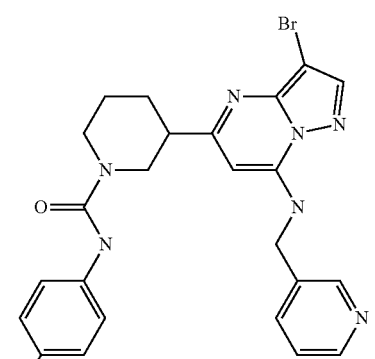 | 1. 7120<br>2. 542.3 |
TABLE 71-continued
| Product | 1. Ex.<br>2. m/z |
|---|---|
| 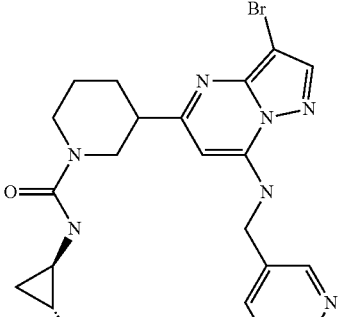 | 1. 7121<br>2. 546.3 |
| 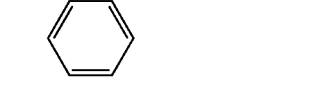 | 1. 7122<br>2. 550.3 |
| 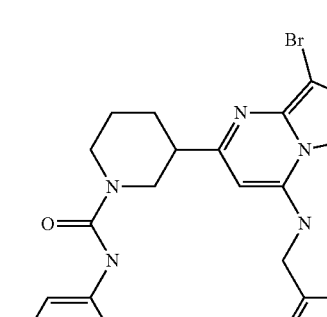 | 1. 7123<br>2. 552.3 |

US 8,673,924 B2
TABLE 71-continued
| Product | 1. Ex. 2. m/z |
|---|---|
| 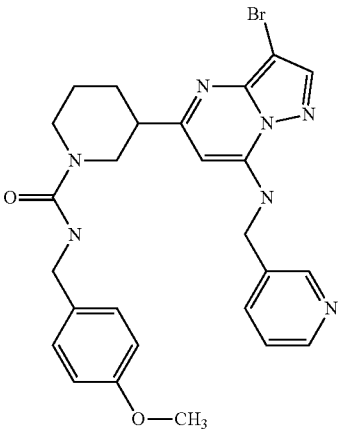 [SMILES: COc1ccc(CNC(=O)N2CCCC(c3cc(NCc4cccnc4)n4ncc(Br)c4n3)C2)cc1] | 1. 7124  2. 552.3 |
| 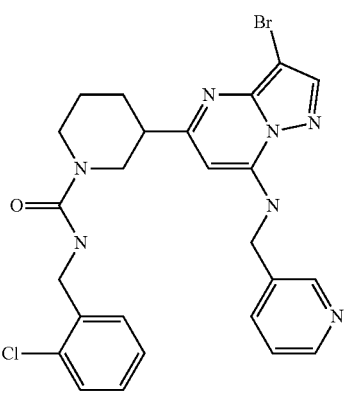 [SMILES: O=C(NCc1ccccc1Cl)N1CCCC(c2cc(NCc3cccnc3)n3ncc(Br)c3n2)C1] | 1. 7125  2. 556.31 |
| 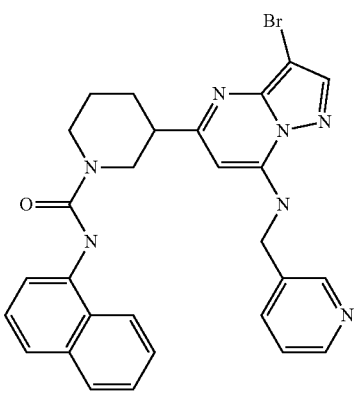 [SMILES: O=C(Nc1cccc2ccccc12)N1CCCC(c2cc(NCc3cccnc3)n3ncc(Br)c3n2)C1] | 1. 7126  2. 558.31 |
TABLE 71-continued
| Product | 1. Ex. 2. m/z |
|---|---|
| 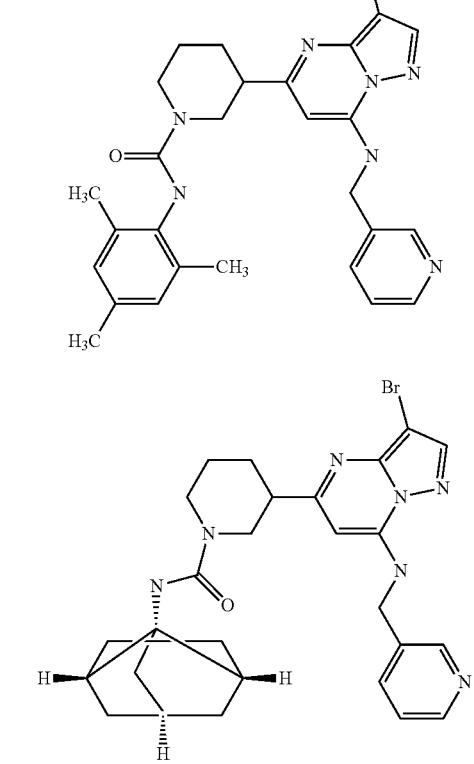 | 1. 7127  2. 550.3 |
| 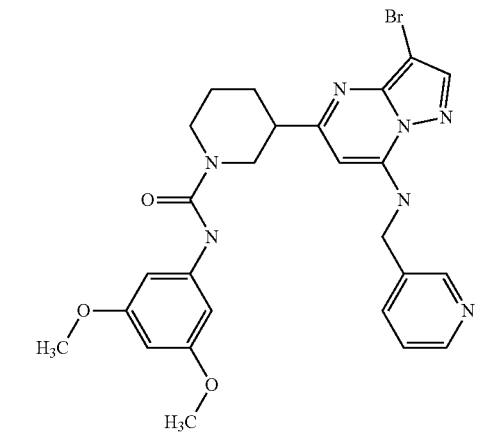 [SMILES: COc1cc(NC(=O)N2CCCC(c3cc(NCc4cccnc4)n4ncc(Br)c4n3)C2)cc(OC)c1] | 1. 7128  2. 566.31 |
| 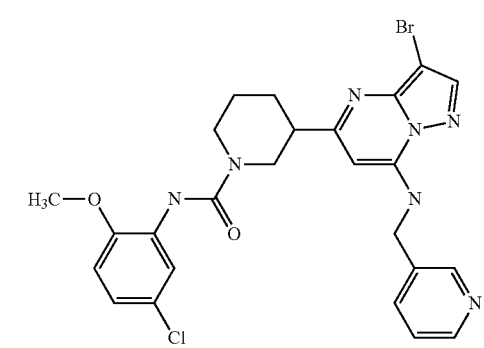 [SMILES: COc1ccc(Cl)cc1NC(=O)N1CCCC(c2cc(NCc3cccnc3)n3ncc(Br)c3n2)C1] | 1. 7129  2. 565.31 |
| 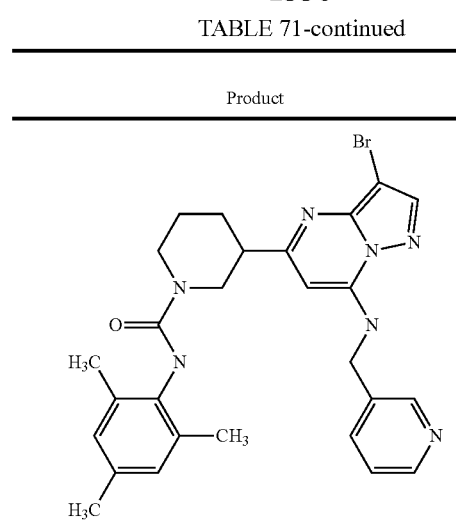 | 1. 7130  2. 572.31 |

TABLE 71-continued
| Product | 1. Ex. 2. m/z |
|---|---|
| | 1. 7131  2. 576.32 |
| | 1. 7132  2. 576.32 |
| | 1. 7133  2. 576.32 |
| | 1. 7134  2. 584.32 |
| | 1. 7135  2. 585.3 |
| | 1. 7136  2. 590.32 |
| | 1. 7137  2. 590.32 |
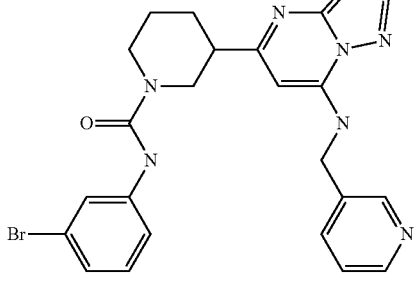
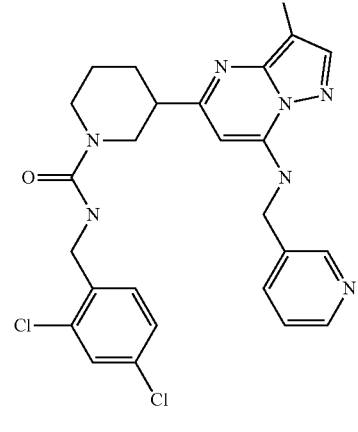
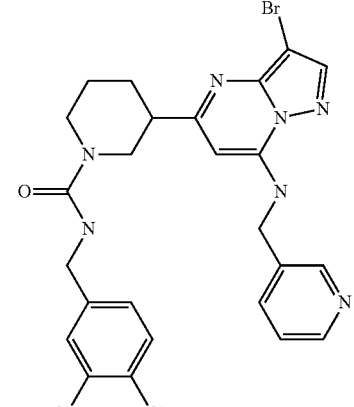

TABLE 71-continued

| Product | 1. Ex. 2. m/z |
|---|---|
| (structure with Br-pyrazolopyrimidine, piperidine urea, 3,4,5-trimethoxyphenyl, pyridin-3-ylmethylamino) | 1. 7138 2. 598.33 |
| (structure with Br-pyrazolopyrimidine, piperidine urea, diphenylmethyl, pyridin-3-ylmethylamino) | 1. 7139 2. 598.33 |

TABLE 72

| Product | 1. Ex. 2. m/z |
|---|---|
| (structure with Br-pyrazolopyrimidine, 2-chlorophenyl, 4-(isopropylureidomethyl)benzylamino) | 1. 7201 2. 529.29 |
| (structure with Br-pyrazolopyrimidine, 2-chlorophenyl, 4-(tert-butylureidomethyl)benzylamino) | 1. 7202 2. 543.3 |

TABLE 72-continued

| Product | 1. Ex.<br>2. m/z |
|---|---|
| | 1. 7203<br>2. 543.3 |
| | 1. 7204<br>2. 555.31 |
| | 1. 7205<br>2. 577.32 |

TABLE 72-continued
| Product | 1. Ex.<br>2. m/z |
|---|---|
| 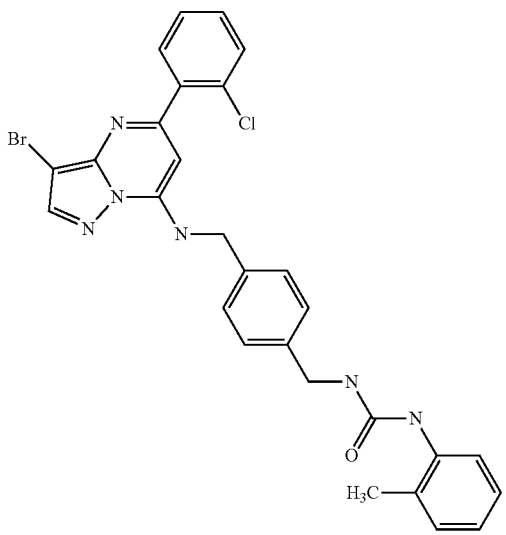 [SMILES: Cc1ccccc1NC(=O)NCc1ccc(CNc2cc(-c3ccccc3Cl)nc3c(Br)cnn23)cc1] | 1. 7206<br>2. 577.32 |
| 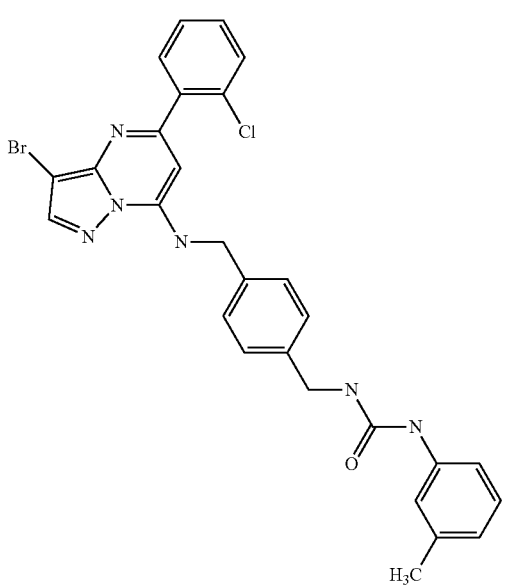 [SMILES: Cc1cccc(NC(=O)NCc2ccc(CNc3cc(-c4ccccc4Cl)nc4c(Br)cnn34)cc2)c1] | 1. 7207<br>2. 577.32 |

TABLE 72-continued
| Product | 1. Ex. 2. m/z |
|---|---|
| 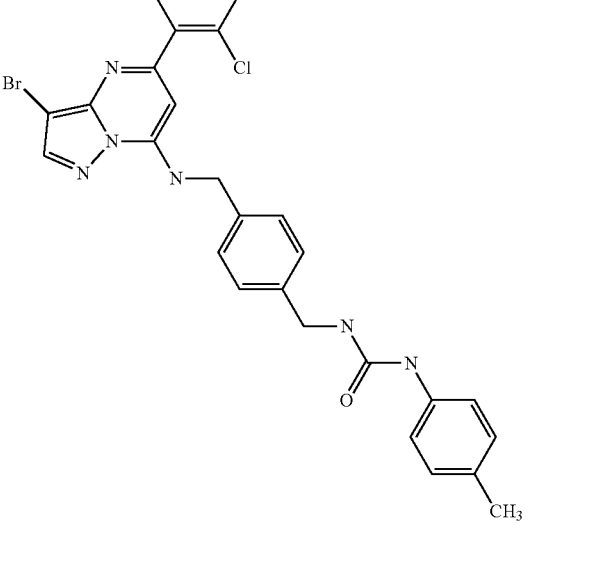 | 1. 7208 2. 577.32 |
| 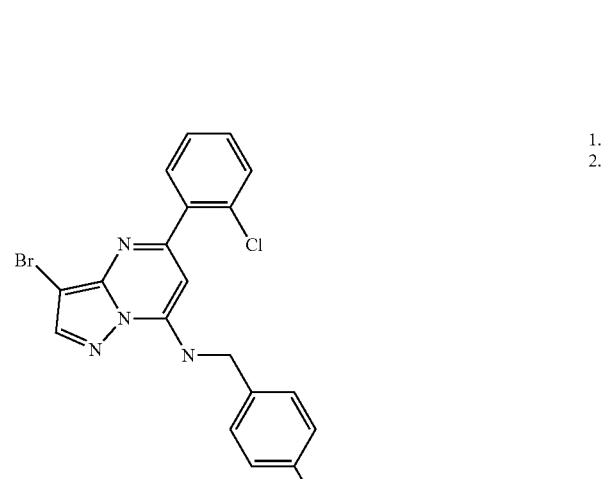 | 1. 7209 2. 581.32 |

TABLE 72-continued
| Product | 1. Ex.<br>2. m/z |
|---|---|
| 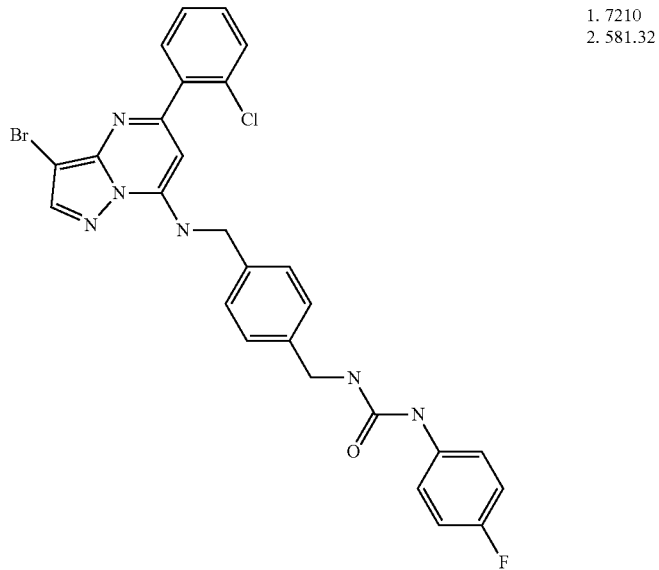 | 1. 7210<br>2. 581.32 |
| 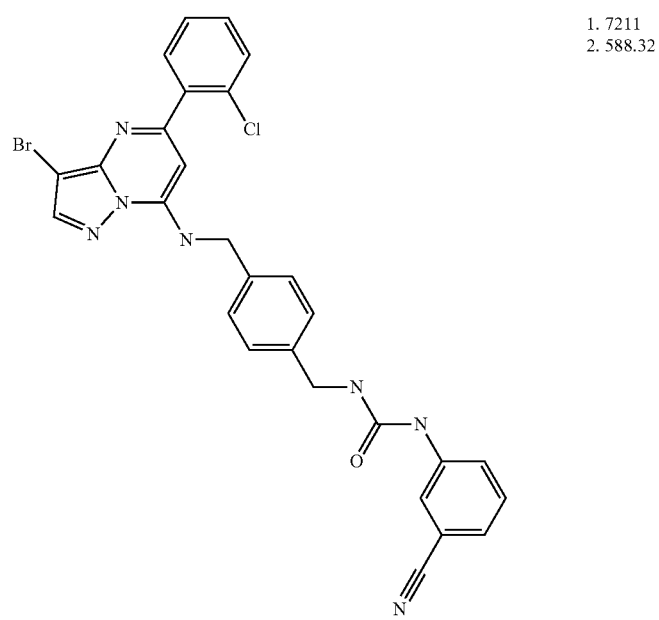 | 1. 7211<br>2. 588.32 |

TABLE 72-continued
| Product | 1. Ex.<br>2. m/z |
|---|---|
| 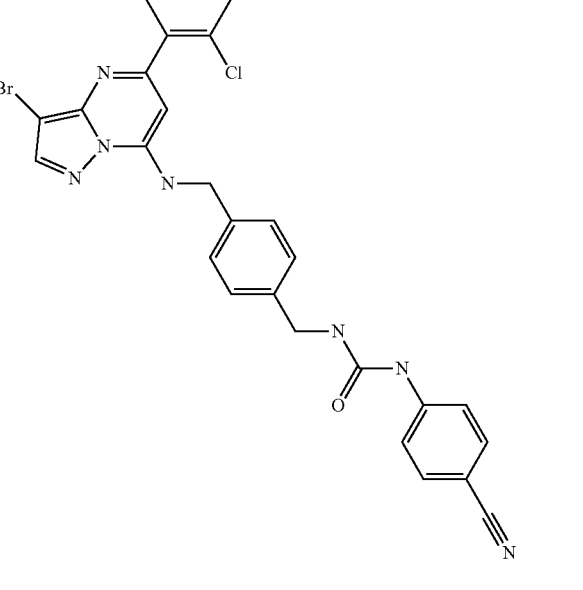 | 1. 7212<br>2. 588.32 |
| 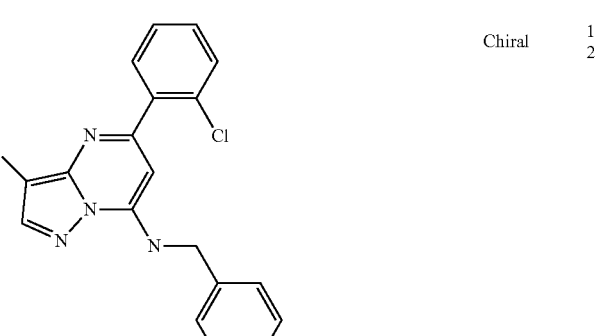 Chiral | 1. 7213<br>2. 591.33 |

TABLE 72-continued
| Product | 1. Ex.<br>2. m/z |
|---|---|
| 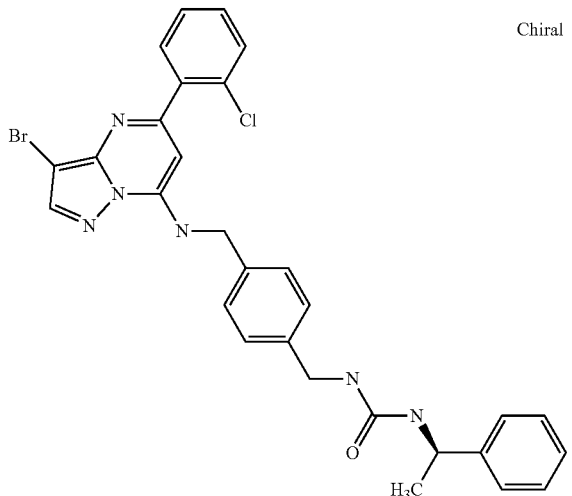 [SMILES: C[C@@H](NC(=O)NCc1ccc(CNc2cc(-c3ccccc3Cl)nc3c(Br)cnn23)cc1)c1ccccc1] | Chiral 1. 7214<br>2. 591.33 |
| 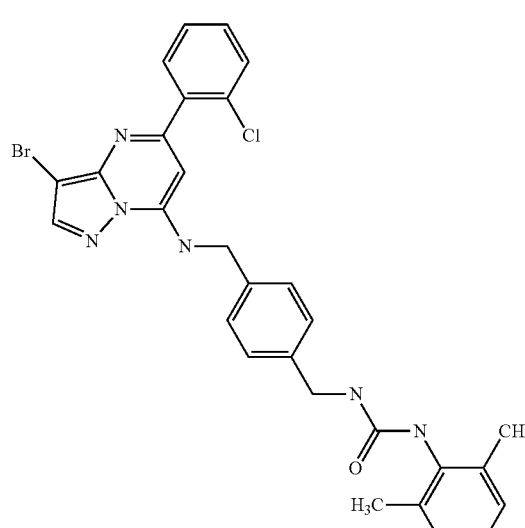 | 1. 7215<br>2. 591.33 |
| 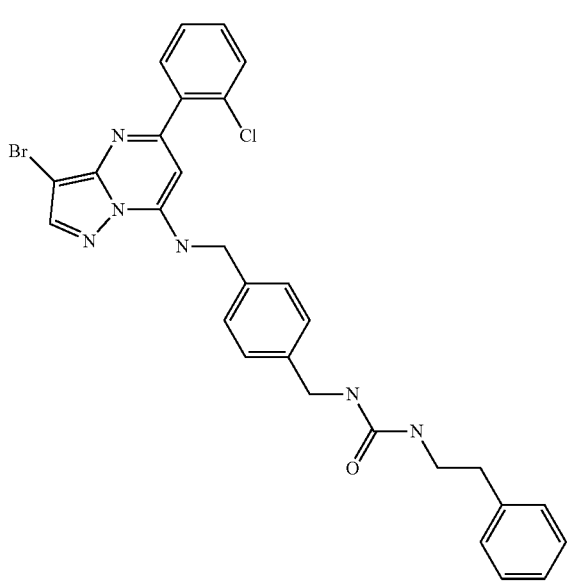 [SMILES: O=C(NCCc1ccccc1)NCc1ccc(CNc2cc(-c3ccccc3Cl)nc3c(Br)cnn23)cc1] | 1. 7216<br>2. 591.33 |

TABLE 72-continued
| Product | 1. Ex.<br>2. m/z |
|---|---|
| 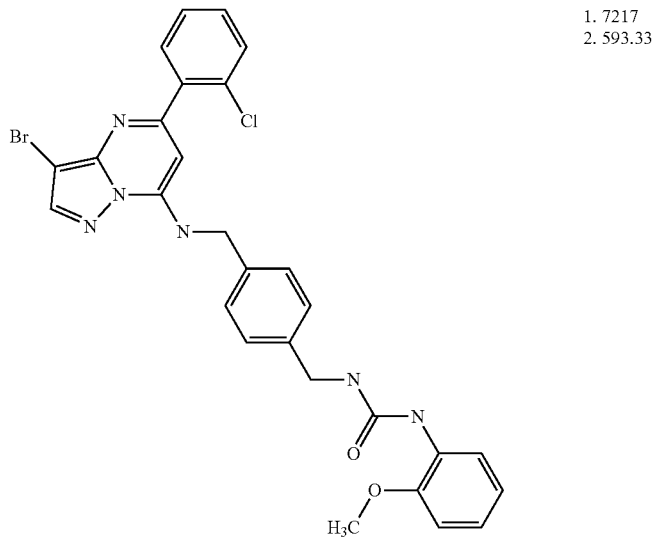 | 1. 7217<br>2. 593.33 |
| 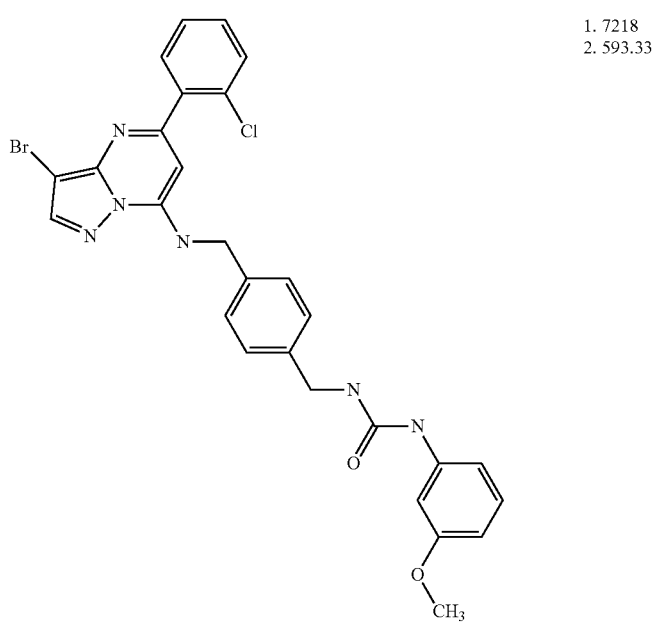 | 1. 7218<br>2. 593.33 |

TABLE 72-continued
| Product | 1. Ex.<br>2. m/z |
|---|---|
| 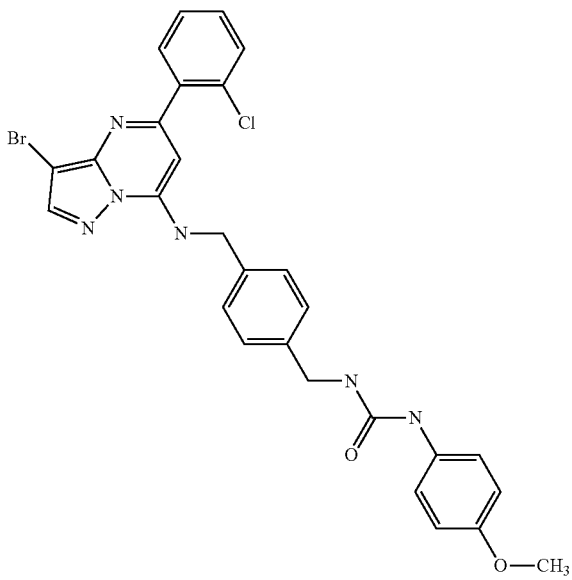 [SMILES: COc1ccc(NC(=O)NCc2ccc(CNc3cc(-c4ccccc4Cl)nc4c(Br)cnn34)cc2)cc1] | 1. 7219<br>2. 593.33 |
| 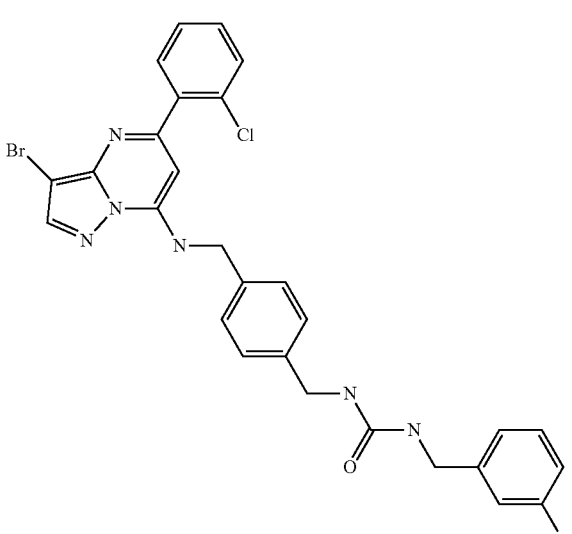 | 1. 7220<br>2. 595.33 |

TABLE 72-continued
| Product | 1. Ex.<br>2. m/z |
|---|---|
| 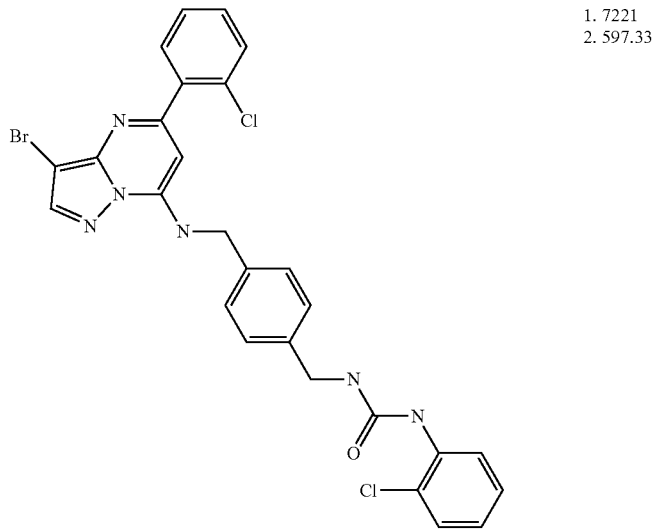 | 1. 7221<br>2. 597.33 |
| 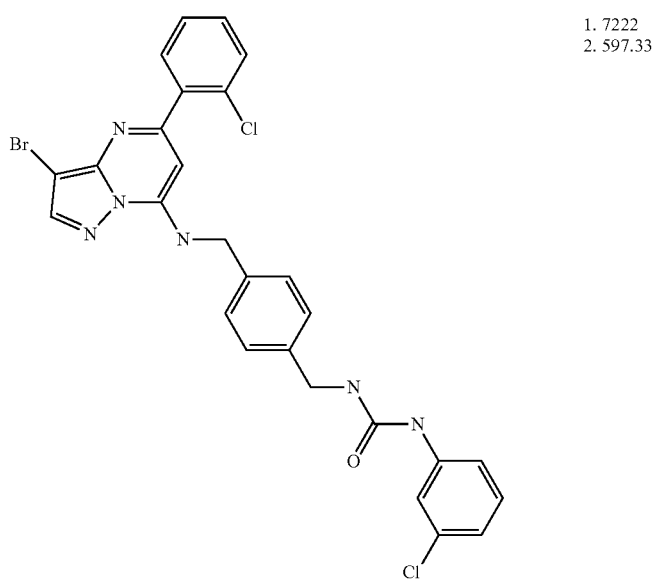 | 1. 7222<br>2. 597.33 |

TABLE 72-continued

| Product | 1. Ex.<br>2. m/z |
|---|---|
| (structure: 3-bromo-5-(2-chlorophenyl)-7-[(4-{[(4-chlorophenyl)carbamoyl]aminomethyl}benzyl)amino]pyrazolo[1,5-a]pyrimidine) | 1. 7223<br>2. 597.33 |
| (structure: 3-bromo-5-(2-chlorophenyl)-7-[(4-{[(3,4-difluorophenyl)carbamoyl]aminomethyl}benzyl)amino]pyrazolo[1,5-a]pyrimidine) | 1. 7224<br>2. 599.33 |

TABLE 72-continued
| Product | 1. Ex.<br>2. m/z |
|---|---|
| 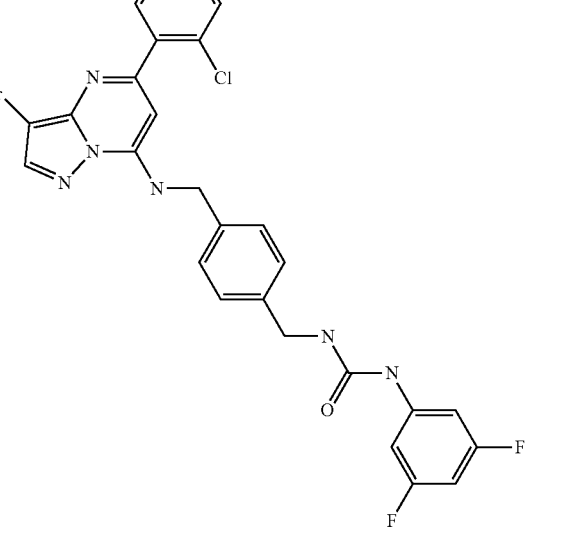 | 1. 7225<br>2. 599.33 |
| 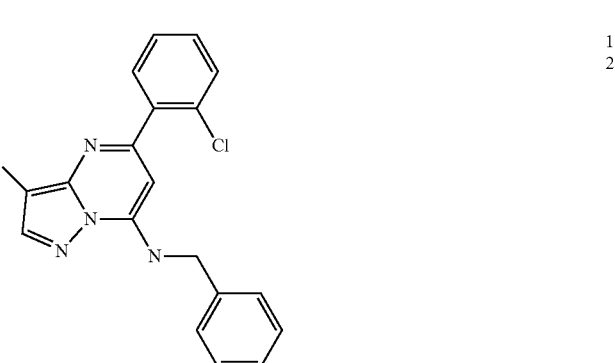 | 1. 7226<br>2. 603.33 |

TABLE 72-continued
| Product | 1. Ex.<br>2. m/z |
|---|---|
| 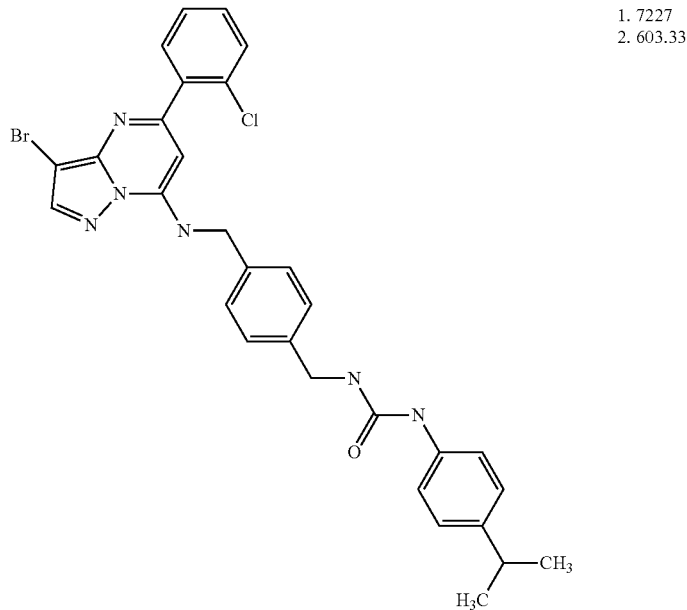 | 1. 7227<br>2. 603.33 |
| 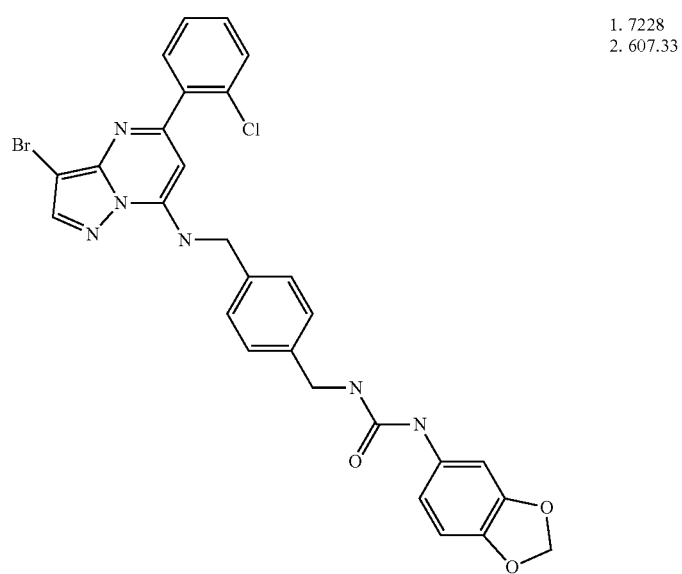 | 1. 7228<br>2. 607.33 |

TABLE 72-continued

| Product | 1. Ex.<br>2. m/z |
|---|---|
| (structure) | 1. 7229<br>2. 607.14 |
| (structure) | 1. 7230<br>2. 611.34 |
| (structure) | 1. 7231<br>2. 613.34 |

TABLE 72-continued
| Product | 1. Ex.<br>2. m/z |
|---|---|
| 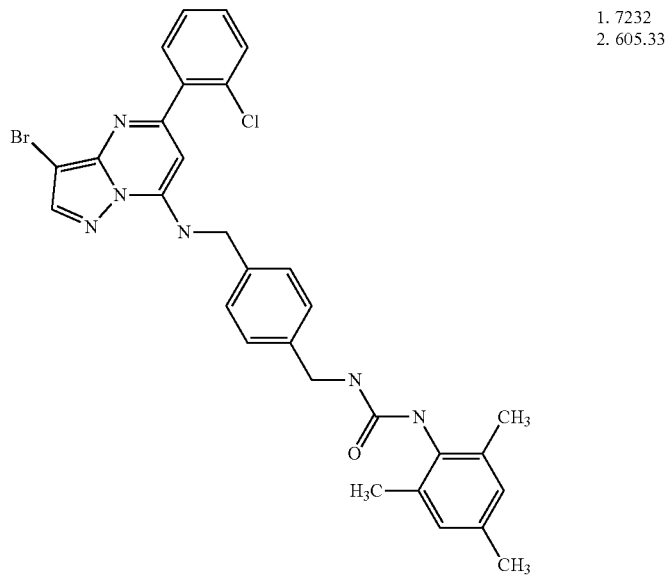 | 1. 7232<br>2. 605.33 |
| 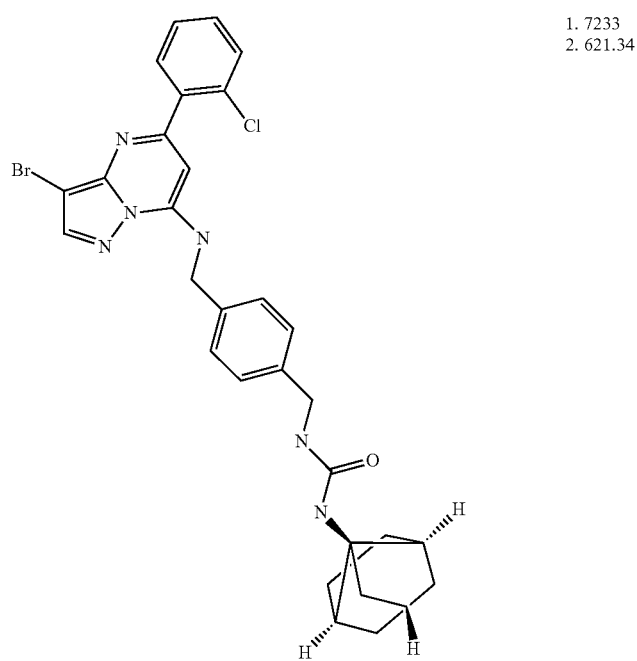 | 1. 7233<br>2. 621.34 |

TABLE 72-continued

| Product | 1. Ex.<br>2. m/z |
|---------|------------------|
|         | 1. 7234<br>2. 623.34 |
|         | 1. 7235<br>2. 627.34 |

TABLE 72-continued
| Product | 1. Ex.<br>2. m/z |
|---|---|
| 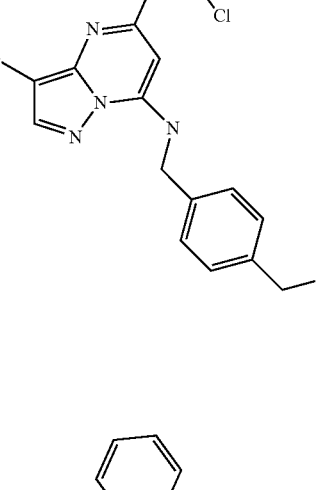 | 1. 7236<br>2. 631.35 |
| 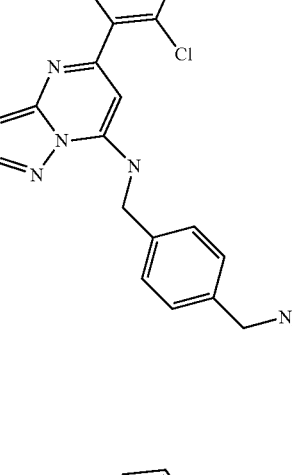 | 1. 7237<br>2. 631.35 |
| 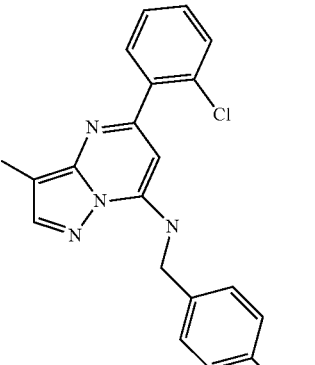 | 1. 7238<br>2. 631.35 |

TABLE 72-continued
| Product | 1. Ex.<br>2. m/z |
|---|---|
| 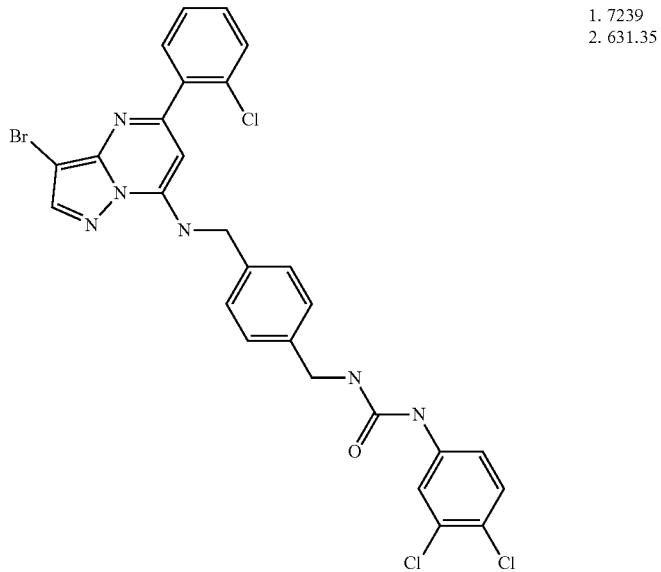 | 1. 7239<br>2. 631.35 |
| 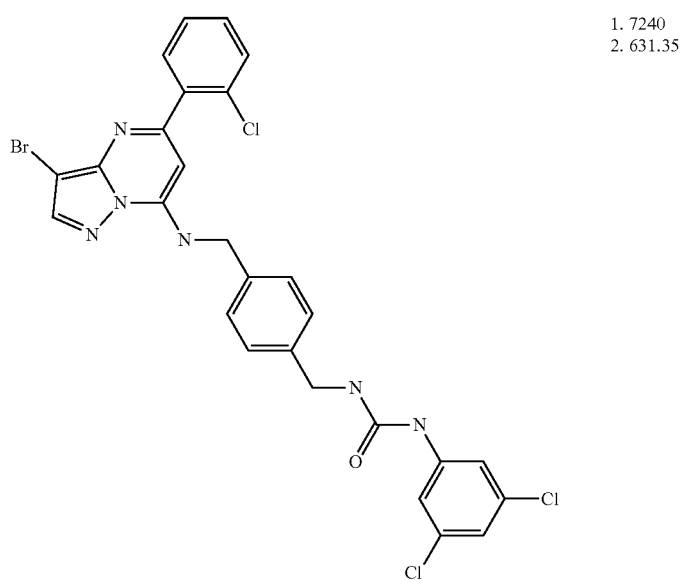 | 1. 7240<br>2. 631.35 |

TABLE 72-continued
| Product | 1. Ex.<br>2. m/z |
|---|---|
| 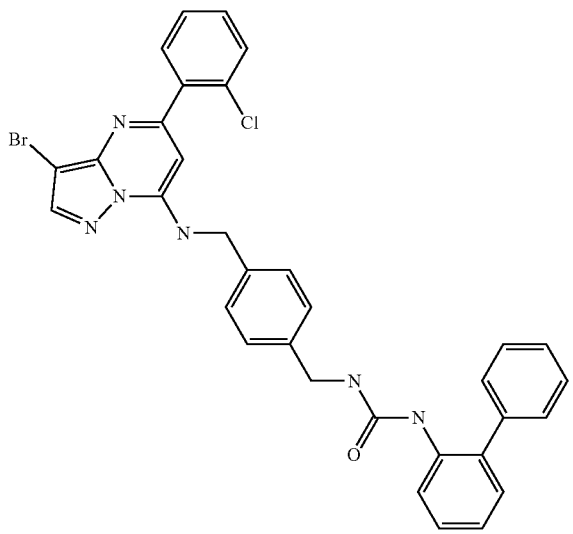 | 1. 7241<br>2. 639.35 |
| 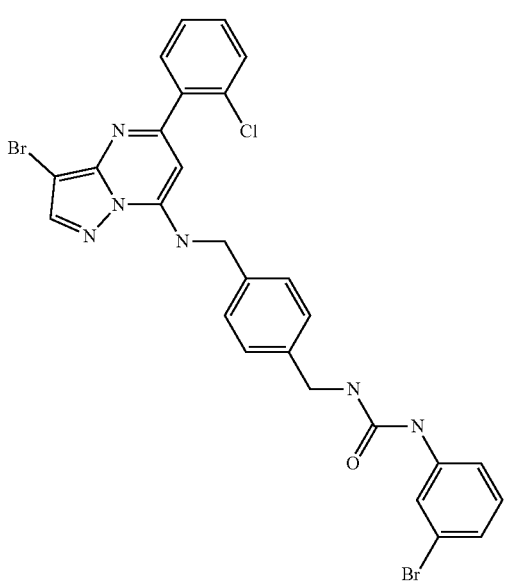 [SMILES: O=C(NCc1ccc(CNc2cc(-c3ccccc3Cl)nc3c(Br)cnn23)cc1)Nc1cccc(Cl)c1] | 1. 7242<br>2. 641.35 |

TABLE 72-continued
| Product | 1. Ex.<br>2. m/z |
|---|---|
| 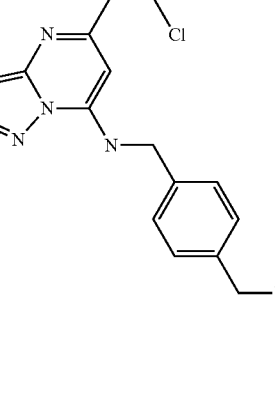 | 1. 7243<br>2. 645.35 |
| 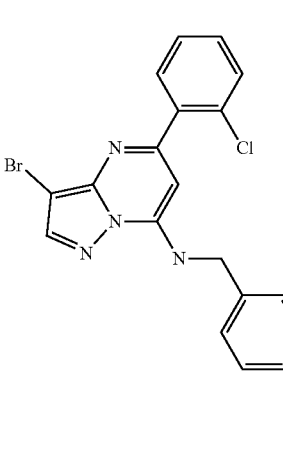 | 1. 7244<br>2. 541.3 |
| 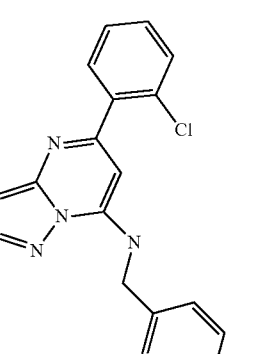 | 1. 7245<br>2. 649.36 |

TABLE 72-continued
| Product | 1. Ex.<br>2. m/z |
|---|---|
| 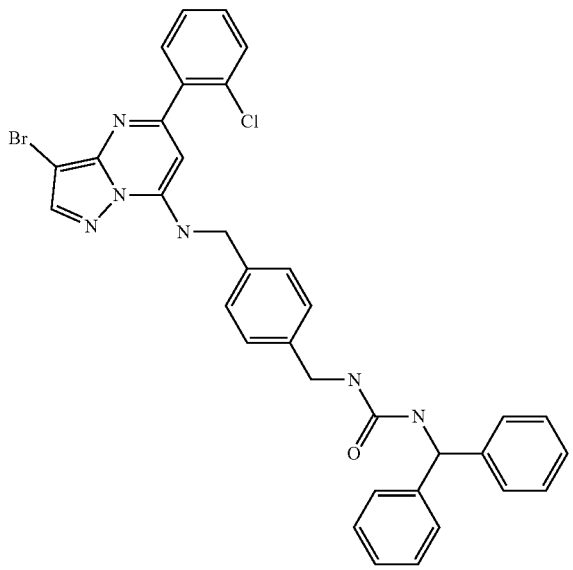 [SMILES: O=C(NCc1ccc(CNc2cc(-c3ccccc3Cl)nc3c(Br)cnn23)cc1)NC(c1ccccc1)c1ccccc1] | 1. 7246<br>2. 653.36 |
| 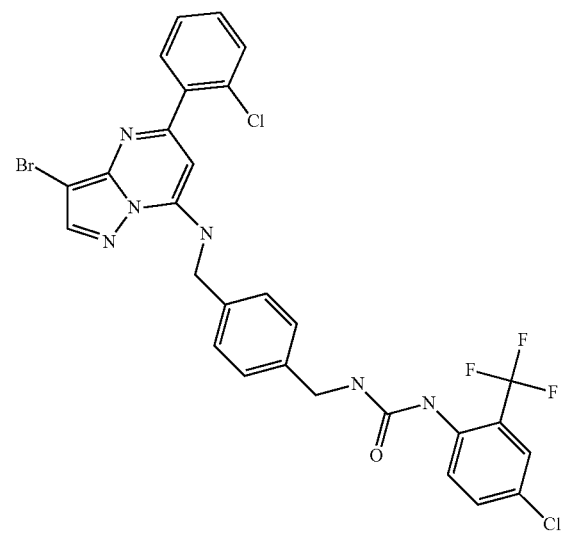 [SMILES: O=C(NCc1ccc(CNc2cc(-c3ccccc3Cl)nc3c(Br)cnn23)cc1)Nc1ccc(Cl)cc1C(F)(F)F] | 1. 7247<br>2. 665.37 |

TABLE 73

| Product | 1. Ex.  2. m/z |
|---|---|
| (structure) | 1. 7301  2. 529.29 |
| (structure) | 1. 7302  2. 541.3 |

TABLE 73-continued

| Product | 1. Ex.  2. m/z |
|---|---|
| (structure) | 1. 7303  2. 563.13 |
| (structure) | 1. 7304  2. 563.31 |

TABLE 73-continued

| Product | 1. Ex.<br>2. m/z |
|---|---|
| (structure) | 1. 7305<br>2. 563.31 |
| (structure) | 1. 7306<br>2. 567.31 |
| (structure) | 1. 7307<br>2. 567.31 |
| (structure) | 1. 7308<br>2. 574.32 |

TABLE 73-continued
| Product | 1. Ex. 2. m/z |
|---|---|
| 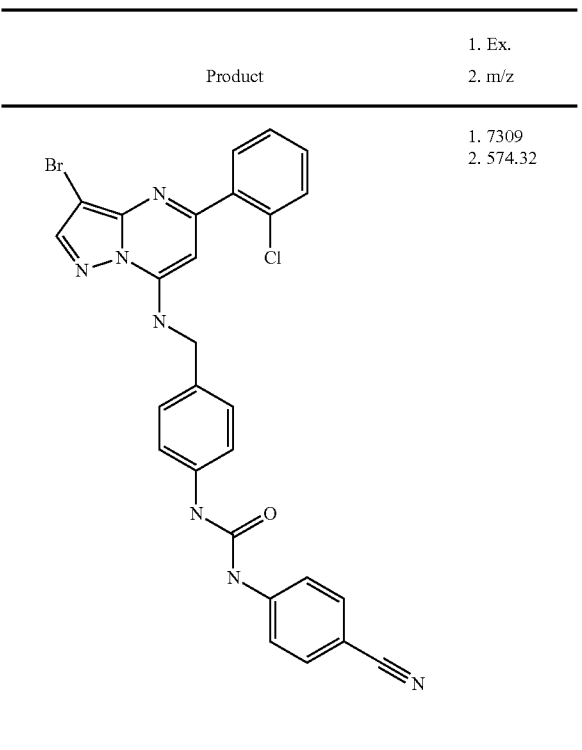 | 1. 7309  2. 574.32 |
| 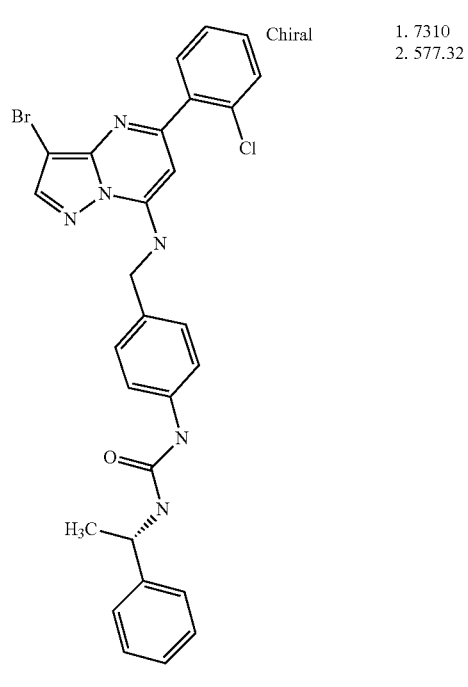 Chiral | 1. 7310  2. 577.32 |
| 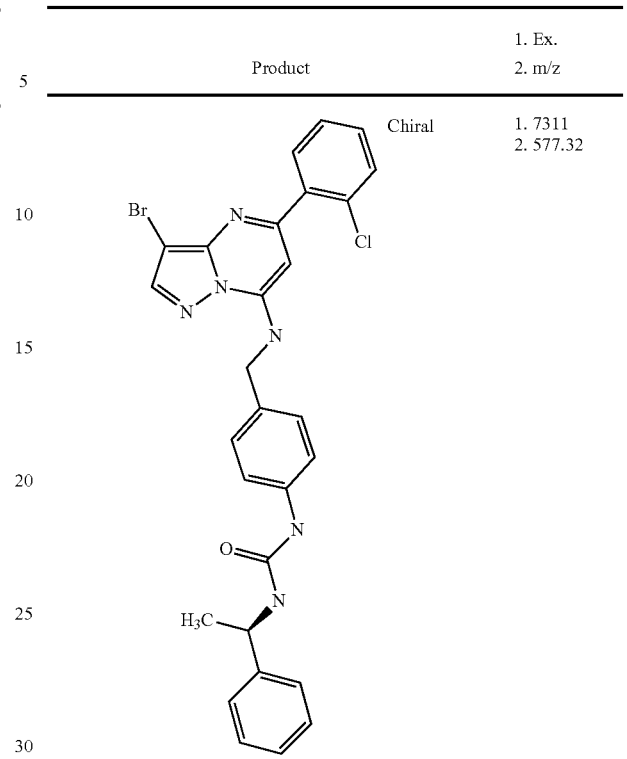 Chiral | 1. 7311  2. 577.32 |
| 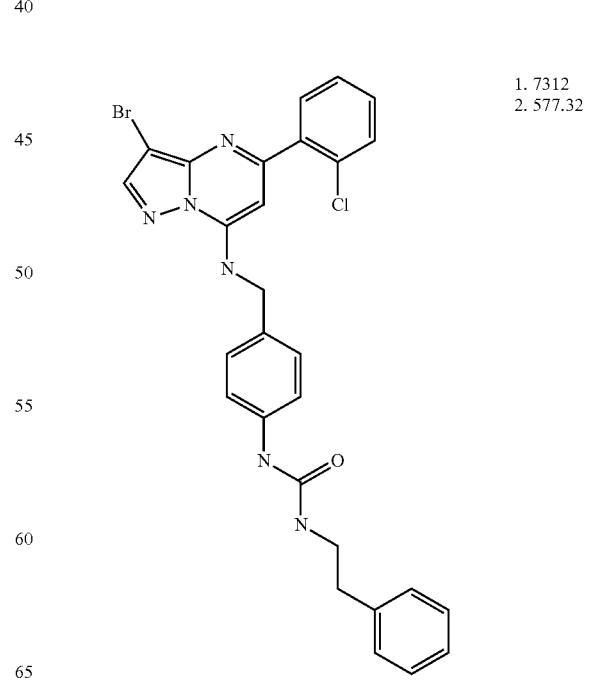 | 1. 7312  2. 577.32 |

TABLE 73-continued
| Product | 1. Ex.<br>2. m/z |
|---|---|
| 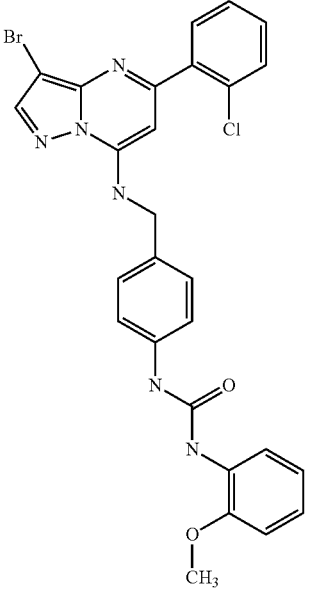 [SMILES: COc1ccccc1NC(=O)Nc1ccc(CNc2cc(-c3ccccc3Cl)nc3c(Br)cnn23)cc1] | 1. 7313<br>2. 579.32 |
| | 1. 7314<br>2. 579.32 |
TABLE 73-continued
| Product | 1. Ex.<br>2. m/z |
|---|---|
| 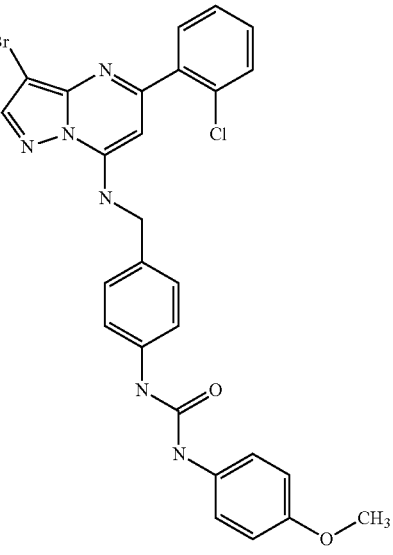 | 1. 7315<br>2. 579.32 |
| 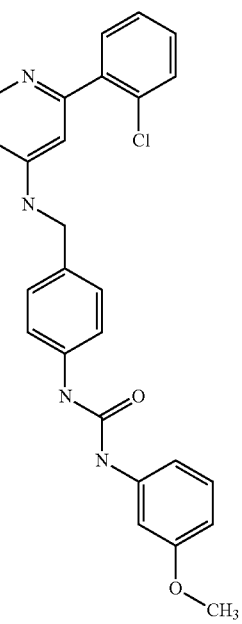 | 1. 7316<br>2. 581.32 |

TABLE 73-continued

| Product | 1. Ex. 2. m/z |
|---|---|
| (structure) | 1. 7317  2. 583.32 |
| (structure) | 1. 7318  2. 583.32 |
| (structure) | 1. 7319  2. 583.32 |
| (structure) | 1. 7320  2. 583.32 |

TABLE 73-continued

| Product | 1. Ex. 2. m/z |
|---|---|
| (structure 1391) | 1. 7321  2. 585.32 |
| (structure 1392) | 1. 7322  2. 589.32 |

TABLE 73-continued

| Product | 1. Ex. 2. m/z |
|---|---|
| (structure) | 1. 7323  2. 591.33 |
| (structure) | 1. 7324  2. 593.33 |

TABLE 73-continued
| Product | 1. Ex. 2. m/z |
|---|---|
| 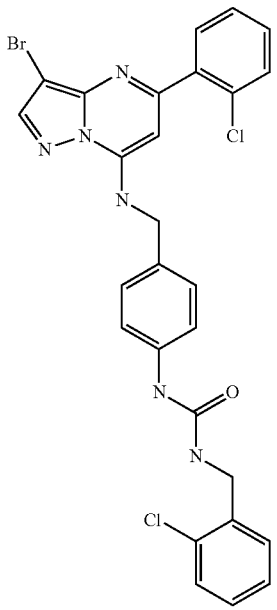 [SMILES: O=C(NCc1ccccc1Cl)Nc1ccc(CNc2cc(-c3ccccc3Cl)nc3c(Br)cnn23)cc1] | 1. 7325<br>2. 597.33 |
| 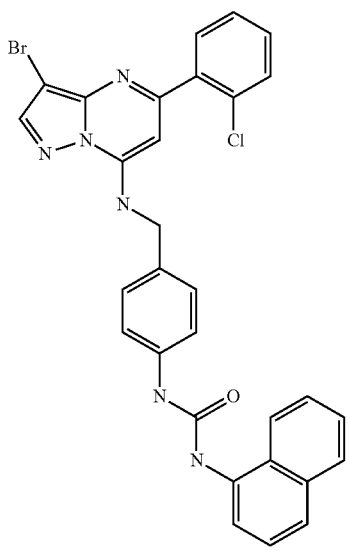 [SMILES: O=C(Nc1ccc(CNc2cc(-c3ccccc3Cl)nc3c(Br)cnn23)cc1)Nc1cccc2ccccc12] | 1. 7326<br>2. 599.33 |
| 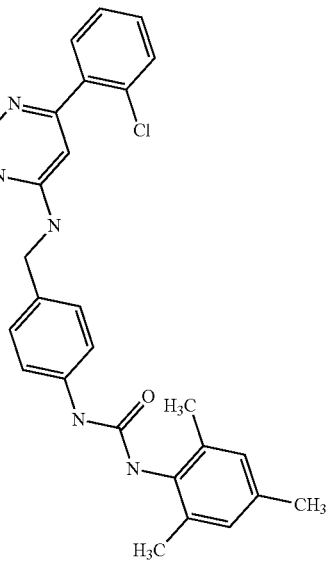 | 1. 7327<br>2. 591.33 |
| 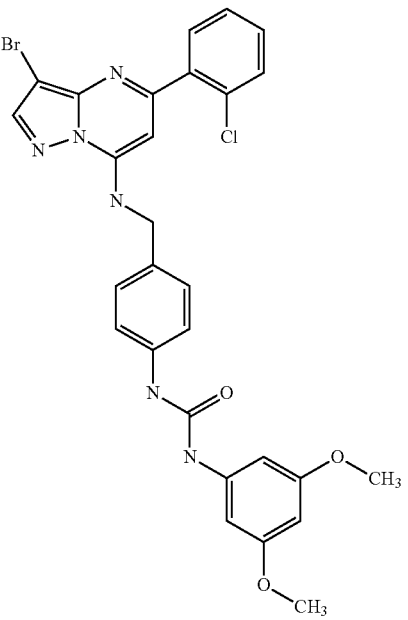 [SMILES: COc1cc(NC(=O)Nc2ccc(CNc3cc(-c4ccccc4Cl)nc4c(Br)cnn34)cc2)cc(OC)c1] | 1. 7328 |

TABLE 73-continued
| Product | 1. Ex. 2. m/z |
|---|---|
| 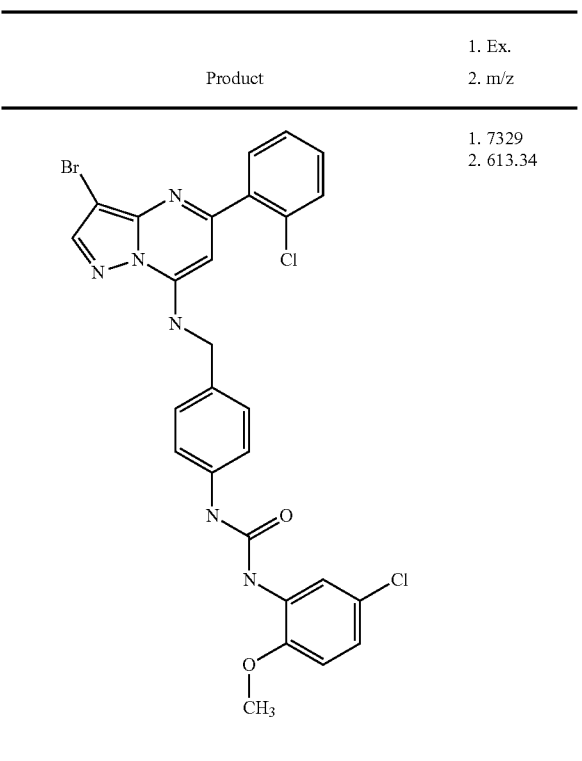 | 1. 7329 2. 613.34 |
| 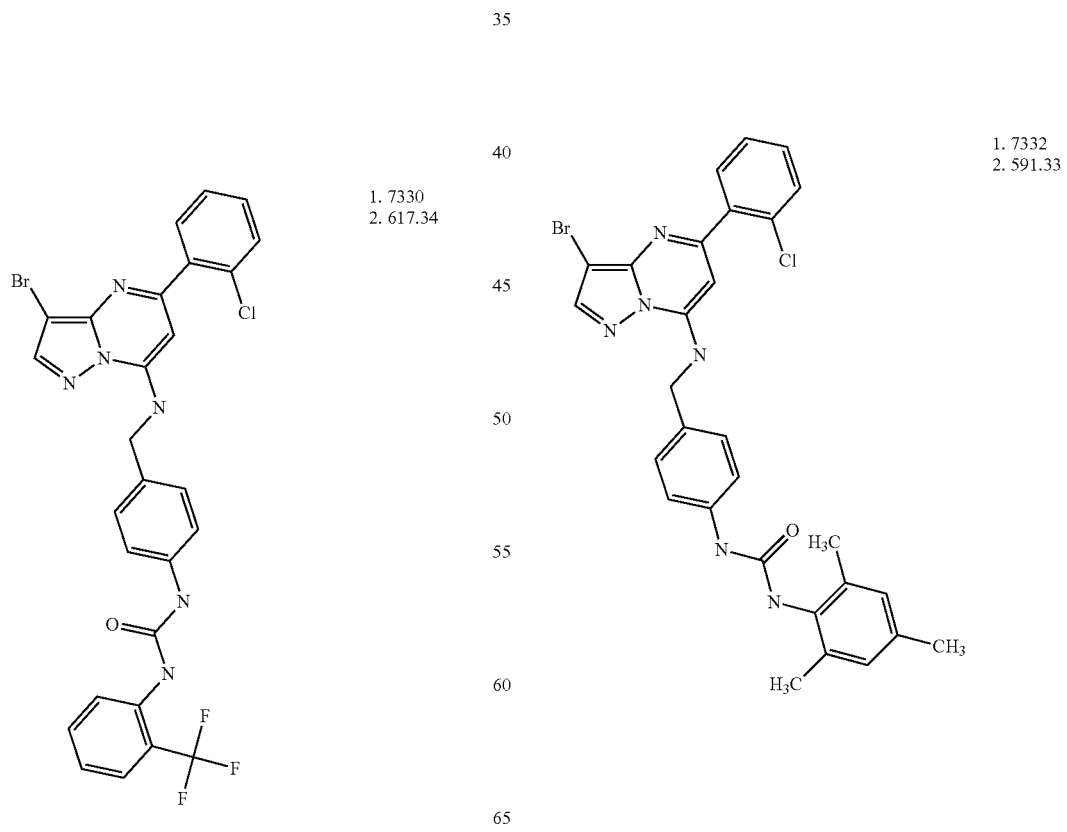 (left structure) | 1. 7330 2. 617.34 |
TABLE 73-continued
| Product | 1. Ex. 2. m/z |
|---|---|
| 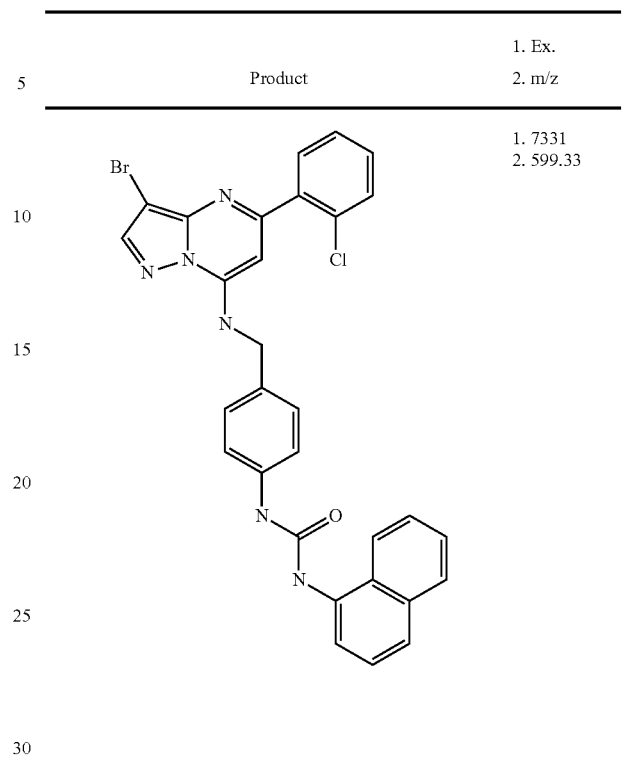 | 1. 7331 2. 599.33 |
| 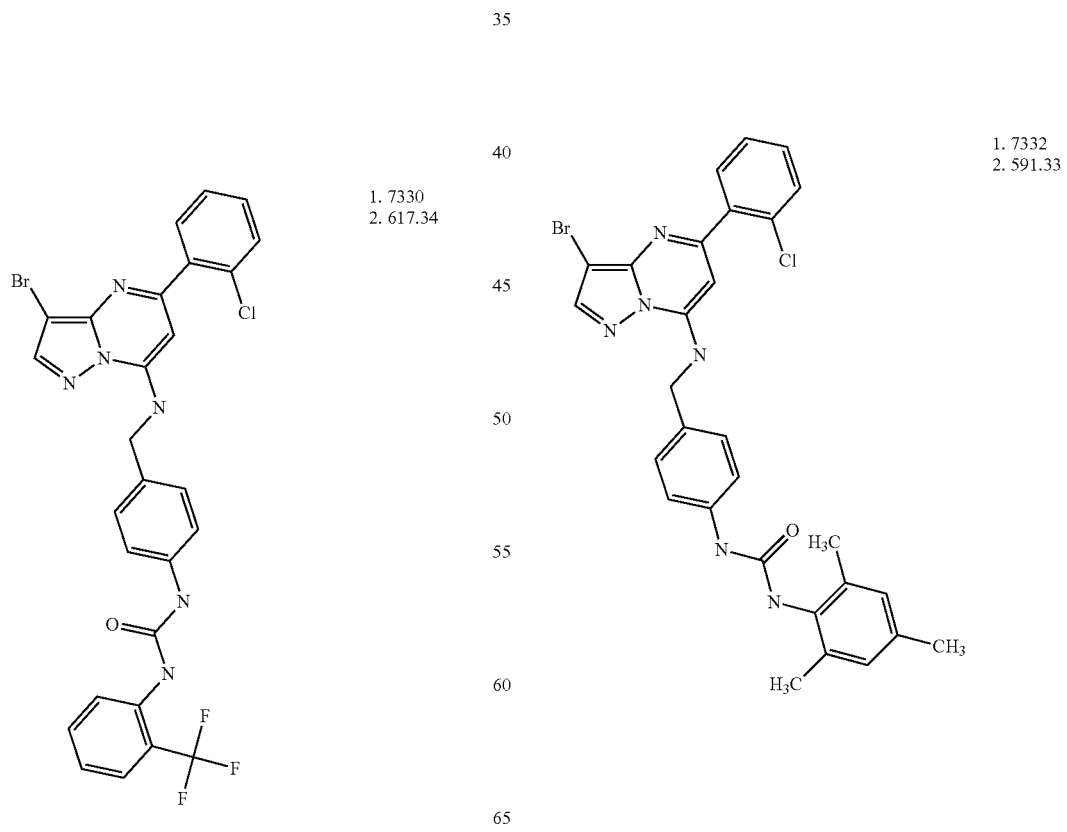 (right structure) | 1. 7332 2. 591.33 |

TABLE 73-continued
| Product | 1. Ex. 2. m/z |
|---|---|
| 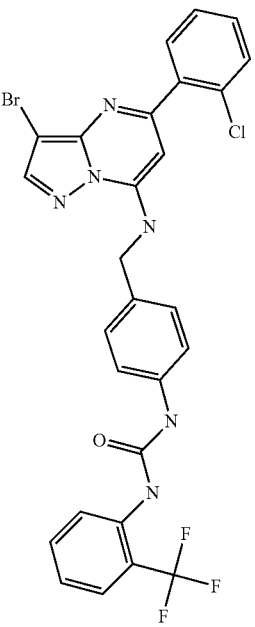 [SMILES: O=C(Nc1ccc(CNc2cc(-c3ccccc3Cl)nc3c(Br)cnn23)cc1)Nc1ccccc1C(F)(F)F] | 1. 7333 2. 609.33 |
| 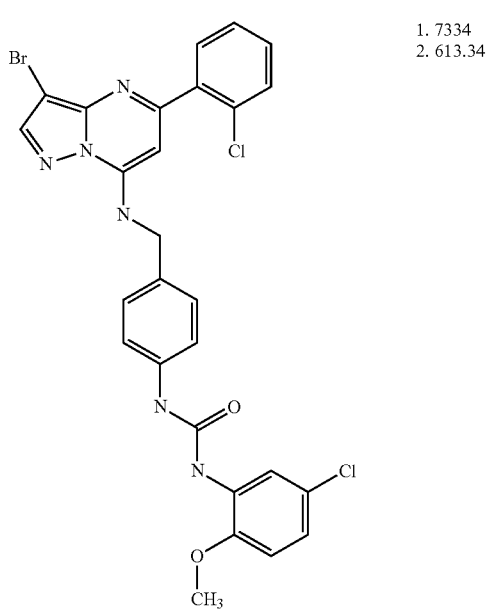 | 1. 7334 2. 613.34 |
TABLE 73-continued
| Product | 1. Ex. 2. m/z |
|---|---|
| | 1. 7335 2. 617.34 |
| | 1. 7336 2. 617.34 |

TABLE 73-continued
| Product | 1. Ex.<br>2. m/z |
|---|---|
| 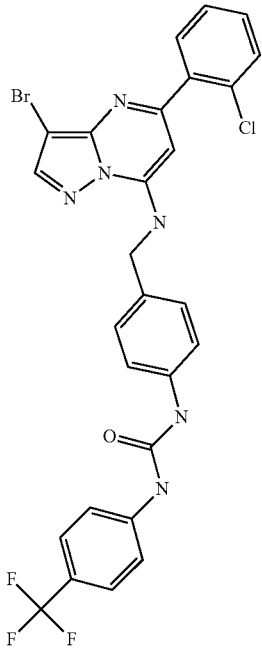 [SMILES: O=C(Nc1ccc(CNc2cc(-c3ccccc3Cl)nc3c(Br)cnn23)cc1)Nc1ccc(C(F)(F)F)cc1] | 1. 7337<br>2. 617.34 |
| | 1. 7338<br>2. 617.34 |
TABLE 73-continued
| Product | 1. Ex.<br>2. m/z |
|---|---|
| 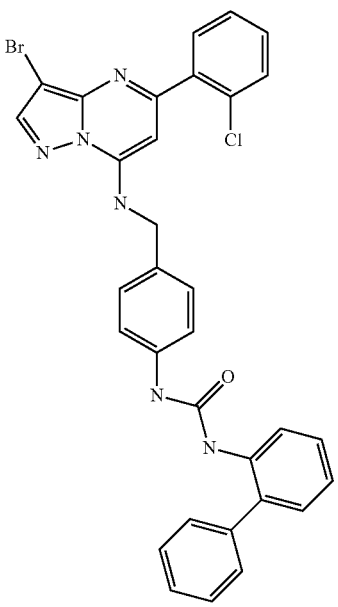 [SMILES: O=C(Nc1ccc(CNc2cc(-c3ccccc3Cl)nc3c(Br)cnn23)cc1)Nc1ccccc1-c1ccccc1] | 1. 7339<br>2. 625.34 |
| | 1. 7340<br>2. 631.35 |

TABLE 73-continued
| Product | 1. Ex.<br>2. m/z |
|---|---|
| 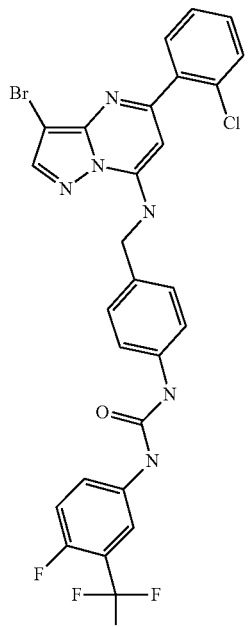 | 1. 7341<br>2. 635.35 |
| 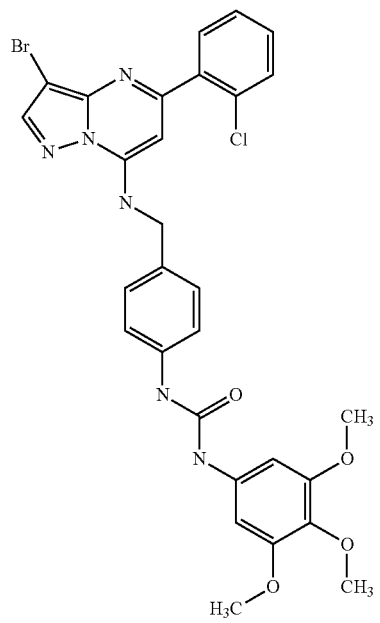 [SMILES: COc1cc(NC(=O)Nc2ccc(CNc3cc(-c4ccccc4Cl)nc4c(Br)cnn34)cc2)cc(OC)c1OC] | 1. 7342<br>2. 639.35 |
TABLE 73-continued
| Product | 1. Ex.<br>2. m/z |
|---|---|
| 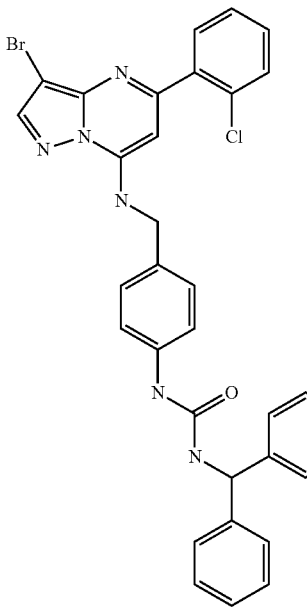 | 1. 7343<br>2. 639.35 |
TABLE 74
| Product | 1. Ex.<br>2. m/z |
|---|---|
| 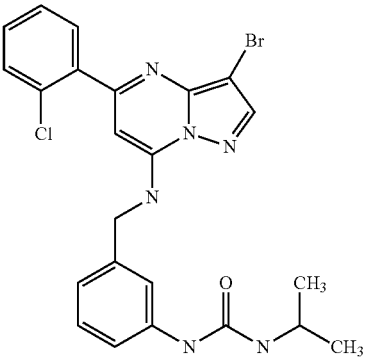 [SMILES: CC(C)NC(=O)Nc1cccc(CNc2cc(-c3ccccc3Cl)nc3c(Br)cnn23)c1] | 1. 7401<br>2. 515.28 |
| 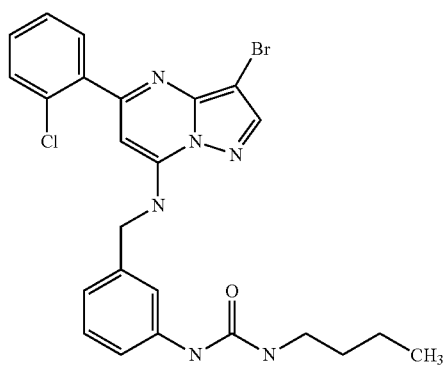 [SMILES: CCCCNC(=O)Nc1cccc(CNc2cc(-c3ccccc3Cl)nc3c(Br)cnn23)c1] | 1. 7402<br>2. 529.29 |

TABLE 74-continued

| Product | 1. Ex. 2. m/z |
|---|---|
| (structure) | 1. 7403  2. 541.3 |
| (structure) | 1. 7404  2. 563.13 |
| (structure) | 1. 7405  2. 563.31 |
| (structure) | 1. 7406  2. 563.31 |
| (structure) | 1. 7407  2. 563.31 |
| (structure) | 1. 7408  2. 567.31 |
| (structure) | 1. 7409  2. 567.31 |
| (structure) | 1. 7410  2. 574.32 |

TABLE 74-continued

| Product | 1. Ex.<br>2. m/z |
|---|---|
| (structure) | 1. 7411<br>2. 574.32 |
| (structure) Chiral | 1. 7412<br>2. 577.14 |
| (structure) Chiral | 1. 7413<br>2. 577.32 |
| (structure) | 1. 7414<br>2. 577.32 |
| (structure) | 1. 7415<br>2. 577.32 |
| (structure) | 1. 7416<br>2. 579.32 |
| (structure) | 1. 7417<br>2. 579.32 |

TABLE 74-continued
| Product | 1. Ex. 2. m/z |
|---|---|
| 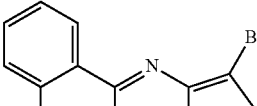 | 1. 7418 2. 579.32 |
| 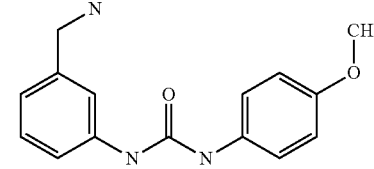 | 1. 7419 2. 581.32 |
| 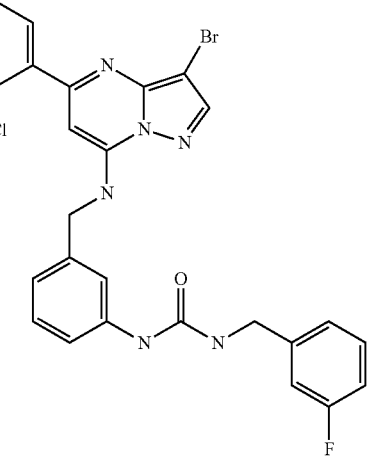 | 1. 7420 2. 583.32 |
| 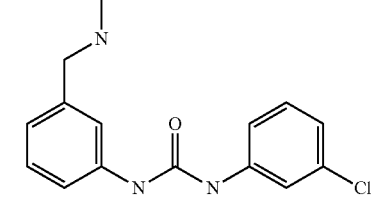 | 1. 7421 2. 583.32 |
| 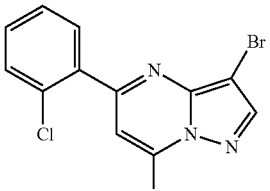 | 1. 7422 2. 585.32 |
| 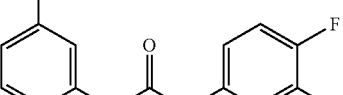 | 1. 7423 2. 585.32 |
| 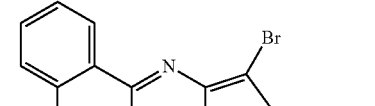 | 1. 7424 2. 589.32 |
| 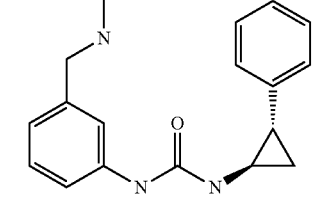 | 1. 7425 2. 591.33 |

TABLE 74-continued
| Product | 1. Ex.<br>2. m/z |
|---|---|
| 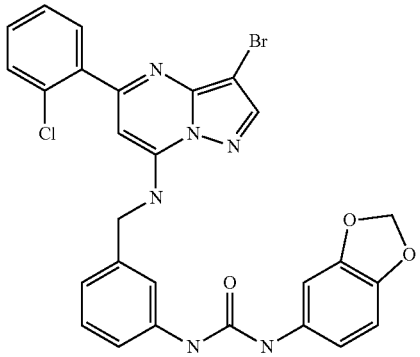 [SMILES: O=C(Nc1cccc(CNc2cc(-c3ccccc3Cl)nc3c(Br)cnn23)c1)Nc1ccc2c(c1)OCO2] | 1. 7426<br>2. 593.33 |
| 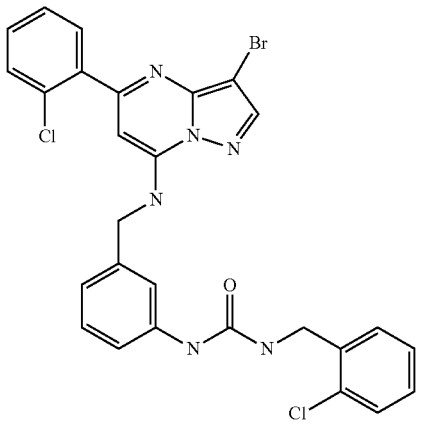 [SMILES: O=C(NCc1ccccc1Cl)Nc1cccc(CNc2cc(-c3ccccc3Cl)nc3c(Br)cnn23)c1] | 1. 7427<br>2. 597.33 |
| 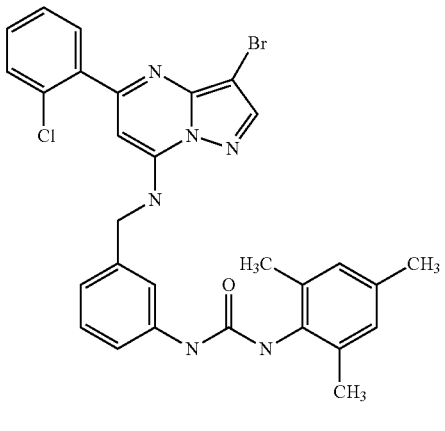 [SMILES: Cc1cc(C)c(NC(=O)Nc2cccc(CNc3cc(-c4ccccc4Cl)nc4c(Br)cnn34)c2)c(C)c1] | 1. 7428<br>2. 591.33 |
| 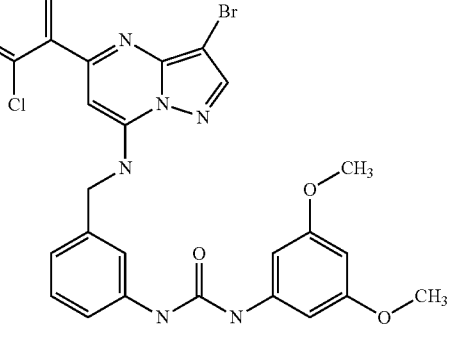 | 1. 7429<br>2. 609.33 |
TABLE 74-continued
| Product | 1. Ex.<br>2. m/z |
|---|---|
| 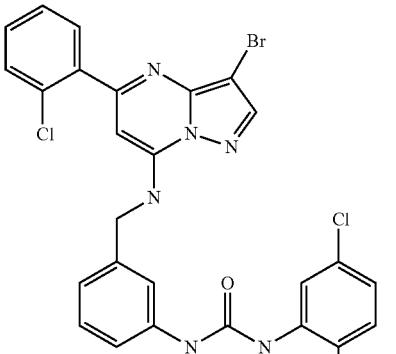 | 1. 7430<br>2. 613.34 |
| 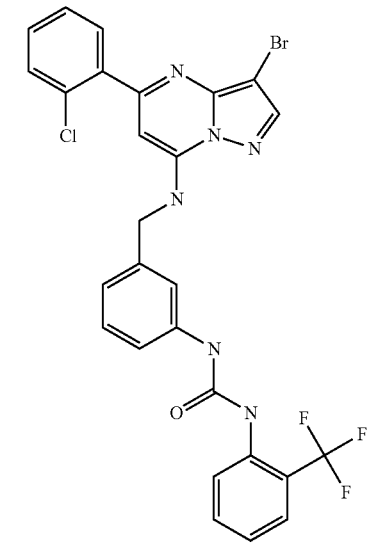 [SMILES: O=C(Nc1cccc(CNc2cc(-c3ccccc3Cl)nc3c(Br)cnn23)c1)Nc1ccccc1C(F)(F)F] | 1. 7431<br>2. 617.34 |
|  | 1. 7432<br>2. 617.34 |

TABLE 74-continued
| Product | 1. Ex. 2. m/z |
|---|---|
| 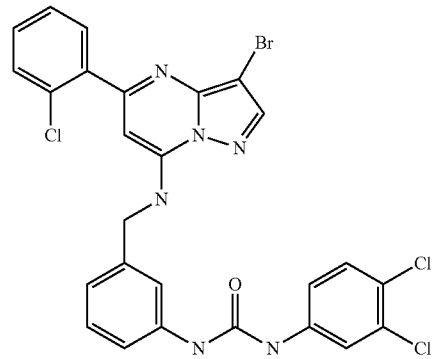 [SMILES: O=C(Nc1cccc(CNc2cc(-c3ccccc3Cl)nc3c(Br)cnn23)c1)Nc1ccc(Cl)c(Cl)c1] | 1. 7433 2. 617.34 |
| 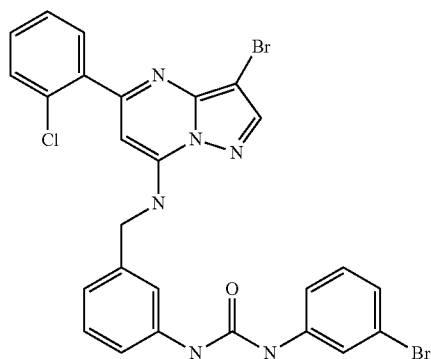 [SMILES: O=C(Nc1cccc(Br)c1)Nc1cccc(CNc2cc(-c3ccccc3Cl)nc3c(Br)cnn23)c1] | 1. 7434 2. 627.34 |
| 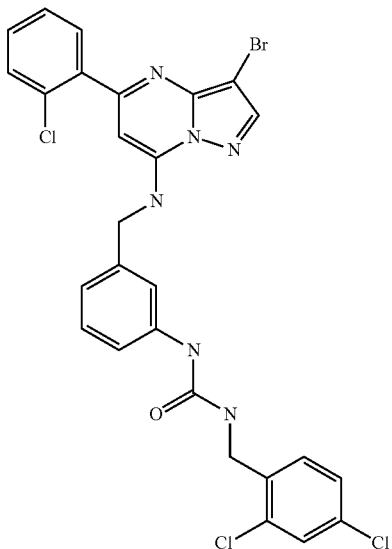 [SMILES: O=C(NCc1ccc(Cl)cc1Cl)Nc1cccc(CNc2cc(-c3ccccc3Cl)nc3c(Br)cnn23)c1] | 1. 7435 2. 631.35 |
TABLE 74-continued
| Product | 1. Ex. 2. m/z |
|---|---|
| 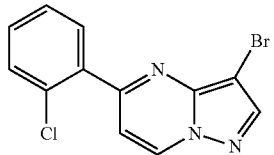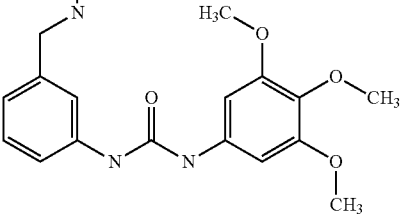 | 1. 7436 2. 639.35 |
| 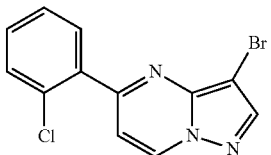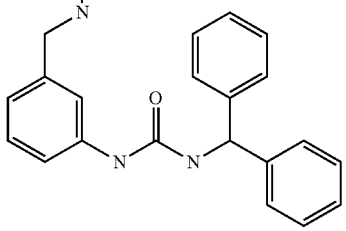 | 1. 7437 2. 693.35 |
| 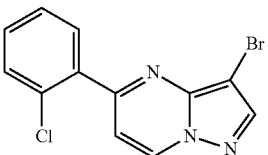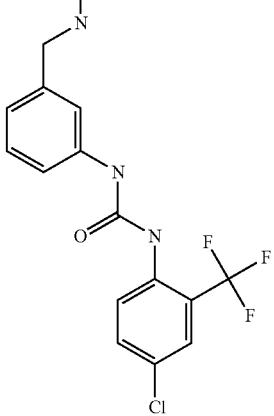 | 1. 7438 2. 651.36 |

TABLE 75

| Product | 1. Ex.<br>2. m/z |
|---|---|
| (structure: 3-bromo-5-(2-chlorophenyl)pyrazolo[1,5-a]pyrimidine-7-yl with N-(CH₂)₄-NH-C(=O)-NH-isopropyl) | 1. 7501<br>2. 481.26 |
| (structure: 3-bromo-5-(2-chlorophenyl)pyrazolo[1,5-a]pyrimidine-7-yl with N-(CH₂)₄-NH-C(=O)-NH-tert-butyl) | 1. 7502<br>2. 495.27 |

TABLE 75-continued

| Product | 1. Ex.<br>2. m/z |
|---|---|
| (structure: 3-bromo-5-(2-chlorophenyl)pyrazolo[1,5-a]pyrimidine-7-yl with N-(CH₂)₄-NH-C(=O)-NH-n-butyl) | 1. 7503<br>2. 495.27 |
| (structure: 3-bromo-5-(2-chlorophenyl)pyrazolo[1,5-a]pyrimidine-7-yl with N-(CH₂)₄-NH-C(=O)-NH-cyclopentyl) | 1. 7504<br>2. 507.28 |

TABLE 75-continued

| Product | 1. Ex.<br>2. m/z |
|---|---|
| (structure: 5-(2-chlorophenyl)-3-bromo-pyrazolo[1,5-a]pyrimidin-7-yl amine linked via butyl chain to N-benzyl urea) | 1. 7505<br>2. 529.29 |
| (structure: 5-(2-chlorophenyl)-3-bromo-pyrazolo[1,5-a]pyrimidin-7-yl amine linked via butyl chain to N-(2-methylphenyl) urea) | 1. 7506<br>2. 529.29 |
| (structure: 5-(2-chlorophenyl)-3-bromo-pyrazolo[1,5-a]pyrimidin-7-yl amine linked via butyl chain to N-(3-methylphenyl) urea) | 1. 7507<br>2. 529.29 |
| (structure: 5-(2-chlorophenyl)-3-bromo-pyrazolo[1,5-a]pyrimidin-7-yl amine linked via butyl chain to N-(4-methylphenyl) urea) | 1. 7508<br>2. 529.29 |
| (structure: 5-(2-chlorophenyl)-3-bromo-pyrazolo[1,5-a]pyrimidin-7-yl amine linked via butyl chain to N-(2-fluorophenyl) urea) | 1. 7509<br>2. 533.29 |
| (structure: 5-(2-chlorophenyl)-3-bromo-pyrazolo[1,5-a]pyrimidin-7-yl amine linked via butyl chain to N-(4-fluorophenyl) urea) | 1. 7510<br>2. 533.29 |

TABLE 75-continued
| Product | 1. Ex.<br>2. m/z |
|---|---|
| 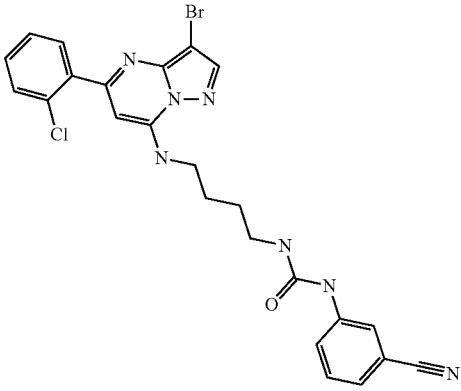 [SMILES: N#Cc1cccc(NC(=O)NCCCCNc2cc(-c3ccccc3Cl)nc3c(Br)cnn23)c1] | 1. 7511<br>2. 540.3 |
| 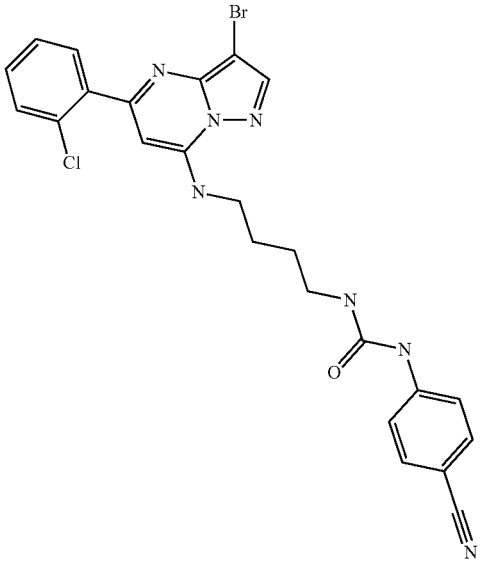 [SMILES: N#Cc1ccc(NC(=O)NCCCCNc2cc(-c3ccccc3Cl)nc3c(Br)cnn23)cc1] | 1. 7512<br>2. 540.3 |
| 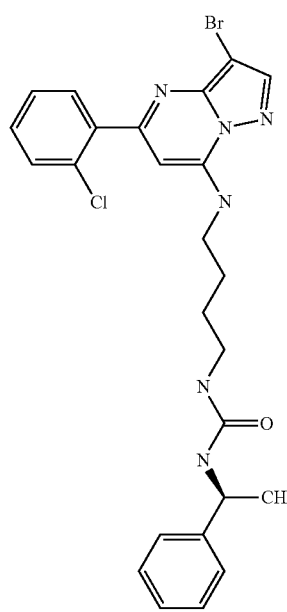 Chiral | 1. 7513<br>2. 543.3 |
TABLE 75-continued
| Product | 1. Ex.<br>2. m/z |
|---|---|
| 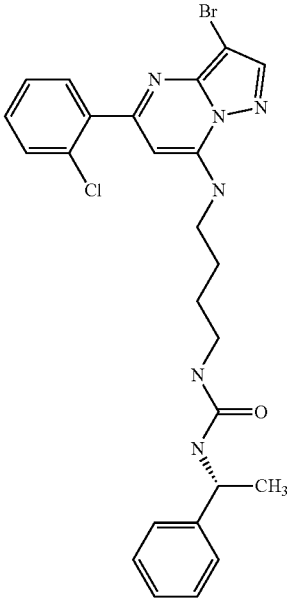 Chiral | 1. 7514<br>2. 543.3 |
| 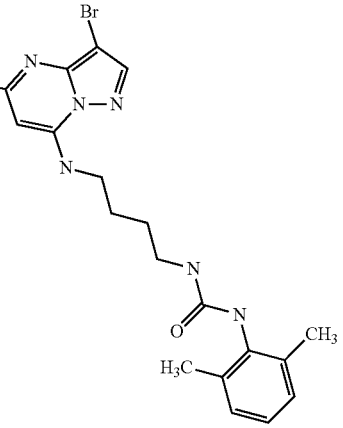 | 1. 7515<br>2. 543.3 |

TABLE 75-continued
| Product | 1. Ex.<br>2. m/z |
|---|---|
| 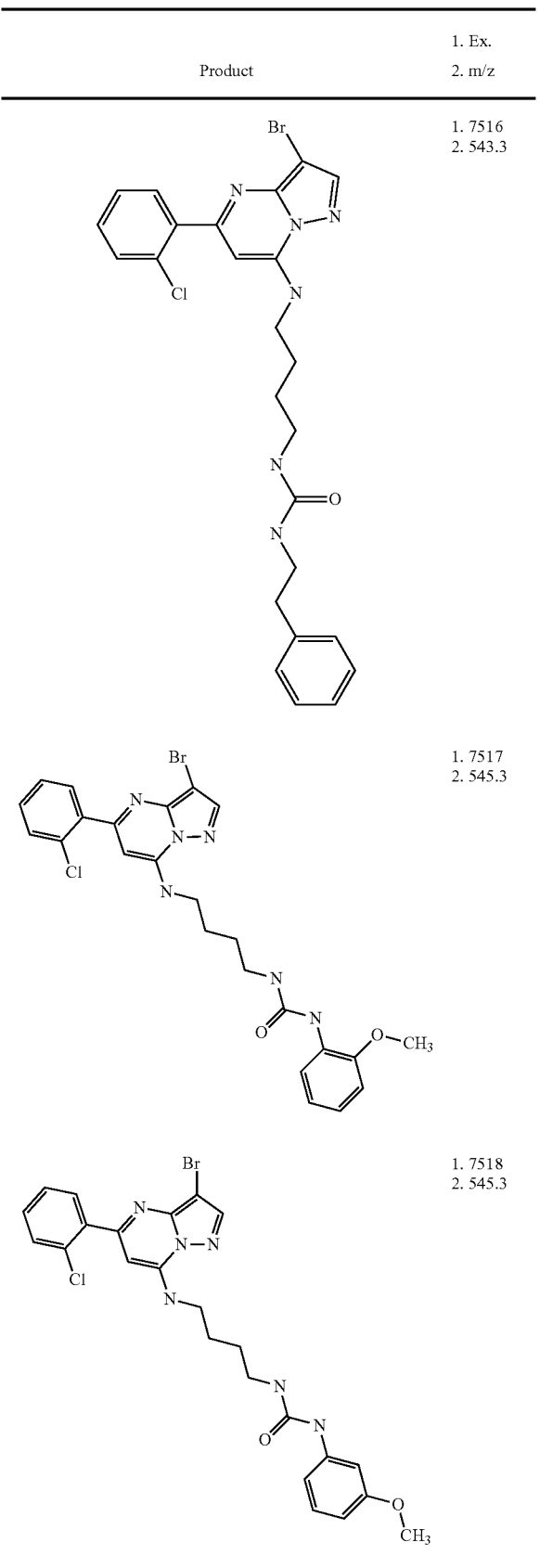 | 1. 7516<br>2. 543.3 |
| | 1. 7517<br>2. 545.3 |
| | 1. 7518<br>2. 545.3 |
TABLE 75-continued
| Product | 1. Ex.<br>2. m/z |
|---|---|
| 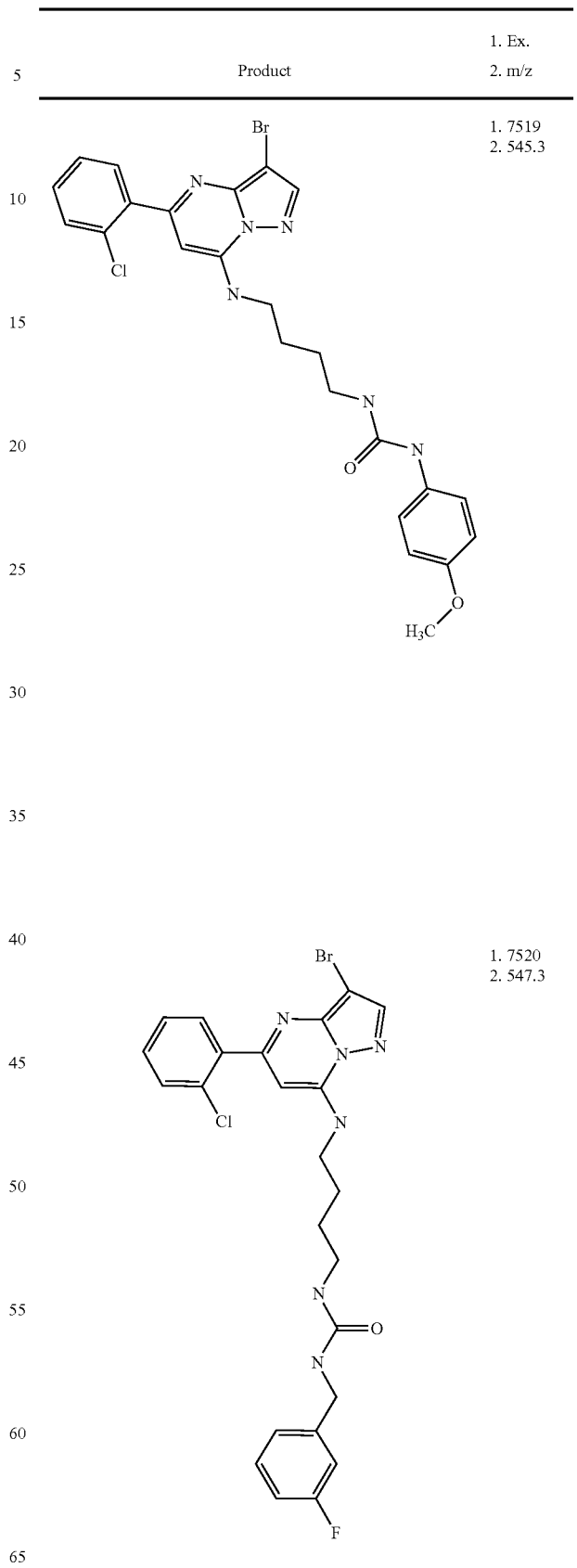 | 1. 7519<br>2. 545.3 |
| | 1. 7520<br>2. 547.3 |

TABLE 75-continued
| Product | 1. Ex. 2. m/z |
|---|---|
| 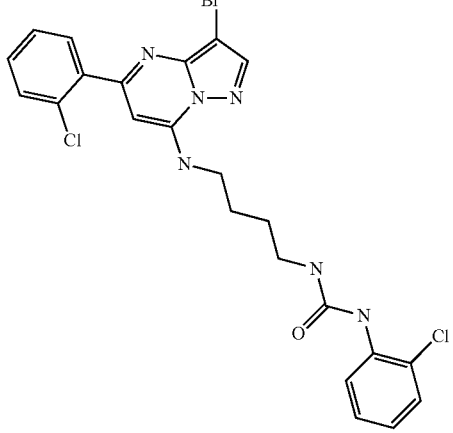 | 1. 7521  2. 549.3 |
| 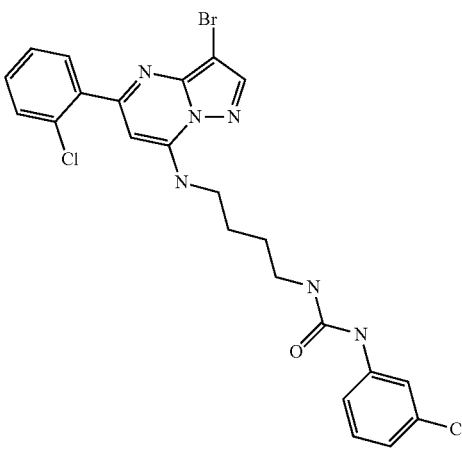 [SMILES: O=C(NCCCCNc1cc(-c2ccccc2Cl)nc2c(Br)cnn12)Nc1cccc(Cl)c1] | 1. 7522  2. 549.3 |
| 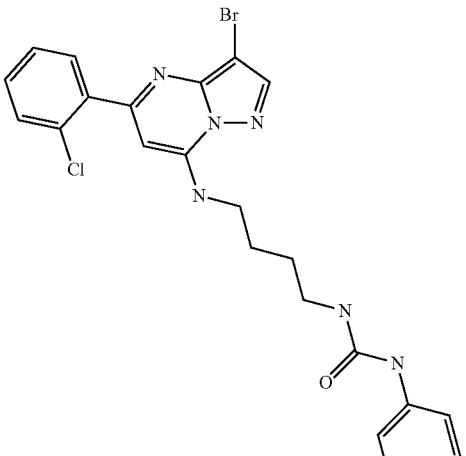 | 1. 7523  2. 549.3 |
TABLE 75-continued
| Product | 1. Ex. 2. m/z |
|---|---|
| 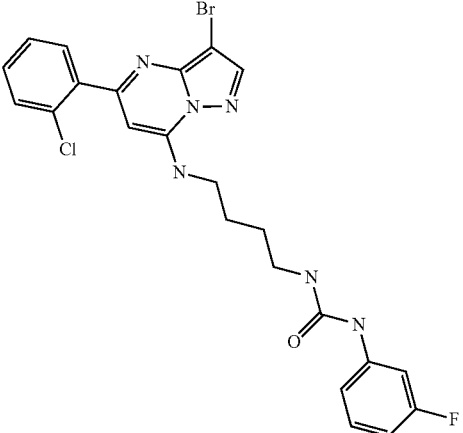 | 1. 7524  2. 551.3 |
| 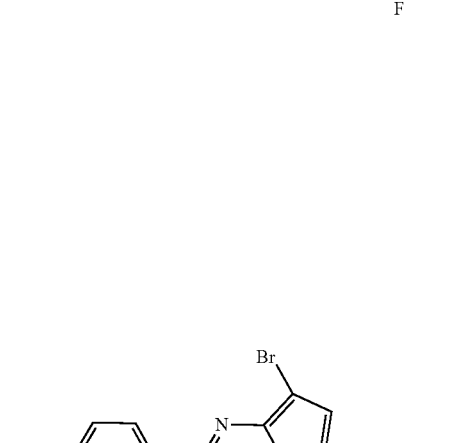 | 1. 7525  2. 551.3 |

TABLE 75-continued
| Product | 1. Ex. 2. m/z |
|---|---|
| 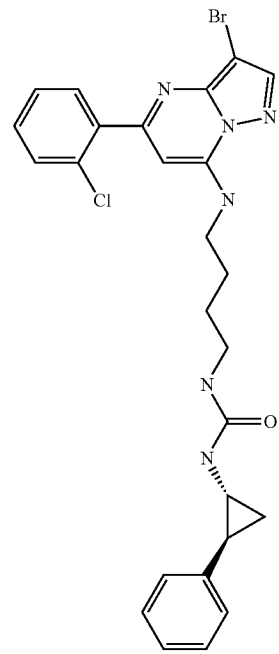 [SMILES: O=C(NCCCCNc1cc(-c2ccccc2Cl)nc2c(Br)cnn12)N[C@@H]1C[C@H]1c1ccccc1] | 1. 7526 2. 555.31 |
| 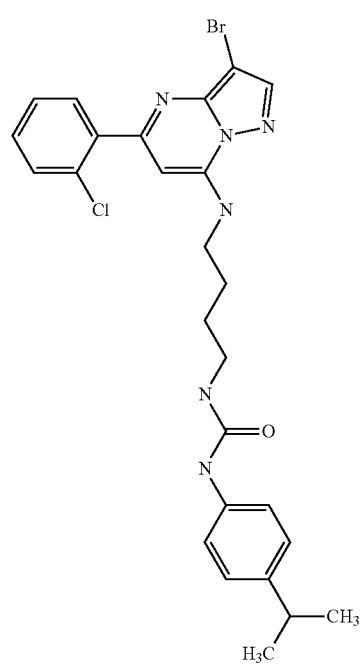 [SMILES: CC(C)c1ccc(NC(=O)NCCCCNc2cc(-c3ccccc3Cl)nc3c(Br)cnn23)cc1] | 1. 7527 2. 557.31 |
| 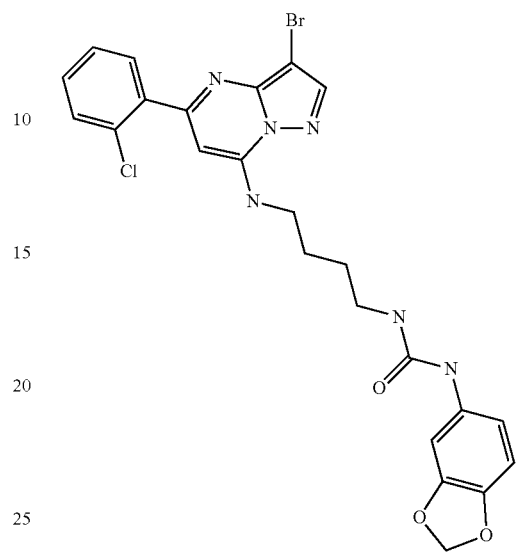 | 1. 7528 2. 559.31 |
| 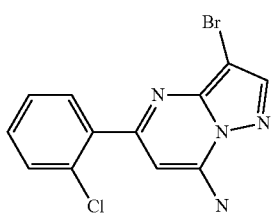 | 1. 7529 2. 560.31 |
| 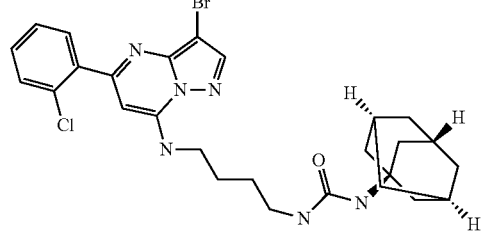 | 1. 7530 2. 573.32 |

TABLE 75-continued
| Product | 1. Ex. 2. m/z |
|---|---|
| 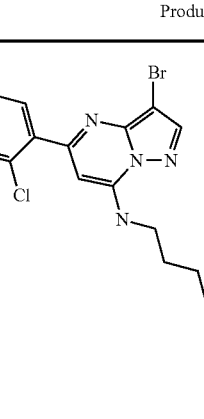 | 1. 7531 2. 579.32 |
| 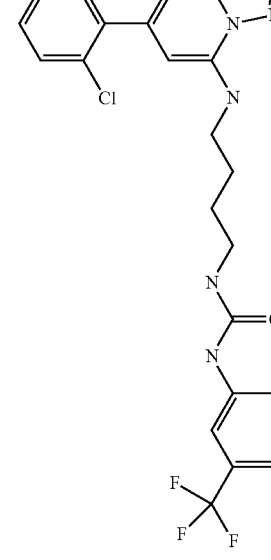 | 1. 7532 2. 583.32 |
| 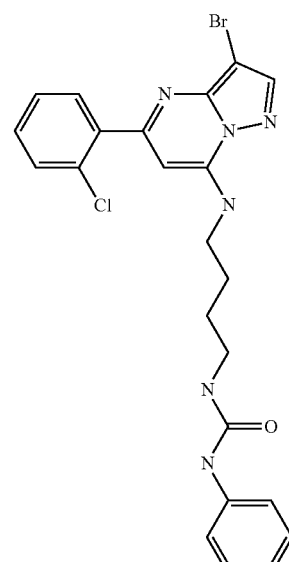 | 1. 7533 2. 583.32 |
| 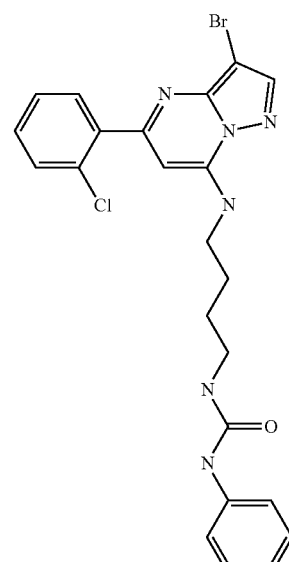 | 1. 7534 2. 583.32 |

TABLE 75-continued

| Product | 1. Ex.<br>2. m/z |
|---|---|
| (structure 1427 top) | 1. 7535<br>2. 583.32 |
| (structure 1427 bottom) | 1. 7536<br>2. 583.32 |

TABLE 75-continued

| Product | 1. Ex.<br>2. m/z |
|---|---|
| (structure 1428 top) | 1. 7537<br>2. 591.33 |
| (structure 1428 bottom) | 1. 7538<br>2. 593.33 |

TABLE 75-continued
| Product | 1. Ex.<br>2. m/z |
|---|---|
| 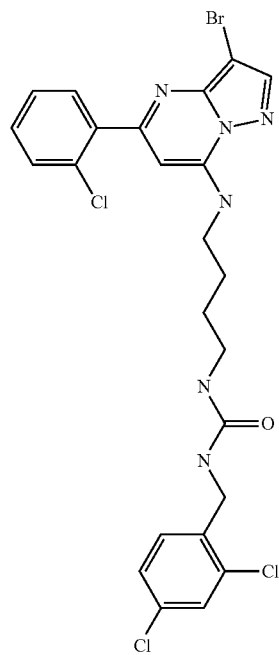 [SMILES: O=C(NCCCCNc1cc(-c2ccccc2Cl)nc2c(Br)cnn12)NCc1ccc(Cl)cc1Cl] | 1. 7539<br>2. 597.33 |
| 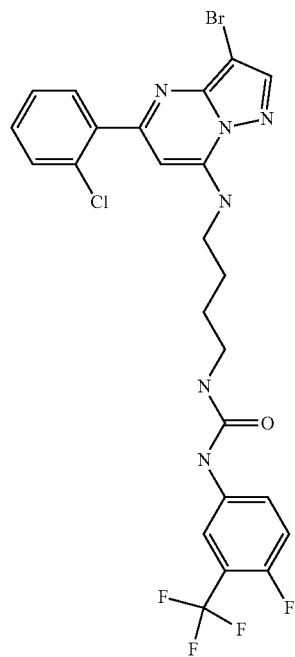 [SMILES: O=C(NCCCCNc1cc(-c2ccccc2Cl)nc2c(Br)cnn12)Nc1ccc(F)c(C(F)(F)F)c1] | 1. 7540<br>2. 601.33 |
TABLE 75-continued
| Product | 1. Ex.<br>2. m/z |
|---|---|
| 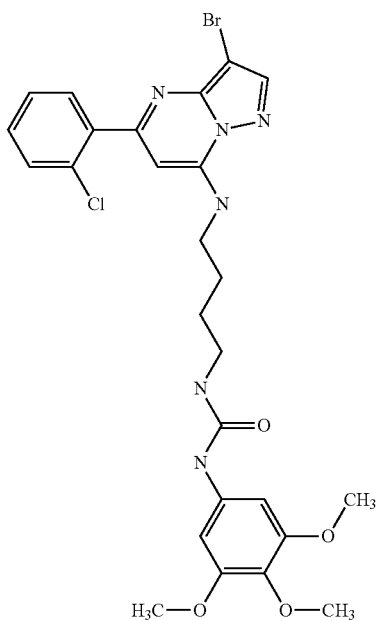 [SMILES: COc1cc(NC(=O)NCCCCNc2cc(-c3ccccc3Cl)nc3c(Br)cnn23)cc(OC)c1OC] | 1. 7541<br>2. 605.33 |
| 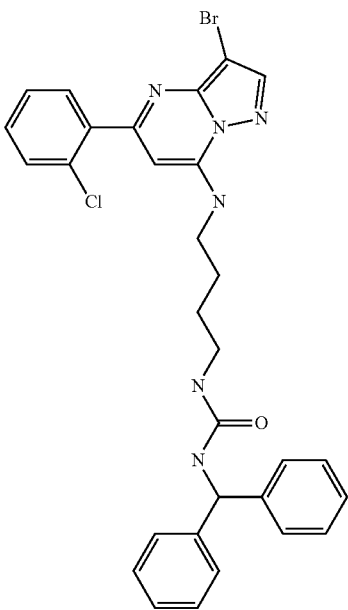 [SMILES: O=C(NCCCCNc1cc(-c2ccccc2Cl)nc2c(Br)cnn12)NC(c1ccccc1)c1ccccc1] | 1. 7542<br>2. 605.33 |

TABLE 75-continued

| Product | 1. Ex.<br>2. m/z |
|---|---|
| (structure) | 1. 7543<br>2. 614.34 |

TABLE 76

| Product | 1. Ex.<br>2. m/z |
|---|---|
| (structure) | 1. 7601<br>2. 453.25 |

TABLE 76-continued

| Product | 1. Ex.<br>2. m/z |
|---|---|
| (structure) | 1. 7602<br>2. 467.26 |
| (structure) | 1. 7603<br>2. 467.26 |
| (structure) | 1. 7604<br>2. 479.26 |

TABLE 76-continued

| Product | 1. Ex.<br>2. m/z |
|---|---|
| (structure) | 1. 7605<br>2. 501.28 |
| (structure) | 1. 7606<br>2. 501.28 |
| (structure) | 1. 7607<br>2. 501.28 |
| (structure) | 1. 7608<br>2. 501.28 |
| (structure) | 1. 7609<br>2. 505.28 |
| (structure) | 1. 7610<br>2. 505.28 |

TABLE 76-continued
| Product | 1. Ex.<br>2. m/z |
|---|---|
| 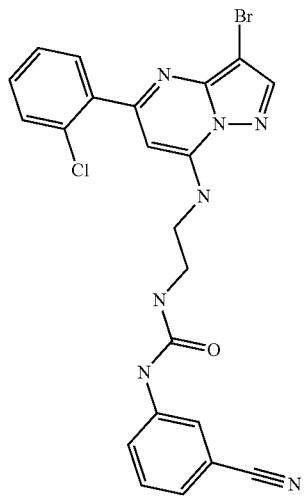 [SMILES: N#Cc1cccc(NC(=O)NCCNc2cc(-c3ccccc3Cl)nc3c(Br)cnn23)c1] | 1. 7611<br>2. 512.28 |
| 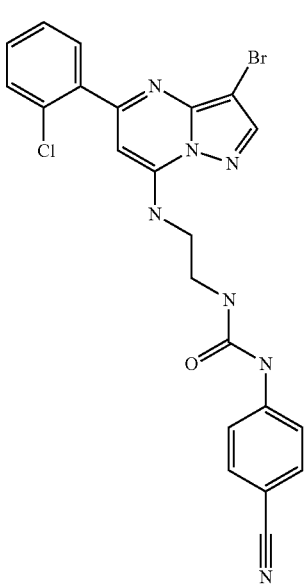 [SMILES: N#Cc1ccc(NC(=O)NCCNc2cc(-c3ccccc3Cl)nc3c(Br)cnn23)cc1] | 1. 7612<br>2. 512.28 |
| 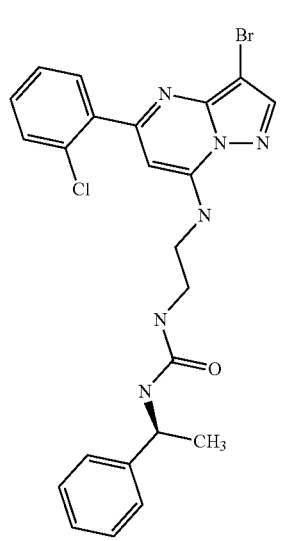 Chiral | 1. 7613<br>2. 515.28 |
TABLE 76-continued
| Product | 1. Ex.<br>2. m/z |
|---|---|
| 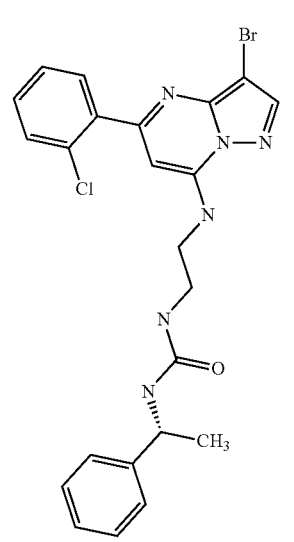 Chiral | 1. 7614<br>2. 515.28 |
| 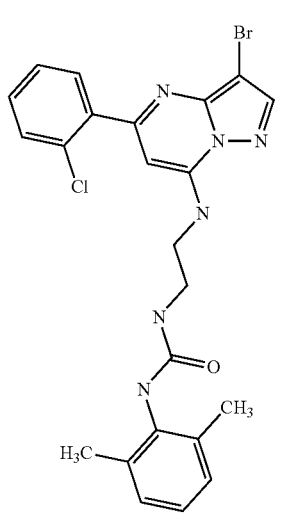 [SMILES: Cc1cccc(C)c1NC(=O)NCCNc1cc(-c2ccccc2Cl)nc2c(Br)cnn12] | 1. 7615<br>2. 515.28 |

TABLE 76-continued

| Product | 1. Ex.<br>2. m/z |
|---|---|
| (structure) | 1. 7616<br>2. 515.28 |
| (structure) | 1. 7617<br>2. 517.28 |
| (structure) | 1. 7618<br>2. 517.28 |
| (structure) | 1. 7619<br>2. 517.28 |
| (structure) | 1. 7620<br>2. 519.29 |

TABLE 76-continued
| Product | 1. Ex. 2. m/z |
|---|---|
| 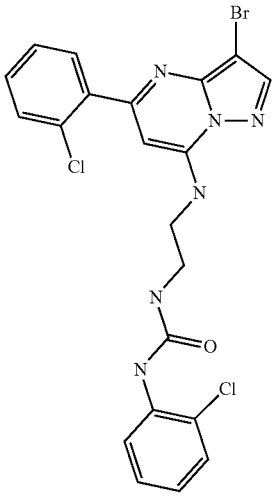 [SMILES: O=C(NCCNc1cc(-c2ccccc2Cl)nc2c(Br)cnn12)Nc1ccccc1Cl] | 1. 7621 2. 521.29 |
| 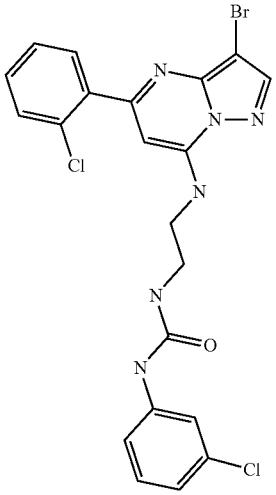 [SMILES: O=C(NCCNc1cc(-c2ccccc2Cl)nc2c(Br)cnn12)Nc1cccc(Cl)c1] | 1. 7622 2. 521.29 |
| 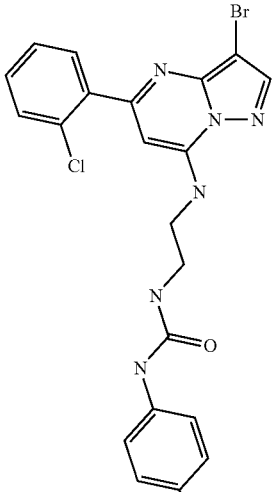 | 1. 7623 2. 521.29 |
TABLE 76-continued
| Product | 1. Ex. 2. m/z |
|---|---|
| 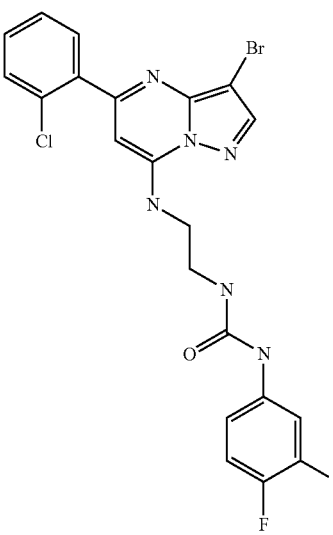 | 1. 7624 2. 523.29 |
| 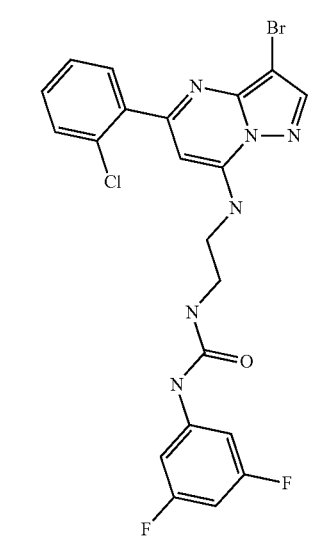 [SMILES: O=C(NCCNc1cc(-c2ccccc2Cl)nc2c(Br)cnn12)Nc1cc(F)cc(F)c1] | 1. 7625 2. 523.29 |

TABLE 76-continued
| Product | 1. Ex.<br>2. m/z |
|---|---|
| 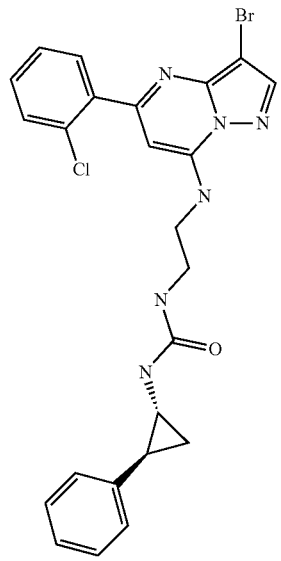 [SMILES: O=C(NCCNc1cc(-c2ccccc2Cl)nc2c(Br)cnn12)N[C@@H]1C[C@H]1c1ccccc1] | 1. 7626<br>2. 527.29 |
| 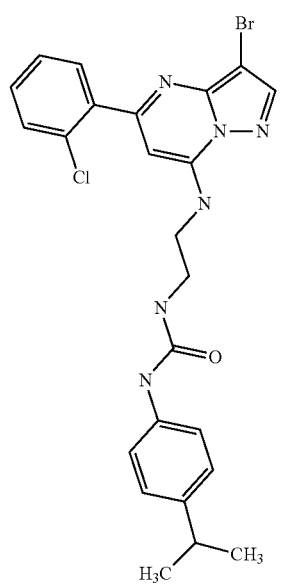 [SMILES: CC(C)c1ccc(NC(=O)NCCNc2cc(-c3ccccc3Cl)nc3c(Br)cnn23)cc1] | 1. 7627<br>2. 529.29 |
TABLE 76-continued
| Product | 1. Ex.<br>2. m/z |
|---|---|
| 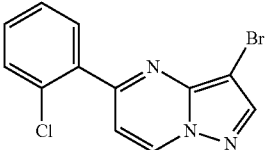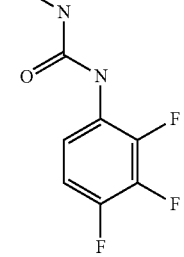 | 1. 7628<br>2. 541.3 |
| 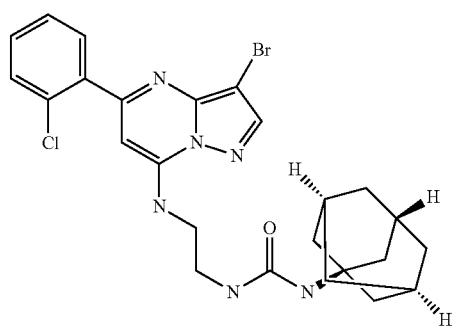 [SMILES: O=C(NCCNc1cc(-c2ccccc2Cl)nc2c(Br)cnn12)N[C@]12C[C@H]3C[C@H](C[C@H](C3)C1)C2] | 1. 7629<br>2. 545.3 |
| 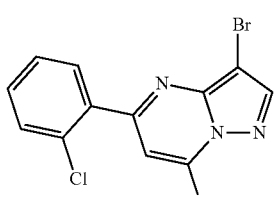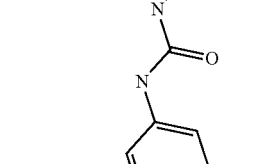 | 1. 7630<br>2. 547.3 |
| 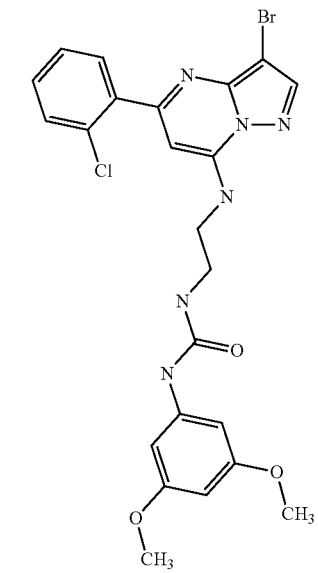 [SMILES: COc1cc(NC(=O)NCCNc2cc(-c3ccccc3Cl)nc3c(Br)cnn23)cc(OC)c1] | |

TABLE 76-continued
| Product | 1. Ex. 2. m/z |
|---|---|
| 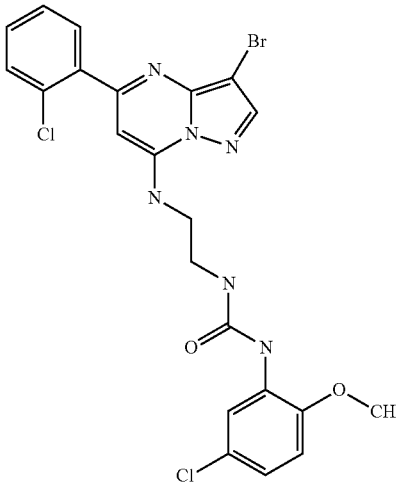 | 1. 7631 2. 551.3 |
| 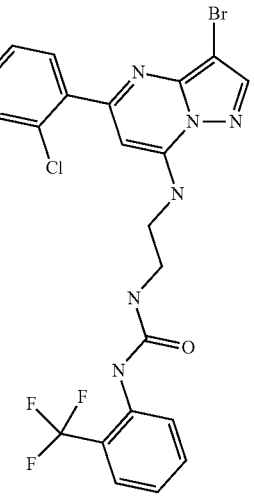 | 1. 7632 2. 555.31 |
| 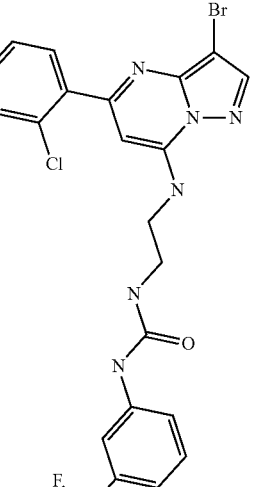 | 1. 7633 2. 555.31 |
| 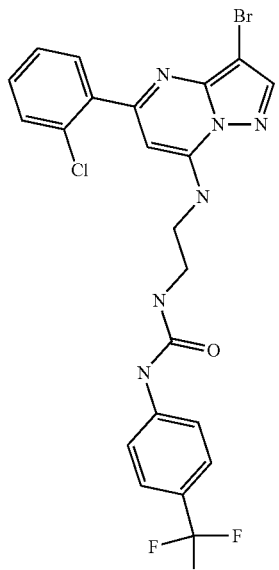 | 1. 7634 2. 555.31 |
| | 1. 7635 2. 555.31 |

TABLE 76-continued
| Product | 1. Ex.<br>2. m/z |
|---|---|
| 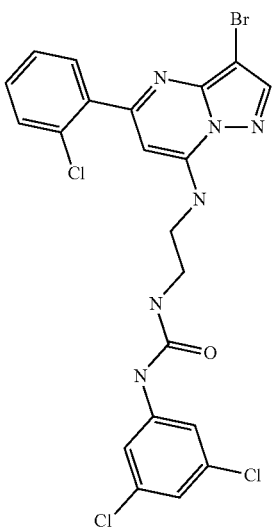 [SMILES: O=C(NCCNc1cc(-c2ccccc2Cl)nc2c(Br)cnn12)Nc1cc(Cl)cc(Cl)c1] | 1. 7636<br>2. 555.31 |
| 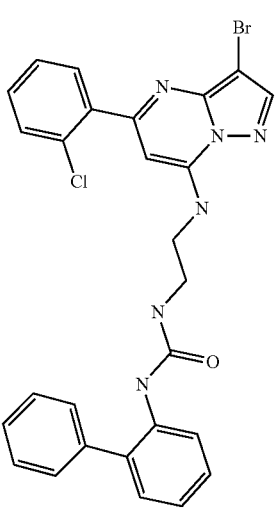 [SMILES: O=C(NCCNc1cc(-c2ccccc2Cl)nc2c(Br)cnn12)Nc1ccccc1-c1ccccc1] | 1. 7637<br>2. 563.31 |
| 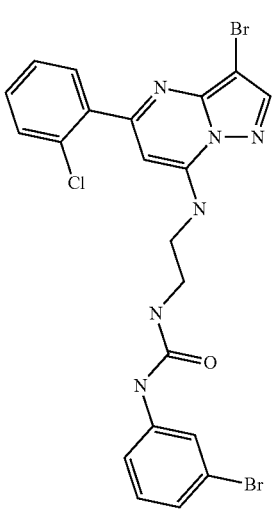 [SMILES: O=C(NCCNc1cc(-c2ccccc2Cl)nc2c(Br)cnn12)Nc1cccc(Br)c1] | 1. 7638<br>2. 565.31 |
TABLE 76-continued
| Product | 1. Ex.<br>2. m/z |
|---|---|
| 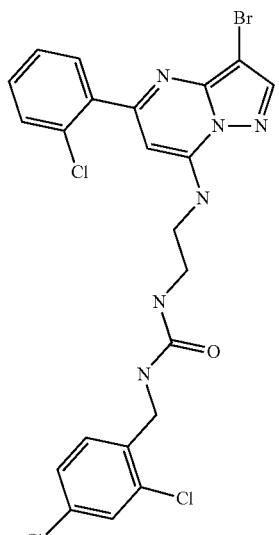 | 1. 7639<br>2. 569.31 |
| 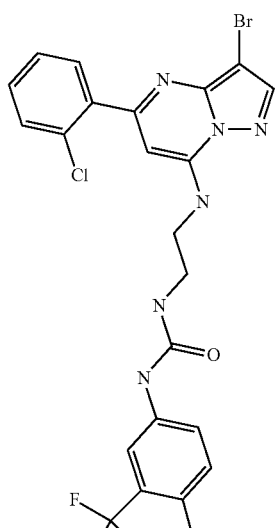 | 1. 7640<br>2. 573.32 |

TABLE 76-continued
| Product | 1. Ex.<br>2. m/z |
|---|---|
| 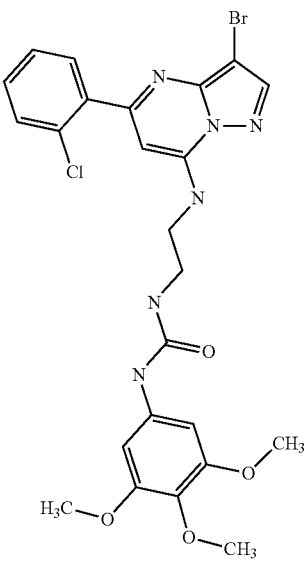 [SMILES: COc1cc(NC(=O)NCCNc2cc(-c3ccccc3Cl)nc3c(Br)cnn23)cc(OC)c1OC] | 1. 7641<br>2. 577.32 |
| 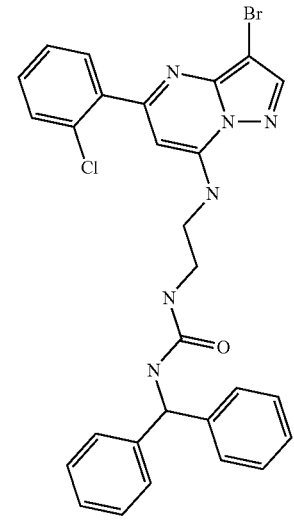 [SMILES: O=C(NCCNc1cc(-c2ccccc2Cl)nc2c(Br)cnn12)NC(c1ccccc1)c1ccccc1] | 1. 7642<br>2. 577.32 |
TABLE 77
| Product | 1. Ex.<br>2. m/z |
|---|---|
| 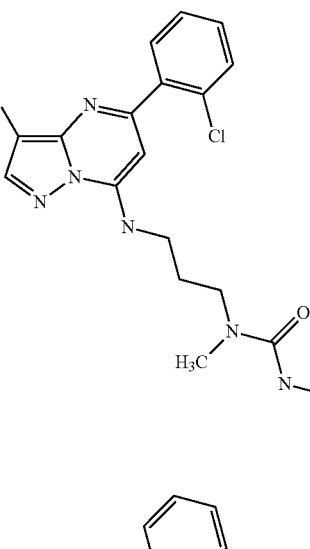 | 1. 7701<br>2. 481.26 |
| 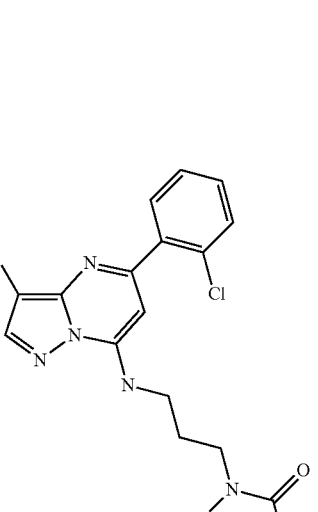 | 1. 7702<br>2. 495.27 |
| 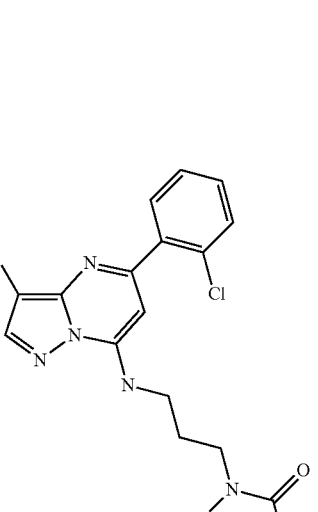 | 1. 7703<br>2. 495.27 |

TABLE 77-continued
| Product | 1. Ex. 2. m/z |
|---|---|
| 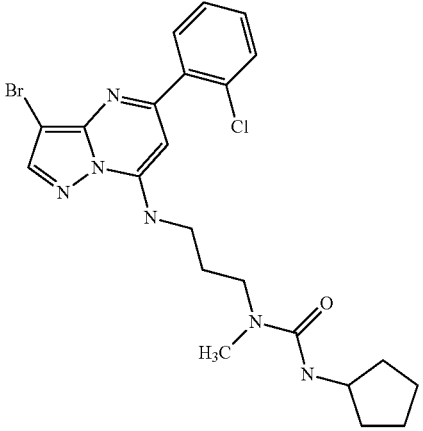 [SMILES: CN(CCCNc1cc(-c2ccccc2Cl)nc2c(Br)cnn12)C(=O)NC1CCCC1] | 1. 7704 2. 507.28 |
| 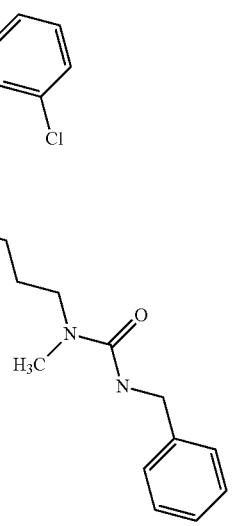 | 1. 7705 2. 529.29 |
| 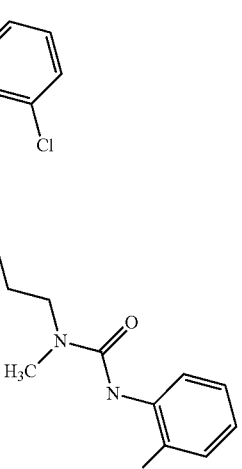 | 1. 7706 2. 529.29 |
TABLE 77-continued
| Product | 1. Ex. 2. m/z |
|---|---|
| 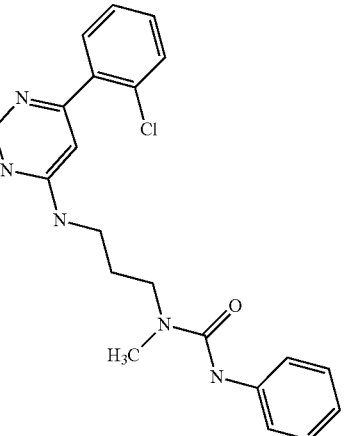 | 1. 7707 2. 529.29 |
| 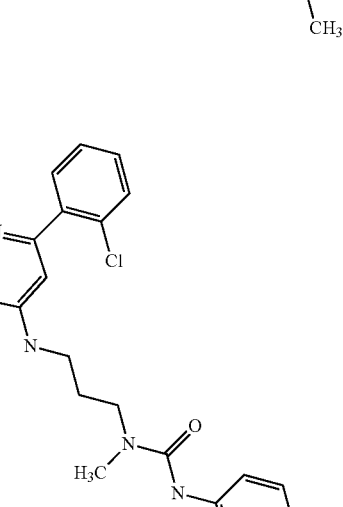 | 1. 7708 2. 529.29 |
| 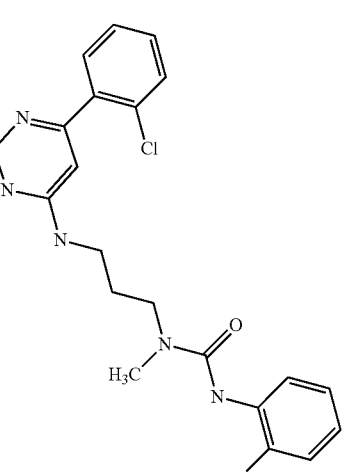 | 1. 7709 2. 533.29 |

TABLE 77-continued
| Product | 1. Ex.<br>2. m/z |
|---------|------------------|
| | 1. 7710<br>2. 533.29 |
TABLE 78
| Product | 1. Ex.<br>2. m/z |
|---------|------------------|
| | 1. 7801<br>2. 507.28 |
| 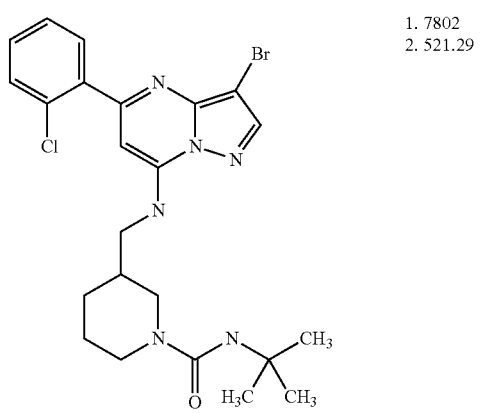 | 1. 7802<br>2. 521.29 |
TABLE 78-continued
| Product | 1. Ex.<br>2. m/z |
|---------|------------------|
| | 1. 7803<br>2. 521.29 |
| 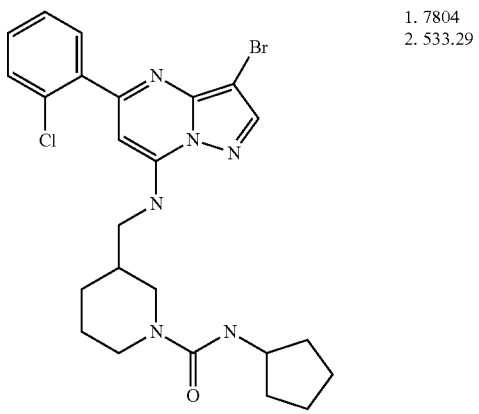 | 1. 7804<br>2. 533.29 |
| 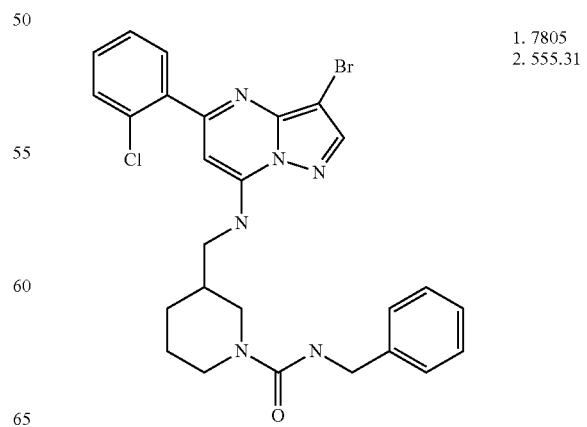 | 1. 7805<br>2. 555.31 |

US 8,673,924 B2
TABLE 78-continued
| Product | 1. Ex. 2. m/z |
|---|---|
| 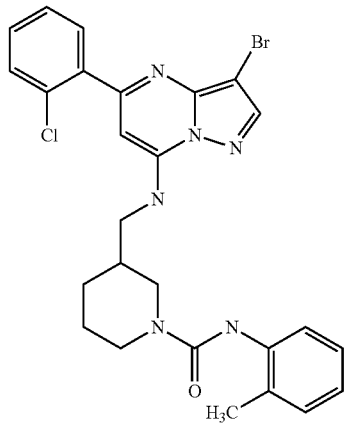 [SMILES: Cc1ccccc1NC(=O)N1CCCC(CNc2cc(-c3ccccc3Cl)nc3c(Br)cnn23)C1] | 1. 7806 2. 555.31 |
| 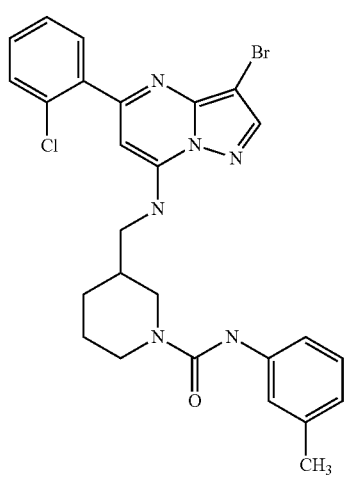 [SMILES: Cc1cccc(NC(=O)N2CCCC(CNc3cc(-c4ccccc4Cl)nc4c(Br)cnn34)C2)c1] | 1. 7807 2. 555.31 |
| 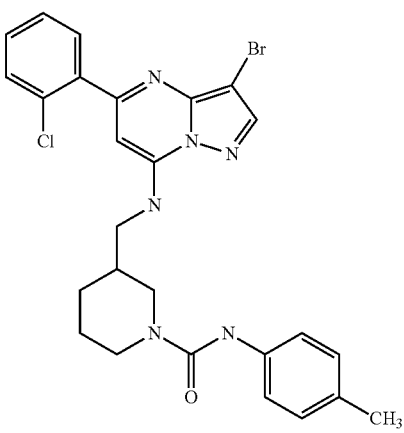 [SMILES: Cc1ccc(NC(=O)N2CCCC(CNc3cc(-c4ccccc4Cl)nc4c(Br)cnn34)C2)cc1] | 1. 7808 2. 555.31 |
TABLE 78-continued
| Product | 1. Ex. 2. m/z |
|---|---|
| 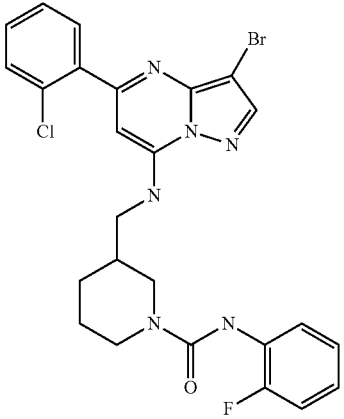 [SMILES: O=C(Nc1ccccc1F)N1CCCC(CNc2cc(-c3ccccc3Cl)nc3c(Br)cnn23)C1] | 1. 7809 2. 559.31 |
| 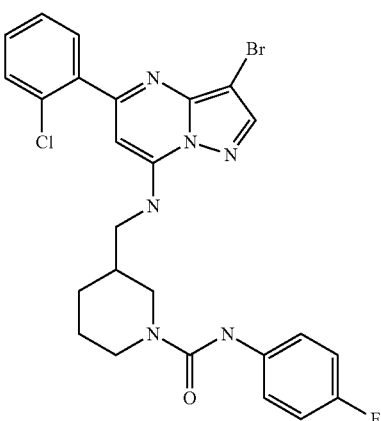 [SMILES: O=C(Nc1ccc(F)cc1)N1CCCC(CNc2cc(-c3ccccc3Cl)nc3c(Br)cnn23)C1] | 1. 7810 2. 559.31 |
| 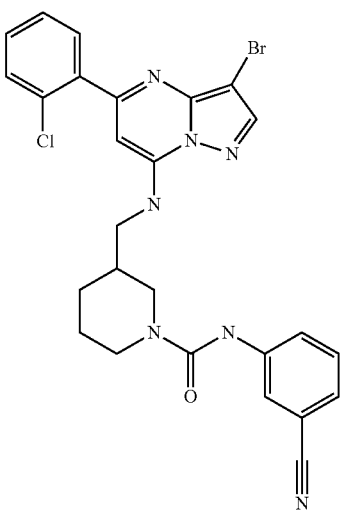 [SMILES: N#Cc1cccc(NC(=O)N2CCCC(CNc3cc(-c4ccccc4Cl)nc4c(Br)cnn34)C2)c1] | 1. 7811 2. 566.31 |

TABLE 78-continued
| Product | 1. Ex. 2. m/z |
|---|---|
| 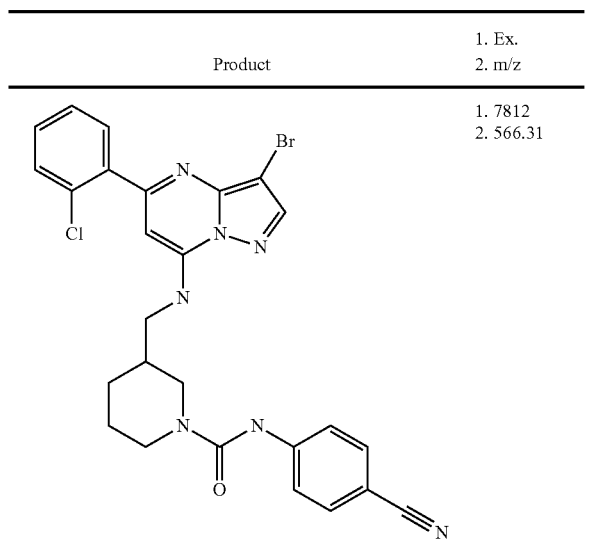 | 1. 7812 2. 566.31 |
| 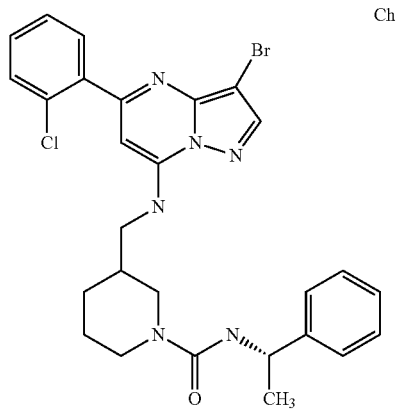 Chiral | 1. 7813 2. 569.31 |
| 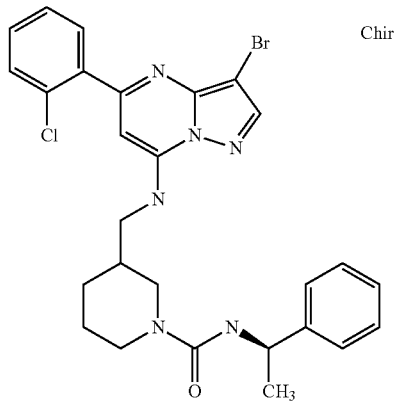 Chiral | 1. 7814 2. 569.31 |
TABLE 78-continued
| Product | 1. Ex. 2. m/z |
|---|---|
| 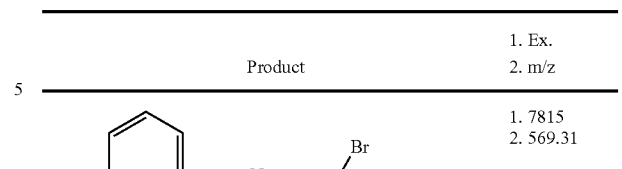 | 1. 7815 2. 569.31 |
| 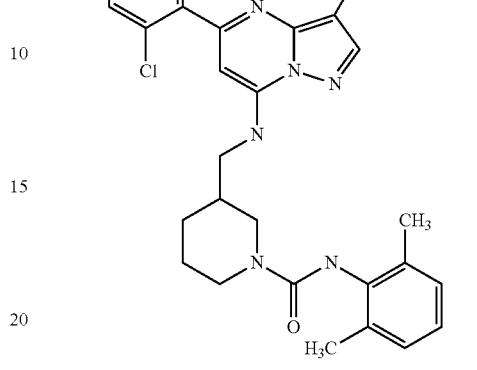 | 1. 7816 2. 569.31 |
| 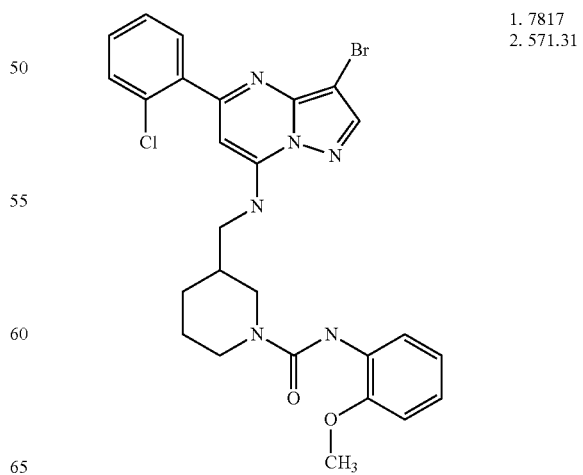 | 1. 7817 2. 571.31 |

TABLE 78-continued
| Product | 1. Ex.<br>2. m/z |
|---|---|
| 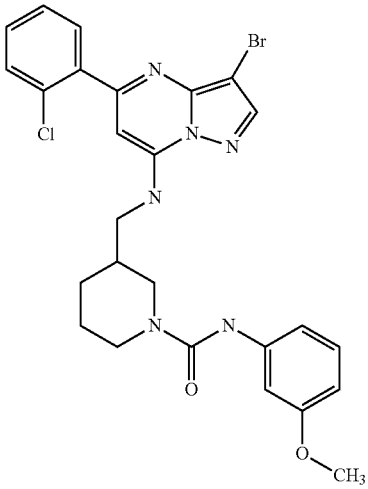 [SMILES: COc1cccc(NC(=O)N2CCCC(CNc3cc(-c4ccccc4Cl)nc4c(Br)cnn34)C2)c1] | 1. 7818<br>2. 571.31 |
| 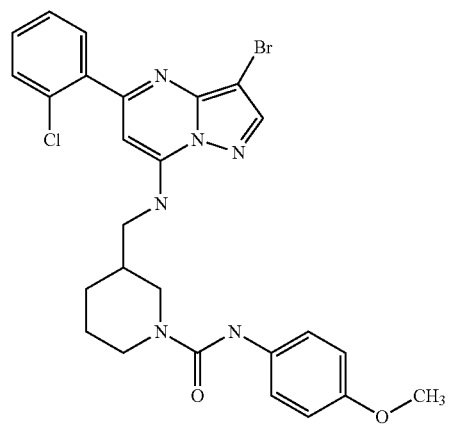 [SMILES: COc1ccc(NC(=O)N2CCCC(CNc3cc(-c4ccccc4Cl)nc4c(Br)cnn34)C2)cc1] | 1. 7819<br>2. 571.31 |
| 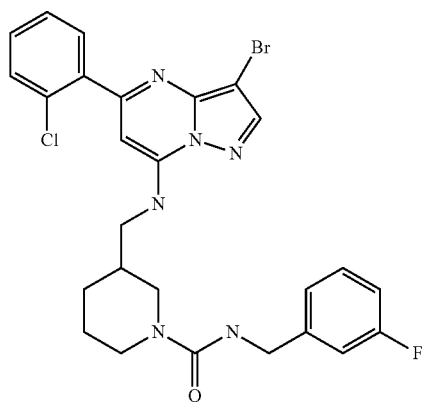 [SMILES: O=C(NCc1cccc(F)c1)N1CCCC(CNc2cc(-c3ccccc3Cl)nc3c(Br)cnn23)C1] | 1. 7820<br>2. 573.32 |
TABLE 78-continued
| Product | 1. Ex.<br>2. m/z |
|---|---|
| 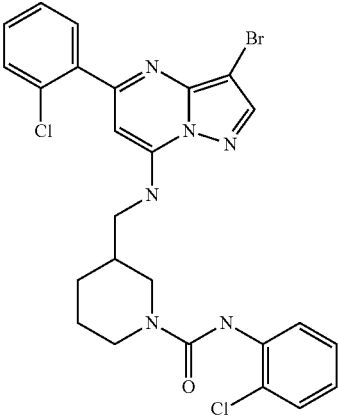 [SMILES: O=C(Nc1ccccc1Cl)N1CCCC(CNc2cc(-c3ccccc3Cl)nc3c(Br)cnn23)C1] | 1. 7821<br>2. 575.32 |
| 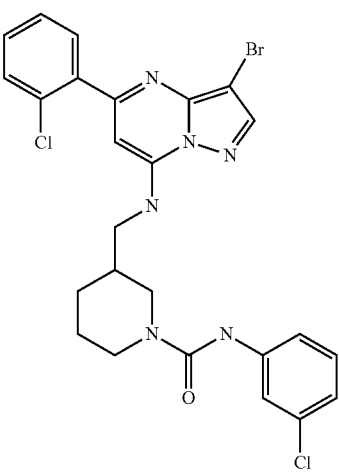 [SMILES: O=C(Nc1cccc(Cl)c1)N1CCCC(CNc2cc(-c3ccccc3Cl)nc3c(Br)cnn23)C1] | 1. 7822<br>2. 575.32 |
| 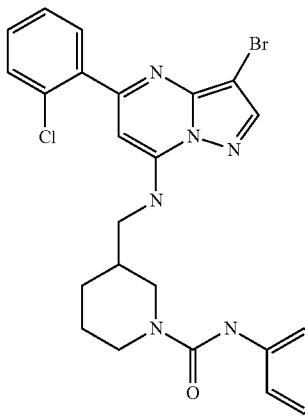 | 1. 7823<br>2. 575.32 |

TABLE 78-continued
| Product | 1. Ex.<br>2. m/z |
|---|---|
| 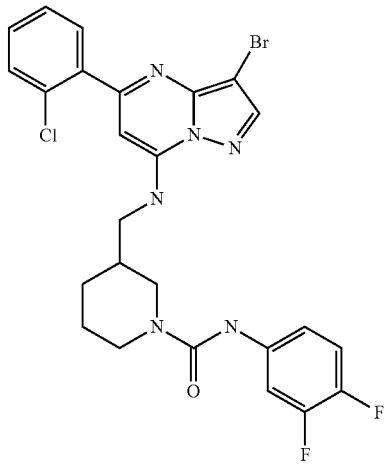 [SMILES: O=C(Nc1ccc(F)c(F)c1)N1CCCC(CNc2cc(-c3ccccc3Cl)nc3c(Br)cnn23)C1] | 1. 7824<br>2. 577.32 |
| 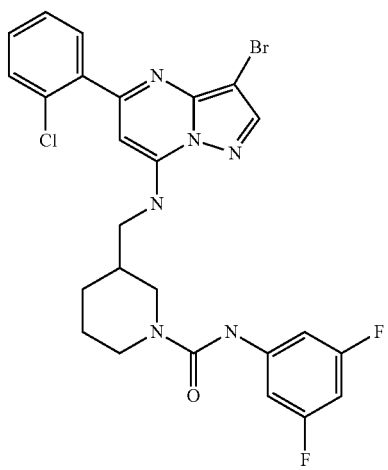 [SMILES: O=C(Nc1cc(F)cc(F)c1)N1CCCC(CNc2cc(-c3ccccc3Cl)nc3c(Br)cnn23)C1] | 1. 7825<br>2. 577.32 |
| 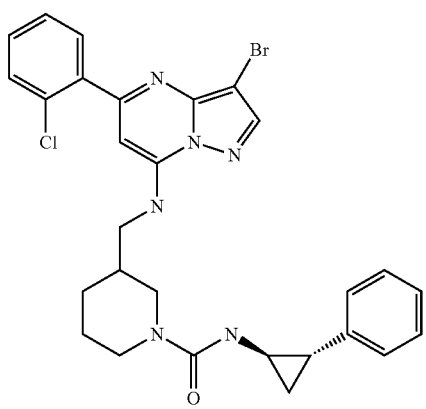 [SMILES: O=C(N[C@@H]1C[C@H]1c1ccccc1)N1CCCC(CNc2cc(-c3ccccc3Cl)nc3c(Br)cnn23)C1] | 1. 7826<br>2. 581.32 |
TABLE 78-continued
| Product | 1. Ex.<br>2. m/z |
|---|---|
| 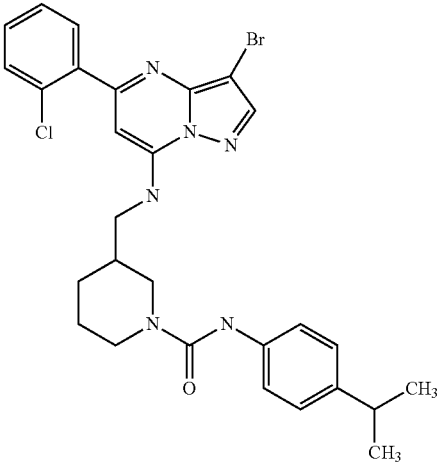 [SMILES: CC(C)c1ccc(NC(=O)N2CCCC(CNc3cc(-c4ccccc4Cl)nc4c(Br)cnn34)C2)cc1] | 1. 7827<br>2. 583.32 |
| | 1. 7828<br>2. 585.32 |
| 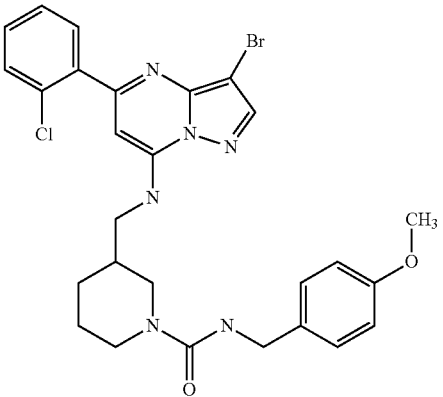 [SMILES: COc1ccc(CNC(=O)N2CCCC(CNc3cc(-c4ccccc4Cl)nc4c(Br)cnn34)C2)cc1] | 1. 7829<br>2. 585.32 |

TABLE 78-continued
| Product | 1. Ex.<br>2. m/z |
|---|---|
| 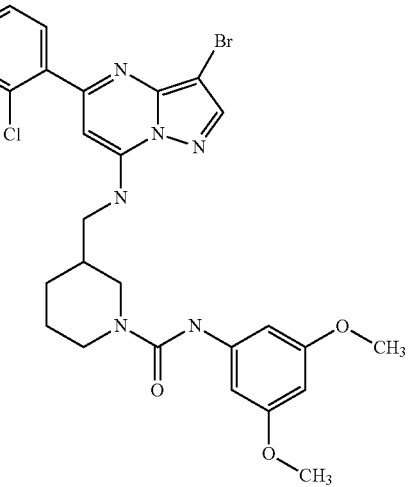 | 1. 7830<br>2. 589.32 |
| 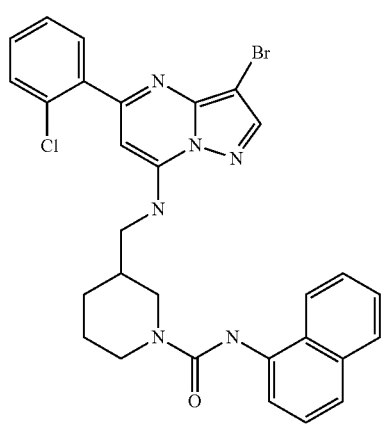 [SMILES: O=C(Nc1cccc2ccccc12)N1CCCC(CNc2cc(-c3ccccc3Cl)nc3c(Br)cnn23)C1] | 1. 7831<br>2. 591.33 |
| 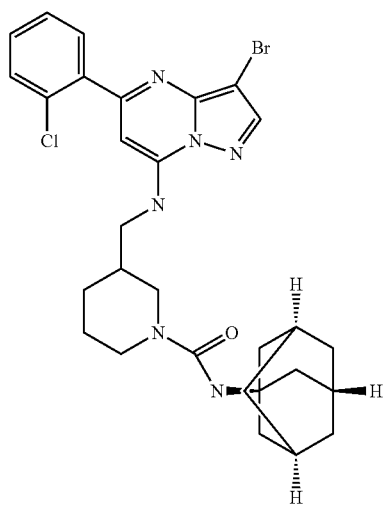 [SMILES: O=C(N[C@]12C[C@H]3C[C@H](C[C@H](C3)C1)C2)N1CCCC(CNc2cc(-c3ccccc3Cl)nc3c(Br)cnn23)C1] | 1. 7832<br>2. 599.33 |
TABLE 78-continued
| Product | 1. Ex.<br>2. m/z |
|---|---|
| 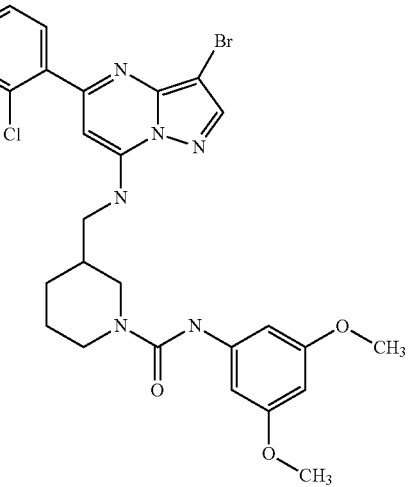 | 1. 7833<br>2. 601.33 |
| 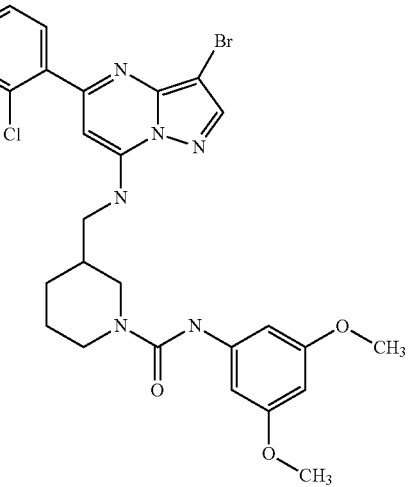 | 1. 7834<br>2. 605.33 |
| 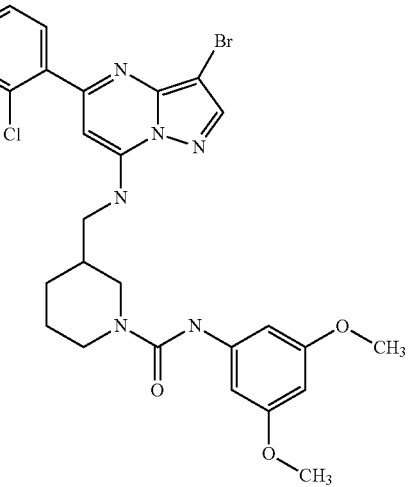 | 1. 7835<br>2. 609.33 |

TABLE 78-continued
| Product | 1. Ex.<br>2. m/z |
|---|---|
| 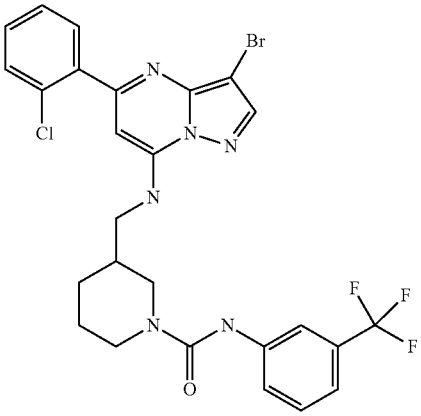 [SMILES: O=C(Nc1cccc(C(F)(F)F)c1)N1CCCC(CNc2cc(-c3ccccc3Cl)nc3c(Br)cnn23)C1] | 1. 7836<br>2. 609.33 |
| 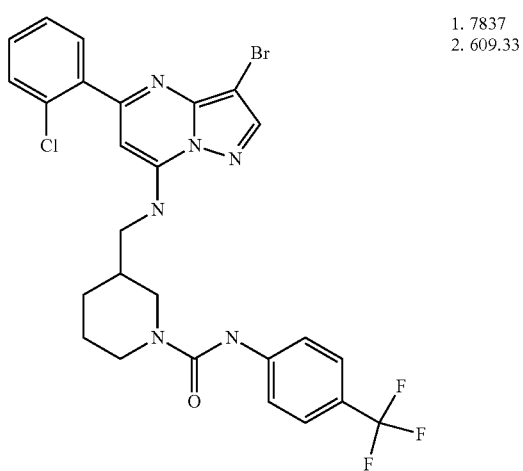 | 1. 7837<br>2. 609.33 |
| 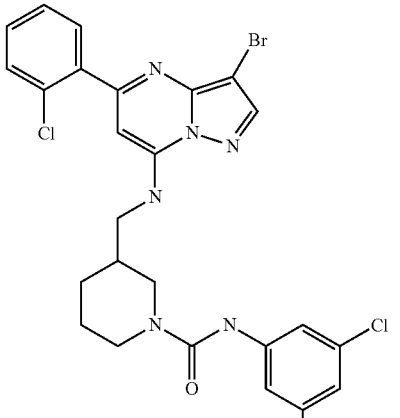 | 1. 7838<br>2. 609.33 |
TABLE 78-continued
| Product | 1. Ex.<br>2. m/z |
|---|---|
| 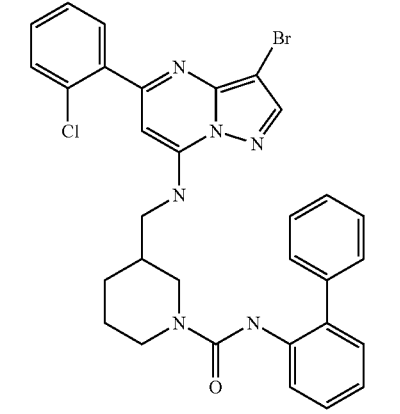 [SMILES: O=C(Nc1ccccc1-c1ccccc1)N1CCCC(CNc2cc(-c3ccccc3Cl)nc3c(Br)cnn23)C1] | 1. 7839<br>2. 609.33 |
| | 1. 7840<br>2. 617.34 |
| 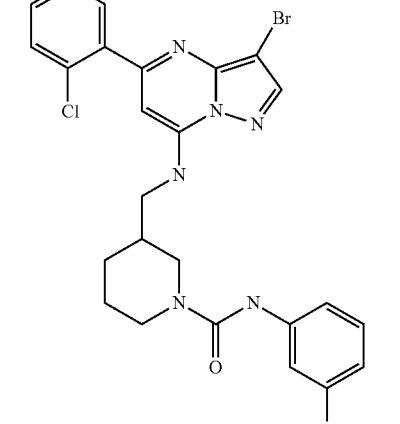 | 1. 7841<br>2. 619.34 |

TABLE 78-continued
| Product | 1. Ex. 2. m/z |
|---|---|
| 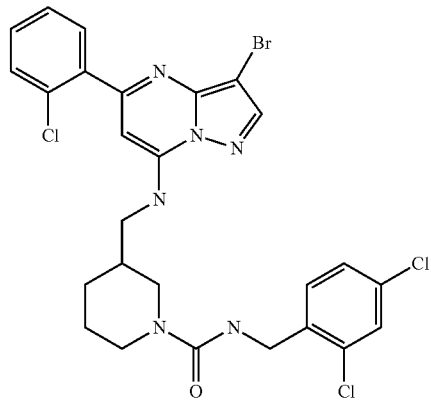 [SMILES: O=C(NCc1ccc(Cl)cc1Cl)N1CCCC(CNc2cc(-c3ccccc3Cl)nc3c(Br)cnn23)C1] | 1. 7842 2. 623.34 |
| 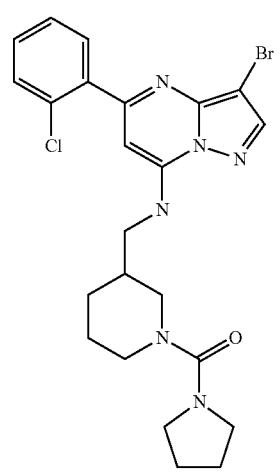 [SMILES: O=C(N1CCCC1)N1CCCC(CNc2cc(-c3ccccc3Cl)nc3c(Br)cnn23)C1] | 1. 7843 2. 519.29 |
| 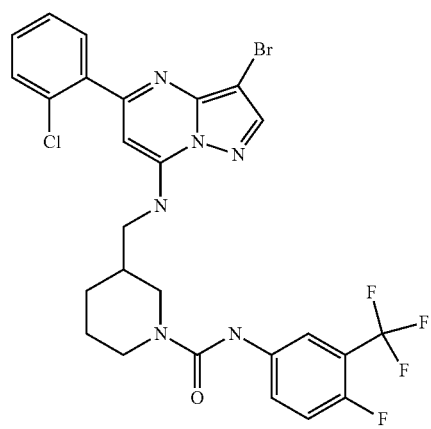 [SMILES: O=C(Nc1ccc(F)c(C(F)(F)F)c1)N1CCCC(CNc2cc(-c3ccccc3Cl)nc3c(Br)cnn23)C1] | 1. 7844 2. 627.34 |
TABLE 78-continued
| Product | 1. Ex. 2. m/z |
|---|---|
| 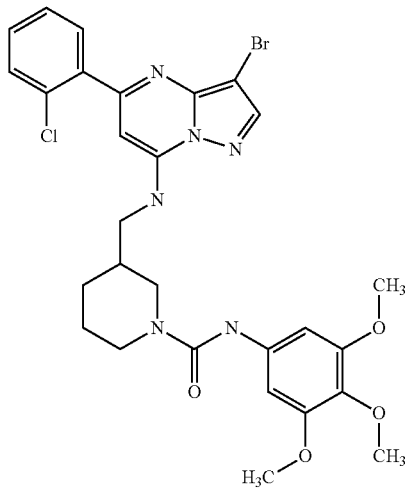 [SMILES: COc1cc(NC(=O)N2CCCC(CNc3cc(-c4ccccc4Cl)nc4c(Br)cnn34)C2)cc(OC)c1OC] | 1. 7845 2. 631.35 |
| 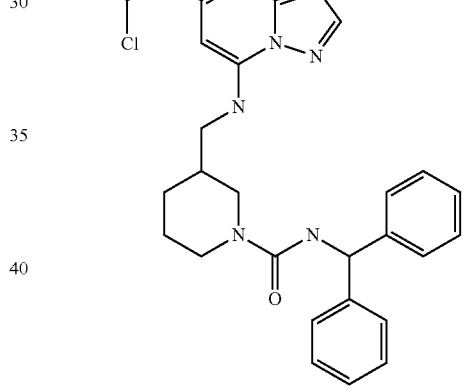 | 1. 7846 2. 631.35 |
| 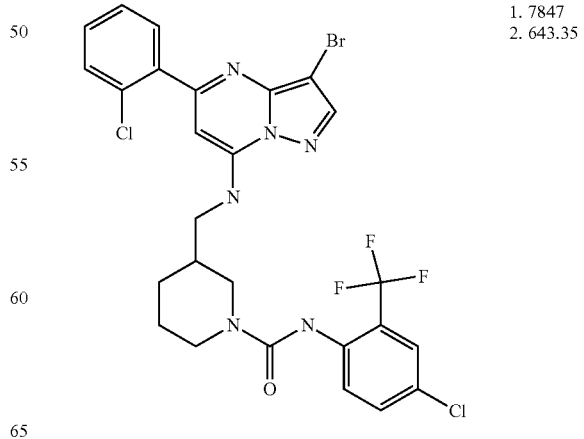 | 1. 7847 2. 643.35 |

TABLE 79

| Product | 1. Ex. 2. m/z |
|---|---|
| (structure with SCH3 group) | 1. 7901 2. 477.26 |
| (structure with thiophen-2-yl group) | 1. 7902 2. 485.27 |
| (structure with thiophen-3-yl group) | 1. 7903 2. 485.27 |

TABLE 79-continued

| Product | 1. Ex. 2. m/z |
|---|---|
| (structure with thiazole group) | 1. 7904 2. 486.27 |
| (structure with 2-hydroxyphenyl group) | 1. 7905 2. 495.27 |
| (structure with cyanophenyl group) | 1. 7906 2. 504.28 |

TABLE 79-continued
| Product | 1. Ex.<br>2. m/z |
|---|---|
| 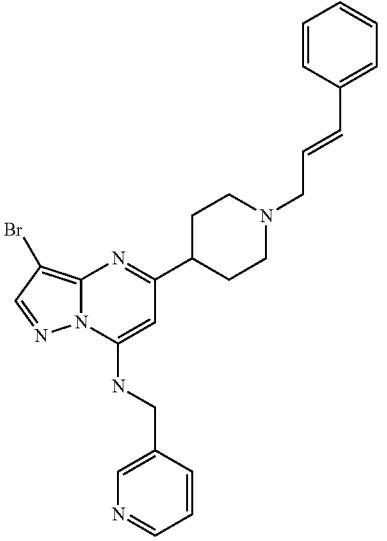 [SMILES: Brc1cnn2c(NCc3cccnc3)cc(C3CCN(C/C=C/c4ccccc4)CC3)nc12] | 1. 7907<br>2. 505.28 |
| 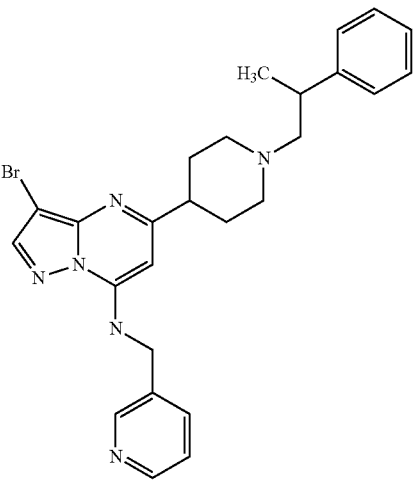 [SMILES: CC(CN1CCC(c2cc(NCc3cccnc3)n3ncc(Br)c3n2)CC1)c1ccccc1] | 1. 7908<br>2. 507.28 |
| 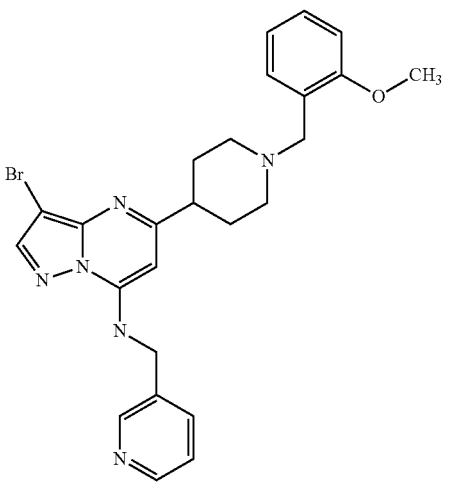 [SMILES: COc1ccccc1CN1CCC(c2cc(NCc3cccnc3)n3ncc(Br)c3n2)CC1] | 1. 7909<br>2. 509.28 |
TABLE 79-continued
| Product | 1. Ex.<br>2. m/z |
|---|---|
| 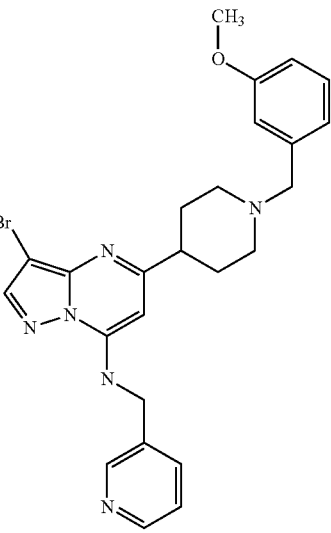 | 1. 7910<br>2. 509.28 |
| 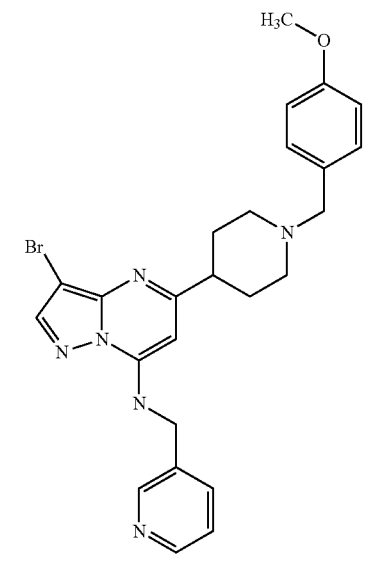 [SMILES: COc1ccc(CN2CCC(c3cc(NCc4cccnc4)n4ncc(Br)c4n3)CC2)cc1] | 1. 7911<br>2. 509.28 |
| 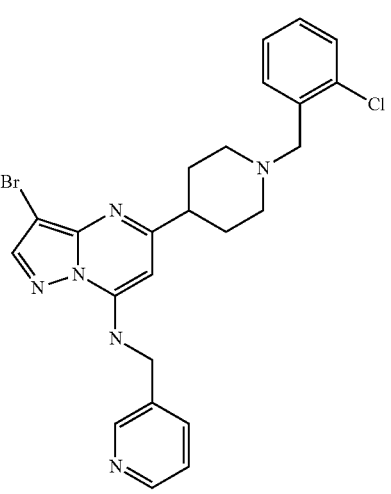 [SMILES: Clc1ccccc1CN1CCC(c2cc(NCc3cccnc3)n3ncc(Br)c3n2)CC1] | 1. 7912<br>2. 513.28 |

TABLE 79-continued
| Product | 1. Ex.<br>2. m/z |
|---|---|
| 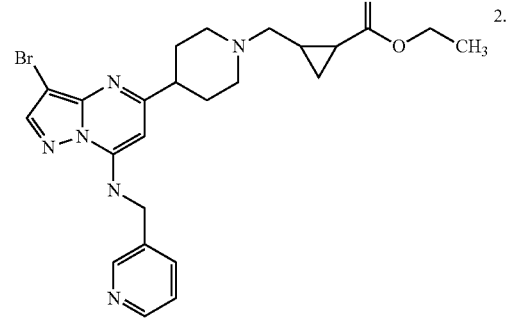 | 1. 7913<br>2. 515.28 |
| 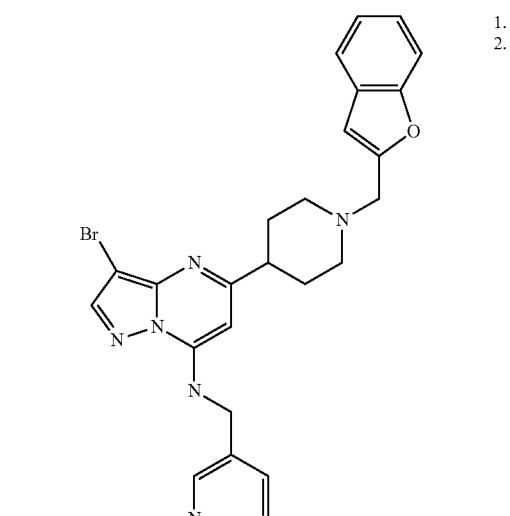 | 1. 7914<br>2. 519.29 |
| 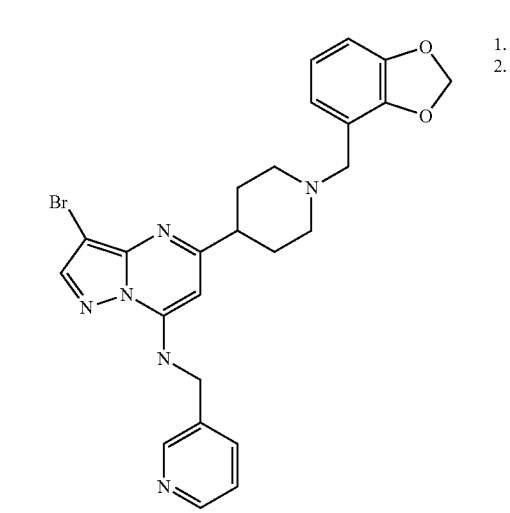 | 1. 7915<br>2. 523.29 |
TABLE 79-continued
| Product | 1. Ex.<br>2. m/z |
|---|---|
| 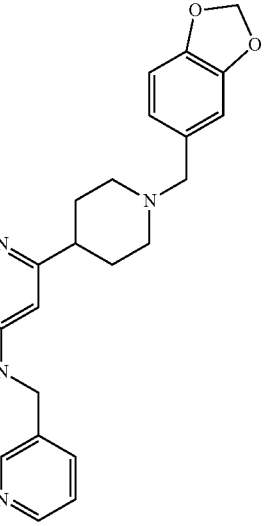 | 1. 7916<br>2. 523.29 |
| 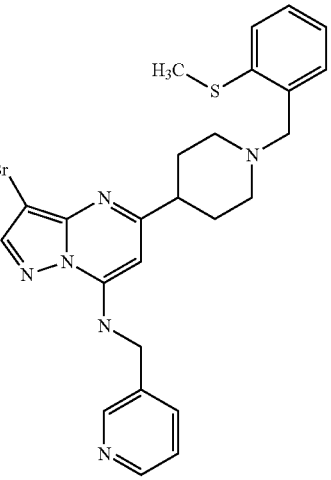 | 1. 7917<br>2. 525.29 |
| 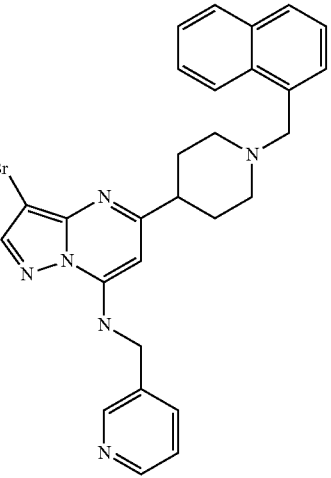 | 1. 7918<br>2. 529.29 |

TABLE 79-continued
| Product | 1. Ex. 2. m/z |
|---|---|
| 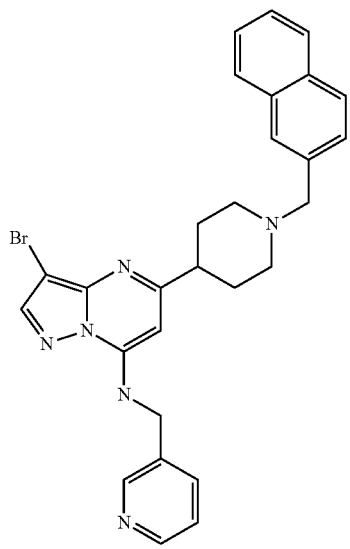 [SMILES: Brc1cnn2c(NCc3cccnc3)cc(C3CCN(Cc4ccc5ccccc5c4)CC3)nc12] | 1. 7919 2. 529.29 |
| 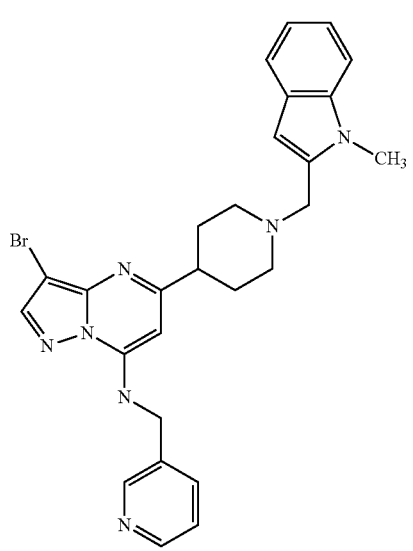 [SMILES: Cn1c(CN2CCC(c3cc(NCc4cccnc4)n4ncc(Br)c4n3)CC2)cc2ccccc21] | 1. 7920 2. 530.29 |
| 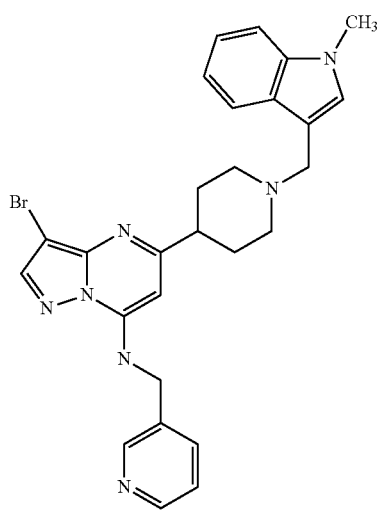 [SMILES: Cn1cc(CN2CCC(c3cc(NCc4cccnc4)n4ncc(Br)c4n3)CC2)c2ccccc21] | 1. 7921 2. 530.29 |
TABLE 79-continued
| Product | 1. Ex. 2. m/z |
|---|---|
| 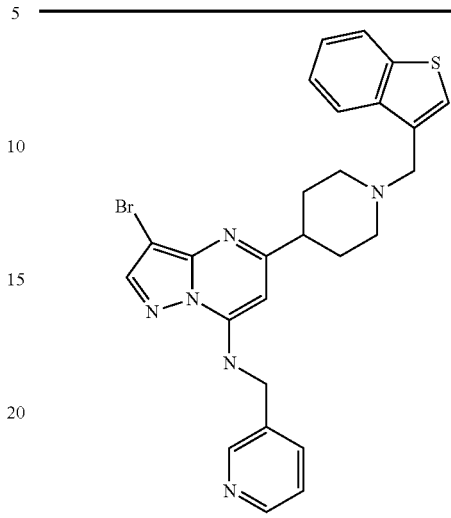 | 1. 7922 2. 535.29 |
| 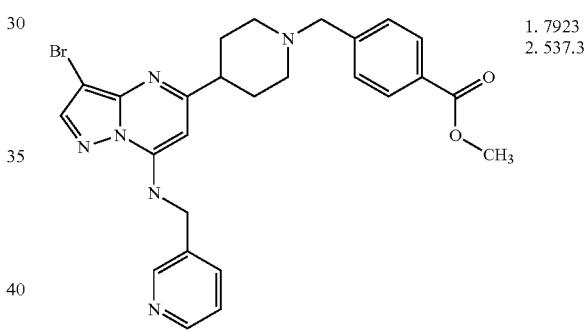 | 1. 7923 2. 537.3 |
| 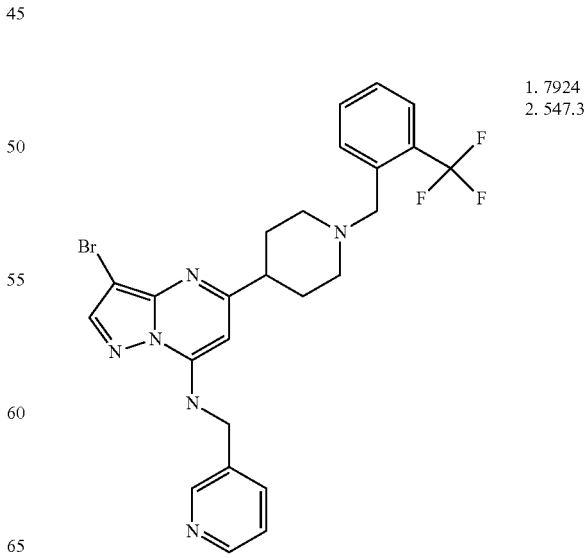 | 1. 7924 2. 547.3 |

TABLE 79-continued
| Product | 1. Ex. 2. m/z |
|---|---|
| 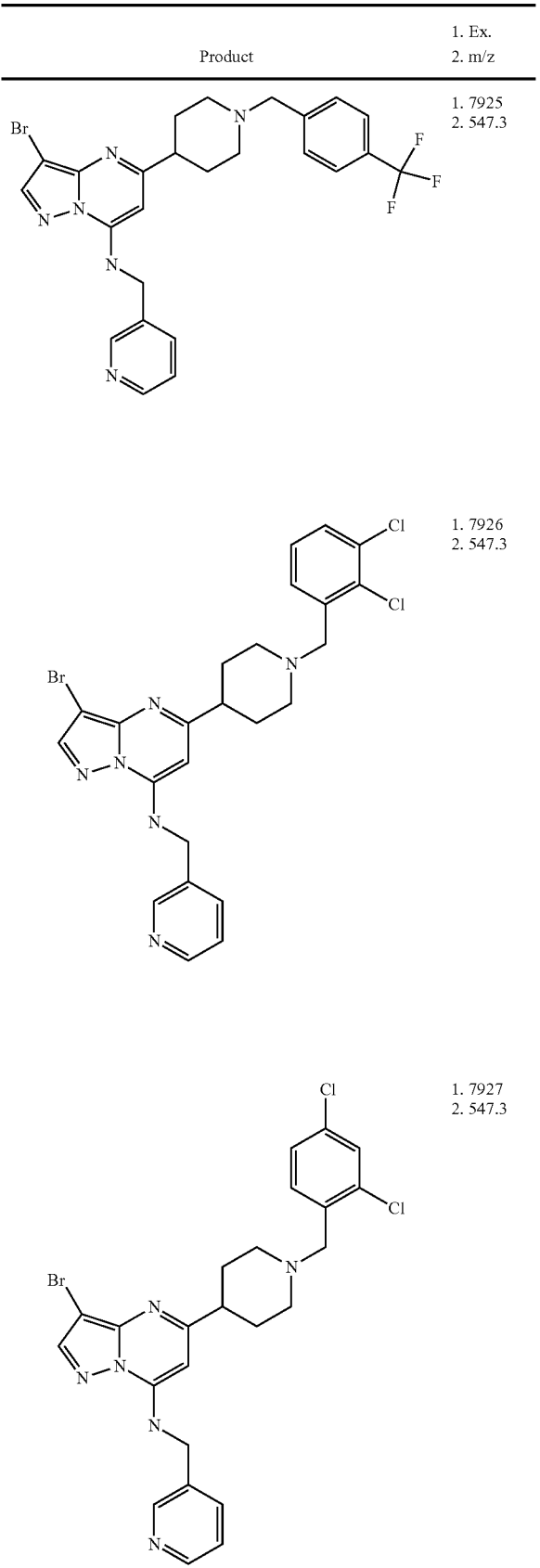 | 1. 7925 2. 547.3 |
| | 1. 7926 2. 547.3 |
| | 1. 7927 2. 547.3 |
TABLE 79-continued
| Product | 1. Ex. 2. m/z |
|---|---|
| 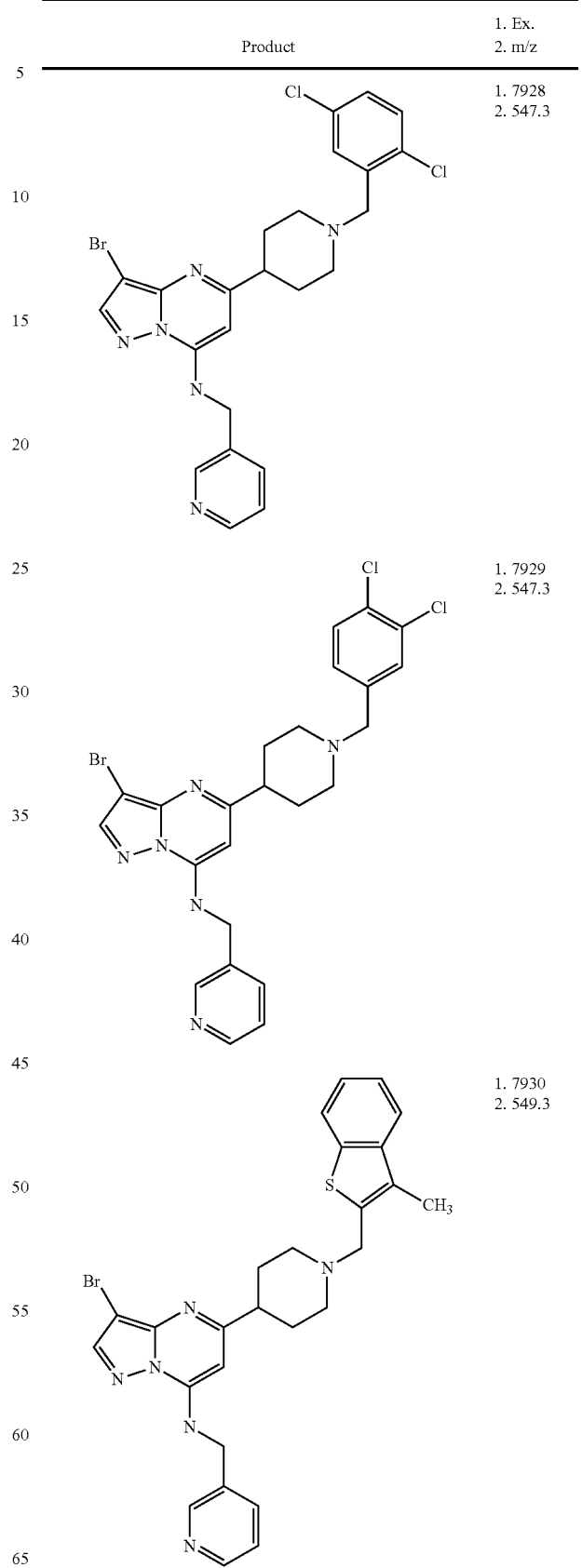 | 1. 7928 2. 547.3 |
| | 1. 7929 2. 547.3 |
| | 1. 7930 2. 549.3 |

TABLE 79-continued
| Product | 1. Ex.<br>2. m/z |
|---|---|
| | 1. 7931<br>2. 555.31 |
| | 1. 7932<br>2. 555.31 |
| | 1. 7933<br>2. 557.31 |
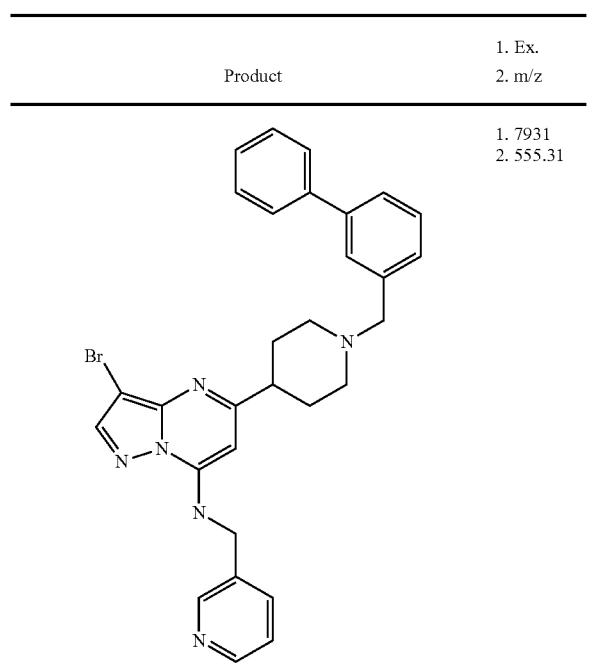
TABLE 79-continued
| Product | 1. Ex.<br>2. m/z |
|---|---|
| | 1. 7934<br>2. 557.31 |
| | 1. 7935<br>2. 557.31 |
| | 1. 7936<br>2. 567.31 |
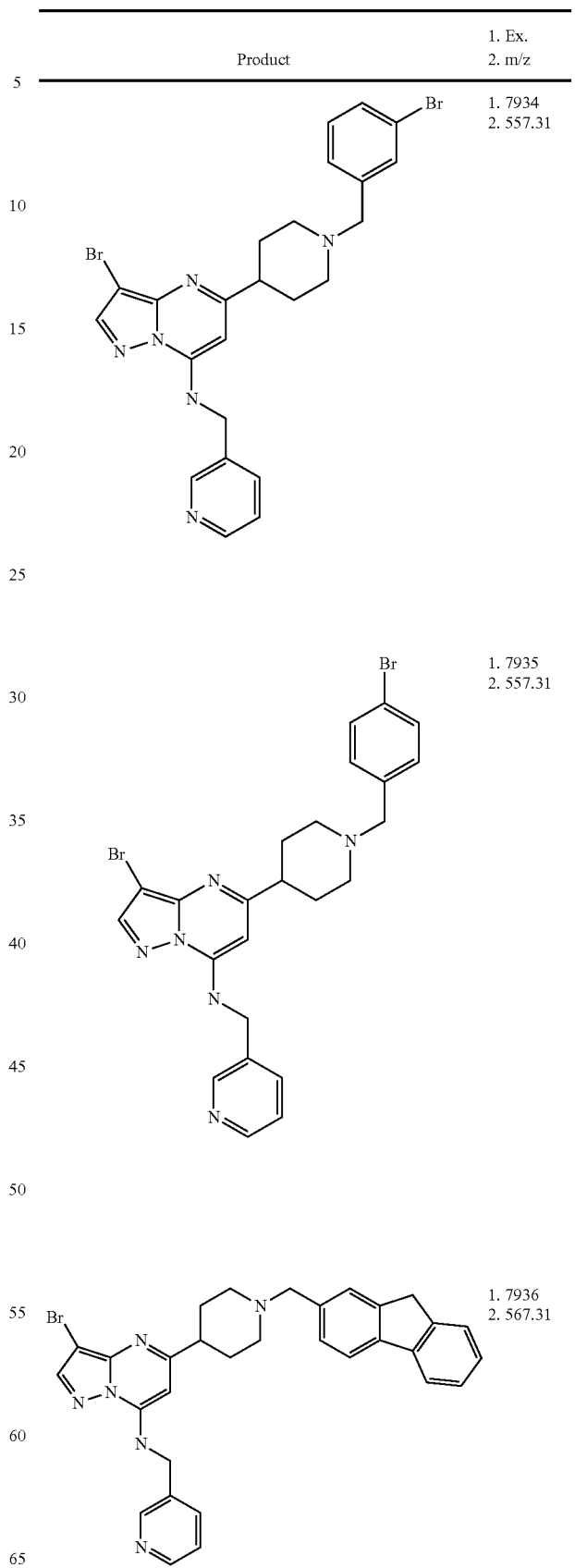

TABLE 79-continued
| Product | 1. Ex. 2. m/z |
|---|---|
| 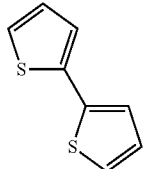 | 1. 7937 2. 567.31 |
| 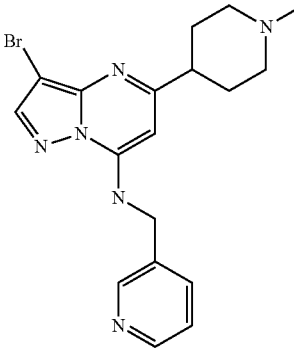 | 1. 7938 2. 569.31 |
| 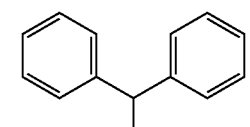 | 1. 7939 2. 571.31 |
| 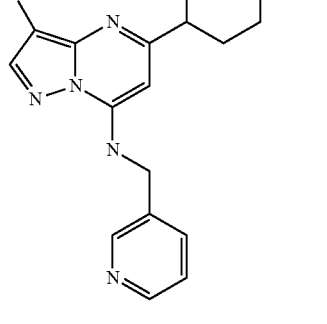 | 1. 7940 2. 571.31 |
| 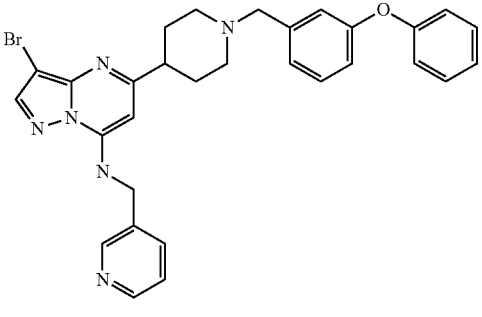 [SMILES: Brc1cnn2c(NCc3cccnc3)cc(C3CCN(Cc4cccc(Oc5ccccc5)c4)CC3)nc12] | 1. 7941 2. 608.33 |
| 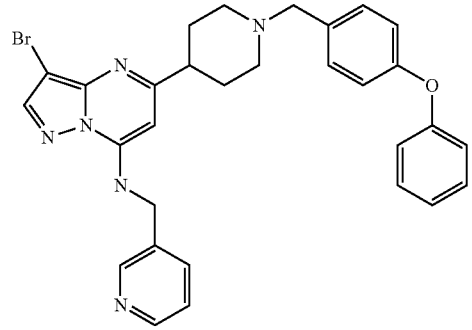 [SMILES: Brc1cnn2c(NCc3cccnc3)cc(C3CCN(Cc4ccc(Oc5ccccc5)cc4)CC3)nc12] | 1. 7942 2. 621.34 |

TABLE 79-continued
| Product | 1. Ex. 2. m/z |
|---|---|
| 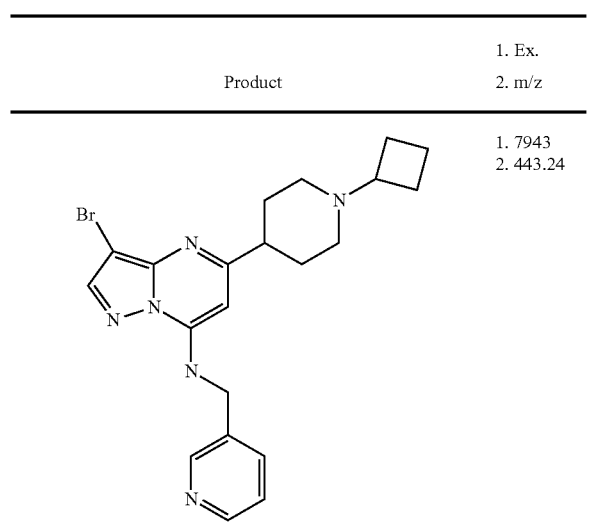 | 1. 7943 2. 443.24 |
| | 1. 7944 2. 457.25 |
| | 1. 7945 2. 471.26 |
TABLE 79-continued
| Product | 1. Ex. 2. m/z |
|---|---|
| 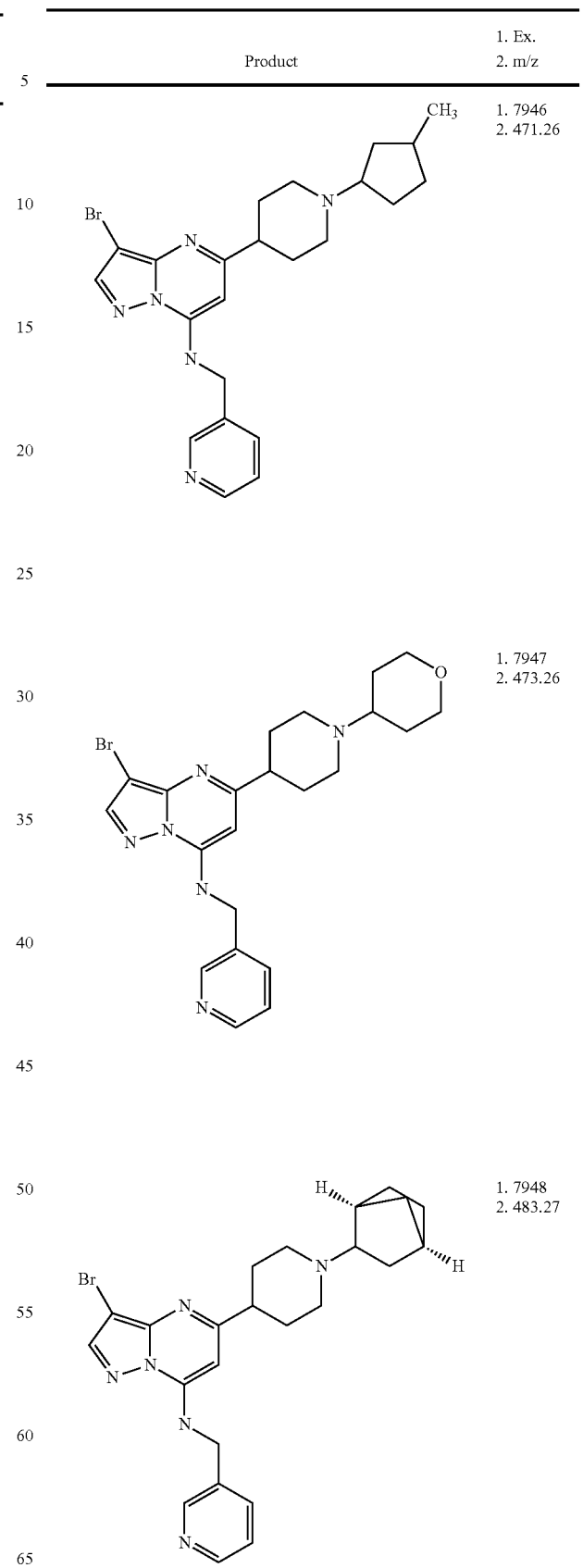 | 1. 7946 2. 471.26 |
| | 1. 7947 2. 473.26 |
| | 1. 7948 2. 483.27 |

TABLE 79-continued
| Product | 1. Ex.<br>2. m/z |
|---|---|
| 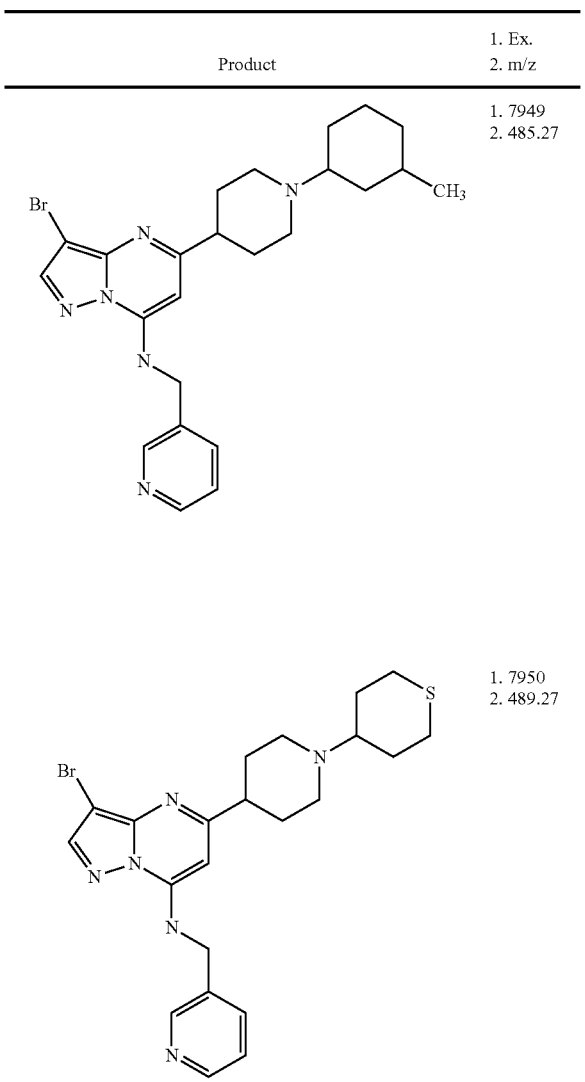 | 1. 7949<br>2. 485.27 |
| | 1. 7950<br>2. 489.27 |
| | 1. 7951<br>2. 499.27 |
TABLE 79-continued
| Product | 1. Ex.<br>2. m/z |
|---|---|
| 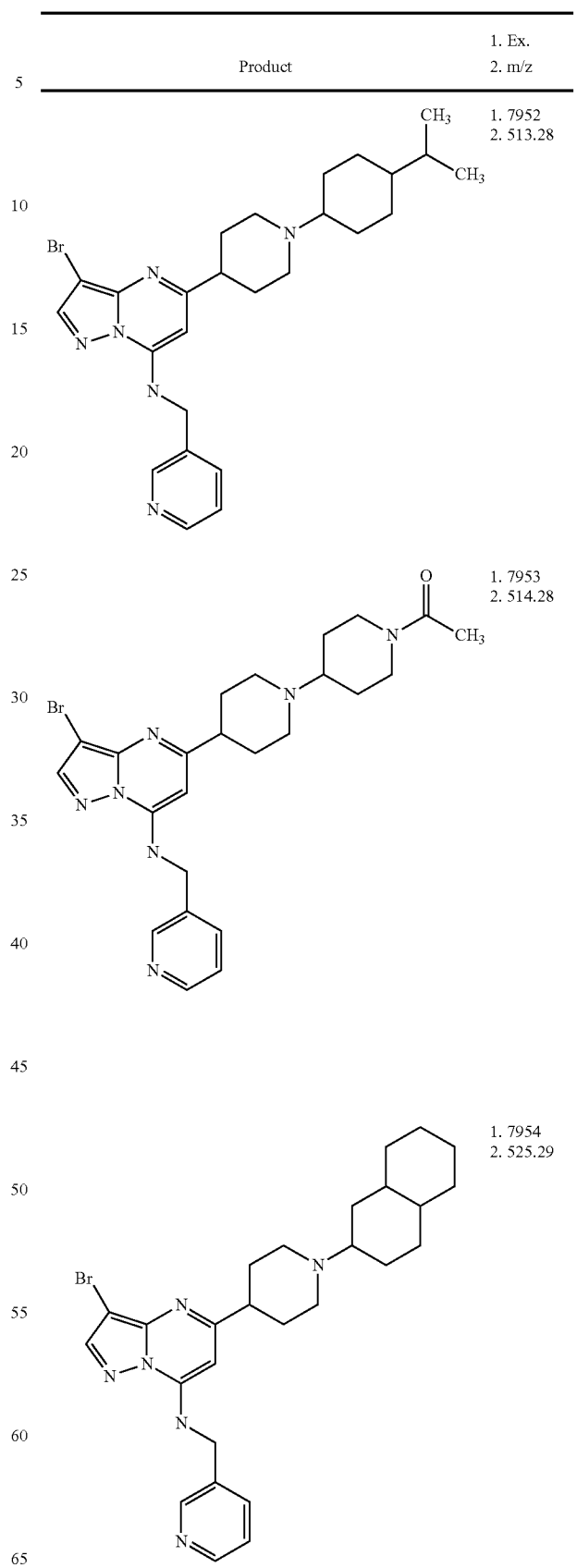 | 1. 7952<br>2. 513.28 |
| | 1. 7953<br>2. 514.28 |
| | 1. 7954<br>2. 525.29 |

TABLE 79-continued
| Product | 1. Ex.<br>2. m/z |
|---|---|
| 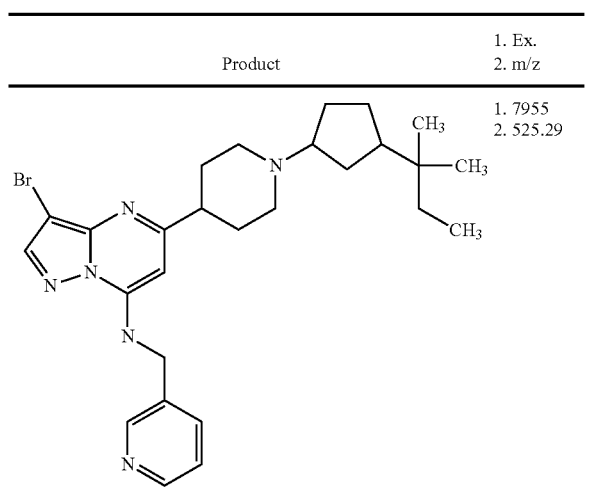 | 1. 7955<br>2. 525.29 |
TABLE 79-continued
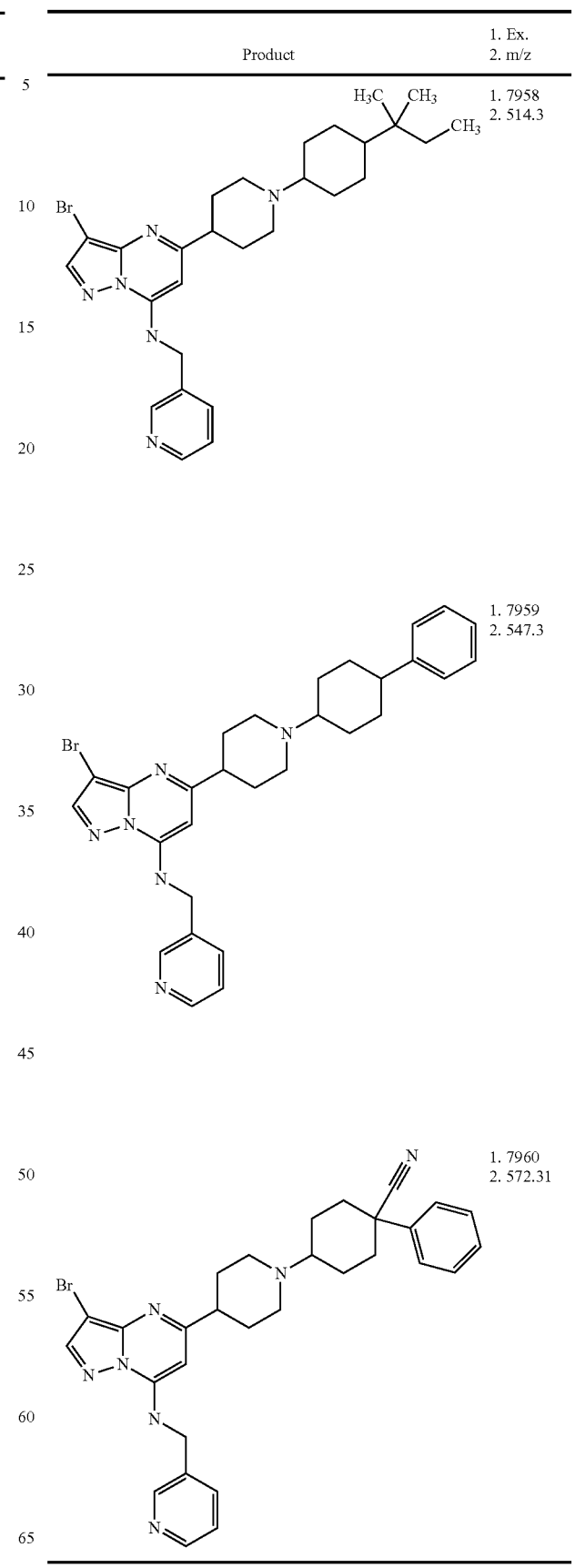
| Product | 1. Ex.<br>2. m/z |
|---|---|
| (structure) | 1. 7958<br>2. 514.3 |
| (structure) | 1. 7959<br>2. 547.3 |
| (structure) | 1. 7960<br>2. 572.31 |
| Product | 1. Ex.<br>2. m/z |
|---|---|
| (structure) | 1. 7956<br>2. 536.29 |
| (structure) | 1. 7957<br>2. 539.3 |

TABLE 80

| Product | 1. Ex. 2. m/z |
|---|---|
| (structure 8001) | 1. 8001 2. 459.25 |
| (structure 8002) | 1. 8002 2. 459.25 |
| (structure 8003) | 1. 8003 2. 469.26 |
| (structure 8004) | 1. 8004 2. 469.26 |

TABLE 80-continued

| Product | 1. Ex. 2. m/z |
|---|---|
| (structure 8005) | 1. 8005 2. 473.26 |
| (structure 8006) | 1. 8006 2. 477.26 |
| (structure 8007) | 1. 8007 2. 485.27 |
| (structure 8008) | 1. 8008 2. 485.27 |

TABLE 80-continued

| Product | 1. Ex. 2. m/z |
|---|---|
| (structure) | 1. 8009  2. 485.27 |
| (structure) | 1. 8010  2. 486.27 |
| (structure) | 1. 8011  2. 493.27 |
| (structure) | 1. 8012  2. 495.27 |

TABLE 80-continued

| Product | 1. Ex. 2. m/z |
|---|---|
| (structure) | 1. 8013  2. 495.27 |
| (structure) | 1. 8014  2. 495.27 |
| (structure) | 1. 8015  2. 495.27 |
| (structure) | 1. 8016  2. 495.27 |

TABLE 80-continued
| Product | 1. Ex.<br>2. m/z |
|---|---|
| | 1. 8017<br>2. 495.27 |
| | 1. 8018<br>2. 502.28 |
| | 1. 8019<br>2. 502.28 |
| | 1. 8020<br>2. 502.28 |
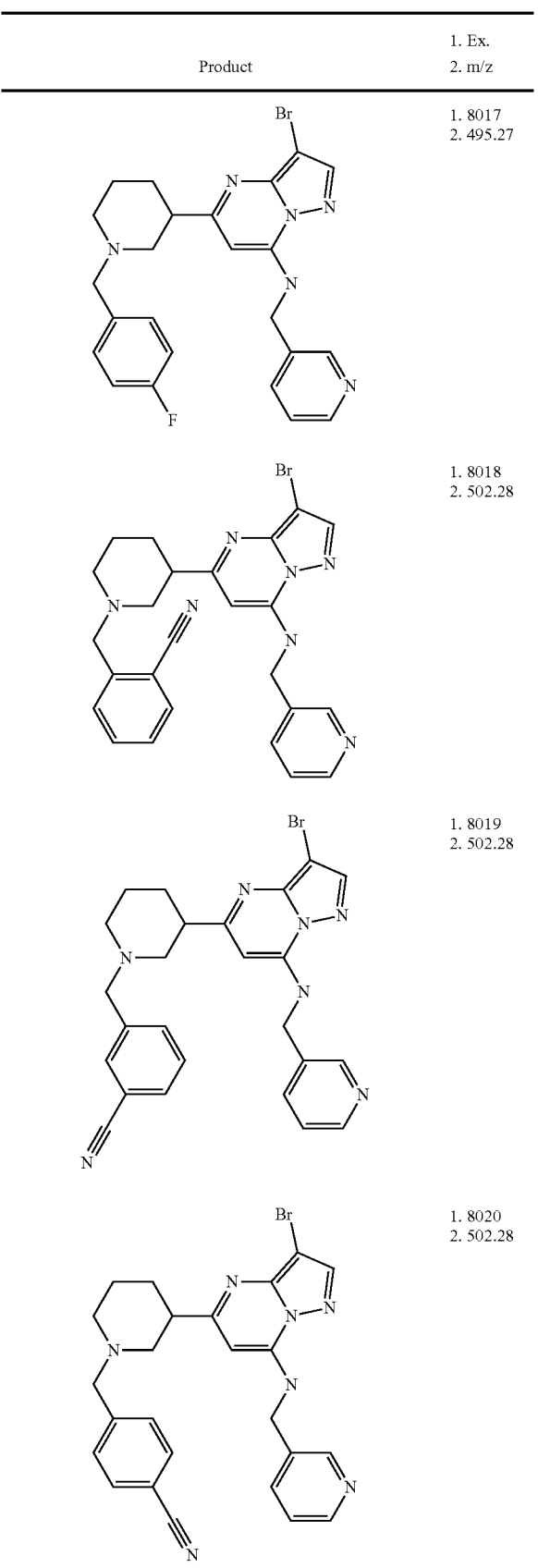
TABLE 80-continued
| Product | 1. Ex.<br>2. m/z |
|---|---|
| | 1. 8021<br>2. 505.28 |
| | 1. 8022<br>2. 505.28 |
| | 1. 8023<br>2. 507.28 |
| | 1. 8024<br>2. 507.28 |
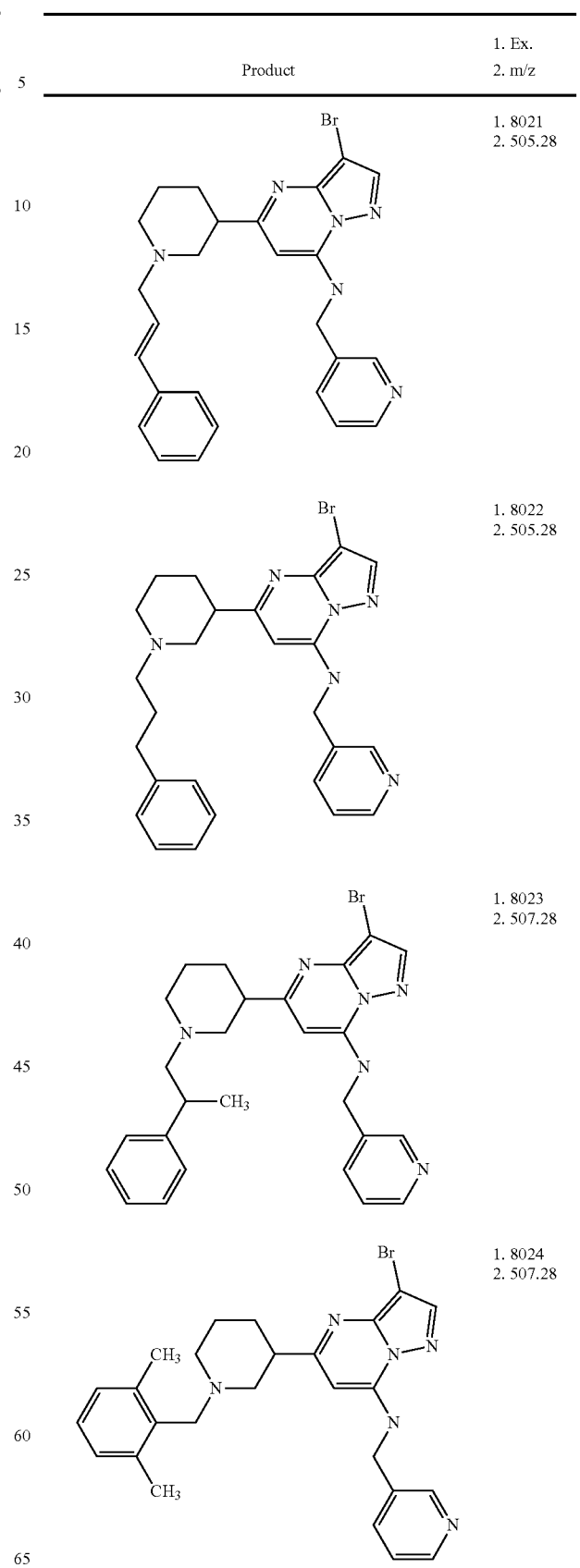

TABLE 80-continued

| Product | 1. Ex. 2. m/z |
|---|---|
| (structure with 2-methoxybenzyl piperidine, bromopyrazolopyrimidine, pyridin-3-ylmethylamine) | 1. 8025  2. 507.28 |
| (structure with 3-methoxybenzyl piperidine, bromopyrazolopyrimidine, pyridin-3-ylmethylamine) | 1. 8026  2. 509.28 |
| (structure with 4-methoxybenzyl piperidine, bromopyrazolopyrimidine, pyridin-3-ylmethylamine) | 1. 8027  2. 509.28 |
| (structure with 2-chlorobenzyl piperidine, bromopyrazolopyrimidine, pyridin-3-ylmethylamine) | 1. 8028  2. 513.28 |
| (structure with 3-chlorobenzyl piperidine, bromopyrazolopyrimidine, pyridin-3-ylmethylamine) | 1. 8029  2. 513.28 |
| (structure with 4-chlorobenzyl piperidine, bromopyrazolopyrimidine, pyridin-3-ylmethylamine) | 1. 8030  2. 513.28 |
| (structure with 2,6-difluorobenzyl piperidine, bromopyrazolopyrimidine, pyridin-3-ylmethylamine) | 1. 8031  2. 515.28 |
| (structure with benzofuran-2-ylmethyl piperidine, bromopyrazolopyrimidine, pyridin-3-ylmethylamine) | 1. 8032  2. 519.29 |

TABLE 80-continued
| Product | 1. Ex. 2. m/z |
|---|---|
| 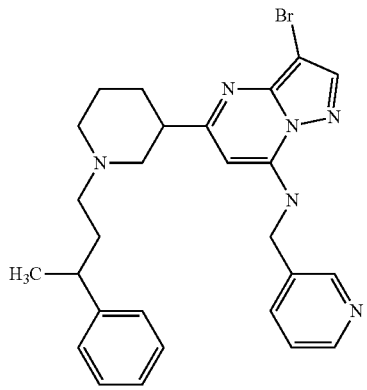 [SMILES: CC(CCN1CCCC(c2cc(NCc3cccnc3)n3ncc(Br)c3n2)C1)c1ccccc1] | 1. 8033 2. 521.29 |
| 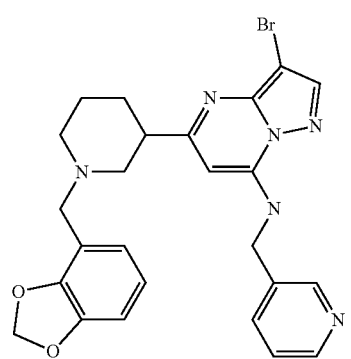 [SMILES: Brc1cnn2c(NCc3cccnc3)cc(C3CCCN(Cc4cccc5c4OCO5)C3)nc12] | 1. 8034 2. 523.29 |
| 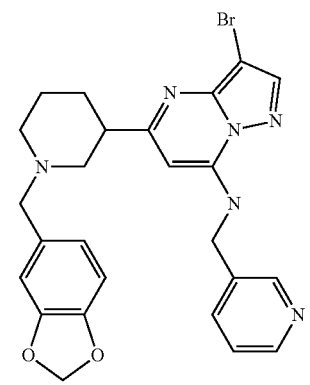 [SMILES: Brc1cnn2c(NCc3cccnc3)cc(C3CCCN(Cc4ccc5c(c4)OCO5)C3)nc12] | 1. 8035 2. 523.29 |
| 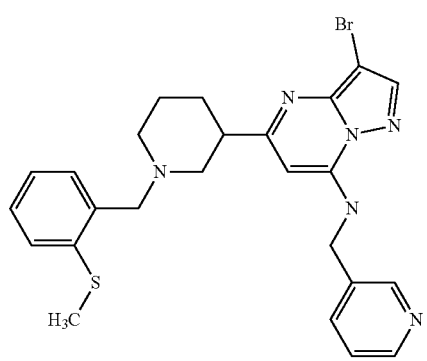 [SMILES: CSc1ccccc1CN1CCCC(c2cc(NCc3cccnc3)n3ncc(Br)c3n2)C1] | 1. 8036 2. 523.29 |
TABLE 80-continued
| Product | 1. Ex. 2. m/z |
|---|---|
| 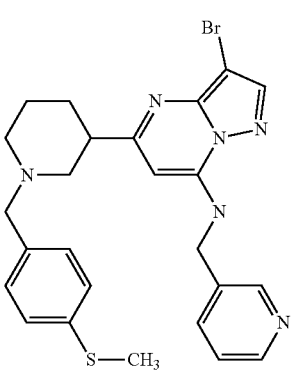 [SMILES: CSc1ccc(CN2CCCC(c3cc(NCc4cccnc4)n4ncc(Br)c4n3)C2)cc1] | 1. 8037 2. 525.29 |
| 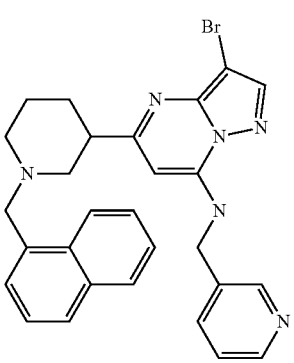 [SMILES: Brc1cnn2c(NCc3cccnc3)cc(C3CCCN(Cc4cccc5ccccc45)C3)nc12] | 1. 8038 2. 529.29 |
| 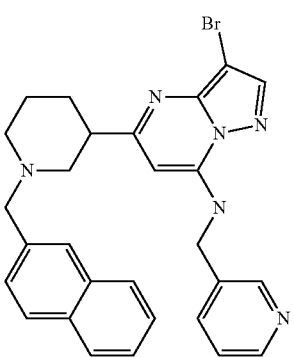 [SMILES: Brc1cnn2c(NCc3cccnc3)cc(C3CCCN(Cc4ccc5ccccc5c4)C3)nc12] | 1. 8039 2. 529.29 |
| 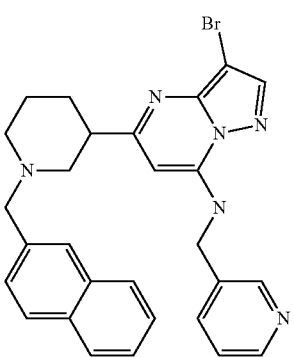 [SMILES: Brc1cnn2c(NCc3cccnc3)cc(C3CCCN(Cc4ccc5ccccc5c4)C3)nc12] | 1. 8040 2. 530.29 |

TABLE 80-continued
| Product | 1. Ex.<br>2. m/z |
|---|---|
| 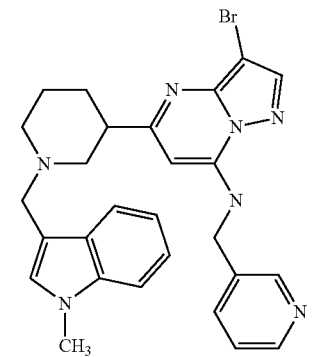 [SMILES: Cn1cc(CN2CCCC(c3cc(NCc4cccnc4)n4ncc(Br)c4n3)C2)c2ccccc21] | 1. 8041<br>2. 530.29 |
| 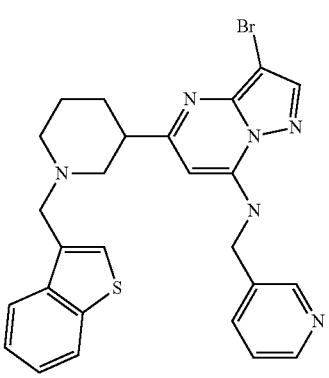 [SMILES: Brc1cnn2c(NCc3cccnc3)cc(C3CCCN(Cc4csc5ccccc45)C3)nc12] | 1. 8042<br>2. 535.29 |
| 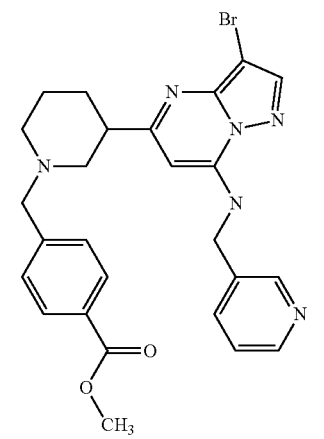 [SMILES: COC(=O)c1ccc(CN2CCCC(c3cc(NCc4cccnc4)n4ncc(Br)c4n3)C2)cc1] | 1. 8043<br>2. 537.3 |
| 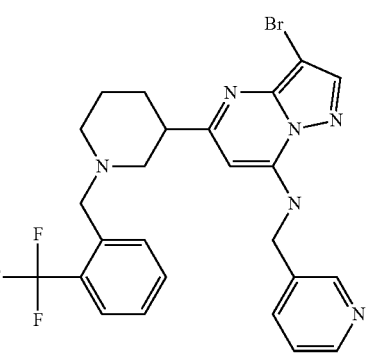 | 1. 8044<br>2. 547.3 |
TABLE 80-continued
| Product | 1. Ex.<br>2. m/z |
|---|---|
| 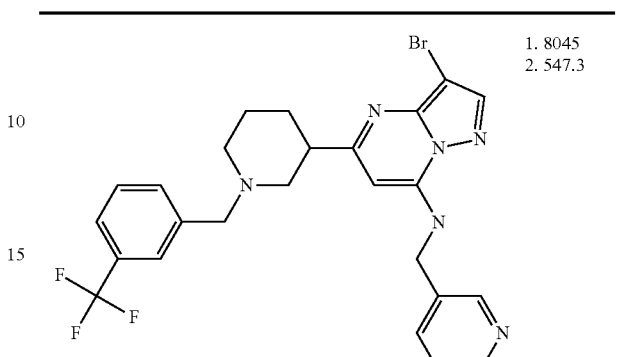 | 1. 8045<br>2. 547.3 |
| 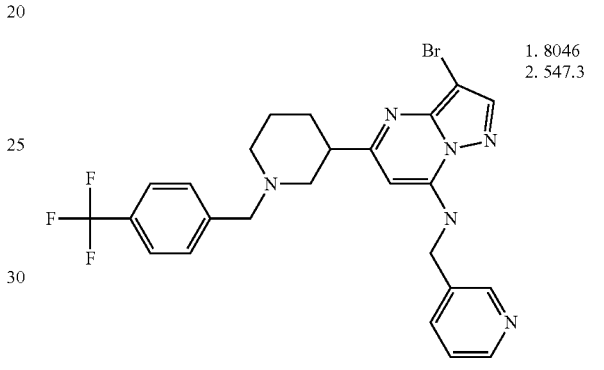 | 1. 8046<br>2. 547.3 |
| 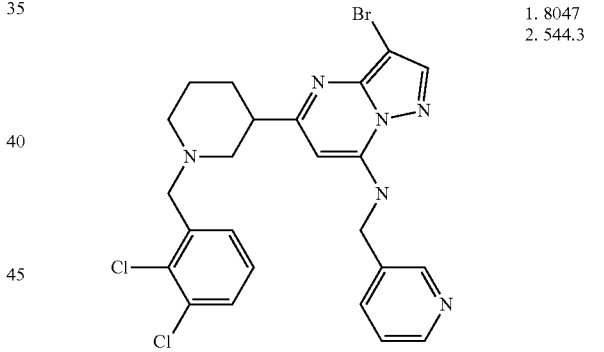 | 1. 8047<br>2. 544.3 |
|  | 1. 8048<br>2. 547.3 |

TABLE 80-continued
| Product | 1. Ex.<br>2. m/z |
|---|---|
| 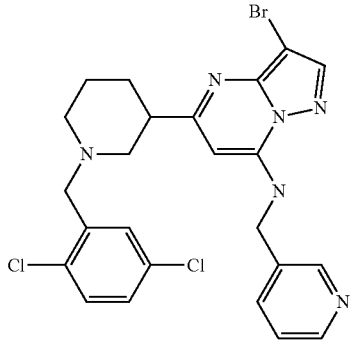 [SMILES: Clc1ccc(Cl)c(CN2CCCC(c3cc(NCc4cccnc4)n4ncc(Br)c4n3)C2)c1] | 1. 8049<br>2. 547.3 |
| 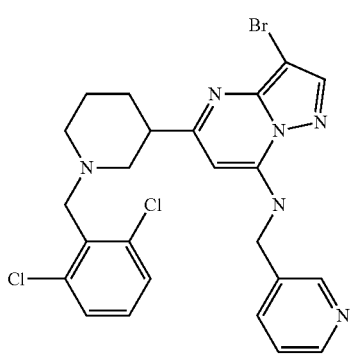 [SMILES: Clc1cccc(Cl)c1CN1CCCC(c2cc(NCc3cccnc3)n3ncc(Br)c3n2)C1] | 1. 8050<br>2. 547.3 |
| 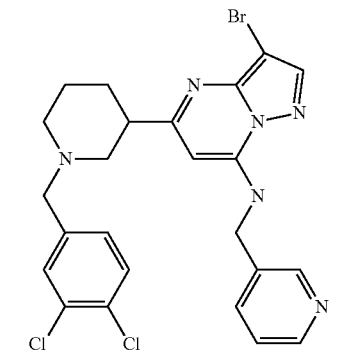 [SMILES: Clc1ccc(CN2CCCC(c3cc(NCc4cccnc4)n4ncc(Br)c4n3)C2)cc1Cl] | 1. 8051<br>2. 548.3 |
| 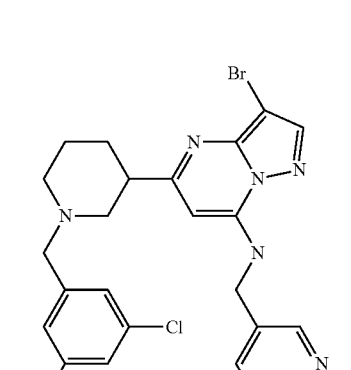 | 1. 8052<br>2. 548.3 |
TABLE 80-continued
| Product | 1. Ex.<br>2. m/z |
|---|---|
| 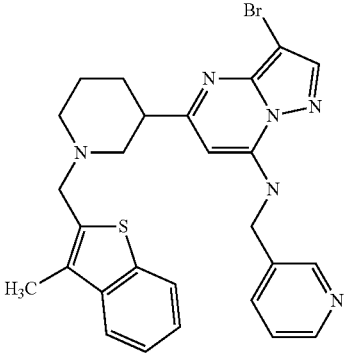 [SMILES: Cc1c(CN2CCCC(c3cc(NCc4cccnc4)n4ncc(Br)c4n3)C2)sc2ccccc12] | 1. 8053<br>2. 547.3 |
| 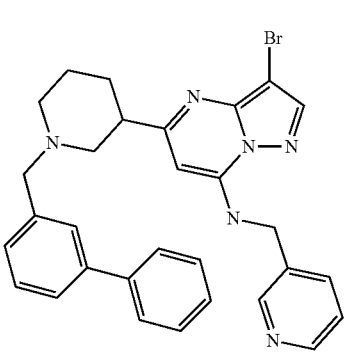 [SMILES: Brc1cnn2c(NCc3cccnc3)cc(C3CCCN(Cc4cccc(-c5ccccc5)c4)C3)nc12] | 1. 8054<br>2. 555.31 |
| 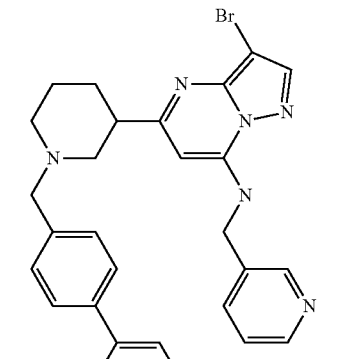 | 1. 8055<br>2. 553.3 |
| 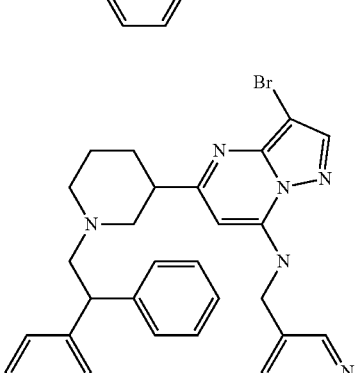 | 1. 8056<br>2. 569.31 |

TABLE 80-continued
| Product | 1. Ex. 2. m/z |
|---|---|
| 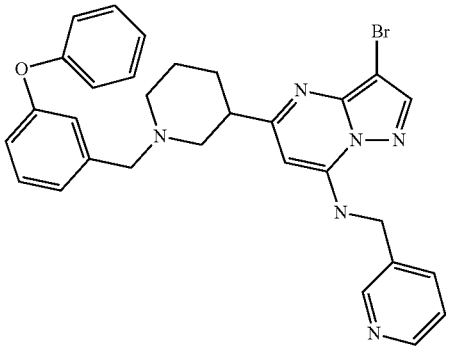 [SMILES: Brc1cnn2c(NCc3cccnc3)cc(C3CCCN(Cc4cccc(Oc5ccccc5)c4)C3)nc12] | 1. 8057 2. 569.31 |
| 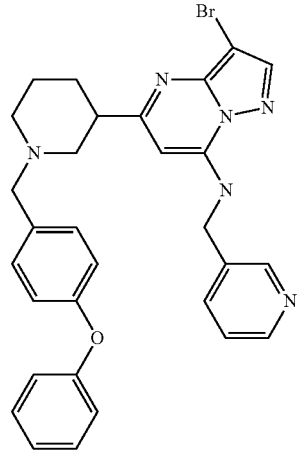 [SMILES: Brc1cnn2c(NCc3cccnc3)cc(C3CCCN(Cc4ccc(Oc5ccccc5)cc4)C3)nc12] | 1. 8058 2. 571.31 |
| 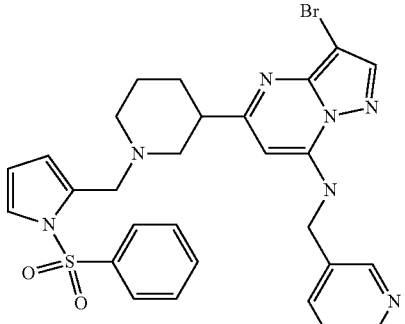 | 1. 8059 2. 608.33 |
| 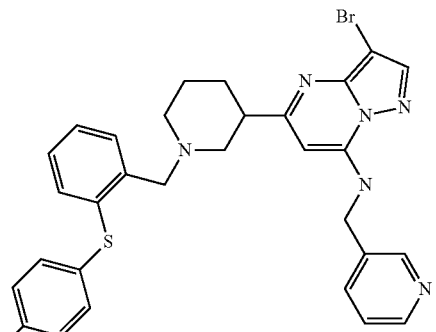 | 1. 8060 2. 621.34 |
TABLE 80-continued
| Product | 1. Ex. 2. m/z |
|---|---|
| 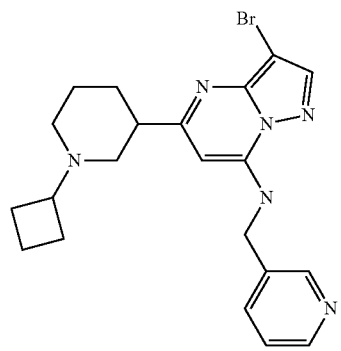 [SMILES: Brc1cnn2c(NCc3cccnc3)cc(C3CCCN(C4CCC4)C3)nc12] | 1. 8061 2. 443.24 |
| 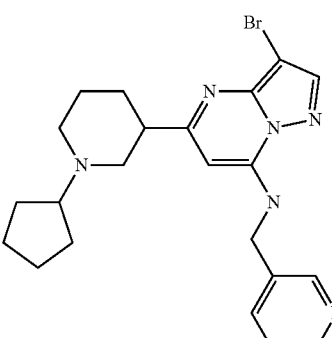 | 1. 8062 2. 457.25 |
| 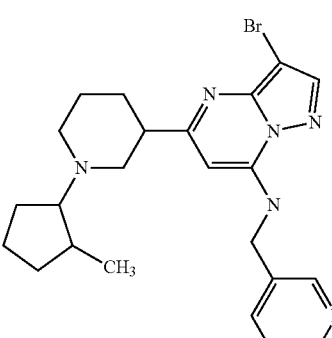 | 1. 8063 2. 471.26 |
| 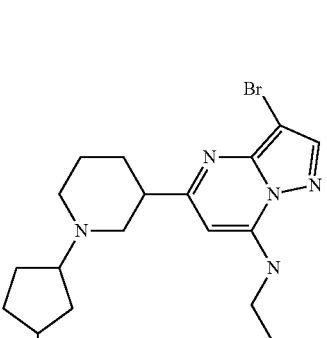 | 1. 8064 2. 471.26 |

TABLE 80-continued

| Product | 1. Ex.<br>2. m/z |
|---|---|
| (structure) | 1. 8065<br>2. 469.26 |
| (structure) | 1. 8066<br>2. 473.26 |
| (structure) | 1. 8067<br>2. 483.27 |
| (structure) | 1. 8068<br>2. 485.27 |

TABLE 80-continued

| Product | 1. Ex.<br>2. m/z |
|---|---|
| (structure) | 1. 8069<br>2. 483.27 |
| (structure) | 1. 8070<br>2. 499.27 |
| (structure) | 1. 8071<br>2. 505.28 |
| (structure) | 1. 8072<br>2. 537.3 |

TABLE 80-continued
| Product | 1. Ex. 2. m/z |
|---|---|
| 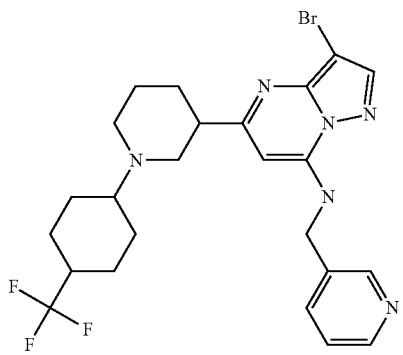 [SMILES: FC(F)(F)C1CCC(N2CCCC(c3cc(NCc4cccnc4)n4ncc(Br)c4n3)C2)CC1] | 1. 8073 2. 537.3 |
| 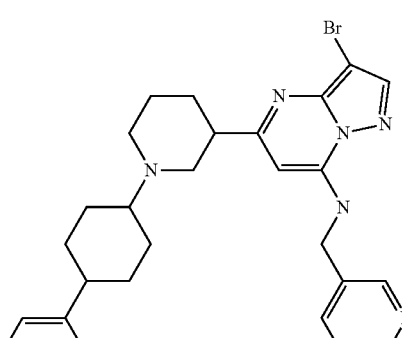 | 1. 8074 2. 547.3 |
TABLE 81
| Product | 1. Ex. 2. m/z |
|---|---|
| 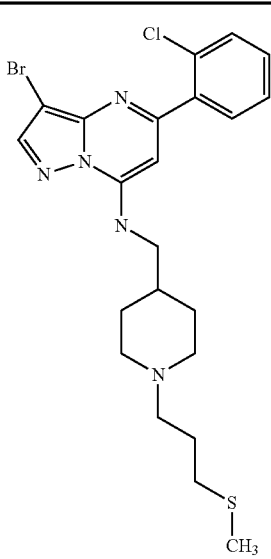 | 1. 8101 2. 510.28 |
TABLE 81-continued
| Product | 1. Ex. 2. m/z |
|---|---|
| 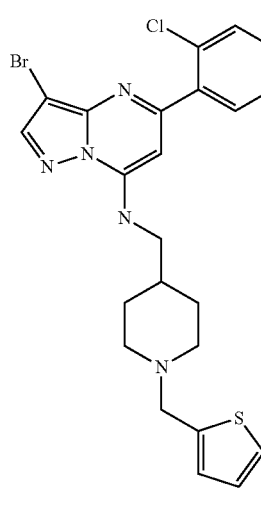 | 1. 8102 2. 518.28 |
| 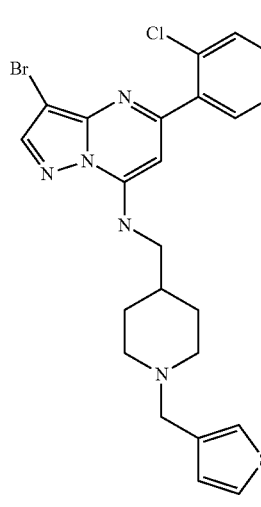 | 1. 8103 2. 518.28 |
| 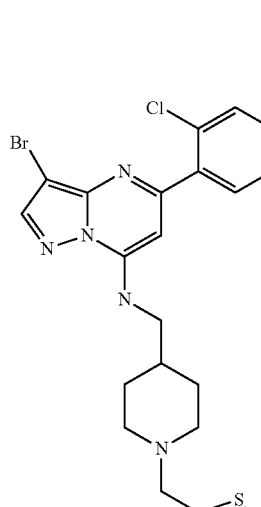 | 1. 8104 2. 519.29 |

TABLE 81-continued

| Product | 1. Ex.<br>2. m/z |
|---|---|
| (structure: 3-bromo-5-(2-chlorophenyl)-N-{[1-(2-phenylethyl)piperidin-4-yl]methyl}pyrazolo[1,5-a]pyrimidin-7-amine) | 1. 8105<br>2. 526.29 |
| (structure: 3-bromo-5-(2-chlorophenyl)-N-{[1-(2-hydroxybenzyl)piperidin-4-yl]methyl}pyrazolo[1,5-a]pyrimidin-7-amine) | 1. 8106<br>2. 528.29 |
| (structure: 4-({4-[({3-bromo-5-(2-chlorophenyl)pyrazolo[1,5-a]pyrimidin-7-yl}amino)methyl]piperidin-1-yl}methyl)benzonitrile) | 1. 8107<br>2. 537.3 |
| (structure: 3-bromo-5-(2-chlorophenyl)-N-{[1-cinnamylpiperidin-4-yl]methyl}pyrazolo[1,5-a]pyrimidin-7-amine) | 1. 8108<br>2. 538.3 |
| (structure: 3-bromo-5-(2-chlorophenyl)-N-{[1-(3-phenylpropyl)piperidin-4-yl]methyl}pyrazolo[1,5-a]pyrimidin-7-amine) | 1. 8109<br>2. 540.3 |

TABLE 81-continued
| Product | 1. Ex.<br>2. m/z |
|---|---|
| 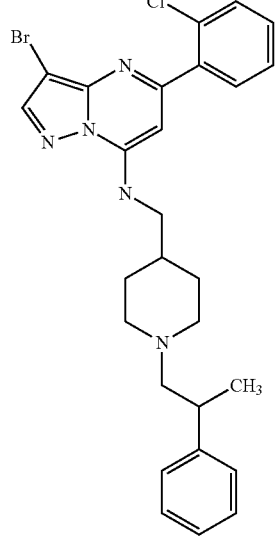 | 1. 8110<br>2. 540.3 |
| 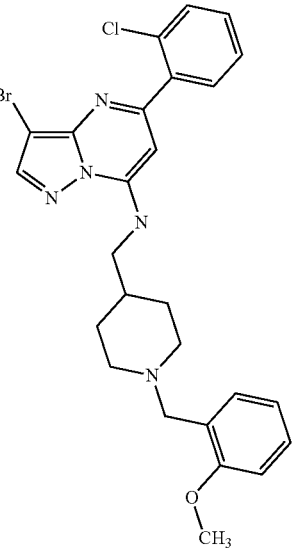 | 1. 8111<br>2. 542.3 |
| 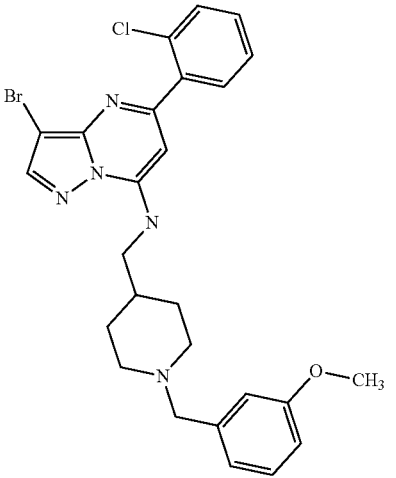 [SMILES: COc1cccc(CN2CCC(CNc3cc(-c4ccccc4Cl)nc4c(Br)cnn34)CC2)c1] | 1. 8112<br>2. 542.3 |
TABLE 81-continued
| Product | 1. Ex.<br>2. m/z |
|---|---|
| 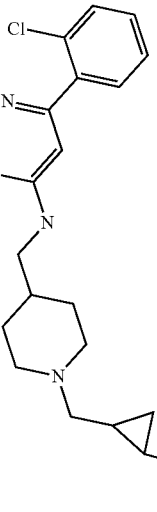 | 1. 8113<br>2. 548.3 |
| 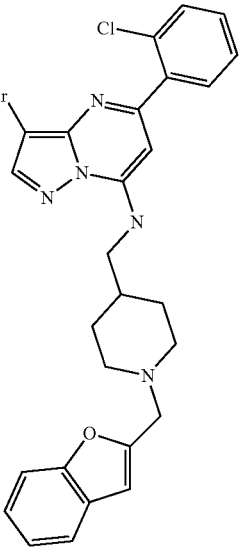 | 1. 8114<br>2. 552.3 |

TABLE 81-continued
| Product | 1. Ex.<br>2. m/z |
|---|---|
| 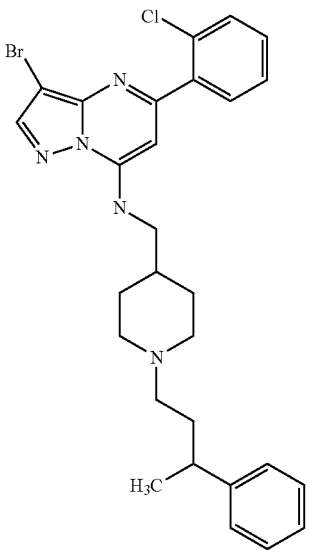 [SMILES: CC(CCN1CCC(CNc2cc(-c3ccccc3Cl)nc3c(Br)cnn23)CC1)c1ccccc1] | 1. 8115<br>2. 554.3 |
| 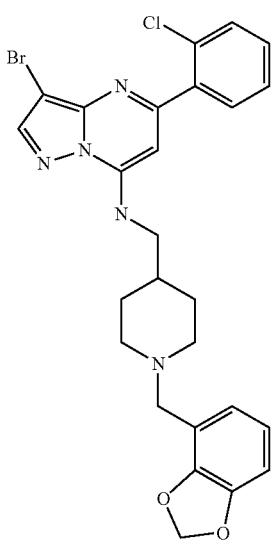 [SMILES: Clc1ccccc1-c1cc(NCC2CCN(Cc3cccc4c3OCO4)CC2)n2ncc(Br)c2n1] | 1. 8116<br>2. 556.31 |
TABLE 81-continued
| Product | 1. Ex.<br>2. m/z |
|---|---|
| 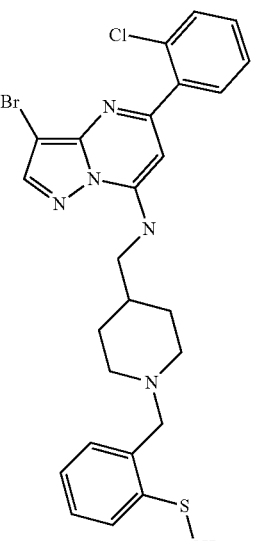 | 1. 8117<br>2. 558.31 |
| 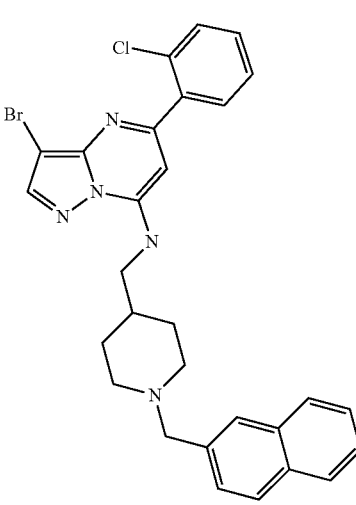 [SMILES: Clc1ccccc1-c1cc(NCC2CCN(Cc3ccc4ccccc4c3)CC2)n2ncc(Br)c2n1] | 1. 8118<br>2. 562.31 |

TABLE 81-continued
| Product | 1. Ex. 2. m/z |
|---|---|
| 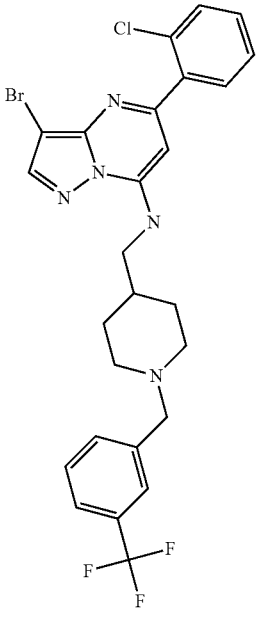 [SMILES: FC(F)(F)c1cccc(CN2CCC(CNc3cc(-c4ccccc4Cl)nc4c(Br)cnn34)CC2)c1] | 1. 8119 2. 580.32 |
| 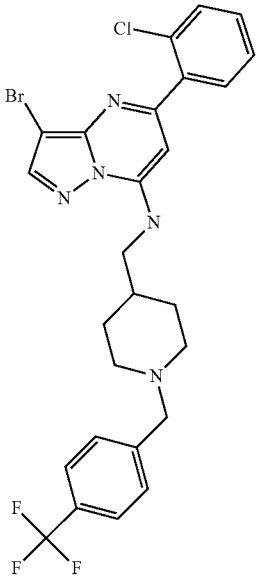 [SMILES: FC(F)(F)c1ccc(CN2CCC(CNc3cc(-c4ccccc4Cl)nc4c(Br)cnn34)CC2)cc1] | 1. 8120 2. 580.32 |
TABLE 81-continued
| Product | 1. Ex. 2. m/z |
|---|---|
| 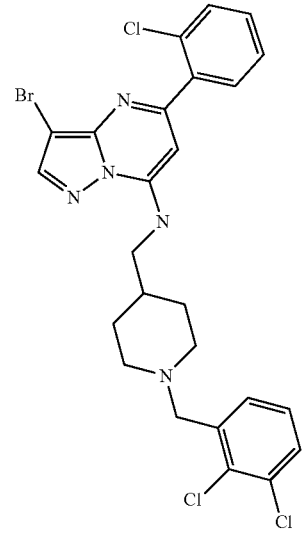 [SMILES: Clc1ccccc1-c1cc(NCC2CCN(Cc3cccc(Cl)c3Cl)CC2)n2ncc(Br)c2n1] | 1. 8121 2. 580.32 |
| 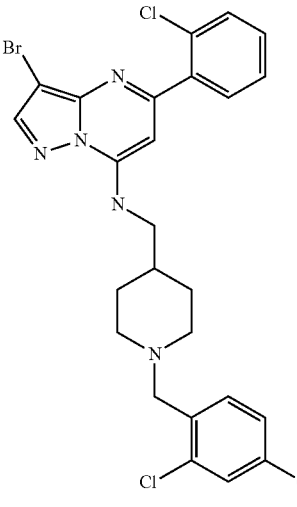 | 1. 8122 2. 580.32 |
| 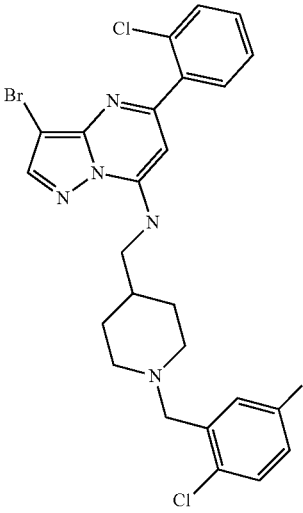 | 1. 8123 2. 580.32 |

TABLE 81-continued
| Product | 1. Ex. 2. m/z |
|---|---|
| 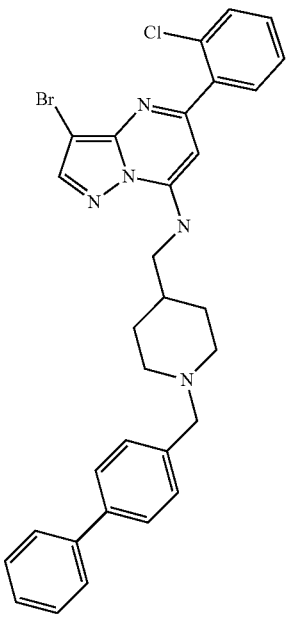 | 1. 8125 2. 580.32 |
| 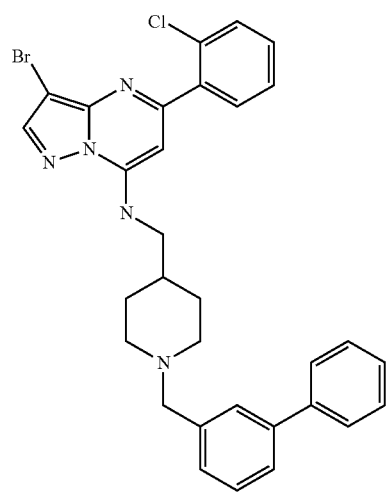 [SMILES: Clc1ccccc1-c1cc(NCC2CCN(Cc3cccc(-c4ccccc4)c3)CC2)n2ncc(Br)c2n1] | 1. 8126 2. 588.32 |
TABLE 81-continued
| Product | 1. Ex. 2. m/z |
|---|---|
| (2-chlorophenyl / biphenyl structure) | 1. 8126 2. 588.32 |
| 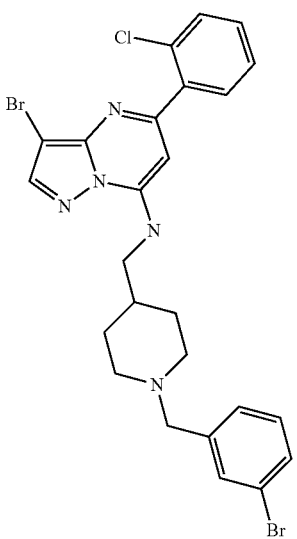 [SMILES: Clc1ccccc1-c1cc(NCC2CCN(Cc3cccc(Br)c3)CC2)n2ncc(Br)c2n1] | 1. 8127 2. 590.32 |

TABLE 81-continued

| Product | 1. Ex.<br>2. m/z |
|---|---|
| (structure) | 1. 8128<br>2. 590.32 |
| (structure) | 1. 8129<br>2. 604.33 |
| (structure) | 1. 8130<br>2. 612.34 |

TABLE 81-continued

| Product | 1. Ex.<br>2. m/z |
|---|---|
| (structure) | 1. 8131<br>2. 654.36 |
| (structure) | 1. 8132<br>2. 476.26 |
| (structure) | 1. 8133<br>2. 580.32 |

TABLE 81-continued
| Product | 1. Ex. 2. m/z |
|---|---|
| 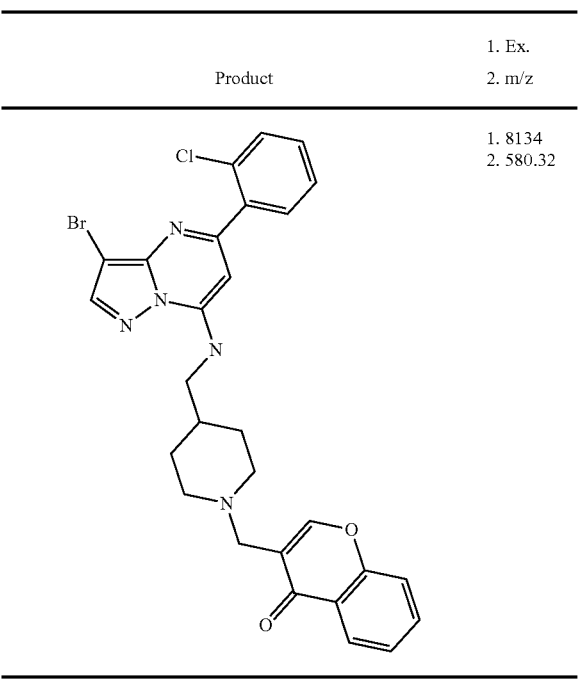 | 1. 8134 2. 580.32 |
TABLE 82
| Product | 1. Ex. 2. m/z |
|---|---|
| 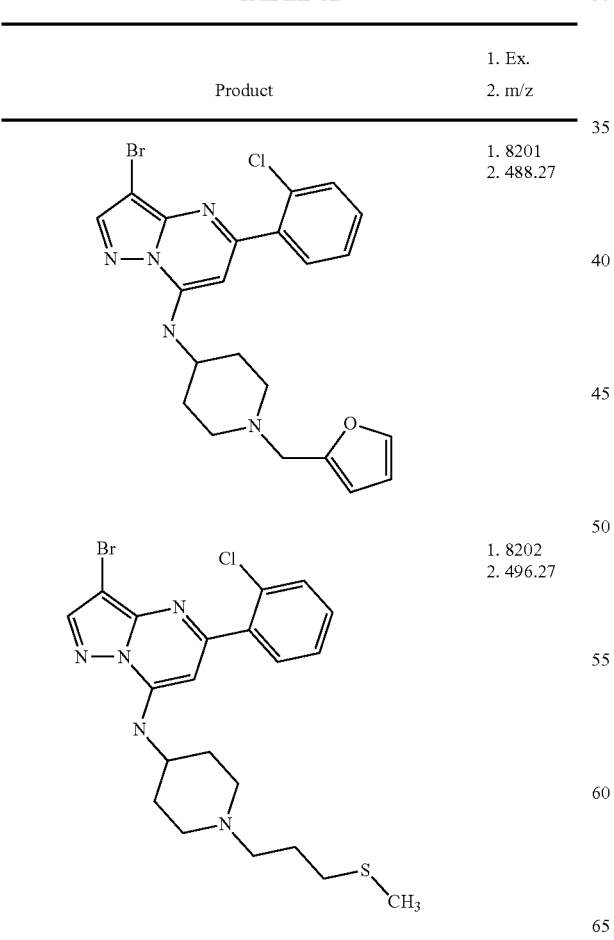 | 1. 8201 2. 488.27 |
| (second structure) | 1. 8202 2. 496.27 |
TABLE 82-continued
| Product | 1. Ex. 2. m/z |
|---|---|
| 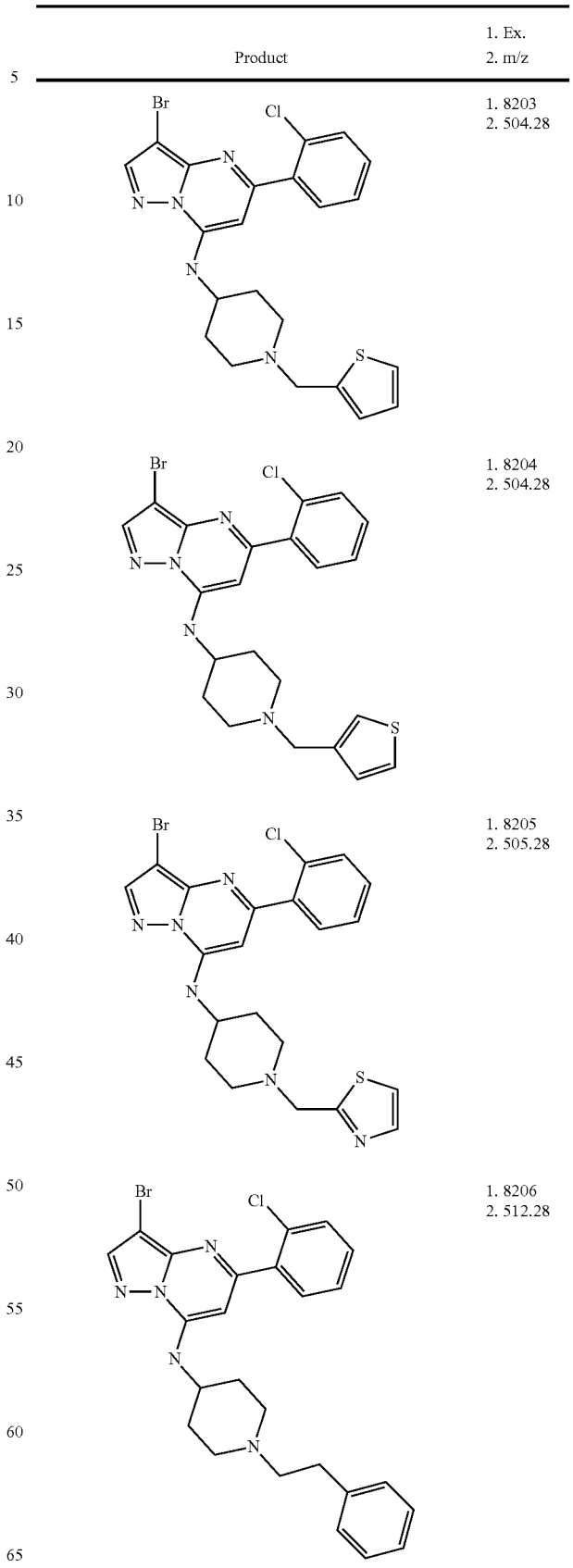 | 1. 8203 2. 504.28 |
| | 1. 8204 2. 504.28 |
| | 1. 8205 2. 505.28 |
| | 1. 8206 2. 512.28 |

TABLE 82-continued
| Product | 1. Ex. 2. m/z |
|---|---|
| 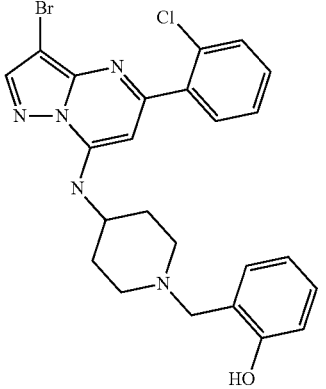 [SMILES: Oc1ccccc1CN1CCC(Nc2cc(-c3ccccc3Cl)nc3c(Br)cnn23)CC1] | 1. 8207 2. 514.28 |
| 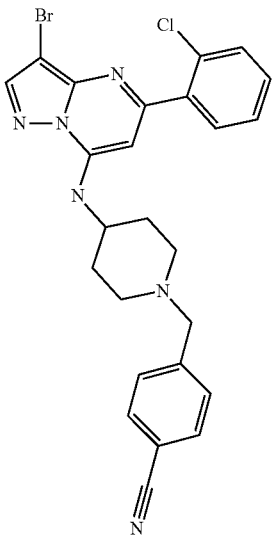 [SMILES: N#Cc1ccc(CN2CCC(Nc3cc(-c4ccccc4Cl)nc4c(Br)cnn34)CC2)cc1] | 1. 8208 2. 523.29 |
| 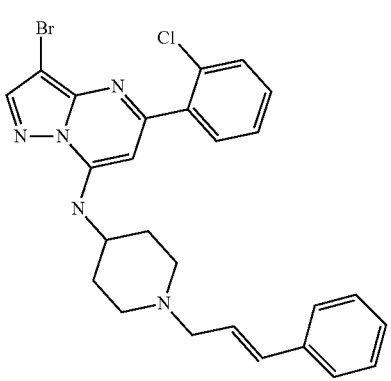 [SMILES: Clc1ccccc1-c1cc(NC2CCN(C/C=C/c3ccccc3)CC2)n2ncc(Br)c2n1] | 1. 8209 2. 524.29 |
TABLE 82-continued
| Product | 1. Ex. 2. m/z |
|---|---|
| 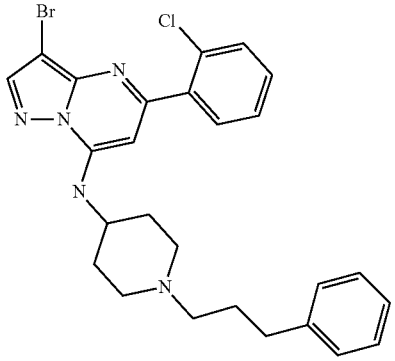 [SMILES: Clc1ccccc1-c1cc(NC2CCN(CCCc3ccccc3)CC2)n2ncc(Br)c2n1] | 1. 8210 2. 526.29 |
| 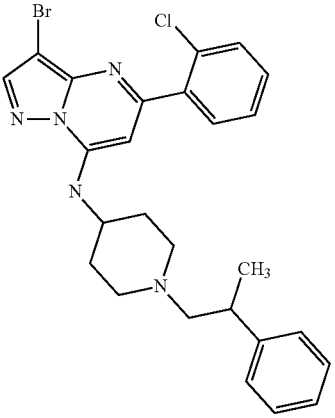 [SMILES: CC(CN1CCC(Nc2cc(-c3ccccc3Cl)nc3c(Br)cnn23)CC1)c1ccccc1] | 1. 8211 2. 526.29 |
| 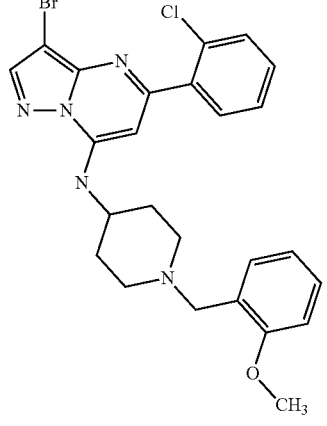 | 1. 8212 2. 528.29 |
| 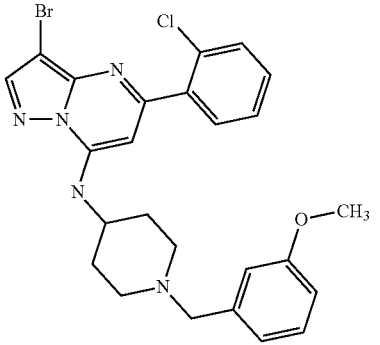 [SMILES: COc1cccc(CN2CCC(Nc3cc(-c4ccccc4Cl)nc4c(Br)cnn34)CC2)c1] | 1. 8213 2. 528.29 |

TABLE 82-continued
| Product | 1. Ex. 2. m/z |
|---|---|
| 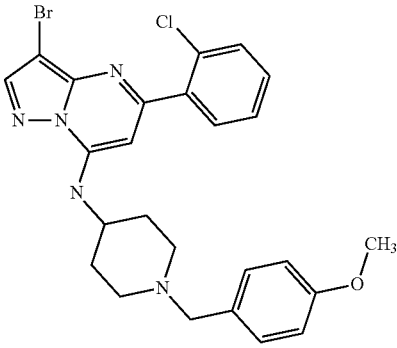 [SMILES: COc1ccc(CN2CCC(Nc3cc(-c4ccccc4Cl)nc4c(Br)cnn34)CC2)cc1] | 1. 8214  2. 528.29 |
| 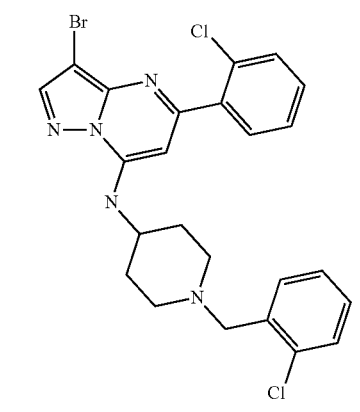 [SMILES: Clc1ccccc1CN1CCC(Nc2cc(-c3ccccc3Cl)nc3c(Br)cnn23)CC1] | 1. 8215  2. 532.29 |
| 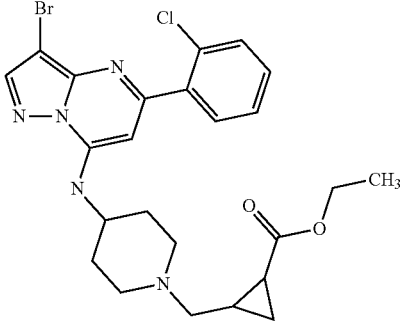 [SMILES: CCOC(=O)C1CC1CN1CCC(Nc2cc(-c3ccccc3Cl)nc3c(Br)cnn23)CC1] | 1. 8216  2. 534.29 |
| 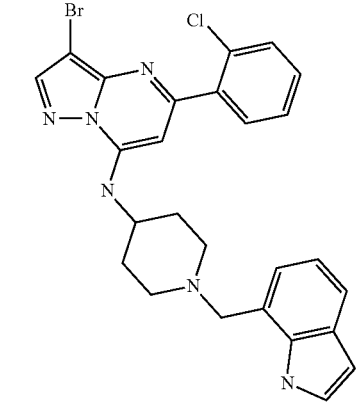 [SMILES: Clc1ccccc1-c1cc(NC2CCN(Cc3cccc4cc[nH]c34)CC2)n2ncc(Br)c2n1] | 1. 8217  2. 537.3 |
TABLE 82-continued
| Product | 1. Ex. 2. m/z |
|---|---|
| 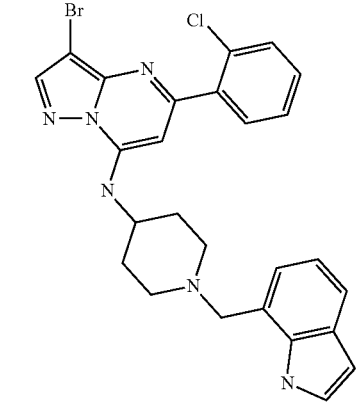 [SMILES: Clc1ccccc1-c1cc(NC2CCN(Cc3cccc4cc[nH]c34)CC2)n2ncc(Br)c2n1] | 1. 8218  2. 538.3 |
| 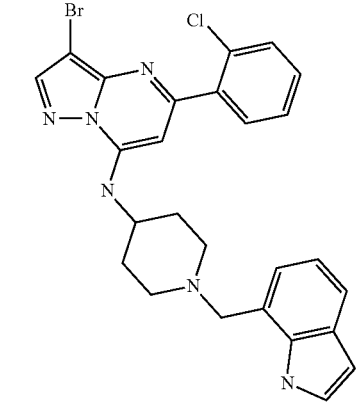 [SMILES: Clc1ccccc1-c1cc(NC2CCN(Cc3cccc4cc[nH]c34)CC2)n2ncc(Br)c2n1] | 1. 8219  2. 542.3 |
| 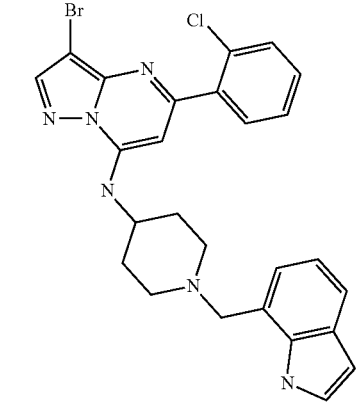 [SMILES: Clc1ccccc1-c1cc(NC2CCN(Cc3cccc4cc[nH]c34)CC2)n2ncc(Br)c2n1] | 1. 8220  2. 542.3 |
| 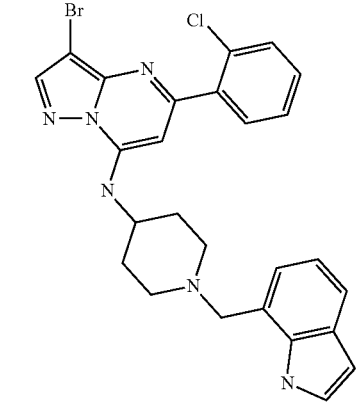 [SMILES: Clc1ccccc1-c1cc(NC2CCN(Cc3cccc4cc[nH]c34)CC2)n2ncc(Br)c2n1] | 1. 8221  2. 544.3 |

TABLE 82-continued
| Product | 1. Ex. 2. m/z |
|---|---|
| 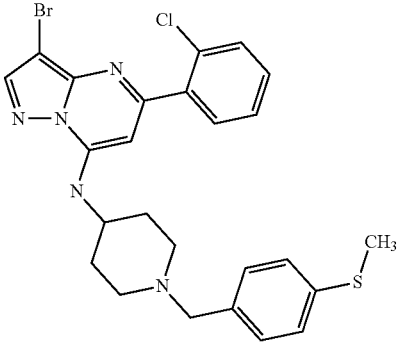 [SMILES: CSc1ccc(CN2CCC(Nc3cc(-c4ccccc4Cl)nc4c(Br)cnn34)CC2)cc1] | 1. 8222 2. 544.3 |
| 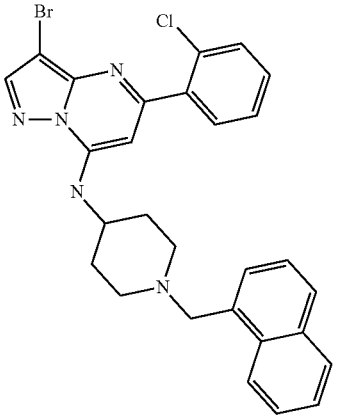 [SMILES: Clc1ccccc1-c1cc(NC2CCN(Cc3cccc4ccccc34)CC2)n2ncc(Br)c2n1] | 1. 8223 2. 548.3 |
| 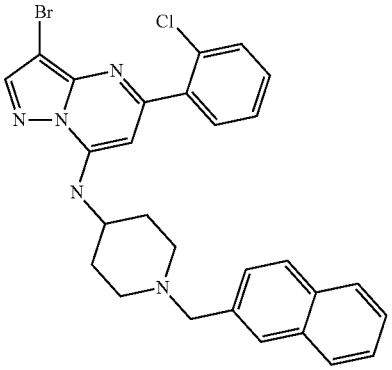 [SMILES: Clc1ccccc1-c1cc(NC2CCN(Cc3ccc4ccccc4c3)CC2)n2ncc(Br)c2n1] | 1. 8224 2. 548.3 |
| 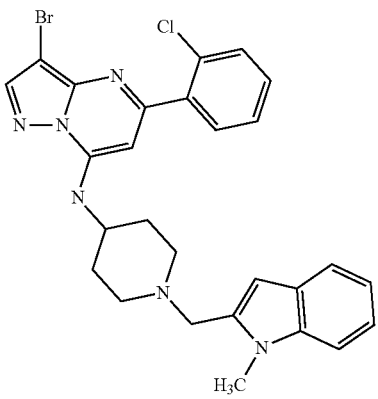 [SMILES: Cn1c(CN2CCC(Nc3cc(-c4ccccc4Cl)nc4c(Br)cnn34)CC2)cc2ccccc21] | 1. 8225 2. 551.3 |
| 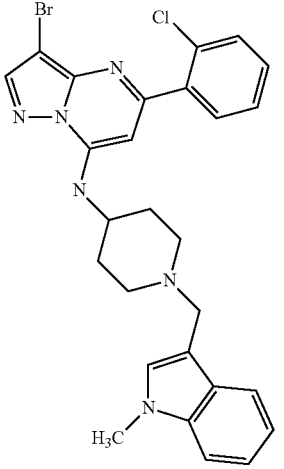 [SMILES: Cn1cc(CN2CCC(Nc3cc(-c4ccccc4Cl)nc4c(Br)cnn34)CC2)c2ccccc21] | 1. 8226 2. 551.3 |
| 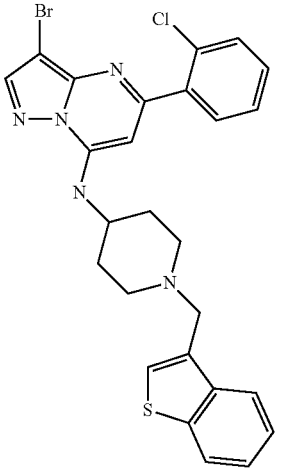 [SMILES: Clc1ccccc1-c1cc(NC2CCN(Cc3csc4ccccc34)CC2)n2ncc(Br)c2n1] | 1. 8227 2. 554.3 |
| 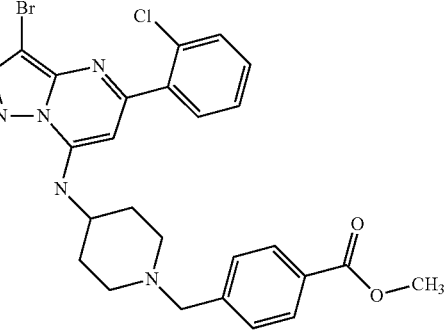 | 1. 8228 2. 556.31 |

TABLE 82-continued
| Product | 1. Ex. 2. m/z |
|---|---|
| 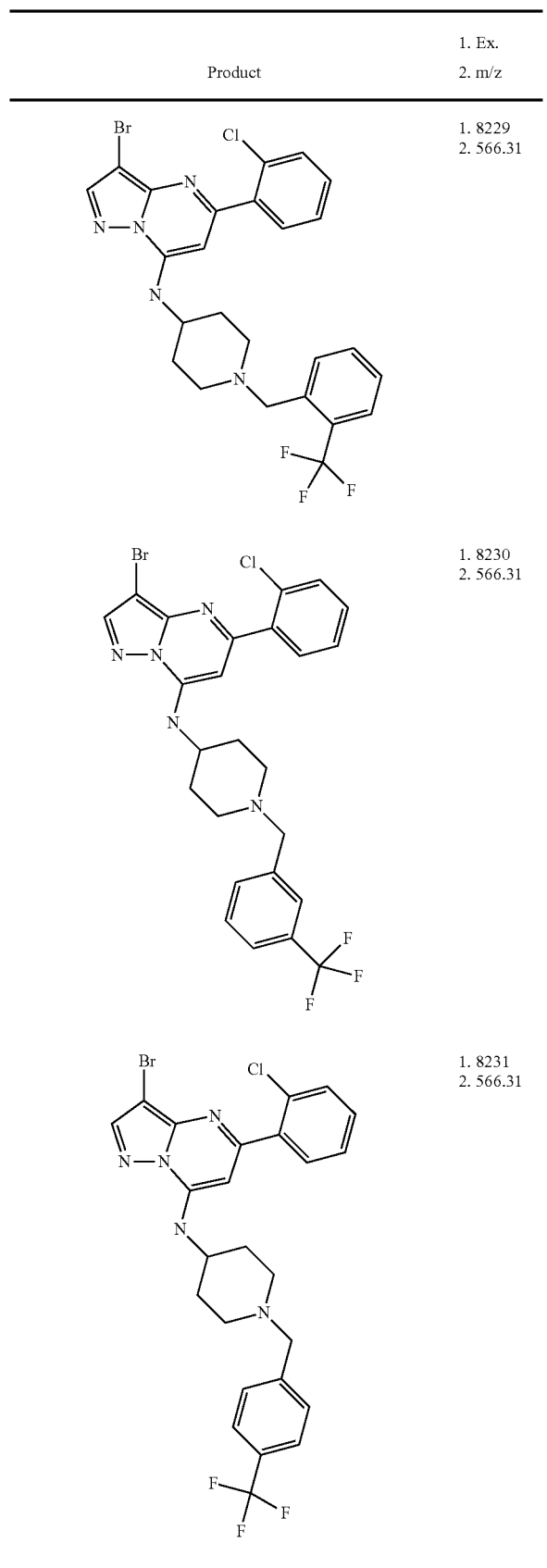 | 1. 8229 2. 566.31 |
| | 1. 8230 2. 566.31 |
| | 1. 8231 2. 566.31 |
TABLE 82-continued
| Product | 1. Ex. 2. m/z |
|---|---|
| 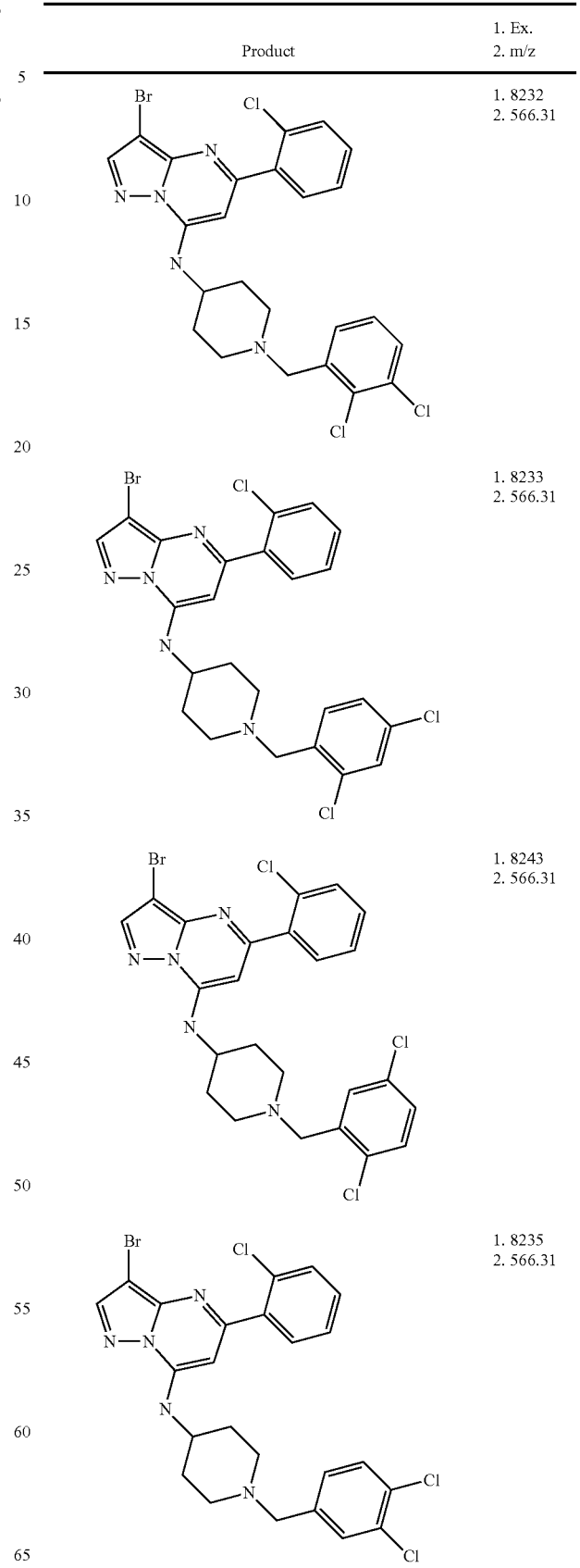 | 1. 8232 2. 566.31 |
| | 1. 8233 2. 566.31 |
| | 1. 8243 2. 566.31 |
| | 1. 8235 2. 566.31 |

TABLE 82-continued
| Product | 1. Ex. 2. m/z |
|---|---|
| 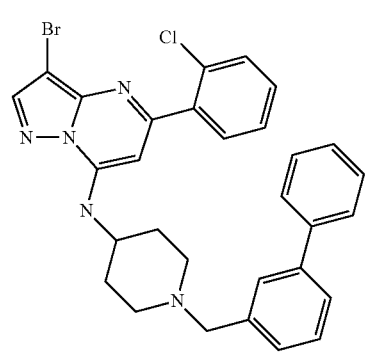 [SMILES: Clc1ccccc1-c1cc(NC2CCN(Cc3cccc(-c4ccccc4)c3)CC2)n2ncc(Br)c2n1] | 1. 8236  2. 568.31 |
| | 1. 8237  2. 574.32 |
| 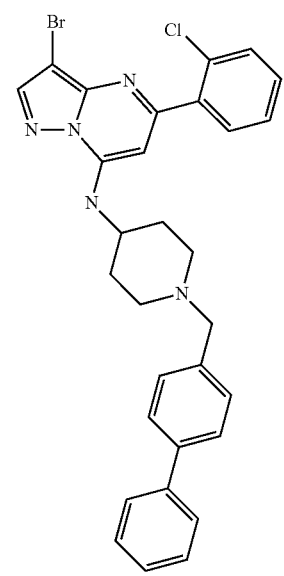 [SMILES: Clc1ccccc1-c1cc(NC2CCN(Cc3ccc(-c4ccccc4)cc3)CC2)n2ncc(Br)c2n1] | 1. 8238  2. 574.32 |
TABLE 82-continued
| Product | 1. Ex. 2. m/z |
|---|---|
| 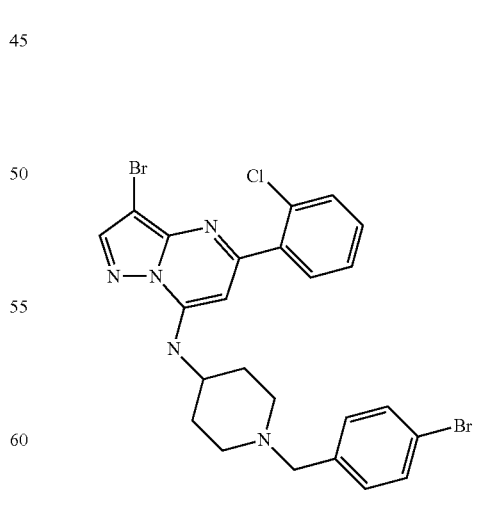 | 1. 8239  2. 576.32 |
| | 1. 8240  2. 576.32 |
| | 1. 8241  2. 576.32 |

TABLE 82-continued

| Product | 1. Ex. 2. m/z |
|---|---|
| (structure) | 1. 8242  2. 586.32 |
| (structure) | 1. 8243  2. 586.32 |
| (structure) | 1. 8244  2. 588.32 |
| (structure) | 1. 8245  2. 590.32 |
| (structure) | 1. 8246  2. 590.32 |
| (structure) | 1. 8247  2. 598.33 |

TABLE 82-continued

| Product | 1. Ex.<br>2. m/z |
|---|---|
| (structure) | 1. 8248<br>2. 627.34 |
| (structure) | 1. 8249<br>2. 640.35 |
| (structure) | 1. 8250<br>2. 462.25 |

TABLE 82-continued

| Product | 1. Ex.<br>2. m/z |
|---|---|
| (structure) | 1. 8251<br>2. 476.26 |
| (structure) | 1. 8252<br>2. 490.27 |
| (structure) | 1. 8253<br>2. 492.27 |
| (structure) | 1. 8254<br>2. 492.27 |

TABLE 82-continued
| Product | 1. Ex.<br>2. m/z |
|---|---|
| 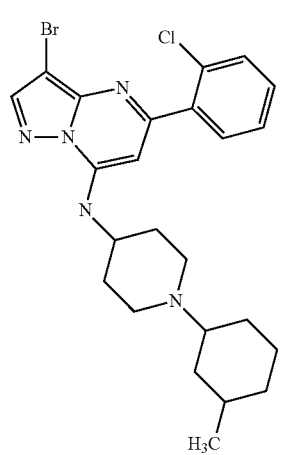 [SMILES: CC1CCCC(N2CCC(Nc3cc(-c4ccccc4Cl)nc4c(Br)cnn34)CC2)C1] | 1. 8255<br>2. 502.28 |
| 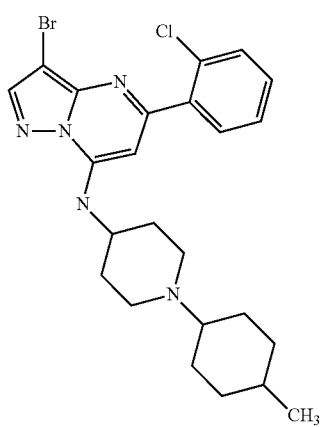 [SMILES: CC1CCC(N2CCC(Nc3cc(-c4ccccc4Cl)nc4c(Br)cnn34)CC2)CC1] | 1. 8256<br>2. 504.28 |
| | 1. 8257<br>2. 504.28 |
TABLE 82-continued
| Product | 1. Ex.<br>2. m/z |
|---|---|
| 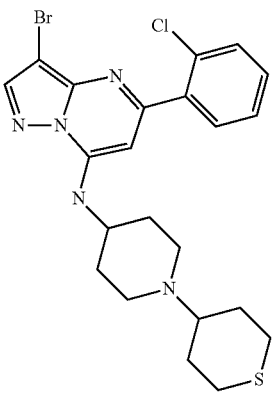 [SMILES: Clc1ccccc1-c1cc(NC2CCN(C3CCSCC3)CC2)n2ncc(Br)c2n1] | 1. 8258<br>2. 508.28 |
| 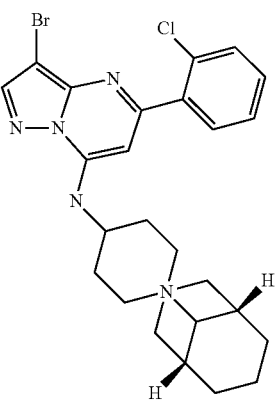 | 1. 8259<br>2. 530.29 |
| 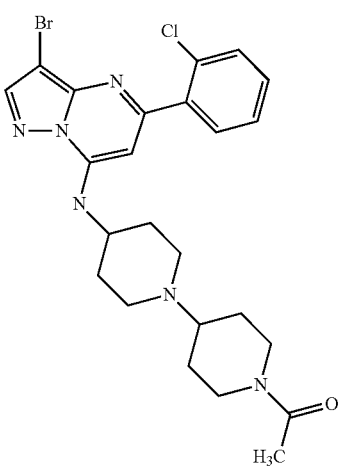 [SMILES: CC(=O)N1CCC(N2CCC(Nc3cc(-c4ccccc4Cl)nc4c(Br)cnn34)CC2)CC1] | 1. 8260<br>2. 533.29 |

TABLE 82-continued
| Product | 1. Ex.<br>2. m/z |
|---|---|
| | 1. 8261<br>2. 544.3 |
| 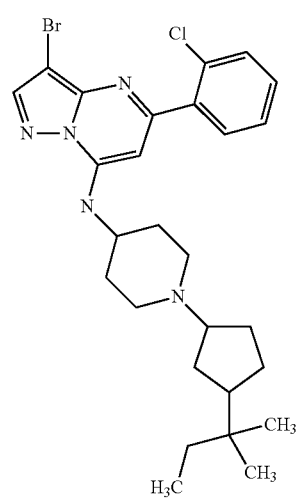 [SMILES: CCC(C)(C)C1CCC(N2CCC(Nc3cc(-c4ccccc4Cl)nc4c(Br)cnn34)CC2)C1] | 1. 8262<br>2. 546.3 |
| | 1. 8263<br>2. 546.3 |
TABLE 82-continued
| Product | 1. Ex.<br>2. m/z |
|---|---|
| | 1. 8264<br>2. 558.31 |
| | 1. 8265<br>2. 558.31 |
| 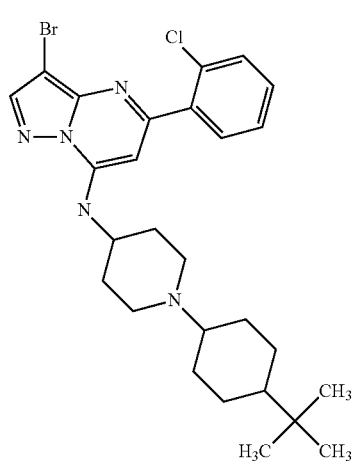 [SMILES: CC(C)(C)C1CCC(N2CCC(Nc3cc(-c4ccccc4Cl)nc4c(Br)cnn34)CC2)CC1] | 1. 8266<br>2. 560.31 |

TABLE 82-continued

| Product | 1. Ex.<br>2. m/z |
|---------|------------------|
| [structure: 3-bromo-5-(2-chlorophenyl)pyrazolo[1,5-a]pyrimidin-7-yl amino piperidine N-(4-phenylcyclohexyl)] | 1. 8267<br>2. 566.31 |
| [structure: 3-bromo-5-(2-chlorophenyl)pyrazolo[1,5-a]pyrimidin-7-yl amino piperidine N-(4-cyano-4-phenylcyclohexyl)] | 1. 8268<br>2. 591.33 |
| [structure: 3-bromo-5-(2-chlorophenyl)pyrazolo[1,5-a]pyrimidin-7-yl amino piperidine N-(1-benzoylpiperidin-4-yl)] | 1. 8269<br>2. 595.33 |

TABLE 82-continued

| Product | 1. Ex.<br>2. m/z |
|---------|------------------|
| [structure: 3-bromo-5-(2-chlorophenyl)pyrazolo[1,5-a]pyrimidin-7-yl amino piperidine N-CH2-(4-acetamidophenyl)] | 1. 8270<br>2. 555.31 |

TABLE 83

| Product | 1. Ex.<br>2. m/z |
|---------|------------------|
| [structure: 3-bromo-5-(2-chlorophenyl)pyrazolo[1,5-a]pyrimidin-7-yl-N-(3-(N-methyl-N-(3-methylbutyl)amino)propyl)amine] | 1. 8301<br>2. 465.882 |

TABLE 83-continued
| Product | 1. Ex. 2. m/z |
|---|---|
| 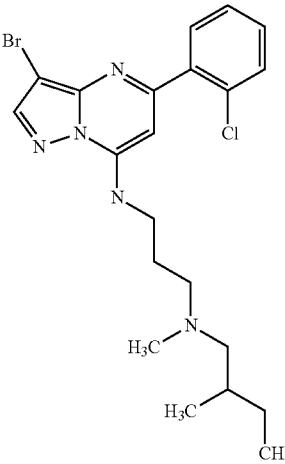 | 1. 8302 2. 465.885 |
| 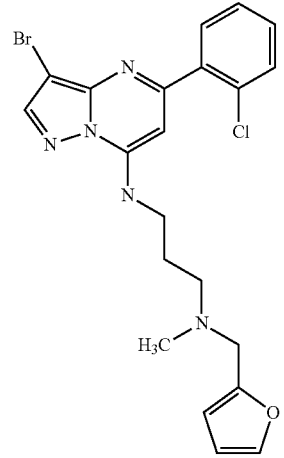 | 1. 8303 2. 475.827 |
| 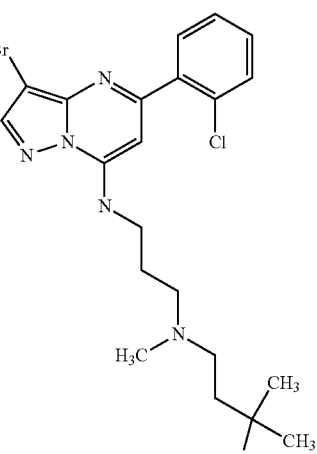 | 1. 8304 2. 479.89 |
TABLE 83-continued
| Product | 1. Ex. 2. m/z |
|---|---|
| 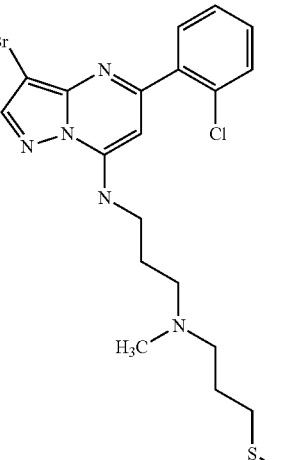 | 1. 8305 2. 483.829 |
| 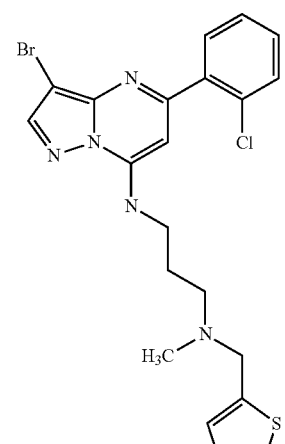 | 1. 8306 2. 491.79 |
| 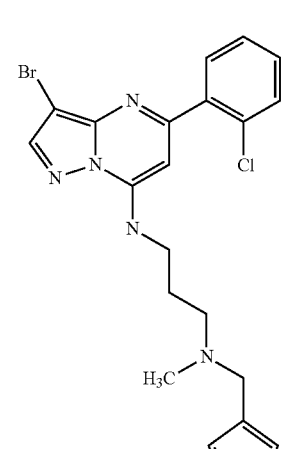 | 1. 8307 2. 491.792 |

TABLE 83-continued
| Product | 1. Ex.<br>2. m/z |
|---|---|
| 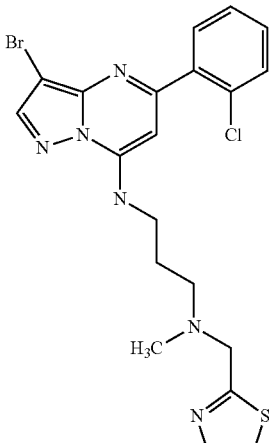 | 1. 8308<br>2. 492.787 |
| 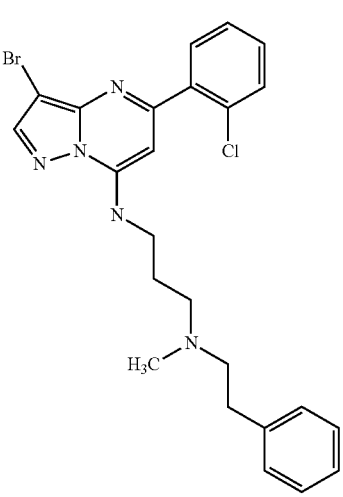 [SMILES: CN(CCCNc1cc(-c2ccccc2Cl)nc2c(Br)cnn12)CCc1ccccc1] | 1. 8309<br>2. 499.846 |
| 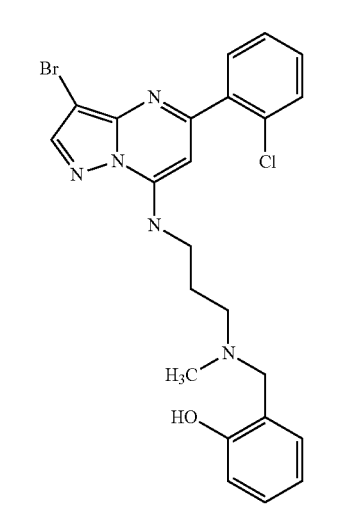 [SMILES: CN(CCCNc1cc(-c2ccccc2Cl)nc2c(Br)cnn12)Cc1ccccc1O] | 1. 8310<br>2. 501.826 |
| 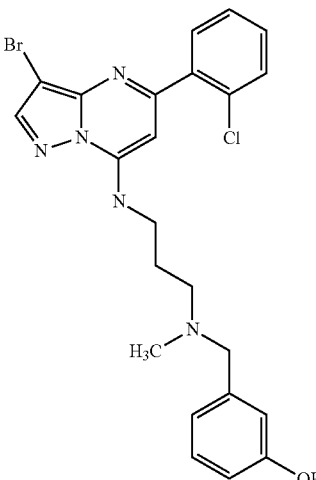 | 1. 8311<br>2. 501.825 |
| 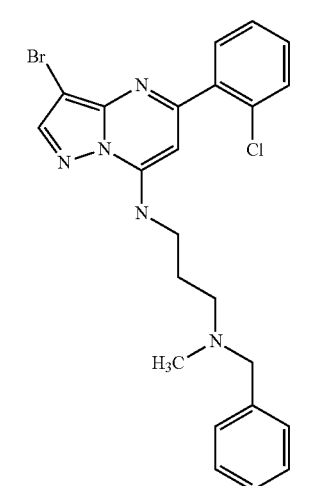 | 1. 8312<br>2. 501.833 |
| 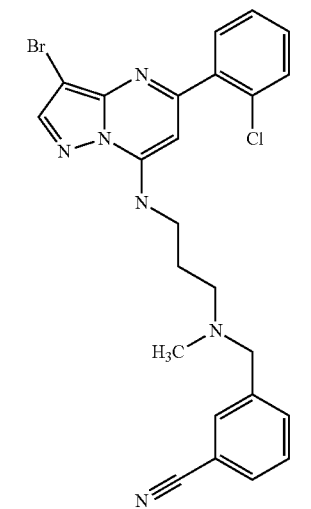 [SMILES: CN(CCCNc1cc(-c2ccccc2Cl)nc2c(Br)cnn12)Cc1cccc(C#N)c1] | 1. 8313<br>2. 510.822 |

TABLE 83-continued
| Product | 1. Ex. 2. m/z |
|---|---|
| 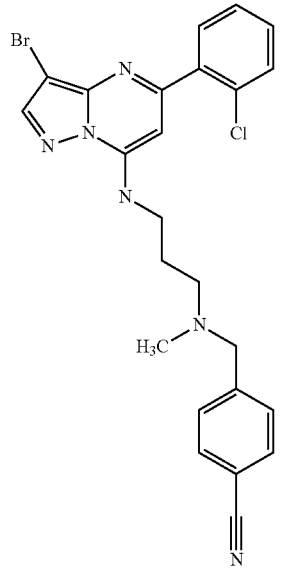 [SMILES: CN(CCCNc1cc(-c2ccccc2Cl)nc2c(Br)cnn12)Cc1ccc(C#N)cc1] | 1. 8314<br>2. 510.821 |
| 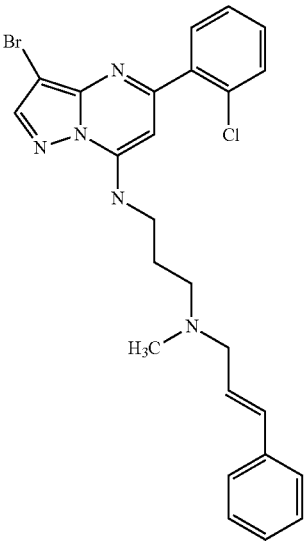 [SMILES: CN(C/C=C/c1ccccc1)CCCNc1cc(-c2ccccc2Cl)nc2c(Br)cnn12] | 1. 8315<br>2. 511.841 |
| 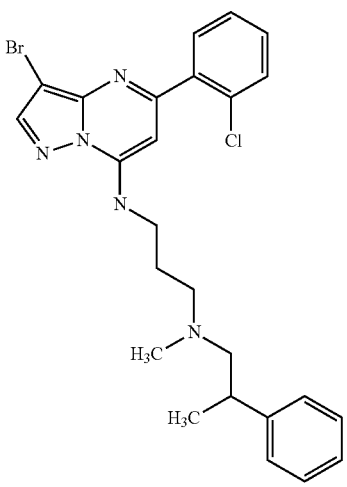 [SMILES: CC(CN(C)CCCNc1cc(-c2ccccc2Cl)nc2c(Br)cnn12)c1ccccc1] | 1. 8316<br>2. 513.855 |
TABLE 83-continued
| Product | 1. Ex. 2. m/z |
|---|---|
| 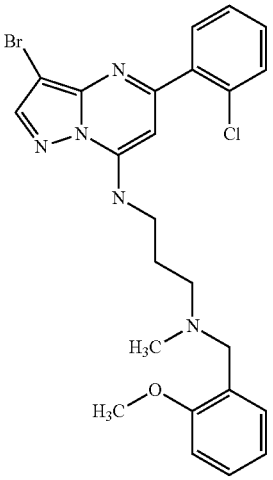 [SMILES: COc1ccccc1CN(C)CCCNc1cc(-c2ccccc2Cl)nc2c(Br)cnn12] | 1. 8317<br>2. 515.832 |
| 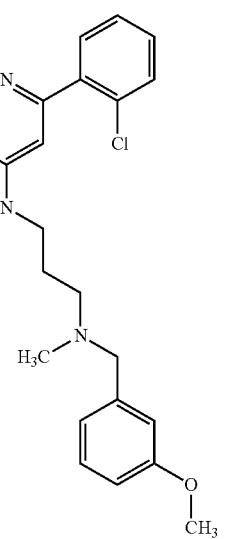 | 1. 8318<br>2. 515.832 |
| 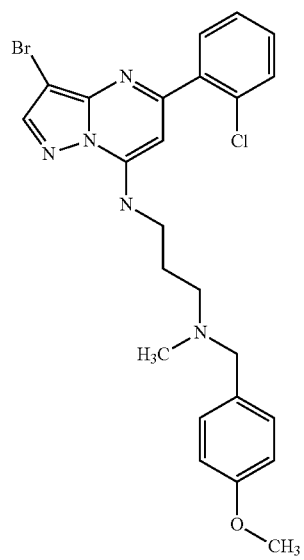 [SMILES: COc1ccc(CN(C)CCCNc2cc(-c3ccccc3Cl)nc3c(Br)cnn23)cc1] | 1. 8319<br>2. 515.837 |

TABLE 83-continued
| Product | 1. Ex.<br>2. m/z |
|---|---|
| 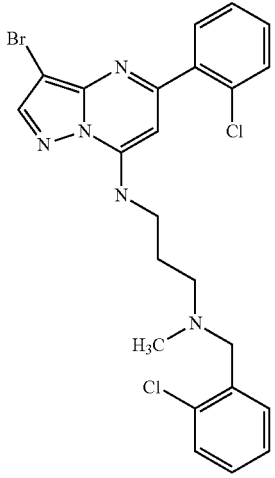 [SMILES: CN(CCCNc1cc(-c2ccccc2Cl)nc2c(Br)cnn12)Cc1ccccc1Cl] | 1. 8320<br>2. 519.782 |
| 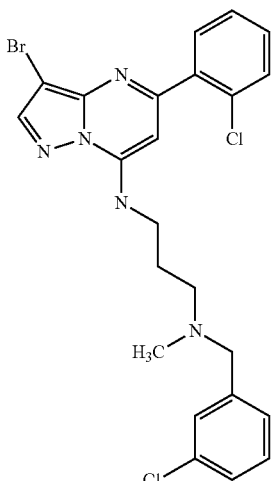 | 1. 8321<br>2. 519.783 |
| 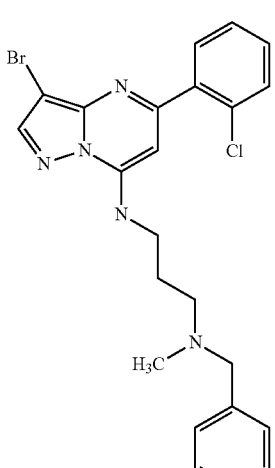 | 1. 8322<br>2. 519.781 |
TABLE 83-continued
| Product | 1. Ex.<br>2. m/z |
|---|---|
| 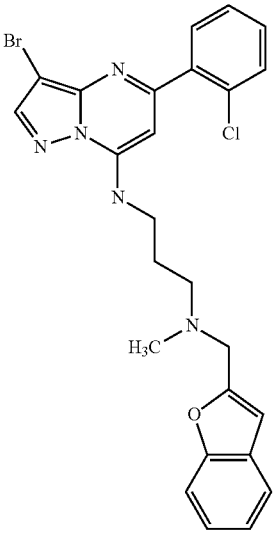 [SMILES: CN(CCCNc1cc(-c2ccccc2Cl)nc2c(Br)cnn12)Cc1cc2ccccc2o1] | 1. 8323<br>2. 525.813 |
| 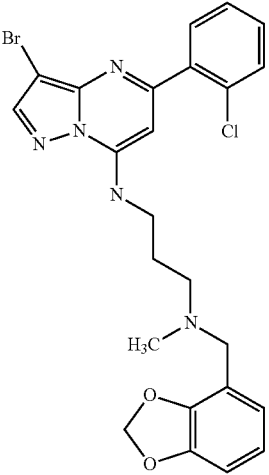 [SMILES: CN(CCCNc1cc(-c2ccccc2Cl)nc2c(Br)cnn12)Cc1cccc2c1OCO2] | 1. 8324<br>2. 529.806 |
| 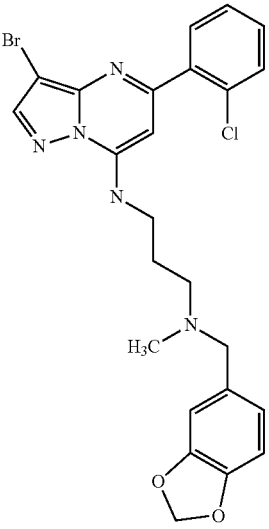 [SMILES: CN(CCCNc1cc(-c2ccccc2Cl)nc2c(Br)cnn12)Cc1ccc2c(c1)OCO2] | 1. 8325<br>2. 529.81 |

TABLE 83-continued
| Product | 1. Ex. 2. m/z |
|---|---|
| 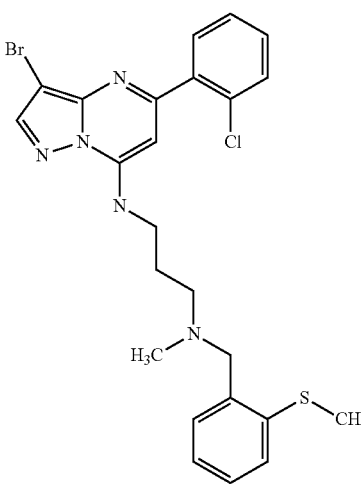 | 1. 8326  2. 531.804 |
| 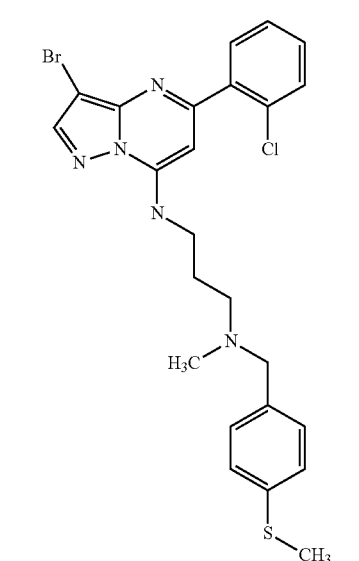 [SMILES: CSc1ccc(CN(C)CCCNc2cc(-c3ccccc3Cl)nc3c(Br)cnn23)cc1] | 1. 8327  2. 531.812 |
| 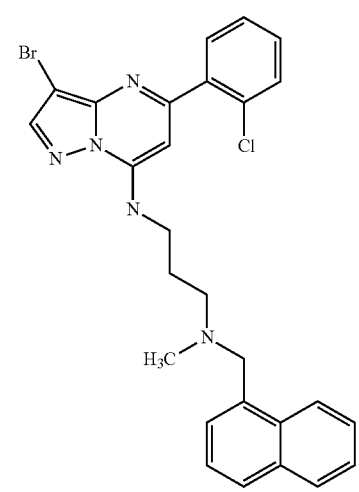 [SMILES: CN(CCCNc1cc(-c2ccccc2Cl)nc2c(Br)cnn12)Cc1cccc2ccccc12] | 1. 8328  2. 535.83 |
TABLE 83-continued
| Product | 1. Ex. 2. m/z |
|---|---|
| 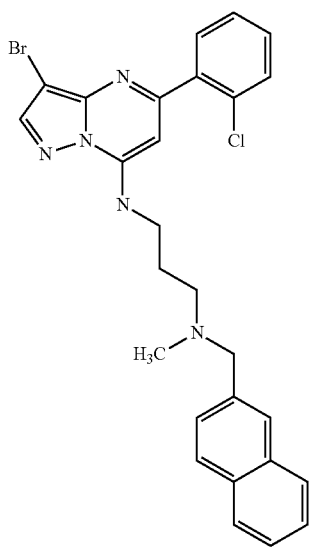 | 1. 8329  2. 535.831 |
| 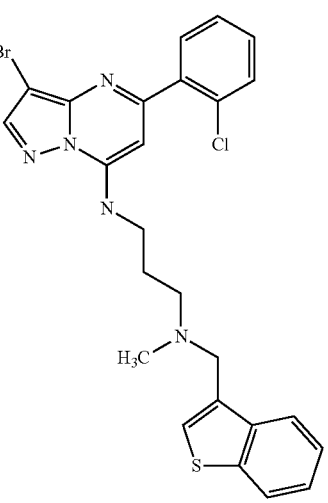 | 1. 8330  2. 541.788 |

TABLE 83-continued

| Product | 1. Ex.<br>2. m/z |
|---|---|
| (structure) | 1. 8331<br>2. 543.821 |
| (structure) | 1. 8332<br>2. 553.797 |

TABLE 83-continued

| Product | 1. Ex.<br>2. m/z |
|---|---|
| (structure) | 1. 8333<br>2. 553.796 |
| (structure) | 1. 8334<br>2. 553.795 |

TABLE 83-continued

| Product | 1. Ex. 2. m/z |
|---|---|
| (structure) | 1. 8335  2. 554.73 |
| (structure) | 1. 8336  2. 554.727 |
| (structure) | 1. 8337  2. 554.738 |
| (structure) | 1. 8338  2. 554.738 |
| (structure) | 1. 8339  2. 554.727 |
| (structure) | 1. 8340  2. 561.836 |

TABLE 83-continued

| Product | 1. Ex.<br>2. m/z |
|---|---|
| (structure) | 1. 8341<br>2. 561.838 |
| (structure) | 1. 8342<br>2. 564.714 |
| (structure) | 1. 8343<br>2. 564.704 |
| (structure) | 1. 8344<br>2. 564.72 |
| (structure) | 1. 8345<br>2. 573.823 |

TABLE 83-continued

| Product | 1. Ex.<br>2. m/z |
|---|---|
| (structure: 3-bromo-5-(2-chlorophenyl)pyrazolo[1,5-a]pyrimidin-7-yl with N-(3-(N-methyl-N-((5-(thiophen-2-yl)thiophen-2-yl)methyl)amino)propyl)amine) | 1. 8346<br>2. 573.735 |
| (structure: 3-bromo-5-(2-chlorophenyl)pyrazolo[1,5-a]pyrimidin-7-yl with N-(3-(N-methyl-N-(2,2-diphenylethyl)amino)propyl)amine) | 1. 8347<br>2. 575.839 |
| (structure: 3-bromo-5-(2-chlorophenyl)pyrazolo[1,5-a]pyrimidin-7-yl with N-(3-(N-methyl-N-(3-phenoxybenzyl)amino)propyl)amine) | 1. 8348<br>2. 577.818 |
| (structure: 3-bromo-5-(2-chlorophenyl)pyrazolo[1,5-a]pyrimidin-7-yl with N-(3-(N-methyl-N-(4-phenoxybenzyl)amino)propyl)amine) | 1. 8349<br>2. 577.814 |

TABLE 83-continued

| Product | 1. Ex. 2. m/z |
|---|---|
| (structure: 3-bromo-5-(2-chlorophenyl)pyrazolo[1,5-a]pyrimidin-7-yl amine with N-(3-(N-methyl-N-(4-(phenylethynyl)benzyl)amino)propyl) linker) | 1. 9350 2. 585.818 |
| (structure: 3-bromo-5-(2-chlorophenyl)pyrazolo[1,5-a]pyrimidin-7-yl amine with N-(3-(N-methyl-N-(2-carboxybenzyl)amino)propyl) linker) | 1. 8351 2. 529.808 |

TABLE 83-continued

| Product | 1. Ex. 2. m/z |
|---|---|
| (structure: 3-bromo-5-(2-chlorophenyl)pyrazolo[1,5-a]pyrimidin-7-yl amine with N-(3-(N-methyl-N-((1-(phenylsulfonyl)-1H-pyrrol-2-yl)methyl)amino)propyl) linker) | 1. 8352 2. 614.763 |
| (structure: 3-bromo-5-(2-chlorophenyl)pyrazolo[1,5-a]pyrimidin-7-yl amine with N-(3-(N-methyl-N-(2-((4-chlorophenyl)thio)benzyl)amino)propyl) linker) | 1. 8353 2. 628.727 |
| (structure: 3-bromo-5-(2-chlorophenyl)pyrazolo[1,5-a]pyrimidin-7-yl amine with N-(3-(N-methyl-N-cyclobutylamino)propyl) linker) | 1. 8354 2. 449.857 |

TABLE 83-continued
| Product | 1. Ex. 2. m/z |
|---|---|
| 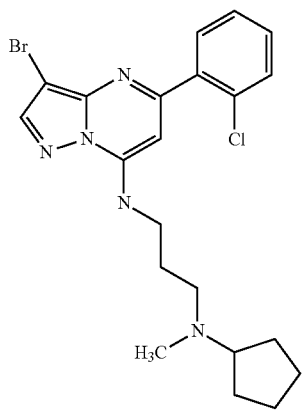 [SMILES: CN(CCCNc1cc(-c2ccccc2Cl)nc2c(Br)cnn12)C1CCCC1] | 1. 8355 2. 463.867 |
| 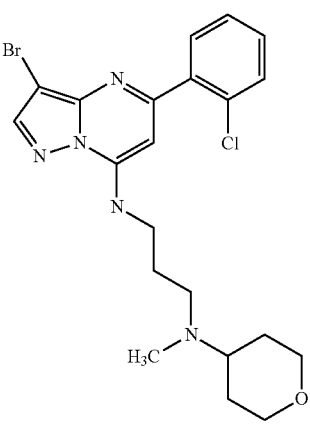 [SMILES: CN(CCCNc1cc(-c2ccccc2Cl)nc2c(Br)cnn12)C1CCOCC1] | 1. 8356 2. 479.856 |
| 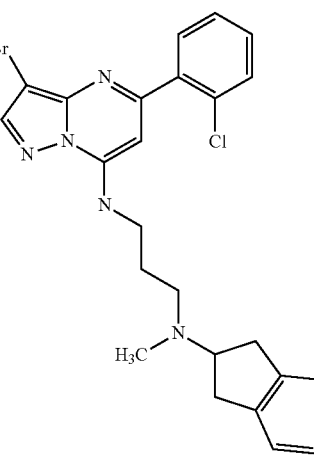 | 1. 8357 2. 511.842 |
TABLE 83-continued
| Product | 1. Ex. 2. m/z |
|---|---|
| 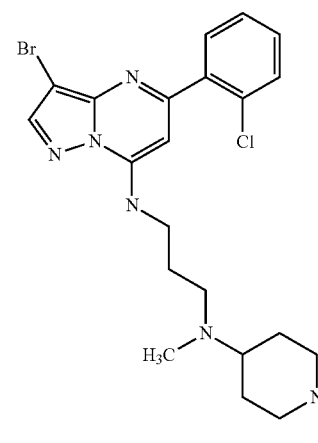 | 1. 8358 2. 520.859 |
| 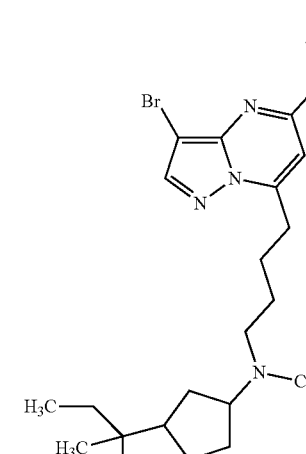 | 1. 8359 2. 533.903 |
| 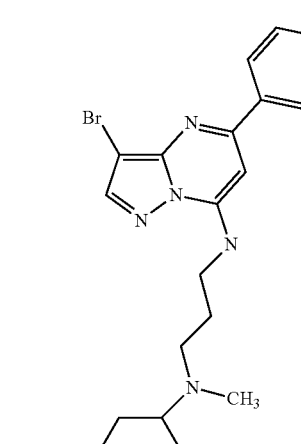 | 1. 8360 2. 545.823 |

TABLE 83-continued
| Product | 1. Ex. 2. m/z |
|---|---|
| 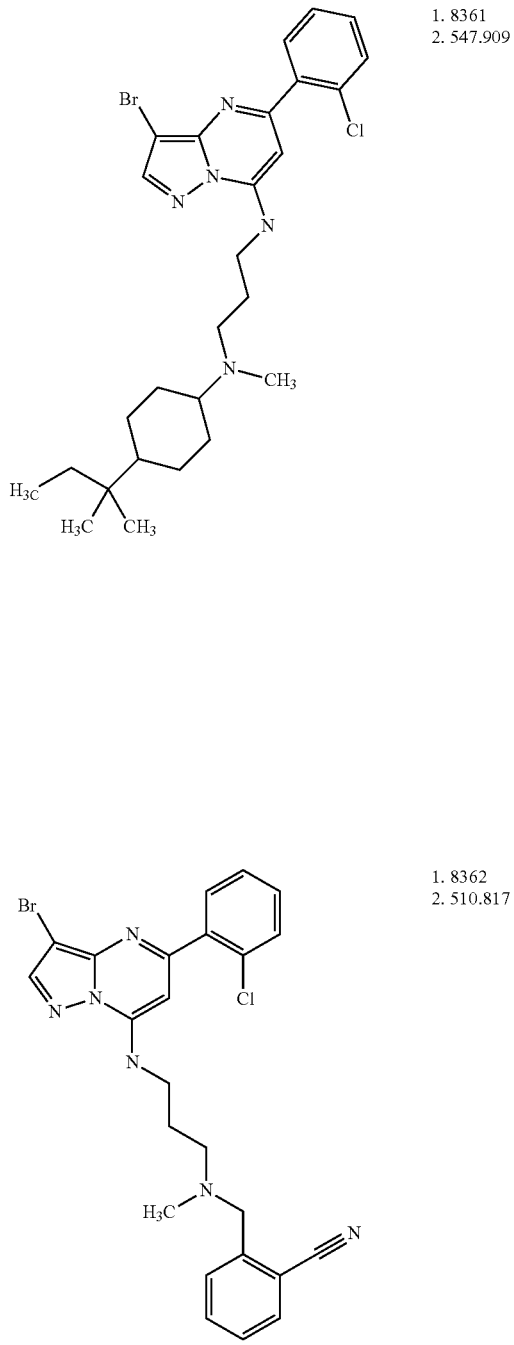 | 1. 8361<br>2. 547.909 |
| | 1. 8362<br>2. 510.817 |
TABLE 83-continued
| Product | 1. Ex. 2. m/z |
|---|---|
| 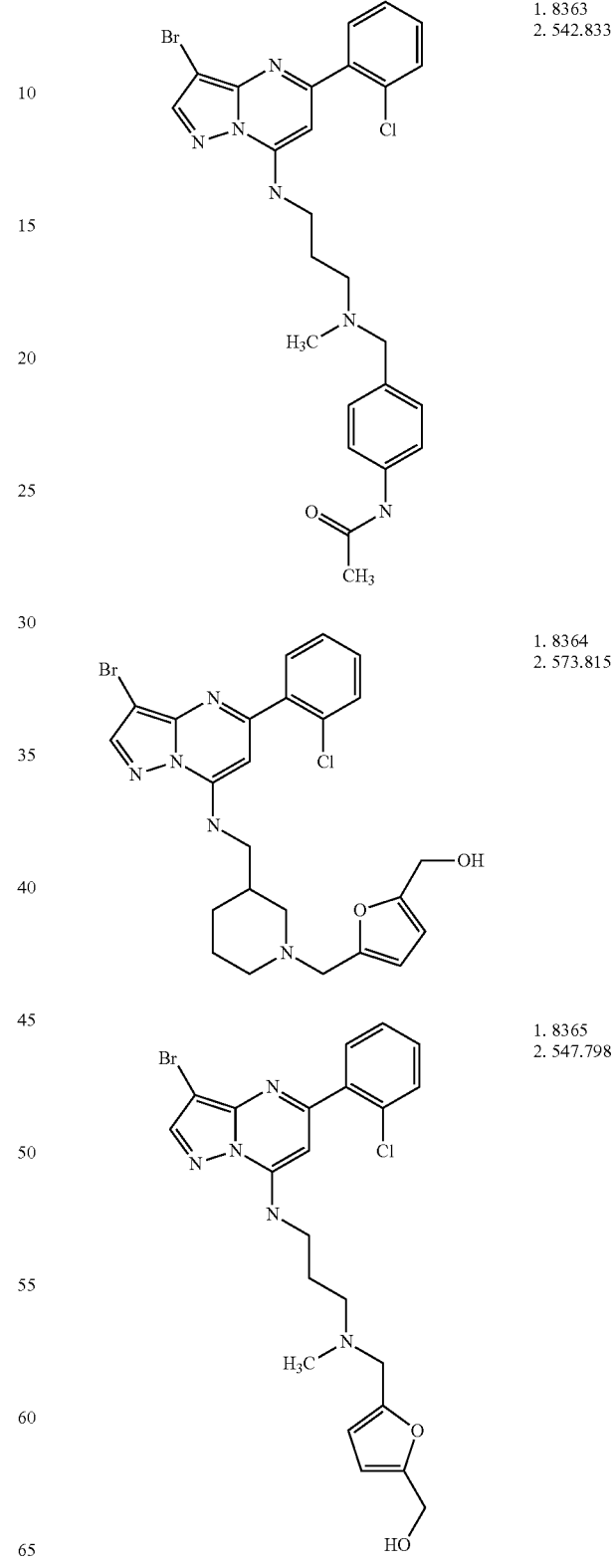 | 1. 8363<br>2. 542.833 |
| | 1. 8364<br>2. 573.815 |
| | 1. 8365<br>2. 547.798 |

TABLE 84
| Product | 1. Ex.<br>2. m/z |
|---|---|
| 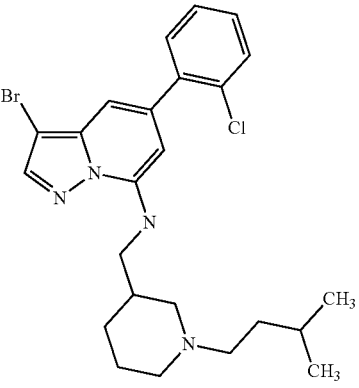 [SMILES: CC(C)CCN1CCCC(CNc2cc(-c3ccccc3Cl)cc3c(Br)cnn23)C1] | 1. 8401<br>2. 491.883 |
| 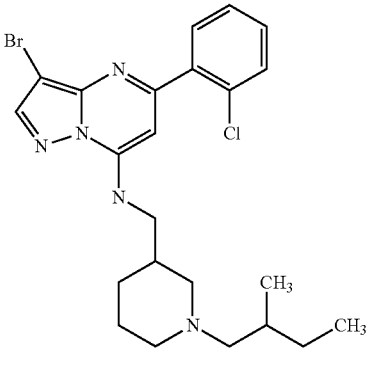 [SMILES: CCC(C)CN1CCCC(CNc2cc(-c3ccccc3Cl)nc3c(Br)cnn23)C1] | 1. 8402<br>2. 491.883 |
| 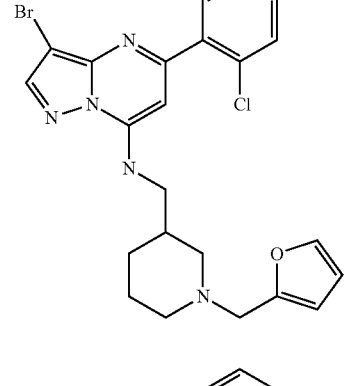 | 1. 8403<br>2. 501.823 |
| 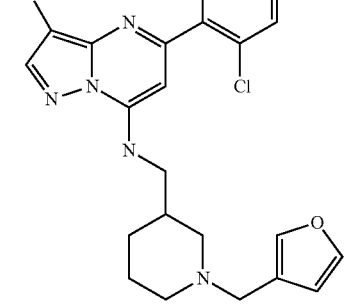 | 1. 8404<br>2. 501.827 |
TABLE 84-continued
| Product | 1. Ex.<br>2. m/z |
|---|---|
| 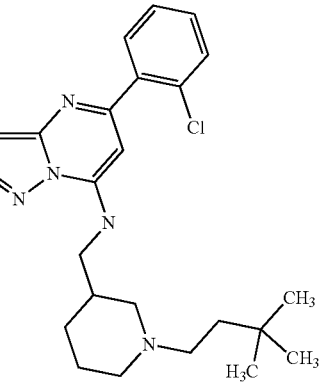 | 1. 8405<br>2. 505.89 |
| 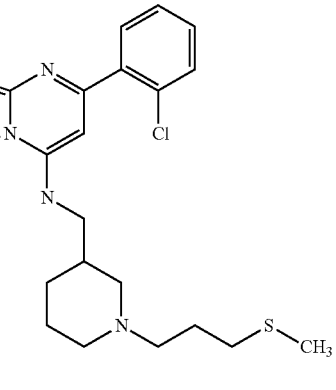 | 1. 8406<br>2. 509.829 |
| 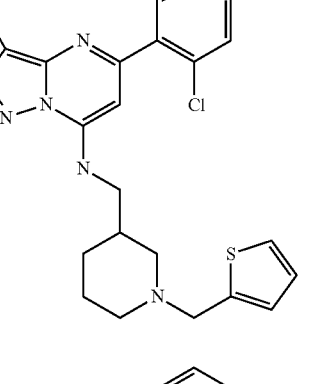 | 1. 8407<br>2. 517.795 |
| 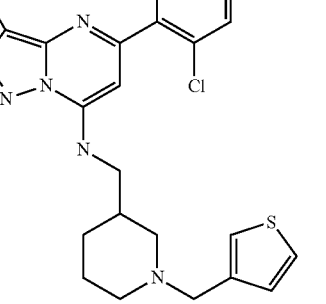 | 1. 8408<br>2. 517.799 |

TABLE 84-continued
| Product | 1. Ex.<br>2. m/z |
|---|---|
| 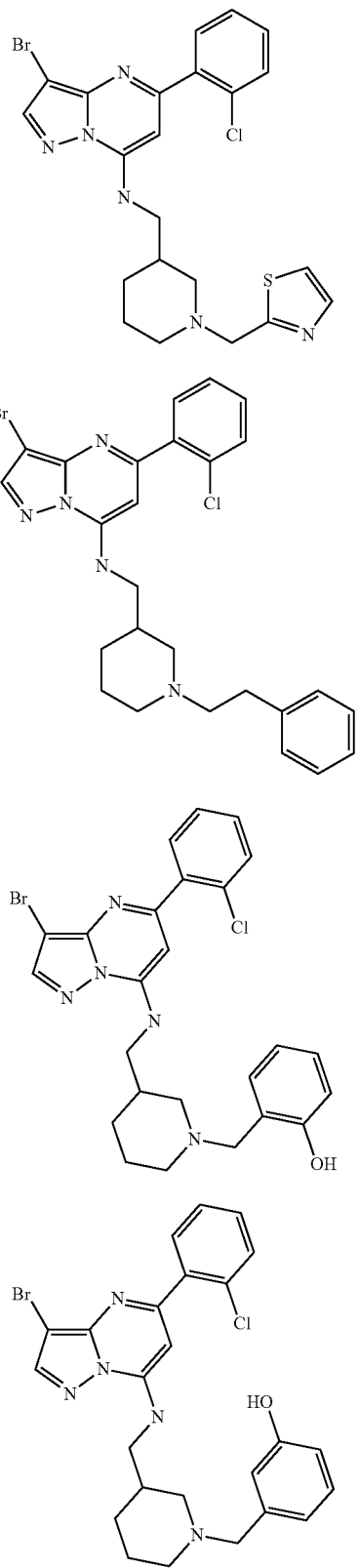 | 1. 8409<br>2. 518.796 |
| | 1. 8410<br>2. 525.851 |
| | 1. 8411<br>2. 527.831 |
| | 1. 8412<br>2. 527.833 |
TABLE 84-continued
| Product | 1. Ex.<br>2. m/z |
|---|---|
| 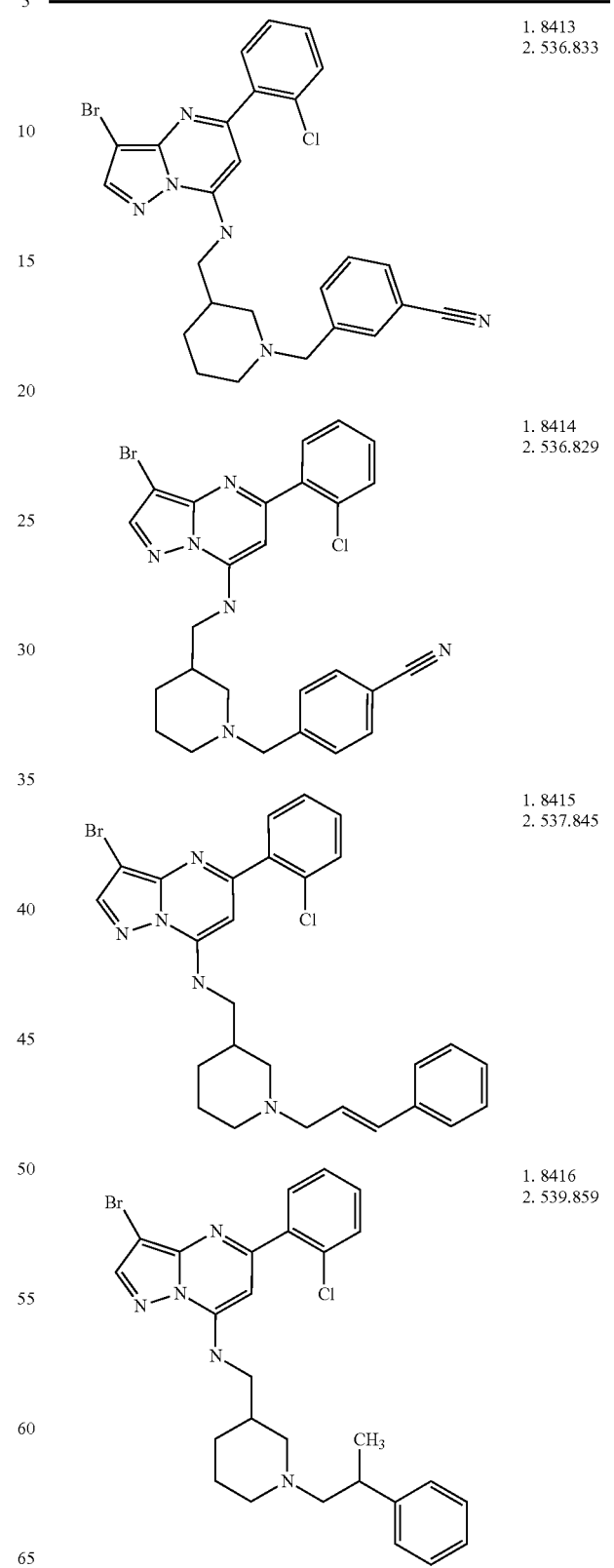 | 1. 8413<br>2. 536.833 |
| | 1. 8414<br>2. 536.829 |
| | 1. 8415<br>2. 537.845 |
| | 1. 8416<br>2. 539.859 |

TABLE 84-continued
| Product | 1. Ex. 2. m/z |
|---|---|
| 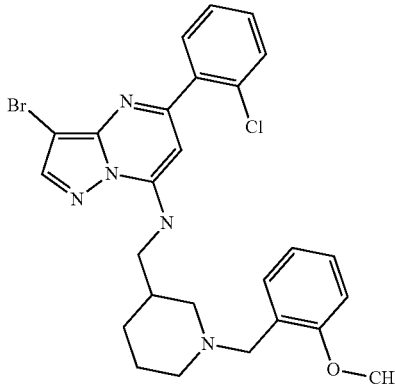 | 1. 8417 2. 541.84 |
| 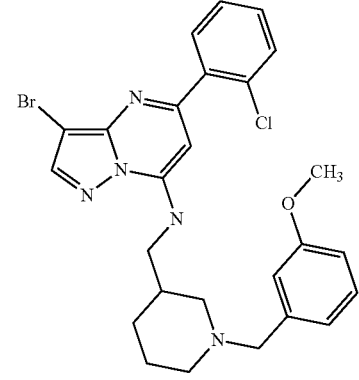 [SMILES: COc1cccc(CN2CCCC(CNc3cc(-c4ccccc4Cl)nc4c(Br)cnn34)C2)c1] | 1. 8418 2. 541.843 |
| 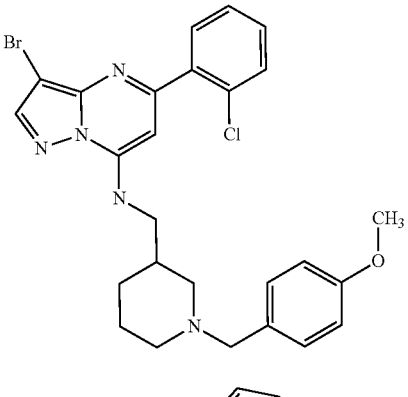 | 1. 8419 2. 541.843 |
| 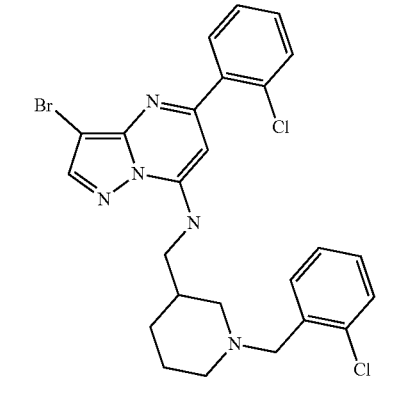 [SMILES: Clc1ccccc1CN1CCCC(CNc2cc(-c3ccccc3Cl)nc3c(Br)cnn23)C1] | 1. 8420 2. 546.786 |
TABLE 84-continued
| Product | 1. Ex. 2. m/z |
|---|---|
| 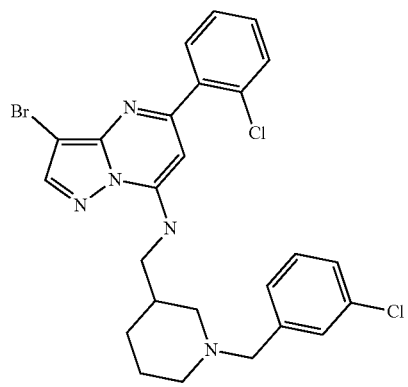 [SMILES: Clc1cccc(CN2CCCC(CNc3cc(-c4ccccc4Cl)nc4c(Br)cnn34)C2)c1] | 1. 8421 2. 546.792 |
| 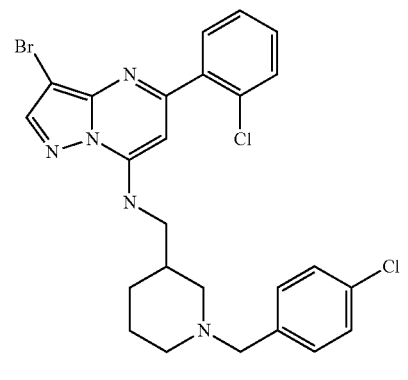 | 1. 8422 2. 546.79 |
| 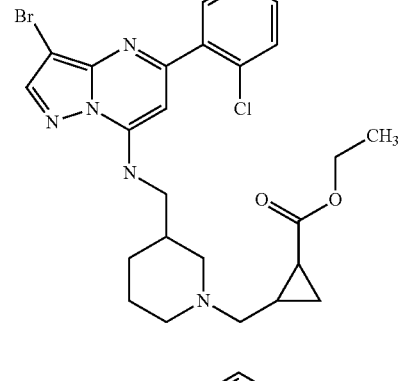 | 1. 8423 2. 547.854 |
| 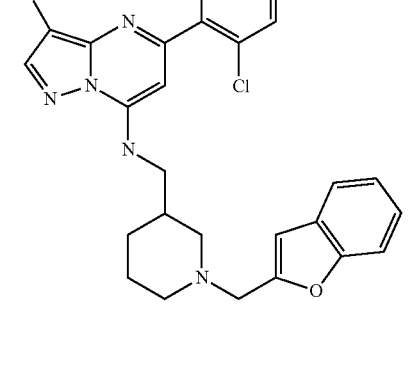 | 1. 8424 2. 551.826 |

TABLE 84-continued
| Product | 1. Ex. 2. m/z |
|---|---|
| 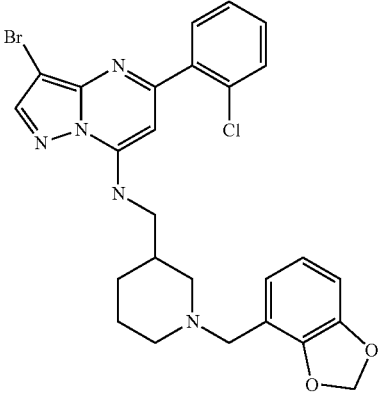 [SMILES: Clc1ccccc1-c1cc(NCC2CCCN(Cc3cccc4c3OCO4)C2)n2ncc(Br)c2n1] | 1. 8425  2. 555.819 |
| 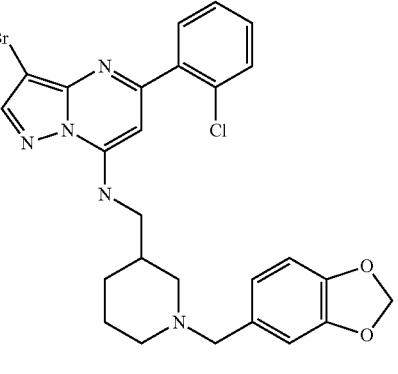 | 1. 8426  2. 555.817 |
| 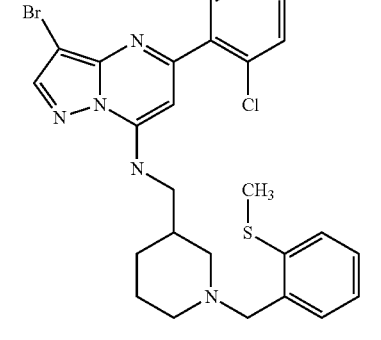 | 1. 8427  2. 557.81 |
| 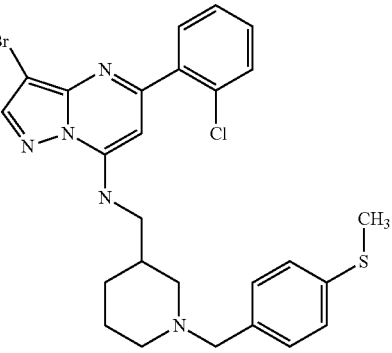 | 1. 8428  2. 557.813 |
| 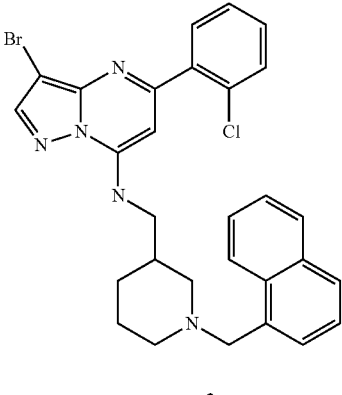 | 1. 8429  2. 561.839 |
| 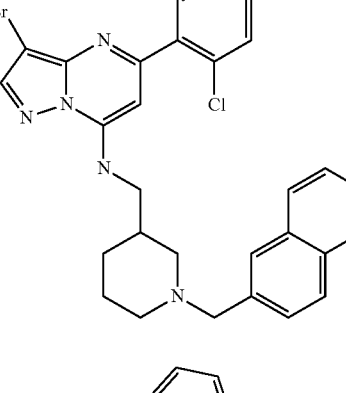 | 1. 8430  2. 561.833 |
| 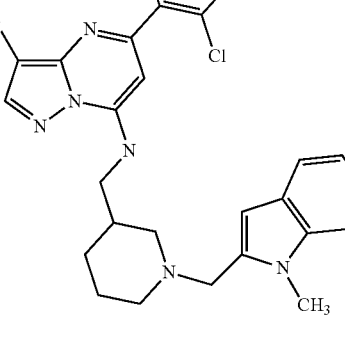 | 1. 8431  2. 564.841 |
| 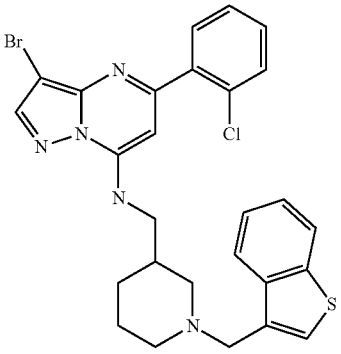 [SMILES: Clc1ccccc1-c1cc(NCC2CCCN(Cc3csc4ccccc34)C2)n2ncc(Br)c2n1] | 1. 8432  2. 567.795 |

TABLE 84-continued
| Product | 1. Ex.<br>2. m/z |
|---|---|
| 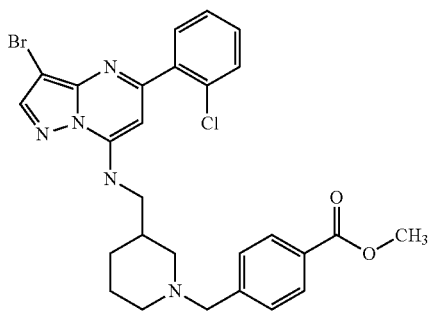 [SMILES: COC(=O)c1ccc(CN2CCCC(CNc3cc(-c4ccccc4Cl)nc4c(Br)cnn34)C2)cc1] | 1. 8433<br>2. 569.823 |
| 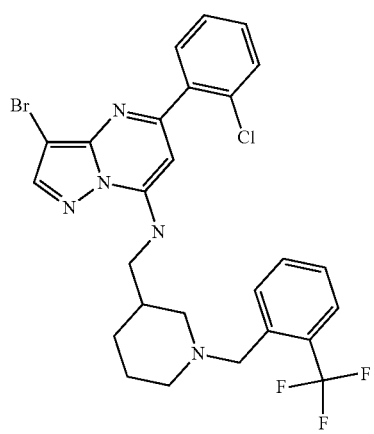 [SMILES: FC(F)(F)c1ccccc1CN1CCCC(CNc2cc(-c3ccccc3Cl)nc3c(Br)cnn23)C1] | 1. 8434<br>2. 579.797 |
| 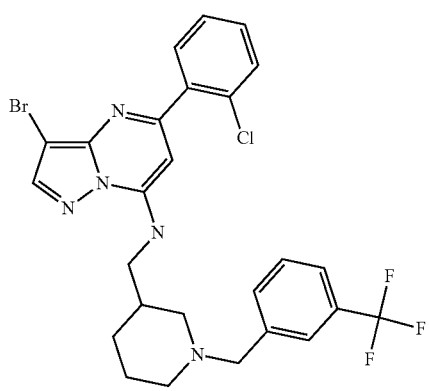 [SMILES: FC(F)(F)c1cccc(CN2CCCC(CNc3cc(-c4ccccc4Cl)nc4c(Br)cnn34)C2)c1] | 1. 8435<br>2. 579.796 |
| 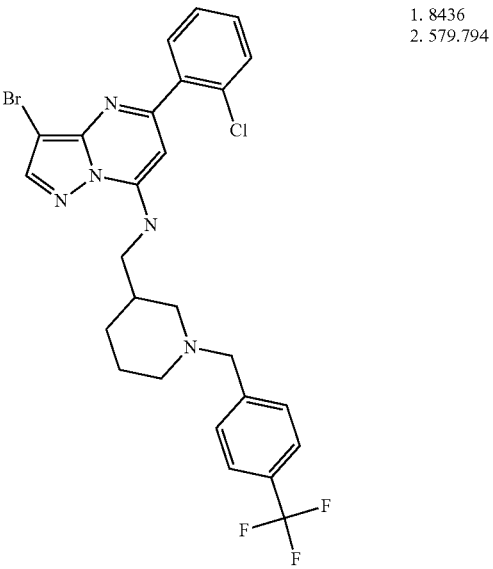 | 1. 8436<br>2. 579.794 |
| 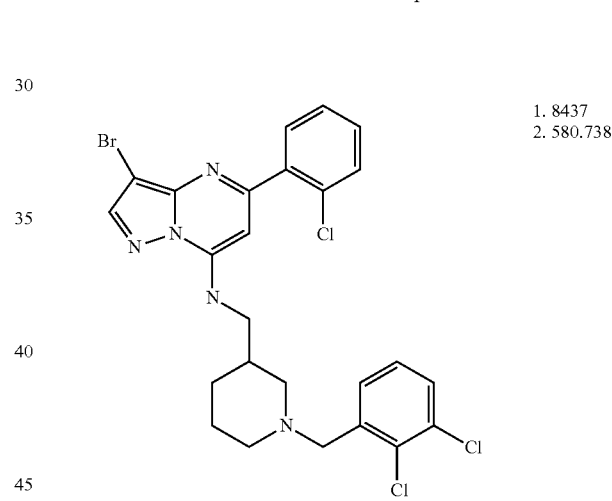 | 1. 8437<br>2. 580.738 |
| 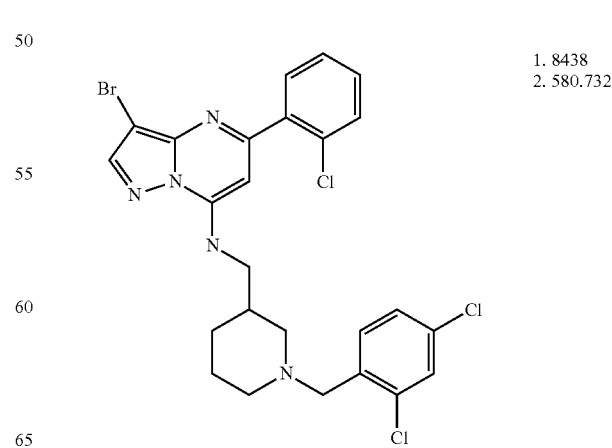 | 1. 8438<br>2. 580.732 |

TABLE 84-continued
| Product | 1. Ex. 2. m/z |
|---|---|
| 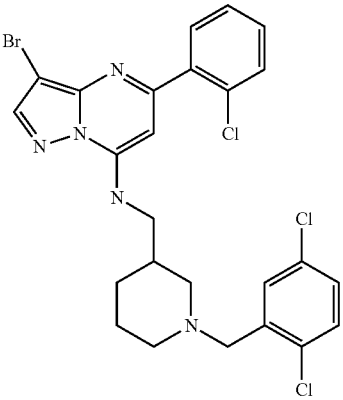 [SMILES: Clc1ccc(Cl)c(CN2CCCC(CNc3cc(-c4ccccc4Cl)nc4c(Br)cnn34)C2)c1] | 1. 8439 2. 580.733 |
| 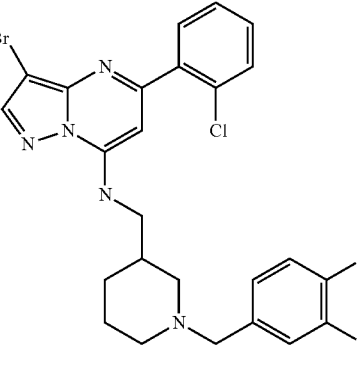 | 1. 8440 2. 580.734 |
| 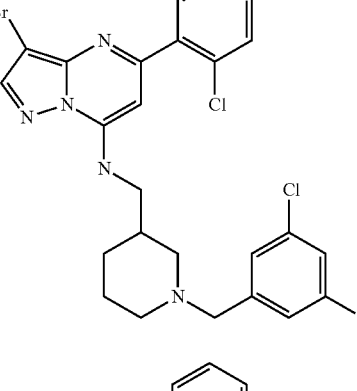 | 1. 8441 2. 580.726 |
| 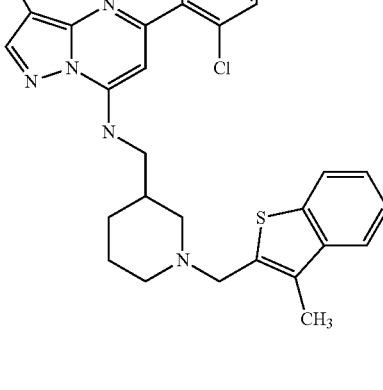 | 1. 8442 2. 581.805 |
| 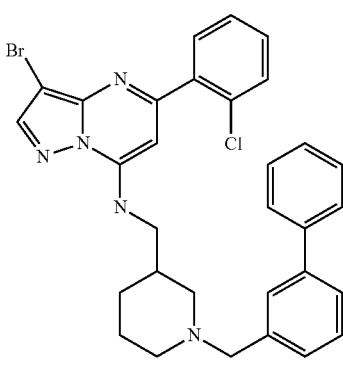 [SMILES: Clc1ccccc1-c1cc(NCC2CCCN(Cc3cccc(-c4ccccc4)c3)C2)n2ncc(Br)c2n1] | 1. 8443 2. 587.844 |
| 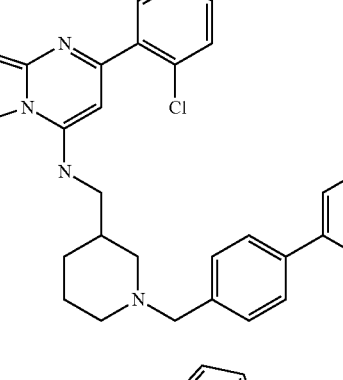 | 1. 8444 2. 587.835 |
| 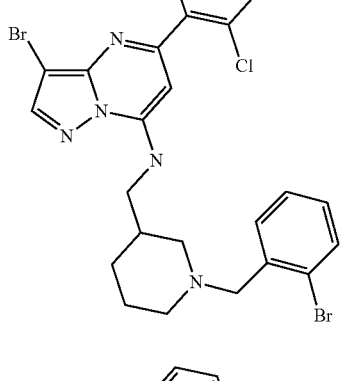 | 1. 8445 2. 590.723 |
| 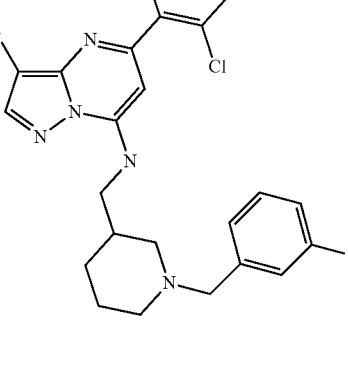 | 1. 8446 2. 590.726 |

TABLE 84-continued
| Product | 1. Ex.<br>2. m/z |
|---|---|
| 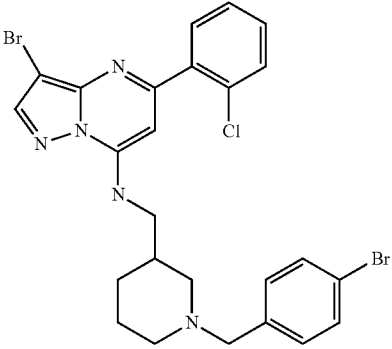 [SMILES: Clc1ccccc1-c1cc(NCC2CCCN(Cc3ccc(Br)cc3)C2)n2ncc(Br)c2n1] | 1. 8447<br>2. 590.724 |
| 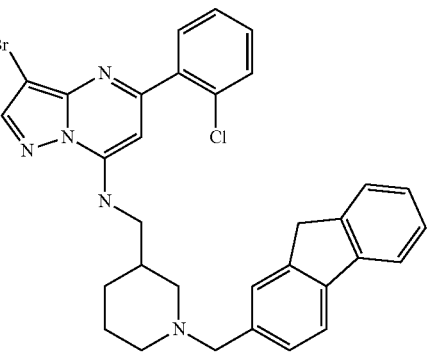 | 1. 8448<br>2. 599.834 |
| 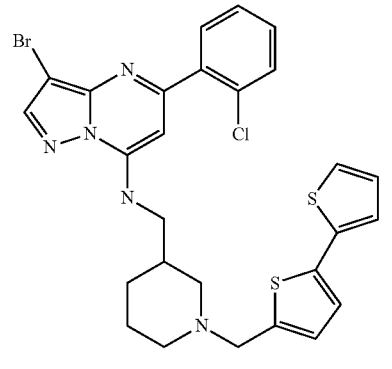 [SMILES: Clc1ccccc1-c1cc(NCC2CCCN(Cc3ccc(-c4cccs4)s3)C2)n2ncc(Br)c2n1] | 1. 8449<br>2. 599.749 |
| 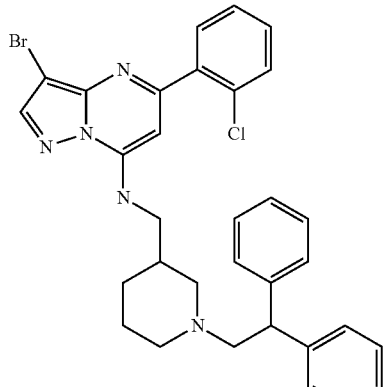 | 1. 8450<br>2. 601.854 |
TABLE 84-continued
| Product | 1. Ex.<br>2. m/z |
|---|---|
| 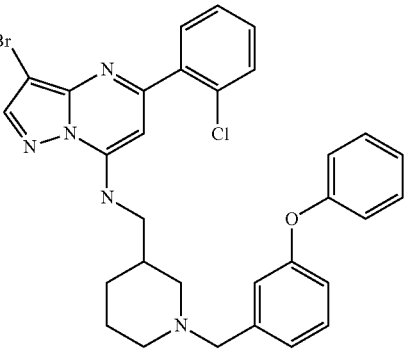 | 1. 8451<br>2. 603.831 |
| 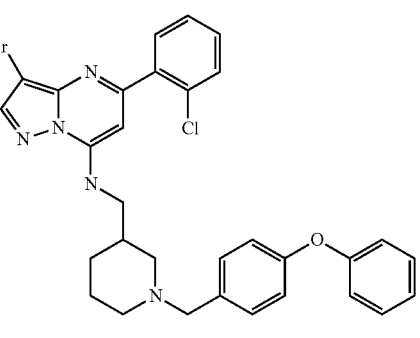 | 1. 8452<br>2. 603.83 |
| 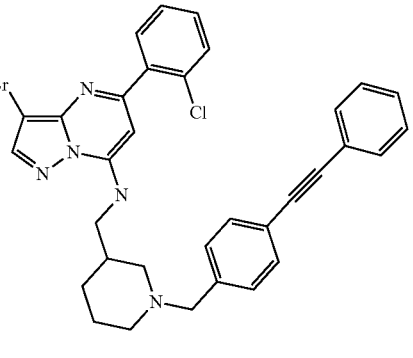 | 1. 8453<br>2. 611.83 |
| 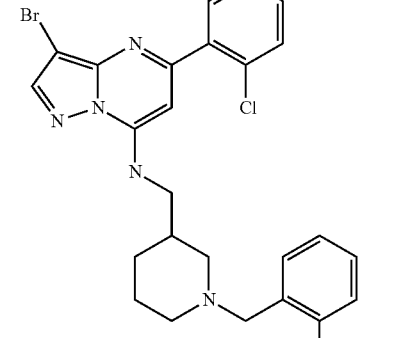 | 1. 8454<br>2. 555.824 |

TABLE 84-continued
| Product | 1. Ex. 2. m/z |
|---|---|
| 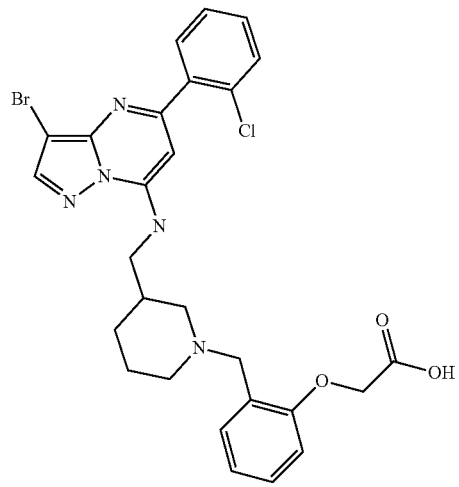 [SMILES: O=C(O)COc1ccccc1CN1CCCC(CNc2cc(-c3ccccc3Cl)nc3c(Br)cnn23)C1] | 1. 8455 2. 585.817 |
| 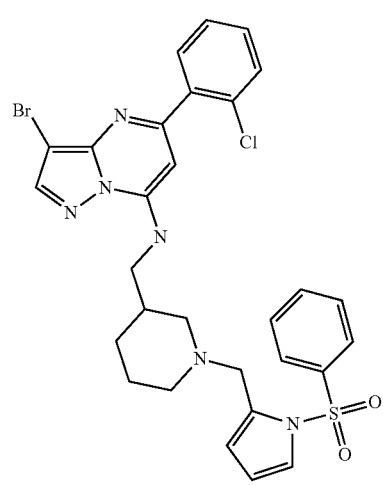 [SMILES: O=S(=O)(c1ccccc1)n1cccc1CN1CCCC(CNc2cc(-c3ccccc3Cl)nc3c(Br)cnn23)C1] | 1. 8456 2. 640.779 |
| 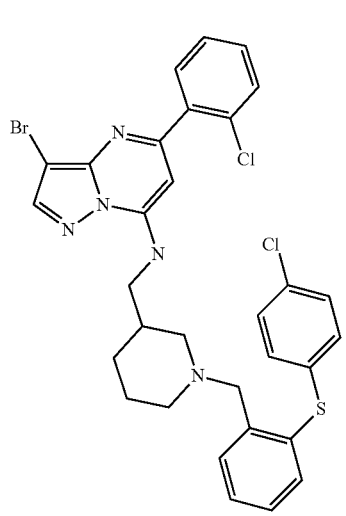 [SMILES: Clc1ccc(Sc2ccccc2CN2CCCC(CNc3cc(-c4ccccc4Cl)nc4c(Br)cnn34)C2)cc1] | 1. 8457 2. 654.746 |
TABLE 84-continued
| Product | 1. Ex. 2. m/z |
|---|---|
| 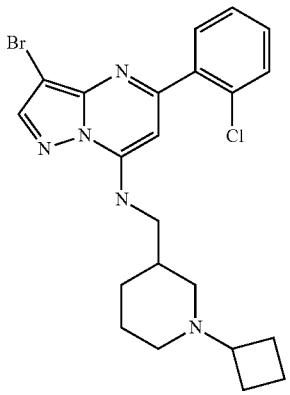 [SMILES: Clc1ccccc1-c1cc(NCC2CCCN(C3CCC3)C2)n2ncc(Br)c2n1] | 1. 8458 2. 475.871 |
| 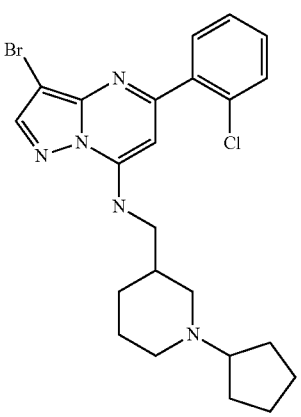 [SMILES: Clc1ccccc1-c1cc(NCC2CCCN(C3CCCC3)C2)n2ncc(Br)c2n1] | 1. 8459 2. 489.879 |
| 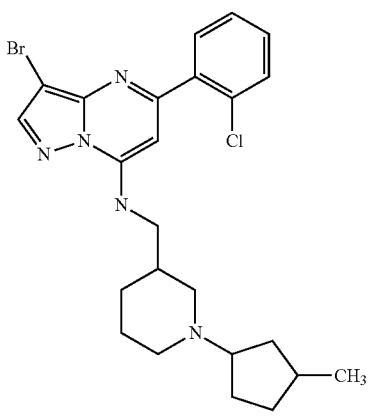 [SMILES: CC1CCC(N2CCCC(CNc3cc(-c4ccccc4Cl)nc4c(Br)cnn34)C2)C1] | 1. 8460 2. 503.885 |

TABLE 84-continued
| Product | 1. Ex.<br>2. m/z |
|---|---|
| 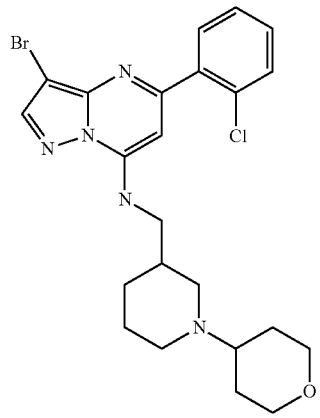 [SMILES: Clc1ccccc1-c1cc(NCC2CCCN(C3CCOCC3)C2)n2ncc(Br)c2n1] | 1. 8461<br>2. 505.866 |
| (structure) | 1. 8462<br>2. 507.828 |
| (structure) | 1. 8463<br>2. 537.859 |
TABLE 84-continued
| Product | 1. Ex.<br>2. m/z |
|---|---|
| 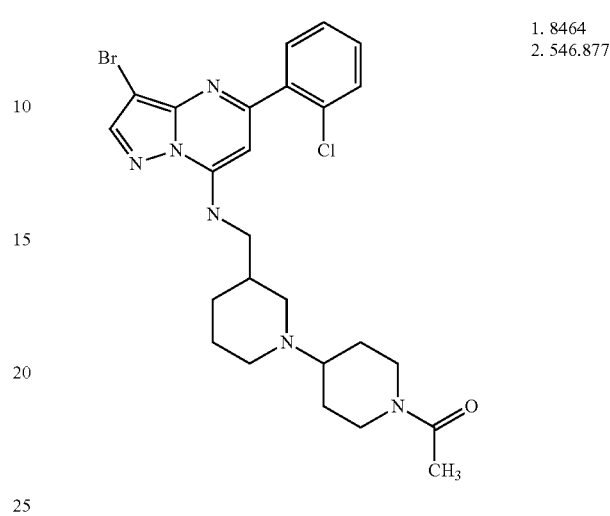 | 1. 8464<br>2. 546.877 |
| 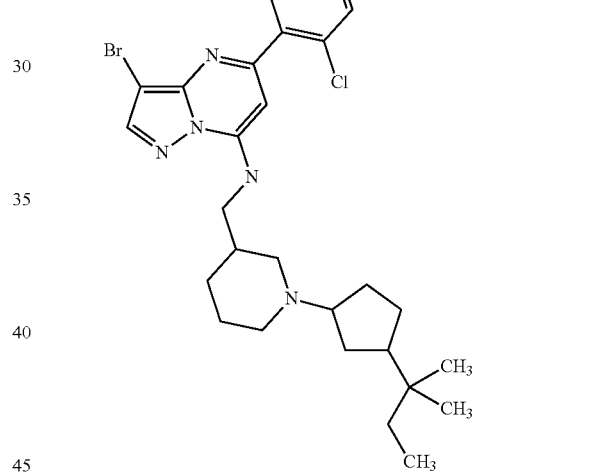 | 1. 8465<br>2. 559.921 |
| 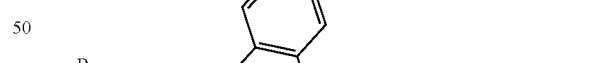 | 1. 8466<br>2. 559.919 |

TABLE 84-continued

| Product | 1. Ex.<br>2. m/z |
|---|---|
| (structure) | 1. 8467<br>2. 573.925 |
| (structure) | 1. 8468<br>2. 579.876 |
| (structure) | 1. 8469<br>2. 536.831 |

TABLE 84-continued

| Product | 1. Ex.<br>2. m/z |
|---|---|
| (structure) | 1. 8470<br>2. 568.843 |

TABLE 85

| Product | 1. Ex.<br>2. m/z |
|---|---|
| (structure) | 1. 8501<br>2. 367.2 |
| (structure) | 1. 8502<br>2. 381.2 |
| (structure) | 1. 8503<br>2. 443.2 |

TABLE 85-continued

| Product | 1. Ex. 2. m/z |
|---|---|
| (structure) | 1. 8504 2. 457.3 |
| (structure) | 1. 8506 2. 443.1 |
| (structure) | 1. 8507 2. 323.1 |
| (structure) | 1. 8508 2. 365.2 |
| (structure) | 1. 8509 2. 379.21 |
| (structure) | 1. 8510 2. 381.21 |
| (structure) | 1. 8511 2. 381.21 |
| (structure) | 1. 8512 2. 393.22 |
| (structure) | 1. 8513 2. 395.22 |

TABLE 85-continued
| Product | 1. Ex. 2. m/z |
|---|---|
| 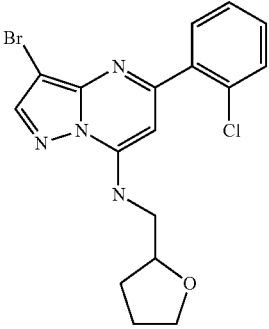 [SMILES: Clc1ccccc1-c1cc(NCC2CCCO2)n2ncc(Br)c2n1] | 1. 8514 2. 397.22 |
| 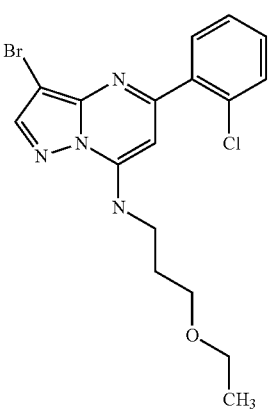 [SMILES: CCOCCCNc1cc(-c2ccccc2Cl)nc2c(Br)cnn12] | 1. 8515 2. 407.22 |
| 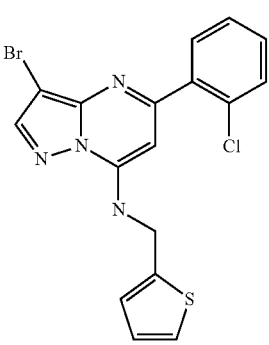 [SMILES: Clc1ccccc1-c1cc(NCc2cccs2)n2ncc(Br)c2n1] | 1. 8516 2. 409.22 |
| 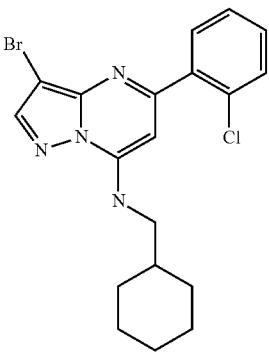 [SMILES: Clc1ccccc1-c1cc(NCC2CCCCC2)n2ncc(Br)c2n1] | 1. 8517 2. 411.23 |
| 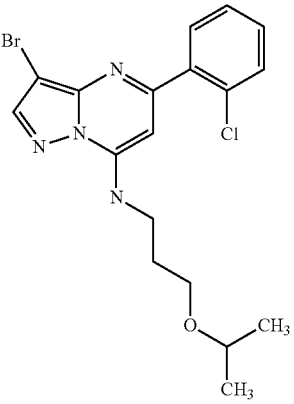 [SMILES: CC(C)OCCCNc1cc(-c2ccccc2Cl)nc2c(Br)cnn12] | 1. 8518 2. 421.23 |
| 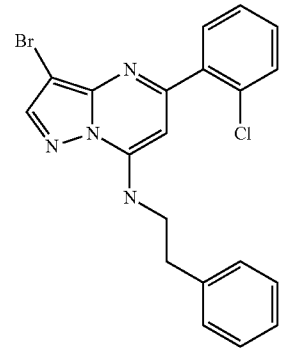 [SMILES: Clc1ccccc1-c1cc(NCCc2ccccc2)n2ncc(Br)c2n1] | 1. 8519 2. 421.23 |
| 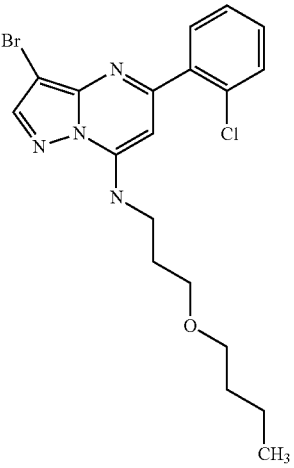 [SMILES: CCCCOCCCNc1cc(-c2ccccc2Cl)nc2c(Br)cnn12] | 1. 8520 2. 425.23 |
| 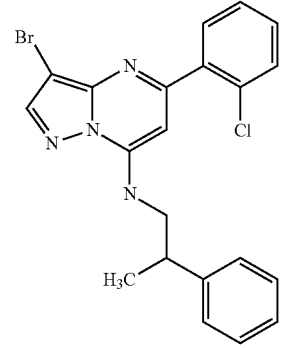 [SMILES: CC(CNc1cc(-c2ccccc2Cl)nc2c(Br)cnn12)c1ccccc1] | 1. 8521 2. 429.24 |

TABLE 85-continued
| Product | 1. Ex.<br>2. m/z |
|---|---|
| 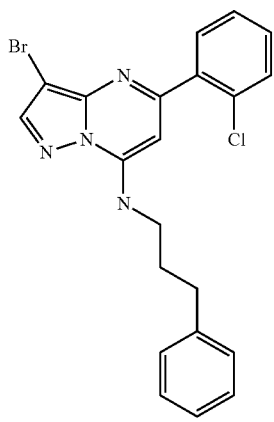 [SMILES: Clc1ccccc1-c1cc(NCCCc2ccccc2)n2ncc(Br)c2n1] | 1. 8522<br>2. 439.24 |
| 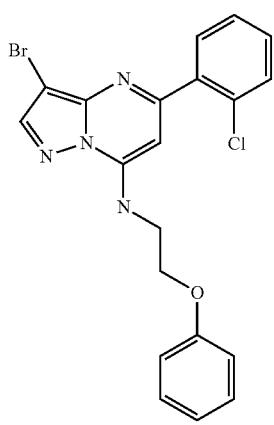 [SMILES: Clc1ccccc1-c1cc(NCCOc2ccccc2)n2ncc(Br)c2n1] | 1. 8523<br>2. 443.24 |
| 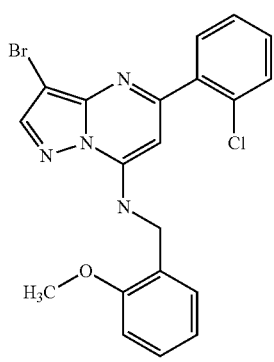 [SMILES: COc1ccccc1CNc1cc(-c2ccccc2Cl)nc2c(Br)cnn12] | 1. 8524<br>2. 443.24 |
TABLE 85-continued
| Product | 1. Ex.<br>2. m/z |
|---|---|
| | 1. 8525<br>2. 445.24 |
| | 1. 8526<br>2. 445.24 |
| | 1. 8527<br>2. 444.24 |

TABLE 85-continued
| Product | 1. Ex. 2. m/z |
|---|---|
| 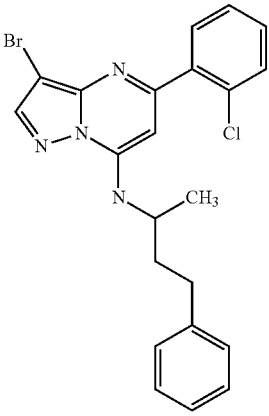 [SMILES: CC(CCc1ccccc1)Nc1cc(-c2ccccc2Cl)nc2c(Br)cnn12] | 1. 8528 2. 444.24 |
| 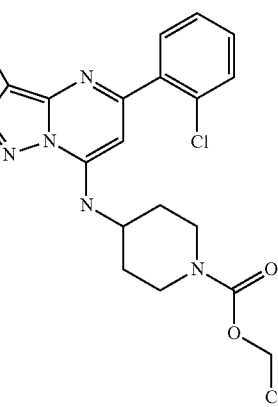 | 1. 8529 2. 446.25 |
| 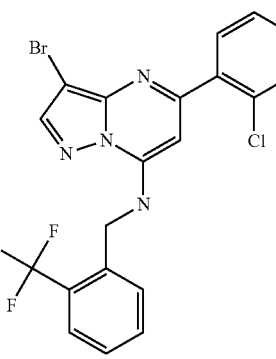 | 1. 8530 2. 457.25 |
TABLE 85-continued
| Product | 1. Ex. 2. m/z |
|---|---|
| 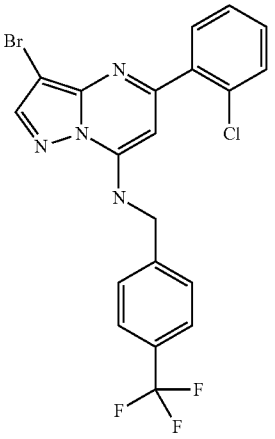 [SMILES: FC(F)(F)c1ccc(CNc2cc(-c3ccccc3Cl)nc3c(Br)cnn23)cc1] | 1. 8531 2. 480.26 |
| 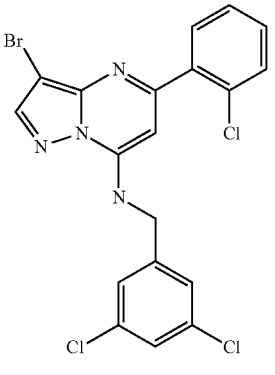 [SMILES: Clc1cc(Cl)cc(CNc2cc(-c3ccccc3Cl)nc3c(Br)cnn23)c1] | 1. 8532 2. 483.27 |
| 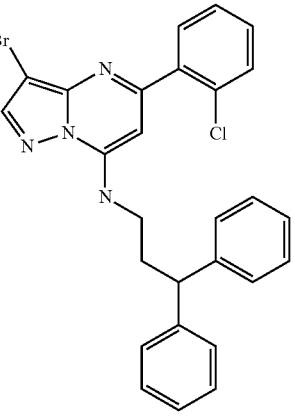 | 1. 8533 2. 483.27 |
| 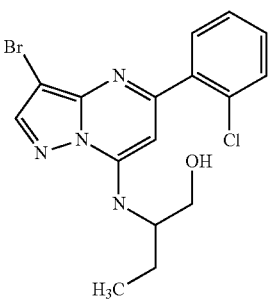 [SMILES: CCC(CO)Nc1cc(-c2ccccc2Cl)nc2c(Br)cnn12] | 1. 8536 2. 431.24 |

TABLE 85-continued
| Product | 1. Ex.<br>2. m/z |
|---|---|
| 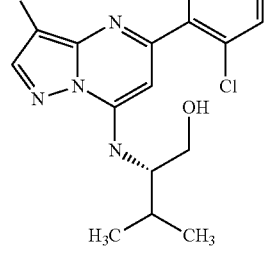 Chiral | 1. 8537<br>2. 429.24 |
| 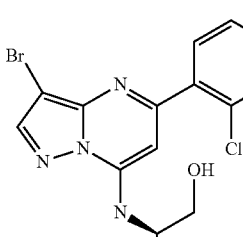 Chiral | 1. 8538<br>2. 397.22 |
| 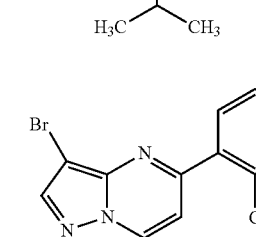 | 1. 8539<br>2. 411.23 |
| 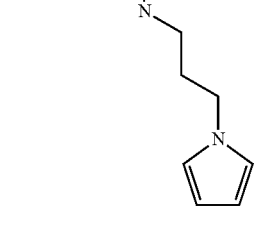 | 1. 8540<br>2. 411.23 |
| 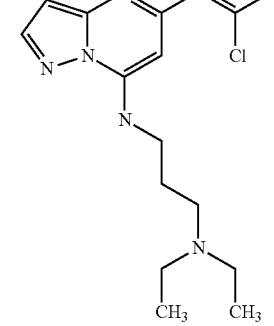 | 1. 8541<br>2. 432.24 |
| 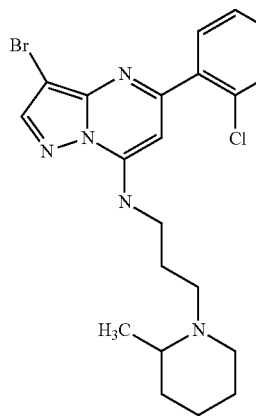 | 1. 8542<br>2. 433.24 |
| 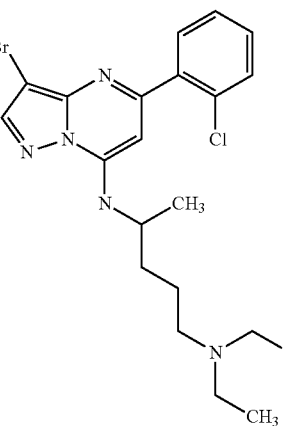 | 1. 8543<br>2. 438.24 |

TABLE 85-continued
| Product | 1. Ex.<br>2. m/z |
|---|---|
| 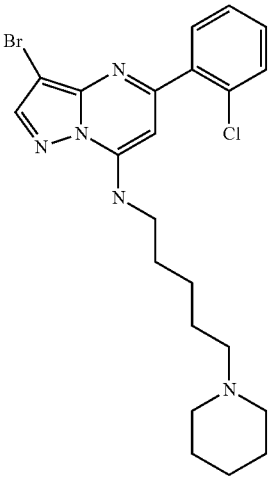 [SMILES: Clc1ccccc1-c1cc(NCCCCCN2CCCCC2)n2ncc(Br)c2n1] | 1. 8545<br>2. 464.26 |
| 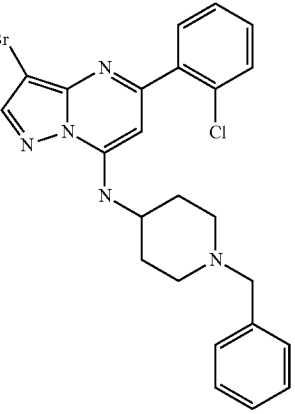 | 1. 8546<br>2. 466.26 |
| 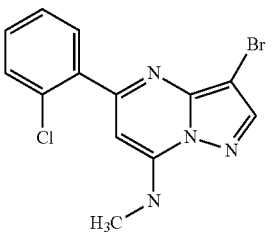 [SMILES: CNc1cc(-c2ccccc2Cl)nc2c(Br)cnn12] | 1. 8547<br>2. 478.26 |
| 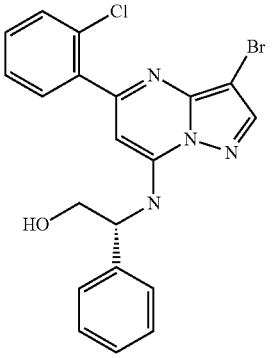 [SMILES: OC[C@H](Nc1cc(-c2ccccc2Cl)nc2c(Br)cnn12)c1ccccc1] | 1. 8548<br>2. 498.27 |
TABLE 85-continued
| Product | 1. Ex.<br>2. m/z |
|---|---|
| 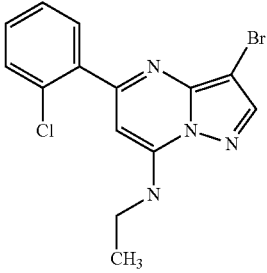 [SMILES: CCNc1cc(-c2ccccc2Cl)nc2c(Br)cnn12] | 1. 8549<br>2. 365.1 |
| 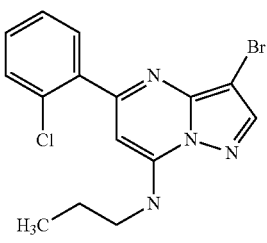 [SMILES: CCCNc1cc(-c2ccccc2Cl)nc2c(Br)cnn12] | 1. 8549<br>2. 337.1 |
| 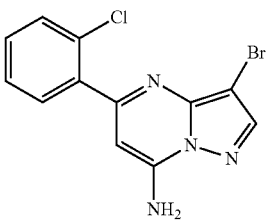 [SMILES: Nc1cc(-c2ccccc2Cl)nc2c(Br)cnn12] | 1. 8550<br>2. 351.1 |
TABLE 86
| Product | 1. Ex.<br>2. m/z |
|---|---|
| 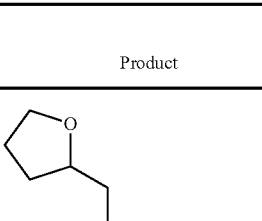 | 1. 8601<br>2. 403.22 |

TABLE 86-continued
| Product | 1. Ex.<br>2. m/z |
|---|---|
| 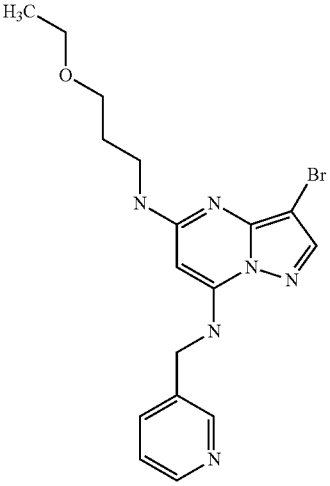 [SMILES: CCOCCCNc1cc(NCc2cccnc2)n2ncc(Br)c2n1] | 1. 8602<br>2. 407.22 |
| 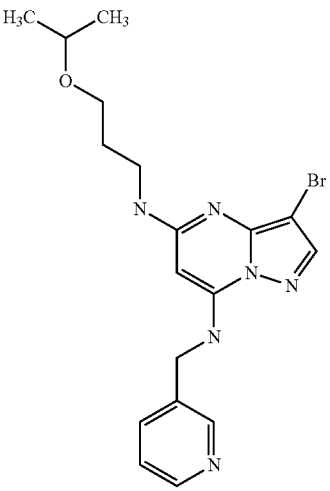 [SMILES: CC(C)OCCCNc1cc(NCc2cccnc2)n2ncc(Br)c2n1] | 1. 8603<br>2. 421.23 |
| 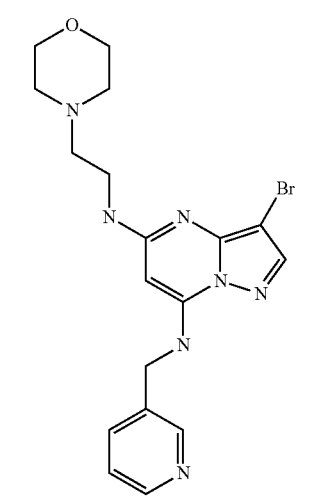 [SMILES: Brc1cnn2c(NCc3cccnc3)cc(NCCN3CCOCC3)nc12] | 1. 8604<br>2. 434.24 |
TABLE 86-continued
| Product | 1. Ex.<br>2. m/z |
|---|---|
| 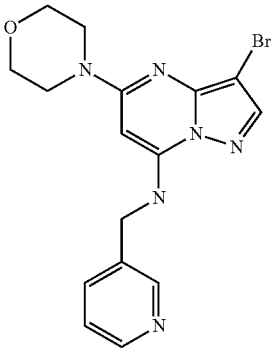 [SMILES: Brc1cnn2c(NCc3cccnc3)cc(N3CCOCC3)nc12] | 1. 8605<br>2. 391.22 |
| 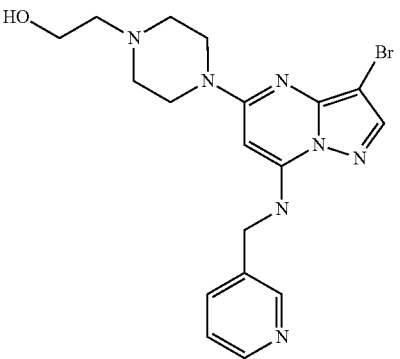 [SMILES: OCCN1CCN(c2cc(NCc3cccnc3)n3ncc(Br)c3n2)CC1] | 1. 8606<br>2. 434.24 |
| 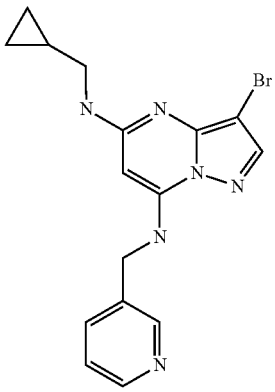 [SMILES: Brc1cnn2c(NCc3cccnc3)cc(NCC3CC3)nc12] | 1. 8607<br>2. 375.21 |
| 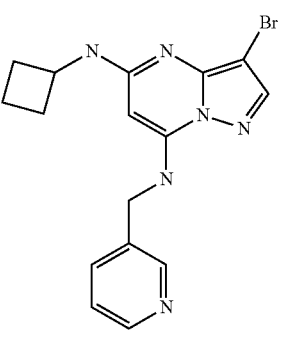 [SMILES: Brc1cnn2c(NCc3cccnc3)cc(NC3CCC3)nc12] | 1. 8608<br>2. 375.21 |

TABLE 86-continued
| Product | 1. Ex.<br>2. m/z |
|---|---|
| 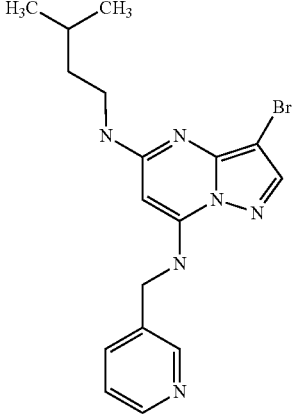 [SMILES: CC(C)CCNc1cc(NCc2cccnc2)n2ncc(Br)c2n1] | 1. 8609<br>2. 391.22 |
| 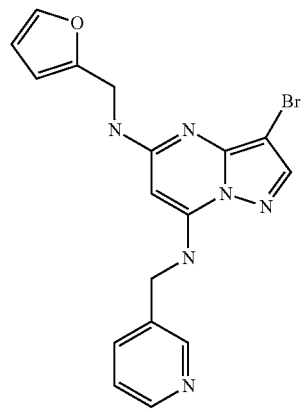 [SMILES: Brc1cnn2c(NCc3cccnc3)cc(NCc3ccco3)nc12] | 1. 8610<br>2. 399.22 |
| 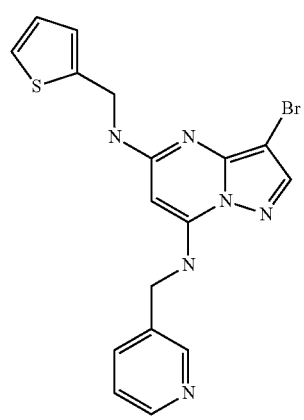 [SMILES: Brc1cnn2c(NCc3cccnc3)cc(NCc3cccs3)nc12] | 1. 8611<br>2. 417.23 |
TABLE 86-continued
| Product | 1. Ex.<br>2. m/z |
|---|---|
| 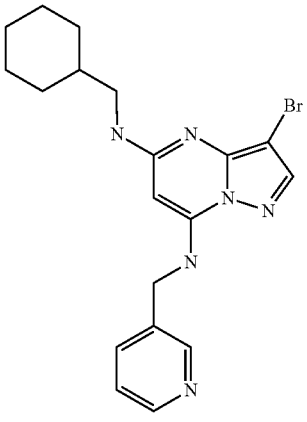 [SMILES: Brc1cnn2c(NCc3cccnc3)cc(NCC3CCCCC3)nc12] | 1. 8612<br>2. 415.23 |
| 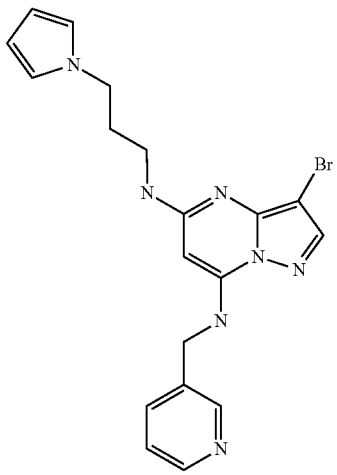 [SMILES: Brc1cnn2c(NCc3cccnc3)cc(NCCCn3cccc3)nc12] | 1. 8613<br>2. 428.24 |
| 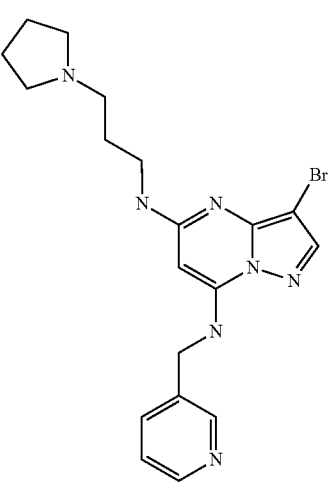 [SMILES: Brc1cnn2c(NCc3cccnc3)cc(NCCCN3CCCC3)nc12] | 1. 8614<br>2. 430.24 |

TABLE 86-continued
| Product | 1. Ex.<br>2. m/z |
|---|---|
| 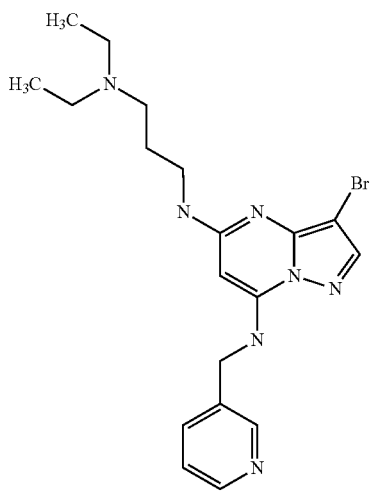 [SMILES: CCN(CC)CCCNc1cc(NCc2cccnc2)n2ncc(Br)c2n1] | 1. 8615<br>2. 434.24 |
| 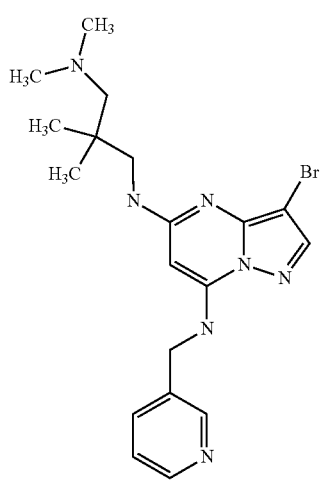 [SMILES: CN(C)CC(C)(C)CNc1cc(NCc2cccnc2)n2ncc(Br)c2n1] | 1. 8616<br>2. 434.24 |
| 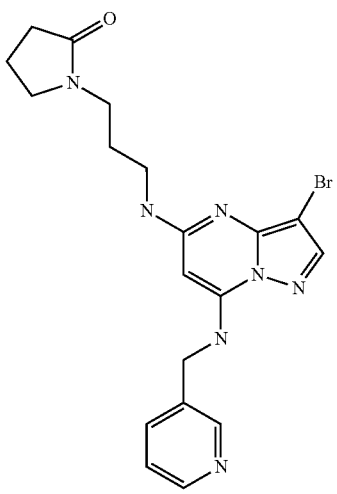 [SMILES: O=C1CCCN1CCCNc1cc(NCc2cccnc2)n2ncc(Br)c2n1] | 1. 8617<br>2. 446.25 |
TABLE 86-continued
| Product | 1. Ex.<br>2. m/z |
|---|---|
| 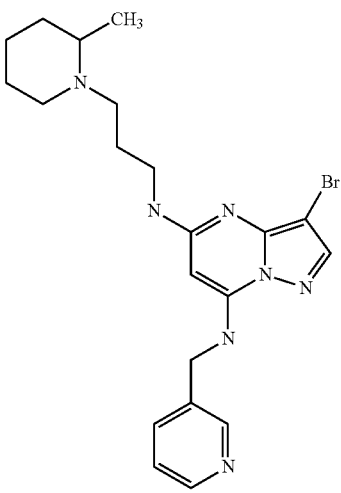 [SMILES: CC1CCCCN1CCCNc1cc(NCc2cccnc2)n2ncc(Br)c2n1] | 1. 8618<br>2. 460.25 |
| 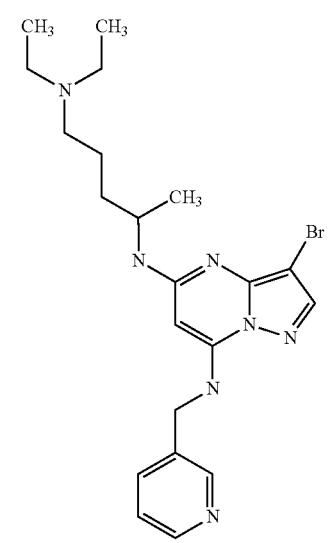 [SMILES: CCN(CC)CCCC(C)Nc1cc(NCc2cccnc2)n2ncc(Br)c2n1] | 1. 8619<br>2. 459.25 |
| 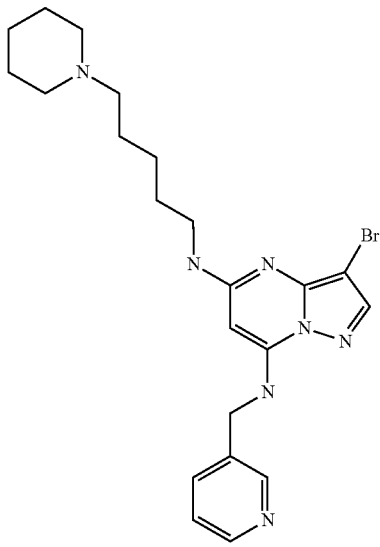 [SMILES: Brc1cnn2c(NCc3cccnc3)cc(NCCCCCN3CCCCC3)nc12] | 1. 8620<br>2. 474.26 |

TABLE 86-continued
| Product | 1. Ex.<br>2. m/z |
|---|---|
| 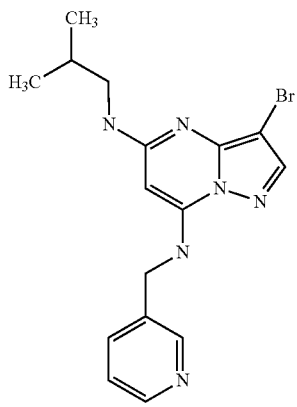 [SMILES: CC(C)CNc1cc(NCc2cccnc2)n2ncc(Br)c2n1] | 1. 8621<br>2. 377.21 |
| 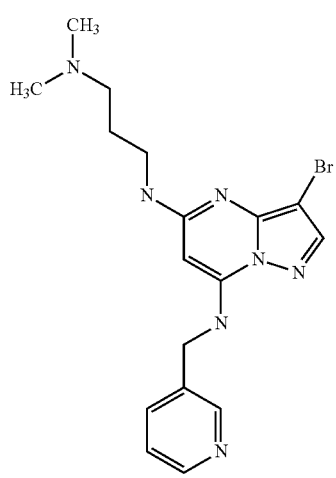 [SMILES: CN(C)CCCNc1cc(NCc2cccnc2)n2ncc(Br)c2n1] | 1. 8622<br>2. 406.22 |
| 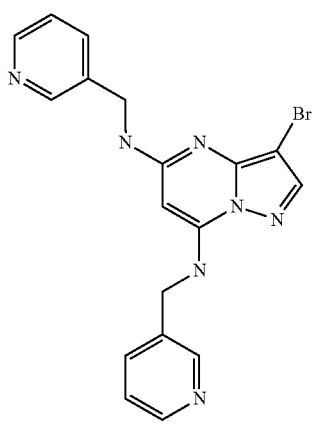 [SMILES: Brc1cnn2c(NCc3cccnc3)cc(NCc3cccnc3)nc12] | 1. 8623<br>2. 412.23 |
TABLE 86-continued
| Product | 1. Ex.<br>2. m/z |
|---|---|
| 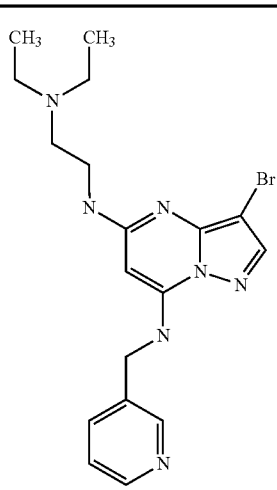 | 1. 8624<br>2. 420.23 |
| 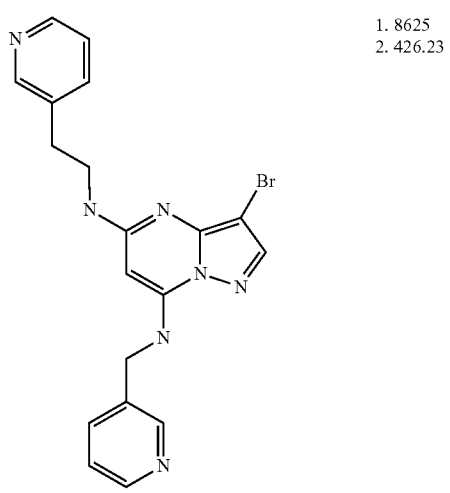 | 1. 8625<br>2. 426.23 |
| 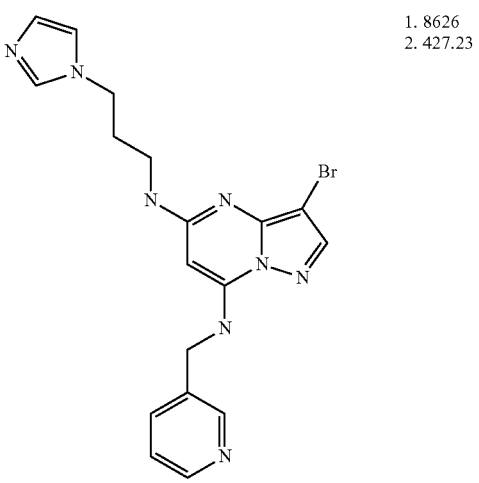 | 1. 8626<br>2. 427.23 |

TABLE 86-continued
| Product | 1. Ex. 2. m/z |
|---|---|
| 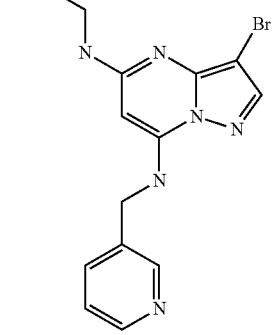 | 1. 8627 2. 431.24 |
| 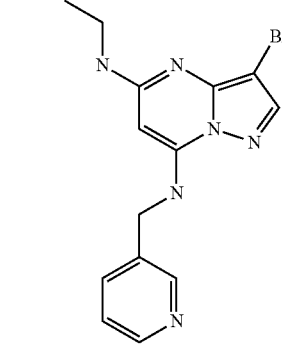 | 1. 8628 2. 446.25 |
| 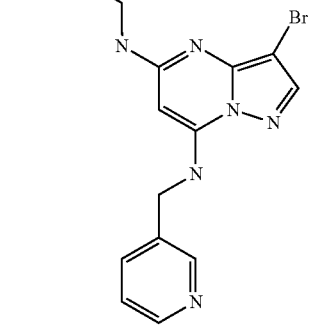 | 1. 8629 2. 446.25 |
TABLE 86-continued
| Product | 1. Ex. 2. m/z |
|---|---|
|  | 1. 8630 2. 407.2 |
| 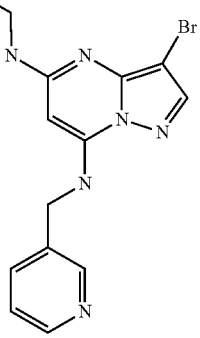 | 1. 8631 2. 407.2 |
|  | 1. 8632 2. 409.2 |

TABLE 86-continued
| Product | 1. Ex. 2. m/z |
|---|---|
| 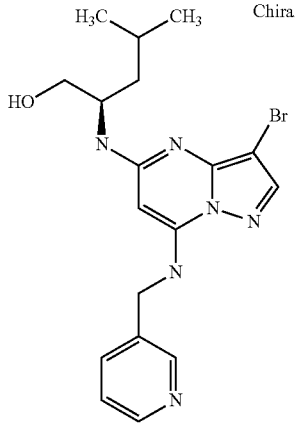 Chiral | 1. 8633  2. 421.2 |
| 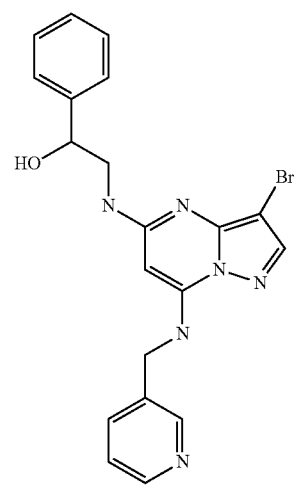 [SMILES: OC(CNc1cc(NCc2cccnc2)n2ncc(Br)c2n1)c1ccccc1] | 1. 8634  2. 439.2 |
| 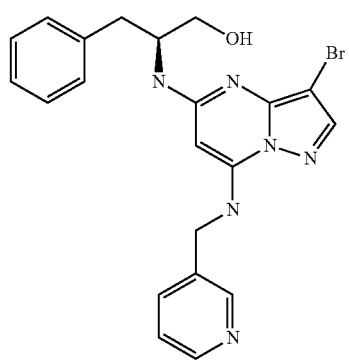 [SMILES: OC[C@H](Cc1ccccc1)Nc1cc(NCc2cccnc2)n2ncc(Br)c2n1] | 1. 8635  2. 455.3 |
TABLE 86-continued
| Product | 1. Ex. 2. m/z |
|---|---|
| 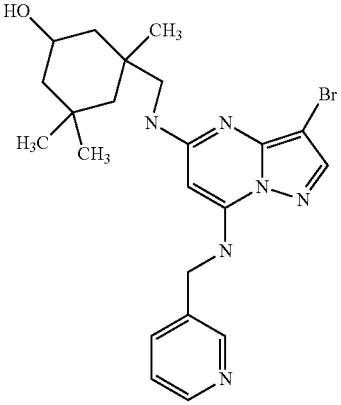 [SMILES: CC1(C)CC(O)CC(C)(CNc2cc(NCc3cccnc3)n3ncc(Br)c3n2)C1] | 1. 8636  2. 475.3 |
| 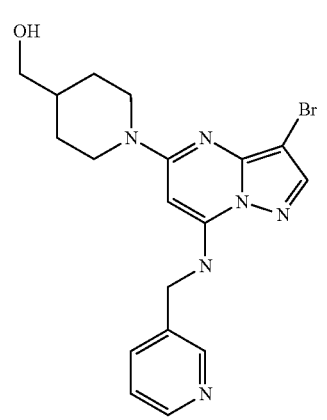 [SMILES: OCC1CCN(c2cc(NCc3cccnc3)n3ncc(Br)c3n2)CC1] | 1. 8637  2. 419.2 |
| 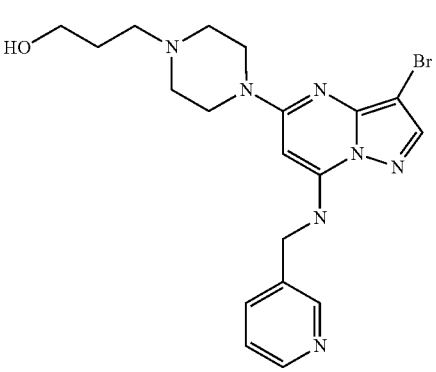 [SMILES: OCCCN1CCN(c2cc(NCc3cccnc3)n3ncc(Br)c3n2)CC1] | 1. 8638  2. 448.2 |
| 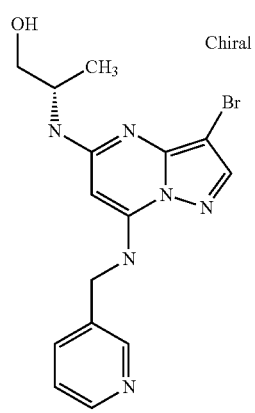 [SMILES: C[C@@H](CO)Nc1cc(NCc2cccnc2)n2ncc(Br)c2n1] Chiral | 1. 8639  2. 379.2 |

TABLE 86-continued
| Product | 1. Ex. 2. m/z |
|---|---|
| 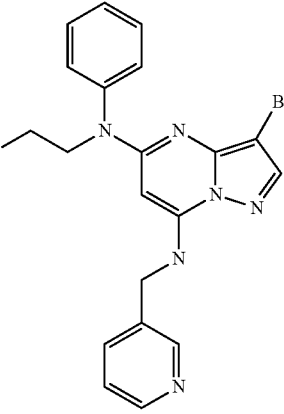 | 1. 8640 2. 437.2 |
| 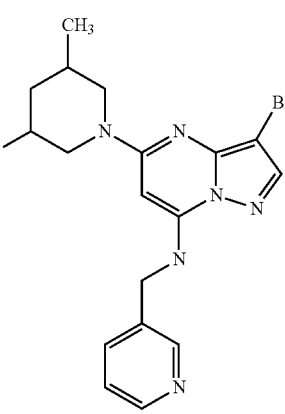 | 1. 8641 2. 415.23 |
| 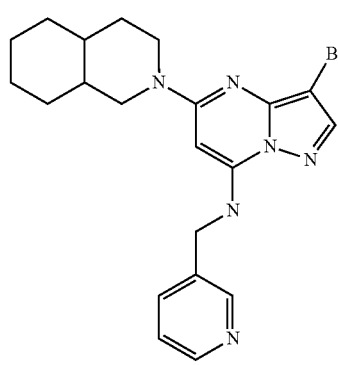 | 1. 8642 2. 443.24 |
| 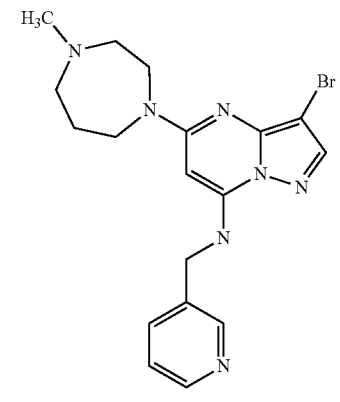 [SMILES: CN1CCCN(c2cc(NCc3cccnc3)n3ncc(Br)c3n2)CC1] | 1. 8643 2. 416.23 |
TABLE 86-continued
| Product | 1. Ex. 2. m/z |
|---|---|
| 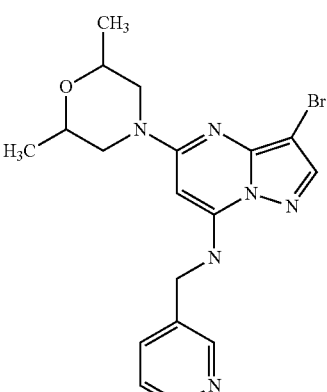 | 1. 8644 2. 417.23 |
| 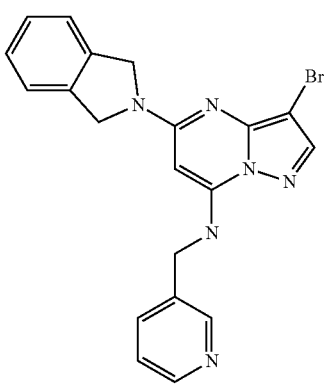 [SMILES: Brc1cnn2c(NCc3cccnc3)cc(N3Cc4ccccc4C3)nc12] | 1. 8645 2. 423.23 |
| 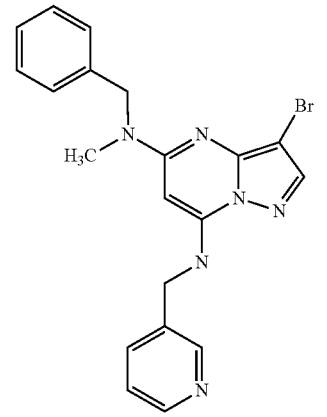 [SMILES: CN(Cc1ccccc1)c1cc(NCc2cccnc2)n2ncc(Br)c2n1] | 1. 8646 2. 423.23 |

TABLE 86-continued
| Product | 1. Ex.<br>2. m/z |
|---|---|
| 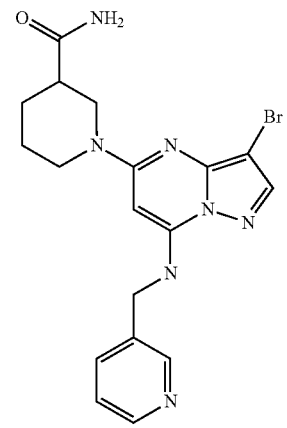 [SMILES: NC(=O)C1CCCN(c2cc(NCc3cccnc3)n3ncc(Br)c3n2)C1] | 1. 8647<br>2. 430.24 |
| 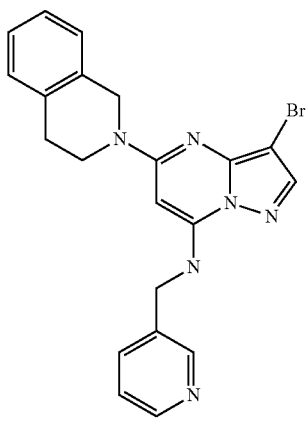 [SMILES: Brc1cnn2c(NCc3cccnc3)cc(N3CCc4ccccc4C3)nc12] | 1. 8648<br>2. 437.24 |
| 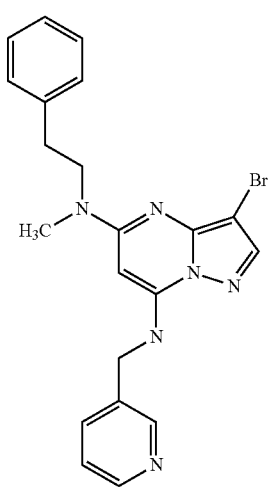 [SMILES: CN(CCc1ccccc1)c1cc(NCc2cccnc2)n2ncc(Br)c2n1] | 1. 8649<br>2. 439.24 |
TABLE 86-continued
| Product | 1. Ex.<br>2. m/z |
|---|---|
| 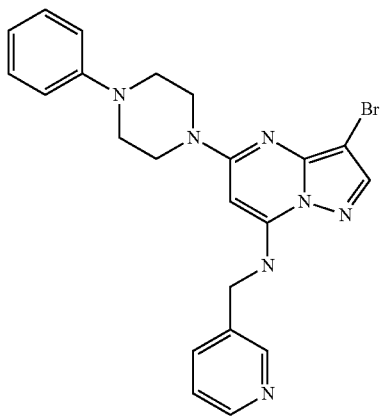 [SMILES: Brc1cnn2c(NCc3cccnc3)cc(N3CCN(c4ccccc4)CC3)nc12] | 1. 8650<br>2. 466.26 |
| 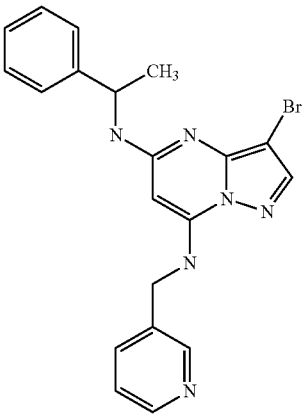 [SMILES: CC(Nc1cc(NCc2cccnc2)n2ncc(Br)c2n1)c1ccccc1] | 1. 8651<br>2. 423.23 |
| 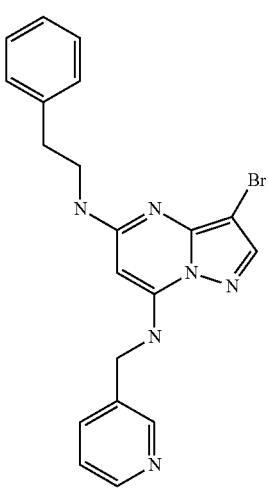 [SMILES: Brc1cnn2c(NCc3cccnc3)cc(NCCc3ccccc3)nc12] | 1. 8652<br>2. 425.23 |

TABLE 86-continued
| Product | 1. Ex.<br>2. m/z |
|---|---|
| 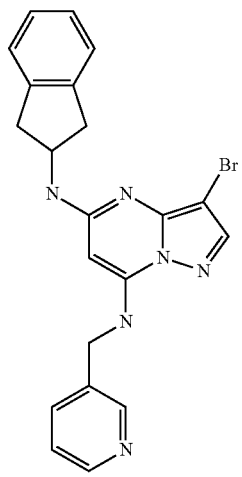 [SMILES: Brc1cnn2c(NCc3cccnc3)cc(NC3Cc4ccccc4C3)nc12] | 1. 8653<br>2. 437.24 |
| 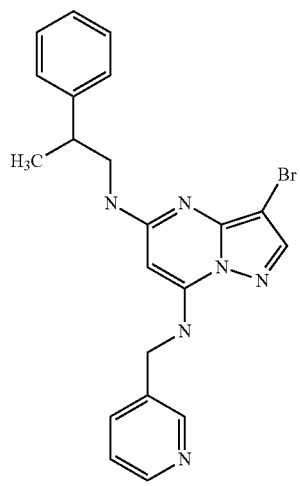 [SMILES: CC(CNc1cc(NCc2cccnc2)n2ncc(Br)c2n1)c1ccccc1] | 1. 8654<br>2. 437.24 |
| 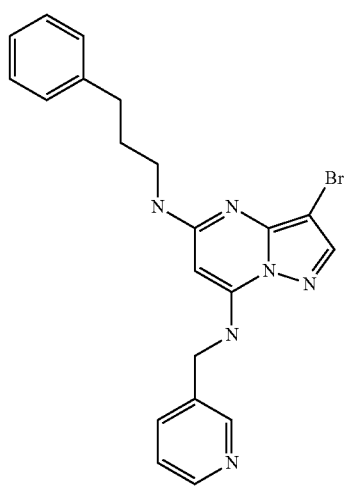 [SMILES: Brc1cnn2c(NCc3cccnc3)cc(NCCCc3ccccc3)nc12] | 1. 8655<br>2. 437.24 |
TABLE 86-continued
| Product | 1. Ex.<br>2. m/z |
|---|---|
| 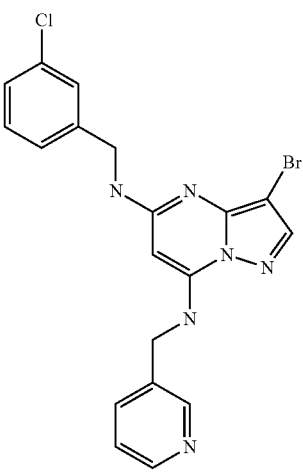 [SMILES: Clc1cccc(CNc2cc(NCc3cccnc3)n3ncc(Br)c3n2)c1] | 1. 8656<br>2. 445.24 |
| 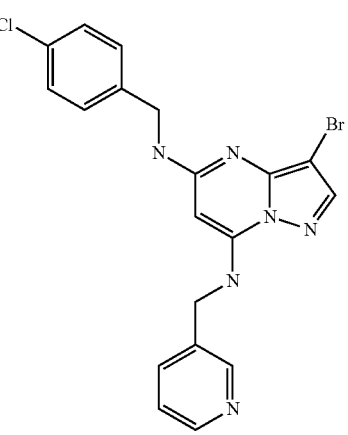 [SMILES: Clc1ccc(CNc2cc(NCc3cccnc3)n3ncc(Br)c3n2)cc1] | 1. 8657<br>2. 445.24 |
| 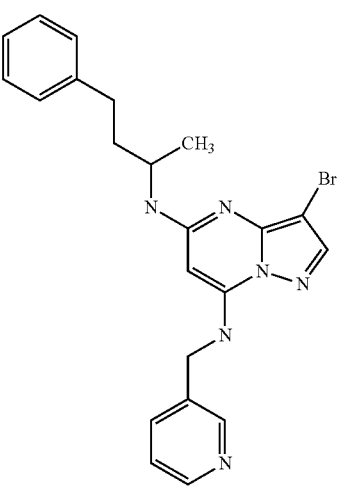 [SMILES: CC(CCc1ccccc1)Nc1cc(NCc2cccnc2)n2ncc(Br)c2n1] | 1. 8658<br>2. 451.25 |

TABLE 86-continued

| Product | 1. Ex. 2. m/z |
|---|---|
| (structure) | 1. 8659 2. 476.26 |
| (structure) | 1. 8660 2. 479.26 |
| (structure) | 1. 8661 2. 477.26 |

TABLE 86-continued

| Product | 1. Ex. 2. m/z |
|---|---|
| (structure) | 1. 8662 2. 479.26 |

What is claimed is:

1. A method of treating chronic lymphocytic leukemia, breast cancer, non-small cell lung cancer, acute myleogenous leukemia, acute lymphoblastic leukemia, or mantle cell lymphoma in a patient in need thereof, comprising administering to said patient a therapeutically effective amount of at least one compound selected from the group consisting of:

1617
-continued
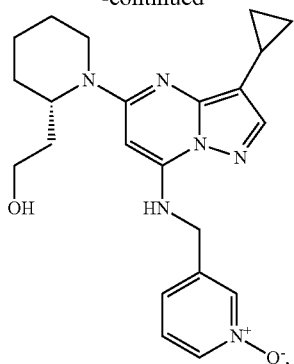
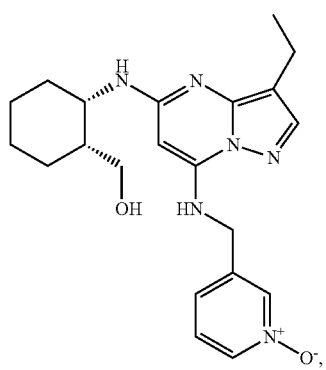
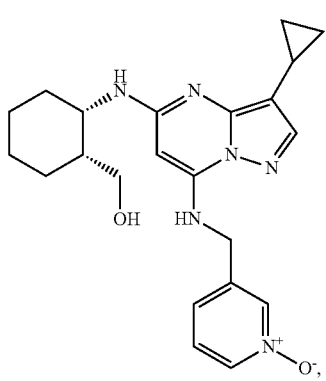
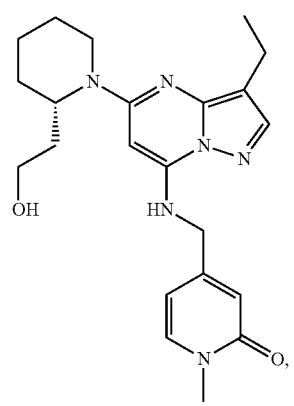
1618
-continued
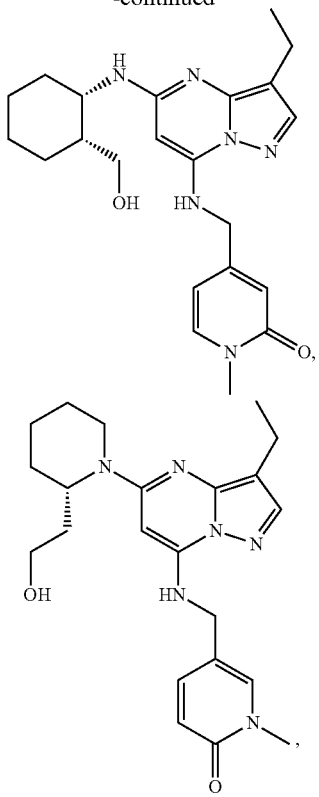
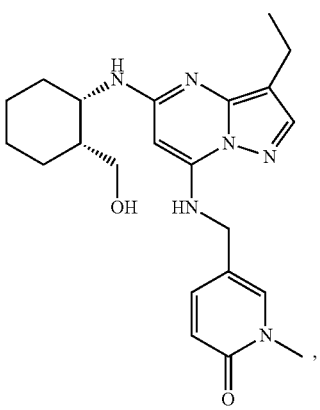
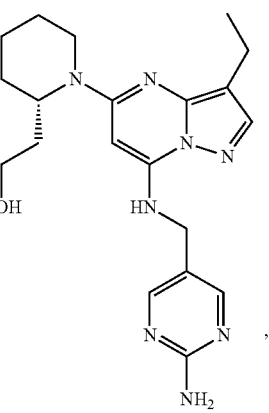

1619
-continued
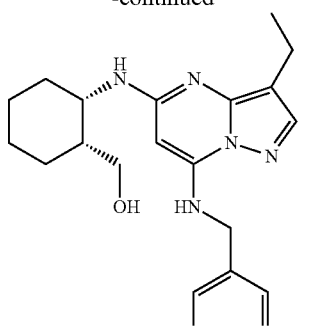
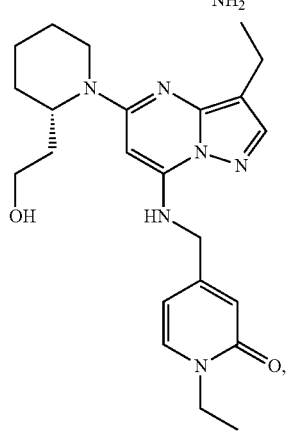
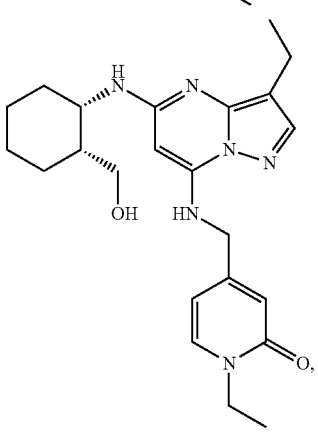
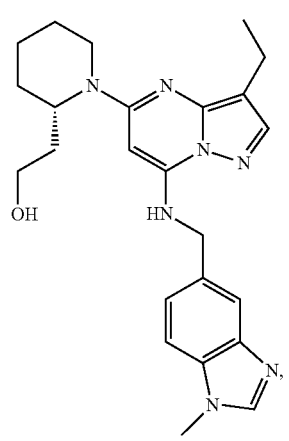
1620
-continued
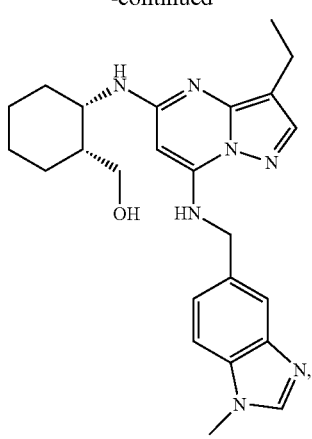
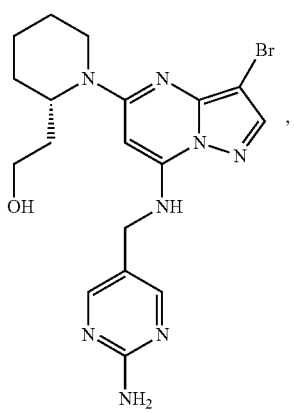
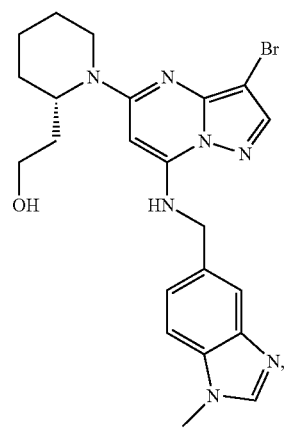
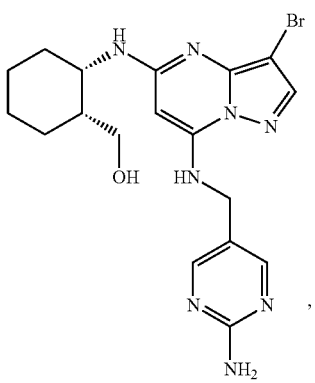

1621
-continued
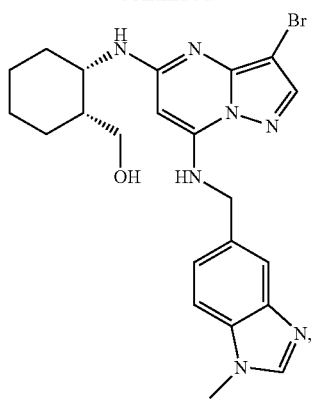
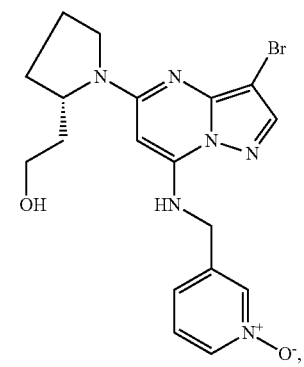
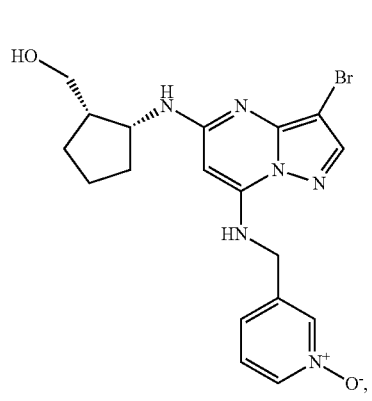
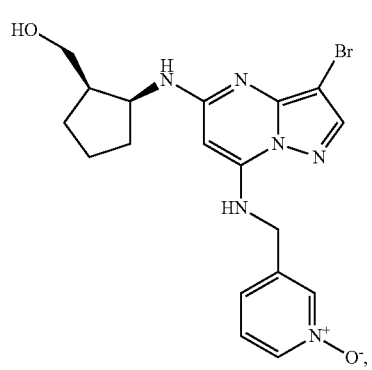
1622
-continued
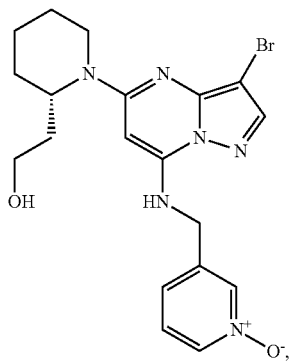
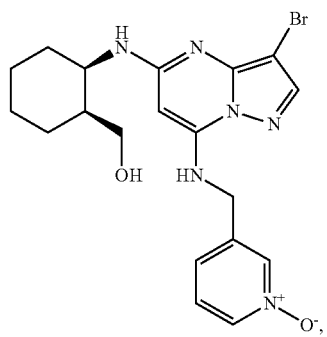
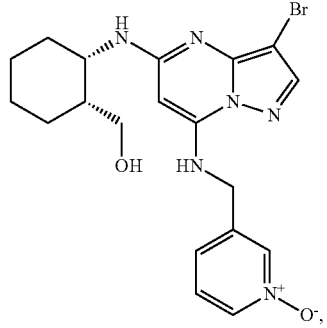
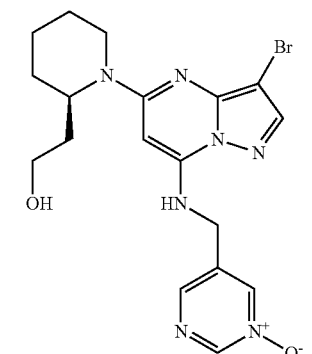

1623
-continued
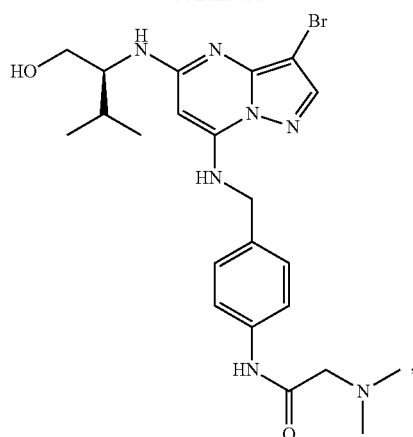
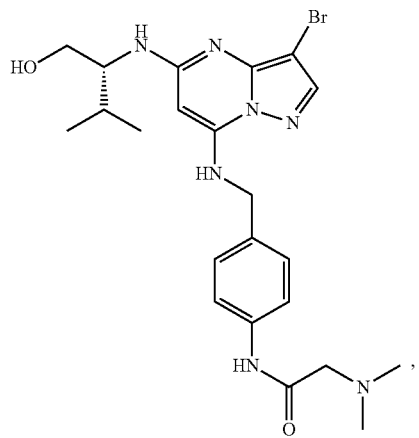
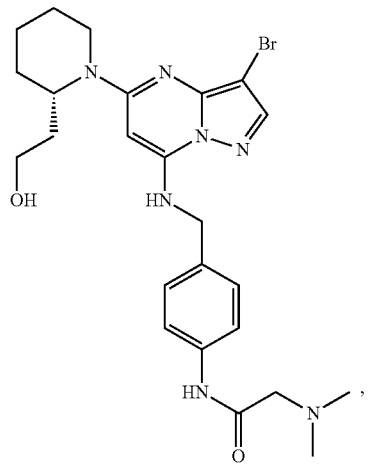
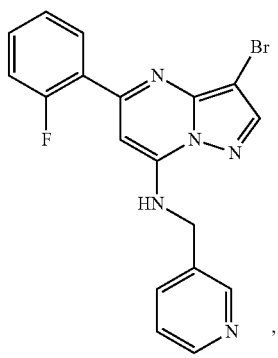
1624
-continued
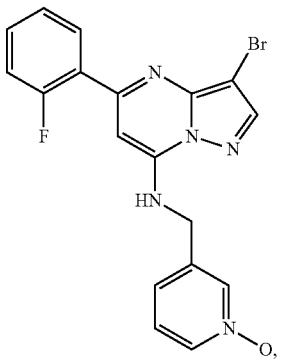
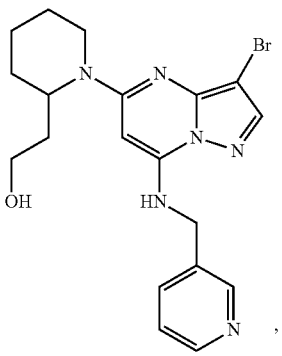
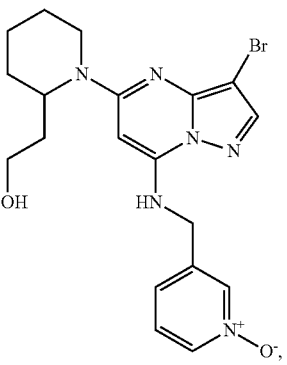
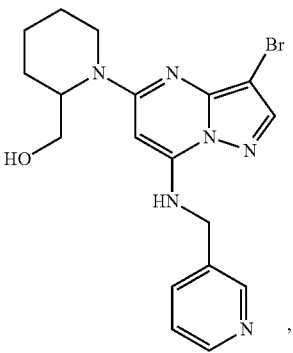

1625
-continued

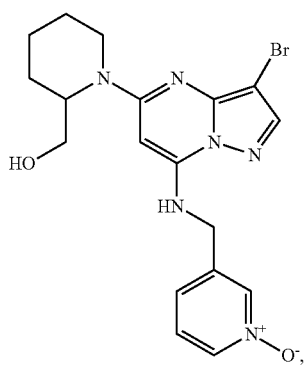

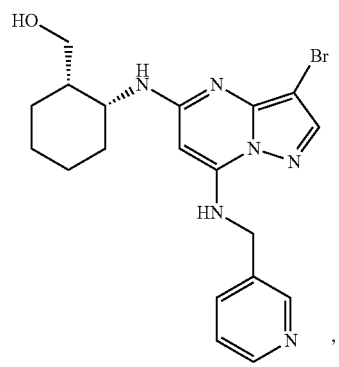

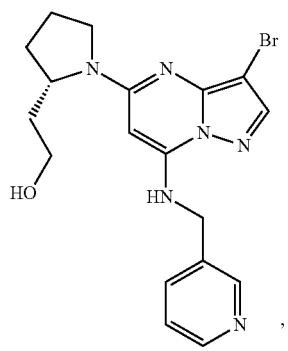

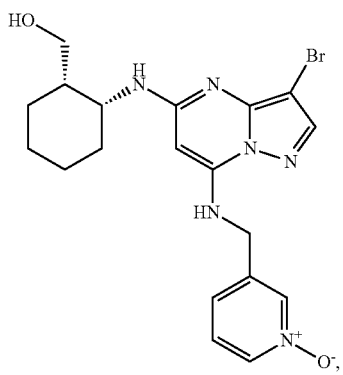
and

1626
-continued

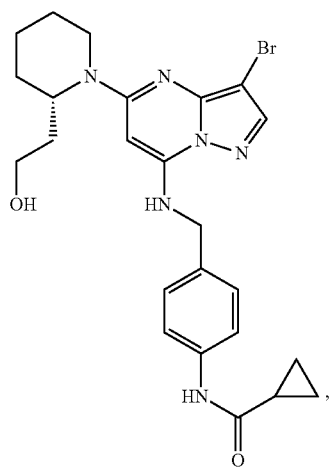

or a pharmaceutically acceptable salt thereof.

2. A method of treating chronic lymphocytic leukemia, breast cancer, non-small cell lung cancer, acute myleogenous leukemia, acute lymphoblastic leukemia, or mantle cell lymphoma in a patient in need thereof, comprising administering to said patient an amount of a first compound, which is a compound selected from the group consisting of:

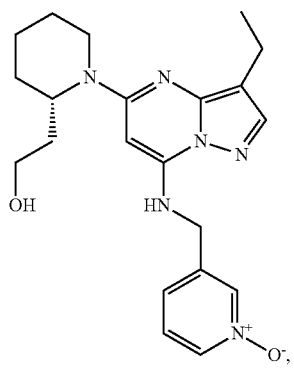

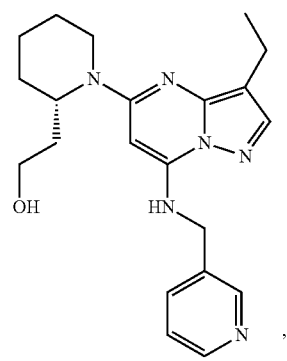

| 1627 | 1628 |
|---|---|
| -continued | -continued |
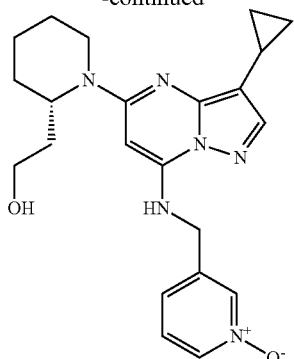
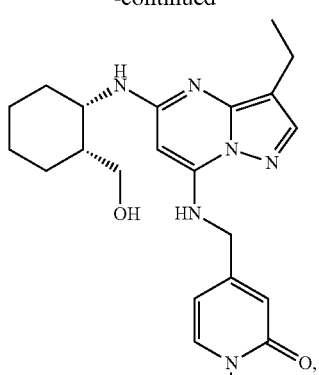

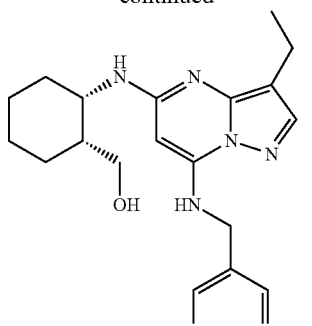
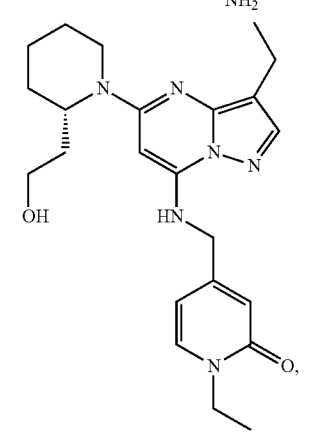
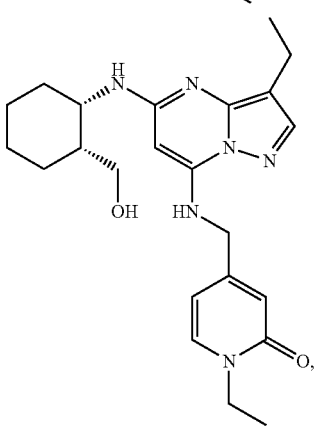
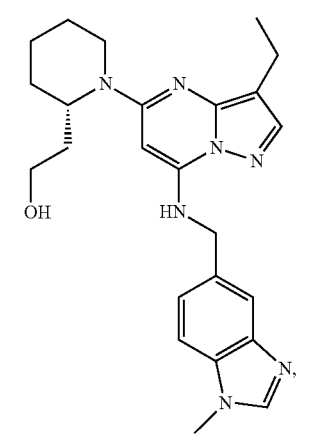
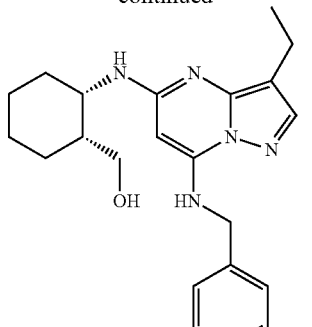
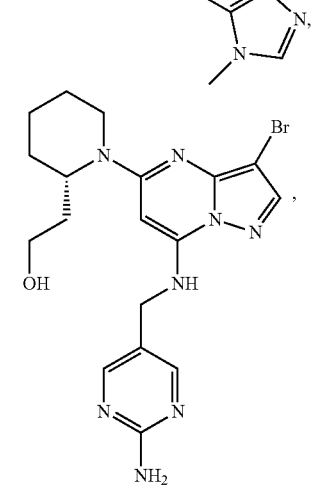
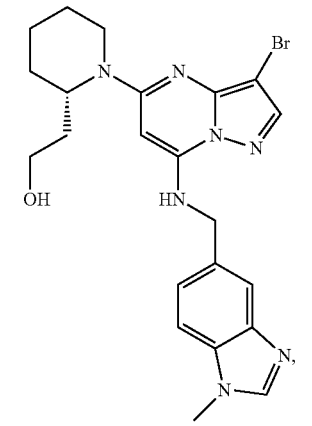
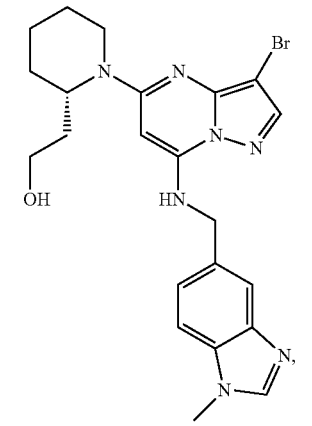

1631
-continued
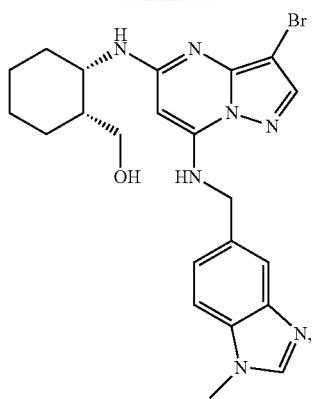
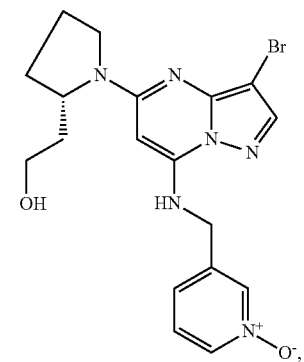
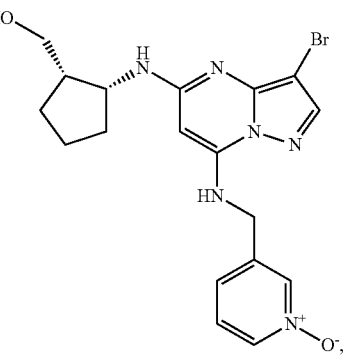
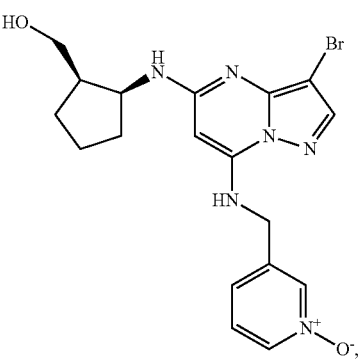
1632
-continued
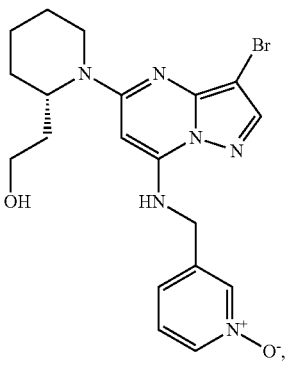
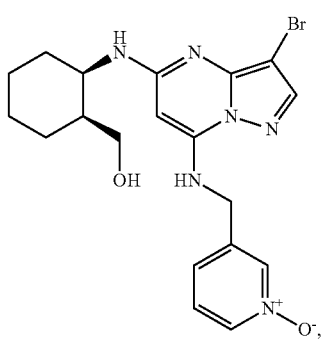
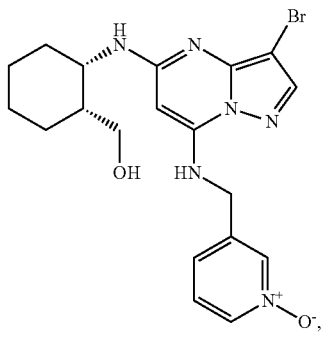
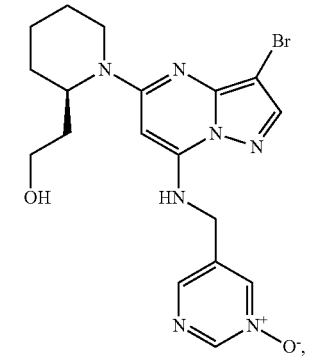

1633
-continued
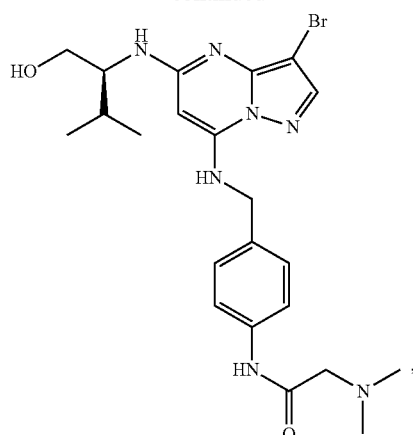
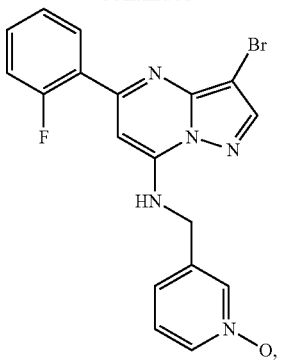
1634
-continued
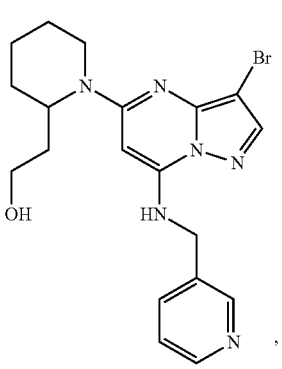
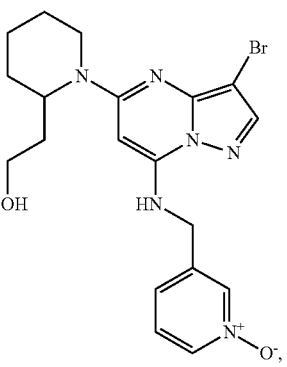
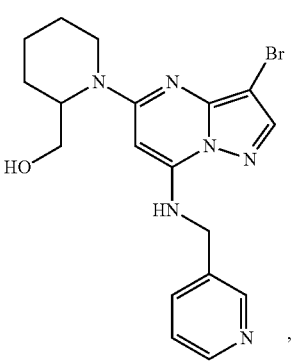

-continued

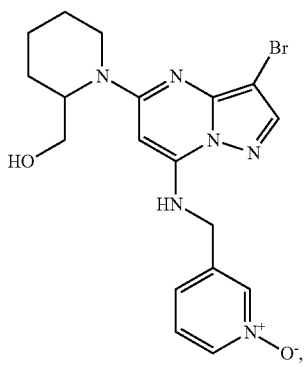

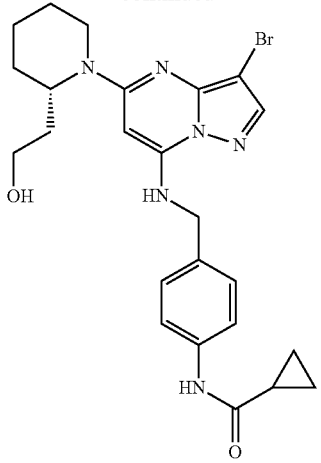 [SMILES: O=C(Nc1ccc(CNc2cc(N3CCCC[C@H]3CCO)nc3c(Br)cnn23)cc1)C1CC1]

or a pharmaceutically acceptable salt thereof; and
an amount of at least one second compound, said second compound being an anti-cancer agent;
wherein the amounts of the first compound and said second compound result in a therapeutic effect.

3. The method of claim 2, further comprising radiation therapy.

4. The method of claim 2, wherein said anti-cancer agent is selected from the group consisting of a cytostatic agent, cisplatin, doxorubicin, pegylated liposomal doxorubicin, liposomal doxorubicin, doxorubicin liposomal, docetaxel, paclitaxel, etoposide, irinotecan, topotecan, epothilones, tamoxifen, 5-fluorouracil, methoxtrexate, temozolomide, cyclophosphamide, 4-[2-[4-[(11R)-3,10-dibromo-8-chloro-6,11-dihydro-5H-benzo[5,6]cyclohepta[1,2-b]pyridin-11-yl-]-1-piperidinyl]-2-oxoethyl]-1-piperidinecarboxamide, tipifarnib, L778,123 (a farnesyl protein transferase inhibitor), BMS 214662 (a farnesyl protein transferase inhibitor), gefitinib, erlotinib, antibodies to EGFR, imatinib, interferon alfa-2b, ara-C, cytoxan, gemcitabine, Uracil mustard, Chlormethine, Ifosfamide, Melphalan, Chlorambucil, Pipobroman, Triethylenemelamine, ispinesib, SB-743921, GSK-923295, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, Pentostatine, Vinblastine, Vincristine, Vindesine, Bleomycin, Dactinomycin, Daunorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, bevacizumab, trastuzumab, tositumomab, bortezomib, ibritumomab, arsenic trioxide, Vinorelbine, Porfimer, cetuximab, Liposomal, Thiotepa, Altretamine, Melphalan, Lerozole, Fulvestrant, Exemestane, Ifosfomide, Rituximab, satriplatin, Gemtuzumab ozogamicin, pemetrexed, panitubimab, sunitinib, sorafenib, dastinib, nilotinib, lapatinib and alemtuzumab.

5. A method of treating chronic lymphocytic leukemia, breast cancer, non-small cell lung cancer, acute myleogenous

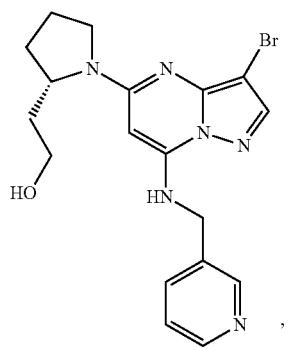

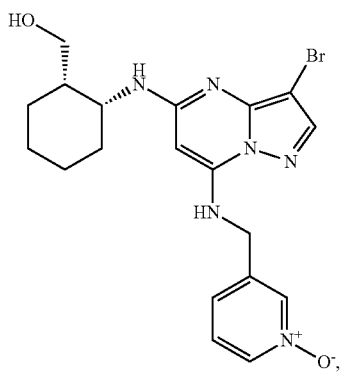

and leukemia, acute lymphoblastic leukemia, or mantle cell lymphoma in a patient in need thereof, comprising administering to said patient: a composition comprising: (i) a therapeutically effective amount of at least one compound selected from the group consisting of:
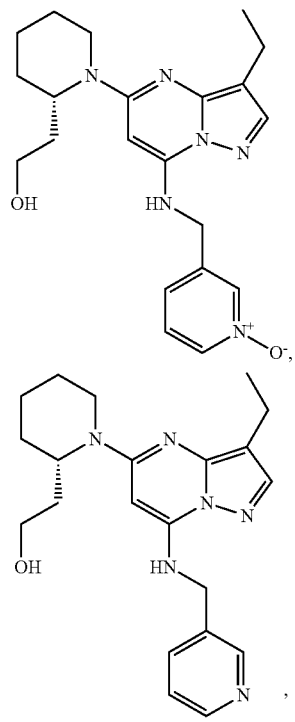
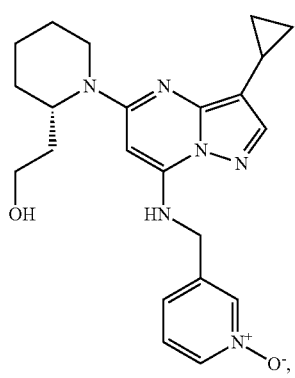
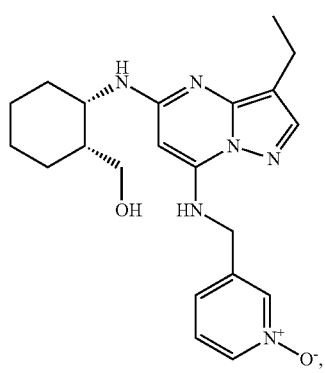
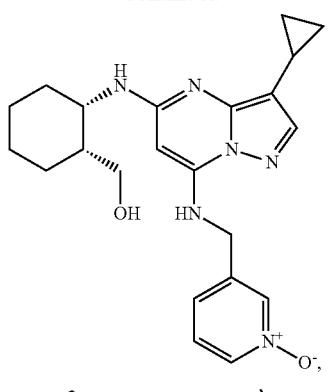
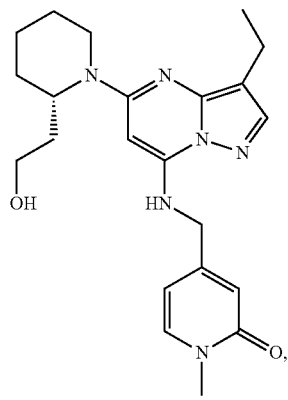
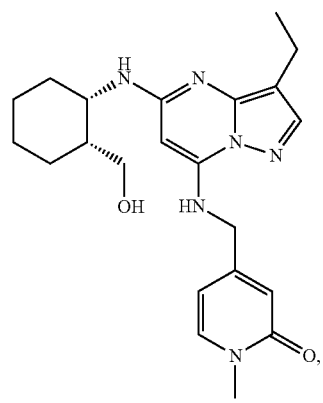
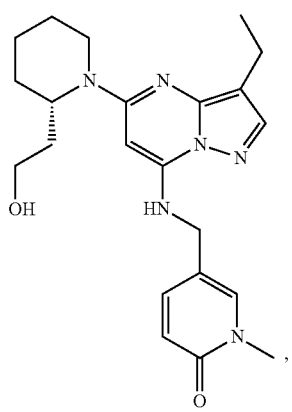

1639
-continued
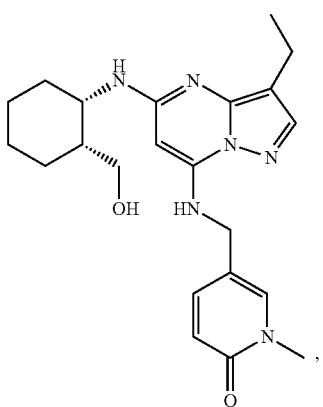
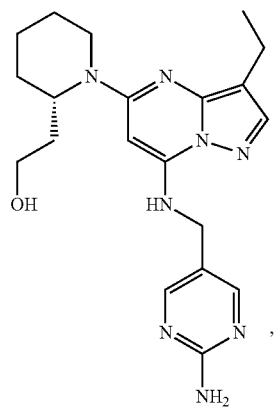
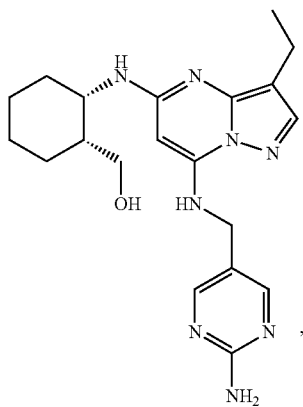
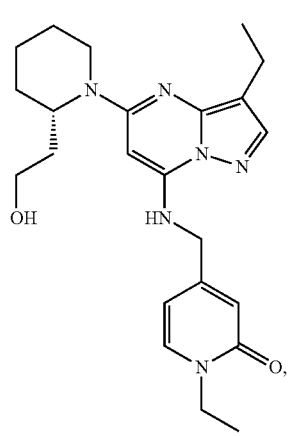
1640
-continued
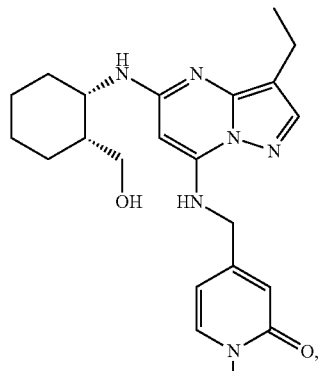
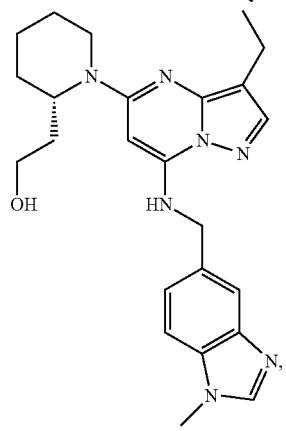
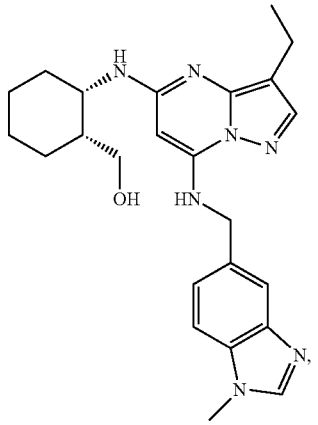
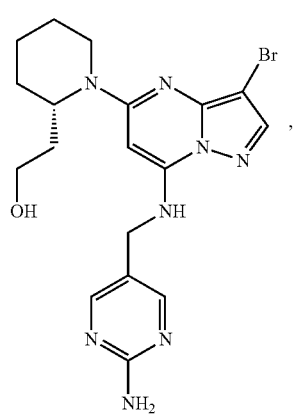

1641
-continued
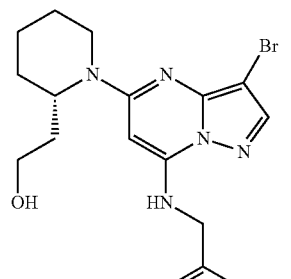
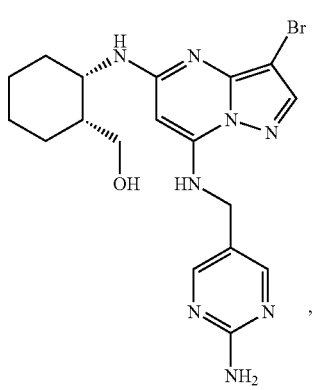
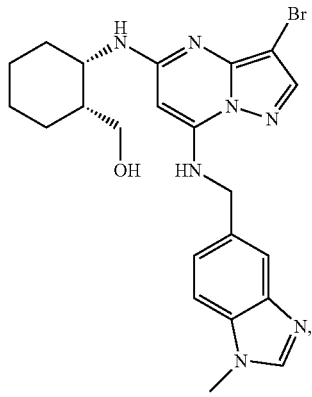
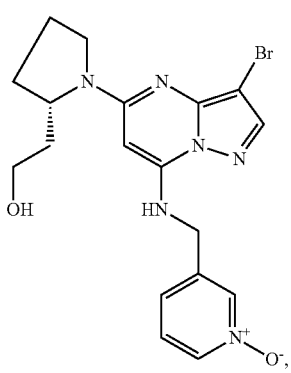
1642
-continued
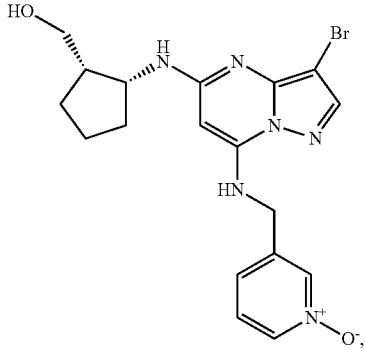
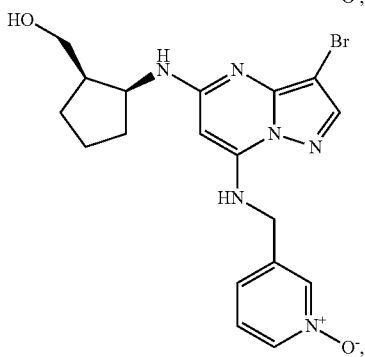
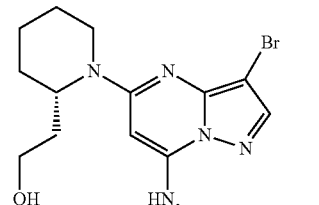
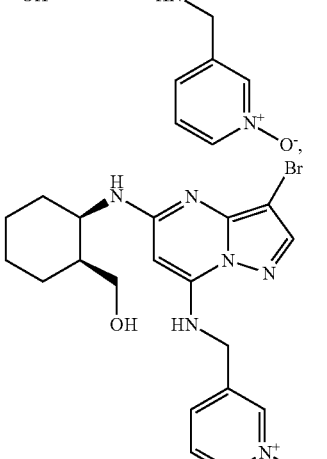
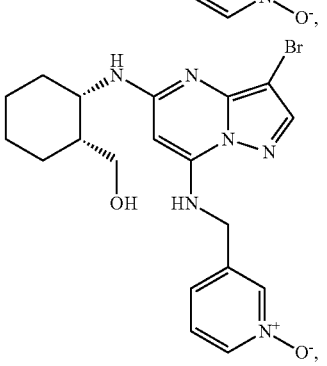

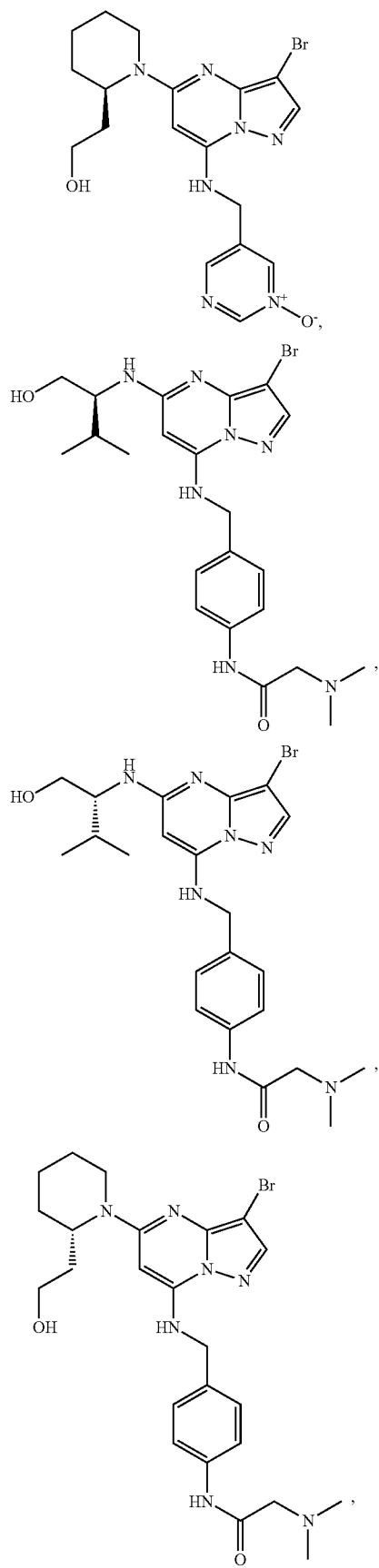
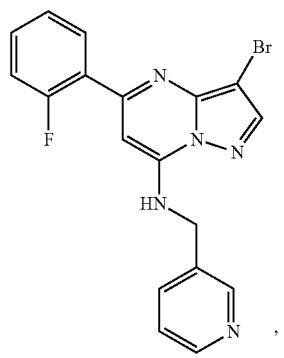

-continued

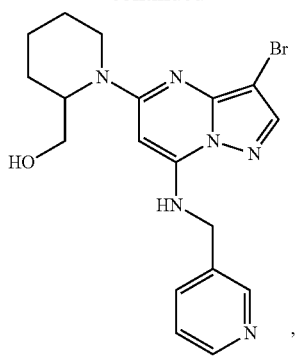

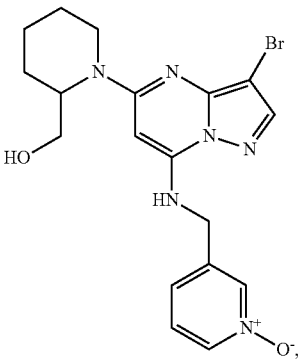

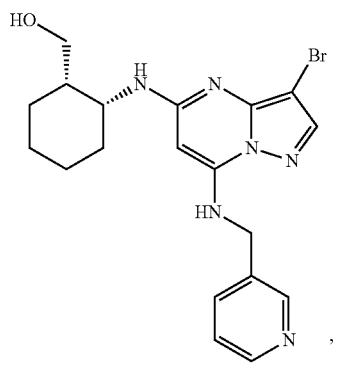

-continued

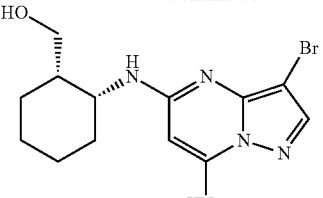

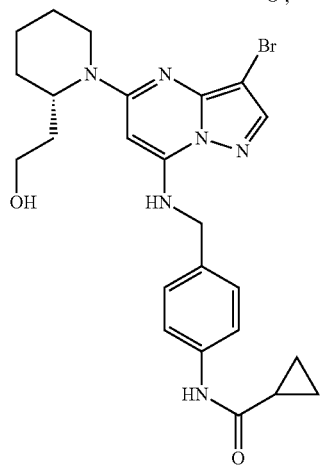

or a pharmaceutically acceptable salt thereof, and (ii) temozolomide.

6. A method of treating chronic lymphocytic leukemia, breast cancer, non-small cell lung cancer, acute myleogenous leukemia, acute lymphoblastic leukemia, or mantle cell lymphoma in a patient in need thereof by inhibiting CDK1 or CDK2, comprising administering to said patient a therapeutically effective amount of the compound:

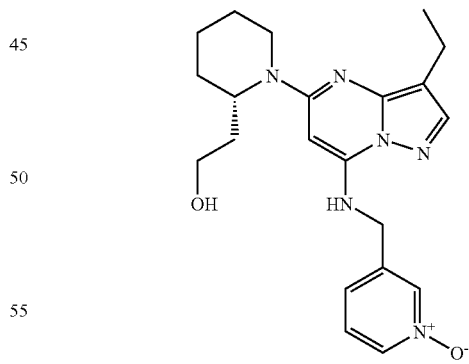

or a pharmaceutically acceptable salt thereof.

7. The method of claim 6 further comprising administering radiation therapy.

8. A method of treating chronic lymphocytic leukemia, breast cancer, non-small cell lung cancer, acute myleogenous leukemia, acute lymphoblastic leukemia, or mantle cell lymphoma in a patient in need thereof, comprising administering to said patient a therapeutically effective amount of the compound:

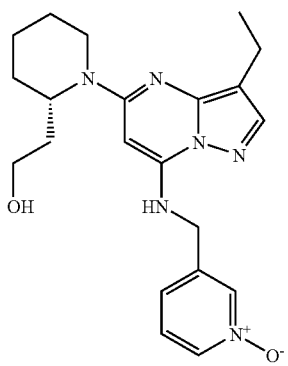

or a pharmaceutically acceptable salt thereof.

9. The method of claim 8 further comprising administering radiation therapy.

10. A method of treating chronic lymphocytic leukemia, breast cancer, non-small cell lung cancer, acute myleogenous leukemia, acute lymphoblastic leukemia, or mantle cell lymphoma in a patient in need thereof, comprising administering to said patient a composition comprising (i) the compound:

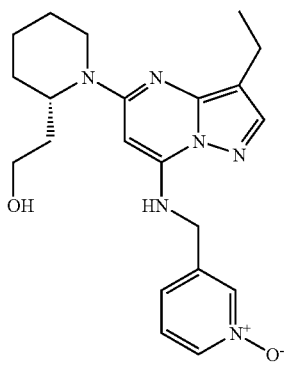

or a pharmaceutically acceptable salt thereof, and (ii) at least one compound selected from the group consisting of a cytostatic agent, cisplatin, doxorubicin, pegylated liposomal doxorubicin, liposomal doxorubicin, doxorubicin liposomal, docetaxel, paclitaxel, etoposide, irinotecan, topotecan, paclitaxel, docetaxel, epothilones, tamoxifen, 5-fluorouracil, methoxtrexate, temozolomide, cyclophosphamide, 4-[2-[4-[(11R)-3,10-dibromo-8-chloro-6,11-dihydro-5H-benzo[5,6]cyclohepta[1,2-b]pyridin-11-yl-]-1-piperidinyl]-2-oxoethyl]-1-piperidinecarboxamide, tipifarnib, L778,123 (a farnesyl protein transferase inhibitor), BMS 214662 (a farnesyl protein transferase inhibitor), gefitinib, erlotinib, antibodies to EGFR, imatinib, interferon alfa-2b, ara-C, cytoxan, gemcitabine, Uracil mustard, Chlormethine, Ifosfamide, Melphalan, Chlorambucil, Pipobroman, Triethylenemelamine, ispinesib, SB-743921, GSK-923295, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, Pentostatine, Vinblastine, Vincristine, Vindesine, Bleomycin, Dactinomycin, Daunorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, bevacizumab, trastuzumab, tositumomab, bortezomib, ibritumomab, arsenic trioxide, Vinorelbine, Porfimer, cetuximab, Liposomal, Thiotepa, Altretamine, Melphalan, Lerozole, Fulvestrant, Exemestane, Ifosfomide, Rituximab, satriplatin, Gemtuzumab ozogamicin, pemetrexed, panitubimab, sunitinib, sorafenib, dastinib, nilotinib, lapatinib and alemtuzumab.

11. The method of claim 10, further comprising the administration of radiation therapy.

12. A method of treating chronic lymphocytic leukemia, breast cancer, non-small cell lung cancer, acute myleogenous leukemia, acute lymphoblastic leukemia, or mantle cell lymphoma in a patient in need thereof comprising administering to said patient a composition comprising (i) the compound:

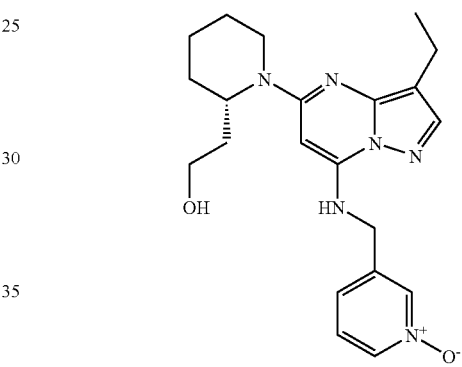

or a pharmaceutically acceptable salt thereof, and (ii) temozolomide.

13. The method of claim 12, further comprising the administration of radiation therapy.

14. A method of treating chronic lymphocytic leukemia, acute myleogenous leukemia, acute lymphoblastic leukemia, or mantle cell lymphoma in a patient in need thereof, comprising administering to said patient a therapeutically effective amount of at least one compound selected from the group consisting of:

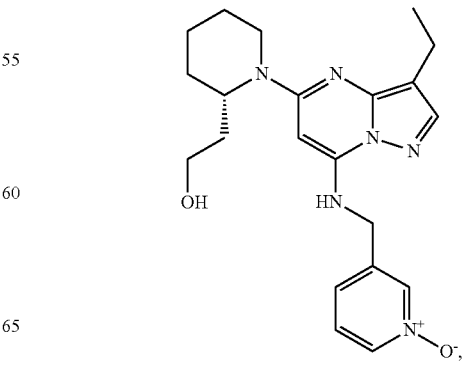

1649
-continued
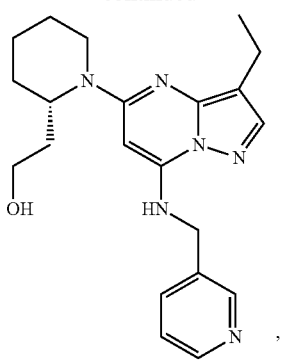
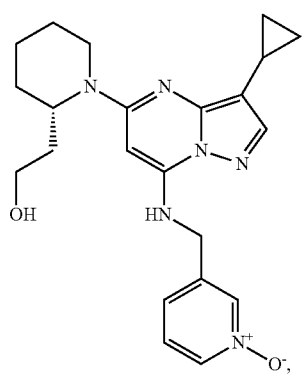
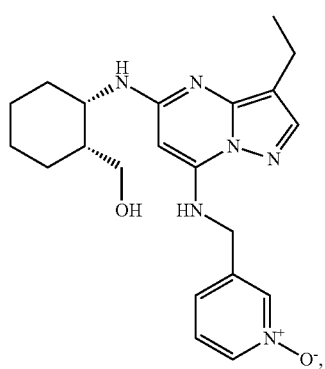
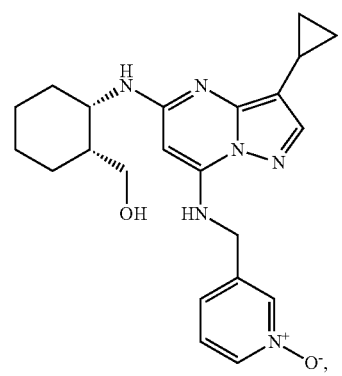
1650
-continued
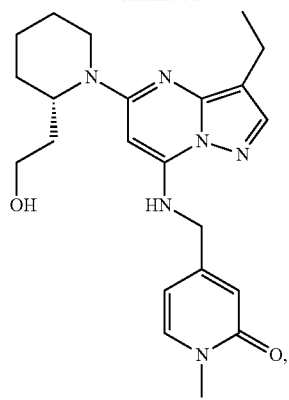
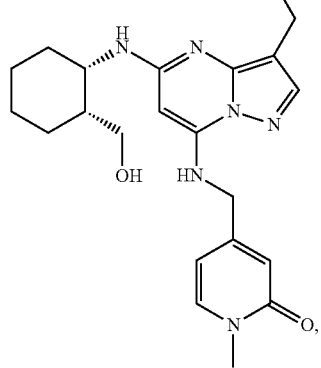
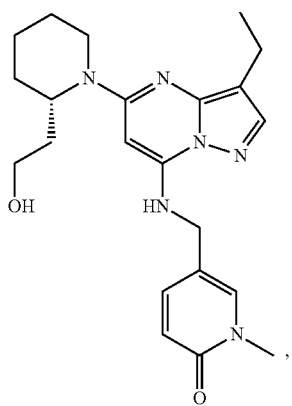
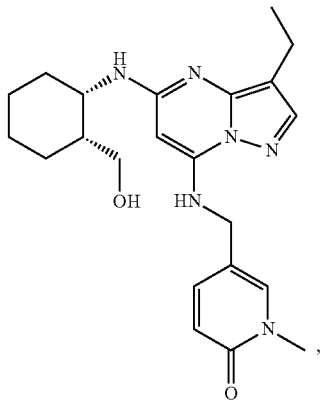

-continued
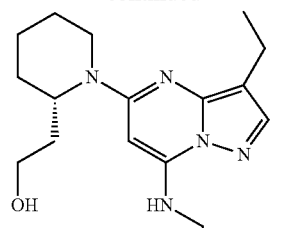
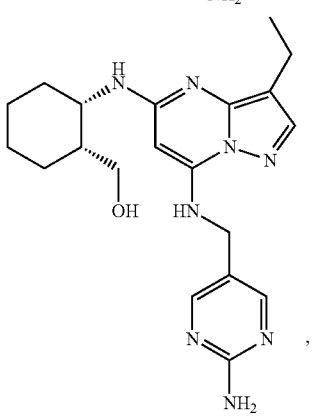
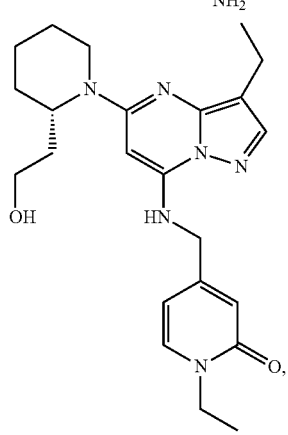
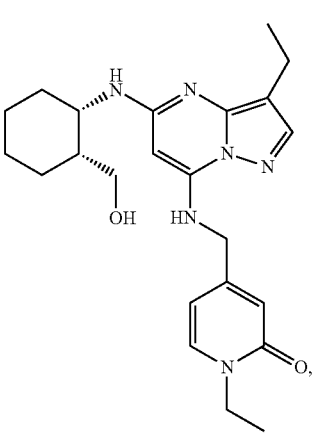
-continued
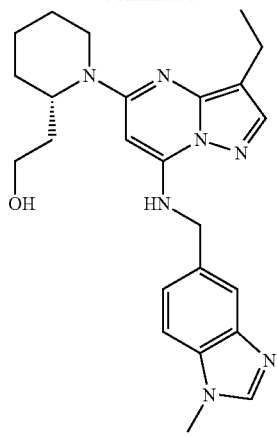
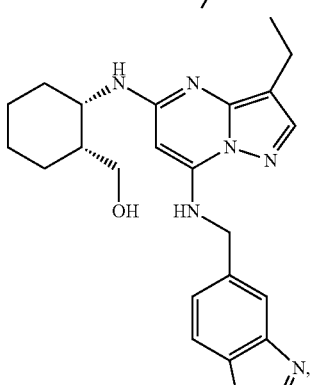
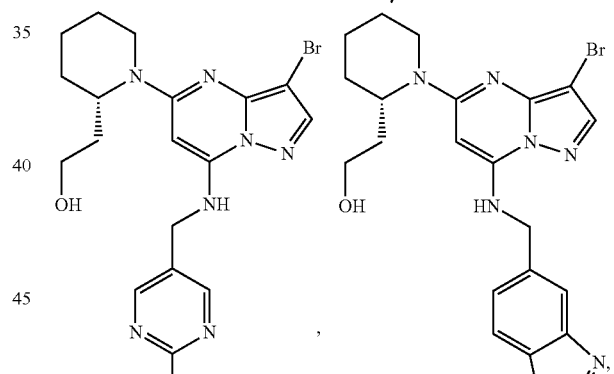
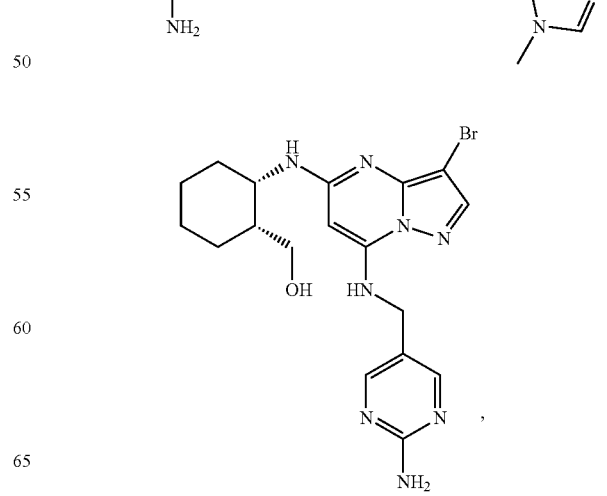

1653
-continued
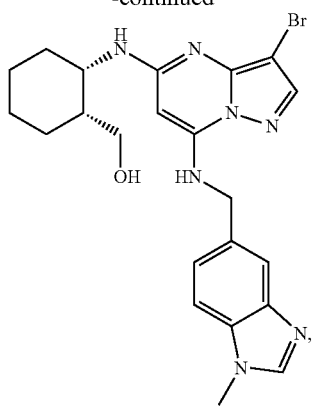
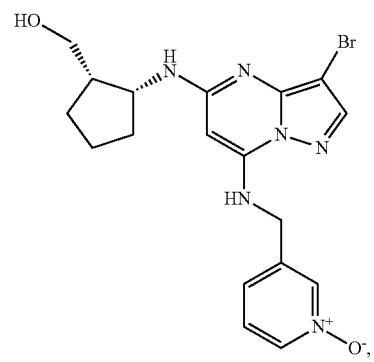
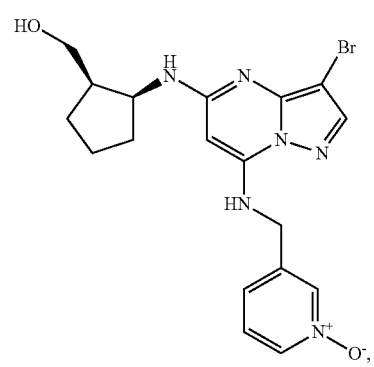
1654
-continued
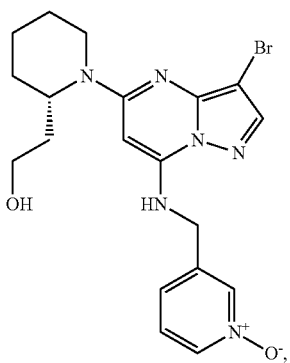
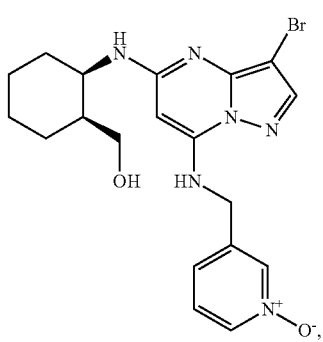
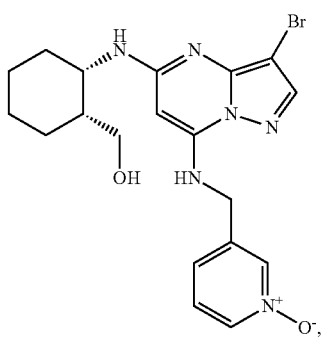

1655
-continued
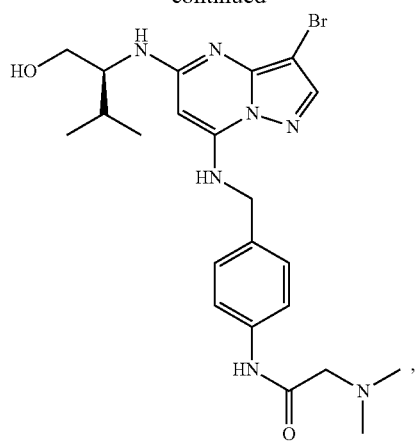
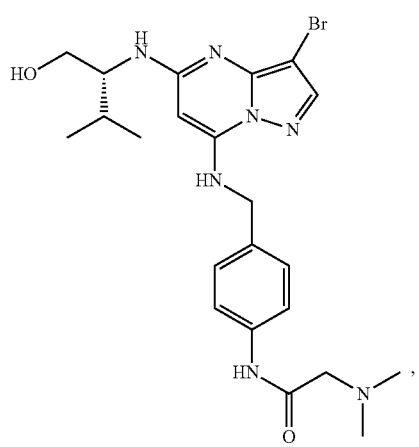
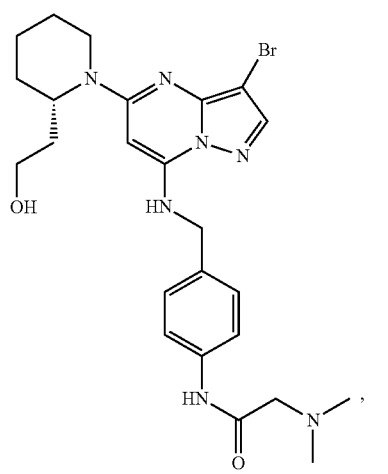
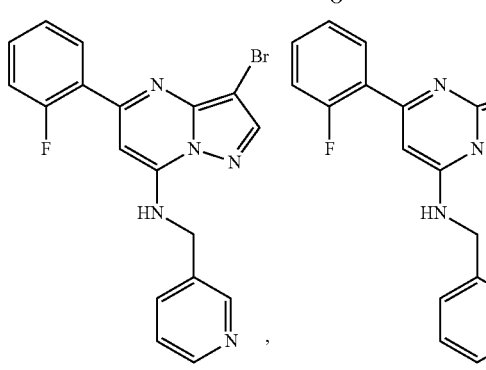
1656
-continued
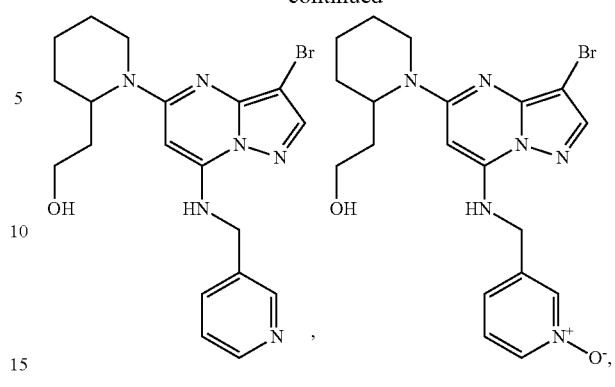
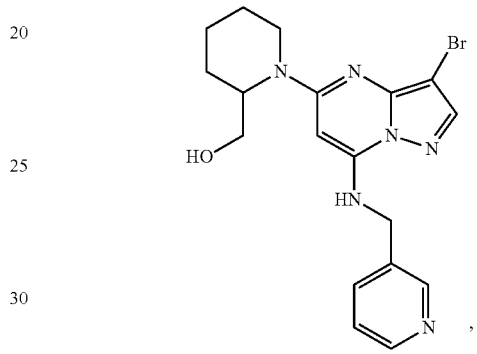
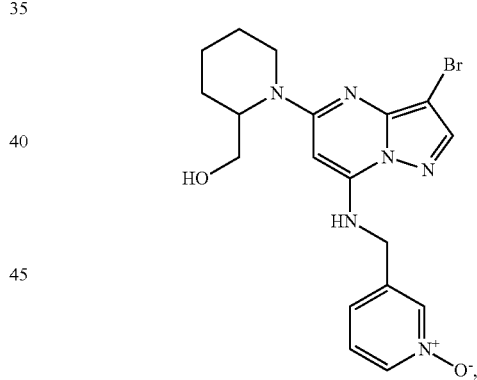
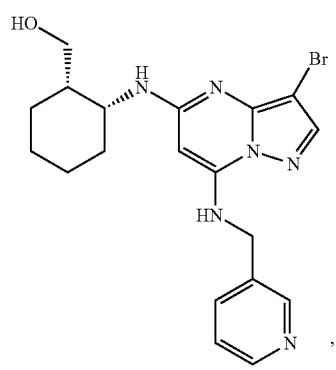

-continued

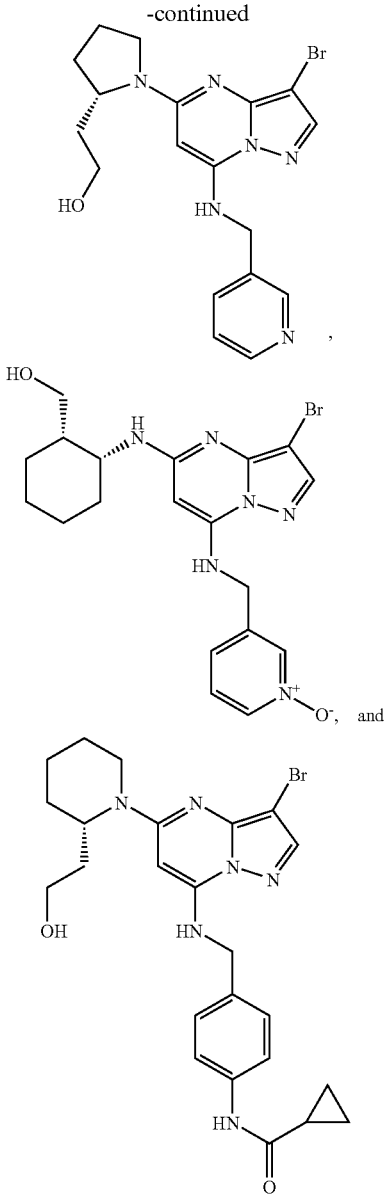

or a pharmaceutically acceptable salt thereof.

15. The method of claim 14 wherein said cancer being treated is chronic lymphocytic leukemia.

16. The method of claim 14 wherein said cancer being treated is acute myleogenous leukemia.

17. The method of claim 14 wherein said cancer being treated is acute lymphoblastic leukemia.

18. The method of claim 14 wherein said cancer being treated is mantle cell leukemia.

19. The method of claim 14 wherein said method further comprises administering at least one anti-cancer agent.

20. The method of claim 19 wherein said anti-cancer agent is selected from the group consisting of a cytostatic agent, cisplatin, doxorubicin, pegylated liposomal doxorubicin, liposomal doxorubicin, doxorubicin liposomal, docetaxel, paclitaxel, etoposide, irinotecan, topotecan, epothilones, tamoxifen, 5-fluorouracil, methoxtrexate, temozolomide, cyclophosphamide, 4-[2-[4-[(11R)-3,10-dibromo-8-chloro-6,11-dihydro-5H-benzo[5,6]cyclohepta[1,2-b]pyridin-11-yl-]-1-piperidinyl]-2-oxoethyl]-1-piperidinecarboxamide, tipifarnib, L778,123 (a farnesyl protein transferase inhibitor), BMS 214662 (a farnesyl protein transferase inhibitor), gefitinib, erlotinib, antibodies to EGFR, imatinib, interferon alfa-2b, ara-C, cytoxan, cyclophosphamide, gemcitabine, Uracil mustard, Chlormethine, Ifosfamide, Melphalan, Chlorambucil, Pipobroman, Triethylenemelamine, ispinesib, SB-743921, GSK-923295, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, Pentostatine, Vinblastine, Vincristine, Vindesine, Bleomycin, Dactinomycin, Daunorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, bevacizumab, trastuzumnab, tositumomab, bortezomib, ibritumomab, arsenic trioxide, Vinorelbine, Porfimer, cetuximab, Liposomal, Thiotepa, Altretamine, Melphalan, Lerozole, Fulvestrant, Exemestane, Ifosfomide, Rituximab, satriplatin, Gemtuzumab ozogamicin, pemetrexed, panitubimab, sunitinib, sorafenib, dastinib, nilotinib, lapatinib and alemtuzumab.

21. A method of treating chronic lymphocytic leukemia, acute myleogenous leukemia, acute lymphoblastic leukemia, or mantle cell lymphoma in a patient in need thereof comprising administering to said patient a composition comprising (i) the compound:

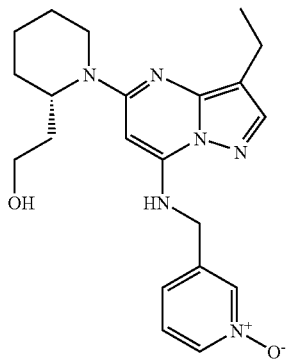 [SMILES: CCc1cnn2c(NCc3ccc[n+]([O-])c3)cc(N3CCCC[C@H]3CCO)nc12]

or a pharmaceutically acceptable salt thereof.

22. The method of claim 21 wherein said cancer is chronic lymphocytic leukemia.

23. The method of claim 21 wherein said cancer is acute myleogenous leukemia.

24. The method of claim 21 wherein said cancer is acute lymphoblastic leukemia.

25. The method of claim 21 wherein said cancer is mantle cell leukemia.

* * * * *